(12) United States Patent
Sekiguchi et al.

(10) Patent No.: US 7,544,690 B2
(45) Date of Patent: Jun. 9, 2009

(54) MCH RECEPTOR ANTAGONISTS

(75) Inventors: Yoshinori Sekiguchi, Tokyo (JP);
Kosuke Kanuma, Tokyo (JP);
Katsunori Omodera, Tokyo (JP);
Thuy-Anh Tran, San Diego, CA (US);
Bryan Aubrey Kramer, San Diego, CA (US); Nigel Robert Arnold Beeley, Solana Beach, CA (US)

(73) Assignee: Taisho Pharmaceutical Co., Ltd., Tokyo (JP)

( * ) Notice: Subject to any disclaimer, the term of this patent is extended or adjusted under 35 U.S.C. 154(b) by 642 days.

(21) Appl. No.: 10/490,996

(22) PCT Filed: Sep. 30, 2002

(86) PCT No.: PCT/US02/31059

§ 371 (c)(1),
(2), (4) Date: Aug. 3, 2004

(87) PCT Pub. No.: WO03/028641

PCT Pub. Date: Apr. 10, 2003

(65) Prior Publication Data

US 2007/0037836 A1 Feb. 15, 2007

Related U.S. Application Data

(60) Provisional application No. 60/326,758, filed on Oct. 2, 2001, provisional application No. 60/326,463, filed on Oct. 1, 2001.

(51) Int. Cl.
*C07D 239/95* (2006.01)
*C07D 403/12* (2006.01)
*A61K 31/517* (2006.01)
*A61K 31/5377* (2006.01)
*A61P 3/04* (2006.01)
*A61P 25/22* (2006.01)
*A61P 25/24* (2006.01)

(52) U.S. Cl. .............. 514/266.1; 514/231.5; 544/291; 544/111

(58) Field of Classification Search ............ 544/291, 544/111; 514/266.1, 231.5
See application file for complete search history.

(56) References Cited

FOREIGN PATENT DOCUMENTS

WO WO 92/07844 5/1992
WO WO 97/20823 A2 6/1997
WO WO 97/20822 * 12/1997

OTHER PUBLICATIONS

Kowalski et al. Expert Opin. Investig. Drugs 13(9), 1113-1122, 2004.*
Nahon, C. R. Biologies, 329, 623-638, 2006.*
Elslager et al., Journal of Medicinal Chemistry, 24(2), 127-140, 1981.*
Yukio Shimomura, et al., "Isolation and Identification of Melanin-Concentrating Hormone as the Endogenous Ligand of the SLC-1 Receptor," Biochemical and Biophysical Research Communications, Aug. 11, 1999, pp. 622-626, vol. 261, No. 3, Aug. 11, 1999.
Yumiko Saito, et al., "Melanin-concentrating Hormone Receptor: An Orphan Receptor Fits the Key," TEM, 2000, pp. 299-3-03, vol. 11, No. 8.
Beth Borowsky, et al., "Antidepressant, anxiolytic and anorectic effects of melanin-concentrating hormone-1 receptor antagonist," Nature Medicine, Aug. 2002, pp. 825-830, vol. 8., No. 8.
Masako Shimada, et al., "Mice lacking melanin-concentrating hormone and hypophagic and lean," Nature, Dec. 17, 1998, pp. 670-674, vol. 396.
Jay C. Erickson, et al., Sensitivity to leptin and susceptibility to seizures of mice lacking neuropeptide Y, Nature, May 30, 1996, pp. 415-418, vol. 381.
Thierry Pedrazzini, "Cardiovascular response, feeding behavior and locomotor activity in mice lacking the NPY Y1 receptor," Nature Medicine, Jun. 1998, pp. 722-726, vol. 4, No. 6.
Donald J. Marsh, et al., "Role of the Y5 neuropeptide Y receptor in feeding and obesity," Nature Medicine, Jun. 1988, pp. 718-721, vol. 4, No. 6.
Health Implications of Obesity, "National Institutes of Health Consensus Development Conference Statement," (online), originally published Feb. 1985, pp. 1-7, vol. 5, No. 9.
KM Flegal, MD, "Overweight and Obesity in the United States: prevalence and trends," International Journal of Obesity, 1998, pp. 39-47, vol. 22.
Patsy M. Nishina, et al., "Atherosclerosis in Genetically Obese Mice: The Mutants Obese, Diabetes, Fat, Tubby, and Lethal Yellow," Metabolism, May 1994, pp. 554-558, vol. 43, No. 5.

* cited by examiner

*Primary Examiner*—Venkataraman Balasubram
(74) *Attorney, Agent, or Firm*—Sughrue Mion, PLLC

(57) ABSTRACT

The present invention relates to novel compounds of the formula (I) which act as MCH receptor antagonists. These compositions are useful in pharmaceutical compositions whose use includes prophylaxis or treatment of obesity, obesity related disorders, anxiety, or depression.

4 Claims, 1 Drawing Sheet

SEQUENCE LISTING

```
<160> NUMBER OF SEQ ID NOS: 12

<210> SEQ ID NO 1
<211> LENGTH: 30
<212> TYPE: DNA
<213> ORGANISM: Artificial Sequence
<220> FEATURE:
<223> OTHER INFORMATION: PCR primer

<400> SEQUENCE: 1
gtgaagcttg cctctggtgc ctgcaggagg                              30

<210> SEQ ID NO 2
<211> LENGTH: 31
<212> TYPE: DNA
<213> ORGANISM: Artificial Sequence
<220> FEATURE:
```

```
<223> OTHER INFORMATION: PCR primer

<400> SEQUENCE: 2
gcagaattcc cggtggcgtg ttgtggtgcc c                            31

<210> SEQ ID NO 3
<211> LENGTH: 24
<212> TYPE: DNA
<213> ORGANISM: Artificial Sequence
<220> FEATURE:
<223> OTHER INFORMATION: PCR primer

<400> SEQUENCE: 3
catgagctgg tggatcatga aggg                                    24

<210> SEQ ID NO 4
<211> LENGTH: 24
<212> TYPE: DNA
<213> ORGANISM: Artificial Sequence
<220> FEATURE:
<223> OTHER INFORMATION: PCR primer

<400> SEQUENCE: 4
atgaagggca tgcccaggag aaag                                    24

<210> SEQ ID NO 5
<211> LENGTH: 1349
<212> TYPE: DNA
<213> ORGANISM: Artificial Sequence
<220> FEATURE:
<223> OTHER INFORMATION: Mutant MCH receptor

<400> SEQUENCE: 5
atggacctgg aagcctcgct gctgcccact ggtcccaatg ccagcaacac ctctgatggc     60
cccgataacc tcacttcggc aggatcacct cctcgcacgg ggagcatctc ctacatcaac    120
atcatcatgc cttcggtgtt cggcaccatc tgcctcctgg gcatcatcgg aactccacg     180 gtcatcttcg cggtcgtgaa gaagtccaag ctgcactggt gcaacaacgt ccccgacatc    240
ttcatcatca acctctcggt agtagatctc ctctttctcc tgggcatgcc cttcatgatc    300
caccagctca tgggcaatgg ggtgtggcac tttggggaga ccatgtgcac cctcatcacg    360
gccatggatg ccaatagtca gttcaccagc acctacatcc tgaccgccat ggccattgac    420
cgctacctgg ccactgtcca ccccatctct ccacgaagt tccggaagcc ctctgtggcc    480
accctggtga tctgcctcct gtgggccctc ccttcatca gcatccccc tgtgtggctg     540 tatgccagac tcatcccctt ccaggaggt gcagtgggct gcggcatacg cctgcccaac    600
ccagacactg acctctactg gttcacccctg taccagtttt tcctggcctt tgccctgcct   660
tttgtggtca tcacagccgc atacgtgagg atcctgcaga aggtgaagtc ctctggaatc    720
cgagtgggct cctctaagag gaagaagtct gagaagaagg tcacccgcac agccatcgcc    780
atctgtctgg tcttctttgt gtgctgggca ccctactatg tgctacagct gacccagttg    840
tccatcagcc gcccgaccct cacctttgtc tacttataca tgcgggccat cagcttgggc    900
tatgccaaca gctgcctcaa ccccttgtg tacatcgtgc tctgtgagac gttccgcaaa    960
cgcttggtcc tgtcggtgaa gcctgcagcc caggggcagc ttcgcgctgt cagcaacgct   1020
cagacggctg acgaggagag gacagaaagc aaaggcacct gatacttccc ctgccaccct   1080
gcacacctcc aagtcagggc accaacacac gccaccggga gagatgctga gaaaaaccca   1140
agaccgctcg ggaaatgcag gaaggccggg ttgtgagggg ttgttgcaat gaaataaata   1200
```

```
cattccatgg gctcacacgt tgctggggag gcctggagtc aggtttgggg ttttcagata    1260
tcagaaatcc cttgggggag caggatgaga cctttggata aacagaagc tgagcaagag     1320 aacatgttgg tttggataac cggttgcac                                      1349
```

<210> SEQ ID NO 6
<211> LENGTH: 353
<212> TYPE: PRT
<213> ORGANISM: Artificial Sequence
<220> FEATURE:
<223> OTHER INFORMATION: Mutant MCH receptor

<400> SEQUENCE: 6

```
Met Asp Leu Glu Ala Ser Leu Leu Pro Thr Gly Pro Asn Ala Ser Asn
1               5                   10                  15

Thr Ser Asp Gly Pro Asp Asn Leu Thr Ser Ala Gly Ser Pro Pro Arg
            20                  25                  30

Thr Gly Ser Ile Ser Tyr Ile Asn Ile Ile Met Pro Ser Val Phe Gly
        35                  40                  45

Thr Ile Cys Leu Leu Gly Ile Ile Gly Asn Ser Thr Val Ile Phe Ala
    50                  55                  60

Val Val Lys Lys Ser Lys Leu His Trp Cys Asn Asn Val Pro Asp Ile
65                  70                  75                  80

Phe Ile Ile Asn Leu Ser Val Val Asp Leu Leu Phe Leu Leu Gly Met
                85                  90                  95

Pro Phe Met Ile His Gln Leu Met Gly Asn Gly Val Trp His Phe Gly
            100                 105                 110

Glu Thr Met Cys Thr Leu Ile Thr Ala Met Asp Ala Asn Ser Gln Phe
        115                 120                 125

Thr Ser Thr Tyr Ile Leu Thr Ala Met Ala Ile Asp Arg Tyr Leu Ala
    130                 135                 140

Thr Val His Pro Ile Ser Ser Thr Lys Phe Arg Lys Pro Ser Val Ala
145                 150                 155                 160

Thr Leu Val Ile Cys Leu Leu Trp Ala Leu Ser Phe Ile Ser Ile Thr
                165                 170                 175

Pro Val Trp Leu Tyr Ala Arg Leu Ile Pro Phe Pro Gly Gly Ala Val
            180                 185                 190

Gly Cys Gly Ile Arg Leu Pro Asn Pro Asp Thr Asp Leu Tyr Trp Phe
        195                 200                 205

Thr Leu Tyr Gln Phe Phe Leu Ala Phe Ala Leu Pro Phe Val Val Ile
    210                 215                 220

Thr Ala Ala Tyr Val Arg Ile Leu Gln Lys Val Lys Ser Ser Gly Ile
225                 230                 235                 240

Arg Val Gly Ser Ser Lys Arg Lys Ser Glu Lys Lys Val Thr Arg
                245                 250                 255

Thr Ala Ile Ala Ile Cys Leu Val Phe Phe Val Cys Trp Ala Pro Tyr
            260                 265                 270

Tyr Val Leu Gln Leu Thr Gln Leu Ser Ile Ser Arg Pro Thr Leu Thr
        275                 280                 285

Phe Val Tyr Leu Tyr Asn Ala Ala Ile Ser Leu Gly Tyr Ala Asn Ser
    290                 295                 300

Cys Leu Asn Pro Phe Val Tyr Ile Val Leu Cys Glu Thr Phe Arg Lys
305                 310                 315                 320

Arg Leu Val Leu Ser Val Lys Pro Ala Ala Gln Gly Gln Leu Arg Ala
                325                 330                 335
```

```
Val Ser Asn Ala Gln Thr Ala Asp Glu Glu Arg Thr Glu Ser Lys Gly
            340                 345                 350

Thr

<210> SEQ ID NO 7
<211> LENGTH: 70
<212> TYPE: DNA
<213> ORGANISM: Artificial Sequence
<220> FEATURE:
<223> OTHER INFORMATION: PCR primer

<400> SEQUENCE: 7
gatcctgcag aaggtgaagt cctctggaat ccgagtgggc tcctctaaga ggaagaagtc    60
tgagaagaag                                                          70

<210> SEQ ID NO 8
<211> LENGTH: 71
<212> TYPE: DNA
<213> ORGANISM: Artificial Sequence
<220> FEATURE:
<223> OTHER INFORMATION: PCR primer

<400> SEQUENCE: 8
gtgaccttct tctcagactt cttcctctta gaggagccca ctcggattcc agaggacttc    60
accttctgca g                                                        71

<210> SEQ ID NO 9
<211> LENGTH: 30
<212> TYPE: DNA
<213> ORGANISM: Artificial Sequence
<220> FEATURE:
<223> OTHER INFORMATION: PCR primer

<400> SEQUENCE: 9
gtgaagcttg cccgggcagg atggacctgg                                    30

<210> SEQ ID NO 10
<211> LENGTH: 24
<212> TYPE: DNA
<213> ORGANISM: Artificial Sequence
<220> FEATURE:
<223> OTHER INFORMATION: PCR primer

<400> SEQUENCE: 10
atctagaggt gcctttgctt tctg                                          24

<210> SEQ ID NO 11
<211> LENGTH: 2133
<212> TYPE: DNA
<213> ORGANISM: Homo Sapiens

<400> SEQUENCE: 11
atggacctgg aagcctcgct gctgcccact ggtcccaatg ccagcaacac ctctgatggc    60
cccgataacc tcacttcggc aggatcacct cctcgcacgg ggagcatctc ctacatcaac   120
atcatcatgc cttcggtgtt cggcaccatc tgcctcctgg gcatcatcgg aactccacg    180 gtcatcttcg cggtcgtgaa gaagtccaag ctgcactggt gcaacaacgt ccccgacatc   240
ttcatcatca acctctcggt agtagatctc ctctttctcc tgggcatgcc cttcatgatc   300
caccagctca tgggcaatgg ggtgtggcac tttgggggaga ccatgtgcac cctcatcacg   360
gccatggatg ccaatagtca gttcaccagc acctacatcc tgaccgccat ggccattgac   420
```

```
cgctacctgg ccactgtcca ccccatctct tccacgaagt tccggaagcc ctctgtggcc      480
accctggtga tctgcctcct gtgggccctc tccttcatca gcatcacccc tgtgtggctg      540
tatgccagac tcatcccctt cccaggaggt gcagtgggct gcggcatacg cctgcccaac      600
ccagacactg acctctactg gttcaccctg taccagtttt tcctggcctt tgccctgcct      660
tttgtggtca tcacagccgc atacgtgagg atcctgcagc gcatgacgtc tcagtggcc       720 cccgcctccc agcgcagcat ccggctgcgg acaaagaggg tgacccgcac agccatcgcc      780
atctgtctgg tcttctttgt gtgctgggca ccctactatg tgctacagct gacccagttg      840
tccatcagcc gcccgaccct cacctttgtc tacttataca atgcggccat cagcttgggc      900
tatgccaaca gctgcctcaa ccccttttgtg tacatcgtgc tctgtgagac gttccgcaaa      960
cgcttggtcc tgtcggtgaa gcctgcagcc caggggcagc ttcgcgctgt cagcaacgct     1020
cagacggctg acgaggagag gacagaaagc aaaggcacct ctagaatggg ctgcacactg     1080
agcgctgagg acaaggcggc cgtggagcgc agcaagatga tcgaccgcaa cctccgggag     1140
gacggagaga aggcagcgcg cgaggtcaag ctgctgctgc tgggtgctgg tgaatccggg     1200
aagagcacaa ttgtgaagca gatgaaaatt atccacgagg ctggctactc agaggaagag     1260
tgtaagcagt acaaagcagt ggtctacagc aacaccatcc agtccatcat tgccatcatt     1320
agagccatgg ggagattgaa aatcgacttt ggagacgctg ctcgtgcgga tgatgctcgc     1380
caactcttcg tgcttgctgg ggctgcagag aaggcttta tgaccgcgga gctcgccggc     1440
gtcataaaga gactgtggaa ggacagcggt gtgcaagcct gcttcaacag atcccgggag     1500
taccagctga cgattcggc ggcgtactac ctgaatgact tggacagaat agcacaacca     1560
aattacatcc caacccagca ggatgttctc agaactagtg tgaaaacgac gggaattgtg     1620
gaaacccact ttactttcaa agatcttcat tttaaaatgt ttgacgtggg aggccagaga     1680
tcagagcgga agaagtggat tcactgcttt gaaggcgtga ctgccatcat cttctgtgtg     1740
gccctgagtg actatgacct ggttcttgct gaggatgaag aaatgaaccg gatgcatgaa     1800
agcatgaagc tgttcgatag catatgtaac aacaagtggt ttacggacac atccatcatc     1860
cttttcctga acaagaagga cctcttcgaa gagaagatca aaagagtcc cctcacgata      1920 tgctatccag aatatgcagg ctcaaacaca tatgaagagg cggctgcgta tatccagtgt     1980
cagtttgaag acctcaataa aggaaggac acaaggaaaa tttacaccca cttcacttgc     2040
gccacggata cgaagaatgt gcagtttgtg ttcgatgctg taacggacgt catcataaag     2100
aataacctaa aagactgtgg tctcttctaa tct                                   2133
```

<210> SEQ ID NO 12
<211> LENGTH: 709
<212> TYPE: PRT
<213> ORGANISM: Homo sapiens

<400> SEQUENCE: 12

```
Met Asp Leu Glu Ala Ser Leu Leu Pro Thr Gly Pro Asn Ala Ser Asn
1               5                   10                  15

Thr Ser Asp Gly Pro Asp Asn Leu Thr Ser Ala Gly Ser Pro Pro Arg
            20                  25                  30

Thr Gly Ser Ile Ser Tyr Ile Asn Ile Ile Met Pro Ser Val Phe Gly
        35                  40                  45

Thr Ile Cys Leu Leu Gly Ile Ile Gly Asn Ser Thr Val Ile Phe Ala
    50                  55                  60
```

-continued

```
Val Val Lys Lys Ser Lys Leu His Trp Cys Asn Asn Val Pro Asp Ile
 65                  70                  75                  80

Phe Ile Ile Asn Leu Ser Val Val Asp Leu Phe Leu Leu Gly Met
                 85                  90                  95

Pro Phe Met Ile His Gln Leu Met Gly Asn Gly Val Trp His Phe Gly
            100                 105                 110

Glu Thr Met Cys Thr Leu Ile Thr Ala Met Asp Ala Asn Ser Gln Phe
            115                 120                 125

Thr Ser Thr Tyr Ile Leu Thr Ala Met Ala Ile Asp Arg Tyr Leu Ala
        130                 135                 140

Thr Val His Pro Ile Ser Ser Thr Lys Phe Arg Lys Pro Ser Val Ala
145                 150                 155                 160

Thr Leu Val Ile Cys Leu Leu Trp Ala Leu Ser Phe Ile Ser Ile Thr
                165                 170                 175

Pro Val Trp Leu Tyr Ala Arg Leu Ile Pro Phe Pro Gly Gly Ala Val
            180                 185                 190

Gly Cys Gly Ile Arg Leu Pro Asn Pro Asp Thr Asp Leu Tyr Trp Phe
        195                 200                 205

Thr Leu Tyr Gln Phe Phe Leu Ala Phe Ala Leu Pro Phe Val Val Ile
    210                 215                 220

Thr Ala Ala Tyr Val Arg Ile Leu Gln Arg Met Thr Ser Ser Val Ala
225                 230                 235                 240

Pro Ala Ser Gln Arg Ser Ile Arg Leu Arg Thr Lys Arg Val Thr Arg
                245                 250                 255

Thr Ala Ile Ala Ile Cys Leu Val Phe Phe Val Cys Trp Ala Pro Tyr
            260                 265                 270

Tyr Val Leu Gln Leu Thr Gln Leu Ser Ile Ser Arg Pro Thr Leu Thr
        275                 280                 285

Phe Val Tyr Leu Tyr Asn Ala Ala Ile Ser Leu Gly Tyr Ala Asn Ser
    290                 295                 300

Cys Leu Asn Pro Phe Val Tyr Ile Val Leu Cys Glu Thr Phe Arg Lys
305                 310                 315                 320

Arg Leu Val Leu Ser Val Lys Pro Ala Ala Gln Gly Gln Leu Arg Ala
                325                 330                 335

Val Ser Asn Ala Gln Thr Ala Asp Glu Glu Arg Thr Glu Ser Lys Gly
            340                 345                 350

Thr Ser Arg Met Gly Cys Thr Leu Ser Ala Glu Asp Lys Ala Ala Val
        355                 360                 365

Glu Arg Ser Lys Met Ile Asp Arg Asn Leu Arg Glu Asp Gly Glu Lys
    370                 375                 380

Ala Ala Arg Glu Val Lys Leu Leu Leu Leu Gly Ala Gly Glu Ser Gly
385                 390                 395                 400

Lys Ser Thr Ile Val Lys Gln Met Lys Ile Ile His Glu Ala Gly Tyr
                405                 410                 415

Ser Glu Glu Glu Cys Lys Gln Tyr Lys Ala Val Val Tyr Ser Asn Thr
            420                 425                 430

Ile Gln Ser Ile Ile Ala Ile Arg Ala Met Gly Arg Leu Lys Ile
        435                 440                 445

Asp Phe Gly Asp Ala Ala Arg Ala Asp Asp Ala Arg Gln Leu Phe Val
    450                 455                 460

Leu Ala Gly Ala Ala Glu Glu Gly Phe Met Thr Ala Glu Leu Ala Gly
465                 470                 475                 480

Val Ile Lys Arg Leu Trp Lys Asp Ser Gly Val Gln Ala Cys Phe Asn
```

-continued

|   |   |   |   | 485 |   |   |   | 490 |   |   |   | 495 |
|---|---|---|---|---|---|---|---|---|---|---|---|---|
| Arg | Ser | Arg | Glu | Tyr | Gln | Leu | Asn | Asp | Ser | Ala | Ala | Tyr | Tyr | Leu | Asn |
| | | | 500 | | | | | 505 | | | | 510 | | | |
| Asp | Leu | Asp | Arg | Ile | Ala | Gln | Pro | Asn | Tyr | Ile | Pro | Thr | Gln | Gln | Asp |
| | | | 515 | | | | | 520 | | | | 525 | | | |
| Val | Leu | Arg | Thr | Arg | Val | Lys | Thr | Thr | Gly | Ile | Val | Glu | Thr | His | Phe |
| | | 530 | | | | | 535 | | | | | 540 | | | |
| Thr | Phe | Lys | Asp | Leu | His | Phe | Lys | Met | Phe | Asp | Val | Gly | Gly | Gln | Arg |
| 545 | | | | | 550 | | | | | 555 | | | | | 560 |
| Ser | Glu | Arg | Lys | Lys | Trp | Ile | His | Cys | Phe | Glu | Gly | Val | Thr | Ala | Ile |
| | | | | 565 | | | | | 570 | | | | | 575 | |
| Ile | Phe | Cys | Val | Ala | Leu | Ser | Asp | Tyr | Asp | Leu | Val | Leu | Ala | Glu | Asp |
| | | | 580 | | | | | 585 | | | | | 590 | | |
| Glu | Glu | Met | Asn | Arg | Met | His | Glu | Ser | Met | Lys | Leu | Phe | Asp | Ser | Ile |
| | | | 595 | | | | | 600 | | | | | 605 | | |
| Cys | Asn | Asn | Lys | Trp | Phe | Thr | Asp | Thr | Ser | Ile | Ile | Leu | Phe | Leu | Asn |
| | | 610 | | | | | 615 | | | | | 620 | | | |
| Lys | Lys | Asp | Leu | Phe | Glu | Glu | Lys | Ile | Lys | Lys | Ser | Pro | Leu | Thr | Ile |
| 625 | | | | | 630 | | | | | 635 | | | | | 640 |
| Cys | Tyr | Pro | Glu | Tyr | Ala | Gly | Ser | Asn | Thr | Tyr | Glu | Glu | Ala | Ala | Ala |
| | | | | 645 | | | | | 650 | | | | | 655 | |
| Tyr | Ile | Gln | Cys | Gln | Phe | Glu | Asp | Leu | Asn | Lys | Arg | Lys | Asp | Thr | Lys |
| | | | | 660 | | | | | 665 | | | | | 670 | |
| Glu | Ile | Tyr | Thr | His | Phe | Thr | Cys | Ala | Thr | Asp | Thr | Lys | Asn | Val | Gln |
| | | | 675 | | | | | 680 | | | | | 685 | | |
| Phe | Val | Phe | Asp | Ala | Val | Thr | Asp | Val | Ile | Ile | Lys | Asn | Asn | Leu | Lys |
| | | | 690 | | | | | 695 | | | | | 700 | | |
| Asp | Cys | Gly | Leu | Phe |
| 705 | | | | |

MCH RECEPTOR ANTAGONISTS

This application is a 371 of PCT/US02/31059 Sep. 30, 2002, which claims priority to United States Provisional Application 60/326463, filed Oct. 1, 2001 and to United States Provisional Application 60/326758, filed Oct. 2, 2001.

FIELD OF THE INVENTION

The present invention relates to compounds which act as antagonists for MCH receptors and to the use of these compounds in pharmaceutical compositions.

BACKGROUND OF THE INVENTION

Melanin Concentrating Hormone (MCH), a cyclic peptide, has been identified as the endogenous ligand of the orphan G-protein coupled receptor SLC-1. See, for example, Shimomura et al., Biochem. Biophys. Res. Commun. 261, 622-26 (1999). Studies have indicated that MCH acts as a neurotransmitter/neuromodulator to alter a number of behavioral responses such as feeding habits. For example, injection of MCH into rats has been reported to increase their consumption of food. Reports indicate that genetically engineered mice which lack MCH show lower body weight and increased metabolism. See Saito et al., TEM, vol. 11, 299 (2000). As such, the literature suggests that discovery of MCH antagonists that interact with SCL-1 expressing cells will be useful in developing obesity treatments. See Shimomura et al., Biochem. Biophys. Res. Commun. 261, 622-26 (1999).

G protein-coupled receptors (GPCRs) share a common structural motif. All these receptors have seven sequences of between 22 to 24 hydrophobic amino acids that form seven alpha helices, each of which spans the membrane. The fourth and fifth transmembrane helices are joined on the extracellular side of the membrane by a strand of amino acids that forms a relatively large loop. Another larger loop, composed primarily of hydrophilic amino acids, joins transmembrane helices five and six on the intracellular side of the membrane. The carboxy terminus of the receptor lies intracellularly, and the amino terminus lies in the extracellular space. It is thought that the loop joining helices five and six, as well as the carboxy terminus, interact with the G protein. Currently, Gq, Gs, Gi, and Go are G proteins that have been identified as possible proteins that interact with the receptor.

Under physiological conditions, GPCRs exist in the cell membrane in equilibrium between two different states or conformations: an "inactive" state and an "active" state. A receptor in an inactive state is unable to link to the intracellular transduction pathway to produce a biological response. Changing the receptor conformation to the active state allows linkage to the transduction pathway and produces a biological response.

A receptor may be stabilized in an active state by an endogenous ligand or an exogenous agonist ligand. Recent discoveries, including but not exclusively limited to, modifications to the amino acid sequence of the receptor, provide alternative mechanisms other than ligands to stabilize the active state conformation. These approaches effectively stabilize the receptor in an active state by simulating the effect of a ligand binding to the receptor. Stabilization by such ligand-independent approaches is termed "constitutive receptor activation." In contrast, antagonists can competitively bind to the receptor at the same site as agonists, but do not activate the intracellular response initiated by the active form of the receptor, and therefore inhibit the intracellular responses by agonists.

Certain 2-aminoquinazoline derivatives have been reported to be NPY antagonists which are said to be effective in the treatment of disorders and diseases associated with the NPY receptor subtype Y5. See WO 97/20823. Quinazoline derivatives have also been found to be useful by enhancing antitumor activity. See WO 92/07844.

Recently, our current knowledge of human obesity has advanced dramatically. Previously, obesity was viewed as an oppugnant behavior of inappropriate eating in the setting of appealing foods. Studies of animal models of obesity, biochemical alterations in both humans and animals, and the complex interactions of psychosocial and cultural factors that create receptiveness to human obesity indicate that this disease in humans is multifaceted and deeply entrenched in biologic systems. Thus, it is almost certain that obesity has multiple causes and that there are different types of obesity. Not only does MCHR1 antagonist have potent and durable anti-obesity effects in rodents, it has surprising antidepressant and anxiolytic properties as well (Borowsky et al., Nature Medicine, 8, 825-830, 2002). MCHR1 antagonists have been reported to show antidepressant and anxiolytic activities in rodent models such as social interaction, forced swimming test and ultrasonic vocalization. These findings indicate that MCHR1 antagonists could be useful for treatment of obesity patients with multiple causes. Moreover, MCHR1 antagonists could be used to treat subjects not only with obesity, but also those with depression and anxiety. These advantages make it different from NPY receptor antagonists, with which anxiogenic-like activity may be expected, as NPY itself has anxiolytic-like effect.

Obesity is also regarded as a chronic disease and the possibly of long-term treatment is a concept that is receiving more attention. In this context, it is noteworthy that the depletion of MCH leads to hypophagia as well as leanness (Shimada et al., Nature, 396, 670-674, 1998). By contrast, NPY (Erickson et al., Nature, 381, 415-418, 1996), as well as the Y1 (Pedrazzini et al., Nature Medicine, 4, 722-726, 1998) and Y5 receptors (Marsh et al., Nature Medicine, 4, 718-721, 1998), disrupted mice maintained a stable body weight or rather became obese. Considering the above reports, MCHR1 antagonists may be more attractive than Y1 or Y5 receptor antagonists in terms of long-term treatment of obese patients.

An increasing number of children and adolescents are overweight. Although not all overweight children will necessarily become overweight adults, the growing occurrence of obesity in childhood is likely to be reflected in increasing obesity in adult years. The high prevalence of obesity in our adult population and the likelihood that the nation of the future will be even more obese demands a re-examination of the health implications of this disease. See, Health Implications of Obesity. NIH Consens. Statement Online 1985 Feb. 11-13; 5(9):1-7.

"Clinical obesity" is a measurement of the excess body fat relative to lean body mass and is defined as a body weight more than 20% above the ideal body weight. Recent estimates suggest that 1 in 2 adults in the United States is clinically obese, an increase of more than 25% over the past decades. Flegal M. D. et al., 22 Int. J. Obes. Relat. Metab. Disor. 39 (1998). Both overweight conditions and clinical obesity are a major health concerns worldwide, in particular because clinical obesity is often accompanied by numerous complications, i.e., hypertension and Type II diabetes, which in turn can cause coronary artery disease, stroke, late-stage complications of diabetes and premature death. (See, e.g., Nishina P. M. et al., 43 Metab. 554 (1994)).

Although the etiologic mechanisms underlying obesity require further clarification, the net effect of such mechanisms leads to an imbalance between energy intake and expenditure. Both genetic and environmental factors are likely to be involved in the pathogenesis of obesity. These include excess caloric intake, decreased physical activity, and metabolic and endocrine abnormalities.

Treatment of overweight conditions and clinical obesity via pharmaceutical agents are not only of importance with respect to the conditions themselves, but also with respect to the possibility of preventing other diseases that are associated with, e.g., clinical obesity, as well as enhancement of the positive feeling of "self" that often accompanies those who are overweight or clinically obese and who encounter a significant reduction in body weight. Given the foregoing discussion, it is apparent that compounds which help in the treatment of such disorders would be useful and would provide an advance in both research and clinical medicine. The present invention is directed to these, as well as other, important ends.

SUMMARY OF THE INVENTION

The present invention, in one aspect, relates to compounds represented by Formula I:

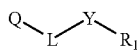
I or a pharmaceutically acceptable salt or prodrug thereof, wherein Q is

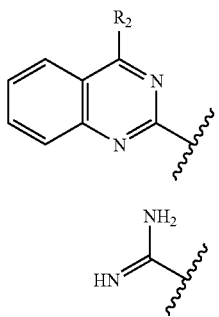

$R_1$ represents (i) $C_1$-$C_{16}$ alkyl,
$C_1$-$C_{16}$ alkyl substituted by substituent(s) independently selected from
  halogen,
  hydroxy,
  oxo,
  $C_1$-$C_3$ alkoxy,
  $C_1$-$C_3$ alkoxy substituted by substituent(s) independently selected from
    carbocyclic aryl,
    heterocyclyl,
    heterocyclyl substituted by $C_1$-$C_3$ alkyl,
  $C_1$-$C_3$ alkylcarbonyloxy,
  carbocyclyloxy,
  carbocyclic aryloxy,
  carbocyclic aryloxy substituted by substituent(s) independently selected from
    halogen,
    nitro,
    carbocyclic aryl,
    carbocyclic aryl substituted by $C_1$-$C_3$ alkoxy,
    $C_1$-$C_4$ alkyl,
    $C_1$-$C_4$ alkyl substituted by substituent(s) independently selected from
      oxo,
      mono- or di-$C_1$-$C_3$ alkylamino,
      mono- or di-$C_1$-$C_3$ alkylamino substituted by carbocyclic aryl,
      mono- or di-$C_1$-$C_3$ alkylamino substituted by halogenated carbocyclic aryl,
      carbocyclic arylcarbonylamino,
      halogenated carbocyclic arylcarbonylamino,
  heterocyclyloxy,
  heterocyclyloxy substituted by $C_1$-$C_3$ alkyl,
  substituted heterocyclyl-ethylideneaminooxy,
  $C_1$-$C_3$ alkoxycarbonyl,
  $C_1$-$C_3$ alkoxycarbonyl substituted by carbocyclic aryl,
  mono- or di-$C_1$-$C_3$ alkylaminocarbonyl,
  mono- or di-$C_1$-$C_3$ alkylamino,
  mono- or di-$C_1$-$C_3$ alkylamino substituted by substituent(s) independently selected from
    cyano,
    carbocyclic aryl,
    heterocyclyl,
  mono- or di-carbocyclic arylamino,
  mono- or di-carbocyclic arylamino substituted by substituent(s) independently selected from
    hydroxy,
    $C_1$-$C_3$ alkyl,
  $C_1$-$C_3$ alkylcalbonylamino,
  $C_1$-$C_3$ alkylcalbonylamino substituted by substituent(s) independently selected from
    $C_1$-$C_3$ alkylcalbonylamino,
    carbocyclic arylcalbonylamino,
    heterocyclyl,
  $C_1$-$C_4$ alkoxycalbonylamino,
  heterocyclyl calbonylamino,
  carbocyclic arylsulfonylamino,
  carbocyclic arylsulfonylamino substituted by substituent(s) independently selected from
    nitro,
    $C_1$-$C_3$ alkyl,
    mono- or di-$C_1$-$C_3$ alkylamino,
  $C_1$-$C_3$ alkylthio,
  $C_1$-$C_3$ alkylthio substituted by substituent(s) independently selected from
    mono- or di-carbocyclic arylaminocarbonyl,
    halogenated mono- or di-carbocyclic arylaminocarbonyl,
    mono- or di-carbocyclic arylamino,
    halogenated mono- or di-carbocyclic arylamino,
    carbocyclic aryl,
    carbocyclic aryl substituted by substituent(s) independently selected from
      halogen,
      $C_1$-$C_3$ alkoxy,
  carbocyclic arylthio,
  carbocyclic arylthio substituted by substituent(s) independently selected from
    halogen,
    $C_1$-$C_3$ alkyl,
  carbocyclic arylsulfonyl,
  halogenated carbocyclic arylsulfonyl,
  heterocyclylthio, heterocyclylthio substituted by substituent(s) independently selected from
  nitro,
  $C_1$-$C_3$ alkyl,
$C_3$-$C_6$ cycloalkyl,
$C_3$-$C_6$ cycloalkyl substituted by $C_1$-$C_3$ alkyl,
$C_3$-$C_6$ cycloalkenyl,
carbocyclyl,
carbocyclyl substituted by substituent(s) independently selected from
  halogen,
  $C_1$-$C_3$ alkyl,
  $C_1$-$C_3$ alkoxy,
  $C_2$-$C_3$ alkenyl,
  $C_2$-$C_3$ alkenyl substituted by carbocyclic aryl,
  $C_2$-$C_3$ alkenyl substituted by carbocyclic aryl substituted $C_1$-$C_3$ alkylsulfinyl,
carbocyclic aryl,
carbocyclic aryl substituted by substituent(s) independently selected from
  halogen,
  hydroxy,
  nitro,
  $C_1$-$C_4$ alkyl,
  $C_1$-$C_4$ alkyl substituted by substituent(s) independently selected from
    halogen,
    hydroxy,
    oxo
    carbocyclic aryl,
    heterocyclyl,
    mono- or di-carbocyclic arylamino,
    mono- or di-carbocyclic arylamino substituted by substituent(s) independently selected from
      halogen,
      nitro,
      $C_1$-$C_3$ alkyl,
      $C_1$-$C_3$ alkoxy,
      halogenated $C_1$-$C_3$ alkoxy,
  $C_1$-$C_4$ alkoxy,
  $C_1$-$C_4$ alkoxy substituted by substituent(s) independently selected from
    halogen,
    carbocyclic aryl,
  carbocyclic aryloxy,
  $C_1$-$C_3$ alkoxycarbonyl,
  $C_1$-$C_3$ alkylcarbonyloxy,
  mono- or di-$C_1$-$C_3$ alkylamino,
  mono- or di-carbocyclic arylamino,
  halogenated mono- or di-carbocyclic arylamino,
  mono- or di-carbocyclic arylaminocarbonyl,
  mono- or di-carbocyclic arylaminocarbonyl substituted by substituent(s) independently selected from
    halogen,
    nitro,
    $C_1$-$C_3$ alkyl,
    $C_1$-$C_3$ alkoxy,
    halogenated $C_1$-$C_3$ alkoxy,
  mercapto,
  $C_1$-$C_3$ alkylthio,
  halogenated $C_1$-$C_3$ alkylthio,
  $C_1$-$C_3$ alkylsulfonyl,
  $C_3$-$C_6$ cycloalkyl,
  carbocyclic aryl,
  heterocyclyl,
  heterocyclyl,
  heterocyclyl substituted by substituent(s) independently selected from
    hydroxy,
    $C_1$-$C_3$ alkyl,
    $C_1$-$C_3$ alkyl substituted by carbocyclic aryl,
    $C_1$-$C_3$ alkoxy,
    $C_1$-$C_3$ alkoxy substituted by carbocyclic aryl,
    carbocyclic aryl,
    halogenated carbocyclic aryl, (ii) $C_2$-$C_8$ alkenyl, $C_2$-$C_8$ alkenyl substituted by substituent(s) independently selected from
  halogen,
  oxo,
  $C_1$-$C_3$ alkoxy,
  $C_1$-$C_3$ alkoxy substituted by carbocyclic aryl,
  carbocyclic aryl,
  carbocyclic aryl substituted by substituent(s) independently selected from
    halogen,
    hydroxy,
    nitro,
    $C_1$-$C_3$ alkyl,
    halogenated $C_1$-$C_3$ alkyl,
    $C_1$-$C_3$ alkoxy,
    halogenated $C_1$-$C_3$ alkoxy,
  heterocyclyl,
  heterocyclyl substituted by substituent(s) independently selected from
    hydroxy,
    nitro,
    $C_1$-$C_3$ alkyl,
    $C_1$-$C_3$ alkoxy, (iii) $C_2$-$C_4$ alkynyl, $C_2$-$C_4$ alkynyl substituted by carbocyclic aryl, (iv) $C_3$-$C_6$ cycloalkyl, $C_3$-$C_6$ cycloalkyl substituted by substituent(s) independently selected from
  $C_1$-$C_3$ alkyl,
  $C_1$-$C_3$ alkyl substituted by substituent(s) independently selected from
    hydroxy,
    oxo,
    carbocyclic aryl,
    mono- or di-$C_1$-$C_3$ alkylamino,
    mono- or di-$C_1$-$C_3$ alkylamino substituted by carbocyclic aryl,
    carbocyclic arylcarbonylamino,
    carbocyclic aryl, (v) $C_3$-$C_6$ cycloalkeyl, $C_3$-$C_6$ cycloalkeyl substituted by $C_1$-$C_3$ alkyl, (vi) carbocyclyl, carbocyclyl substituted by substituent(s) independently selected from
  hydroxy,
  nitro, (vii) carbocyclic aryl, carbocyclic aryl substituted by substituent(s) independently selected from
  halogen, hydroxy,
cyano,
nitro,
$C_1$-$C_9$ alkyl,
$C_1$-$C_9$ alkyl substituted by substituent(s) independently selected from
  halogen,
  hydroxy,
  oxo,
  $C_1$-$C_3$ alkoxy,
  carbocyclic aryloxy,
  mono- or di-$C_1$-$C_3$ alkylamino-N-oxy,
  mono- or di-$C_1$-$C_3$ alkylamino,
  mono- or di-$C_1$-$C_3$ alkylamino substituted by carbocyclic aryl,
  mono- or di-carbocyclic arylamino,
  carbocyclylimino,
  carbocyclylimino substituted by carbocyclic aryl,
  mono- or di-carbocyclic arylamino,
  mono- or di-carbocyclic arylamino substituted by $C_1$-$C_3$ alkoxy,
  mono- or di-carbocyclic arylaminocarbonyl,
  mono- or di-carbocyclic arylaminocarbonyl substituted by $C_1$-$C_3$ alkoxy,
  carbocyclic aryl,
  carbocyclic aryl substituted by substituent(s) independently selected from
    halogen,
    $C_1$-$C_3$ alkyl,
    halogenated $C_1$-$C_3$ alkyl,
  heterocyclyl,
  heterocyclyl substituted by $C_1$-$C_3$ alkyl,
$C_2$-$C_3$ alkenyl,
$C_2$-$C_3$ alkenyl substituted by carbocyclic aryl,
$C_1$-$C_9$ alkoxy,
$C_1$-$C_9$ alkoxy substituted by substituent(s) independently selected from
  hydroxy,
  halogen,
  carboxy,
  mono- or di-$C_1$-$C_3$ alkylamino,
  carbocyclic aryl,
  halogenated carbocyclic aryl,
  heterocyclyl,
  heterocyclyl substituted by substituent(s) independently selected from
    halogen,
    heterocyclyl,
    heterocyclyl substituted by substituent(s) independently selected from
      halogen,
      $C_1$-$C_3$ alkyl,
      halogenated $C_1$-$C_3$ alkyl,
$C_2$-$C_3$ alkenyloxy,
$C_1$-$C_3$ alkylcarbonyloxy,
carbocyclic aryloxy,
carbocyclic aryloxy substituted by substituent(s) independently selected from
  halogen,
  nitro,
  $C_1$-$C_4$ alkyl,
  halogenated $C_1$-$C_4$ alkyl,
  $C_1$-$C_3$ alkoxy,
heterocyclyloxy,
heterocyclyloxy substituted by substituent(s) independently selected from
  halogen,
  $C_1$-$C_3$ alkyl,
  halogenated $C_1$-$C_3$ alkyl,
(carbocyclic aryl)S(O)$_2$O,
carboxy,
$C_1$-$C_3$ alkoxycarbonyl,
mono- or di-$C_1$-$C_3$ alkylaminocarbonyl,
mono- or di-$C_1$-$C_3$ alkylaminocarbonyl substituted by carbocyclic aryl,
mono- or di-carbocyclic arylaminocarbonyl,
mono- or di-carbocyclic arylaminocarbonyl substituted by $C_1$-$C_3$ alkyl,
amino,
mono- or di-$C_1$-$C_4$ alkylamino,
mono- or di-$C_1$-$C_4$ alkylamino substituted by cyano,
mono- or di-carbocyclic arylamino,
$C_1$-$C_3$ alkynylcarbonylamino,
$C_1$-$C_3$ alkynylcarbonylamino substituted by carbocyclic aryl,
carbocyclic arylsulfonylamino,
carbocyclic arylsulfonylamino substituted by $C_1$-$C_3$ alkyl,
(carbocyclic aryl)NHC(O)NH,
(carbocyclic aryl)NHC(O)NH substituted by $C_1$-$C_3$ alkoxy,
(carbocyclic aryl)NHC(O)NH substituted by haloganated $C_1$-$C_3$ alkoxy,
carbocyclic aryl diazo,
carbocyclic aryl diazo substituted by mono- or di-$C_1$-$C_3$ alkylamino,
$C_1$-$C_3$ alkylthio,
halogenated $C_1$-$C_3$ alkylthio,
carbocyclic arylthio,
carbocyclic arylthio substituted by substituent(s) independently selected from
  halogen,
  cyano,
  $C_1$-$C_3$ alkyl,
heterocyclylthio,
$C_1$-$C_3$ alkylsulfonyl,
mono- or di-$C_1$-$C_3$ alkylaminosulfonyl,
carbocyclic aryl,
carbocyclic aryl substituted by substituent(s) independently selected from
  $C_1$-$C_7$ alkyl,
  halogenated $C_1$-$C_7$ alkyl,
  heterocyclyl,
  heterocyclyl substituted by substituent(s) independently selected from
    $C_1$-$C_3$ alkyl,
    carbocyclic aryl,
    halogenated carbocyclic aryl, (viii) heterocyclyl, or heterocyclyl substituted by substituent(s) independently selected from
  halogen,
  hydroxy,
  cyano,
  nitro,
  $C_1$-$C_4$ alkyl,
  $C_1$-$C_4$ alkyl substituted by substituent(s) independently selected from
    halogen,
    hydroxy,
    oxo,
    $C_1$-$C_3$ alkylcarbonyloxy,
    carbocyclic arylcarbonylamino,
    halogenated carbocyclic arylcarbonylamino, $C_1$-$C_3$ alkoxycarbonyl,
$C_1$-$C_3$ alkylthio,
$C_1$-$C_3$ alkylthio substituted by carbocyclic aryl,
$C_1$-$C_3$ alkylthio substituted by halogenated carbocyclic aryl,
carbocyclic aryl,
carbocyclic aryl substituted by substituent(s) independently selected from
  halogen,
  nitro,
  heterocyclyl,
  heterocyclyl substituted by substituent(s) independently selected from
    halogen,
    $C_1$-$C_3$ alkyl,
    halogenated $C_1$-$C_3$ alkyl,
$C_1$-$C_3$ alkoxy,
$C_1$-$C_3$ alkoxy substituted by carbocyclic aryl,
carbocyclic aryloxy,
carbocyclic aryloxy substituted by substituent(s) independently selected from
  halogen,
  $C_1$-$C_3$ alkyl,
mono- or di-$C_1$-$C_3$ alkylamino,
$C_1$-$C_4$ alkylcarbonylamino,
$C_1$-$C_3$ alkylthio,
$C_1$-$C_3$ alkenylthio,
carbocyclic arylthio,
halogenated carbocyclic arylthio,
carbocyclic arylthio substituted by $C_1$-$C_3$ alkoxycarbonyl,
heterocyclylthio,
heterocyclylthio substituted by $C_1$-$C_3$ alkyl,
$C_1$-$C_3$ alkylsulfonyl,
carbocyclic arylsulfonyl,
halogenated carbocyclic arylsulfonyl,
carbocyclic arylsulfonyl substituted by $C_1$-$C_4$ alkyl,
$C_1$-$C_3$ alkoxycarbonyl,
carbocyclic aryl,
carbocyclic aryl substituted by substituent(s) independently selected from
  halogen,
  nitro,
  $C_1$-$C_3$ alkyl,
  halogenated $C_1$-$C_3$ alkyl,
  $C_1$-$C_3$ alkoxy,
  halogenated $C_1$-$C_3$ alkoxy,
  heterocyclyl,
  heterocyclyl substituted by substituent(s) independently selected from
    halogen,
    $C_1$-$C_3$ alkyl,
    halogenated $C_1$-$C_3$ alkyl,
    $C_1$-$C_3$ alkoxy,
    $C_1$-$C_3$ alkoxycarbonyl;
$R_2$ is —NHNH$_2$, —NHNHBoc, —N($R_{2a}$)($R_{2b}$), morpholino, 4-acetyl-piperazyl, or 4-phenyl-piperazyl;

wherein $R_{2a}$ is H or $C_1$-$C_3$ alkyl;

$R_{2b}$ is $C_1$-$C_4$ alkyl, $C_1$-$C_4$ alkyl substituted by substituent(s) independently selected from
  hydroxy,
  $C_1$-$C_3$ alkoxy,
  amino,
  —NHBoc,
  $C_3$-$C_6$ cycloalkyl,
  carbocyclic aryl,
  carbocyclic aryl substituted by substituent(s) independently selected from
    halogen,
    $C_1$-$C_3$ alkyl,
    $C_1$-$C_3$ alkoxy,
    —SO$_2$NH$_2$,
    heterocyclyl,
$C_3$-$C_6$ cycloalkyl, carbocyclic aryl, carbocyclic aryl substituted by substituent(s) independently selected from
  halogen,
  $C_1$-$C_3$ alkyl,
  $C_1$-$C_3$ alkoxy, or a group of Formula IV;

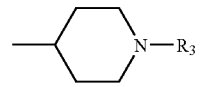

IV wherein Boc is carbamic acid tert-butyl ester and $R_3$ is $C_1$-$C_3$ alkyl or $C_1$-$C_3$ alkyl substituted by substituent(s) independently selected from
  carbocyclic aryl,
  halogenated carbocyclic aryl,
  carbocyclic aryl substituted by $C_1$-$C_3$ alkoxy;

L is selected from Formula V-XIX;

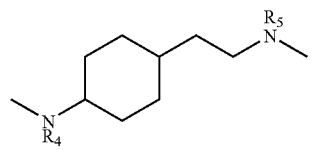

V

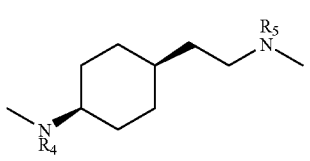

Va

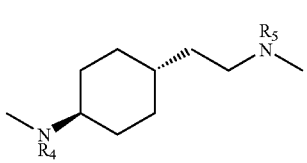

Vb

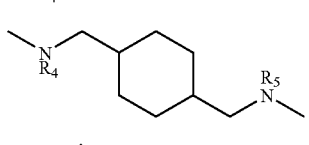

VI

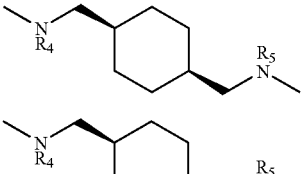

VIa

VIb

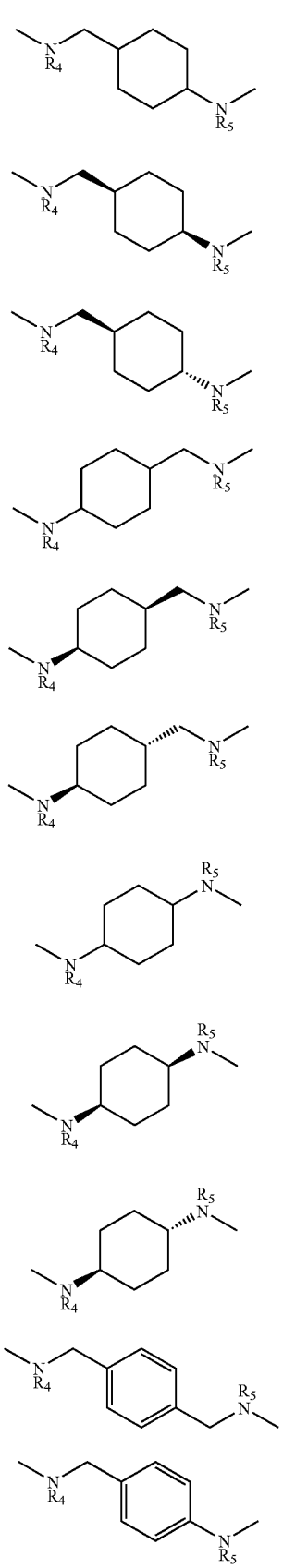
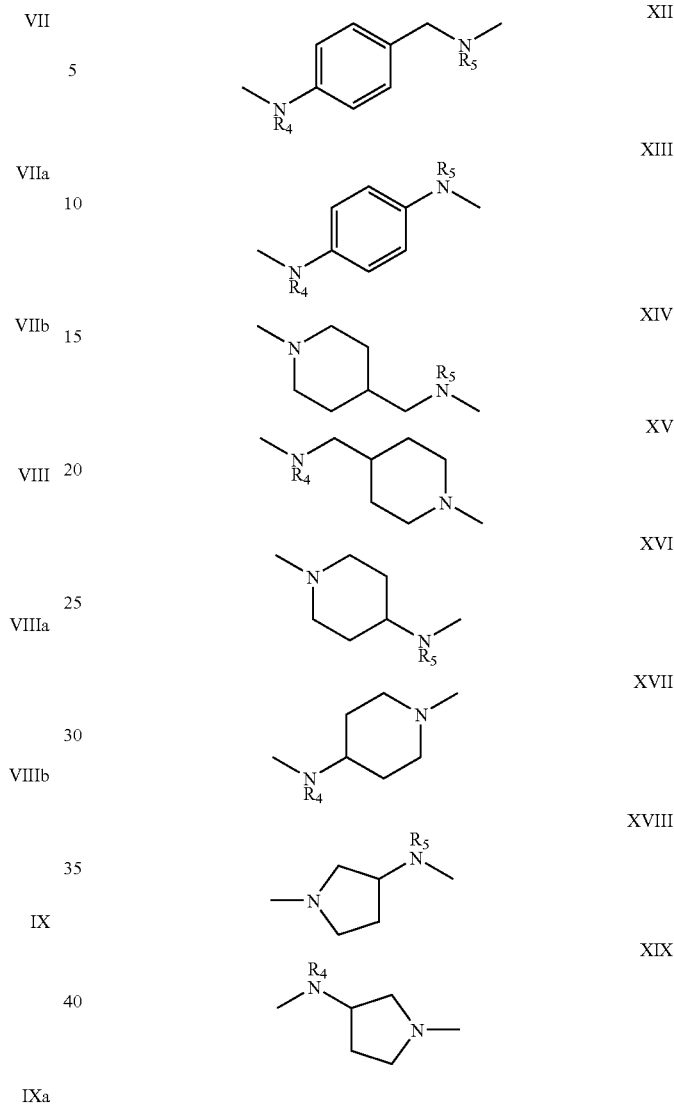

wherein $R_4$ is H or $C_1$-$C_3$ alkyl;

$R_5$ is H, $C_1$-$C_3$ alkyl, or $C_1$-$C_3$ alkyl substituted by a substituted carbocyclic aryl;

Y is —S(O)$_2$—, —C(O)—, or —(CH$_2$)$_m$;

m is 0 or 1;

wherein carbocyclic aryl is phenyl, naphthyl, anthranyl, biphenyl, or phenanthryl; carbocyclyl is 10,11-dihydro-5-oxo-dibenzo[a,d]cycloheptyl, 1-oxo-indanyl, 7,7-dimethyl-2-oxo-bicyclo[2.2.1]heptyl, 9H-fluorenyl, 9-oxo-fluorenyl, acenaphthyl, anthraquinonyl, C-fluoren-9-ylidene, indanyl, indenyl, 1,2,3,4-tetrahydro-naphthyl, or bicyclo[2.2.1]hepteny;

heterocyclyl is 1,2,3,4-tetrahydro-isoquinolyl, 1,2,3-thiadiazolyl, 1,2,3-triazolyl, 1,2-dihydro-3-oxo-pyrazolyl, 1,3,4-thiadiazolyl, 1,3-dioxo-isoindolyl, 1,3-dioxolanyl, 1H-indolyl, 1H-pyrrolo[2,3-c]pyridyl, 1H-pyrrolyl, 1-oxo-3H-isobenzofuranyl, 2,2',5',2"-terthiophenyl, 2,2'-bithiophenyl, 2,3-dihydro-1-oxo-isoindolyl, 2,3-dihydro-benzo[1,4]dioxinyl, 2,3-dihydro-benzofuryl, 2,4-dihydro-3-oxo-pyrazolyl, 2H-benzopyranyl, 2-oxo-benzopyranyl, 2-oxo-pyrrolidinyl, 3,4-dihydro-2H-benzo[1,4]oxazinyl, 3,4-dihydro-2H-benzo[b][1,4]dioxepinyl, 4H-benzo[1,3]dioxinyl, 4H-benzopyranyl, 4-oxo-1,5,6,7-tetrahydro-indolyl, 4-oxo-3,4-dihydrophthalazinyl, 4-oxo-benzopyranyl, 9,10,10-trioxo-thioxanthenyl, 9H-carbazolyl, 9H-xanthenyl, azetidinyl, benzimidazolyl, benzo[1,3]dioxolyl, benzo[2,1,3]oxadiazolyl, benzo[b]thienyl, benzofuryl, benzothiazolyl, cinnolyl, furyl, imidazo[2,1-b]thiazolyl, imidazolyl, isoxazolyl, morpholino, morpholinyl, oxazolyl, oxolanyl, piperazyl, piperidyl, piridyl, pyrazolo[5,1-b]thiazolyl, pyrazolyl, pyridyl, pyrimidyl, pyrrolidyl, quinolyl, quinoxalyl, thiazolidyl, thiazolyl, thienyl, thiolanyl, 2,3-dihydro-benzofuryl, tetrahydrothienyl, or benzofuranyl;

halogen is fluoro, chloro, bromo, or iodo.

Preferred compounds of this invention are those compounds of Formula I wherein,

Q is Formula II;

$R_1$ represents (i) $C_1$-$C_{10}$ alkyl, $C_1$-$C_{10}$ alkyl substituted by substituent(s) independently selected from
  halogen,
  oxo,
  $C_1$-$C_3$ alkoxy,
  $C_1$-$C_3$ alkoxy substituted by carbocyclic aryl,
  $C_1$-$C_3$ alkylcarbonyloxy,
  carbocyclyloxy,
  carbocyclic aryloxy,
  carbocyclic aryloxy substituted by substituent(s) independently selected from
    halogen,
    nitro,
    $C_1$-$C_4$ alkyl,
    $C_1$-$C_4$ alkyl substituted by substituent(s) independently selected from
      oxo,
      carbocyclic arylcarbonylamino,
      halogenated carbocyclic arylcarbonylamino,
  heterocyclyloxy,
  heterocyclyloxy substituted by $C_1$-$C_3$ alkyl,
  substituted heterocyclyl-ethylideneaminooxy,
  $C_1$-$C_3$ alkoxycarbonyl,
  $C_1$-$C_3$ alkoxycarbonyl substituted by carbocyclic aryl,
  mono- or di-$C_1$-$C_3$ alkylaminocarbonyl,
  mono- or di-carbocyclic arylamino,
  mono- or di-carbocyclic arylamino substituted by hydroxy,
  $C_1$-$C_3$ alkylcalbonylamino,
  $C_1$-$C_3$ alkylcalbonylamino substituted by substituent(s) independently selected from
    $C_1$-$C_3$ alkylcalbonylamino,
    carbocyclic arylcalbonylamino,
    heterocyclyl,
  $C_1$-$C_4$ alkoxycalbonylamino,
  heterocyclyl calbonylamino,
  carbocyclic arylsulfonylamino,
  carbocyclic arylsulfonylamino substituted by substituent(s) independently selected from
    nitro,
    $C_1$-$C_3$ alkyl,
    mono- or di-$C_1$-$C_3$ alkylamino,
    $C_1$-$C_3$ alkylthio,
    $C_1$-$C_3$ alkylthio substituted by substituent(s) independently selected from
      mono- or di-carbocyclic arylaminocarbonyl,
      halogenated mono- or di-carbocyclic arylaminocarbonyl,
      carbocyclic aryl,
      carbocyclic aryl substituted by substituent(s) independently selected from
        halogen,
        $C_1$-$C_3$ alkoxy,
  carbocyclic arylthio,
  carbocyclic arylthio substituted by substituent(s) independently selected from
    halogen,
    $C_1$-$C_3$ alkyl,
  carbocyclic arylsulfonyl,
  halogenated carbocyclic arylsulfonyl,
  heterocyclylthio,
  heterocyclylthio substituted by substituent(s) independently selected from
    nitro,
    $C_1$-$C_3$ alkyl,
  $C_3$-$C_6$ cycloalkyl,
  $C_3$-$C_6$ cycloalkyl substituted by $C_1$-$C_3$ alkyl,
  $C_3$-$C_6$ cycloalkenyl,
  carbocyclyl,
  carbocyclyl substituted by substituent(s) independently selected from
    halogen,
    $C_1$-$C_3$ alkyl,
    $C_1$-$C_3$ alkoxy,
    $C_2$-$C_3$ alkenyl,
    $C_2$-$C_3$ alkenyl substituted by carbocyclic aryl,
    $C_2$-$C_3$ alkenyl substituted by carbocyclic aryl substituted $C_1$-$C_3$ alkylsulfinyl,
  carbocyclic aryl,
  carbocyclic aryl substituted by substituent(s) independently selected from
    halogen,
    hydroxy,
    nitro,
    $C_1$-$C_4$ alkyl,
    $C_1$-$C_4$ alkyl substituted by substituent(s) independently selected from
      oxo,
      carbocyclic aryl,
      heterocyclyl,
    $C_1$-$C_4$ alkoxy,
    $C_1$-$C_4$ alkoxy substituted by substituent(s) independently selected from
      halogen,
      carbocyclic aryl,
    carbocyclic aryloxy,
    $C_1$-$C_3$ alkylcarbonyloxy,
    mono- or di-carbocyclic arylamino,
    halogenated mono- or di-carbocyclic arylamino,
    mono- or di-carbocyclic arylaminocarbonyl,
    mono- or di-carbocyclic arylaminocarbonyl substituted by substituent(s) independently selected from
      halogen,
      nitro,
      $C_1$-$C_3$ alkyl,
      $C_1$-$C_3$ alkoxy,
      halogenated $C_1$-$C_3$ alkoxy,
    mercapto,
    $C_1$-$C_3$ alkylthio,
    halogenated $C_1$-$C_3$ alkylthio,
    $C_1$-$C_3$ alkylsulfonyl,
    $C_3$-$C_6$ cycloalkyl,
    carbocyclic aryl,
    heterocyclyl,
  heterocyclyl,
  heterocyclyl substituted by substituent(s) independently selected from
    hydroxy, $C_1$-$C_3$ alkyl,
$C_1$-$C_3$ alkyl substituted by carbocyclic aryl,
$C_1$-$C_3$ alkoxy,
$C_1$-$C_3$ alkoxy substituted by carbocyclic aryl,
carbocyclic aryl,
halogenated carbocyclic aryl, (ii) $C_2$-$C_6$ alkenyl, $C_2$-$C_6$ alkenyl substituted by substituent(s) independently selected from
oxo,
carbocyclic aryl,
carbocyclic aryl substituted by substituent(s) independently selected from
halogen,
nitro,
$C_1$-$C_3$ alkyl,
halogenated $C_1$-$C_3$ alkyl,
$C_1$-$C_3$ alkoxy,
halogenated $C_1$-$C_3$ alkoxy,
heterocyclyl,
heterocyclyl substituted by substituent(s) independently selected from
hydroxy,
$C_1$-$C_3$ alkyl,
$C_1$-$C_3$ alkoxy, (iii) $C_3$-$C_6$ cycloalkyl, $C_3$-$C_6$ cycloalkyl substituted by substituent(s) independently selected from
$C_1$-$C_3$ alkyl,
$C_1$-$C_3$ alkyl substituted by substituent(s) independently selected from
oxo,
carbocyclic aryl,
carbocyclic arylcarbonylamino,
carbocyclic aryl, (iv) carbocyclyl, carbocyclyl substituted by nitro, (v) carbocyclic aryl, carbocyclic aryl substituted by substituent(s) independently selected from
halogen,
hydroxy,
cyano,
nitro,
$C_1$-$C_9$ alkyl,
$C_1$-$C_9$ alkyl substituted by substituent(s) independently selected from
halogen,
oxo,
carbocyclic aryloxy,
carbocyclylimino,
carbocyclylimino substituted by carbocyclic aryl,
mono- or di-carbocyclic arylaminocarbonyl,
mono- or di-carbocyclic arylaminocarbonyl substituted by $C_1$-$C_3$ alkoxy,
carbocyclic aryl,
carbocyclic aryl substituted by substituent(s) independently selected from
halogen,
$C_1$-$C_3$ alkyl,
halogenated $C_1$-$C_3$ alkyl,
heterocyclyl,
heterocyclyl substituted by $C_1$-$C_3$ alkyl,
$C_1$-$C_7$ alkoxy,
$C_1$-$C_7$ alkoxy substituted by substituent(s) independently selected from
halogen,
carbocyclic aryl,
$C_1$-$C_3$ alkylcarbonyloxy,
carbocyclic aryloxy,
carbocyclic aryloxy substituted by $C_1$-$C_3$ alkoxy,
$C_1$-$C_3$ alkoxycarbonyl,
mono- or di-$C_1$-$C_3$ alkylaminocarbonyl,
mono- or di-$C_1$-$C_3$ alkylaminocarbonyl substituted by carbocyclic aryl,
mono- or di-carbocyclic arylaminocarbonyl,
mono- or di-carbocyclic arylaminocarbonyl substituted by $C_1$-$C_3$ alkyl,
amino,
mono- or di-$C_1$-$C_3$ alkylamino,
$C_1$-$C_3$ alkynylcarbonylamino,
$C_1$-$C_3$ alkynylcarbonylamino substituted by carbocyclic aryl,
carbocyclic arylsulfonylamino,
carbocyclic arylsulfonylamino substituted by $C_1$-$C_3$ alkyl,
(carbocyclic aryl)NHC(O)NH,
(carbocyclic aryl)NHC(O)NH substituted by $C_1$-$C_3$ alkoxy,
(carbocyclic aryl)NHC(O)NH substituted by haloganated $C_1$-$C_3$ alkoxy,
$C_1$-$C_3$ alkylthio,
halogenated $C_1$-$C_3$ alkylthio,
carbocyclic arylthio,
carbocyclic arylthio substituted by cyano,
$C_1$-$C_3$ alkylsulfonyl,
mono- or di-$C_1$-$C_3$ alkylaminosulfonyl,
carbocyclic aryl,
carbocyclic aryl substituted by substituent(s) independently selected from
$C_1$-$C_7$ alkyl,
halogenated $C_1$-$C_7$ alkyl,
heterocyclyl,
heterocyclyl substituted by substituent(s) independently selected from
$C_1$-$C_3$ alkyl,
carbocyclic aryl,
halogenated carbocyclic aryl, (vi) heterocyclyl, or heterocyclyl substituted by substituent(s) independently selected from
halogen,
nitro,
$C_1$-$C_4$ alkyl,
$C_1$-$C_4$ alkyl substituted by substituent(s) independently selected from
halogen,
oxo,
$C_1$-$C_3$ alkylthio,
$C_1$-$C_3$ alkylthio substituted by carbocyclic aryl,
$C_1$-$C_3$ alkylthio substituted by halogenated carbocyclic aryl,
carbocyclic aryl,
halogenated carbocyclic aryl,
heterocyclyl,
$C_1$-$C_3$ alkoxy,
carbocyclic aryloxy, carbocyclic aryloxy substituted by substituent(s) independently selected from
  halogen,
  $C_1$-$C_3$ alkyl,
$C_1$-$C_3$ alkylthio,
$C_1$-$C_3$ alkenylthio,
carbocyclic arylthio,
$C_1$-$C_3$ alkylsulfonyl,
carbocyclic arylsulfonyl,
halogenated carbocyclic arylsulfonyl,
carbocyclic arylsulfonyl substituted by $C_1$-$C_4$ alkyl,
carbocyclic aryl,
carbocyclic aryl substituted by substituent(s) independently selected from
  halogen,
  nitro,
  $C_1$-$C_3$ alkyl,
  $C_1$-$C_3$ alkoxy,
heterocyclyl,
heterocyclyl substituted by substituent(s) independently selected from
  $C_1$-$C_3$ alkyl,
  halogenated $C_1$-$C_3$ alkyl;
$R_2$ is —NHNH$_2$, —NHNHBoc, —N($R_{2a}$)($R_{2b}$), morpholino, 4-acetyl-piperazyl, or 4-phenyl-piperazyl;
wherein $R_{2a}$ is H or $C_1$-$C_3$ alkyl;
$R_{2b}$ is $C_1$-$C_4$ alkyl, $C_1$-$C_4$ alkyl substituted by substituent(s) independently selected from
  hydroxy,
  $C_1$-$C_3$ alkoxy,
  amino,
  —NHBoc,
  $C_3$-$C_6$ cycloalkyl,
  carbocyclic aryl,
  carbocyclic aryl substituted by substituent(s) independently selected from
    halogen,
    $C_1$-$C_3$ alkyl,
    $C_1$-$C_3$ alkoxy,
    —SO$_2$NH$_2$,
  heterocyclyl,
$C_3$-$C_6$ cycloalkyl, carbocyclic aryl, carbocyclic aryl substituted by substituent(s) independently selected from
  halogen,
  $C_1$-$C_3$ alkyl,
  $C_1$-$C_3$ alkoxy,
or a group of Formula IV;
  wherein Boc is carbamic acid tert-butyl ester and $R_3$ is $C_1$-$C_3$ alkyl or $C_1$-$C_3$ alkyl substituted by substituent(s) independently selected from
    carbocyclic aryl,
    halogenated carbocyclic aryl,
    carbocyclic aryl substituted by $C_1$-$C_3$ alkoxy;
  L is selected from Formula V-XIX;
    wherein $R_4$ is H or $C_1$-$C_3$ alkyl;
  $R_5$ is H, $C_1$-$C_3$ alkyl, or $C_1$-$C_3$ alkyl substituted by a substituted carbocyclic aryl;
    Y is —C(O)—;
  wherein carbocyclic aryl is phenyl, naphthyl, anthranyl, or biphenyl;
  carbocyclyl is 10,11-dihydro-5-oxo-dibenzo[a,d]cycloheptyl, 1-oxo-indanyl, 9H-fluorenyl, 9-oxo-fluorenyl, acenaphthyl, anthraquinonyl, C-fluoren-9-ylidene, indanyl, indenyl, 1,2,3,4-tetrahydro-naphthyl, or bicyclo[2.2.1]heptenyl;

heterocyclyl is 1,2,3-thiadiazolyl, 1,2,3-triazolyl, 1,2-dihydro-3-oxo-pyrazolyl, 1,3-dioxo-isoindolyl, 1H-indolyl, 1H-pyrrolyl, 1-oxo-3H-isobenzofuranyl, 2,3-dihydro-benzo[1,4]dioxinyl, 2,3-dihydro-benzofuryl, 2,4-dihydro-3-oxo-pyrazolyl, 2H-benzopyranyl, 2-oxo-benzopyranyl, 2-oxo-pyrrolidinyl, 3,4-dihydro-2H-benzo[b][1,4]dioxepinyl, 4-oxo-1,5,6,7-tetrahydro-indolyl, 4-oxo-3,4-dihydro-phthalazinyl, 4-oxo-benzopyranyl, 9,10,10-trioxo-thioxanthenyl, 9H-xanthenyl, azetidinyl, benzimidazolyl, benzo[1,3]dioxolyl, benzo[2,1,3]oxadiazolyl, benzo[b]thienyl, cinnolyl, furyl, imidazolyl, isoxazolyl, morpholino, morpholinyl, oxazolyl, oxolanyl, piperidyl, piridyl, pyrazolyl, pyridyl, pyrimidyl, pyrrolidyl, quinolyl, quinoxalyl, thiazolidyl, thiazolyl, thienyl, thiolanyl, tetrahydro-thienyl, benzofuranyl, or benzothiazolyl;
  halogen is fluoro, chloro, bromo, or iodo.
Other preferred compounds of this invention are those compounds of Formula I wherein,
  Q is Formula II;
  $R_1$ represents
(i) $C_1$-$C_{10}$ alkyl,
$C_1$-$C_{10}$ alkyl substituted by substituent(s) independently selected from
  oxo,
  di-propylaminocarbonyl,
  methoxy substituted by carbocyclic aryl,
  methylcarbonyloxy,
  carbocyclic aryloxy,
  halogenated carbocyclic aryloxy,
  carbocyclic aryloxy substituted by nitro,
  heterocyclyloxy substituted by methyl,
  substituted heterocyclyl-ethylideneaminooxy,
  tert-butoxycarbonylamino,
  carbocyclic arylcarbonylamino,
  $C_1$-$C_2$ alkylthio,
  $C_1$-$C_2$ alkylthio substituted by substituent(s) independently selected from
    halogenated carbocyclic aryl,
    carbocyclic aryl substituted by methoxy,
  carbocyclic arylthio,
  hetrocyclylthio substituted by nitro,
  hetrocyclylthio substituted by methyl,
  $C_5$-$C_6$ cycloalkyl,
  $C_5$-$C_6$ cycloalkenyl,
  carbocyclyl substituted by substituent(s) independently selected from
    halogen,
    methyl,
    methoxy,
    ethenyl substituted by carbocyclic aryl substituted methylsulfinyl,
  carbocyclic aryl,
  carbocyclic aryl substituted by substituent(s) independently selected from
    halogen,
    hydroxy,
    nitro,
    $C_1$-$C_4$ alkyl,
    $C_1$-$C_4$ alkyl substituted by substituent(s) independently selected from
      oxo,
      carbocyclic aryl,
      heterocyclyl,
    $C_1$-$C_4$ alkoxy,
    halogenated $C_1$-$C_4$ alkoxy,
    $C_1$-$C_4$ alkoxy substituted by carbocyclic aryl, carbocyclic aryloxy,
halogenated mono-carbocyclic arylaminocarbonyl,
carbocyclic aryl,
heterocyclyl,
heterocyclyl,
heterocyclyl substituted by substituent(s) independently selected from
  $C_1$-$C_2$ alkyl,
  $C_1$-$C_2$ substituted by carbocyclic aryl,
  methoxy,
  methoxy substituted by carbocyclic aryl,
  carbocyclic aryl,
  halogenated carbocyclic aryl, (ii) $C_2$-$C_3$ alkenyl substituted by substituent(s) independently selected from
  carbocyclic aryl,
  halogenated carbocyclic aryl,
  carbocyclic aryl substituted by nitro, (iii) $C_3$-$C_6$ cycloalkyl, $C_3$-$C_6$ cycloalkyl substituted by substituent(s) independently selected from
  methyl substituted by oxo,
  methyl substituted by carbocyclic aryl,
  carbocyclic aryl, (iv) carbocyclyl, (v) carbocyclic aryl, carbocyclic aryl substituted by substituent(s) independently selected from
  halogen,
  hydroxy,
  cyano,
  nitro,
  $C_1$-$C_9$ alkyl,
  $C_1$-$C_9$ alkyl substituted by substituent(s) independently selected from
    halogen,
    oxo,
    carbocyclic aryl,
    carbocyclic aryl substituted by methyl,
    carbocyclic aryloxy,
  $C_1$-$C_7$ alkoxy,
  halogenated $C_1$-$C_7$ alkoxy,
  $C_1$-$C_7$ alkoxy substituted by carbocyclic aryl,
  methylcarbonyloxy,
  carbocyclic aryloxy,
  carbocyclic aryloxy substituted by methoxy,
  amino,
  di-methylamino,
  propargynylcarbonylamino substituted by carbocyclic aryl,
  carbocyclic arylsulfonylamino substituted by methyl,
  (carbocyclic aryl)NHC(O)NH substituted by halogenated methoxy,
  halogenated methylthio,
  carbocyclic arylthio substituted by cyano,
  di-propylamino sulfonyl,
  mono- or di-ethylaminocarbonyl substituted by carbocyclic aryl,
  carbocyclic aryl,
  heterocyclyl substituted by methyl,
  heterocyclyl substituted by halogenated carbocyclic aryl, (vi) heterocyclyl, or heterocyclyl substituted by substituent(s) independently selected from
  halogen,
  nitro,
  $C_1$-$C_4$ alkyl,
  $C_1$-$C_4$ alkyl substituted by substituent(s) independently selected from
    halogen,
    methylthio substituted by halogenated carbocyclic aryl,
    carbocyclic aryl,
    halogenated carbocyclic aryl,
    heterocyclyl,
  methoxy,
  carbocyclic aryloxy,
  carbocyclic aryloxy substituted by methyl,
  $C_1$-$C_3$ alkylthio,
  propenylthio,
  carbocyclic arylthio,
  $C_1$-$C_3$ alkylsulfonyl,
  carbocyclic arylsulfonyl substituted by $C_1$-$C_4$ alkyl,
  carbocyclic aryl,
  halogenated carbocyclic aryl,
  carbocyclic aryl substituted by methyl,
  carbocyclic aryl substituted by nitro,
  heterocyclyl;

$R_2$ is methylamino or dimethylamino;
L is selected from Formula Va, VIIIa, or IXa;
wherein $R_4$ and $R_5$ are independently selected from H or $C_1$-$C_3$ alkyl;
Y is —C(O)—;
wherein carbocyclic aryl is phenyl, naphthyl, anthranyl, or biphenyl;
carbocyclyl is 1-oxo-indanyl, 9-oxo-fluorenyl, indenyl, anthraquinonyl, C-fluoren-9-ylidene, 1,2,3,4-tetrahydro-naphthyl, or bicyclo[2.2.1]heptenyl;
heterocyclyl is 1,2,3-thiadiazolyl, 1,2,3-triazolyl, 1,2-dihydro-3-oxo-pyrazolyl, 1,3-dioxo-isoindolyl, 1H-indolyl, 1H-pyrrolyl, 1-oxo-3H-isobenzofuranyl, 2,3-dihydro-benzo[1,4]dioxinyl, 2,4-dihydro-3-oxo-pyrazolyl, 2H-benzopyranyl, 2-oxo-benzopyranyl, 3,4-dihydro-2H-benzo[b][1,4]dioxepinyl, 4-oxo-3,4-dihydro-phthalazinyl, 4-oxo-benzopyranyl, 9,10,10-trioxo-thioxanthenyl, 9H-xanthenyl, azetidinyl, benzimidazolyl, benzo[1,3]dioxolyl, benzo[2,1,3]oxadiazolyl, benzo[b]thienyl, furyl, imidazolyl, isoxazolyl, morpholino, morpholinyl, oxolanyl, piperidyl, piridyl, pyrazolyl, pyridyl, quinolyl, quinoxalyl, thiazolidyl, thiazolyl, thienyl, thiolanyl, 2,3-dihydro-1-oxo-isoindolyl, 2,3-dihydro-benzofuryl, 2-oxo-pyrrolidinyl, 4-oxo-1,5,6,7-tetrahydro-indolyl, cinnolyl, pyrimidyl, pyrrolidyl, tetrahydro-thienyl, benzofuranyl, or benzothiazolyl;
halogen is fluoro, chloro, bromo, or iodo.

Other more preferred compounds of this invention are those compounds of Formula I wherein,
Q is Formula II;
$R_1$ represents (i) $C_1$-$C_{10}$ alkyl substituted by substituent(s) independently selected from
  oxo,
  di-propylaminocarbonyl,
  methoxy substituted by carbocyclic aryl,
  methylcarbonyloxy,
  carbocyclic aryloxy,
  halogenated carbocyclic aryloxy,
  carbocyclic aryloxy substituted by nitro,
  heterocyclyloxy substituted by methyl, tert-butoxycarbonylamino,
carbocyclic arylcarbonylamino,
$C_1$-$C_2$ alkylthio,
$C_1$-$C_2$ alkylthio substituted by substituent(s) independently selected from
   halogenated carbocyclic aryl,
   carbocyclic aryl substituted by methoxy,
carbocyclic arylthio,
hetrocyclylthio substituted by nitro,
hetrocyclylthio substituted by methyl,
$C_5$-$C_6$ cycloalkenyl,
carbocyclyl substituted by substituent(s) independently selected from
   halogen,
   methyl,
   methoxy,
   ethenyl substituted by carbocyclic aryl substituted methylsulfinyl,
carbocyclic aryl substituted by substituent(s) independently selected from
   halogen,
   hydroxy,
   nitro,
   $C_1$-$C_4$ alkyl,
   $C_1$-$C_4$ alkyl substituted by substituent(s) independently selected from
      oxo,
      carbocyclic aryl,
      heterocyclyl,
      $C_1$-$C_4$ alkoxy,
      halogenated $C_1$-$C_4$ alkoxy,
      $C_1$-$C_4$ alkoxy substituted by carbocyclic aryl,
      carbocyclic aryloxy,
      halogenated mono-carbocyclic arylaminocarbonyl,
      carbocyclic aryl,
      heterocyclyl,
   heterocyclyl substituted by substituent(s) independently selected from
      $C_1$-$C_2$ alkyl,
      $C_1$-$C_2$ substituted by carbocyclic aryl,
      methoxy,
      methoxy substituted by carbocyclic aryl,
      carbocyclic aryl,
      halogenated carbocyclic aryl,
(ii) $C_2$-$C_3$ alkenyl substituted by substituent(s) independently selected from
   carbocyclic aryl,
   halogenated carbocyclic aryl,
   carbocyclic aryl substituted by nitro,
(iii) $C_3$-$C_6$ cycloalkyl substituted by substituent(s) independently selected from
   methyl substituted by oxo,
   methyl substituted by carbocyclic aryl,
   carbocyclic aryl,
(iv) carbocyclyl,
(v) carbocyclic aryl substituted by substituent(s) independently selected from
   halogen,
   hydroxy,
   cyano,
   nitro,
   $C_1$-$C_9$ alkyl,
   $C_1$-$C_9$ alkyl substituted by substituent(s) independently selected from
      halogen,
      oxo,
      carbocyclic aryl,
      carbocyclic aryl substituted by methyl,
      carbocyclic aryloxy,
   $C_1$-$C_7$ alkoxy,
   halogenated $C_1$-$C_7$ alkoxy,
   $C_1$-$C_7$ alkoxy substituted by carbocyclic aryl,
   methylcarbonyloxy,
   carbocyclic aryloxy,
   carbocyclic aryloxy substituted by methoxy,
   amino,
   di-methylamino,
   propargynylcarbonylamino substituted by carbocyclic aryl,
   carbocyclic arylsulfonylamino substituted by methyl,
   (carbocyclic aryl)NHC(O)NH substituted by halogenated methoxy,
   halogenated methylthio,
   carbocyclic arylthio substituted by cyano,
   di-propylamino sulfonyl,
   mono- or di-ethylaminocarbonyl substituted by carbocyclic aryl,
   carbocyclic aryl,
   heterocyclyl substituted by methyl,
   heterocyclyl substituted by halogenated carbocyclic aryl,
(vi) or heterocyclyl substituted by substituent(s) independently selected from
   halogen,
   nitro,
   $C_1$-$C_4$ alkyl,
   $C_1$-$C_4$ alkyl substituted by substituent(s) independently selected from
      halogen,
      methylthio substituted by halogenated carbocyclic aryl,
      carbocyclic aryl,
      halogenated carbocyclic aryl,
      heterocyclyl,
   methoxy,
   carbocyclic aryloxy,
   carbocyclic aryloxy substituted by methyl,
   $C_1$-$C_3$ alkylthio,
   propenylthio,
   carbocyclic arylthio,
   $C_1$-$C_3$ alkylsulfonyl,
   carbocyclic arylsulfonyl,
   carbocyclic arylsulfonyl substituted by $C_1$-$C_4$ alkyl,
   carbocyclic aryl,
   halogenated carbocyclic aryl,
   carbocyclic aryl substituted by methyl,
   carbocyclic aryl substituted by nitro,
   heterocyclyl;
$R_2$ is methylamino or dimethylamino;
L is selected from Formula XX-XXII;

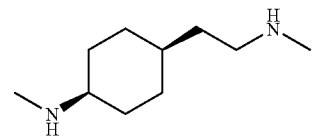

XX

-continued

XXI

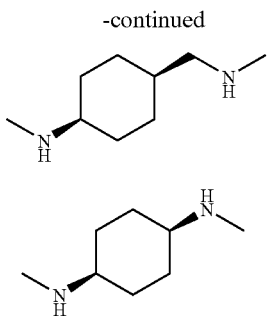

XXII

Y is —C(O)—;
wherein carbocyclic aryl is phenyl, naphthyl, or biphenyl;
carbocyclyl is 1-oxo-indanyl, 9-oxo-fluorenyl, indenyl, anthraquinonyl, C-fluoren-9-ylidene, 1,2,3,4-tetrahydronaphthyl, or bicyclo[2.2.1]heptenyl;
heterocyclyl is 1,2,3-thiadiazolyl, 1,2,3-triazolyl, 1,2-dihydro-3-oxo-pyrazolyl, 1H-indolyl, 1H-pyrrolyl, 2,4-dihydro-3-oxo-pyrazolyl, 2H-benzopyranyl, 4-oxo-benzopyranyl, azetidinyl, benzo[b]thienyl, furyl, isoxazolyl, morpholinyl, piperidyl, piridyl, pyrazolyl, pyridyl, quinolyl, thiazolidyl, thiazolyl, thienyl, thiolanyl, 2,3-dihydro-1-oxo-isoindolyl, 2,3-dihydro-benzofuryl, 2-oxo-benzopyranyl, 2-oxo-pyrrolidinyl, 4-oxo-1,5,6,7-tetrahydro-indolyl, 9H-xanthenyl, cinnolyl, imidazolyl, morpholino, pyrimidyl, pyrrolidyl, tetrahydro-thienyl, benzofuranyl, or benzothiazolyl;
halogen is fluoro, chloro, bromo, or iodo.
Further other more preferred compounds of this invention are those compounds of Formula I wherein,
Q is Formula II;
$R_1$ represents (i) $C_1$-$C_5$ alkyl substituted by substituent(s) independently selected from
oxo,
di-propylaminocarbonyl,
methoxy substituted by carbocyclic aryl,
methylcarbonyloxy,
carbocyclic aryloxy,
halogenated carbocyclic aryloxy,
carbocyclic aryloxy substituted by nitro,
heterocyclyloxy substituted by methyl,
substituted heterocyclyl-ethylideneaminooxy,
tert-butoxycarbonylamino,
carbocyclic arylcarbonylamino,
$C_1$-$C_2$ alkylthio,
$C_1$-$C_2$ alkylthio substituted by substituent(s) independently selected from
halogenated carbocyclic aryl,
carbocyclic aryl substituted by methoxy,
carbocyclic arylthio,
hetrocyclylthio substituted by nitro,
hetrocyclylthio substituted by methyl,
cyclohexenyl,
carbocyclyl substituted by substituent(s) independently selected from
halogen,
methyl,
methoxy,
ethenyl substituted by carbocyclic aryl substituted methylsulfinyl,
carbocyclic aryl substituted by substituent(s) independently selected from
halogen,
hydroxy,
nitro,
$C_1$-$C_4$ alkyl,
$C_1$-$C_4$ alkyl substituted by substituent(s) independently selected from
oxo,
carbocyclic aryl,
heterocyclyl,
$C_1$-$C_2$ alkoxy,
halogenated $C_1$-$C_2$ alkoxy,
$C_1$-$C_2$ alkoxy substituted by carbocyclic aryl,
carbocyclic aryloxy,
halogenated mono-carbocyclic arylaminocarbonyl,
carbocyclic aryl,
heterocyclyl,
heterocyclyl substituted by substituent(s) independently selected from
$C_1$-$C_2$ alkyl,
$C_1$-$C_2$ substituted by carbocyclic aryl,
methoxy,
methoxy substituted by carbocyclic aryl,
carbocyclic aryl,
halogenated carbocyclic aryl, (ii) $C_2$-$C_3$ alkenyl substituted by substituent(s) independently selected from
carbocyclic aryl,
halogenated carbocyclic aryl,
carbocyclic aryl substituted by nitro, (iii) $C_3$-$C_6$ cycloalkyl substituted by substituent(s) independently selected from
methyl substituted by oxo,
methyl substituted by carbocyclic aryl,
carbocyclic aryl, (iv) carbocyclyl, (v) carbocyclic aryl substituted by substituent(s) independently selected from
halogen,
hydroxy,
cyano,
nitro,
$C_1$-$C_4$ alkyl,
$C_1$-$C_2$ alkyl substituted by substituent(s) independently selected from
halogen,
oxo,
carbocyclic aryl,
carbocyclic aryl substituted by methyl,
carbocyclic aryloxy,
$C_1$-$C_2$ alkoxy,
halogenated $C_1$-$C_2$ alkoxy,
$C_1$-$C_2$ alkoxy substituted by carbocyclic aryl,
methylcarbonyloxy,
carbocyclic aryloxy,
carbocyclic aryloxy substituted by methoxy,
amino,
di-methylamino,
propargynylcarbonylamino substituted by carbocyclic aryl,
carbocyclic arylsulfonylamino substituted by methyl,
(carbocyclic aryl)NHC(O)NH substituted by halogenated methoxy,
halogenated methylthio, carbocyclic arylthio substituted by cyano,
di-propylamino sulfonyl,
mono- or di-ethylaminocarbonyl substituted by carbocyclic aryl,
carbocyclic aryl,
heterocyclyl substituted by methyl,
heterocyclyl substituted by halogenated carbocyclic aryl, (vi) or heterocyclyl substituted by substituent(s) independently selected from
halogen,
nitro,
$C_1$-$C_4$ alkyl,
$C_1$-$C_4$ alkyl substituted by substituent(s) independently selected from
halogen,
methylthio substituted by halogenated carbocyclic aryl,
carbocyclic aryl,
halogenated carbocyclic aryl,
heterocyclyl,
methoxy,
carbocyclic aryloxy,
carbocyclic aryloxy substituted by methyl,
$C_1$-$C_3$ alkylthio,
propenylthio,
carbocyclic arylthio,
$C_1$-$C_3$ alkylsulfonyl,
carbocyclic arylsulfonyl,
carbocyclic arylsulfonyl substituted by methyl,
carbocyclic aryl,
halogenated carbocyclic aryl,
carbocyclic aryl substituted by methyl,
carbocyclic aryl substituted by nitro,
heterocyclyl;
$R_2$ is methylamino or dimethylamino;
L is selected from Formula XX-XXII;
Y is —C(O)—;
wherein carbocyclic aryl is phenyl, naphthyl, or biphenyl;
carbocyclyl is 1-oxo-indanyl, indenyl, 9-oxo-fluorenyl, 1,2,3,4-tetrahydro-naphthyl, or bicyclo[2.2.1]hepteny;
heterocyclyl is 1H-indolyl, 2,4-dihydro-3-oxo-pyrazolyl, furyl, pyrazolyl, pyridyl, thienyl, 1,2,3-triazolyl, 1H-pyrrolyl, 2,3-dihydro-1-oxo-isoindolyl, 2,3-dihydro-benzofuryl, 2H-benzopyranyl, 2-oxo-benzopyranyl, 4-oxo-1,5,6,7-tetrahydro-indolyl, imidazolyl, isoxazolyl, morpholino, morpholinyl, pyrazolyl, pyrimidyl, quinolyl, thiazolyl, tetrahydro-thienyl, benzofuranyl, or benzothiazolyl;
halogen is fluoro, chloro, bromo, or iodo.

The following compounds are specially preffered;

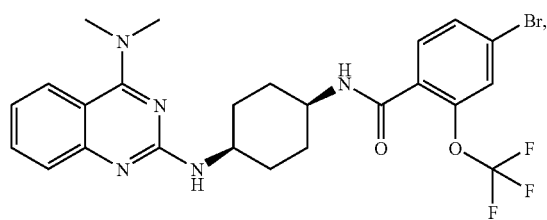

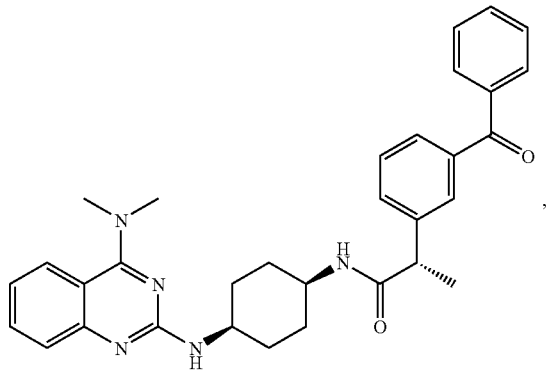

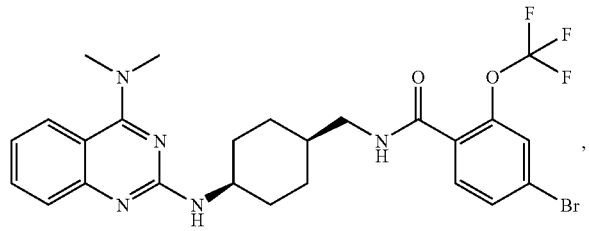

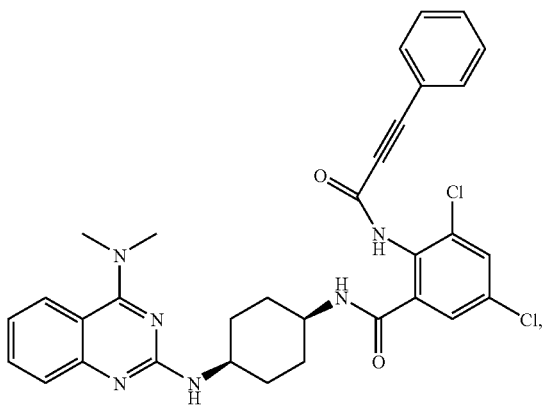

-continued
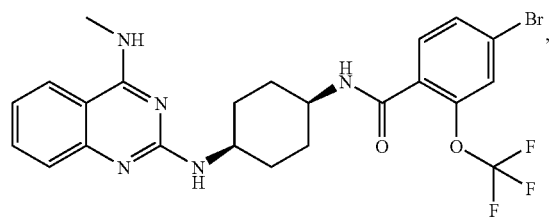 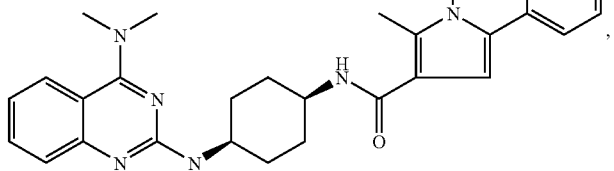
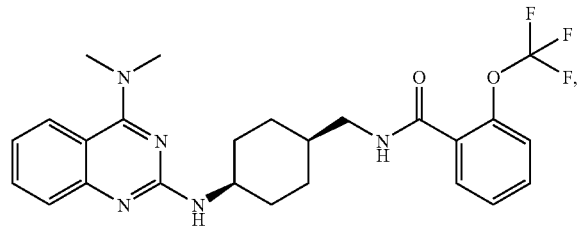 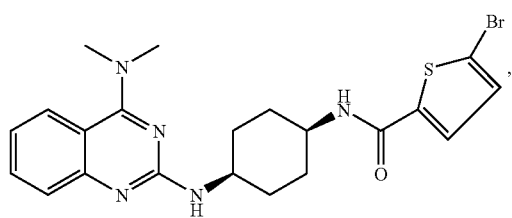
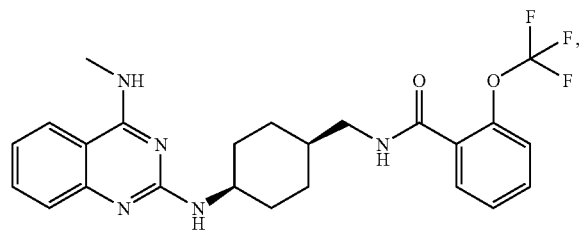 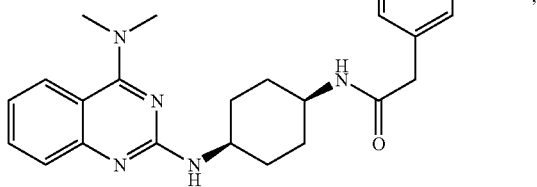
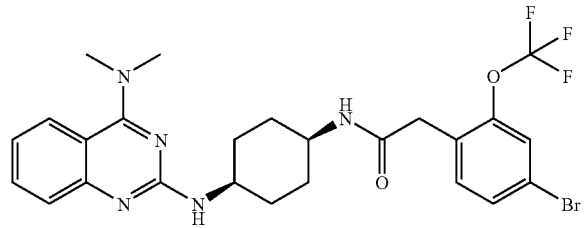 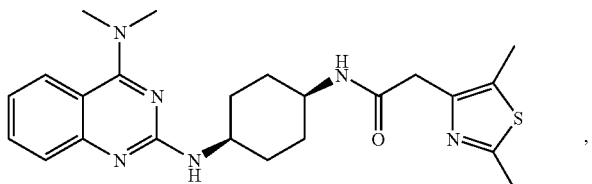
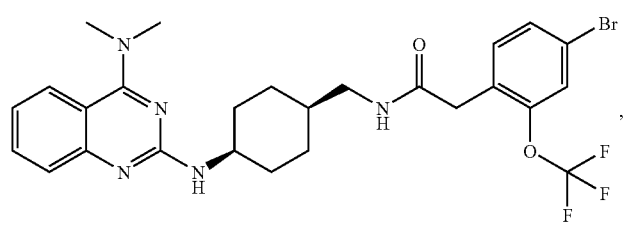 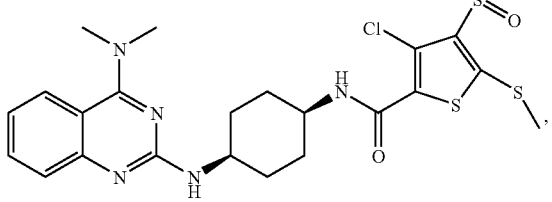

-continued
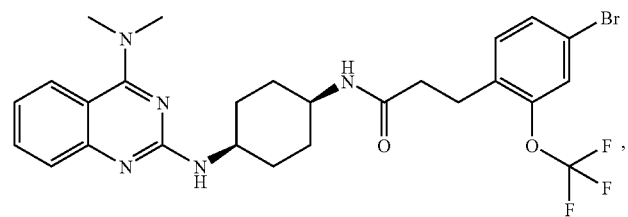
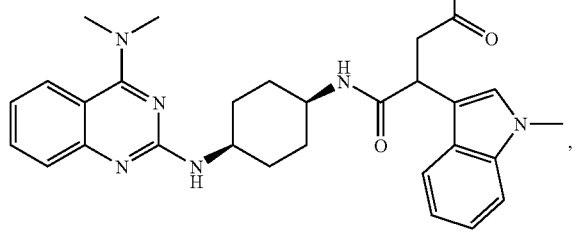
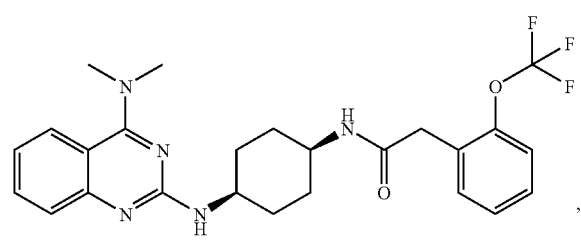
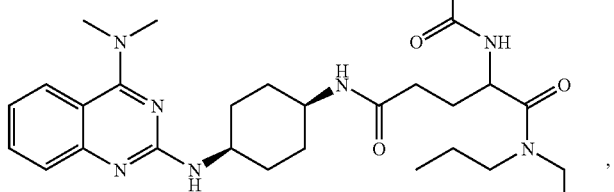
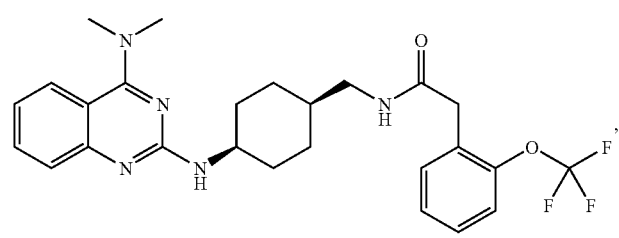
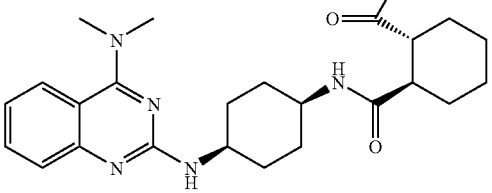
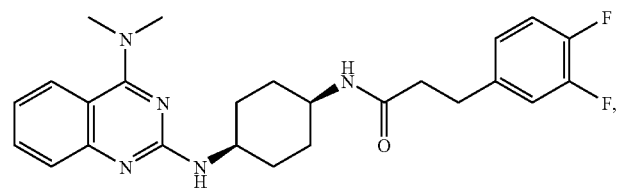
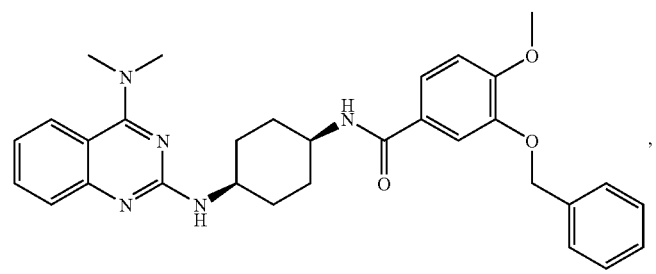

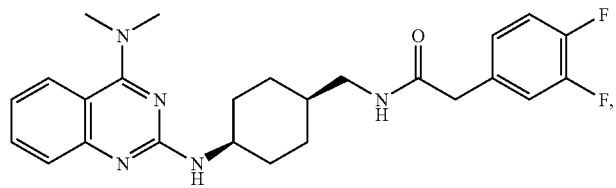
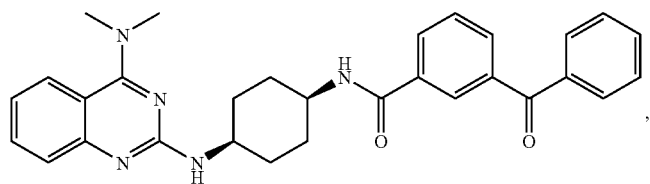
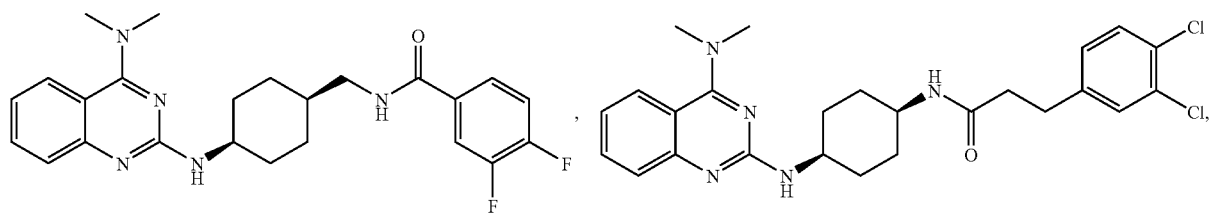
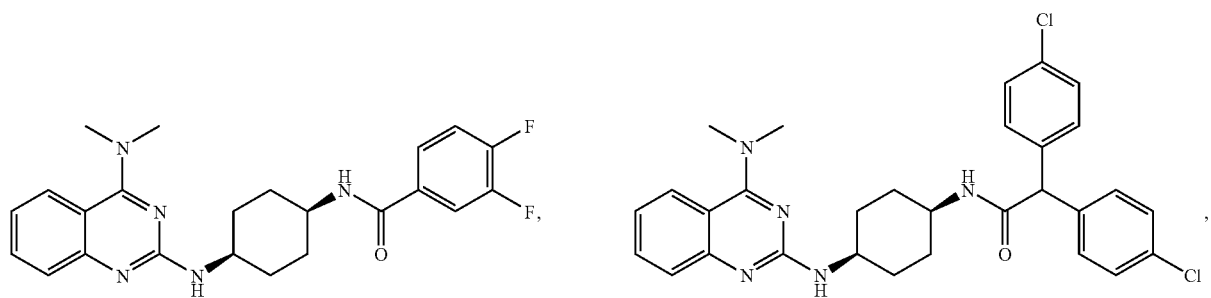
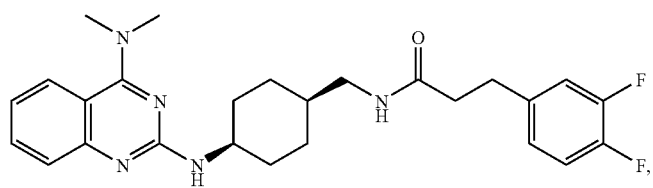
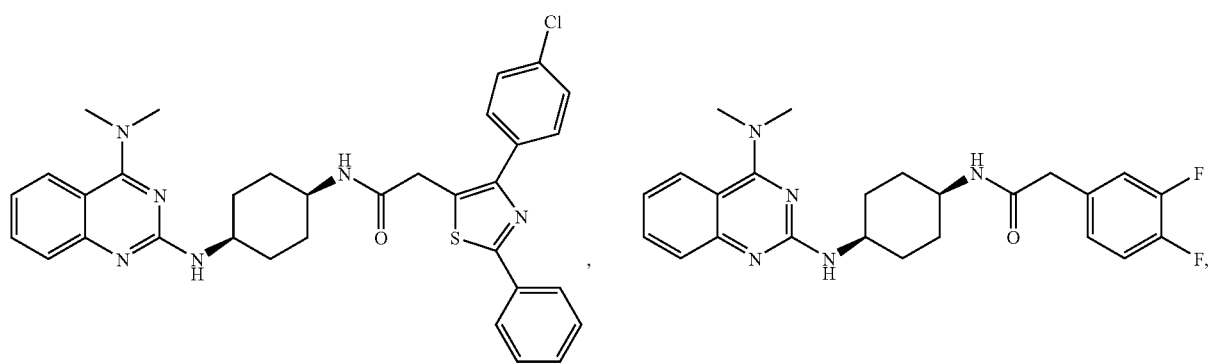

-continued
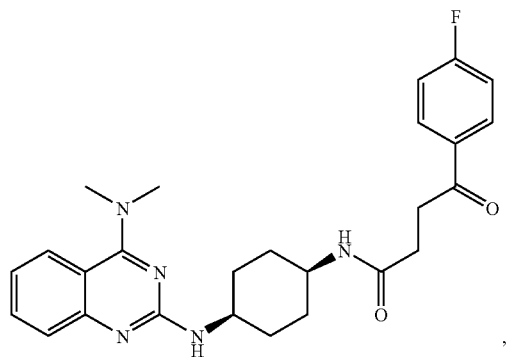 , 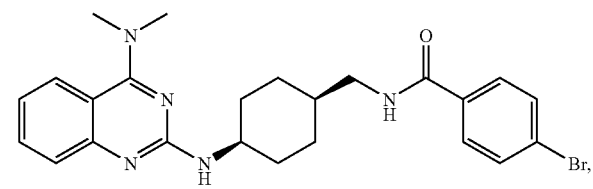
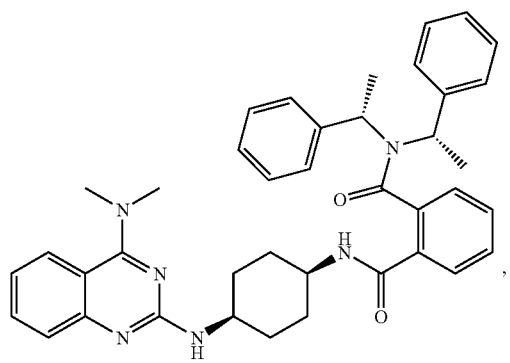 , 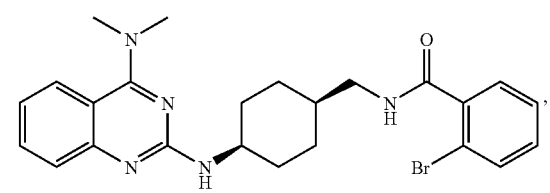
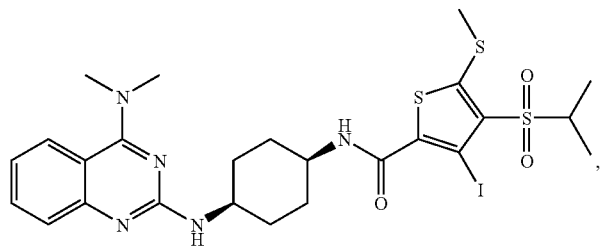 , 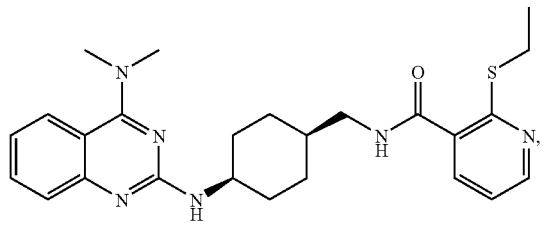
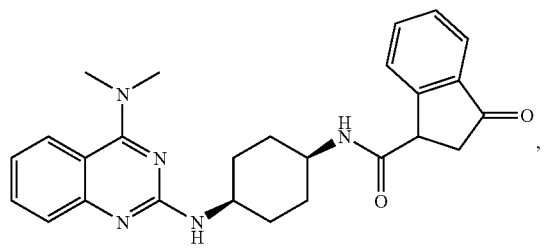 , 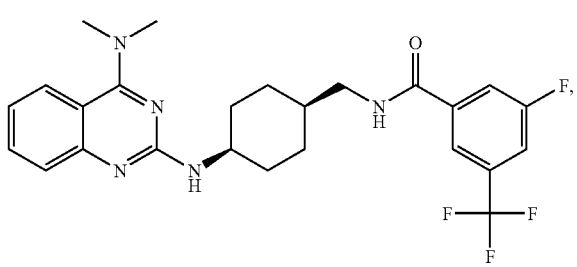
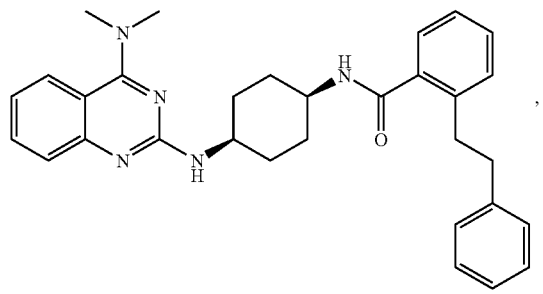 , 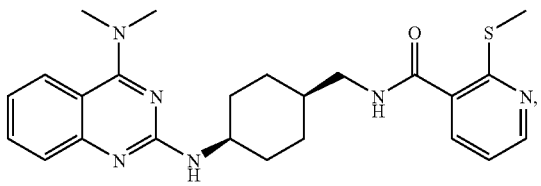

-continued
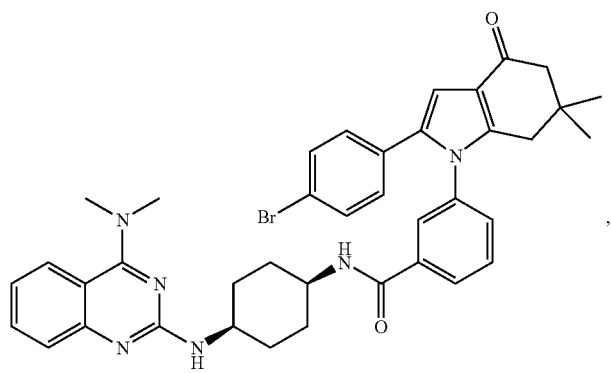
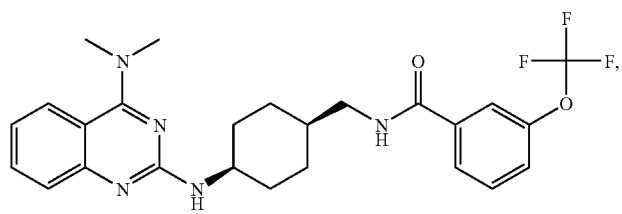
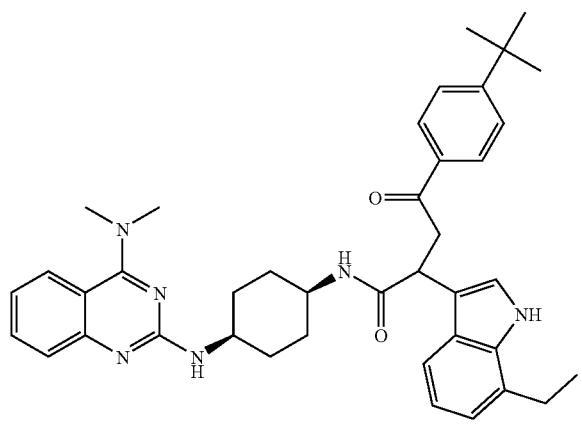
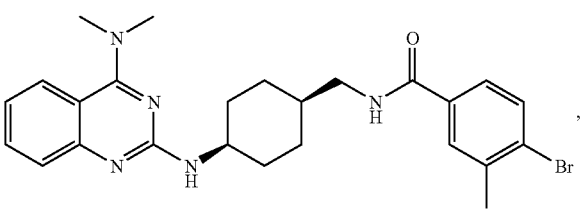
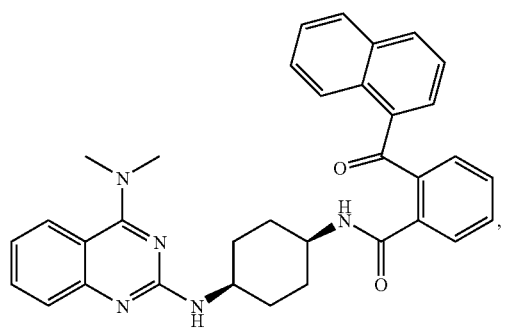
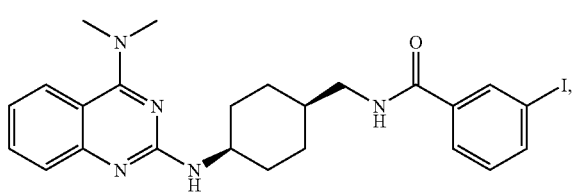
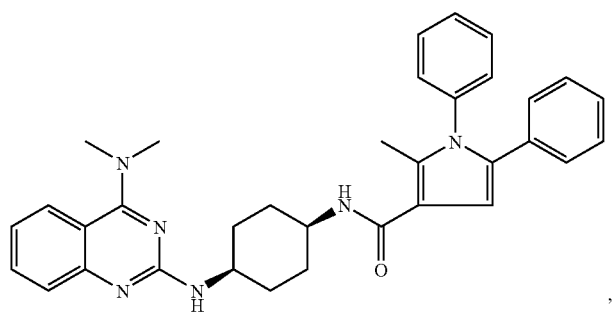
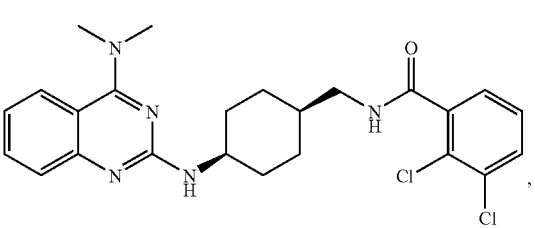

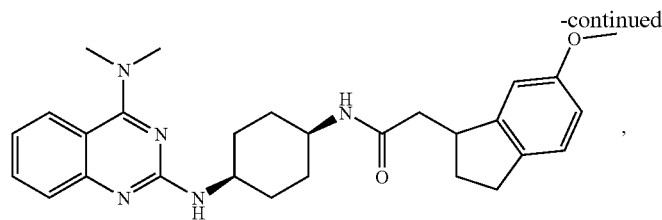
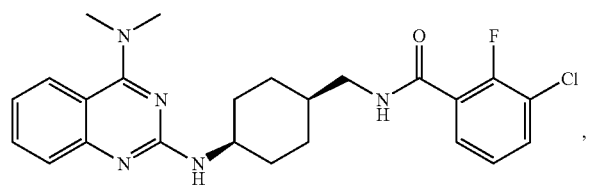
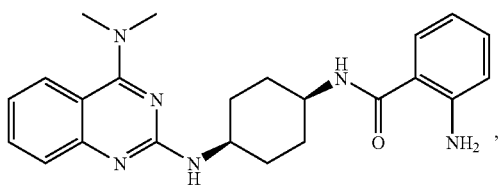
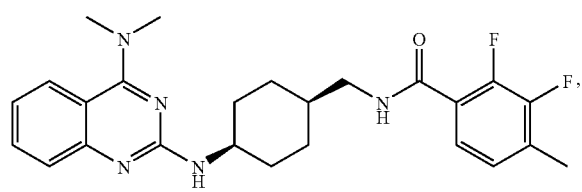
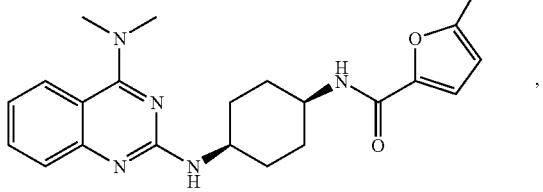
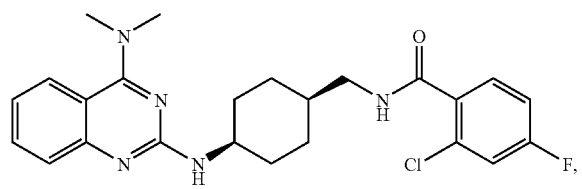
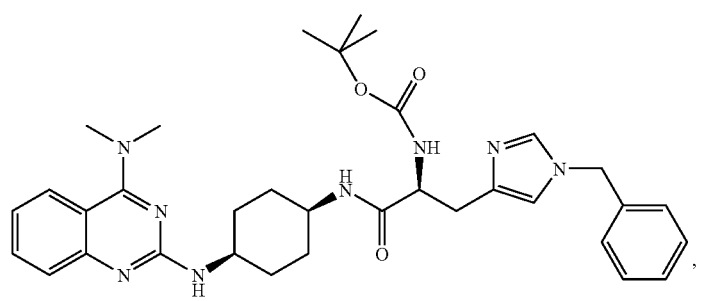
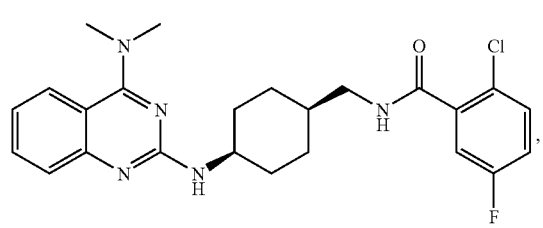
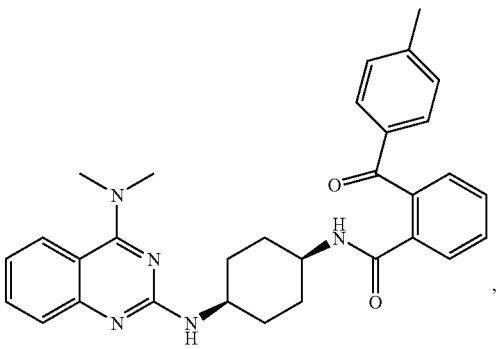

-continued
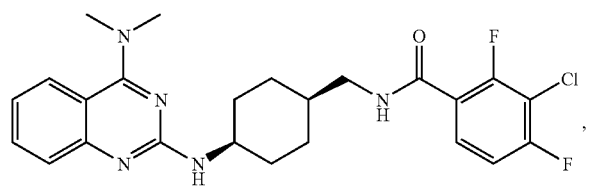
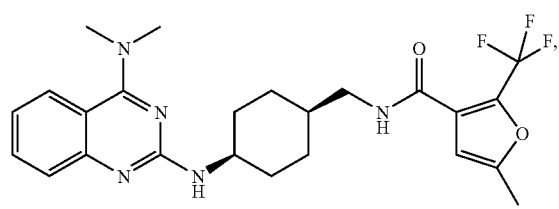
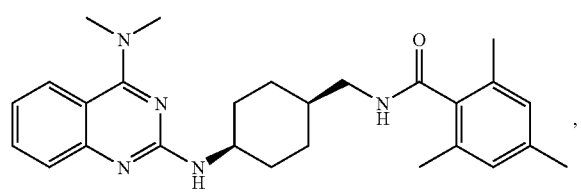
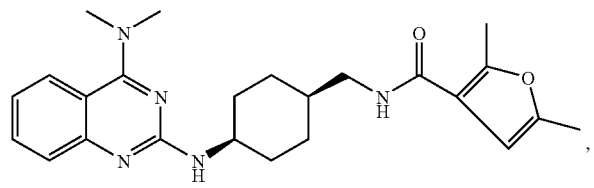
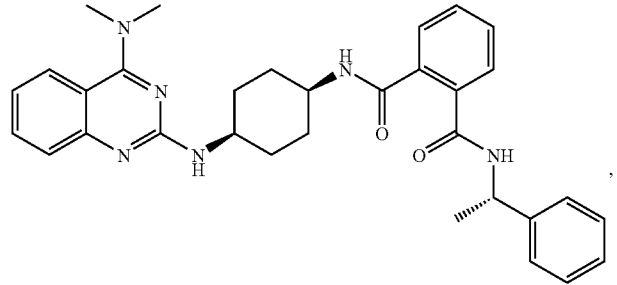
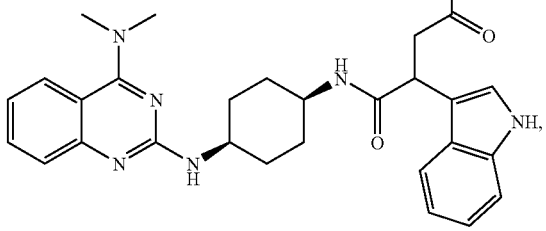
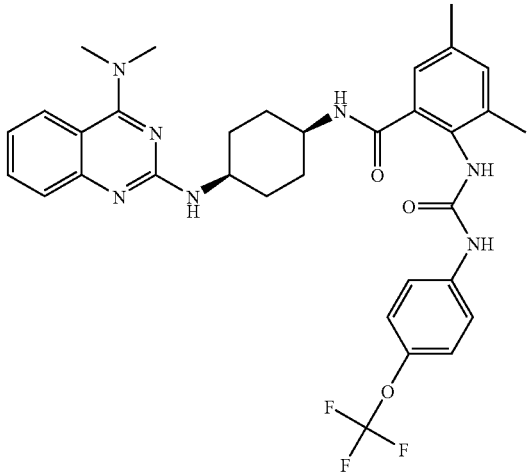
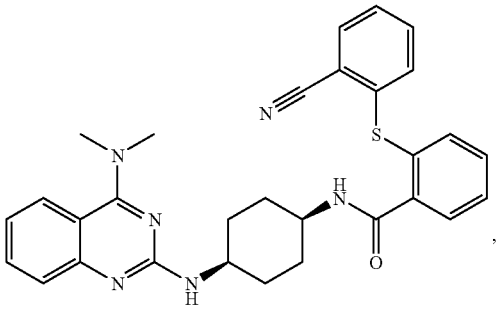

-continued
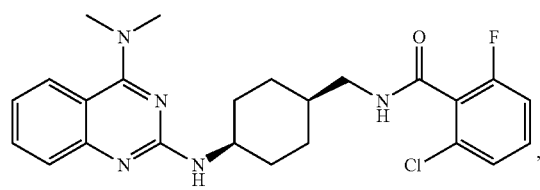
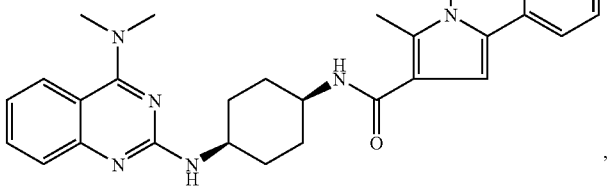
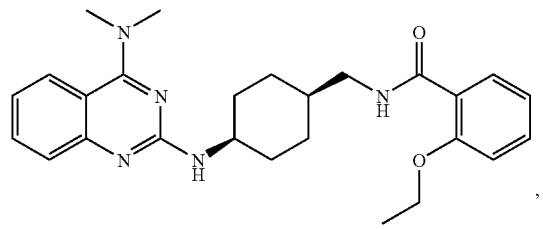
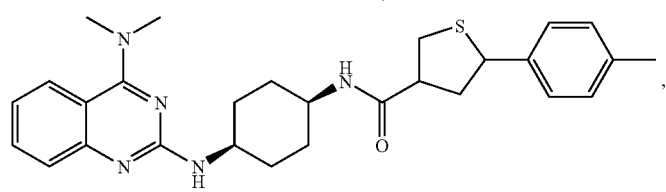
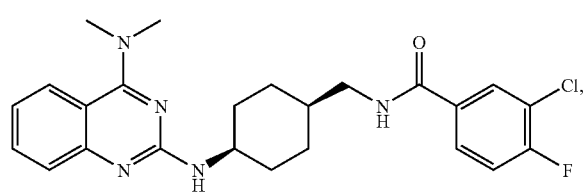
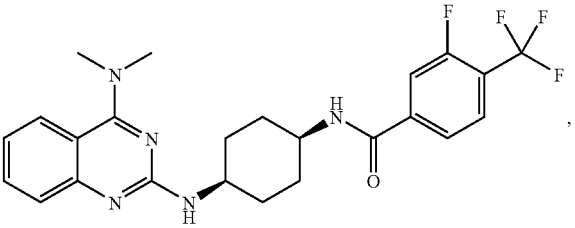
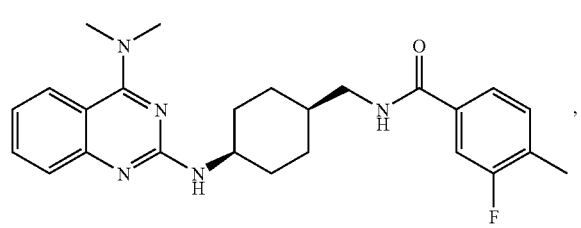
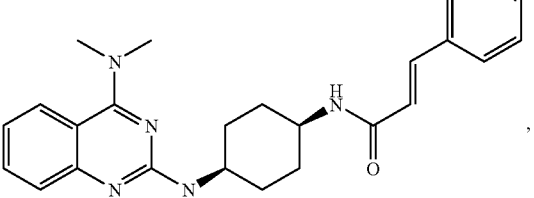
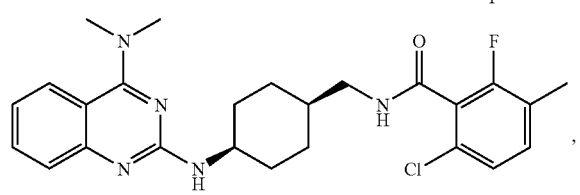
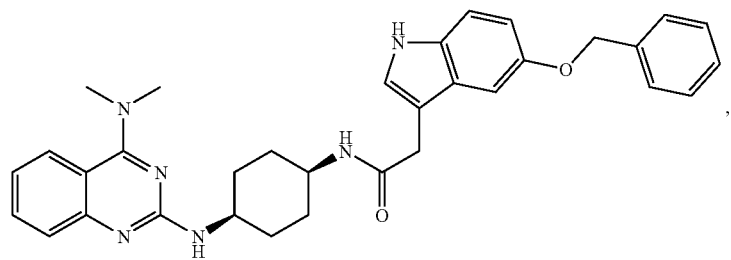

-continued
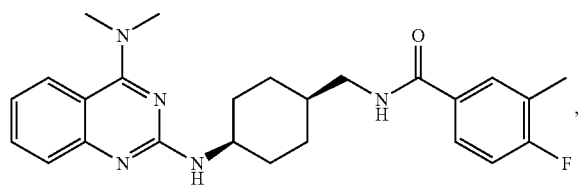
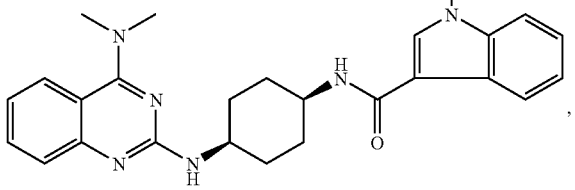
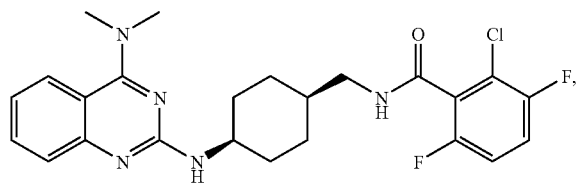
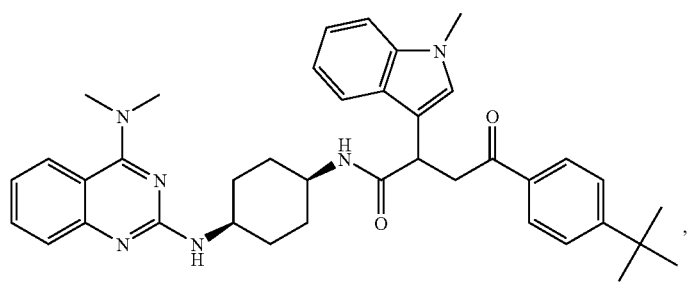
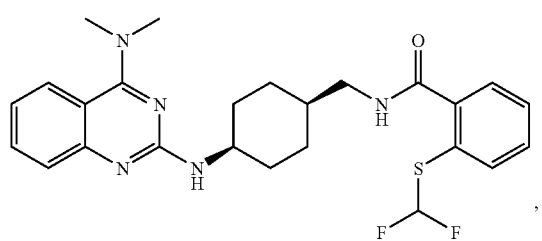
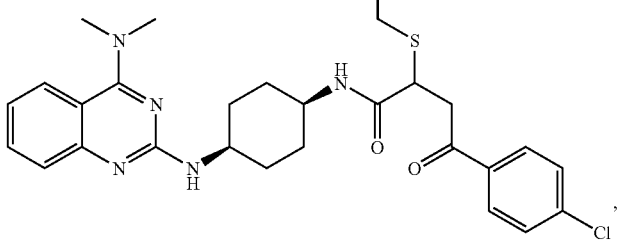
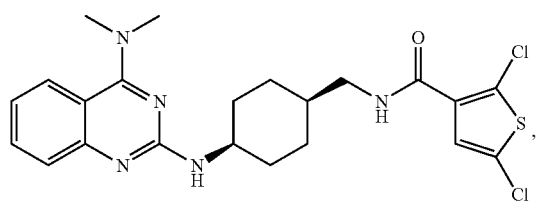
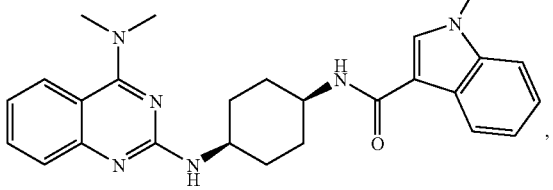

-continued
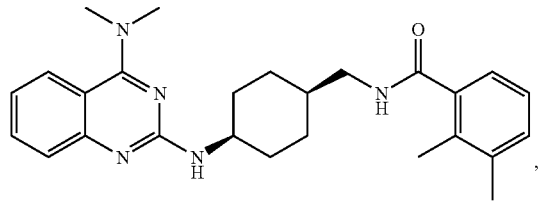,
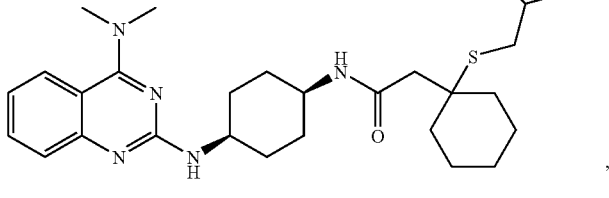,
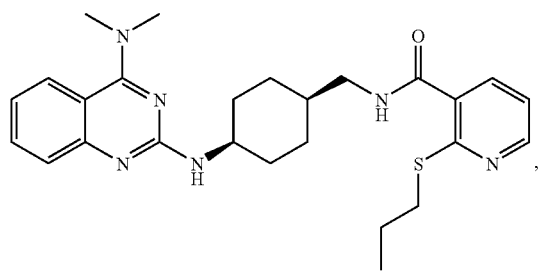,
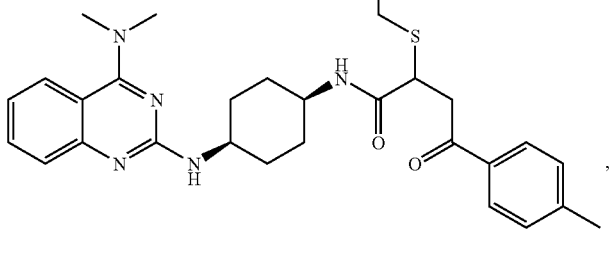,
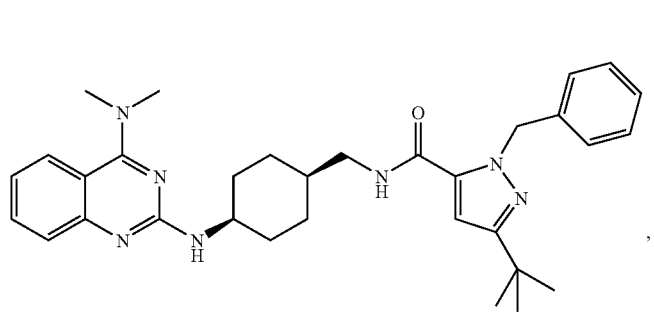,
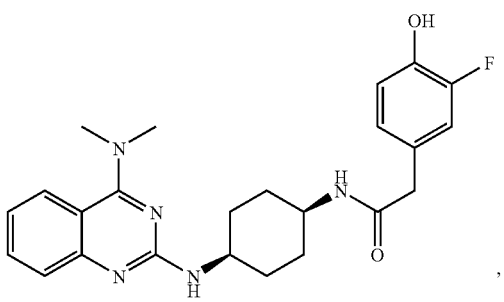,
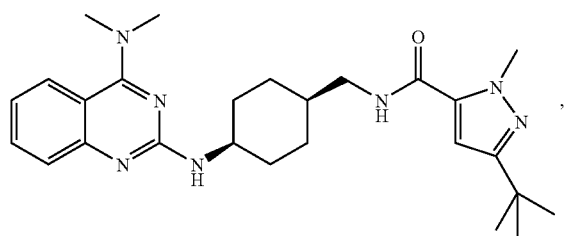,
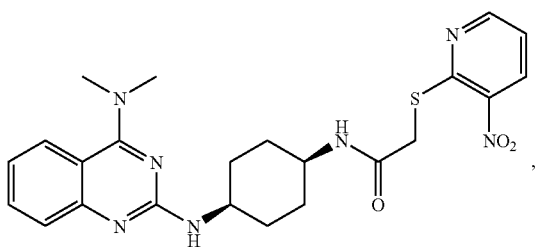, -continued
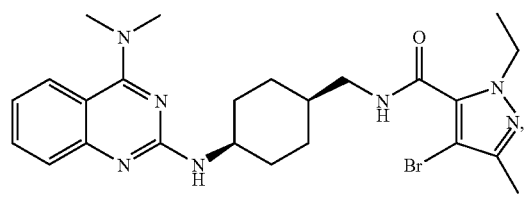
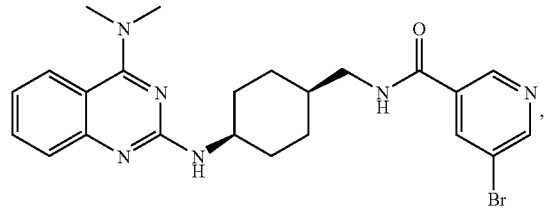
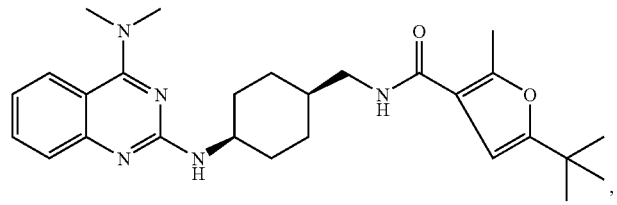
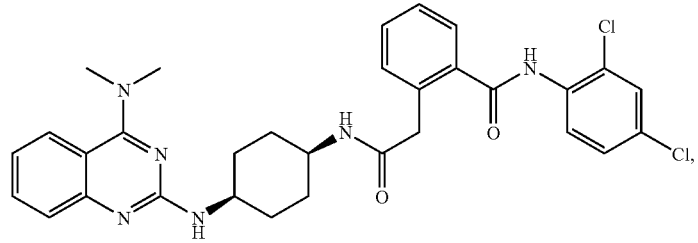
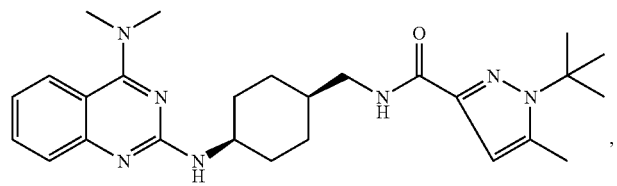
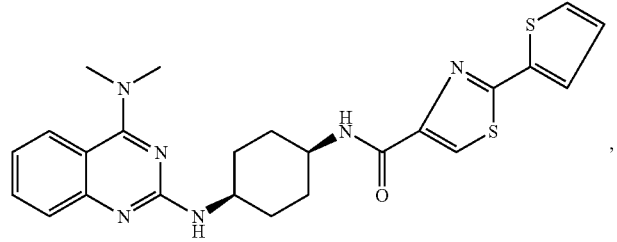
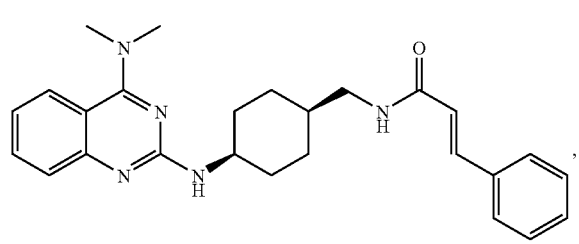
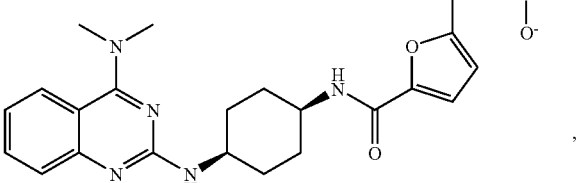
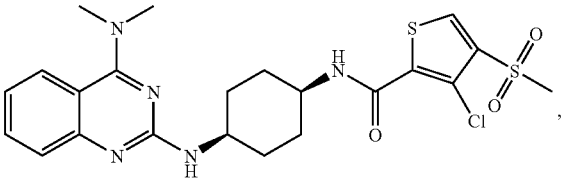
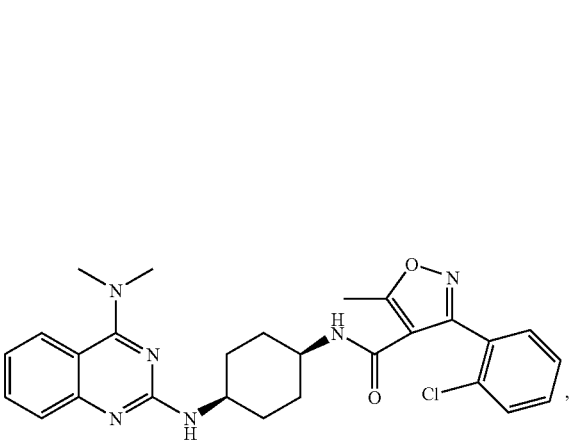

-continued
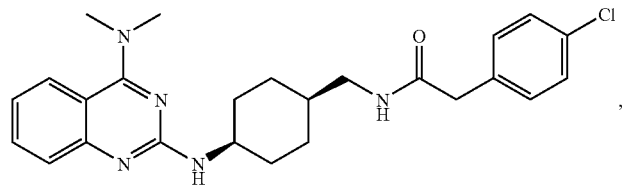
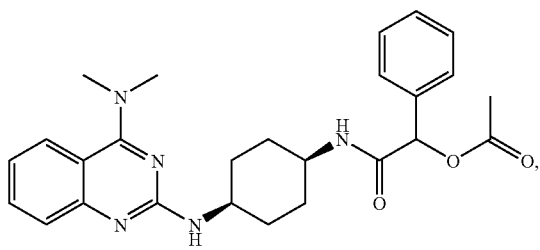
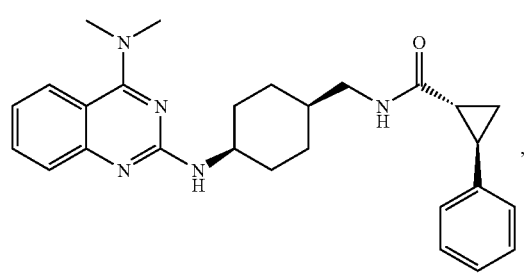
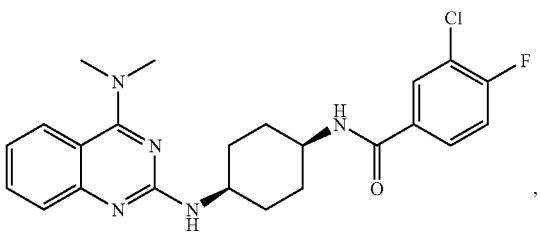
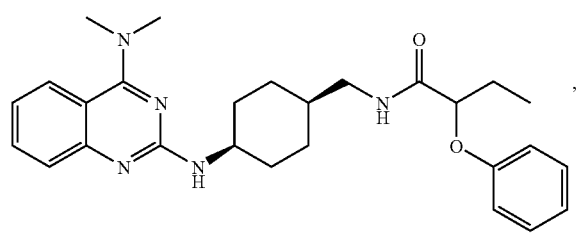
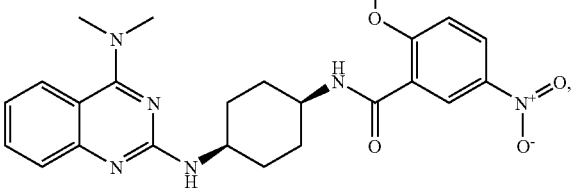
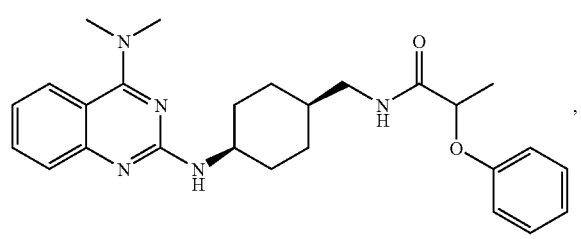
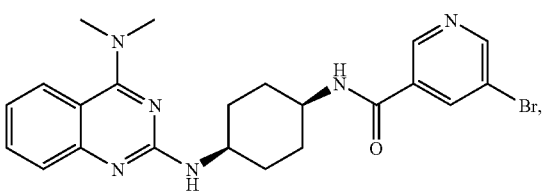
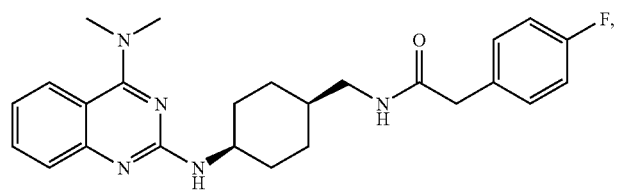
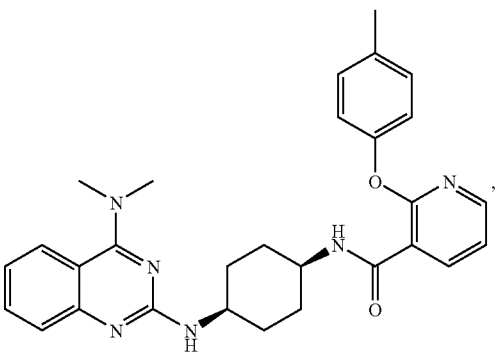

-continued
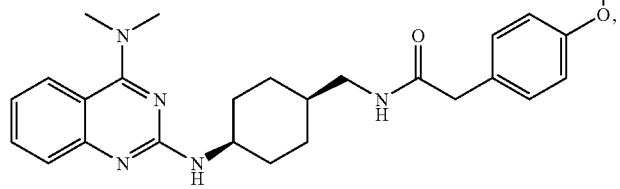
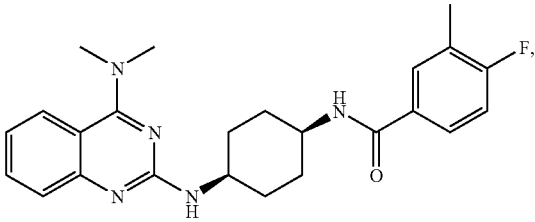
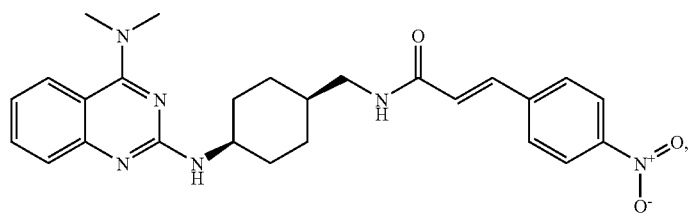
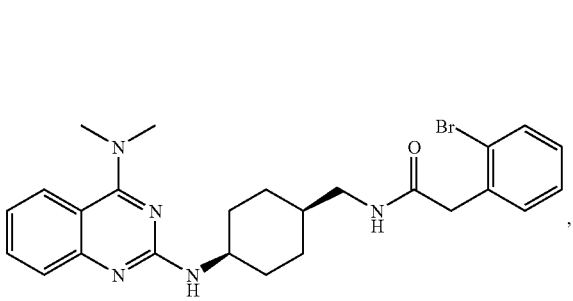
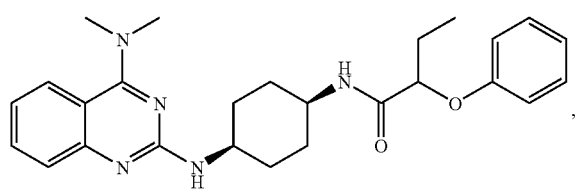
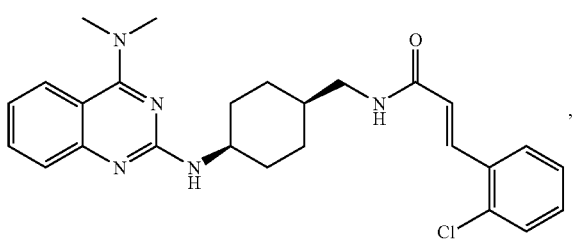
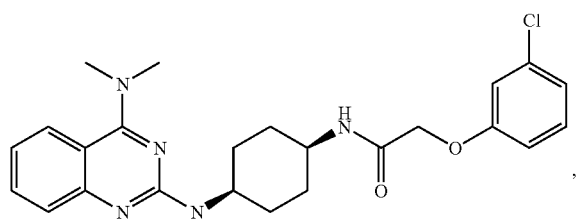
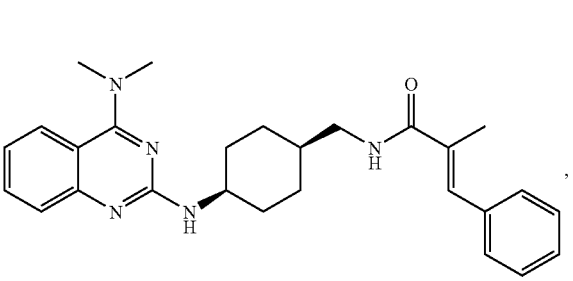
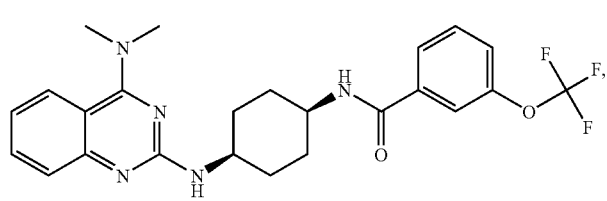
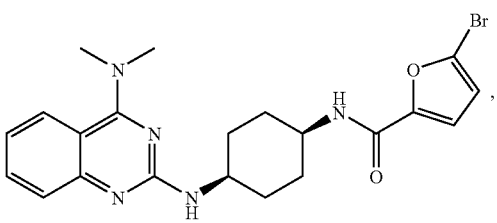

-continued
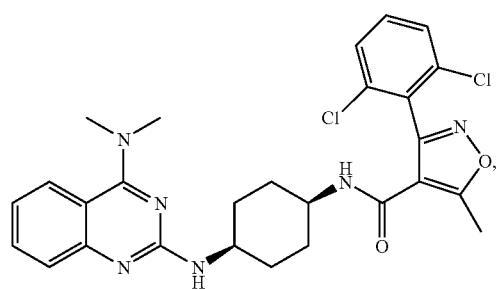
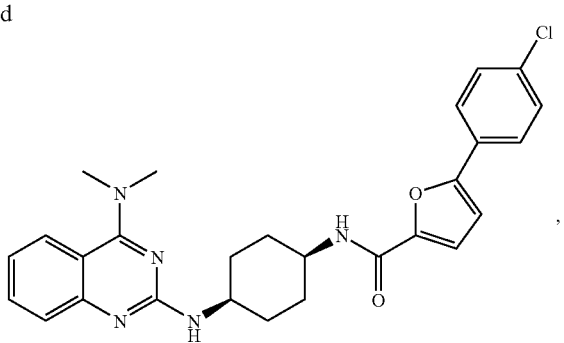
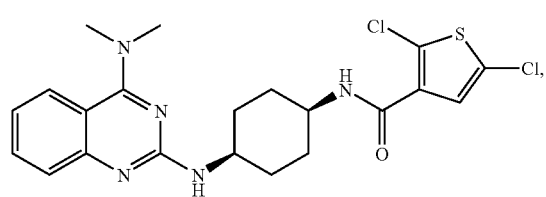
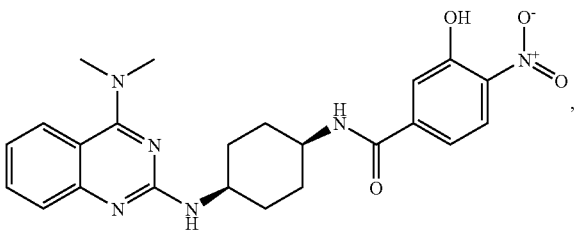
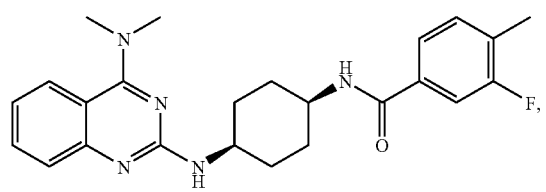
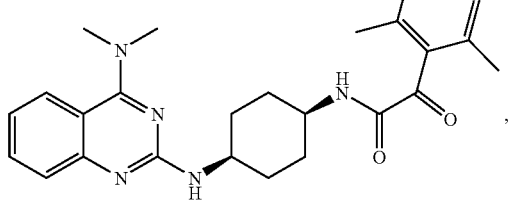
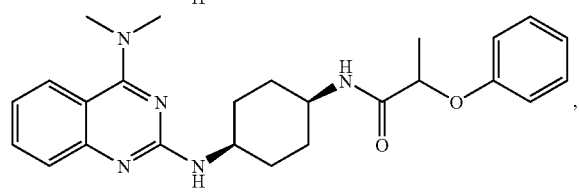
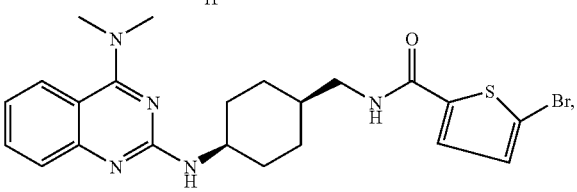
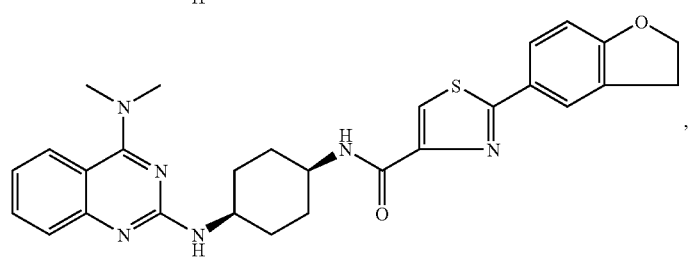
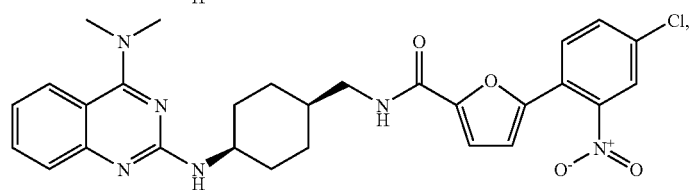
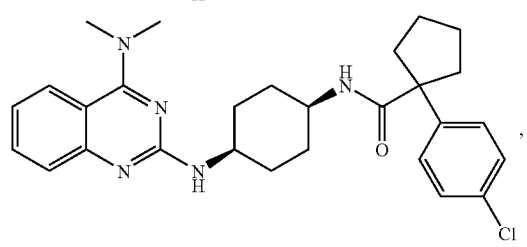
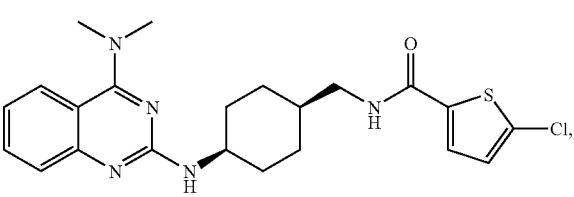

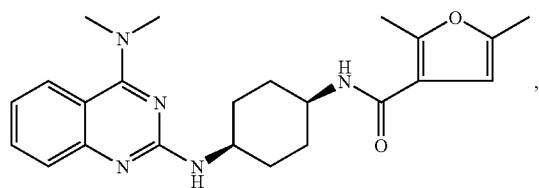
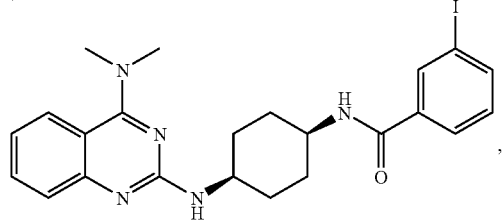
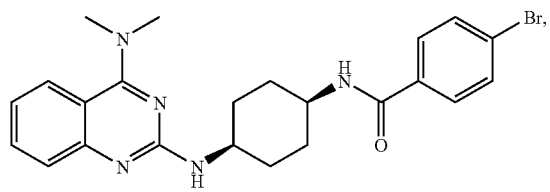
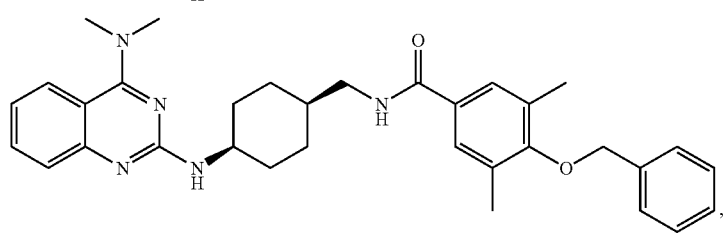
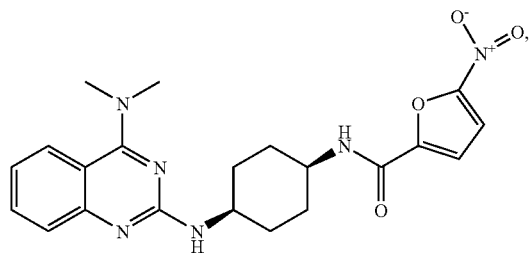
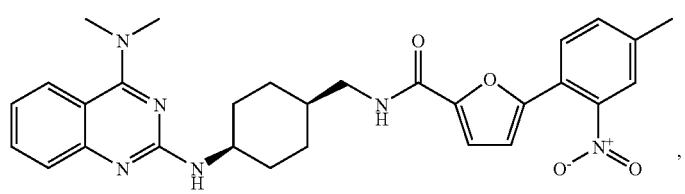
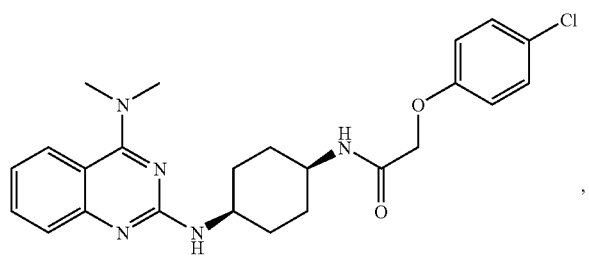
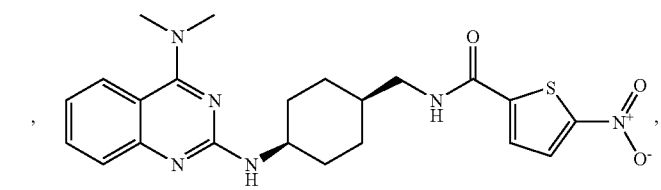

-continued
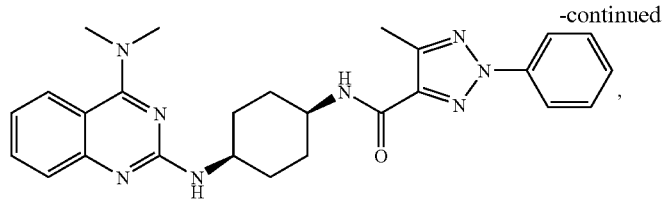
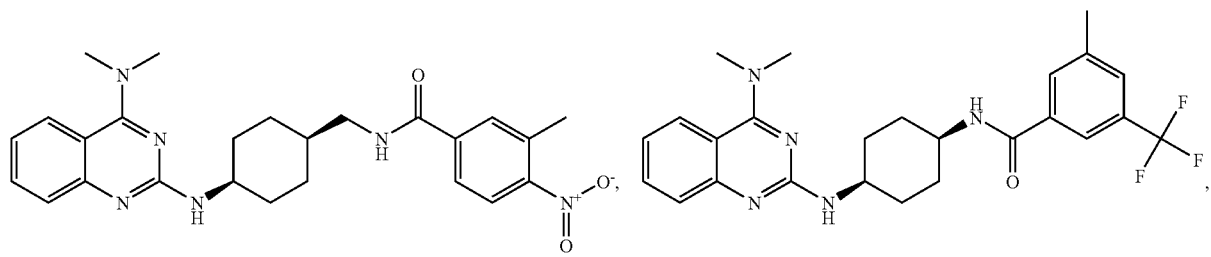
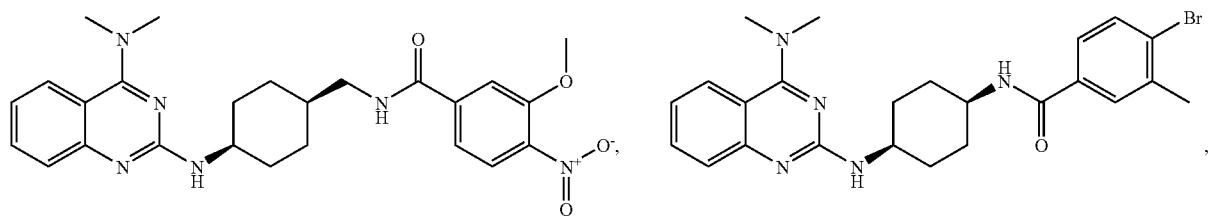
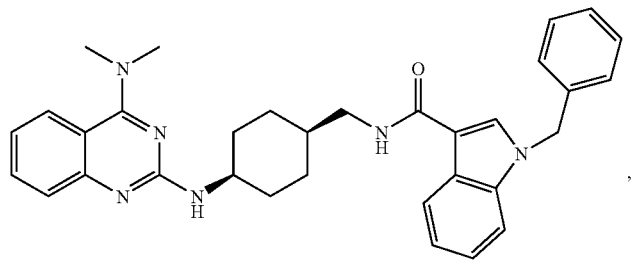
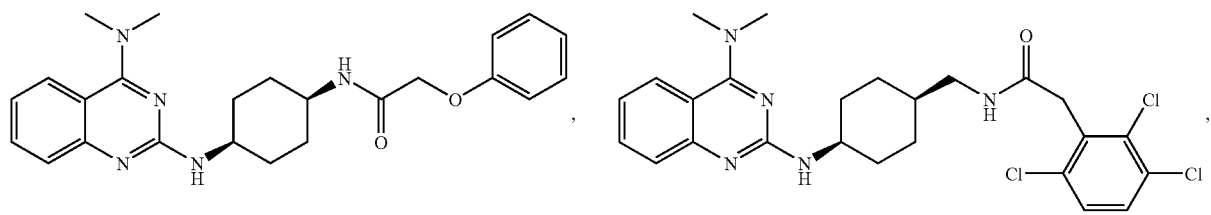
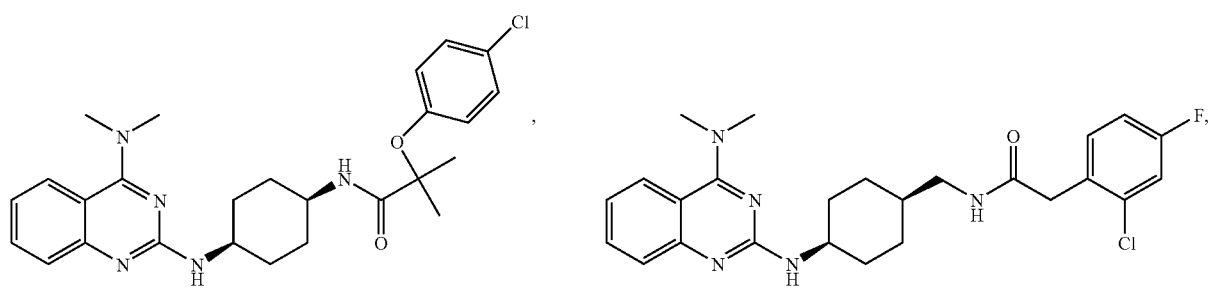

-continued
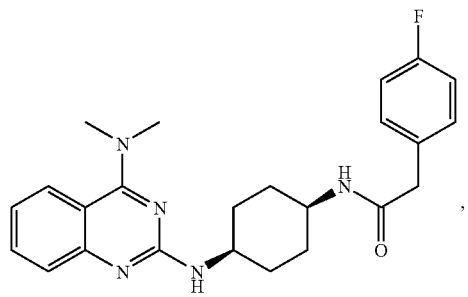 , 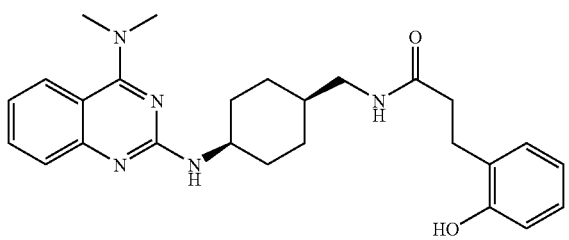 ,
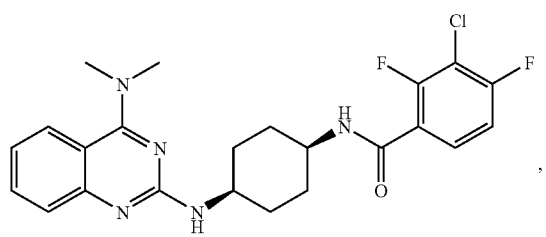 , 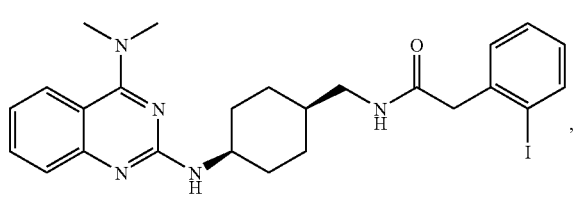 ,
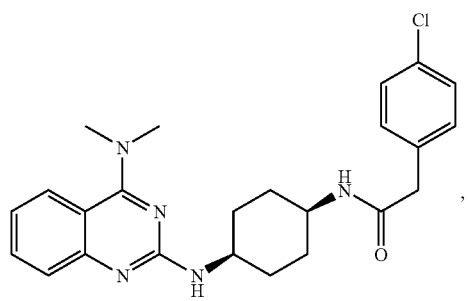 , 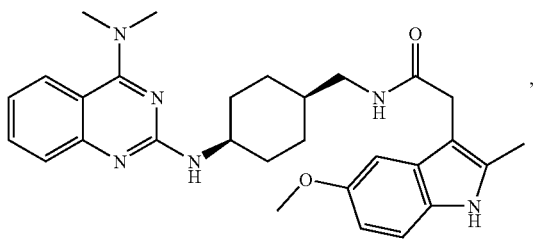 ,
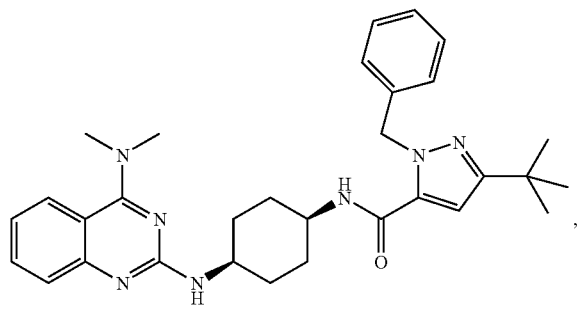 ,
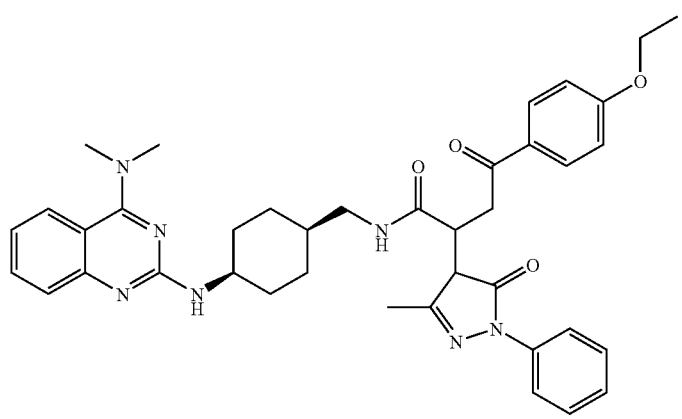 , 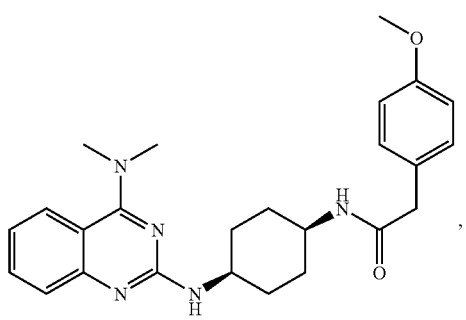 , -continued
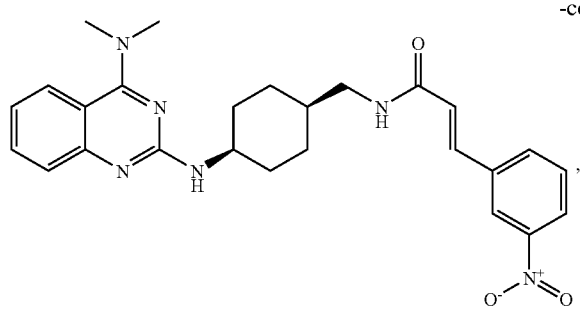
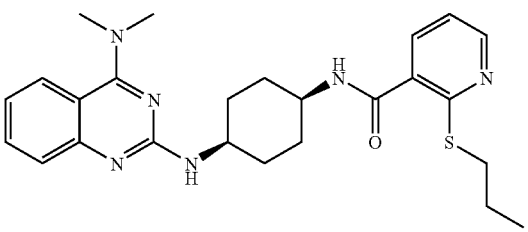
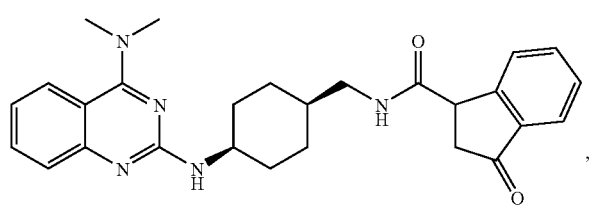
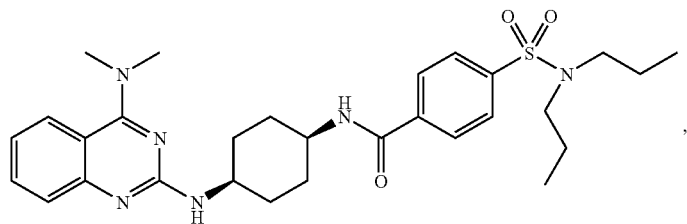
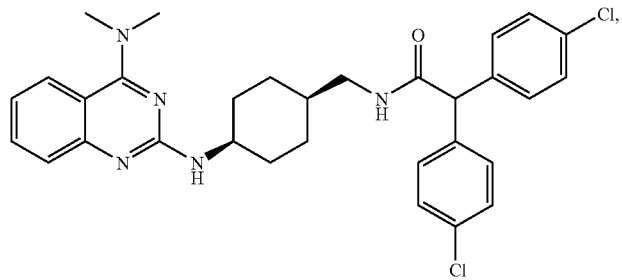
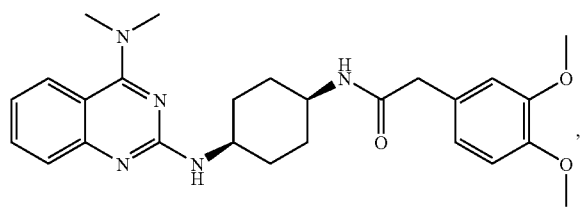
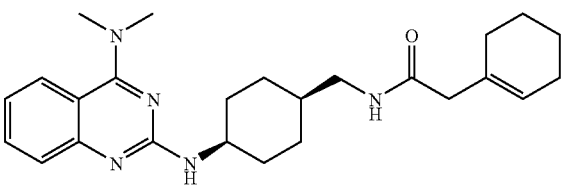
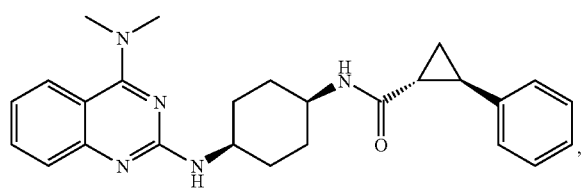
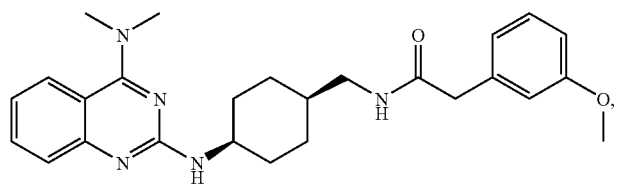

-continued
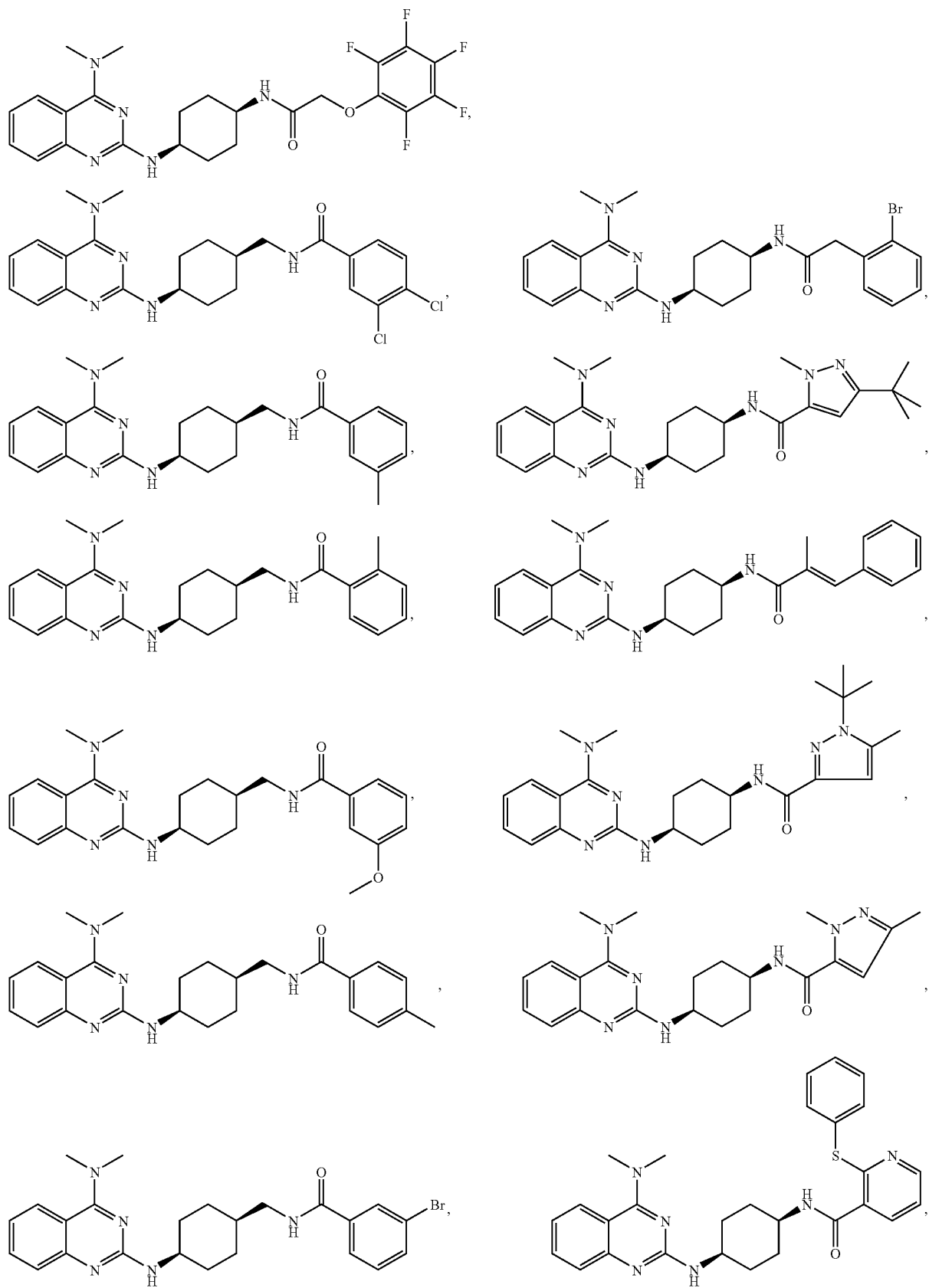

-continued
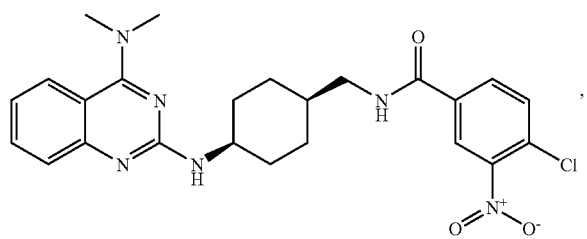
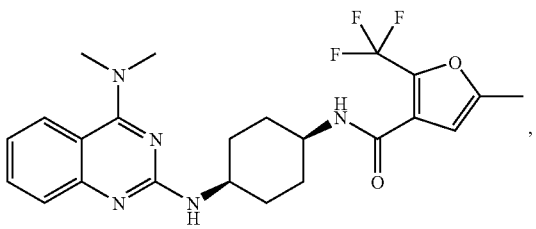
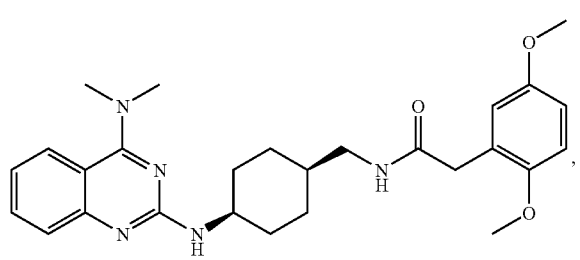
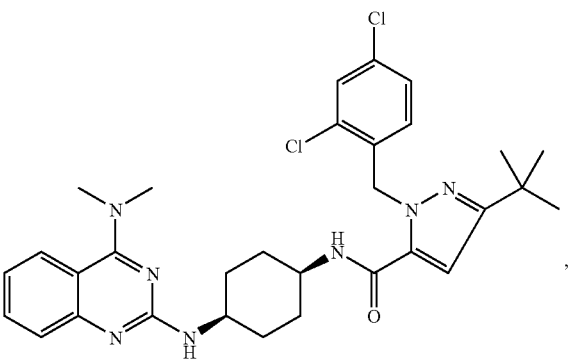
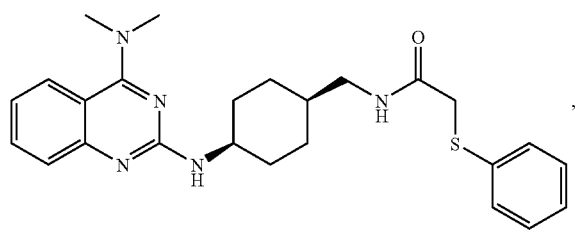
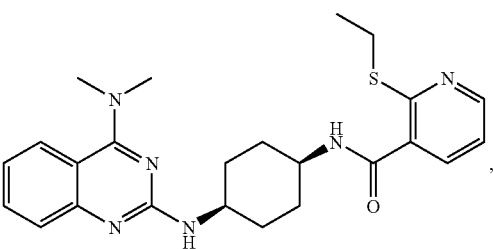
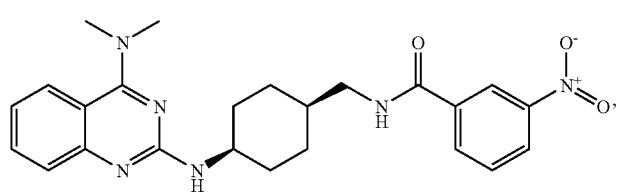
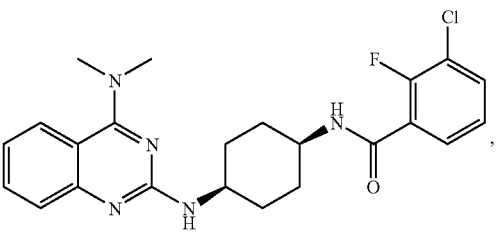
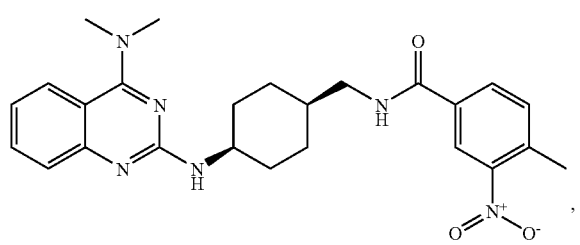
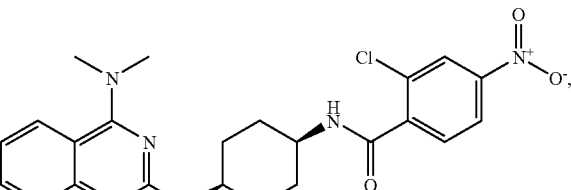
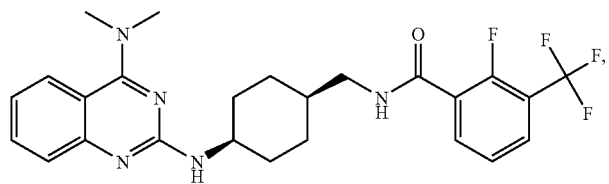

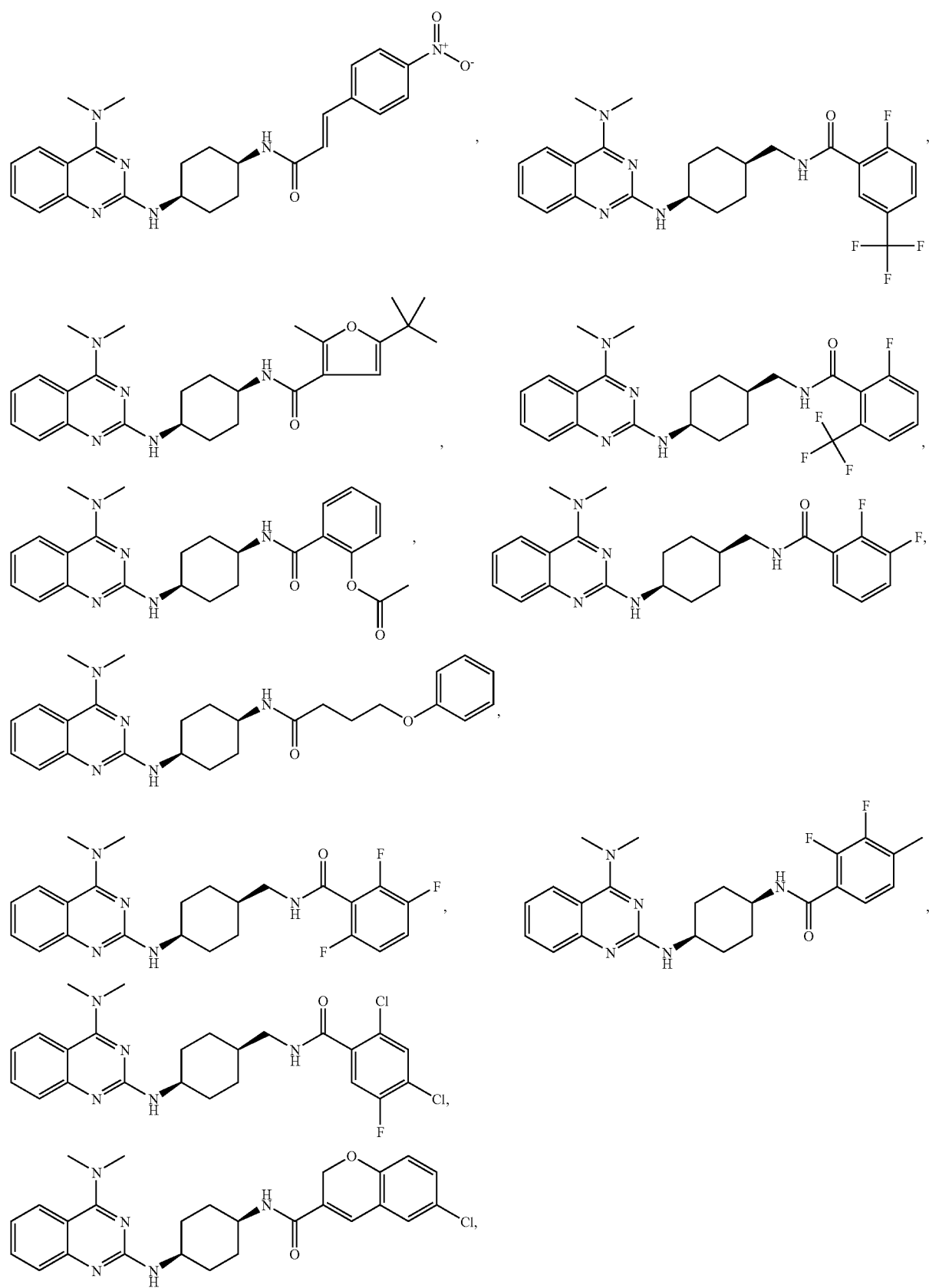

-continued
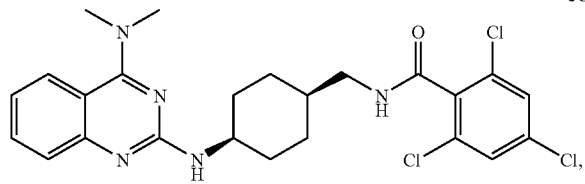
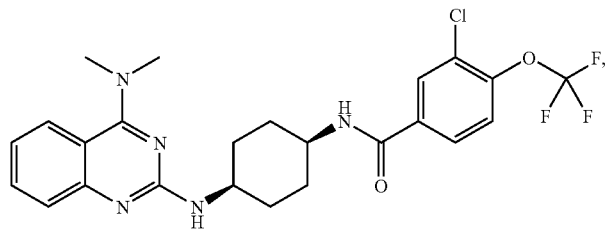
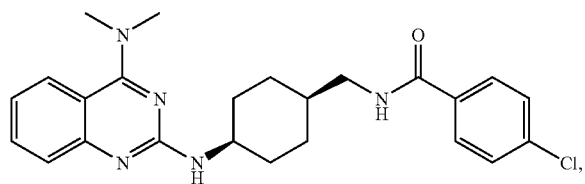
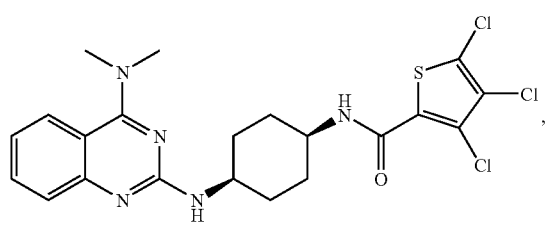
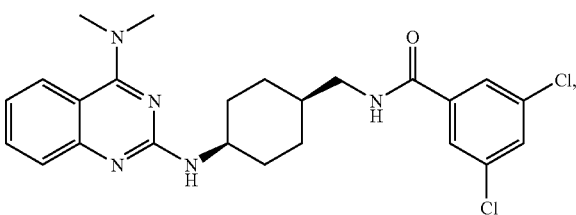
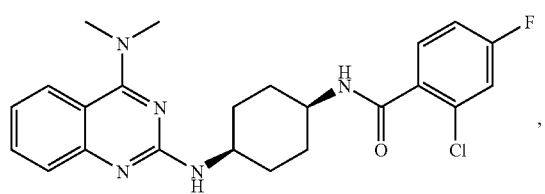
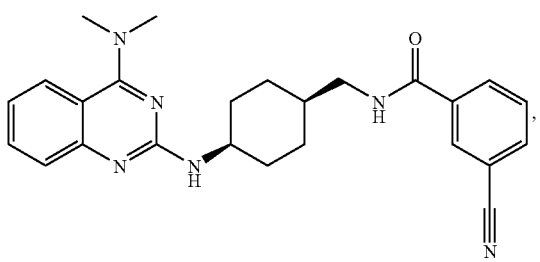
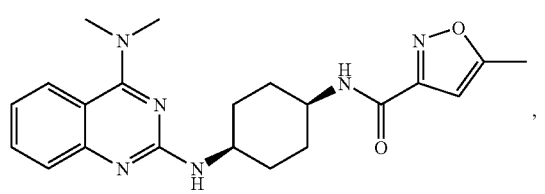
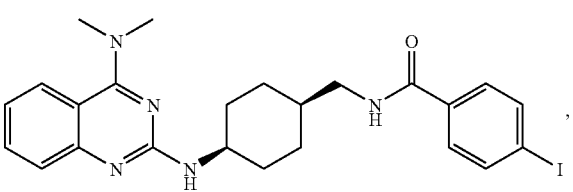
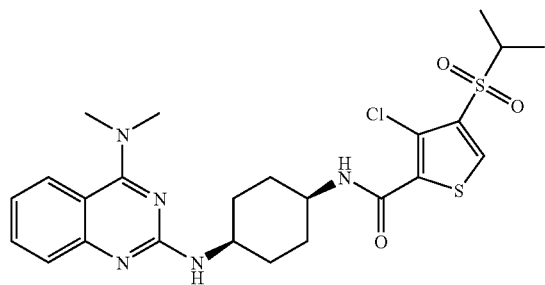
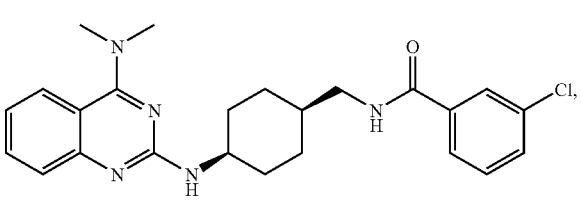

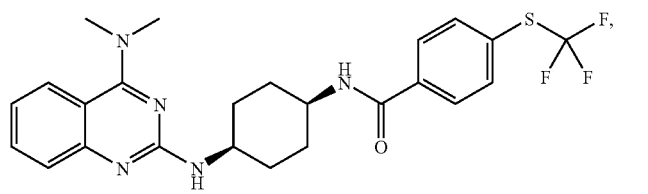
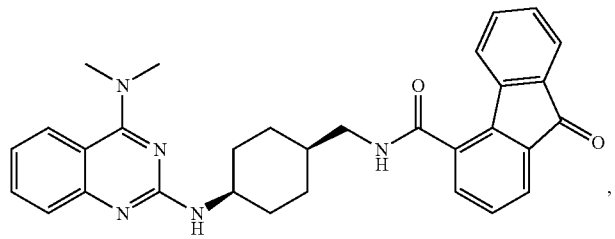
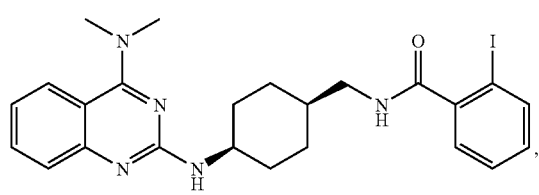
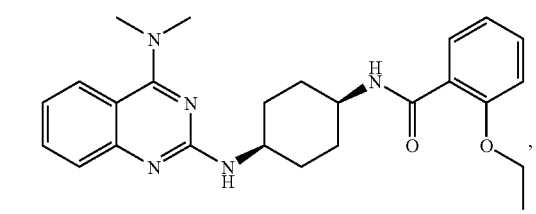
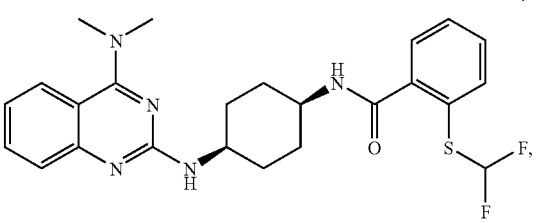
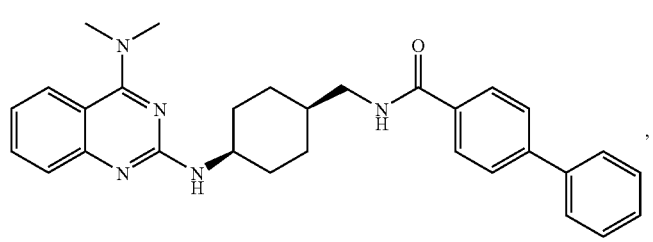
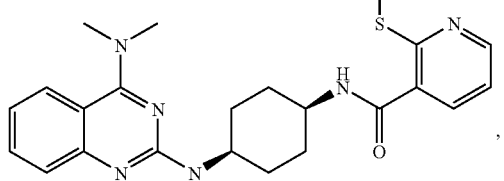
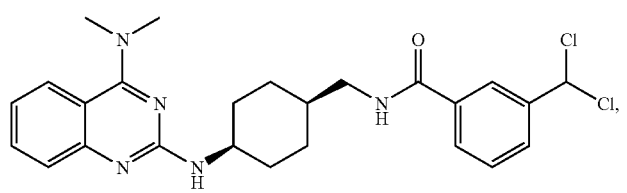
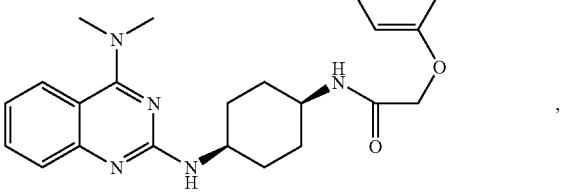
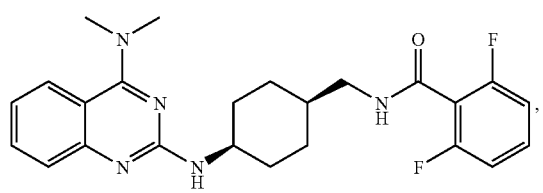
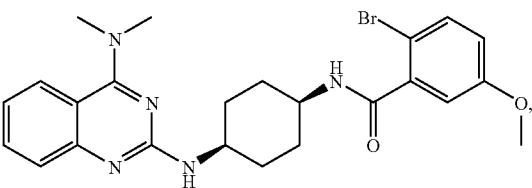
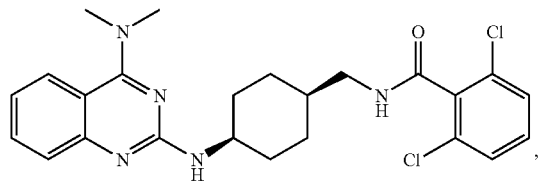

-continued
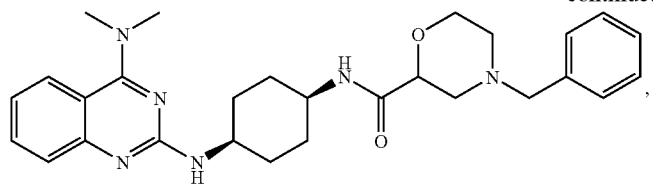
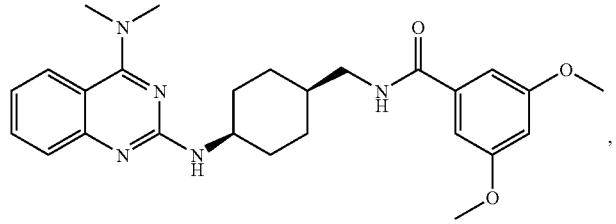
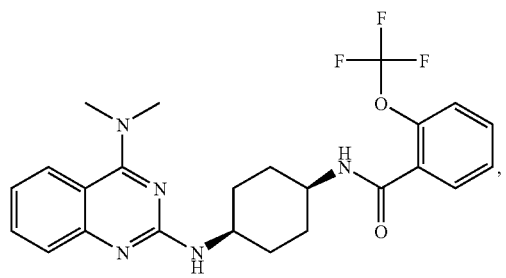
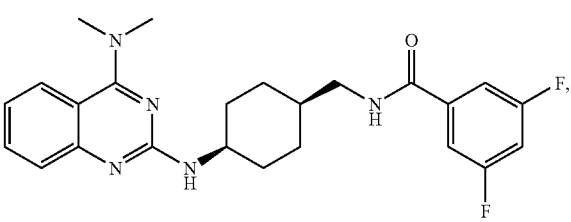
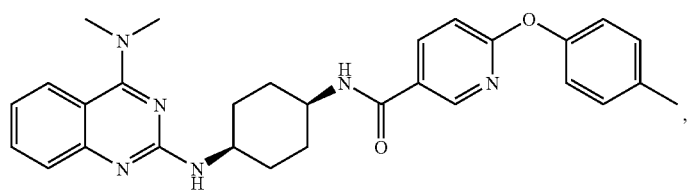
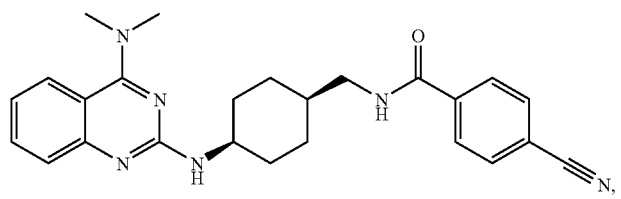
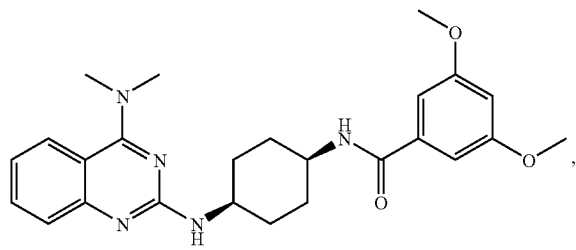
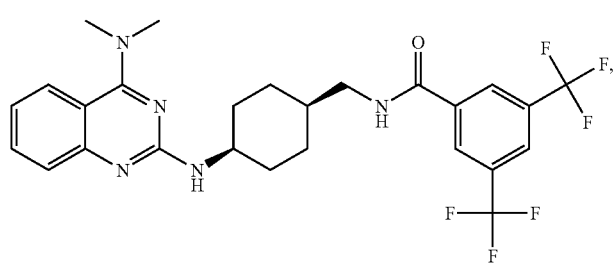
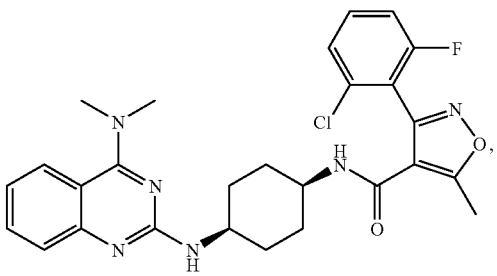

-continued
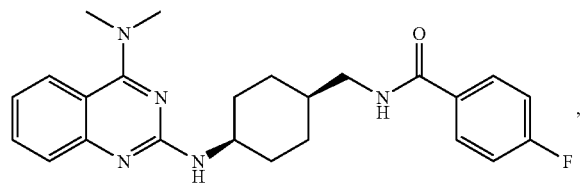
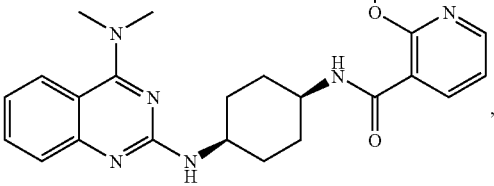
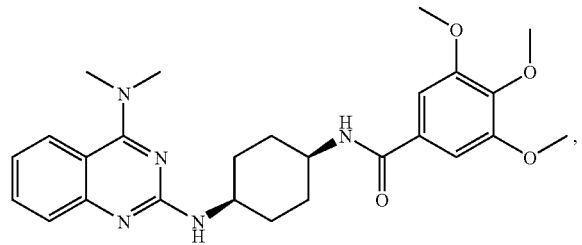
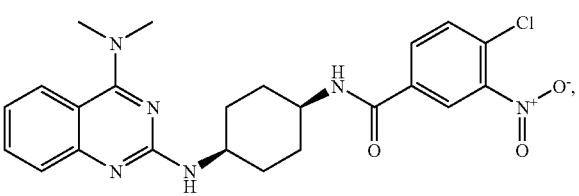
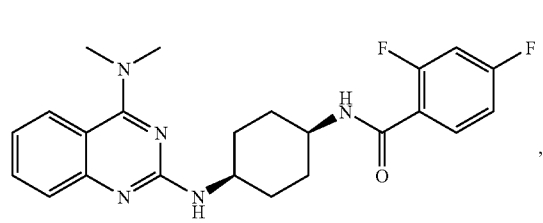
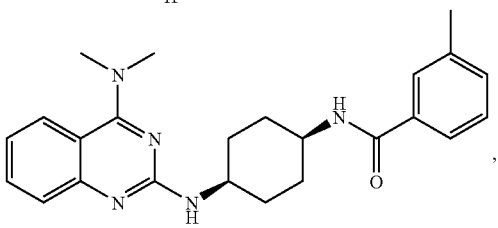
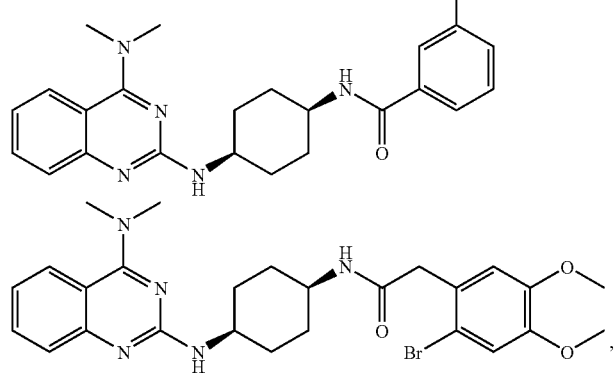
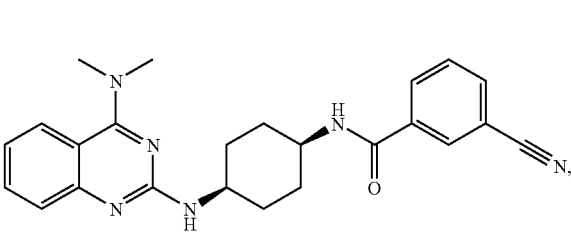
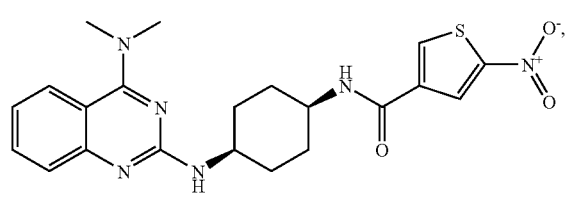
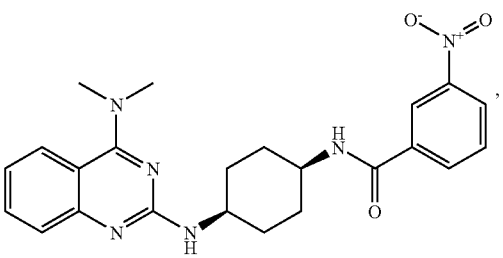

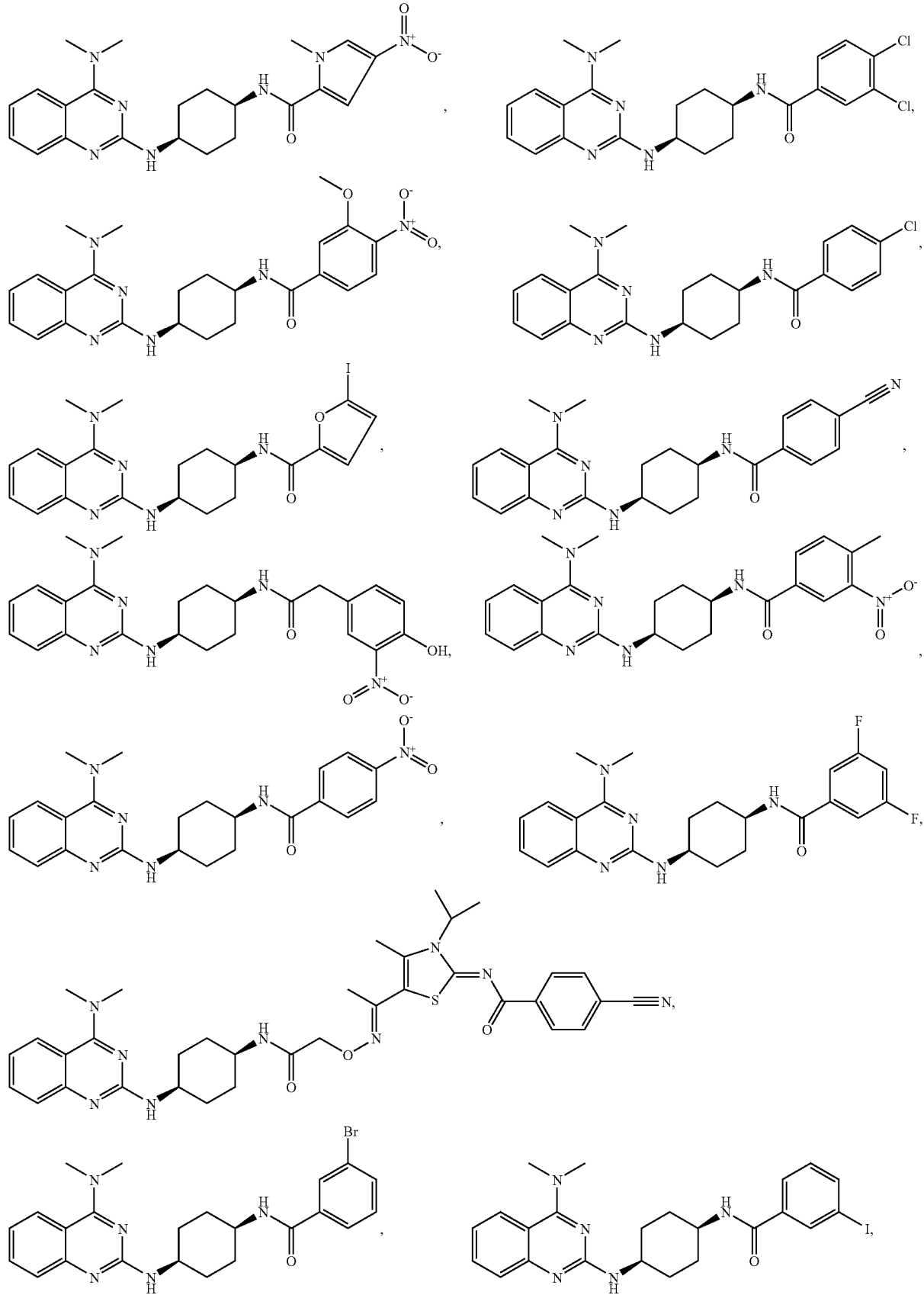

-continued
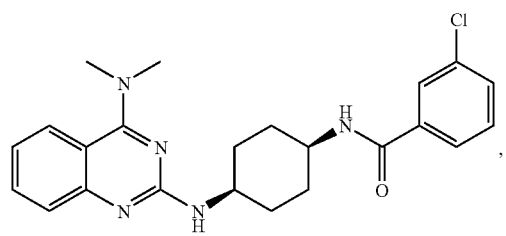
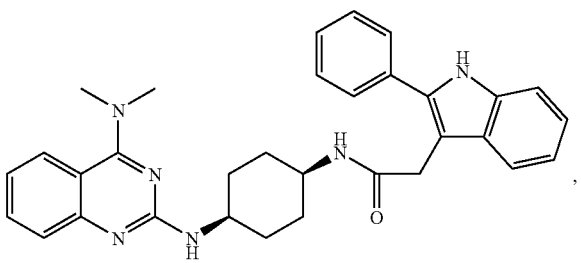
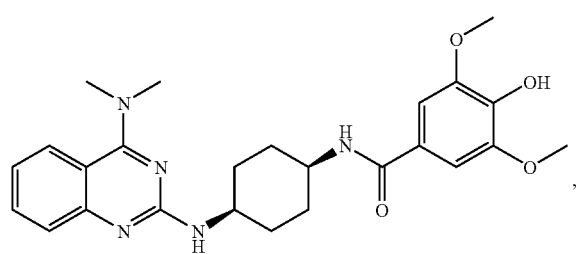
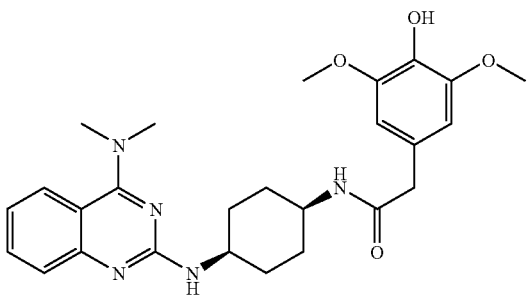
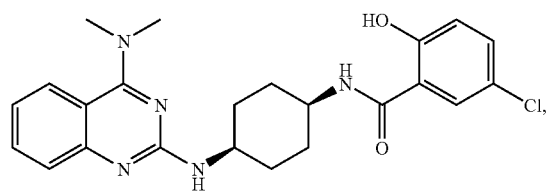
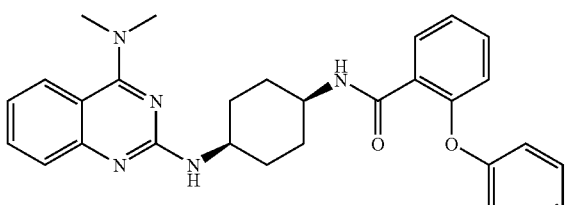
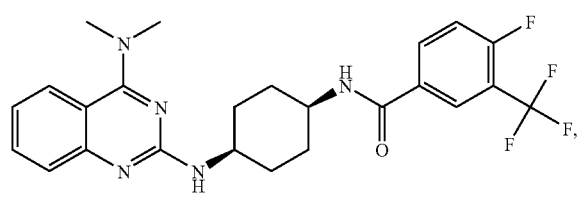
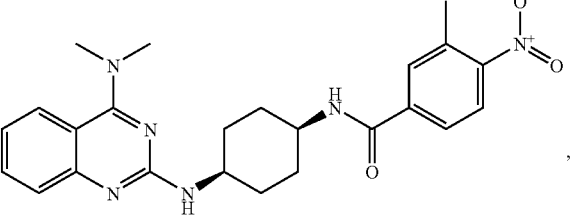
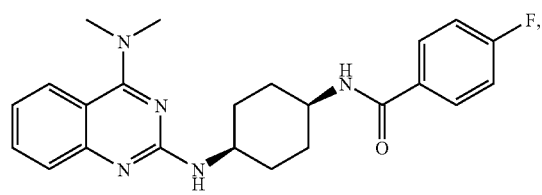
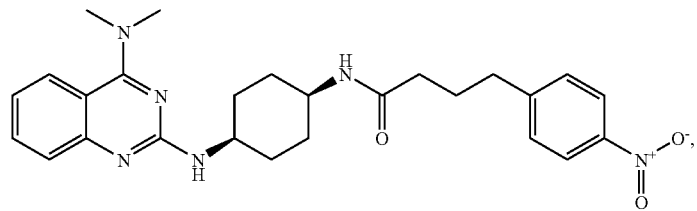
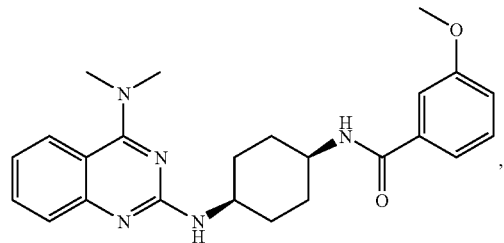

-continued
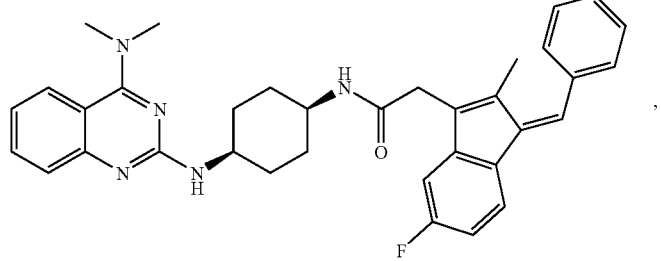
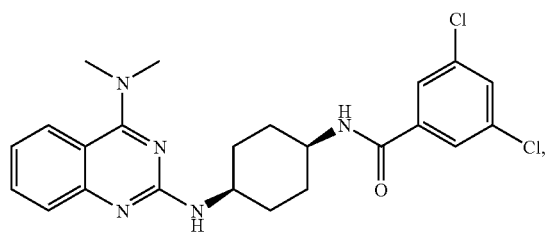
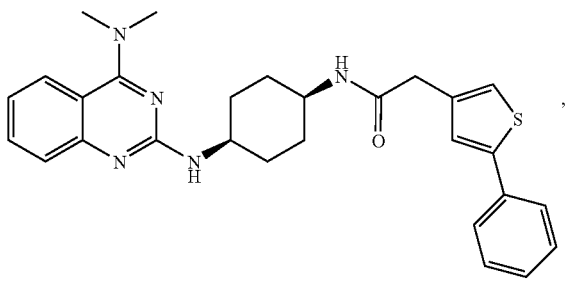
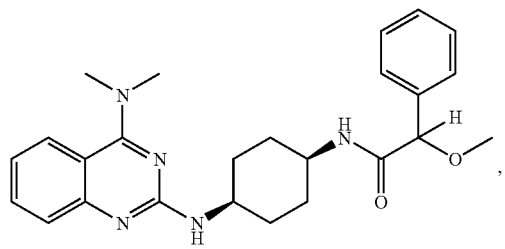
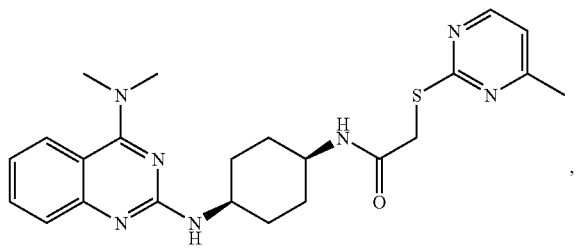
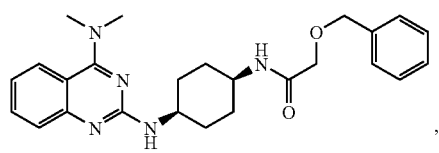
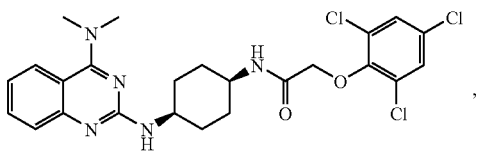
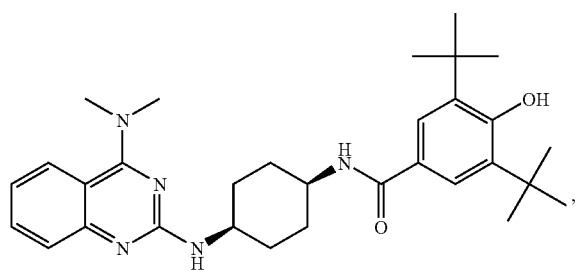
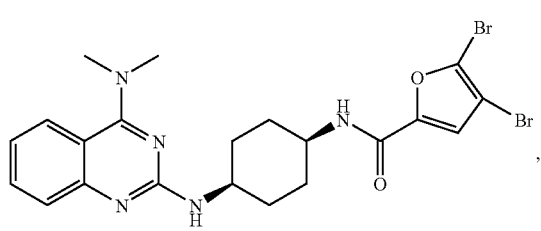
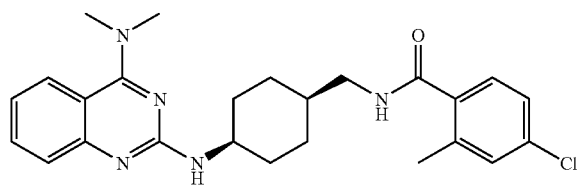
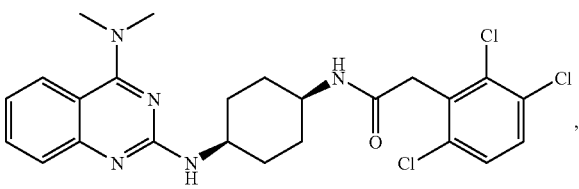

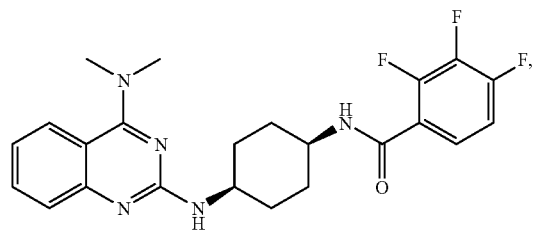
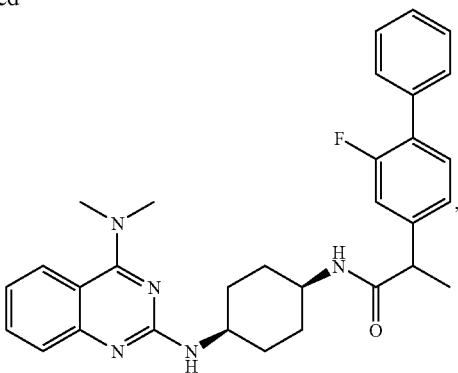
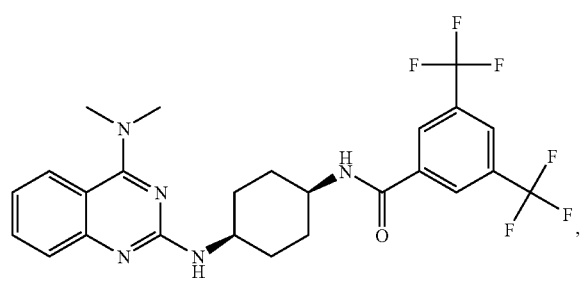
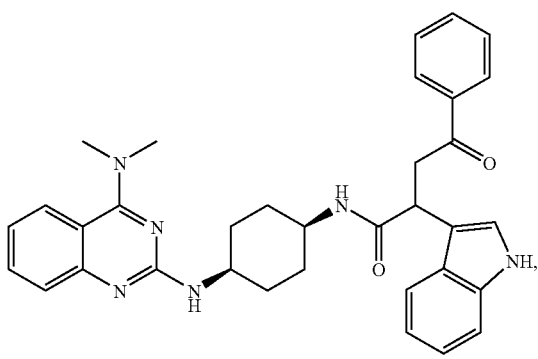
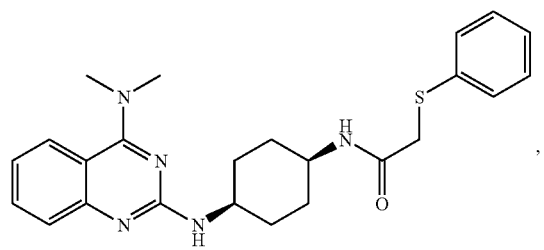
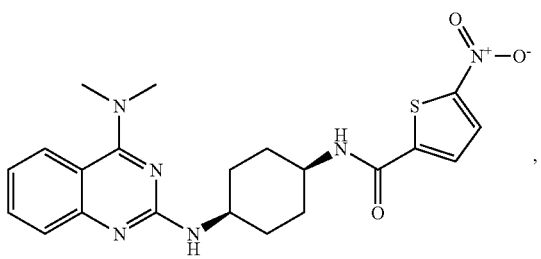
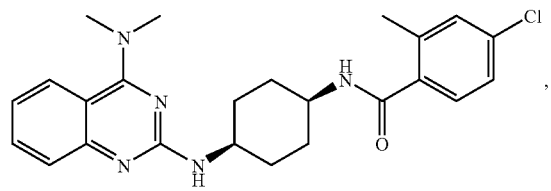
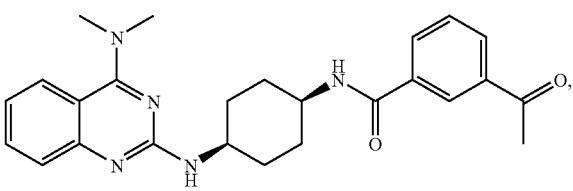
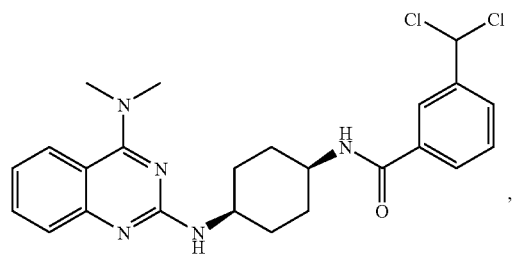
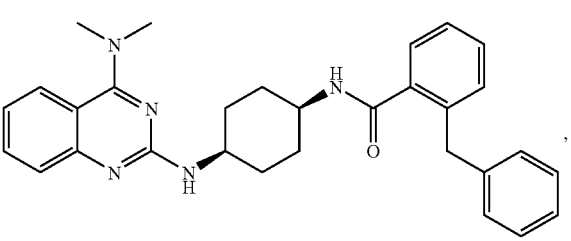

-continued
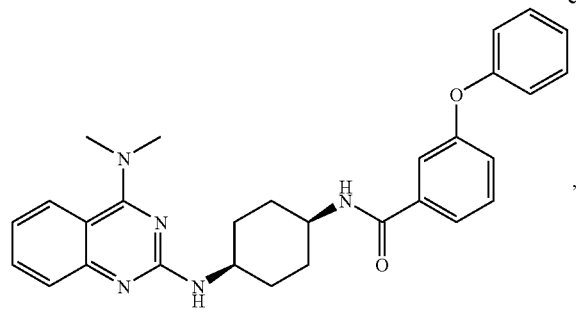
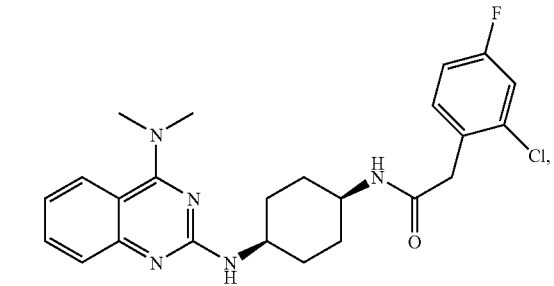
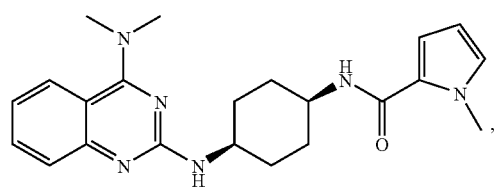
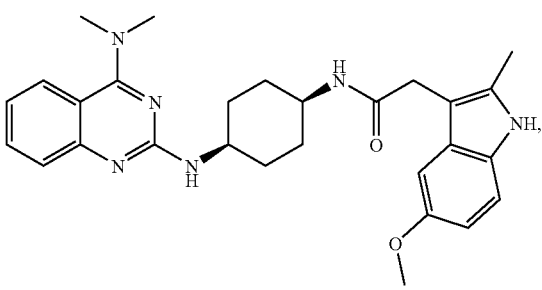
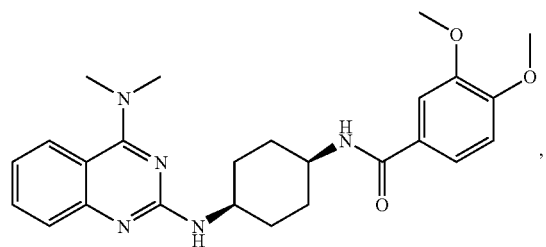
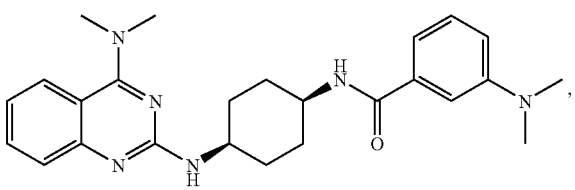
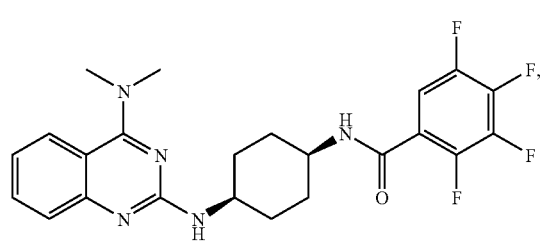
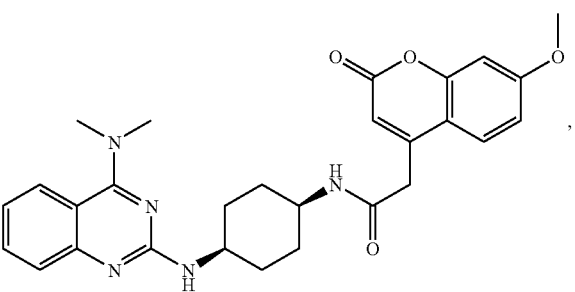
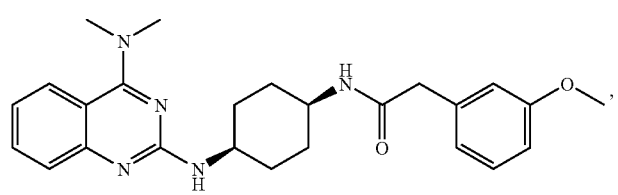
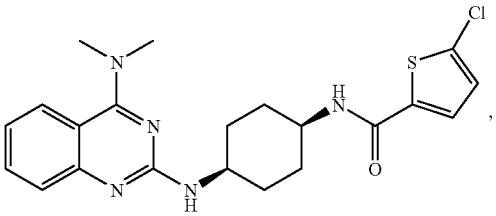
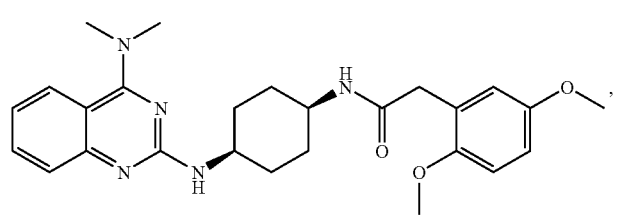
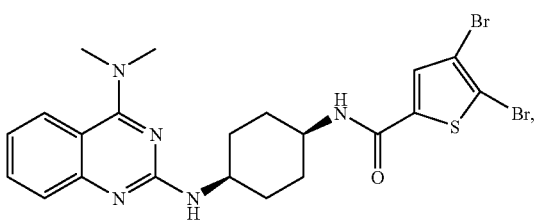

-continued
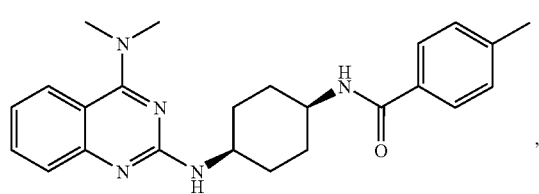
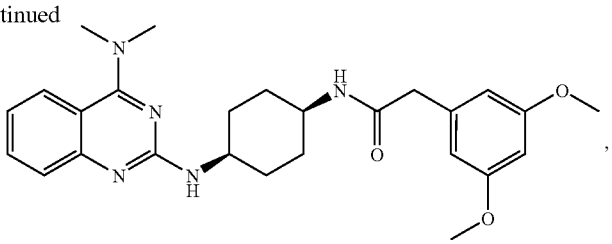
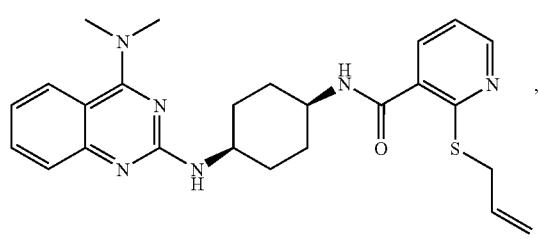
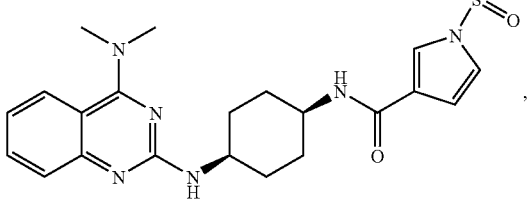
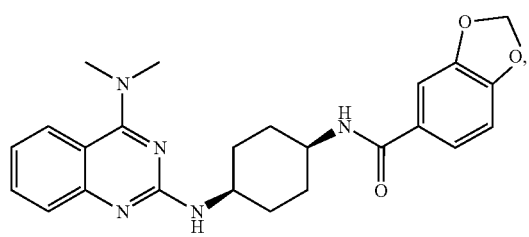
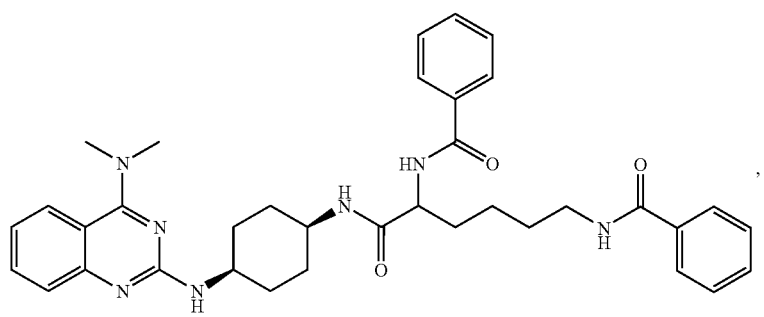
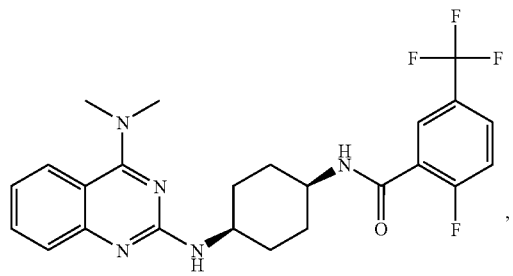
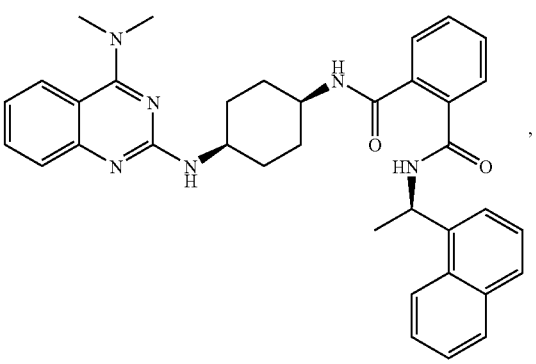

-continued
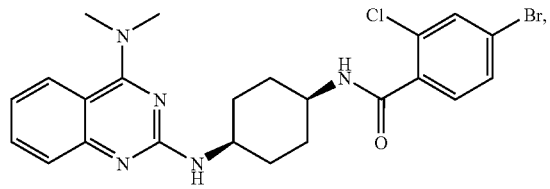
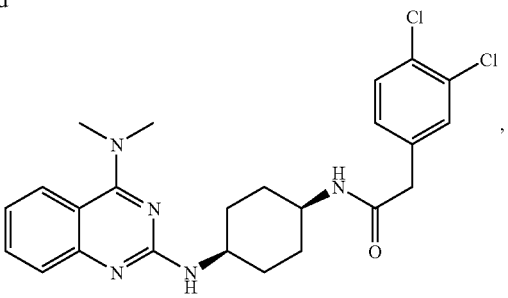
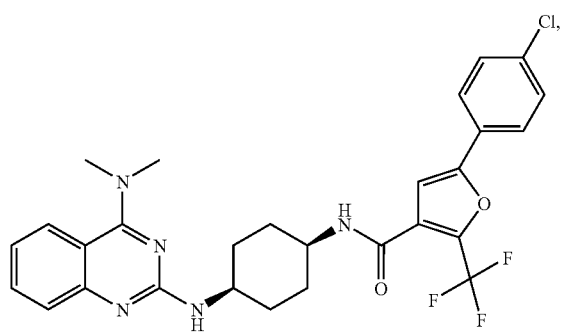
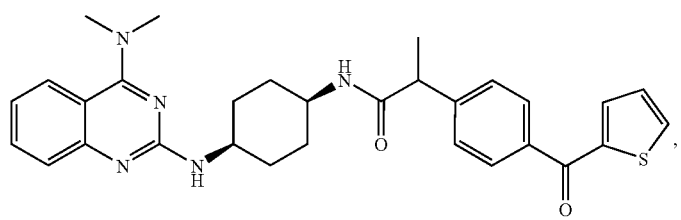
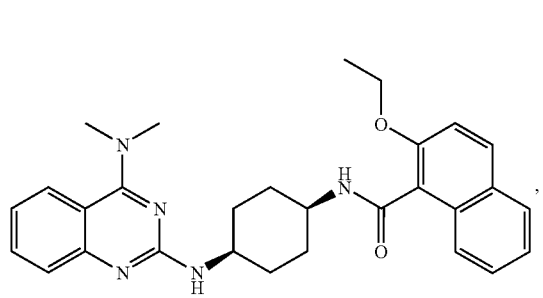
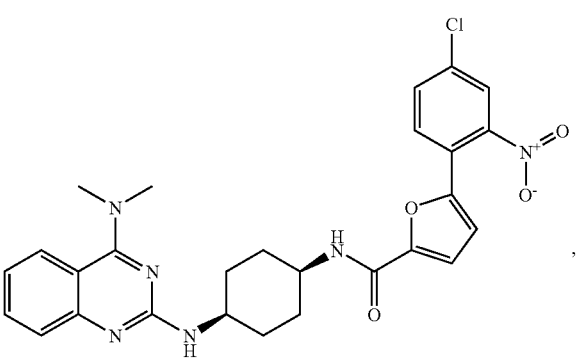
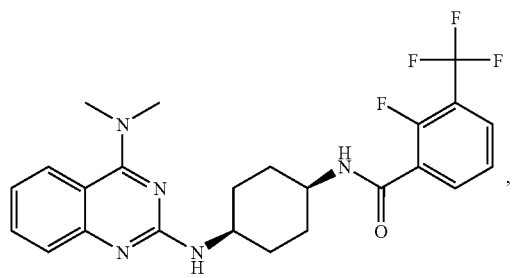
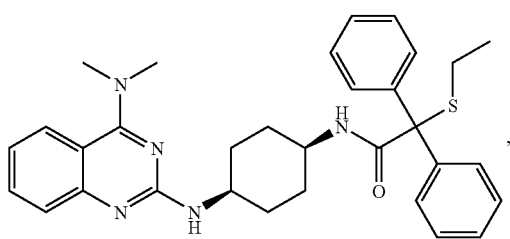

-continued
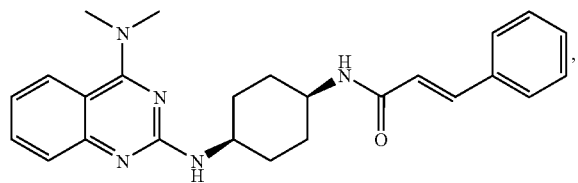
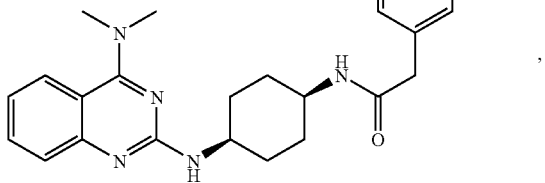
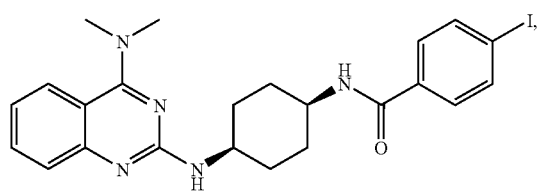
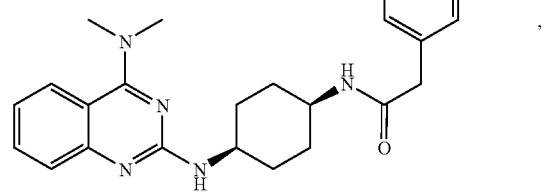
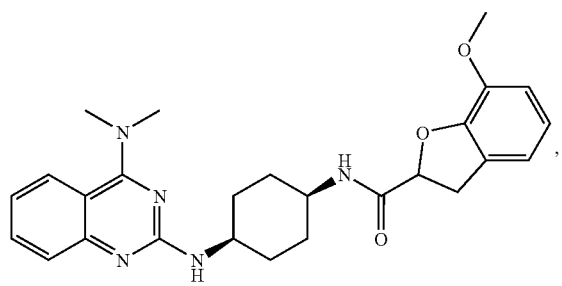
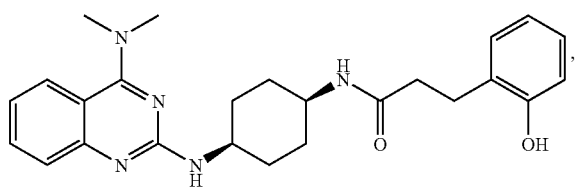
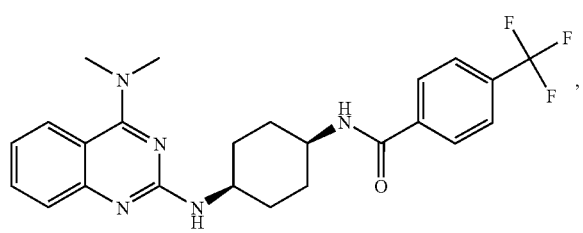
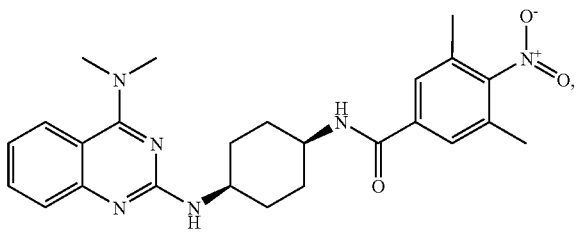
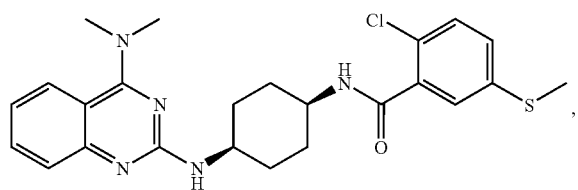
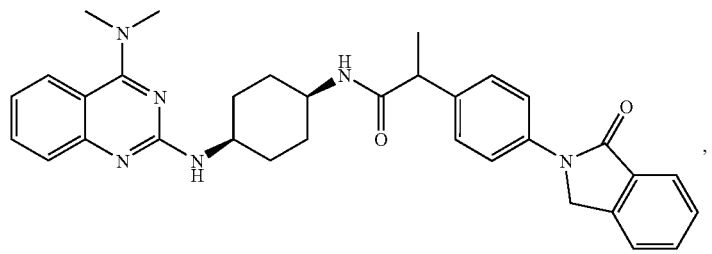

-continued
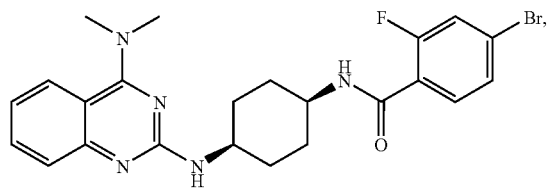
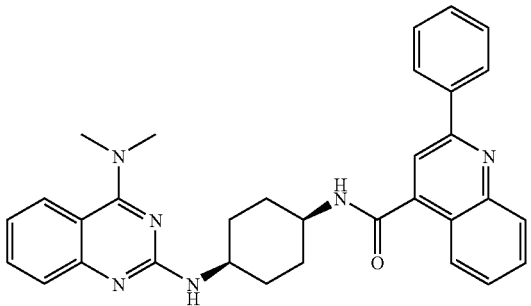
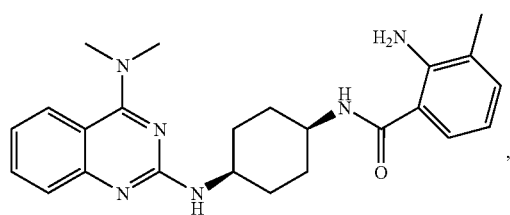
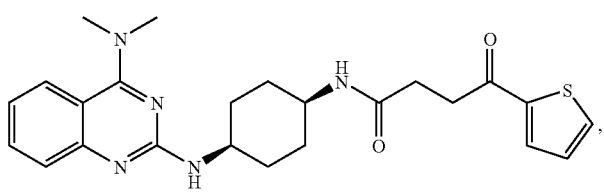
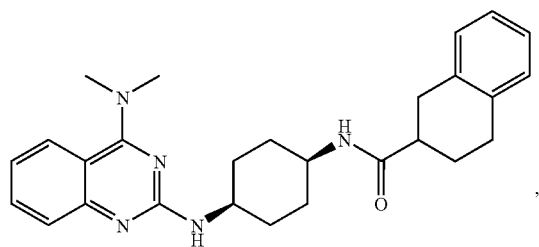
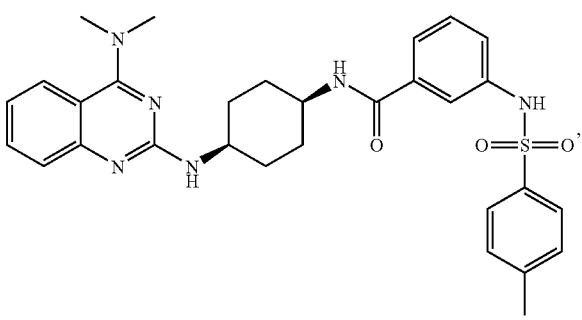
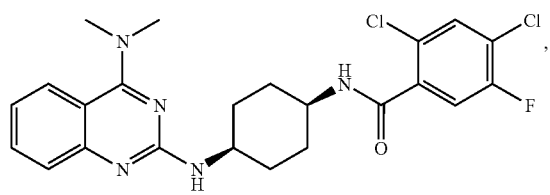
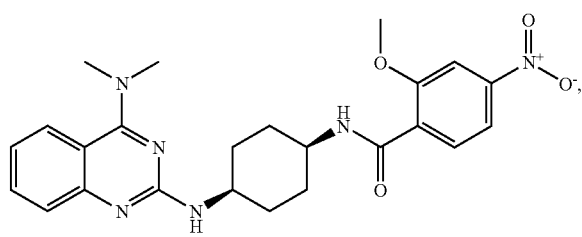
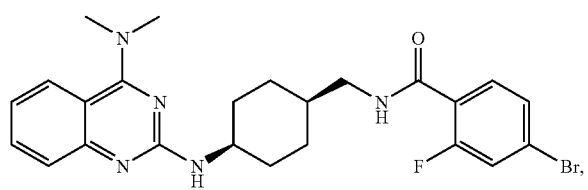
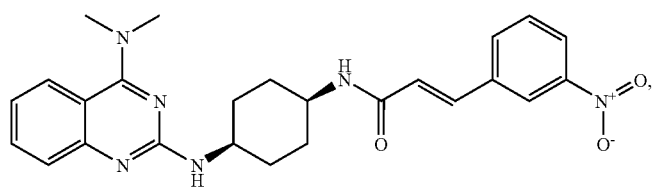

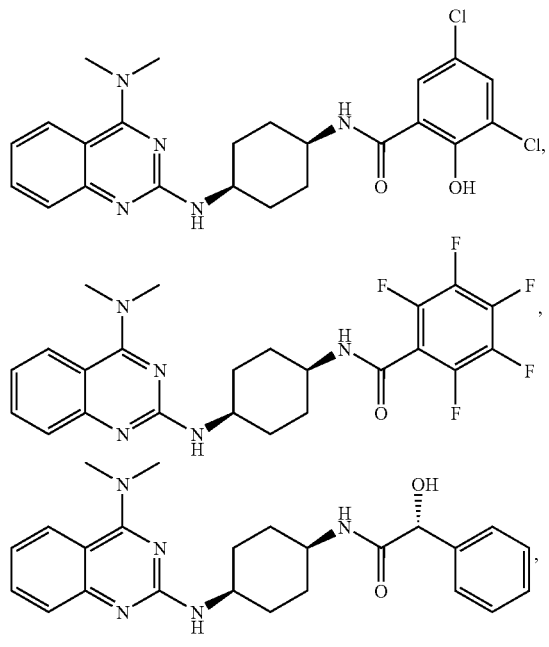
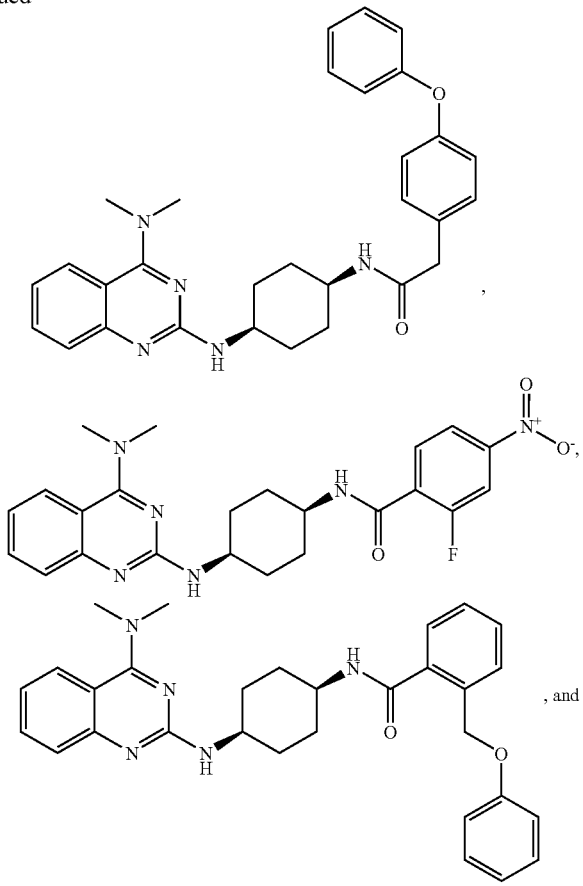
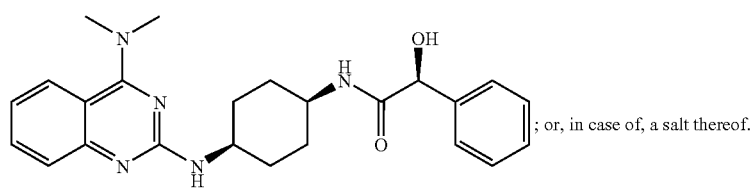

; or, in case of, a salt thereof.

Other more preferred compounds of this invention are those compounds of Formula I wherein,
Q is Formula II;
$R_1$ represents (i) $C_1$-$C_{10}$ alkyl, $C_1$-$C_{10}$ alkyl substituted by substituent(s) independently selected from
$C_5$-$C_6$ cycloalkyl,
carbocyclic aryl,
heterocyclyl, (ii) $C_3$-$C_6$ cycloalkyl, (iii) carbocyclic aryl, (iv) or heterocyclyl;
$R_2$ is methylamino or dimethylamino;
L is selected from Formula XX-XXII;
Y is —C(O)—;
wherein carbocyclic aryl is phenyl, naphthyl, anthranyl, or biphenyl;
heterocyclyl is 1,3-dioxo-isoindolyl, 1H-indolyl, 1-oxo-3H-isobenzofuranyl, 2,3-dihydro-benzo[1,4]dioxinyl, 3,4-dihydro-2H-benzo[b][1,4]dioxepinyl, 4-oxo-3,4-dihydrophthalazinyl, 9,10,10-trioxo-thioxanthenyl, 9H-xanthenyl, benzimidazolyl, benzo[1,3]dioxolyl, benzo[2,1,3]oxadiazolyl, benzo[b]thienyl, furyl, imidazolyl, isoxazolyl, morpholino, oxolanyl, piperidyl, pyridyl, quinoxalyl, thienyl, quinolyl, or benzothiazolyl;
halogen is fluoro, chloro, bromo, or iodo.

Further other more preferred compounds of this invention are those compounds of Formula I wherein,
Q is Formula II;
$R_1$ represents (i) $C_1$-$C_4$ alkyl, $C_1$-$C_4$ alkyl substituted by substituent(s) independently selected from
cyclopentyl,
carbocyclic aryl,
heterocyclyl, (ii) carbocyclic aryl, (iii) or heterocyclyl;
$R_2$ is methylamino or dimethylamino;

L is selected from Formula XX-XXII;
Y is —C(O)—;
wherein carbocyclic aryl is phenyl, naphthyl, anthranyl, or biphenyl;
heterocyclyl is 9H-xanthenyl, benzo[1,3]dioxolyl, benzo[2,1,3]oxadiazolyl, benzo[b]thienyl, thienyl, 1H-indolyl, quinoxalyl, quinolyl, or benzothiazolyl;
halogen is fluoro, chloro, bromo, or iodo.
The following compounds are specially preffered;
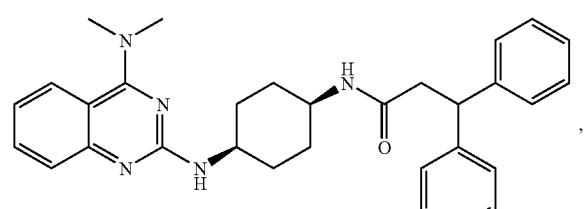
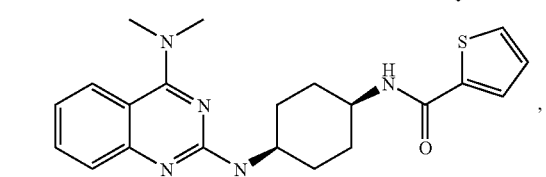
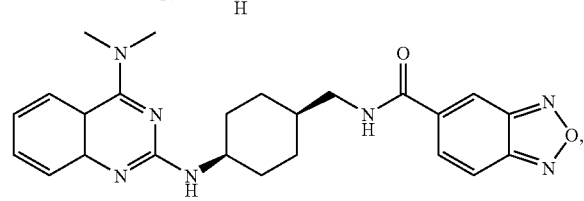
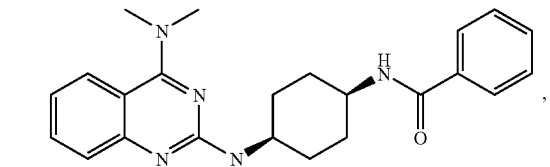
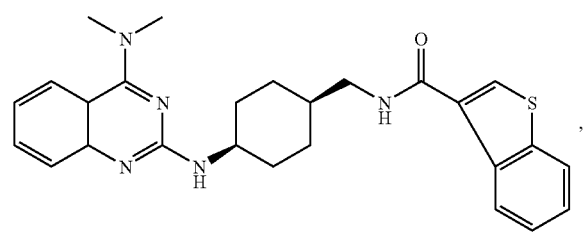
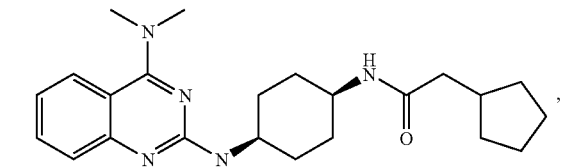
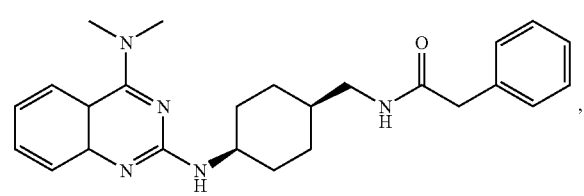
-continued
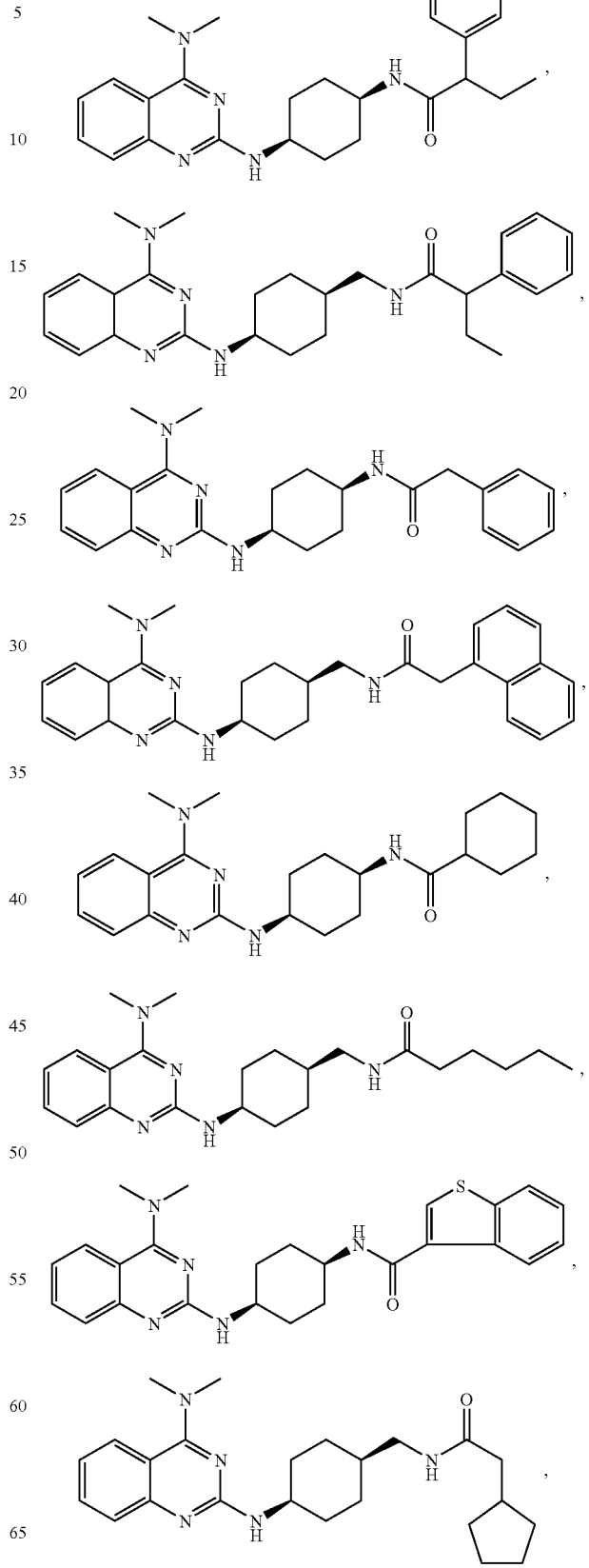

-continued
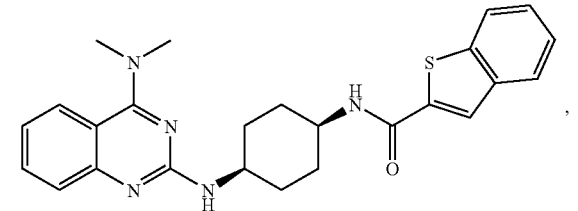,
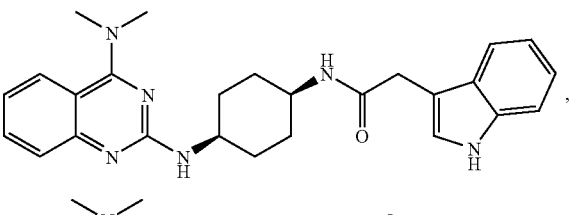,
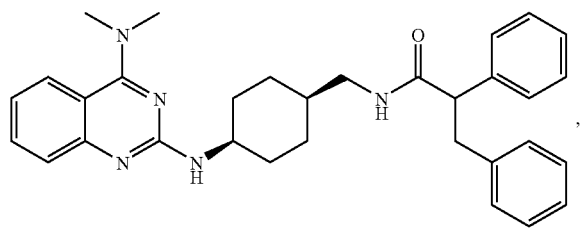,
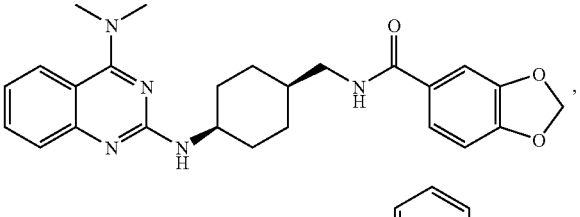,
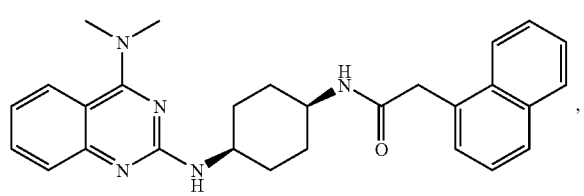,
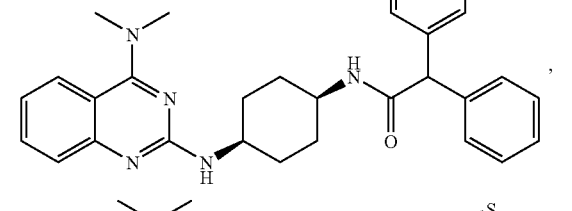,
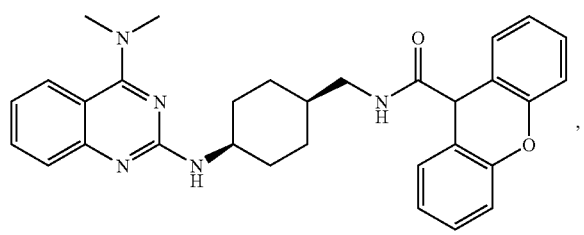,
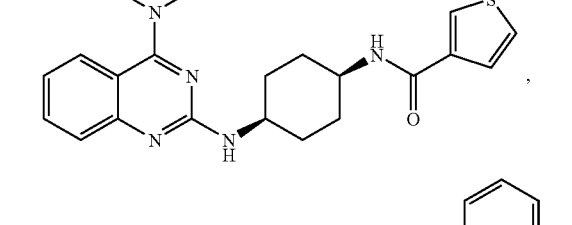,
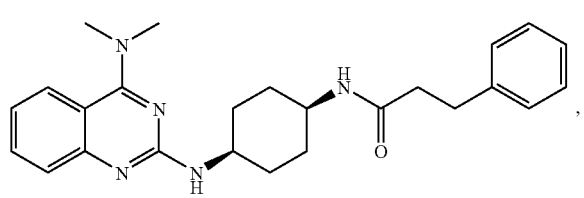,
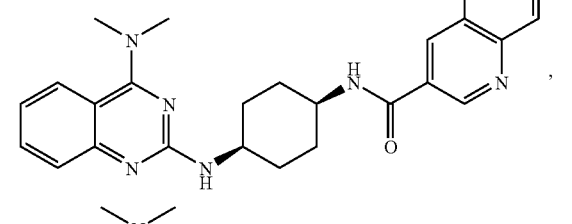,
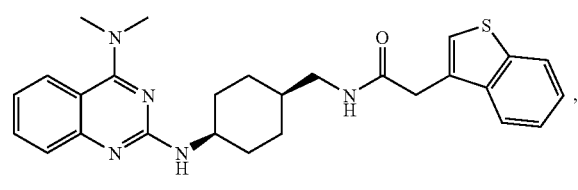,
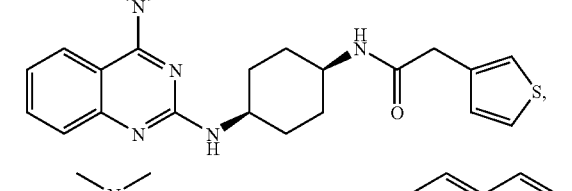,
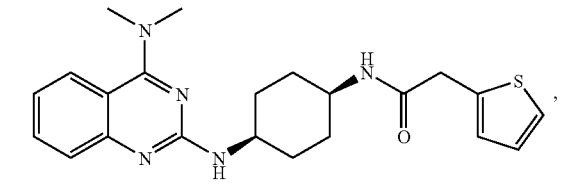,
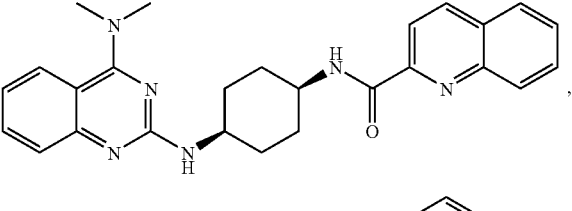,
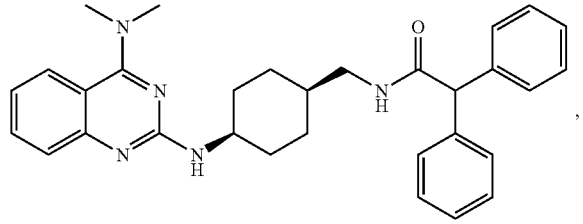,
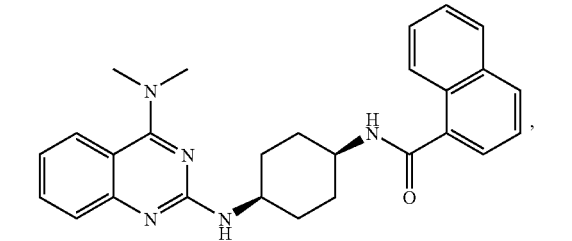, 101
-continued
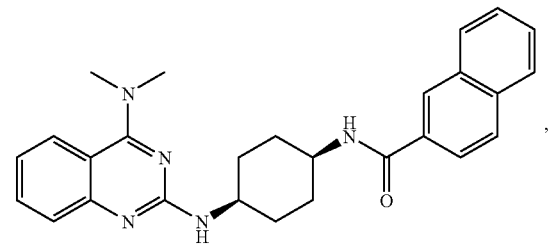
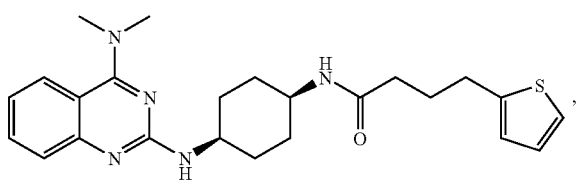
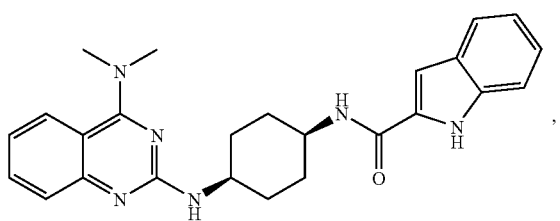
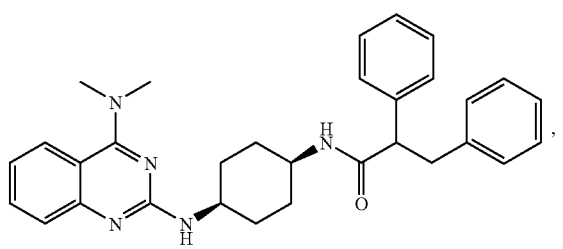
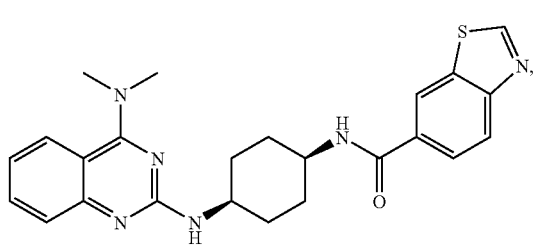
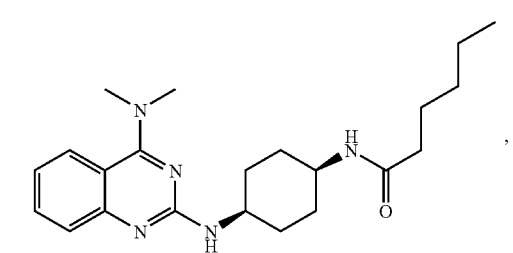
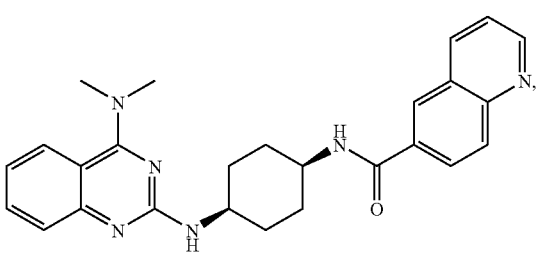
102
-continued
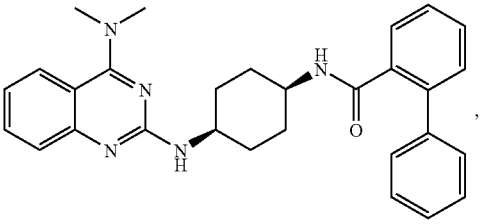
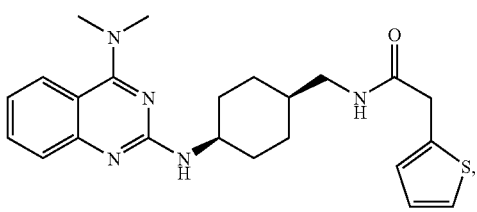
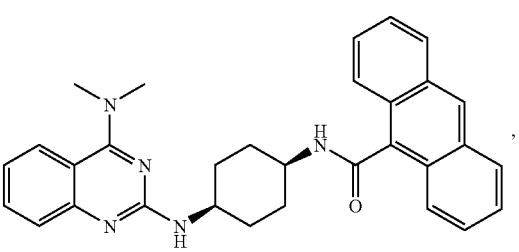
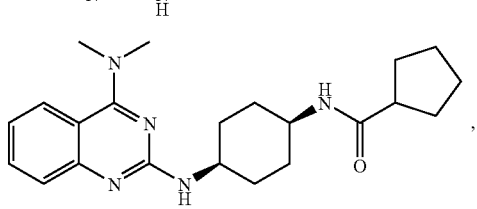
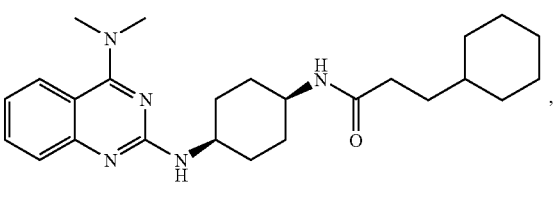
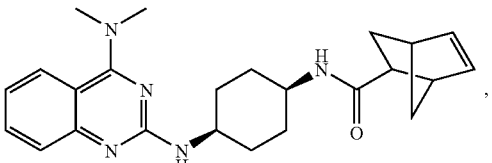
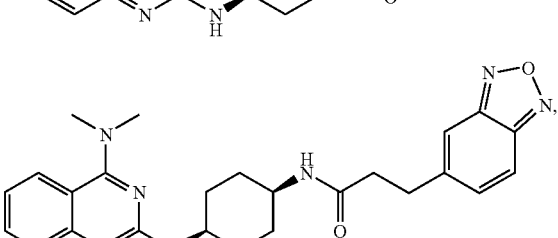
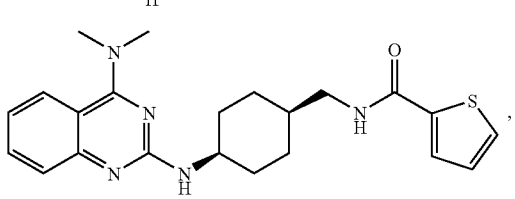

-continued

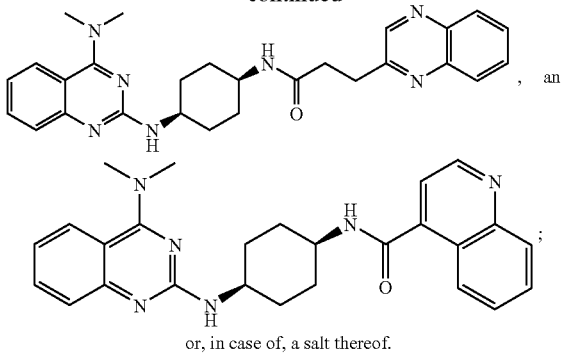

, and or, in case of, a salt thereof.

Preferred compounds of this invention are those compounds of Formula I wherein,
Q is Formula II;
$R_1$ represents (i) $C_1$-$C_{10}$ alkyl, $C_1$-$C_{10}$ alkyl substituted by substituent(s) independently selected from
halogen,
hydroxy,
oxo,
$C_1$-$C_3$ alkoxy,
$C_1$-$C_3$ alkoxy substituted by substituent(s) independently selected from
carbocyclic aryl,
heterocyclyl,
heterocyclyl substituted by $C_1$-$C_3$ alkyl,
carbocyclic aryloxy,
carbocyclic aryloxy substituted by substituent(s) independently selected from
halogen,
halogen,
nitro,
carbocyclic aryl,
carbocyclic aryl substituted by $C_1$-$C_3$ alkoxy,
$C_1$-$C_4$ alkyl,
$C_1$-$C_4$ alkyl substituted by substituent(s) independently selected from
mono- or di-$C_1$-$C_3$ alkylamino,
mono- or di-$C_1$-$C_3$ alkylamino substituted by carbocyclic aryl,
mono- or di-$C_1$-$C_3$ alkylamino substituted by halogenated carbocyclic aryl,
mono- or di-$C_1$-$C_3$ alkylamino,
mono- or di-$C_1$-$C_3$ alkylamino substituted by substituent(s) independently selected from
cyano,
carbocyclic aryl,
heterocyclyl,
mono- or di-carbocyclic arylamino,
mono- or di-carbocyclic arylamino substituted by $C_1$-$C_3$ alkyl,
$C_1$-$C_3$ alkylcalbonylamino,
$C_1$-$C_4$ alkoxycalbonylamino,
carbocyclic arylsulfonylamino,
carbocyclic arylsulfonylamino substituted by substituent(s) independently selected from
nitro,
$C_1$-$C_3$ alkyl,
mono- or di-$C_1$-$C_3$ alkylamino,
$C_1$-$C_3$ alkylthio,
$C_1$-$C_3$ alkylthio substituted by substituent(s) independently selected from
mono- or di-carbocyclic arylamino,
halogenated mono- or di-carbocyclic arylamino,
carbocyclic aryl,
carbocyclic aryl substituted by substituent(s) independently selected from
halogen,
$C_1$-$C_3$ alkoxy,
carbocyclic arylthio,
carbocyclic arylthio substituted by substituent(s) independently selected from
halogen,
$C_1$-$C_3$ alkyl,
carbocyclic arylsulfonyl,
halogenated carbocyclic arylsulfonyl,
heterocyclylthio,
$C_3$-$C_6$ cycloalkyl,
$C_3$-$C_6$ cycloalkyl substituted by $C_1$-$C_3$ alkyl,
carbocyclyl,
carbocyclyl substituted by substituent(s) independently selected from
halogen,
$C_1$-$C_3$ alkyl,
$C_2$-$C_3$ alkenyl,
$C_2$-$C_3$ alkenyl substituted by carbocyclic aryl,
$C_2$-$C_3$ alkenyl substituted by carbocyclic aryl substituted $C_1$-$C_3$ alkylsulfinyl,
carbocyclic aryl,
carbocyclic aryl substituted by substituent(s) independently selected from
halogen,
hydroxy,
nitro,
$C_1$-$C_4$ alkyl,
$C_1$-$C_4$ alkyl substituted by substituent(s) independently selected from
halogen,
hydroxy,
carbocyclic aryl,
mono- or di-carbocyclic arylamino,
mono- or di-carbocyclic arylamino substituted by substituent(s) independently selected from
halogen,
nitro,
$C_1$-$C_3$ alkyl,
$C_1$-$C_3$ alkoxy,
halogenated $C_1$-$C_3$ alkoxy,
$C_1$-$C_3$ alkoxy,
$C_1$-$C_3$ alkoxy substituted by substituent(s) independently selected from
halogen,
carbocyclic aryl,
carbocyclic aryloxy,
$C_1$-$C_3$ alkoxycarbonyl,
mono- or di-$C_1$-$C_3$ alkylamino,
$C_1$-$C_3$ alkylthio,
halogenated $C_1$-$C_3$ alkylthio,
$C_1$-$C_3$ alkylsulfonyl, $C_3$-$C_6$ cycloalkyl,
carbocyclic aryl,
heterocyclyl,
heterocyclyl substituted by substituent(s) independently selected from
  $C_1$-$C_3$ alkyl,
  $C_1$-$C_3$ alkoxy,
  $C_1$-$C_3$ alkoxy substituted by carbocyclic aryl,
  carbocyclic aryl,
  halogenated carbocyclic aryl, (ii) $C_2$-$C_9$ alkenyl, $C_2$-$C_8$ alkenyl substituted by substituent(s) independently selected from
  halogen,
  $C_1$-$C_3$ alkoxy,
  $C_1$-$C_3$ alkoxy substituted by carbocyclic aryl,
  carbocyclic aryl,
  carbocyclic aryl substituted by substituent(s) independently selected from
    halogen,
    hydroxy,
    $C_1$-$C_3$ alkoxy,
    halogenated $C_1$-$C_3$ alkoxy,
  heterocyclyl,
  heterocyclyl substituted by nitro, (iii) $C_2$-$C_4$ alkynyl, $C_2$-$C_4$ alkynyl substituted by carbocyclic alkyl, (iv) $C_3$-$C_6$ cycloalkyl, $C_3$-$C_6$ cycloalkyl substituted by substituent(s) independently selected from
  $C_1$-$C_3$ alkyl,
  $C_1$-$C_3$ alkyl substituted by substituent(s) independently selected from
    hydroxy,
    oxo,
    carbocyclic aryl,
    mono- or di-$C_1$-$C_3$ alkylamino,
    mono- or di-$C_1$-$C_3$ alkylamino substituted by carbocyclic aryl,
    carbocyclic aryl, (v) $C_3$-$C_6$ cycloalkeyl, $C_3$-$C_6$ cycloalkeyl substituted by $C_1$-$C_3$ alkyl, (vi) carbocyclyl, carbocyclyl substituted by substituent(s) independently selected from
  hydroxy,
  nitro, (vii) carbocyclic aryl, carbocyclic aryl substituted by substituent(s) independently selected from
  halogen,
  hydroxy,
  cyano,
  nitro,
  $C_1$-$C_9$ alkyl,
  $C_1$-$C_9$ alkyl substituted by substituent(s) independently selected from
    halogen,
    hydroxy,
    oxo,
    $C_1$-$C_3$ alkoxy,
    carbocyclic aryloxy,
    mono- or di-$C_1$-$C_3$ alkylamino-N-oxy,
    mono- or di-$C_1$-$C_3$ alkylamino,
    mono- or di-$C_1$-$C_3$ alkylamino substituted by carbocyclic aryl,
    mono- or di-carbocyclic arylamino,
    mono- or di-carbocyclic arylamino substituted by $C_1$-$C_3$ alkoxy,
    carbocyclic aryl,
    halogenated carbocyclic aryl,
    heterocyclyl,
    heterocyclyl substituted by $C_1$-$C_3$ alkyl,
  $C_2$-$C_3$ alkenyl,
  $C_2$-$C_3$ alkenyl substituted by carbocyclic aryl,
  $C_1$-$C_9$ alkoxy,
  $C_1$-$C_9$ alkoxy substituted by substituent(s) independently selected from
    hydroxy,
    halogen,
    carboxy,
    mono- or di-$C_1$-$C_3$ alkylamino,
    carbocyclic aryl,
    halogenated carbocyclic aryl,
    heterocyclyl,
    heterocyclyl substituted by substituent(s) independently selected from
      heterocyclyl,
      heterocyclyl substituted by substituent(s) independently selected from
        halogen,
        $C_1$-$C_3$ alkyl,
        halogenated $C_1$-$C_3$ alkyl,
  $C_2$-$C_3$ alkenyloxy,
  $C_1$-$C_3$ alkylcarbonyloxy,
  carbocyclic aryloxy,
  carbocyclic aryloxy substituted by substituent(s) independently selected from
    halogen,
    $C_1$-$C_4$ alkyl,
    halogenated $C_1$-$C_4$ alkyl,
    $C_1$-$C_3$ alkoxy,
  heterocyclyloxy,
  heterocyclyloxy substituted by substituent(s) independently selected from
    halogen,
    $C_1$-$C_3$ alkyl,
    halogenated $C_1$-$C_3$ alkyl,
  (carbocyclic aryl)S(O)$_2$O,
  carboxy,
  $C_1$-$C_3$ alkoxycarbonyl,
  mono- or di-$C_1$-$C_3$ alkylaminocarbonyl,
  mono- or di-$C_1$-$C_3$ alkylaminocarbonyl substituted by carbocyclic aryl,
  amino,
  mono- or di-$C_1$-$C_4$ alkylamino,
  mono- or di-$C_1$-$C_4$ alkylamino substituted by cyano,
  mono- or di-carbocyclic arylamino,
  $C_1$-$C_3$ alkylcarbonylamino,
  carbocyclic arylsulfonylamino,
  carbocyclic arylsulfonylamino substituted by $C_1$-$C_3$ alkyl,
  (carbocyclic aryl)NHC(O)NH,
  (carbocyclic aryl)NHC(O)NH substituted by $C_1$-$C_3$ alkoxy,
  (carbocyclic aryl)NHC(O)NH substituted by haloganated $C_1$-$C_3$ alkoxy,
  $C_1$-$C_3$ alkylthio, halogenated $C_1$-$C_3$ alkylthio,
carbocyclic arylthio,
halogenated carbocyclic arylthio,
carbocyclic arylthio substituted by $C_1$-$C_3$ alkyl,
heterocyclylthio,
$C_1$-$C_3$ alkylsulfonyl,
mono- or di-$C_1$-$C_3$ alkylaminosulfonyl,
carbocyclic aryl,
carbocyclic aryl substituted by substituent(s) independently selected from
  $C_1$-$C_7$ alkyl,
  halogenated $C_1$-$C_7$ alkyl,
heterocyclyl,
heterocyclyl substituted by substituent(s) independently selected from
  $C_1$-$C_3$ alkyl,
  carbocyclic aryl,
  halogenated carbocyclic aryl, (viii) heterocyclyl, or heterocyclyl substituted by substituent(s) independently selected from
  halogen,
  hydroxy,
  cyano,
  nitro,
  $C_1$-$C_4$ alkyl,
  $C_1$-$C_4$ alkyl substituted by substituent(s) independently selected from
    halogen,
    hydroxy,
    oxo,
    $C_1$-$C_3$ alkylcarbonyloxy,
    $C_1$-$C_3$ alkoxycarbonyl,
    $C_1$-$C_3$ alkylthio substituted by carbocyclic aryl,
    $C_1$-$C_3$ alkylthio substituted by halogenated carbocyclic aryl,
    carbocyclic aryl,
    carbocyclic aryl substituted by substituent(s) independently selected from
      halogen,
      nitro,
    heterocyclyl,
    $C_1$-$C_3$ alkoxy,
    $C_1$-$C_3$ alkoxy substituted by carbocyclic aryl,
    carbocyclic aryloxy,
    carbocyclic aryloxy substituted by $C_1$-$C_3$ alkyl,
    mono- or di-$C_1$-$C_3$ alkylamino,
    $C_1$-$C_4$ alkylcarbonylamino,
    $C_1$-$C_3$ alkylthio,
    carbocyclic arylthio,
    halogenated carbocyclic arylthio,
    carbocyclic arylthio substituted by $C_1$-$C_3$ alkoxycarbonyl,
    heterocyclylthio,
    heterocyclylthio substituted by $C_1$-$C_3$ alkyl,
    $C_1$-$C_3$ alkylsulfonyl,
    carbocyclic arylsulfonyl,
    carbocyclic arylsulfonyl substituted by $C_1$-$C_4$ alkyl,
    $C_1$-$C_3$ alkoxycarbonyl,
    carbocyclic aryl,
    carbocyclic aryl substituted by substituent(s) independently selected from
      halogen,
      nitro,
      $C_1$-$C_3$ alkyl,
      halogenated $C_1$-$C_3$ alkyl,
      $C_1$-$C_3$ alkoxy,
      halogenated $C_1$-$C_3$ alkoxy,
    heterocyclyl,
    heterocyclyl substituted by substituent(s) independently selected from
      $C_1$-$C_3$ alkyl,
      halogenated $C_1$-$C_3$ alkyl,
      $C_1$-$C_3$ alkoxy,
      $C_1$-$C_3$ alkoxycarbonyl;

$R_2$ is —NHNH$_2$, —NHNHBoc, —N($R_{2a}$)($R_{2b}$), morpholino, 4-acetyl-piperazyl, or 4-phenyl-piperazyl;

wherein $R_{2a}$ is H or $C_1$-$C_3$ alkyl;

$R_{2b}$ is $C_1$-$C_4$ alkyl, $C_1$-$C_4$ alkyl substituted by substituent(s) independently selected from
  hydroxy,
  $C_1$-$C_3$ alkoxy,
  amino,
  —NHBoc,
  $C_3$-$C_6$ cycloalkyl,
  carbocyclic aryl,
  carbocyclic aryl substituted by substituent(s) independently selected from
    halogen,
    $C_1$-$C_3$ alkyl,
    $C_1$-$C_3$ alkoxy,
    —SO$_2$NH$_2$,
  heterocyclyl, $C_3$-$C_6$ cycloalkyl, carbocyclic aryl, carbocyclic aryl substituted by substituent(s) independently selected from
  halogen,
  $C_1$-$C_3$ alkyl,
  $C_1$-$C_3$ alkoxy, or a group of Formula IV;

wherein Boc is carbamic acid tert-butyl ester and $R_3$ is $C_1$-$C_3$ alkyl or $C_1$-$C_3$ alkyl substituted by substituent(s) independently selected from
  carbocyclic aryl,
  halogenated carbocyclic aryl,
  carbocyclic aryl substituted by $C_1$-$C_3$ alkoxy;

L is selected from Formula V-XIX;

wherein $R_4$ is H or $C_1$-$C_3$ alkyl;

$R_5$ is H, $C_1$-$C_3$ alkyl, or $C_1$-$C_3$ alkyl substituted by a substituted carbocyclic aryl;

Y is —(CH$_2$)$_m$, m is 0 or 1;

wherein carbocyclic aryl is phenyl, naphthyl, phenanthryl, or biphenyl;

carbocyclyl is 9H-fluorenyl, 9-oxo-fluorenyl, acenaphthyl, anthraquinonyl, indanyl, or indenyl;

heterocyclyl is 1,2,3-thiadiazolyl, 1,2,3-triazolyl, 1,2-dihydro-3-oxo-pyrazolyl, 1,3,4-thiadiazolyl, 1,3-dioxo-isoindolyl, 1,3-dioxolanyl, 1H-indolyl, 1H-pyrrolo[2,3-c]pyridyl, 1H-pyrrolyl, 2,2',5',2"-terthiophenyl, 2,2'-bithiophenyl, 2,3-dihydro-1-oxo-isoindolyl, 2,3-dihydro-benzo[1,4]dioxinyl, 2,3-dihydro-benzofuryl, 2,4-dihydro-3-oxo-pyrazolyl, 2H-benzopyranyl, 2-oxo-pyrrolidinyl, 3,4-dihydro-2H-benzo[1,4]oxazinyl, 3,4-dihydro-2H-benzo[b][1,4]dioxepinyl, 4H-benzo[1,3]dioxinyl, 4H-benzopyranyl, 4-oxo-1,5,6,7-tetrahydro-indolyl, 4-oxo-benzopyranyl, 9H-carbazolyl, 9H-xanthenyl, azetidinyl, benzimidazolyl, benzo[1,3]dioxolyl, benzo[b]thienyl, benzofuryl, benzothiazolyl, furyl, imidazo[2,1-b]thiazolyl, imidazolyl, isoxazolyl, morpholino, morpholinyl, oxolanyl, piperazyl, piperidyl, pyrazolo[5,1-b]thiazolyl, pyrazolyl, pyridyl, pyrimidyl, pyrrolidyl, quinolyl, quinoxalyl, thiazolidyl, thiazolyl, thienyl, or thiolanyl;

halogen is fluoro, chloro, bromo, or iodo.

Other preferred compounds of this invention are those compounds of Formula I wherein,
$Q$ is Formula II;
$R_1$ represents (i) $C_1$-$C_{10}$ alkyl substituted by substituent(s) independently selected from
methoxy,
methoxy substituted by carbocyclic aryl,
carbocyclic aryloxy,
halogenated carbocyclic aryloxy,
mono-$C_1$-$C_2$ alkylamino substituted by cyano,
mono- or di-$C_1$-$C_2$ alkylamino substituted by carbocyclic aryl,
mono-carbocyclic arylamino,
mono-carbocyclic arylamino substituted by methyl,
carbocyclic arylsulfonylamino substituted by methyl,
carbocyclic aryl,
carbocyclic aryl substituted by substituent(s) independently selected from
halogen,
nitro,
$C_1$-$C_4$ alkyl,
$C_1$-$C_4$ alkyl substituted by carbocyclic aryl,
$C_1$-$C_4$ alkyl substituted by hydroxy,
$C_1$-$C_2$ alkoxy,
halogenated $C_1$-$C_2$ alkoxy,
heterocyclyl substituted by carbocyclic aryl, (ii) $C_2$-$C_8$ alkenyl substituted by substituent(s) independently selected from
methoxy substituted by carbocyclic aryl,
carbocyclic aryl,
carbocyclic aryl substituted by methoxy, (iii) $C_2$-$C_4$ alkynyl substituted by carbocyclic aryl, (iv) cyclohexyl substituted by carbocyclic arylmethyl, (v) carbocyclyl, (vi) carbocyclic aryl,
carbocyclic aryl substituted by substituent(s) independently selected from
halogen,
hydroxy,
cyano,
amino,
$C_1$-$C_9$ alkyl,
halogenated $C_1$-$C_9$ alkyl,
$C_1$-$C_9$ alkoxy,
$C_1$-$C_9$ alkoxy substituted by substituent(s) independently selected from
halogen,
halogenated carbocyclic aryl,
propenyloxy,
methylamino,
di-$C_1$-$C_2$ alkylamino,
di-$C_1$-$C_2$ alkylamino substituted by cyano,
methylthio,
halogenated methylthio, (vii) heterocyclyl,
or heterocyclyl substituted by substituent(s) independently selected from
halogen,
$C_1$-$C_4$ alkyl,
$C_1$-$C_4$ alkyl substituted by hydroxy,
$C_1$-$C_4$ alkyl substituted by carbocyclic aryl,
methoxy,
$C_1$-$C_2$ alkoxycarbonyl,
carbocyclic arylthio substituted by methoxycarbonyl,
carbocyclic aryl,
carbocyclic aryl substituted by substituent(s) independently selected from
halogen,
halogenated methyl,
heterocyclyl;
$R_2$ is methylamino or dimethylamino;
L is selected from Formula Va, VIIIa, or IXa;
wherein $R_4$ and $R_5$ are independently selected from H or $C_1$-$C_3$ alkyl;
Y is —$(CH_2)_m$, m is 0 or 1;
wherein carbocyclic aryl is phenyl, naphthyl, phenanthryl, or biphenyl;
carbocyclyl is 9H-fluorenyl, acenaphthyl, or anthraquinonyl;
heterocyclyl is 1,2,3-thiadiazolyl, 1,2,3-triazolyl, 1,2-dihydro-3-oxo-pyrazolyl, 1,3-dioxolanyl, 1H-indolyl, 1H-pyrrolyl, 2,2',5',2''-terthiophenyl, 2,2'-bithiophenyl, 2,3-dihydro-benzo[1,4]dioxinyl, 3,4-dihydro-2H-benzo[1,4]oxazinyl, 4-oxo-benzopyranyl, 9H-carbazolyl, 9H-xanthenyl, benzimidazolyl, benzo[1,3]dioxolyl, benzo[b]thienyl, benzofuryl, benzothiazolyl, furyl, imidazolyl, isoxazolyl, oxolanyl, pyrazolo[5,1-b]thiazolyl, pyrazolyl, pyridyl, pyrimidyl, quinolyl, quinoxalyl, thiazolidyl, thiazolyl, thienyl, 2H-benzopyranyl, 4H-benzo[1,3]dioxinyl, azetidinyl, imidazo[2,1-b]thiazolyl, morpholinyl, or 2,3-dihydro-benzofuryl;
halogen is fluoro, chloro, bromo, or iodo.

Other more preferred compounds of this invention are those compounds of Formula I wherein,
$Q$ is Formula II;
$R_1$ represents (i) $C_1$-$C_7$ alkyl substituted by substituent(s) independently selected from
methoxy,
methoxy substituted by carbocyclic aryl,
carbocyclic aryloxy,
halogenated carbocyclic aryloxy,
mono-ethylamino substituted by cyano,
di-methylamino substituted by carbocyclic aryl,
mono-carbocyclic arylamino,
mono-carbocyclic arylamino substituted by methyl,
carbocyclic arylsulfonylamino substituted by methyl,
carbocyclic aryl,
carbocyclic aryl substituted by substituent(s) independently selected from
halogen,
nitro,
$C_1$-$C_4$ alkyl,
$C_1$-$C_4$ alkyl substituted by carbocyclic aryl,
$C_1$-$C_4$ alkyl substituted by hydroxy,
metoxy,
halogenated methoxy,
heterocyclyl substituted by carbocyclic aryl, (ii) $C_2$-$C_7$ alkenyl substituted by substituent(s) independently selected from
methoxy substituted by carbocyclic aryl,
carbocyclic aryl,
carbocyclic aryl substituted by methoxy, (iii) butynyl substituted by carbocyclic aryl, (iv) cyclohexyl substituted by carbocyclic arylmethyl, (v) carbocyclyl, (vi) carbocyclic aryl, carbocyclic aryl substituted by substituent(s) independently selected from
- halogen,
- hydroxy,
- cyano,
- amino,
- $C_1$-$C_2$ alkyl,
- halogenated methyl,
- $C_1$-$C_3$ alkoxy,
- $C_1$-$C_3$ alkoxy substituted by substituent(s) independently selected from
  - halogen,
  - halogenated carbocyclic aryl,
- propenyloxy,
- di-$C_1$-$C_2$ alkylamino,
- di-$C_1$-$C_2$ alkylamino substituted by cyano,
- methylthio,
- halogenated methylthio, (vii) heterocyclyl, or heterocyclyl substituted by substituent(s) independently selected from
- halogen,
- $C_1$-$C_3$ alkyl,
- $C_1$-$C_3$ alkyl substituted by hydroxy,
- $C_1$-$C_3$ alkyl substituted by carbocyclic aryl,
- methoxy,
- ethoxycarbonyl,
- carbocyclic arylthio substituted by methoxycarbonyl,
- carbocyclic aryl,
- carbocyclic aryl substituted by substituent(s) independently selected from
  - halogen,
  - halogenated methyl,
- heterocyclyl;

$R_2$ is methylamino or dimethylamino;

L is selected from Formula XX-XXII;

Y is —$(CH_2)_m$, m is 0 or 1;

wherein carbocyclic aryl is phenyl, naphthyl, or biphenyl;

carbocyclyl is acenaphthyl;

heterocyclyl is 1H-indolyl, 1H-pyrrolyl, 2,3-dihydro-benzo[1,4]dioxinyl, 9H-carbazolyl, benzo[1,3]dioxolyl, furyl, pyrazolyl, thienyl, 4-oxo-benzopyranyl, azetidinyl, imidazo[2,1-b]thiazolyl, pyridyl, imidazolyl, 2,3-dihydro-benzofuryl, or benzo[b]thienyl;

halogen is fluoro, chloro, bromo, or iodo.

The following compounds are specially preffered;

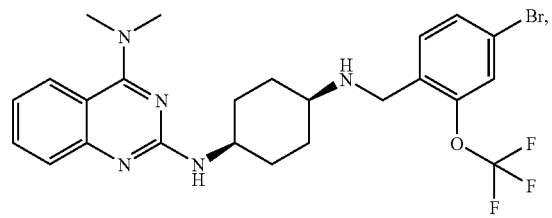

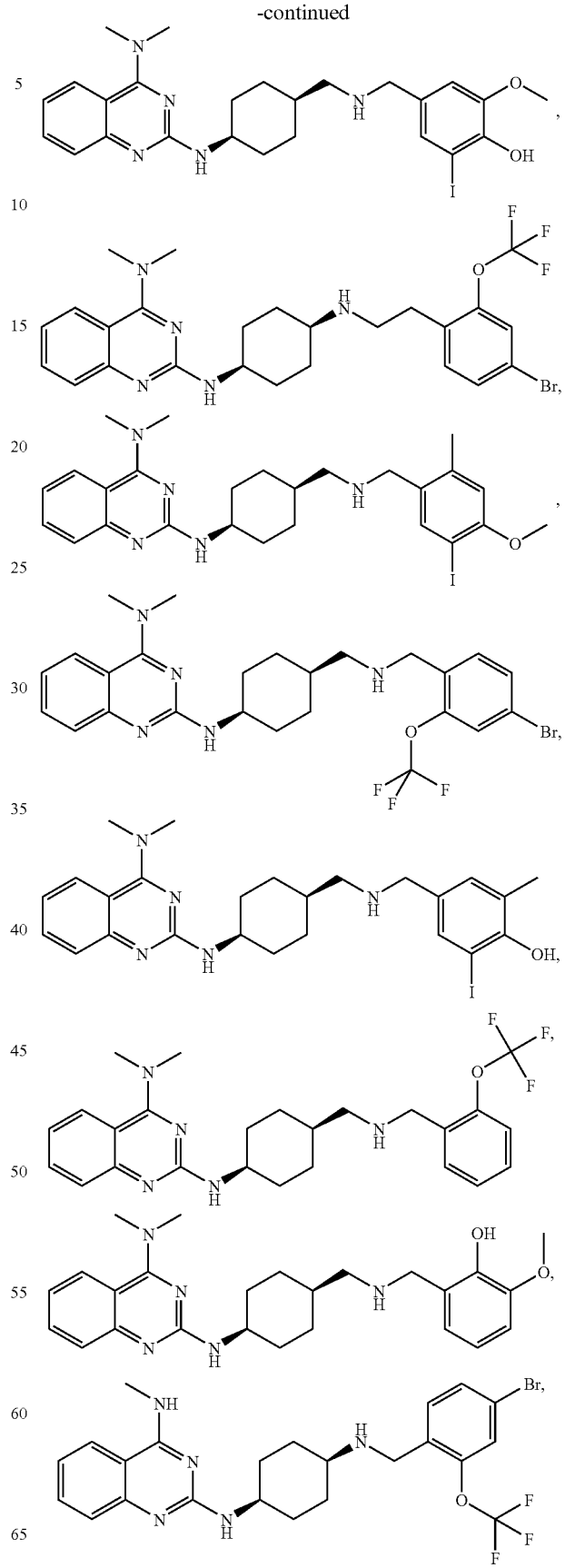

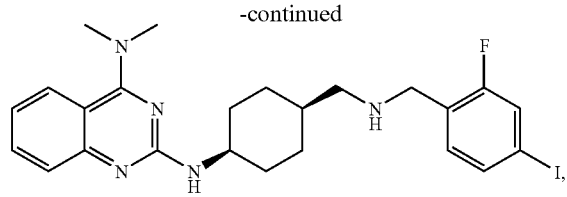
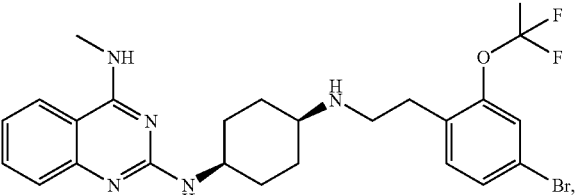
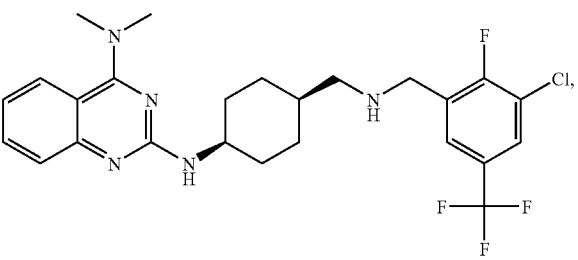
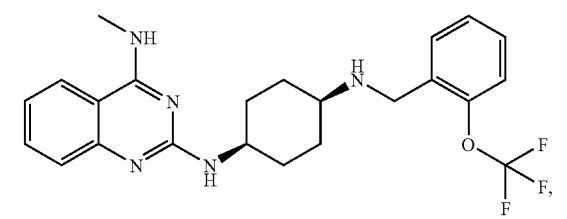
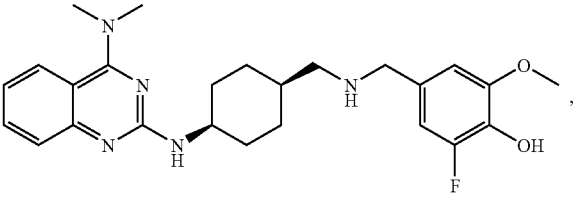
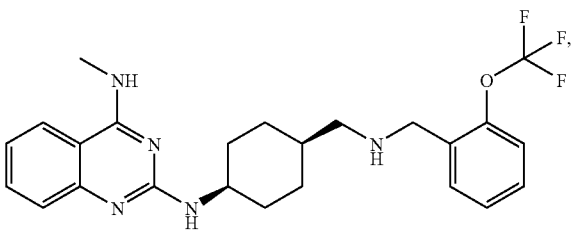
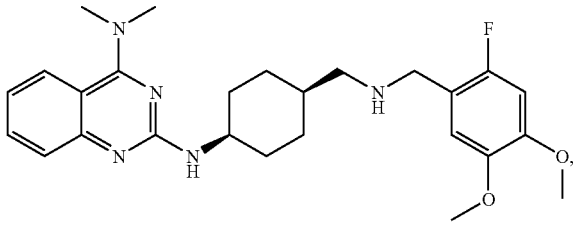
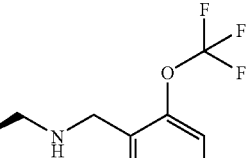
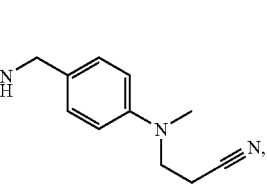

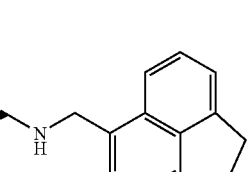
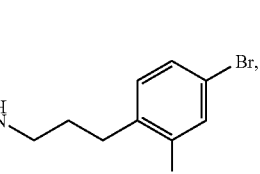

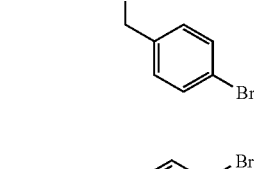
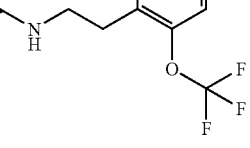

115                                    116
-continued                             -continued
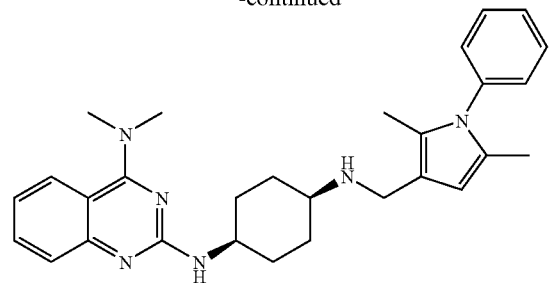
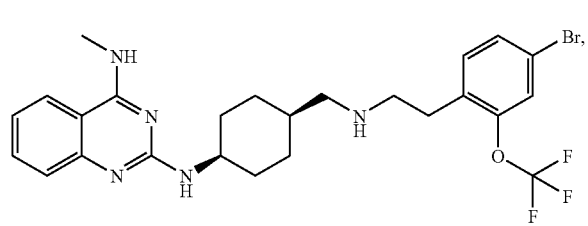     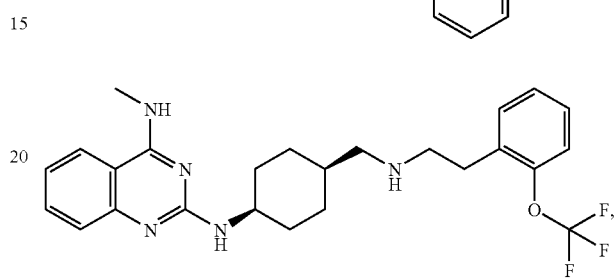
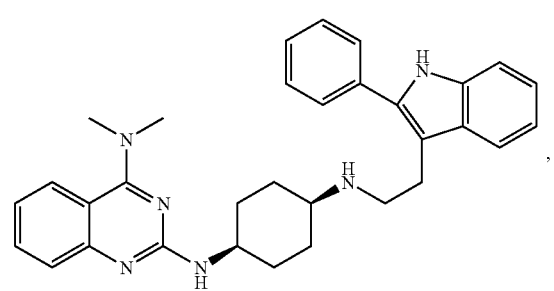     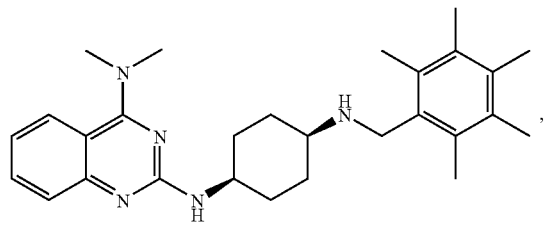
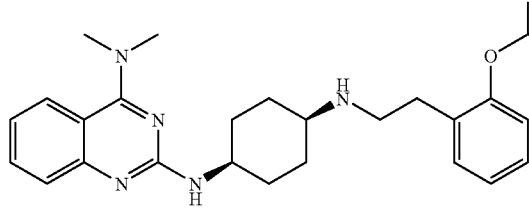     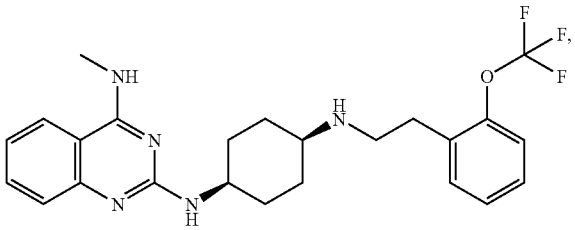
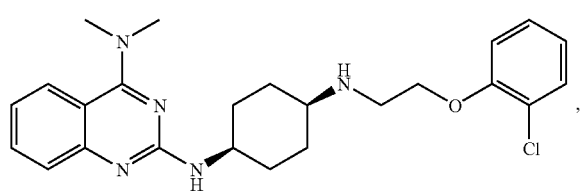     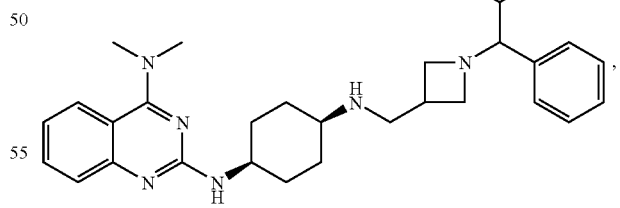
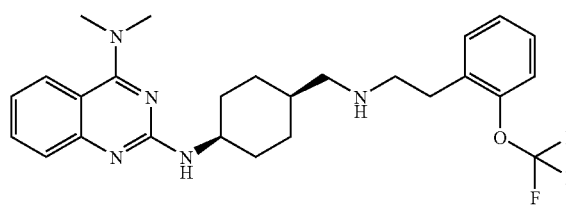    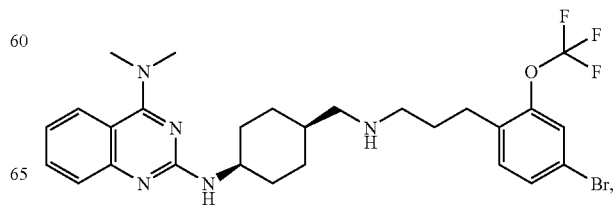

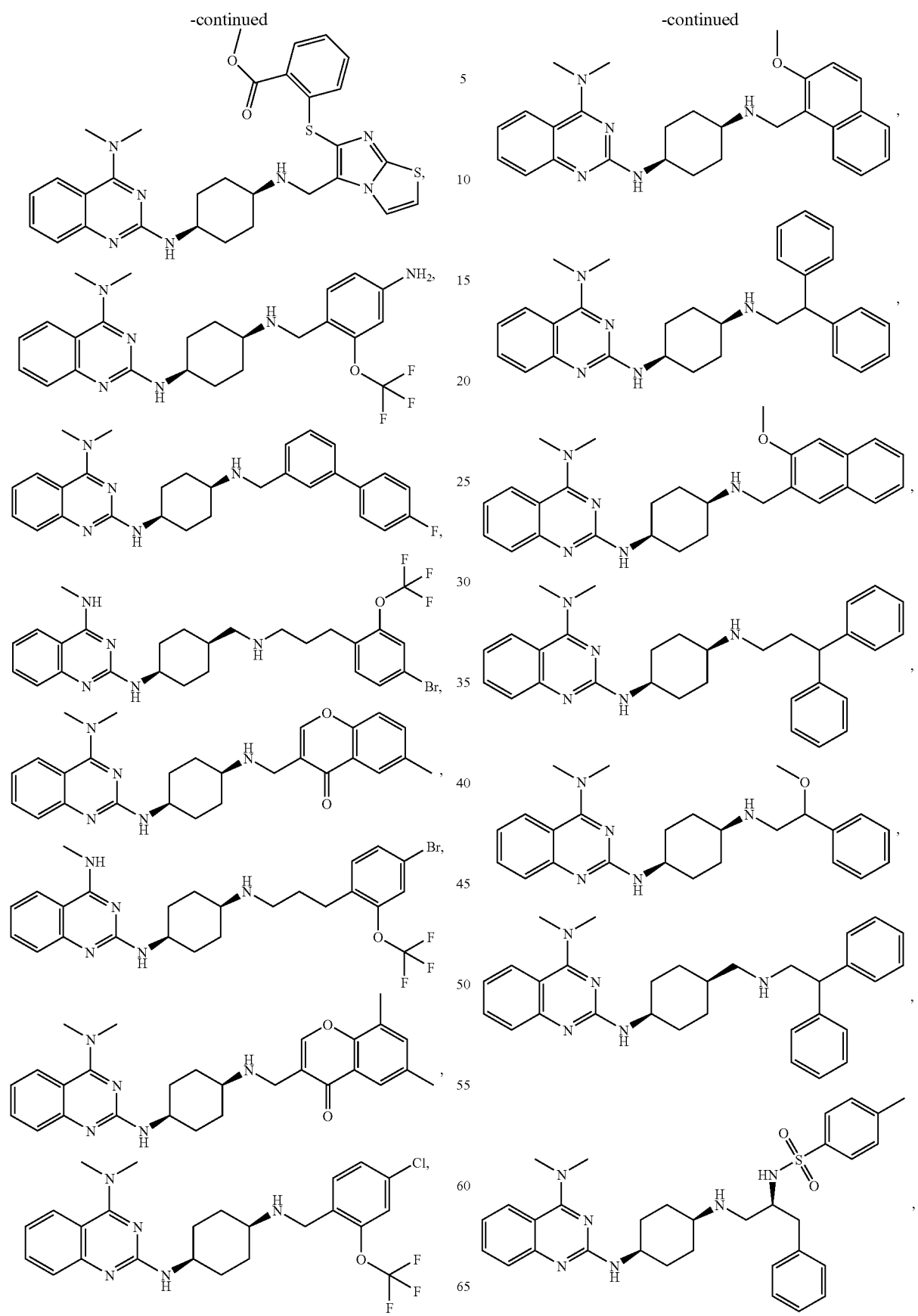

-continued
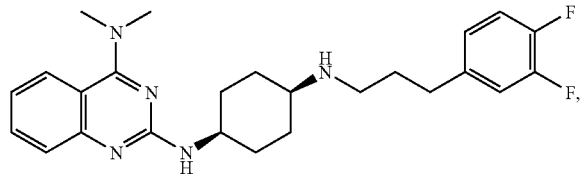
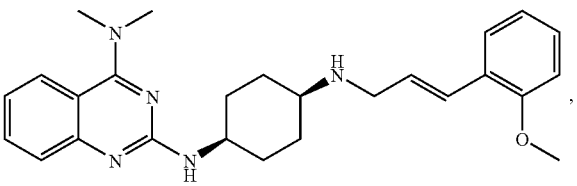
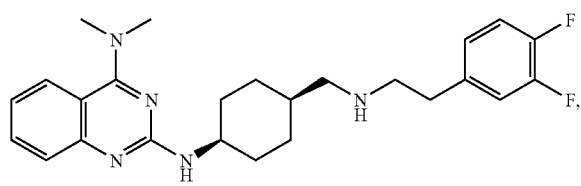
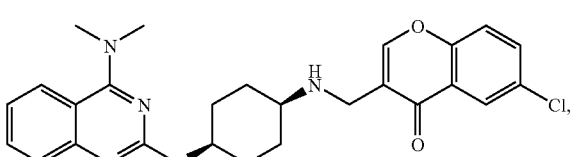
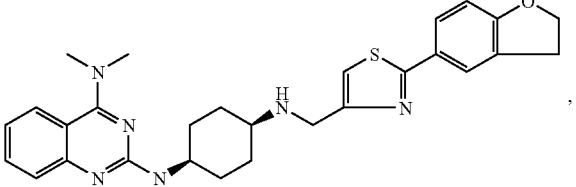
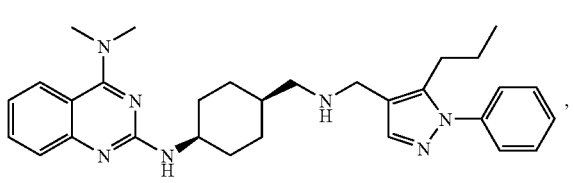
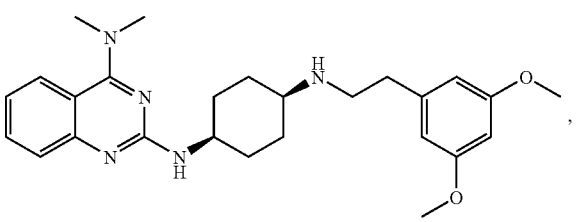
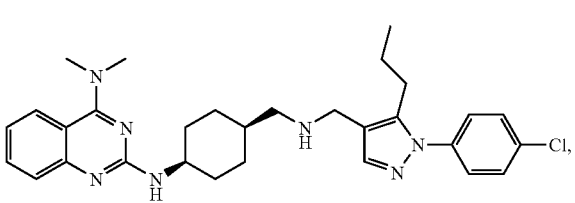

121
-continued
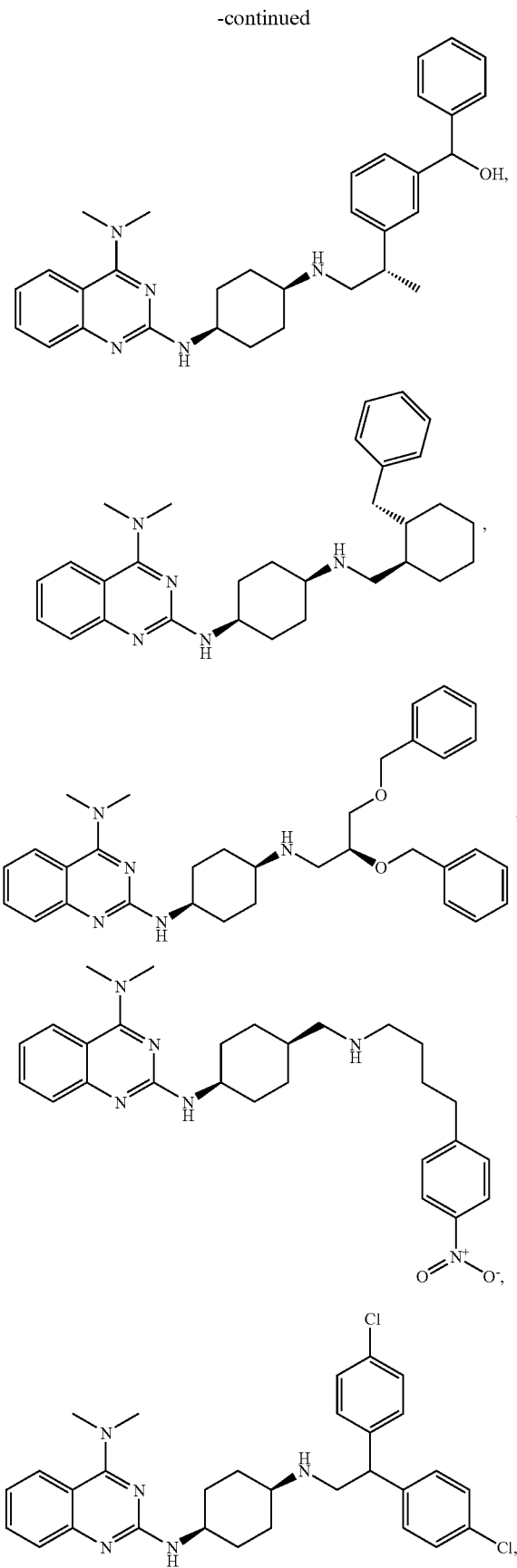
122
-continued
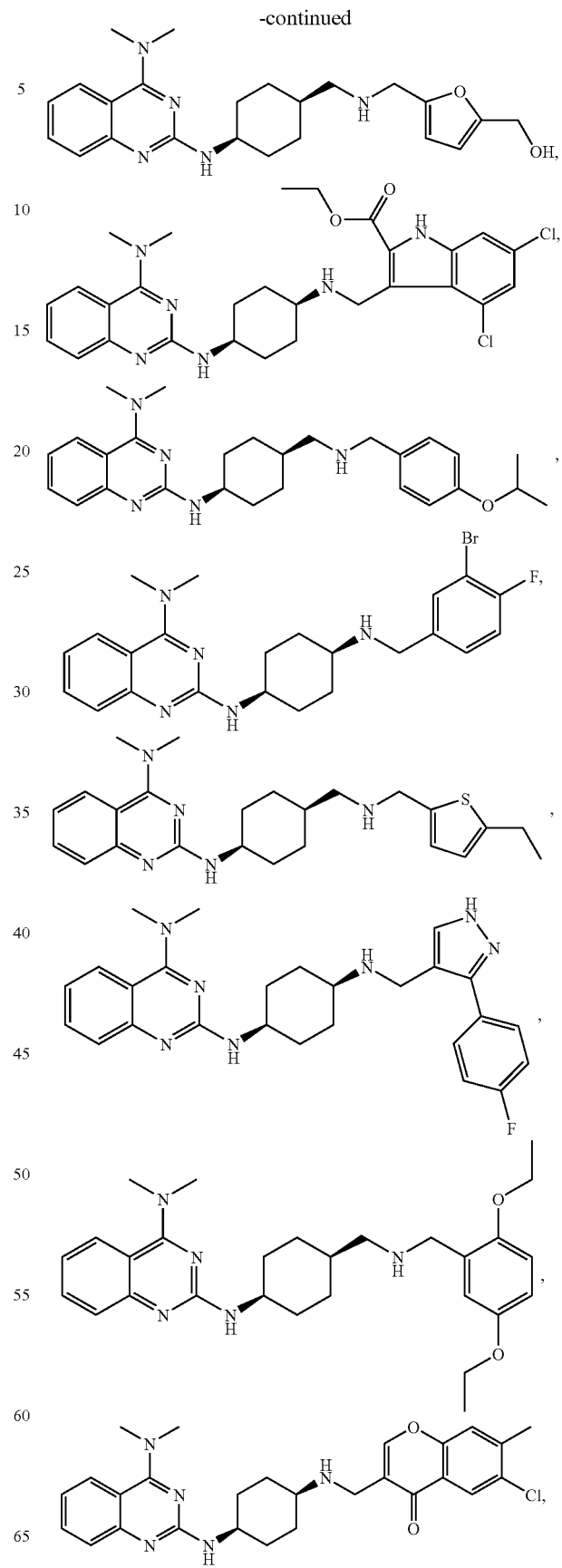

123
-continued
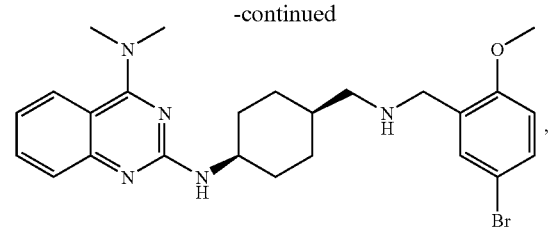
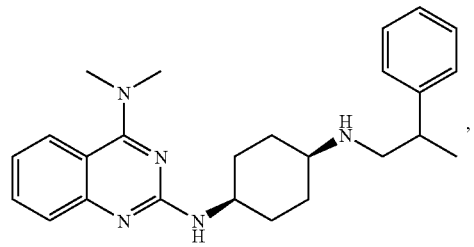
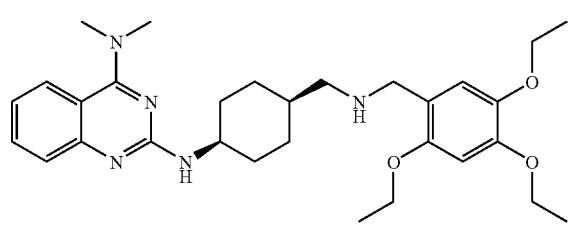
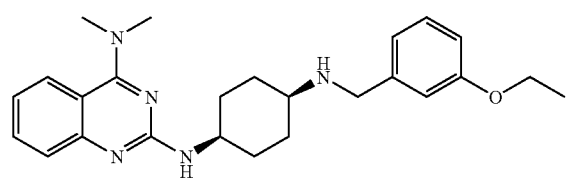
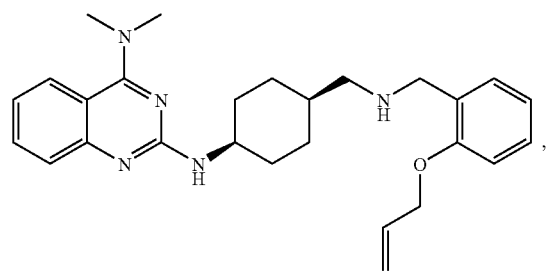
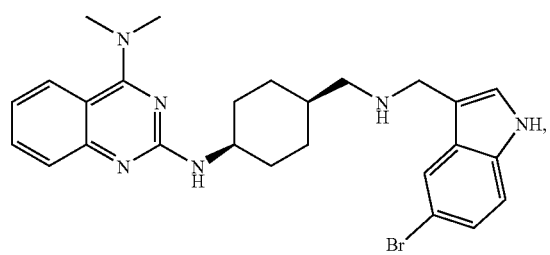
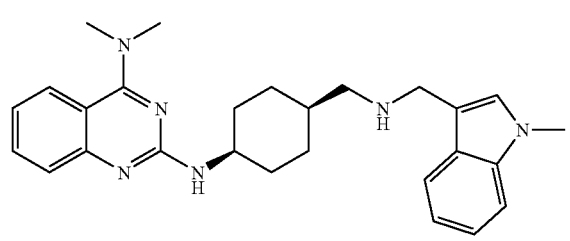
124
-continued
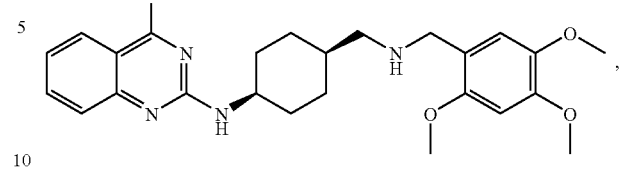
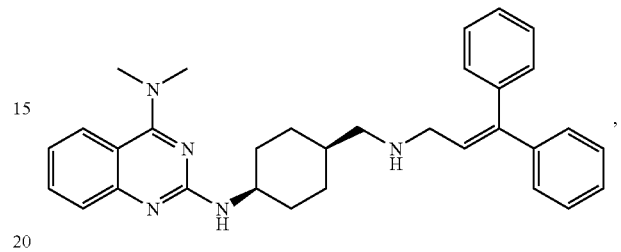
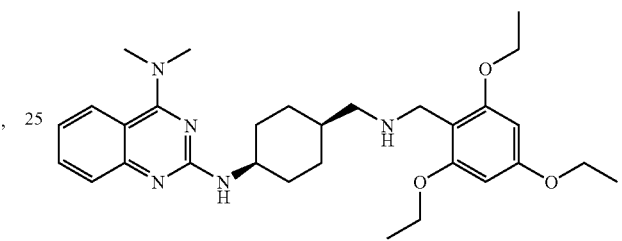
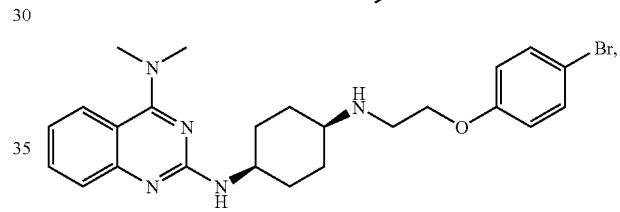
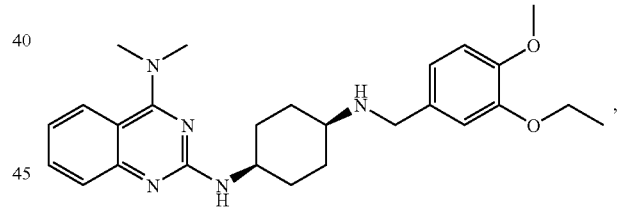
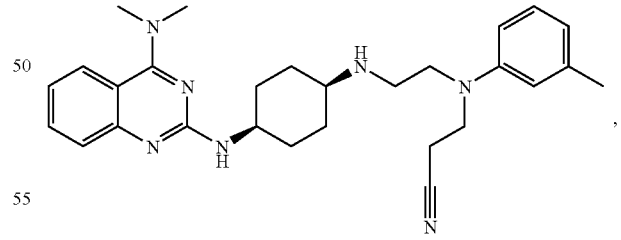
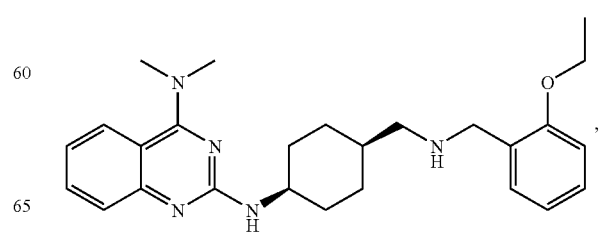

-continued
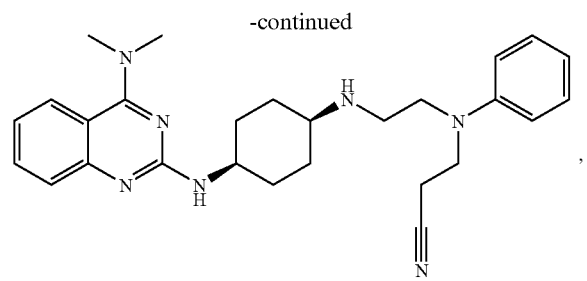
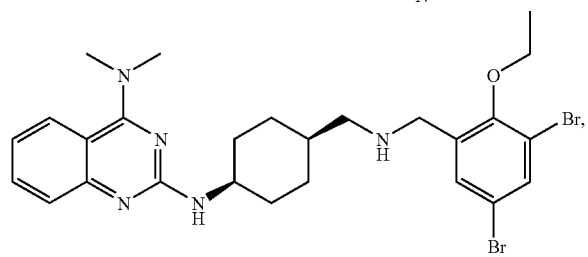
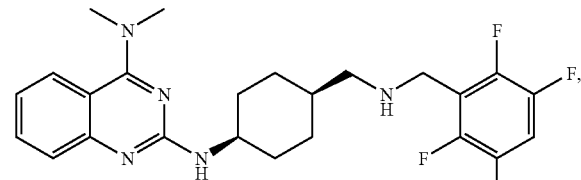
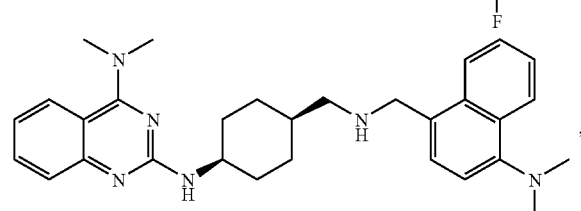
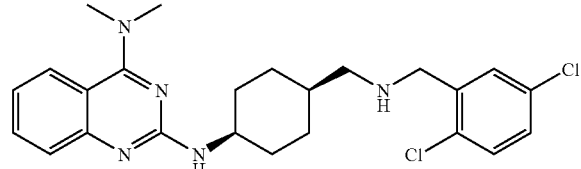
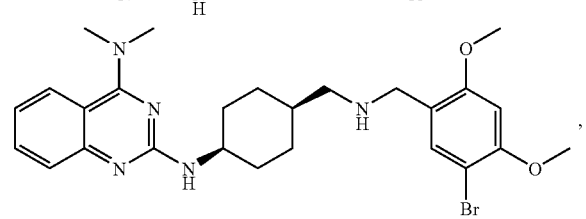
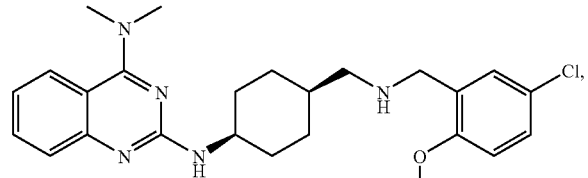
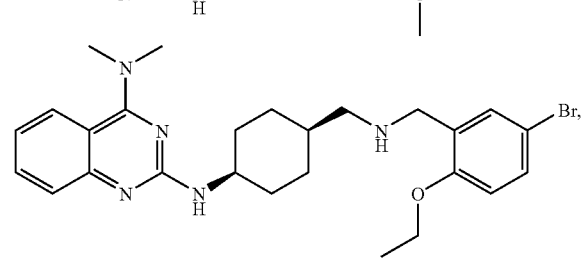
-continued
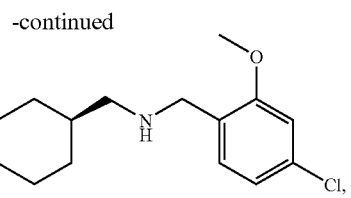
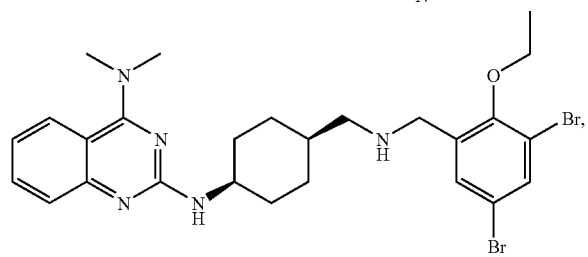
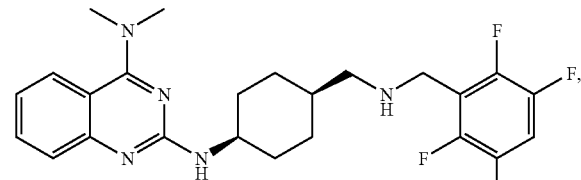
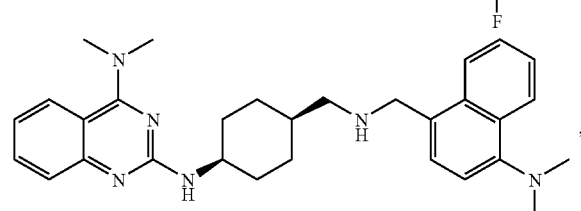
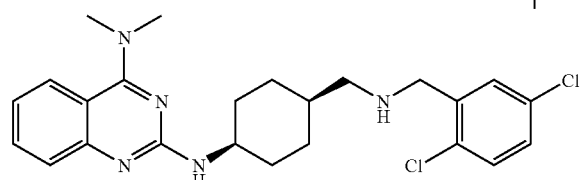
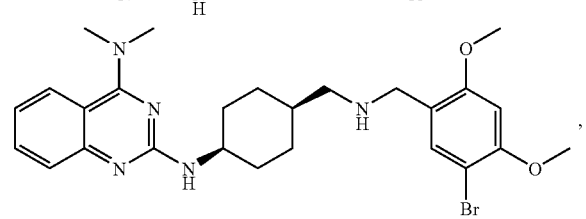
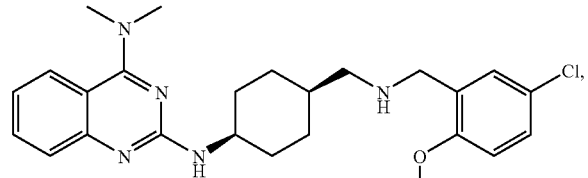
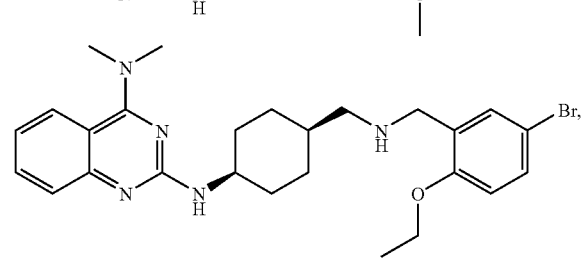

127
-continued
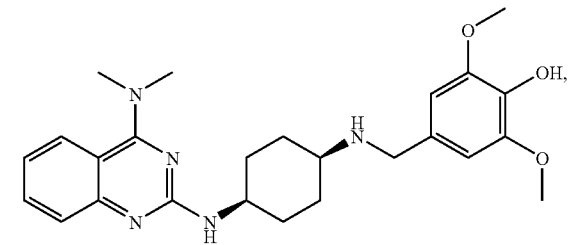
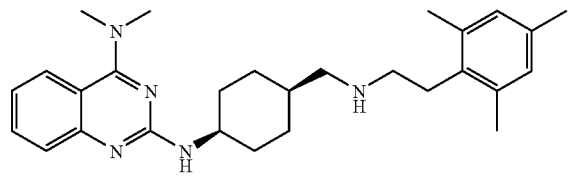
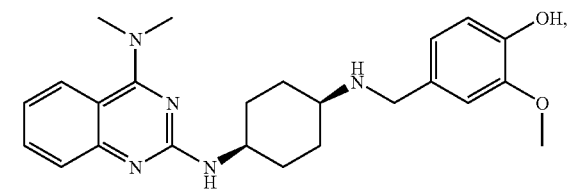
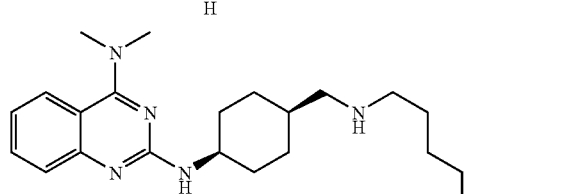
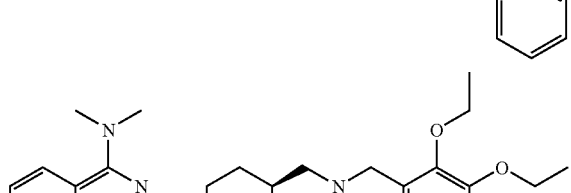
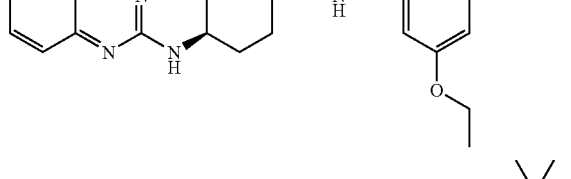
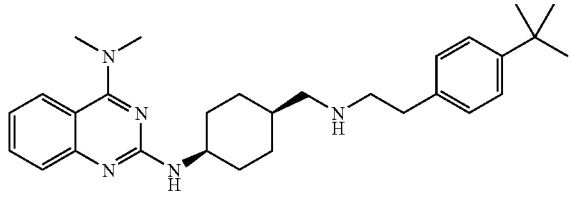
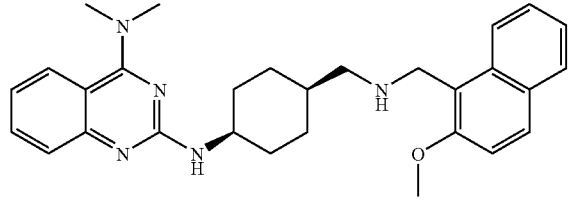
128
-continued
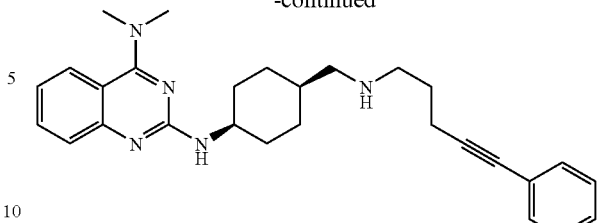
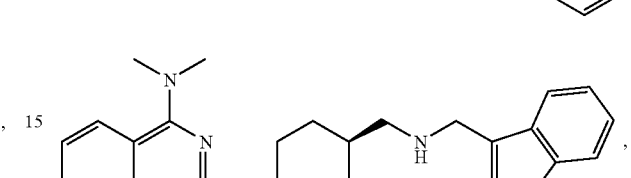

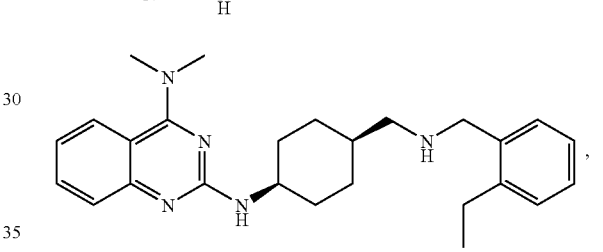
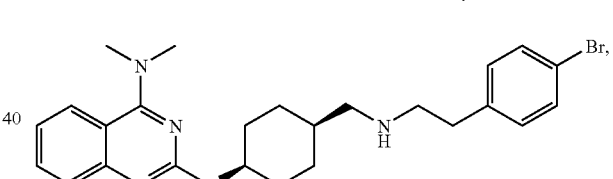
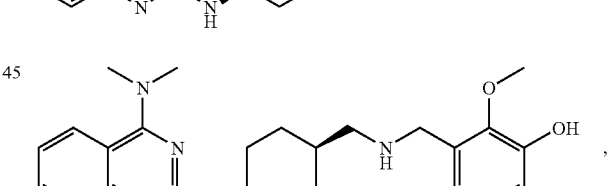
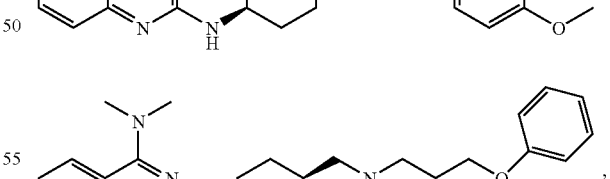
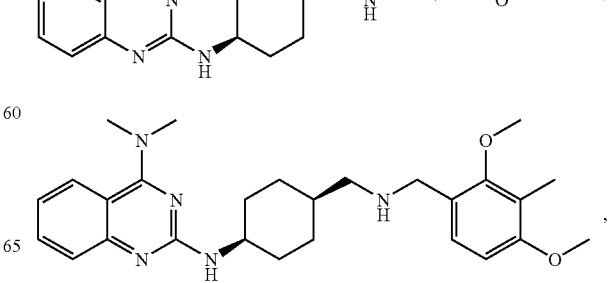

-continued
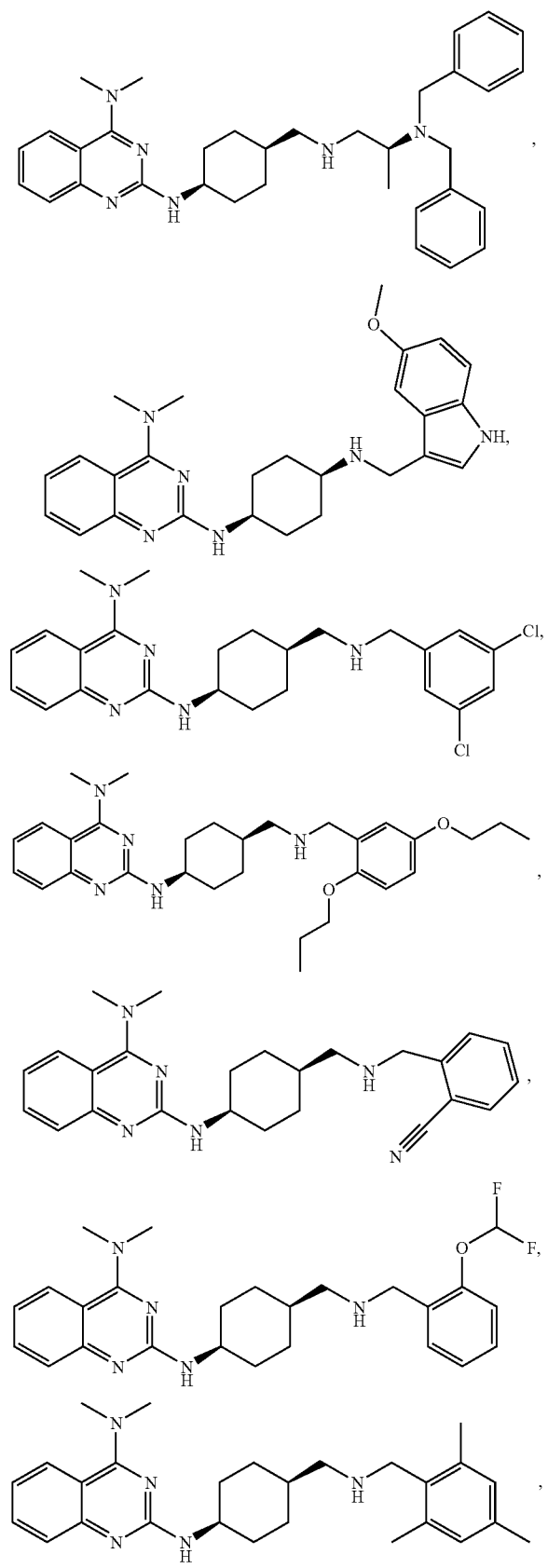
-continued
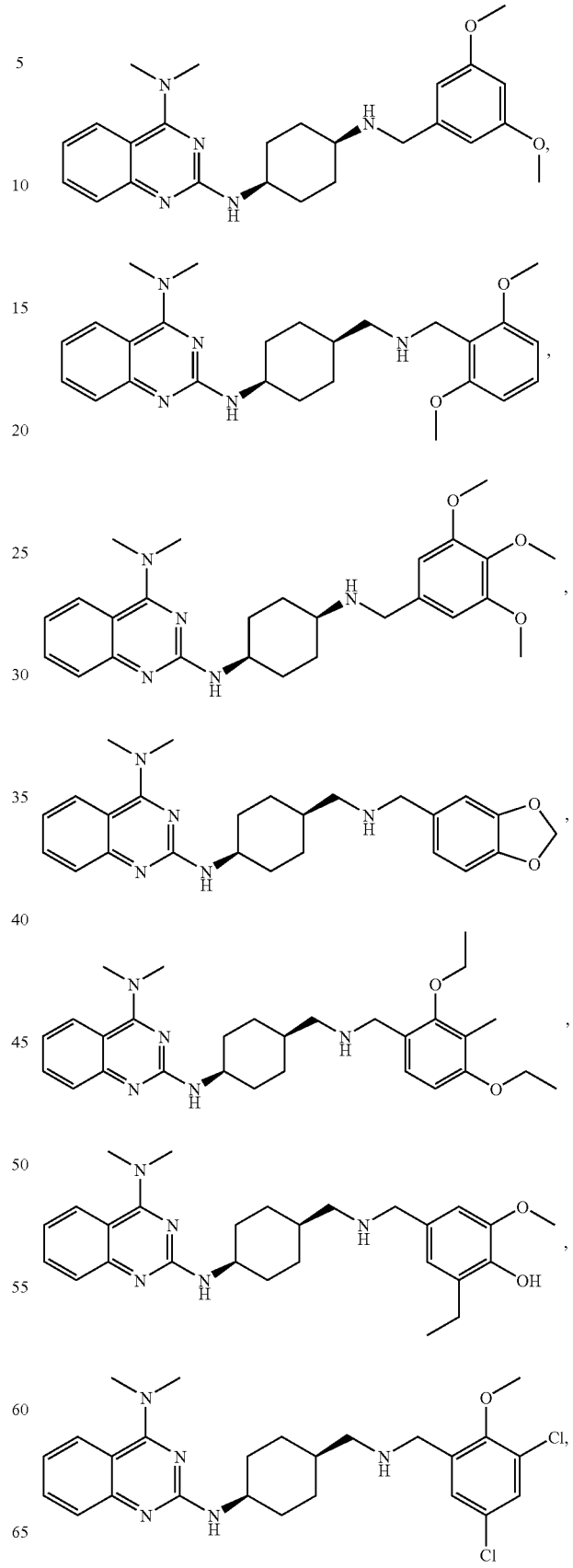

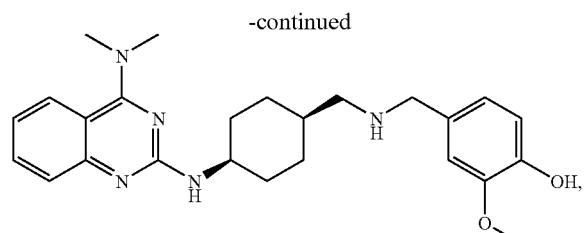,
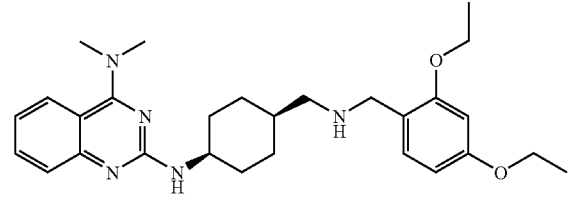,
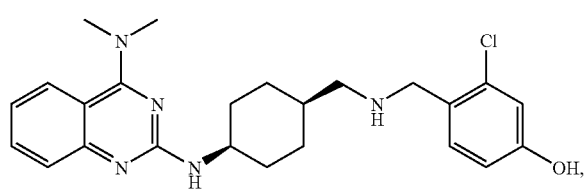,
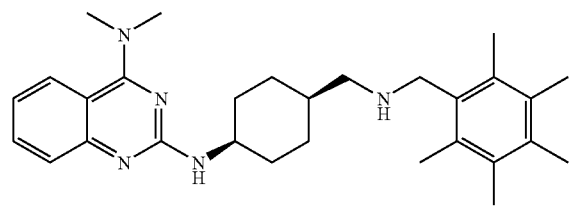,
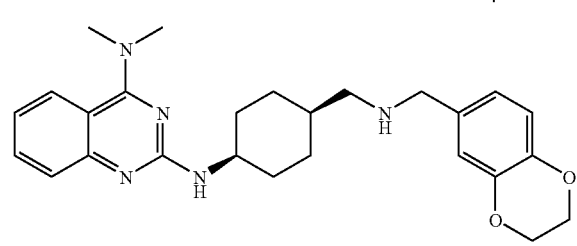,
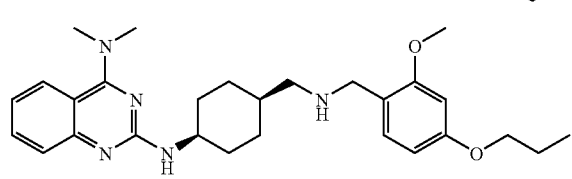,
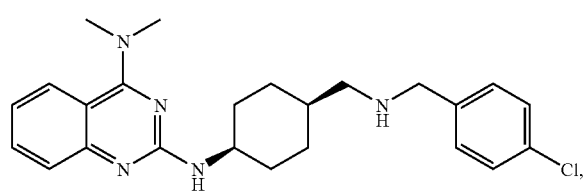,
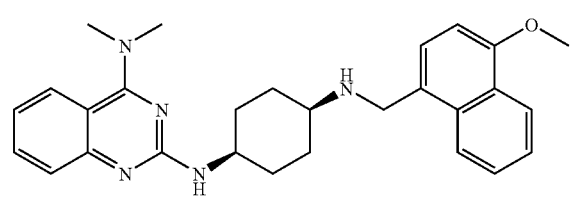,
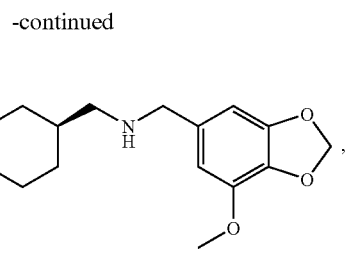,
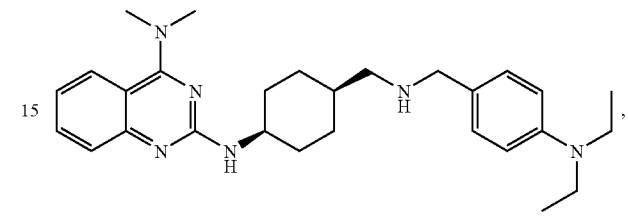,
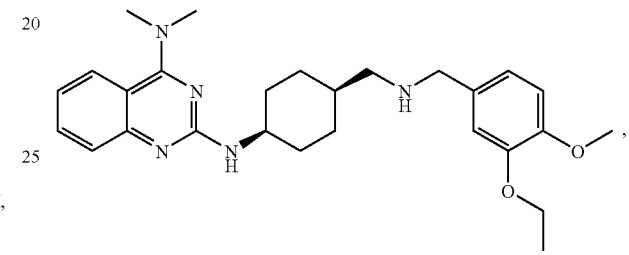,
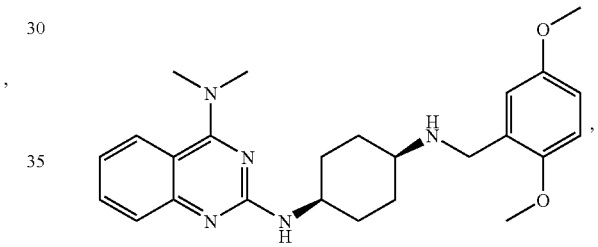,
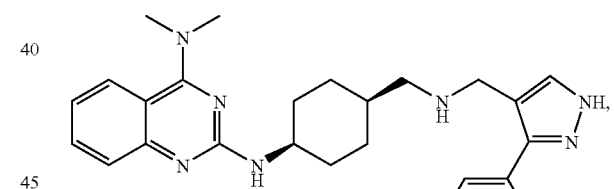,
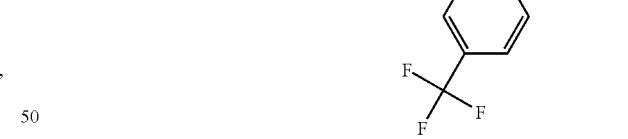,
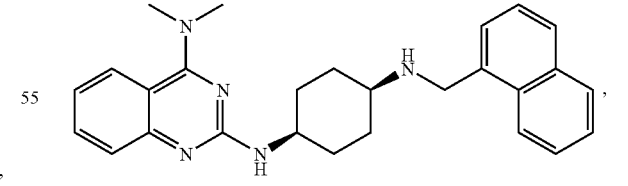,
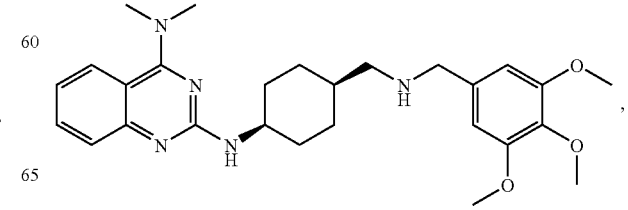, -continued
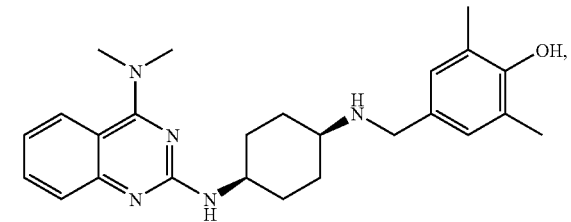
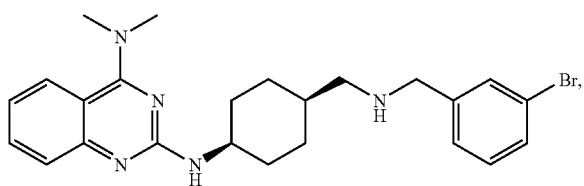
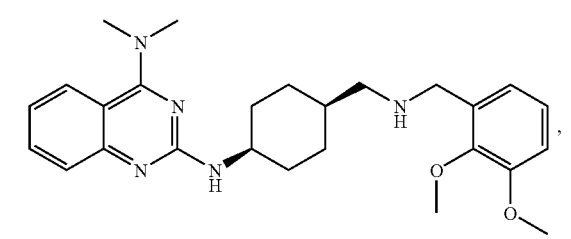
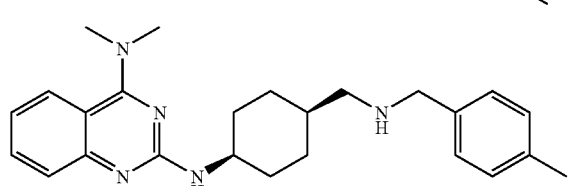
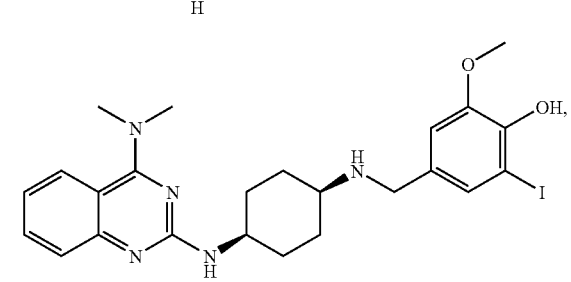
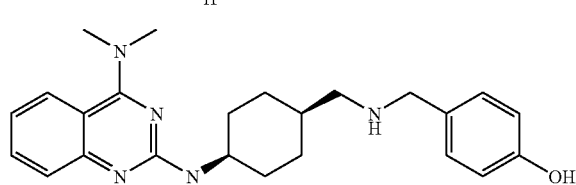
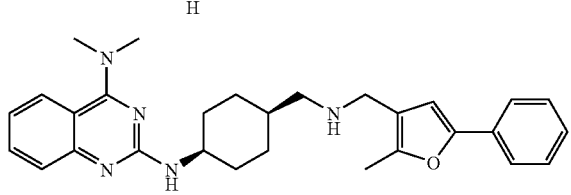
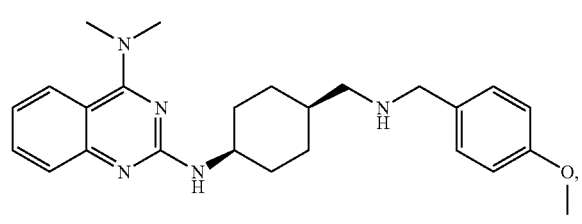
-continued
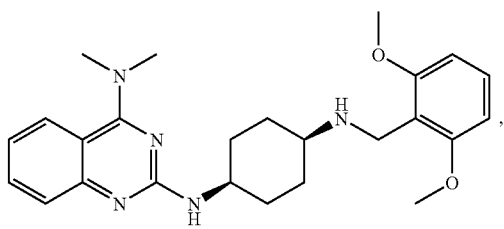
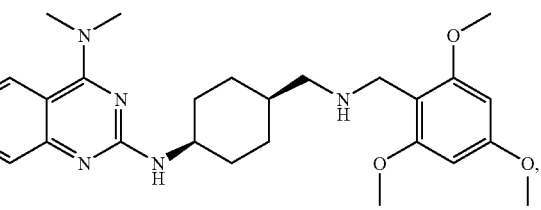
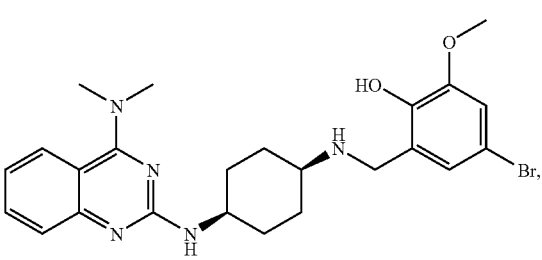
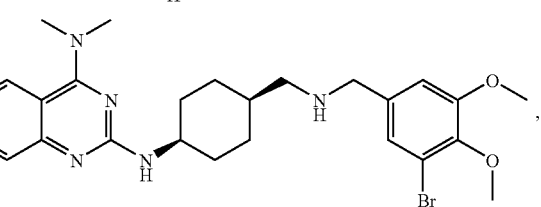
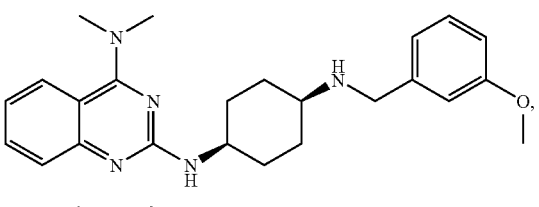
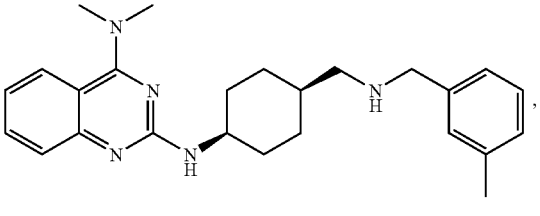
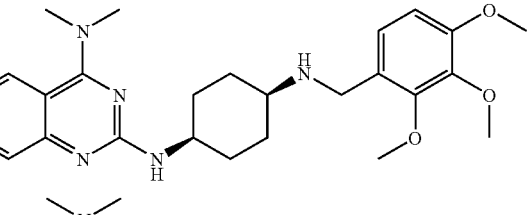
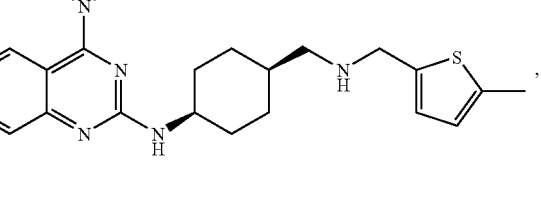

-continued
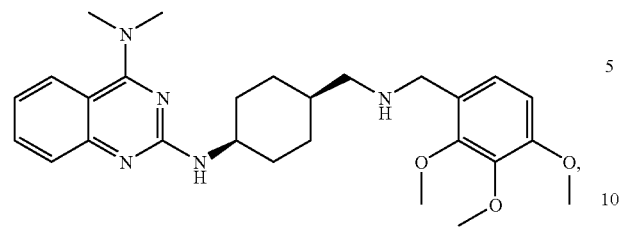
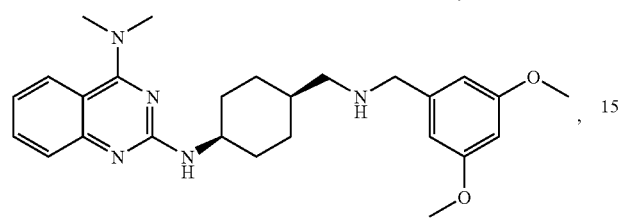
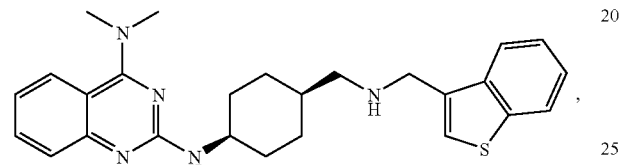
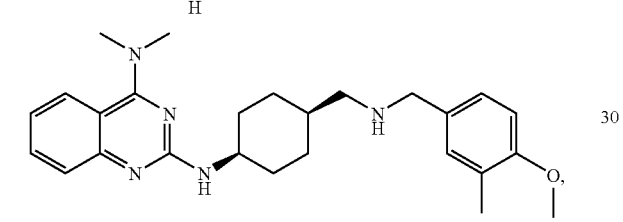

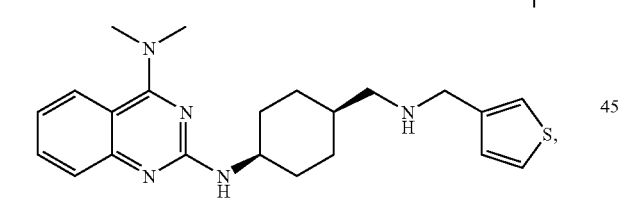

-continued
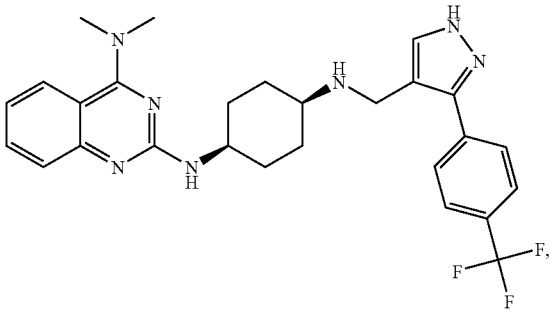
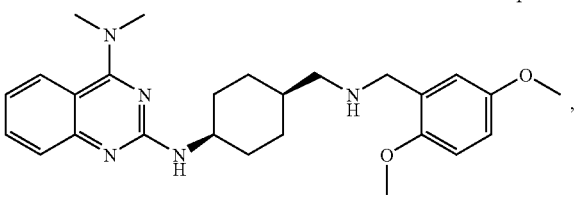
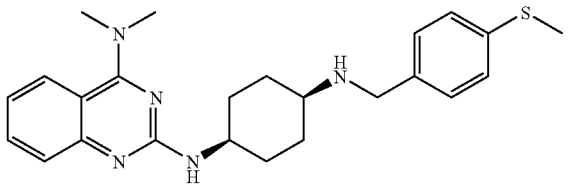
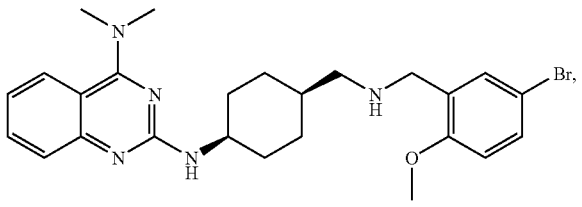
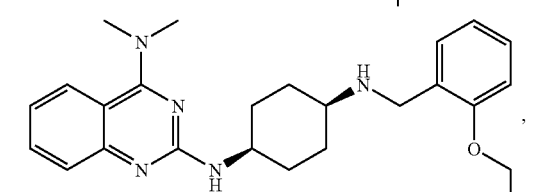
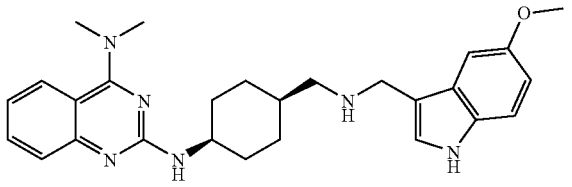
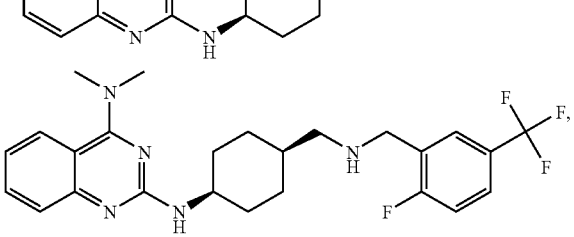

-continued
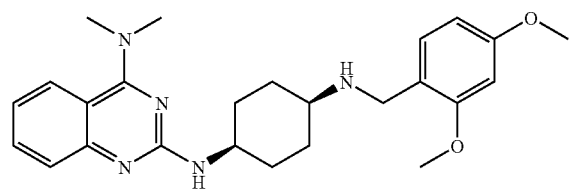
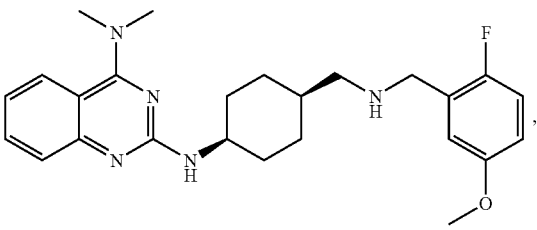
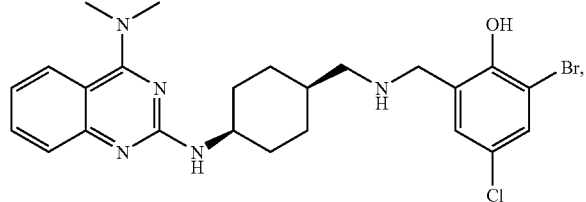
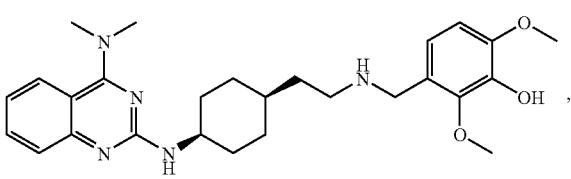
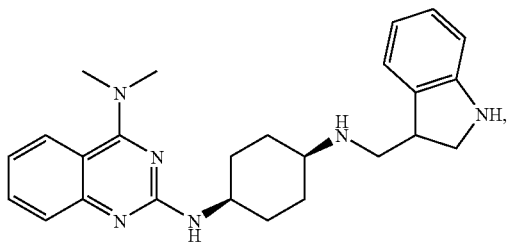
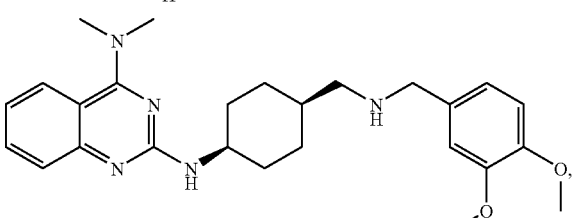
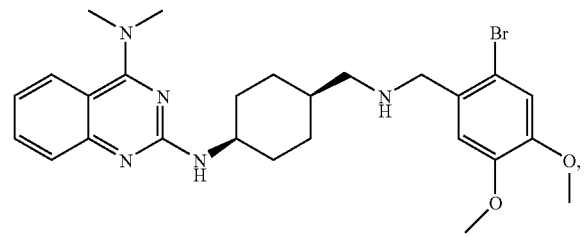
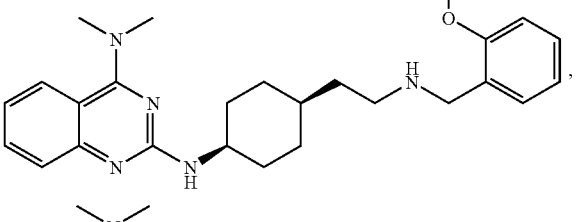
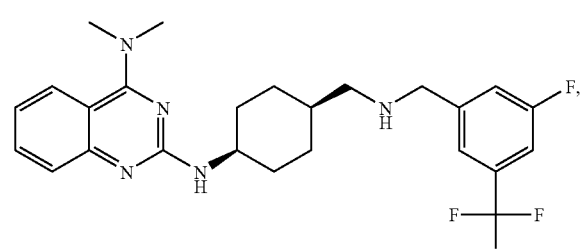
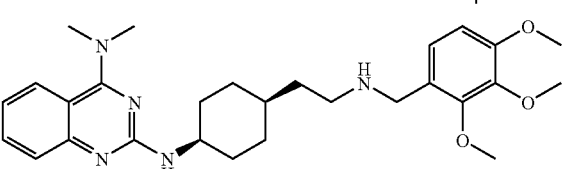
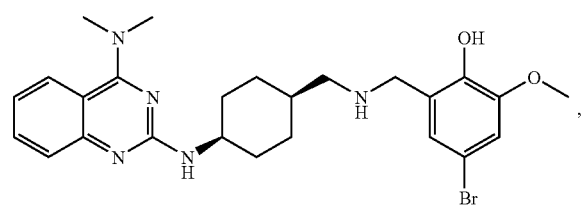
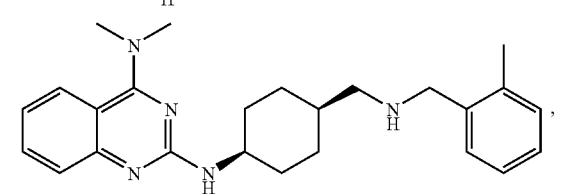
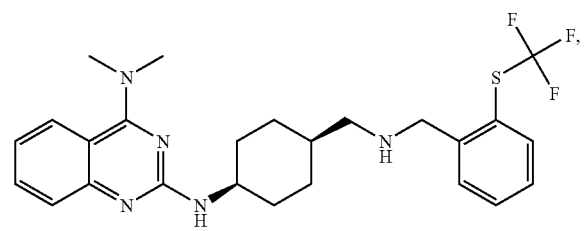
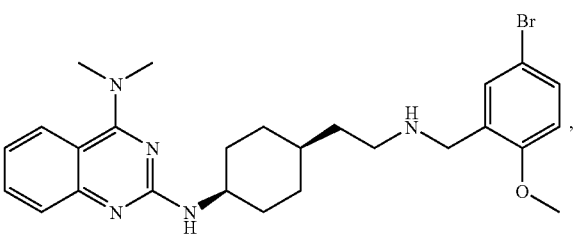

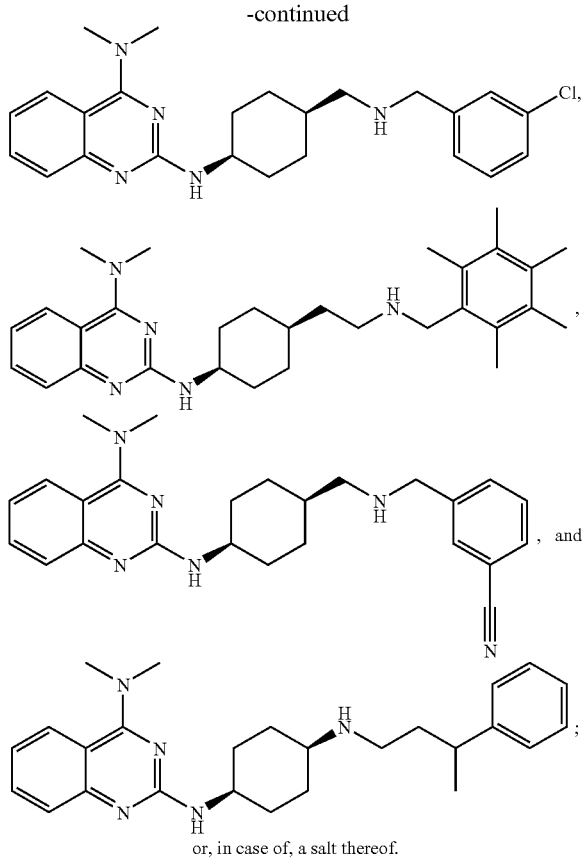

or, in case of, a salt thereof.

Preferred compounds of this invention are those compounds of Formula I wherein,

Q is Formula II;

$R_1$ represents (i) $C_1$-$C_{16}$ alkyl, $C_1$-$C_{16}$ alkyl substituted by substituent(s) independently selected from
halogen,
carbocyclyl,
carbocyclic aryl,
carbocyclic aryl substituted by substituent(s) independently selected from
halogen,
nitro,
$C_1$-$C_3$ alkyl,
halogenated $C_1$-$C_3$ alkyl, (ii) $C_2$-$C_3$ alkenyl, $C_2$-$C_3$ alkenyl substituted by carbocyclic aryl, (iii) carbocyclic aryl, carbocyclic aryl substituted by substituent(s) independently selected from
halogen,
cyano,
nitro,
$C_1$-$C_5$ alkyl,
$C_1$-$C_5$ alkyl substituted by substituent(s) independently selected from
halogen,
oxo,
$C_2$-$C_3$ alkenyl,
$C_1$-$C_4$ alkoxy,
$C_1$-$C_4$ alkoxy substituted by substituent(s) independently selected from
halogen,
heterocyclyl,
halogenated heterocyclyl,
carbocyclic aryloxy,
carbocyclic aryloxy substituted by substituent(s) independently selected from
halogen,
nitro,
heterocyclyloxy,
heterocyclyloxy substituted by substituent(s) independently selected from
halogen,
$C_1$-$C_3$ alkyl,
halogenated $C_1$-$C_3$ alkyl,
$C_1$-$C_3$ alkoxycarbonyl,
mono- or di-$C_1$-$C_4$ alkylamino,
$C_1$-$C_3$ alkylcarbonylamino,
carbocyclic aryl diazo,
carbocyclic aryl diazo substituted by mono- or di-$C_1$-$C_3$ alkylamino,
$C_1$-$C_3$ alkylsulfonyl,
carbocyclic aryl, (iv) heterocyclyl, or heterocyclyl substituted by substituent(s) independently selected from
halogen,
$C_1$-$C_3$ alkyl,
$C_1$-$C_3$ alkyl substituted by substituent(s) independently selected from
halogen,
oxo,
carbocyclic arylcarbonylamino,
halogenated carbocyclic arylcarbonylamino,
heterocyclyl,
heterocyclyl substituted by substituent(s) independently selected from
halogen,
$C_1$-$C_3$ alkyl,
halogenated $C_1$-$C_3$ alkyl,
$C_1$-$C_3$ alkoxy,
$C_1$-$C_3$ alkylcarbonylamino,
carbocyclic arylsulfonyl,
$C_1$-$C_3$ alkoxycarbonyl,
carbocyclic aryl,
halogenated carbocyclic aryl,
heterocyclyl,
heterocyclyl substituted by substituent(s) independently selected from
halogen,
$C_1$-$C_3$ alkyl,
halogenated $C_1$-$C_3$ alkyl;

$R_2$ is —NHNH$_2$, —NNHBoc, —N(R$_{2a}$)(R$_{2b}$), morpholino, 4-acetyl-piperazyl, or 4-phenyl-piperazyl;

wherein $R_{2a}$ is H or $C_1$-$C_3$ alkyl;

$R_{2b}$ is $C_1$-$C_4$ alkyl, $C_1$-$C_4$ alkyl substituted by substituent(s) independently selected from hydroxy, $C_1$-$C_3$ alkoxy, amino, —NHBoc, $C_3$-$C_6$ cycloalkyl, carbocyclic aryl, carbocyclic aryl substituted by substituent(s) independently selected from halogen, $C_1$-$C_3$ alkyl, $C_1$-$C_3$ alkoxy,

—SO$_2$NH$_2$, heterocyclyl, $C_3$-$C_6$ cycloalkyl, carbocyclic aryl, carbocyclic aryl substituted by substituent(s) independently selected from halogen, $C_1$-$C_3$ alkyl, $C_1$-$C_3$ alkoxy, or a group of Formula IV;

wherein Boc is carbamic acid tert-butyl ester and $R_3$ is $C_1$-$C_3$ alkyl or $C_1$-$C_3$ alkyl substituted by substituent(s) independently selected from carbocyclic aryl, halogenated carbocyclic aryl, carbocyclic aryl substituted by $C_1$-$C_3$ alkoxy;

L is selected from Formula V-XIX;

wherein $R_4$ is H or $C_1$-$C_3$ alkyl;

$R_5$ is H, $C_1$-$C_3$ alkyl, or $C_1$-$C_3$ alkyl substituted by a substituted carbocyclic aryl;

Y is —S(O)$_2$—;

wherein carbocyclic aryl is phenyl, naphthyl, or biphenyl;

carbocyclyl is 7,7-dimethyl-2-oxo-bicyclo[2.2.1]heptyl;

heterocyclyl is 1,2,3,4-tetrahydro-isoquinolyl, 1,2,3-thiadiazolyl, 1H-pyrrolyl, benzo[2,1,3]oxadiazolyl, benzo[b]thienyl, furyl, imidazolyl, isoxazolyl, pyrazolyl, pyridyl, quinolyl, thiazolyl, or thienyl;

halogen is fluoro, chloro, bromo, or iodo.

The following compounds are specially preffered;

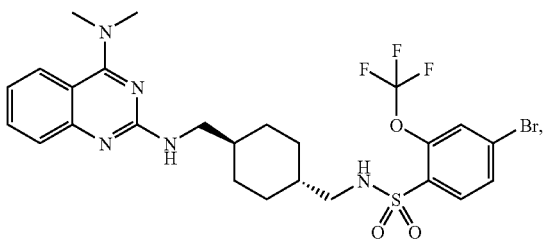
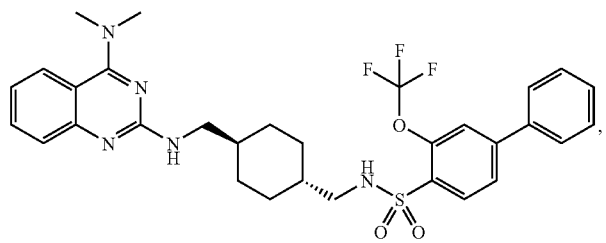
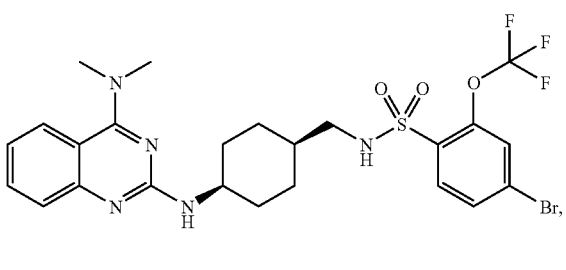
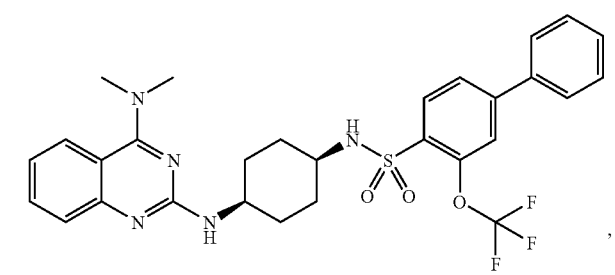
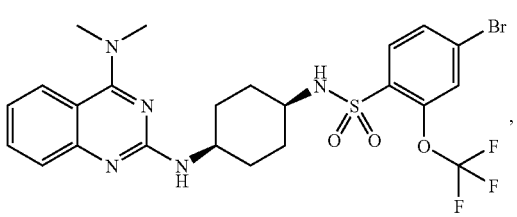
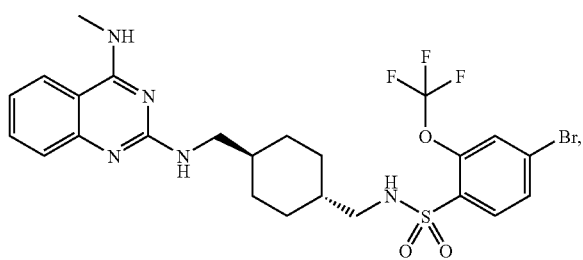
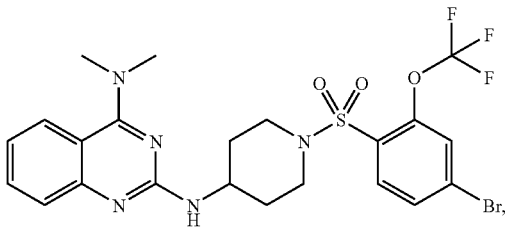

-continued

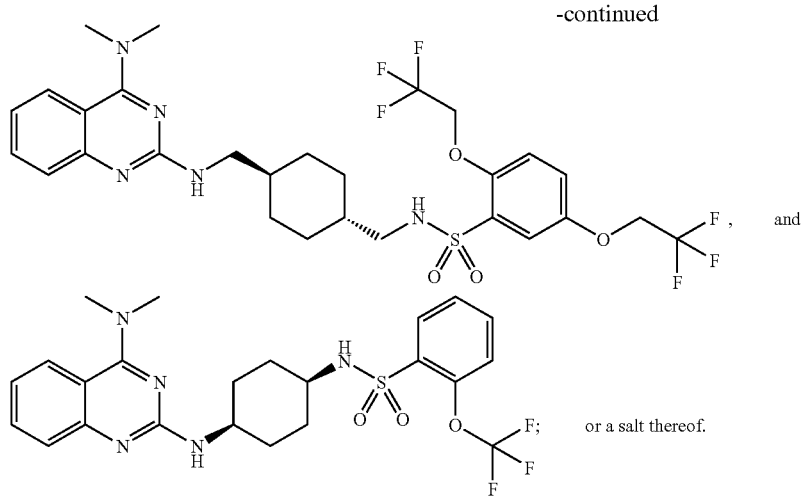

or a salt thereof.

Preferred compounds of this invention are those compounds of Formula I wherein,

Q is Fomura II;

$R_1$ is selected from H, —$CO_2{}^t$Bu, or —$CO_2$Bn (Bn is a benzyl group);

$R_2$ is methylamino or dimethylamino;

L is selected from Formula XX-XXII;

Y is a single bond;

or a salt thereof.

Also provided in accordance with the present invention are methods of modulating G-protein receptor SLC-1 comprising contacting the SLC-1 receptor with a compound of the invention.

The present invention further provides pharmaceutical compositions containing MCH receptor antagonists of the invention.

DETAILED DESCRIPTION

Figure 1:
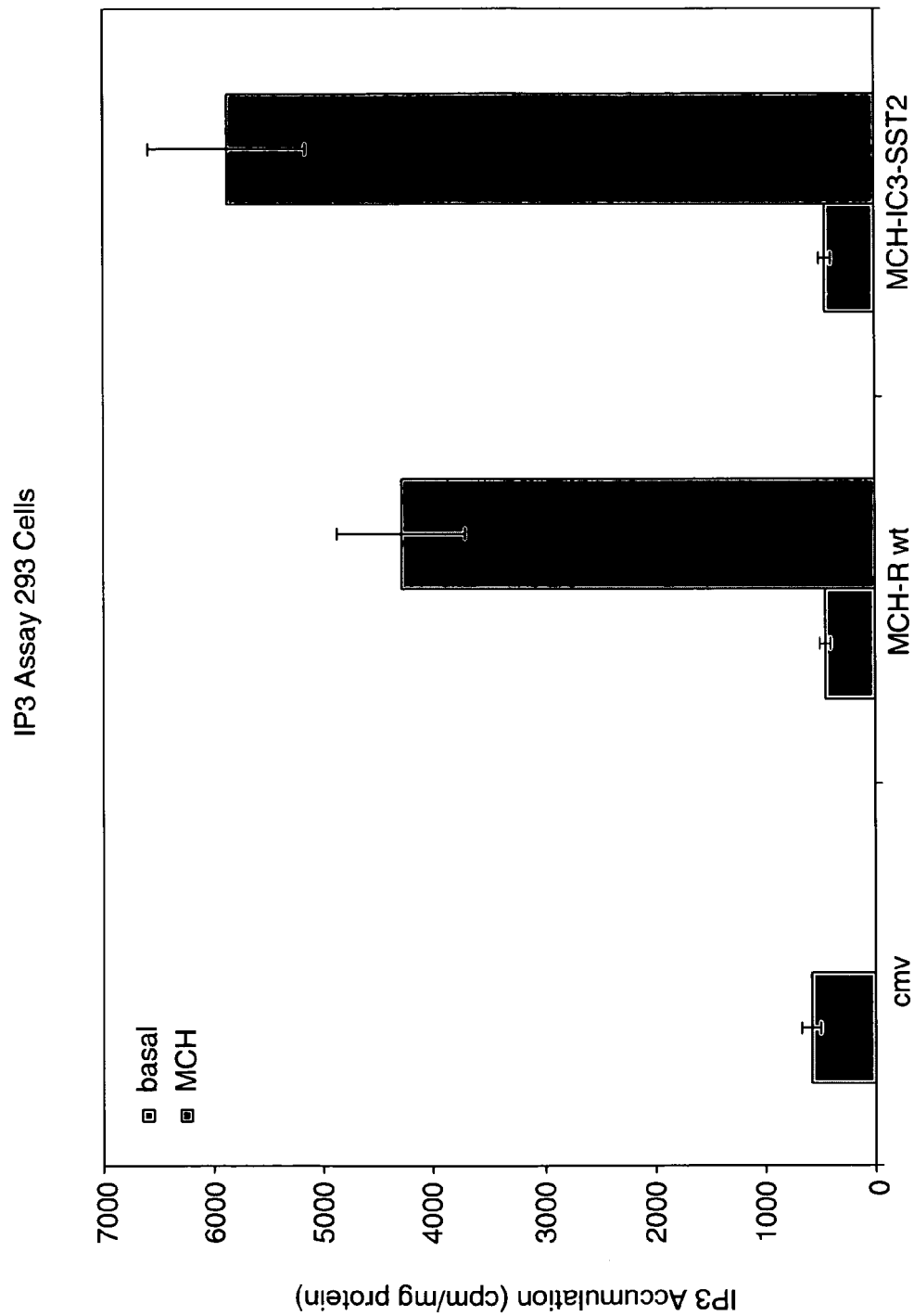
FIG. 1 provides an illustration of $IP_3$ production from several non-endogenous, constitutively activated version of MCH receptor as compared with the endogenous version of this receptor.

The present invention relates to MCH receptor antagonist compounds, and methods of modulating MCH receptors by contacting the receptors with one or more compounds of the invention.

The term "antagonist" is intended to mean moieties that competitively bind to the receptor at the same site as agonists (for example, the endogenous ligand), but which do not activate the intracellular response initiated by the active form of the receptor, and can thereby inhibit the intracellular responses by agonists or partial agonists. Antagonists do not diminish the baseline intracellular response in the absence of an agonist or partial agonist. As used herein, the term "agonist" is intended to mean moieties that activate the intracellular response when they bind to the receptor, or enhance GTP binding to membranes. In the context of the present invention, a pharmaceutical composition comprising a MCH receptor antagonist of the invention can be utilized for modulating the activity of the MCH receptor, decreasing body weight and/or affecting metabolism such that the recipient loses weight and/or maintains weight. Such pharmaceutical compositions can be used in the context of disorders and/or diseases where weight gain is a component of the disease and/or disorder such as, for example, obesity.

As used herein, the term "contact" or "contacting" shall mean bringing the indicated moieties together, whether in an in vitro system or an in vivo system. Thus, "contacting" an MCH receptor with a compound of the invention includes the administration of a compound of the invention to an animal having an MCH receptor, as well as, for example, introducing a compound of the invention into a sample containing a cellular or more purified preparation containing an MCH receptor.

Compounds of the invention include those having Formula I, shown below:

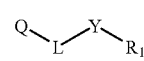

I wherein Q can be either Foemura II or III:

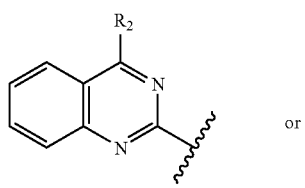

II

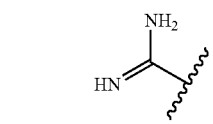

III $R_1$ represents (i) $C_1$-$C_{16}$ alkyl, $C_1$-$C_{16}$ alkyl substituted by substituent(s) independently selected from halogen,
hydroxy,
oxo,
$C_1$-$C_3$ alkoxy,
$C_1$-$C_3$ alkoxy substituted by substituent(s) independently selected from
  carbocyclic aryl,
  heterocyclyl,
  heterocyclyl substituted by $C_1$-$C_3$ alkyl,
$C_1$-$C_3$ alkylcarbonyloxy,
carbocyclyloxy,
carbocyclic aryloxy,
carbocyclic aryloxy substituted by substituent(s) independently selected from
  halogen,
  nitro,
  carbocyclic aryl,
  carbocyclic aryl substituted by $C_1$-$C_3$ alkoxy,
  $C_1$-$C_4$ alkyl,
  $C_1$-$C_4$ alkyl substituted by substituent(s) independently selected from
    oxo,
    mono- or di-$C_1$-$C_3$ alkylamino,
    mono- or di-$C_1$-$C_3$ alkylamino substituted by carbocyclic aryl,
    mono- or di-$C_1$-$C_3$ alkylamino substituted by halogenated carbocyclic aryl,
    carbocyclic arylcarbonylamino,
    halogenated carbocyclic arylcarbonylamino,
heterocyclyloxy,
heterocyclyloxy substituted by $C_1$-$C_3$ alkyl,
substituted heterocyclyl-ethylideneaminooxy,
$C_1$-$C_3$ alkoxycarbonyl,
$C_1$-$C_3$ alkoxycarbonyl substituted by carbocyclic aryl,
mono- or di-$C_1$-$C_3$ alkylaminocarbonyl,
mono- or di-$C_1$-$C_3$ alkylamino,
mono- or di-$C_1$-$C_3$ alkylamino substituted by substituent(s) independently selected from
  cyano,
  carbocyclic aryl,
  heterocyclyl,
mono- or di-carbocyclic arylamino,
mono- or di-carbocyclic arylamino substituted by substituent(s) independently selected from
  hydroxy,
  $C_1$-$C_3$ alkyl,
$C_1$-$C_3$ alkylcalbonylamino,
$C_1$-$C_3$ alkylcalbonylamino substituted by substituent(s) independently selected from
  $C_1$-$C_3$ alkylcalbonylamino,
  carbocyclic arylcalbonylamino,
  heterocyclyl,
$C_1$-$C_4$ alkoxycalbonylamino,
heterocyclyl calbonylamino,
carbocyclic arylsulfonylamino,
carbocyclic arylsulfonylamino substituted by substituent(s) independently selected from
  nitro,
  $C_1$-$C_3$ alkyl,
  mono- or di-$C_1$-$C_3$ alkylamino,
$C_1$-$C_3$ alkylthio,
$C_1$-$C_3$ alkylthio substituted by substituent(s) independently selected from
  mono- or di-carbocyclic arylaminocarbonyl,
  halogenated mono- or di-carbocyclic arylaminocarbonyl,
  mono- or di-carbocyclic arylamino,
  halogenated mono- or di-carbocyclic arylamino,
carbocyclic aryl,
carbocyclic aryl substituted by substituent(s) independently selected from
  halogen,
  $C_1$-$C_3$ alkoxy,
carbocyclic arylthio,
carbocyclic arylthio substituted by substituent(s) independently selected from
  halogen,
  $C_1$-$C_3$ alkyl,
carbocyclic arylsulfonyl,
halogenated carbocyclic arylsulfonyl,
heterocyclylthio,
heterocyclylthio substituted by substituent(s) independently selected from
  nitro,
  $C_1$-$C_3$ alkyl,
  $C_3$-$C_6$ cycloalkyl,
  $C_3$-$C_6$ cycloalkyl substituted by $C_1$-$C_3$ alkyl,
  $C_3$-$C_6$ cycloalkenyl,
carbocyclyl,
carbocyclyl substituted by substituent(s) independently selected from
  halogen,
  $C_1$-$C_3$ alkyl,
  $C_1$-$C_3$ alkoxy,
  $C_2$-$C_3$ alkenyl,
  $C_2$-$C_3$ alkenyl substituted by carbocyclic aryl,
  $C_2$-$C_3$ alkenyl substituted by carbocyclic aryl substituted $C_1$-$C_3$ alkylsulfinyl,
carbocyclic aryl,
carbocyclic aryl substituted by substituent(s) independently selected from
  halogen,
  hydroxy,
  nitro,
  $C_1$-$C_4$ alkyl,
  $C_1$-$C_4$ alkyl substituted by substituent(s) independently selected from
    halogen,
    hydroxy,
    oxo,
    carbocyclic aryl,
    heterocyclyl,
    mono- or di-carbocyclic arylamino,
    mono- or di-carbocyclic arylamino substituted by substituent(s) independently selected from
      halogen,
      nitro,
      $C_1$-$C_3$ alkyl,
      $C_1$-$C_3$ alkoxy,
      halogenated $C_1$-$C_3$ alkoxy,
  $C_1$-$C_4$ alkoxy,
  $C_1$-$C_4$ alkoxy substituted by substituent(s) independently selected from
    halogen,
    carbocyclic aryl,
  carbocyclic aryloxy,
  $C_1$-$C_3$ alkoxycarbonyl,
  $C_1$-$C_3$ alkylcarbonyloxy,
  mono- or di-$C_1$-$C_3$ alkylamino,
  mono- or di-carbocyclic arylamino,
  halogenated mono- or di-carbocyclic arylamino,
  mono- or di-carbocyclic arylaminocarbonyl, mono- or di-carbocyclic arylaminocarbonyl substituted by substituent(s) independently selected from
halogen,
nitro,
$C_1$-$C_3$ alkyl,
$C_1$-$C_3$ alkoxy,
halogenated $C_1$-$C_3$ alkoxy,
mercapto,
$C_1$-$C_3$ alkylthio,
halogenated $C_1$-$C_3$ alkylthio,
$C_1$-$C_3$ alkylsulfonyl,
$C_3$-$C_6$ cycloalkyl,
carbocyclic aryl,
heterocyclyl,
heterocyclyl,
heterocyclyl substituted by substituent(s) independently selected from
hydroxy,
$C_1$-$C_3$ alkyl,
$C_1$-$C_3$ alkyl substituted by carbocyclic aryl,
$C_1$-$C_3$ alkoxy,
$C_1$-$C_3$ alkoxy substituted by carbocyclic aryl,
carbocyclic aryl,
halogenated carbocyclic aryl, (ii) $C_2$-$C_8$ alkenyl, $C_2$-$C_8$ alkenyl substituted by substituent(s) independently selected from
halogen,
oxo,
$C_1$-$C_3$ alkoxy,
$C_1$-$C_3$ alkoxy substituted by carbocyclic aryl,
carbocyclic aryl,
carbocyclic aryl substituted by substituent(s) independently selected from
halogen,
hydroxy,
nitro,
$C_1$-$C_3$ alkyl,
halogenated $C_1$-$C_3$ alkyl,
$C_1$-$C_3$ alkoxy,
halogenated $C_1$-$C_3$ alkoxy,
heterocyclyl,
heterocyclyl substituted by substituent(s) independently selected from
hydroxy,
nitro,
$C_1$-$C_3$ alkyl,
$C_1$-$C_3$ alkoxy, (iii) $C_2$-$C_4$ alkynyl, $C_2$-$C_4$ alkynyl substituted by carbocyclic aryl, (iv) $C_3$-$C_6$ cycloalkyl, $C_3$-$C_6$ cycloalkyl substituted by substituent(s) independently selected from
$C_1$-$C_3$ alkyl,
$C_1$-$C_3$ alkyl substituted by substituent(s) independently selected from
hydroxy,
oxo,
carbocyclic aryl,
mono- or di-$C_1$-$C_3$ alkylamino,
mono- or di-$C_1$-$C_3$ alkylamino substituted by carbocyclic aryl,
carbocyclic arylcarbonylamino,
carbocyclic aryl, (v) $C_3$-$C_6$ cycloalkeyl, $C_3$-$C_6$ cycloalkeyl substituted by $C_1$-$C_3$ alkyl, (vi) carbocyclyl, carbocyclyl substituted by substituent(s) independently selected from
hydroxy,
nitro, (vii) carbocyclic aryl, carbocyclic aryl substituted by substituent(s) independently selected from
halogen,
hydroxy,
cyano,
nitro,
$C_1$-$C_9$ alkyl,
$C_1$-$C_9$ alkyl substituted by substituent(s) independently selected from
halogen,
hydroxy,
oxo,
$C_1$-$C_3$ alkoxy,
carbocyclic aryloxy,
mono- or di-$C_1$-$C_3$ alkylamino-N-oxy,
mono- or di-$C_1$-$C_3$ alkylamino,
mono- or di-$C_1$-$C_3$ alkylamino substituted by carbocyclic aryl,
mono- or di-carbocyclic arylamino,
carbocyclylimino,
carbocyclylimino substituted by carbocyclic aryl,
mono- or di-carbocyclic arylamino,
mono- or di-carbocyclic arylamino substituted by $C_1$-$C_3$ alkoxy,
mono- or di-carbocyclic arylaminocarbonyl,
mono- or di-carbocyclic arylaminocarbonyl substituted by $C_1$-$C_3$ alkoxy,
carbocyclic aryl,
carbocyclic aryl substituted by substituent(s) independently selected from
halogen,
$C_1$-$C_3$ alkyl,
halogenated $C_1$-$C_3$ alkyl,
heterocyclyl,
heterocyclyl substituted by $C_1$-$C_3$ alkyl,
$C_2$-$C_3$ alkenyl,
$C_2$-$C_3$ alkenyl substituted by carbocyclic aryl,
$C_1$-$C_9$ alkoxy,
$C_1$-$C_9$ alkoxy substituted by substituent(s) independently selected from
hydroxy,
halogen,
carboxy,
mono- or di-$C_1$-$C_3$ alkylamino,
carbocyclic aryl,
halogenated carbocyclic aryl,
heterocyclyl,
heterocyclyl substituted by substituent(s) independently selected from
halogen,
heterocyclyl,
heterocyclyl substituted by substituent(s) independently selected from
halogen,
$C_1$-$C_3$ alkyl,
halogenated $C_1$-$C_3$ alkyl, C$_2$-C$_3$ alkenyloxy,
C$_1$-C$_3$ alkylcarbonyloxy,
carbocyclic aryloxy,
carbocyclic aryloxy substituted by substituent(s) independently selected from
    halogen,
    nitro,
    C$_1$-C$_4$ alkyl,
    halogenated C$_1$-C$_4$ alkyl,
    C$_1$-C$_3$ alkoxy,
heterocyclyloxy,
heterocyclyloxy substituted by substituent(s) independently selected from
    halogen,
    C$_1$-C$_3$ alkyl,
    halogenated C$_1$-C$_3$ alkyl,
(carbocyclic aryl)S(O)$_2$O,
carboxy,
C$_1$-C$_3$ alkoxycarbonyl,
mono- or di-C$_1$-C$_3$ alkylaminocarbonyl,
mono- or di-C$_1$-C$_3$ alkylaminocarbonyl substituted by carbocyclic aryl,
mono- or di-carbocyclic arylaminocarbonyl,
mono- or di-carbocyclic arylaminocarbonyl substituted by C$_1$-C$_3$ alkyl,
amino,
mono- or di-C$_1$-C$_4$ alkylamino,
mono- or di-C$_1$-C$_4$ alkylamino substituted by cyano,
mono- or di-carbocyclic arylamino,
C$_1$-C$_3$ alkynylcarbonylamino,
C$_1$-C$_3$ alkynylcarbonylamino substituted by carbocyclic aryl,
carbocyclic arylsulfonylamino,
carbocyclic arylsulfonylamino substituted by C$_1$-C$_3$ alkyl,
(carbocyclic aryl)NHC(O)NH,
(carbocyclic aryl)NHC(O)NH substituted by C$_1$-C$_3$ alkoxy,
(carbocyclic aryl)NHC(O)NH substituted by haloganated C$_1$-C$_3$ alkoxy,
carbocyclic aryl diazo,
carbocyclic aryl diazo substituted by mono- or di-C$_1$-C$_3$ alkylamino,
C$_1$-C$_3$ alkylthio,
halogenated C$_1$-C$_3$ alkylthio,
carbocyclic arylthio,
carbocyclic arylthio substituted by substituent(s) independently selected from
    halogen,
    cyano,
    C$_1$-C$_3$ alkyl,
heterocyclylthio,
C$_1$-C$_3$ alkylsulfonyl,
mono- or di-C$_1$-C$_3$ alkylaminosulfonyl,
carbocyclic aryl,
carbocyclic aryl substituted by substituent(s) independently selected from
    C$_1$-C$_7$ alkyl,
    halogenated C$_1$-C$_7$ alkyl,
    heterocyclyl,
    heterocyclyl substituted by substituent(s) independently selected from
        C$_1$-C$_3$ alkyl,
        carbocyclic aryl,
        halogenated carbocyclic aryl,
(viii) heterocyclyl,
or heterocyclyl substituted by substituent(s) independently selected from
    halogen,
    hydroxy,
    cyano,
    nitro,
    C$_1$-C$_4$ alkyl,
    C$_1$-C$_4$ alkyl substituted by substituent(s) independently selected from
        halogen,
        hydroxy,
        oxo,
        C$_1$-C$_3$ alkylcarbonyloxy,
        carbocyclic arylcarbonylamino,
        halogenated carbocyclic arylcarbonylamino,
        C$_1$-C$_3$ alkoxycarbonyl,
        C$_1$-C$_3$ alkylthio,
        C$_1$-C$_3$ alkylthio substituted by carbocyclic aryl,
        C$_1$-C$_3$ alkylthio substituted by halogenated carbocyclic aryl,
        carbocyclic aryl,
        carbocyclic aryl substituted by substituent(s) independently selected from
            halogen,
            nitro,
        heterocyclyl,
        heterocyclyl substituted by substituent(s) independently selected from
            halogen,
            C$_1$-C$_3$ alkyl,
            halogenated C$_1$-C$_3$ alkyl,
    C$_1$-C$_3$ alkoxy,
    C$_1$-C$_3$ alkoxy substituted by carbocyclic aryl,
    carbocyclic aryloxy,
    carbocyclic aryloxy substituted by substituent(s) independently selected from
        halogen,
        C$_1$-C$_3$ alkyl,
    mono- or di-C$_1$-C$_3$ alkylamino,
    C$_1$-C$_4$ alkylcarbonylamino,
    C$_1$-C$_3$ alkylthio,
    C$_1$-C$_3$ alkenylthio,
    carbocyclic arylthio,
    halogenated carbocyclic arylthio,
    carbocyclic arylthio substituted by C$_1$-C$_3$ alkoxycarbonyl,
    heterocyclylthio,
    heterocyclylthio substituted by C$_1$-C$_3$ alkyl,
    C$_1$-C$_3$ alkylsulfonyl,
    carbocyclic arylsulfonyl,
    halogenated carbocyclic arylsulfonyl,
    carbocyclic arylsulfonyl substituted by C$_1$-C$_4$ alkyl,
    C$_1$-C$_3$ alkoxycarbonyl,
    carbocyclic aryl,
    carbocyclic aryl substituted by substituent(s) independently selected from
        halogen,
        nitro,
        C$_1$-C$_3$ alkyl,
        halogenated C$_1$-C$_3$ alkyl,
        C$_1$-C$_3$ alkoxy,
        halogenated C$_1$-C$_3$ alkoxy,
    heterocyclyl,
    heterocyclyl substituted by substituent(s) independently selected from
        halogen, C₁-C₃ alkyl,
halogenated C₁-C₃ alkyl,
C₁-C₃ alkoxy,
C₁-C₃ alkoxycarbonyl;

$R_2$ is —NHNH₂, —NHNHBoc, —N($R_{2a}$)($R_{2b}$), morpholino, 4-acetyl-piperazyl, or 4-phenyl-piperazyl;

wherein $R_{2a}$ is H or C₁-C₃ alkyl;

$R_{2b}$ is C₁-C₄ alkyl, C₁-C₄ alkyl substituted by substituent(s) independently selected from
hydroxy,
C₁-C₃ alkoxy,
amino,
—NHBoc,
C₃-C₆ cycloalkyl,
carbocyclic aryl,
carbocyclic aryl substituted by substituent(s) independently selected from
halogen,
C₁-C₃ alkyl,
C₁-C₃ alkoxy,
—SO₂NH₂,
heterocyclyl, C₃-C₆ cycloalkyl, carbocyclic aryl, carbocyclic aryl substituted by substituent(s) independently selected from
halogen,
C₁-C₃ alkyl,
C₁-C₃ alkoxy, or a group of Formula IV;

IV wherein Boc is carbamic acid tert-butyl ester and $R_3$ is C₁-C₃ alkyl or C₁-C₃ alkyl substituted by substituent(s) independently selected from
carbocyclic aryl,
halogenated carbocyclic aryl,
carbocyclic aryl substituted by C₁-C₃ alkoxy;

L is selected from Formula V-XIX;

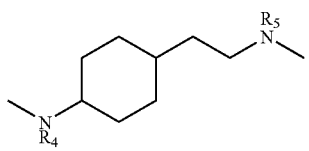

V

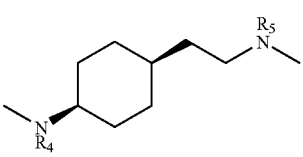

Va

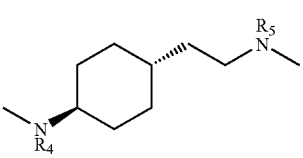

Vb

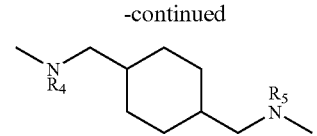

VI

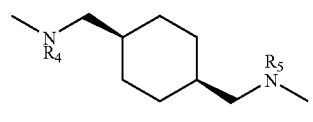

VIa

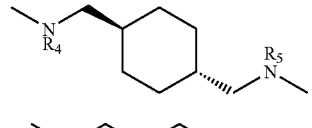

VIb

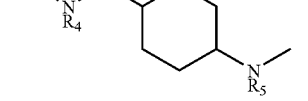

VII

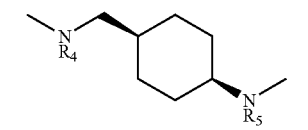

VIIa

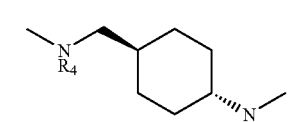

VIIb

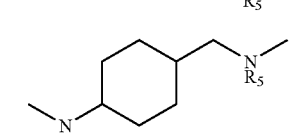

VIII

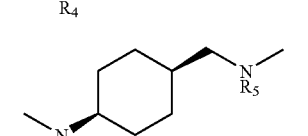

VIIIa

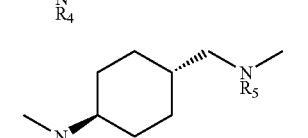

VIIIb

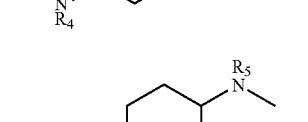

IX

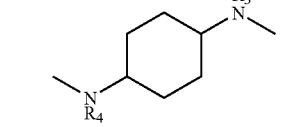

IXa

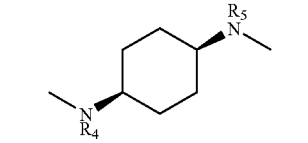

IXb

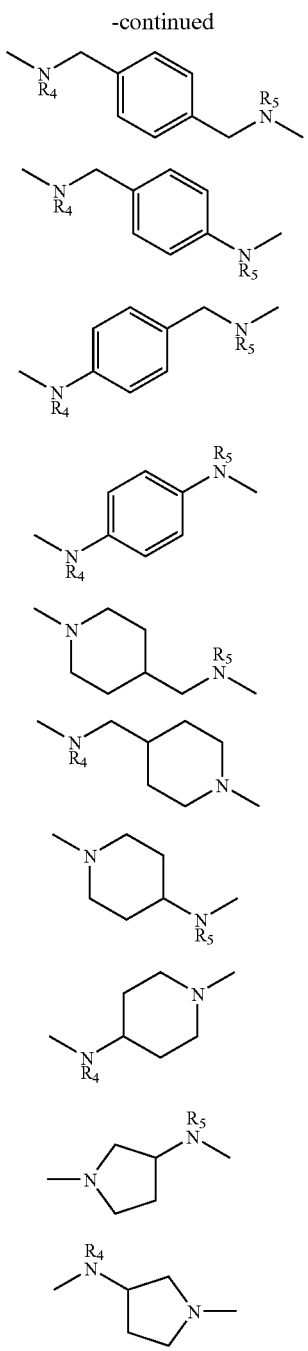

wherein $R_4$ is H or $C_1$-$C_3$ alkyl;
$R_5$ is H, $C_1$-$C_3$ alkyl, or $C_1$-$C_3$ alkyl substituted by a substituted carbocyclic aryl;
Y is —S(O)$_2$—, —C(O)—, or —(CH$_2$)$_m$—;
m is 0 or 1;
wherein carbocyclic aryl is phenyl, naphthyl, anthranyl, biphenyl, or phenanthryl;
carbocyclyl is 10,11-dihydro-5-oxo-dibenzo [a,d]cycloheptyl, 1-oxo-indanyl, 7,7-dimethyl-2-oxo-bicyclo[2.2.1]heptyl, 9H-fluorenyl, 9-oxo-fluorenyl, acenaphthyl, anthraquinonyl, C-fluoren-9-ylidene, indanyl, indenyl, 1,2,3,4-tetrahydro-naphthyl, or bicyclo[2.2.1]hepteny;
heterocyclyl is 1,2,3,4-tetrahydro-isoquinolyl, 1,2,3-thiadiazolyl, 1,2,3-triazolyl, 1,2-dihydro-3-oxo-pyrazolyl, 1,3,4-thiadiazolyl, 1,3-dioxo-isoindolyl, 1,3-dioxolanyl, 1H-indolyl, 1H-pyrrolo[2,3-c]pyridyl, 1H-pyrrolyl, 1-oxo-3H-isobenzofuranyl, 2,2',5',2"-terthiophenyl, 2,2'-bithiophenyl, 2,3-dihydro-1-oxo-isoindolyl, 2,3-dihydro-benzo[1,4]dioxinyl, 2,3-dihydro-benzofuryl, 2,4-dihydro-3-oxo-pyrazolyl, 2H-benzopyranyl, 2-oxo-benzopyranyl, 2-oxo-pyrrolidinyl, 3,4-dihydro-2H-benzo[1,4]oxazinyl, 3,4-dihydro-2H-benzo[b][1,4]dioxepinyl, 4H-benzo[1,3]dioxinyl, 4H-benzopyranyl, 4-oxo-1,5,6,7-tetrahydro-indolyl, 4-oxo-3,4-dihydro-phthalazinyl, 4-oxo-benzopyranyl, 9,10,10-trioxo-thioxanthenyl, 9H-carbazolyl, 9H-xanthenyl, azetidinyl, benzimidazolyl, benzo[1,3]dioxolyl, benzo[2,1,3]oxadiazolyl, benzo[b]thienyl, benzofuryl, benzothiazolyl, cinnolyl, furyl, imidazo[2,1-b]thiazolyl, imidazolyl, isoxazolyl, morpholino, morpholinyl, oxazolyl, oxolanyl, piperazyl, piperidyl, piridyl, pyrazolo[5,1-b]thiazolyl, pyrazolyl, pyridyl, pyrimidyl, pyrrolidyl, quinolyl, quinoxalyl, thiazolidyl, thiazolyl, thienyl, thiolanyl, 2,3-dihydro-benzofuryl, tetrahydrothienyl, or benzofuranyl;
halogen is fluoro, chloro, bromo, or iodo.

Preferred compounds of this invention are those compounds of Formula I wherein,
Q is Formula II;
$R_1$ represents
(i) $C_1$-$C_{10}$ alkyl,
$C_1$-$C_{10}$ alkyl substituted by substituent(s) independently selected from
halogen,
oxo,
$C_1$-$C_3$ alkoxy,
$C_1$-$C_3$ alkoxy substituted by carbocyclic aryl,
$C_1$-$C_3$ alkylcarbonyloxy,
carbocyclyloxy,
carbocyclic aryloxy,
carbocyclic aryloxy substituted by substituent(s) independently selected from
halogen,
nitro,
$C_1$-$C_4$ alkyl,
$C_1$-$C_4$ alkyl substituted by substituent(s) independently selected from
oxo,
carbocyclic arylcarbonylamino,
halogenated carbocyclic arylcarbonylamino,
heterocyclyloxy,
heterocyclyloxy substituted by $C_1$-$C_3$ alkyl,
substituted heterocyclyl-ethylideneaminooxy,
$C_1$-$C_3$ alkoxycarbonyl,
$C_1$-$C_3$ alkoxycarbonyl substituted by carbocyclic aryl,
mono- or di-$C_1$-$C_3$ alkylaminocarbonyl,
mono- or di-carbocyclic arylamino,
mono- or di-carbocyclic arylamino substituted by hydroxy,
$C_1$-$C_3$ alkylcalbonylamino,
$C_1$-$C_3$ alkylcalbonylamino substituted by substituent(s) independently selected from
$C_1$-$C_3$ alkylcalbonylamino,
carbocyclic arylcalbonylamino,
heterocyclyl,
$C_1$-$C_4$ alkoxycalbonylamino,
heterocyclyl calbonylamino,
carbocyclic arylsulfonylamino,
carbocyclic arylsulfonylamino substituted by substituent(s) independently selected from
nitro,
$C_1$-$C_3$ alkyl,
mono- or di-$C_1$-$C_3$ arylamino, $C_1$-$C_3$ alkylthio,
$C_1$-$C_3$ alkylthio substituted by substituent(s) independently selected from
  mono- or di-carbocyclic arylaminocarbonyl,
  halogenated mono- or di-carbocyclic arylaminocarbonyl,
  carbocyclic aryl,
  carbocyclic aryl substituted by substituent(s) independently selected from
    halogen,
    $C_1$-$C_3$ alkoxy,
carbocyclic arylthio,
carbocyclic arylthio substituted by substituent(s) independently selected from
  halogen,
  $C_1$-$C_3$ alkyl,
carbocyclic arylsulfonyl,
halogenated carbocyclic arylsulfonyl,
heterocyclylthio,
heterocyclylthio substituted by substituent(s) independently selected from
  nitro,
  $C_1$-$C_3$ alkyl,
$C_3$-$C_6$ cycloalkyl,
$C_3$-$C_6$ cycloalkyl substituted by $C_1$-$C_3$ alkyl,
$C_3$-$C_6$ cycloalkenyl,
carbocyclyl,
carbocyclyl substituted by substituent(s) independently selected from
  halogen,
  $C_1$-$C_3$ alkyl,
  $C_1$-$C_3$ alkoxy,
  $C_2$-$C_3$ alkenyl,
  $C_2$-$C_3$ alkenyl substituted by carbocyclic aryl,
  $C_2$-$C_3$ alkenyl substituted by carbocyclic aryl substituted $C_1$-$C_3$ alkylsulfinyl,
carbocyclic aryl,
carbocyclic aryl substituted by substituent(s) independently selected from
  halogen,
  hydroxy,
  nitro,
  $C_1$-$C_4$ alkyl,
  $C_1$-$C_4$ alkyl substituted by substituent(s) independently selected from
    oxo,
    carbocyclic aryl,
    heterocyclyl,
  $C_1$-$C_4$ alkoxy,
  $C_1$-$C_4$ alkoxy substituted by substituent(s) independently selected from
    halogen,
    carbocyclic aryl,
  carbocyclic aryloxy,
  $C_1$-$C_3$ alkylcarbonyloxy,
  mono- or di-carbocyclic arylamino,
  halogenated mono- or di-carbocyclic arylamino,
  mono- or di-carbocyclic arylaminocarbonyl,
  mono- or di-carbocyclic arylaminocarbonyl substituted by substituent(s) independently selected from
    halogen,
    nitro,
    $C_1$-$C_3$ alkyl,
    $C_1$-$C_3$ alkoxy,
    halogenated $C_1$-$C_3$ alkoxy,
  mercapto,
  $C_1$-$C_3$ alkylthio,
  halogenated $C_1$-$C_3$ alkylthio,
  $C_1$-$C_3$ alkylsulfonyl,
  $C_3$-$C_6$ cycloalkyl,
  carbocyclic aryl,
  heterocyclyl,
  heterocyclyl substituted by substituent(s) independently selected from
    hydroxy,
    $C_1$-$C_3$ alkyl,
    $C_1$-$C_3$ alkyl substituted by carbocyclic aryl,
    $C_1$-$C_3$ alkoxy,
    $C_1$-$C_3$ alkoxy substituted by carbocyclic aryl,
    carbocyclic aryl,
    halogenated carbocyclic aryl, (ii) $C_2$-$C_6$ alkenyl, $C_2$-$C_6$ alkenyl substituted by substituent(s) independently selected from
  oxo,
  carbocyclic aryl,
  carbocyclic aryl substituted by substituent(s) independently selected from
    halogen,
    nitro,
    $C_1$-$C_3$ alkyl,
    halogenated $C_1$-$C_3$ alkyl,
    $C_1$-$C_3$ alkoxy,
    halogenated $C_1$-$C_3$ alkoxy,
  heterocyclyl,
  heterocyclyl substituted by substituent(s) independently selected from
    hydroxy,
    $C_1$-$C_3$ alkyl,
    $C_1$-$C_3$ alkoxy, (iii) $C_3$-$C_6$ cycloalkyl, $C_3$-$C_6$ cycloalkyl substituted by substituent(s) independently selected from
  $C_1$-$C_3$ alkyl,
  $C_1$-$C_3$ alkyl substituted by substituent(s) independently selected from
    oxo,
    carbocyclic aryl,
  carbocyclic arylcarbonylamino,
  carbocyclic aryl, (iv) carbocyclyl, carbocyclyl substituted by nitro, (v) carbocyclic aryl, carbocyclic aryl substituted by substituent(s) independently selected from
  halogen,
  hydroxy,
  cyano,
  nitro,
  $C_1$-$C_9$ alkyl,
  $C_1$-$C_9$ alkyl substituted by substituent(s) independently selected from
    halogen,
    oxo,
    carbocyclic aryloxy,
    carbocyclylimino,
    carbocyclylimino substituted by carbocyclic aryl,
    mono- or di-carbocyclic arylaminocarbonyl, mono- or di-carbocyclic arylaminocarbonyl substituted by $C_1$-$C_3$ alkoxy,
carbocyclic aryl,
carbocyclic aryl substituted by substituent(s) independently selected from
  halogen,
  $C_1$-$C_3$ alkyl,
  halogenated $C_1$-$C_3$ alkyl,
  heterocyclyl,
  heterocyclyl substituted by $C_1$-$C_3$ alkyl,
$C_1$-$C_7$ alkoxy,
$C_1$-$C_7$ alkoxy substituted by substituent(s) independently selected from
  halogen,
  carbocyclic aryl,
$C_1$-$C_3$ alkylcarbonyloxy,
carbocyclic aryloxy,
carbocyclic aryloxy substituted by $C_1$-$C_3$ alkoxy,
$C_1$-$C_3$ alkoxycarbonyl,
mono- or di-$C_1$-$C_3$ alkylaminocarbonyl,
mono- or di-$C_1$-$C_3$ alkylaminocarbonyl substituted by carbocyclic aryl,
mono- or di-carbocyclic arylaminocarbonyl,
mono- or di-carbocyclic arylaminocarbonyl substituted by
  $C_1$-$C_3$ alkyl,
amino,
mono- or di-$C_1$-$C_3$ alkylamino,
$C_1$-$C_3$ alkynylcarbonylamino,
$C_1$-$C_3$ alkynylcarbonylamino substituted by carbocyclic aryl,
carbocyclic arylsulfonylamino,
carbocyclic arylsulfonylamino substituted by $C_1$-$C_3$ alkyl,
(carbocyclic aryl)NHC(O)NH,
(carbocyclic aryl)NHC(O)NH substituted by $C_1$-$C_3$ alkoxy,
(carbocyclic aryl)NHC(O)NH substituted by halogenated $C_1$-$C_3$ alkoxy,
$C_1$-$C_3$ alkylthio,
halogenated $C_1$-$C_3$ alkylthio,
carbocyclic arylthio,
carbocyclic arylthio substituted by cyano,
$C_1$-$C_3$ alkylsulfonyl,
mono- or di-$C_1$-$C_3$ alkylaminosulfonyl,
carbocyclic aryl,
carbocyclic aryl substituted by substituent(s) independently selected from
  $C_1$-$C_7$ alkyl,
  halogenated $C_1$-$C_7$ alkyl,
  heterocyclyl,
  heterocyclyl substituted by substituent(s) independently selected from
    $C_1$-$C_3$ alkyl,
    carbocyclic aryl,
    halogenated carbocyclic aryl,
(vi) heterocyclyl,
or heterocyclyl substituted by substituent(s) independently selected from
  halogen,
  nitro,
  $C_1$-$C_4$ alkyl,
  $C_1$-$C_4$ alkyl substituted by substituent(s) independently selected from
    halogen,
    oxo,
    $C_1$-$C_3$ alkylthio,
    $C_1$-$C_3$ alkylthio substituted by carbocyclic aryl,
    $C_1$-$C_3$ alkylthio substituted by halogenated carbocyclic aryl,
    carbocyclic aryl,
    halogenated carbocyclic aryl,
    heterocyclyl,
  $C_1$-$C_3$ alkoxy,
  carbocyclic aryloxy,
  carbocyclic aryloxy substituted by substituent(s) independently selected from
    halogen,
    $C_1$-$C_3$ alkyl,
    $C_1$-$C_3$ alkylthio,
    $C_1$-$C_3$ alkenylthio,
    carbocyclic arylthio,
    $C_1$-$C_3$ alkylsulfonyl,
    carbocyclic arylsulfonyl,
    halogenated carbocyclic arylsulfonyl,
    carbocyclic arylsulfonyl substituted by $C_1$-$C_4$ alkyl,
    carbocyclic aryl,
    carbocyclic aryl substituted by substituent(s) independently selected from
      halogen,
      nitro,
      $C_1$-$C_3$ alkyl,
      $C_1$-$C_3$ alkoxy,
      heterocyclyl,
      heterocyclyl substituted by substituent(s) independently selected from
        $C_1$-$C_3$ alkyl,
        halogenated $C_1$-$C_3$ alkyl;
$R_2$ is —$NHNH_2$, —NHNHBoc, —N($R_{2a}$)($R_{2b}$), morpholino, 4-acetyl-piperazyl, or 4-phenyl-piperazyl;

wherein $R_{2a}$ is H or $C_1$-$C_3$ alkyl;

$R_{2b}$ is $C_1$-$C_4$ alkyl, $C_1$-$C_4$ alkyl substituted by substituent(s) independently selected from
  hydroxy,
  $C_1$-$C_3$ alkoxy,
  amino,
  —NHBoc,
  $C_3$-$C_6$ cycloalkyl,
  carbocyclic aryl,
  carbocyclic aryl substituted by substituent(s) independently selected from
    halogen,
    $C_1$-$C_3$ alkyl,
    $C_1$-$C_3$ alkoxy,
    —$SO_2NH_2$,
  heterocyclyl, $C_3$-$C_6$ cycloalkyl, carbocyclic aryl, carbocyclic aryl substituted by substituent(s) independently selected from
  halogen,
  $C_1$-$C_3$ alkyl,
  $C_1$-$C_3$ alkoxy, or a group of Formula IV;
  wherein Boc is carbamic acid tert-butyl ester and $R_3$ is
    $C_1$-$C_3$ alkyl or $C_1$-$C_3$ alkyl substituted by substituent(s) independently selected from
    carbocyclic aryl,
    halogenated carbocyclic aryl,
    carbocyclic aryl substituted by $C_1$-$C_3$ alkoxy;
  L is selected from Formula V-XIX;
    wherein $R_4$ is H or $C_1$-$C_3$ alkyl;
  $R_5$ is H, $C_1$-$C_3$ alkyl, or $C_1$-$C_3$ alkyl substituted by a substituted carbocyclic aryl;
  Y is —C(O)—;

wherein carbocyclic aryl is phenyl, naphthyl, anthranyl, or biphenyl;

carbocyclyl is 10,11-dihydro-5-oxo-dibenzo[a,d]cycloheptyl, 1-oxo-indanyl, 9H-fluorenyl, 9-oxo-fluorenyl, acenaphthyl, anthraquinonyl, C-fluoren-9-ylidene, indanyl, indenyl, 1,2,3,4-tetrahydro-naphthyl, or bicyclo[2.2.1]hepteny;

heterocyclyl is 1,2,3-thiadiazolyl, 1,2,3-triazolyl, 1,2-dihydro-3-oxo-pyrazolyl, 1,3-dioxo-isoindolyl, 1H-indolyl, 1H-pyrrolyl, 1-oxo-3H-isobenzofuranyl, 2,3-dihydro-benzo[1,4]dioxinyl, 2,3-dihydro-benzofuryl, 2,4-dihydro-3-oxo-pyrazolyl, 2H-benzopyranyl, 2-oxo-benzopyranyl, 2-oxo-pyrrolidinyl, 3,4-dihydro-2H-benzo[b][1,4]dioxepinyl, 4-oxo-1,5,6,7-tetrahydro-indolyl, 4-oxo-3,4-dihydro-phthalazinyl, 4-oxo-benzopyranyl, 9,10,10-trioxo-thioxanthenyl, 9H-xanthenyl, azetidinyl, benzimidazolyl, benzo[1,3]dioxolyl, benzo[2,1,3]oxadiazolyl, benzo[b]thienyl, cinnolyl, furyl, imidazolyl, isoxazolyl, morpholino, morpholinyl, oxazolyl, oxolanyl, piperidyl, piridyl, pyrazolyl, pyridyl, pyrimidyl, pyrrolidyl, quinolyl, quinoxalyl, thiazolidyl, thiazolyl, thienyl, thiolanyl, tetrahydro-thienyl, benzofuranyl, or benzothiazolyl;

halogen is fluoro, chloro, bromo, or iodo.

Other preferred compounds of this invention are those compounds of Formula I wherein, Q is Formula II;

$R_1$ represents (i) $C_1$-$C_{10}$ alkyl, $C_1$-$C_{10}$ alkyl substituted by substituent(s) independently selected from
  oxo,
  di-propylaminocarbonyl,
  methoxy substituted by carbocyclic aryl,
  methylcarbonyloxy,
  carbocyclic aryloxy,
  halogenated carbocyclic aryloxy,
  carbocyclic aryloxy substituted by nitro,
  heterocyclyloxy substituted by methyl,
  substituted heterocyclyl-ethylideneaminooxy,
  tert-butoxycarbonylamino,
  carbocyclic arylcarbonylamino,
  $C_1$-$C_2$ alkylthio,
  $C_1$-$C_2$ alkylthio substituted by substituent(s) independently selected from
    halogenated carbocyclic aryl,
    carbocyclic aryl substituted by methoxy,
  carbocyclic arylthio,
  hetrocyclylthio substituted by nitro,
  hetrocyclylthio substituted by methyl,
  $C_5$-$C_6$ cycloalkyl,
  $C_5$-$C_6$ cycloalkenyl,
  carbocyclyl substituted by substituent(s) independently selected from
    halogen,
    methyl,
    methoxy,
    ethenyl substituted by carbocyclic aryl substituted methylsulfinyl,
  carbocyclic aryl,
  carbocyclic aryl substituted by substituent(s) independently selected from
    halogen,
    hydroxy,
    nitro,
    $C_1$-$C_4$ alkyl,
    $C_1$-$C_4$ alkyl substituted by substituent(s) independently selected from
      oxo,
      carbocyclic aryl,
      heterocyclyl,
    $C_1$-$C_4$ alkoxy,
    halogenated $C_1$-$C_4$ alkoxy,
    $C_1$-$C_4$ alkoxy substituted by carbocyclic aryl,
    carbocyclic aryloxy,
    halogenated mono-carbocyclic arylaminocarbonyl,
    carbocyclic aryl,
    heterocyclyl,
  heterocyclyl,
  heterocyclyl substituted by substituent(s) independently selected from
    $C_1$-$C_2$ alkyl,
    $C_1$-$C_2$ substituted by carbocyclic aryl,
    methoxy,
    methoxy substituted by carbocyclic aryl,
    carbocyclic aryl,
    halogenated carbocyclic aryl, (ii) $C_2$-$C_3$ alkenyl substituted by substituent(s) independently selected from
  carbocyclic aryl,
  halogenated carbocyclic aryl,
  carbocyclic aryl substituted by nitro, (iii) $C_3$-$C_6$ cycloalkyl, $C_3$-$C_6$ cycloalkyl substituted by substituent(s) independently selected from
  methyl substituted by oxo,
  methyl substituted by carbocyclic aryl,
  carbocyclic aryl, (iv) carbocyclyl, (v) carbocyclic aryl, carbocyclic aryl substituted by substituent(s) independently selected from
  halogen,
  hydroxy,
  cyano,
  nitro,
  $C_1$-$C_9$ alkyl,
  $C_1$-$C_9$ alkyl substituted by substituent(s) independently selected from
    halogen,
    oxo,
    carbocyclic aryl,
    carbocyclic aryl substituted by methyl,
    carbocyclic aryloxy,
  $C_1$-$C_7$ alkoxy,
  halogenated $C_1$-$C_7$ alkoxy,
  $C_1$-$C_7$ alkoxy substituted by carbocyclic aryl,
  methylcarbonyloxy,
  carbocyclic aryloxy,
  carbocyclic aryloxy substituted by methoxy,
  amino,
  di-methylamino,
  propargynylcarbonylamino substituted by carbocyclic aryl,
  carbocyclic arylsulfonylamino substituted by methyl,
  (carbocyclic aryl)NHC(O)NH substituted by halogenated methoxy,
  halogenated methylthio,
  carbocyclic arylthio substituted by cyano,
  di-propylamino sulfonyl, mono- or di-ethylaminocarbonyl substituted by carbocyclic aryl,
carbocyclic aryl,
heterocyclyl substituted by methyl,
heterocyclyl substituted by halogenated carbocyclic aryl, (vi) heterocyclyl, or heterocyclyl substituted by substituent(s) independently selected from
  halogen,
  nitro,
  $C_1$-$C_4$ alkyl,
  $C_1$-$C_4$ alkyl substituted by substituent(s) independently selected from
    halogen,
    methylthio substituted by halogenated carbocyclic aryl,
    carbocyclic aryl,
    halogenated carbocyclic aryl,
    heterocyclyl,
  methoxy,
  carbocyclic aryloxy,
  carbocyclic aryloxy substituted by methyl,
  $C_1$-$C_3$ alkylthio,
  propenylthio,
  carbocyclic arylthio,
  $C_1$-$C_3$ alkylsulfonyl,
  carbocyclic arylsulfonyl substituted by $C_1$-$C_4$ alkyl,
  carbocyclic aryl,
  halogenated carbocyclic aryl,
  carbocyclic aryl substituted by methyl,
  carbocyclic aryl substituted by nitro,
  heterocyclyl;
$R_2$ is methylamino or dimethylamino;
L is selected from Formula Va, VIIIa, or IXa;
  wherein $R_4$ and $R_5$ are independently selected from H or $C_1$-$C_3$ alkyl;
  Y is —C(O)—;
  wherein carbocyclic aryl is phenyl, naphthyl, anthranyl, or biphenyl;
  carbocyclyl is 1-oxo-indanyl, 9-oxo-fluorenyl, indenyl, anthraquinonyl, C-fluoren-9-ylidene, 1,2,3,4-tetrahydronaphthyl, or bicyclo[2.2.1]heptenyl;
  heterocyclyl is 1,2,3-thiadiazolyl, 1,2,3-triazolyl, 1,2-dihydro-3-oxo-pyrazolyl, 1,3-dioxo-isoindolyl, 1H-indolyl, 1H-pyrrolyl, 1-oxo-3H-isobenzofuranyl, 2,3-dihydro-benzo[1,4]dioxinyl, 2,4-dihydro-3-oxo-pyrazolyl, 2H-benzopyranyl, 2-oxo-benzopyranyl, 3,4-dihydro-2H-benzo[b][1,4]dioxepinyl, 4-oxo-3,4-dihydro-phthalazinyl, 4-oxobenzopyranyl, 9,10,10-trioxo-thioxanthenyl, 9H-xanthenyl, azetidinyl, benzimidazolyl, benzo[1,3]dioxolyl, benzo[2,1,3]oxadiazolyl, benzo[b]thienyl, furyl, imidazolyl, isoxazolyl, morpholino, morpholinyl, oxolanyl, piperidyl, piridyl, pyrazolyl, pyridyl, quinolyl, quinoxalyl, thiazolidyl, thiazolyl, thienyl, thiolanyl, 2,3-dihydro-1-oxo-isoindolyl, 2,3-dihydro-benzofuryl, 2-oxo-pyrrolidinyl, 4-oxo-1,5,6,7-tetrahydro-indolyl, cinnolyl, pyrimidyl, pyrrolidyl, tetrahydro-thienyl, benzofuranyl, or benzothiazolyl;
  halogen is fluoro, chloro, bromo, or iodo.

Other more preferred compounds of this invention are those compounds of Formula I wherein,
Q is Formula II;
$R_1$ represents (i) $C_1$-$C_{10}$ alkyl substituted by substituent(s) independently selected from
  oxo,
  di-propylaminocarbonyl,
  methoxy substituted by carbocyclic aryl,
  methylcarbonyloxy,
  carbocyclic aryloxy,
  halogenated carbocyclic aryloxy,
  carbocyclic aryloxy substituted by nitro,
  heterocyclyloxy substituted by methyl,
  substituted heterocyclyl-ethylideneaminooxy,
  tert-butoxycarbonylamino,
  carbocyclic arylcarbonylamino,
  $C_1$-$C_2$ alkylthio,
  $C_1$-$C_2$ alkylthio substituted by substituent(s) independently selected from
    halogenated carbocyclic aryl,
    carbocyclic aryl substituted by methoxy,
  carbocyclic arylthio,
  hetrocyclylthio substituted by nitro,
  hetrocyclylthio substituted by methyl,
  $C_5$-$C_6$ cycloalkenyl,
  carbocyclyl substituted by substituent(s) independently selected from
    halogen,
    methyl,
    methoxy,
    ethenyl substituted by carbocyclic aryl substituted methylsulfinyl,
  carbocyclic aryl substituted by substituent(s) independently selected from
    halogen,
    hydroxy,
    nitro,
    $C_1$-$C_4$ alkyl,
    $C_1$-$C_4$ alkyl substituted by substituent(s) independently selected from
      oxo,
      carbocyclic aryl,
      heterocyclyl,
    $C_1$-$C_4$ alkoxy,
    halogenated $C_1$-$C_4$ alkoxy,
    $C_1$-$C_4$ alkoxy substituted by carbocyclic aryl,
    carbocyclic aryloxy,
    halogenated mono-carbocyclic arylaminocarbonyl,
    carbocyclic aryl,
    heterocyclyl,
  heterocyclyl substituted by substituent(s) independently selected from
    $C_1$-$C_2$ alkyl,
    $C_1$-$C_2$ substituted by carbocyclic aryl,
    methoxy,
    methoxy substituted by carbocyclic aryl,
    carbocyclic aryl,
    halogenated carbocyclic aryl, (ii) $C_2$-$C_3$ alkenyl substituted by substituent(s) independently selected from
  carbocyclic aryl,
  halogenated carbocyclic aryl,
  carbocyclic aryl substituted by nitro, (iii) $C_3$-$C_6$ cycloalkyl substituted by substituent(s) independently selected from
  methyl substituted by oxo,
  methyl substituted by carbocyclic aryl,
  carbocyclic aryl, (iv) carbocyclyl, (v) carbocyclic aryl substituted by substituent(s) independently selected from
  halogen, hydroxy,
cyano,
nitro,
$C_1$-$C_9$ alkyl,
$C_1$-$C_9$ alkyl substituted by substituent(s) independently selected from
halogen,
oxo,
carbocyclic aryl,
carbocyclic aryl substituted by methyl,
carbocyclic aryloxy,
$C_1$-$C_7$ alkoxy,
halogenated $C_1$-$C_7$ alkoxy,
$C_1$-$C_7$ alkoxy substituted by carbocyclic aryl,
methylcarbonyloxy,
carbocyclic aryloxy,
carbocyclic aryloxy substituted by methoxy,
amino,
di-methylamino,
propargynylcarbonylamino substituted by carbocyclic aryl,
carbocyclic arylsulfonylamino substituted by methyl,
(carbocyclic aryl)NHC(O)NH substituted by halogenated methoxy,
halogenated methylthio,
carbocyclic arylthio substituted by cyano,
di-propylamino sulfonyl,
mono- or di-ethylaminocarbonyl substituted by carbocyclic aryl,
carbocyclic aryl,
heterocyclyl substituted by methyl,
heterocyclyl substituted by halogenated carbocyclic aryl, (vi) or heterocyclyl substituted by substituent(s) independently selected from
halogen,
nitro,
$C_1$-$C_4$ alkyl,
$C_1$-$C_4$ alkyl substituted by substituent(s) independently selected from
halogen,
methylthio substituted by halogenated carbocyclic aryl,
carbocyclic aryl,
halogenated carbocyclic aryl,
heterocyclyl,
methoxy,
carbocyclic aryloxy,
carbocyclic aryloxy substituted by methyl,
$C_1$-$C_3$ alkylthio,
propenylthio,
carbocyclic arylthio,
$C_1$-$C_3$ alkylsulfonyl,
carbocyclic arylsulfonyl,
carbocyclic arylsulfonyl substituted by $C_1$-$C_4$ alkyl,
carbocyclic aryl,
halogenated carbocyclic aryl,
carbocyclic aryl substituted by methyl,
carbocyclic aryl substituted by nitro,
heterocyclyl;

$R_2$ is methylamino or dimethylamino;
L is selected from Formula XX-XXII;

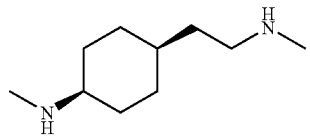

XX

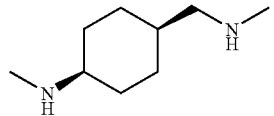

XXI

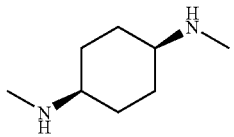

XXII

Y is —C(O)—;
wherein carbocyclic aryl is phenyl, naphthyl, or biphenyl;
carbocyclyl is 1-oxo-indanyl, 9-oxo-fluorenyl, indenyl, anthraquinonyl, C-fluoren-9-ylidene, 1,2,3,4-tetrahydronaphthyl, or bicyclo[2.2.1]hepteny;
heterocyclyl is 1,2,3-thiadiazolyl, 1,2,3-triazolyl, 1,2-dihydro-3-oxo-pyrazolyl, 1H-indolyl, 1H-pyrrolyl, 2,4-dihydro-3-oxo-pyrazolyl, 2H-benzopyranyl, 4-oxo-benzopyranyl, azetidinyl, benzo[b]thienyl, furyl, isoxazolyl, morpholinyl, piperidyl, piridyl, pyrazolyl, pyridyl, quinolyl, thiazolidyl, thiazolyl, thienyl, thiolanyl, 2,3-dihydro-1-oxo-isoindolyl, 2,3-dihydro-benzofuryl, 2-oxo-benzopyranyl, 2-oxo-pyrrolidinyl, 4-oxo-1,5,6,7-tetrahydro-indolyl, 9H-xanthenyl, cinnolyl, imidazolyl, morpholino, pyrimidyl, pyrrolidyl, tetrahydro-thienyl, benzofuranyl, or benzothiazolyl;
halogen is fluoro, chloro, bromo, or iodo.

Further other more preferred compounds of this invention are those compounds of Formula I wherein,
Q is Formula II;
$R_1$ represents (i) $C_1$-$C_5$ alkyl substituted by substituent(s) independently selected from
oxo,
di-propylaminocarbonyl,
methoxy substituted by carbocyclic aryl,
methylcarbonyloxy,
carbocyclic aryloxy,
halogenated carbocyclic aryloxy,
carbocyclic aryloxy substituted by nitro,
heterocyclyloxy substituted by methyl,
substituted heterocyclyl-ethylideneaminooxy,
tert-butoxycarbonylamino,
carbocyclic arylcarbonylamino,
$C_1$-$C_2$ alkylthio,
$C_1$-$C_2$ alkylthio substituted by substituent(s) independently selected from
halogenated carbocyclic aryl,
carbocyclic aryl substituted by methoxy, carbocyclic arylthio,
hetrocyclylthio substituted by nitro,
hetrocyclylthio substituted by methyl,
cyclohexenyl,
carbocyclyl substituted by substituent(s) independently selected from
  halogen,
  methyl,
  methoxy,
  ethenyl substituted by carbocyclic aryl substituted methylsulfinyl,
carbocyclic aryl substituted by substituent(s) independently selected from
  halogen,
  hydroxy,
  nitro,
  $C_1$-$C_4$ alkyl,
  $C_1$-$C_4$ alkyl substituted by substituent(s) independently selected from
    oxo,
    carbocyclic aryl,
    heterocyclyl,
  $C_1$-$C_2$ alkoxy,
  halogenated $C_1$-$C_2$ alkoxy,
  $C_1$-$C_2$ alkoxy substituted by carbocyclic aryl,
  carbocyclic aryloxy,
  halogenated mono-carbocyclic arylaminocarbonyl,
  carbocyclic aryl,
  heterocyclyl,
heterocyclyl substituted by substituent(s) independently selected from
  $C_1$-$C_2$ alkyl,
  $C_1$-$C_2$ substituted by carbocyclic aryl,
  methoxy,
  methoxy substituted by carbocyclic aryl,
  carbocyclic aryl,
  halogenated carbocyclic aryl, (ii) $C_2$-$C_3$ alkenyl substituted by substituent(s) independently selected from
  carbocyclic aryl,
  halogenated carbocyclic aryl,
  carbocyclic aryl substituted by nitro, (iii) $C_3$-$C_6$ cycloalkyl substituted by substituent(s) independently selected from
  methyl substituted by oxo,
  methyl substituted by carbocyclic aryl,
  carbocyclic aryl, (iv) carbocyclyl, (v) carbocyclic aryl substituted by substituent(s) independently selected from
  halogen,
  hydroxy,
  cyano,
  nitro,
  $C_1$-$C_4$ alkyl,
  $C_1$-$C_2$ alkyl substituted by substituent(s) independently selected from
    halogen,
    oxo,
    carbocyclic aryl,
    carbocyclic aryl substituted by methyl,
    carbocyclic aryloxy,
  $C_1$-$C_2$ alkoxy,
  halogenated $C_1$-$C_2$ alkoxy,
  $C_1$-$C_2$ alkoxy substituted by carbocyclic aryl,
  methylcarbonyloxy,
  carbocyclic aryloxy,
  carbocyclic aryloxy substituted by methoxy,
  amino,
  di-methylamino,
  propargynylcarbonylamino substituted by carbocyclic aryl,
  carbocyclic arylsulfonylamino substituted by methyl,
  (carbocyclic aryl)NHC(O)NH substituted by halogenated methoxy,
  halogenated methylthio,
  carbocyclic arylthio substituted by cyano,
  di-propylamino sulfonyl,
  mono- or di-ethylaminocarbonyl substituted by carbocyclic aryl,
  carbocyclic aryl,
  heterocyclyl substituted by methyl,
  heterocyclyl substituted by halogenated carbocyclic aryl,
(vi) or heterocyclyl substituted by substituent(s) independently selected from
  halogen,
  nitro,
  $C_1$-$C_4$ alkyl,
  $C_1$-$C_4$ alkyl substituted by substituent(s) independently selected from
    halogen,
    methylthio substituted by halogenated carbocyclic aryl,
    carbocyclic aryl,
    halogenated carbocyclic aryl,
    heterocyclyl,
  methoxy,
  carbocyclic aryloxy,
  carbocyclic aryloxy substituted by methyl,
  $C_1$-$C_3$ alkylthio,
  propenylthio,
  carbocyclic arylthio,
  $C_1$-$C_3$ alkylsulfonyl,
  carbocyclic arylsulfonyl,
  carbocyclic arylsulfonyl substituted by methyl,
  carbocyclic aryl,
  halogenated carbocyclic aryl,
  carbocyclic aryl substituted by methyl,
  carbocyclic aryl substituted by nitro,
  heterocyclyl;
$R_2$ is methylamino or dimethylamino;
L is selected from Formula XX-XXII;
Y is —C(O)—;
wherein carbocyclic aryl is phenyl, naphthyl, or biphenyl;
carbocyclyl is 1-oxo-indanyl, indenyl, 9-oxo-fluorenyl, 1,2,3,4-tetrahydro-naphthyl, or bicyclo[2.2.1]hepteny;
heterocyclyl is 1H-indolyl, 2,4-dihydro-3-oxo-pyrazolyl, furyl, pyrazolyl, pyridyl, thienyl, 1,2,3-triazolyl, 1H-pyrrolyl, 2,3-dihydro-1-oxo-isoindolyl, 2,3-dihydro-benzofuryl, 2H-benzopyranyl, 2-oxo-benzopyranyl, 4-oxo-1,5,6,7-tetrahydro-indolyl, imidazolyl, isoxazolyl, morpholino, morpholinyl, pyrazolyl, pyrimidyl, quinolyl, thiazolyl, tetrahydro-thienyl, benzofuranyl, or benzothiazolyl;
halogen is fluoro, chloro, bromo, or iodo.

The following compounds are specially preffered;
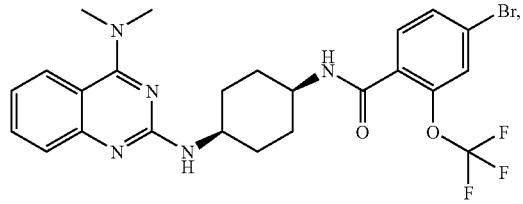
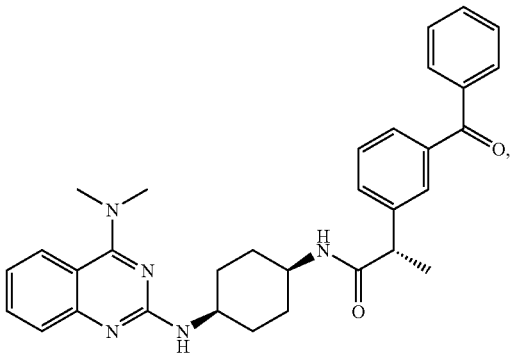
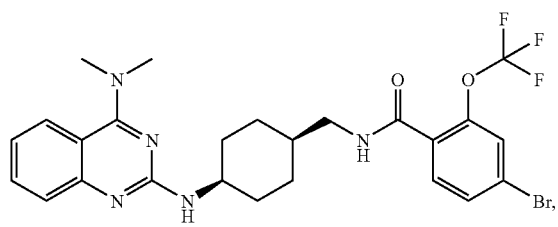
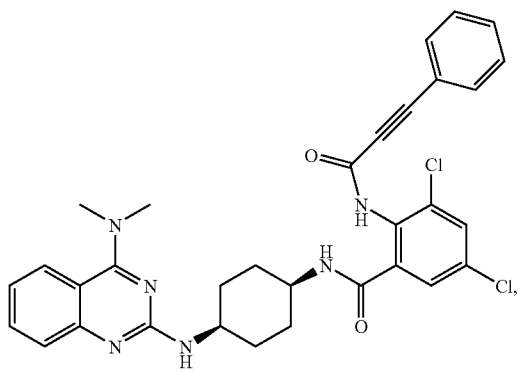
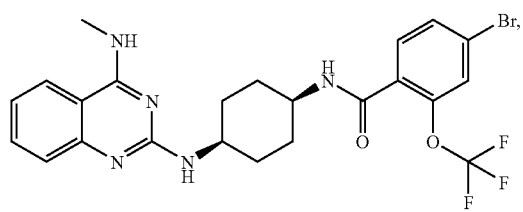
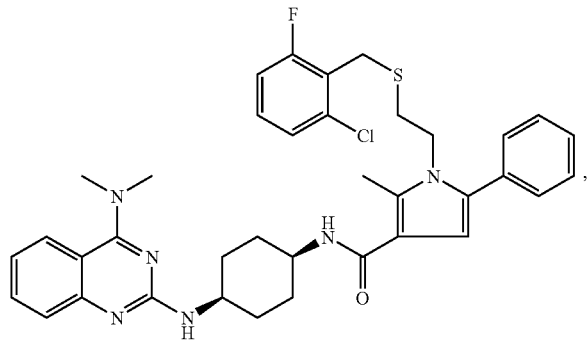
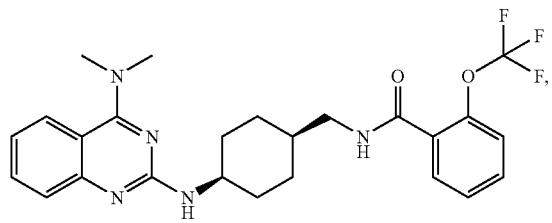
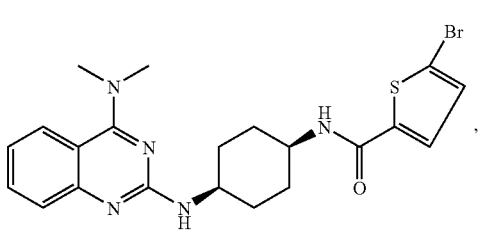

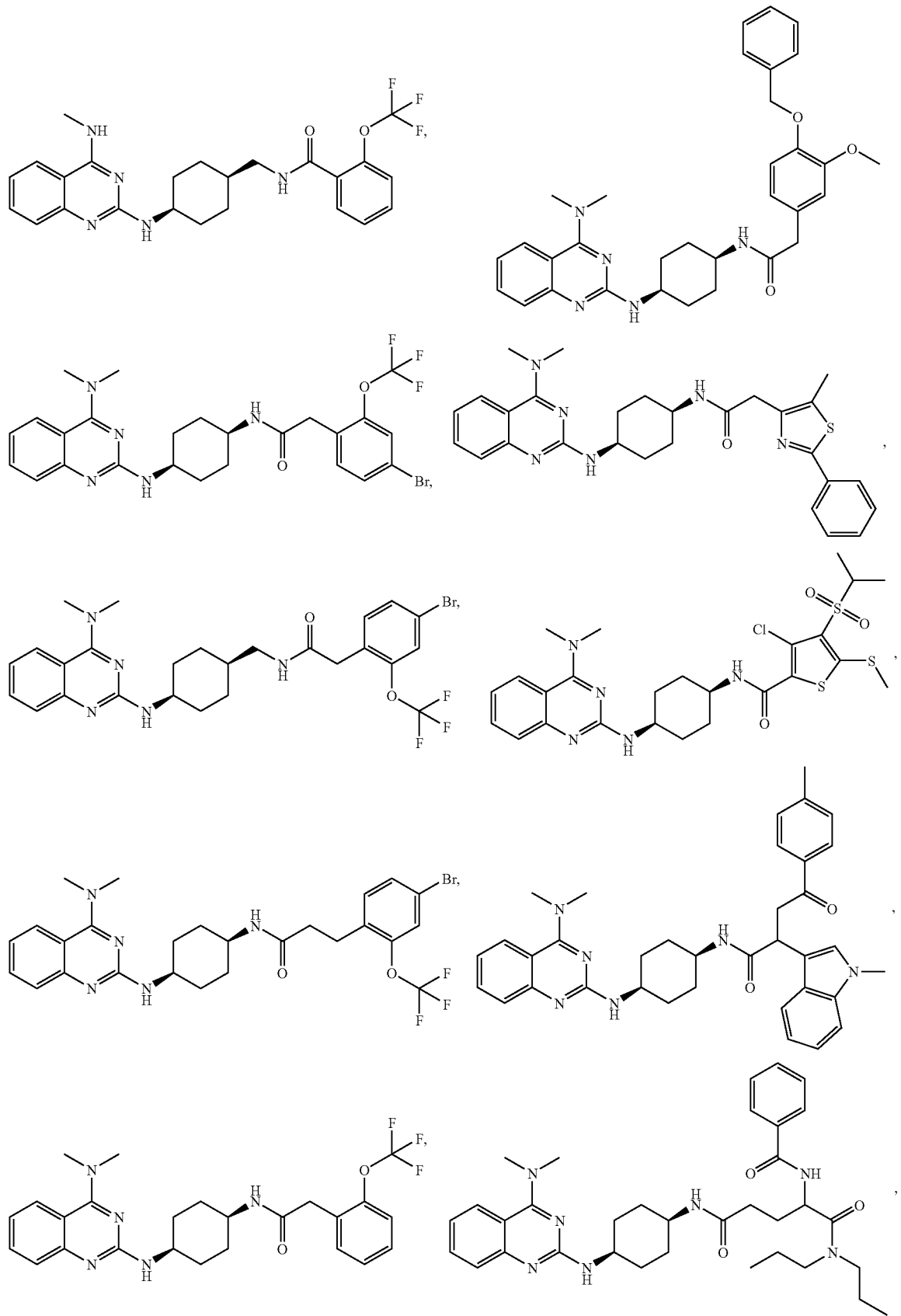

-continued
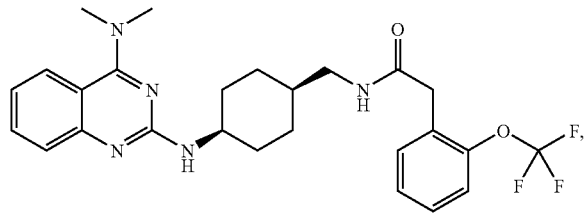
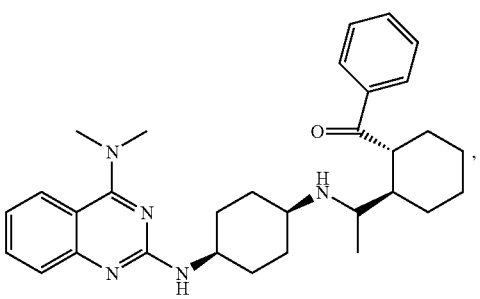
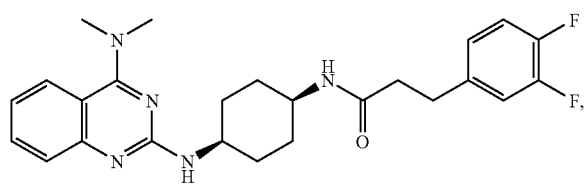
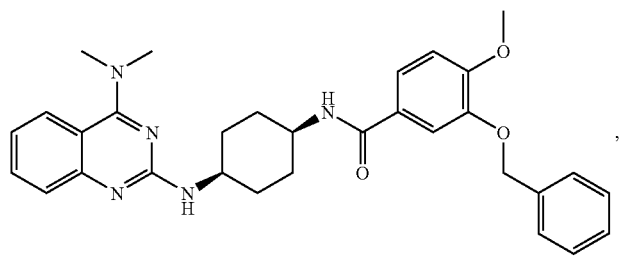
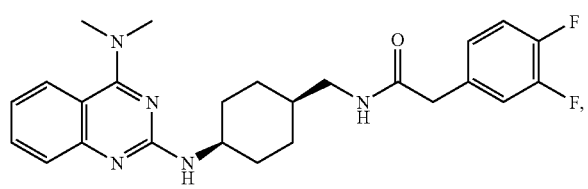
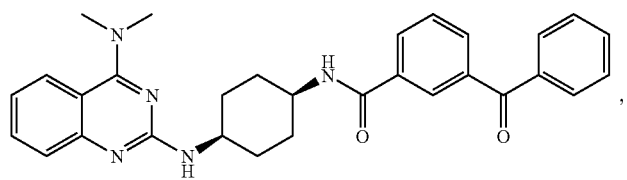
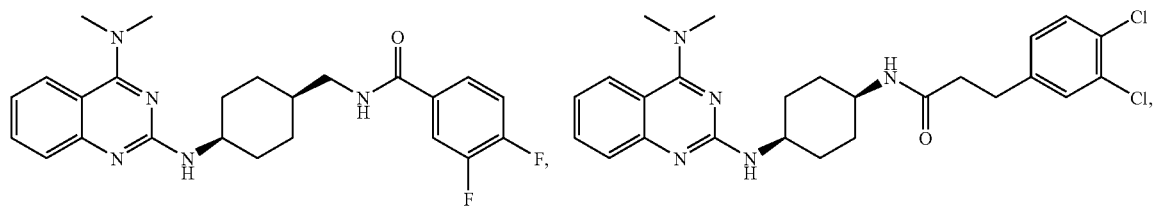
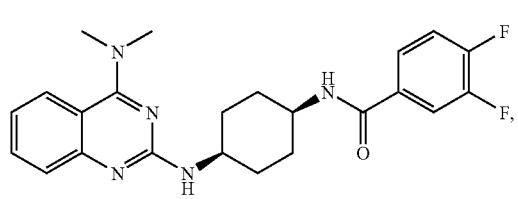
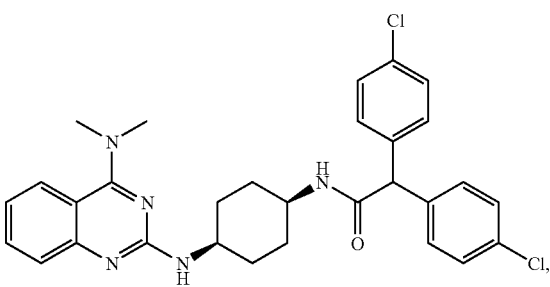

-continued
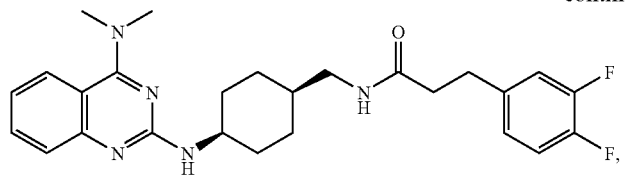
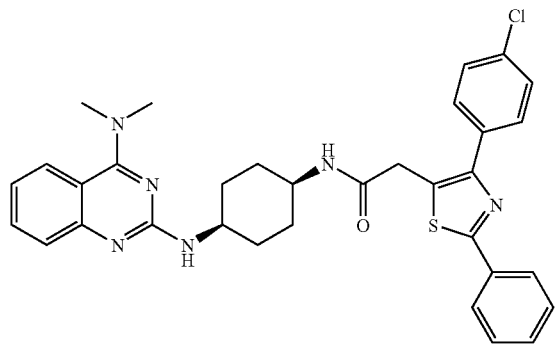
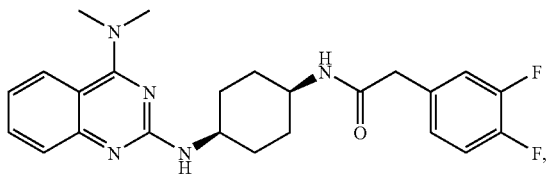
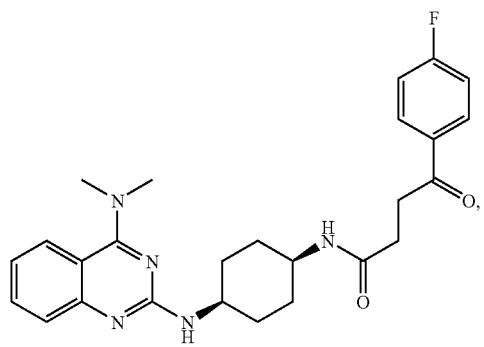
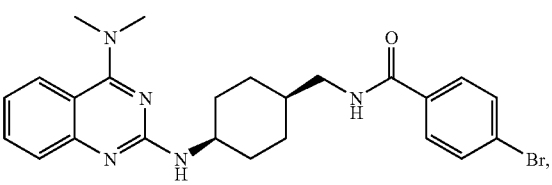
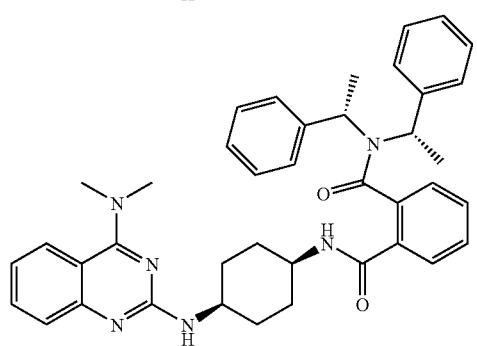
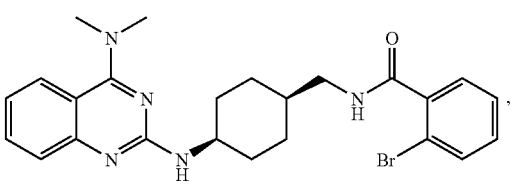
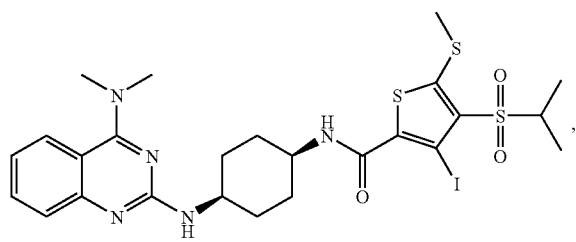
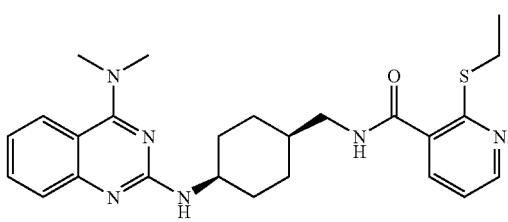
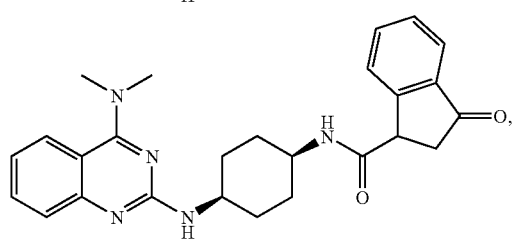
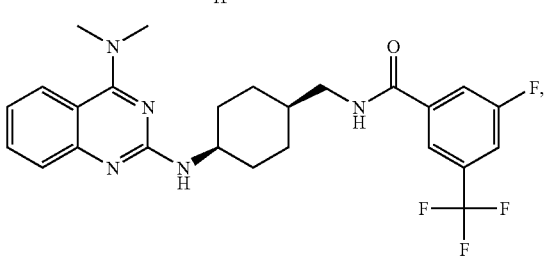

-continued
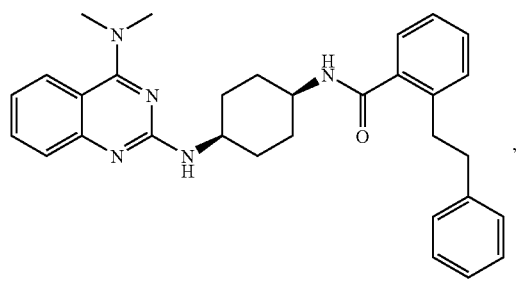
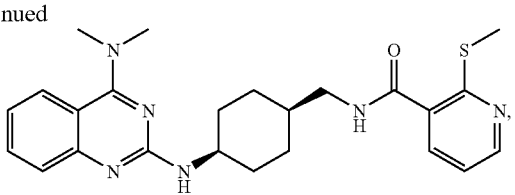
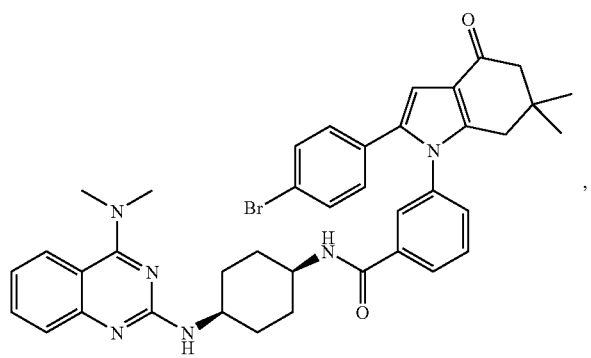
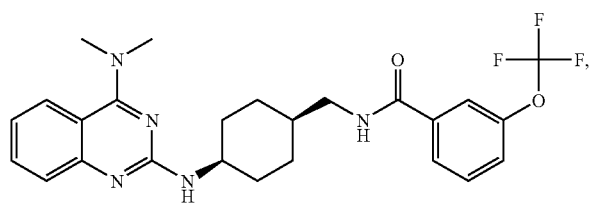
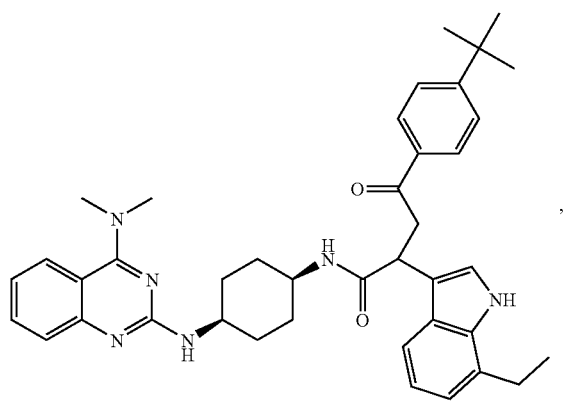
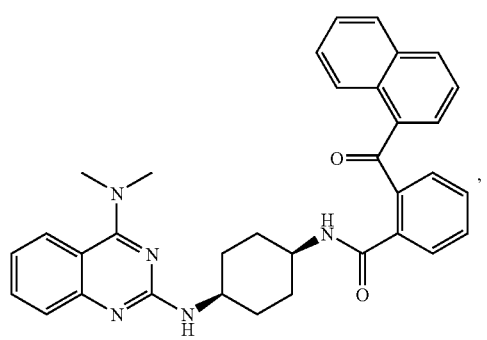
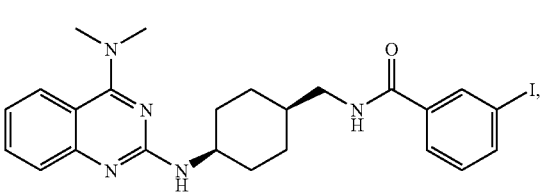

-continued
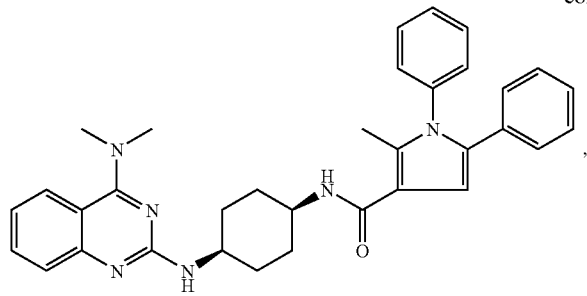
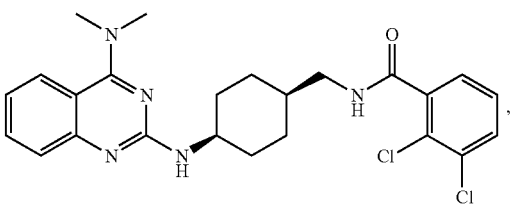
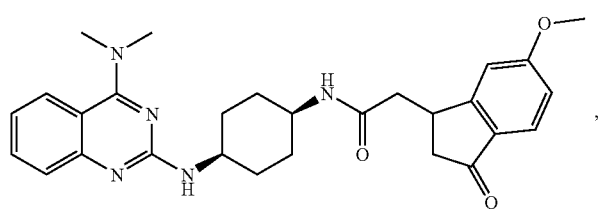
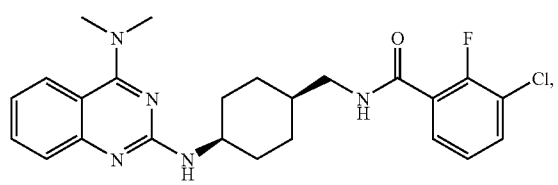
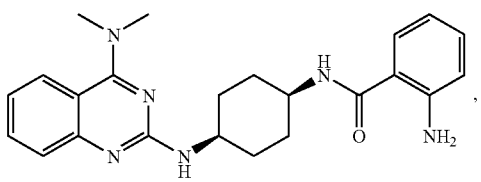
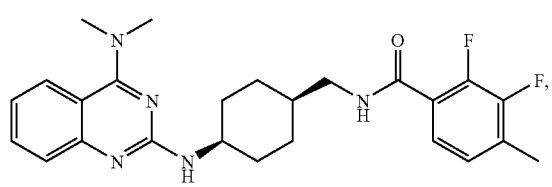
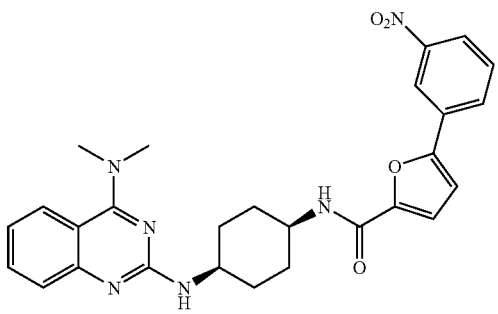
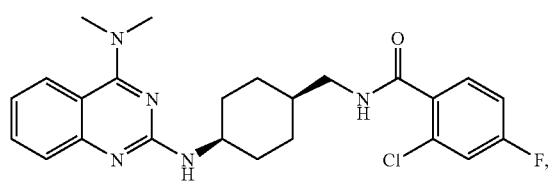
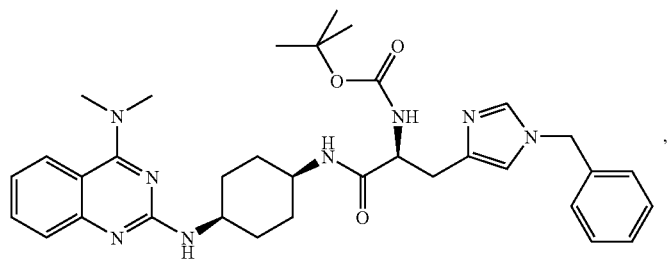

-continued
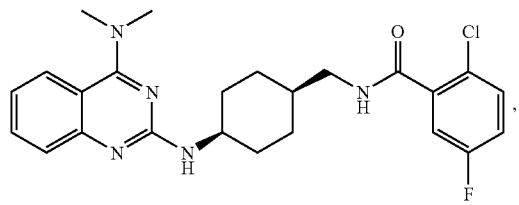
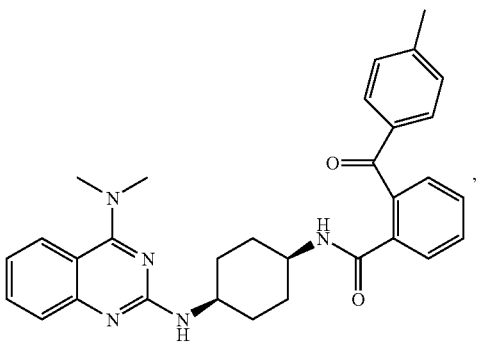
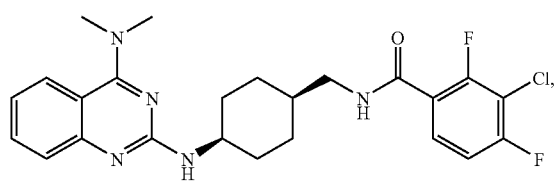
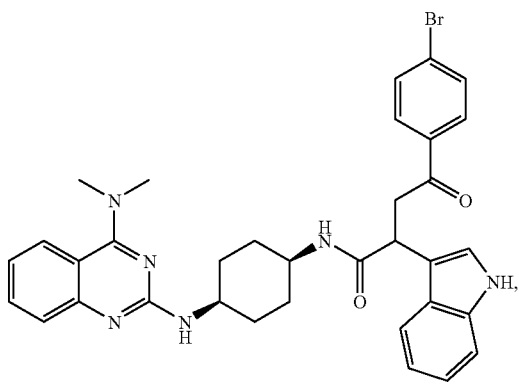
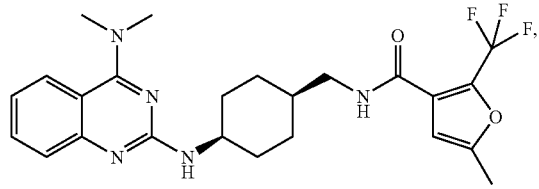
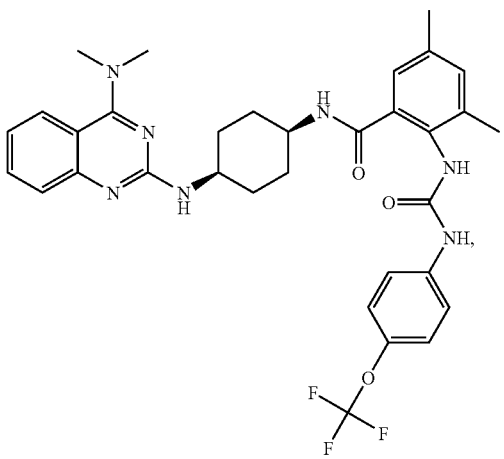
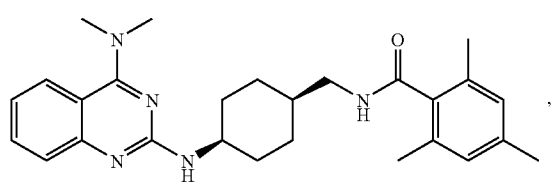
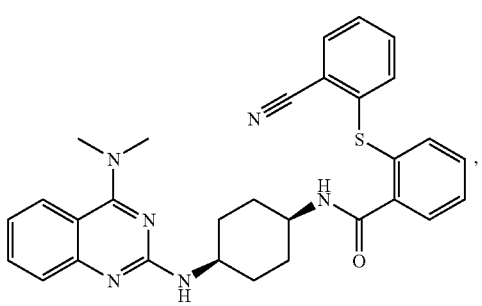

181
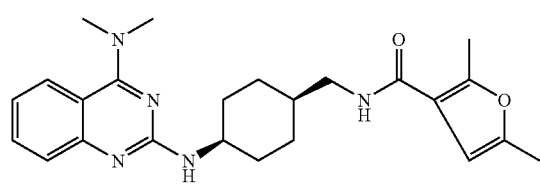
182
-continued
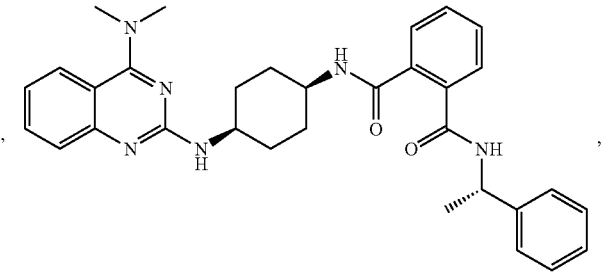
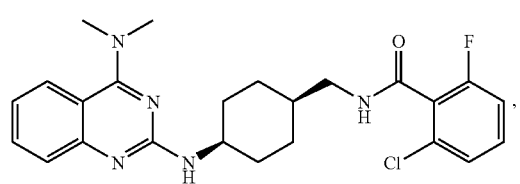
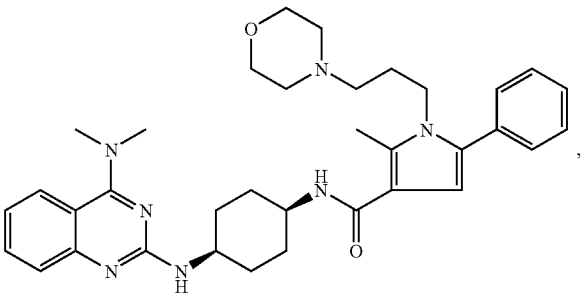
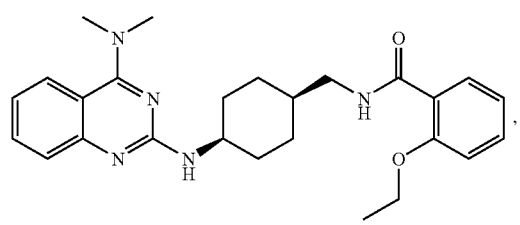
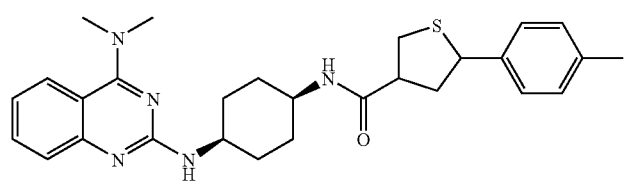
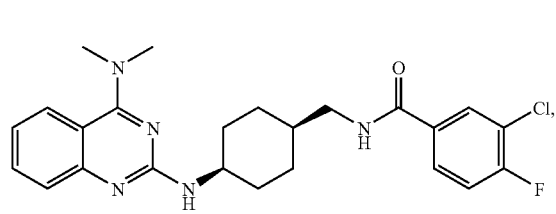
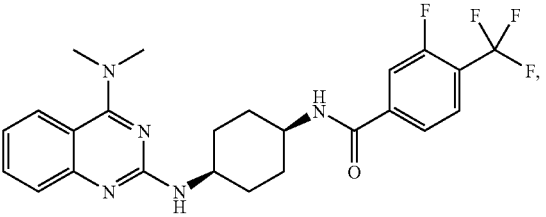
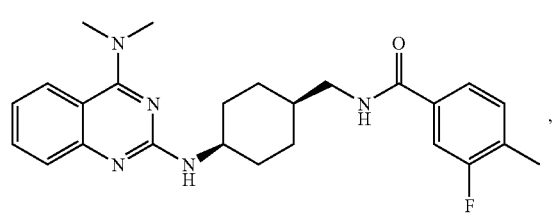
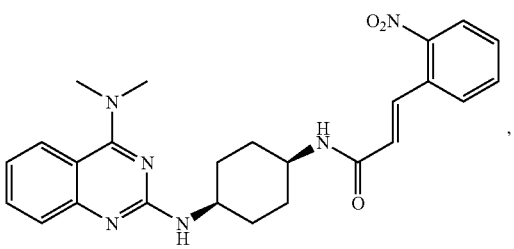
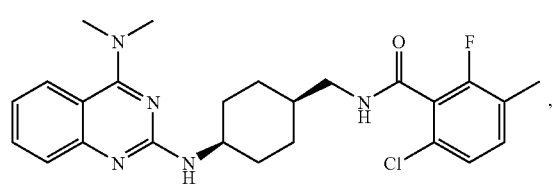

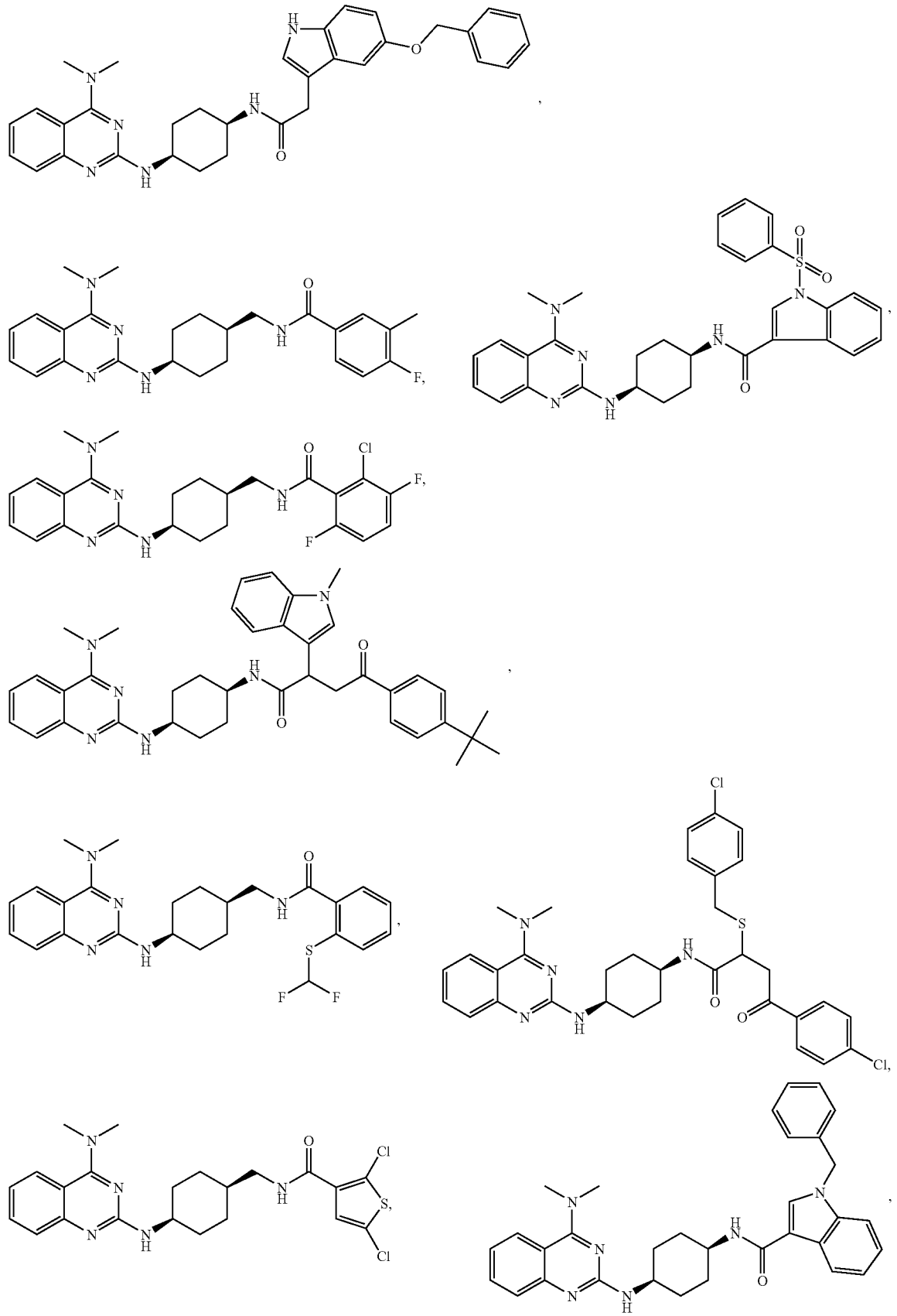

-continued
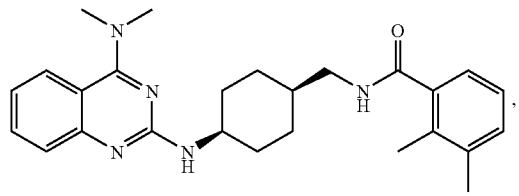
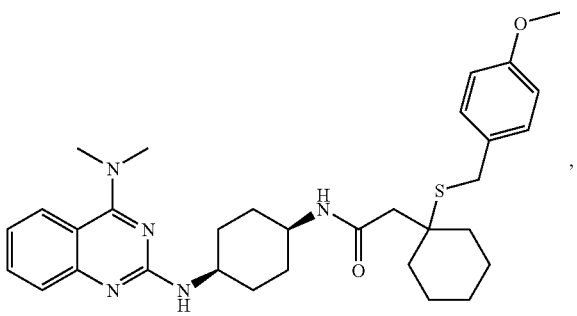
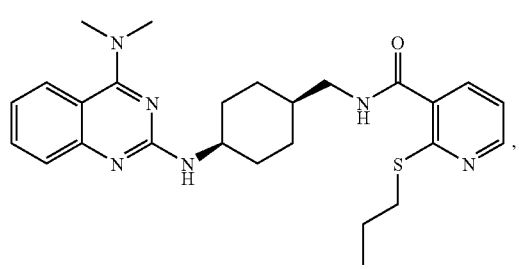
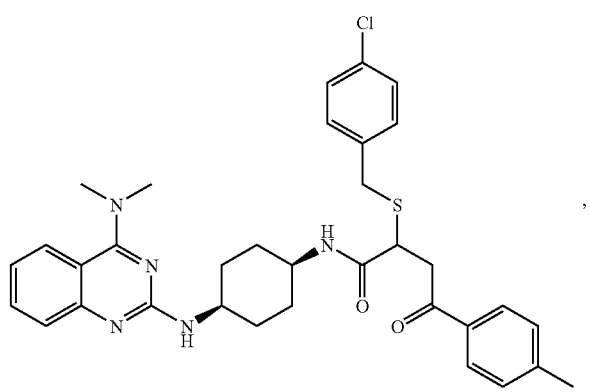
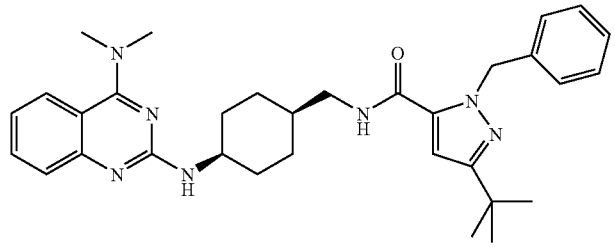
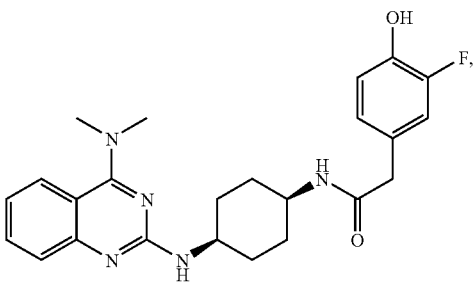
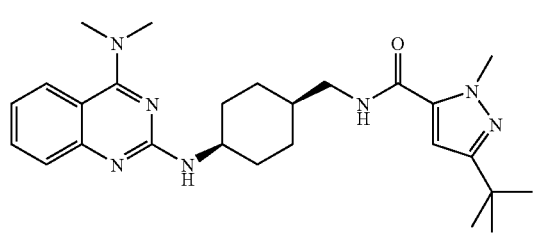
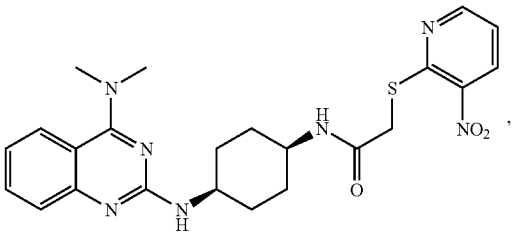
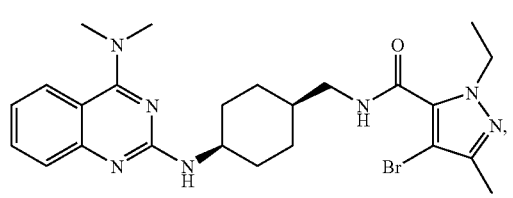
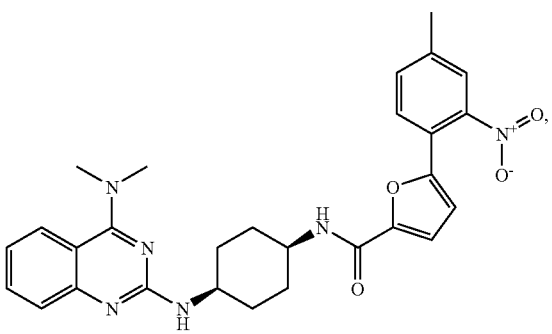

187
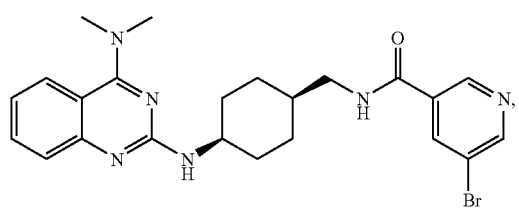
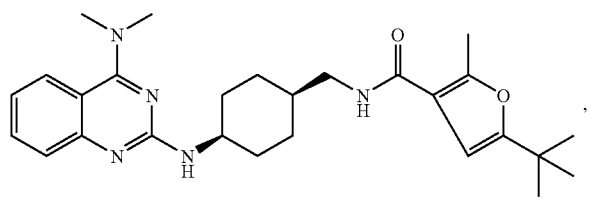
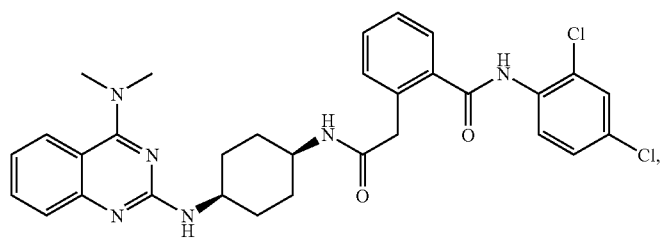
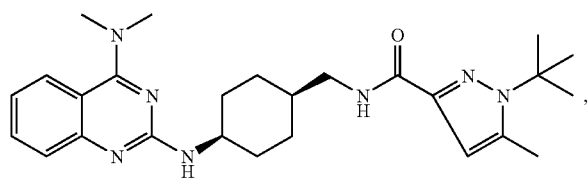
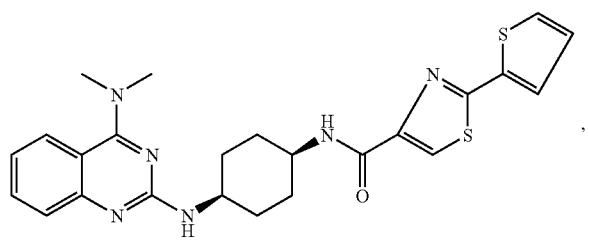
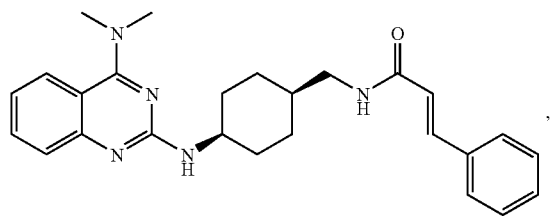
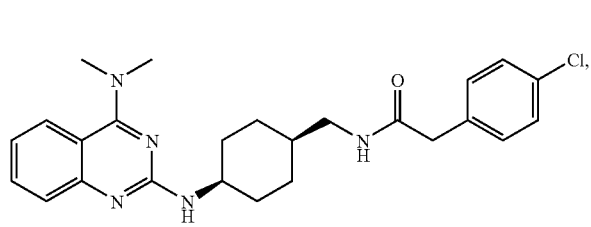
188
-continued
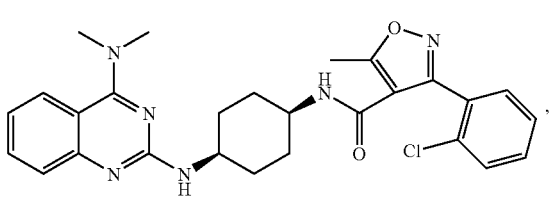
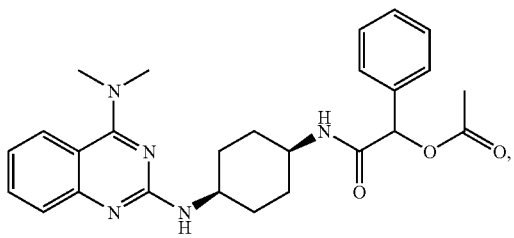

-continued
| 189 | 190 |
|---|---|
| 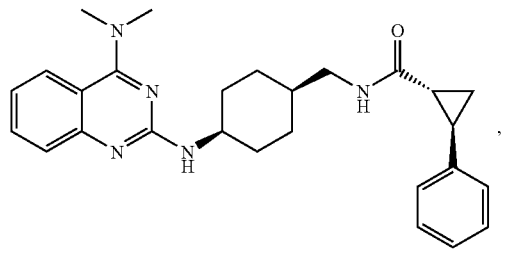 | 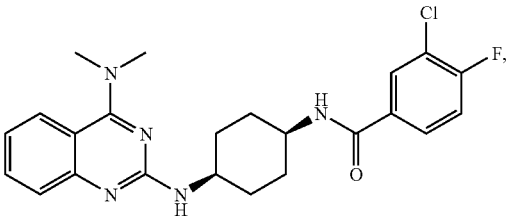 |
| 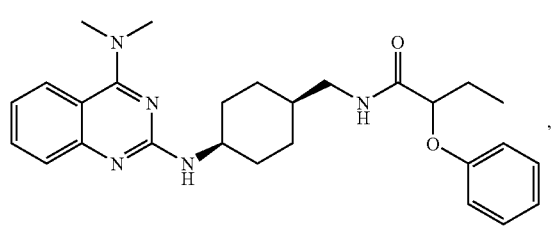 |  |
| 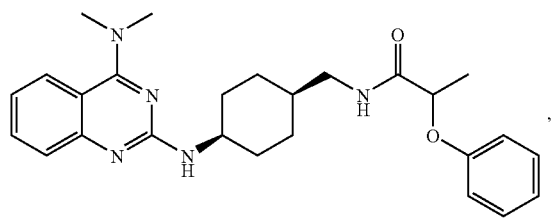 | 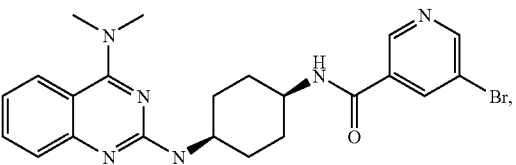 |
| 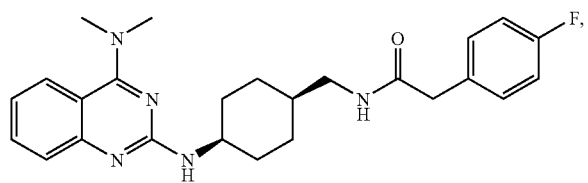 |  |
| 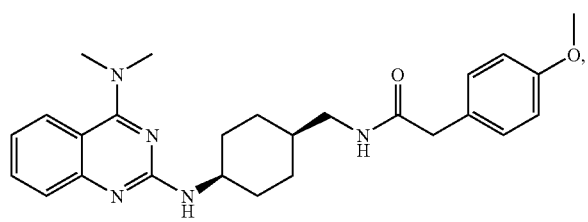 | 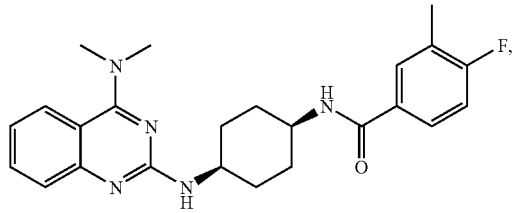 |
| 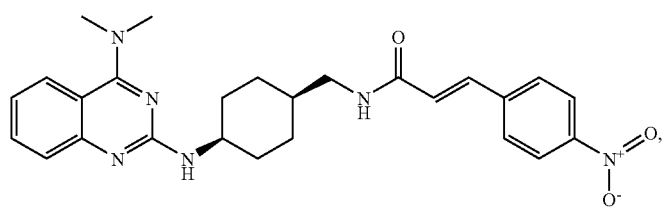 | |

-continued
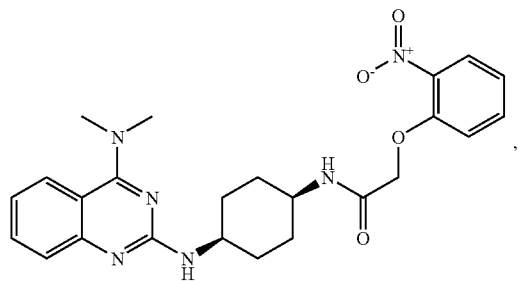
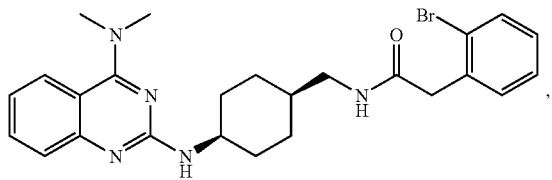
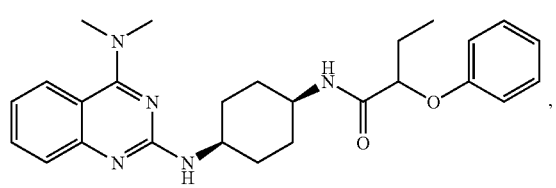
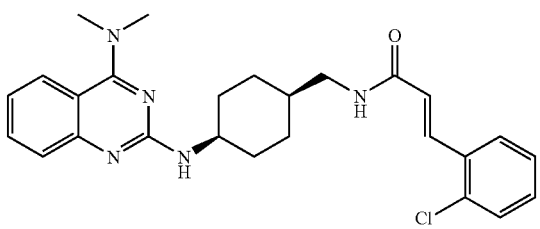
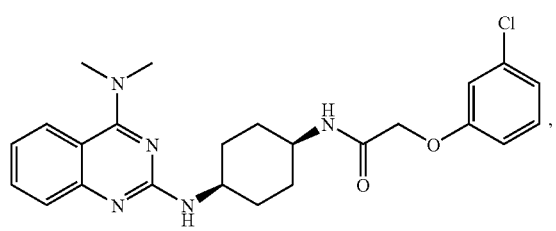
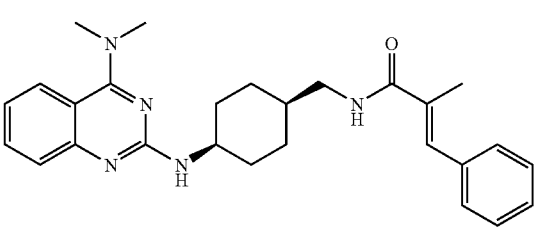
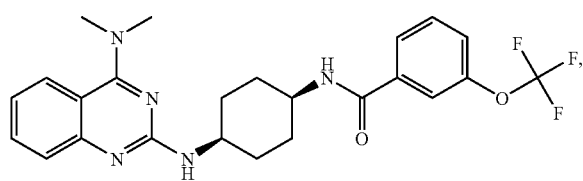
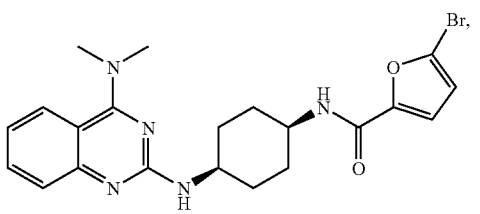
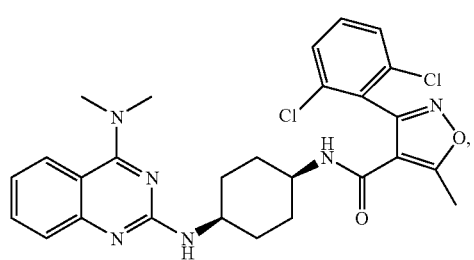
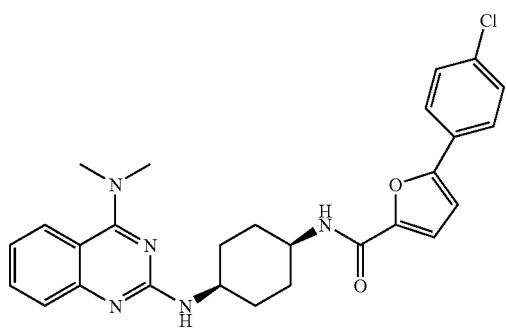
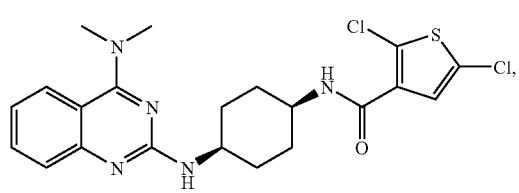
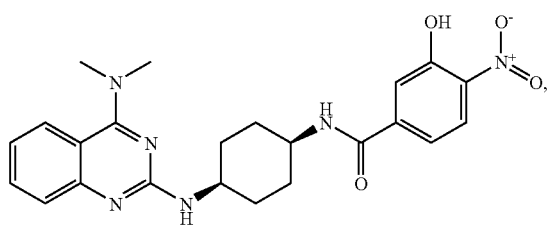

-continued
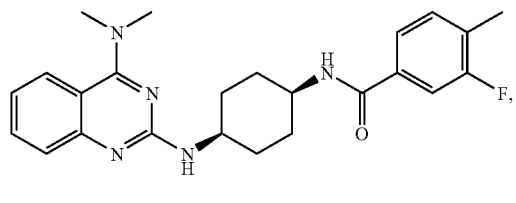
,
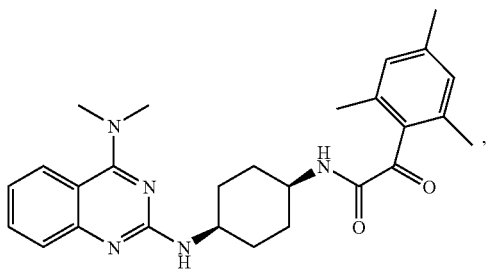
,
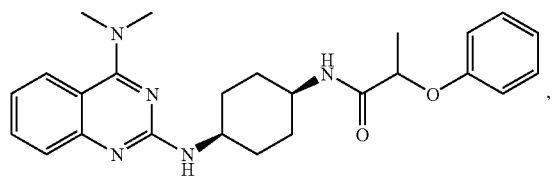
,
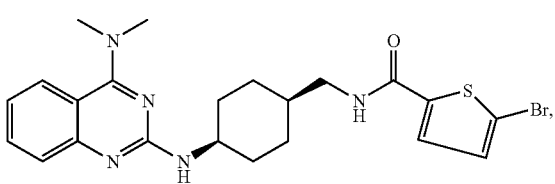
,
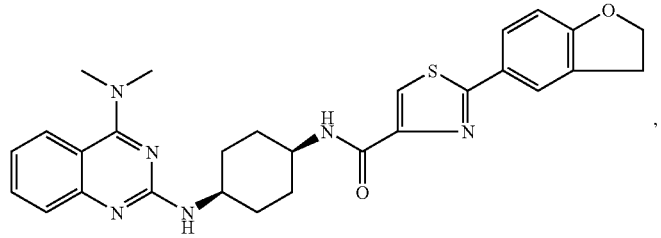
,
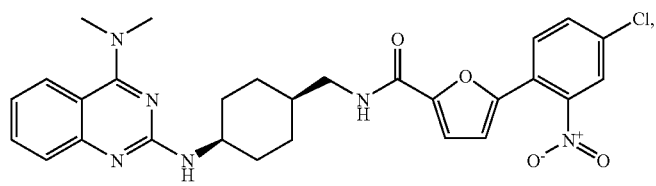
,
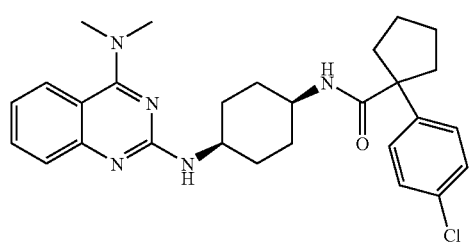
,
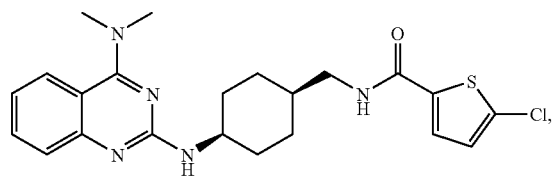
,
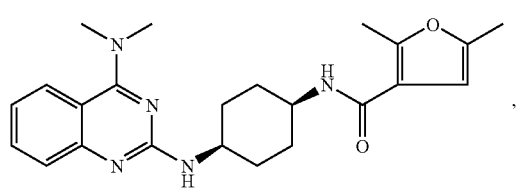
,
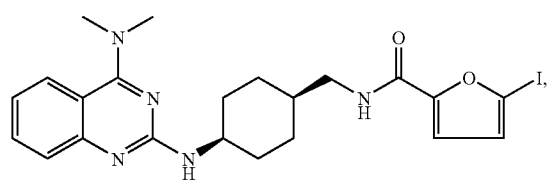
,
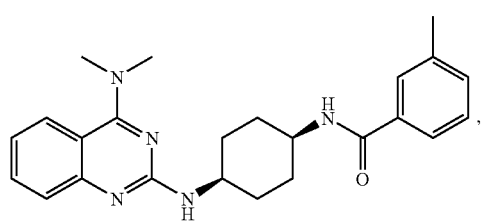
,
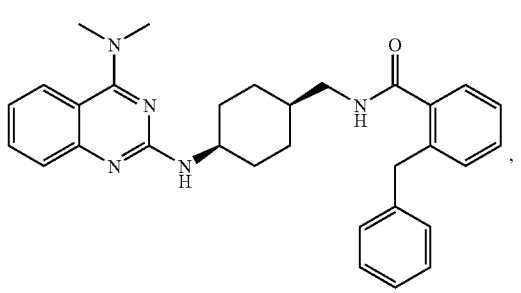
,

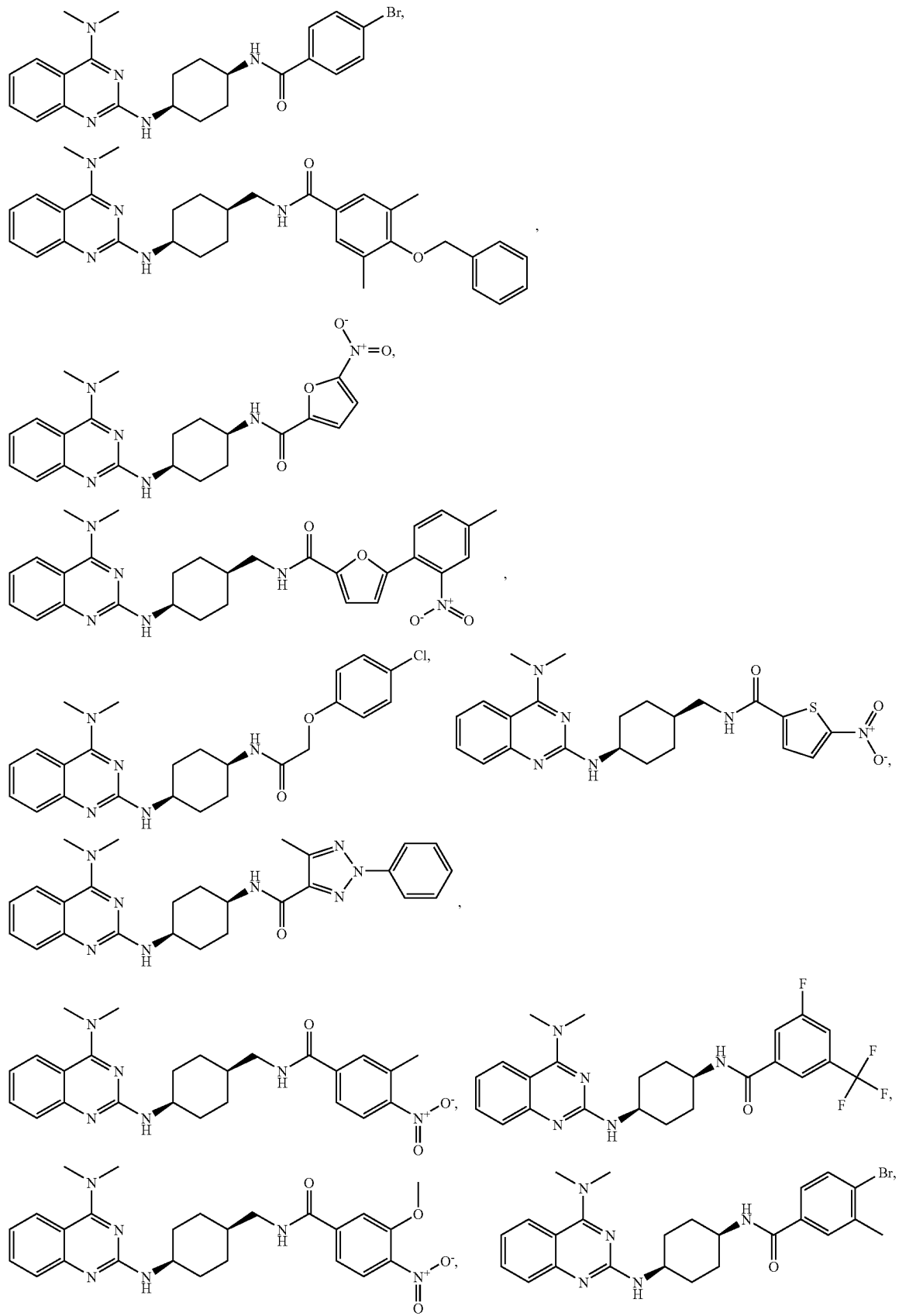

-continued
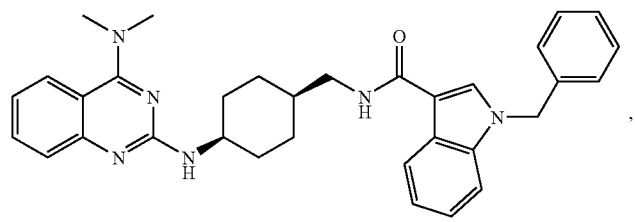
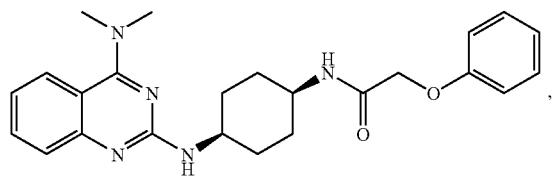
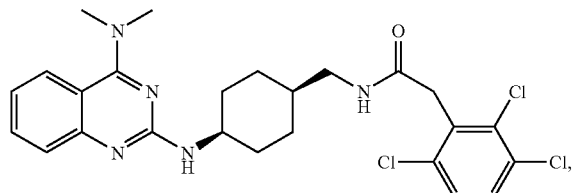
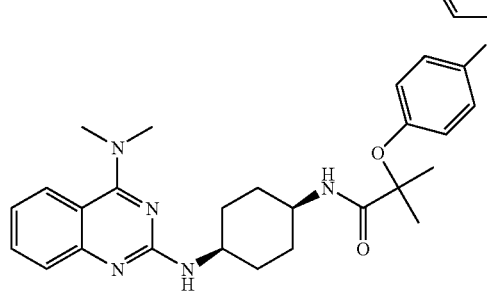
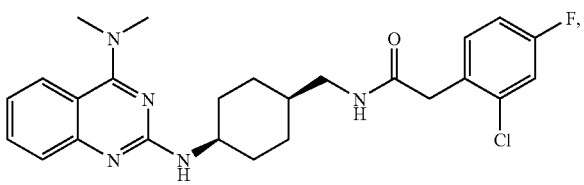
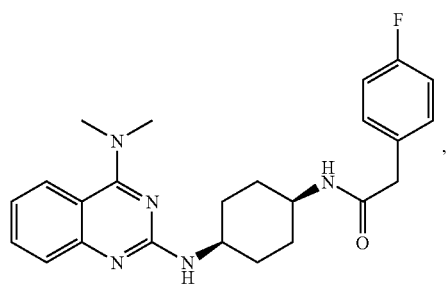
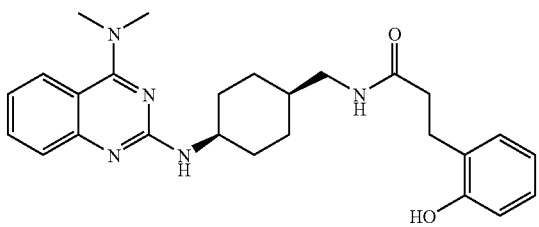
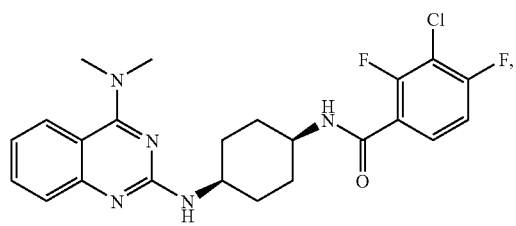
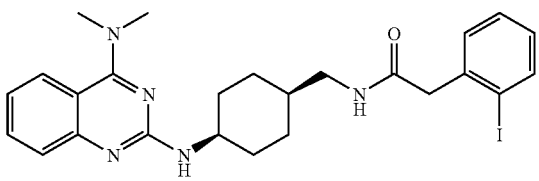
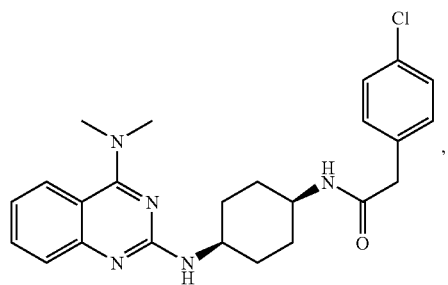
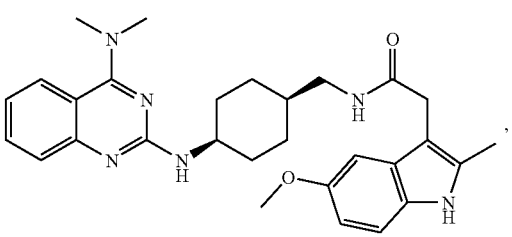

-continued
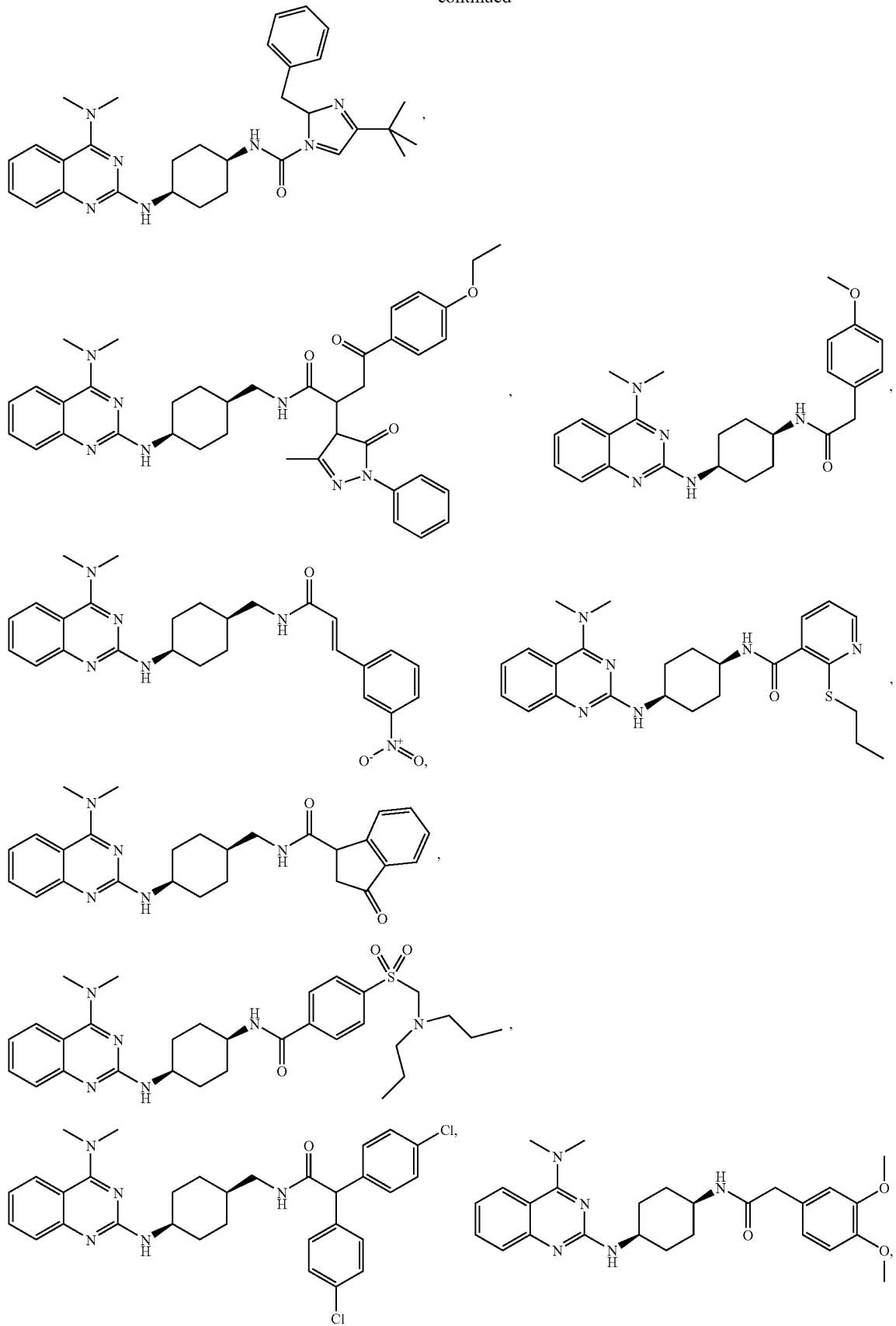

-continued
201
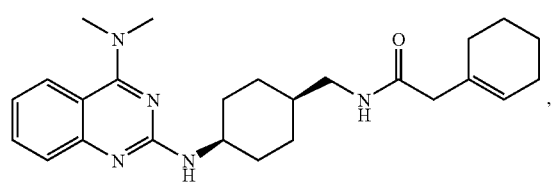
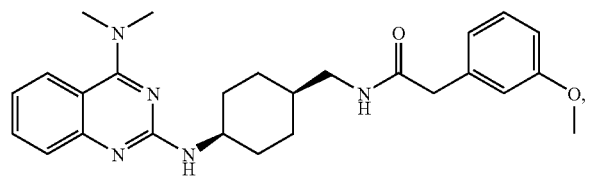
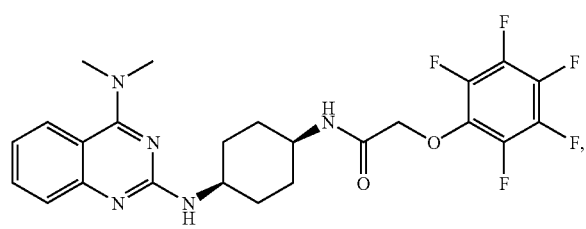
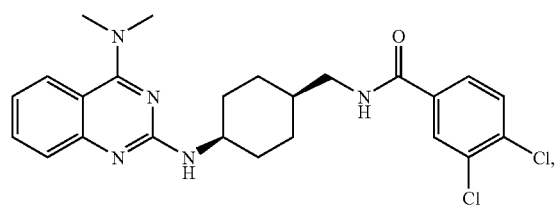
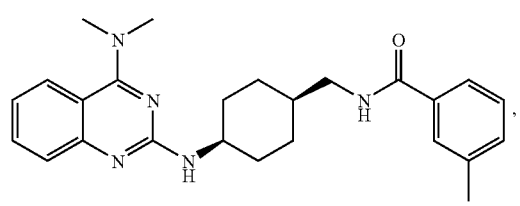
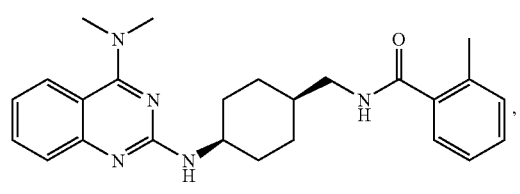
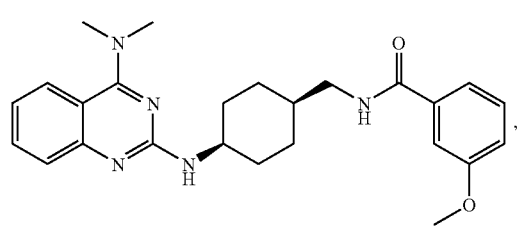
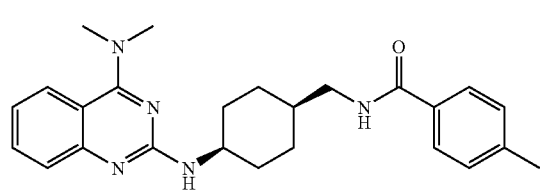
202
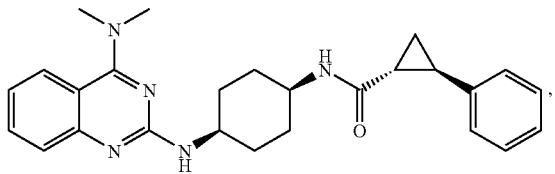
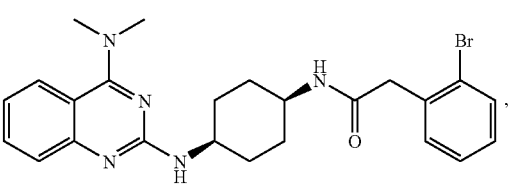
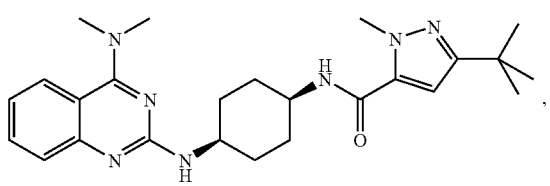
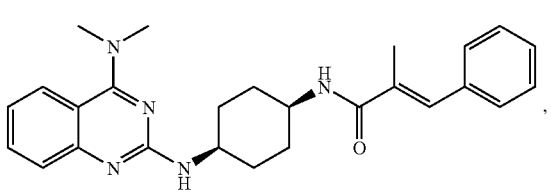
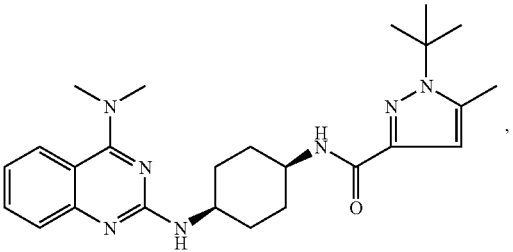
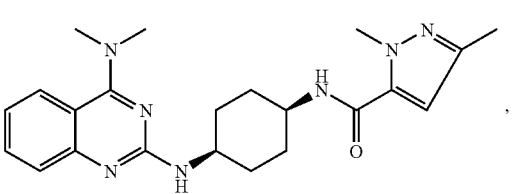

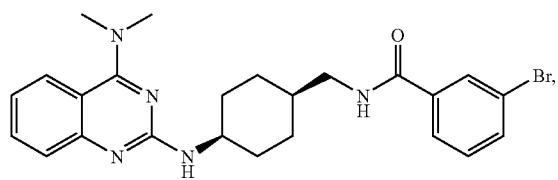,
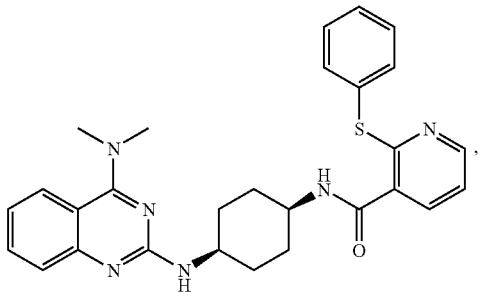,
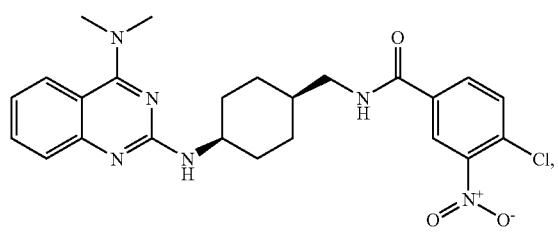,
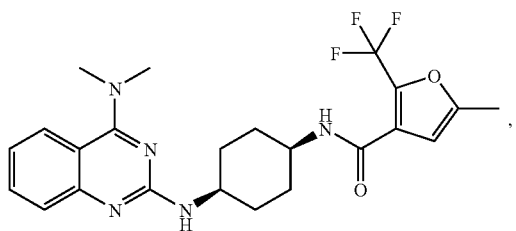,
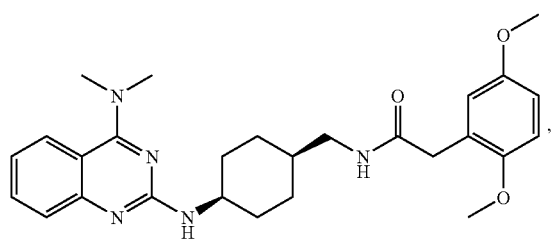,
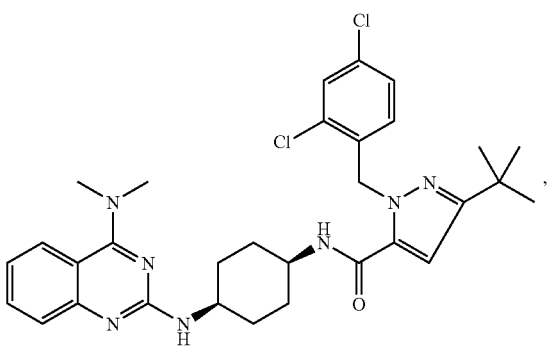,
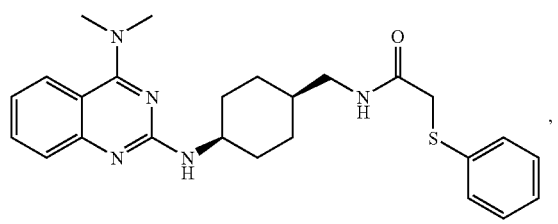,
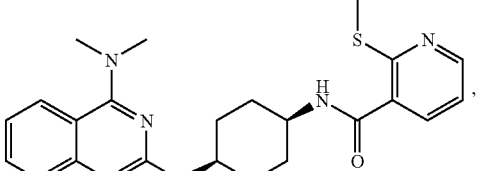,
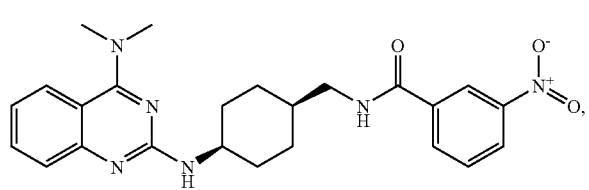,
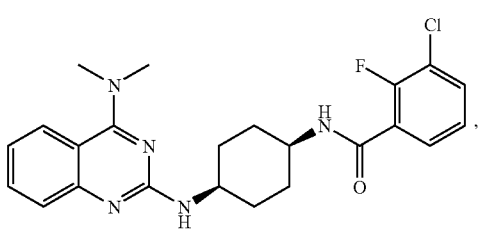,
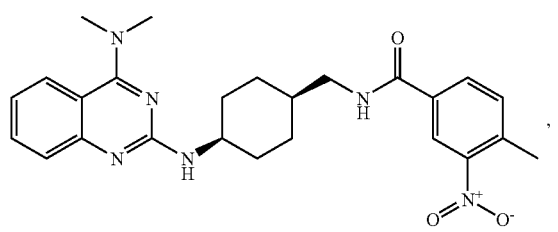,
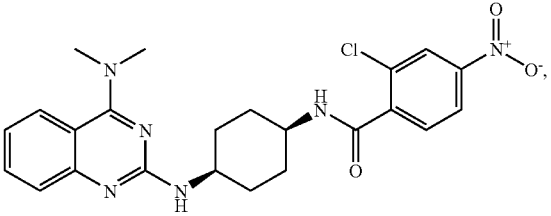, -continued
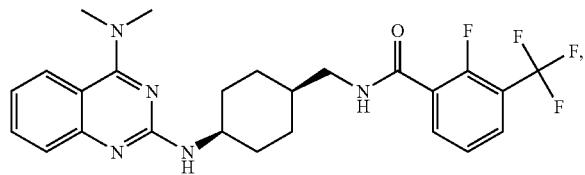
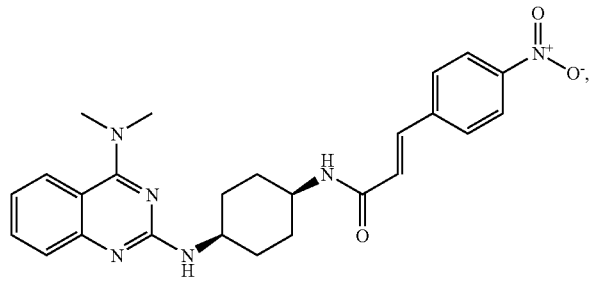
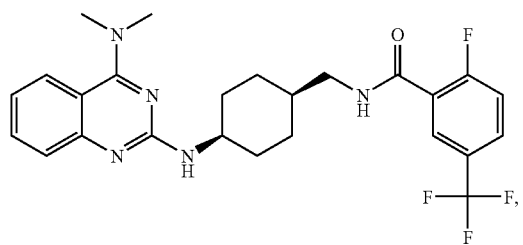
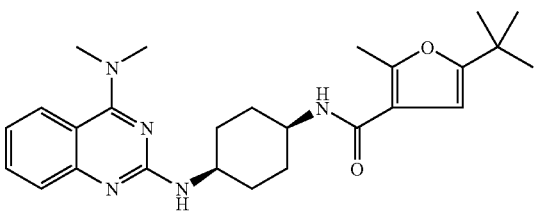
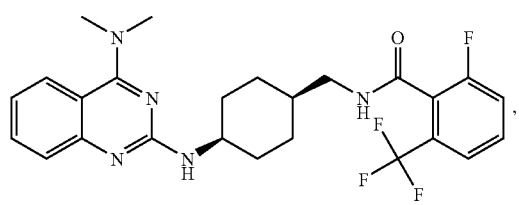
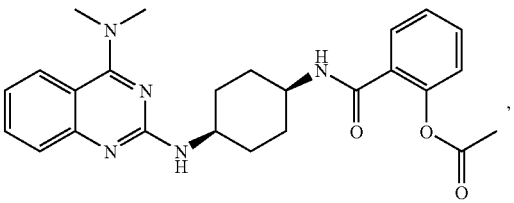
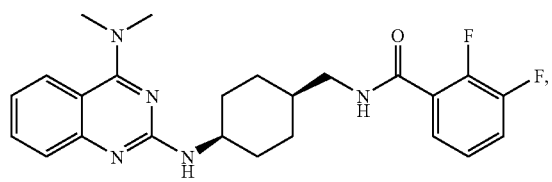
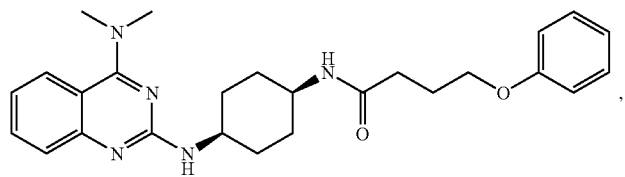
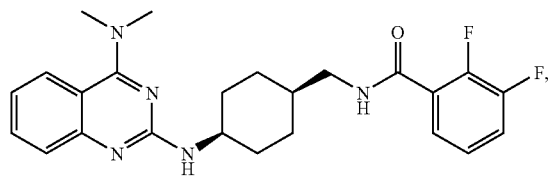
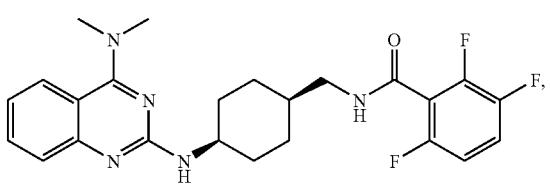
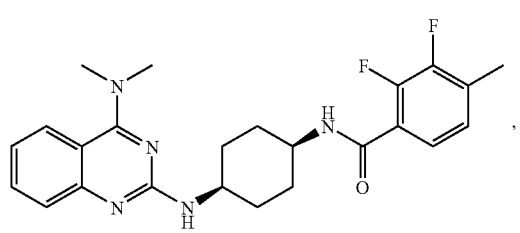
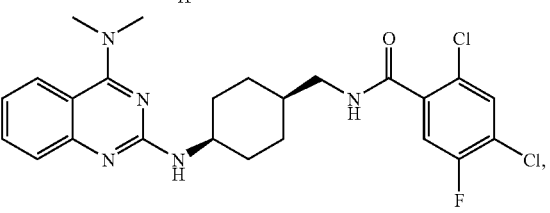

-continued
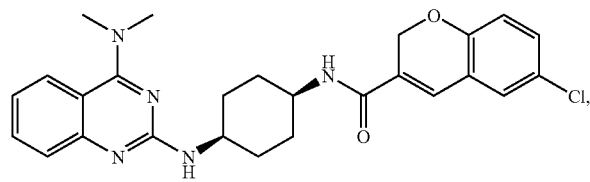
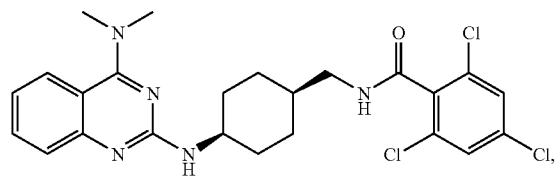
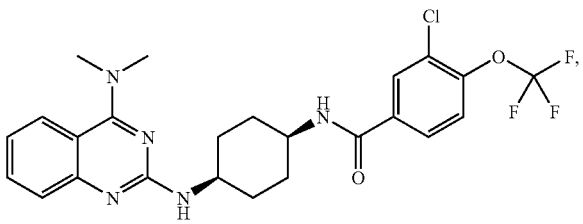
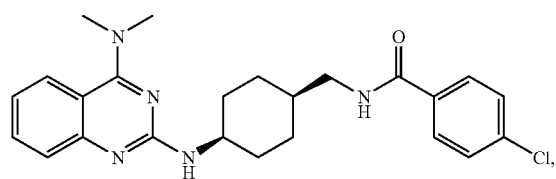
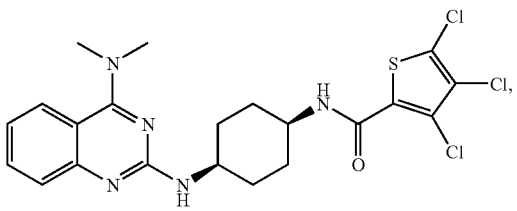
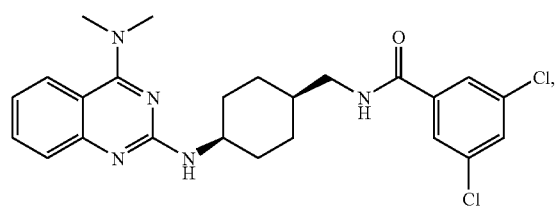
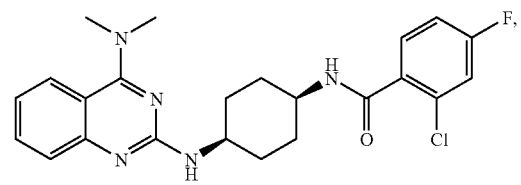
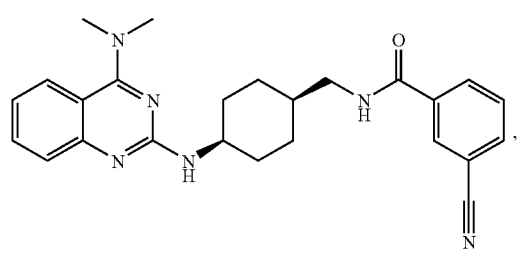
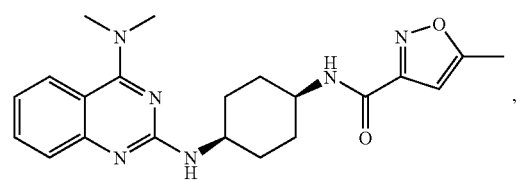
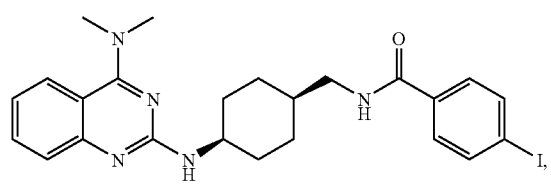
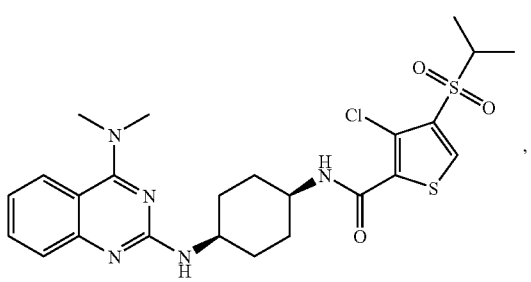
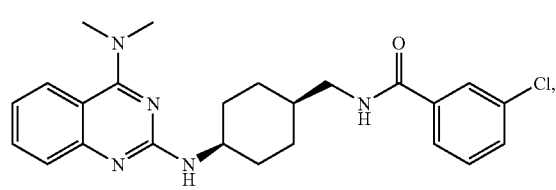
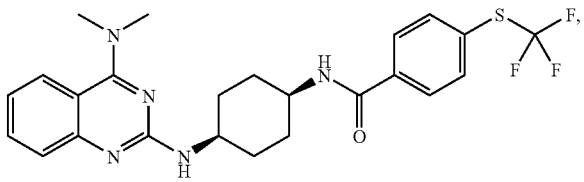

-continued
| 209 | 210 |
|---|---|
| 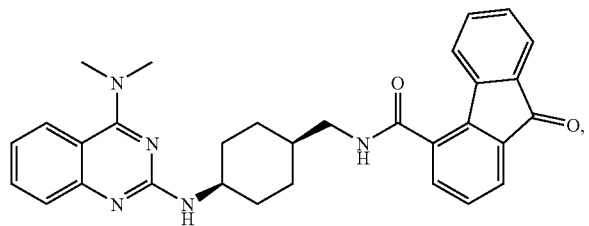 | 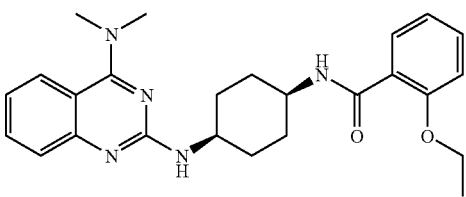 |
| 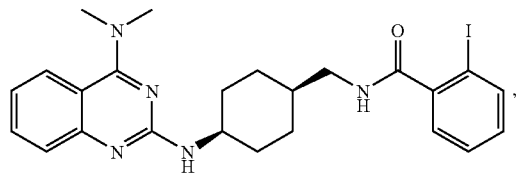 | 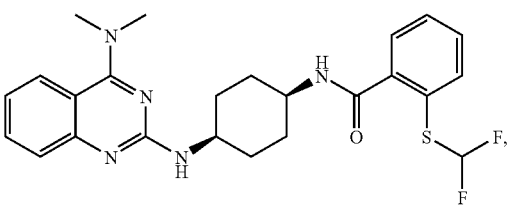 |
| 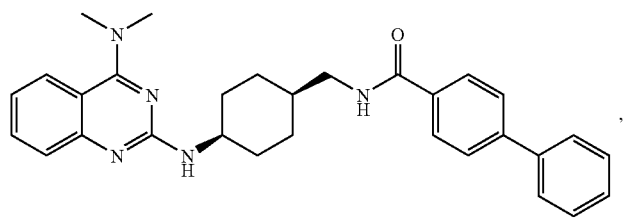 | |
| 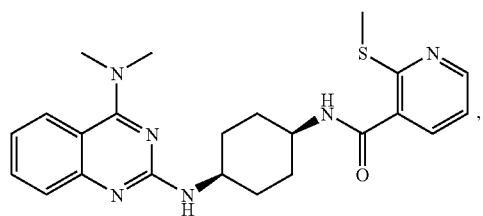 | 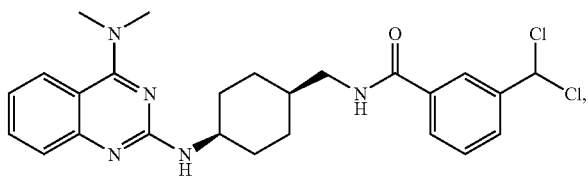 |
| 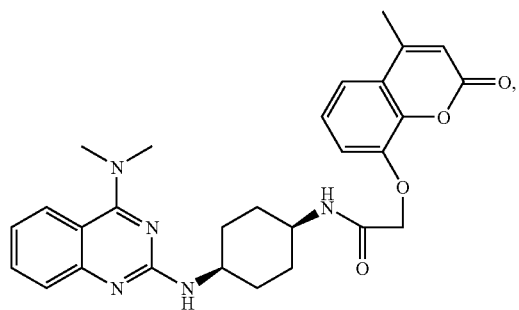 | 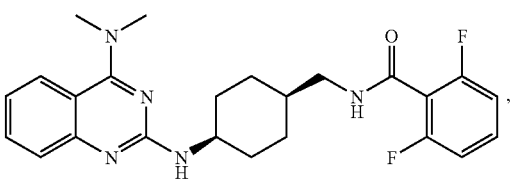 |
| 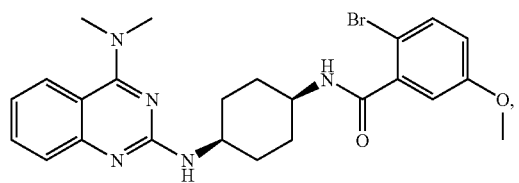 | 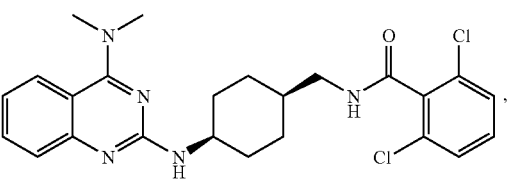 |
| 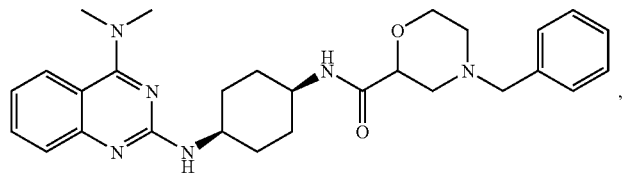 | |

-continued
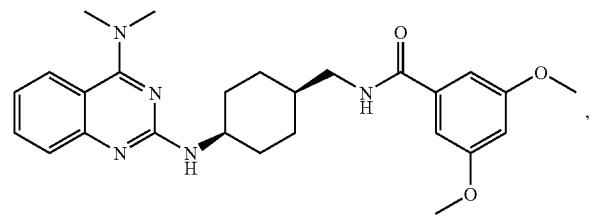
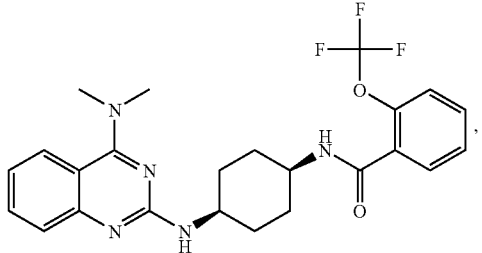
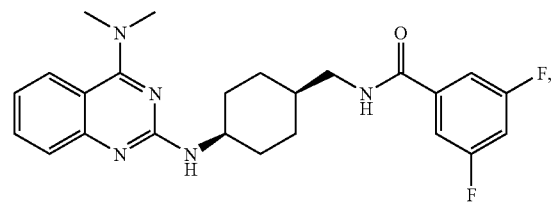
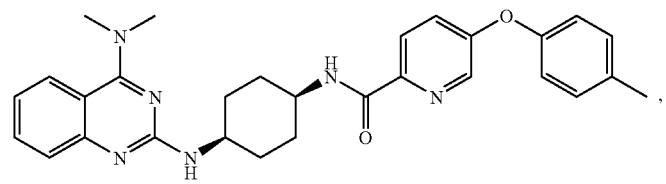
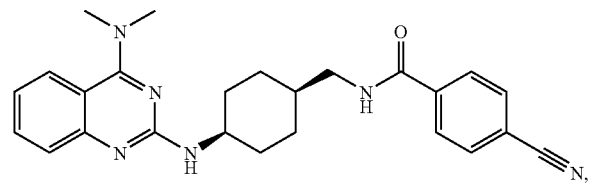
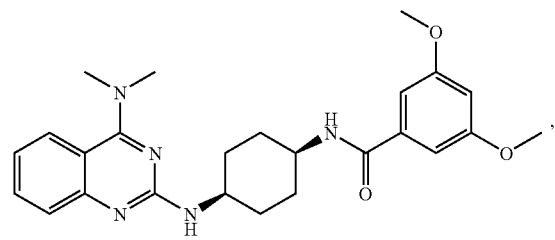
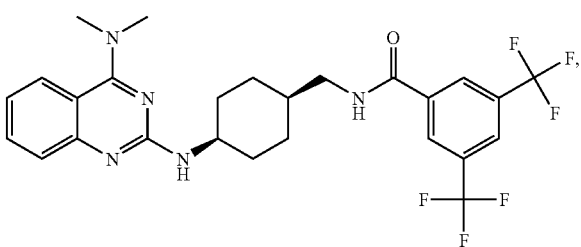
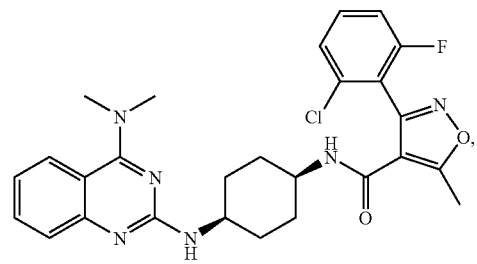
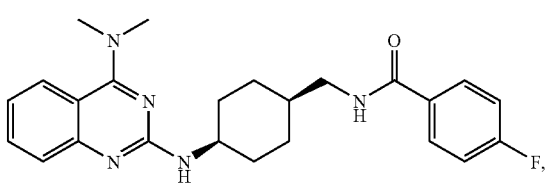
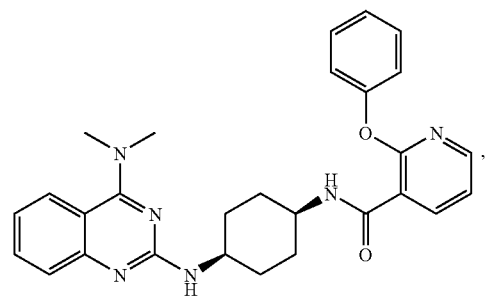
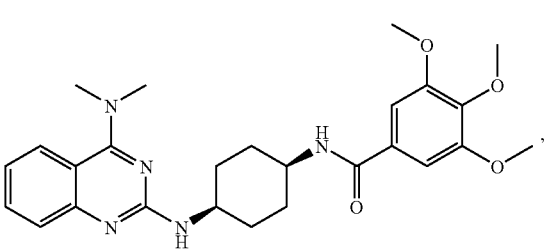

213
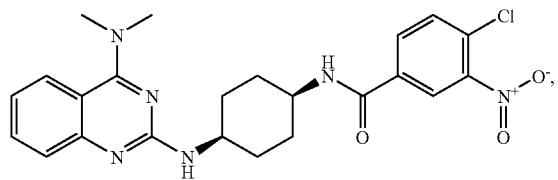
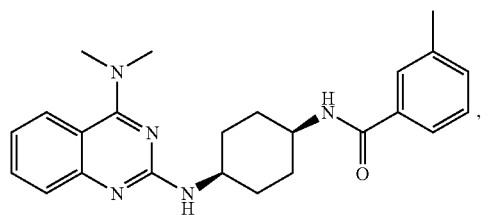
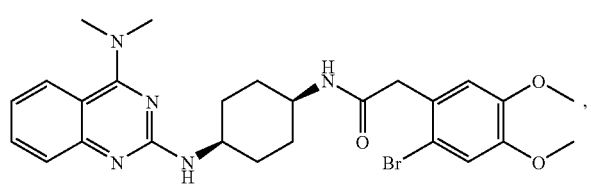
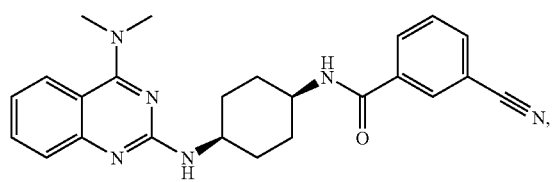
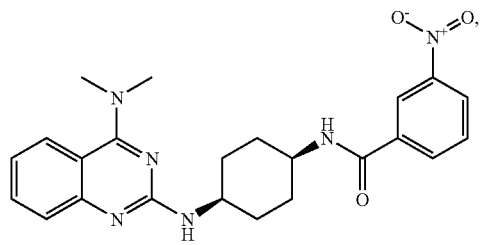
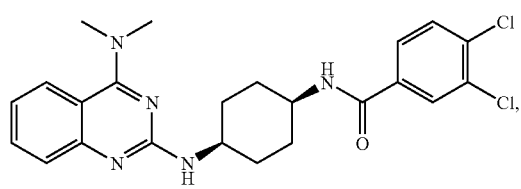
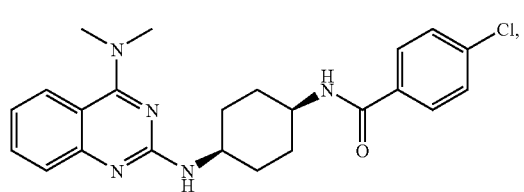
214
-continued
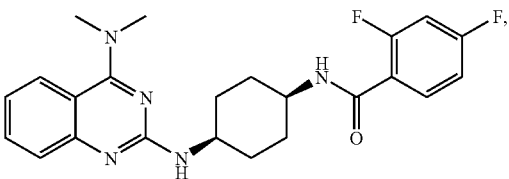
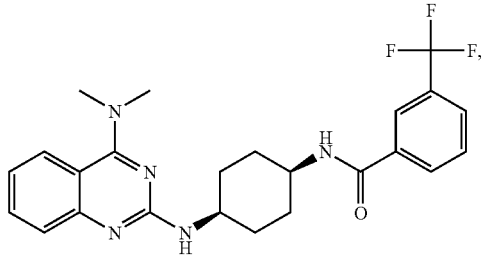
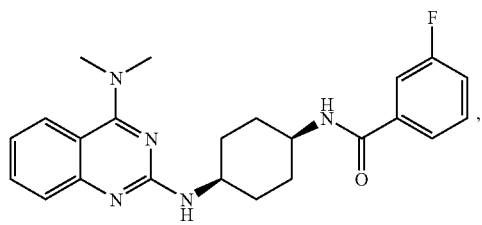
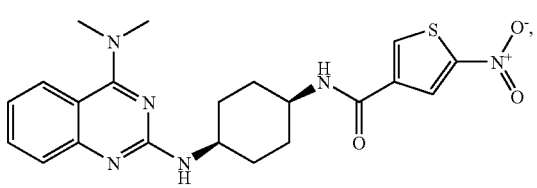
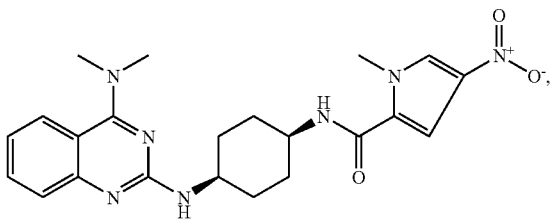
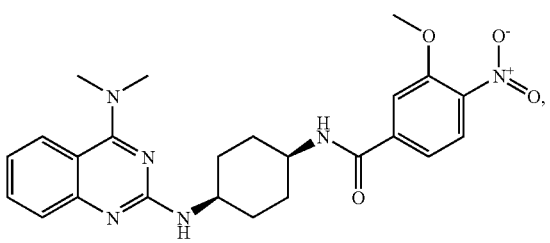
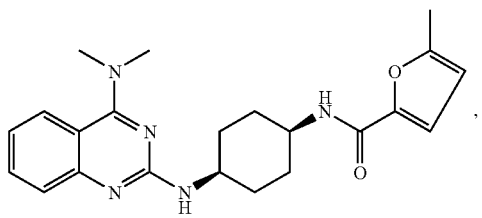

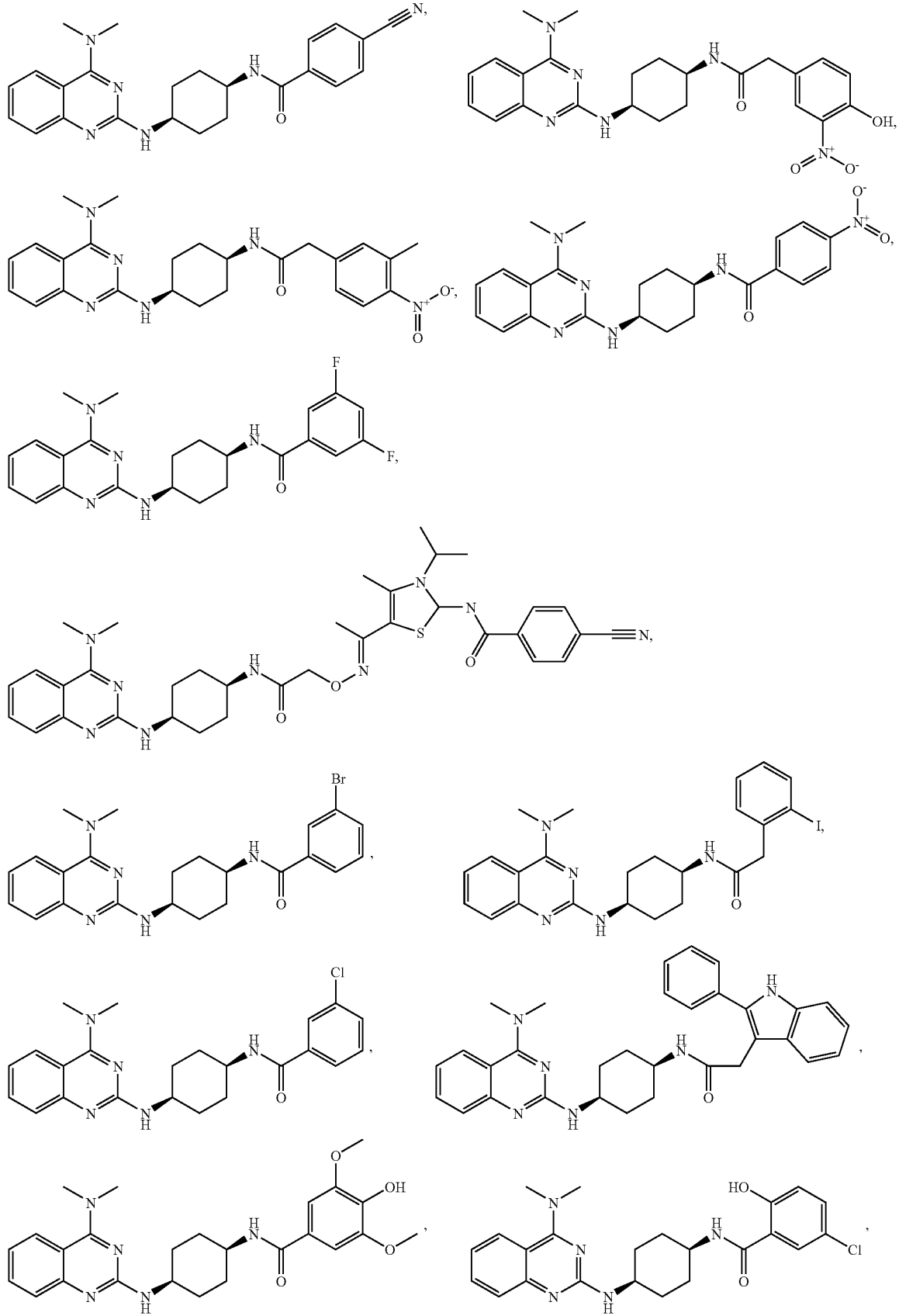

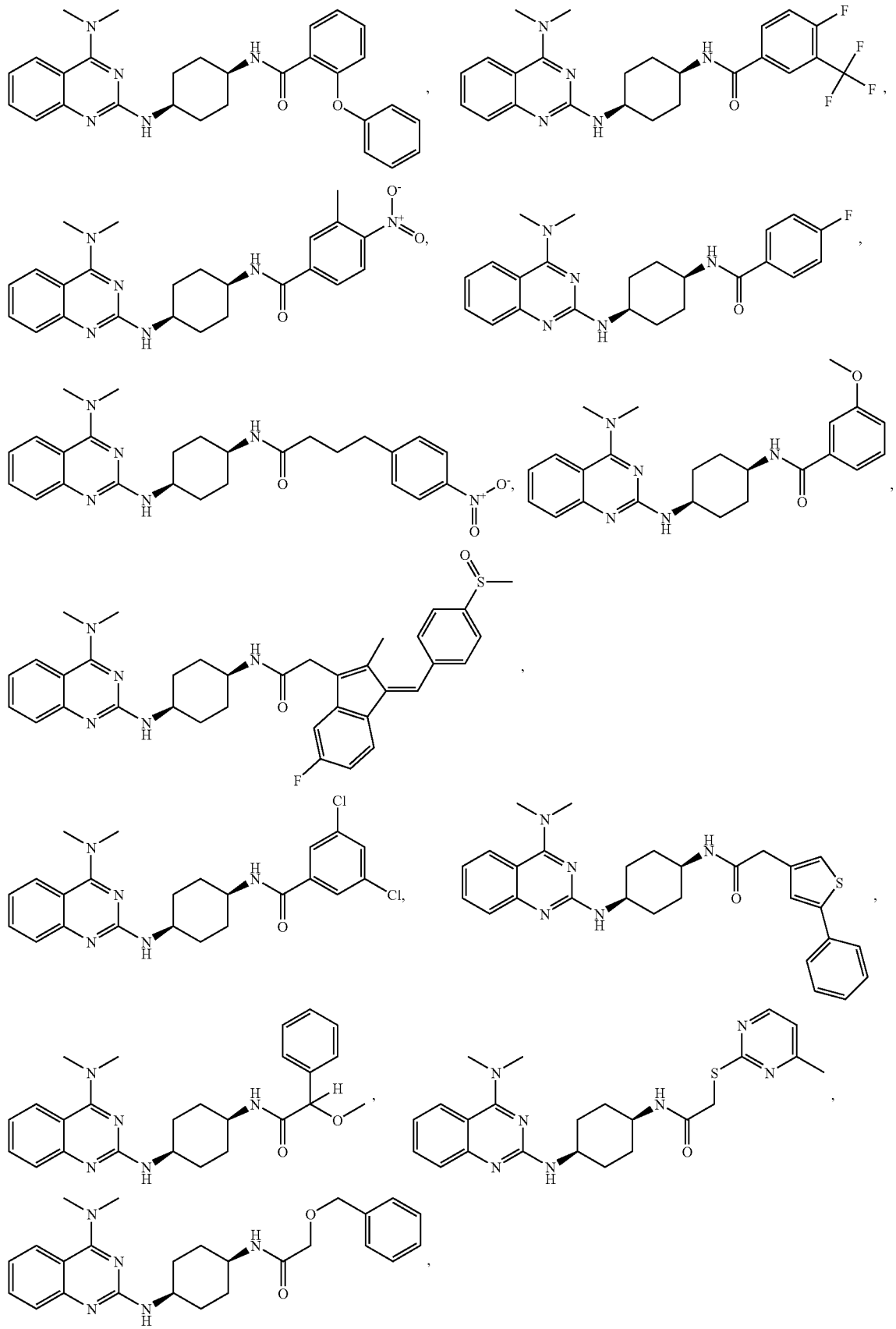

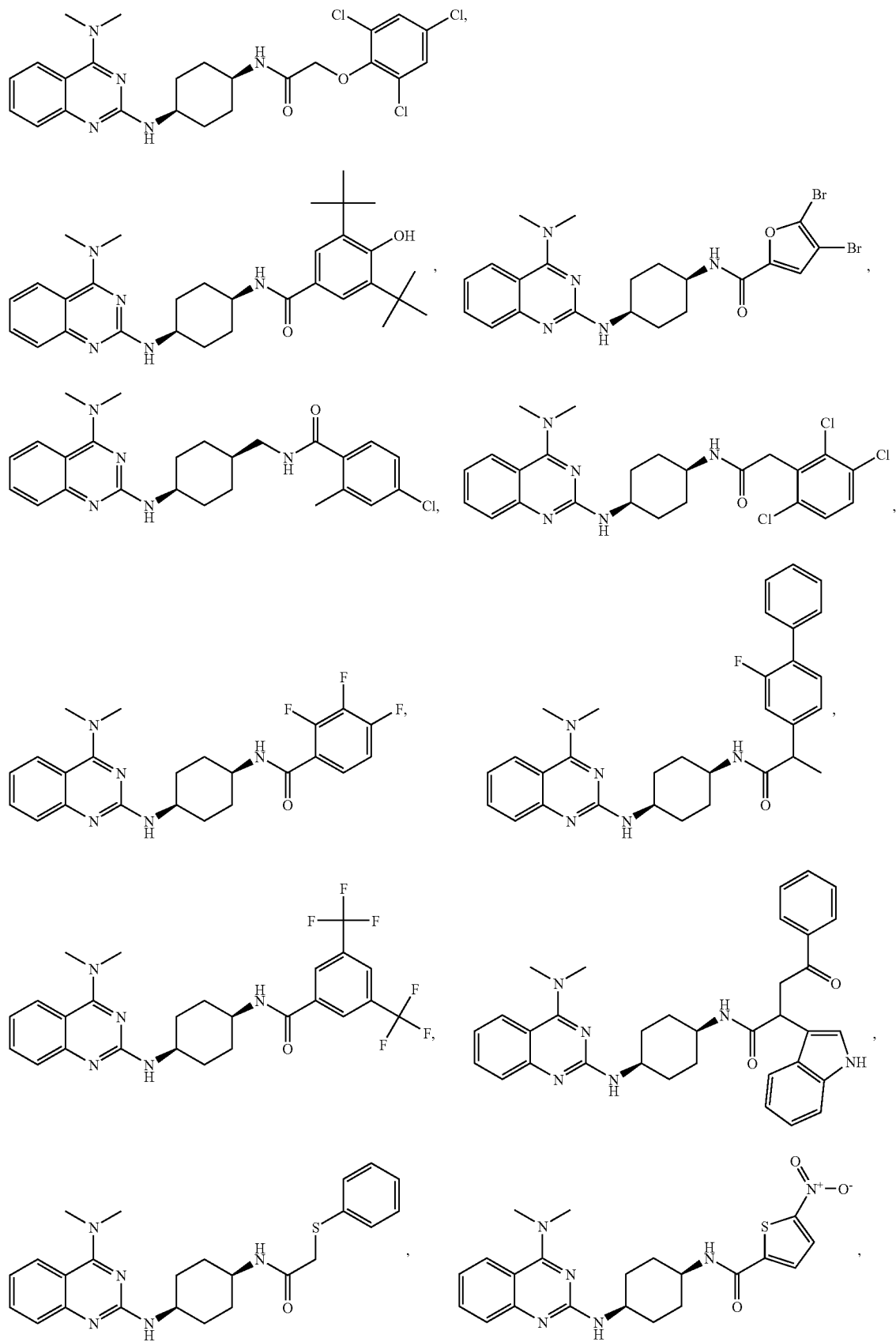

221 222
-continued
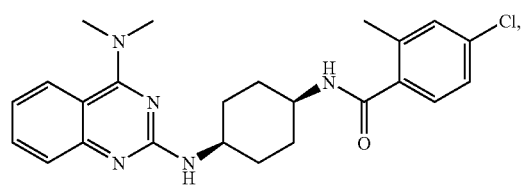
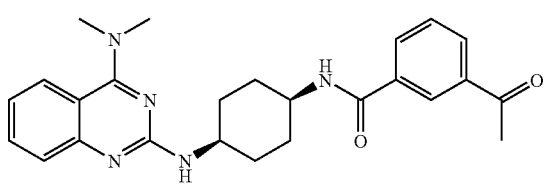
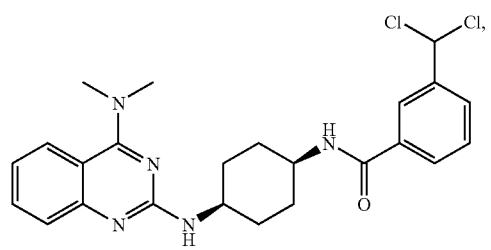
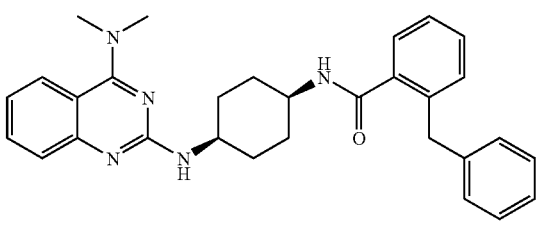
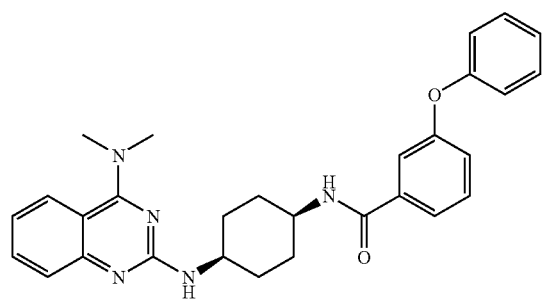
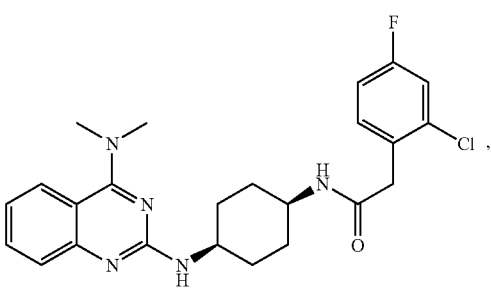
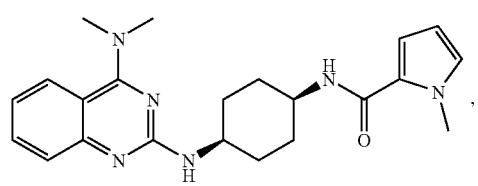
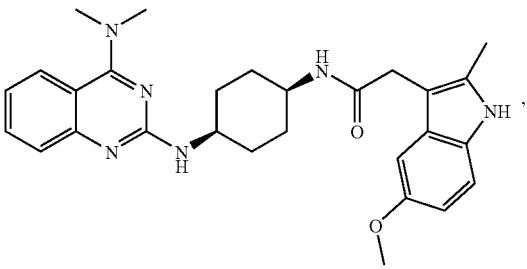
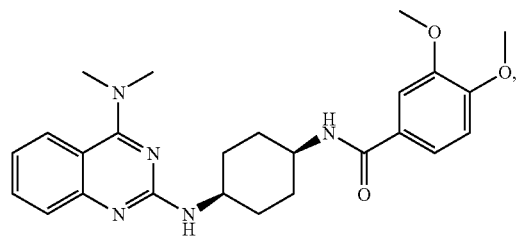
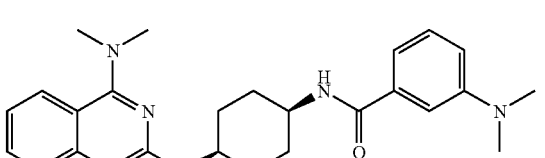
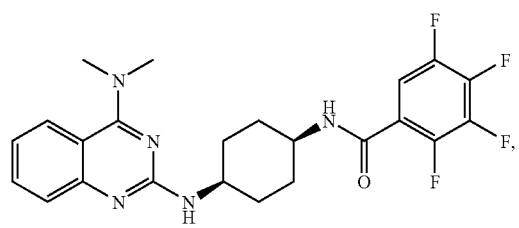
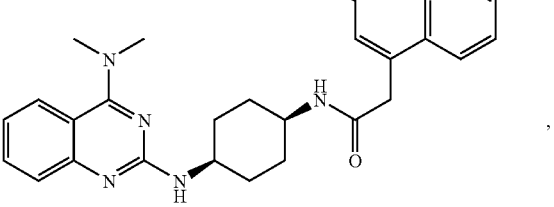

-continued
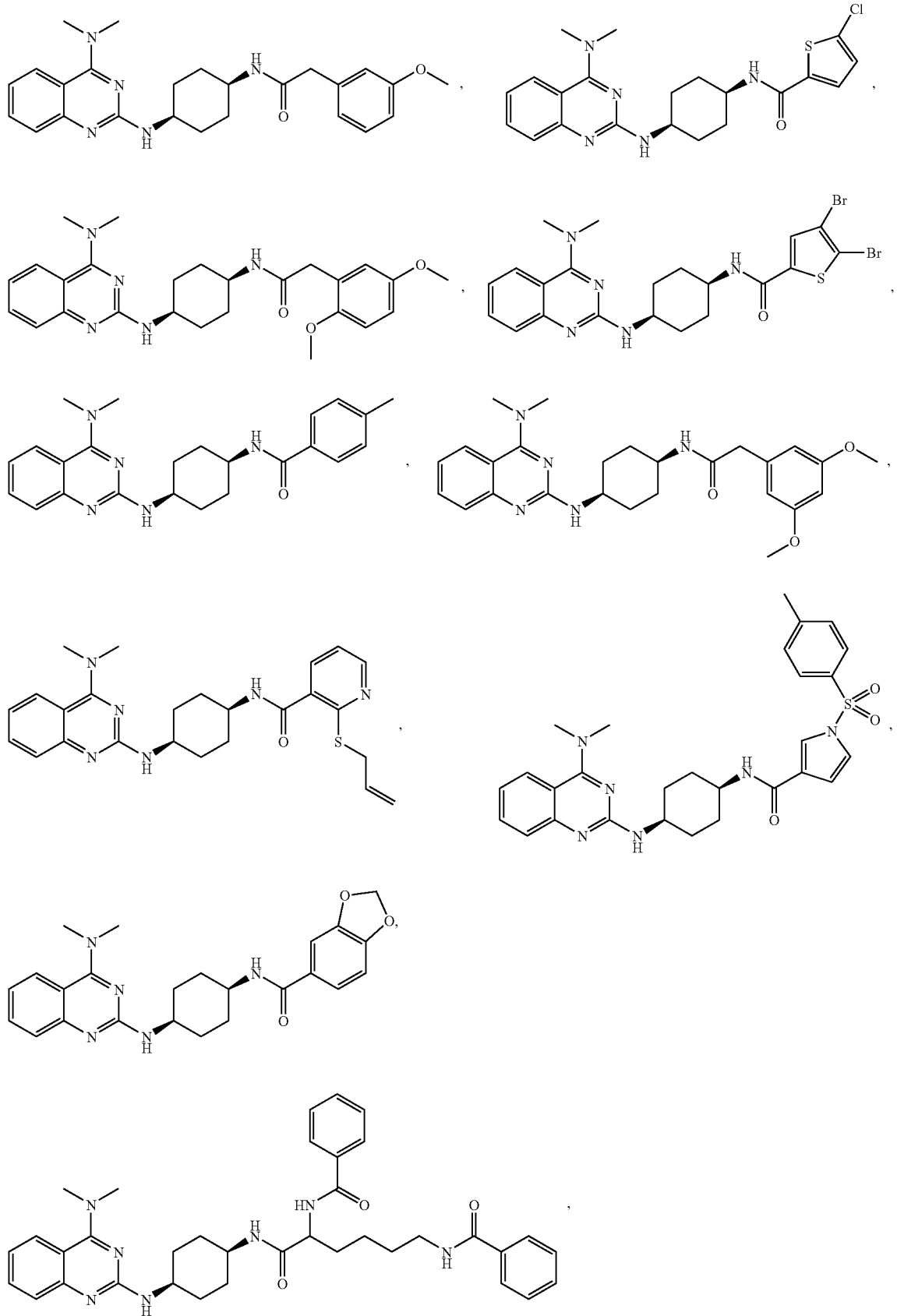

-continued
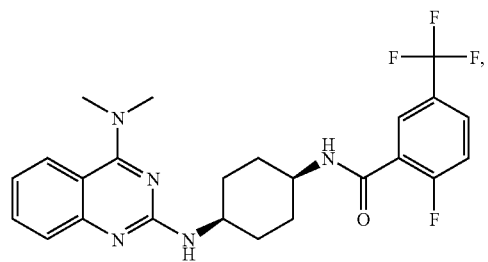
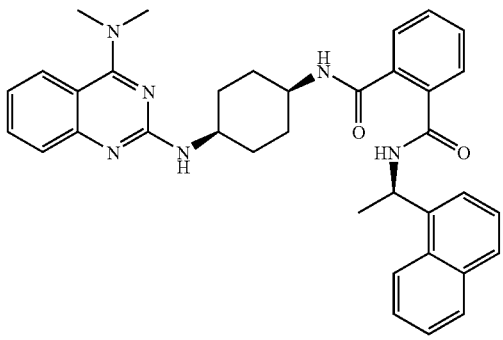
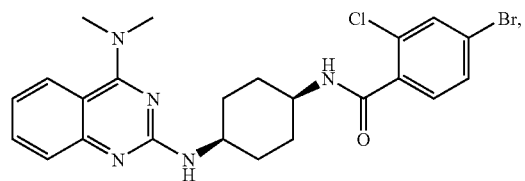
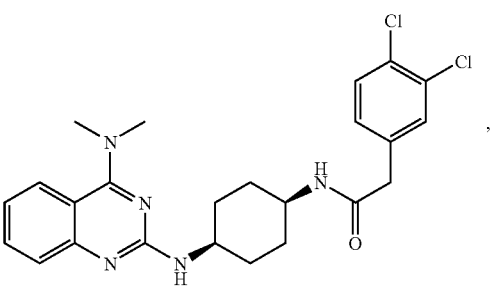
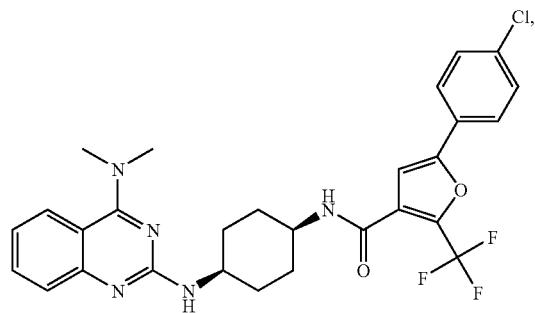
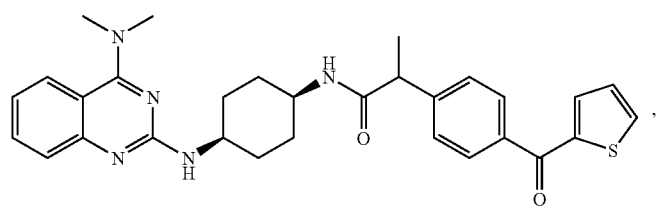
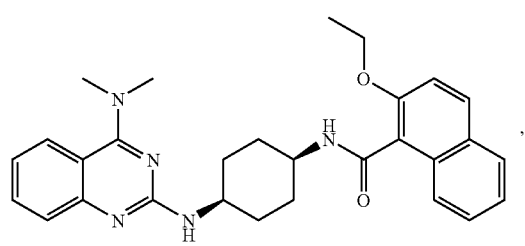
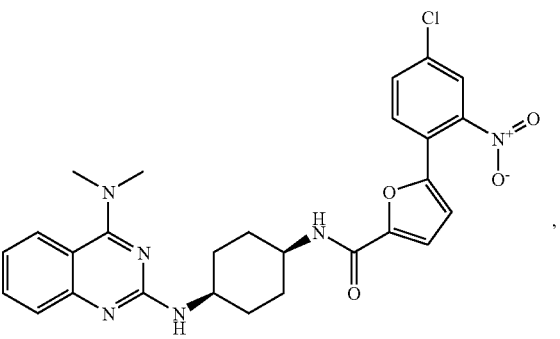

-continued
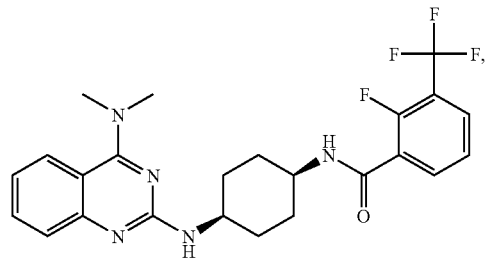
,
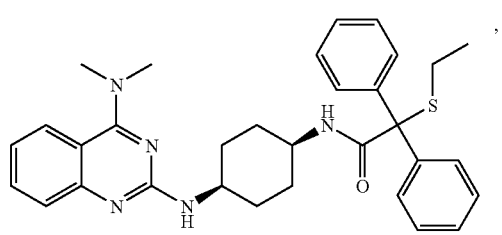
,
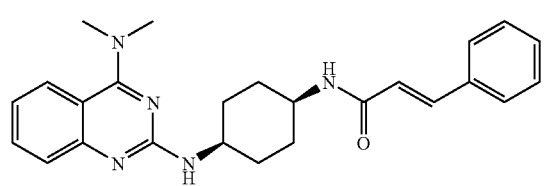
,
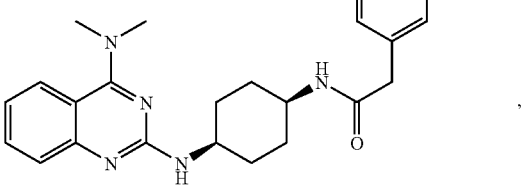
,
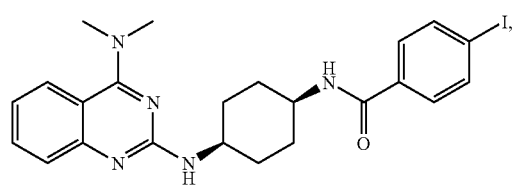
,
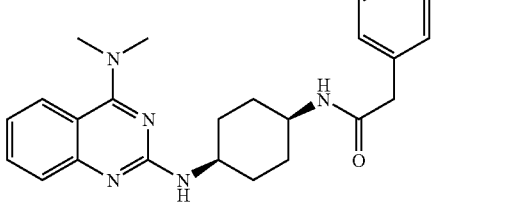
,
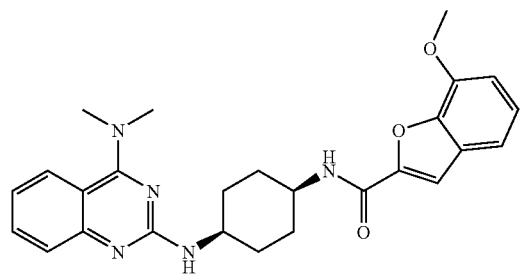
,
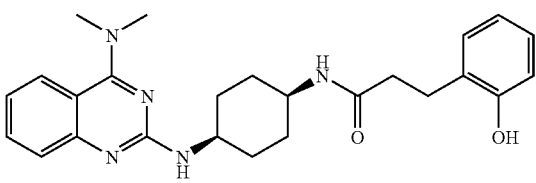
,
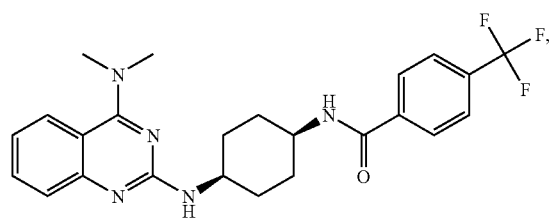
,
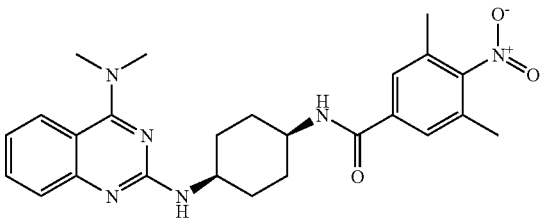
,
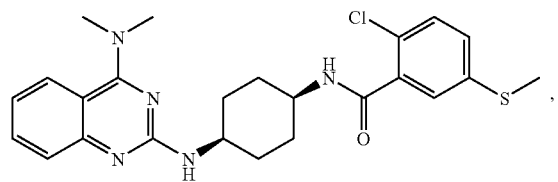
, -continued
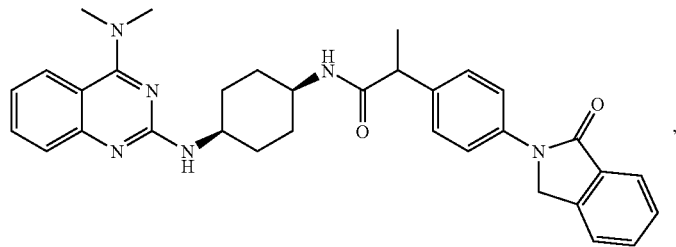
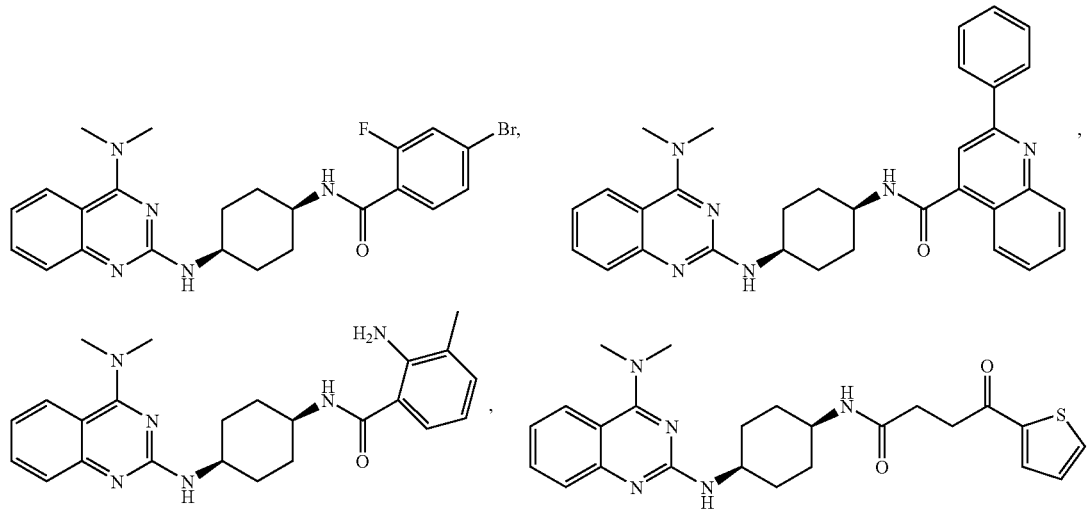
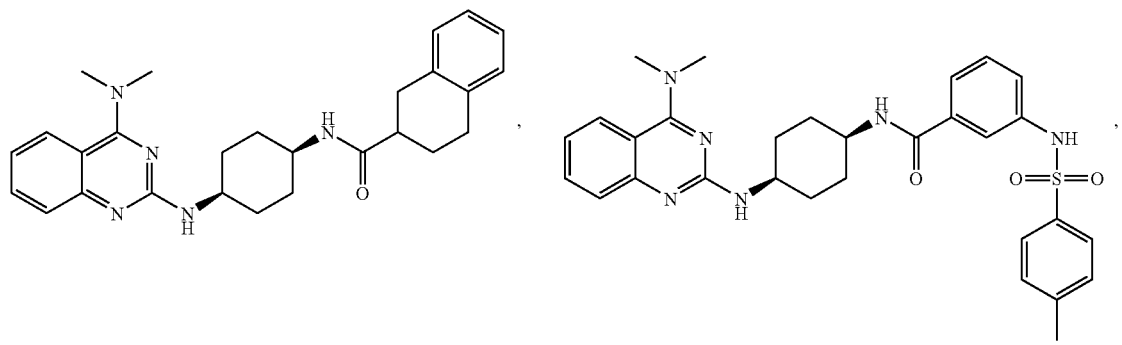
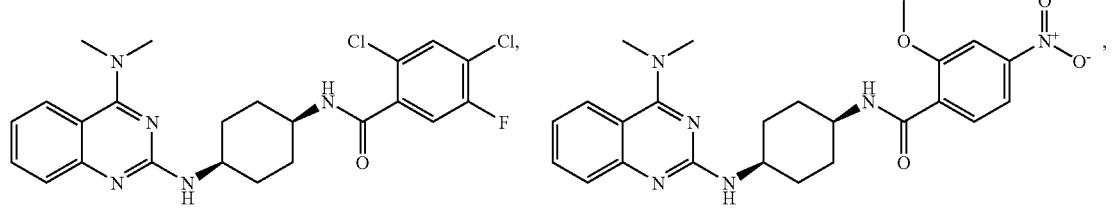
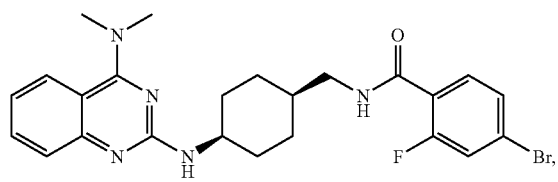
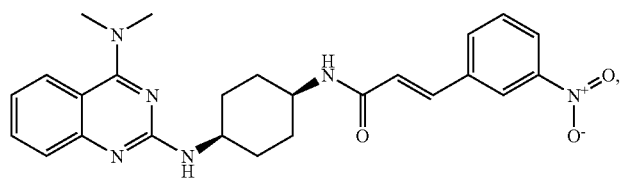

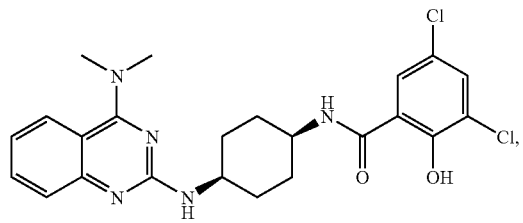

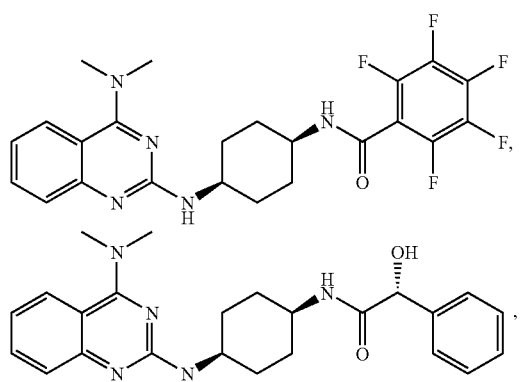

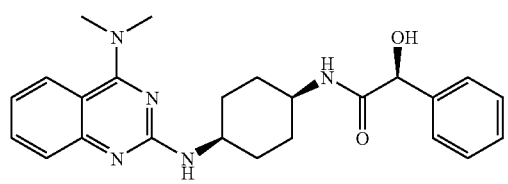

; or, in case of, a salt thereof.

Other more preferred compounds of this invention are those compounds of Formula I wherein,
Q is Formula II;
R$_1$ represents (i) C$_1$-C$_{10}$ alkyl, C$_1$-C$_{10}$ alkyl substituted by substituent(s) independently selected from
C$_5$-C$_6$ cycloalkyl,
carbocyclic aryl,
heterocyclyl, (ii) C$_3$-C$_6$ cycloalkyl, (iii) carbocyclic aryl, (iv) or heterocyclyl;
R$_2$ is methylamino or dimethylamino;
L is selected from Formula XX-XXII;
Y is —C(O)—;
wherein carbocyclic aryl is phenyl, naphthyl, anthranyl, or biphenyl;
heterocyclyl is 1,3-dioxo-isoindolyl, 1H-indolyl, 1-oxo-3H-isobenzofuranyl, 2,3-dihydro-benzo[1,4]dioxinyl, 3,4-dihydro-2H-benzo[b] [1,4]dioxepinyl, 4-oxo-3,4-dihydrophthalazinyl, 9,10,10-trioxo-thioxanthenyl, 9H-xanthenyl, benzimidazolyl, benzo[1,3]dioxolyl, benzo[2,1,3]oxadiazolyl, benzo[b]thienyl, furyl, imidazolyl, isoxazolyl, morpholino, oxolanyl, piperidyl, pyridyl, quinoxalyl, thienyl, quinolyl, or benzothiazolyl;
halogen is fluoro, chloro, bromo, or iodo.

Further other more preferred compounds of this invention are those compounds of Formula I wherein,
Q is Formula II;
R$_1$ represents (i) C$_1$-C$_4$ alkyl, C$_1$-C$_4$ alkyl substituted by substituent(s) independently selected from
cyclopentyl,
carbocyclic aryl,
heterocyclyl, (ii) carbocyclic aryl, (iii) or heterocyclyl;
R$_2$ is methylamino or dimethylamino;

L is selected from Formula XX-XXII;
Y is —C(O)—;
wherein carbocyclic aryl is phenyl, naphthyl, anthranyl, or biphenyl;
heterocyclyl is 9H-xanthenyl, benzo[1,3]dioxolyl, benzo[2,1,3]oxadiazolyl, benzo[b]thienyl, thienyl, 1H-indolyl, quinoxalyl, quinolyl, or benzothiazolyl;
halogen is fluoro, chloro, bromo, or iodo.
The following compounds are specially preffered;
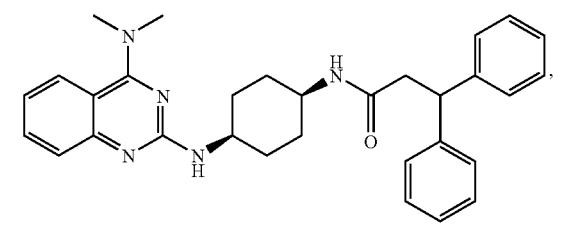
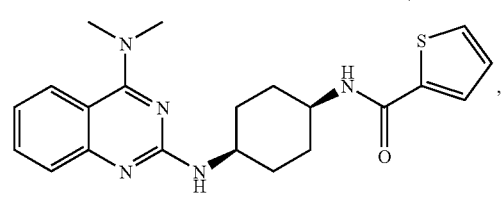
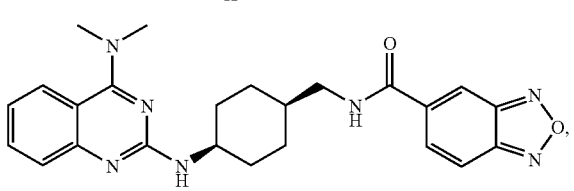
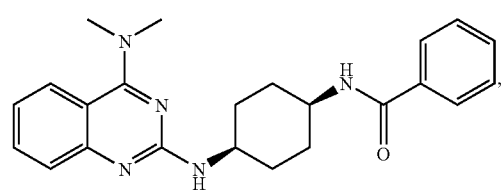
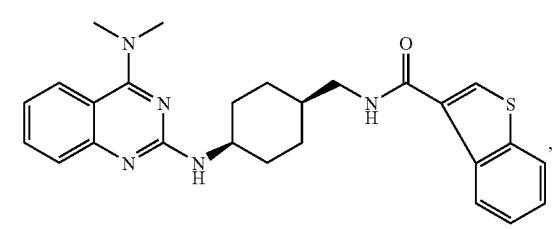
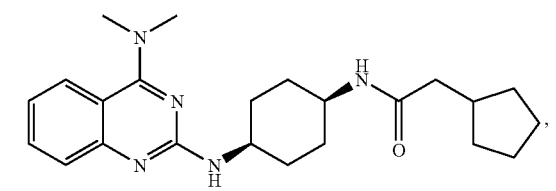
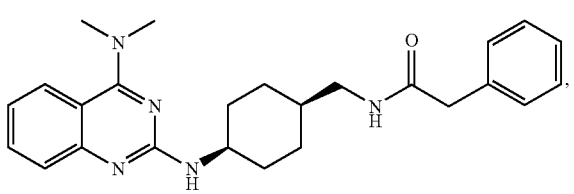
-continued
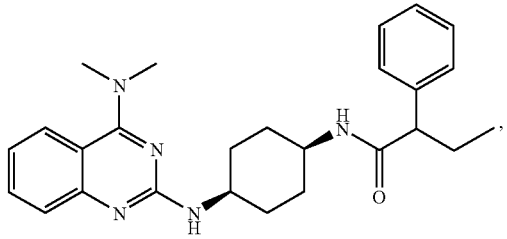
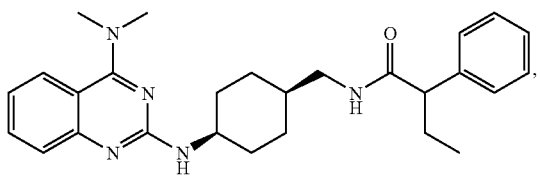
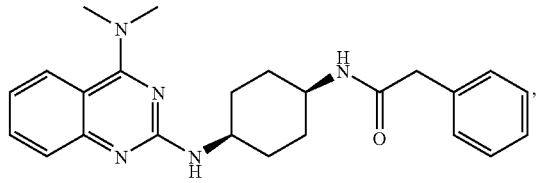
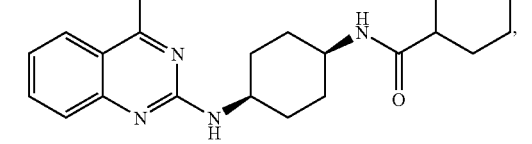

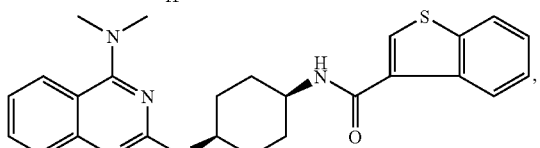
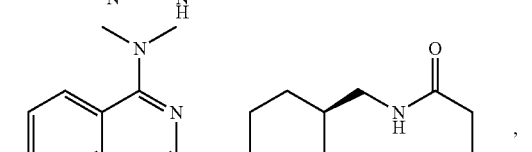
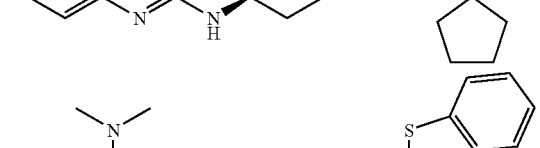
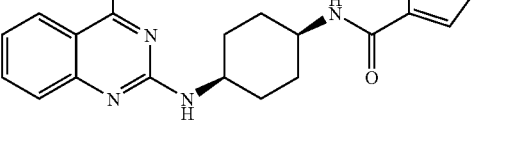

-continued
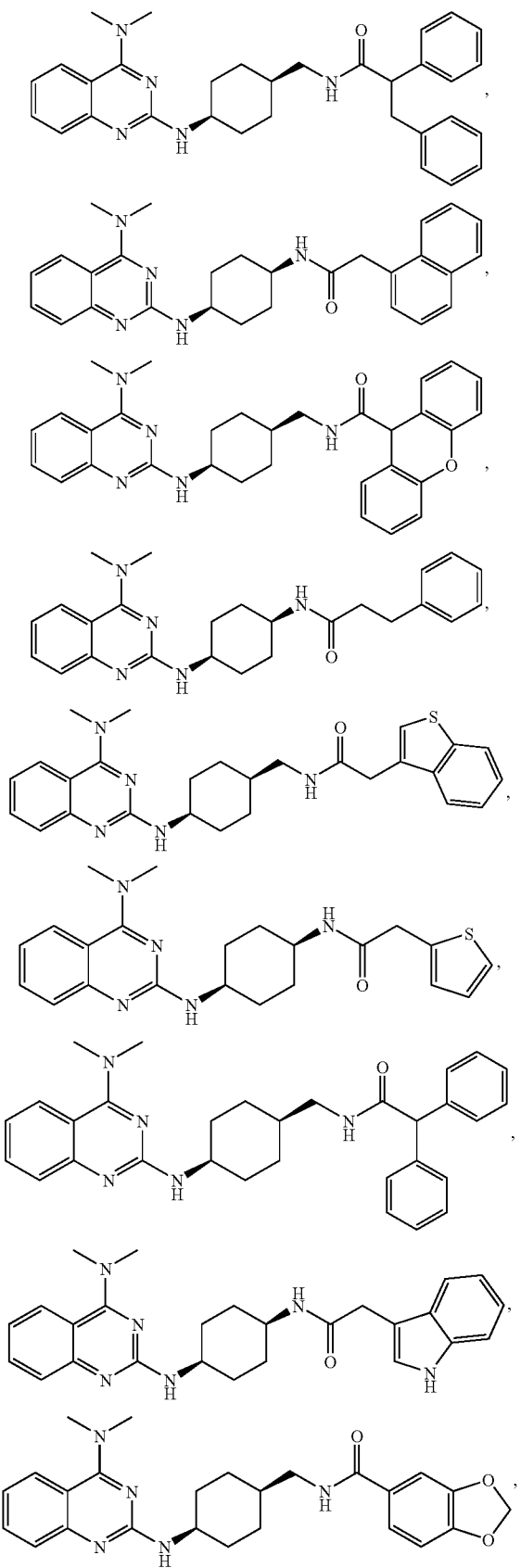
-continued
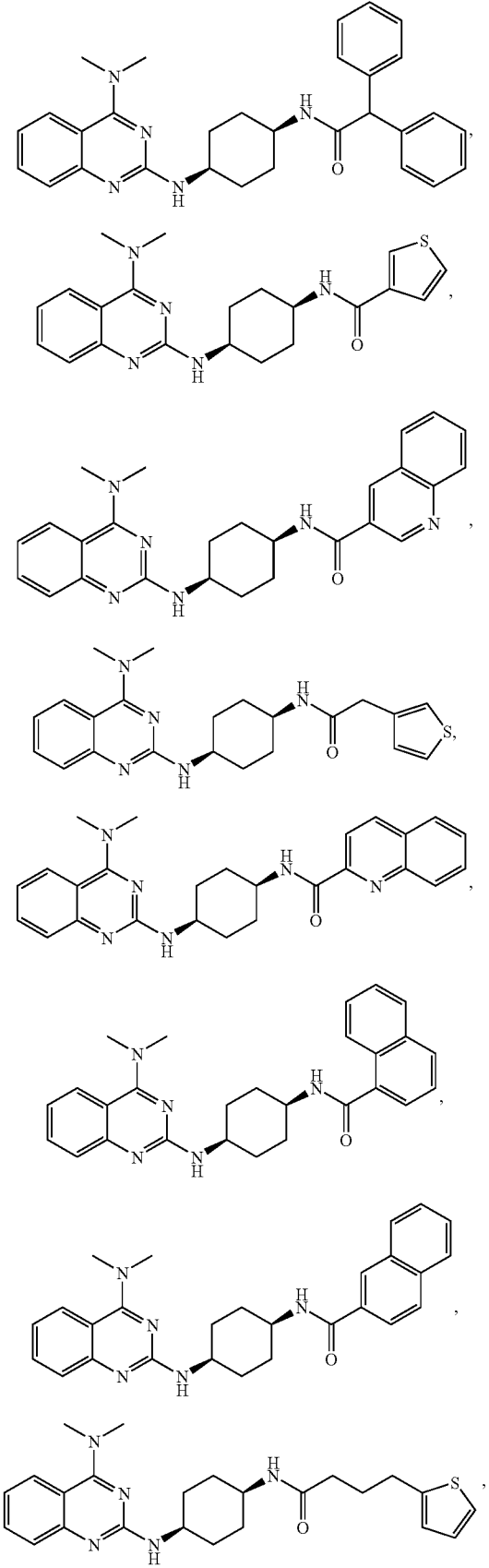

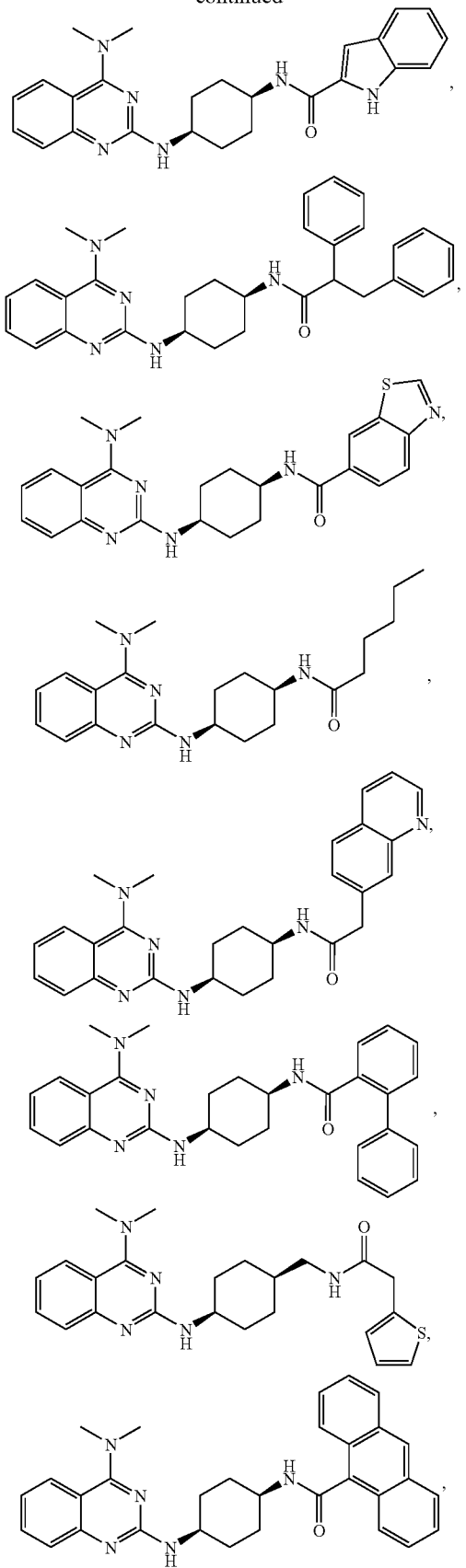

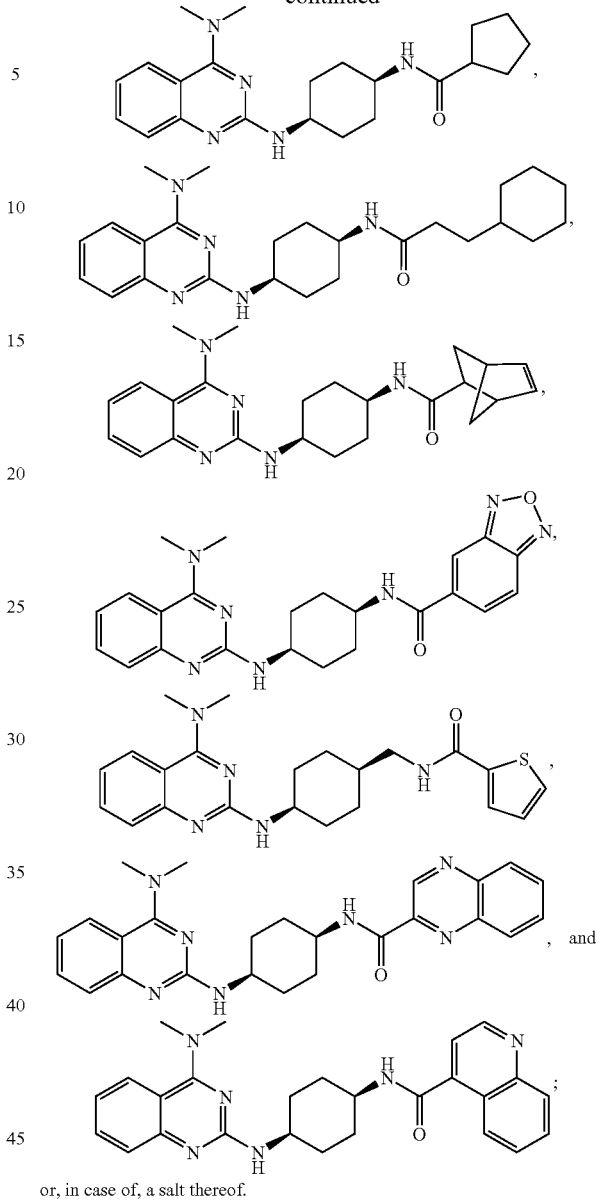

or, in case of, a salt thereof.

Preferred compounds of this invention are those compounds of Formula I wherein,
Q is Formula II;
$R_1$ represents (i) $C_1$-$C_{10}$ alkyl, $C_1$-$C_{10}$ alkyl substituted by substituent(s) independently selected from
  halogen,
  hydroxy,
  oxo,
  $C_1$-$C_3$ alkoxy,
  $C_1$-$C_3$ alkoxy substituted by substituent(s) independently selected from
    carbocyclic aryl,
    heterocyclyl,
    heterocyclyl substituted by $C_1$-$C_3$ alkyl, carbocyclic aryloxy,
carbocyclic aryloxy substituted by substituent(s) independently selected from
  halogen,
  nitro,
  carbocyclic aryl,
  carbocyclic aryl substituted by $C_1$-$C_3$ alkoxy,
  $C_1$-$C_4$ alkyl,
  $C_1$-$C_4$ alkyl substituted by substituent(s) independently selected from
    mono- or di-$C_1$-$C_3$ alkylamino,
    mono- or di-$C_1$-$C_3$ alkylamino substituted by carbocyclic aryl,
    mono- or di-$C_1$-$C_3$ alkylamino substituted by halogenated carbocyclic aryl,
mono- or di-$C_1$-$C_3$ alkylamino,
mono- or di-$C_1$-$C_3$ alkylamino substituted by substituent(s) independently selected from
  cyano,
  carbocyclic aryl,
  heterocyclyl,
mono- or di-carbocyclic arylamino,
mono- or di-carbocyclic arylamino substituted by $C_1$-$C_3$ alkyl,
$C_1$-$C_3$ alkylcalbonylamino,
$C_1$-$C_4$ alkoxycalbonylamino,
carbocyclic arylsulfonylamino,
carbocyclic arylsulfonylamino substituted by substituent(s) independently selected from
  nitro,
  $C_1$-$C_3$ alkyl,
  mono- or di-$C_1$-$C_3$ alkylamino,
$C_1$-$C_3$ alkylthio,
$C_1$-$C_3$ alkylthio substituted by substituent(s) independently selected from
  mono- or di-carbocyclic arylamino,
  halogenated mono- or di-carbocyclic arylamino,
  carbocyclic aryl,
  carbocyclic aryl substituted by substituent(s) independently selected from
    halogen,
    $C_1$-$C_3$ alkoxy,
carbocyclic arylthio,
carbocyclic arylthio substituted by substituent(s) independently selected from
  halogen,
  $C_1$-$C_3$ alkyl,
carbocyclic arylsulfonyl,
halogenated carbocyclic arylsulfonyl,
heterocyclylthio,
$C_3$-$C_6$ cycloalkyl,
$C_3$-$C_6$ cycloalkyl substituted by $C_1$-$C_3$ alkyl,
carbocyclyl,
carbocyclyl substituted by substituent(s) independently selected from
  halogen,
  $C_1$-$C_3$ alkyl,
  $C_2$-$C_3$ alkenyl,
  $C_2$-$C_3$ alkenyl substituted by carbocyclic aryl,
  $C_2$-$C_3$ alkenyl substituted by carbocyclic aryl substituted $C_1$-$C_3$ alkylsulfinyl,
carbocyclic aryl,
carbocyclic aryl substituted by substituent(s) independently selected from
  halogen,
  hydroxy,
  nitro,
  $C_1$-$C_4$ alkyl,
  $C_1$-$C_4$ alkyl substituted by substituent(s) independently selected from
    halogen,
    hydroxy,
    carbocyclic aryl,
    mono- or di-carbocyclic arylamino,
    mono- or di-carbocyclic arylamino substituted by substituent(s) independently selected from
      halogen,
      nitro,
      $C_1$-$C_3$ alkyl,
      $C_1$-$C_3$ alkoxy,
      halogenated $C_1$-$C_3$ alkoxy,
  $C_1$-$C_3$ alkoxy,
  $C_1$-$C_3$ alkoxy substituted by substituent(s) independently selected from
    halogen,
    carbocyclic aryl,
  carbocyclic aryloxy,
  $C_1$-$C_3$ alkoxycarbonyl,
  mono- or di-$C_1$-$C_3$ alkylamino,
  $C_1$-$C_3$ alkylthio,
  halogenated $C_1$-$C_3$ alkylthio,
  $C_1$-$C_3$ alkylsulfonyl,
  $C_3$-$C_6$ cycloalkyl,
  carbocyclic aryl,
  heterocyclyl,
heterocyclyl,
heterocyclyl substituted by substituent(s) independently selected from
  $C_1$-$C_3$ alkyl,
  $C_1$-$C_3$ alkoxy,
  $C_1$-$C_3$ alkoxy substituted by carbocyclic aryl,
  carbocyclic aryl,
  halogenated carbocyclic aryl, (ii) $C_2$-$C_8$ alkenyl,
$C_2$-$C_8$ alkenyl substituted by substituent(s) independently selected from
  halogen,
  $C_1$-$C_3$ alkoxy,
  $C_1$-$C_3$ alkoxy substituted by carbocyclic aryl,
  carbocyclic aryl,
  carbocyclic aryl substituted by substituent(s) independently selected from halogen,
    hydroxy,
    $C_1$-$C_3$ alkoxy,
    halogenated $C_1$-$C_3$ alkoxy,
  heterocyclyl,
  heterocyclyl substituted by nitro, (iii) $C_2$-$C_4$ alkynyl,
$C_2$-$C_4$ alkynyl substituted by carbocyclic aryl, (iv) $C_3$-$C_6$ cycloalkyl,
$C_3$-$C_6$ cycloalkyl substituted by substituent(s) independently selected from
  $C_1$-$C_3$ alkyl,
  $C_1$-$C_3$ alkyl substituted by substituent(s) independently selected from
    hydroxy,
    oxo,
    carbocyclic aryl, mono- or di-C$_1$-C$_3$ akylamino,
mono- or di-C$_1$-C$_3$ alkylamino substituted by carbocyclic aryl,
carbocyclic aryl, (v) C$_3$-C$_6$ cycloalkeyl, C$_3$-C$_6$ cycloalkeyl substituted by C$_1$-C$_3$ alkyl, (vi) carbocyclyl, carbocyclyl substituted by substituent(s) independently selected from
  hydroxy,
  nitro, (vii) carbocyclic aryl, carbocyclic aryl substituted by substituent(s) independently selected from
  halogen,
  hydroxy,
  cyano,
  nitro,
  C$_1$-C$_9$ alkyl,
  C$_1$-C$_9$ alkyl substituted by substituent(s) independently selected from
    halogen,
    hydroxy,
    oxo,
    C$_1$-C$_3$ alkoxy,
    carbocyclic aryloxy,
    mono- or di-C$_1$-C$_3$ alkylamino-N-oxy,
    mono- or di-C$_1$-C$_3$ alkylamino,
    mono- or di-C$_1$-C$_3$ alkylamino substituted by carbocyclic aryl,
    mono- or di-carbocyclic arylamino,
    mono- or di-carbocyclic arylamino substituted by C$_1$-C$_3$ alkoxy,
    carbocyclic aryl,
    halogenated carbocyclic aryl,
    heterocyclyl,
    heterocyclyl substituted by C$_1$-C$_3$ alkyl,
  C$_2$-C$_3$ alkenyl,
  C$_2$-C$_3$ alkenyl substituted by carbocyclic aryl,
  C$_1$-C$_9$ alkoxy,
  C$_1$-C$_9$ alkoxy substituted by substituent(s) independently selected from
    hydroxy,
    halogen,
    carboxy,
    mono- or di-C$_1$-C$_3$ alkylamino,
    carbocyclic aryl,
    halogenated carbocyclic aryl,
    heterocyclyl,
    heterocyclyl substituted by substituent(s) independently selected from
      heterocyclyl,
      heterocyclyl substituted by substituent(s) independently selected from
        halogen,
        C$_1$-C$_3$ alkyl,
        halogenated C$_1$-C$_3$ alkyl,
  C$_2$-C$_3$ alkenyloxy,
  C$_1$-C$_3$ alkylcarbonyloxy,
  carbocyclic aryloxy,
  carbocyclic aryloxy substituted by substituent(s) independently selected from
    halogen,
    C$_1$-C$_4$ alkyl,
    halogenated C$_1$-C$_4$ alkyl,
    C$_1$-C$_3$ alkoxy,
  heterocyclyloxy,
  heterocyclyloxy substituted by substituent(s) independently selected from
    halogen,
    C$_1$-C$_3$ alkyl,
    halogenated C$_1$-C$_3$ alkyl,
  (carbocyclic aryl)S(O)$_2$O,
  carboxy,
  C$_1$-C$_3$ alkoxycarbonyl,
  mono- or di-C$_1$-C$_3$ alkylaminocarbonyl,
  mono- or di-C$_1$-C$_3$ alkylaminocarbonyl substituted by carbocyclic aryl,
  amino,
  mono- or di-C$_1$-C$_4$ alkylamino,
  mono- or di-C$_1$-C$_4$ alkylamino substituted by cyano,
  mono- or di-carbocyclic arylamino,
  C$_1$-C$_3$ alkylcarbonylamino,
  carbocyclic arylsulfonylamino,
  carbocyclic arylsulfonylamino substituted by C$_1$-C$_3$ alkyl,
  (carbocyclic aryl)NHC(O)NH,
  (carbocyclic aryl)NHC(O)NH substituted by C$_1$-C$_3$ alkoxy,
  (carbocyclic aryl)NHC(O)NH substituted by haloganated C$_1$-C$_3$ alkoxy,
  C$_1$-C$_3$ alkylthio,
  halogenated C$_1$-C$_3$ alkylthio,
  carbocyclic arylthio,
  halogenated carbocyclic arylthio,
  carbocyclic arylthio substituted by C$_1$-C$_3$ alkyl,
  heterocyclylthio,
  C$_1$-C$_3$ alkylsulfonyl,
  mono- or di-C$_1$-C$_3$ alkylaminosulfonyl,
  carbocyclic aryl,
  carbocyclic aryl substituted by substituent(s) independently selected from
    C$_1$-C$_7$ alkyl,
    halogenated C$_1$-C$_7$ alkyl,
  heterocyclyl,
  heterocyclyl substituted by substituent(s) independently selected from
    C$_1$-C$_3$ alkyl,
    carbocyclic aryl,
    halogenated carbocyclic aryl, (viii) heterocyclyl, or heterocyclyl substituted by substituent(s) independently selected from
  halogen,
  hydroxy,
  cyano,
  nitro,
  C$_1$-C$_4$ alkyl,
  C$_1$-C$_4$ alkyl substituted by substituent(s) independently selected from
    halogen,
    hydroxy,
    oxo,
    C$_1$-C$_3$ alkylcarbonyloxy,
    C$_1$-C$_3$ alkoxycarbonyl,
    C$_1$-C$_3$ alkylthio,
    C$_1$-C$_3$ alkylthio substituted by carbocyclic aryl,
    C$_1$-C$_3$ alkylthio substituted by halogenated carbocyclic aryl,
    carbocyclic aryl, carbocyclic aryl substituted by substituent(s) independently selected from
halogen,
nitro,
heterocyclyl,
$C_1$-$C_3$ alkoxy,
$C_1$-$C_3$ alkoxy substituted by carbocyclic aryl,
carbocyclic aryloxy,
carbocyclic aryloxy substituted by $C_1$-$C_3$ alkyl,
mono- or di-$C_1$-$C_3$ alkylamino,
$C_1$-$C_4$ alkylcarbonylamino,
$C_1$-$C_3$ alkylthio,
carbocyclic arylthio,
halogenated carbocyclic arylthio,
carbocyclic arylthio substituted by $C_1$-$C_3$ alkoxycarbonyl,
heterocyclylthio,
heterocyclylthio substituted by $C_1$-$C_3$ alkyl,
$C_1$-$C_3$ alkylsulfonyl,
carbocyclic arylsulfonyl,
carbocyclic arylsulfonyl substituted by $C_1$-$C_4$ alkyl,
$C_1$-$C_3$ alkoxycarbonyl,
carbocyclic aryl,
carbocyclic aryl substituted by substituent(s) independently selected from
halogen,
nitro,
$C_1$-$C_3$ alkyl,
halogenated $C_1$-$C_3$ alkyl,
$C_1$-$C_3$ alkoxy,
halogenated $C_1$-$C_3$ alkoxy,
heterocyclyl,
heterocyclyl substituted by substituent(s) independently selected from
$C_1$-$C_3$ alkyl,
halogenated $C_1$-$C_3$ alkyl,
$C_1$-$C_3$ alkoxy,
$C_1$-$C_3$ alkoxycarbonyl;
$R_2$ is —$NHNH_2$, —NHNHBoc, —$N(R_{2a})(R_{2b})$, morpholino, 4-acetyl-piperazyl, or 4-phenyl-piperazyl;
wherein $R_{2a}$ is H or $C_1$-$C_3$ alkyl;

$R_{2b}$ is $C_1$-$C_4$ alkyl, $C_1$-$C_4$ alkyl substituted by substituent(s) independently selected from
hydroxy,
$C_1$-$C_3$ alkoxy,
amino,
—NHBoc,
$C_3$-$C_6$ cycloalkyl,
carbocyclic aryl,
carbocyclic aryl substituted by substituent(s) independently selected from
halogen,
$C_1$-$C_3$ alkyl,
$C_1$-$C_3$ alkoxy,
—$SO_2NH_2$,
heterocyclyl, $C_3$-$C_6$ cycloalkyl, carbocyclic aryl, carbocyclic aryl substituted by substituent(s) independently selected from
halogen,
$C_1$-$C_3$ alkyl,
$C_1$-$C_3$ alkoxy,
or a group of Formula IV;
wherein Boc is carbamic acid tert-butyl ester and $R_3$ is $C_1$-$C_3$ alkyl or $C_1$-$C_3$ alkyl substituted by substituent(s) independently selected from
carbocyclic aryl,
halogenated carbocyclic aryl,
carbocyclic aryl substituted by $C_1$-$C_3$ alkoxy;
L is selected from Formula V-XIX;
wherein $R_4$ is H or $C_1$-$C_3$ alkyl;
$R_5$ is H, $C_1$-$C_3$ alkyl, or $C_1$-$C_3$ alkyl substituted by a substituted carbocyclic aryl;
Y is —$(CH_2)_m$, m is 0 or 1;
wherein carbocyclic aryl is phenyl, naphthyl, phenanthryl, or biphenyl;
carbocyclyl is 9H-fluorenyl, 9-oxo-fluorenyl, acenaphthyl, anthraquinonyl, indanyl, or indenyl;
heterocyclyl is 1,2,3-thiadiazolyl, 1,2,3-triazolyl, 1,2-dihydro-3-oxo-pyrazolyl, 1,3,4-thiadiazolyl, 1,3-dioxo-isoindolyl, 1,3-dioxolanyl, 1H-indolyl, 1H-pyrrolo[2,3-c]pyridyl, 1H-pyrrolyl, 2,2',5',2"-terthiophenyl, 2,2'-bithiophenyl, 2,3-dihydro-1-oxo-isoindolyl, 2,3-dihydro-benzo[1,4]dioxinyl, 2,3-dihydro-benzofuryl, 2,4-dihydro-3-oxo-pyrazolyl, 2H-benzopyranyl, 2-oxo-pyrrolidinyl, 3,4-dihydro-2H-benzo[1,4]oxazinyl, 3,4-dihydro-2H-benzo[b][1,4]dioxepinyl, 4H-benzo[1,3]dioxinyl, 4H-benzopyranyl, 4-oxo-1,5,6,7-tetrahydro-indolyl, 4-oxo-benzopyranyl, 9H-carbazolyl, 9H-xanthenyl, azetidinyl, benzimidazolyl, benzo[1,3]dioxolyl, benzo[b]thienyl, benzofuryl, benzothiazolyl, furyl, imidazo[2,1-b]thiazolyl, imidazolyl, isoxazolyl, morpholino, morpholinyl, oxolanyl, piperazyl, piperidyl, pyrazolo[5,1-b]thiazolyl, pyrazolyl, pyridyl, pyrimidyl, pyrrolidyl, quinolyl, quinoxalyl, thiazolidyl, thiazolyl, thienyl, or thiolanyl;
halogen is fluoro, chloro, bromo, or iodo.
Other preferred compounds of this invention are those compounds of Formula I wherein,
Q is Formula II;
$R_1$ represents (i) $C_1$-$C_{10}$ alkyl substituted by substituent(s) independently selected from
methoxy,
methoxy substituted by carbocyclic aryl,
carbocyclic aryloxy,
halogenated carbocyclic aryloxy,
mono-$C_1$-$C_2$ aklylamino substituted by cyano,
mono- or di-$C_1$-$C_2$ alkylamino substituted by carbocyclic aryl,
mono-carbocyclic arylamino,
mono-carbocyclic arylamino substituted by methyl,
carbocyclic arylsulfonylamino substituted by methyl,
carbocyclic aryl,
carbocyclic aryl substituted by substituent(s) independently selected from
halogen,
nitro,
$C_1$-$C_4$ alkyl,
$C_1$-$C_4$ alkyl substituted by carbocyclic aryl,
$C_1$-$C_4$ alkyl substituted by hydroxy,
$C_1$-$C_2$ alkoxy,
halogenated $C_1$-$C_2$ alkoxy,
heterocyclyl substituted by carbocyclic aryl, (ii) $C_2$-$C_8$ alkenyl substituted by substituent(s) independently selected from
methoxy substituted by carbocyclic aryl,
carbocyclic aryl,
carbocyclic aryl substituted by methoxy, (iii) $C_2$-$C_4$ alkynyl substituted by carbocyclic aryl, (iv) cyclohexyl substituted by carbocyclic arylmethyl, (v) carbocyclyl, (vi) carbocyclic aryl, carbocyclic aryl substituted by substituent(s) independently selected from
  halogen,
  hydroxy,
  cyano,
  amino,
  $C_1$-$C_9$ alkyl,
  halogenated $C_1$-$C_9$ alkyl,
  $C_1$-$C_9$ alkoxy,
  $C_1$-$C_9$ alkoxy substituted by substituent(s) independently selected from
    halogen,
    halogenated carbocyclic aryl,
  propenyloxy,
  methylamino,
  di-$C_1$-$C_2$ alkylamino,
  di-$C_1$-$C_2$ alkylamino substituted by cyano,
  methylthio,
  halogenated methylthio, (vii) heterocyclyl, or heterocyclyl substituted by substituent(s) independently selected from
  halogen,
  $C_1$-$C_4$ alkyl,
  $C_1$-$C_4$ alkyl substituted by hydroxy,
  $C_1$-$C_4$ alkyl substituted by carbocyclic aryl,
  methoxy,
  $C_1$-$C_2$ alkoxycarbonyl,
  carbocyclic arylthio substituted by methoxycarbonyl,
  carbocyclic aryl,
  carbocyclic aryl substituted by substituent(s) independently selected from
    halogen,
    halogenated methyl,
    heterocyclyl;
$R_2$ is methylamino or dimethylamino;
L is selected from Formula Va, VIIIa, or IXa;
  wherein $R_4$ and $R_5$ are independently selected from H or $C_1$-$C_3$ alkyl;
  Y is —$(CH_2)_m$, m is 0 or 1;
  wherein carbocyclic aryl is phenyl, naphthyl, phenanthryl, or biphenyl;
  carbocyclyl is 9H-fluorenyl, acenaphthyl, or anthraquinonyl;
  heterocyclyl is 1,2,3-thiadiazolyl, 1,2,3-triazolyl, 1,2-dihydro-3-oxo-pyrazolyl, 1,3-dioxolanyl, 1H-indolyl, 1H-pyrrolyl, 2,2',5',2''-terthiophenyl, 2,2'-bithiophenyl, 2,3-dihydro-benzo[1,4]dioxinyl, 3,4-dihydro-2H-benzo[1,4]oxazinyl, 4-oxo-benzopyranyl, 9H-carbazolyl, 9H-xanthenyl, benzimidazolyl, benzo[1,3]dioxolyl, benzo[b]thienyl, benzofuryl, benzothiazolyl, furyl, imidazolyl, isoxazolyl, oxolanyl, pyrazolo[5,1-b]thiazolyl, pyrazolyl, pyridyl, pyrimidyl, quinolyl, quinoxalyl, thiazolidyl, thiazolyl, thienyl, 2H-benzopyranyl, 4H-benzo[1,3]dioxinyl, azetidinyl, imidazo[2,1-b]thiazolyl, morpholinyl, or 2,3-dihydro-benzofuryl;
  halogen is fluoro, chloro, bromo, or iodo.

Other more preferred compounds of this invention are those compounds of Formula I wherein,
  Q is Formula II;
  $R_1$ represents (i) $C_1$-$C_7$ alkyl substituted by substituent(s) independently selected from
  methoxy,
  methoxy substituted by carbocyclic aryl,
  carbocyclic aryloxy,
  halogenated carbocyclic aryloxy,
  mono-ethylamino substituted by cyano,
  di-methylamino substituted by carbocyclic aryl,
  mono-carbocyclic arylamino,
  mono-carbocyclic arylamino substituted by methyl,
  carbocyclic arylsulfonylamino substituted by methyl,
  carbocyclic aryl,
  carbocyclic aryl substituted by substituent(s) independently selected from
    halogen,
    nitro,
    $C_1$-$C_4$ alkyl,
    $C_1$-$C_4$ alkyl substituted by carbocyclic aryl,
    $C_1$-$C_4$ alkyl substituted by hydroxy,
    metoxy,
    halogenated methoxy,
    heterocyclyl substituted by carbocyclic aryl, (ii) $C_2$-$C_7$ alkenyl substituted by substituent(s) independently selected from
  methoxy substituted by carbocyclic aryl,
  carbocyclic aryl,
  carbocyclic aryl substituted by methoxy, (iii) butynyl substituted by carbocyclic aryl, (iv) cyclohexyl substituted by carbocyclic arylmethyl, (v) carbocyclyl, (vi) carbocyclic aryl, carbocyclic aryl substituted by substituent(s) independently selected from
  halogen,
  hydroxy,
  cyano,
  amino,
  $C_1$-$C_2$ alkyl,
  halogenated methyl,
  $C_1$-$C_3$ alkoxy,
  $C_1$-$C_3$ alkoxy substituted by substituent(s) independently selected from
    halogen,
    halogenated carbocyclic aryl,
  propenyloxy,
  di-$C_1$-$C_2$ alkylamino,
  di-$C_1$-$C_2$ alkylamino substituted by cyano,
  methylthio,
  halogenated methylthio, (vii) heterocyclyl, or heterocyclyl substituted by substituent(s) independently selected from
  halogen,
  $C_1$-$C_3$ alkyl,
  $C_1$-$C_3$ alkyl substituted by hydroxy,
  $C_1$-$C_3$ alkyl substituted by carbocyclic aryl,
  methoxy,
  ethoxycarbonyl,
  carbocyclic arylthio substituted by methoxycarbonyl,
  carbocyclic aryl,
  carbocyclic aryl substituted by substituent(s) independently selected from
    halogen,
    halogenated methyl,
    heterocyclyl;
$R_2$ is methylamino or dimethylamino;
L is selected from Formula XX-XXII;

Y is —(CH$_2$)$_m$, m is 0 or 1;

wherein carbocyclic aryl is phenyl, naphthyl, or biphenyl;

carbocyclyl is acenaphthyl;

heterocyclyl is 1H-indolyl, 1H-pyrrolyl, 2,3-dihydro-benzo[1,4]dioxinyl, 9H-carbazolyl, benzo[1,3]dioxolyl, furyl, pyrazolyl, thienyl, 4-oxo-benzopyranyl, azetidinyl, imidazo[2,1-b]thiazolyl, pyridyl, imidazolyl, 2,3-dihydro-benzofuryl, or benzo[b]thienyl;

halogen is fluoro, chloro, bromo, or iodo.

The following compounds are specially preffered;

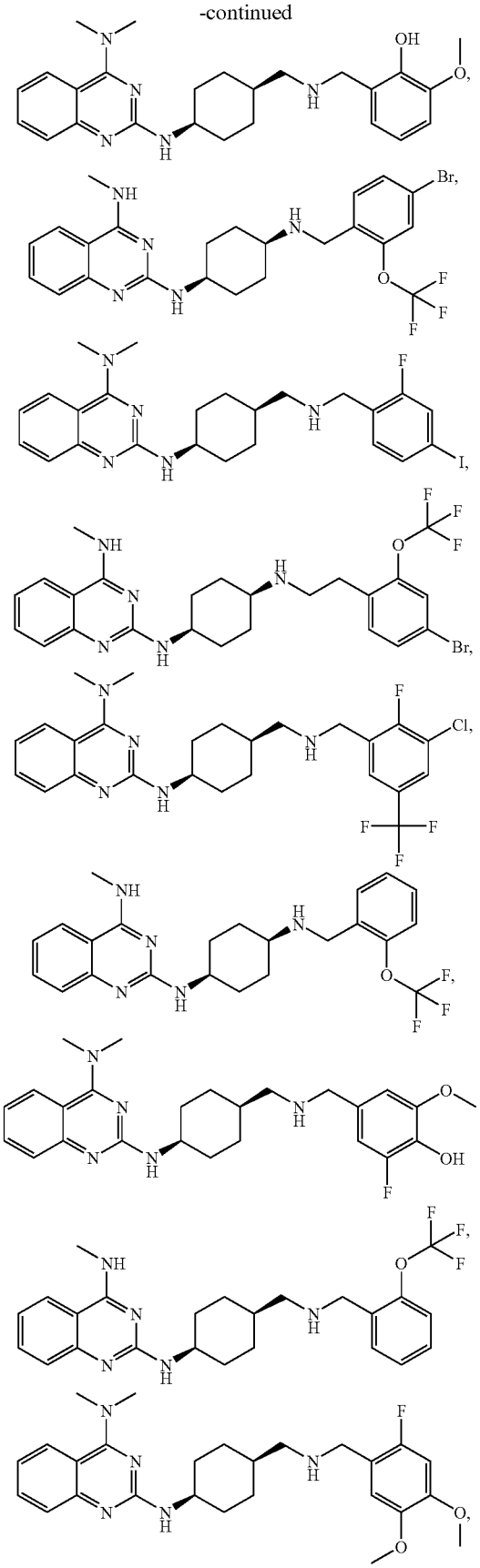

249
-continued
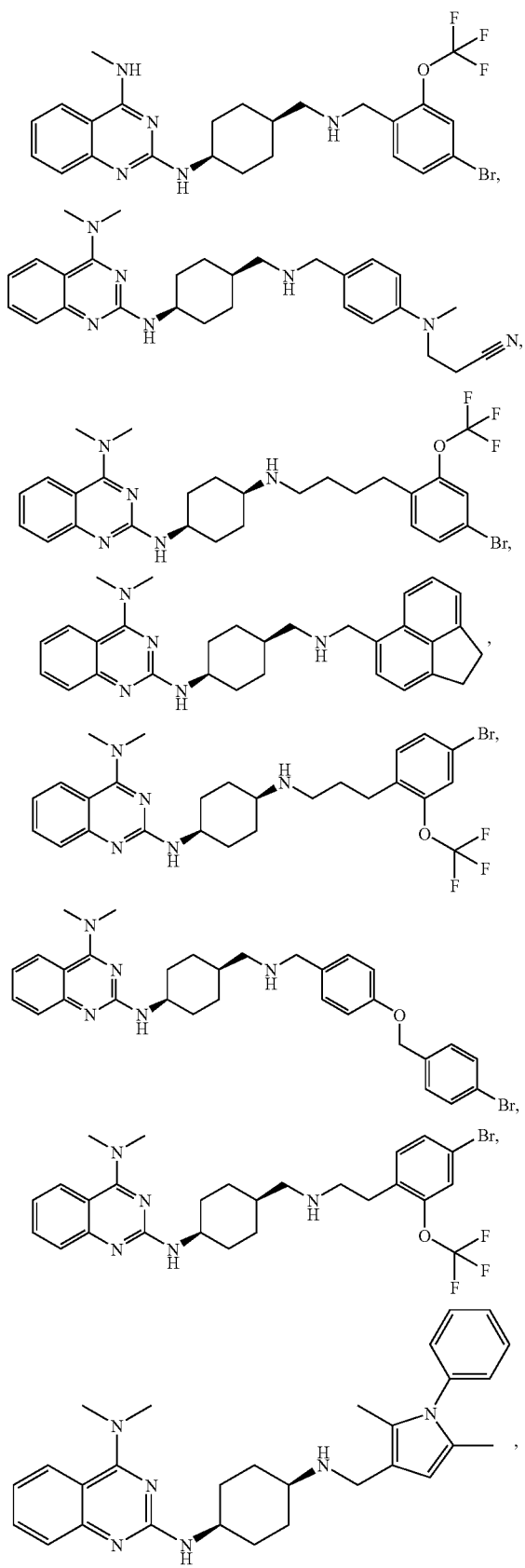
250
-continued
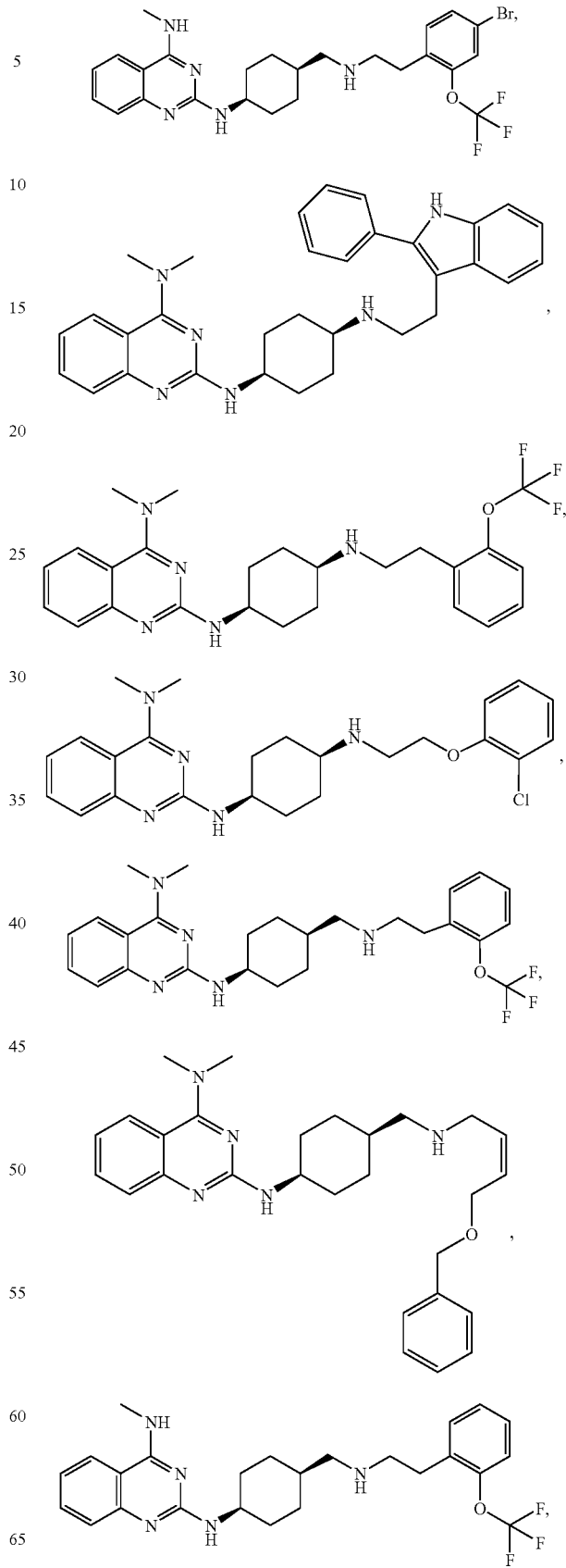

251
-continued
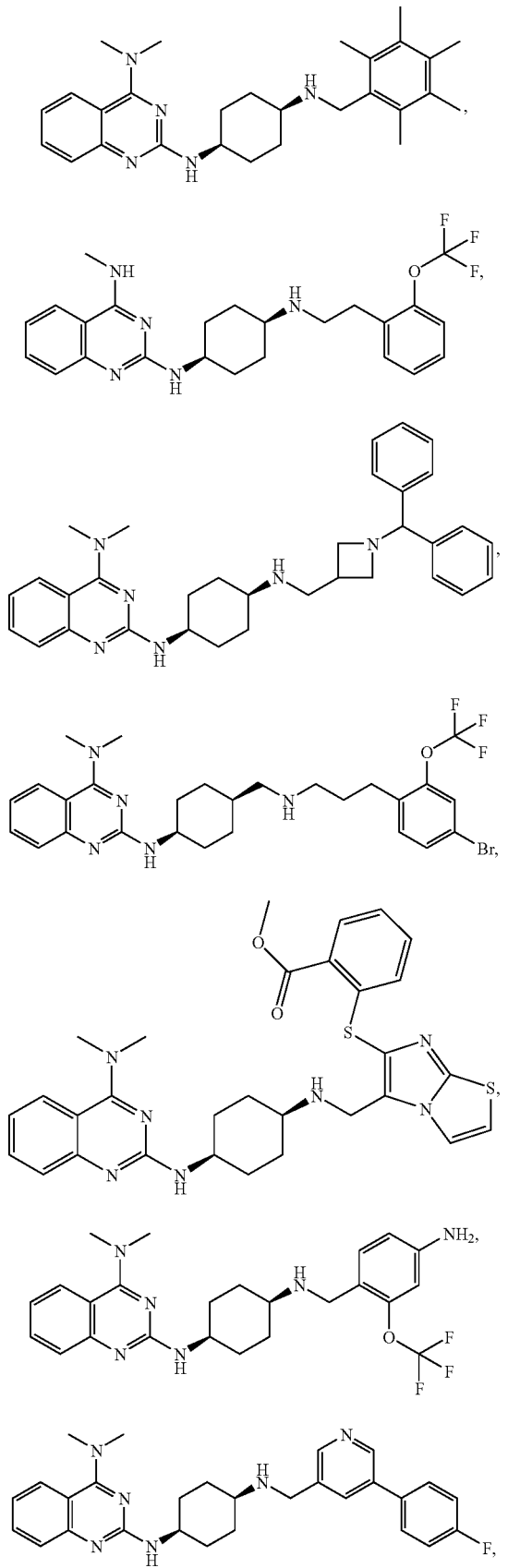
252
-continued
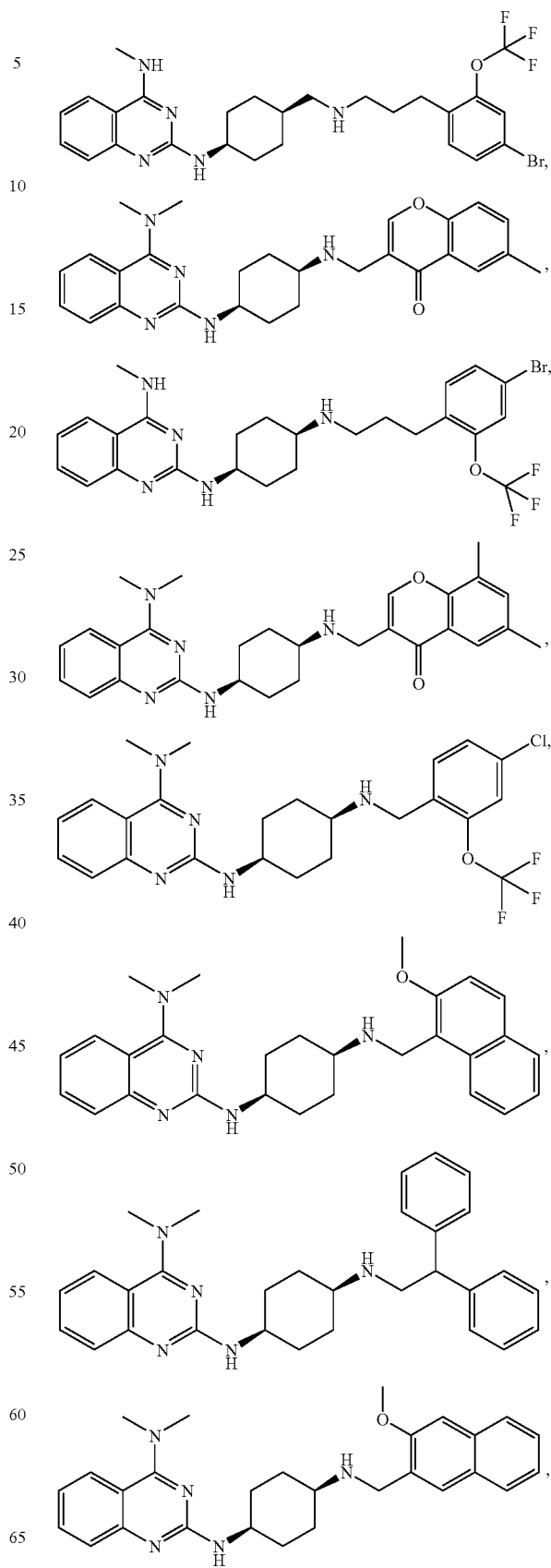

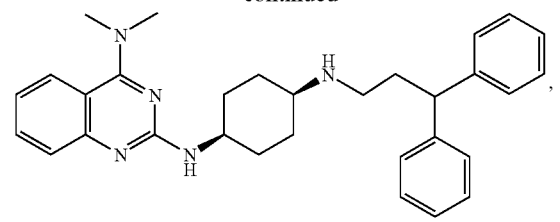
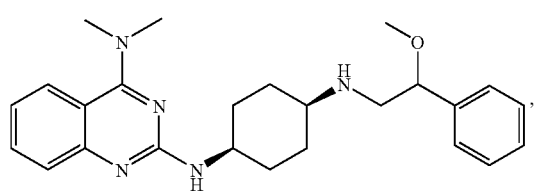
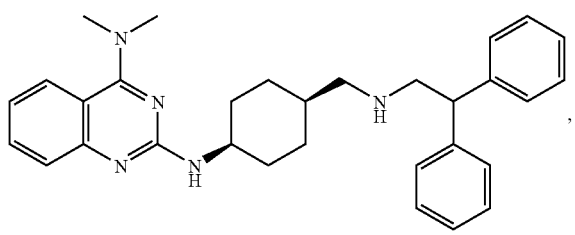
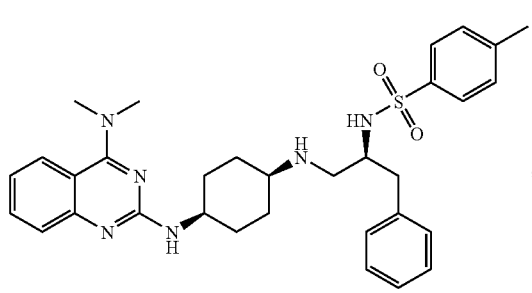
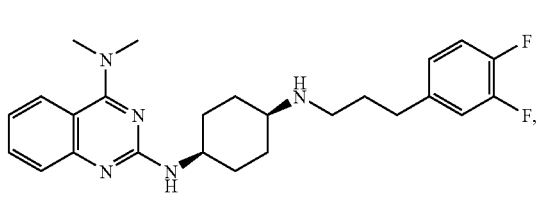
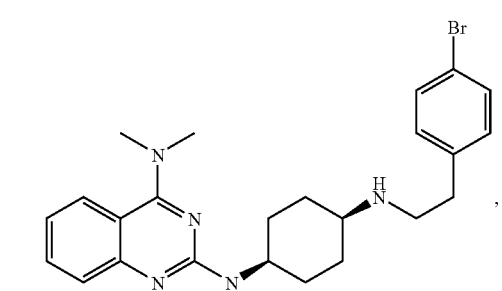
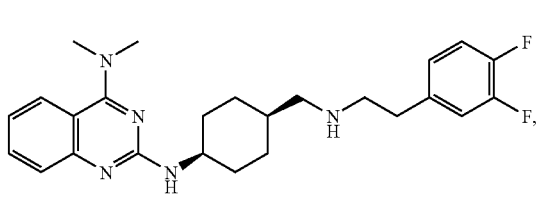
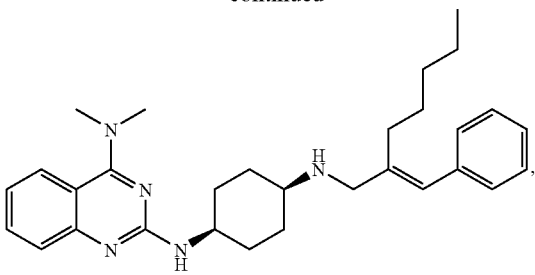
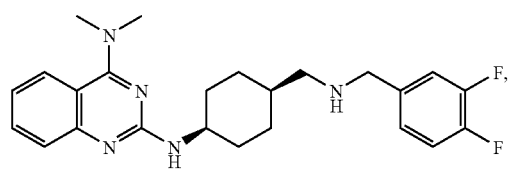
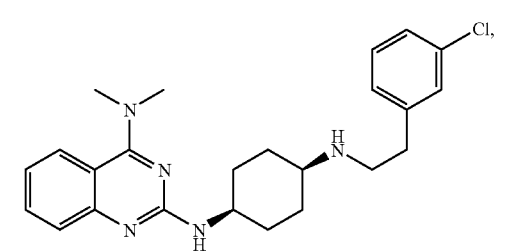
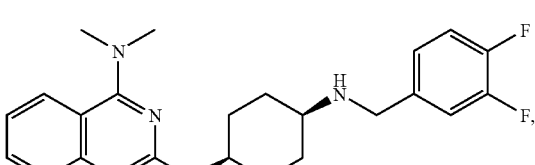
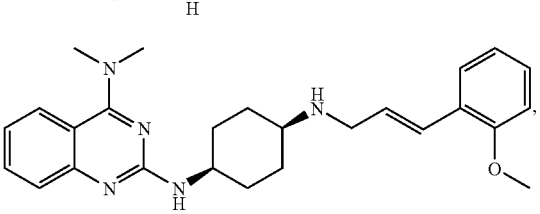
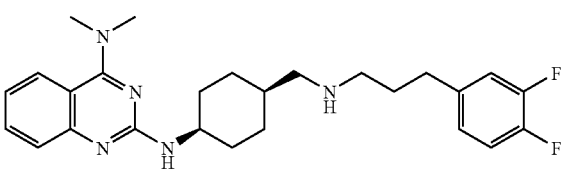
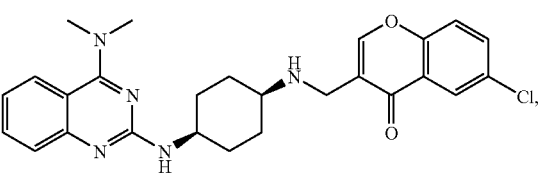
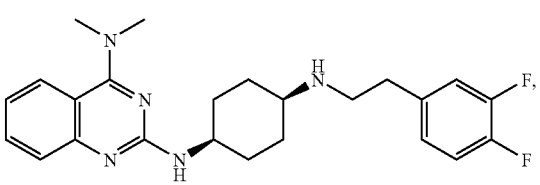

-continued
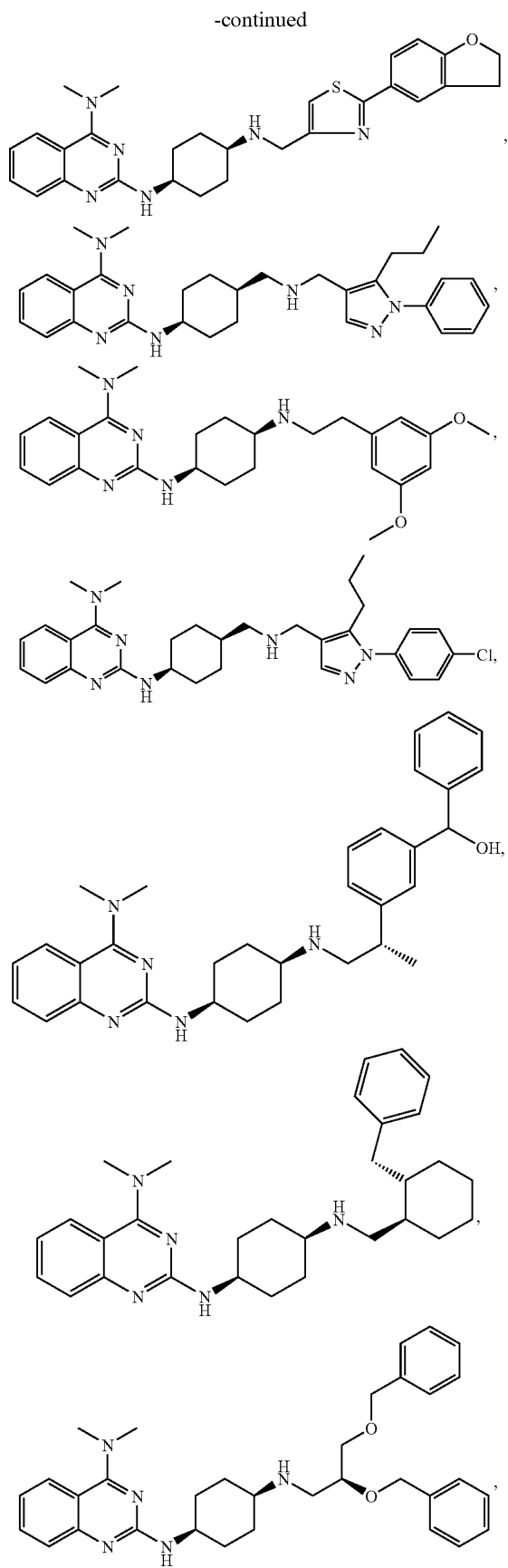
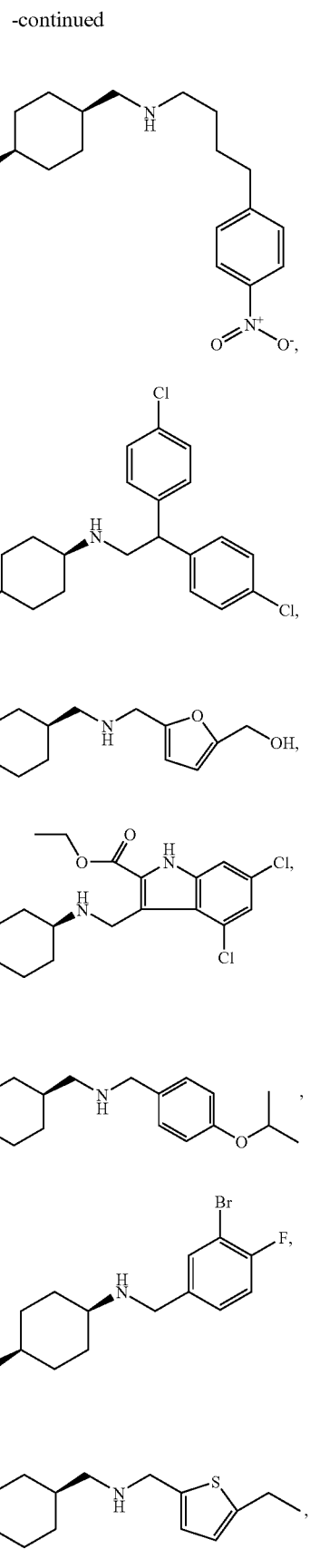

257
-continued
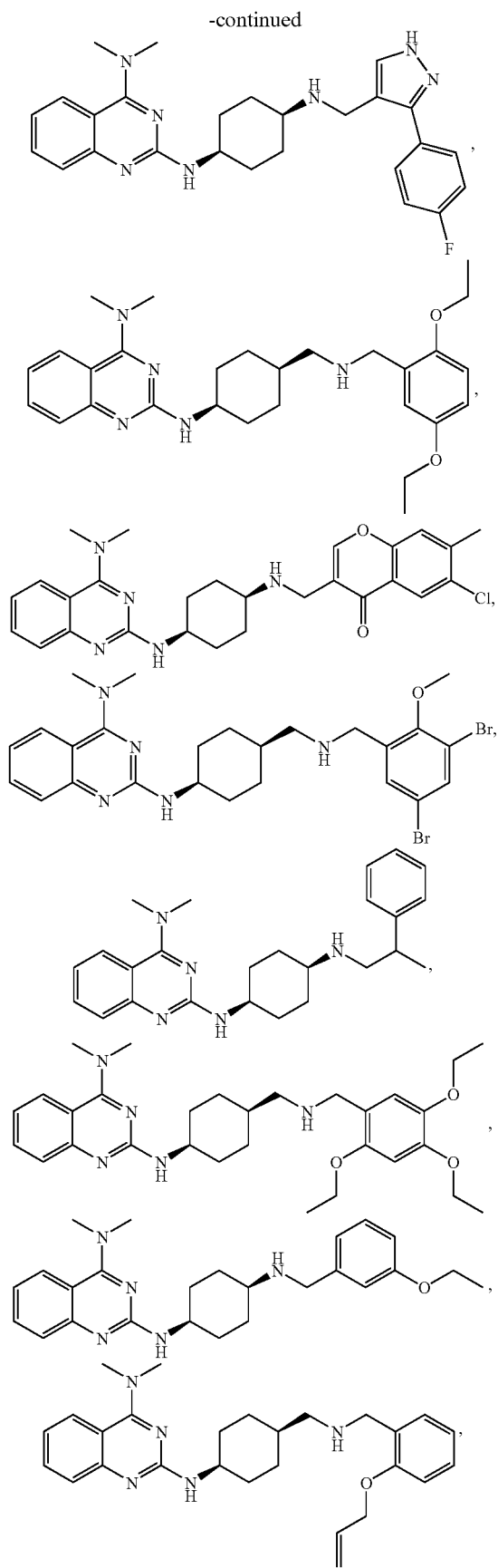
258
-continued
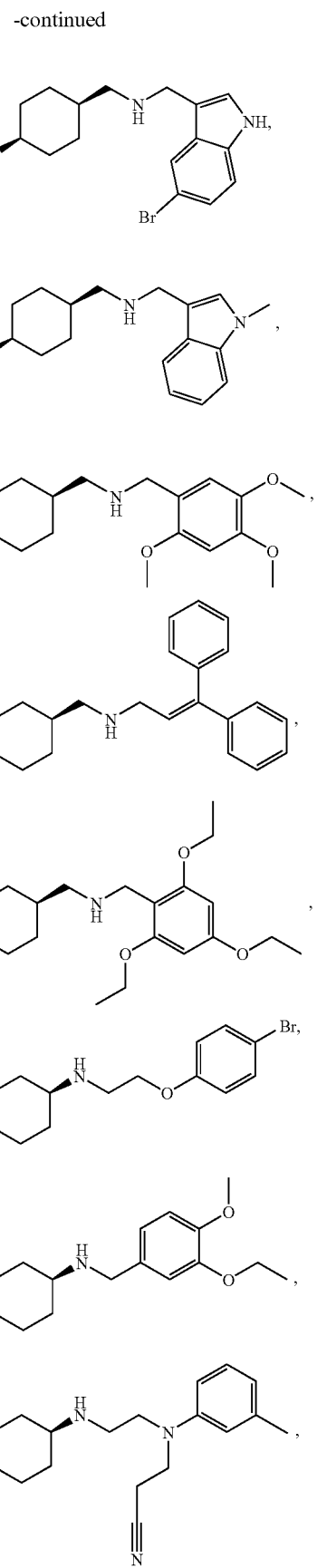

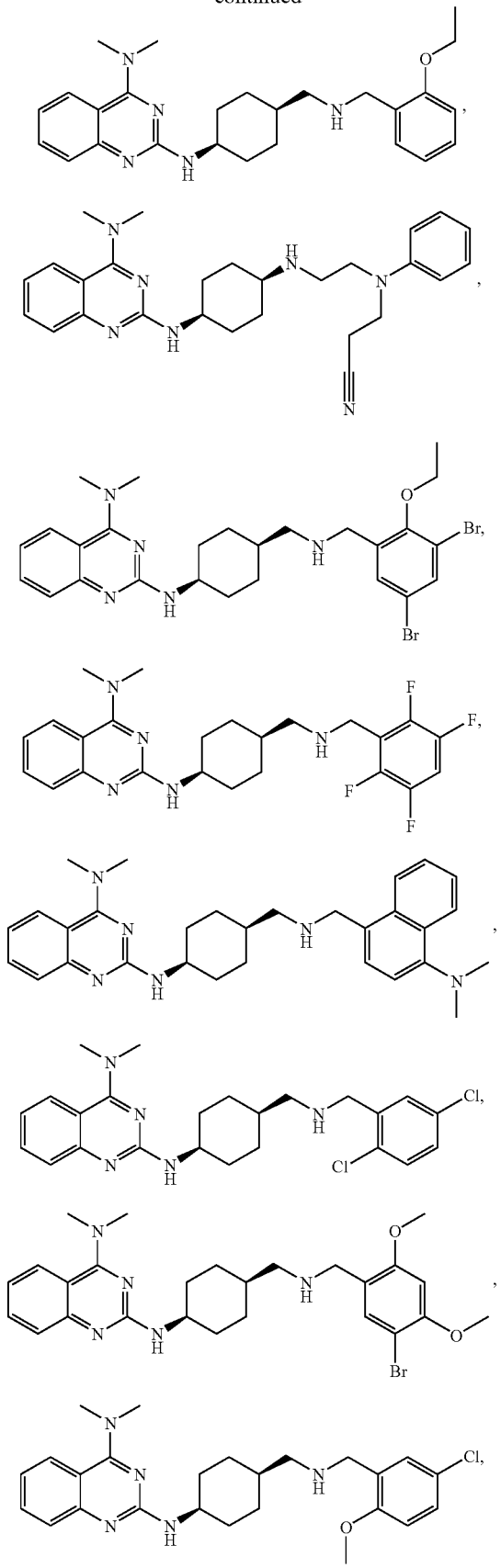
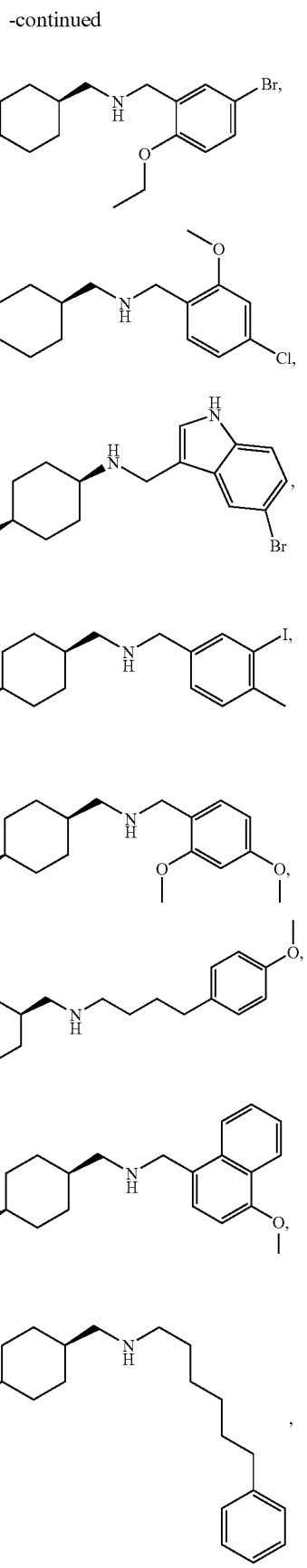

-continued
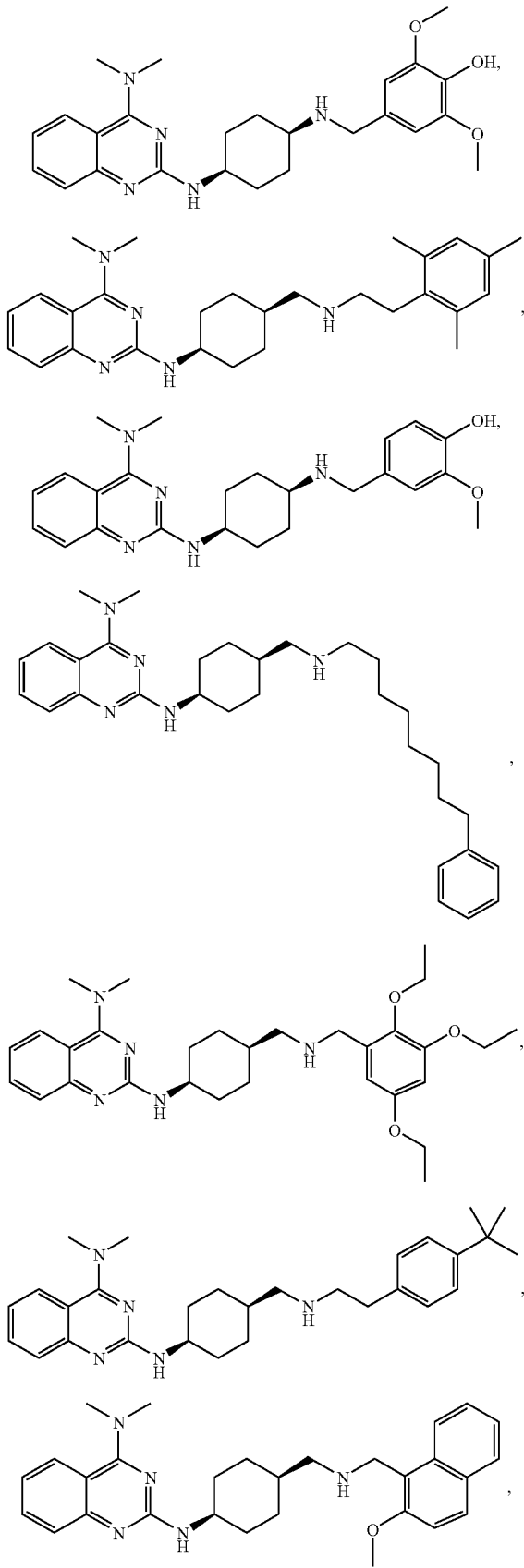
-continued
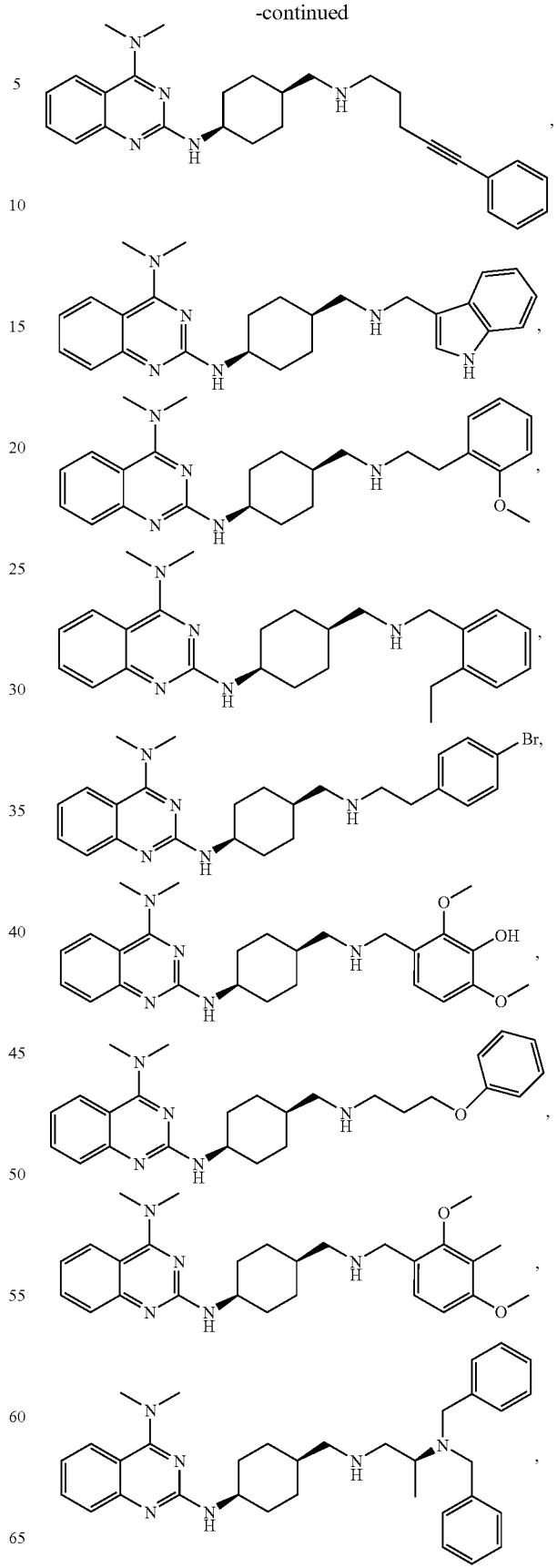

-continued
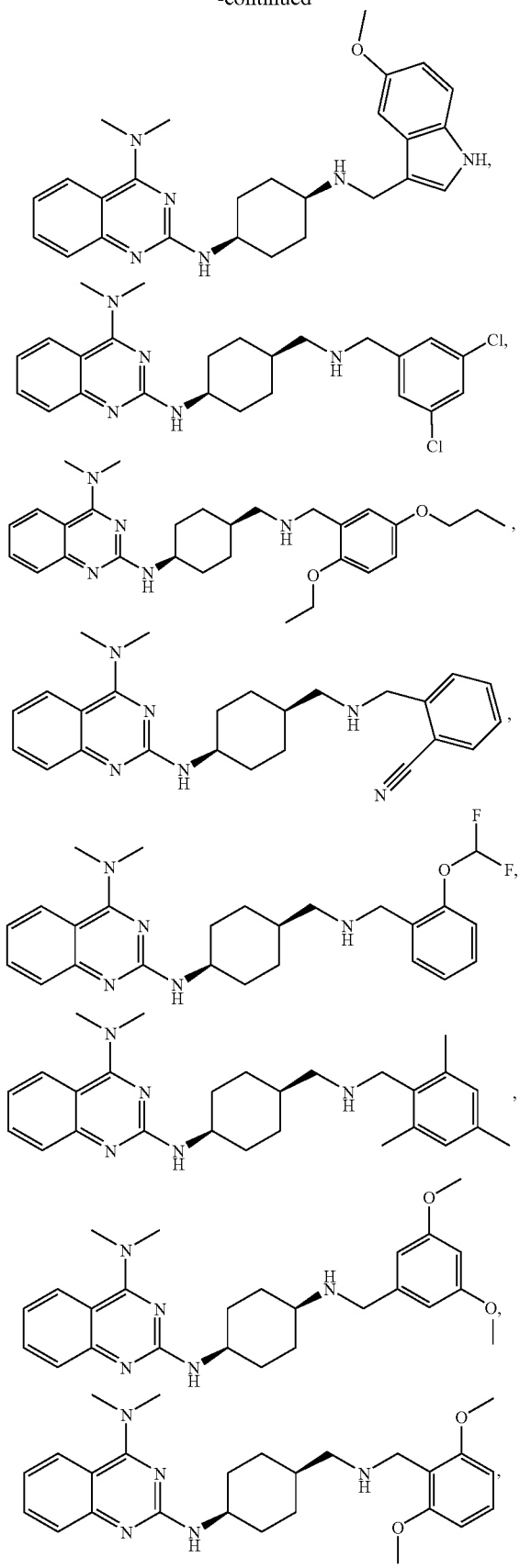
-continued
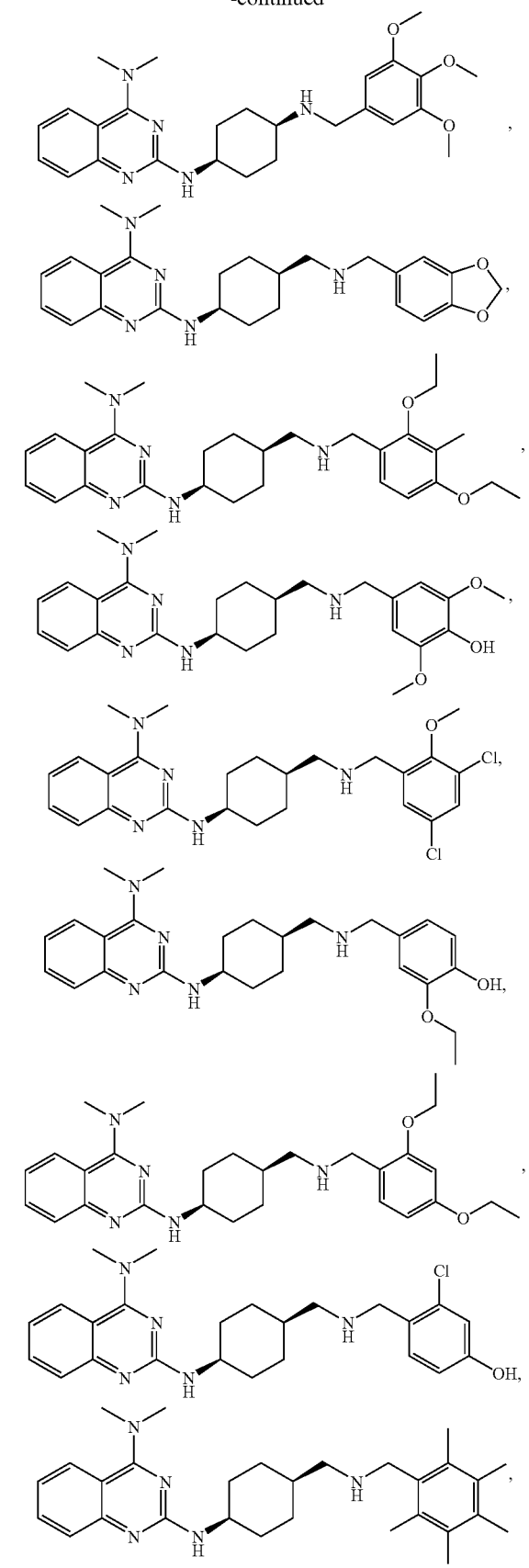

-continued
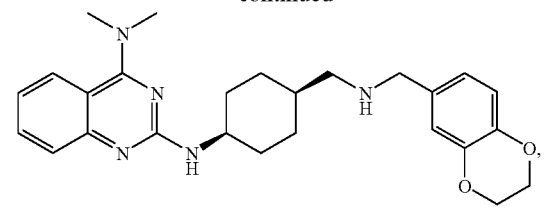
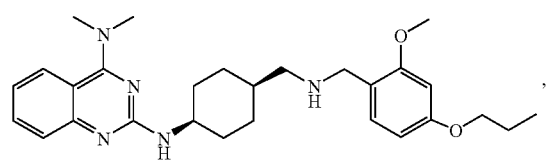
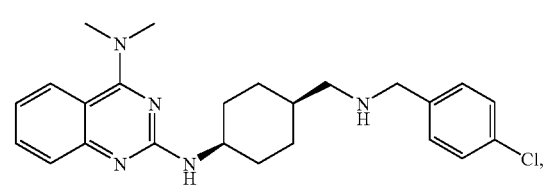
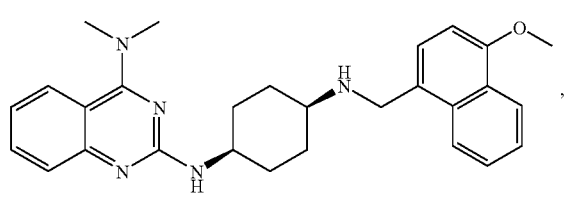
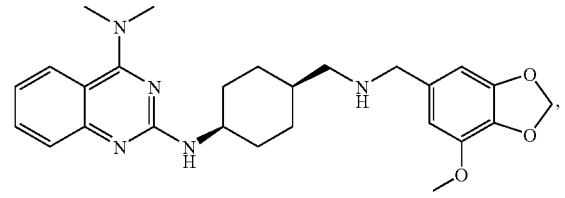
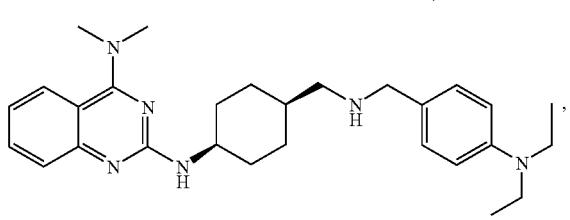
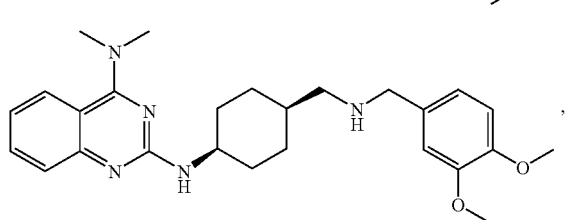
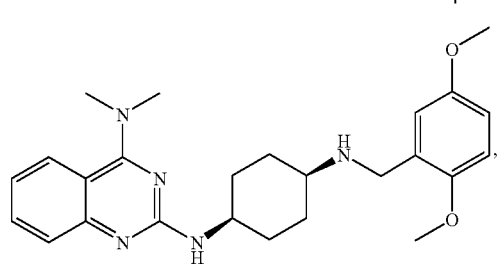
-continued
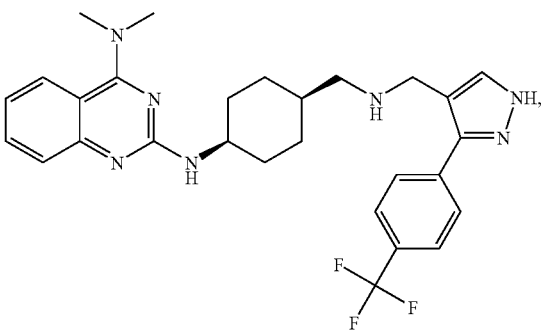
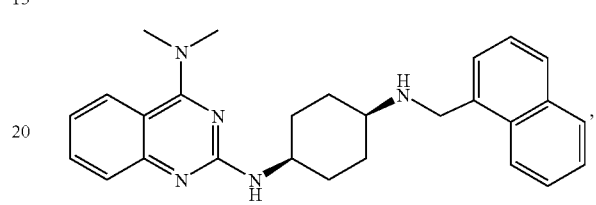
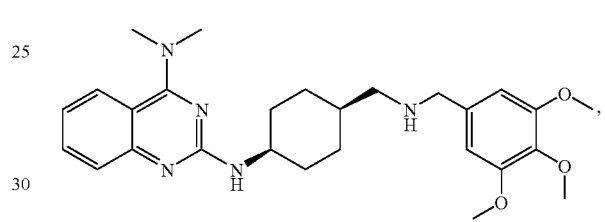

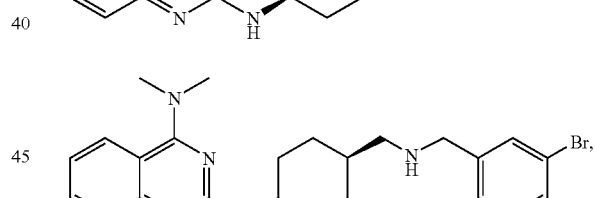
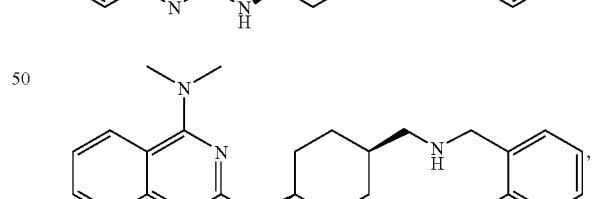

267
-continued
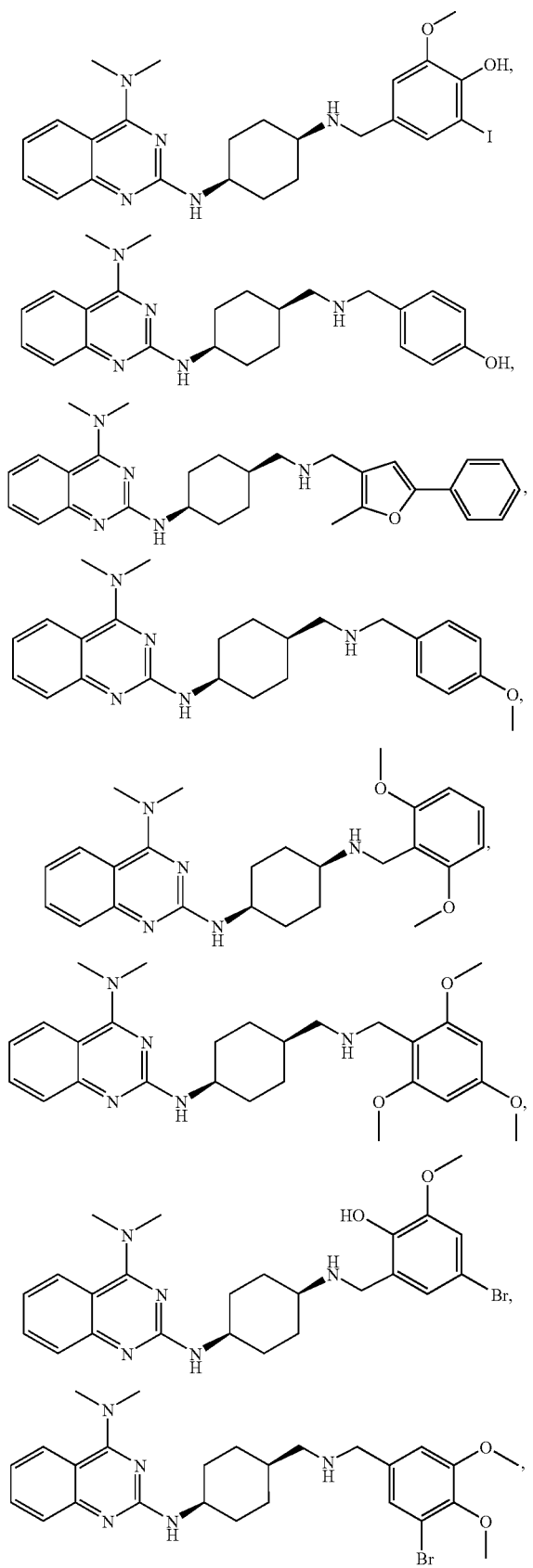
268
-continued
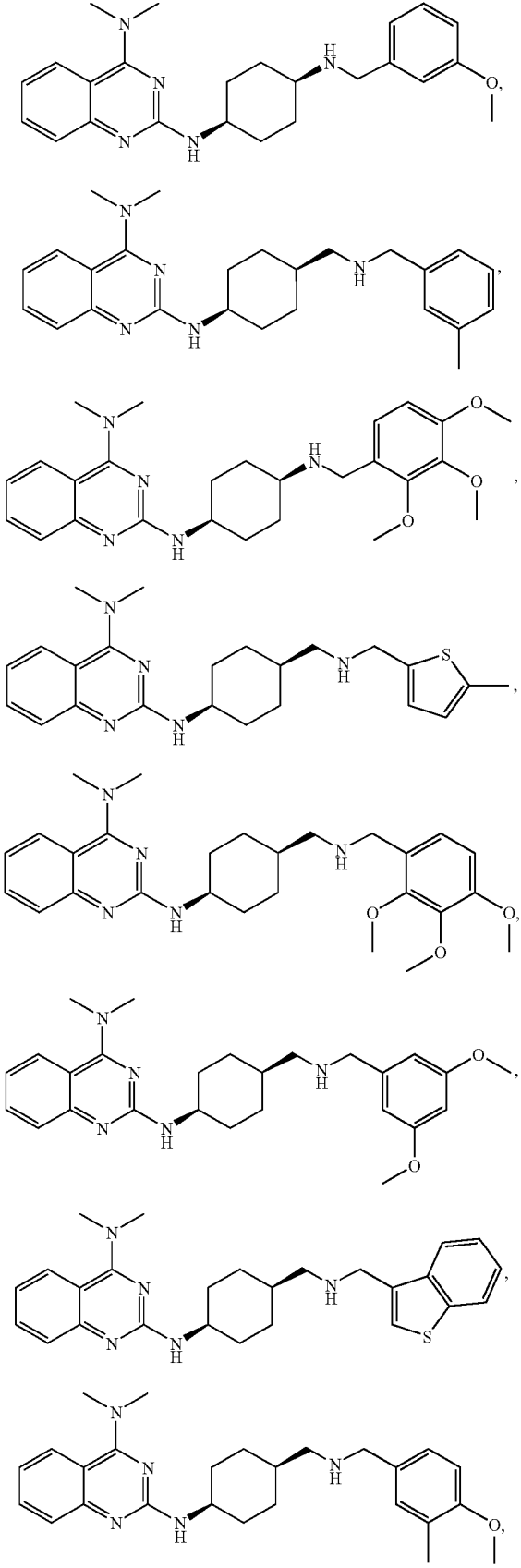

269
-continued
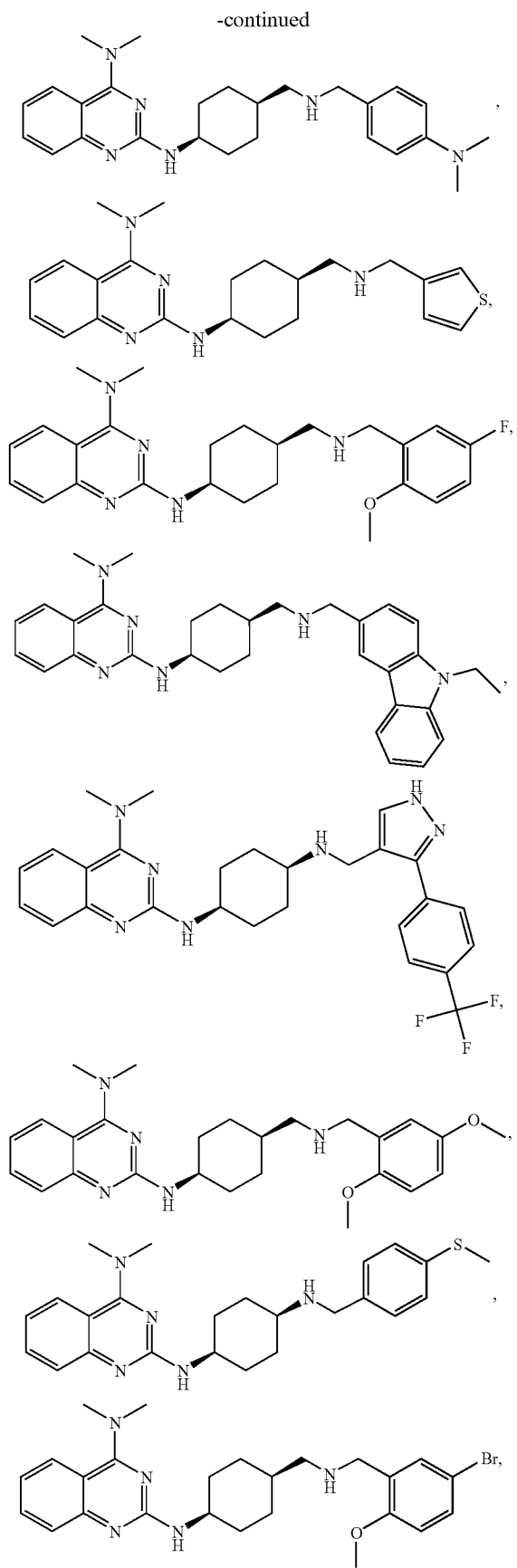
270
-continued
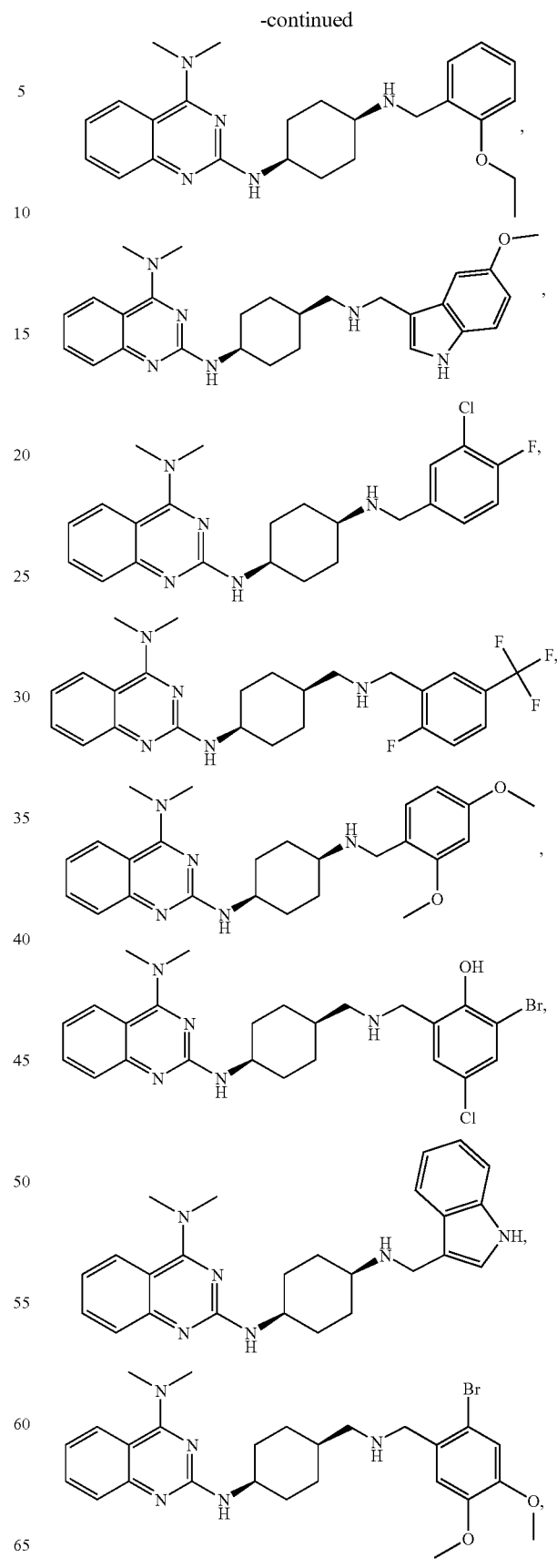

-continued
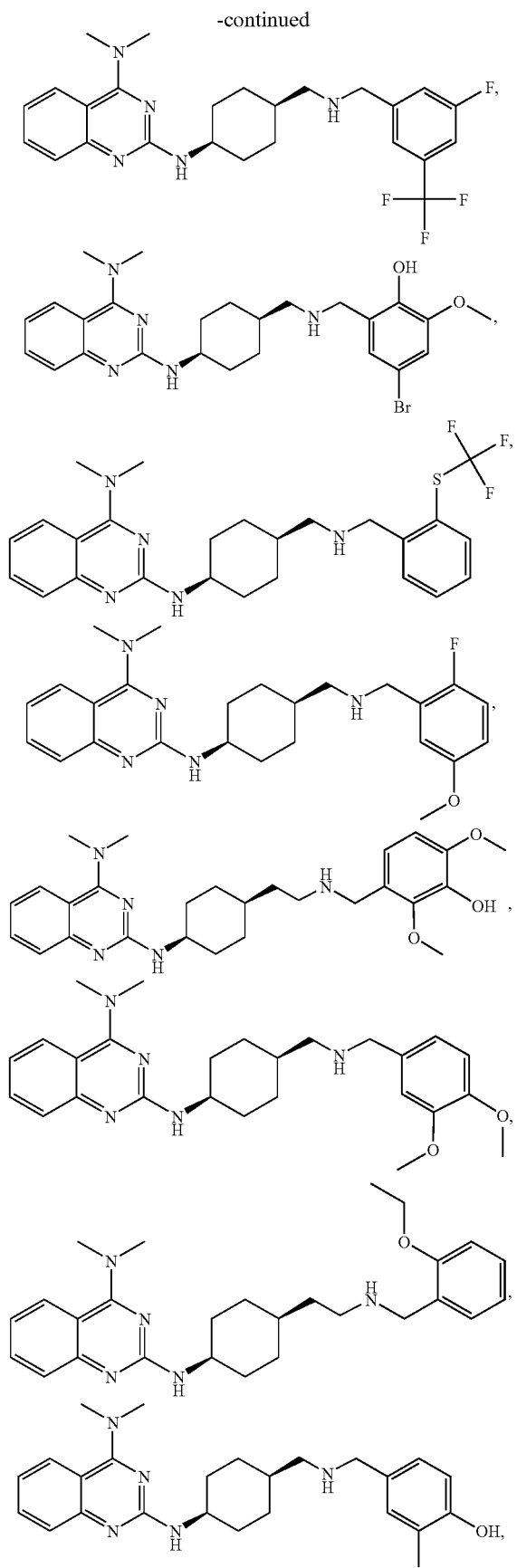
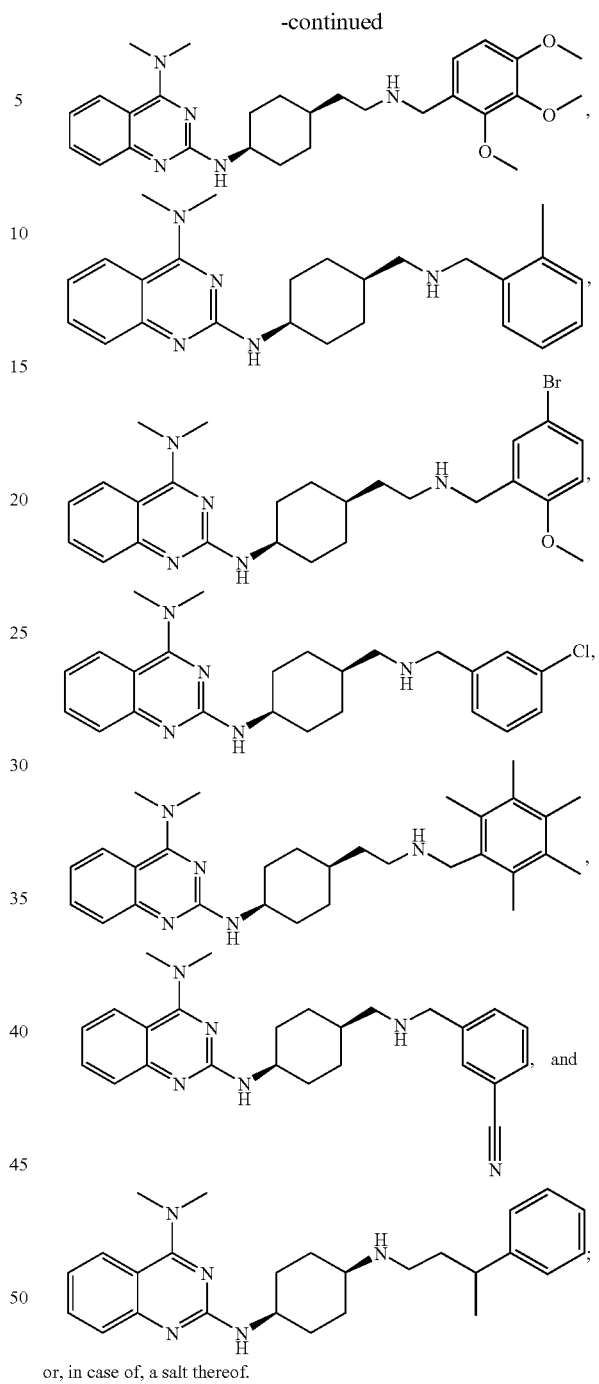
or, in case of, a salt thereof.
Preferred compounds of this invention are those compounds of Formula I wherein,
Q is Formula II;
$R_1$ represents
(i) $C_1$-$C_{16}$ alkyl,
$C_1$-$C_{16}$ alkyl substituted by substituent(s) independently selected from
halogen,
carbocyclyl,
carbocyclic aryl, carbocyclic aryl substituted by substituent(s) independently selected from
  halogen,
  nitro,
  $C_1$-$C_3$ alkyl,
  halogenated $C_1$-$C_3$ alkyl,
(ii) $C_2$-$C_3$ alkenyl,
$C_2$-$C_3$ alkenyl substituted by carbocyclic aryl,
(iii) carbocyclic aryl,
carbocyclic aryl substituted by substituent(s) independently selected from
  halogen,
  cyano,
  nitro,
  $C_1$-$C_5$ alkyl,
  $C_1$-$C_5$ alkyl substituted by substituent(s) independently selected from
    halogen,
    oxo,
    $C_2$-$C_3$ alkenyl,
    $C_1$-$C_4$ alkoxy,
  $C_1$-$C_4$ alkoxy substituted by substituent(s) independently selected from
    halogen,
    heterocyclyl,
    halogenated heterocyclyl,
  carbocyclic aryloxy,
  carbocyclic aryloxy substituted by substituent(s) independently selected from
    halogen,
    nitro,
  heterocyclyloxy,
  heterocyclyloxy substituted by substituent(s) independently selected from
    halogen,
    $C_1$-$C_3$ alkyl,
    halogenated $C_1$-$C_3$ alkyl,
  $C_1$-$C_3$ alkoxycarbonyl,
  mono- or di-$C_1$-$C_4$ alkylamino,
  $C_1$-$C_3$ alkylcarbonylamino,
  carbocyclic aryl diazo,
  carbocyclic aryl diazo substituted by mono- or di-$C_1$-$C_3$ alkylamino,
  $C_1$-$C_3$ alkylsulfonyl,
  carbocyclic aryl,
(iv) heterocyclyl,
or heterocyclyl substituted by substituent(s) independently selected from
  halogen,
  $C_1$-$C_3$ alkyl,
  $C_1$-$C_3$ alkyl substituted by substituent(s) independently selected from
    halogen,
    oxo,
    carbocyclic arylcarbonylamino,
    halogenated carbocyclic arylcarbonylamino,
    heterocyclyl,
    heterocyclyl substituted by substituent(s) independently selected from
      halogen,
      $C_1$-$C_3$ alkyl,
      halogenated $C_1$-$C_3$ alkyl,
  $C_1$-$C_3$ alkoxy,
  $C_1$-$C_3$ alkylcarbonylamino,
  carbocyclic arylsulfonyl,
  $C_1$-$C_3$ alkoxycarbonyl,
  carbocyclic aryl,
  halogenated carbocyclic aryl,
  heterocyclyl,
  heterocyclyl substituted by substituent(s) independently selected from
    halogen,
    $C_1$-$C_3$ alkyl,
    halogenated $C_1$-$C_3$ alkyl;
    $R_2$ is —NHNH$_2$, —NHNHBoc, —N($R_{2a}$)($R_{2b}$); morpholino, 4-acetyl-piperazyl, or 4-phenyl-piperazyl;
wherein $R_{2a}$ is H or $C_1$-$C_3$ alkyl;
$R_{2b}$ is $C_1$-$C_4$ alkyl, $C_1$-$C_4$ alkyl substituted by substituent(s) independently selected from
  hydroxy,
  $C_1$-$C_3$ alkoxy,
  amino,
  —NHBoc,
  $C_3$-$C_6$ cycloalkyl,
  carbocyclic aryl,
  carbocyclic aryl substituted by substituent(s) independently selected from
    halogen,
    $C_1$-$C_3$ alkyl,
    $C_1$-$C_3$ alkoxy,
    —SO$_2$NH$_2$,
  heterocyclyl,
$C_3$-$C_6$ cycloalkyl, carbocyclic aryl, carbocyclic aryl substituted by substituent(s) independently selected from
  halogen,
  $C_1$-$C_3$ alkyl,
  $C_1$-$C_3$ alkoxy,
or a group of Formula IV;
  wherein Boc is carbamic acid tert-butyl ester and $R_3$ is $C_1$-$C_3$ alkyl or $C_1$-$C_3$ alkyl substituted by substituent(s) independently selected from
    carbocyclic aryl,
    halogenated carbocyclic aryl,
    carbocyclic aryl substituted by $C_1$-$C_3$ alkoxy;
  L is selected from Formula V-XIX;
  wherein $R_4$ is H or $C_1$-$C_3$ alkyl;
  $R_5$ is H, $C_1$-$C_3$ alkyl, or $C_1$-$C_3$ alkyl substituted by a substituted carbocyclic aryl;
  Y is —S(O)$_2$—;
wherein carbocyclic aryl is phenyl, naphthyl, or biphenyl;
carbocyclyl is 7,7-dimethyl-2-oxo-bicyclo[2.2.1]heptyl;
heterocyclyl is 1,2,3,4-tetrahydro-isoquinolyl, 1,2,3-thiadiazolyl, 1H-pyrrolyl, benzo[2,1,3]oxadiazolyl, benzo[b]thienyl, furyl, imidazolyl, isoxazolyl, pyrazolyl, pyridyl, quinolyl, thiazolyl, or thienyl;
halogen is fluoro, chloro, bromo, or iodo.

The following compounds are specially preffered;
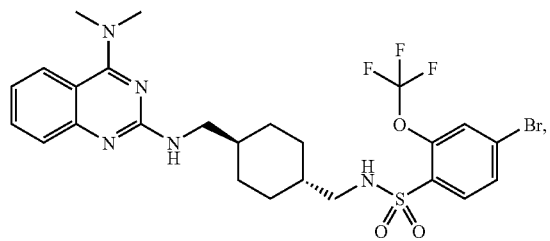
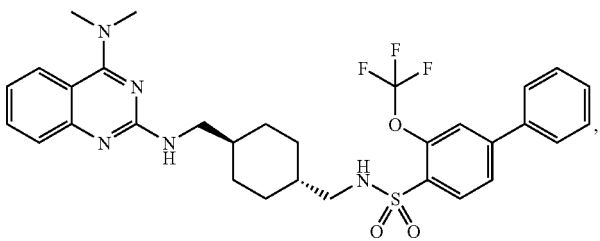
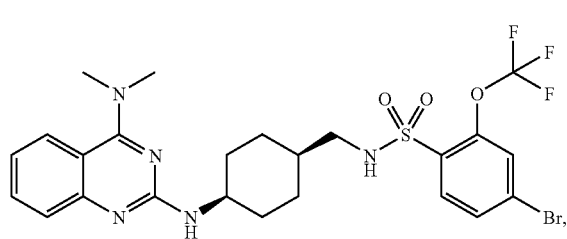
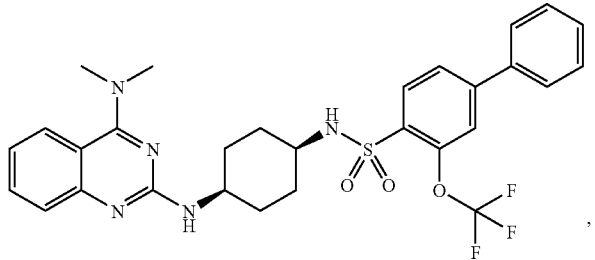
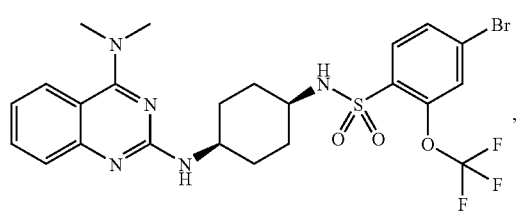
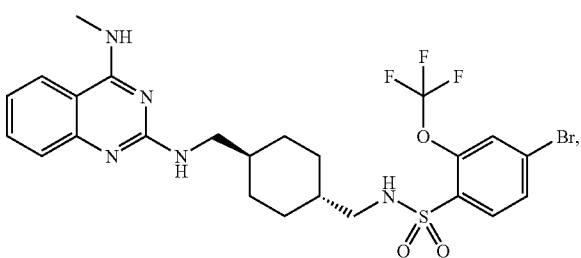
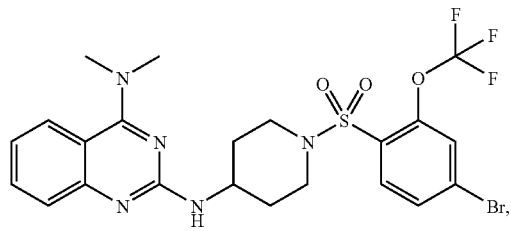
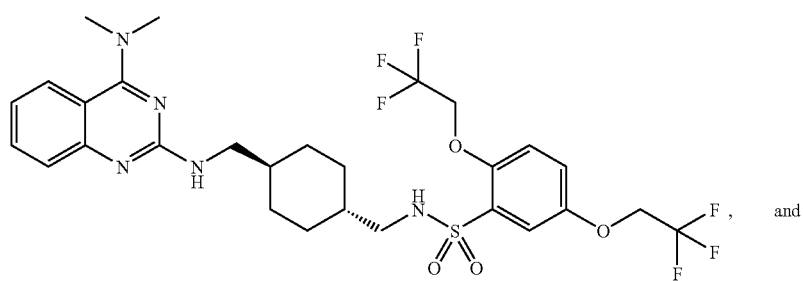 and
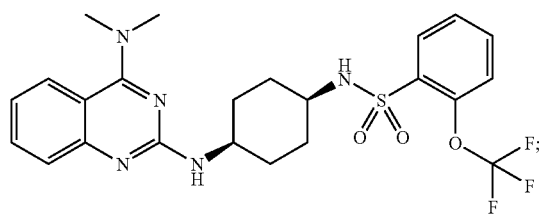 or a salt thereof.

Preferred compounds of this invention are those compounds of Formula I wherein,

Q is Fomura II;
$R_1$ is selected from H, —$CO_2^tBu$, or —$CO_2Bn$ (Bn is a benzyl group);
$R_2$ is methylamino or dimethylamino;
L is selected from Formula XX-XXII;
Y is a single bond;
or a salt thereof.

One embodiment of the invention includes any compound of the invention which selectively binds an MCH receptor, such selective binding is preferably demonstrated by a Ki for one or more other GPCR(s), preferably NPY, being at least 10-fold greater than the Ki for any particular MCH receptor, preferable MCHR1.

As used herein, the term "alkyl" is intended to denote hydrocarbon compounds including straight chain and branched chain, including for example but not limited to methyl, ethyl, n-propyl, isopropyl, n-butyl, sec-butyl, tert-butyl, n-pentyl, isopentyl, tert-pentyl, n-hexyl, and the like.

The term "alkoxy" is intended to denote substituents of the formula

—O-alkyl.

At various places in the present specification substituents of compounds of the invention are disclosed in groups. It is specifically intended that the invention include each and every individual subcombination of the members of such groups.

G-protein coupled receptors (GPCRs) represent a major class of cell surface receptors with which many neurotransmitters interact to mediate their effects. GPCRs are predicted to have seven membrane-spanning domains and are coupled to their effectors via G-proteins linking receptor activation with intracellular biochemical sequelae such as stimulation of adenylyl cyclase. Melanin Concentrating Hormone (MCH), a cyclic peptide, has been identified as the endogenous ligand of the orphan G-protein coupled receptor SLC-1. See, for example, Shimomura et al., Biochem. Biophys. Res. Commun. 261, 622-26 (1999). Studies have indicated that MCH acts as a neurotransmitter/modulator/regulator to alter a number of behavioral responses.

Mammalian MCH (19 amino acids) is highly conserved between rat, mouse, and human, exhibiting 100% amino acid identity, but its physiological roles are less clear. MCH has been reported to participate in a variety of processes including feeding, water balance, energy metabolism, general arousal/attention state, memory and cognitive functions, and psychiatric disorders. For reviews, see 1. Baker, Int. Rev. Cytol. 126:1-47 (1991); 2. Baker, TEM 5:120-126 (1994); 3. Nahon, Critical Rev. in Neurobiol 221:221-262, (1994); 4. Knigge et al., Peptides 18(7):1095-1097, (1996). The role of MCH in feeding or body weight regulation is supported by Qu et al., Nature 380:243-247, (1996), demonstrating that MCH is over expressed in the hypothalamus of ob/ob mice compared with ob/+mice, and that fasting further increased MCH mRNA in both obese and normal mice during fasting. MCH also stimulated feeding in normal rats when injected into the lateral ventricles as reported by Rossi et al., Endocrinology 138:351-355, (1997). MCH also has been reported to functionally antagonize the behavioral effects of α-MSH; see: Miller et al., Peptides 14:1-10, (1993); Gonzalez et al, Peptides 17:171-177, (1996); and Sanchez et al., Peptides 18:3933-396, (1997). In addition, stress has been shown to increase POMC mRNA levels while decreasing the MCH precursor pre-proMCH (ppMCH) mRNA levels; Presse et al., Endocrinology 131:1241-1250, (1992). Thus MCH may serve as an integrative neuropeptide involved in the reaction to stress, as well as in the regulation of feeding and sexual activity; Baker, Int. Rev. Cytol. 126:1-47, (1991); Knigge et al., Peptides 17:1063-1073, (1996).

The localization and biological activities of MCH peptide suggest that the modulation of MCH receptor activity may be useful in a number of therapeutic applications. MCH is expressed in the lateral hypothalamus, a brain area implicated in the regulation of thirst and hunger: Grillon et al., Neuropeptides 31:131-136, (1997); recently orexins A and B, which are potent orexigenic agents, have been shown to have very similar localization to MCH in the lateral hypothalamus; Sakurai et al., Cell 92:573-585 (1998). MCH mRNA levels in this brain region are increased in rats after 24 hours of food-deprivation; Herve and Fellmann, Neurpeptides 31:237-242 (1997); after insulin injection, a significant increase in the abundance and staining intensity of MCH immunoreactive perikarya and fibres was observed concurrent with a significant increase in the level of MCH mRNA; Bahjaoui-Bouhaddi et al., Neuropeptides 24:251-258, (1994). Consistent with the ability of MCH to stimulate feeding in rats; Rossi et al., Endocrinology 138:351-355, (1997); is the observation that MCH mRNA levels are upregulated in the hypothalami of obese ob/ob mice; Qu et al., Nature 380:243-247, (1996); and decreased in the hypothalami of rats treated with leptin, whose food intake and body weight gains are also decreased; Sahu, Endocrinology 139:795-798, (1998). MCH appears to act as a functional antagonist of the melanocortin system in its effects on food intake and on hormone secretion within the HPA (hypothalamopituitary/adrenal axis); Ludwig et al., Am. J. Physiol. Endocrinol. Metab. 274:E627-E633, (1998). Together these data suggest a role for endogenous MCH in the regulation of energy balance and response to stress, and provide a rationale for the development of specific compounds acting at MCH receptors for use in the treatment of obesity and stress-related disorders.

Accordingly, a MCH receptor antagonist is desirable for the prophylaxis or treatment of obesity or obesity related disorders. An obesity related disorder is a disorder that has been directly or indirectly associated to obesity, such as, type II diabetes, syndrome X, impaired glucose tolerance, dyslipidaemia, hypertension, coronary heart disease and other cardiovascular disorders including atherosclerosis, insulin resistance associated with obesity and psoriasis, for treating diabetic complications and other diseases such as polycystic ovarian syndrome (PCOS), certain renal diseases including diabetic nephropathy, glomerulonephritis, glomerular sclerosis, nephrotic syndrome, hypertensive nephrosclerosis, end-stage renal diseases and microalbuminuria as well as certain eating disorders.

In species studied to date, a major portion of the neurons of the MCH cell group occupies a rather constant location in those areas of the lateral hypothalamus and subthalamus where they lie and may be a part of some of the so-called "extrapyramidal" motor circuits. These involve substantial striato- and pallidofugal pathways involving the thalamus and cerebral cortex, hypothalamic areas, and reciprocal connections to subthalamic nucleus, substantia nigra, and mid-brain centers; Bittencourt et al., J. Comp. Neurol. 319:218-245, (1992). In their location, the MCH cell group may offer a bridge or mechanism for expressing hypothalamic visceral activity with appropriate and coordinated motor activity. Clinically it may be of some value to consider the involvement of this MCH system in movement disorders, such as Parkinson's disease and Huntingdon's Chorea in which extrapyramidal circuits are known to be involved.

Human genetic linkage studies have located authentic hMCH loci on chromosome 12 (12q23-24) and the variant hMCH loci on chromosome 5 (5q12-13) (Pedeutour et al., 1994). Locus 12q23-24 coincides with a locus to which autosomal dominant cerebellar ataxia type II (SCA2) has been mapped; Auburger et al., Cytogenet. Cell. Genet. 61:252-256, (1992); Twells et al., Cytogenet. Cell. Genet. 61:262-265, (1992). This disease comprises neurodegenerative disorders, including an olivopontocerebellar atrophy. Furthermore, the gene for Darier's disease, has been mapped to locus 12q23-24; Craddock et al., Hum. Mol. Genet. 2:1941-1943, (1993). Dariers' disease is characterized by abnormalities I keratinocyte adhesion and mental illnesses in some families. In view of the functional and neuroanatomical patterns of the MCH neural system in the rat and human brains, the MCH gene may represent a good candidate for SCA2 or Darier's disease. Interestingly, diseases with high social impact have been mapped to this locus. Indeed, the gene responsible for chronic or acute forms of spinal muscular atrophies has been assigned to chromosome 5q12-13 using genetic linkage analysis; Melki et al., Nature (London) 344:767-768, (1990); Westbrook et al., Cytogenet. Cell. Genet. 61:225-231, (1992). Furthermore, independent lines of evidence support the assignment of a major schizophrenia locus to chromosome 5q11.2-13.3; Sherrington et al., Nature (London) 336:164-167, (1988); Bassett et al., Lancet 1:799-801, (1988); Gilliam et al., Genomics 5:940-944, (1989). The above studies suggest that MCH may play a role in neurodegenerative diseases and disorders of emotion.

Additional therapeutic applications for MCH-related compounds are suggested by the observed effects of MCH in other biological systems. For example, MCH may regulate reproductive functions in male and female rats. MCH transcripts and MCH peptide were found within germ cells in testes of adult rats, suggesting that MCH may participate in stem cell renewal and/or differentiation of early spermatocytes; Hervieu et al., Biology of Reduction 54:1161-1172, (1996). MCH injected directly into the medial preoptic area (MPOA) or ventromedial nucleus (VMN) stimulated sexual activity in female rats; Gonzalez et al., Peptides 17:171-177, (1996). In ovariectomized rats primed with estradiol, MCH stimulated luteinizing hormone (LH) release while anti-MCH antiserum inhibited LH release; Gonzalez et al., Neuroendocrinology 66:254-262, (1997). The zona incerta, which contains a large population of MCH cell bodies, has previously been identified as a regulatory site for the pre-ovulatory LH surge; MacKenzie et al., Neuroendocrinology 39:289-295, (1984). MCH has been reported to influence release of pituitary hormones including ACTH and oxytocin. MCH analogues may also be useful in treating epilepsy. In the PTZ seizure model, injection of MCH prior to seizure induction prevented seizure activity in both rats and guinea pigs, suggesting that MCH-containing neurons may participate in the neural circuitry underlying PTZ-induced seizure; Knigge and Wagner, Peptides 18:1095-1097, (1997). MCH has also been observed to affect behavioral correlates of cognitive functions. MCH treatment hastened extinction of the passive avoidance response in rats; McBride et al., Peptides 15:757-759, (1994); raising the possibility that MCH receptor antagonists may be beneficial for memory storage and/or retention. A possible role for MCH in the modulation or perception of pain is supported by the dense innervation of the periaqueductal grey (PAG) by MCH-positive fibers. Finally, MCH may participate in the regulation of fluid intake. ICV infusion of MCH in conscious sheep produced diuretic, natriuretic, and kaliuretic changes in response to increased plasma volume; Parkes, J. Neuroendocrinol. 8:57-63, (1996). Together with anatomical data reporting the presence of MCH in fluid regulatory areas of the brain, the results indicate that MCH may be an important peptide involved in the central control of fluid homeostasis in mammals.

In a recent citation MCHR1 antagonists surprisingly demonstrated their use as an anti-depressants and/or anti-anxiety agents. MCHR1 antagonists have been reported to show anti-depressant and anxiolytic activities in rodent models, such as, social interaction, forced swimming test and ultrasonic vocalization. Therefore, MCHR1 antagonists could be useful to independently treat subjects with depression and/or anxiety. Also, MCHR1 antagonists could be useful to treat subjects that suffer from depression and/or anxiety and obesity.

This invention provides a method of treating an abnormality in a subject wherein the abnormality is alleviated by decreasing the activity of a mammalian MCH1 receptor which comprises administering to the subject an amount of a compound which is a mammalian MCH1 receptor antagonist effective to treat the abnormality. In separate embodiments, the abnormality is a regulation of a steroid or pituitary hormone disorder, an epinephrine release disorder, an anxiety disorder, genta gastrointestinal disorder, a cardiovascular disorder, an electrolyte balance disorder, hypertension, diabetes, a respiratory disorder, asthma, a reproductive function disorder, an immune disorder, an endocrine disorder, a musculoskeletal disorder, a neuroendocrine disorder, a cognitive disorder, a memory disorder, a sensory modulation and transmission disorder, a motor coordination disorder, a sensory integration disorder, a motor integration disorder, a dopaminergic function disorder, a sensory transmission disorder, an olfaction disorder, a sympathetic innervation disorder, an affective disorder, a stress-related disorder, a fluid-balance disorder, a seizure disorder, pain, psychotic behavior, morphine tolerance, opiate addiction or migraine.

Compositions of the invention may conveniently be administered in unit dosage form and may be prepared by any of the methods well known in the pharmaceutical art, for example, as described in *Remington's Pharmaceutical Sciences* (Mack Pub. Co., Easton, Pa., 1980).

The compounds of the invention can be employed as the sole active agent in a pharmaceutical or can be used in combination with other active ingredients which could facilitate the therapeutic effect of the compound.

Compounds of the present invention or a solvate or physiologically functional derivative thereof can be used as active ingredients in pharmaceutical compositions, specifically as a MCH receptor antagonists. By the term "active ingredient" is defined in the context of a "pharmaceutical composition" and shall mean a component of a pharmaceutical composition that provides the primary pharmaceutical benefit, as opposed to an "inactive ingredient" which would generally be recognized as providing no pharmaceutical benefit. The term "pharmaceutical composition" shall mean a composition comprising at one active ingredient and at least one ingredient that is not an active ingredient (for example and not limitation, a filler, dye, or a mechanism for slow release), whereby the composition is amenable to use for a specified, efficacious outcome in a mammal (for example, and not limitation, a human).

Pharmaceutical compositions, including, but not limited to, pharmaceutical compositions, comprising at least one compound of the present invention and/or an acceptable salt or solvate thereof (e.g., a pharmaceutically acceptable salt or solvate) as an active ingredient combined with at least one carrier or excipient (e.g., pharmaceutical carrier or excipient) may be used in the treatment of clinical conditions for which a MCH receptor antagonist is indicated. At least one compound of the present invention may be combined with the carrier in either solid or liquid form in a unit dose formulation. The pharmaceutical carrier must be compatible with the other ingredients in the composition and must be tolerated by the individual recipient. Other physiologically active ingredients may be incorporated into the pharmaceutical composition of the invention if desired, and if such ingredients are compatible with the other ingredients in the composition. Formulations may be prepared by any suitable method, typically by uniformly mixing the active compound(s) with liquids or finely divided solid carriers, or both, in the required proportions, and then, if necessary, forming the resulting mixture into a desired shape.

Conventional excipients, such as binding agents, fillers, acceptable wetting agents, tabletting lubricants, and disintegrants may be used in tablets and capsules for oral administration. Liquid preparations for oral administration may be in the form of solutions, emulsions, aqueous or oily suspensions, and syrups. Alternatively, the oral preparations may be in the form of dry powder that can be reconstituted with water or another suitable liquid vehicle before use. Additional additives such as suspending or emulsifying agents, non-aqueous vehicles (including edible oils), preservatives, and flavorings and colorants may be added to the liquid preparations. Parenteral dosage forms may be prepared by dissolving the compound of the invention in a suitable liquid vehicle and filter sterilizing the solution before filling and sealing an appropriate vial or ampoule. These are just a few examples of the many appropriate methods well known in the art for preparing dosage forms.

It is noted that when the MCH receptor antagonists are utilized as active ingredients in a pharmaceutical composition, these are not intended for use only in humans, but in other non-human mammals as well. Indeed, recent advances in the area of animal health-care mandate that consideration be given for the use of MCH receptor antagonists for the treatment of obesity in domestic animals (e.g., cats and dogs), and MCH receptor antagonists in other domestic animals where no disease or disorder is evident (e.g., food-oriented animals such as cows, chickens, fish, etc.). Those of ordinary skill in the art are readily credited with understanding the utility of such compounds in such settings.

Pharmaceutically acceptable salts of the compounds of the invention can be prepared by reacting the free acid or base forms of these compounds with the appropriate base or acid in water, in an organic solvent, or in a mixture of the two; generally, nonaqueous media like ether, ethyl acetate, ethanol, isopropanol, dioxane, or acetonitrile are preferred. For instance, when the compound (I) possesses an acidic functional group, it can form an inorganic salt such as an alkali metal salt (e.g., sodium salt, potassium salt, etc.), an alkaline earth metal salt (e.g. calcium salt, magnesium salt, barium salt, etc.), and an ammonium salt. When the compound (I) possesses a basic functional group, it can form an inorganic salt (e.g., hydrochloride, sulfate, phosphate, hydrobromate, etc.) or an organic salt (e.g., acetate, maleate, fumarate, succinate, methanesulfonate, p-toluenesulfonate, citrate, tartrate, etc.).

When a compound of the invention contains optical isomers, stereoisomers, regio isomers, rotational isomers, a single substance and a mixture of them are included as a compound of the invention. For example, when a chemical formula is represented as showing no stereochemical designation(s), such as Formula IX, then all possible stereoisomer, optical isomers and mixtures thereof are considered within the scope of that formula. Accordingly, Formula XXII, specifically designates the cis relationship between the two amino groups on the cyclohexyl ring and therefore this formula is also fully embraced by Formula IX.

The novel substituted quinazolines of the present invention can be readily prepared according to a variety of synthetic manipulations, all of which would be familiar to one skilled in the art. Preferred methods for the preparation of compounds of the present invention include, but are not limited to, those described in Scheme 1-31.

The common intermediate (E) of the novel substituted quinazolines can be prepared as shown in Scheme 1. Commercially available 1H,3H-quinazoline-2,4-dione (A) is converted to 2,4-dihalo-quinazoline (B) by a halogenating agent with or without a base (wherein X is halogen such as chloro, bromo, or iodo). The halogenating agent includes phosphorous oxychloride ($POCl_3$), phosphorous oxybromide ($POBr_3$), or phosphorus pentachloride ($PCl_5$). The base includes a tertiary amine (preferably N,N-diisopropylethylamine, etc.) or an aromatic amine (preferably N,N-dimethylaniline, etc.). Reaction temperature ranges from about 100° C. to 200° C., preferably about 140° C. to 180° C. The halogen of 4-position of 2,4-dihalo-quinazoline (B) is selectively substituted by a primary or secondary amine ($HNR_{2a}R_{2b}$, wherein $R_{2a}$ and $R_{2b}$ are as defined above) with or without a base in an inert solvent to provide the corresponding 4-substitued amino adduct (C). The base includes an alkali metal carbonate (preferably sodium carbonate or potassium carbonate, etc.), an alkali metal hydroxide (preferably sodium hydroxide, etc.), or a tertiary amine (preferably N,N-diisopropylethylamine, triethylamine, or N-methylmorpholine, etc.). The inert solvent includes lower alkyl alcohol solvents (preferably methanol, ethanol, 2-propanol, or butanol, etc.), ethereal solvents (preferably tetrahydrofuran or dioxane, etc.), or amide solvents (preferably N,N-dimethylformamide or 1-methyl-pyrrolidin-2-one, etc.). Reaction temperature ranges from about 0° C. to 200° C., preferably about 10° C. to 150° C.

In turn, this is substituted by the mono-protected diamine ($R_4HN$-A-$NR_5P$, wherein $R_4HN$-A-$NR_5P$ is as defined below, $R_4$ and $R_5$ are as defined above, and P is a protective group) with or without a base in an inert solvent to provide 2,4-disubstituted amino quinazoline (D). The base includes an alkali metal carbonate (preferably sodium carbonate or potassium carbonate, etc.), an alkali metal hydroxide (preferably sodium hydroxide, etc.), or a tertiary amine (preferably N,N-diisopropylethylamine, triethylamine, or N-methylmorpholine, etc.). The inert solvent includes lower alkyl alcohol solvents (preferably methanol, ethanol, 2-propanol, or butanol, etc.) or amide solvents (preferably N,N-dimethylformamide or 1-methyl-pyrrolidin-2-one, etc.). Reaction temperature ranges from about 50° C. to 200° C., preferably about 80° C. to 150° C. Also this reaction can be carried out under microwave conditions. Representative protecting groups suitable for a wide variety of synthetic transformations are disclosed in Greene and Wuts, *Protective Groups in Organic Synthesis*, second edition, John Wiley & Sons, New York, 1991, the disclosure of which is incorporated herein by reference in its entirety. The deprotection of the protective group leads to the common intermediate (E) of the novel substituted quinazolines.

Scheme 1

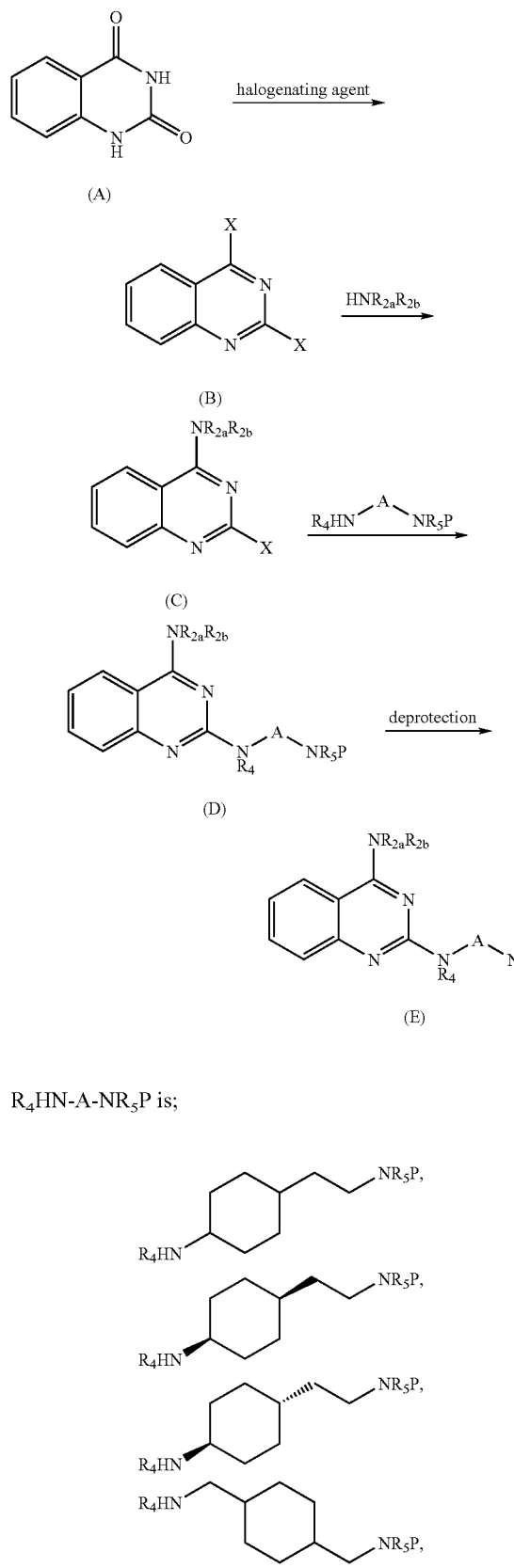

R₄HN-A-NR₅P is;

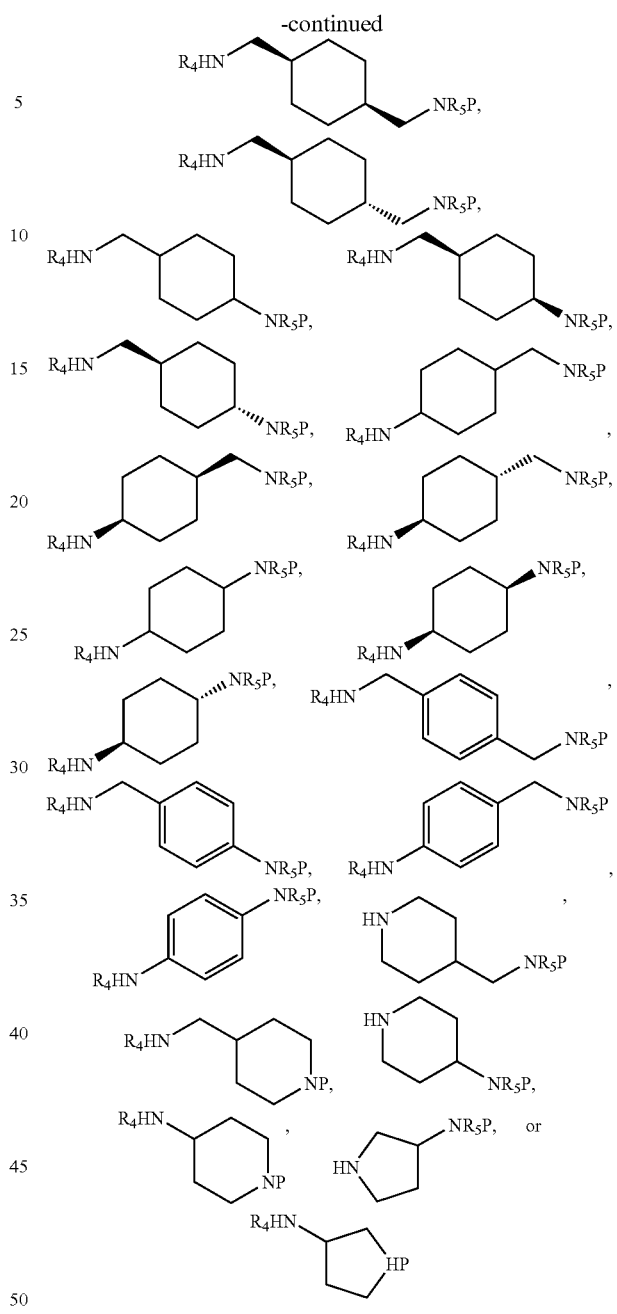

The conversion of the common intermediate (E) to the novel substituted quinazolines (F-H) of the present invention is outlined in Scheme 2.

The amine (E) is reacted with a sulfonyl chloride ($R_1SO_2Cl$) and a base in an inert solvent to provide the novel sulfonamide (F) of the present invention. The base includes an alkali metal carbonate (preferably sodium carbonate or potassium carbonate, etc.), an alkali metal hydrogencarbonate (preferably sodium hydrogencarbonate or potassium hydrogencarbonate, etc.), an alkali hydroxide (preferably sodium hydroxide or potassium hydroxide, etc.), a tertiary amine (preferably N,N-diisopropylethylamine, triethylamine, or N-methylmorpholine, etc.), or an aromatic amine (preferably pyridine or imidazole, etc.). The inert solvent includes lower halocarbon solvents (preferably dichloromethane, dichloroethane, or chloroform, etc.), ethereal solvents (preferably tetrahydrofuran or dioxane), alcohol solvents (preferably 2-propanol, etc.), or aromatic solvents (preferably toluene or pyridine, etc.). Reaction temperature ranges from about −20° C. to 50° C., preferably about 0° C. to 40° C.

The amine (E) is reacted with a carboxylic acid ($R_1CO_2H$) and a dehydrating condensing agent in an inert solvent with or without a base to provide the novel amide (G) of the present invention. The dehydrating condensing agent includes dicyclohexylcarbodiimide (DCC), 1-ethyl-3-(3-dimethylaminopropyl)carbodiimide hydrochloride (EDC.HCl), bromo-tris-pyrrolidino-phosnium hexafluorophosphate (PyBroP), O-(7-azabenzotriazol-1-yl)-1,1,3,3-tetramethyluronium hexafluorophosphate (HATU), or 1-cyclohexyl-3-methylpolystyrene-carbodiimide. The base includes a tertiary amine (preferably N,N-diisopropylethylamine or triethylamine, etc.). The inert solvent includes lower halocarbon solvents (preferably dichloromethane, dichloroethane, or chloroform, etc.), ethereal solvents (preferably tetrahydrofuran or dioxane), nitrile solvents (preferably acetonitrile, etc.), or amide solvents (preferably N,N-dimethylformamide, etc.). In case of need, 1-hydroxybenzotriazole (HOBT), HOBT-6-carboxaamidomethyl polystyrene, or 1-hydroxy-7-azabenzotriazole (HOAT) can be used as a reactant agent. Reaction temperature ranges from about −20° C. to 50° C., preferably about 0° C. to 40° C.

Alternatively, the novel amide (G) of the present invention can be obtained by amidation reaction using an acid chloride ($R_1COCl$) and a base in an inert solvent. The base includes an alkali metal carbonate (preferably sodium carbonate or potassium carbonate, etc.), an alkali metal hydrogencarbonate (preferably sodium hydrogencarbonate or potassium hydrogencarbonate, etc.), an alkali hydroxide (preferably sodium hydroxide or potassium hydroxide, etc.), a tertiary amine (preferably N,N-diisopropylethylamine, triethylamine, or N-methylmorpholine, etc.), or an aromatic amine (preferably pyridine, imidazole, poly-(4-vinylpyridine), etc.). The inert solvent includes lower halocarbon solvents (preferably dichloromethane, dichloroethane, or chloroform, etc.), ethereal solvents (preferably tetrahydrofuran or dioxane), amide solvents (preferably N,N-dimethylformamide, etc.), or aromatic solvents (preferably toluene or pyridine, etc.). Reaction temperature ranges from about −20° C. to 50° C., preferably about 0° C. to 40° C.

The novel amide (G) of the present invention is reacted with a reducing agent in an inert solvent to provide the novel amine (H) of the present invention. The reducing agent includes alkali metal aluminum hydrides (preferably lithium aluminum hydride), alkali metal borohydrides (preferably lithium borohydride), alkali metal trialkoxyaluminum hydrides (preferably lithium tri-tert-butoxyaluminum hydride), dialkylaluminum hydrides (preferably di-isobutylaluminum hydride), borane, dialkylboranes (preferably di-isoamyl borane), alkali metal trialkylboron hydrides (preferably lithium triethylboron hydride). The inert solvent includes ethereal solvents (preferably tetrahydrofuran or dioxane) or aromatic solvents (preferably toluene, etc.). Reaction temperature ranges from about −78° C. to 200° C., preferably about 50° C. to 120° C.

Alternatively, the novel amine (H) of the present invention can be obtained by reductive amination reaction using aldehyde ($R_1CHO$) and a reducing agent in an inert solvent with or without an acid. The reducing agent includes sodium triacetoxyborohydride, sodium cyanoborohydride, sodium borohydride, or boran-pyridine complex, preferably sodium triacetoxyborohydride or sodium cyanoborohydride. The inert solvent includes lower alkyl alcohol solvents (preferably methanol or ethanol, etc.), lower halocarbon solvents (preferably dichloromethane, dichloroethane, or chloroform, etc.), ethereal solvents (preferably tetrahydrofuran or dioxane), or aromatic solvents (preferably toluene, etc.). The acid includes an inorganic acid (preferably hydrochloric acid or sulfuric acid) or an organic acid (preferably acetic acid). Reaction temperature ranges from about −20° C. to 120° C., preferably about 0° C. to 100° C. Also this reaction can be carried out under microwave conditions.

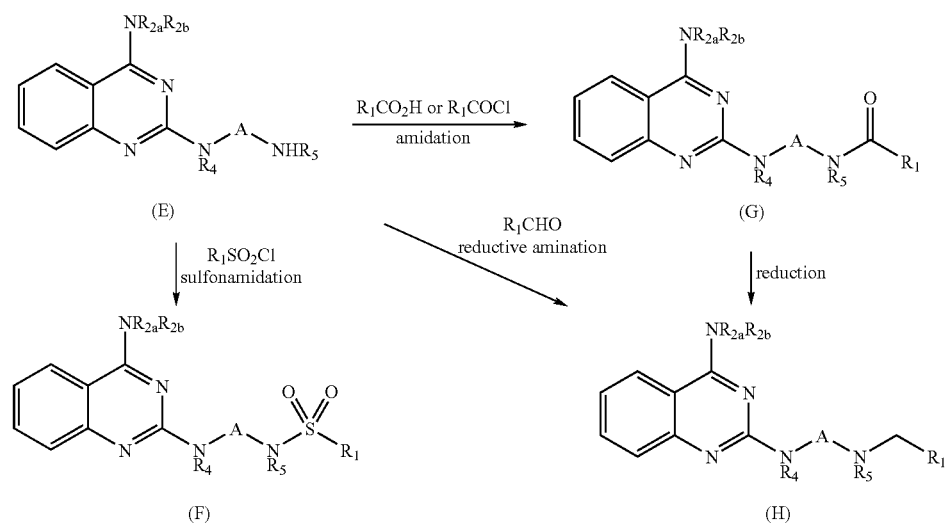

Scheme 2

Compounds of Formula (I) can be prepared as shown in Scheme 3. The amine of commercially available trans-4-aminomethyl-cyclohexancarboxylic acid is protected as tert-butyl carbamate. The carboxylic acid is reduced to the alcohol by sodium borohydride via the mixed acid anhydride. Tosylation of the alcohol with tosylchloride followed by azidation give the adide, which is converted to the amine by lithium aluminum hydride reduction. The coupling of the amine with the quinazoline core (C), which is synthesized in Scheme 1, gives 2,4-disubstituted amino quinazoline. The deprotection of Boc-group is achieved by an acid to give compounds of Formula (I).

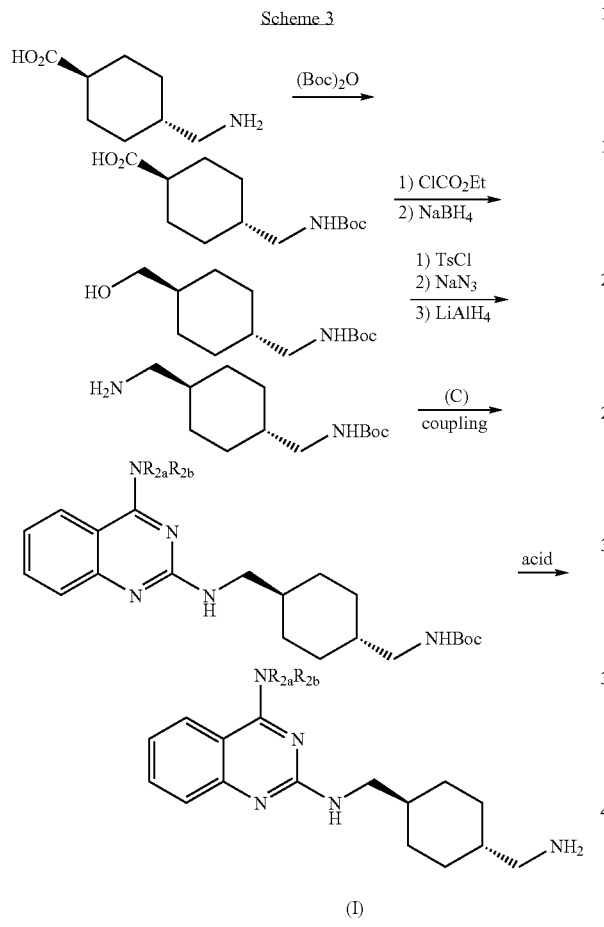

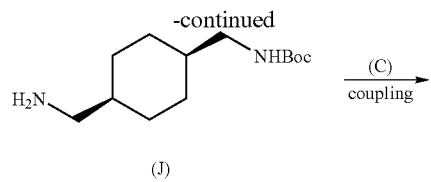

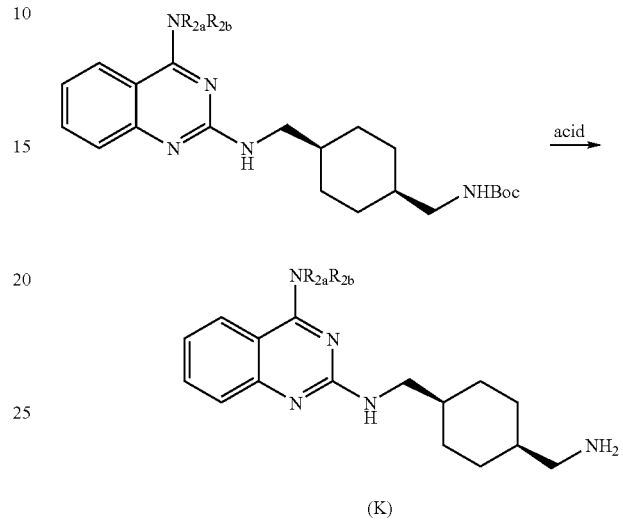

Compounds of Formula (K) can be prepared as shown in Scheme 4. Known cis-(4-aminomethyl-cyclohexylmethyl)-carbamic acid tert-butyl ester (J), synthesis of which is described in WO 01/2710, can be leaded to compounds of Formula (K) according to the method of scheme 3.

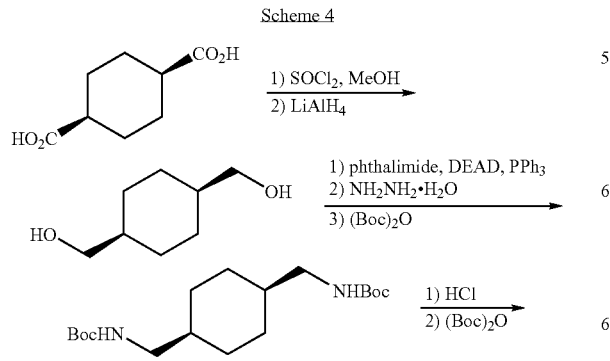

Compounds of Formula (L) can be prepared as shown in Scheme 5. The amine of cis-[4-(2-amino-ethyl)-cyclohexyl]-carbamic acid tert-butyl ester is protected as benzyl carbamate. The deprotection of Boc-group is achieved by an acid to give the amine. The coupling of the amine with quinazoline core (C), which is synthesized as scheme 1, gives 2,4-disubstituted amino quinazoline. The deprotection of Z-group is achieved by hydrogen reduction to give compounds of Formula (L).

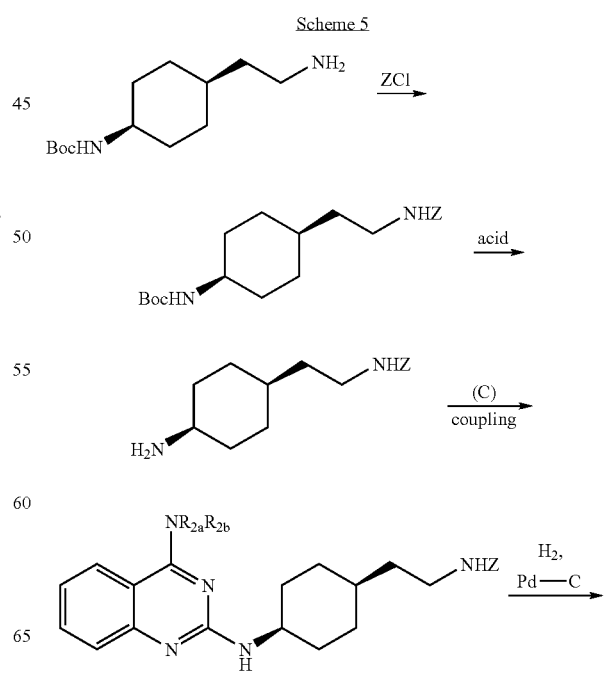

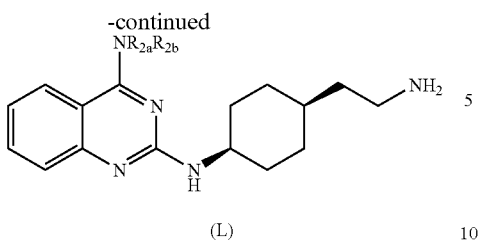

(L)

Compounds of Formula (N) can be prepared as shown in Scheme 6. The amine of commercially available trans-4-aminomethyl-cyclohexanecarboxylic acid is protected as tert-butyl carbamate. The carboxylic acid is transformed to benzyl carbamate (M) by curtius rearrangement. The deprotection of Z-group is achieved by hydrogen reduction to give the amine. The amine is converted to compounds of Formula (N) according to the method of scheme 3.

Scheme 6

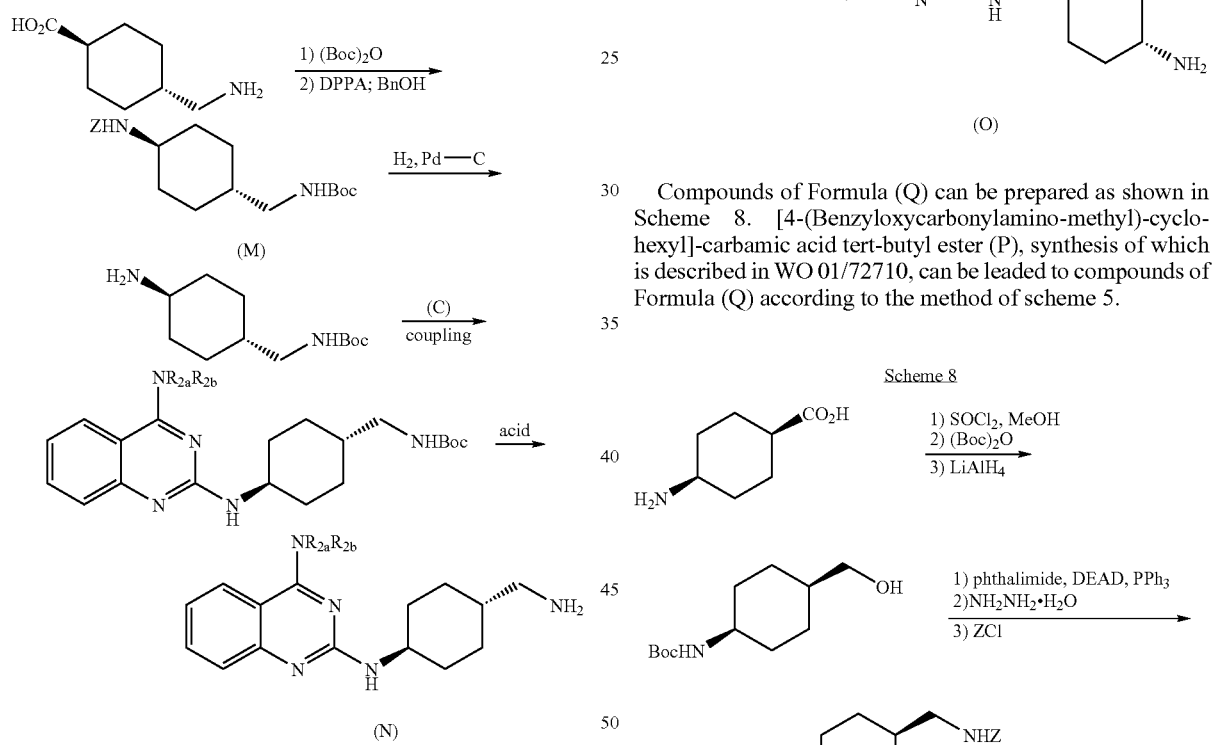

(N)

Compounds of Formula (O) can be prepared from the compound of Formula (M), which is described in Scheme 6, as shown in Scheme 7. The compound of Formula (M) can be leaded to compounds of Formula (O) according to the method of scheme 5.

Scheme 7

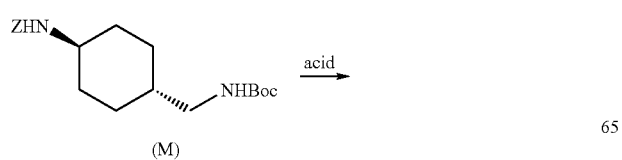

(M)

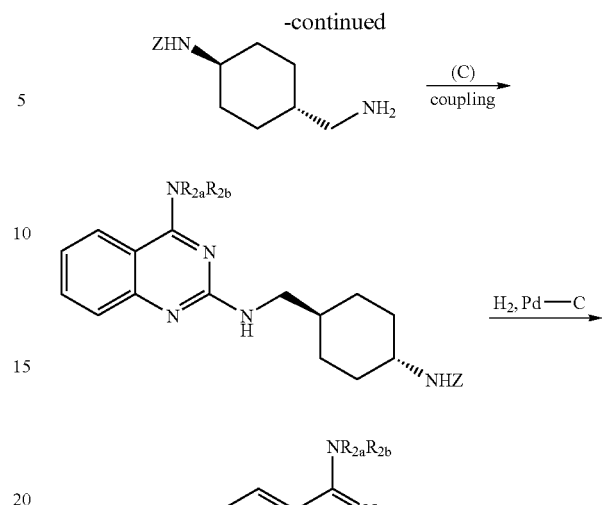

(O)

Compounds of Formula (Q) can be prepared as shown in Scheme 8. [4-(Benzyloxycarbonylamino-methyl)-cyclohexyl]-carbamic acid tert-butyl ester (P), synthesis of which is described in WO 01/72710, can be leaded to compounds of Formula (Q) according to the method of scheme 5.

Scheme 8

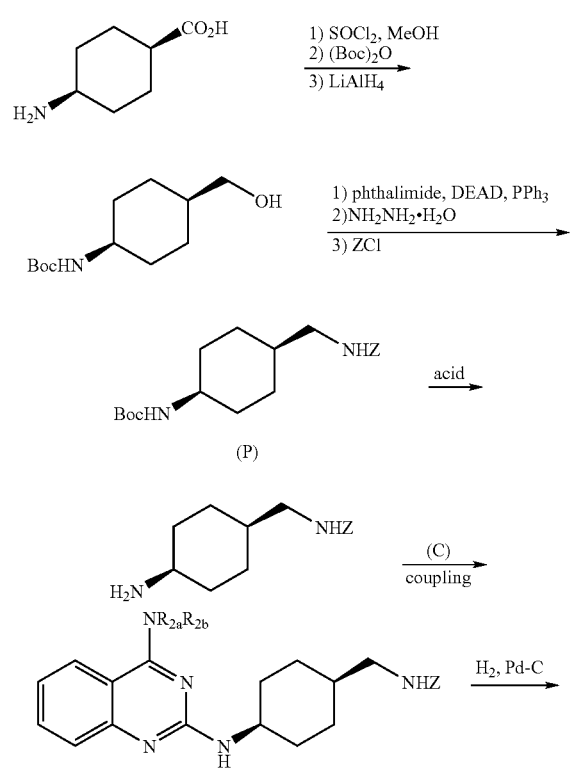

(P)

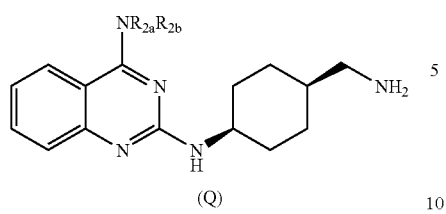

Alternatively compounds of Formula (Q) can be prepared as shown in Scheme 9. The amine of commercially available cis-4-amino-cyclohexanecarboxylic acid is protected as tert-butyl carbamate. The carboxylic acid (R) is converted to the amide (S) by aqueous ammonia via the mixed acid anhydride. The deprotection of Boc-group is achieved by an acid to give the amine. The coupling of the amine with quinazoline core (C), which is synthesized as scheme 1, gives 2,4-disubstituted amino quinazoline. The amide is reduced to compounds of Formula (Q).

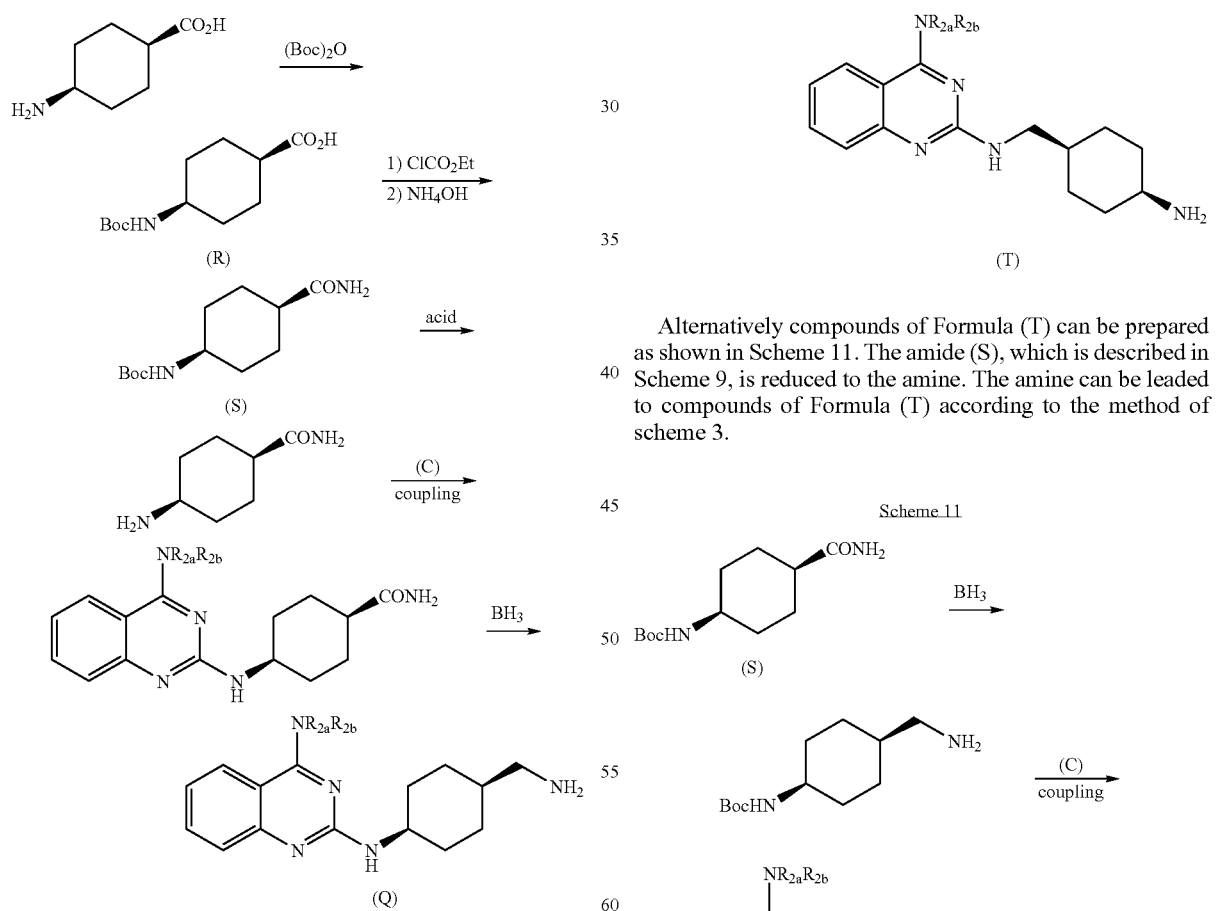

Compounds of Formula (T) can be prepared from the compound of Formula (P), which is described in Scheme 8, as shown in Scheme 10. The compound of Formula (P) can be leaded to compounds of Formula (T) according to the method of scheme 6.

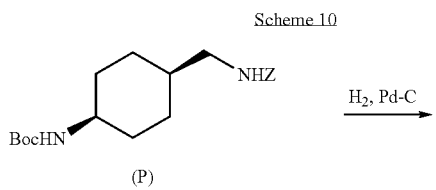

Alternatively compounds of Formula (T) can be prepared as shown in Scheme 11. The amide (S), which is described in Scheme 9, is reduced to the amine. The amine can be leaded to compounds of Formula (T) according to the method of scheme 3.

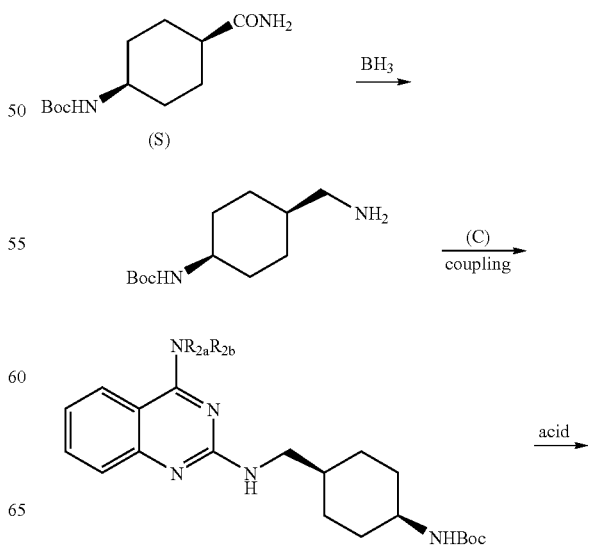

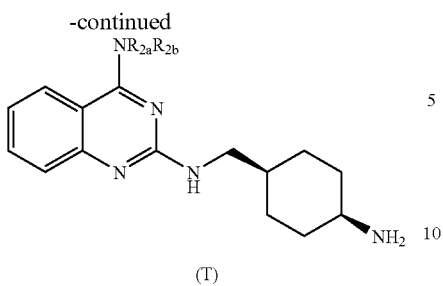

(T)

Compounds of Formula (V) can be prepared as shown in Scheme 12. The mono-protection of commercially available trans-cyclohexane-1,4-diamine can be achieved by the method described in *Synthetic communications,* 20, 2559-2564 (1990). The conversion to compounds of Formula (V) can be accomplished according to the method of scheme 3.

Scheme 12

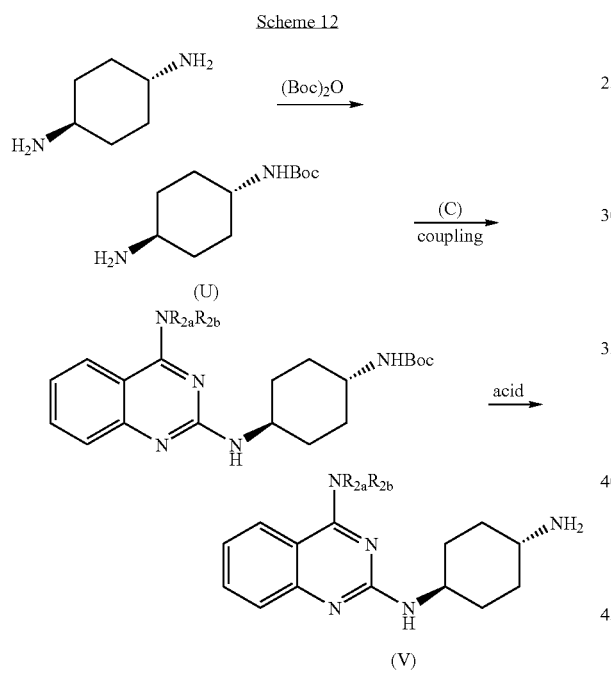

Compounds of Formula (X) can be prepared as shown in Scheme 13. The dicarboxylic acid of commercially available cis-cyclohexane-1,4-dicarboxylic acid is transformed to dibenzyl carbamate by curtius rearrangement. The deprotection of Z-group is achieved by hydrogen reduction to give the diamine. The mono-protection of the diamine can be achieved according to the method of scheme 12 to give the compound (W). The conversion to compounds of Formula (X) can be accomplished according to the method of scheme 3.

Scheme 13

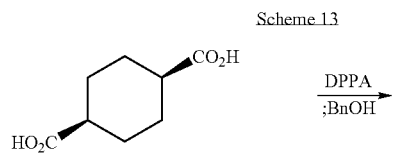

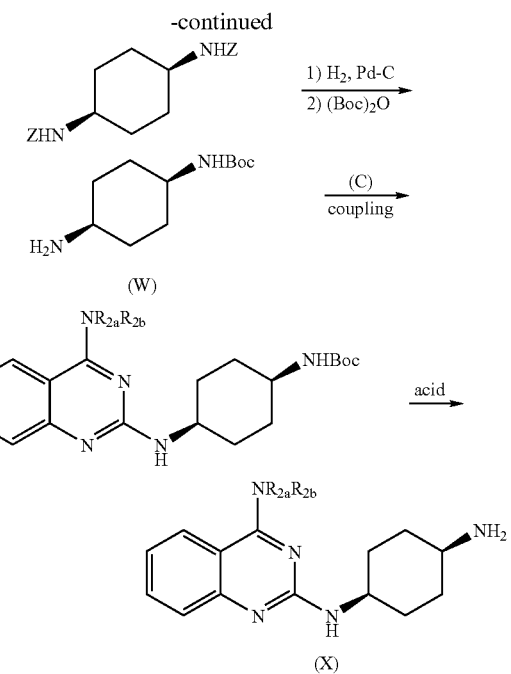

(W)

Alternatively the compound of Formula (W) can be prepared as shown in Scheme 14. The carboxylic acid (R), which is described in Scheme 9, is transformed to benzyl carbamate by curtius rearrangement. The deprotection of Z-group is achieved by hydrogen reduction to give the compound of Formula (W).

Scheme 14

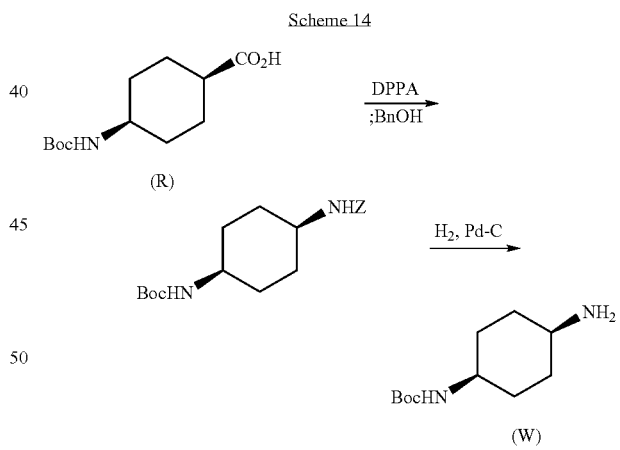

(W)

Compounds of Formula (Y) can be prepared according to the method described in Scheme 12 by using commercially available 4-aminomethyl-benzylamine as a starting material (Scheme 15).

Scheme 15

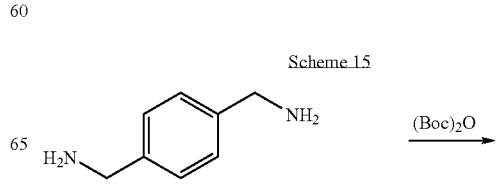

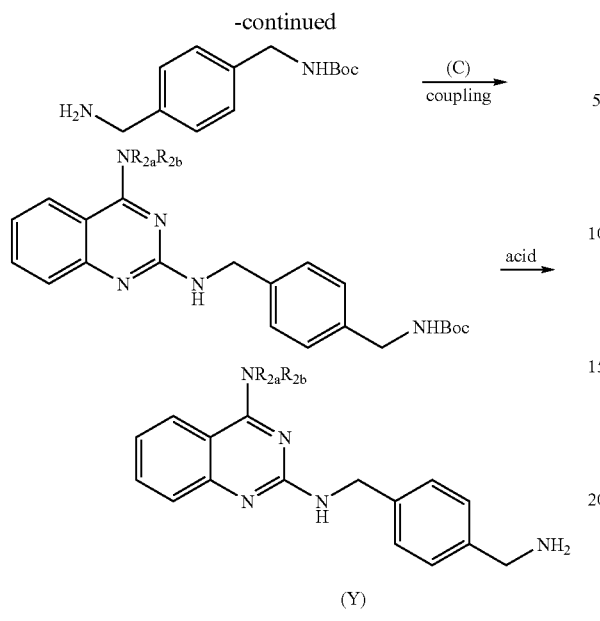

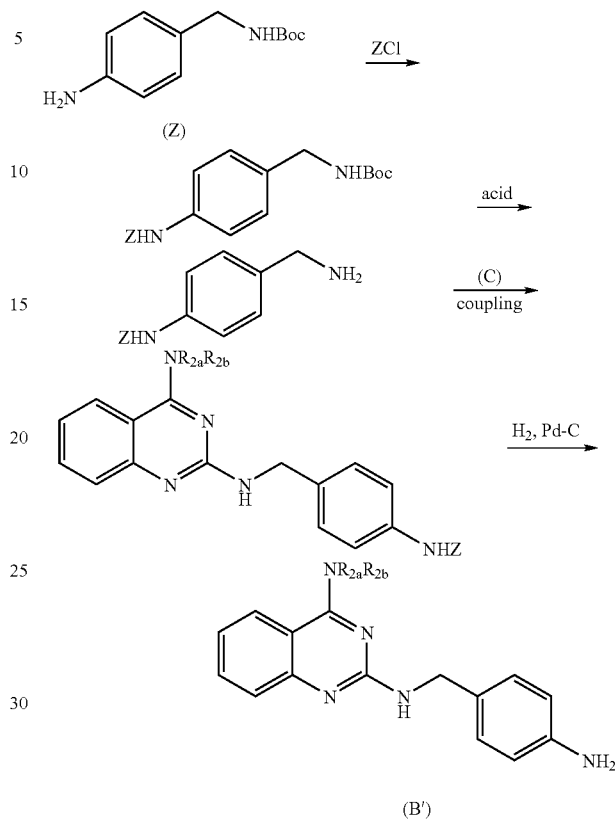

Compounds of Formula (A') can be prepared as shown in Scheme 16. The mono-protection of commercially available 4-aminomethyl-phenylamine can be achieved by using an equimolecular amount of (Boc)$_2$O to give mono-tert-butyl carbamate (Z). The amine can be leaded to compounds of Formula (A') according to the method of scheme 3.

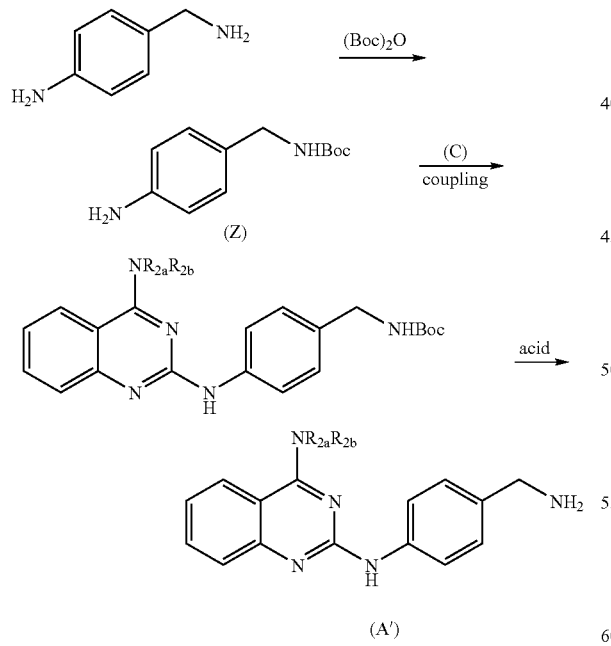

Compounds of Formula (B') can be prepared from the compound of Formula (Z), which is described in Scheme 16, as shown in Scheme 17. The compound of Formula (Z) can be leaded to compounds of Formula (B') according to the method of scheme 5.

Compounds of Formula (C') can be prepared according to the method described in Scheme 3 by using commercially available (4-amino-phenyl)-carbamic acid tert-butyl ester as a starting material (Scheme 18).

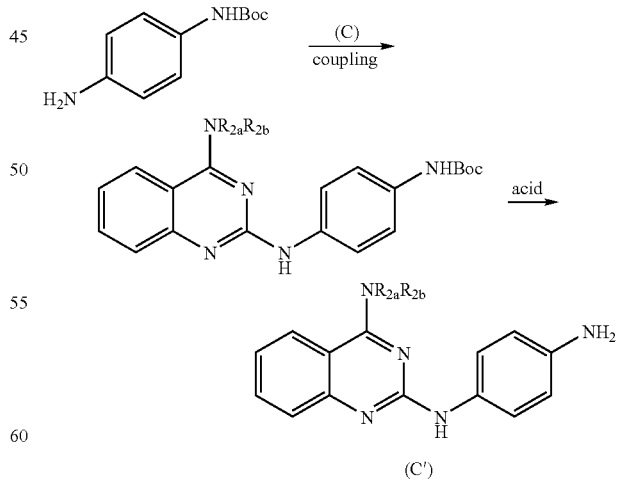

Compounds of Formula (E') can be prepared as shown in Scheme 19. The selective protection of the secondary amine in the presence of the primary amine of commercially available 4-(aminomethyl)piperidin is achieved by the method described in *Synthetic communications*, 22, 2357-2360 (1992) to give the amine (D'). The amine is converted to compounds of Formula (E') according to the method of scheme 3.

Scheme 19

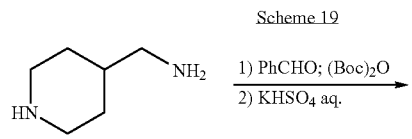

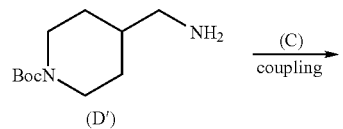

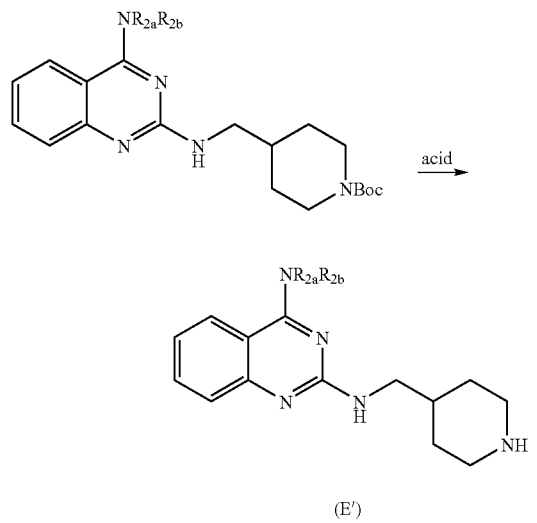

Compounds of Formula (F') can be prepared from the compound of Formula (D'), which is described in Scheme 19, as shown in Scheme 20. The compound of Formula (D') can be leaded to compounds of Formula (F') according to the method of Scheme 5.

Scheme 20

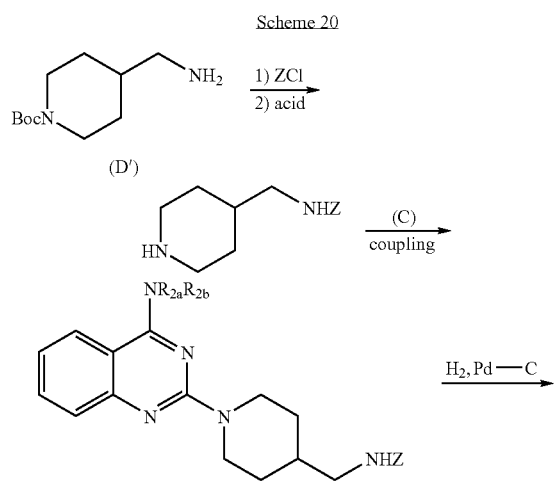

-continued

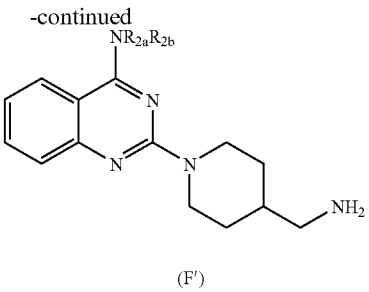

Compounds of Formula (G') can be prepared according to the method described in Scheme 5 by using commercially available 1-benzyl-piperidin-4-ylamine as a starting material (Scheme 21).

Scheme 21

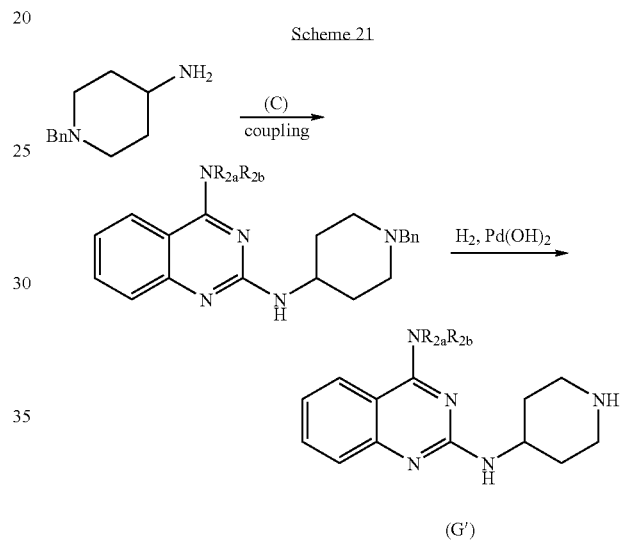

Compounds of Formula (H') can be prepared as shown in Scheme 22. The amine of commercially available 1-benzyl-piperidin-4-ylamine is protected as tert-butyl carbamate. The deprotection of benzyl group is achieved by hydrogen reduction to give the amine. The amine can be leaded to compounds of Formula (H') according to the method of scheme 3.

Scheme 22

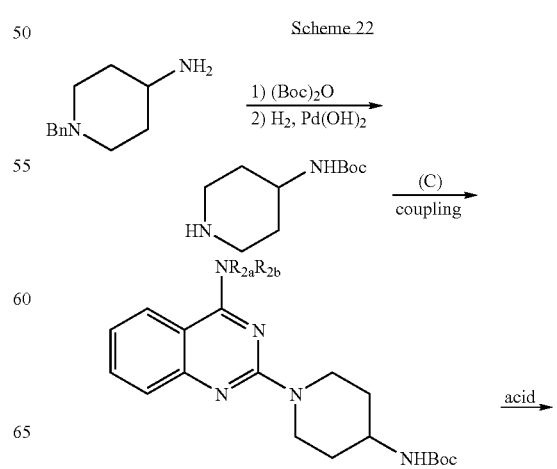

-continued

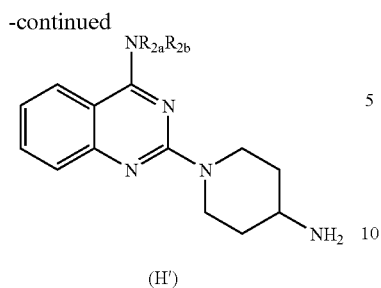

(H')

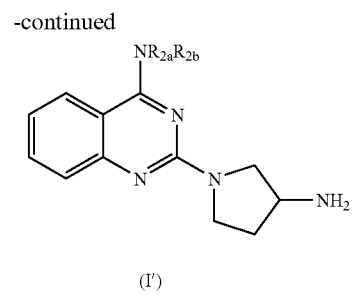

(I')

Compounds of Formula (I') can be prepared according to the method described in Scheme 3 by using commercially available pyrrolidin-3-yl-carbamic acid tert-butyl ester as a starting material (Scheme 23).

Scheme 23

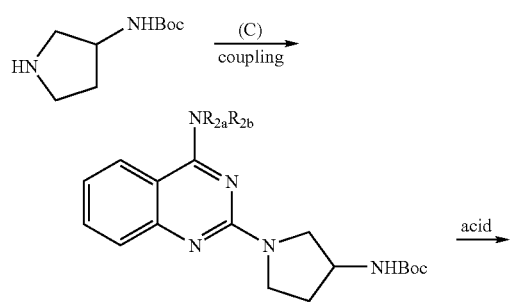

Alternatively, the novel sulfonamide (F), the novel amide (G), and the novel amine (H) of the present invention are directly synthesized from the quinazoline core (C), which is synthesized in Scheme 1, as shown in Scheme 24. This coupling is performed with or without a base in an inert solvent. The base includes an alkali metal carbonate (preferably sodium carbonate or potassium carbonate, etc.), an alkali metal hydroxide (preferably sodium hydroxide, etc.), or a tertiary amine (preferably N,N-diisopropylethylamine, triethylamine, or N-methylmorpholine, etc.). The inert solvent includes lower alkyl alcohol solvents (preferably methanol, ethanol, 2-propanol, or butanol, etc.) or amide solvents (preferably N,N-dimethylformamide or 1-methyl-pyrrolidin-2-one, etc.). Reaction temperature ranges from about 50° C. to 200° C., preferably about 80° C. to 180° C. Also this reaction can be carried out under microwave conditions.

Scheme 24

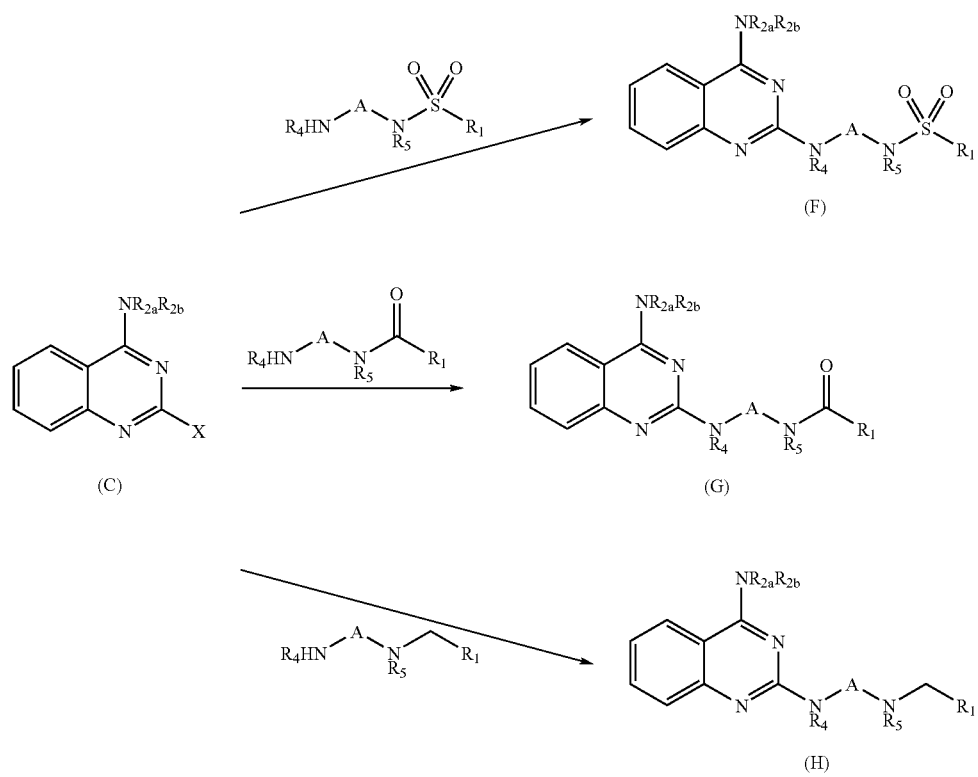

Compounds of Formula (K') can be prepared as shown in Scheme 25. Commercially available trans-4-aminomethyl-cyclohexanecarboxylic acid is reacted with sulfonyl chloride ($R_1SO_2Cl$) to give the sulfonamide. The carboxylic acid is converted to the amide via the mixed acid anhydride. The amide is reduced to the amine (J') by borane reduction. The coupling of the amine with the quinazoline core (C), which is synthesized in Scheme 1, gives the novel sulfonamide (K') of the present invention.

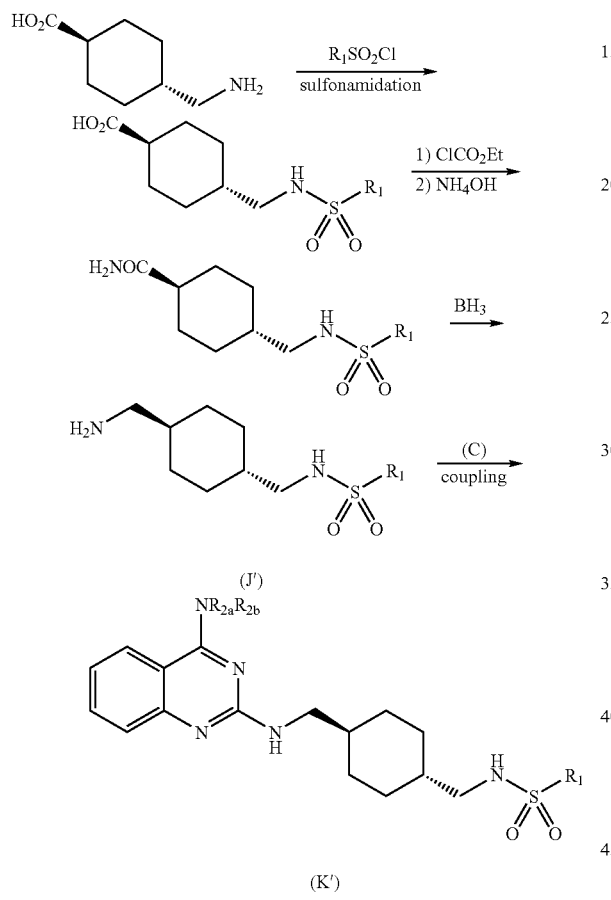

Compounds of Formula (L') can be prepared from the compound of Formula (U), which is described in Scheme 12, as shown in Scheme 26. The amine (U) is reacted with sulfonyl chloride ($R_1SO_2Cl$) to give the sulfonamide. The deprotection of Boc-group is achieved by an acid to give the amine. The coupling of the amine with quinazoline core (C), which is synthesized as scheme 1, gives the novel sulfonamide (L') of the present invention.

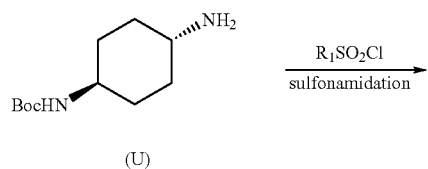

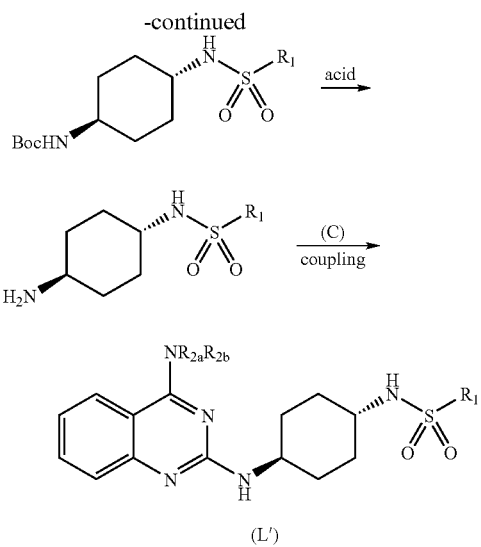

Compounds of Formula (M') can be prepared according to the method described in Scheme 26 by using the compound of Formula (D'), which is described in Scheme 19, as a starting material (Scheme 27).

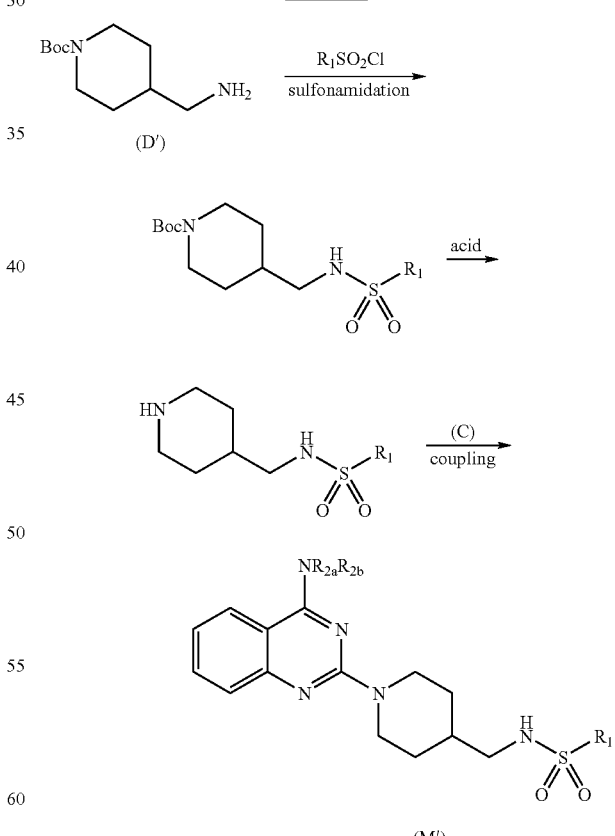

Compounds of Formula (N') can be prepared according to the method described in Scheme 26 by using commercially available pyrrolidin-3-yl-carbamic acid tert-butyl ester as a starting material (Scheme 28).

Scheme 28

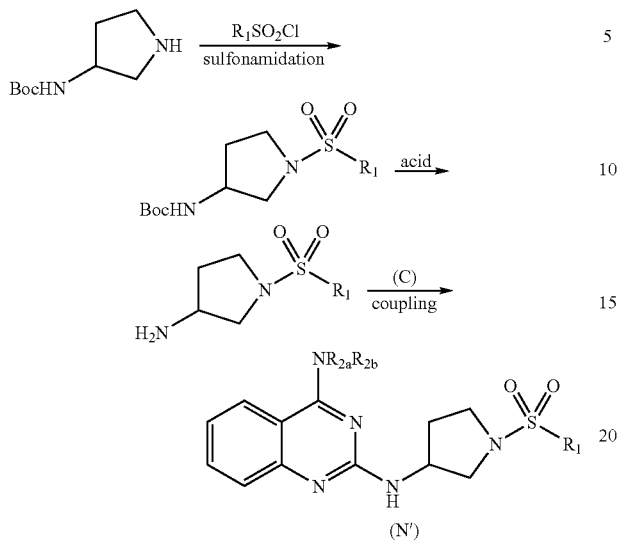

Compounds of Formula (O) can be prepared from the compound of Formula (Z), which is described in Scheme 16, as shown in Scheme 29. The aniline (Z) is reacted with carboxylic acid ($R_1CO_2H$) to give the amide. The deprotection of Boc-group is achieved by an acid to give the amine. The coupling of the amine with quinazoline core (C), which is synthesized as scheme 1, gives the novel sulfonamide (O') of the present invention.

Scheme 29

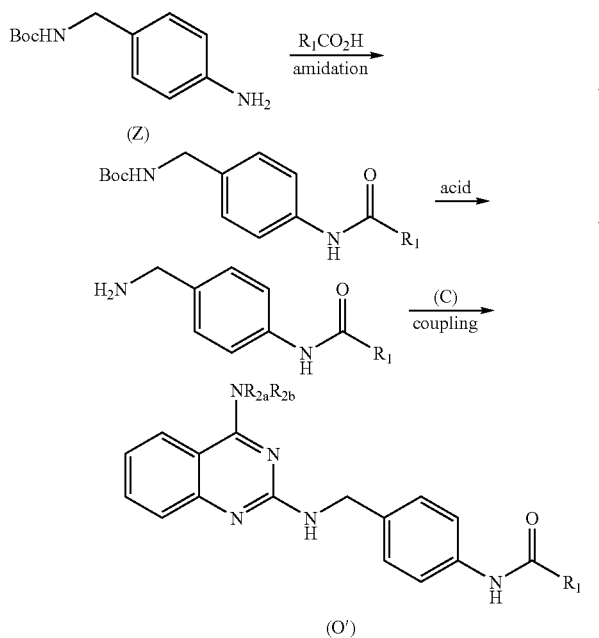

Compounds of Formula (P') can be prepared as shown in Scheme 30. The amine (W), which is synthesized in Scheme 13, is subjected to reductive amination by aldehyde ($R_1CHO$). The deprotection of Boc-group is achieved by an acid to give the amine. The coupling of the amine with quinazoline core (C), which is synthesized as scheme 1, gives the novel amine (P') of the present invention.

Scheme 30

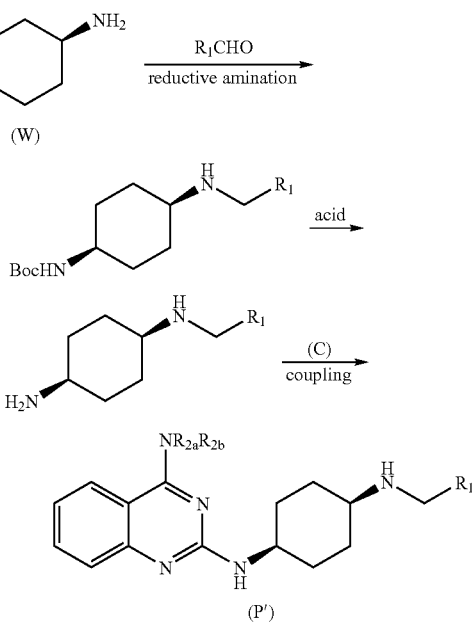

Scheme 31 shows the preparation of compounds (Q') of the invention where Q of Formula I has Formula III. The compound (J'), which is synthesized in Scheme 25, is reacted with (1-tert-butoxycarbonylamino-1 trifluorometlanesulfonylimino-methyl)-carbamic acid tert-butyl ester. The deprotection of Boc-group is achieved by an acid to give the novel guanidine (Q') of the present invention.

Scheme 31

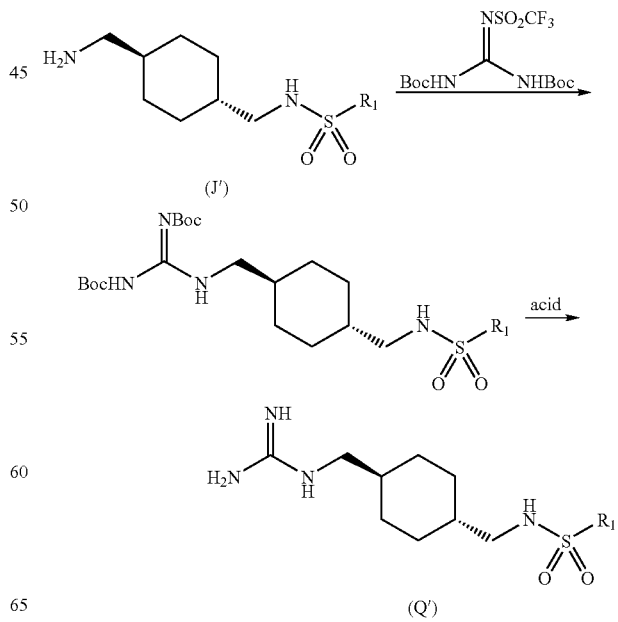

EXAMPLES

The compounds of the invention and their synthesis are further illustrated by the following examples. The following examples are provided to further define the invention without, however, limiting the invention to the particulas of these examples. "Ambient temperature" as referred to in the following example is meant to indicate a temperature falling between 0° C. and 40° C.

Abbreviations used in the instant specification, particularly the Schemes and Examples, are as follows:

$^1$H NMR: proton nuclear magnetic resonance spectrum
AcOH: acetic acid
APCI: atmospheric pressure chemical ionization
(Boc)$_2$O: di-tertiary-butyl dicarbonate
BuLi: butyl lithium
BuOH: butanol
CaCl$_2$: calcium chloride
CDCl$_3$: deuterated chloroform
CF$_3$CO$_2$H: trifluoroacetic acid
CH$_2$Cl$_2$: dichloromethane
CHCl$_3$: chloroform
CI: chemical ionization
CuCl: copper (1) chloride
D$_2$O: deuterium oxide
DMAP: 4-dimethylaminopyridine
DMF: N,N-dimethylformamide
DMSO: dimethyl sulfoxide
EDC: 1-(3-dimethylaminopropyl)-3-ethylcarbodiimide hydrochloride
ESI: electrospray ionization
Et$_2$O: diethyl ether
EtOAc: acetic acid ethyl ester
EtOH: ethanol
FAB: fast atom bombardment
H$_2$SO$_4$: sulfuric acid
HATU: O-(7-azabenzotriazol-1-yl)-N,N,N',N'-tetramethyluronium-hexafluorophosphate
HCHO: formaldehyde
HCl: hydrogen chloride
HOAt: 1-hydroxy-7-azabenzotriazole
HOBt: 1-hydroxybenzotriazole
HPLC: high performance liquid chromatography
K$_2$CO$_3$: potassium carbonate
KHSO$_4$: potassium bisulfate
Me$_2$NH: dimethylamine
MeNH$_2$: methylamine
MeOH: methanol
MgSO$_4$: magnesium sulfate
Na$_2$CO$_3$: sodium carbonate
Na$_2$SO$_4$.10H$_2$O: sodium sulfate decahydrate
NaBH(OAc)$_3$: sodium triacetoxyborohydride
NaBH$_3$CN: sodium cyanoborohydride
NaBH$_4$: sodium borohydride
NaHCO$_3$: sodium hydrogencarbonate
NaN$_3$: sodium azide
NaNO$_2$: sodium nitrate
Pd(OH)$_2$: palladium hydroxide
Pd/C: palladium carbon
POCl$_3$: phosphoryl chloride
PVP: poly(4-vinylpyridine)
PyBroP: bromo-tris-pyrrolidino phosphonium hexafluoro phosphate
SOCl$_2$: thionyl chloride
t-BuOH: tertiary butanol
TFA: trifluoroacetic acid
THF: tetrahydrofuran
WSC: water solubule carbodiimide
ZCl: benzyloxycarbonyl chloride
s: singlet
d: doublet
t: triplet
q: qualtet
dd: doublet doublet
dt: doublet triplet
ddd: doublet doublet doublet
brs: broad singlet
m: multiplet
J: coupling constant
Hz: Hertz The analytical condition of high performance liquid chromatography is as follows:
 Solvent A: 0.050% TFA in water
 Solvent B: 0.035% TFA in acetonitrile
 5-100% B over 5 min, flow rate 3.5 ml/min Example 1

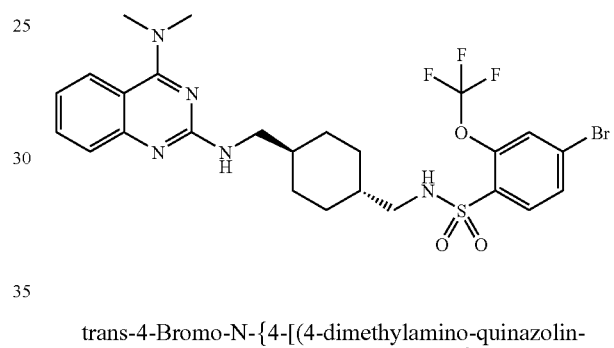

trans-4-Bromo-N-{4-[(4-dimethylamino-quinazolin-2-ylamino)-methyl]-cyclohexylmethyl}-2-trifluoromethoxy-benzenesulfonamide Step A: Synthesis of 2,4-dichloro-quinazoline.

To a suspension of 1H-quinazoline-2,4-dione (150 g, 925 mmol) in POCl$_3$ (549 mL, 5.89 mol) was added dimethylphenyl-amine (123 mL, 962 mmol). The mixture was stirred at reflux for 7 hr and concentrated. The solution was poured into ice water, and the aqueous layer was extracted with CHCl$_3$ (three times). The combined organic layer was dried over MgSO$_4$, filtered, concentrated, and purified by flash chromatography (silica gel, 50% CHCl$_3$ in hexane to 10% EtOAc in CHCl$_3$) to give 2,4-dichloro-quinazoline (159 g, 86%) as a pale yellow solid.

CI MS m/e 199, M$^+$; $^1$H NMR (300 MHz, CDCl$_3$) δ 8.27 (dt, J=8.3, 1.1 Hz, 1 H), 7.95-8.04 (m, 2 H), 7.71-7.81 (m, 1 H).

Step B: Synthesis of (2-chloro-quinazolin-4-yl)-dimethylamine.

A solution of 2,4-dichloro-quinazoline (102 g, 530 mmol) in THF (1.2 L) was cooled to 4° C. and 50% aqueous Me$_2$NH (139 mL, 1.33 mol) was added. The mixture was stirred at ambient temperature for 80 min. The solution was alkalized with saturated aqueous NaHCO$_3$ (pH=9), and the aqueous layer was extracted with CHCl$_3$ (three times). The combined organic layer was dried over MgSO$_4$, filtered, and concentrated. The residue was suspended in 50% Et$_2$O in hexane (250 mL) and stirred at ambient temperature for 30 min. The solid was collected by filtration, washed with 50% Et$_2$O in hexane, and dried at 80° C. to give (2-chloro-quinazolin-4-yl)-dimethyl-amine (104 g, 94%) as a pale yellow solid.

ESI MS m/e 207, M+; $^1$H NMR (300 MHz, CDCl$_3$) δ 8.00 (d, J=8.4 Hz, 1 H), 7.73-7.78 (m, 2 H), 7.68 (ddd, J=8.4, 6.9, 1.4 Hz, 1 H), 3.41 (s, 6 H).

Step C: Synthesis of trans-4-(tert-butoxycarbonylamino-methyl)-cyclohexanecarboxylic acid.

To a solution of trans-4-aminomethyl-cyclohexanecarboxylic acid (150 g, 954 mmol) in 1.32 M aqueous sodium hydroxide (750 mL) were added t-BuOH (1680 mL) and (Boc)$_2$O (215 g, 985 mmol). The reaction mixture was stirred at ambient temperature for 18 hr. To the reaction mixture was added H$_2$O (2.8 L), and cooled at 5° C. The aqueous layer was acidified with saturated aqueous KHSO$_4$ (pH=3), extracted with EtOAc (three times). The combined organic layer was washed with saturated aqueous NaRCO$_3$ and brine, dried over MgSO$_4$, filtered, concentrated and dried under reduced pressure to give trans-4-(tert-butoxycarbonylamino-methyl)-cyclohexanecarboxylic acid (165 g, 67%) as a white solid.

ESI MS m/e 280, M+Na+; $^1$H NMR (300 MHz, CDCl$_3$) δ 4.60 (brs, 1 H), 2.98 (t, J=6.3 Hz, 2 H), 2.19-2.33 (m, 1 H), 1.99-2.11 (m, 2 H), 1.77-1.90 (m, 2 H), 1.44 (s, 9 H), 1.34-1.52 (m, 3 H), 0.86-1.05 (m, 2 H).

Step D: Synthesis of trans-(4-hydroxymethyl-cyclohexylmethyl)-carbamic acid tert-butyl ester.

A suspension of trans-4-(tert-butoxycarbonylamino-methyl)-cyclohexane-carboxylic acid (155 g, 603 mmol) in CH$_2$Cl$_2$ (1.35 L) was cooled at −65° C. and triethylamine (126 mL, 904 mmol) and a solution of ethyl chloroformate (58 mL, 751 mmol) in CH$_2$Cl$_2$ (200 mL) were added below −60° C. The reaction mixture was stirred at 0° C. for 50 min. The mixture was acidified with saturated aqueous KHSO$_4$ (pH=3), and the aqueous layer was extracted with CHCl$_3$ (three times). The combined organic layer was washed with saturated aqueous Na$_2$CO$_3$ and brine, dried over MgSO$_4$, filtered, and concentrated to give a colorless oil. A solution of the above oil in THF (1.5 L) was cooled at −65° C. and NaBH$_4$ (26.6 g, 703 mmol) and MeOH (45 mL) were added. The mixture was stirred at −40° C. for 25 min, and stirred at 4° C. for 3 hr. The mixture was acidified with saturated aqueous KHSO$_4$ (pH=3), and the aqueous layer was extracted with EtOAc (three times). The combined organic layer was washed with saturated aqueous Na$_2$CO$_3$ and brine, dried over MgSO$_4$, filtered, and concentrated, and purified by flash chromatography (silica gel, 17% MeOH in CHCl$_3$) to give trans-(4-hydroxymethyl-cyclohexylmethyl)-carbamic acid tert-butyl ester (123 g, 84%) as a white solid.

ESI MS m/e 266, M+Na+; $^1$H NMR (300 MHz, CDCl$_3$) δ 4.59 (brs, 1 H), 3.46 (d, J=6.4 Hz, 2 H), 2.98 (t, J=6.3 Hz, 2 H), 1.75-1.94 (m, 4 H), 1.45 (s, 9 H), 1.24-1.70 (m, 3 H), 0.81-1.12 (m, 4 H).

Step E: Synthesis of trans-(4-azidomethyl-cyclohexylmethyl)-carbamic acid tert-butyl ester.

A solution of trans-(4-hydroxymethyl-cyclohexylmethyl)-carbamic acid tert-butyl ester (123 g, 505 mmol) in pyridine (1 L) was cooled at 4° C. and a solution of p-toluenesulfonyl chloride (125 g, 657 mmol) in pyridine (200 ml) was added below 10° C. The mixture was stirred at ambient temperature for 15 hr and concentrated. After dissolution with EtOAc and H$_2$O, the organic layer was separated. The aqueous layer was extracted with EtOAc (three times), the combined organic layer was washed with H$_2$O, dried over MgSO$_4$, filtered, and concentrated to give a pale yellow oil. To a solution of the above oil in DMF (1.6 L) was added NaN$_3$ (98.8 g, 1.52 mol). The reaction mixture was stirred at ambient temperature for 14 hr and concentrated. After dissolution with CHCl$_3$ and saturated aqueous NaHCO$_3$, the organic layer was separated. The aqueous layer was extracted with CHCl$_3$ (three times), the combined organic layer was dried over MgSO$_4$, filtered, concentrated, and purified by flash chromatography (silica gel, 17% EtOAc in hexane) to give trans-(4-azidomethyl-cyclohexylmethyl)-carbamic acid tert-butyl ester (124 g, 91%) as a colorless oil.

ESI MS m/e 291, M+Na+; $^1$H NMR (300 MHz, CDCl$_3$) δ 4.59 (brs, 1 H), 3.13 (d, J=6.5 Hz, 2 H), 2.98 (t, J=6.4 Hz, 2 H), 1.70-1.90 (m, 4 H), 1.44 (s, 9 H), 1.25-1.65 (m, 2 H), 0.87-1.07 (m, 4 H).

Step F: Synthesis of trans-(4-aminomethyl-cyclohexylmethyl)-carbamic acid tert-butyl ester.

A suspension of lithium aluminum hydride (2.76 g, 72.6 mmol) in THF (225 mL) was cooled at 0° C. and a solution of trans-(4-azidomethyl-cyclohexylmethyl)-carbamic acid tert-butyl ester (15.0 g, 55.9 mmol) in THF (75 mL) was added over 1 hr. The reaction mixture was stirred at ambient temperature for 6 hr. The reaction was quenched with Na$_2$SO$_4$.10H$_2$O, filtered through a pad of celite, and concentrated. The residue was purified by flash chromatography (silica gel, 50% MeOH in CHCl$_3$) to give trans-(4-aminomethyl-cyclohexylmethyl)-carbamic acid tert-butyl ester (12.3 g, 91%) as a pale yellow oil.

ESI MS m/e 243, M+H+; $^1$H NMR (300 MHz, CDCl$_3$) δ 4.60 (brs, 1 H), 2.97 (t, J=6.3 Hz, 2 H), 2.53 (d, J=6.4 Hz, 2 H), 1.70-1.92 (m, 4 H), 1.44 (s, 9 H), 1.08-1.54 (m, 4 H), 0.81-1.02 (m, 4 H).

Step G: Synthesis of trans-{4-[(4-dimethylamino-quinazolin-2-ylamino)-methyl]-cyclohexylmethyl}-carbamic acid tert-butyl ester A mixture of (2-chloro-quinazolin-4-yl)-dimethyl-amine (15.2 g, 73.3 mmol) and trans-(4-aminomethyl-cyclohexylmethyl)-carbamic acid tert-butyl ester (14.8 g, 61.0 mmol) in 2-propanol (80 mL) was stirred at reflux for 4 days, poured into saturated aqueous NaHCO$_3$, and the aqueous layer was extracted with CHCl$_3$ (three times). The combined organic layer was dried over MgSO$_4$, filtered, concentrated, and purified by flash chromatography (NH-silica gel, 33% EtOAc in hexane) to give trans-{4-[(4-dimethylamino-quinazolin-2-ylamino)-methyl]-cyclohexylmethyl}-carbamic acid tert-butyl ester (20.4 g, 81%) as a pale yellow solid.

ESI MS m/e 414, M+H+; $^1$H NMR (300 MHz, CDCl$_3$) δ 7.81 (d, J=8.2 Hz, 1 H), 7.40-7.52 (m, 2 H), 6.98-7.06 (m, 1 H), 4.93 (brs, 1 H), 4.59 (brs, 1 H), 3.35 (t, J=6.2 Hz, 2 H), 3.26 (s, 6 H), 2.97 (t, J=6.2 Hz, 2 H), 1.72-1.95 (m, 4 H), 1.44 (s, 9 H), 1.30-1.62 (m, 2 H), 0.84-1.12 (m, 4 H).

Step H: Synthesis of trans-4-bromo-N-{4-[(4-dimethylamino-quinazolin-2-ylamino)-methyl]-cyclohexylmethyl}-2-trifluoromethoxy-benzenesulfonamide hydrochloride.

To a suspension of trans-{4-[(4-dimethylamino-quinazolin-2-ylamino)-methyl]cyclohexylmethyl}-carbamic acid tert-butyl ester (3.84 g, 9.28 mmol) in EtOAc (50 mL) was added 4 M hydrogen chloride in EtOAc (38 mL). The mixture was stirred at ambient temperature for 40 min and concentrated to give a white solid. To a suspension of the solid in CH$_2$Cl$_2$ (50 mL) was added diisopropylethylamine (6.46 mL, 37.1 mmol). The mixture was cooled at 4° C. and a solution of 4-bromo-2-trifluoromethoxy-benzenesulfonyl chloride (3.31 g, 9.75 mmol) in CH$_2$Cl$_2$ (10 mL) was added below 5° C. The reaction mixture was stirred at 4° C. for 1.5 hr. The reaction was quenched with saturated aqueous NaHCO$_3$ The aqueous layer was extracted with CHCl$_3$ (three times). The combined organic layer was dried over MgSO$_4$, filtered, concentrated, and purified by flash chromatography (NH-silica gel, 20% EtOAc in hexane) to give trans-4-bromo-N-{4-[(4-dimethylamino-quinazolin-2-ylamino)-methyl]-cyclohexylmethyl}-2-trifluoromethoxy-benzenesulfonamide (3.45 g, 60%) as a pale yellow solid.

ESI MS m/e 616, M+H$^+$; $^1$H NMR (300 MHz, CDCl$_3$) δ 7.89 (d, J=8.9 Hz, 1 H), 7.81 (d, J=7.6 Hz, 1 H), 7.35-7.61 (m, 4 H), 7.02 (t, J=6.8 Hz, 1 H), 4.96 (brs, 1 H), 3.35 (t, J=6.1 Hz, 2 H), 3.26 (s, 6 H), 2.79 (d, J=6.7 Hz, 2 H), 1.32-1.98 (m, 6 H), 0.72-1.12 (m, 4 H).

Example 2

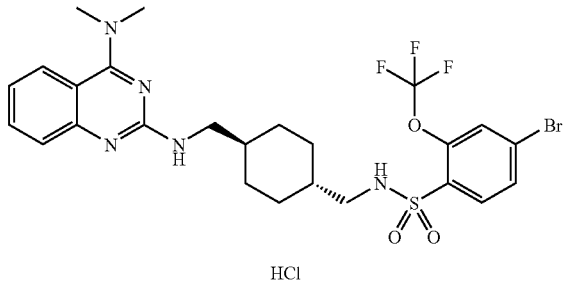

HCl trans-4-Bromo-N-{4-[(4-dimethylamino-quinazolin-2-ylamino)-methyl]-cyclohexylmethyl}-2-trifluoromethoxy-benzenesulfonamide hydrochloride Step A: Synthesis of trans-4-bromo-N-{4-[(4-dimethylamino-quinazolin-2-ylamino)-methyl]-cyclohexylmethyl}-2-trifluoromethoxy-benzenesulfonamide hydrochloride.

A solution of trans-4-bromo-N-{4-[(4-dimethylamino-quinazolin-2-ylamino)-methyl]-cyclohexylmethyl}-2-trifluoromethoxy-benzenesulfonamide obtained step H of example 1 (3.45 g, 5.61 mmol) in EtOAc (100 mL) was cooled on an ice-bath and 4 M hydrogen chloride in EtOAc (1.66 mL) was added. The mixture was stirred at ambient temperature for 1 hr and concentrated to give a white solid. The solid was recrystallized from 16% EtOH in Et$_2$O, and dried under reduced pressure to give trans-4-bromo-N-{4-[(4-dimethylamino-quinazolin-2-ylamino)-methyl]-cyclohexylmethyl}-2-trifluoromethoxy-benzenesulfonamide hydrochloride (2.76 g, 75%) as a white solid.

ESI MS m/e 616, M+H$^+$; $^1$H NMR (300 MHz, CDCl$_3$) δ 13.50 (brs, 1H), 8.42 (t, J=6.0 Hz, 1 H), 7.86-7.94 (m, 2 H), 7.51-7.68 (m, 4H), 7.21-7.28 (m, 1 H), 4.83 (d, J=6.4 Hz, 1 H), 3.51 (s, 6H), 3.35 (t, J=6.0 Hz, 2H), 2.78 (t, J=6.4 Hz, 2H), 1.73-1.95 (m, 4H), 1.35-1.65 (m, 2H), 0.81-1.12 (m, 4H).

Example 3

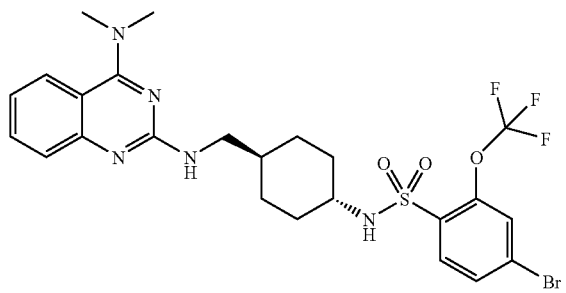

trans-4-Bromo-N-9-{4-[(4-dimethylamino-quinazolin-2-ylamino)-methyl]-cyclohexyl}-2-trifluoromethoxy-benzenesulfonamide Step A: Synthesis of trans-[4-(tert-butoxycarbonylamino-methyl)-cyclohexyl]-carbamic acid benzyl ester.

To a suspension of trans-4-aminomethyl-cyclohexanecarboxylic acid (15.0 g, 95.4 mmol) in CHCl$_3$ (150 mL) were added 1 M aqueous sodium hydroxide (150 mL) and (Boc)$_2$O (21.9 g, 100 mmol) successively. The reaction mixture was stirred at ambient temperature for 15 hr, and partitioned between CHCl$_3$ and water. The aqueous layer was acidified with saturated aqueous KHSO$_4$ (pH=3), extracted with CHCl$_3$ (three times). The combined organic layer was washed with brine, dried over MgSO$_4$, filtered, and concentrated to give a white solid. To a suspension of the above solid in benzene (75 mL) were added phosphorazidic acid diphenyl ester (16.2 g, 58.9 mmol) and triethylamine (5.94 g, 58.7 mmol). The reaction mixture was stirred at reflux for 3 hr (Caution! Vigorous exothermic reaction). Benzyl alcohol (6.65 g, 61.5 mmol) was added, the reaction mixture was stirred at reflux for 24 hr, concentrated. After dissolution with EtOAc and H$_2$O, the organic layer was separated. The aqueous layer was extracted with EtOAc (twice), the combined organic layer was washed with 1 M aqueous KHSO$_4$, saturated aqueous NaHCO$_3$ and brine, dried over MgSO$_4$, filtered, concentrated, and purified by flash chromatography (silica gel, 33% EtOAc in hexane) to give a white solid. A suspension of the above solid in Et$_2$O was stirred at ambient temperature for 30 min and filtered. The filtrate was washed with Et$_2$O and dried under reduced pressure to give trans-[4-(tert-butoxycarbonylamino-methyl)-cyclohexyl]-carbamic acid benzyl ester (17.4 g, 50%) as a white solid.

ESI MS m/e 385, M+Na$^+$; $^1$H NMR (300 MHz, CDCl$_3$) δ 7.22-7.41 (m, 5 H), 5.09 (s, 2 H), 4.20-4.68 (m, 2 H), 3.23-3.60 (m, 1 H), 2.96 (t, 2H, J=6.4 Hz), 1.62-2.18 (m, 4 H), 1.44 (s, 9 H), 1.30-1.60 (m, 1 H), 0.90-1.23 (m, 4 H).

Step B: Synthesis of trans-(4-aminomethyl-cyclohexyl)-carbamic acid benzyl ester hydrochloride.

To a suspension of trans-[4-(tert-butoxycarbonylamino-methyl)-cyclohexyl]-carbamic acid benzyl ester (4.00 g, 11.0 mmol) in EtOAc (40 mL) was added 4 M hydrogen chloride in EtOAc (10 mL). To the reaction mixture was added CHCl$_3$ (10 mL) and the mixture was stirred at ambient temperature for 3 hr. To the reaction mixture was 4 M hydrogen chloride in EtOAc (20 mL) and the mixture was stirred at ambient temperature for 1.5 hr, filtered, washed with EtOAc, and dried under reduced pressure to give trans-(4-aminomethyl-cyclohexyl)-carbamic acid benzyl ester hydrochloride (2.96 g, 90%) as a white solid.

ESI MS m/e 263, M (free)+H$^+$; $^1$H NMR (300 MHz, DMSO-d$_6$) δ 8.12 (brs, 3 H), 7.25-7.40 (m, 5 H), 7.21 (d, 1 H, J=7.8 Hz), 5.00 (s, 2 H), 3.17-3.30 (m, 1 H), 2.62 (d, 2 H, J=7.0 Hz), 1.64-1.88 (m, 4 H), 1.42-1.60 (m, 1 H), 0.90-1.21 (m, 4 H).

Step C: Synthesis of trans-{4-[(4-dimethylamino-quinazolin-2-ylamino)-methyl]-cyclohexyl}-carbamic acid benzyl ester.

A mixture of (2-chloro-quinazolin-4-yl)-dimethyl-amine (1.50 g, 7.22 mmol) and trans-(4-aminomethyl-cyclohexyl)-carbamic acid benzyl ester hydrochloride (2.59 g, 8.67 mmol) in 2-propanol (15 mL) was stirred at reflux for 8 days and dissolved in CHCl$_3$ and MeOH. The mixture was poured into saturated aqueous NaHCO$_3$, and the aqueous layer was extracted with CHCl$_3$ (three times). The combined organic layer was dried over MgSO$_4$, filtered, concentrated, and purified by flash chromatography (H-silica gel, 33% EtOAc in hexane) to give trans-{4-[(4-dimethylamino-quinazolin-2-ylamino)-methyl]-cyclohexyl}-carbamic acid benzyl ester (1.20 g, 38%) as a pale yellow solid.

ESI MS m/e 434, M+H$^+$; $^1$H NMR (300 MHz, CDCl$_3$) δ 7.76-7.82 (m, 1 H), 7.40-7.50 (m, 2 H), 7.25-7.40 (m, 5 H), 6.95-7.04 (m, 1 H), 5.08 (s, 2 H), 4.82-5.05 (m, 1 H), 4.40-4.70 (m, 1 H), 3.40-3.60 (m, 1 H), 3.35 (t, 2H, J=6.3 Hz), 3.26 (s, 6 H), 1.96-2.18 (m, 2 H), 1.80-1.96 (m, 2 H), 1.45-1.61 (m, 1 H), 1.00-1.20 (m, 4 H).

Step D: Synthesis of trans-4-bromo-N-{4-[(4-dimethylamino-quinazolin-2-ylamino)-methyl]-cyclohexyl}-2-trifluoromethyl-benzenesulfonamide.

To a suspension of trans-{4-[(4-dimethylamino-quinazolin-2-ylamino)-methyl]-cyclohexyl}-carbamic acid benzyl ester (500 mg, 1.15 mmol) in MeOH (5 mL) was added 5% Pd/C (50 mg). The mixture was stirred at ambient temperature under hydrogen atmosphere for 2 hr, at 50° C. for 8 hr, and at ambient temperature for 10.5 hr, filtered, and concentrated to give a colorless oil. To a solution of the above oil in $CH_2Cl_2$ (5 mL) was added diisopropylethylamine (420 μL, 2.41 mmol). The mixture was cooled to 4° C. and a solution of 4-bromo-2-trifluoromethoxy-benzenesulfonyl chloride (431 mg, 1.27 mmol) in $CH_2Cl_2$ (2 mL) was added below 5° C. The reaction mixture was stirred at 4° C. for 1.5 hr. The reaction was quenched with saturated aqueous $NaHCO_3$ The aqueous layer was extracted with $CHCl_3$ (three times). The combined organic layer was dried over $MgSO_4$, filtered, concentrated, and purified by flash chromatography (NH-silica gel, 33% to 50% EtOAc in hexane) to give trans-4-bromo-N-{4-[(4-dimethylamino-quinazolin-2-ylamino)-methyl]-cyclohexyl}-2-trifluoromethoxy-benzenesulfonamide (560 mg, 81%) as a pale yellow solid.

ESI MS m/e 602, M+H$^+$; $^1$H NMR (300 MHz, CDCl$_3$) δ 7.90 (d, 1 H, J=8.9 Hz), 7.80 (dd, 1 H, J=8.4, 0.9 Hz), 7.38-7.58 (m, 4 H), 7.01 (ddd, 1 H, J=8.4, 6.7, 1.6 Hz), 4.85-5.04 (m, 1 H), 3.31 (t, 2 H, J=6.3 Hz), 3.24 (s, 6 H), 3.07-3.20 (m, 1 H), 1.70-1.90 (m, 4 H), 1.42-1.58 (m, 1 H), 0.90-1.28 (m, 4 H).

Example 4

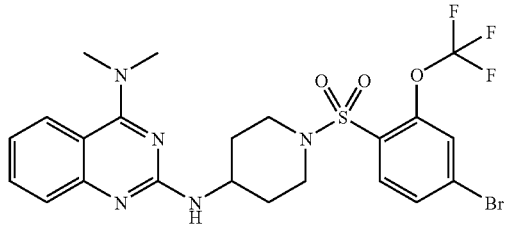

$N^2$-[1-(4-Bromo-2-trifluoromethoxy-benzenesulfonyl)-piperidin-4-yl]-$N^4$,$N^4$-dimethyl-quinazoline-2,4-diamine Step A: Synthesis of IV-(1-benzyl-piperidin-4-yl)-$N^4$,$N^4$-dimethyl-quinazoline-2,4-diamine.

Using the procedure for the step G of example 1, the title compound was obtained.

ESI MS m/e 362, M+H$^+$; $^1$H NMR (300 MHz, CDCl$_3$) δ 7.80 (d, J=7.6 Hz, 1 H), 7.20-7.52 (m, 7 H), 6.97-7.05 (m, 1 H), 4.74-4.90 (m, 1 H), 3.90-4.05 (m, 1 H), 3.53 (s, 2 H), 3.26 (s, 6 H), 2.78-2.90 (m, 2 H), 2.02-2.24 (m, 4 H), 1.48-1.62 (m, 2 H).

Step B: Synthesis of IV-[1-(4-bromo-2-trifluoromethoxy-benzenesulfonyl)-piperidin-4-yl]-$N^4$,$N^4$-dimethyl-quinazoline-2,4-diamine.

To a solution of $N^2$-(1-benzyl-piperidin-4-yl)-$N^4$,$N^4$-dimethyl-quinazoline-2,4-diamine (500 mg, 1.38 mmol) in MeOH (5 mL) was added 20% Pd(OH)$_2$ (100 mg). The mixture was stirred at ambient temperature under hydrogen atmosphere for 1.5 hr, at 50° C. for 8 hr, at ambient temperature for 16.5 hr, filtered through a pad of celite, and concentrated. To a solution of the residue in $CH_2Cl_2$ (5 mL) was added diisopropylethylamine (510 μL, 2.93 mmol). The mixture was cooled to 4° C. and a solution of 4-bromo-2-trifluoromethoxy-benzenesulfonyl chloride (493 mg, 1.45 mmol) in $CH_2Cl_2$ (2 mL) was added below 5° C. The reaction mixture was stirred at 4° C. for 2 hr. The reaction was quenched with saturated aqueous $NaHCO_3$ The aqueous layer was extracted with $CHCl_3$ (three times). The combined organic layer was dried over $MgSO_4$, filtered, concentrated, and purified by flash chromatography (NH-silica gel, 33% EtOAc in hexane) to give $N^2$-[1-(4-bromo-2-trifluoromethoxy-benzenesulfonyl)-piperidin-4-yl]-$N^4$,$N^4$-dimethyl-quinazoline-2,4-diamine (339 mg, 43%) as a pale yellow solid.

ESI MS m/e 596, M+Na$^+$; $^1$H NMR (300 MHz, CDCl$_3$) δ 7.87 (d, J=8.2 Hz, 1 H), 7.81 (dd, J=8.3, 1.0 Hz, 1 H), 7.36-7.61 (m, 4 H), 7.04 (ddd, J=8.3, 6.8, 1.4 Hz, 1 H), 4.77 (d, J=7.8 Hz, 1 H), 3.97-4.14 (m, 1 H), 3.68-3.86 (m, 2 H), 3.25 (s, 6 H), 2.87-3.01 (m, 2 H), 2.10-2.23 (m, 2 H), 1.51-1.70 (m, 2 H).

Example 5

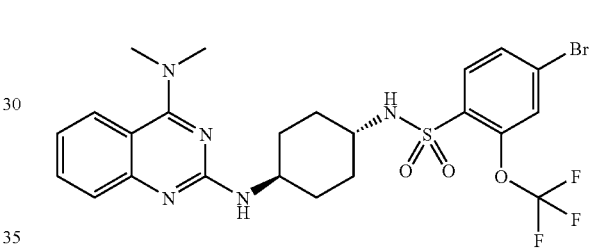

trans-4-Bromo-N-[4-(4-dimethylamino-quinazolin-2-ylamino)-cyclohexyl]-2-trifluoromethoxy-benzenesulfonamide Step A: Synthesis of trans-(4-amino-cyclohexyl)-carbamic acid tert-butyl ester.

To a solution of trans-cyclohexane-1,4-diamine (15.0 g, 131 mmol) in 1,4-dioxane (85 mL) was added (Boc)$_2$O (3.61 g, 16.5 mmol) dropwise over 4 hr. The mixture was stirred at ambient temperature for 19 hr and concentrated. To the residue was added H$_2$O and the insoluble material was removed by filtration. The filtrate was extracted with CHCl$_3$ (three times). The combined organic layer was dried over MgSO$_4$, filtered, concentrated to give trans-(4-amino-cyclohexyl)-carbamic acid tert-butyl ester (3.15 g, 11% based on diamine, 89% based on (Boc)$_2$O) as a white solid.

ESI MS m/e 215, M+H$^+$; $^1$H NMR (300 MHz, CDCl$_3$) δ 4.43 (brs, 1 H), 3.36 (brs, 1 H), 2.57-2.70 (m, 1 H), 1.78-2.04 (m, 4 H), 1.44 (s, 9 H), 1.05-1.38 (m, 4 H).

Step B: Synthesis of trans-[4-(4-dimethylamino-quinazolin-2-ylamino)-cyclohexyl]-carbamic acid tert-butyl ester.

Using the procedure for the step G of example 1, the title compound was obtained ESI MS m/e 408, M+Na$^+$; $^1$H NMR (300 MHz, CDCl$_3$) δ 7.80 (d, J=8.2 Hz, 1 H), 7.39-7.52 (m, 2 H), 7.02 (ddd, 1H, J=8.3, 6.3, 1.9 Hz, 1 H), 4.68-4.78 (m, 1 H), 4.43 (brs, 1 H), 3.89 (brs, 1 H), 3.46 (brs, 1 H), 3.25 (s, 6 H), 2.15-2.24 (m, 2 H), 1.97-2.10 (m, 2 H), 1.45 (s, 9 H), 1.21-1.35 (m, 4 H).

Step C: Synthesis of trans-4-bromo-N-[4-(4-dimethylamino-quinazolin-2-ylamino)-cyclohexyl]-2-trifluoromethoxy-benzenesulfonamide.

To a solution of trans-[4-(4-dimethylamino-quinazolin-2-ylamino)-cyclohexyl]-carbamic acid tert-butyl ester (500 mg, 1.30 mmol) in EtOAc (5 mL) was added 4 M hydrogen chloride in EtOAc (5 mL). The mixture was stirred at ambient temperature for 1 hr and concentrated to give a white solid. To a suspension of the above solid in $CH_2Cl_2$ (7 mL) was added diisopropylethylamine (905 µL, 5.20 mmol). The mixture was cooled to 4° C. and a solution of 4-bromo-2-trifluoromethoxy-benzenesulfonyl chloride (462 mg, 1.36 mmol) in $CH_2Cl_2$ (2 mL) was added below 5° C. The reaction mixture was stirred at 4° C. for 1.5 hr. To the reaction mixture was added a solution of 4-bromo-2-trifluoromethoxy-benzenesulfonyl chloride (88 mg, 0.26 mmol) in $CH_2Cl_2$ (0.5 mL) and the mixture was stirred at 4° C. for 1 hr. To the reaction mixture was added diisopropylethylamine (230 µL, 1.32 mmol) and the mixture was stirred at 4° C. for 1.5 hr. The reaction was quenched with saturated aqueous $NaHCO_3$ The aqueous layer was extracted with $CHCl_3$ (three times). The combined organic layer was dried over $MgSO_4$, filtered, concentrated, and purified by flash chromatography (NH-silica gel, 50% EtOAc in hexane) to give trans-4-bromo-N-[4-(4-dimethylamino-quinazolin-2-ylamino)-cyclohexyl]-2-trifluoromethoxy-benzenesulfonamid (339 mg, 44%) as a white solid.

ESI MS m/e 588, M+H$^+$; $^1$H NMR (300 MHz, CDCl$_3$) δ 7.92 (d, J=8.9 Hz, 1 H), 7.80 (dd, J=8.3, 0.7 Hz, 1 H), 7.37-7.59 (m, 4 H), 6.99-7.06 (m, 1 H), 4.64-4.75 (m, 1 H), 3.78-3.94 (m, 1 H), 3.17-3.30 (m, 7 H), 2.09-2.20 (m, 2 H), 1.85-1.97 (m, 2 H), 1.12-1.47 (m, 4 H).

Example 6

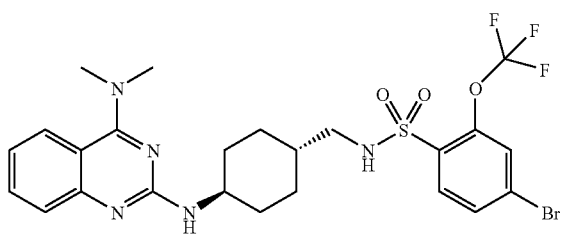

trans-4-Bromo-N-[4-(4-dimethylamino-quinazolin-2-ylamino)-cyclohexylmethyl]-2-trifluoromethoxy-benzenesulfonamide Step A: Synthesis of trans-(4-amino-cyclohexylmethyl)-carbamic acid tert-butyl ester.

To a suspension of trans-[4-(tert-butoxycarbonylamino-methyl)-cyclohexyl]-carbamic acid benzyl ester (4.00 g, 11.0 mmol) in MeOH (40 mL) was added 5% Pd/C (400 mg). The mixture was stirred at ambient temperature under hydrogen atmosphere for 1 hr, filtered through a pad of celite, and concentrated to give a white solid. A suspension of the above solid in hexane (15 mL) was stirred at ambient temperature for 30 min. The solid was collected by filtration, washed with hexane, dried under reduced pressure to give trans-(4-amino-cyclohexylmethyl)-carbamic acid tert-butyl ester (2.52 g, 100%) as a white solid.

ESI MS m/e 229, M+H$^+$; $^1$H NMR (300 MHz, CDCl$_3$) δ 4.56-4.88 (m, 1 H), 3.00 (t, J=6.5 Hz, 2 H), 2.54-2.65 (m, 1 H), 1.70-1.94 (m, 4 H), 1.44 (s, 9 H), 1.18-1.50 (m, 1 H), 0.92-1.15 (m, 4 H).

Step B: Synthesis of trans-[4-(4-dimethylamino-quinazolin-2-ylamino)-cyclohexylmethyl]-carbamic acid tert-butyl ester.

Using the procedure for the step G of example 1, the title compound was obtained ESI MS m/e 422, M+Na$^+$; $^1$H NMR (300 MHz, CDCl$_3$) 7.81 (d, J=7.9 Hz, 1 H), 7.38-7.52 (m, 2 H), 6.96-7.07 (m, 1 H), 4.55-4.84 (m, 2 H), 3.75-3.97 (m, 1 H), 3.26 (s, 6 H), 3.01 (t, J=6.4 Hz, 2 H), 2.15-2.30 (m, 2 H), 1.75-1.88 (m, 2 H), 1.45 (s, 9 H), 1.35-1.54 (m, 1 H), 1.00-1.30 (m, 4 H).

Step C: Synthesis of trans-4-bromo-N-[4-(4-dimethylamino-quinazolin-2-ylamino)-cyclohexylmethyl]-2-trifluoromethoxy-benzenesulfonamide.

To a suspension of trans-[4-(4-dimethylamino-quinazolin-2-ylamino)-cyclohexylmethyl]-carbamic acid tert-butyl ester (500 mg, 1.25 mmol) in EtOAc (5 mL) was added 4 M hydrogen chloride in EtOAc (5 mL). The mixture was stirred at ambient temperature for 1 hr and concentrated to give a white solid. To a suspension of the above solid in $CH_2Cl_2$ (7 mL) was added diisopropylethylamine (905 µL, 5.20 mmol). The mixture was cooled to 4° C. and a solution of 4-bromo-2-trifluoromethoxy-benzenesulfonyl chloride (446 mg, 1.31 mmol) in $CH_2Cl_2$ (2 mL) was added below 5° C. The reaction mixture was stirred at 4° C. for 1.5 hr. To the reaction mixture was added a solution of 4-bromo-2-trifluoromethoxy-benzenesulfonyl chloride (85 mg, 0.25 mmol) in $CH_2Cl_2$ (0.5 mL) and the mixture was stirred at 4° C. for 1 hr. To the reaction mixture was added diisopropylethylamine (220 µL, 1.26 mmol) and the mixture was stirred at 4° C. for 1 hr. The reaction was quenched with saturated aqueous $NaHCO_3$. The aqueous layer was extracted with $CHCl_3$ (three times). The combined organic layer was dried over $MgSO_4$, filtered, concentrated, and purified by flash chromatography (NH-silica gel, 50% EtOAc in hexane) to give trans-4-bromo-N-[4-(4-dimethylamino-quinazolin-2-ylamino)-cyclohexylmethyl]-2-trifluoromethoxy-benzenesulfonamide (624 mg, 83%) as a pale yellow solid.

ESI MS m/e 602, M+H$^+$; $^1$H NMR (300 MHz, CDCl$_3$) δ 7.89 (d, J=8.9 Hz, 1 H), 7.80 (d, J=8.5 Hz, 1 H), 7.39-7.60 (m, 4 H), 7.04 (ddd, J=8.2, 6.8, 1.6 Hz, 1 H), 3.71-3.92 (m, 1 H), 3.30 (s, 6 H), 2.85 (d, J=6.5 Hz, 2 H), 2.10-2.22 (m, 2 H), 1.70-1.86 (m, 2 H), 1.37-1.53 (m, 1 H), 0.98-1.32 (m, 4 H).

Example 7

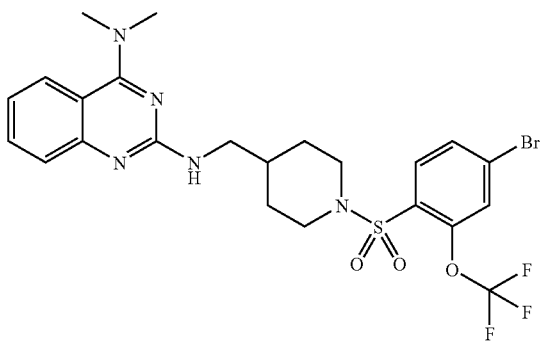

N²-[1-(4-Bromo-2-trifluoromethoxybenzenesulfonyl)-piperidin-4-ylmethyl]-N⁴,N⁴-dimethyl-quinazoline-2,4-diamine Step A: Synthesis of 4-aminomethyl-piperidine-1-carboxylic acid tert-butyl ester.

To a solution of C-piperidin-4-yl-methylamine (15.0 g, 131 mmol) in toluene (165 mL) was added benzaldehyde (13.9 g, 131 mmol) and the mixture was stirred at reflux with a Dean-Stark trap under N₂ atmosphere for 3 hr, and cooled on an ice-bath. To the reaction mixture was added (Boc)₂O (31.5 g, 144 mmol) dropwise over 15 min. The mixture was stirred at ambient temperature for 2.5 days, and concentrated. To the residue was added 1 M aqueous KHSO₄ and the mixture was stirred at ambient temperature for 7 hr, the aqueous layer was washed with EtO (twice), alkalized with sodium hydroxide, and extracted with CHCl₃ (five times). The combined organic layer was dried over MgSO₄, filtered, concentrated. The precipitate was suspended in hexane (10 mL) and the suspension was stirred at ambient temperature for 10 min. The solid was collected by filtration and dried under reduced pressure to give 4-aminomethyl-piperidine-1-carboxylic acid tert-butyl ester (25.8 g, 92%) as a white solid.

ESI MS m/e 215, M+H⁺; ¹H NMR (300 MHz, CDCl₃) δ 3.85-4.22 (m, 2 H), 2.90 (d, J=6.8 Hz, 2 H), 2.50-2.80 (m, 2 H), 1.70-2.02 (m, 3 H), 1.45 (s, 9 H), 1.10-1.28 (m, 2 H).

Step B: Synthesis of 4-[(4-dimethylamino-quinazolin-2-ylamino)-methyl]-piperidine-1-carboxylic acid tert-butyl ester.

Using the procedure for the step G of example 1, the title compound was obtained ESI MS m/e 386, M+H⁺; ¹H NMR (300 MHz, CDCl₃) δ 7.81 (d, J=8.4 Hz, 1 H), 7.41-7.53 (m, 2 H), 6.99-7.06 (m, 1 H), 5.16 (brs, 1 H), 4.00-4.20 (m, 2 H), 3.41 (t, J=6.1 Hz, 2 H), 3.26 (s, 6 H), 2.60-2.77 (m, 2 H), 1.67-1.84 (m, 3 H), 1.45 (s, 9 H), 1.11-1.28 (m, 2 H).

Step C: Synthesis of N²-[1-(4-bromo-2-trifluoromethoxy-benzenesulfonyl)-piperidin-4-ylmethyl]-N⁴,N⁴-dimethyl-quinazoline-2,4-diamine.

To a suspension of 4-[(4-dimethylamino-quinazolin-2-ylamino)-methyl]-piperidine-1-carboxylic acid tert-butyl ester (500 mg, 1.30 mmol) in EtOAc (5 mL) was added 4 M hydrogen chloride in EtOAc (5 mL). The mixture was stirred at ambient temperature for 1 hr and concentrated to give a white solid. To a suspension of the above solid in CH₂Cl₂ (5 mL) was added diisopropylethylamine (480 μL, 2.76 mmol). The mixture was cooled to 4° C. and a solution of 4-bromo-2-trifluoromethoxy-benzenesulfonyl chloride (462 mg, 1.36 mmol) in CH₂Cl₂ (2 mL) was added below 5° C. The reaction mixture was stirred at 4° C. for 3 hr. The reaction was quenched with saturated aqueous NaHCO₃ The aqueous layer was extracted with CHCl₃ (three times). The combined organic layer was dried over MgSO₄, filtered, concentrated, and purified by flash chromatography (NH-silica gel, 14% to 20% EtOAc in hexane) to give N²-[1-(4-bromo-2-trifluoromethoxy-benzenesulfonyl)-piperidin-4-ylmethyl]-N⁴,N⁴-dimethyl-quinazoline-2,4-diamine (420 mg, 55%) as a yellow solid.

ESI MS m/e 588, M+H⁺, ¹H NMR (300 MHz, CDCl₃) δ 7.85 (d, J=8.9 Hz, 1 H), 7.81 (dd, J=8.7, 0.9 Hz, 1 H), 7.40-7.56 (m, 4 H), 7.04 (ddd, J=8.2, 6.7, 1.6 Hz, 1 H), 5.10-5.46 (brs, 1 H), 3.85 (d, J=12.4 Hz, 2 H), 3.40 (t, J=6.4 Hz, 2 H), 3.27 (s, 6 H), 2.56-2.67 (m, 2 H), 1.64-1.91 (m, 3 H), 1.23-1.43 (m, 2 H).

Example 8

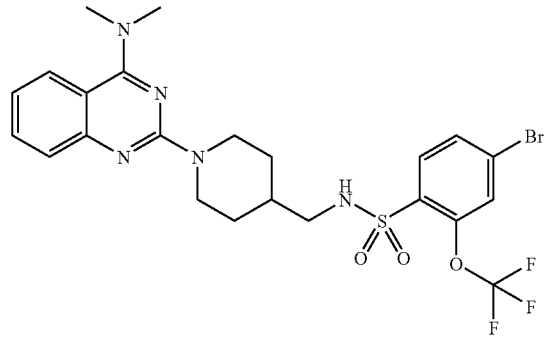

4-Bromo-N-[1-(4-dimethylamino-quinazolin-2-yl)-piperidin-4-ylmethyl]-2-trifluoromethoxy-benzenesulfonamide Step A: Synthesis of 4-(benzyloxycarbonylamino-methyl)-piperidine-1-carboxylic acid tert-butyl ester.

To a solution of 4-aminomethyl-piperidine-1-carboxylic acid tert-butyl ester (7.00 g, 32.7 mmol) in CHCl₃ (70 mL) was added triethylamine (3.64 g, 36.0 mmol). The resulting solution was cooled to 4° C. and ZCl (6.13 g, 35.9 mmol) was added below 8° C. over 15 min. The reaction mixture was stirred at ambient temperature for 18 hr, and poured into saturated aqueous NaHCO₃. The aqueous layer was extracted with CHCl₃ (three times), dried over MgSO₄, filtered, concentrated, and purified by flash chromatography (silica gel, 33% to 50% EtOAc in hexane) to give 4-(benzyloxycarbonylamino-methyl)-piperidine-1-carboxylic acid tert-butyl ester (10.7 g, 94%) as a colorless oil.

ESI MS m/e 371, M+Na⁺; ¹H NMR (300 MHz, CDCl₃) δ 7.26-7.37 (m, 5 H), 5.09 (s, 2 H), 4.84-5.01 (m, 1 H), 3.95-4.22 (m, 2 H), 2.98-3.16 (m, 2 H), 2.66 (t, J=12.4 Hz, 2 H), 1.58-1.72 (m, 3 H), 1.45 (s, 9 H), 0.98-1.18 (m, 2 H).

Step B: Synthesis of piperidin-4-ylmethyl-carbamic acid benzyl ester hydrochloride.

A solution of 4-(benzyloxycarbonylamino-methyl)-piperidine-1-carboxylic acid tert-butyl ester (10.2 g, 29.3 mmol) in EtOAc (100 mL) was cooled on an ice-bath and 4 M hydrogen chloride in EtOAc (100 mL) was added. The mixture was stirred at ambient temperature for 1 hr and concentrated. The residue was suspended in hexane (30 mL) and the mixture was stirred at ambient temperature for 30 min. The solid was collected by filtration, washed with hexane, and dried under reduced pressure to give piperidin-4-ylmethyl-carbamic acid benzyl ester hydrochloride (7.24 g, 87%) as a white solid.

ESI MS m/e 271, M (free)+Na⁺; ¹H NMR (300 MHz, DMSO-d₆) δ 9.10 (brs, 2 H), 7.20-7.50 (m, 6 H), 5.02 (s, 2 H), 3.15-3.28 (m, 2 H), 2.68-3.02 (m, 4 H), 1.56-1.82 (m, 3 H), 1.20-1.52 (m, 2 H).

Step C: Synthesis of [1-(4-dimethylamino-quinazolin-2-yl)-piperidin-4-ylmethyl]-carbamic acid benzyl ester.

Using the procedure for the step C of example 3, the title compound was obtained ESI MS m/e 420, M+H⁺; ¹H NMR (300 MHz, CDCl₃) δ 7.78 (d, J=8.2 Hz, 1 H), 7.21-7.49 (m, 7 H), 6.95-7.04 (m, 1

H), 5.06-5.17 (m, 2 H), 4.83-4.98 (m, 3 H), 3.24 (s, 6 H), 3.00-3.16 (m, 2 H), 2.77-2.91 (m, 2 H), 1.58-1.97 (m, 3 H), 1.12-1.33 (m, 2 H).

Step D: Synthesis of 4-bromo-N-[1-(4-dimethylamino-quinazolin-2-yl)-piperidin-4-ylmethyl]-2-trifluoromethoxy-benzenesulfonamide.

Using the procedure for the step D of example 3, the title compound was obtained ESI MS m/e 588, M+H$^+$; $^1$H NMR (300 MHz, CDCl$_3$) δ 7.87 (d, J=8.7 Hz, 1 H), 7.78 (d, J=8.2 Hz, 1 H), 7.44-7.59 (m, 4 H), 6.97-7.06 (m, 1 H), 4.94-5.04 (m, 1 H), 4.89 (d, J=13.2 Hz, 2 H), 3.25 (s, 6 H), 2.75-2.88 (m, 4 H), 1.64-1.82 (m, 3 H), 1.05-1.28 (m, 2 H).

Example 9

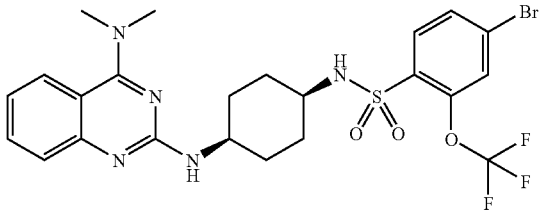

cis-4-Bromo-N-[4-(4-dimethylamino-quinazolin-2-ylamino)-cyclohexyl]-2-trifluoromethoxy-benzene-sulfonamide Step A: Synthesis of cis-(4-benzyloxycarbonylamino-cyclohexyl)-carbamic acid benzyl ester.

To a suspension of cis-cyclohexane-1,4-dicarboxylic acid (25.0 g, 145 mmol) in benzene (125 mL) were added phosphorazidic acid diphenyl ester (81.9 g, 298 mmol) and triethylamine (30.1 g, 297 mmol). The reaction mixture was stirred at reflux for 2.5 hr (Caution! Vigorous exothermic reaction). Benzyl alcohol (32.2 g, 298 mmol) was added and the mixture was stirred at reflux for 24 hr. The reaction mixture was concentrated and the residue was dissolved in EtOAc and H$_2$O. The organic layer was separated and the aqueous layer was extracted with EtOAc (twice). The combined organic layer was washed with 1 M aqueous KHSO$_4$, saturated aqueous NaHCO$_3$, and brine, dried over MgSO$_4$, filtered, concentrated, and purified by flash chromatography (silica gel, 33% EtOAc in hexane) to give cis-(4-benzyloxycarbonylamino-cyclohexyl)-carbamic acid benzyl ester (52.0 g, 94%) as a colorless oil.

ESI MS m/e 405, M+Na$^+$; $^1$H NMR (300 MHz, CDCl$_3$) δ 7.15-7.40 (m, 10 H), 5.07 (s, 4 H), 4.70-5.00 (m, 2 H), 3.52-3.80 (m, 2 H), 1.60-1.80 (m, 4 H), 1.45-1.60 (m, 4 H).

Step B: Synthesis of cis-(4-amino-cyclohexyl)-carbamic acid tert-butyl ester.

To a solution of cis-(4-benzyloxycarbonylamino-cyclohexyl)-carbamic acid benzyl ester (91.7 g, 240 mmol) in MeOH (460 mL) was added 5% Pd/C (9.17 g). The reaction mixture was stirred at ambient temperature under hydrogen atmosphere for 2.5 days, filtered through a pad of celite, and concentrated to give a diamine as a colorless oil. To a solution of the diamine in MeOH (550 mL) was added a solution of (Boc)$_2$O (6.59 g, 30.2 mmol) in MeOH (80 mL) dropwise over 4 hr. The reaction mixture was stirred at ambient temperature for 1.5 days and concentrated. After dissolution with H$_2$O, the aqueous layer was extracted with CHCl$_3$ (three times). The combined organic layer was dried over MgSO$_4$, filtered, and concentrated to give cis-(4-amino-cyclohexyl)-carbamic acid tert-butyl ester (7.78 g, 15%, crude) as a colorless oil. The aqueous layer was concentrated and the residue was dissolved in MeOH, dried over MgSO$_4$, filtered, and concentrated to give a recovered diamine (32.9 g) as a colorless oil. To a solution of the recovered diamine (32.9 g, 288 mmol) in MeOH (660 mL) was added a solution of (Boc)$_2$O (6.29 g, 28.8 mmol) in MeOH (80 mL) dropwise over 5 hr. The reaction mixture was stirred at ambient temperature for 10 hr and concentrated. After dissolution with H$_2$O, the aqueous layer was extracted with CHCl$_3$ (three times). The combined organic layer was dried over MgSO$_4$, filtered, and concentrated to give cis-(4-amino-cyclohexyl)-carbamic acid tert-butyl ester (8.16 g, 16%, crude) as a colorless oil. The aqueous layer was concentrated and the residue was dissolved in MeOH, dried over MgSO$_4$, filtered, and concentrated to give a recovered diamine (23.1 g) as a colorless oil. To a solution of the recovered diamine (23.1 g, 202 mmol) in MeOH (462 mL) was added a solution of (Boc)$_2$O (4.42 g, 20.3 mmol) in MeOH (56 mL) dropwise over 4 hr. The reaction mixture was stirred at ambient temperature for 3.5 days and concentrated. After dissolution with H$_2$O, the aqueous layer was extracted with CHCl$_3$ (three times). The combined organic layer was dried over MgSO$_4$, filtered, and concentrated to give cis-(4-amino-cyclohexyl)-carbamic acid tert-butyl ester (5.01 g, 10% based on starting material) as a colorless oil. The aqueous layer was concentrated and the residue was dissolved in MeOH, dried over MgSO$_4$, filtered, and concentrated to give a recovered diamine (16.0 g) as a colorless oil. To a solution of the recovered diamine (16.0 g, 140 mmol) in MeOH (320 mL) was added a solution of (Boc)$_2$O (3.06 g, 14.0 mmol) in MeOH (40 mL) dropwise over 4 hr. The reaction mixture was stirred at ambient temperature for 13 hr and concentrated. After dissolution with H$_2$O, the aqueous layer was extracted with CHCl$_3$ (three times). The combined organic layer was dried over MgSO$_4$, filtered, and concentrated to give cis-(4-amino-cyclohexyl)-carbamic acid tert-butyl ester (3.53 g, 7% based on the starting material) as a colorless oil. The aqueous layer was concentrated and the residue was dissolved in MeOH, dried over MgSO$_4$, filtered, and concentrated to give a recovered diamine (11.1 g) as a colorless oil.

ESI MS m/e 215, M+H$^+$; $^1$H NMR (300 MHz, CDCl$_3$) δ 4.30-4.82 (m, 1 H), 3.50-3.80 (m, 1 H), 2.78-2.95 (m, 1 H), 1.44 (s, 9 H), 1.20-1.80 (m, 8 H).

Step C: Synthesis of cis-N$^2$-(4-amino-cyclohexyl)-N$^4$,N$^4$-dimethyl-quinazoline-2,4-diamine.

A mixture of (2-chloro-quinazolin-4-yl)-dimethyl-amine obtained in step B of example 1 (3.00 g, 14.4 mmol) and cis-(4-amino-cyclohexyl)-carbamic acid tert-butyl ester (3.72 g, 17.4 mmol) in 2-propanol (10 mL) was stirred at reflux for 5.5 days, poured into saturated aqueous NaHCO$_3$, and the aqueous layer was extracted with CHCl$_3$ (three times). The combined organic layer was dried over MgSO$_4$, filtered, concentrated, and purified by flash chromatography (NH-silica, 20% EtOAc in hexane) to give cis-[4-(4-dimethylamino-quinazolin-2-ylamino)-cyclohexyl]-carbamic acid tert-butyl ester including solvent (5.44 g) as a colorless oil. To a solution of the above material (5.44 g) in EtOAc (10 mL) was added 4 M hydrogen chloride in EtOAc (50 mL). The reaction mixture was stirred at ambient temperature for 2 hr, and concentrated. The residue was alkalized with saturated aqueous NaHCO$_3$, and the precipitate was collected by filtration to give cis-N$^2$-(4-amino-cyclohexyl)-N$^4$,N$^4$-dimethylquinazoline-2,4-diamine (2.26 g, 55%) as a white solid. The aqueous layer was extracted CHCl$_3$ (three times). The combined organic layer was dried over MgSO$_4$, filtered, and concentrated to give cis-N$^2$-(4-amino-cyclohexyl)-N$^4$,N$^4$-diethyl-quinazoline-2,4-diamine (687 mg, 17%) as a white solid.

ESI MS m/e 285, M; $^1$H NMR (300 MHz, DMSO-d$_6$) δ 7.86 (d, J=7.5 Hz, 1 H), 7.47 (t, J=8.3 Hz, 1 H), 7.29 (d, J=8.3 Hz, 1 H), 7.01 (t, J=7.6 Hz, 1 H), 6.56 (d, J=7.5 Hz, 1 H), 3.83-4.06 (m, 1 H), 3.38-3.52 (m, 1 H), 3.20 (s, 6 H), 1.22-1.82 (m, 8 H).

Step D: Synthesis of cis-4-bromo-N-[4-(4-dimethylamino-quinazolin-2-ylamino)-cyclohexyl]-2-trifluoromethoxy-benzenesulfonamide.

To a suspension of cis-N$^2$-(4-amino-cyclohexyl)-N$^4$,N$^4$-dimethyl-quinazoline-2,4-diamine (680 mg, 2.38 mmol) in CH$_2$Cl$_2$ (7 mL) was added diisopropylethylamine (620 μL, 3.56 mmol). The mixture was cooled on an ice-bath and a solution of 4-bromo-2-trifluoromethoxy-benzenesulfonyl chloride (849 mg, 2.50 mmol) in CH$_2$Cl$_2$ (3 mL) was added dropwise. The reaction mixture was stirred on an ice-bath for 6.5 hr. The reaction was quenched with saturated aqueous NaHCO$_3$ The aqueous layer was extracted with CHCl$_3$ (three times). The combined organic layer was dried over MgSO$_4$, filtered, concentrated, and purified by flash chromatography (NH-silica gel, 33% EtOAc in hexane) to give cis-4-bromo-N-[4-(4-dimethylamino-quinazolin-2-ylamino)-cyclohexyl]-2-trifluoromethoxy-benzenesulfonamide (782 mg, 56%) as a pale yellow solid.

ESI MS m/e 588, M$^+$; $^1$H NMR (300 MHz, CDCl$_3$) δ 7.92 (d, J=8.9 Hz, 1 H), 7.81 (dd, J=8.3, 1.2 Hz, 1 H), 7.41-7.58 (m, 4 H), 7.04 (ddd, J=8.3, 6.6, 1.6 Hz, 1 H), 4.00-4.12 (m, 1 H), 3.36-3.45 (m, 1 H), 3.31 (s, 6 H), 1.54-1.84 (m, 8 H).

Example 10

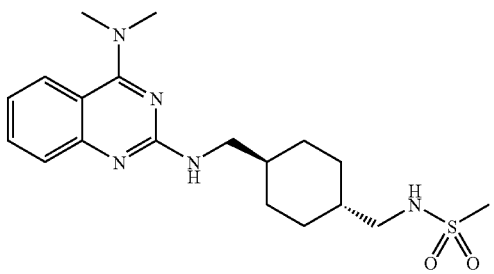

trans-N-{4-[(4-Dimethylamino-quinazolin-2-ylamino)-methyl]-cyclohexylmethyl}-methane-sulfonamide Step A: Synthesis of trans-N-{4-[(4-dimethylamino-quinazolin-2-ylamino)-methyl]-cyclohexylmethyl}-methane sulfonamide.

Using the procedure for the step H of example 1, the title compound was obtained.

ESI MS m/e 392, M+H$^+$; $^1$H NMR (300 MHz, CDCl$_3$) δ 7.81 (d, J=7.8 Hz, 1 H), 7.38-7.53 (m, 2 H), 7.02 (ddd, J=8.3, 6.6, 1.6 Hz, 1 H), 5.07 (brs, 1 H), 4.61 (brs, 1 H), 3.36 (t, J=6.2 Hz, 2 H), 3.27 (s, 6 H), 2.94 (s, 3 H), 2.91-3.01 (m, 2 H), 1.76-1.98 (m, 4 H), 1.37-1.64 (m, 2 H), 0.85-1.12 (m, 4 H).

Example 11

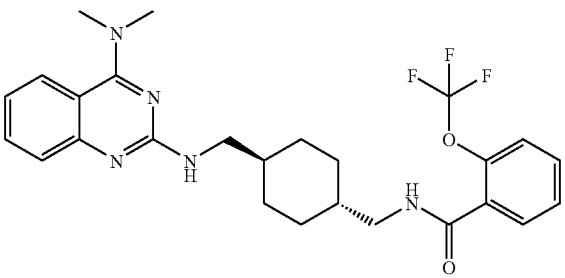

trans-N-{4-[(4-dimethylamino-quinazolin-2-ylamino)-methyl]-cyclohexylmethyl}-2-trifluoromethoxy-benzamide Step A: Synthesis of trans-N-{4-[(4-dimethylamino-quinazolin-2-ylamino)-methyl]-cyclohexylmethyl}-2-trifluoromethoxy-benzamide.

To a suspension of trans-{4-[(4-dimethylamino-quinazolin-2-ylamino)-methyl]cyclohexylmethyl}-carbamic acid tert-butyl ester obtained in step G of example 1 (800 mg, 1.93 mmol) in EtOAc (10 mL) was added 4 M hydrogen chloride in EtOAc (10 mL). The mixture was stirred at ambient temperature for 60 min and concentrated to give a white solid. To a suspension of the solid in CH$_2$Cl$_2$ (10 mL) was added diisopropylethylamine (706 μL, 4.05 mmol). The mixture was cooled at 4° C. and a solution of 2-(trifluoromethoxy)benzoyl chloride (455 mg, 2.03 mmol) in CH$_2$Cl$_2$ (4 mL) was added below 5° C. The reaction mixture was stirred at 4° C. for 90 min. The reaction was quenched with saturated aqueous NaHCO$_3$ The aqueous layer was extracted with CHCl$_3$ (three times). The combined organic layer was dried over MgSO$_4$, filtered, concentrated, and purified by flash chromatography (NH-silica gel, 33% EtOAc in hexane) to give trans-N-{4-[(4-dimethylamino-quinazolin-2-ylamino)-methyl]-cyclohexylmethyl}-2-trifluoromethoxy-benzamide (772 mg, 80%) as a pale yellow solid.

ESI MS m/e 502, M+H$^+$; $^1$H NMR (300 MHz, CDCl$_3$) δ 7.90 (dd, J=7.4, 1.6, Hz, 1 H), 7.81 (d, J=8.1 Hz, 1 H), 7.33-7.55 (m, 4 H), 7.29 (d, J=8.8, Hz, 1 H), 6.96-7.08 (m, 1 H), 6.55 (brs, 1 H), 4.97 (brs, 1 H), 3.28-3.43 (m, 4 H), 3.26 (s, 6 H), 1.76-2.10 (m, 4 H), 1.44-1.72 (m, 2 H), 0.90-1.21 (m, 4 H).

Example 12

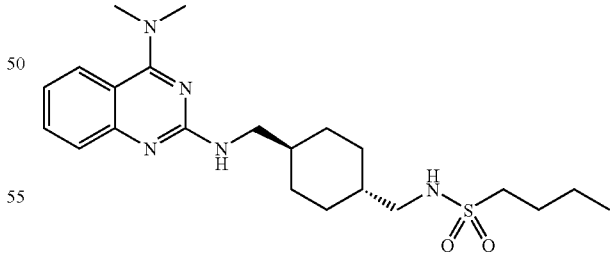

trans-Butane-1-sulfonic acid {4-[(4-dimethylamino-quinazolin-2-ylamino)-methyl]-cyclohexylmethyl}-amide Step A: Synthesis of trans-butane-1-sulfonic acid {4-[(4-dimethylamino-quinazolin-2-ylamino)-methyl]-cyclohexylmethyl}-amide.

Using the procedure for the step H of example 1, the title compound was obtained.

ESI MS m/e 434, M+H⁺; ¹H NMR (300 MHz, CDCl₃) δ 7.81 (d, J=8.2 Hz, 1 H), 7.35-7.54 (m, 2 H), 6.97-7.07 (m, 1 H), 4.41 (t, J=6.1 Hz, 1 H), 3.36 (t, J=6.1 Hz, 2 H), 3.27 (s, 6 H), 2.89-3.05 (m, 4 H), 1.71-1.97 (m, 6 H), 1.37-1.65 (m, 4 H), 0.82-1.12 (m, 7 H).

Example 13

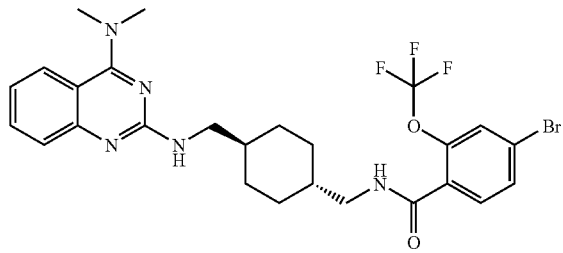

trans-4-Bromo-N-{4-[(4-dimethylamino-quinazolin-2-ylamino)-methyl]-cyclohexylmethyl}-2-trifluoromethoxy-benzamide Step A: Synthesis of 4-bromo-2-trifluoromethoxy-benzaldehyde.

A solution of 4-bromo-1-iodo-2-trifluoromethoxy-benzene (1.00 g, 2.72 mmol) in THF (15 mL) was cooled to −78° C., and 2.66 M BuLi in hexane (2.05 mL, 5.44 mmol) was added dropwise. The reaction mixture was stirred at −78° C. for 1.5 h, and N-formylmorpholine (0.57 mL, 5.63 mmol) was added. The reaction mixture was stirred at −78° C. for 15 min and at ambient temperature for 80 min. The reaction was quenched with 0.25 M aqueous citric acid (10 mL), and the resulting mixture was extracted with EtOAc (three times). The combined organic layer was dried over MgSO₄, filtered, concentrated, and purified by flash chromatography (silica gel, 2% to 5% EtOAc in hexane) to give 4-bromo-2-trifluoromethoxy-benzaldehyde (560 mg, 77%) as a pale brown solid.

CI MS m/e 269, M+H⁺; ¹H NMR (300 MHz, CDCl₃) δ 10.33 (s, 1 H), 7.85 (d, J=8.1 Hz, 1 H), 7.50-7.67 (m, 2 H).

Step B: Synthesis of 4-bromo-2-trifluoromethoxy-benzoic acid.

A solution of 4-bromo-2-trifluoromethoxy-benzaldehyde (550 mg, 2.04 mmol) in 1,4-dioxane (27 mL) and H₂O (9 mL) was cooled at 4° C. To the solution were added amidosulfuric acid (296 mg, 3.05 mmol) and sodium dihydrogen phosphate dihydrate (1.4 g, 8.98 mmol). The mixture was stirred at 4° C. for 15 min. To the reaction mixture was added a solution of sodium chlorite (238 mg, 2.63 mmol) in H₂O (1.5 mL) and stirred at 4° C. for 15 min. To the reaction mixture was added Na₂CO₃ (304 mg, 2.41 mmol) and stirred at 4° C. for 15 min. The mixture was acidified with conc-HCl (pH=1), and the aqueous layer was extracted with CHCl₃ (three times). The combined organic layer was dried over MgSO₄, filtered, concentrated, and purified by flash chromatography (silica gel, 1% MeOH in CHCl₃) to give 4-bromo-2-trifluoromethoxy-benzoic acid (471 mg, 81%) as a white solid.

ESI MS m/e 284, M⁺; ¹H NMR (300 MHz, CDCl₃) δ 7.98 (d, J=8.4 Hz, 1 H), 7.53-7.62 (m, 2 H).

Step C: Synthesis of trans-4-bromo-N-{4-[(4-dimethylamino-quinazolin-2-ylamino)-methyl]-cyclohexylmethyl}-2-trifluoromethoxy-benzamide.

To a solution of 4-bromo-2-trifluoromethoxy-benzoic acid (454 mg, 1.59 mmol) in CH₂Cl₂ (6 mL) were added DMF (1.5 μL, 0.02 mmol) and SOCl₂ (158 μL, 2.17 mmol). The mixture was stirred at reflux for 1 hr and concentrated to give acid chloride as a pale yellow oil. To a suspension of trans-{4-[(4-dimethylamino-quinazolin-2-ylamino)-methyl]cyclohexylmethyl}-carbamic acid tert-butyl ester obtained in step G of example 1 (624 mg, 1.51 mmol) in EtOAc (10 mL) was added 4 M hydrogen chloride in EtOAc (8 mL). The mixture was stirred at ambient temperature for 40 min and concentrated to give a white solid. To a suspension of the solid in CH₂Cl₂ (6 mL) was added diisopropylethylamine (552 μL, 3.17 mmol). The mixture was cooled at 4° C. and a solution of acid chloride in CH₂Cl₂ (6 mL) was added below 5° C. The reaction mixture was stirred at 4° C. for 2.5 hr. The reaction was quenched with saturated aqueous NaHCO₃ The aqueous layer was extracted with CHCl₃ (three times). The combined organic layer was dried over MgSO₄, filtered, concentrated, and purified by flash chromatography (NH-silica gel, 33% EtOAc in hexane) to give trans-4-bromo-N-{4-[(4-dimethylamino-quinazolin-2-ylamino)-methyl]-cyclohexylmethyl}-2-trifluoromethoxy-benzamide (309 mg, 35%) as a pale yellow solid.

ESI MS m/e 580, M+H⁺; ¹H NMR (300 MHz, CDCl₃) δ 7.89 (d, J=8.4 Hz, 1 H), 7.81 (d, J=8.2 Hz, 1 H), 7.39-7.67 (m, 4 H), 7.02 (ddd, J=8.2, 6.4, 1.9 Hz, 1 H), 6.53 (brs, 1 H), 4.99 (brs, 1 H), 3.37 (t, J=6.5 Hz, 2 H), 3.32 (t, J=6.3 Hz, 2 H), 3.27 (s, 6 H), 1.76-2.02 (m, 4 H), 1.48-1.67 (m, 2 H), 0.94-1.16 (m, 4 H).

Example 14

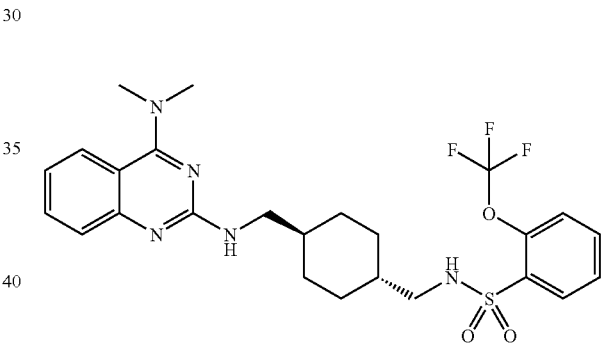

trans-N-{4-[(4-Dimethylamino-quinazolin-2-ylamino)-methyl]-cyclohexylmethyl}-2-trifluoromethoxy-benzenesulfonamide Step A: Synthesis of trans-N-{4-[(4-dimethylamino-quinazolin-2-ylamino)-methyl]-cyclohexylmethyl}-2-trifluoromethoxy-benzenesulfonamide.

To a suspension of trans-{4-[(4-dimethylamino-quinazolin-2-ylamino)-methyl]cyclohexylmethyl}-carbamic acid tert-butyl ester obtained in step G of example 1 (500 mg, 1.21 mmol) in EtOAc (8 mL) was added 4 M hydrogen chloride in EtOAc (7 mL). The mixture was stirred at ambient temperature for 40 min and concentrated to give a white solid. To a suspension of the solid in CH₂Cl₂ (7 mL) was added pyridine (215 μL, 2.66 mmol). The mixture was cooled at 4° C. and a solution of 2-trifluoromethoxy-benzenesulfonyl chloride (331 mg, 1.27 mmol) in CH₂Cl₂ (2 mL) was added below 5° C. The reaction mixture was stirred at 4° C. for 2 hr. The reaction was quenched with saturated aqueous NaHCO₃ The aqueous layer was extracted with CHCl₃ (three times). The combined organic layer was dried over MgSO₄, filtered, concentrated, and purified by flash chromatography (NH-silica gel, 20% EtOAc in hexane) to give trans-N-{4-[(4-dimethylamino-quinazolin-2-ylamino)-methyl]-cyclohexylmethyl}-2-trifluoromethoxy-benzenesulfonamide (231 mg, 36%) as a pale yellow solid.

ESI MS m/e 538, M+H$^+$; $^1$H NMR (300 MHz, CDCl$_3$) δ 8.03 (dd, J=8.0, 1.6 Hz, 1 H), 7.81 (d, J=8.2 Hz, 1 H), 7.57-7.66 (m, 1 H), 7.36-7.52 (m, 4 H), 7.02 (ddd, J=8.3, 6.5, 1.7 Hz, 1 H), 4.94 (brs, 1 H), 4.66 (brs, 1 H), 3.34 (t, J=6.4 Hz, 2 H), 3.26 (s, 6 H), 2.78 (t, J=6.2 Hz, 2 H), 1.68-2.01 (m, 4 H), 1.29-1.60 (m, 2 H), 0.79-1.07 (m, 4 H).

Example 15

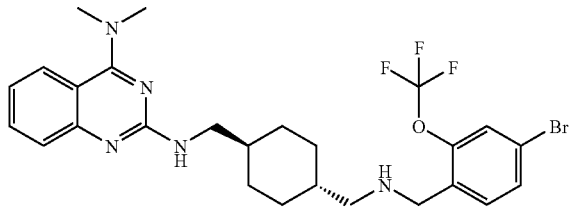

trans-N$^2$-{4-[(4-Bromo-2-trifluoromethoxy-benzylamino)-methyl]-cyclohexylmethyl}-N',N-dimethyl-quinazoline-2,4-diamine Step A: Synthesis of trans-N$^4$-(4-aminomethyl-cyclohexylmethyl)-N$^4$,N$^4$-dimethyl-quinazoline-2,4-diamine.

To a suspension of trans-{4-[(4-dimethylamino-quinazolin-2-ylamino)-methyl]-cyclohexylmethyl}-carbamic acid tert-butyl ester (20.1 g, 48.6 mmol) in EtOAc (200 mL) was added 4 M hydrogen chloride in EtOAc (200 mL). The mixture was stirred at ambient temperature for 90 min and concentrated to give a solid. The solid was alkalized with saturated aqueous NaHCO$_3$ (pH=9), concentrated, and purified by flash chromatography (NH silica gel, 33% MeOH in CHCl$_3$) to give trans-N$^2$-(4-aminomethyl-cyclohexylmethyl)-N$^4$,N$^4$-dimethyl-quinazoline-2,4-diamine (14.7 g, 97%) as a white solid.

ESI MS m/e 314, M+H$^+$; $^1$H NMR (300 MHz, CDCl$_3$) δ 7.81 (d, J=8.2 Hz, 1 H), 7.42-7.52 (m, 2 H), 7.01 (ddd, J=8.2, 6.2, 0.9 Hz, 1 H), 4.95 (brs, 1 H), 3.36 (t, J=6.3 Hz, 2 H), 3.26 (s, 6 H), 2.52 (d, J=6.4 Hz, 2 H), 1.75-1.96 (m, 5 H), 1.48-1.66 (m, 1 H), 0.82-1.40 (m, 6 H).

Step B: Synthesis of trans-N$^2$-{4-[(4-bromo-2-trifluoromethoxy-benzylamino)-methyl]-cyclohexylmethyl}-N$^4$,N$^4$-dimethyl-quinazoline-2,4-diamine.

To a solution of trans-N$^2$-(4-aminomethyl-cyclohexylmethyl)-N$^4$,N$^4$-dimethyl-quinazoline-2,4-diamine (500 mg, 1.59 mmol) in CH$_2$Cl$_2$ (5 mL) were added 4-bromo-2-trifluoromethoxy-benzaldehyde obtained in step A of example 13 (428 mg, 1.59 mmol), acetic acid (95 mg, 1.59 mmol), and NaBH(OAc)$_3$ (505 mg, 2.38 mmol). The reaction mixture was stirred at ambient temperature for 4 hr. The reaction was quenched with saturated aqueous NaHCO$_3$. The aqueous layer was extracted with CHCl$_3$ (three times). The combined organic layer was dried over MgSO$_4$, filtered, concentrated, and purified by flash chromatography (NH-silica gel, 50% EtOAc in hexane) to give trans-N$^2$-{4-[(4-bromo-2-trifluoromethoxy-benzylamino)-methyl]-cyclohexylmethyl}-N$^4$,N$^4$-dimethyl-quinazoline-2,4-diamine (783 mg, 89%) as a pale yellow solid.

ESI MS m/e 566, M+H$^+$; $^1$H NMR (300 MHz, CDCl$_3$) δ 7.80 (d, J=8.2 Hz, 1 H), 7.34-7.52 (m, 5 H), 7.01 (ddd, J=8.3, 6.2, 2.0 Hz, 1 H), 5.00 (brs, 1 H), 3.77 (s, 2 H), 3.36 (t, J=6.3 Hz, 2 H), 3.26 (s, 6 H), 2.43 (d, J=6.7 Hz, 2 H), 1.76-1.95 (m, 4 H), 1.34-1.65 (m, 2 H), 0.83-1.12(m, 4 H).

Example 16

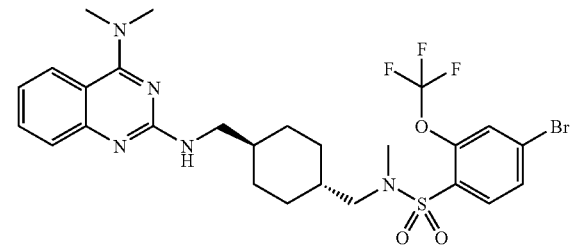

trans-4-Bromo-N-{4-[(4-dimethylamino-quinazolin-2-ylamino)-methyl]-cyclohexylmethyl}-N-methyl-2-trifluoromethoxy-benzenesulfonamide Step A: Synthesis of trans-4-bromo-N-{4-[(4-dimethylamino-quinazolin-2-ylamino)-methyl]-cyclohexylmethyl}-N-methyl-2-trifluoromethoxy-benzenesulfonamide.

To a solution of trans-4-bromo-N-{4-[(4-dimethylamino-quinazolin-2-ylamino)-methyl]-cyclohexylmethyl}-2-trifluoromethoxy-benzenesulfonamide obtained in step H of example 1 (380 mg, 0.61 mmol) in DMF (2 mL) was added 60% sodium hydride in oil (24.6 mg, 0.61 mmol). The reaction mixture was stirred at ambient temperature for 80 min. The reaction mixture was cooled at 0° C. and iodomethane (38.3 μL, 0.61 mmol) was added and stirred at ambient temperature for 3 hr. The reaction was quenched with saturated aqueous NaHCO$_3$. The aqueous layer was extracted with EtOAc (three times). The combined organic layer was dried over MgSO$_4$, filtered, concentrated, and purified by flash chromatography (NH-silica gel, 25% EtOAc in hexane, and silica gel, 5% MeOH in CHCl$_3$) to give trans-4-bromo-N-{4-[(4-dimethylamino-quinazolin-2-ylamino)-methyl]-cyclohexylmethyl}-N-methyl-2-trifluoromethoxy-benzenesulfonamide (268 mg, 69%) as a pale yellow solid.

ESI MS m/e 630, M+H$^+$; $^1$H NMR (300 MHz, CDCl$_3$) δ 7.88 (d, J=9.2 Hz, 1 H), 7.81 (d, J=8.4 Hz, 1 H), 7.41-7.57 (m, 4 H), 7.03 (ddd, J=8.4, 6.3, 1.8 Hz, 1 H), 3.37 (t, J=6.2 Hz, 2 H), 3.27 (s, 6 H), 2.97 (d, J=7.5 Hz, 2H), 2.81 (s, 3H), 1.73-1.97 (m, 4H), 1.46-1.66 (m, 2H), 0.83-1.12 (m, 4H).

Example 17

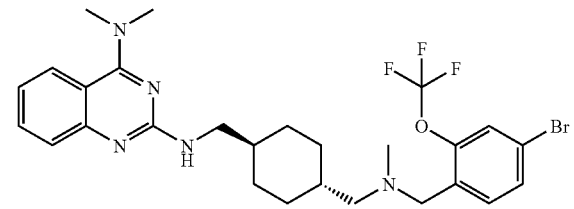

trans-N$^2$-(4-{[(4-Bromo-2-trifluoromethoxy-benzyl)-methyl-amino]-methyl}-cyclohexylmethyl)-N$^4$,N$^4$-dimethyl-quinazoline-2,4-diamine Step A: Synthesis of trans-N$^2$-(4-{[(4-bromo-2-trifluoromethoxy-benzyl)-methyl-amino]-methyl}-cyclohexylmethyl)-N$^4$,N$^4$-dimethyl-quinazoline-2,4-diamine.

To a solution of trans-N$^2$-{4-[(4-bromo-2-trifluoromethoxy-benzylamino)-methyl]-cyclohexylmethyl}-N$^4$, N⁴-dimethyl-quinazoline-2,4-diamine obtained in step B of example 15 (290 mg, 0.52 mmol) in CH₂Cl₂ (3 mL) were added 37% aqueous formaldehyde (42 mg, 0.52 mmol), acetic acid (31 mg, 0.52 mmol), and NaBH(OAc)₃ (165 mg, 0.78 mmol). The reaction mixture was stirred at ambient temperature for 19 hr. The reaction was quenched with saturated aqueous NaHCO₃ The aqueous layer was extracted with CHCl₃ (three times). The combined organic layer was dried over MgSO₄, filtered, concentrated, and purified by flash chromatography (NH-silica gel, 25% EtOAc in hexane) to give trans-N²-(4-{[(4-bromo-2-trifluoromethoxy-benzyl)-methyl-amino]-methyl}-cyclohexylmethyl)-N⁴,N⁴-dimethyl-quinazoline-2,4-diamine (153 mg, 51%) as a pale yellow solid.

ESI MS m/e 580, M+H⁺; ¹H NMR (300 MHz, CDCl₃) δ 7.81 (d, J=7.6 Hz, 1 H), 7.34-7.53 (m, 5 H), 7.02 (ddd, J=8.3, 6.2, 2.0 Hz, 1 H), 3.44 (s, 2 H), 3.36 (t, J=6.3 Hz, 2 H), 3.27 (s, 6 H), 2.14 (s, 3 H), 2.11-2.18 (m, 2 H), 1.81-1.96 (m, 4 H), 1.36-1.66 (m, 2 H), 0.73-1.13 (m, 4 H).

Example 18

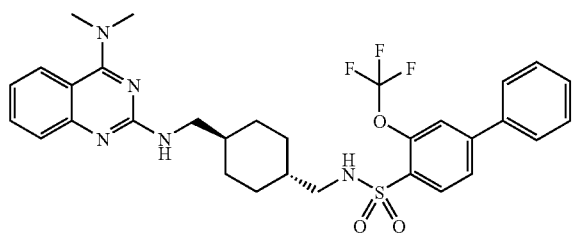

trans-3-Trifluoromethoxy-biphenyl-4-sulfonic acid {4-[(4-dimethylamino-quinazolin-2-ylamino)-methyl]-cyclohexylmethyl}-amide Step A: Synthesis of trans-3-trifluoromethoxy-biphenyl-4-sulfonic acid {4-[(4-dimethylamino-quinazolin-2-ylamino)-methyl]-cyclohexylmethyl}-amide.

To a solution of trans-4-bromo-N-{4-[(4-dimethylamino-quinazolin-2-ylamino)-methyl]-cyclohexylmethyl}-2-trifluoromethoxy-benzenesulfonamide obtained in step H of example 1 (122 mg, 0.198 mmol) in toluene (2.7 mL) were added MeOH (0.9 mL), 2 M aqueous K₂CO₃ (0.9 mL), phenylboronic acid (29.0 mg, 0.237 mmol), and tetrakis(triphenylphosphine)palladium (23.0 mg, 0.02 mmol). The reaction mixture was stirred at 130° C. for 10 hr. The mixture was poured into water, and the aqueous layer was extracted with CHCl₃ (three times). The combined organic layer was dried over MgSO₄, filtered, concentrated, and purified by flash chromatography H-silica gel, 25% EtOAc in hexane and silica gel, 9% MeOH in CHCl₃) to give trans-3-trifluoromethoxy-biphenyl-4-sulfonic acid {4-[(4-dimethylamino-quinazolin-2-ylamino)-methyl]-cyclohexylmethyl}-amide (77 mg, 0.125 mmol) as a white solid.

ESI MS m/e 614, M+H⁺; ¹H NMR (200 MHz, CDCl₃) δ 8.07 (d, J=8.4 Hz, 1 H), 7.82 (d, J=8.8 Hz, 1 H), 7.38-7.67 (m, 9 H), 7.03 (ddd, J=8.4, 6.2, 2.2 Hz, 1 H), 5.11 (brs, 1 H), 4.71 (brs, 1 H), 3.35 (t, J=6.2 Hz, 2 H), 3.27 (s, 6 H), 2.73-2.90 (m, 2 H), 1.67-2.03 (m, 4 H), 1.30-1.64 (m, 2 H), 0.75-1.16 (m, 4 H).

Example 19

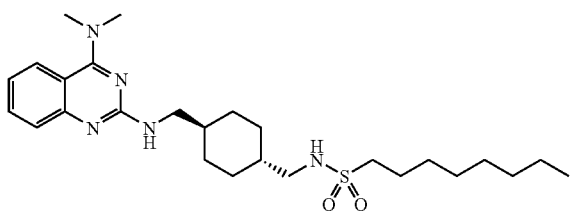

trans-Octane-1-sulfonic acid{4-[(4-dimethylamino-quinazolin-2-ylamino)-methyl]-cyclohexylmethyl}-amide Step A: Synthesis of trans-octane-1-sulfonic acid{4-[(4-dimethylamino-quinazolin-2-ylamino)-methyl]-cyclohexylmethyl}-amide.

Using the procedure for the step H of example 1, the title compound was obtained.

ESI MS m/e 490, M+H⁺; ¹H NMR (300 MHz, CDCl₃) δ 7.81 (d, J=7.8 Hz, 1 H), 7.38-7.54 (m, 2 H), 7.02 (ddd, J=8.3, 6.6, 1.7 Hz, 1 H), 5.01 (brs, 1 H), 4.45 (t, J=6.2 Hz, 1 H), 3.36 (t, J=6.2 Hz, 2 H), 3.26 (s, 6 H), 2.86-3.04 (m, 4 H), 1.70-1.96 (m, 6 H), 1.12-1.65 (m, 11 H), 0.76-1.11 (m, 8 H).

Example 20

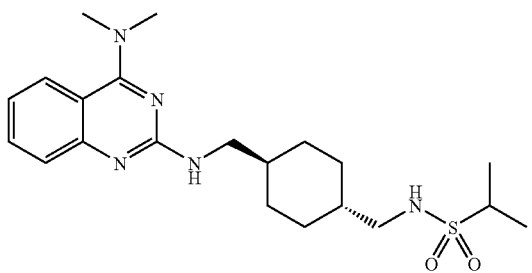

trans-Propane-2-sulfonic acid {4-[(4-dimethylamino-quinazolin-2-ylamino)-methyl]-cyclohexylmethyl}-amide Step A: Synthesis of trans-propane-2-sulfonic acid {4-[(4-dimethylamino-quinazolin-2-ylamino)-methyl]-cyclohexylmethyl}-amide.

To a suspension of trans-N²-(4-aminomethyl-cyclohexylmethyl)-N⁴,N⁴-dimethyl-quinazoline-2,4-diamine obtained in step A of example 15 (227 mg, 0.72 mmol) in CH₂Cl₂ (4 mL) was added diisopropylethylamine (263 μL, 1.51 mmol). The mixture was cooled at 4° C. and a solution of 2-propanesulfonyl chloride (108 mg, 0.76 mmol) in CH₂Cl₂ (1 mL) was added below 5° C. The reaction mixture was stirred at ambient temperature for 12 hr. The reaction was quenched with saturated aqueous NaHCO₃ The aqueous layer was extracted with CHCl₃ (three times). The combined organic layer was dried over MgSO₄, filtered, concentrated, and purified by flash chromatography (NH-silica gel, 66% EtOAc in hexane) to give trans-propane-2-sulfonic acid {4-[(4-dimethylamino-quinazolin-2-ylamino)-methyl]-cyclohexylmethyl}-amide (135 mg, 45%) as a pale yellow solid.

ESI MS m/e 420, M+H⁺; ¹H NMR (300 MHz, CDCl₃) δ 7.81 (d, J=7.8 Hz, 1 H), 7.39-7.52 (m, 2 H), 7.02 (ddd, J=8.3, 6.5, 1.7 Hz, 1 H), 5.02 (brs, 1 H), 4.22 (t, J=6.2 Hz, 1 H), 3.36 (t, J=6.2 Hz, 2 H), 3.27 (s, 6 H), 3.09-3.21 (m, 1 H), 2.97 (t, J=6.5 Hz, 2 H), 1.75-1.97 (m, 4 H), 1.39-1.64 (m, 2 H), 1.37 (d, J=6.8 Hz, 6 H), 0.85-1.12 (m, 4 H).

Example 21

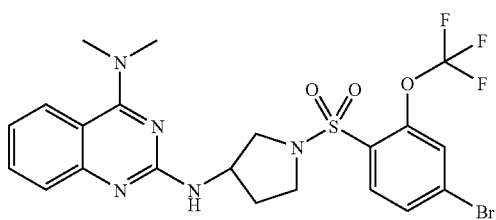

N²-[1-(4-Bromo-2-trifluoromethoxy-benzenesulfonyl)-pyrrolidin-3-yl]-N⁴,N⁴-dimethyl-quinazoline-2,4-diamine Step A: Synthesis of 1-(4-bromo-2-trifluoromethoxy-benzenesulfonyl)-pyrrolidin-3-ylamine hydrochloride.

To a solution of pyrrolidin-3-yl-carbamic acid tert-butyl ester (1.00 g, 5.37 mmol) in CH₂Cl₂ (10 mL) was added diisopropylethylamine (1.96 mL, 5.92 mmol). The mixture was cooled at 0° C. and a solution of 4-bromo-2-trifluoromethoxy-benzenesulfonyl chloride (2.01 g, 5.92 mmol) in CH₂Cl₂ (10 mL) was added below 10° C. The reaction mixture was stirred at 4° C. for 15 min, dissolved in CHCl₃ and saturated aqueous NaHCO₃. The two phases were separated, the aqueous layer was extracted with CHCl₃ (twice). The combined organic layer was dried over MgSO₄, filtered, concentrated, and dried under reduced pressure to give a pale brown solid. To a solution of the above solid in CHCl₃ (50 mL) was added 4 M hydrogen chloride in EtOAc (50 mL). The mixture was stirred at ambient temperature for 1 hr, filtered, washed with EtOAc, and dried under reduced pressure to give 1-(4-bromo-2-trifluoromethoxy-benzenesulfonyl)-pyrrolidin-3-ylamine hydrochloride (1.83 g, 80%) as a white solid.

ESI MS m/e 388, M⁺; ¹H NMR (300 MHz, DMSO-d₆) δ 8.44 (brs, 3 H), 7.82-7.94 (m, 3 H), 3.76-3.84 (m, 1 H), 3.42-3.58 (m, 2 H), 3.23-3.40 (m, 2 H), 2.10-2.23 (m, 1 H), 1.88-2.02 (m, 1 H).

Step B: Synthesis of N²-[1-(4-bromo-2-trifluoromethoxy-benzenesulfonyl)-pyrrolidin-3-yl]-N⁴,N⁴-dimethyl-quinazoline-2,4-diamine Using the procedure for the step C of example 3, the title compound was obtained.

ESI MS m/e 560, M+H⁺; ¹H NMR (300 MHz, CDCl₃) δ 7.82-7.89 (m, 2 H), 7.40-7.75 (m, 4 H), 7.08 (ddd, J=8.3, 6.8, 1.5 Hz, 1 H), 4.83 (brs, 1 H), 4.53-4.64 (m, 1 H), 3.75 (dd, J=10.3, 5.8 Hz, 1 H), 3.48-3.64 (m, 2 H), 3.44 (dd, J=10.3, 4.4 Hz, 1 H), 3.27 (s, 6 H), 2.21-2.36 (m, 1 H), 1.86-2.00 (m, 1 H).

Example 22

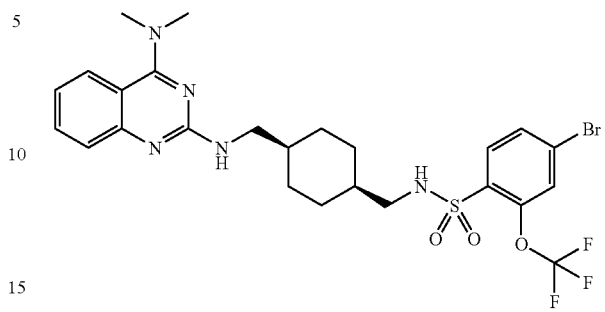

cis-4-Bromo-N-{4-[(4-dimethylamino-quinazolin-2-ylamino)-methyl]-cyclohexylmethyl}-2-trifluoromethoxy-benzenesulfonamide Step A: Synthesis of cis-[4-(tert-butoxycarbonylamino-methyl)-cyclohexylmethyl]-carbamic acid tert-butyl ester.

To MeOH (220 mL) cooled at 0° C. was added thionyl chloride (52 mL) below 10° C. over 2.5 hr and the solution was stirred at 0° C. for 1 hr. To the reaction mixture was added cis-cyclohexane-1,4-dicarboxylic acid (30.0 g, 174 mmol) and the mixture was stirred at ambient temperature for 14 hr and concentrated. The residue was dissolved in CHCl₃, poured into saturated aqueous NaHCO₃, and the aqueous layer was extracted with CHCl₃ (three times). The combined organic layer was dried over MgSO₄, filtered, concentrated. A suspension of lithium aluminum hydride (13.2 g, 348 mmol) in THF (400 mL) was cooled at −20° C. A solution of the above residue in THF (200 mL) was added dropwise, and the mixture was stirred at ambient temperature for 3 hr. The reaction was quenched with Na₂SO₄.10H₂O, filtered through a pad of celite, and concentrated. To a solution of the above residue in toluene (500 mL) was added triphenylphosphine (37.2 g, 142 mmol). To the mixture cooled at 4° C. were added phthalimide (20.9 g, 142 mmol) and 40% diethyl azodicarboxylate (DEAD) in toluene (61.7 mL, 136 mmol) over 25 min. The reaction mixture was stirred at ambient temperature for 12 hr, poured into H₂O. The aqueous layer was extracted with CHCl₃ (three times). The combined organic layer was dried over MgSO₄, filtered, concentrated. The precipitate was suspended in Et₂O, filtered, washed with MeOH and Et₂O, and dried under reduced pressure to give a white solid (16.5 g). To a suspension of the above solid (16.5 g, 410 mmol) in EtOH (735 mL) was added hydrazine hydrate (20.5 g, 410 mmol). The mixture was stirred at reflux for 2.5 hr, cooled, and concentrated. The precipitate was dissolved in 10% aqueous sodium hydroxide (120 mL) and 1,4-dioxane (160 mL). To the mixture cooled on an ice-bath was added (Boc)₂O (30.4 g, 139 mmol) and the mixture was stirred at ambient temperature for 2.5 hr, and poured into H₂O. The aqueous layer was extracted with CHCl₃ (ten times). The combined organic layer was dried over MgSO₄, filtered and concentrated. The precipitate was suspended in hexane, filtered, washed with hexane, and dried under reduced pressure to give cis-[4-(tert-butoxycarbonylamino-methyl)-cyclohexylmethyl]-carbamic acid tert-butyl ester (5.10 g, 9%) as a white solid.

ESI MS m/e 365, M+Na⁺; ¹H NMR (300 MHz, CDCl₃) δ 4.49-4.59 (m, 2 H), 3.05 (t, J=6.6 Hz, 4 H), 1.29-1.69 (m, 28 H).

Step C: Synthesis of cis-(4-aminomethyl-cyclohexylmethyl)-carbamic acid tert-butyl ester.

To a solution of cis-[4-(tert-butoxycarbonylamino-methyl)-cyclohexylmethyl]-carbamic acid tert-butyl ester (2.55 g, 7.45 mmol) in CH$_2$Cl$_2$ (40 mL) was added 4 M hydrogen chloride in EtOAc (4 mL). The reaction mixture was stirred at ambient temperature for 5 hr and concentrated. The residue was dissolved in 1,4-dioxane (20 mL) and 10% aqueous sodium hydroxide (40 mL) and the resulting solution was cooled on an ice-bath. (Boc)$_2$O (829 mg, 3.80 mmol) was added dropwise and the mixture was stirred at ambient temperature for 3 h. The aqueous layer was extracted with CHCl$_3$ (three times). The combined organic layer was dried over MgSO$_4$, filtered and concentrated, and purified by flash chromatography (silica gel, 9% MeOH in CHCl$_3$) to give cis-(4-aminomethyl-cyclohexylmethyl)-carbamic acid tert-butyl ester (255 mg, 14%) as a pale yellow oil.

ESI MS m/e 243, M+H$^+$; $^1$H NMR (300 MHz, CDCl$_3$) δ 4.58 (brs, 1 H), 3.06 (t, J=6.7 Hz, 2 H), 2.60 (d, J=5.9 Hz, 2 H), 1.28-1.70 (m, 19 H).

Step D: Synthesis of cis-{4-[(4-dimethylamino-quinazolin-2-ylamino)-methyl]-cyclohexylmethyl}-carbamic acid tert-butyl ester.

Using the procedure for the step G of example 1, the title compound was obtained.

ESI MS m/e 414, M+H$^+$; $^1$H NMR (300 MHz, CDCl$_3$) δ 7.81 (d, J=7.8 Hz, 1 H), 7.42-7.52 (m, 2 H), 7.02 (ddd, J=8.3, 6.3, 1.9 Hz, 1 H), 4.52 (brs, 1 H), 3.45 (t, J=6.6 Hz, 2 H), 3.27 (s, 6 H), 3.08 (t, J=6.5 Hz, 2 H), 1.34-1.86 (m, 19 H).

Step E: Synthesis of cis-4-bromo-N-{4-[(4-dimethylamino-quinazolin-2-ylamino)-methyl]-cyclohexylmethyl}-2-trifluoromethoxy-benzenesulfonamide.

Using the procedure for the step H of example 1, the title compound was obtained.

ESI MS m/e 616, M+H$^+$; $^1$H NMR (300 MHz, CDCl$_3$) δ 7.90 (d, J=8.9 Hz, 1 H), 7.81 (d, J=7.8 Hz, 1 H), 7.41-7.58 (m, 4 H), 7.03 (ddd, J=8.2, 6.6, 1.5 Hz, 1 H), 3.41 (t, J=6.5 Hz, 2-H), 3.50 (s, 6 H), 2.90 (d, J=7.3 Hz, 2 H), 1.32-1.86 (m, 10 H).

Example 23

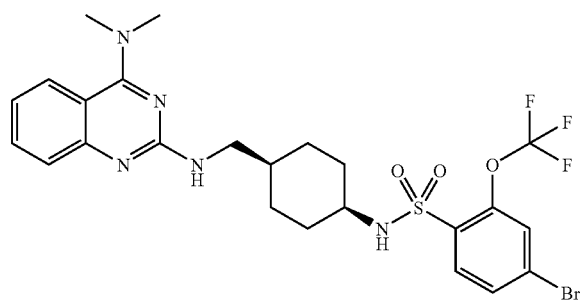

cis-4-Bromo-N-{4-[(4-dimethylamino-quinazolin-2-ylamino)-methyl]-cyclohexyl}-2-trifluoromethoxy-benzenesulfonamide Step A: Synthesis of cis-(4-hydroxymethyl-cyclohexyl)-carbamic acid tert-butyl ester.

A suspension of cis-4-amino-cyclohexanecarboxylic acid (244 g, 1.70 mol) in MeOH (2.45 L) was cooled to −8° C. Thionyl chloride (45.0 mL, 617 mmol) was added dropwise. The resulting solution was stirred at ambient temperature for 4.5 hr and concentrated to give a white solid. To a suspension of the above solid in CHCl$_3$ (3.00 L) were added triethylamine (261 mL, 1.87 mol) and (Boc)$_2$O (409 g, 1.87 mol) successively. The reaction mixture was stirred at ambient temperature for 5 hr and poured into water. The aqueous layer was extracted with CHCl$_3$ (three times). The combined organic layer was dried over MgSO$_4$, filtered, concentrated, and purified by flash chromatography (silica gel, CHCl$_3$ only to 10% MeOH in CHCl$_3$) to give a colorless oil (531 g). To a suspension cooled at −4° C. of lithium aluminum hydride (78.3 g, 2.06 mol) in Et$_2$O (7.9 L) was added a solution of above oil (530.9 g) in Et$_2$O (5.3 L) below 0° C. The resulting suspension was stirred at ambient temperature for 2 hr. The reaction mixture was cooled on an ice-bath, quenched with cold water, filtered through a pad of celite. The filtrate was dried over MgSO$_4$, filtered, and concentrated. The precipitate was suspended in hexane (300 mL), filtered, washed with hexane, and dried under reduced pressure to give cis-(4-hydroxymethyl-cyclohexyl)-carbamic acid tert-butyl ester (301 g, 77%) as a white solid.

ESI MS m/e 252, M+Na$^+$; $^1$H NMR (300 MHz, CDCl$_3$) δ 4.30-4.82 (m, 1 H), 3.75 (brs, 1 H), 3.51 (d, J=6.2 Hz, 1 H), 1.52-1.77 (m, 7 H), 1.45 (s, 9 H), 1.16-1.36 (m, 2 H).

Step B: Synthesis of cis-[4-(benzyloxycarbonylamino-methyl)-cyclohexyl]-carbamic acid tert-butyl ester.

To a solution of cis-(4-hydroxymethyl-cyclohexyl)-carbamic acid tert-butyl ester (17.7 g, 77.2 mmol) in THF (245 mL) were added triphenylphosphine (20.2 g, 77.0 mmol) and phthalimide (11.4 g, 77.5 mmol) successively. The resulting suspension was cooled on an ice-bath and 40% diethyl azodicarboxylate (DEAD) in toluene was added over 1 hr. The reaction mixture was stirred at ambient temperature for 2.5 days, concentrated, and purified by flash chromatography (silica gel, 33% EtOAc in hexane) to give a white solid. To a suspension of above solid (27.5 g) in EtOH (275 mL) was added hydrazine hydrate (5.76 g, 115 mmol). The mixture was stirred at reflux for 2.25 hr, cooled, concentrated. The precipitate was dissolved in 10% aqueous sodium hydroxide (350 mL). The aqueous layer was extracted with CHCl$_3$ (three times). The combined organic layer was dried over MgSO$_4$, filtered and concentrated. To a solution of the above residue in CHCl$_3$ (275 mL) was added triethylamine (8.54 g, 84.4 mmol). The resulting solution was cooled to 0° C. and ZCl (14.4 g, 84.4 mmol) was added below 5° C. The reaction mixture was stirred at ambient temperature for 16 hr, and poured into saturated aqueous NaHCO$_3$. The aqueous layer was extracted with CHCl$_3$ (three times). The combined organic layer was dried over MgSO$_4$, filtered, concentrated, and purified by flash chromatography (silica gel, 2% MeOH in CHCl$_3$) to give cis-[4-(benzyloxycarbonylamino-methyl)-cyclohexyl]-carbamic acid tert-butyl ester (25.3 g, 91%) as a colorless oil.

ESI MS m/e 385, M+Na$^+$; $^1$H NMR (300 MHz, CDCl$_3$) δ 7.27-7.38 (m, 5 H), 5.09 (s, 2 H), 4.76-4.92 (m, 1 H), 4.42-4.76 (m, 1 H), 3.72 (brs, 1 H), 3.10 (t, J=6.4 Hz, 2 H), 1.48-1.75 (m, 7 H), 1.44 (s, 9 H), 1.13-1.31 (m, 2 H).

Step C: Synthesis of cis-{4-[(4-dimethylamino-quinazolin-2-ylamino)-methyl]-cyclohexyl}-carbamic acid tert-butyl ester.

A mixture of cis-[4-(benzyloxycarbonylamino-methyl)-cyclohexyl]-carbamic acid tert-butyl ester (4.00 g, 11.0 mmol) and 5% Pd/C (400 mg) in MeOH (40 mL) was stirred under hydrogen atmosphere at ambient temperature for 8.5 hr and at 50° C. for 12 hr, filtered through a pad of celite, and concentrated. The precipitate was suspended in hexane and the suspension was stirred at ambient temperature for 30 min. The solid was collected by filtration, washed with hexane, and dried (3.03 g). A mixture of (2-chloro-quinazolin-4-yl)-dimethyl-amine obtained in step B of example 1 (1.00 g, 4.82 mmol) and the above solid (1.65 g, 7.23 mmol) in 2-propanol (10 mL) was stirred at reflux for 5 days, poured into saturated aqueous NaHCO$_3$, and the aqueous layer was extracted with CHCl$_3$ (three times). The combined organic layer was dried over MgSO$_4$, filtered, concentrated, and purified by flash chromatography (NH-silica gel, 20% EtOAc in hexane) to give cis-{4-[(4-dimethylamino-quinazolin-2-ylamino)-methyl]-cyclohexyl}-carbamic acid tert-butyl ester (629 mg, 43%) as a pale yellow solid.

ESI MS m/e 400, M+H$^+$; $^1$H NMR (300 MHz, CDCl$_3$) δ 7.81 (d, J=8.2 Hz, 1 H), 7.42-7.56 (m, 2 H), 6.98-7.06 (m, 1 H), 4.64-4.75 (m, 1 H), 3.67-3.82 (m, 1 H), 3.29-3.44 (m, 2 H), 3.28 (s, 6 H), 1.50-1.78 (m, 7 H), 1.45 (s, 9 H), 1.21-1.42 (m, 2 H).

Step D: Synthesis of cis-4-bromo-N-{4-[(4-dimethylamino-quinazolin-2-ylamino)-methyl]-cyclohexyl}-2-trifluoromethoxy-benzenesulfonamid.

Using the procedure for the step H of example 1, the title compound was obtained.

ESI MS m/e 602, M+H$^+$; $^1$H NMR (300 MHz, CDCl$_3$) δ 7.91 (d, J=8.9 Hz, 1 H), 7.82 (dd, J=8.0, 1.0 Hz, 1 H), 7.42-7.56 (m, 4 H), 7.04 (ddd, J=8.3, 6.6, 1.6 Hz, 1 H), 3.44-3.50 (m, 1 H), 3.40 (t, J=6.0 Hz, 2 H), 3.28 (s, 6 H), 1.22-1.78 (m, 9 H).

Example 24

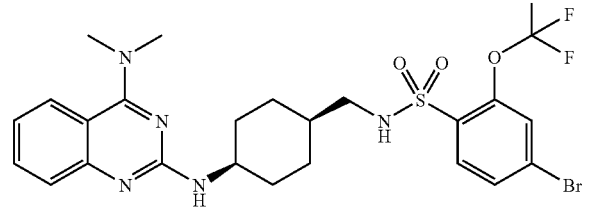

cis-4-Bromo-N-[4-(4-dimethylamino-quinazolin-2-ylamino)-cyclohexylmethyl]-2-trifluoromethoxy-benzenesulfonamide Step A: Synthesis of cis-(4-amino-cyclohexylmethyl)-carbamic acid benzyl ester.

To a solution of cis-[4-(benzyloxycarbonylamino-methyl)-cyclohexyl]-carbamic acid tert-butyl ester obtained in step C of example 23 (12.9 g, 35.6 mmol) in EtOAc (129 mL) was added 4 M hydrogen chloride in EtOAc (129 mL). The reaction mixture was stirred at ambient temperature for 3 hr, filtered, washed with EtOAc, and dried under reduced pressure. The solid was dissolved in saturated aqueous NaHCO$_3$. The aqueous layer was extracted with CHCl$_3$ (five times), dried over MgSO$_4$, filtered and concentrated, and dried under reduced pressure to give cis-(4-amino-cyclohexylmethyl)-carbamic acid benzyl ester (8.88 g, 95%) as a colorless oil.

ESI MS m/e 263, M+H$^+$; $^1$H NMR (300 MHz, CDCl$_3$) δ 7.36 (s, 5 H), 5.12 (brs, 3 H), 2.96-3.32 (m, 3 H), 1.36-1.98 (m, 9 H).

Step B: Synthesis of cis-[4-(4-dimethylamino-quinazolin-2-ylamino)-cyclohexylmethyl]-carbamic acid benzyl ester.

Using the procedure for the step G of example 1, the title compound was obtained.

ESI MS m/e 434, M+H$^+$; $^1$H NMR (300 MHz, CDCl$_3$) δ 7.81 (d, J=9.0 Hz, 1 H), 7.26-7.52 (m, 7 H), 7.01 (ddd, J=8.2, 6.5, 1.7 Hz, 1 H), 5.10 (s, 2 H), 4.93-5.06 (m, 1 H), 4.82-4.93 (m, 1 H), 4.18-4.28 (m, 1 H), 3.26 (s, 6 H), 3.11 (t, J=6.3 Hz, 2 H), 1.80-1.93 (m, 2 H), 1.52-1.73 (m, 5 H), 1.23-1.40 (m, 2 H).

Step C: Synthesis of cis-4-bromo-N-[4-(4-dimethylamino-quinazolin-2-ylamino)-cyclohexylmethyl]-2-trifluoromethoxy-benzenesulfonamide.

Using the procedure for the step D of example 3, the title compound was obtained.

ESI MS m/e 602, M+H$^+$; $^1$H NMR (300 MHz, CDCl$_3$) δ 7.90 (d, J=8.9 Hz, 1 H), 7.81 (dd, J=8.3, 1.3 Hz, 1 H), 7.38-7.59 (m, 4 H), 7.02 (ddd, J=8.2, 6.8, 1.2 Hz, 1 H), 4.75-5.24 (m, 1 H), 4.16-4.27 (m, 1 H), 3.27 (s, 6 H), 2.86 (d, J=6.4 Hz, 2 H), 1.78-1.91 (m, 2 H), 1.51-1.70 (m, 5 H), 1.21-1.38 (m, 2 H).

Example 25

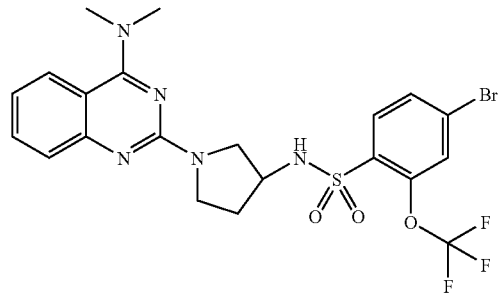

4-Bromo-N-[1-(4-dimethylamino-quinazolin-2-yl)-pyrrolidin-3-yl]-2-trifluoromethoxy-benzenesulfonamide Step A: Synthesis of [1-(4-dimethylamino-quinazolin-2-yl)-pyrrolidin-3-yl]-carbamic acid tert-butyl ester.

Using the procedure for the step G of example 1, the title compound was obtained.

ESI MS m/e 358, M+H$^+$; $^1$H NMR (300 MHz, CDCl$_3$) δ 7.81 (d, J=8.2 Hz, 1 H), 7.45-7.54 (m, 2 H), 6.98-7.05 (m, 1 H), 4.67-4.80 (m, 1 H), 4.25-4.40 (m, 1 H), 3.85-3.94 (m, 1 H), 3.68-3.79 (m, 2 H), 3.52-3.62 (m, 1 H), 3.27 (s, 6 H), 2.16-2.28 (m, 1 H), 1.86-2.01 (m, 1 H), 1.45 (s, 9 H).

Step B: Synthesis of 4-bromo-N-[1-(4-dimethylamino-quinazolin-2-yl)-pyrrolidin-3-yl]-2-trifluoromethoxy-benzenesulfonamide.

Using the procedure for the step H of example 1, the title compound was obtained.

ESI MS m/e 560, M+H$^+$; $^1$H NMR (300 MHz, CDCl$_3$) δ 7.94 (d, J=8.4 Hz, 1 H), 7.81 (d, J=8.1 Hz, 1 H), 7.44-7.58 (m, 4 H), 7.03 (ddd, J=8.4, 5.7, 2.6 Hz, 1 H), 4.76-5.04 (m, 1 H), 3.96-4.11 (m, 1 H), 3.70-3.82 (m, 2 H), 3.58-3.68 (m, 1 H), 3.45-3.54 (m, 1 H), 3.25 (s, 6 H), 2.11-2.24 (m, 1 H), 1.86-1.99 (m, 1 H).

Example 26

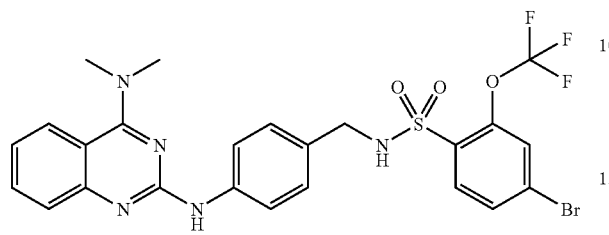

4-Bromo-N-[4-(4-dimethylamino-quinazolin-2-ylamino)-benzyl]-2-trifluoromethoxy-benzene sulfonamide Step A: Synthesis of (4-amino-benzyl)-carbamic acid tert-butyl ester.

To a solution of 4-aminomethyl-phenylamine (1.00 g, 8.19 mmol) in CHCl₃ (10 mL) was added triethylamine (870 mg, 8.60 mmol). After cooling on an ice-bath, (Boc)₂O (1.88 g, 8.61 mmol) was added dropwise. The reaction mixture was stirred at ambient temperature for 55 min and poured into saturated aqueous NaHCO₃. The aqueous layer was extracted with CHCl₃ (three times). The combined organic layer was dried over MgSO₄, filtered, concentrated, and purified by flash chromatography (silica gel, 9% MeOH in CHCl₃) to give (4-amino-benzyl)-carbamic acid tert-butyl ester (1.79 g, 99%) as a yellow solid.

ESI MS m/e 245, M+Na⁺; ¹H NMR (200 MHz, CDCl₃) δ 7.07 (d, J=8.4 Hz, 2 H), 6.63 (d, J=8.4 Hz, 2 H), 4.76 (brs, 1 H), 4.18 (d, J=5.3 Hz, 2 H), 3.65 (brs, 2 H), 1.45 (s, 9 H).

Step B: Synthesis of 4-bromo-N-[4-(4-dimethylamino-quinazolin-2-ylamino)-benzyl]-2-trifluoromethoxy-benzenesulfonamide.

A mixture of (2-chloro-quinazolin-4-yl)-dimethyl-amine obtained in step B of example 1 (1.00 g, 4.82 mmol) and (4-amino-benzyl)-carbamic acid tert-butyl ester (1.28 g, 5.76 mmol) in 2-propanol (10 mL) was stirred at reflux for 3 hr, cooled, poured into saturated aqueous NaHCO₃, and the aqueous layer was extracted with CHCl₃ (three times). The combined organic layer was dried over MgSO₄, filtered, concentrated, and purified by flash chromatography (NH-silica gel, 20% EtOAc in hexane) to give a pale yellow solid (2.32 g). To a solution of the above solid (750 mg, 1.91 mmol) in EtOAc (7 mL) was added 4 M hydrogen chloride in EtOAc (7 mL). The mixture was stirred at ambient temperature for 2 hr, concentrated to give a white solid. To a suspension of the above solid in CH₂Cl₂ (5 mL) was added diisopropylethylamine (730 μL, 4.19 mmol). The mixture was cooled on an ice-bath and a solution of 4-bromo-2-trifluoromethoxy-benzenesulfonyl chloride (777 mg, 2.29 mmol) in CH₂Cl₂ (2 mL) was added dropwise. The reaction mixture was stirred on an ice-bath for 9 hr, poured into saturated aqueous NaHCO₃. The aqueous layer was extracted with CHCl₃ (three times). The combined organic layer was dried over MgSO₄, filtered, concentrated, and purified by medium-pressure liquid chromatography (NH-silica gel, 20% EtOAc in hexane) to give 4-bromo-N-[4-(4-dimethylamino-quinazolin-2-ylamino)-benzyl]-2-trifluoromethoxy-benzenesulfonamide (519 mg, 56%) as a pale yellow solid.

ESI MS m/e 618, M+Na⁺; ¹H NMR (300 MHz, CDCl₃) δ 7.88 (t, J=9.0 Hz, 2 H), 7.64 (d, J=8.6 Hz, 2 H), 7.48-7.61 (m, 4 H), 6.98-7.20 (m, 4 H), 4.96 (brs, 1 H), 4.13 (s, 2 H), 3.34 (s, 6 H).

Example 27

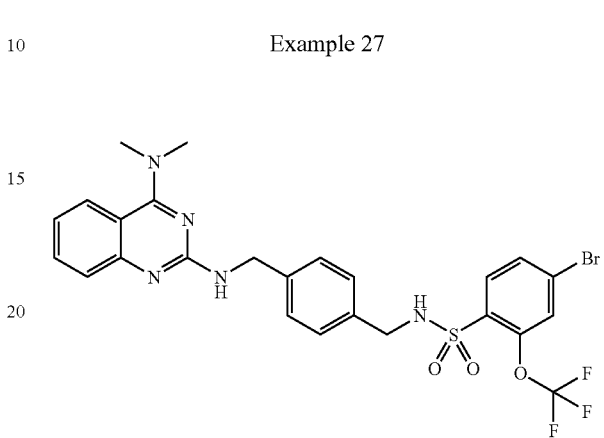

4-Bromo-N-{4-[(4-dimethylamino-quinazolin-2-ylamino)-methyl]-benzyl}-2-trifluoromethoxy-benzenesulfonamide Step A: Synthesis of (4-aminomethyl-benzyl)-carbamic acid tert-butyl ester.

To a solution of 4-aminomethyl-benzylamine (15.0 g, 110 mmol) in CHCl₃ (85 mL) was added a solution of (Boc)₂O (3.03 g, 13.9 mmol) in CHCl₃ (45 mL) dropwise over 3.5 hr. The reaction mixture was stirred at ambient temperature for 13 hr, and concentrated. After dissolution with H₂O, the aqueous layer was extracted with EtOAc (three times). The combined organic layer was washed with H₂O (three times), dried over MgSO₄, filtered, and concentrated to give (4-aminomethyl-benzyl)-carbamic acid tert-butyl ester (3.20 g, 12%) as a white solid.

ESI MS m/e 237, M+H⁺; ¹H NMR (300 MHz, CDCl₃) δ 7.21-7.30 (m, 4 H), 4.86-5.02 (m, 1 H), 4.29 (d, J=5.8 Hz, 2 H), 3.84 (s, 2 H), 1.46 (s, 9 H).

Step B: Synthesis of {4-[(4-dimethylamino-quinazolin-2-ylamino)-methyl]-benzyl}-carbamic acid tert-butyl ester.

Using the procedure for the step G of example 1, the title compound was obtained.

ESI MS m/e 408, M+H⁺; ¹H NMR (300 MHz, CDCl₃) δ 7.85 (d, J=8.2 Hz, 1 H), 7.47-7.55 (m, 2 H), 7.37 (d, J=8.0 Hz, 2 H), 7.24 (d, J=8.0 Hz, 2 H), 7.05-7.10 (m, 1 H), 5.35-5.45 (m, 1 H), 4.90-5.04 (m, 1 H), 4.72 (d, J=5.8 Hz, 2 H), 4.31 (d, J=5.8 Hz, 2 H), 3.27 (s, 6 H), 1.49 (s, 9 H).

Step C: Synthesis of 4-bromo-N-{4-[(4-dimethylamino-quinazolin-2-ylamino)-methyl]-benzyl}-2-trifluoromethoxy-benzenesulfonamide.

Using the procedure for the step H of example 1, the title compound was obtained.

ESI MS m/e 610, M+H⁺; ¹H NMR (300 MHz, CDCl₃) δ 7.83 (d, J=8.4 Hz, 2 H), 7.44-7.54 (m, 4 H), 7.29 (d, J=7.9 Hz,

2 H), 7.11 (d, J=8.1 Hz, 2 H), 7.06 (ddd, J=8.3, 6.3, 2.0 Hz, 1 H), 4.67 (d, J=5.9 Hz, 2 H), 4.15 (s, 2 H), 3.26 (s, 6 H).

Example 28

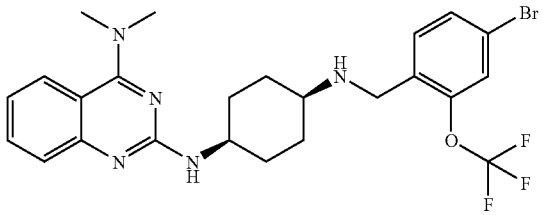

cis-$N^2$-[4-(4-Bromo-2-trifluoromethoxy-benzylamino)-cyclohexyl]-$N^4,N^4$-dimethyl-quinazoline-2,4-diamine Step A: Synthesis of cis-$N^2$-[4-(4-bromo-2-trifluoromethoxy-benzylamino)-cyclohexyl]-$N^4,N^4$-dimethyl-quinazoline-2,4-diamine.

Using the procedure for the step B of example 15, the title compound was obtained.

ESI MS m/e 560, M+Na$^+$; $^1$H NMR (300 MHz, CDCl$_3$) δ 7.80 (dd, J=7.9, 0.9 Hz, 1 H), 7.36-7.51 (m, 5 H), 7.01 (ddd, J=8.3, 6.4, 1.9 Hz, 1 H), 4.95-5.18 (m, 1 H), 4.08-4.22 (m, 1 H), 3.81 (s, 2 H), 3.25 (s, 6 H), 2.55-2.70 (m, 1 H), 1.65-1.90 (m, 6 H), 1.29-1.65 (m, 2 H).

Example 29

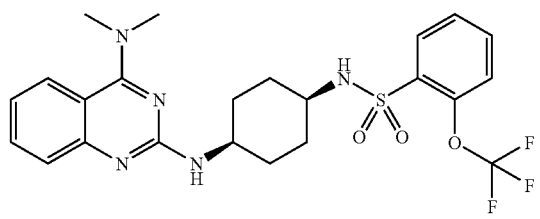

cis-N-[4-(4-Dimethylamino-quinazolin-2-ylamino)-cyclohexyl]-2-trifluoromethoxy-benzenesulfonamide Step A: Synthesis of cis-N-[4-(4-dimethylamino-quinazolin-2-ylamino)-cyclohexyl]-2-trifluoromethoxy-benzenesulfonamide.

Using the procedure for the step A of example 20, the title compound was obtained.

ESI MS m/e 532, M+Na$^+$; $^1$H NMR (300 MHz, CDCl$_3$) δ 8.06 (dd, J=8.1, 1.9 Hz, 1 H), 7.81 (dd, J=8.4, 1.4 Hz, 1 H), 7.36-7.66 (m, 5 H), 7.03 (ddd, J=8.3, 6.7, 1.5 Hz, 1 H), 4.72-5.07 (m, 2 H), 3.95-4.10 (m, 1 H), 3.32-3.48 (m, 1 H), 3.25 (s, 6 H), 1.37-2.17 (m, 8 H).

Example 30

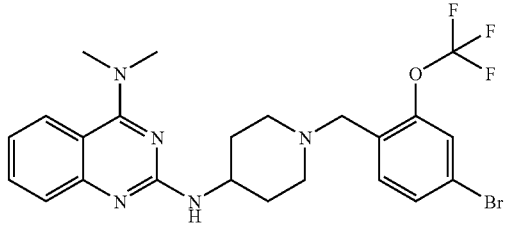

$N^2$-[1-(4-Bromo-2-trifluoromethoxy-benzyl)-piperidin-4-yl]-$N^4,N^4$-dimethyl-quinazoline-2,4-diamine Step A: Synthesis of $N^2$-(1-benzyl-piperidin-4-yl)-$N^4,N^4$-dimethyl-quinazoline-2,4-diamine.

Using the procedure for the step G of example 1, the title compound was obtained.

ESI MS m/e 362, M+H$^+$; $^1$H NMR (300 MHz, CDCl$_3$) δ 7.80 (d, J=7.6 Hz, 1 H), 7.20-7.52 (m, 7 H), 6.97-7.05 (m, 1 H), 4.74-4.90 (m, 1 H), 3.90-4.05 (m, 1 H), 3.53 (s, 2 H), 3.26 (s, 6 H), 2.78-2.90 (m, 2 H), 2.02-2.24 (m, 4 H), 1.48-1.62 (m, 2 H).

Step B: Synthesis of $N^4,N^4$-dimethyl-$N^2$-piperidin-4-yl-quinazoline-2,4-diamine.

To a solution of $N^2$-(1-benzyl-piperidin-4-yl)-$N^4,N^4$-dimethyl-quinazoline-2,4-diamine (1.80 g, 4.98 mmol) in MeOH (18 mL) was added 20% Pd(OH)$_2$ (360 mg). The mixture was stirred at 50° C. under hydrogen atmosphere for 3 days, filtered through a pad of celite, and concentrated to give $N^4,N^4$-dimethyl-$N^2$-piperidin-4-yl-quinazoline-2,4-diamine (1.33 g, 99%) as a pale yellow solid.

ESI MS m/e 272, M+H$^+$; $^1$H NMR (300 MHz, CDCl$_3$) δ 7.86 (d, J=8.6 Hz, 1 H), 7.43-7.62 (m, 2 H), 7.15 (t, J=8.2 Hz, 1 H), 4.12-4.29 (m, 1 H), 3.29-3.47 (m, 2 H), 3.37 (s, 6 H), 2.96-3.12 (m, 2 H), 2.20-2.34 (m, 2 H), 1.79-1.97 (m, 2 H).

Step C: Synthesis of $N^2$-[1-(4-bromo-2-trifluoromethoxy-benzyl)-piperidin-4-yl]-$N^4,N^4$-dimethyl-quinazoline-2,4-diamine.

Using the procedure for the step B of example 15, the title compound was obtained.

ESI MS m/e 546, M+Na$^+$; $^1$H NMR (300 MHz, CDCl$_3$) δ 7.80 (dd, J=8.7, 0.9 Hz, 1 H), 7.34-7.54 (m, 5 H), 7.01 (ddd, J=8.3, 6.6, 1.6 Hz, 1 H), 4.76-4.95 (m, 1 H), 3.87-4.06 (m, 1 H), 3.52 (s, 2 H), 3.25 (s, 6 H), 2.71-2.86 (m, 2 H), 2.17-2.33 (m, 2 H), 1.97-2.12 (m, 2 H), 1.44-1.61 (m, 2 H).

Example 31

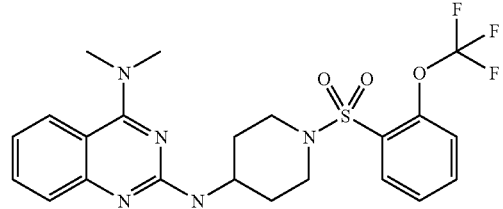

$N^4,N^4$-Dimethyl-$N^2$-[1-(2-trifluoromethoxy-benzenesulfonyl)-piperidin-4-yl]-quinazoline-2,4-diamine Step A: Synthesis of $N^4,N^4$-dimethyl-$N^2$-[1-(2-trifluoromethoxy-benzenesulfonyl)-piperidin-4-yl]-quinazoline-2,4-diamine.

Using the procedure for the step A of example 20, the title compound was obtained.

ESI MS m/e 518, M+Na⁺; ¹H NMR (300 MHz, CDCl₃) δ 8.02 (dd, J=7.9, 1.9 Hz, 1 H), 7.81 (dd, J=8.4, 0.7 Hz, 1 H), 7.34-7.67 (m, 5 H), 7.04 (ddd, J=8.3, 6.7, 1.5 Hz, 1 H), 4.81 (brs, 1 H), 3.95-4.12 (m, 1 H), 3.78 (d, J=12.8 Hz, 2 H), 3.25 (s, 6 H), 2.85-3.05 (m, 2 H), 2.05-2.28 (m, 2 H), 1.50-1.71 (m, 2 H).

Example 32

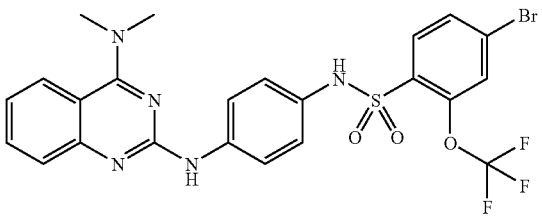

4-Bromo-N-[4-(4-dimethylamino-quinazolin-2-ylamino)-phenyl]-2-trifluoromethoxy-benzenesulfonamide Step A: Synthesis of [4-(4-dimethylamino-quinazolin-2-ylamino)-phenyl]-carbamic acid tert-butyl ester.

Using the procedure for the step G of example 1, the title compound was obtained.

ESI MS m/e 402, M+Na⁺; ¹H NMR (300 MHz, CDCl₃) δ 10.05 (brs, 1 H), 7.94 (d, J=8.4 Hz, 1 H), 7.50-7.66 (m, 4 H), 7.23-7.38 (m, 3 H), 6.57-6.64 (m, 1 H), 3.48 (s, 6 H), 1.53 (s, 9 H).

Step B: Synthesis of 4-bromo-N-[4-(4-dimethylamino-quinazolin-2-ylamino)-phenyl]-2-trifluoromethoxy-benzenesulfonamide To a suspension of [4-(4-dimethylamino-quinazolin-2-ylamino)-phenyl]-carbamic acid tert-butyl ester (380 mg, 1.00 mmol) in EtOAc (4 mL) and CH₂Cl₂ (4 mL) was added 4 M hydrogen chloride in EtOAc (4 mL). The mixture was stirred at ambient temperature for 4 hr and concentrated to give a white solid. The solid was alkalized with saturated aqueous NaHCO₃ filtered, washed with H₂O and hexane, and dried at 50° C. under reduced pressure. To a solution of 4-bromo-2-trifluoromethoxy-benzenesulfonyl chloride (680 mg, 2.00 mmol) in CH₂Cl₂ (30 mL) was added PVP (8 mL). To the resulting suspension was added a solution of the above solid in CH₂Cl₂ (5 mL). The mixture was stirred at ambient temperature for 10.5 hr and filtered. The filtrate was washed with saturated aqueous NaHCO₃, dried over MgSO₄, filtered, concentrated, and purified by medium-pressure liquid chromatography (NH-silica gel, EtOAc) to give a solid. The solid was washed with Et₂O and dried at 50° C. under reduced pressure to give 4-bromo-N-[4-(4-dimethylamino-quinazolin-2-ylamino)-phenyl]-2-trifluoromethoxy-benzenesulfonamide (202 mg, 35%) as a pale yellow solid.

ESI MS m/e 582, M+H⁺; ¹H NMR (300 MHz, CDCl₃) δ 7.88 (d, J=8.4 Hz, 1 H), 7.73 (d, J=8.4 Hz, 1 H), 7.64 (d, J=8.9 Hz, 2 H), 7.51-7.58 (m, 3 H), 7.44 (dd, J=8.4, 1.7 Hz, 1 H), 7.07-7.24 (m, 1 H), 7.02 (d, J=8.9 Hz, 2 H), 3.32 (s, 6 H).

Example 33

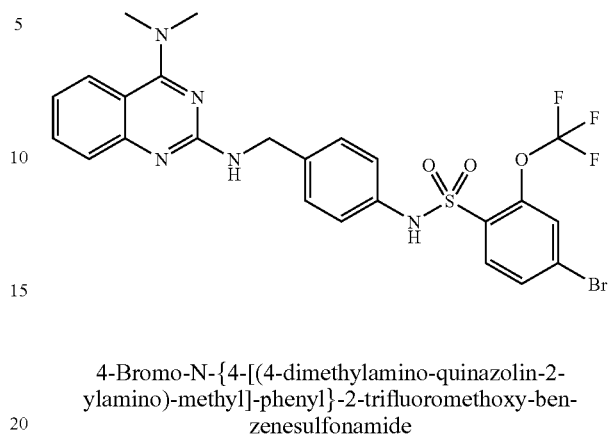

4-Bromo-N-{4-[(4-dimethylamino-quinazolin-2-ylamino)-methyl]-phenyl}-2-trifluoromethoxy-benzenesulfonamide Step A: Synthesis of [4-(tert-butoxycarbonylamino-methyl)-phenyl]-carbamic acid benzyl ester.

To a solution of 4-aminomethyl-phenylamine (3.00 g, 24.6 mmol) in CHCl₃ (30 mL) was added triethylamine (2.61 g, 25.8 mmol). After cooling on an ice-bath, (Boc)₂O (5.63 g, 25.8 mmol) was added dropwise. The reaction mixture was stirred at ambient temperature for 55 min and poured into saturated aqueous NaHCO₃. The aqueous layer was extracted with CHCl₃ (three times) and the combined organic layer was dried over MgSO₄, filtered, and concentrated to give a pale yellow oil. To a solution of the above oil in CHCl₃ (30 mL) was added diisopropylethylamine (3.33 g, 25.8 mmol). The resulting solution was cooled to 4° C. and ZCl (4.40 g, 25.8 mmol) was added below 10° C. over 5 min. The reaction mixture was stirred at ambient temperature for 12 hr, and poured into saturated aqueous NaHCO₃. The aqueous layer was extracted with CHCl₃ (three times). The combined organic layer was dried over MgSO₄, filtered, concentrated, and purified by flash chromatography (silica gel, 2% MeOH in CHCl₃) to give [4-(tert-butoxycarbonylamino-methyl)-phenyl]-carbamic acid benzyl ester (2.64 g, 30%) as a white solid.

ESI MS m/e 379, M+Na⁺; ¹H NMR (300 MHz, CDCl₃) δ 7.11-7.44 (m, 9 H), 6.76 (brs, 1 H), 5.19 (s, 2 H), 4.81 (brs, 1 H), 4.25 (d, J=5.1 Hz, 2 H), 1.45 (s, 9 H).

Step B: Synthesis of (4-aminomethyl-phenyl)-carbamic acid benzyl ester hydrochloride.

A solution of [4-(tert-butoxycarbonylamino-methyl)-phenyl]-carbamic acid benzyl ester (1.25 g, 3.51 mmol) in EtOAc (20 mL) was cooled on an ice-bath and 4 M hydrogen chloride in EtOAc (20 mL) was added. The mixture was stirred at ambient temperature for 20 min. The precipitate was collected by filtration, washed with EtOAc, and dried under reduced pressure to give (4-aminomethyl-phenyl)-carbamic acid benzyl ester hydrochloride (957 mg, 93%) as a white solid.

ESI MS m/e 279, M+Na⁺; ¹H NMR (300 MHz, DMSO-d₆) δ 9.90 (s, 1 H), 8.37 (brs, 3H), 7.29-7.55 (m, 9 H), 5.15 (s, 2 H), 3.85-4.01 (m, 2 H).

Step C: Synthesis of {4-[(4-dimethylamino-quinazolin-2-ylamino)-methyl]-phenyl}-carbamic acid benzyl ester.

Using the procedure for the step C of example 3, the title compound was obtained.

ESI MS m/e 428, M+H+; 1H NMR (300 MHz, CDCl3) δ 7.82 (d, J=7.5 Hz, 1 H), 7.25-7.52 (m, 11 H), 6.98-7.07 (m, 1 H), 6.74 (brs, 1 H), 5.28 (brs, 1 H), 5.19 (s, 2 H), 4.65 (d, J=5.9 Hz, 2 H), 3.25(s, 6 H).

Step D: Synthesis of 4-bromo-N-{4-[(4-dimethylamino-quinazolin-2-ylamino)-methyl]-phenyl}-2-trifluoromethoxy-benzenesulfonamide.

To a solution of {4-[(4-dimethylamino-quinazolin-2-ylamino)-methyl]-phenyl}-carbamic acid benzyl ester (318 mg, 0.744 mmol) in MeOH (3 mL) was added 5% Pd/C (30 mg). The mixture was stirred at 50° C. under hydrogen atmosphere for 41.5 hr, filtered through a pad of celite, and concentrated. To a solution of 4-bromo-2-trifluoromethoxy-benzenesulfonyl chloride (505 mg, 1.49 mmol) in CH2Cl2 (12 mL) was added PVP (6 mL). To the resulting suspension was added a solution of the above residue in CH2Cl2 (10 mL). The mixture was stirred at ambient temperature for 1.5 days, filtered, poured into saturated aqueous NaHCO3. The aqueous layer was extracted with CHCl3 (three times). The combined organic layer was dried over MgSO4, filtered, concentrated, and purified by medium-pressure liquid chromatography (NH-silica gel, 33% EtOAc in hexane) to give 4-bromo-N-{4-[(4-dimethylamino-quinazolin-2-ylamino)-methyl]-phenyl}-2-trifluoromethoxy-benzenesulfonamide (330 mg, 74%) as a pale brown solid.

ESI MS m/e 596, M+H+; 1H NMR (300 MHz, CDCl3) δ 7.83 (d, J=8.4 Hz, 1 H), 7.77 (d, J=8.4 Hz, 1 H), 7.41-7.60 (m, 4 H), 7.22 (d, J=8.6 Hz, 2 H), 7.08-7.18 (m, 1 H), 6.99 (d, J=8.6 Hz, 2 H), 4.56 (d, J=5.6 Hz, 2 H), 3.34 (s, 6 H).

Example 34

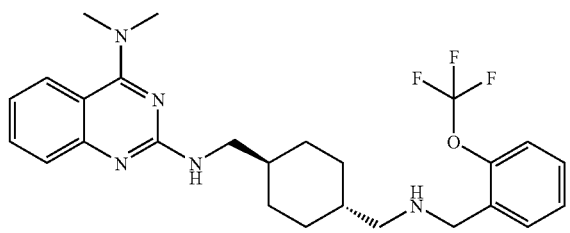

trans-N4,N4-Dimethyl-N2-{4-[(2-trifluoromethoxy-benzylamino)-methyl]-cyclohexylmethyl}-quinazoline-2,4-diamine Step A: Synthesis of trans-N4,N4-dimethyl-N2-{4-[(2-trifluoromethoxy-benzylamino)-methyl]-cyclohexylmethyl}-quinazoline-2,4-diamine.

Using the procedure for the step B of example 15, the title compound was obtained.

ESI MS m/e 510, M+Na+; 1H NMR (300 MHz, CDCl3) δ 7.80 (d, J=8.2 Hz, 1 H), 7.39-7.57 (m, 3 H), 7.15-7.35 (m, 3 H), 7.02 (ddd, J=8.3, 6.0, 2.2 Hz, 1 H), 3.83 (s, 2 H), 3.35 (t, J=6.3 Hz, 2 H), 3.27 (s, 6 H), 2.45 (d, J=6.5 Hz, 2 H), 1.69-2.04 (m, 4 H), 1.37-1.69 (m, 2 H), 0.84-1.12 (m, 4 H).

Example 35

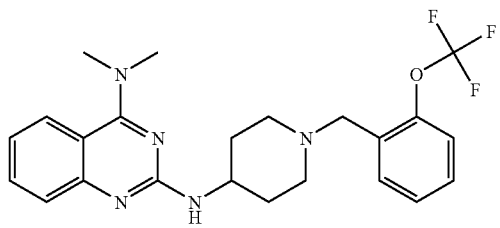

N4,N4-Dimethyl-N2-[1-(2-trifluoromethoxy-benzyl)-piperidin-4-yl]-quinazoline-2,4-diamine Step A: Synthesis of N4,N4-dimethyl-N2-[1-(2-trifluoromethoxy-benzyl)-piperidin-4-yl]-quinazoline-2,4-diamine.

Using the procedure for the step B of example 15, the title compound was obtained.

ESI MS m/e 468, M+Na+; 1H NMR (300 MHz, CDCl3) δ 7.80 (d, J=7.8 Hz, 1 H), 7.37-7.63 (m, 3 H), 7.17-7.35 (m, 3 H), 7.02 (ddd, J=8.3, 6.4, 1.9 Hz, 1 H), 5.12 (brs, 1 H), 3.86-4.07 (m, 1 H), 3.60 (s, 2 H), 3.26 (s, 6 H), 2.74-2.94 (m, 2 H), 2.18-2.37 (m, 2 H), 1.98-2.15 (m, 2 H), 1.45-1.69 (m, 2 H).

Example 36

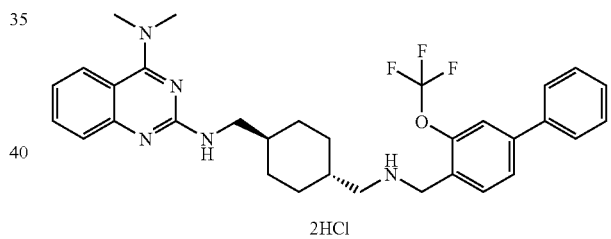

trans-N4,N4-Dimethyl-N2-(4-{[(3-trifluoromethoxy-biphenyl-4-ylmethyl)-amino]-methyl}-cyclohexylmethyl)-quinazoline-2,4-diamine dihydrochloride Step A: Synthesis of trans-N4,N4-dimethyl-N2-(4-{[(3-trifluoromethoxy-biphenyl-4-ylmethyl)-amino]-methyl}-cyclohexylmethyl)-quinazoline-2,4-diamine-dihydrochloride To a solution of trans-N2-{4-[(4-bromo-2-trifluoromethoxy-benzylamino)-methyl]-cyclohexylmethyl}-N4,N4-dimethyl-quinazoline-2,4-diamine obtained in step B of example 15 (300 mg, 0.529 mol) in toluene (6.6 mL) were added MeOH (2.2 mL), 2 M aqueous K2CO3 (2.2 mL), phenylboronic acid (77 mg, 0.635 mmol), and tetrakis (triphenylphosphine) palladium (61 mg, 0.053 mmol). The reaction mixture was stirred at 130° C. for 12 hr. The mixture was poured into water, and the aqueous layer was extracted with CHCl3 (three times). The combined organic layer was dried over MgSO4, filtered, concentrated and, purified by flash chromatography (NH-silica gel, 33% CHCl3 in hexane and silica gel, 9% MeOH in CHCl3) to give pale yellow oil. To a solution of above oil in EtOAc (2 mL) was added 4 M hydrogen chloride in EtOAc (0.1 mL). The mixture was stirred at ambient temperature for 20 min and concentrated. A solution of the residue in Et$_2$O (2 mL) was stirred at ambient temperature for 30 min. The precipitate was collected by filtration, washed with Et$_2$O, and dried under reduced pressure to give trans-$N^4,N^4$-dimethyl-$N^2$-(4-{[(3-trifluoromethoxy-biphenyl-4-ylmethyl)-amino]-methyl}-cyclohexylmethyl)-quinazoline-2,4-diamine dihydrochloride (70 mg, 21%) as a white solid.

ESI MS m/e 564, M (free)+H$^+$; $^1$H NMR (300 MHz, CDCl$_3$) δ 13.27 (s, 1 H), 9.96 (brs, 2 H), 8.17-8.32 (m, 2 H), 7.89 (d, J=7.9 Hz, 1 H), 7.34-7.64 (m, 9 H), 7.20 (t, J=7.7 Hz, 1 H), 4.29 (brs, 2 H), 3.50 (s, 6 H), 3.28 (t, J=6.1 Hz, 2 H), 2.69 (brs, 2 H), 1.79-2.11 (m, 4 H), 1.44-1.68 (m, 2 H), 0.91-1.16 (m, 4 H).

Example 37

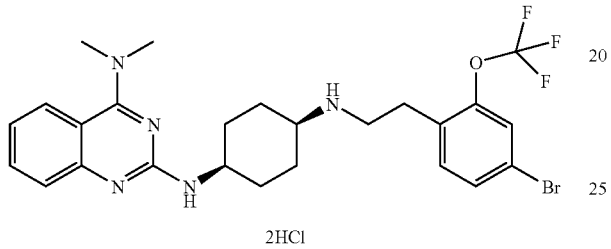

2HCl cis-$N^2$-{4-[2-(4-Bromo-2-trifluoromethoxy-phenyl)-ethylamino]-cyclohexyl}-$N^4,N^4$-dimethyl-quinazoline-2,4-diamine dihydrochloride Step A: Synthesis of (4-bromo-2-trifluoromethoxy-phenyl)-acetaldehyde.

To a suspension of (methoxymethyl) triphenylphosphonium chloride (5.29 g, 14.9 mol) in Et$_2$O (50 mL) was added 1.8 M phenyl lithium in 30% Et$_2$O in cyclohexane (8.58 mL, 15.5 mmol). The mixture was stirred at ambient temperature for 10 min. To the reaction mixture was added 4-bromo-2-trifluoromethoxy-benzaldehyde (4 g, 14.9 mmol) in Et$_2$O (18 mL). The mixture was stirred at ambient temperature for 4 hr, filtrated, and concentrated. To the above residue was added 10% H$_2$SO$_4$ in AcOH (40 mL). The mixture was stirred at ambient temperature for 90 min. The solution was poured into H$_2$O, and the aqueous layer was extracted with CHCl$_3$ (three times). The combined organic layer was washed with saturated aqueous NaHCO$_3$, washed with brine, dried over MgSO$_4$, filtered, concentrated, and purified by flash chromatography (silica gel, 9% EtOAc in hexane) to give (4-bromo-2-trifluoromethoxy-phenyl)-acetaldehyde (1.25 g, 30%) as a pale brown oil.

ESI MS m/e 284, M+H$^+$; $^1$H NMR (200 MHz, CDCl$_3$) δ 9.74 (t, J=1.5 Hz, 1 H), 7.41-7.51 (m, 2 H), 7.16 (d, J=8.4 Hz, 1 H), 3.75 (d, J=1.5 Hz, 2 H).

Step B: Synthesis of cis-$N^2${4-[2-(4-bromo-2-trifluoromethoxy-phenyl)-ethylamino]-cyclohexyl}-$N^4,N^4$-dimethyl-quinazoline-2,4-diamine dihydrochloride.

To a suspension of cis-$N^2$-(4-amino-cyclohexyl)-$N^4,N^4$-dimethyl-quinazoline-2,4-diamine obtained in step C of example 9 (300 mg, 1.05 mmol) in CH$_2$Cl$_2$ (3 mL) were added (4-bromo-2-trifluoromethoxy-phenyl)-acetaldehyde (357 mg, 1.26 mmol), AcOH (76 mg, 1.26 mmol), and NaBH(OAc)$_3$ (334 mg, 1.57 mmol). The reaction mixture was stirred at ambient temperature for 4.5 hr. The reaction was quenched with saturated aqueous NaHCO$_3$ The aqueous layer was extracted with CHCl$_3$ (three times). The combined organic layer was dried over MgSO$_4$, filtered, concentrated, and purified by flash chromatography (NH-silica gel, 50% EtOAc in hexane) to give a pale yellow solid. To a solution of above solid in EtOAc (0.8 mL) was added 4 M hydrogen chloride in EtOAc (0.25 mL). The mixture was stirred at ambient temperature for 30 min and concentrated. A solution of the residue in Et$_2$O (2 mL) was stirred at ambient temperature for 30 min. The precipitate was collected by filtration, washed with Et$_2$O, and dried under reduced pressure to give cis-$N^2$-{4-[2-(4-bromo-2-trifluoromethoxy-phenyl)-ethylamino]-cyclohexyl}-$N^4,N^4$-dimethyl-quinazoline-2,4-diamine dihydrochloride (161 mg, 25%) as a white solid.

ESI MS m/e 552, M (free)$^+$; $^1$H NMR (200 MHz, CDCl$_3$) δ 12.66 (brs, 1 H), 9.91 (brs, 2 H), 8.71 (brs, 1 H), 7.93 (d, J=6.6 Hz, 1 H), 7.19-7.77 (m, 6 H), 4.31 (brs, 1 H), 3.54 (s, 6 H), 3.09-3.78 (m, 5 H), 2.00-2.48 (m, 6 H), 1.62-1.96 (m, 2 H).

Example 38

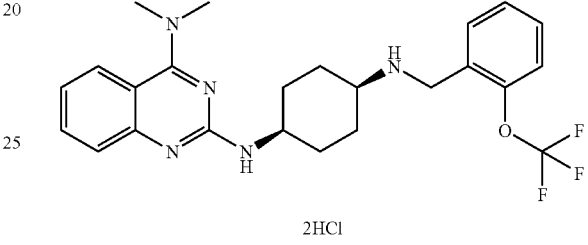

2HCl cis-$N^4,N^4$-Dimethyl-$N^2$-[4-(2-trifluoromethoxy-benzylamino)-cyclohexyl]-quinazoline-2,4-diamine dihydrochloride Step A: Synthesis of cis-$N^4,N^4$-dimethyl-$N^2$-[4-(2-trifluoromethoxy-benzylamino)-cyclohexyl]-quinazoline-2,4-diamine dihydrochloride.

Using the procedure for the step B of example 37, the title compound was obtained.

ESI MS m/e 460, M (free)+H$^+$; $^1$H NMR (300 MHz, CDCl$_3$) δ 8.68 (d, J=7.6 Hz, 1 H), 8.19-8.33 (m, 1 H), 7.95 (d, J=8.2 Hz, 1 H), 7.66 (t, J=7.7 Hz, 1 H), 7.47 (d, J=8.1 Hz, 1 H), 7.18-7.44 (m, 4 H), 4.35 (s, 2 H), 4.15-4.47 (m, 1 H), 3.53 (s, 6 H), 3.02-3.31 (m, 1 H), 1.95-2.37 (m, 6 H), 1.51-1.85 (m, 2 H).

Example 39

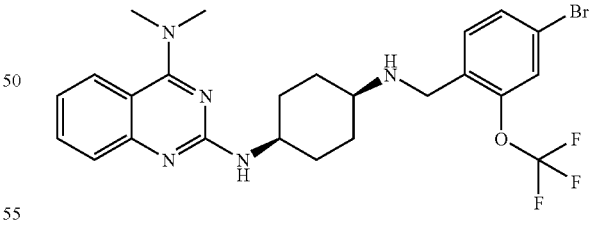

2HCl cis-$N^2$-[4-(4-Bromo-2-trifluoromethoxy-benzylamino)-cyclohexyl]-$N^4,N^4$-dimethyl-quinazoline-2,4-diamine dihydrochloride Step A: Synthesis of cis-$N^2$-[4-(4-bromo-2-trifluoromethoxy-benzylamino)-cyclohexyl]-$N^4,N^4$-dimethyl-quinazoline-2,4-diamine dihydrochloride.

Using the procedure for the step A of example 2, the title compound was obtained.

ESI MS m/e 538, M (free)+H+; 1H NMR (300 MHz, CDCl3) δ 8.77 (d, J=7.5 Hz, 1 H), 8.11 (d, J=8.4 Hz, 1 H), 7.92 (d, J=8.6 Hz, 1 H), 7.67 (t, J=7.7 Hz, 1 H), 7.41-7.53 (m, 2 H), 7.37 (s, 1 H), 7.28 (t, J=7.8 Hz, 1 H), 4.19-4.40 (m, 1 H), 4.26 (s, 2 H), 3.52 (s, 7 H), 3.07-3.25 (m, 1 H), 2.00-2.39 (m, 6 H), 1.61-1.88 (m, 2 H).

Example 40

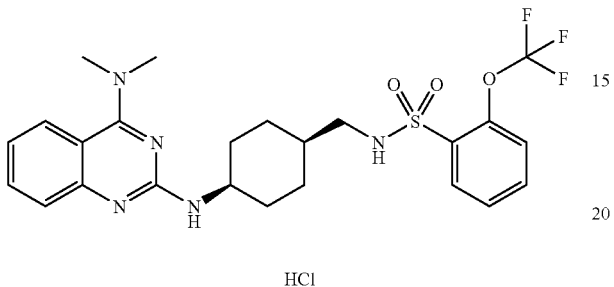

HCl cis-N-[4-(4-Dimethylamino-quinazolin-2-ylamino)-cyclohexylmethyl]-2-trifluoromethoxy-benzene-sulfonamide hydrochloride Step A: Synthesis of cis-N-[4-(4-dimethylamino-quinazolin-2-ylamino)-cyclohexylmethyl]-2-trifluoromethoxy-benzenesulfonamide hydrochloride.

To a solution of cis-[4-(4-dimethylamino-quinazolin-2-ylamino)-cyclohexylmethyl]-carbamic acid benzyl ester obtained in step B of example 24 (4.57 g, 10.5 mmol) in MeOH (46 mL) was added 5% Pd/C (460 mg). The mixture was stirred at 50° C. under hydrogen atmosphere for 3 days, filtered, and concentrated to give a white solid (3.79 g). To a solution of the above solid (500 mg, 1.67 mmol) in CH2Cl2 (5 mL) was added diisopropylethylamine (440 μL, 2.53 mmol). The mixture was cooled on an ice-bath and a solution of 2-trifluoromethoxy-benzenesulfonyl chloride (457 mg, 1.75 mmol) in CH2Cl2 (2 mL) was added dropwise. The reaction mixture was stirred on an ice-bath for 10 hr. The reaction was quenched with saturated aqueous NaHCO3 The aqueous layer was extracted with CHCl3 (three times). The combined organic layer was dried over MgSO4, filtered, concentrated, purified by medium-pressure liquid chromatography (NH-silica gel, 33% EtOAc in hexane), and concentrated. To a solution of the residue in EtOAc (1 mL) was added 4 M hydrogen chloride in EtOAc (5 mL). The reaction mixture was stirred at ambient temperature for 30 min, and concentrated. A solution of the residue in Et2O (10 mL) was stirred at ambient temperature for 1 hr and the precipitate was collected by filtration to give cis-N-[4-(4-dimethylamino-quinazolin-2-ylamino)-cyclohexylmethyl]-2-trifluoromethoxy-benzenesulfonamide hydrochloride (262 mg, 34%) as a white solid.

ESI MS m/e 524, M (free)+W; 1H NMR (300 MHz, CDCl3) δ 13.18 (s, 1 H), 8.75 (d, J=7.6 Hz, 1 H), 8.03 (dd, J=8.0, 1.7 Hz, 1 H), 7.89 (d, J=8.2 Hz, 1 H), 7.56-7.71 (m, 2 H), 7.34-7.55 (m, 3 H), 7.24 (t, J=7.5 Hz, 1 H), 4.99 (t, J=6.5 Hz, 1 H), 4.20-4.33 (m, 1 H), 3.50 (s, 6 H), 2.88 (t, J=6.3 Hz, 2 H), 1.78-1.99 (m, 2 H), 1.38-1.77 (m, 7 H).

Example 41

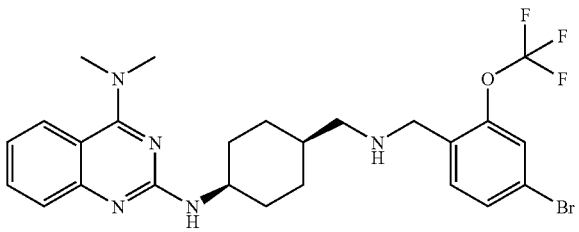

2HCl cis-N2-{4-[(4-Bromo-2-trifluoromethoxy-benzylamino)-methyl]-cyclohexyl}-N4,N4-dimethyl-quinazoline-2,4-diamine dihydrochloride Step A: Synthesis of cis-N2-{4-[(4-bromo-2-trifluoromethoxy-benzylamino)-methyl]-cyclohexyl}-N4,N4-dimethyl-quinazoline-2,4-diamine dihydrochloride.

To a solution of cis-[4-(4-dimethylamino-quinazolin-2-ylamino)-cyclohexylmethyl]-carbamic acid benzyl ester obtained in step B of example 24 (4.57 g, 10.5 mmol) in MeOH (46 mL) was added 5% Pd/C (460 mg). The mixture was stirred at 50° C. under hydrogen atmosphere for 3 days, filtered, and concentrated to give a colorless solid (3.79 g). To a solution of the above solid (500 mg, 1.67 mmol) in CH2Cl2 (5 mL) were added 4-bromo-2-trifluoromethoxy-benzaldehyde obtained in step A of example 13 (449 mg, 1.67 mmol), AcOH (100 mg, 1.67 mmol), and NaBH(OAc)3 (531 g, 2.51 mmol). The reaction mixture was stirred at ambient temperature with CaCl2 tube for 9 hr, poured into saturated aqueous NaHCO3, and the aqueous layer was extracted with CHCl3 (three times). The combined organic layer was dried over MgSO4, filtered, concentrated, purified by medium-pressure liquid chromatography (NH-silica gel, 25% EtOAc in hexane), and concentrated. To a solution of the residue in EtOAc (1 mL) was added 4 M hydrogen chloride in EtOAc (5 mL). The reaction mixture was stirred at ambient temperature for 30 min, and concentrated. A solution of the residue in Et2O (10 mL) was stirred at ambient temperature for 1 hr and the precipitate was collected by filtration to give cis-N2-{4-[(4-bromo-2-trifluoromethoxy-benzylamino)-methyl]-cyclohexyl}-N4,N4-dimethyl-quinazoline-2,4-diamine dihydrochloride (147 mg, 34%) as a white solid.

ESI MS m/e 552, M (free)+W; 1H NMR (300 MHz, CDCl3) δ 12.62 (s, 1 H), 10.07 (brs, 2 H), 8.66 (d, J=7.6 Hz, 1 H), 8.22 (d, J=8.4 Hz, 1 H), 7.90 (d, J=8.4 Hz, 1 H), 7.65 (t, J=7.6 Hz, 1 H), 7.52 (dd, J=8.3, 1.8 Hz, 1 H), 7.33-7.48 (m, 2 H), 7.26 (t, J=7.5 Hz, 1 H), 4.11-4.36 (m, 3 H), 3.51 (s, 6 H), 2.76-2.97 (m, 2 H), 1.51-2.27 (m, 9 H).

Example 42

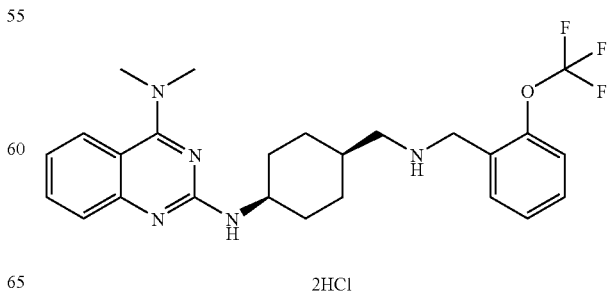

2HCl cis-N⁴,N⁴-Dimethyl-N²-{4-[(2-trifluoromethoxy-benzylamino)-methyl]-cyclohexyl}-quinazoline-2,4-diamine dihydrochloride Step A: Synthesis of cis-N⁴,N⁴-dimethyl-N²-{4-[(2-trifluoromethoxy-benzylamino)-methyl]-cyclohexyl}-quinazoline-2,4-diamine dihydrochloride.

Using the procedure for the step A of example 41, the title compound was obtained.

ESI MS m/e 474, M (free)+H⁺; ¹H NMR (300 MHz, CDCl₃) δ 12.81 (s, 1 H), 9.97 (brs, 1 H), 8.69 (d, J=7.5 Hz, 1 H), 8.16-8.28 (m, 1 H), 7.90 (d, J=8.4 Hz, 1 H), 7.63 (t, J=7.6 Hz, 1 H), 7.18-7.51 (m, 4 H), 4.31 (brs, 2 H), 4.15-4.30 (m, 1 H), 3.50 (s, 6 H), 2.70-2.94 (m, 2 H), 1.41-2.28 (m, 10 H).

Example 43

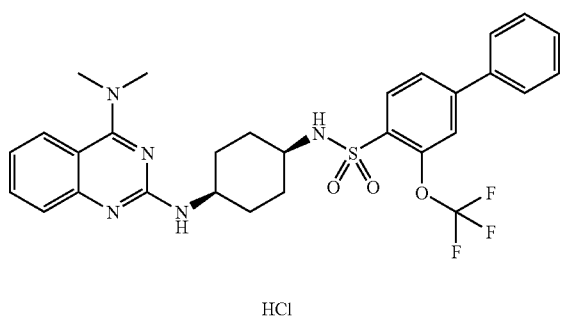

HCl cis-3-Trifluoromethoxy-biphenyl-4-sulfonic acid [4-(4-dimethylamino-quinazolin-2-ylamino)-cyclohexyl]-amide hydrochloride Step A: Synthesis of cis-3-trifluoromethoxy-biphenyl-4-sulfonic acid [4-(4-dimethylamino-quinazolin-2-ylamino)-cyclohexyl]-amide hydrochloride.

Using the procedure for the step A of example 36, the title compound was obtained.

ESI MS m/e 586, M (free)+H⁺; ¹H NMR (300 MHz, CDCl₃) δ 13.20 (brs, 1 H), 8.82 (d, J=8.1 Hz, 1 H), 8.09 (d, J=8.6 Hz, 1 H), 7.88 (d, J=7.8 Hz, 1 H), 7.40-7.73 (m, 8 H), 7.25 (t, J=8.4 Hz, 1 H), 5.41 (d, J=8.6 Hz, 1 H), 4.07-4.22 (m, 1 H), 3.49 (s, 6 H), 3.37-3.62 (m, 1 H), 1.57-2.01 (m, 8 H).

Example 44

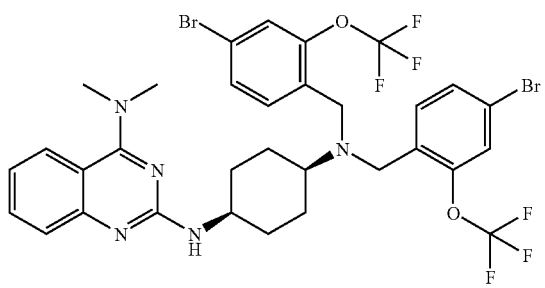

2HCl cis-N²-{4-[Bis-(4-bromo-2-trifluoromethoxy-benzyl)-amino]-cyclohexyl}-N⁴,N⁴-dimethyl-quinazoline-2,4-diamine dihydrochloride Step A: Synthesis of cis-N²-{4-[bis-(4-bromo-2-trifluoromethoxy-benzyl)-amino]-cyclohexyl}-N⁴,N⁴-dimethyl-quinazoline-2,4-diamine dihydrochloride.

Using the procedure for the step B of example 37, the title compound was obtained.

ESI MS m/e 790, M (free)+H⁺; ¹H NMR (300 MHz, CDCl₃) δ 12.50-12.82 (m, 2 H), 9.50-9.69 (m, 1 H), 8.39 (d, J=8.1 Hz, 2 H), 7.91 (d, J=8.1 Hz, 1 H), 7.66 (t, J=7.8 Hz, 1 H), 7.48 (t, J=8.7 Hz, 2 H), 7.07-7.43 (m, 4 H), 4.06-4.67 (m, 5 H), 3.51 (s, 6 H), 2.97-3.27 (m, 1 H), 2.21-2.59 (m, 4 H), 1.89-2.17 (m, 2 H), 1.36-1.82 (m, 2 H)

Example 45

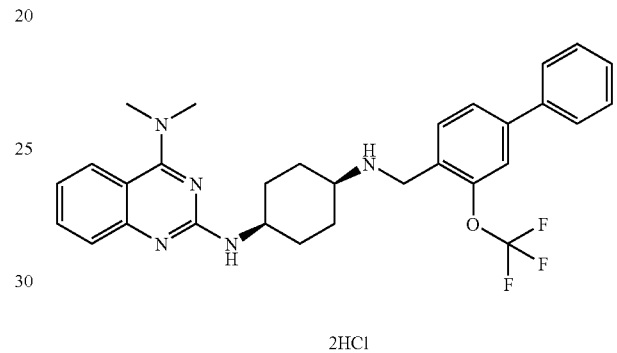

2HCl cis-N⁴,N⁴-Dimethyl-N²-{4-[(3-trifluoromethoxy-biphenyl-4-ylmethyl)-amino]-cyclohexyl}-quinazoline-2,4-diamine dihydrochloride Step A: Synthesis of cis-N⁴,N⁴-dimethyl-N²-{4-[(3-trifluoromethoxy-biphenyl-4-ylmethyl)-amino]-cyclohexyl}-quinazoline-2,4-diamine dihydrochloride.

Using the procedure for the step A of example 43, the title compound was obtained.

ESI MS m/e 536, M (free)+H⁺; ¹H NMR (300 MHz, CDCl₃) δ 12.63 (brs, 1 H), 10.07 (brs, 2 H), 8.68 (d, J=7.3 Hz, 1 H), 8.33 (d, J=8.1 Hz, 1 H), 7.90 (d, J=8.4 Hz, 1 H), 7.17-7.68 (m, 10 H), 4.40 (s, 2 H), 4.19-4.33 (m, 1 H), 3.50 (s, 6 H), 3.16-3.37 (m, 1 H), 2.03-2.48 (m, 6 H), 1.64-1.88 (m, 2 H).

Example 46

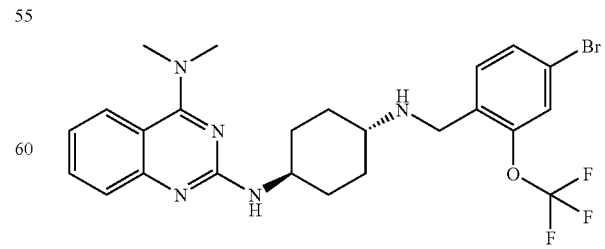

2HCl trans-N²-[4-(4-Bromo-2-trifluoromethoxy-benzylamino)-cyclohexyl]-N⁴,N⁴-dimethyl-quinazoline-2,4-diamine dihydrochloride Step A: Synthesis of trans-N²-[4-(4-bromo-2-trifluoromethoxy-benzylamino)-cyclohexyl]-N⁴,N⁴-dimethyl-quinazoline-2,4-diamine dihydrochloride.

Using the procedure for the step B of example 37, the title compound was obtained.

ESI MS m/e 537, M (free)⁺; ¹H NMR (300 MHz, CDCl₃) δ 13.00 (brs, 1 H), 10.08 (brs, 2 H), 8.40 (d, J=7.2 Hz, 1 H), 8.05 (d, J=8.2 Hz, 1 H), 7.91 (d, J=8.4 Hz, 1 H), 7.65 (t, J=7.7 Hz, 1 H), 7.38-7.57 (m, 3 H), 7.26 (t, J=7.6 Hz, 1 H), 4.17 (s, 2 H), 3.83-4.06 (m, 1 H), 3.53 (s, 6 H), 2.76-2.99 (m, 1 H), 2.09-2.46 (m, 4 H), 1.74-2.00 (m, 2 H), 1.28-1.58 (m, 2 H).

Example 47

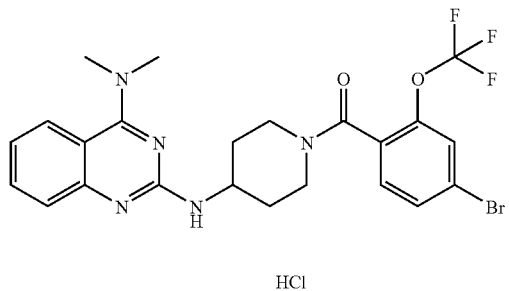

HCl 1-(4-Bromo-2-trifluoromethoxy-phenyl)-1-[4-(4-dimethylamino-quinazolin-2-ylamino)-piperidin-1-yl]-methanone hydrochloride Step A: Synthesis of (4-bromo-2-trifluoromethoxy-phenyl)-[4-(4-dimethylamino-quinazolin-2-ylamino)-piperidin-1-yl]-methanone hydrochloride.

To a solution of 4-bromo-2-trifluoromethoxy-benzoic acid obtained in step B of example 13 (440 mg, 1.47 mmol) in CH₂Cl₂ (5 mL) were added DMF (1.1 μL, 15 μmol) and SOCl₂ (175 μL, 2.09 mmol). The mixture was stirred at reflux for 30 min and concentrated to give acid chloride as a pale yellow oil. To a solution of N⁴,N⁴-dimethyl-N²-piperidin-4-yl-quinazoline-2,4-diamine obtained in step B of example 30 (400 mg, 1.47 mmol) in CH₂Cl₂ (4 mL) was added diisopropylethylamine (538 μL, 3.08 mmol). The mixture was cooled at 4° C. and a solution of above acid chloride in CH₂Cl₂ (3 mL) was added below 5° C. The reaction mixture was stirred at 4° C. for 3 hr. The reaction was quenched with saturated aqueous NaHCO₃, and the aqueous layer was extracted with CHCl₃ (three times). The combined organic layer was dried over MgSO₄, filtered, concentrated, and purified by flash chromatography (NH-silica gel, 25% EtOAc in hexane) to give a pale yellow oil. To a solution of above oil in EtOAc (1 mL) was added 4 M hydrogen chloride in EtOAc (0.26 mL). The mixture was stirred at ambient temperature for 50 min and concentrated. A solution of the residue in Et₂O (5 mL) was stirred at ambient tempareture for 30 min. The precipitate was collected by filtration, washed with Et₂O, and dried under reduced pressure to give (4-bromo-2-trifluoromethoxy-phenyl)-[4-(4-dimethylamino-quinazolin-2-ylamino)-piperidin-1-yl]-methanone hydrochloride (126 mg, 16%) as a white solid.

ESI MS m/e 538, M (free)+H⁺; ¹H NMR (200 MHz, CDCl₃) δ 13.35 (brs, 1 H), 9.06 (d, J=7.5 Hz, 1 H), 7.93 (d, J=8.4 Hz, 1 H), 7.67 (dt, J=7.7, 0.9 Hz, 1 H), 7.43-7.61 (m, 3 H), 7.18-7.41 (m, 2 H), 4.00-4.44 (m, 2 H), 3.54 (s, 6 H), 3.03-3.78 (m, 3 H), 1.52-2.24 (m, 4 H).

Example 48

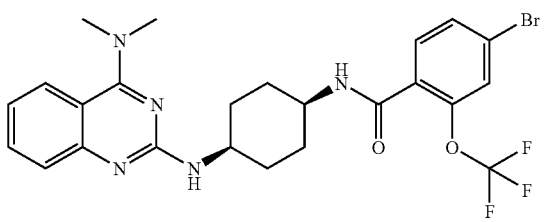

HCl cis-4-Bromo-N-[4-(4-dimethylamino-quinazolin-2-ylamino)-cyclohexyl]-2-trifluoromethoxy-benzamide dihydrochloride Step A: Synthesis of 4-bromo-N-[4-(4-dimethylamino-quinazolin-2-ylamino)-cyclohexyl]-2-trifluoromethoxy-benzamide dihydrochloride.

Using the procedure for the step A of example 47, the title compound was obtained.

ESI MS m/e 551, M (free)⁺; ¹H NMR (200 MHz, CDCl₃) δ 13.24 (brs, 1 H), 8.95 (d, J=7.9 Hz, 1 H), 7.92 (d, J=8.4 Hz, 1 H), 7.71 (d, J=8.4 Hz, 1 H), 7.60-7.67 (m, 1 H), 7.44-7.58 (m, 3 H), 7.20-7.34 (m, 1 H), 6.57 (d, J=8.4 Hz, 1 H), 4.00-4.41 (m, 2 H), 3.53 (s, 6 H), 1.66-2.04 (m, 8 H).

Example 49

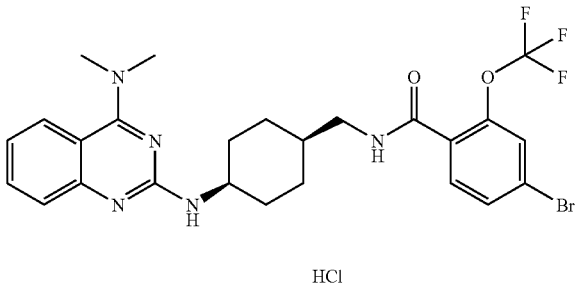

HCl cis-4-Bromo-N-[4-(4-dimethylamino-quinazolin-2-ylamino)-cyclohexylmethyl]-2-trifluoromethoxy-benzamide hydrochloride Step A: Synthesis of 4-bromo-N-[4-(4-dimethylamino-quinazolin-2-ylamino)-cyclohexylmethyl]-2-trifluoromethoxy-benzamide hydrochloride.

Using the procedure for the step A of example 47, the title compound was obtained.

ESI MS m/e 565, M (free)⁺; ¹H NMR (200 MHz, CDCl₃) δ 13.20 (brs, 1 H), 8.93 (d, J=7.9 Hz, 1 H), 7.90 (d, J=8.4 Hz, 1 H), 7.84 (d, J=8.4 Hz, 1 H), 7.42-7.70 (m, 4 H), 7.18-7.34 (m, 1 H), 6.87 (t, J=5.5 Hz, 1 H), 4.34 (brs, 1 H), 3.51 (s, 6 H), 3.43 (t, J=5.7 Hz, 2 H), 1.52-2.17 (m, 9 H).

Example 50

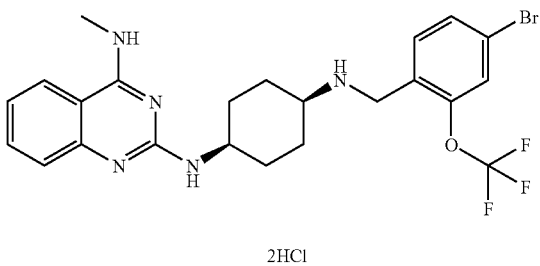

2HCl cis-N$^2$-[4-(4-Bromo-2-trifluoromethoxy-benzylamino)-cyclohexyl]-IV-methyl-quinazoline-2,4-diamine dihydrochloride Step A: Synthesis of (2-chloro-quinazolin-4-yl)-methyl-amine.

A solution of 2,4-dichloro-quinazoline obtained in step A of example 1 (125 g, 628 mmol) in THF (1 L) was cooled to 4° C. and 40% aqueous MeNH$_2$ (136 mL, 1.57 mol) was added. The mixture was stirred at ambient temperature for 80 min. The solution was alkalized with saturated aqueous NaHCO$_3$ (pH=9) and concentrated. The precipitate was collected by filtration, washed with H$_2$O and hexane, and dried at 80° C. to give (2-chloro-quinazolin-4-yl)-methyl-amine (114 g, 94%) as a white solid.

ESI MS m/e 193, M$^+$; $^1$H NMR (300 MHz, CDCl$_3$) δ 7.68-7.78 (m, 3 H), 7.39-7.48 (m, 1 H), 6.34 (brs, 1 H), 3.22 (d, J=4.8 Hz, 3 H).

Step B: Synthesis of cis-[4-(4-methylamino-quinazolin-2-ylamino)-cyclohexyl]-carbamic acid tert-butyl ester.

Using the procedure for the step G of example 1, the title compound was obtained.

ESI MS m/e 372, M+H$^+$; $^1$H NMR (300 MHz, CDCl$_3$) δ 7.36-7.56 (m, 3 H), 7.06 (ddd, J=8.2, 6.8, 1.3 Hz, 1 H), 5.71 (brs, 1 H), 5.10 (brs, 1 H), 4.45-4.72 (m, 1 H), 4.00-4.26 (m, 1 H), 3.49-3.76 (m, 1 H), 3.12 (d, J=4.8 Hz, 3 H), 1.50-1.93 (m, 8 H), 1.46 (s, 9 H).

Step C: Synthesis of cis-N$^2$-[4-(4-bromo-2-trifluoromethoxy-benzylamino)-cyclohexyl]-N$^4$-methyl-quinazoline-2,4-diamine dihydrochloride.

To a suspension of cis-[4-(4-methylamino-quinazolin-2-ylamino)-cyclohexyl]-carbamic acid tert-butyl ester (1.75 g, 4.71 mmol) in EtOAc (5 mL) and CHCl$_3$ (10 mL) was added 4 M hydrogen chloride in EtOAc (15 mL). The reaction mixture was stirred at ambient temperature for 2 hr, and concentrated. The residue was alkalized with saturated aqueous NaHCO$_3$ and the aqueous layer was extracted with CHCl$_3$ (three times). The combined organic layer was dried over MgSO$_4$, filtered, concentrated (2.15 g). To a suspension of the above residue (300 mg, 1.11 mmol) in CH$_2$Cl$_2$ (3 mL) were added 4-bromo-2-trifluoromethoxy-benzaldehyde obtained in Step A of Example 13 (297 mg, 1.10 mmol), AcOH (66 mg, 1.10 mmol), and NaBH(OAc)$_3$ (351 mg, 1.66 mmol). The reaction mixture was stirred at ambient temperature with CaCl$_2$ tube for 4 hr, poured into saturated aqueous NaHCO$_3$, and the aqueous layer was extracted with CHCl$_3$ (three times). The combined organic layer was dried over MgSO$_4$, filtered, concentrated, purified by medium-pressure liquid chromatography (NH-silica gel, 50% EtOAc in hexane), and concentrated to give a pale yellow oil (91 mg). To a solution of the residue (71 mg) in EtOAc (1 mL) was added 4 M hydrogen chloride in EtOAc (5 mL). The reaction mixture was stirred at ambient temperature for 30 min, and concentrated. A solution of the residue in Et$_2$O (10 mL) was stirred at ambient temperature for 1 hr and the precipitate was collected by filtration to give cis-N$^2$-[4-(4-bromo-2-trifluoromethoxy-benzylamino)-cyclohexyl]-N-4-methyl-quinazoline-2,4-diamine dihydrochloride (62 mg, 20%) as a white solid.

ESI MS m/e 524, M (free)+H$^+$; $^1$H NMR (300 MHz, CDCl$_3$) δ 7.34-7.57 (m, 6 H), 7.05 (ddd, J=8.2, 6.8, 1.4 Hz, 1 H), 5.52 (brs, 1 H), 4.09-4.27 (m, 1 H), 3.82 (s, 2 H), 3.12 (d, J=4.8 Hz, 3 H), 2.57-2.72 (m, 1 H), 1.41-1.94 (m, 8 H).

Example 51

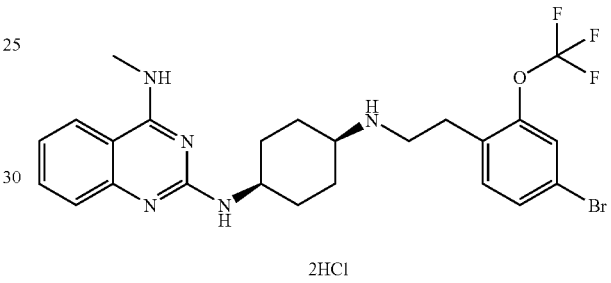

2HCl cis-N$^2$-{4-[2-(4-Bromo-2-trifluoromethoxy-phenyl)-ethylamino]-cyclohexyl}-N$^4$-methyl-quinazoline-2,4-diamine dihydrochloride Step A: Synthesis of cis-N$^2$-{4-[2-(4-bromo-2-trifluoromethoxy-phenyl)-ethylamino]-cyclohexyl}-N$^4$-methyl-quinazoline-2,4-diamine dihydrochloride.

Using the procedure for the step C of example 50, the title compound was obtained.

ESI MS m/e 538, M (free)+H$^+$; $^1$H NMR (300 MHz, CDCl$_3$) δ 12.18 (brs, 1 H), 9.93 (brs, 3 H), 8.74 (d, J=6.2 Hz, 1 H), 7.71-7.94 (m, 1 H), 7.60 (t, 1H, J=7.7 Hz, 1 H), 7.21-7.45 (m, 5 H), 3.94-4.26 (m, 1 H), 3.35-3.58 (m, 2 H), 3.08-3.33 (m, 3 H), 2.94 (brs, 3 H), 1.64-2.42 (m, 8 H).

Example 52

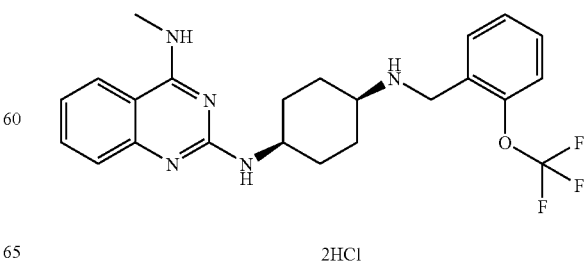

2HCl cis-N⁴-Methyl-N²-[4-(2-trifluoromethoxy-benzy-
lamino)-cyclohexyl]-quinazoline-2,4-diamine dihy-
drochloride Step A: Synthesis of cis-N⁴-methyl-N²-[4-(2-trifluo-
romethoxy-benzylamino)-cyclohexyl]-quinazoline-2,4-di-
amine dihydrochloride.

Using the procedure for the step C of example 50, the title compound was obtained.

ESI MS m/e 446, M (free)+H⁺; ¹H NMR (300 MHz, CDCl₃) δ 7.36-7.56 (m, 4 H), 7.17-7.33 (m, 3 H), 7.04 (ddd, 1H, J=8.2, 6.8, 1.4 Hz, 1 H), 5.66 (brs, 1 H), 5.18 (brs, 1 H), 4.11-4.27 (m, 1 H), 3.87 (s, 2 H), 3.10 (d, J=4.8 Hz, 3 H), 2.60-2.74 (m, 1 H), 1.45-1.95 (m, 8 H).

Example 53

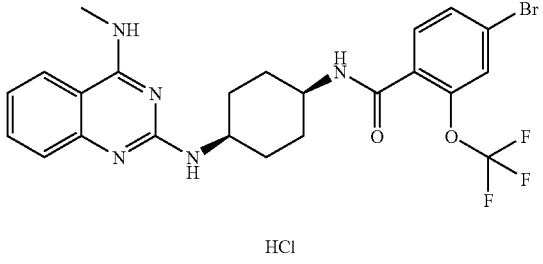

HCl cis-4-Bromo-N-[4-(4-methylamino-quinazolin-2-
ylamino)-cyclohexyl]-2-trifluoromethoxy-benzamide
hydrochloride Step A: Synthesis of cis-4-bromo-N-[4-(4-methylamino-
quinazolin-2-ylamino)-cyclohexyl]-2-trifluoromethoxy-
benzamide hydrochloride.

To a suspension of cis-[4-(4-methylamino-quinazolin-2-ylamino)-cyclohexyl]-carbamic acid tert-butyl ester obtained in step B of example 50 (1.75 g, 4.71 mmol) in EtOAc (5 mL) and CHCl₃ (10 mL) was added 4 M hydrogen chloride in EtOAc (15 mL). The reaction mixture was stirred at ambient temperature for 2 hr, and concentrated. The residue was alkalized with saturated aqueous NaHCO₃ and the aqueous layer was extracted with CHCl₃ (three times). The combined organic layer was dried over MgSO₄, filtered, concentrated. To a solution of 4-bromo-2-trifluoromethoxy-benzoic acid obtained in step B of example 13 (331 mg, 1.16 mmol) in CH₂Cl₂ (5 mL) were added DMF (1 μL, 0.01 mmol) and SOCl₃ (120 μL, 1.65 mmol). The mixture was stirred at reflux for 30 min and concentrated to give acid chloride as a pale yellow oil. To a suspension of cis-N²-(4-amino-cyclohexyl)-N-4-methyl-quinazoline-2,4-diamine (300 mg, 1.11 mmol) in CH₂Cl₂ (3 mL) was added diisopropylethylamine (410 μL, 2.35 mmol). The mixture was cooled on an ice-bath and a solution of the above residue in CH₂Cl₂ (3 mL) was added dropwise. The reaction mixture was stirred on an ice-bath for 3.5 hr. The reaction was quenched with saturated aqueous NaHCO₃ The aqueous layer was extracted with CHCl₃ (three times). The combined organic layer was dried over MgSO₄, filtered, concentrated, and purified by flash chromatography (NH-silica gel, 50% EtOAc in hexane) to give a pale yellow solid.

To a solution of the residue (116 mg) in EtOAc (1 mL) was added 4 M hydrogen chloride in EtOAc (5 mL). The reaction mixture was stirred at ambient temperature for 30 min, and concentrated. A solution of the residue in Et₂O (10 mL) was stirred at ambient temperature for 1 hr and the precipitate was collected by filtration to give 4-bromo-N-[4-(4-methy-lamino-quinazolin-2-ylamino)-cyclohexyl]-2-trifluo-romethoxy-benzamide (102 mg, 16%) as a white solid.

ESI MS m/e 538, M (free)+H⁺; ¹H NMR (300 MHz, CDCl₃) δ 12.72 (s, 1 H), 8.66 (d, J=7.1 Hz, 1 H), 8.35 (brs, 1 H), 8.16 (d, J=7.7 Hz, 1 H), 7.74 (d, J=8.4 Hz, 1 H), 7.48-7.60 (m, 2 H), 7.40-7.43 (m, 1 H), 7.30 (d, J=8.4 Hz, 1 H), 7.19 (t, J=7.8 Hz, 1 H), 6.57 (d, J=8.1 Hz, 1 H), 4.34 (brs, 1 H), 4.15 (brs, 1 H), 3.22 (d, J=3.9 Hz, 3 H), 1.90 (m, 8 H).

Example 54

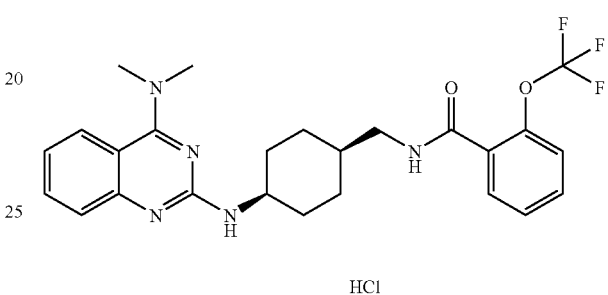

HCl cis-N-[4-(4-Dimethylamino-quinazolin-2-ylamino)-
cyclohexylmethyl]-2-trifluoromethoxy-benzamide
hydrochloride Step A: Synthesis of cis-N-[4-(4-dimethylamino-quinazolin-
2-ylamino)-cyclohexylmethyl]-2-trifluoromethoxy-benza-
mide hydrochloride.

To a solution of cis-[4-(4-dimethylamino-quinazolin-2-ylamino)-cyclohexylmethyl]-carbamic acid benzyl ester obtained in step B of example 24 (4.57 g, 10.5 mmol) in MeOH (46 mL) was added 5% Pd/C (460 mg). The mixture was stirred at 50° C. under hydrogen atmosphere for 3 days, filtered, and concentrated to give a white solid (3.79 g). To a solution of the above solid (300 mg, 1.00 mmol) in CH₂Cl₂ (3 mL) was added triethylamine (280 μL, 2.01 mmol). The mixture was cooled on an ice-bath and a solution of 2-trifluo-romethoxy-benzoyl chloride (236 mg, 1.05 mmol) in CH₂Cl₂ (2 mL) was added dropwise. The reaction mixture was stirred on an ice-bath for 5 hr. The reaction was quenched with saturated aqueous NaHCO₃. The aqueous layer was extracted with CHCl₃ (three times). The combined organic layer was dried over MgSO₄, filtered, concentrated, purified by flash chromatography (NH-silica gel, 33% EtOAc in hexane and silica gel, 10% MeOH in CHCl₃), and concentrated. To a solution of the residue in EtOAc (1 mL) was added 4 M hydrogen chloride in EtOAc (5 mL). The reaction mixture was stirred at ambient temperature for 30 min, and concentrated. A solution of the residue in Et₂O (10 mL) was stirred at ambient temperature for 1 hr and the precipitate was collected by filtration to give cis-N-[4-(4-dimethylamino-quinazolin-2-ylamino)-cyclohexylmethyl]-2-trifluo-romethoxy-benzamide hydrochloride (134 mg, 31%) as a white solid.

ESI MS m/e 510, M (free)+Na⁺; ¹H NMR (300 MHz, CDCl₃) δ 13.29 (s, 1 H), 8.89 (d, J=7.9 Hz, 1 H), 7.93 (dd, J=7.7, 1.8 Hz, 1 H), 7.89 (d, J=8.4 Hz, 1 H), 7.63 (t, J=7.3 Hz, 1 H), 7.52 (d, J=7.9 Hz, 1 H), 7.47 (dd, J=8.1, 1.9 Hz, 1 H), 7.39 (t, J=7.6 Hz, 1 H), 7.29 (d, J=9.0 Hz, 1 H), 7.23 (d, J=7.3 Hz, 1 H), 6.77 (t, J=5.6 Hz, 1 H), 4.18-4.36 (m, 1 H), 3.51 (s, 6 H), 3.42 (t, J=6.3 Hz, 2 H), 1.35-2.02 (m, 9 H).

Example 55

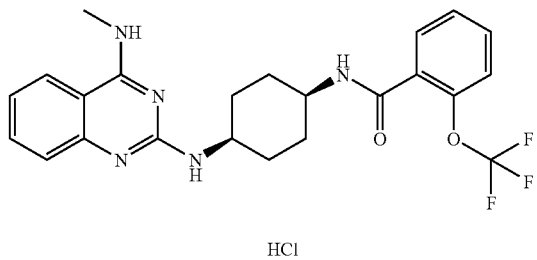

HCl cis-N-[4-(4-Methylamino-quinazolin-2-ylamino)-cyclohexyl]-2-trifluoromethoxy-benzamide hydrochloride Step A: Synthesis of cis-N-[4-(4-methylamino-quinazolin-2-ylamino)-cyclohexyl]-2-trifluoromethoxy-benzamide hydrochloride.

Using the procedure for the step A of example 54, the title compound was obtained.

ESI MS m/e 460, M (free)+H⁺; ¹H NMR (300 MHz, CDCl₃) δ 12.61 (s, 1 H), 8.70 (d, J=4.4 Hz, 1 H), 8.57 (d, J=7.6 Hz, 1 H), 8.26 (d, J=8.1 Hz, 1 H), 7.82 (dd, J=7.7, 1.8 Hz, 1 H), 7.08-7.57 (m, 6 H), 6.60 (d, J=8.1 Hz, 1 H), 4.25-4.45 (m, 1 H), 4.01-4.25 (m, 1 H), 3.20 (d, J=4.5 Hz, 3 H), 1.53-2.18 (m, 8 H).

Example 56

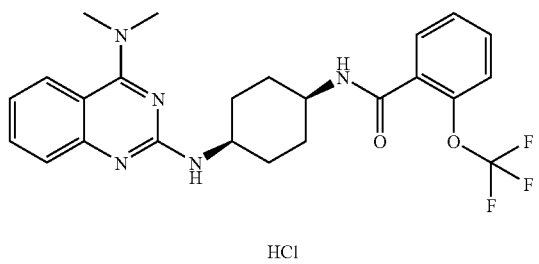

HCl cis-N-[4-(4-Dimethylamino-quinazolin-2-ylamino)-cyclohexyl]-2-trifluoromethoxy-benzamide hydrochloride Step A: Synthesis of cis-N-[4-(4-dimethylamino-quinazolin-2-ylamino)-cyclohexyl]-2-trifluoromethoxy-benzamide hydrochloride.

To a suspension of polymer supported DMA (2.45 g, 7.35 mmol) in CH₂Cl₂ (6 mL) were added 2-trifluoromethoxy-benzoyl chloride (472 mg, 2.10 mmol) and cis-N²-(4-amino-cyclohexyl)-N⁴,N⁴-dimethylquiazoline-2,4-diamine obtained in step C of example 9 (300 mg, 1.05 mmol). The mixture was stirred at ambient temperature for 24 h, filtered, poured into saturated aqueous NaHCO₃. The aqueous layer was extracted with CHCl₃ (three times). The combined organic layer was dried over MgSO₄, filtered, concentrated, purified by medium-pressure liquid chromatography (NH-silica gel, 25% EtOAc in hexane), and concentrated. To a solution of the residue in EtOAc (1 mL) was added 4 M hydrogen chloride in EtOAc (10 mL). The reaction mixture was stirred at ambient temperature for 1 hr, and concentrated. A solution of the residue in Et₂O (10 mL) was stirred at ambient temperature for 1 hr and the precipitate was collected by filtration to give cis-N-[4-(4-dimethylaminoquinazolin-2-ylamino)-cyclohexyl]-2-trifluoromethoxy-benzamide hydrochloride (145 mg, 27%) as a white solid.

ESI MS m/e 474, M+H⁺; ¹H NMR (300 MHz, CDCl₃) δ 13.22 (s, 1 H), 8.88 (d, J=7.5 Hz, 1 H), 7.90 (d, J=8.2 Hz, 1 H), 7.79 (dd, J=7.6, 1.9 Hz, 1 H), 7.64 (t, J=7.5 Hz, 1 H), 7.52 (d, J=8.7 Hz, 1 H), 7.47 (dd, J=8.1, 1.9 Hz, 1 H), 7.37 (dt, J=7.5, 1.2 Hz, 1 H), 7.20-7.33 (m, 2 H), 6.66 (d, J=8.4 Hz, 1 H), 4.06-4.36 (m, 2 H), 3.52 (s, 6 H), 1.55-2.21 (m, 8 H).

Example 57

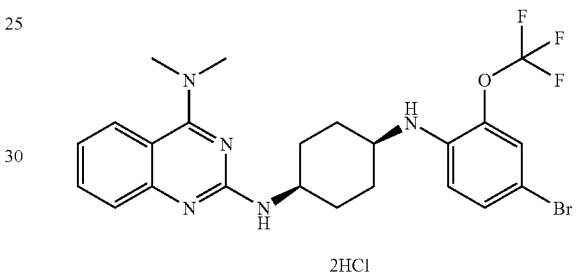

2HCl cis-N²-[4-(4-Bromo-2-trifluoromethoxy-phenylamino)-cyclohexyl]-N⁴,N⁴-dimethyl-quinazoline-2,4-diamine dihydrochloride Step A: Synthesis of cis-N²-[4-(4-bromo-2-trifluoromethoxy-phenylamino)-cyclohexyl]-N⁴,N⁴-dimethyl-quinazoline-2,4-diamine dihydrochloride.

To a glass flask were added 18-crown-6 (647 mg, 2.45 mmol), 4-Bromo-1-iodo-2-trifluoromethoxy-benzene (770 mg, 2.10 mmol), cis-N²-(4-amino-cyclohexyl)-N⁴,N⁴-dimethyl-quinazoline-2,4-diamine obtained in step C of example 9 (500 mg, 1.75 mmol), sodium tert-butoxide (235 mg, 2.45 mmol), tris(dibenzylideneacetone)dipalladium (160 mg, 0.175 mmol), (R)-(+)-2,2'-Bis(diphenylphosphino)-1,1'-binaphthyl (160 mg, 0.175 mmol) and THF (3.5 mL). The reaction mixture was stirred at reflux 18 hr. The mixture was filtered through a pad of celite, concentrated, and purified by flash chromatography (NH-silica gel, 33% EtOAc in hexane) to give a pale yellow oil. To a solution of above oil in Et₂O (2 mL) was added 4 M hydrogen chloride in EtOAc (0.3 mL). The mixture was stirred at ambient temperature for 30 min and concentrated. A solution of the residue in Et₂O (2 mL) was stirred at ambient tempareture for 15 min. The precipitate was collected by filtration, washed with Et₂O, and dried under reduced pressure to give cis-N²-[4-(4-bromo-2-trifluoromethoxy-phenylamino)-cyclohexyl]-N⁴,N⁴-dimethyl-quinazoline-2,4-diamine dihydrochloride (189 mg, 18%) as a white solid.

ESI MS m/e 524, M (free)+H⁺; ¹H NMR (300 MHz, CDCl₃) δ 13.04 (s, 1 H), 8.85 (d, J=7.9 Hz, 1 H), 7.90 (d, J=8.1

Hz, 1 H), 7.61-7.70 (m, 1 H), 7.53 (d, J=7.6 Hz, 1 H), 7.22-7.31 (m, 1 H), 6.94 (s, 1 H), 6.79 (s, 1 H), 6.65 (s, 1 H), 4.28 (brs, 1 H), 3.52 (s, 6 H), 3.30-3.45 (m, 2 H), 1.64-2.08 (m, 8 H).

Example 58

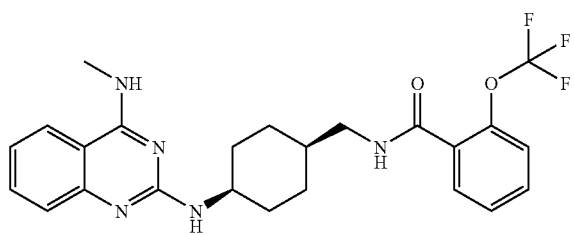

HCl cis-N-[4-(4-Methylamino-quinazolin-2-ylamino)-cyclohexylmethyl]-2-trifluoromethoxy-benzamid hydrochloride Step A: Synthesis of cis-[4-(4-methylamino-quinazolin-2-ylamino)-cyclohexylmethyl]-carbamic acid benzyl ester.

Using the procedure for the step G of Example 1, the title compound was obtained.

ESI MS m/e 420, M (free)+H$^+$; $^1$H NMR (300 MHz, CDCl$_3$) δ 7.20-7.59 (m, 8 H), 7.04 (ddd, J=8.2, 6.8, 1.3 Hz, 1 H), 5.54-5.76 (m, 1 H), 5.10 (s, 2 H), 4.78-5.24 (m, 2 H), 4.18-4.36 (m, 1 H), 3.11 (d, J=4.8 Hz, 3 H), 2.92-3.16 (m, 2 H), 1.06-1.94 (m, 9 H).

Step B: Synthesis of cis-N-[4-(4-methylamino-quinazolin-2-ylamino)-cyclohexylmethyl]-2-trifluoromethoxy-benzamid hydrochloride To a solution of cis-[4-(4-methylamino-quinazolin-2-ylamino)-cyclohexylmethyl]-carbamic acid benzyl ester (2.73 g, 6.50 mmol) in MeOH (27 mL) was added 10% Pd/C (273 mg). The mixture was stirred at 50° C. under hydrogen atmosphere for 14 hr, filtered, and concentrated to give a colorless solid (1.95 g). To a suspension of polymer supported DMAP (2.45 g, 7.35 mmol) in CH$_2$Cl$_2$ (10 mL) were added 2-trifluoromethoxy-benzoyl chloride (472 mg, 2.10 mmol) and the above solid (300 mg, 1.05 mmol). The mixture was stirred at ambient temperature for 2.5 days, filtered, poured into saturated aqueous NaHCO$_3$. The aqueous layer was extracted with CHCl$_3$ (three times). The combined organic layer was dried over MgSO$_4$, filtered, concentrated, purified by medium-pressure liquid chromatography (NH-silica gel, 50% EtOAc in hexane) and flash chromatography (silica gel, 20% MeOH in CHCl$_3$), and concentrated. To a solution of the residue in EtOAc (1 mL) was added 4 M hydrogen chloride in EtOAc (5 mL). The reaction mixture was stirred at ambient temperature for 30 min, and concentrated. A solution of the residue in Et$_2$O (5 mL) was stirred at ambient temperature for 1 hr and the precipitate was collected by filtration to give cis-N-[4-(4-methylamino-quinazolin-2-ylamino)-cyclohexylmethyl]-2-trifluoromethoxy-benzamide hydrochloride (20 mg, 4%) as a white solid.

ESI MS m/e 474, M+H$^+$; $^1$H NMR (500 MHz, CDCl$_3$) δ 12.82 (s, 1 H), 8.63 (d, J=7.3 Hz, 1 H), 7.97-8.12 (m, 2 H), 7.91 (dd, J=7.6, 1.5 Hz, 1 H), 7.54 (t, J=7.6 Hz, 1 H), 7.48 (dt, J=7.9, 1.8 Hz, 1 H), 7.38 (t, J=7.0 Hz, 1 H), 7.26-7.35 (m, 2 H), 7.19 (t, J=7.6 Hz, 1 H), 6.77 (t, J=5.8 Hz, 1 H), 4.30-4.41 (m, 1 H), 3.41 (t, J=6.4 Hz, 2 H), 3.20 (d, J=3.7 Hz, 3 H), 1.48-2.01 (m, 9 H).

Example 59

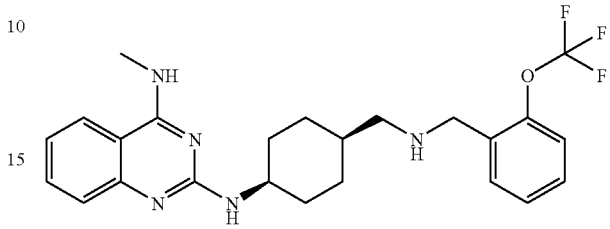

2HCl cis-N$^4$-Methyl-N$^2$-{4-[(2-trifluoromethoxy-benzylamino)-methyl]-cyclohexyl}-quinazoline-2,4-diamine dihydrochloride Step A: Synthesis of cis-N$^4$-methyl-N$^2$-{4-[(2-trifluoromethoxy-benzylamino)-methyl]-cyclohexyl}-quinazoline-2,4-diamine dihydrochloride.

To a solution of cis-[4-(4-methylamino-quinazolin-2-ylamino)-cyclohexylmethyl]-carbamic acid benzyl ester obtained in step A of example 58 (2.73 g, 6.50 mmol) in MeOH (27 mL) was added 10% Pd/C (273 mg). The mixture was stirred at 50° C. under hydrogen atmosphere for 14 hr, filtered, and concentrated to give a colorless solid (1.95 g). To a solution of the above solid (300 mg, 1.05 mmol) in MeOH (3 mL) were added 2-trifluoromethoxy-benzaldehyde (200 mg, 1.05 mmol), AcOH (63 mg, 1.05 mmol), and NaBH$_3$CN (99 mg, 1.58 mmol). The reaction mixture was stirred at ambient temperature with CaCl$_2$ tube for 4 hr, poured into 1 M aqueous sodium hydroxide, and the aqueous layer was extracted with CHCl$_3$ (three times). The combined organic layer was dried over MgSO$_4$, filtered, concentrated, purified by medium-pressure liquid chromatography (NH-silica gel, 50% EtOAc in hexane) and flash chromatography (silica gel, 10% MeOH in CHCl$_3$), and concentrated. To a solution of the residue in EtOAc (1 mL) was added 4 M hydrogen chloride in EtOAc (5 mL). The reaction mixture was stirred at ambient temperature for 30 min, and concentrated. A solution of the residue in Et$_2$O (10 mL) was stirred at ambient temperature for 1 hr and the precipitate was collected by filtration to give cis-N$^4$-methyl-N$^2$-{4-[(2-trifluoromethoxy-benzylamino)-methyl]-cyclohexyl}-quinazoline-2,4-diamine dihydrochloride (175 mg, 33%) as a white solid.

ESI MS m/e 460, M (free)+H$^+$; $^1$H NMR (300 MHz, CDCl$_3$) δ 11.49 (brs, 1 H), 9.74 (brs, 1 H), 9.57 (d, J=4.4 Hz, 1 H), 8.43 (d, J=8.4 Hz, 1 H), 8.27 (d, J=8.4 Hz, 1 H), 8.13 (dd, J=7.5, 1.8 Hz, 1 H), 7.24-7.51 (m, 4 H), 6.95-7.16 (m, 2 H), 4.28 (s, 2 H), 4.13-4.38 (m, 1 H), 2.99 (d, J=4.5 Hz, 3 H), 2.92 (d, J=4.8 Hz, 2 H), 1.41-2.19 (m, 9 H).

Example 60

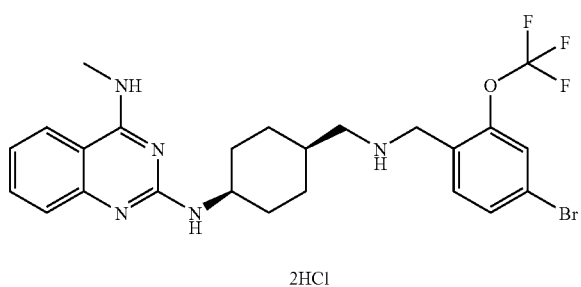

2HCl cis-$N^2$-{4-[(4-Bromo-2-trifluoromethoxy-benzylamino)-methyl]-cyclohexyl}-$N^4$-methyl-quinazoline-2,4-diamine dihydrochloride Step A: Synthesis of cis-$N^2$-{4-[(4-bromo-2-trifluoromethoxy-benzylamino)-methyl]-cyclohexyl}-$N^4$-methyl-quinazoline-2,4-diamine dihydrochloride.

Using the procedure for the step A of Example 59, the title compound was obtained.

ESI MS m/e 538, M (free)+$H^+$; $^1H$ NMR (500 MHz, CDCl$_3$) δ 11.23 (brs, 1 H), 9.75 (brs, 2 H), 9.46 (brs, 1 H), 8.43 (d, J=7.9 Hz, 1 H), 8.29 (d, J=8.5 Hz, 1 H), 8.08 (d, J=8.5 Hz, 1 H), 7.55 (dd, J=8.6, 1.8 Hz, 1 H), 7.44-7.52 (m, 2 H), 7.14 (t, J=7.3 Hz, 1 H), 7.07 (d, J=7.9 Hz, 1 H), 4.24 (s, 2 H), 4.19-4.30 (m, 1 H), 2.88-3.05 (m, 5 H), 1.38-1.84 (m, 9 H).

Example 61

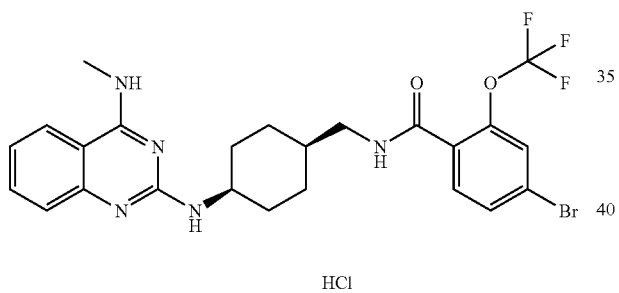

HCl cis-4-Bromo-N-[4-(4-methylamino-quinazolin-2-ylamino)-cyclohexylmethyl]-2-trifluoromethoxy-benzamide hydrochloride Step A: Synthesis of cis-4-bromo-N-[4-(4-methylamino-quinazolin-2-ylamino)-cyclohexylmethyl]-2-trifluoromethoxy-benzamide hydrochloride.

To a solution of cis-[4-(4-Methylamino-quinazolin-2-ylamino)-cyclohexylmethyl]-carbamic acid benzyl ester obtained in step A of example 58 (2.73 g, 6.50 mmol) in MeOH (27 mL) was added 10% Pd/C (273 mg). The mixture was stirred at 50° C. under hydrogen atmosphere for 14 hr, filtered, and concentrated to give cis-$N^2$-(4-Aminomethyl-cyclohexyl)-N-4-methyl-quinazoline-2,4-diamine (1.95 g) as a white solid. To a solution of 4-bromo-2-trifluoromethoxy-benzoic acid obtained in step B of example 13 (599 mg, 2.10 mmol) in CH$_2$Cl$_2$ (6 mL) was added DMF (1 μL, 14.7 μmol) and SOCl$_2$ (190 μL, 2.60 mmol). The mixture was stirred at reflux for 30 min and concentrated to give acid chloride as a pale yellow oil. To a suspension of polymer supported DMAP (2.45 g, 7.35 mmol) in CH$_2$Cl$_2$ (6 mL) were added above acid chloride and cis-$N^2$-(4-aminomethyl-cyclohexyl)-$N^4$-methyl-quinazoline-2,4-diamine (300 mg). The mixture was stirred at ambient temperature for 24 hr, filtered, poured into saturated aqueous NaHCO$_3$. The aqueous layer was extracted with CHCl$_3$ (three times). The combined organic layer was dried over MgSO$_4$, filtered, concentrated, purified by medium-pressure liquid chromatography (NH-silica gel, 50% EtOAc in hexane), and concentrated. To a solution of the residue in EtOAc (1 mL) was added 4 M hydrogen chloride in EtOAc (10 mL). The reaction mixture was stirred at ambient temperature for 1 hr, and concentrated. A solution of the residue in Et$_2$O (10 mL) was stirred at ambient temperature for 1 hr and the precipitate was collected by filtration to give cis-4-bromo-N-[4-(4-methylamino-quinazolin-2-ylamino)-cyclohexylmethyl]-2-trifluoromethoxy-benzamide hydrochloride (47 mg, 8%) as a white solid.

ESI MS m/e 551, M (free)+; $^1H$ NMR (500 MHz, CDCl$_3$) δ 12.61 (s, 1 H), 8.56 (d, J=7.3 Hz, 1 H), 8.40 (brs, 1 H), 8.15 (d, J=8.5 Hz, 1 H), 7.78 (d, J=8.5 Hz, 1 H), 7.47-7.55 (m, 2 H), 7.42 (t, J=1.5 Hz, 1 H), 7.26 (d, J=8.5 Hz, 1 H), 7.17 (t, J=7.6 Hz, 1 H), 6.88 (t, J=5.8 Hz, 1 H), 4.32-4.44 (m, 1 H), 3.40 (t, J=6.1 Hz, 2 H), 3.20 (d, J=4.3 Hz, 3 H), 1.49-2.00 (m, 8 H).

Example 62

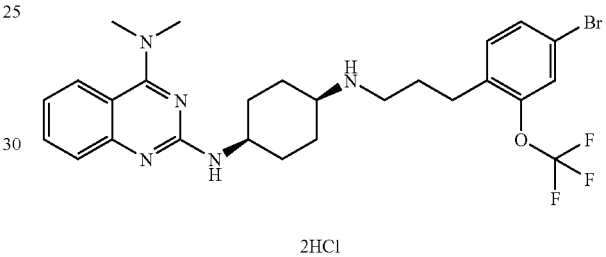

2HCl cis-$N^2$-{4-[3-(4-Bromo-2-trifluoromethoxy-phenyl)-propylamino]-cyclohexyl}-$N^4$,$N^4$-dimethyl-quinazoline-2,4-diamine dihydrochloride Step A: Synthesis of (E)-3-(4-bromo-2-trifluoromethoxyphenyl)-acrylic acid ethyl ester.

To a solution of (ethoxy-methoxymethyl-phosphinoyl)-acetic acid ethyl ester (3.45 g, 15.4 mmol) in THF (230 mL) was added 60% sodium hydride in oil (370 mg, 15.4 mmol). The mixture was stirred at ambient temperature for 50 min and cooled at 4° C. To the reaction mixture was added 4-bromo-2-trifluoromethoxy-benzaldehyde (3 g, 11.2 mmol) in THF (100 mL). The mixture was stirred at ambient temperature for 15 hr. The solution was poured into H$_2$O, and the aqueous layer was extracted with EtOAc (three times). The combined organic layer was dried over MgSO$_4$, filtered, concentrated, and purified by flash chromatography (silica gel, 5% EtOAc in hexane) to give (E)-3-(4-Bromo-2-trifluoromethoxy-phenyl)-acrylic acid ethyl ester (2.98 g, 79%) as a colorless oil.

CI MS m/e 339, M+$H^+$; $^1H$ NMR (300 MHz, CDCl$_3$) δ 7.85 (d, J=15.8 Hz, 1 H), 7.42-7.58 (m, 3 H), 6.48 (d, J=15.8 Hz, 1 H), 4.29 (q, J=7.0 Hz, 2 H), 1.35 (t, J=7.0 Hz, 3 H).

Step B: Synthesis of 3-(4-bromo-2-trifluoromethoxy-phenyl)-propan-1-ol.

A suspension of lithium aluminum hydride (834 mg, 22.0 mmol) in Et$_2$O (20 mL) was cooled at 4° C. A solution of (E)-3-(4-bromo-2-trifluoromethoxy-phenyl)-acrylic acid ethyl ester (2.98 g, 8.79 mmol) in Et$_2$O (9 mL) was added dropwise, and the mixture was stirred at ambient temperature for 90 min. The reaction was quenched with EtOAc (6 mL) and saturated aqueous NH$_4$Cl was added dropwise. The aqueous layer was extracted with EtOAc (three times). The combined organic layer was washed with 1 M aqueous HCl, dried over MgSO$_4$, filtered, concentrated, and purified by flash chromatography (silica gel, 25% EtOAc in hexane) to give 3-(4-bromo-2-trifluoromethoxy-phenyl)-propan-1-ol (1.14 g, 43%) as a colorless oil.

ESI MS m/e 298, M$^+$; $^1$H NMR (300 MHz, CDCl$_3$) δ 7.10-7.43 (m, 3 H), 3.68 (t, J=6.4 Hz, 2 H), 2.67-2.80 (m, 2 H), 1.75-1.94 (m, 2 H).

Step C: Synthesis of 3-(4-bromo-2-trifluoromethoxy-phenyl)-propionaldehyde.

A solution of 3-(4-bromo-2-trifluoromethoxy-phenyl)-propan-1-ol (1.03 g, 3.44 mmol) in CH$_2$Cl$_2$ (47 mL) was cooled at 4° C. and added celite (1.4 g) and pyridinium chlorochromate (1.11 g, 5.16 mmol). The reaction mixture was stirred at ambient temperature for 6 hr and filtered through a pad of celite, concentrated, and purified by flash chromatography (silica gel, 16% EtOAc in hexane) to give 3-(4-bromo-2-trifluoromethoxy-phenyl)-propionaldehyde (659 mg, 64%) as a colorless oil.

CI MS m/e 297, M+H$^+$; $^1$H NMR (300 MHz, CDCl$_3$) δ 9.80 (t, J=1.1 Hz, 1 H), 7.32-7.42 (m, 2 H), 7.17 (d, J=8.4, Hz, 1 H), 2.96 (t, J=7.4 Hz, 2 H), 2.72-2.81 (m, 2 H).

Step D: Synthesis of cis-N$^2$-{4-[3-(4-bromo-2-trifluoromethoxy-phenyl)-propylamino]-cyclohexyl}-N$^4$,N$^4$-dimethyl-quinazoline-2,4-diamine dihydrochloride.

Using the procedure for the step B of example 37, the title compound was obtained.

ESI MS m/e 566, M (free)+H$^+$; $^1$H NMR (300 MHz, CDCl$_3$) δ 8.81 (d, J=7.2 Hz, 1 H), 7.91 (d, J=7.9 Hz, 1 H), 7.60-7.70 (m, 1 H), 7.49 (d, J=8.4 Hz, 1 H), 7.12-7.42 (m, 5 H), 4.31 (brs, 1 H), 3.52 (s, 6 H), 3.23 (brs, 1 H), 3.02-3.14 (m, 2 H), 2.78 (t, J=7.8 Hz, 2 H), 1.97-2.36 (m, 8 H), 1.59-1.85 (m, 2 H).

Example 63

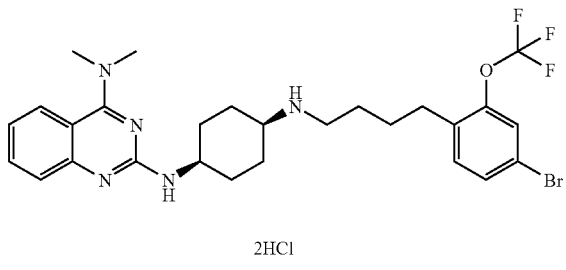

cis-N$^2$-{4-[4-(4-Bromo-2-trifluoromethoxy-phenyl)-butylamino]-cyclohexyl}-N$^4$,N$^4$-dimethyl-quinazoline-2,4-diamine dihydrochloride Step A: Synthesis of (E)-4-(4-bromo-2-trifluoromethoxy-phenyl)-but-2-enoic acid ethyl ester.

Using the procedure for the step A of example 62, the title compound was obtained.

ESI MS m/e 352, N; $^1$H NMR (300 MHz, CDCl$_3$) δ 7.33-7.53 (m, 3 H), 6.64 (d, J=16.2 Hz, 1 H), 6.37 (dt, J=16.0, 7.1 Hz, 1 H), 4.18 (q, J=7.2 Hz, 2 H), 3.28 (dd, J=7.1, 1.5 Hz, 2 H), 1.29 (t, J=7.2 Hz, 3 H).

Step B: Synthesis of 4-(4-bromo-2-trifluoromethoxy-phenyl)-butan-1-ol.

Using the procedure for the step B of example 62, the title compound was obtained.

ESI MS m/e 312, M$^+$; $^1$H NMR (200 MHz, CDCl$_3$) δ 7.10-7.42 (m, 3 H), 3.68 (t, J=5.1 Hz, 2 H), 2.60-2.82 (m, 2 H), 1.50-1.79 (m, 4 H), 1.10-1.50 (brs, 1 H).

Step C: Synthesis of 4-(4-bromo-2-trifluoromethoxy-phenyl)-butyraldehyde.

Using the procedure for the step C of example 62, the title compound was obtained.

ESI MS m/e 311, M+H$^+$; $^1$H NMR (200 MHz, CDCl$_3$) δ 9.79 (s, 1 H), 7.02-7.22 (m, 3 H), 2.60-2.84 (m, 2 H), 2.49 (t, J=5.9 Hz, 2 H), 1.80-2.03 (m, 2 H).

Step D: Synthesis of cis-N$^2$-{4-[4-(4-bromo-2-trifluoromethoxy-phenyl)-butylamino]-cyclohexyl}-N$^4$,N$^4$-dimethyl-quinazoline-2,4-diamine dihydrochloride.

To a suspension of cis-N$^2$-(4-amino-cyclohexyl)-N$^4$,N$^4$-dimethyl-quinazoline-2,4-diamine obtained in step C of example 9 (240 mg, 0.84 mmol) in MeOH (3 mL) were added 4-(4-bromo-2-trifluoromethoxy-phenyl)-butyraldehyde (262 mg, 0.84 mmol), acetic acid (79 mg, 1.26 mmol), and NaBH$_3$CN (79 mg, 1.26 mmol). The reaction mixture was stirred at ambient temperature for 8 hr. The reaction was quenched with saturated aqueous NaHCO$_3$ The aqueous layer was extracted with CHCl$_3$ (three times). The combined organic layer was dried over MgSO$_4$, filtered, concentrated, and purified by medium-pressure liquid chromatography (NH-silica gel, 50% EtOAc in hexane) to give a pale yellow solid. To a solution of above solid in EtOAc (2 mL) was added 4 M hydrogen chloride in EtOAc (10 mL). The mixture was stirred at ambient temperature for 1 hr and concentrated. A solution of the residue in Et$_2$O (20 mL) was stirred at ambient tempareture for 1 hr. The solid was collected by filtration, washed with Et$_2$O, and dried under reduced pressure to give cis-N$^2$-{4-[4-(4-bromo-2-trifluoromethoxy-phenyl)-butylamino]-cyclohexyl}-N$^4$,N$^4$-dimethyl-quinazoline-2,4-diamine dihydrochloride (220 mg, 40%) as a white solid.

ESI MS m/e 580, M (free)+H$^+$; $^1$H NMR (200 MHz, CDCl$_3$) δ 12.73 (brs, 1 H), 9.55 (brs, 2 H), 8.66-8.88 (m, 1 H), 7.92 (d, J=7.9 Hz, 1 H), 7.66 (t, J=7.3 Hz, 1 H), 7.48 (d, J=7.7 Hz, 1 H), 7.12-7.40 (m, 3 H), 4.20-4.42 (m, 1 H), 3.52 (s, 6 H), 2.92-3.42 (m, 3 H), 2.60-2.78 (m, 2 H), 1.58-2.59 (m, 12 H).

Example 64

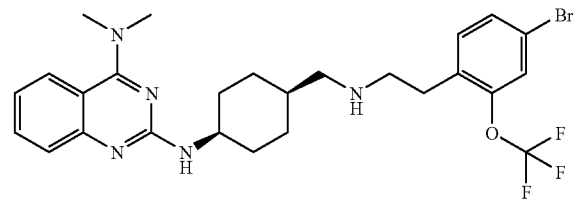

cis-N$^2$-(4-{[2-(4-Bromo-2-trifluoromethoxy-phenyl)-ethylamino]-methyl}-cyclohexyl)-N$^4$,N$^4$-dimethyl-quinazoline-2,4-diamine dihydrochloride Step A: Synthesis of N$^2$-(4-aminomethyl-cyclohexyl)-N$^4$,N$^4$-dimethyl-quinazoline-2,4-diamine.

To a solution of cis-[4-(4-dimethylamino-quinazolin-2-ylamino)-cyclohexylmethyl]-carbamic acid benzyl ester obtained in step B of example 24 (12.1 g, 27.9 mmol) in MeOH (120 mL) was added 10% Pd/C (1.21 g). The mixture was stirred at 50° C. under hydrogen atmosphere for 19 hr, filtered, concentrated, and purified by flash chromatography (NH-silica gel, 66% EtOAc in hexane to 15% MeOH in chloroform) to give $N^2$-(4-aminomethyl-cyclohexyl)-$N^4,N^4$-dimethyl-quinazoline-2,4-diamine (6.9 g, 83%) as a yellow solid.

CI MS m/e 300, M+H[+]; $^1$H NMR (300 MHz, CDCl$_3$) δ 7.81 (d, J=8.4 Hz, 1 H), 7.40-7.51 (m, 2 H), 6.98-7.04 (m, 1 H), 5.04 (d, J=7.3 Hz, 1 H), 4.24-4.30 (m, 1 H), 3.27 (s, 6 H), 2.60 (d, J=6.4 Hz, 2 H), 1.81-1.96 (m, 2 H), 1.57-1.76 (m, 4 H), 0.90-1.51 (m, 5 H).

Step B: Synthesis of cis-$N^2$-(4-{[2-(4-bromo-2-trifluoromethoxy-phenyl)-ethylamino]-methyl}-cyclohexyl)-$N^4$,$N^4$-dimethyl-quinazoline-2,4-diamine dihydrochloride.

Using the procedure for the step B of example 37, the title compound was obtained.

ESI MS m/e 566, M (free)+H[+]; $^1$H NMR (300 MHz, CDCl$_3$) δ 12.45 (s, 1 H), 9.74 (brs, 2 H), 8.70 (d, J=7.6 Hz, 1 H), 7.90 (d, J=8.4 Hz, 1 H), 7.66 (t, J=7.6 Hz, 1 H), 7.17-7.52 (m, 4 H), 4.30 (brs, 1 H), 3.52 (s, 6 H), 3.32-3.50 (m, 2 H), 3.17 (brs, 2 H), 3.01 (brs, 2 H), 1.56-2.10 (m, 9 H).

Example 65

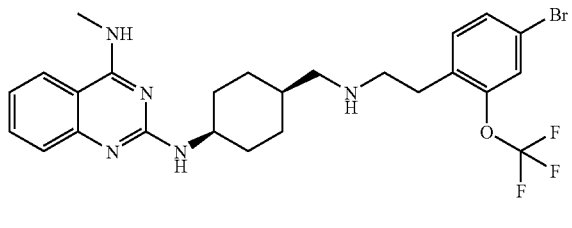

2HCl cis-$N^2$-(4-{[2-(4-Bromo-2-trifluoromethoxy-phenyl)-ethylamino]-methyl}-cyclohexyl)-$N^4$-methyl-quinazoline-2,4-diamine dihydrochloride Step A: Synthesis of cis-$N^2$-(4-{[2-(4-bromo-2-trifluoromethoxy-phenyl)-ethylamino]-methyl}-cyclohexyl)-N-4-methyl-quinazoline-2,4-diamine dihydrochloride.

Using the procedure for the step A of example 59, the title compound was obtained.

ESI MS m/e 552 M (free)+W; $^1$H NMR (300 MHz, CDCl$_3$) δ 11.66 (s, 1 H), 9.62 (brs, 1 H), 9.40 (brs, 1 H), 8.05-8.50 (m, 2 H), 7.21-7.58 (m, 4 H), 6.96-7.21 (m, 2 H), 4.26 (brs, 1 H), 3.41 (brs, 2 H), 2.75-3.31 (m, 7 H), 1.30-2.24 (m, 9 H).

Example 66

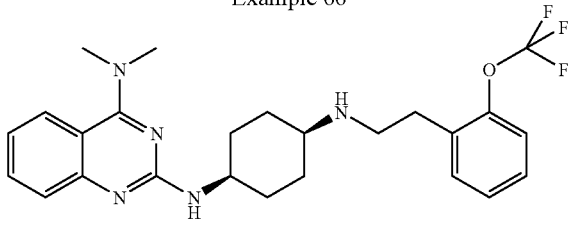

2HCl cis-$N^4$,$N^4$-Dimethyl-$N^2$-{4-[2-(2-trifluoromethoxy-phenyl)-ethylamino]-cyclohexyl}-quinazoline-2,4-diamine dihydrochloride Step A: Synthesis of cis-$N^4$,$N^4$-dimethyl-$N^2$-{4-[2-(2-trifluoromethoxy-phenyl)-ethylamino]-cyclohexyl}-quinazoline-2,4-diamine dihydrochloride.

To a solution of cis-$N^2$-{4-[2-(4-bromo-2-trifluoromethoxy-phenyl)-ethylamino]-cyclohexyl}-$N^4$,$N^4$-dimethyl-quinazoline-2,4-diamine dihydrochloride obtained in step B of example 37 (250 mg, 0.4 mmol) in EtOH (5 mL) was added 10% Pd/C (75 mg). The mixture was stirred at ambient temperature under hydrogen atmosphere for 17 hr, filtered, poured into saturated aqueous NaHCO$_3$. The aqueous layer was extracted with CHCl$_3$ (three times). The combined organic layer was dried over MgSO$_4$, filtered, concentrated, and purified by flash chromatography (NH-silica gel, 50% EtOAc in hexane) to give a colorless oil. To a solution of above oil in EtOAc (4 mL) was added 4 M hydrogen chloride in EtOAc (0.25 mL). The mixture was stirred at ambient temperature for 1 hr and concentrated. The residue was suspended with Et$_2$O (15 mL) and stirred at ambient tempareture for 1 hr. The solid was collected by filtration, washed with Et$_{2O}$, and dried under reduced pressure to give cis-$N^4$,$N^4$-dimethyl-$N^2$-{4-[2-(2-trifluoromethoxy-phenyl)-ethylamino]-cyclohexyl}-quinazoline-2,4-diamine dihydrochloride (104 mg, 48%) as a white solid.

ESI MS m/e 474, M (free)+H[+]; $^1$H NMR (300 MHz, CDCl$_3$) δ 12.62 (s, 1 H), 9.78 (brs, 2 H), 8.71 (brs, 1 H), 7.93 (d, J=8.4 Hz, 1 H), 7.39-7.77 (m, 3 H), 7.14-7.37 (m, 4 H), 4.33 (brs, 1 H), 3.15-3.71 (m, 11 H), 1.93-2.53 (m, 6 H), 1.62-1.89 (m, 2 H).

Example 67

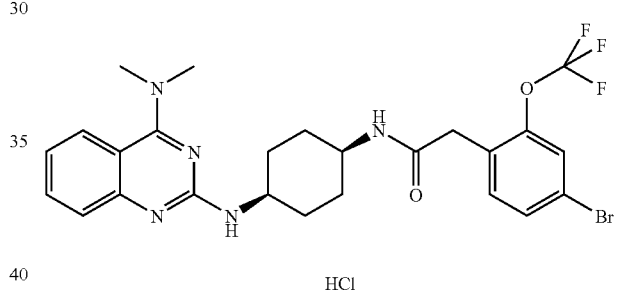

HCl cis-2-(4-Bromo-2-trifluoromethoxy-phenyl)-N-[4-(4-dimethylamino-quinazolin-2-ylamino)-cyclohexyl]-acetamide hydrochloride Step A: Synthesis of (4-bromo-2-trifluoromethoxy-phenyl)-acetic acid.

Using the procedure for the step B of example 13, the title compound was obtained ESI MS m/e 298, M[+]; $^1$H NMR (300 MHz, CDCl$_3$) δ 7.39-7.47 (m, 2 H), 7.22 (d, J=8.1 Hz, 1 H), 3.70 (s, 2 H).

Step B: Synthesis of cis-2-(4-bromo-2-trifluoromethoxy-phenyl)-N-[4-(4-dimethylamino-quinazolin-2-ylamino)-cyclohexyl]-acetamide hydrochloride.

Using the procedure for the step A of example 47, the title compound was obtained.

ESI MS m/e 566, M (free)+H[+]; $^1$H NMR (300 MHz, CDCl$_3$) δ 13.15 (s, 1 H), 8.91 (d, J=7.7 Hz, 1 H), 7.89 (d, J=8.4 Hz, 1 H), 7.61-7.70 (m, 1 H), 7.48-7.56 (m, 1 H), 7.39-7.45 (m, 1 H), 7.21-7.33 (m, 2 H), 6.02 (d, J=8.8 Hz, 1 H), 4.19-4.33 (m, 1 H), 3.82-4.03 (m, 1 H), 3.53 (s, 2 H), 3.51 (s, 6 H), 1.64-1.97 (m, 8 H).

Example 68

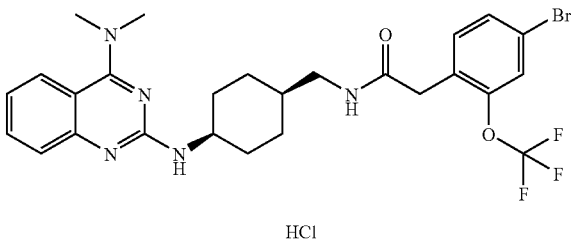

HCl cis-2-(4-Bromo-2-trifluoromethoxy-phenyl)-N-[4-(4-dimethylamino-quinazolin-2-ylamino)-cyclohexylmethyl]-acetamide hydrochloride Step A: Synthesis of cis-2-(4-bromo-2-trifluoromethoxy-phenyl)-N-[4-(4-dimethylamino-quinazolin-2-ylamino)-cyclohexylmethyl]-acetamide hydrochloride.

Using the procedure for the step A of example 47, the title compound was obtained.

ESI MS m/e 580, M (free)+H$^+$; $^1$H NMR (300 MHz, CDCl$_3$) δ 12.85 (brs, 1 H), 9.08 (d, J=8.4 Hz, 1 H), 7.90 (d, J=8.8 Hz, 1 H), 7.58-7.72 (m, 1 H), 7.19-7.54 (m, 5 H), 6.81-6.98 (m, 1 H), 4.28-4.51 (m, 1 H), 3.83 (s, 2 H), 3.51 (s, 6 H), 3.29-3.34 (m, 2 H), 1.42-2.03 (m, 9 H).

Example 69

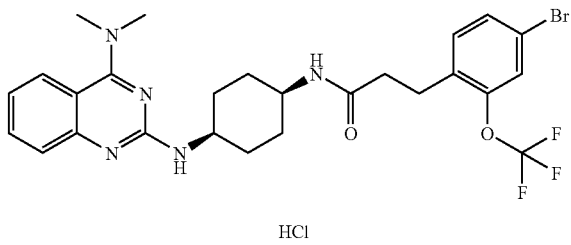

HCl cis-3-(4-Bromo-2-trifluoromethoxy-phenyl)-N-[4-(4-dimethylamino-quinazolin-2-ylamino)cyclohexyl]-propionamide hydrochloride Step A: Synthesis of 3-(4-bromo-2-trifluoromethoxy-phenyl)-propionic acid.

To a solution of 3-(4-bromo-2-trifluoromethoxy-phenyl)-propan-1-ol obtained in step B of example 62 (1 g, 3.34 mmol) in acetone (15 mL) was added Jones reagent (4 mL) at 4° C. The mixture was stirred at ambient temperature for 2 hr. The solution was poured into water (50 mL), and the aqueous layer was extracted with Et$_2$O (three times). The combined organic layer was dried over MgSO$_4$, filtered, concentrated, and purified by flash chromatography (silica gel, 25% EtOAc in hexane) to give 3-(4-Bromo-2-trifluoromethoxy-phenyl)-propionic acid (930 mg, 89%) as a colorless oil.

ESI MS m/e 313, M$^+$; $^1$H NMR (200 MHz, CDCl$_3$) δ 7.31-7.50 (m, 2 H), 7.10-7.29 (m, 1 H), 2.97 (t, J=7.7 Hz, 2 H), 2.65 (t, J=7.7 Hz, 2 H).

Step B: Synthesis of cis-3-(4-bromo-2-trifluoromethoxy-phenyl)-N-[4-(4-dimethylamino-quinazolin-2-ylamino)cyclohexyl]-propionamide hydrochloride.

Using the procedure for the step A of example 47, the title compound was obtained.

ESI MS m/e 580, M (free)+H$^+$; $^1$H NMR (300 MHz, CDCl$_3$) δ 13.12 (brs, 1 H), 8.92 (d, J=7.9 Hz, 1 H), 7.90 (d, J=8.3 Hz, 1 H), 7.47-7.73 (m, 2 H), 7.15-7.44 (m, 3 H), 5.92 (d, J=8.4 Hz, 1 H), 4.18-4.38 (m, 1 H), 3.76-4.03 (m, 1 H), 3.51 (s, 6 H), 2.98 (t, J=7.7 Hz, 2 H), 2.44 (t, J=7.7 Hz, 2 H), 1.55-1.96 (m, 9 H).

Example 70

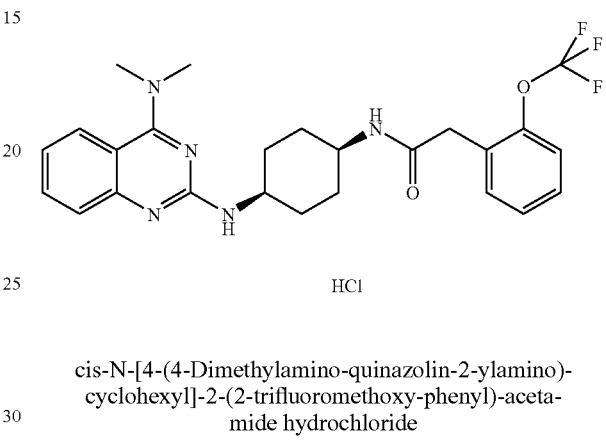

HCl cis-N-[4-(4-Dimethylamino-quinazolin-2-ylamino)-cyclohexyl]-2-(2-trifluoromethoxy-phenyl)-acetamide hydrochloride Step A: Synthesis of cis-N-[4-(4-dimethylamino-quinazolin-2-ylamino)-cyclohexyl]-2-(2-trifluoromethoxy-phenyl)-acetamide hydrochloride.

Using the procedure for the step A of example 47, the title compound was obtained.

ESI MS m/e 488, M (free)+H$^+$; $^1$H NMR (300 MHz, CDCl$_3$) δ 13.20 (s, 1 H), 8.84 (d, J=7.6 Hz, 1 H), 7.89 (d, J=8.7 Hz, 1 H), 7.60-7.70 (m, 1H), 7.49-7.56 (m, 1 H), 7.20-7.43 (m, 5 H), 5.98 (d, J=7.6 Hz, 1 H), 4.23 (brs, 1 H), 3.84-4.03 (m, 1 H), 3.59 (s, 2 H), 3.50 (s, 6 H), 1.62-1.98 (m, 8 H).

Example 71

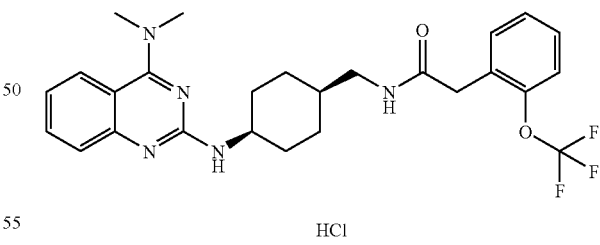

HCl cis-N-[4-(4-Dimethylamino-quinazolin-2-ylamino)-cyclohexylmethyl]-2-(2-trifluoromethoxy-phenyl)-acetamide hydrochloride Step A: Synthesis of cis-N-[4-(4-dimethylamino-quinazolin-2-ylamino)-cyclohexylmethyl]-2-(2-trifluoromethoxy-phenyl)-acetamide hydrochloride Using the procedure for the step A of example 47, the title compound was obtained.

ESI MS m/e 502, M (free)+H⁺; ¹H NMR (300 MHz, CDCl₃) δ 12.99 (s, 1 H), 8.99 (d, J=8.5 Hz, 1 H), 7.90 (d, J=8.2 Hz, 1 H), 7.63 (t, J=7.62 Hz, 1 H), 7.38-7.54 (m, 2 H), 7.16-7.34 (m, 4 H), 6.55 (brs, 1 H), 4.28-4.43 (m, 1 H), 3.81 (s, 2 H), 3.51 (s, 6 H), 3.27 (s, 2 H), 1.46-1.99 (m, 9 H).

Example 72

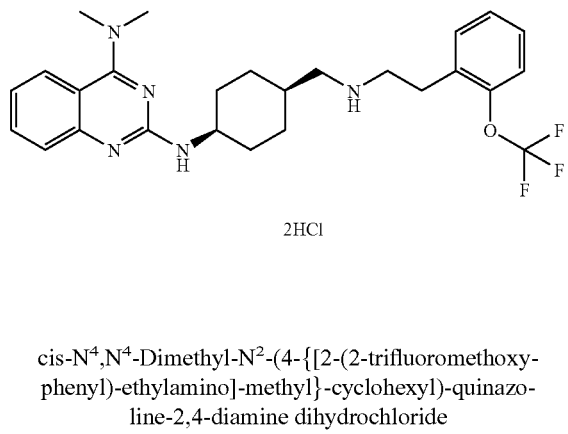

2HCl cis-N⁴,N⁴-Dimethyl-N²-(4-{[2-(2-trifluoromethoxy-phenyl)-ethylamino]-methyl}-cyclohexyl)-quinazoline-2,4-diamine dihydrochloride Step A: cis-N⁴,N⁴-dimethyl-N²-(4-{[2-(2-trifluoromethoxy-phenyl)-ethylamino]-methyl}-cyclohexyl)-quinazoline-2,4-diamine dihydrochloride To a solution of cis-N-[4-(4-dimethylamino-quinazolin-2-ylamino)-cyclohexylmethyl]-2-(2-trifluoromethoxy-phenyl)-acetamide (free) obtained in step A of example 71 (246 mg, 0.5 mmol) in THF (3.5 mL) was added 1 M borane-THF complex (2.45 mL, 2.45 mmol). The mixture was stirred at reflux for 2.5 h, and concentrated. To a solution of above residue in THF (3.5 mL) was added 1 M hydrochloric acid (4.41 mL, 4.41 mmol). The mixture was stirred at reflux for 1 hr, and cooled to ambient temperature. To the reaction mixture was added 2 M aqueous sodium hydroxide, and the aqueous layer was extracted with CHCl₃ (three times). The combined organic layer was dried over MgSO₄, filtered, concentrated, and purified by medium-pressure liquid chromatography (NH-silica gel, 50% EtOAc in hexane) to give a colorless oil. To a solution of above oil in EtOAc (4 mL) was added 4 M hydrogen chloride in EtOAc (0.25 mL). The mixture was stirred at ambient temperature for 1 hr and concentrated. A solution of the residue in Et₂O (15 mL) was stirred at ambient tempareture for 1 hr. The precipitate was collected by filtration, washed with Et₂O, and dried under reduced pressure to give cis-N⁴,N⁴-dimethyl-N²-{4-[2-(2-trifluoromethoxy-phenyl)-ethylamino]-cyclohexyl}-quinazoline-2,4-diamine dihydrochloride (81 mg, 30%) as a white solid.

FAB MS m/e 488, M+H⁺; ¹H NMR (300 MHz, CDCl₃) δ 12.56 (s, 1 H), 9.72 (brs, 1 H), 8.72 (d, J=7.7 Hz, 1 H), 7.90 (d, J=8.2 Hz, 1 H), 7.66 (t, J=7.7 Hz, 1 H), 7.42-7.54 (m, 2 H), 7.15-7.32 (m, 4 H), 4.22-4.35 (m, 1 H), 3.51 (s, 6 H), 3.38-3.59 (m, 2 H), 3.11-3.30 (m, 2 H), 2.92-3.07 (m, 2 H), 2.21 (brs, 1 H), 1.50-2.01 (m, 8 H).

Example 73

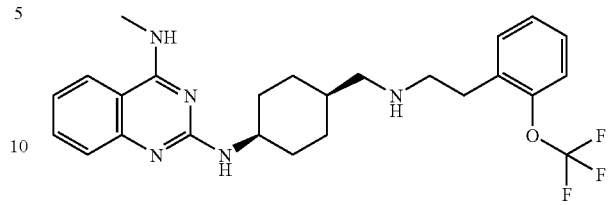

2HCl cis-N⁴-Methyl-N²-(4-{[2-(2-trifluoromethoxy-phenyl)-ethylamino]-methyl}-cyclohexyl)-quinazoline-2,4-diamine dihydrochloride Step A: Synthesis of cis-N⁴-methyl-N³-(4-{[2-(2-trifluoromethoxy-phenyl)-ethylamino]-methyl}-cyclohexyl)-quinazoline-2,4-diamine dihydrochloride.

Using the procedure for the step A of example 66, the title compound was obtained.

ESI MS m/e 474, M (free)+H⁺; ¹H NMR (200 MHz, CDCl₃) δ 11.72 (s, 1 H), 9.23-9.94 (m, 3 H), 8.00-8.66 (m, 2 H), 6.64-7.66 (m, 7 H), 4.26 (brs, 1 H), 2.73-3.65 (m, 9 H), 1.27-2.44 (m, 9 H).

Example 74

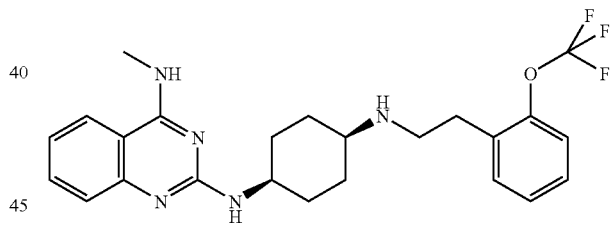

2HCl cis-A-Methyl-N²-{4-[2-(2-trifluoromethoxy-phenyl)-ethylamino]-cyclohexyl}-quinazoline-2,4-diamine dihydrochloride Step A: Synthesis of cis-N⁴-methyl-N²-{4-[2-(2-trifluoromethoxy-phenyl)-ethylamino]-cyclohexyl}-quinazoline-2,4-diamine dihydrochloride.

Using the procedure for the step A of example 66, the title compound was obtained.

ESI MS m/e 460, M (free)+H⁺; ¹H NMR (200 MHz, CDCl₃) δ 12.20 (brs, 1 H), 9.84 (brs, 3 H), 8.59-8.79 (m, 1 H), 7.79-8.02 (m, 1 H), 7.10-7.70 (m, 7 H), 3.95-4.26 (m, 1 H), 3.09-3.54 (m, 5 H), 2.82-3.03 (m, 3 H), 1.57-2.43 (m, 8 H).

Example 75

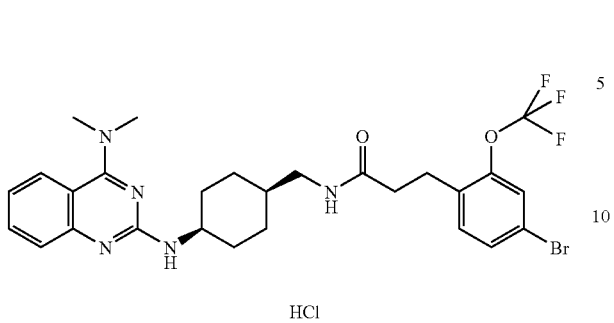

HCl cis-3-(4-Bromo-2-trifluoromethoxy-phenyl)-N-[4-(4-dimethylamino-quinazolin-2-ylamino)-cyclohexylmethyl]-propionamide hydrochloride Step A: Synthesis of cis-3-(4-bromo-2-trifluoromethoxy-phenyl)-N-[4-(4-dimethylamino-quinazolin-2-ylamino)-cyclohexylmethyl]-propionamide hydrochloride.

Using the procedure for the step A of example 47, the title compound was obtained.

ESI MS m/e 594, M (free)+; $^1$H NMR (300 MHz, CDCl$_3$) δ 12.72 (s, 1H), 9.01 (d, J=8.7 Hz, 1 H), 7.90 (d, J=8.2 Hz, 1 H), 7.65 (t, J=7.6 Hz, 1 H), 7.47 (d, J=7.6 Hz, 1 H), 7.21-7.41 (m, 3 H), 6.96 (brs, 1 H), 4.31-4.44 (m, 1 H), 3.51 (s, 6 H), 3.23-3.35 (m, 2 H), 3.03 (t, J=7.6 Hz, 2 H), 2.76 (t, J=7.6 Hz, 2 H), 1.38-1.98 (m, 9 H).

Example 76

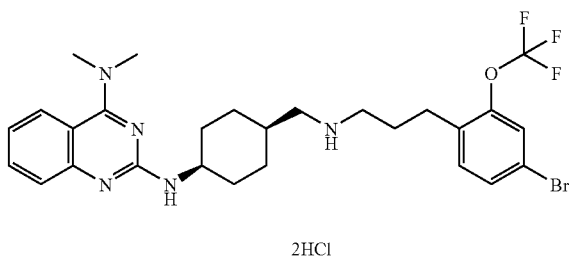

2HCl cis-N$^2$-(4-{[3-(4-Bromo-2-trifluoromethoxy-phenyl)-propylamino]-methyl}-cyclohexyl)-N$^4$,N$^4$-dimethyl-quinazoline-2,4-diamine dihydrochloride Step A: Synthesis of cis-N$^2$-(4-{[3-(4-bromo-2-trifluoromethoxy-phenyl)-propylamino]-methyl}-cyclohexyl)-N$^4$,N$^4$-dimethyl-quinazoline-2,4-diamine dihydrochloride.

Using the procedure for the step A of example 72, the title compound was obtained.

ESI MS m/e 580, M (free)+H+; $^1$H NMR (200 MHz, CDCl$_3$) δ 12.56 (s, 1 H), 9.40-9.71 (m, 2 H), 8.56-8.76 (m, 1 H), 7.91 (d, J=8.4 Hz, 1 H), 7.66 (t, J=7.6 Hz, 1 H), 7.13-7.47 (m, 5 H), 4.17-4.39 (m, 1 H), 3.51 (s, 6 H), 2.83-3.16 (m, 4 H), 2.67-2.82 (m, 2 H), 1.38-2.53 (m, 11 H).

Example 77

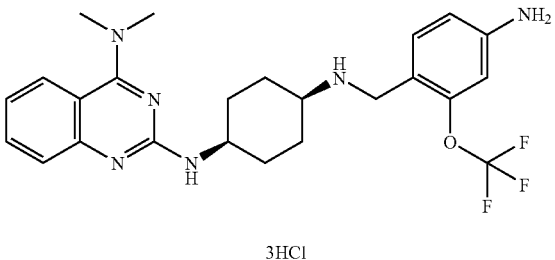

3HCl cis-N$^2$-[4-(4-Amino-2-trifluoromethoxy-benzylamino)-cyclohexyl]-N$^4$,N$^4$-dimethyl-quinazoline-2,4-diamine trihydrochloride Step A: Synthesis of cis-N$^2$-[4-(4-amino-2-trifluoromethoxy-benzylamino)-cyclohexyl]-N$^4$,N$^4$-dimethyl-quinazoline-2,4-diamine trihydrochloride.

To a solution of cis-N$^2$-[4-(4-bromo-2-trifluoromethoxy-benzylamino)-cyclohexyl]-N$^4$,N$^4$-dimethyl-quinazoline-2,4-diamine obtained in step A of example 28 (1.5 g, 2.79 mmol) in EtOH (25 mL) were added copper powder (443 mg, 6.93 mmol), CuCl (690 mg, 2.79 mmol), and 28% aqueous NH$_3$ (25 mL). The reaction mixture was stirred at reflux for 3.5 hr. The mixture was poured into water, and the aqueous layer was extracted with CHCl$_3$ (three times). The combined organic layer was dried over MgSO$_4$, filtered, concentrated, and purified by medium-pressure liquid chromatography (NH-silica gel, 50% EtOAc in hexane) to give a colorless oil. To a solution of above oil in EtOAc (4 mL) was added 4 M hydrogen chloride in EtOAc (0.25 mL). The mixture was stirred at ambient temperature for 1 hr and concentrated. A solution of the residue in Et$_2$O (15 mL) was stirred at ambient tempareture for 1 hr. The precipitate was collected by filtration, washed with Et$_2$O, and dried under reduced pressure to give cis-N$^2$-[4-(4-amino-2-trifluoromethoxy-benzylamino)-cyclohexyl]-N$^4$,N$^4$-dimethyl-quinazoline-2,4-diamine trihydrochloride (104 mg, 6%) as a white solid.

ESI MS m/e 475, M (free)+H+; $^1$H NMR (300 MHz, DMSO-d$_6$) δ 13.08 (brs, 1 H), 9.15 (brs, 2 H), 8.32-8.48 (m, 1 H), 8.19 (d, J=8.1 Hz, 1 H), 7.73-7.85 (m, 1 H), 7.46 (d, J=8.4 Hz, 1 H), 7.37 (t, J=7.4 Hz, 2 H), 6.56-6.71 (m, 2 H), 3.94-4.26 (m, 3 H), 3.49 (s, 6 H), 3.02-3.24 (m, 1 H), 1.59-2.09 (m, 8 H).

Example 78

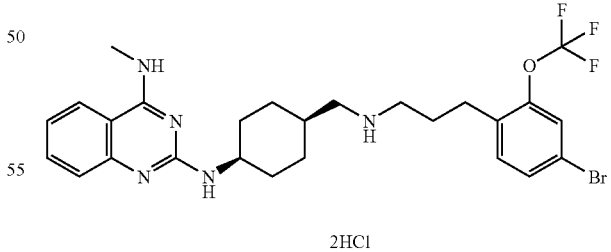

2HCl cis-N$^2$-(4-{[3-(4-Bromo-2-trifluoromethoxy-phenyl)-propylamino]-methyl}-cyclohexyl)-N$^4$-methyl-quinazoline-2,4-diamine dihydrochloride Step A: Synthesis of N$^2$-(4-aminomethyl-cyclohexyl)-N$^4$-methyl-quinazoline-2,4-diamine Using the procedure for the step A of example 64, the title compound was obtained.

ESI MS m/e 286, M+H⁺; ¹H NMR (300 MHz, CDCl₃) δ 7.35-7.59 (m, 3 H), 6.97-7.11 (m, 1 H), 5.59 (brs, 1 H), 5.00-5.18 (m, 1 H), 4.21-4.39 (m, 1 H), 3.13 (d, J=4.8 Hz, 3 H), 2.61 (d, J=6.2 Hz, 2 H), 1.57-1.99 (m, 5H), 1.04-1.52 (m, 4 H).

Step B: Synthesis of cis-N²-(4-{[3-(4-bromo-2-trifluoromethoxy-phenyl)-propylamino]-methyl}-cyclohexyl)-N⁴-methyl-quinazoline-2,4-diamine dihydrochloride.

Using the procedure for the step D of example 63, the title compound was obtained.

ESI MS m/e 566, M (free)+H⁺; ¹H NMR (300 MHz, CDCl₃) δ 11.63 (s, 1 H), 9.45 (brs, 3 H), 8.41 (d, J=8.5 Hz, 1 H), 8.32 (d, J=7.9 Hz, 1 H), 7.46 (t, J=7.54 Hz, 1 H), 7.24-7.39 (m, 3 H), 6.99-7.17 (m, 2 H), 4.13-4.35 (m, 1 H), 2.85-3.12 (m, 7 H), 2.75 (t, J=7.6 Hz, 2 H), 2.27-2.47 (m, 2 H), 1.97-2.18 (m, 1 H), 1.37-1.91 (m, 8 H).

Example 79

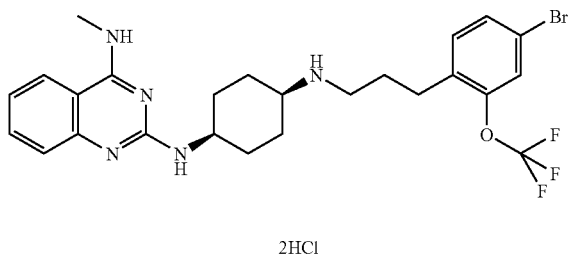

2HCl cis-N²-{4-[3-(4-Bromo-2-trifluoromethoxy-phenyl)-propylamino]-cyclohexyl}-N⁴-methyl-quinazoline-2,4-diamine dihydrochloride Step A: Synthesis of cis-N²-{4-[3-(4-bromo-2-trifluoromethoxy-phenyl)-propylamino]-cyclohexyl}-N⁴-methyl-quinazoline-2,4-diamine dihydrochloride To a suspension of cis-[4-(4-methylamino-quinazolin-2-ylamino)-cyclohexyl]-carbamic acid tert-butyl ester obtained in step B of example 50 (8.68 g, 23.4 mmol) in CHCl₃ (87 mL) was added 4 M hydrogen chloride in EtOAc (100 mL). The reaction mixture was stirred at ambient temperature for 2 hr, and concentrated. The residue was alkalized with saturated aqueous NaHCO₃ and the aqueous layer was extracted with CHCl₃ (three times). The combined organic layer was dried over MgSO₄, filtered, concentrated (10.57 g). To a suspension of the above residue (594 mg) in MeOH (6 mL) were added 3-(4-bromo-2-trifluoromethoxy-phenyl)-propionaldehyde obtained in step C of example 62 (650 mg, 2.19 mmol), AcOH (132 mg, 2.19 mmol), and NaBH₃CN (207 mg, 3.29 mmol). The reaction mixture was stirred at ambient temperature for 16 hr, poured into saturated aqueous NaHCO₃, and the aqueous layer was extracted with CHCl₃ (three times). The combined organic layer was dried over MgSO₄, filtered, concentrated, purified by medium-pressure liquid chromatography (NH-silica gel, 50% EtOAc in hexane and silica gel, 16% MeOH in CHCl₃) to give a yellow oil. To a solution of the residue in EtOAc (6 mL) was added 4 M hydrogen chloride in EtOAc (0.14 mL). The reaction mixture was stirred at ambient temperature for 30 min, and concentrated. A solution of the residue in Et₂O (10 mL) was stirred at ambient temperature for 1 hr and the precipitate was collected by filtration to give cis-N²-{4-[3-(4-bromo-2-trifluoromethoxy-phenyl)-propylamino]-cyclohexyl}-N⁴-methyl-quinazoline-2,4-diamine dihydrochloride (59 mg, 7%) as a white solid.

ESI MS m/e 552, M (free)+H⁺; ¹H NMR (300 MHz, CDCl₃) δ 12.37 (s, 1 H), 9.78 (brs, 1 H), 9.59 (brs, 2 H), 8.68 (d, J=8.2 Hz, 1 H), 7.55-7.67 (m, 2 H), 7.27-7.43 (m, 5 H), 3.78-3.96 (m, 1 H), 2.94-3.24 (m, 3 H), 2.50-2.89 (m, 5 H), 2.09-2.50 (m, 6 H), 1.60-1.98 (m, 4 H).

Example 80

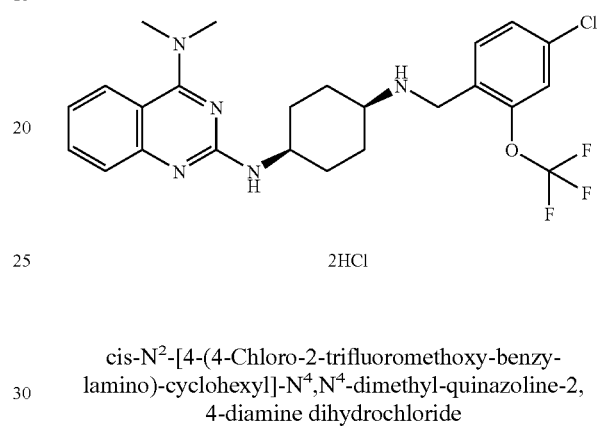

2HCl cis-N²-[4-(4-Chloro-2-trifluoromethoxy-benzylamino)-cyclohexyl]-N⁴,N⁴-dimethyl-quinazoline-2,4-diamine dihydrochloride Step A: Synthesis of cis-N²-[4-(4-chloro-2-trifluoromethoxy-benzylamino)-cyclohexyl]-N⁴,N⁴-dimethyl-quinazoline-2,4-diamine dihydrochloride.

A mixture of conc. HCl (420 μL) and NaNO₂ (44 mg, 0.64 mmol) were stirred at 70° C. for 10 min. To the reaction mixture was added a solution of cis-N²-[4-(4-amino-2-trifluoromethoxy-benzylamino)-cyclohexyl]-N⁴,N⁴-dimethyl-quinazoline-2,4-diamine (free) obtained in step A of example 77 in AcOH (15 mL), and stirred at ambient temperature for 10 min. To the reaction mixture was added a solution of CuCl (146 mg, 1.47 mmol) in conc. HCl (1 mL), and stirred at 80° C. for 6 hr. The reaction mixture was alkalized with saturated aqueous NaHCO₃, and the aqueous layer was extracted with CHCl₃ (three times). The combined organic layer was dried over MgSO₄, filtered, concentrated, purified by medium-pressure liquid chromatography (NH-silica gel, 50% EtOAc in hexane) to give a yellow oil. To a solution of above oil in EtOAc (2 mL) was added 4 M hydrogen chloride in EtOAc (10 mL). The mixture was stirred at ambient temperature for 1 hr and concentrated. A solution of the residue in Et₂O (20 mL) was stirred at ambient tempareture for 1 hr. The precipitate was collected by filtration, washed with Et₂O, and dried under reduced pressure to give cis-N²-[4-(4-chloro-2-trifluoromethoxy-benzylamino)-cyclohexyl]-N⁴,N⁴-dimethyl-quinazoline-2,4-diamine dihydrochloride (70 mg, 29%) as a white solid.

ESI MS m/e 494, M (free)+H⁺; ¹H NMR (300 MHz, CDCl₃) δ 12.66 (s, 1 H), 9.82-10.28 (m, 2 H), 8.78 (d, J=7.6 Hz, 1 H), 8.24 (d, J=8.3 Hz, 1 H), 7.92 (d, J=8.2 Hz, 1 H), 7.67 (t, J=7.6 Hz, 1 H), 7.47 (d, J=8.1 Hz, 1 H), 7.18-7.41 (m, 3 H), 4.20-4.44 (m, 3 H), 3.52 (s, 6 H), 3.23 (brs, 1 H), 2.02-2.65 (m, 6 H), 1.75 (t, J=12.8 Hz, 2 H).

Example 81

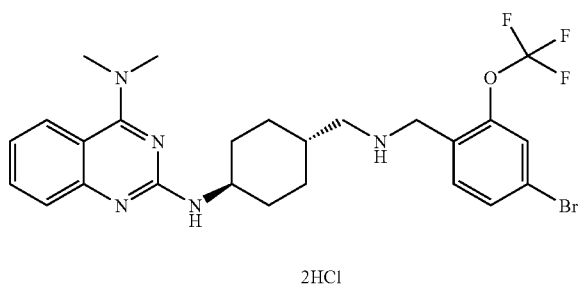

2HCl trans-$N^2$-{4-[(4-Bromo-2-trifluoromethoxy-benzylamino)-methyl]-cyclohexyl}-$N^4$,$N^4$-dimethyl-quinazoline-2,4-diamine dihydrochloride Step A: Synthesis of $N^2$-(4-aminomethyl-cyclohexyl)-$N^4$,$N^4$-dimethyl-quinazoline-2,4-diamine To a suspension of trans-[4-(4-dimethylamino-quinazolin-2-ylamino)-cyclohexylmethyl]-carbamic acid tert-butyl ester obtained in step B of example 6 (400 mg, 1.00 mmol) in EtOAc (10 mL) was added 4 M hydrogen chloride in EtOAc (5 mL). The mixture was stirred at ambient temperature for 80 min. The reaction mixture was alkalized with 2 M aqueous sodium hydroxide, and the aqueous layer was extracted with CHCl₃ (three times). The combined organic layer was dried over MgSO₄, filtered, concentrated, purified by medium-pressure liquid chromatography (NH-silica gel, 33% EtOAc in hexane to 3% MeOH in CHCl₃) to give $N^2$-(4-aminomethyl-cyclohexyl)-$N^4$,$N^4$-dimethyl-quinazoline-2,4-diamine (250 mg, 83%) as a pale yellow oil.

ESI MS m/e 300, M+H⁺; ¹H NMR (300 MHz, CDCl₃) δ 7.80 (d, J=9.3 Hz, 1 H), 7.38-7.53 (m, 2 H), 6.97-7.05 (m, 1 H), 4.77 (d, J=9.3 Hz, 1 H), 3.73-4.02 (m, 1 H), 3.26 (s, 6 H), 2.57 (d, J=6.2 Hz, 2 H), 2.13-2.31 (m, 2 H), 1.75-1.96 (m, 2 H), 0.92-1.45 (m, 7 H).

Step B: Synthesis of trans-$N^2$-{4-[(4-bromo-2-trifluoromethoxy-benzylamino)-methyl]-cyclohexyl}-$N^4$,$N^4$-dimethyl-quinazoline-2,4-diamine dihydrochloride Using the procedure for the step B of example 37, the title compound was obtained ESI MS m/e 552, M (free)+H⁺; ¹H NMR (300 MHz, CDCl₃) δ 12.72 (s, 1 H), 10.19 (brs, 2 H), 8.18 (d, J=8.9 Hz, 1 H), 8.06 (d, J=7.9 Hz, 1 H), 7.91 (d, J=8.3 Hz, 1 H), 7.42-7.65 (m, 3 H), 7.35 (d, J=8.3 Hz, 1 H), 7.23 (t, J=7.5 Hz, 1 H), 4.18-4.29 (m, 2 H), 3.69-3.89 (m, 1 H), 3.52 (s, 6 H), 2.64-2.81 (m, 2 H), 1.90-2.24 (m, 5 H), 1.02-1.56 (m, 4 H).

Example 82

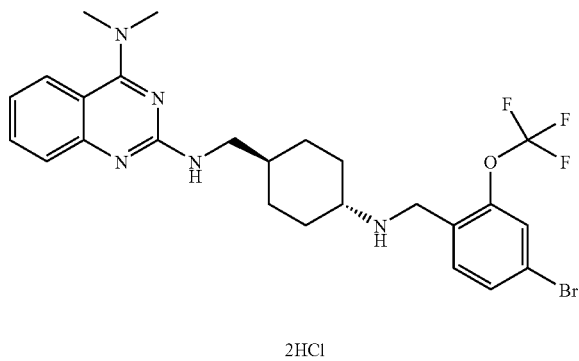

2HCl trans-$N^2$-[4-(4-Bromo-2-trifluoromethoxy-benzylamino)-cyclohexylmethyl]-$N^4$,$N^4$-dimethyl-quinazoline-2,4-diamine dihydrochloride Step A: Synthesis of trans-$N^2$-(4-amino-cyclohexylmethyl)-$N^4$,$N^4$-dimethyl-quinazoline-2,4-diamine.

To a solution of trans-{4-[(4-dimethylamino-quinazolin-2-ylamino)-methyl]-cyclohexyl}-carbamic acid benzyl ester obtained in step C of example 3 (330 mg, 0.76 mmol) in MeOH (3.3 mL) was added 10% Pd/C (33 mg). The mixture was stirred at ambient temperature under hydrogen atmosphere for 25 hr, filtered, concentrated, and purified by flash chromatography (NH-silica gel, 50% EtOAc in hexane) to give trans-$N^2$-(4-amino-cyclohexylmethyl)-$N^4$,$N^4$-dimethyl-quinazoline-2,4-diamine (250 mg, 98%) as a pale yellow oil.

ESI MS m/e 300, M+H⁺; ¹H NMR (300 MHz, CDCl₃) δ 7.80 (d, J=8.1 Hz, 1 H), 7.40-7.55 (m, 2 H), 6.95-7.07 (m, 1 H), 4.86-5.02 (m, 1 H), 3.36 (t, J=6.3 Hz, 2 H), 3.26 (s, 6 H), 2.53-2.70 (m, 1 H), 1.77-1.98 (m, 4 H), 0.93-1.64 (m, 7 H).

Step B: Synthesis of trans-$N^2$-[4-(4-bromo-2-trifluoromethoxy-benzylamino)-cyclohexylmethyl]-$N^4$,$N^4$-dimethyl-quinazoline-2,4-diamine dihydrochloride Using the procedure for the step B of example 37, the title compound was obtained.

ESI MS m/e 552, M (free)⁺; ¹H NMR (300 MHz, CDCl₃) δ 13.21 (s, 1 H), 10.03 (brs, 2 H), 8.34-8.47 (m, 1 H), 8.07 (d, J=8.4 Hz, 1 H), 7.91 (d, J=8.4 Hz, 1 H), 7.38-7.71 (m, 4 H), 7.20-7.34 (m, 1 H), 4.03-4.20 (m, 2 H), 3.51 (s, 6 H), 3.28-3.42 (m, 2 H), 2.65-2.92 (m, 1 H), 2.16-2.35 (m, 2 H), 1.86-2.05 (m, 2 H), 1.56-1.83 (m, 3 H), 0.89-1.16 (m, 2 H).

Example 83

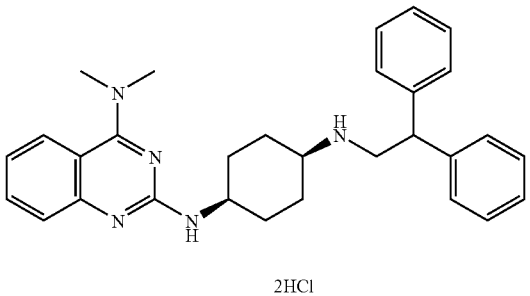

2HCl cis-$N^2$-[4-(2,2-Diphenyl-ethylamino)-cyclohexyl]-$N^4$,$N^4$-dimethyl-quinazoline-2,4-diamine dihydrochloride Step A: Synthesis of cis-$N^2$-[4-(2,2-diphenyl-ethylamino)-cyclohexyl]-$N^4$,$N^4$-dimethyl-quinazoline-2,4-diamine dihydrochloride Using the procedure for the step B of example 37, the title compound was obtained.

ESI MS m/e 466, M (free)+H⁺; ¹H NMR (300 MHz, CDCl₃) δ 12.60 (brs, 1 H), 8.76-9.28 (m, 3 H), 7.91 (d, J=8.3 Hz, 1 H), 7.59-7.71 (m, 2 H), 7.14-7.51 (m, 10 H), 5.00 (t, J=7.7 Hz, 1 H), 4.30-4.40 (m, 1 H), 3.72 (d, J=7.4 Hz, 2 H), 3.51 (s, 6 H), 3.19-3.43 (m, 1 H), 1.85-2.31 (m, 6 H), 1.52-1.76 (s, 2 H).

Example 84

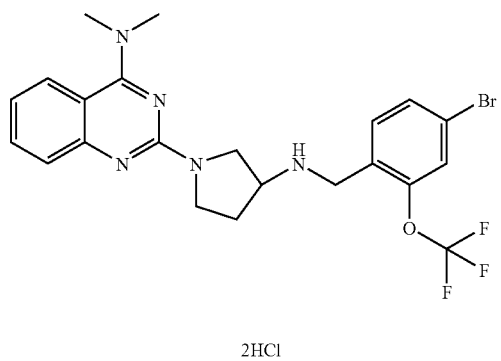

2HCl

{2-[3-(4-Bromo-2-trifluoromethoxy-benzylamino)-pyrrolidin-1-yl]-quinazolin-4-yl}-dimethyl-amine dihydrochloride Step A: Synthesis of [2-(3-amino-pyrrolidin-1-yl)-quinazolin-4-yl]-dimethyl-amine.

Using the procedure for the step A of example 81, the title compound was obtained ESI MS m/e 258, M+H$^+$; $^1$H NMR (300 MHz, CDCl$_3$) δ 7.80 (d, J=8.2 Hz, 1 H), 7.41-7.57 (m, 2 H), 6.93-7.06 (m, 1 H), 3.61-4.02 (m, 4 H), 3.40 (dd, J=11.0, 4.97 Hz, 1 H), 3.26 (s, 6 H), 2.09-2.30 (m, 1 H), 1.68-1.87 (m, 1 H), 1.22-1.63 (m, 2 H).

Step B: Synthesis of {2-[3-(4-bromo-2-trifluoromethoxy-benzylamino)-pyrrolidin-1-yl]-quinazolin-4-yl}-dimethyl-amine dihydrochloride Using the procedure for the step B of example 37, the title compound was obtained.

ESI MS m/e 510, M (free)+H$^+$; $^1$H NMR (300 MHz, CDCl$_3$) δ 8.05-8.61 (m, 2 H), 7.61-7.96 (m, 2 H), 7.33-7.57 (m, 2 H), 7.17-7.31 (m, 1 H), 4.42-4.64 (m, 2 H), 4.34 (s, 2 H), 3.58-4.24 (m, 3 H), 3.46 (s, 6 H), 2.81 (brs, 1 H), 2.31-2.60 (m, 1 H).

Example 85

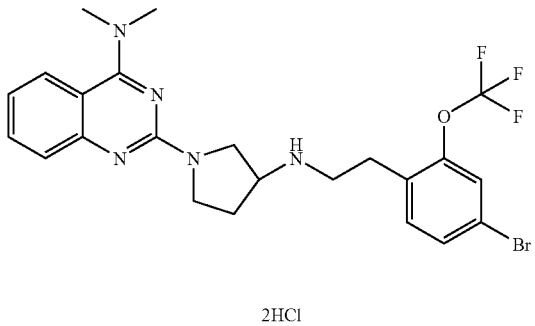

2HCl (2-{3-[2-(4-Bromo-2-trifluoromethoxy-phenyl)-ethylamino]-pyrrolidin-1-yl}-quinazolin-4-yl)-dimethyl-amine dihydrochloride Step A: Synthesis of (2-{3-[2-(4-bromo-2-trifluoromethoxy-phenyl)-ethylamino]-pyrrolidin-1-yl}-quinazolin-4-yl)-dimethyl-amine dihydrochloride Using the procedure for the step B of example 37, the title compound was obtained.

ESI MS m/e 524, M (free)$^+$; $^1$H NMR (300 MHz, CDCl$_3$) δ 8.15-8.53 (m, 1 H), 7.70-7.93 (m, 1 H), 7.62 (t, J=7.6 Hz, 1 H), 7.11-7.46 (m, 4 H), 3.60-4.70 (m, 5 H), 3.45 (s, 6 H), 3.04-3.59 (m, 4 H), 2.29-2.98 (m, 2 H).

Example 86

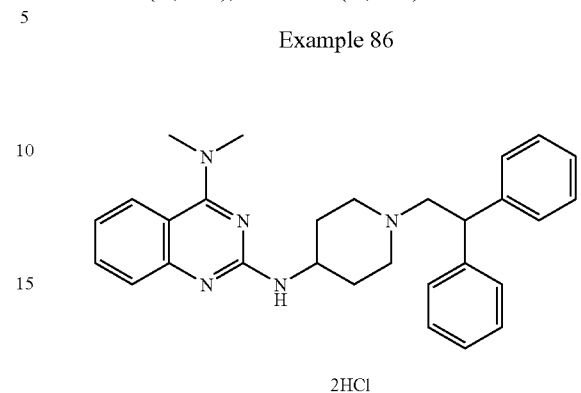

2HCl

N$^2$-[1-(2,2-Diphenyl-ethyl)-piperidin-4-yl]-N$^4$,N$^4$-dimethyl-quinazoline-2,4-diamine dihydrochloride Step A: Synthesis of N$^2$-[1-(2,2-diphenyl-ethyl)-piperidin-4-yl]-N$^4$,N$^4$-dimethyl-quinazoline-2,4-diamine dihydrochloride Using the procedure for the step B of example 37, the title compound was obtained ESI MS m/e 452, M (free)+H$^+$; $^1$H NMR (300 MHz, CDCl$_3$) δ 12.54 (brs, 1 H), 12.42 (s, 1 H), 9.82 (d, J=8.4 Hz, 1 H), 7.92 (d, J=8.1 Hz, 1 H), 7.66-7.74 (m, 1 H); 7.40-7.54 (m, 5 H), 7.27-7.39 (m, 5 H), 7.14-7.26 (m, 2 H), 5.17 (t, J=6.3 Hz, 1 H), 4.39-4.56 (m, 1 H), 3.70-3.87 (m, 2 H), 3.34-3.60 (m, 7 H), 3.07-3.25 (m, 2 H), 2.55-2.87 (m, 2 H), 1.61-1.94 (m, 4 H).

Example 87

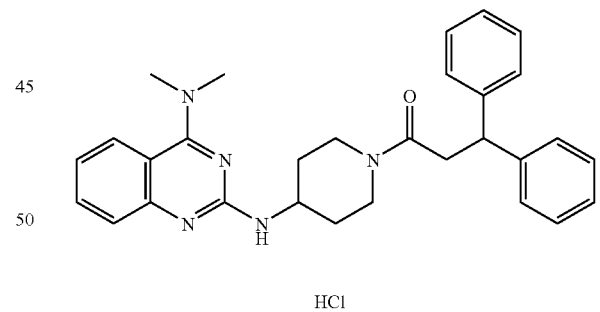

HCl

1-[4-(4-Dimethylamino-quinazolin-2-ylamino)-piperidin-1-yl]-3,3-diphenyl-propan-1-one hydrochloride Step A: Synthesis of 1-[4-(4-dimethylamino-quinazolin-2-ylamino)-piperidin-1-yl]-3,3-diphenyl-propan-1-one hydrochloride Using the procedure for the step A of example 47, the title compound was obtained.

ESI MS m/e 502, M+Na$^+$; $^1$H NMR (300 MHz, CDCl$_3$) δ 13.45 (brs, 1 H), 8.73 (d, J=6.9 Hz, 1 H), 7.89 (d, J=8.2 Hz, 1

H), 7.61-7.70 (m, 1 H), 7.56 (d, J=7.6 Hz, 1 H), 7.25-7.39 (m, 11 H), 4.67 (t, J=7.5 Hz, 1 H), 3.97-4.14 (m, 2 H), 3.70-3.89 (m, 1 H), 3.50 (s, 6 H), 3.13-3.30 (m, 2 H), 2.99-3.12 (m, 2 H), 1.31-1.99 (m, 4 H).

Example 88

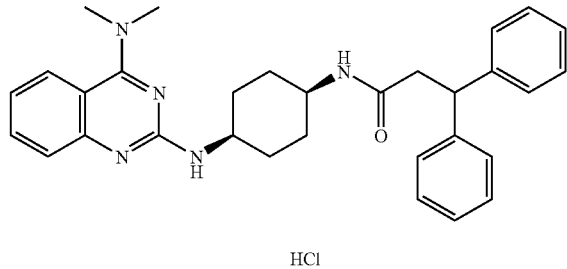

HCl cis-N-[4-(4-Dimethylamino-quinazolin-2-ylamino)-cyclohexyl]-3,3-diphenyl-propionamide hydrochloride Step A: Synthesis of cis-N-[4-(4-dimethylamino-quinazolin-2-ylamino)-cyclohexyl]-3,3-diphenyl-propionamide hydrochloride Using the procedure for the step A of example 47, the title compound was obtained.

ESI MS m/e 494, M (free)+H$^+$; $^1$H NMR (300 MHz, CDCl$_3$) δ 13.20 (s, 1 H), 8.77 (d, J=8.2 Hz, 1 H), 7.88 (d, J=7.7 Hz, 1 H), 7.60-7.69 (m, 1 H), 7.53 (d, J=17.1 Hz, 1 H), 7.12-7.33 (m, 11 H), 5.72 (d, J=9.2 Hz, 1 H), 4.57 (t, J=8.0 Hz, 1 H), 4.11-4.23 (m, 1 H), 3.72-3.87 (m, 1 H), 3.49 (s, 6 H), 2.88 (d, J=7.9 Hz, 2 H), 1.47-1.85 (m, 8 H).

Example 89

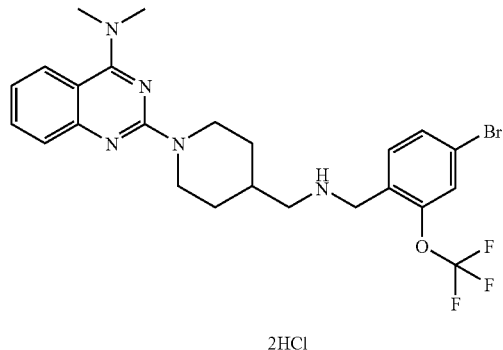

2HCl (2-{4-[(4-Bromo-2-trifluoromethoxy-benzylamino)-methyl]-piperidin-1-yl}-quinazolin-4-yl)-dimethyl-amine dihydrochloride Step A: Synthesis of [2-(4-aminomethyl-piperidin-1-yl)-quinazolin-4-yl]-dimethyl-amine Using the procedure for the step A of example 64, the title compound was obtained.

ESI MS m/e 286, M+H$^+$; $^1$H NMR (300 MHz, CDCl$_3$) δ 7.79 (d, J=8.3 Hz, 1 H), 7.42-7.52 (m, 1 H), 7.23-7.36 (m, 1 H), 6.94-7.07 (m, 1 H), 4.94 (d, J=12.7 Hz, 2 H), 3.26 (s, 6 H), 2.74-3.01 (m, 2 H), 2.61 (d, J=6.6 Hz, 2 H), 1.46-1.99 (m, 4 H), 1.01-1.39 (m, 3 H).

Step B: Synthesis of (2-{4-[(4-bromo-2-trifluoromethoxy-benzylamino)-methyl]-piperidin-1-yl}-quinazolin-4-yl)-dimethyl-amine dihydrochloride Using the procedure for the step B of example 37, the title compound was obtained.

ESI MS m/e 538, M (free)+H$^+$; $^1$H NMR (300 MHz, CDCl$_3$) δ 12.66 (s, 1 H), 8.50 (d, J=8.1 Hz, 1 H), 8.23 (d, J=8.6 Hz, 1 H), 7.88 (d, J=8.4 Hz, 1 H), 7.66 (t, J=7.9 Hz, 1 H), 7.50 (dd, J=8.4, 1.9 Hz, 1 H), 7.36-7.41 (m, 1 H), 7.24-7.34 (m, 1 H), 5.01 (brs, 2 H), 4.27 (s, 2 H), 3.49 (s, 6 H), 3.05-3.37 (m, 2 H), 2.44-2.92 (m, 3 H), 1.82-2.37 (m, 2 H), 1.14-1.62 (m, 2 H).

Example 90

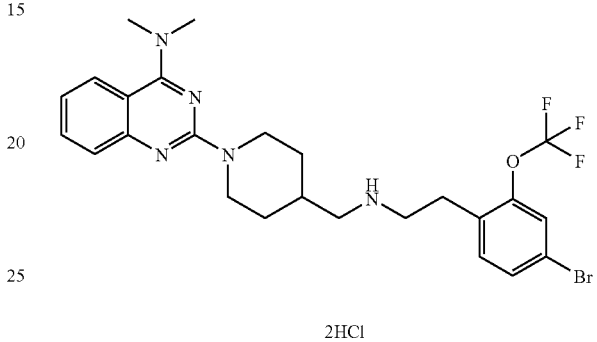

2HCl

[2-(4-{[2-(4-Bromo-2-trifluoromethoxy-phenyl)-ethylamino]-methyl}-piperidin-1-yl)-quinazolin-4-yl]-dimethyl-amine dihydrochloride Step A: Synthesis of [2-(4-{[2-(4-bromo-2-trifluoromethoxy-phenyl)-ethylamino]-methyl}-piperidin-1-yl)-quinazolin-4-yl]-dimethyl-amine dihydrochloride.

Using the procedure for the step B of example 37, the title compound was obtained.

ESI MS m/e 552, M (free)+H; $^1$H NMR (300 MHz, CDCl$_3$) δ 12.63 (s, 1 H), 8.48 (d, J=8.2 Hz, 1 H), 7.79-7.97 (d, J=7.5 Hz, 1 H), 7.58-7.73 (m, 1 H), 7.19-7.48 (m, 4 H), 5.02 (brs, 2 H), 3.49 (s, 6 H), 2.82-3.69 (m, 6 H), 1.98-2.79 (m, 5 H), 1.52 (brs, 2 H).

Example 91

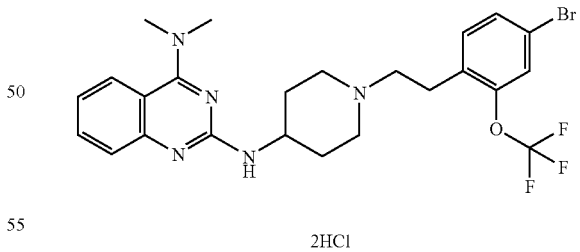

2HCl

N$^2$-{1-[2-(4-Bromo-2-trifluoromethoxy-phenyl)-ethyl]-piperidin-4-yl}-N$^4$,N$^4$-dimethyl-quinazoline-2,4-diamine dihydrochloride Step A: Synthesis of N$^2$-{1-[2-(4-bromo-2-trifluoromethoxy-phenyl)-ethyl]-piperidin-4-yl}-N$^4$,N$^4$-dimethyl-quinazoline-2,4-diamine dihydrochloride.

Using the procedure for the step B of example 37, the title compound was obtained.

ESI MS m/e 538, M (free)+H⁺; ¹H NMR (300 MHz, CDCl₃) δ 12.61 (brs, 1 H), 12.43 (s, 1 H), 9.97 (d, J=8.1 Hz, 1 H), 7.94 (d, J=7.9 Hz, 1 H), 7.65-7.76 (m, 1 H), 7.28-7.52 (m, 5 H), 4.48-4.62 (m, 1 H), 3.12-3.73 (m, 14 H), 2.68-2.92 (m, 2 H), 1.96-2.13 (m, 2 H).

Example 92

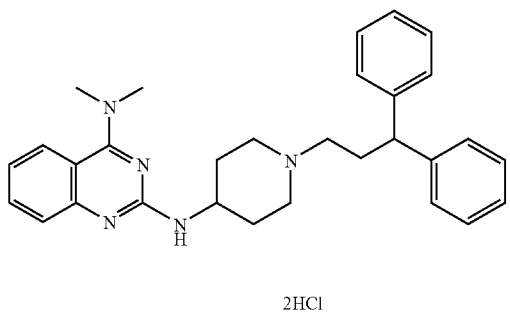

2HCl $N^2$-[1-(3,3-Diphenyl-propyl)-piperidin-4-yl]-$N^4$,$N^4$-dimethyl-quinazoline-2,4-diamine dihydrochloride Step A: Synthesis of $N^2$-[1-(3,3-diphenyl-propyl)-piperidin-4-yl]-$N^4$,$N^4$-dimethyl-quinazoline-2,4-diamine dihydrochloride.

Using the procedure for the step A of example 72, the title compound was obtained.

ESI MS m/e 466, M (free)+H⁺; ¹H NMR (300 MHz, CDCl₃) δ 12.42 (s, 1 H), 12.26 (brs, 1 H), 9.87 (d, J=8.2 Hz, 1 H), 7.93 (d, J=8.2 Hz, 1 H), 7.65-7.74 (m, 1 H), 7.47 (d, J=8.2 Hz, 1 H), 7.13-7.37 (m, 11 H), 4.44-4.60 (m, 1 H), 3.98 (t, J=7.9 Hz, 1 H), 3.28-3.65 (m, 10 H), 2.93-3.09 (m, 2 H), 2.63-2.88 (m, 4 H), 1.84-2.02 (m, 2 H).

Example 93

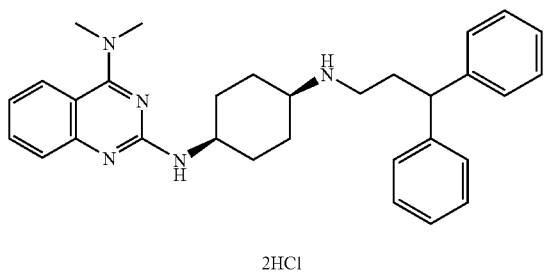

2HCl cis-$N^2$-[4-(3,3-Diphenyl-propylamino)-cyclohexyl]-$N^4$,$N^4$-dimethyl-quinazoline-2,4-diamine dihydrochloride Step A: Synthesis of cis-$N^2$-[4-(3,3-diphenyl-propylamino)-cyclohexyl]-$N^4$,$N^4$-dimethyl-quinazoline-2,4-diamine dihydrochloride.

Using the procedure for the step A of example 72, the title compound was obtained.

ESI MS m/e 480, M (free)+H⁺; ¹H NMR (300 MHz, CDCl₃) δ 12.58 (s, 1 H), 9.53 (s, 2H), 8.58 (d, J=7.9 Hz, 1 H), 7.91 (d, J=8.1 Hz, 1 H), 7.64 (t, J=7.7 Hz, 1 H), 7.48 (d, J=7.9 Hz, 1 H), 7.08-7.33 (m, 11 H), 4.18-4.33 (m, 1 H), 4.11 (t, J=7.7 Hz, 1 H), 3.50 (s, 6 H), 3.16 (brs, 1 H), 2.96 (brs, 2 H), 2.64-2.84 (m, 2 H), 1.87-2.25 (m, 6 H), 1.53-1.75 (m, 2 H).

Example 94

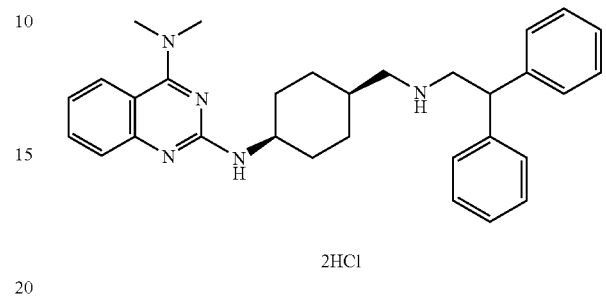

2HCl cis-$N^2$-{4-[(2,2-Diphenyl-ethylamino)-methyl]-cyclohexyl}-$N^4$,$N^4$-dimethyl-quinazoline-2,4-diamine dihydrochloride Step A: Synthesis of cis-$N^2$-{4-[(2,2-diphenyl-ethylamino)-methyl]-cyclohexyl}-$N^4$,$N^4$-dimethyl-quinazoline-2,4-diamine dihydrochloride Using the procedure for the step B of example 37, the title compound was obtained.

ESI MS m/e 480, M (free)+H⁺; ¹H NMR (300 MHz, CDCl₃) δ 12.78 (s, 1 H), 8.94 (brs, 2 H), 8.80 (d, J=8.4 Hz, 1 H), 7.89 (d, J=8.1 Hz, 1 H), 7.60-7.69 (m, 1 H), 7.44-7.58 (m, 2 H), 7.18-7.42 (m, 9 H), 4.91 (t, J=8.0 Hz, 1 H), 4.19-4.34 (m, 1 H), 3.61-3.76 (m, 2 H), 3.50 (s, 6 H), 2.81-2.97 (m, 2 H), 2.04-2.19 (m, 1 H), 1.74-1.91 (m, 2 H), 1.45-1.69 (m, 6 H).

Example 95

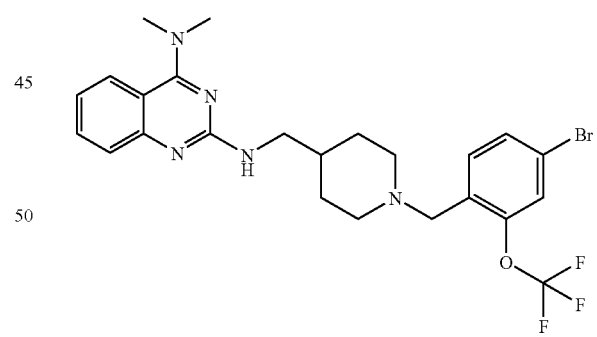

2HCl $N^2$-[1-(4-Bromo-2-trifluoromethoxy-benzyl)-piperidin-4-ylmethyl]-$N^4$,$N^4$-dimethyl-quinazoline-2,4-diamine dihydrochloride Step A: Synthesis of $N^4$,$N^4$-dimethyl-$N^2$-piperidin-4-ylmethyl-quinazoline-2,4-diamine.

Using the procedure for the step A of example 81, the title compound was obtained.

ESI MS m/e 408, M+Na⁺; ¹H NMR (300 MHz, CDCl₃) δ 7.82 (d, J=8.3 Hz, 1 H), 7.39-7.59 (m, 2 H), 6.96-7.12 (m, 1 H), 4.79-5.11 (m, 1 H), 3.94-4.31 (m, 2 H), 3.42 (t, J=5.9 Hz, 2 H), 3.27 (s, 6 H), 2.70 (t, J=12.1 Hz, 2 H), 1.63-1.92 (m, 3 H), 1.46 (s, 9 H), 0.99-1.37 (m, 2 H).

Step B: Synthesis of N²-[1-(4-bromo-2-trifluoromethoxy-benzyl)-piperidin-4-ylmethyl]-N⁴,N⁴-dimethyl-quinazoline-2,4-diamine dihydrochloride.

Using the procedure for the step B of example 37, the title compound was obtained.

ESI MS m/e 538, M (free)+H⁺; ¹H NMR (300 MHz, CDCl₃) δ 13.13 (s, 1 H), 12.69 (brs, 1 H), 8.73 (t, J=6.3 Hz, 1 H), 8.19 (d, J=8.2 Hz, 1 H), 7.90 (d, J=7.6 Hz, 1 H), 7.45-7.73 (m, 4 H), 7.22-7.33 (m, 1 H), 4.10-4.24 (m, 2 H), 3.36-3.67 (m, 10 H), 2.61-2.86 (m, 2 H), 1.80-2.33 (m, 5 H).

Example 96

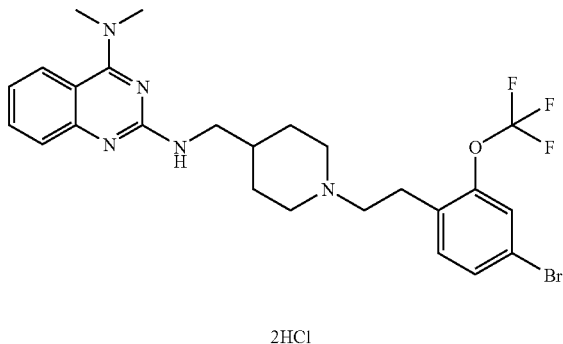

2HCl

N²-{1-[2-(4-Bromo-2-trifluoromethoxy-phenyl)-ethyl]-piperidin-4-ylmethyl}-N⁴,N⁴-dimethyl-quinazoline-2,4-diamine dihydrochloride Step A: Synthesis of N²-{1-[2-(4-bromo-2-trifluoromethoxy-phenyl)-ethyl]-piperidin-4-ylmethyl}-N⁴,N⁴-dimethyl-quinazoline-2,4-diamine dihydrochloride Using the procedure for the step B of example 37, the title compound was obtained.

ESI MS m/e 552, M (free)+H⁺; ¹H NMR (300 MHz, CDCl₃) δ 13.16 (brs, 1 H), 8.74 (m, 1 H), 7.92 (d, J=8.2 Hz, 1 H), 7.67 (t, J=7.5 Hz, 1 H), 7.53 (d, J=7.6 Hz, 1 H), 7.22-7.46 (m, 5 H), 3.44-3.71 (m, 10 H), 3.26-3.39 (m, 2 H), 3.01-3.15 (m, 2 H), 2.63-2.86 (m, 2 H), 1.87-2.33 (m, 5 H).

Example 97

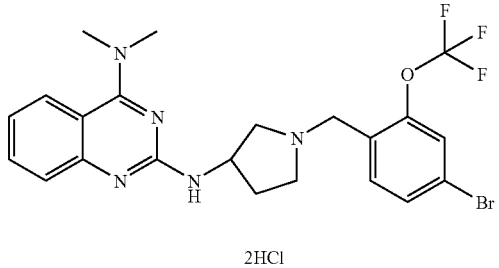

2HCl

N²-[1-(4-Bromo-2-trifluoromethoxy-benzyl)-pyrrolidin-3-yl]-N⁴,N⁴-dimethyl-quinazoline-2,4-diamine dihydrochloride Step A: Synthesis of N²-(1-benzyl-pyrrolidin-3-yl)-N⁴,N⁴-dimethyl-quinazoline-2,4-diamine.

A mixture of (2-chloro-quinazolin-4-yl)-dimethyl-amine obtained in step B of example 1 (5.1 g, 28.9 mmol) and 1-benzyl-pyrrolidin-3-ylamine (5.1 g, 28.9 mmol) in BuOH (8 mL) was stirred at reflux for 26 hr, poured into saturated aqueous NaHCO₃, and the aqueous layer was extracted with CHCl₃ (three times). The combined organic layer was dried over MgSO₄, filtered, concentrated, and purified by flash chromatography (NH-silica gel, 10% to 16% EtOAc in hexane) to give N²-(1-benzyl-pyrrolidin-3-yl)-N⁴,N⁴-dimethyl-quinazoline-2,4-diamine (3.37 g, 50%) as a pale yellow solid.

ESI MS m/e 348, M+H⁺; ¹H NMR (300 MHz, CDCl₃) δ 7.80 (d, J=9.0 Hz, 1 H), 7.46 (m, 2 H), 7.18-7.38 (m, 5 H), 7.02 (ddd, J=8.3, 6.3, 1.9 Hz, 1 H), 5.30 (brs, 1 H), 4.59-4.75 (m, 1 H), 3.63 (d, J=2.5 Hz, 2 H), 3.25 (s, 6 H), 2.88 (dd, J=9.6, 6.6 Hz, 1 H), 2.70-2.81 (m, 2 H), 2.28-2.60 (m, 3 H), 1.64-1.78 (m, 1 H).

Step B: Synthesis of N⁴,N⁴-dimethyl-N²-pyrrolidin-3-yl-quinazoline-2,4-diamine.

To a solution of N²-(1-benzyl-pyrrolidin-3-yl)-N⁴,N⁴-dimethyl-quinazoline-2,4-diamine (3.3 g, 9.5 mmol) in MeOH (33 mL) was added Pd(OH)₂ (660 mg). The mixture was stirred at ambient temperature under hydrogen atmosphere for 13 hr, and stirred at 50° C. for 6 hr. The mixture was filtered, concentrated, and purified by medium-pressure liquid chromatography (NH-silica gel, 1% to 3% MeOH in CHCl₃) to give N⁴,N⁴-dimethyl-N²-pyrrolidin-3-yl-quinazoline-2,4-diamine (2.3 g, 93%) as a yellow oil.

ESI MS m/e 258, M+H⁺; ¹H NMR (300 MHz, CDCl₃) δ 7.82 (d, J=7.8 Hz, 1 H), 7.42-7.54 (m, 2 H), 7.03 (ddd, J=8.3, 6.4, 1.8 Hz, 1 H), 5.03 (brs, 1 H), 4.52 (brs, 1 H), 3.26 (s, 6 H), 2.83-3.24 (m, 4 H), 1.97-2.30 (m, 2 H), 1.57-1.77 (m, 1 H).

Step C: Synthesis of N²-[1-(4-bromo-2-trifluoromethoxy-benzyl)-pyrrolidin-3-yl]-N⁴,N⁴-dimethyl-quinazoline-2,4-diamine dihydrochloride Using the procedure for the step B of example 37, the title compound was obtained.

ESI MS m/e 510, M (free)+H⁺; ¹H NMR (300 MHz, CDCl₃) δ 13.22 (brs, 1 H), 12.87 (s, 1 H), 9.68 (d, J=7.4 Hz, 1 H), 8.11 (d, J=8.4 Hz, 1 H), 7.95 (d, J=8.4 Hz, 1 H), 7.71 (t, J=8.3 Hz, 1 H), 7.43-7.63 (m, 3 H), 7.28-7.38 (m, 1 H), 4.94-5.15 (m, 1 H), 4.41 (s, 2 H), 4.00-4.17 (m, 1 H), 3.26-3.82 (m, 8 H), 3.00-3.16 (m, 1 H), 2.59-2.82 (m, 1 H), 2.18-2.37 (m, 1 H).

Example 98

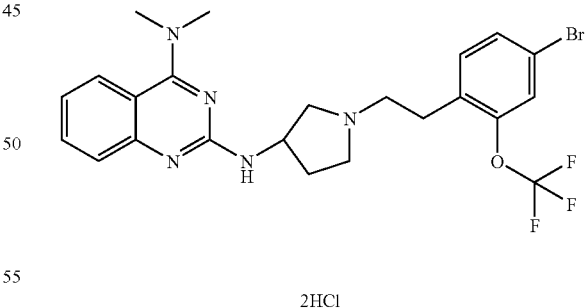

2HCl

N²-{1-[2-(4-Bromo-2-trifluoromethoxy-phenyl)-ethyl]-pyrrolidin-3-yl}-N⁴,N⁴-dimethyl-quinazoline-2,4-diamine dihydrochloride Step A: Synthesis of N²-{1-[2-(4-bromo-2-trifluoromethoxy-phenyl)-ethyl]-pyrrolidin-3-yl}-N⁴,N⁴-dimethyl-quinazoline-2,4-diamine dihydrochloride.

Using the procedure for the step B of example 37, the title compound was obtained.

ESI MS m/e 524, M (free)+H+; 1H NMR (300 MHz, CDCl3) δ 9.61-9.78 (m, 1 H), 7.96 (d, J=8.4 Hz, 1 H), 7.71 (t, J=7.7 Hz, 1 H), 7.55 (d, J=8.2 Hz, 1 H), 7.29-7.47 (m, 4 H), 4.89-5.12 (m, 1 H), 4.07-4.28 (m, 1 H), 2.99-3.97 (m, 13 H), 2.55-2.79 (m, 1 H), 2.22-2.42 (m, 1 H).

Example 99

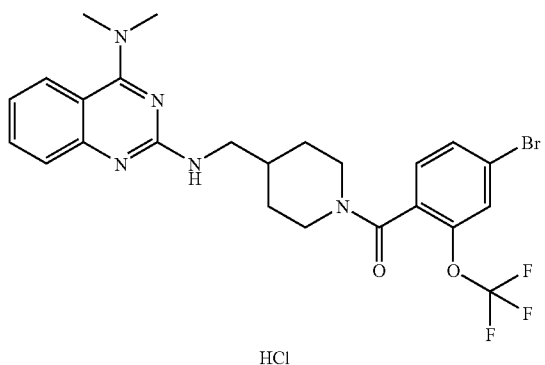

HCl 1-(4-Bromo-2-trifluoromethoxy-phenyl)-1-{4-[(4-dimethylamino-quinazolin-2-ylamino)-methyl]-piperidin-1-yl}-methanone hydrochloride Step A: Synthesis of 1-(4-bromo-2-trifluoromethoxy-phenyl)-1-{4-[(4-dimethylamino-quinazolin-2-ylamino)-methyl]-piperidin-1-yl}-methanone hydrochloride.

Using the procedure for the step A of example 47, the title compound was obtained.

ESI MS m/e 552, M (free)+H+; 1H NMR (300 MHz, CDCl3) δ 13.44 (brs, 1 H), 8.53-8.77 (m, 1 H), 7.90 (d, J=8.5 Hz, 1 H), 7.66 (t, J=7.7 Hz, 1 H), 7.43-7.61 (m, 3 H), 7.19-7.37 (m, 1 H), 4.69-4.85 (m, 1 H), 3.20-3.63 (m, 10 H), 2.61-3.13 (m, 2 H), 1.76-2.14 (m, 3 H), 1.08-1.48 (m, 2 H).

Example 100

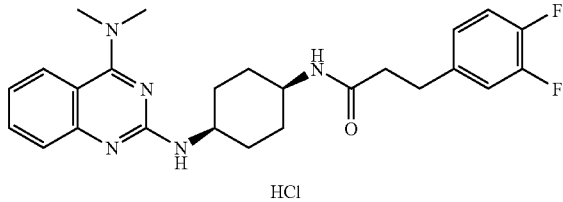

HCl cis-3-(3,4-Difluoro-phenyl)-N-[4-(4-dimethylamino-quinazolin-2-ylamino)-cyclohexyl]-propionamide hydrochloride Step A: Synthesis of cis-3-(3,4-difluoro-phenyl)-N-[4-(4-dimethylamino-quinazolin-2-ylamino)-cyclohexyl]-propionamide hydrochloride.

Using the procedure for the step A of example 47, the title compound was obtained.

ESI MS m/e 454, M (free)+H+; 1H NMR (300 MHz, CDCl3) δ 13.05 (s, 1 H), 8.87 (d, J=8.1 Hz, 1 H), 7.89 (d, J=8.2 Hz, 1 H), 7.65 (t, J=7.7 Hz, 1 H), 7.51 (d, J=7.3 Hz, 1H), 7.20-7.27 (m, 1 H), 6.88-7.09 (m, 3 H), 5.97 (d, J=8.5 Hz, 1 H), 4.26 (brs, 1 H), 3.91 (brs, 1 H), 3.51 (s, 6 H), 2.92 (t, J=7.6 Hz, 2 H), 2.44 (t, J=7.6 Hz, 2 H), 1.61-1.93 (brs, 8 H).

Example 101

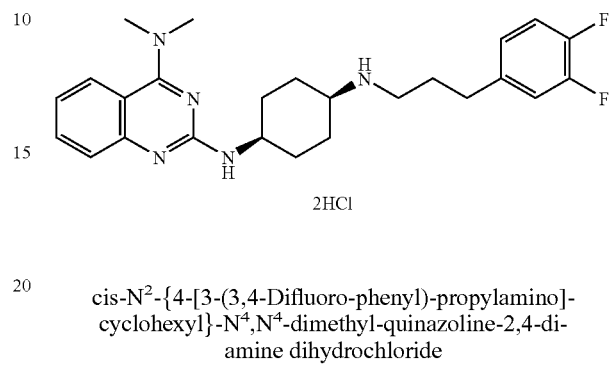

2HCl cis-N2-{4-[3-(3,4-Difluoro-phenyl)-propylamino]-cyclohexyl}-N4,N4-dimethyl-quinazoline-2,4-diamine dihydrochloride Step A: Synthesis of cis-N2-{4-[3-(3,4-difluoro-phenyl)-propylamino]-cyclohexyl}-N4,N4-dimethyl-quinazoline-2,4-diamine dihydrochloride.

Using the procedure for the step A of example 72, the title compound was obtained.

ESI MS m/e 440, M (free)+H+; 1H NMR (300 MHz, CDCl3) δ 12.62 (s, 1 H), 9.54 (s, 2 H), 8.72 (d, J=7.6 Hz, 1 H), 7.91 (d, J=8.4 Hz, 1 H), 7.62-7.70 (m, 1 H), 7.48 (d, J=7.6 Hz, 1 H), 7.24-7.33 (m, 1 H), 6.90-7.06 (m, 3 H), 4.29 (brs, 1 H), 3.52 (s, 6 H), 3.00-3.42 (m, 3 H), 2.67-2.81 (m, 2 H), 1.93-2.43 (m, 8 H), 1.60-1.80 (m, 2 H).

Example 102

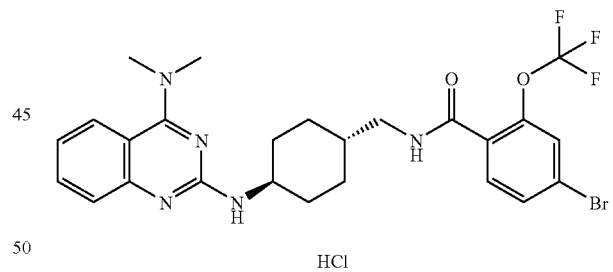

HCl trans-4-Bromo-N-[4-(4-dimethylamino-quinazolin-2-ylamino)-cyclohexylmethyl]-2-trifluoromethoxy-benzamide hydrochloride Step A: Synthesis of N2-(4-aminomethyl-cyclohexyl)-N4,N4-dimethyl-quinazoline-2,4-diamine.

Using the procedure for the step A of example 81, the title compound was obtained.

ESI MS m/e 300, M+H+; 1H NMR (300 MHz, CDCl3) δ 7.79 (d, J=8.4 Hz, 1 H), 7.45 (m, 2 H), 7.00 (ddd, J=8.4, 6.3, 1.9 Hz, 1 H), 4.80 (d, J=8.2 Hz, 1 H), 3.82-3.94 (m, 1 H), 3.24 (s, 6 H), 2.56 (d, J=6.2 Hz, 2 H), 2.14-2.28 (m, 2 H), 1.78-1.92 (m, 2 H), 0.95-1.42 (m, 7 H).

Step B: Synthesis of trans-4-bromo-N-[4-(4-dimethylamino-quinazolin-2-ylamino)-cyclohexylmethyl]-2-trifluoromethoxy-benzamide hydrochloride.

Using the procedure for the step A of example 47, the title compound was obtained.

ESI MS m/e 566, M+H⁺; ¹H NMR (300 MHz, CDCl₃) δ 13.48 (s, 1 H), 8.34 (d, J=7.5 Hz, 1 H), 7.83-7.94 (m, 2 H), 7.43-7.69 (m, 4 H), 7.20-7.29 (m, 1 H), 6.49-6.62 (m, 1 H), 3.72-3.93 (m, 1 H), 3.50 (s, 6 H), 3.39 (t, J=6.3 Hz, 2 H), 2.09-2.22 (m, 2 H), 1.85-1.98 (m, 2 H), 1.37-1.69 (m, 3 H), 1.08-1.28 (m, 2 H).

Example 103

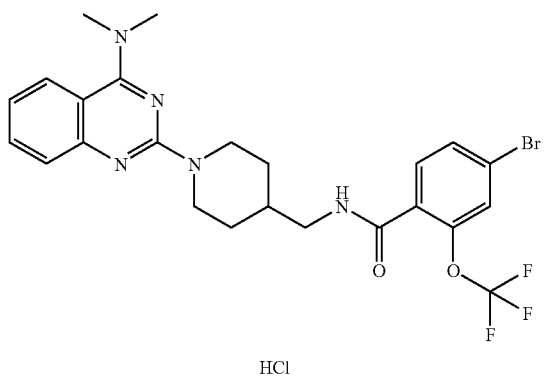

HCl

4-Bromo-N-[1-(4-dimethylamino-quinazolin-2-yl)-piperidin-4-ylmethyl]-2-trifluoromethoxy-benzamide hydrochloride Step A: Synthesis of 4-bromo-N-[1-(4-dimethylamino-quinazolin-2-yl)-piperidin-4-ylmethyl]-2-trifluoromethoxy-benzamide hydrochloride.

Using the procedure for the step A of example 47, the title compound was obtained.

ESI MS m/e 552, M (free)⁺; ¹H NMR (300 MHz, CDCl₃) δ 13.50 (s, 1 H), 8.73 (d, J=8.5 Hz, 1 H), 7.86 (d, J=8.4 Hz, 1 H), 7.81 (d, J=8.4 Hz, 1 H), 7.62-7.71 (m, 1 H), 7.53 (dd, J=8.4, 1.87 Hz, 1 H), 7.45 (s, 1 H), 7.23-7.32 (m, 1 H), 6.77-6.87 (m, 1 H), 3.30-3.55 (m, 10 H), 2.96-3.27 (m, 2 H), 1.89-2.15 (m, 3 H), 1.28-1.57 (m, 2 H).

Example 104

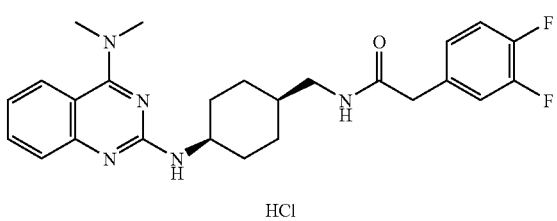

HCl cis-2-(3,4-Difluoro-phenyl)-N-[4-(4-dimethylamino-quinazolin-2-ylamino)-cyclohexylmethyl]-acetamide hydrochloride Step A: Synthesis of cis-2-(3,4-difluoro-phenyl)-N-[4-(4-dimethylamino-quinazolin-2-ylamino)-cyclohexylmethyl]-acetamide hydrochloride Using the procedure for the step A of example 47, the title compound was obtained.

ESI MS m/e 454, M (free)+H⁺; ¹H NMR (300 MHz, CDCl₃) δ 12.66 (s, 1 H), 9.08 (d, J=8.9 Hz, 1 H), 7.90 (d, J=8.1 Hz, 1 H), 7.66 (ddd, J=8.4, 7.2, 1.2 Hz, 1 H), 7.48 (dd, J=8.4, 0.9 Hz, 1 H), 7.32-7.41 (m, 1 H), 7.12-7.31 (m, 3 H), 6.97-7.08 (m, 1 H), 4.35-4.48 (m, 1 H), 3.78 (s, 2 H), 3.52 (s, 6 H), 3.28-3.36 (m, 2 H), 1.42-2.05 (m, 9 H).

Example 105

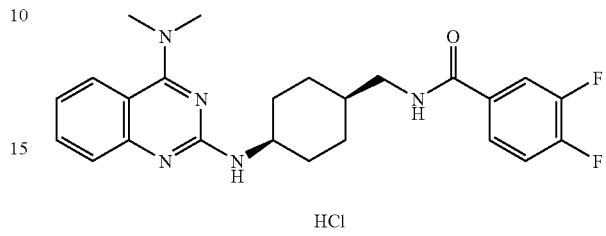

HCl cis-N²-[4-(4-Dimethylamino-quinazolin-2-ylamino)-cyclohexylmethyl]-3,4-difluoro-benzamide hydrochloride Step A: Synthesis of cis-N-[4-(4-dimethylamino-quinazolin-2-ylamino)-cyclohexylmethyl]-3,4-difluoro-benzamide hydrochloride.

Using the procedure for the step A of example 47, the title compound was obtained.

ESI MS m/e 440, M (free)+H⁺; ¹H NMR (300 MHz, CDCl₃) δ 12.89 (s, 1 H), 9.11 (d, J=8.2 Hz, 1 H), 7.88 (m, 3 H), 7.64 (ddd, J=8.4, 7.2, 1.2 Hz, 1 H), 7.49 (dd, J=8.4, 0.9 Hz, 1 H), 7.18-7.29 (m, 2 H), 6.96-7.07 (m, 1 H), 4.29-4.44 (m, 1 H), 3.51 (s, 8 H), 1.55-2.02(m, 9 H).

Example 106

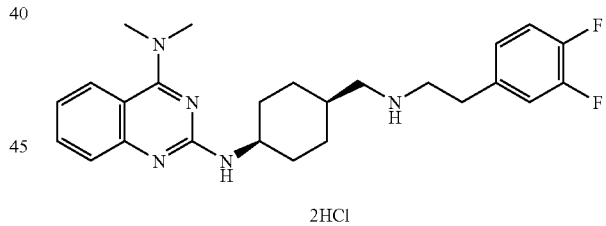

2HCl cis-N²-(4-{[2-(3,4-Difluoro-phenyl)-ethylamino]-methyl}-cyclohexyl)-N⁴,N⁴-dimethyl-quinazoline-2,4-diamine dihydrochloride Step A: Synthesis of cis-N²-(4-{[2-(3,4-difluoro-phenyl)-ethylamino]-methyl}-cyclohexyl)-N⁴,N⁴-dimethyl-quinazoline-2,4-diamine dihydrochloride.

Using the procedure for the step A of example 72, the title compound was obtained.

ESI MS m/e 440, M (free)+H⁺; ¹H NMR (300 MHz, CDCl₃) δ 12.43 (s, 1 H), 9.64 (brs, 2 H), 8.66 (d, J=8.3 Hz, 1 H), 7.91 (d, J=8.3 Hz, 1 H), 7.67 (t, J=7.8 Hz, 1 H), 7.46 (d, J=8.3 Hz, 1 H), 7.28 (t, J=7.8 Hz, 1 H), 6.97-7.17 (m, 3 H), 4.24-4.37 (m, 1 H), 3.52 (s, 6 H), 3.30-3.44 (m, 2 H), 2.94-3.25 (m, 4 H), 1.57-2.28 (m, 9 H).

Example 107

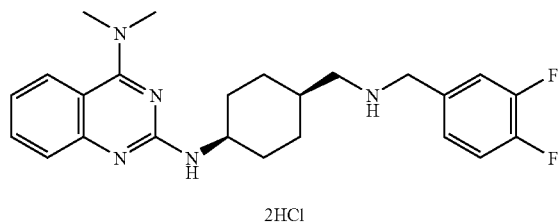

2HCl cis-N²-{4-[(3,4-Difluoro-benzylamino)-methyl]-cyclohexyl}-N⁴,N⁴-dimethyl-quinazoline-2,4-diamine dihydrochloride Step A: Synthesis of cis-N²-{4-[(3,4-difluoro-benzylamino)-methyl]-cyclohexyl}-N⁴,N⁴-dimethyl-quinazoline-2,4-diamine dihydrochloride Using the procedure for the step A of example 72, the title compound was obtained.

ESI MS m/e 426, M (free)+H⁺; ¹H NMR (300 MHz, DMSO-d₆) δ 9.39 (s, 2 H), 8.44 (m, 1 H), 8.17 (d, J=8.4 Hz, 1 H), 7.72-7.88 (m, 2 H), 7.27-7.61 (m, 4 H), 4.11-4.31 (m, 3 H), 3.48 (s, 6 H), 2.81 (d, J=6.1 Hz, 2 H), 1.32-2.03 (m, 9 H).

Example 108

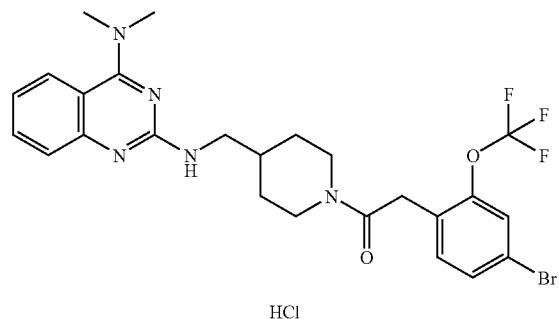

HCl 2-(4-Bromo-2-trifluoromethoxy-phenyl)-1-{4-[(4-dimethylamino-quinazolin-2-ylamino)-methyl]-piperidin-1-yl}-ethanone hydrochloride Step A: Synthesis of 2-(4-bromo-2-trifluoromethoxy-phenyl)-1-{4-[(4-dimethylamino-quinazolin-2-ylamino)-methyl]-piperidin-1-yl}-ethanone hydrochloride.

Using the procedure for the step A of example 47, the title compound was obtained.

ESI MS m/e 566, M (free)+H⁺; ¹H NMR (300 MHz, CDCl₃) δ 13.48 (s, 1 H), 8.65 (t, J=5.8 Hz, 1 H), 7.90 (d, J=8.4 Hz, 1 H), 7.53-7.70 (m, 2 H), 7.37-7.44 (m, 2 H), 7.20-7.32 (m, 2 H), 4.59-4.72 (m, 1 H), 3.80-3.94 (m, 1 H), 3.68 (d, J=6.1 Hz, 2 H), 3.25-3.58 (m, 8 H), 2.94-3.12 (m, 1 H), 2.50-2.68 (m, 1 H), 1.75-2.03 (m, 3 H), 1.06-1.32 (m, 2 H).

Example 109

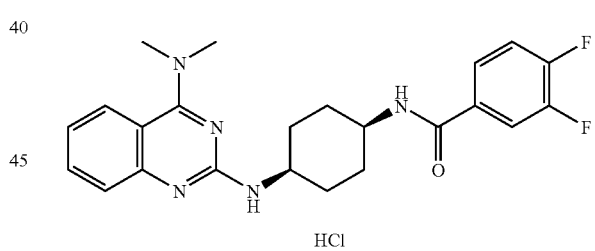

HCl trans-2-(4-Bromo-2-trifluoromethoxy-phenyl)-N-[4-(4-dimethylamino-quinazolin-2-ylamino)-cyclohexylmethyl]-acetamide Step A: Synthesis of trans-2-(4-bromo-2-trifluoromethoxy-phenyl)-N-[4-(4-dimethylamino-quinazolin-2-ylamino)-cyclohexylmethyl]-acetamide.

Using the procedure for the step A of example 47, the title compound was obtained.

ESI MS m/e 580, M (free)⁺; ¹H NMR (300 MHz, CDCl₃) δ 8.28 (d, J=6.7 Hz, 1 H), 7.87-7.90 (d, J=8.5 Hz, 1 H), 7.52-7.66 (m, 2 H), 7.39-7.44 (m, 2 H), 7.20-7.33 (m, 2 H), 5.85-5.98 (m, 1 H), 3.70-3.91 (m, 1 H), 3.58 (s, 2 H), 3.50 (s, 6 H), 3.16 (t, J=6.5 Hz, 2 H), 2.03-2.20 (m, 2 H), 1.28-1.88 (m, 5 H), 0.96-1.18 (m, 2 H).

Example 110 cis-N-[4-(4-Dimethylamino-quinazolin-2-ylamino)-cyclohexyl]-3,4-difluoro-benzamide hydrochloride Step A: Synthesis of cis-N-[4-(4-dimethylamino-quinazolin-2-ylamino)-cyclohexyl]-3,4-difluoro-benzamide hydrochloride.

Using the procedure for the step A of example 47, the title compound was obtained.

ESI MS m/e 448, M (free)+Na⁺; ¹H NMR (300 MHz, CDCl₃) δ 13.01 (s, 1 H), 8.96 (d, J=8.1 Hz, 1 H), 7.91 (d, J=8.2 Hz, 1 H), 7.55-7.79 (m, 4 H), 7.49-7.54 (m, 1 H), 7.15-7.32 (m, 2 H), 6.76 (d, J=8.4 Hz, 1 H), 4.30-4.41 (m, 1 H), 4.03-4.22 (m, 1 H), 3.52 (s, 6 H), 1.67-2.07 (m, 8 H).

Example 111

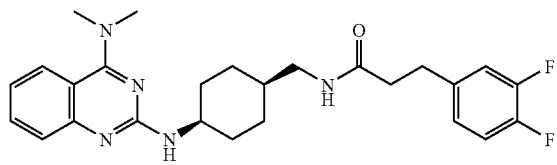

HCl cis-3-(3,4-Difluoro-phenyl)-N-[4-(4-dimethylamino-quinazolin-2-ylamino)-cyclohexylmethyl]-propionamide hydrochloride Step A: Synthesis of cis-3-(3,4-difluoro-phenyl)-N-[4-(4-dimethylamino-quinazolin-2-ylamino)-cyclohexylmethyl]-propionamide hydrochloride.

Using the procedure for the step A of example 47, the title compound was obtained.

ESI MS m/e 468, M (free)+H$^+$; $^1$H NMR (300 MHz, CDCl$_3$) δ 12.70 (s, 1 H), 9.00 (d, J=8.3 Hz, 1 H), 7.90 (d, J=8.3 Hz, 1 H), 7.66 (ddd, J=8.3, 7.2, 1.0 Hz, 1 H), 7.48 (dd, J=8.3, 1.0 Hz, 1 H), 7.11-7.31 (m, 2 H), 6.84-7.06 (m, 3 H), 4.32-4.44 (m, 1 H), 3.51 (s, 6H), 3.26-3.33 (m, 2 H), 2.96 (t, J=7.5 Hz, 2 H), 2.76 (t, J=7.4 Hz, 2 H), 1.34-1.94 (m, 9 H).

Example 112

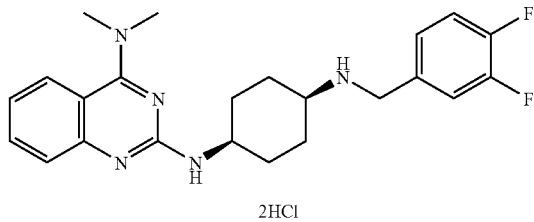

2HCl cis-N$^2$-[4-(3,4-Difluoro-benzylamino)-cyclohexyl]-N$^4$,N$^4$-dimethyl-quinazoline-2,4-diamine dihydrochloride Step A: Synthesis of cis-N$^2$-[4-(3,4-difluoro-benzylamino)-cyclohexyl]-N$^4$,N$^4$-dimethyl-quinazoline-2,4-diamine dihydrochloride.

Using the procedure for the step A of example 72, the title compound was obtained.

ESI MS m/e 434, M (free)+Na$^+$; $^1$H NMR (300 MHz, DMSO-d$_6$) δ 13.03 (s, 1 H), 9.50 (brs, 2 H), 8.31-8.40 (m, 1 H), 8.19 (d, J=8.2 Hz, 1 H), 7.73-7.90 (m, 2 H), 7.29-7.60 (m, 4 H), 4.04-4.28 (m, 3 H), 3.46 (s, 6 H), 3.06-3.22 (m, 1 H), 1.61-2.10 (m, 8 H).

Example 113

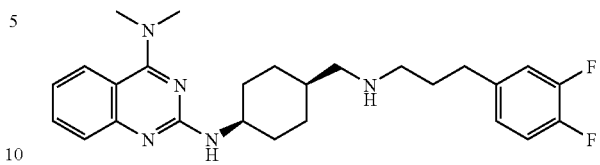

2HCl cis-N$^2$-(4-{[3-(3,4-Difluoro-phenyl)-propylamino]-methyl}-cyclohexyl)-N$^4$,N$^4$-dimethyl-quinazoline-2,4-diamine dihydrochloride Step A: Synthesis of cis-N$^2$-(4-{[3-(3,4-difluoro-phenyl)-propylamino]-methyl}-cyclohexyl)-N$^4$,N$^4$-dimethyl-quinazoline-2,4-diamine dihydrochloride.

Using the procedure for the step A of example 72, the title compound was obtained.

ESI MS m/e 454, M (free)+H$^+$; $^1$H NMR (300 MHz, CDCl$_3$) δ 12.50 (s, 1 H), 9.43 (brs, 2 H), 8.60 (d, J=7.93 Hz, 1 H), 7.90 (d, J=8.2 Hz, 1 H), 7.65 (ddd, J=8.2, 7.2, 1.1 Hz, 1 H), 7.46 (d, J=8.6 Hz, 1 H), 7.23-7.30 (m, 1 H), 6.91-7.08 (m, 3 H), 4.22-4.34 (m, 1 H), 3.51 (s, 6 H), 2.87-3.07 (m, 4 H), 2.68 (t, J=7.7 Hz, 2 H), 1.53-2.43 (m, 11 H).

Example 114

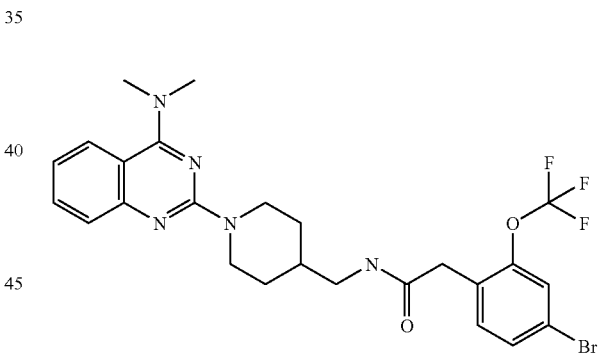

HCl 2-(4-Bromo-2-trifluoromethoxy-phenyl)-N-[1-(4-dimethylamino-quinazolin-2-yl)-piperidin-4-ylmethyl]-acetamide hydrochloride Step A: Synthesis of 2-(4-bromo-2-trifluoromethoxy-phenyl)-N-[1-(4-dimethylamino-quinazolin-2-yl)-piperidin-4-ylmethyl]-acetamide hydrochloride Using the procedure for the step A of example 47, the title compound was obtained.

ESI MS m/e 588, M (free)+Na$^+$; $^1$H NMR (300 MHz, CDCl$_3$) δ 13.32 (s, 1 H), 8.68 (d, J=8.4 Hz, 1 H), 7.86 (d, J=7.4 Hz, 1 H), 7.65 (ddd, J=8.4, 7.1, 1.2 Hz, 1 H), 7.23-7.42 (m, 4 H), 6.59-6.69 (m, 1 H), 3.60 (s, 2 H), 3.48 (s, 7 H), 2.90-3.37 (m, 5 H), 1.78-2.08 (m, 3 H), 1.19-1.46 (m, 2 H).

Example 115

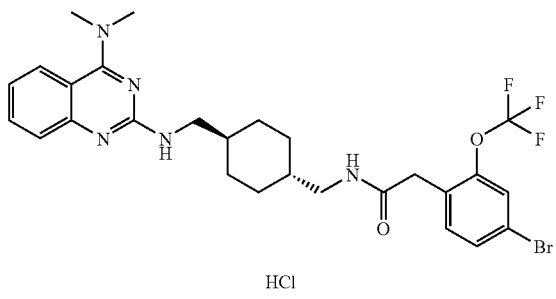

trans-2-(4-Bromo-2-trifluoromethoxphenyl)-N-{4-[(4-dimethylamino-quinazolin-2-ylamino)-methyl]-cyclohexylmethyl}-acetamide hydrochloride Step A: Synthesis of tarns-2-(4-bromo-2-trifluoromethoxyphenyl)-N-{4-[(4-dimethylamino-quinazolin-2-ylamino)-methyl]-cyclohexylmethyl}-acetamide hydrochloride.

Using the procedure for the step A of example 47, the title compound was obtained.

ESI MS m/e 616, M (free)+Na$^+$; $^1$H NMR (300 MHz, CDCl$_3$) δ 8.37-8.49 (m, 1 H), 7.89 (d, J=8.5 Hz, 1 H), 7.53-7.68 (m, 2 H), 7.40-7.45 (m, 2 H), 7.20-7.32 (m, 2 H), 5.60-5.71 (m, 1 H), 3.55 (s, 2 H), 3.50 (s, 6 H), 3.35 (t, J=6.1 Hz, 2 H), 3.08 (t, J=6.4 Hz, 2 H), 0.77-2.00 (m, 10 H).

Example 116

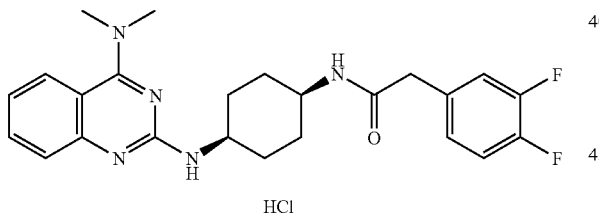

cis-2-(3,4-Difluoro-phenyl)-N-[4-(4-dimethylamino-quinazolin-2-ylamino)-cyclohexyl]-acetamide hydrochloride Step A: Synthesis of cis-2-(3,4-difluoro-phenyl)-N-[4-(4-dimethylamino-quinazolin-2-ylamino)-cyclohexyl]-acetamide hydrochloride Using the procedure for the step A of example 47, the title compound was obtained.

ESI MS m/e 440, M (free)+H$^+$; $^1$H NMR (300 MHz, CDCl$_3$) δ 13.01 (s, 1 H), 8.85 (d, J=8.2 Hz, 1 H), 7.89 (d, J=8.2 Hz, 1 H), 7.65 (ddd, J=8.2, 7.1, 1.2 Hz, 1 H), 7.52 (d, J=8.2 Hz, 1 H), 6.95-7.33 (m, 4 H), 6.32 (d, J=7.6 Hz, 1 H), 4.19-4.34 (m, 1 H), 3.82-4.01 (m, 1 H), 3.51 (s, 6 H), 3.47 (s, 2 H), 1.61-2.01 (m, 8 H).

Example 117

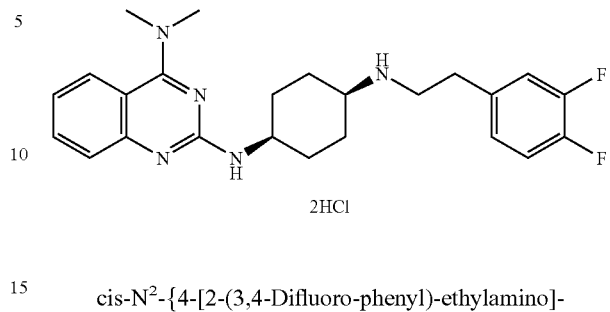

cis-N$^2$-{4-[2-(3,4-Difluoro-phenyl)-ethylamino]-cyclohexyl}-N$^4$,N$^4$-dimethyl-quinazoline-2,4-diamine dihydrochloride Step A: Synthesis of cis-N$^2$-{4-[2-(3,4-difluoro-phenyl)-ethylamino]-cyclohexyl}-N$^4$,N$^4$-dimethyl-quinazoline-2,4-diamine dihydrochloride.

Using the procedure for the step A of example 72, the title compound was obtained.

ESI MS m/e 426, M (free)+H$^+$; $^1$H NMR (300 MHz, CDCl$_3$) δ 12.51 (s, 1 H), 9.70 (brs, 2 H), 8.67 (d, J=7.5 Hz, 1 H), 7.92 (d, J=8.0 Hz, 1 H), 7.68 (t, J=8.0 Hz, 1 H), 7.52 (d, J=8.4 Hz, 1 H), 7.30 (t, J=7.8 Hz, 1 H), 6.97-7.22 (m, 3 H), 4.34 (brs, 1 H), 3.53 (s, 6 H), 3.12-3.41 (m, 5 H), 1.62-2.40 (m, 8 H).

Example 118

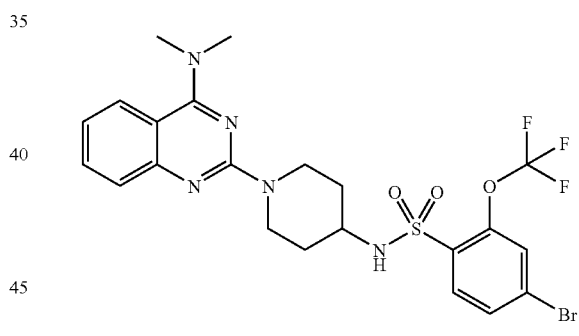

4-Bromo-N-[1-(4-dimethylamino-quinazolin-2-yl)-piperidin-4-yl]-2-trifluoromethoxy-benzenesulfonamide Step A: Synthesis of [2-(4-amino-piperidin-1-yl)-quinazolin-4-yl]-dimethyl-amine.

To a solution of 1-benzyl-piperidin-4-ylamine (2.00 g, 10.5 mmol) in THF (20 mL) was added (Boc)$_2$O (2.52 g, 11.5 mmol). The mixture was stirred at ambient temperature for 40 min, and concentrated. To a solution of the residue in MeOH (20 mL) was added 20% Pd(OH)$_2$ (400 mg). The mixture was stirred at ambient temperature under hydrogen atmosphere for 20 hr. Additionally, 20% Pd(OH)$_2$ (400 mg) was added and the mixture was stirred at ambient temperature under hydrogen atmosphere for 7 hr, at 50° C. for 4.5 hr, and at ambient temperature for 12 hr, filtered through a pad of celite, and concentrated to give a white solid. A mixture of (2-chloro-quinazolin-4-yl)-dimethyl-amine obtained in step B of example 1 (1.10 g, 5.30 mmol) and the above solid (1.27 g, 6.34 mmol) in 2-propanol (11 mL) was stirred at reflux for 20 hr. The precipitate was collected by filtration, washed with 2-propanol, dissolved in 50% MeOH in $CHCl_3$ (60 mL). The solution was poured into saturated aqueous $NaHCO_3$, and the aqueous layer was extracted with $CHCl_3$ (three times). The combined organic layer was dried over $MgSO_4$, filtered, concentrated, and purified by flash chromatography (NH-silica gel, EtOAc to $CHCl_3$) to give [2-(4-amino-piperidin-1-yl)-quinazolin-4-yl]-dimethyl-amine (864 mg, 68%) as a colorless oil.

ESI MS m/e 272, M+H$^+$; $^1$H NMR (300 MHz, $CDCl_3$) δ 7.79 (d, J=8.2 Hz, 1 H), 7.45-7.55 (m, 2 H), 6.96-7.05 (m, 1 H), 4.83 (d, J=13.4 Hz, 2 H), 3.26 (s, 6 H), 2.84-3.03 (m, 3 H), 1.85-1.95 (m, 2 H), 1.20-1.50 (m, 4 H).

Step B: Synthesis of 4-bromo-N-[1-(4-dimethylamino-quinazolin-2-yl)-piperidin-4-yl]-2-trifluoromethoxy-benzenesulfonamide.

Using the procedure for the step A of example 20, the title compound was obtained.

ESI MS m/e 574, M+H$^+$; $^1$H NMR (300 MHz, $CDCl_3$) δ 7.94 (d, J=8.7 Hz, 1 H), 7.80 (d, J=8.2 Hz, 1 H), 7.39-7.61 (m, 4 H), 6.98-7.07 (m, 1 H), 4.60-4.81 (m, 3 H), 3.39-3.61 (m, 1 H), 3.25 (s, 6 H), 2.98-3.08 (m, 2 H), 1.73-1.92 (m, 2 H), 1.33-1.54 (m, 2 H).

Example 119

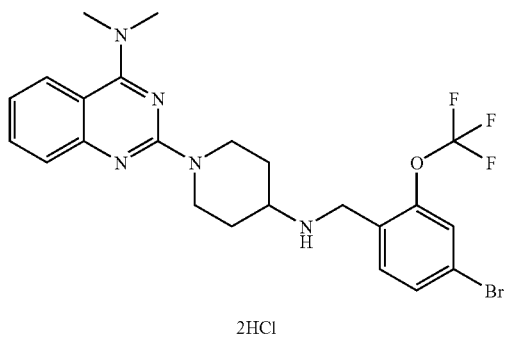

2HCl

{2-[4-(4-Bromo-2-trifluoromethoxy-benzylamino)-piperidin-1-yl]-quinazolin-4-yl}-dimethyl-amine dihydrochloride Step A: Synthesis of {2-[4-(4-bromo-2-trifluoromethoxy-benzylamino)-piperidin-1-yl]-quinazolin-4-yl}-dimethyl-amine dihydrochloride.

Using the procedure for the step B of example 37, the title compound was obtained.

ESI MS m/e 524, M (free)+H$^+$; $^1$H NMR (300 MHz, $CDCl_3$) δ 8.43 (d, J=8.1 Hz, 1 H), 8.20 (d, J=8.4 Hz, 1 H), 7.90 (d, J=8.4 Hz, 1 H), 7.67 (t, J=7.5 Hz, 1 H), 7.26-7.49 (m, 3 H), 5.13 (brs, 2 H), 4.27 (s, 2 H), 3.08-3.60 (s, 9 H), 2.08-2.78 (m, 4 H).

Example 120

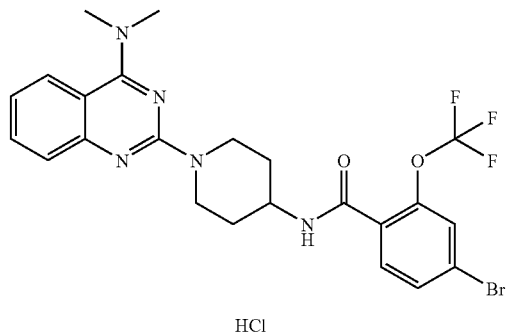

HCl

4-Bromo-N-[1-(4-dimethylamino-quinazolin-2-yl)-piperidin-4-yl]-2-trifluoromethoxy-benzamide hydrochloride Step A: Synthesis of 4-bromo-N-[1-(4-dimethylamino-quinazolin-2-yl)-piperidin-4-yl]-2-trifluoromethoxy-benzamide hydrochloride.

Using the procedure for the step A of example 47, the title compound was obtained.

ESI MS m/e 560, M (free) Na$^+$; $^1$H NMR (300 MHz, $CDCl_3$) δ 13.68 (s, 1 H), 8.73 (d, J=7.8 Hz, 1 H), 7.80-7.91 (m, 2 H), 7.68 (ddd, J=8.4, 7.1, 1.3 Hz, 1 H), 7.55 (dd, J=8.4, 1.9 Hz, 1 H), 7.42-7.46 (m, 1 H), 7.29 (ddd, J=8.4, 7.1, 1.3 Hz, 1 H), 6.67 (d, J=7.3 Hz, 1 H), 5.04 (brs, 2 H), 4.23-4.42 (m, 1 H), 3.27-3.61 (m, 8 H), 2.19-2.36 (m, 2 H), 1.57-1.81 (m, 2 H).

Example 121

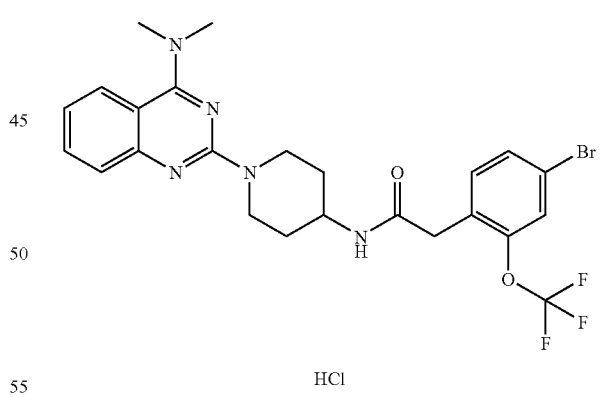

HCl 2-(4-Bromo-2-trifluoromethoxy-phenyl)-N-[1-(4-dimethylamino-quinazolin-2-yl)-piperidin-4-yl]-acetamide hydrochloride Step A: Synthesis of 2-(4-bromo-2-trifluoromethoxy-phenyl)-N-[1-(4-dimethylamino-quinazolin-2-yl)-piperidin-4-yl]-acetamide hydrochloride.

Using the procedure for the step A of example 47, the title compound was obtained.

ESI MS m/e 574, M (free)+Na⁺; $^1$H NMR (300 MHz, CDCl₃) δ 13.08 (s, 1 H), 8.61 (d, J=8.4 Hz, 1 H), 7.86 (d, J=7.5 Hz, 1 H), 7.56-7.68 (m, 2 H), 7.21-7.39 (m, 4 H), 4.70-5.10 (m, 2 H), 4.04-4.22 (m, 1 H), 3.68 (s, 2 H), 3.34-3.61 (m, 8 H), 1.59-2.19 (m, 4 H).

Example 122-301

To a solution of amine obtained in step A of example 15 (30 µmol) and pyridine (120 µmol) in CH₂Cl₂ (400 µL) was added an appropriate sulfonyl chloride (60 µmol) in CH₂Cl₂ (200 µL) at 25° C. After stirring at the same temperature for 20 hr, the reaction mixture was concentrated by a stream of dry N₂. To the residue was partitionated between CHCl₃ and saturated aqueous NH₄Cl. The aqueous layer was extracted with CHCl₃. The combined organic layers were dried over MgSO₄. After concentration by a stream of dry N₂, dry CH₂Cl₂ (600 µL) and PSA (300 µL) were added to the residue. After the stirring at 25° C. for 20 hr, the reaction mixture was filtrated and purified by flash chromatography (NH-silica gel, 33% MeOH in CHCl₃) to give the desired product.

Example 302-588

To a solution of amine obtained in step C of example 9 or step A of example 64 (30 µmol) in CH₂Cl₂ (200 µL) were added poly(4-vinylpyridine) (75 µL) in CH₂Cl₂ (200 µL) and acid chloride (60 µmol) in CH₂Cl₂ (200 µL) at 25° C. After stirring at the same temperature for 20 hr, the reaction mixture was filtered and concentrated by a stream of dry N₂. To the residue were added dry CH₂Cl₂ (600 µL) and PSA (300 µL). After the stirring at 25° C. for 20 hr, the reaction mixture was filtrated and purified by flash chromatography (NH-silica gel, 33% MeOH in CHCl₃) to give the desired product.

Example 589-1136

To a solution of carboxylic acid (200 µL, 60 µmol) in CH₂Cl₂ (200 µL) were added 1-cyclohexyl-3-methylpolystyrene-carbodiimide (150 µL, 126 µmol) in CH₂Cl₂ (200 µL) and amine obtained in step C of example 9 or step A of example 64 (30 µmol) in CH₂Cl₂ (200 µL) at 25° C. After stirring at the same temperature for 20 hr, the reaction mixture was filtered through NH-silica gel, and concentrated by a stream of dry N₂. To the residue were added dry CH₂Cl₂ (700 µL) and polystyrene linked benzaldehyde (75 µL, 60 µmol). After the stirring at 50° C. for 20 hr, the reaction mixture was filtrated, and concentrated by a stream of dry N₂ to give the desired product.

Example 1137-1745

To a solution of the amide product in THF (200 µl) was added 1 M borane-THF complex in THF (300 µl, 300 µmol). The mixture was stirred at 80° C. for 1 hr, and concentrated by a stream of dry N₂. To the residue were added 1 M aqueous HCl (300 µl) and THF (300 µl). The mixture was stirred at 80° C. for 1 hr, and concentrated by a stream of dry N₂. To the residue was partitionated between CHCl₃ and 2 M aqueous sodium hydroxide. The aqueous layer was extracted with CHCl₃. The combined organic layers were dried over MgSO₄. The mixture was concentrated by a stream of dry N₂, and the purified by flash chromatography (silica gel, 2% to 7% 2 M NH₃/MeOH in CHCl₃) to give the desired product.

Example 1746-2184

To a solution of amine obtained in step C of example 9 or step A of example 64 (36 µmol) in MeOH (200 µL) were added aldehyde (30 µmol) in MeOH (200 µL) and AcOH (90 µmol) at 25° C. The reaction mixture was stirred at the same temperature for 1 hr. To the mixture was added NaBH₃CN (120 µmol) in MeOH (200 µL). After stirring at the same temperature for 20 hr, the reaction mixture was concentrated by a stream of dry N₂. To the residue was partitionated between CHCl₃ and 2 M aqueous sodium hydroxide. The aqueous layer was extracted with CHCl₃. The combined organic layers were dried over MgSO₄. The mixture was concentrated by a stream of dry N₂, and purified by flash chromatography (silica gel, 2% to 7% 2 M NH₃/MeOH in CHCl₃) to give the desired product.

Example 2185-2328

To a solution of alcohol (35 µmol) in CH₂Cl₂ (200 µL) was added Dess-Martin periodinane (63 µmol) in CH₂Cl₂ (200 µL) at 25° C., and the reaction mixture was stirred at the same temperature for 20 hr. To the reaction mixture were added amine obtained in step C of example 9 or step A of example 64 (36 µmol) in MeOH (200 µL) and AcOH (90 µL), and the mixture was stirred at the same temperature for 1 hr. To the mixture was added NaBH₃CN (120 µmol) in MeOH (200 µL). After stirring at the same temperature for 20 hr, the reaction mixture was concentrated by a stream of dry N₂. To the residue was partitionated between CHCl₃ and 2 M aqueous sodium hydroxide. The aqueous layer was extracted with CHCl₃. The combined organic layers were dried over MgSO₄. The mixture was concentrated by a stream of dry N₂, and purified by flash chromatography (silica gel, 2% to 7% 2 M NH₃/MeOH in CHCl₃) to give the desired product.

| Example No. | Structure | APCI-MS |
|---|---|---|
| 122 | 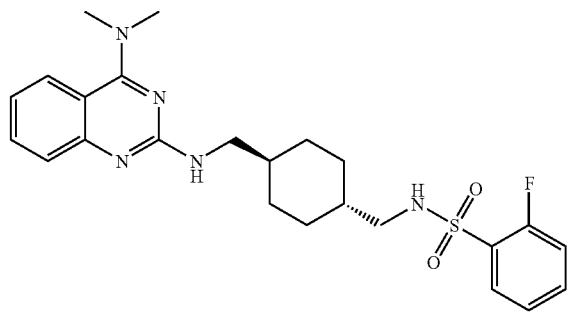 | 472 (M + H) |

-continued
| Example No. | Structure | APCI-MS |
|---|---|---|
| 123 | 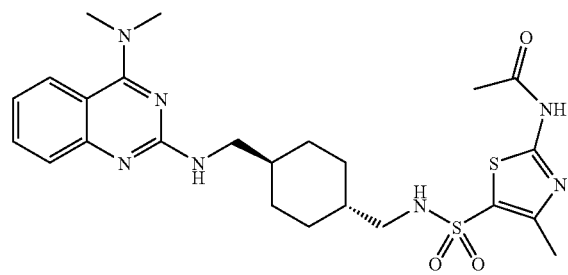 | 532 (M + H) |
| 124 | 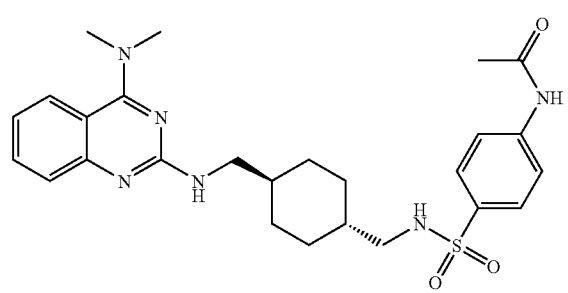 | 511 (M + H) |
| 125 | 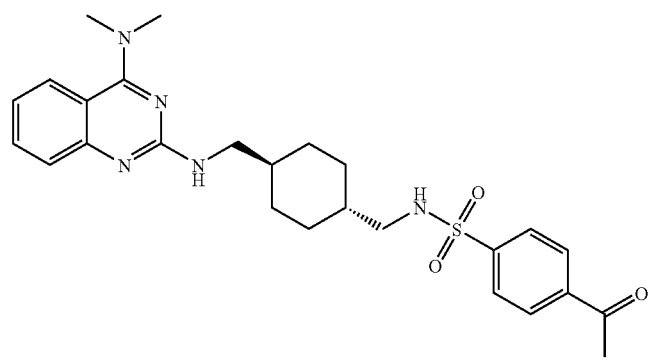 | 496 (M + H) |
| 126 | 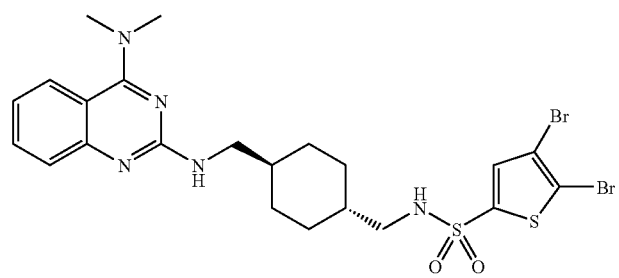 | 616 (M + H) |
| 127 | 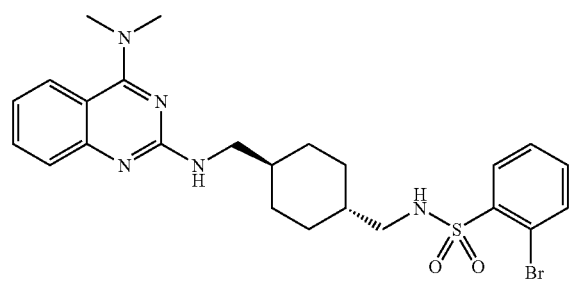 | 532 (M + H) |

-continued
| Example No. | Structure | APCI-MS |
|---|---|---|
| 128 | 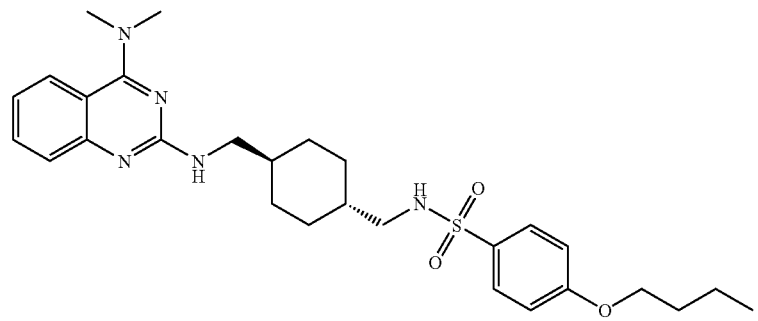 | 526 (M + H) |
| 129 | 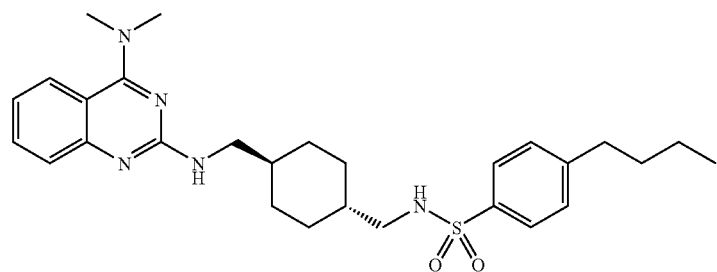 | 510 (M + H) |
| 130 | 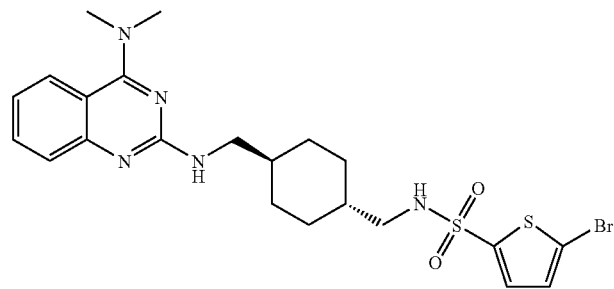 | 538 (M + H) |
| 131 | 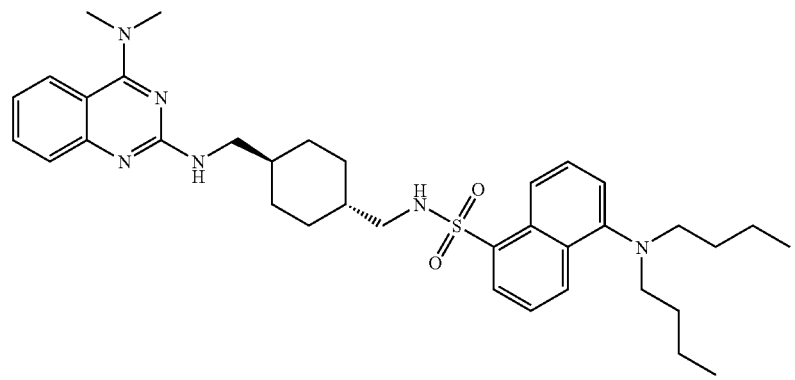 | 631 (M + H) |
| 132 | 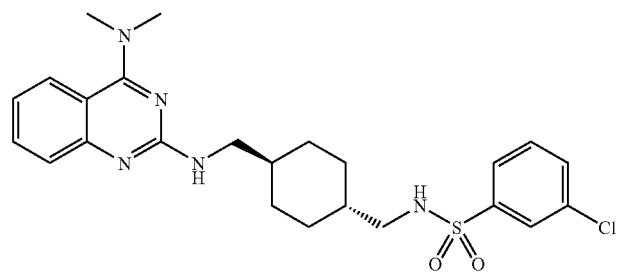 | 488 (M + H) |

| Example No. | Structure | APCI-MS |
|---|---|---|
| 133 | 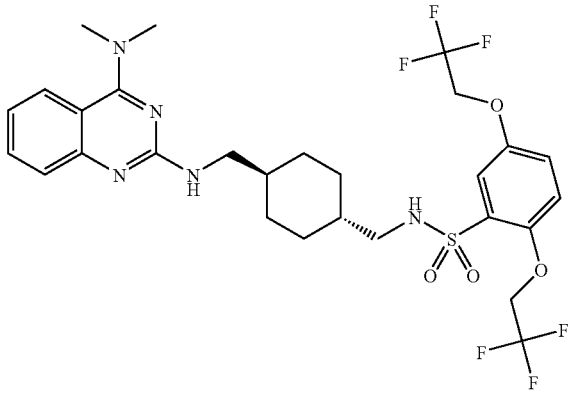 | 650 (M + H) |
| 134 | 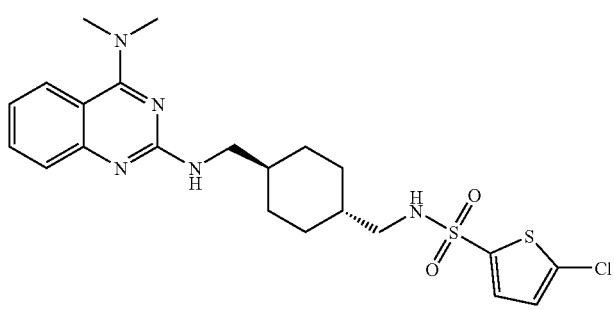 | 494 (M + H) |
| 135 | 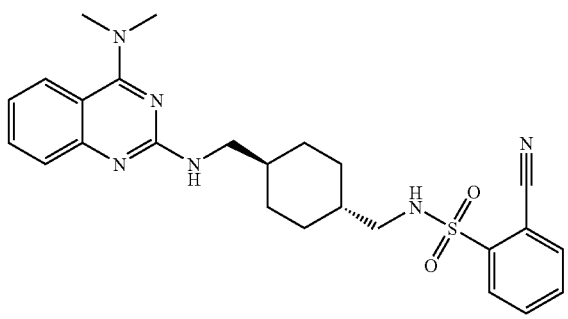 | 479 (M + H) |
| 136 | 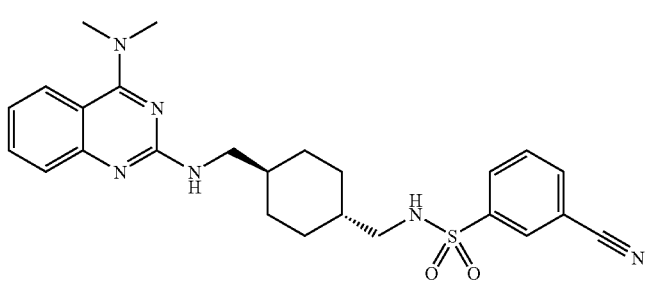 | 479 (M + H) |

-continued
| Example No. | Structure | APCI-MS |
|---|---|---|
| 137 | 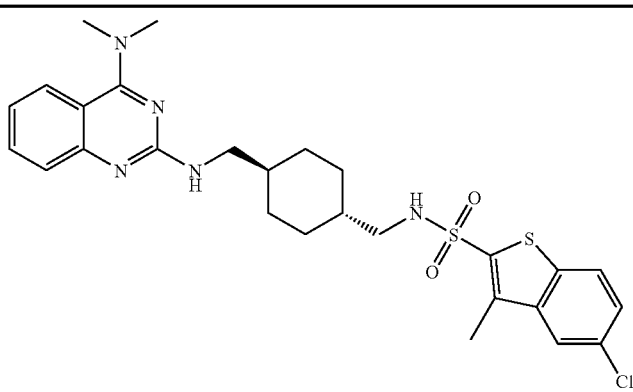 | 558 (M + H) |
| 138 | 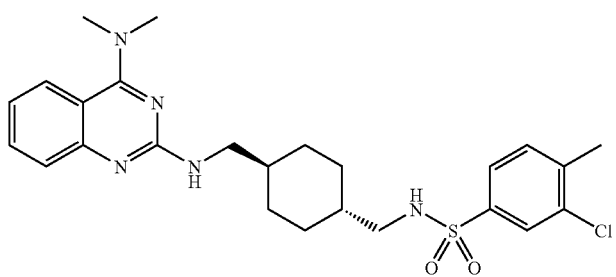 | 502 (M + H) |
| 139 | 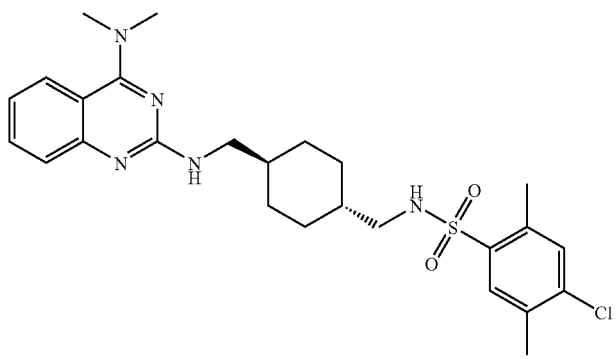 | 516 (M + H) |
| 140 | 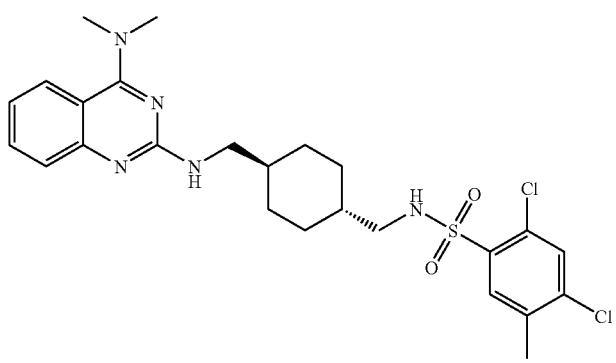 | 536 (M + H) |

-continued
| Example No. | Structure | APCI-MS |
| --- | --- | --- |
| 141 | 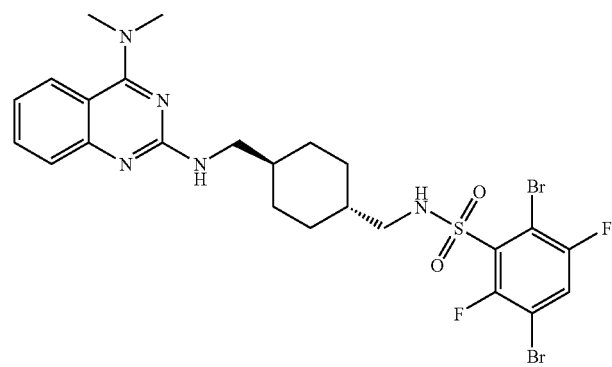 | 646 (M + H) |
| 142 | 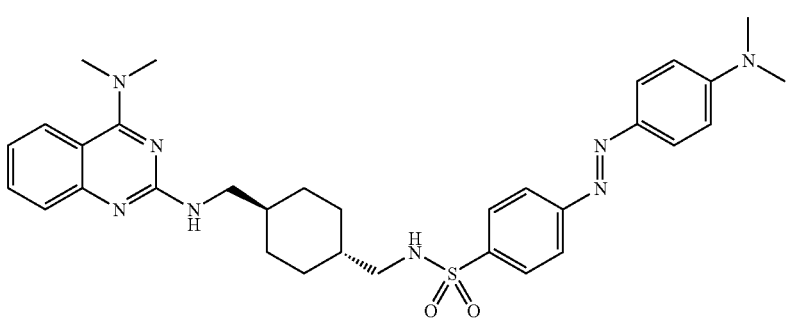 | 601 (M + H) |
| 143 | 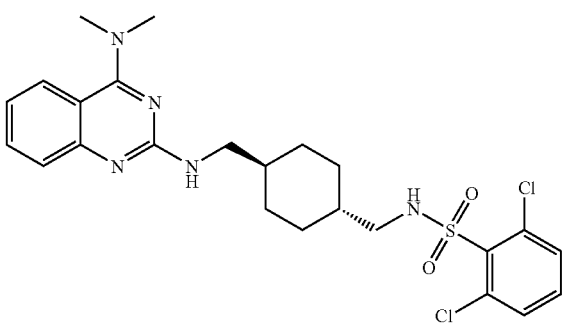 | 522 (M + H) |
| 144 | 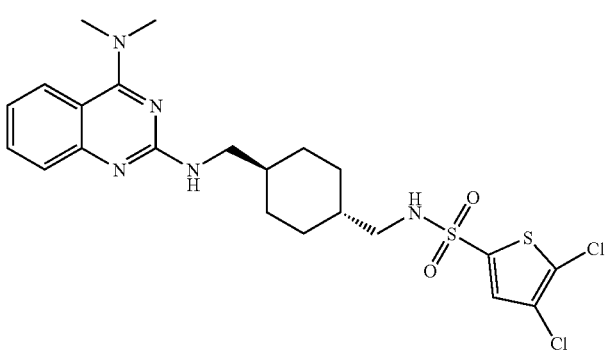 | 528 (M + H) |

-continued
| Example No. | Structure | APCI-MS |
|---|---|---|
| 145 | 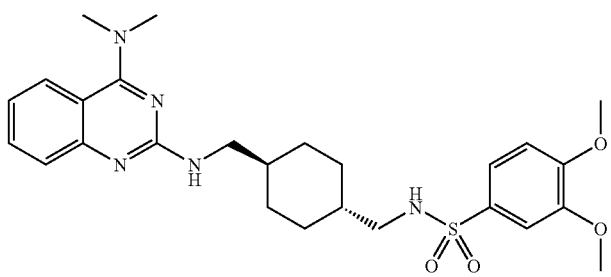 | 514 (M + H) |
| 146 | 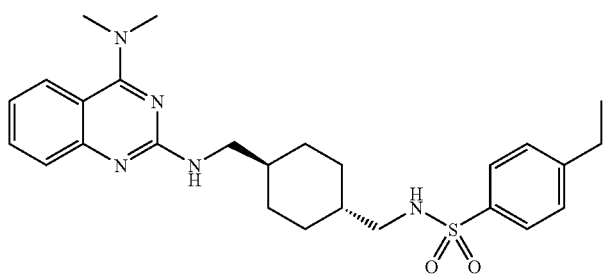 | 482 (M + H) |
| 147 | 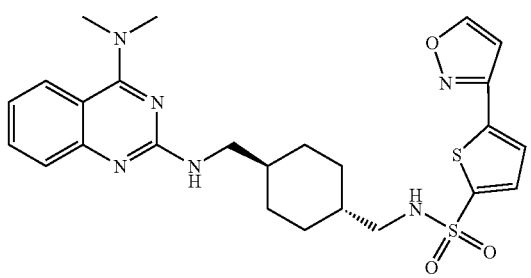 | 527 (M + H) |
| 148 | 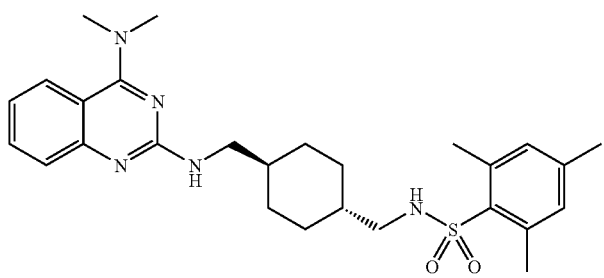 | 496 (M + H) |
| 149 | 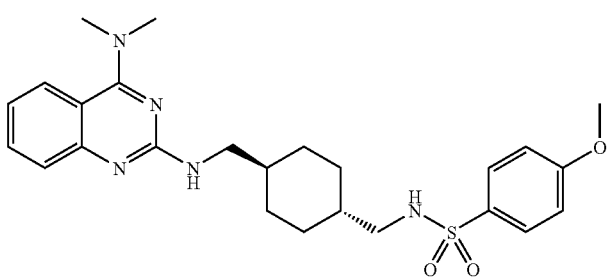 | 484 (M + H) |

-continued
| Example No. | Structure | APCI-MS |
|---|---|---|
| 150 | 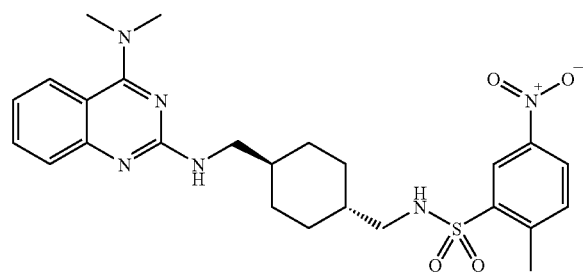 | 513 (M + H) |
| 151 | 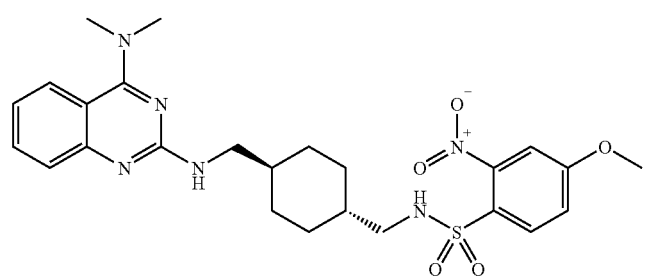 | 529 (M + H) |
| 152 | 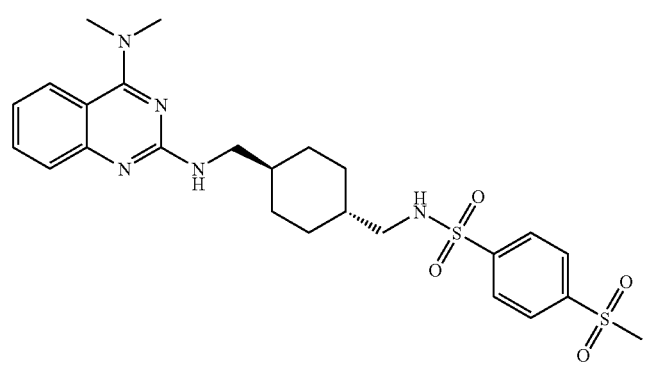 | 532 (M + H) |
| 153 | 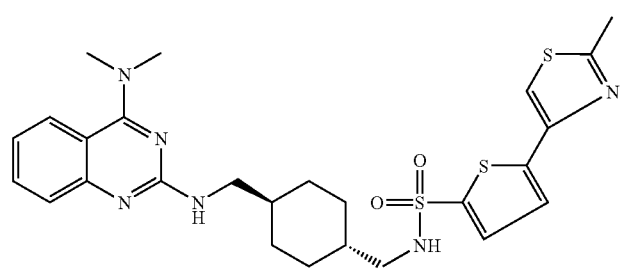 | 557 (M + H) |
| 154 | 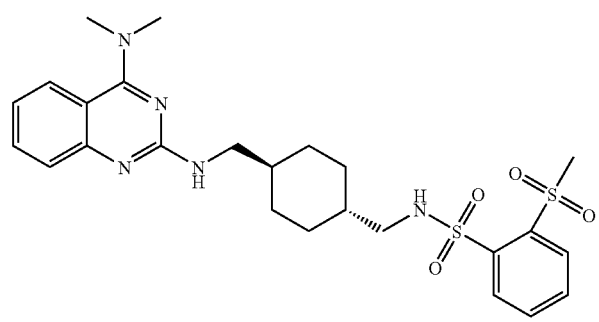 | 532 (M + H) |

-continued

| Example No. | Structure | APCI-MS |
|---|---|---|
| 155 | 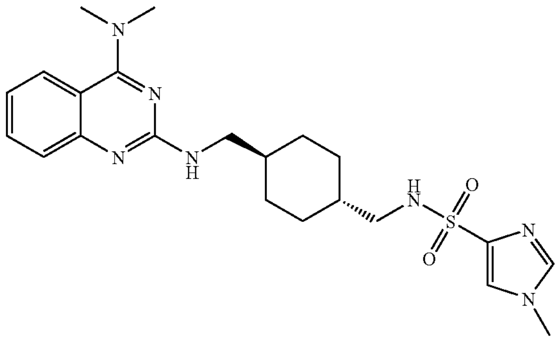 | 458 (M + H) |
| 156 | 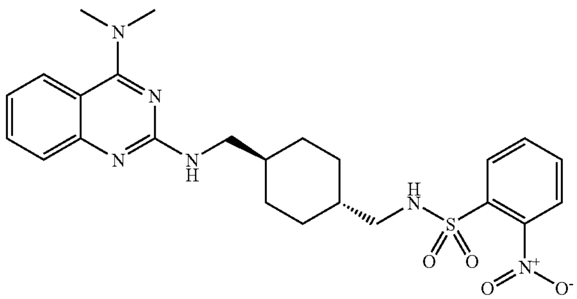 | 499 (M + H) |
| 157 | 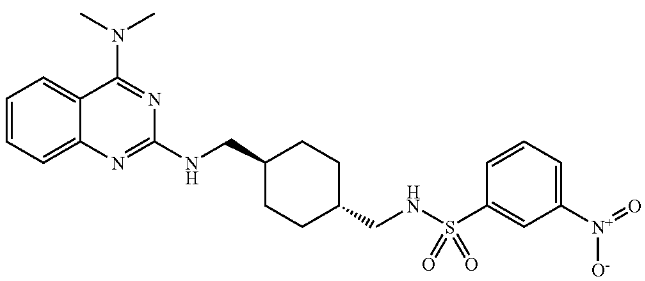 | 499 (M + H) |
| 158 | 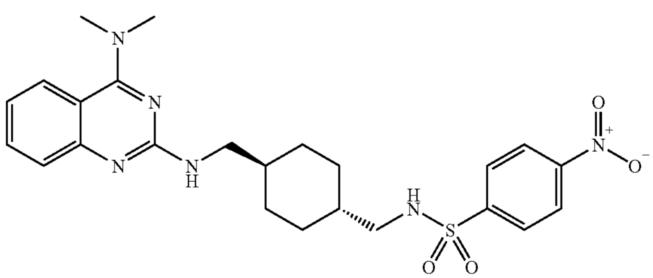 | 499 (M + H) |
| 159 | 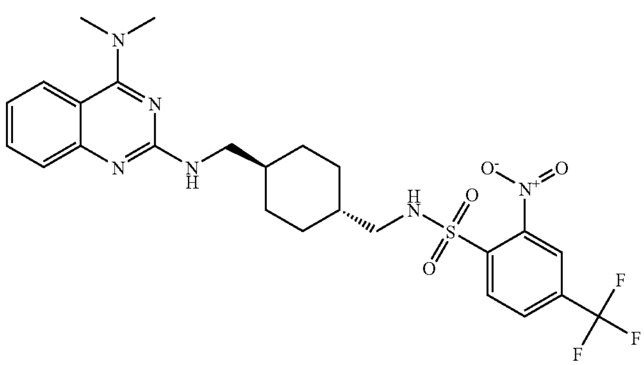 | 567 (M + H) |

| Example No. | Structure | APCI-MS |
|---|---|---|
| 160 | 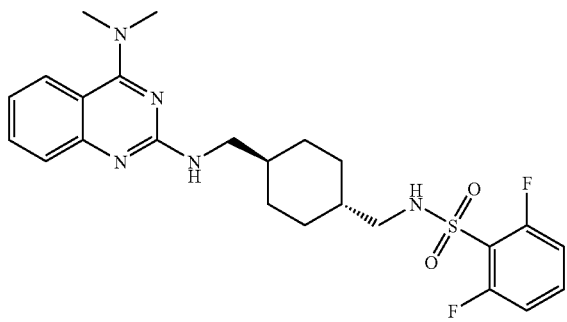 | 490 (M + H) |
| 161 | 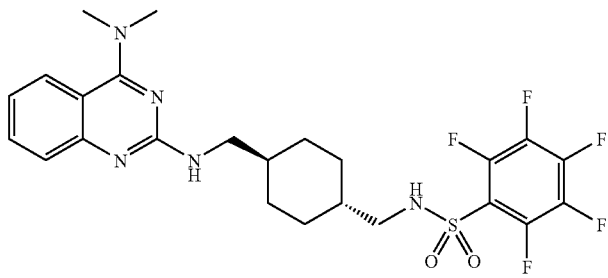 | 544 (M + H) |
| 162 | 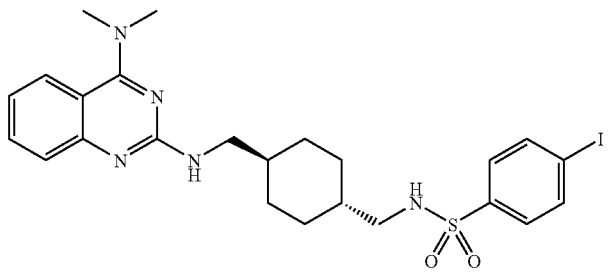 | 580 (M + H) |
| 163 | 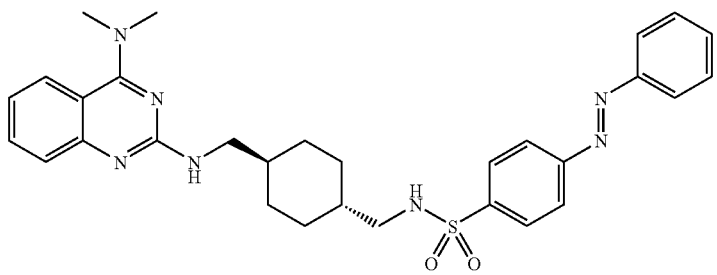 | 558 (M + H) |
| 164 | 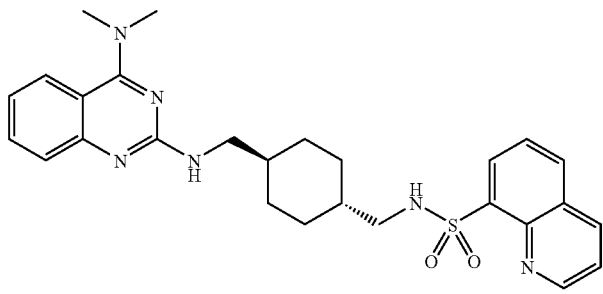 | 505 (M + H) |

-continued
| Example No. | Structure | APCI-MS |
|---|---|---|
| 165 | 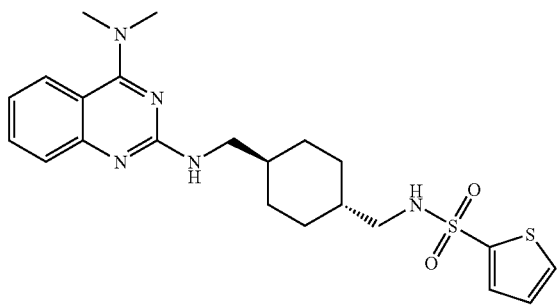 | 460 (M + H) |
| 166 | 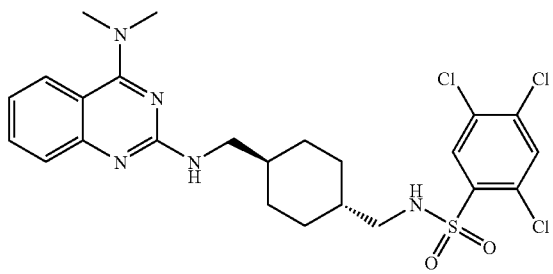 | 556 (M + H) |
| 167 | 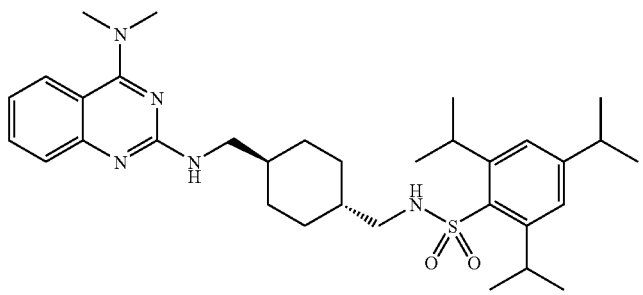 | 580 (M + H) |
| 168 | 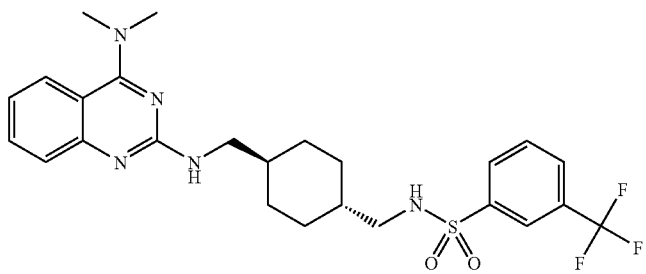 | 522 (M + H) |
| 169 | 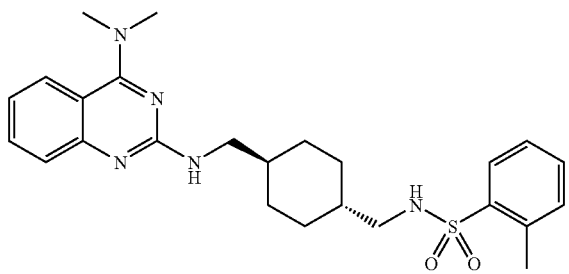 | 468 (M + H) |

| Example No. | Structure | APCI-MS |
|---|---|---|
| 170 | 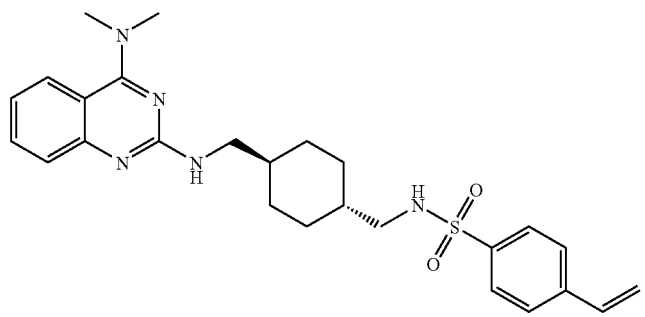 | 480 (M + H) |
| 171 | 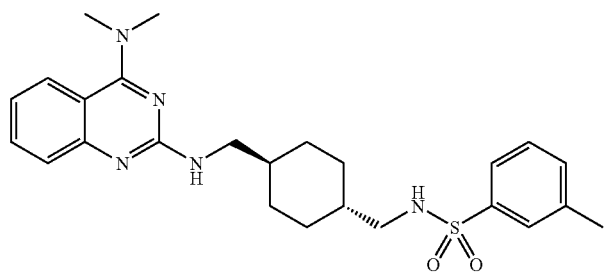 | 468 (M + H) |
| 172 | 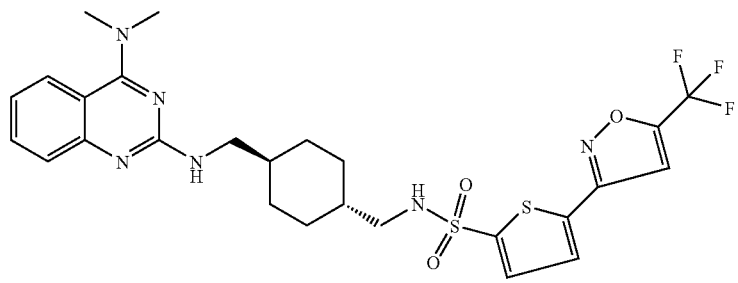 | 595 (M + H) |
| 173 | 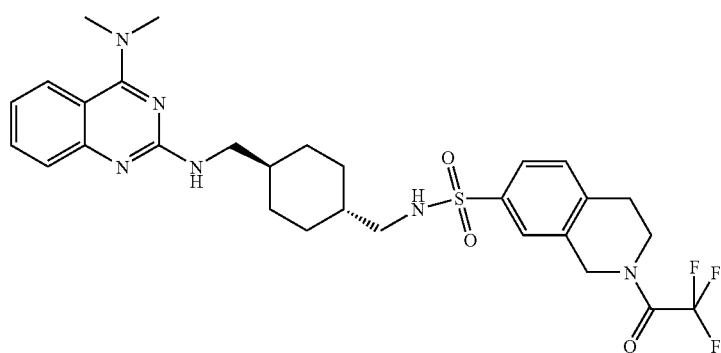 | 605 (M + H) |
| 174 | 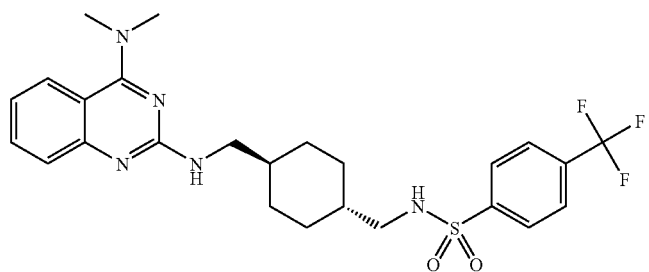 | 522 (M + H) |

-continued
| Example No. | Structure | APCI-MS |
|---|---|---|
| 175 | 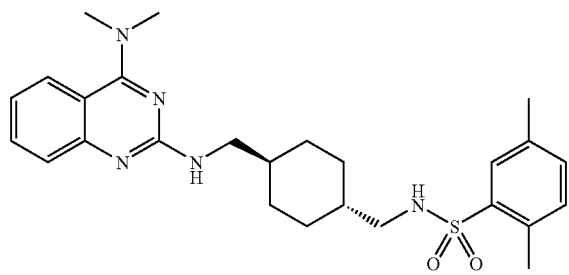 | 482 (M + H) |
| 176 | 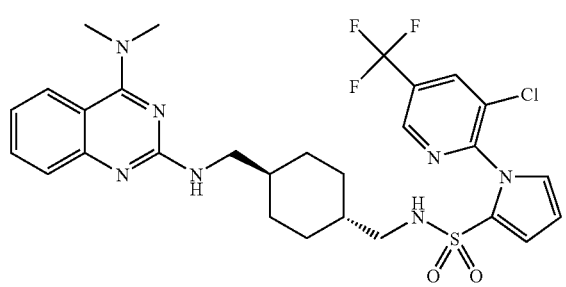 | 622 (M + H) |
| 177 | 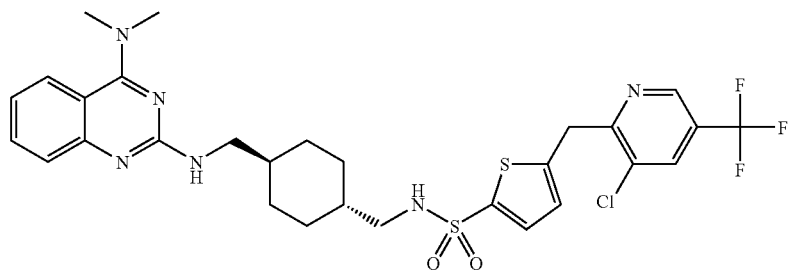 | 653 (M + H) |
| 178 | 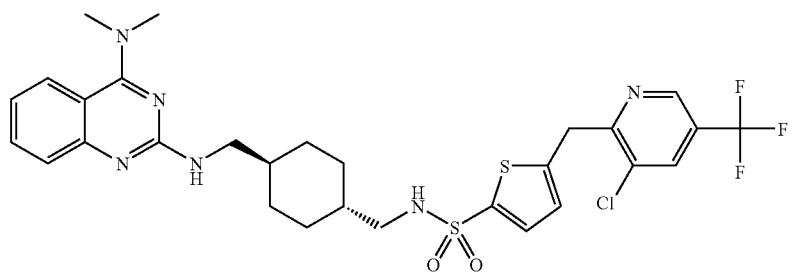 | 544 (M + H) |
| 179 | 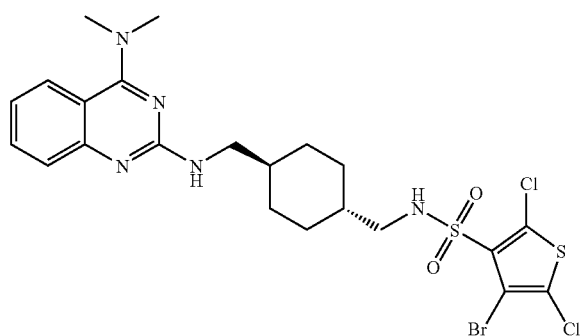 | 606 (M + H) |

-continued
| Example No. | Structure | APCI-MS |
|---|---|---|
| 180 | 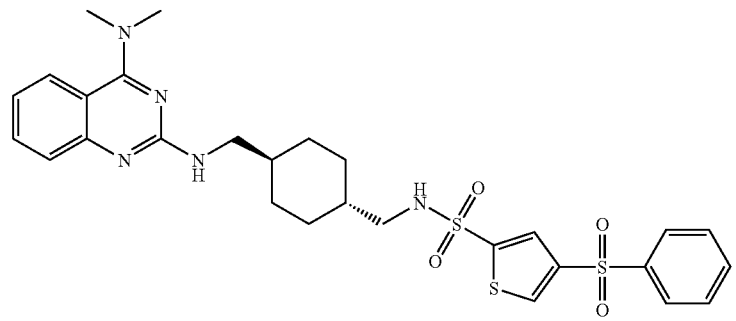 | 600 (M + H) |
| 181 | 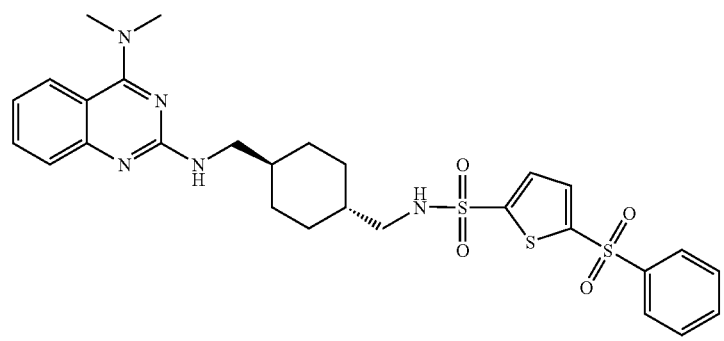 | 600 (M + H) |
| 182 | 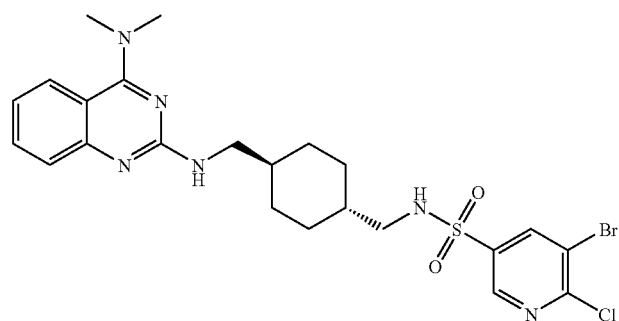 | 567 (M + H) |
| 183 | 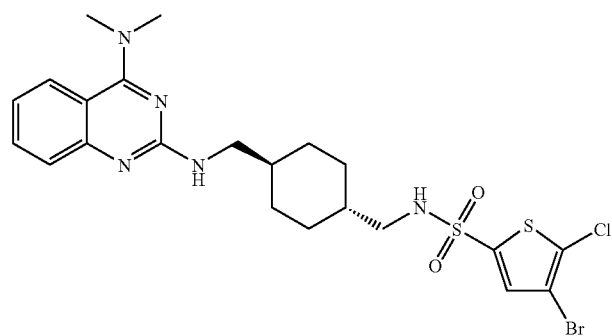 | 572 (M + H) |

-continued
| Example No. | Structure | APCI-MS |
|---|---|---|
| 184 | 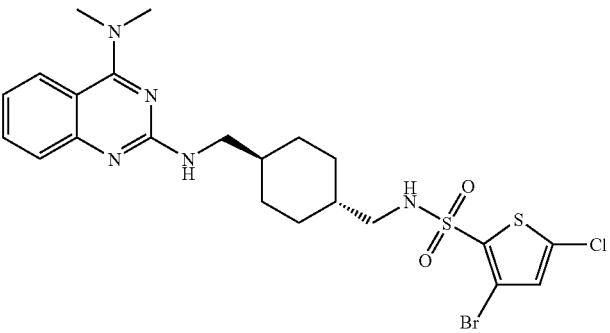 | 572 (M + H) |
| 185 | 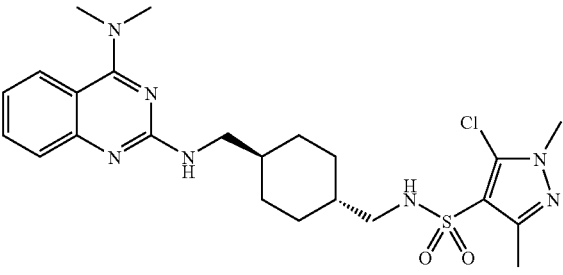 | 506 (M + H) |
| 186 | 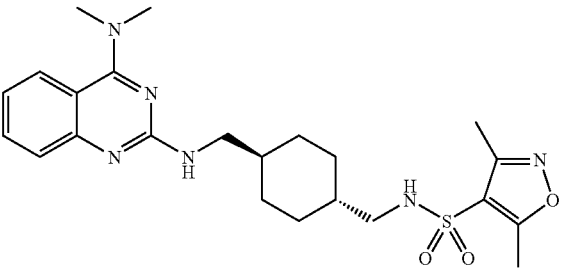 | 473 (M + H) |
| 187 | 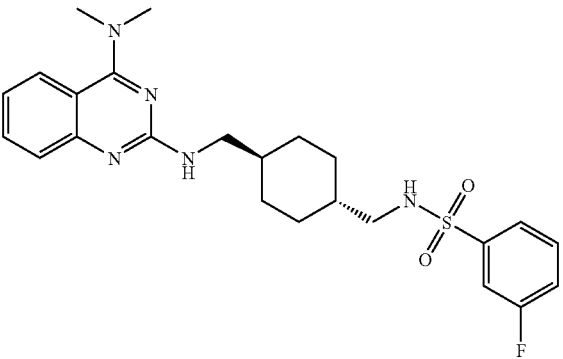 | 472 (M + H) |
| 188 | 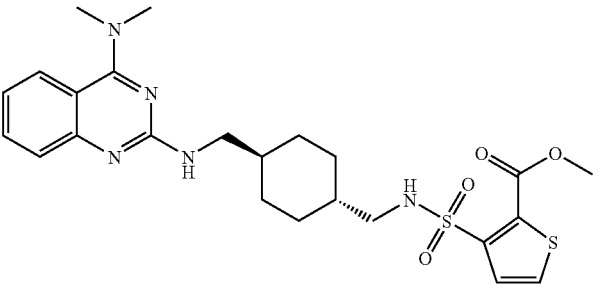 | 518 (M + H) |

-continued
| Example No. | Structure | APCI-MS |
|---|---|---|
| 189 | 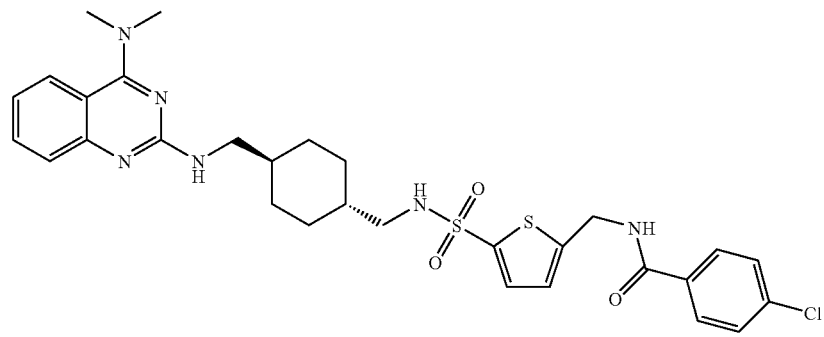 | 627 (M + H) |
| 190 | 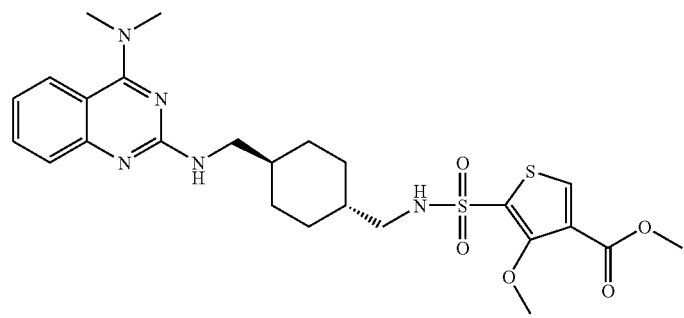 | 548 (M + H) |
| 191 | 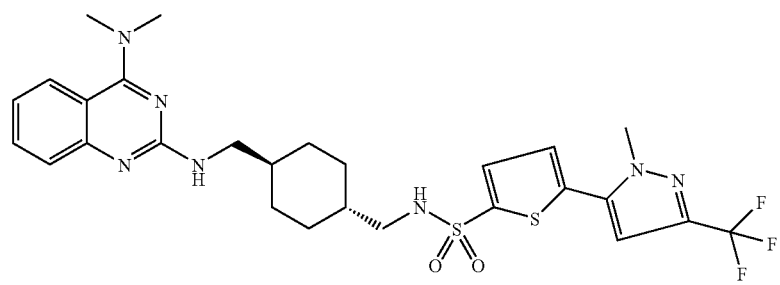 | 608 (M + H) |
| 192 | 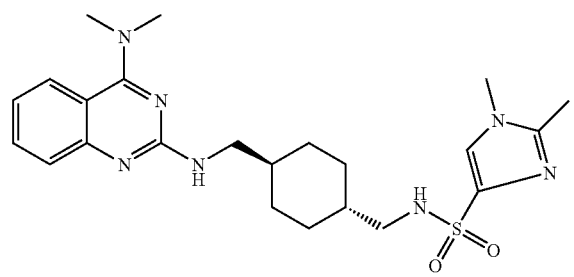 | 472 (M + H) |
| 193 | 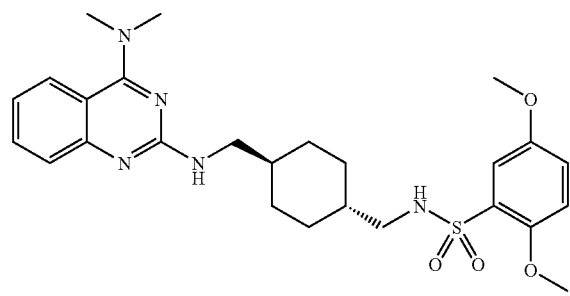 | 514 (M + H) |

-continued

| Example No. | Structure | APCI-MS |
| --- | --- | --- |
| 194 | 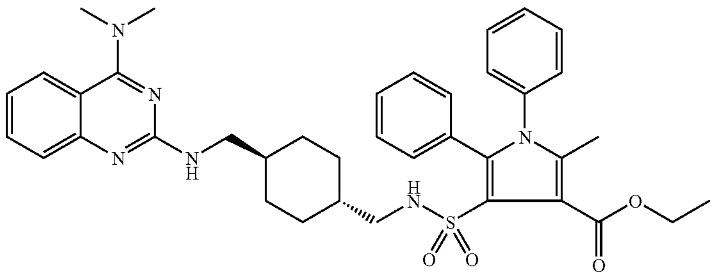 | 681 (M + H) |
| 195 | 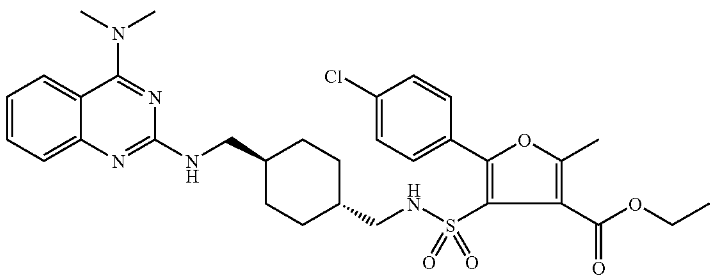 | 640 (M + H) |
| 196 | 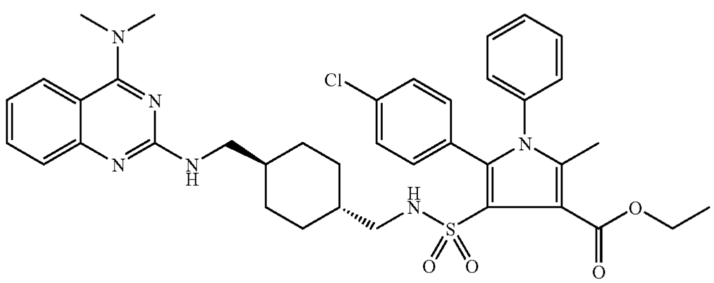 | 715 (M + H) |
| 197 | 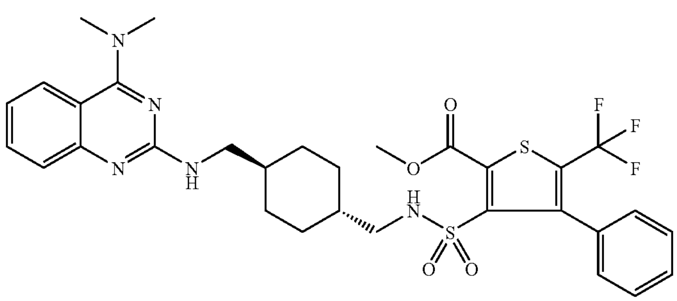 | 662 (M + H) |
| 198 | 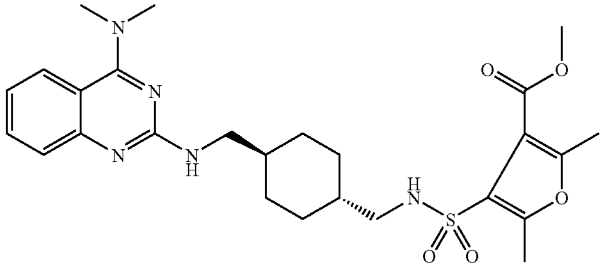 | 530 (M + H) |

-continued
| Example No. | Structure | APCI-MS |
|---|---|---|
| 199 | 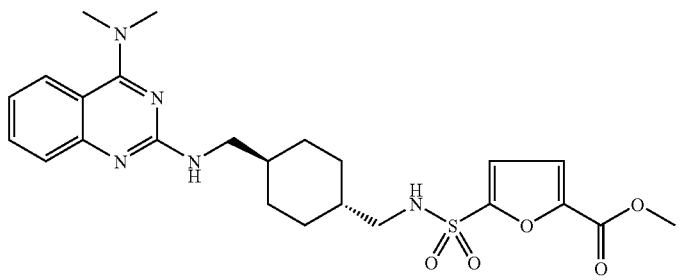 | 502 (M + H) |
| 200 | 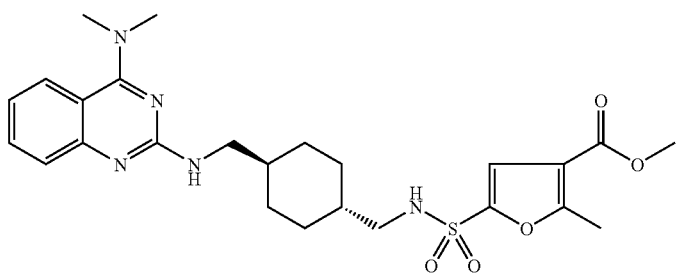 | 516 (M + H) |
| 201 | 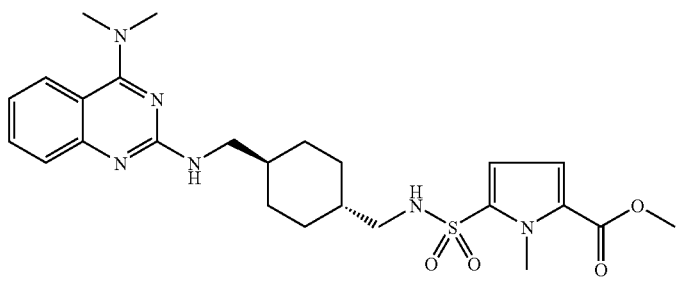 | 515 (M + H) |
| 202 | 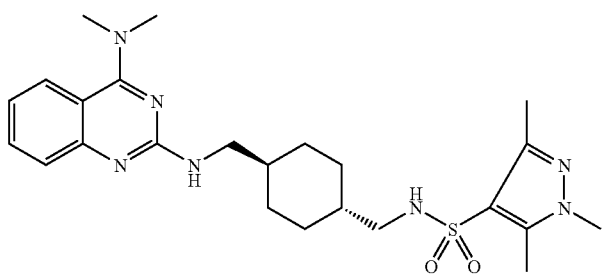 | 486 (M + H) |
| 203 | 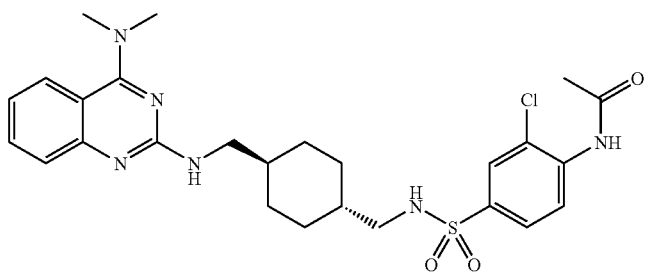 | 545 (M + H) |

-continued
| Example No. | Structure | APCI-MS |
|---|---|---|
| 204 | 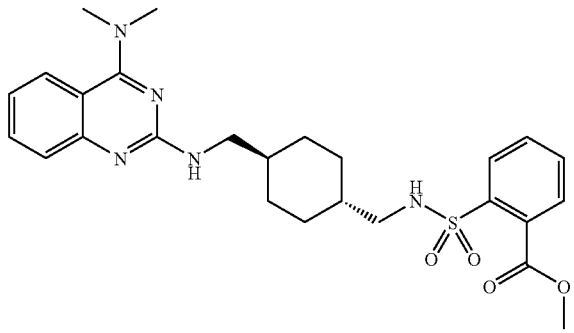 | 512 (M + H) |
| 205 | 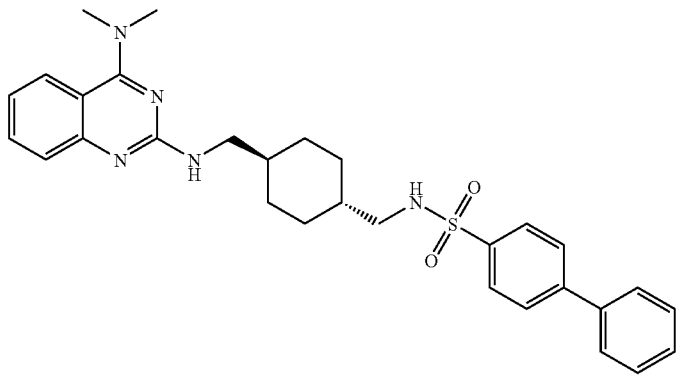 | 530 (M + H) |
| 206 | 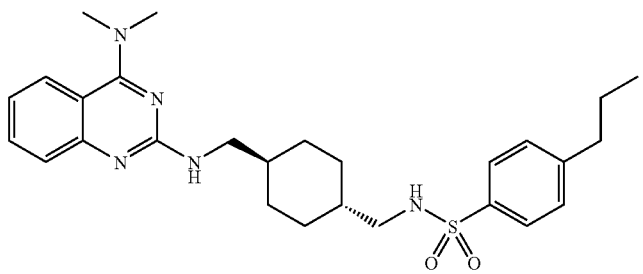 | 496 (M + H) |
| 207 | 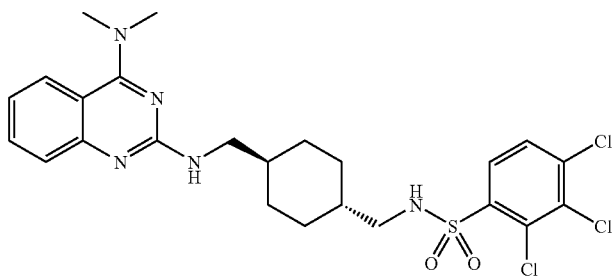 | 556 (M + H) |
| 208 | 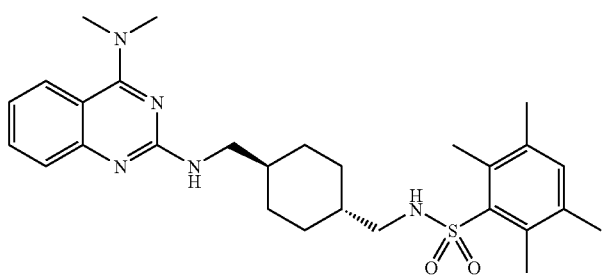 | 510 (M + H) |

-continued
| Example No. | Structure | APCI-MS |
|---|---|---|
| 209 | 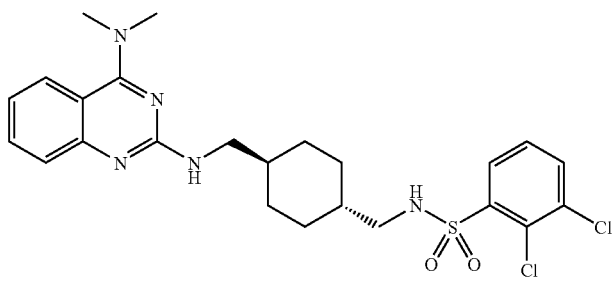 | 522 (M + H) |
| 210 | 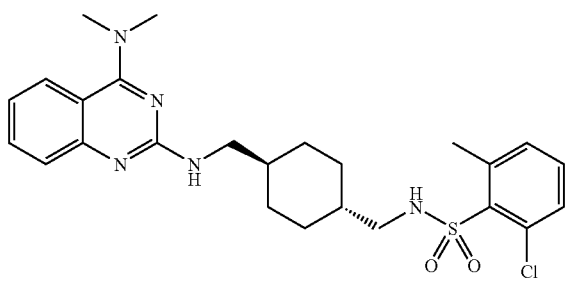 | 502 (M + H) |
| 211 | 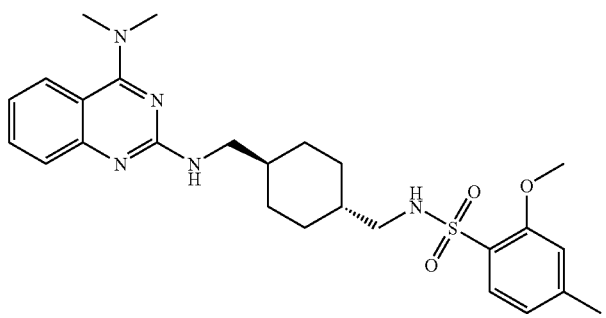 | 498 (M + H) |
| 212 | 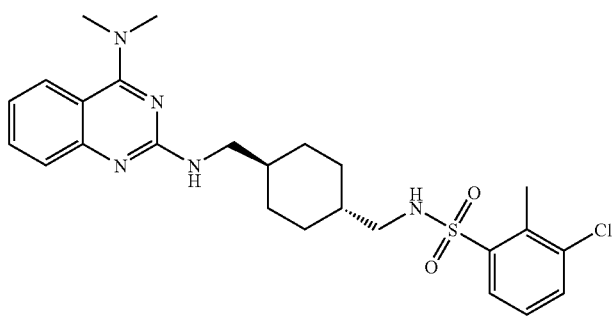 | 502 (M + H) |
| 213 | 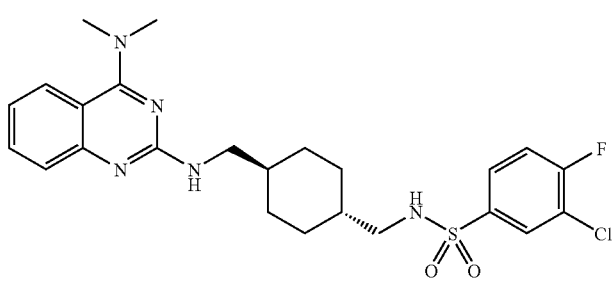 | 506 (M + H) |

-continued
| Example No. | Structure | APCI-MS |
|---|---|---|
| 214 | 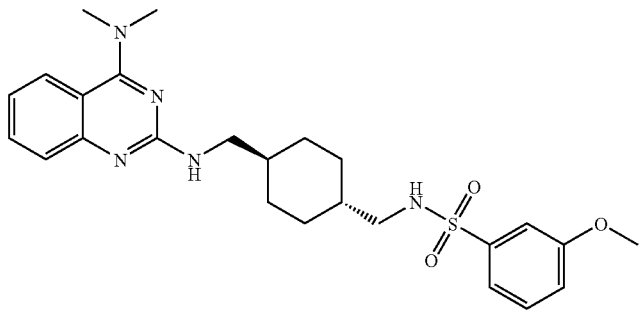 | 484 (M + H) |
| 215 | 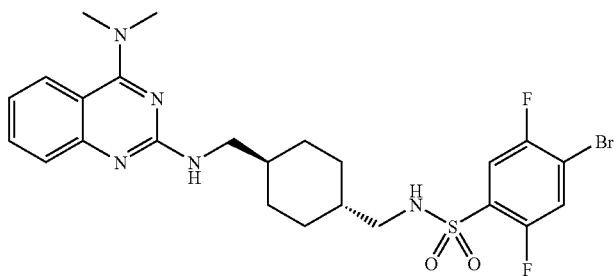 | 568 (M + H) |
| 216 | 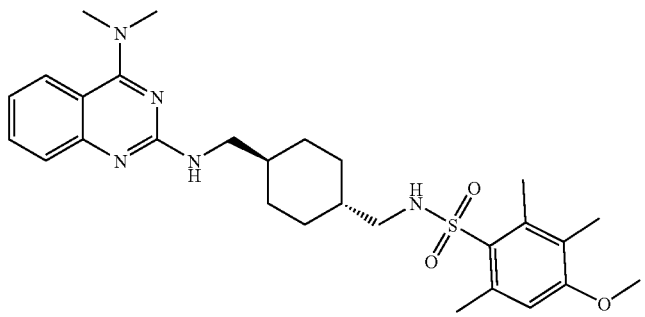 | 526 (M + H) |
| 217 | 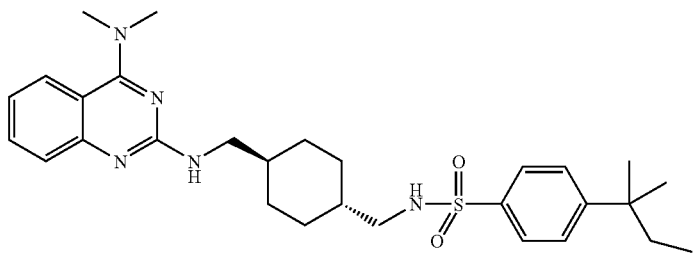 | 524 (M + H) |
| 218 | 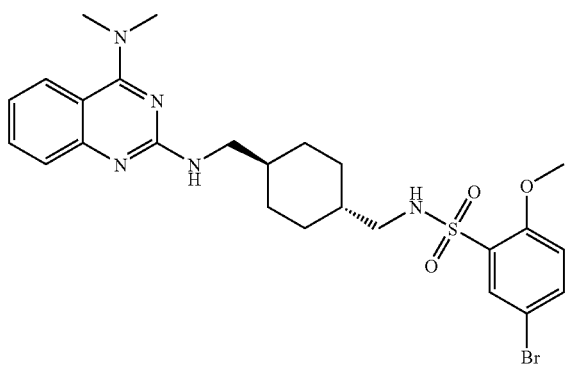 | 562 (M + H) |

-continued

| Example No. | Structure | APCI-MS |
|---|---|---|
| 219 | 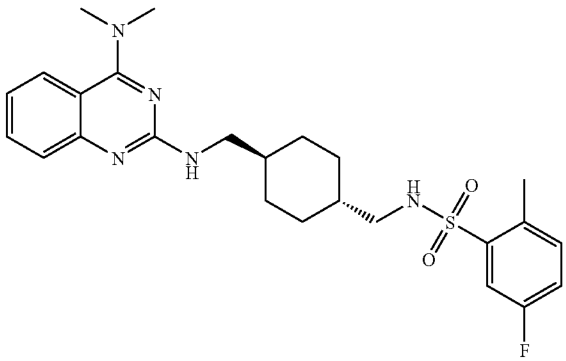 | 486 (M + H) |
| 220 | 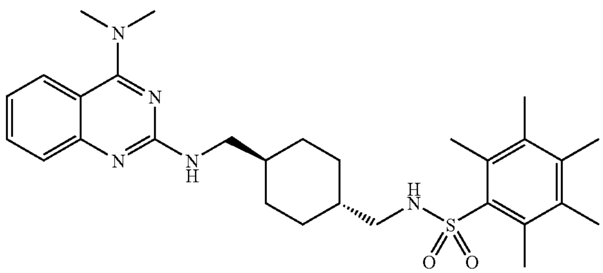 | 524 (M + H) |
| 221 | 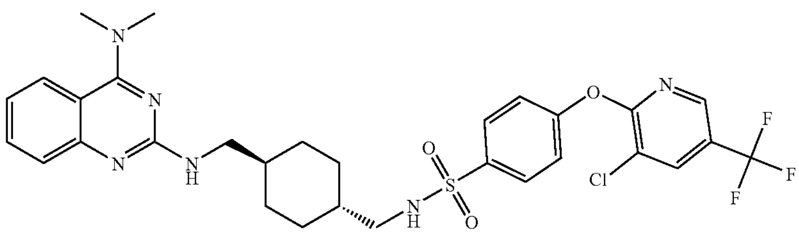 | 649 (M + H) |
| 222 | 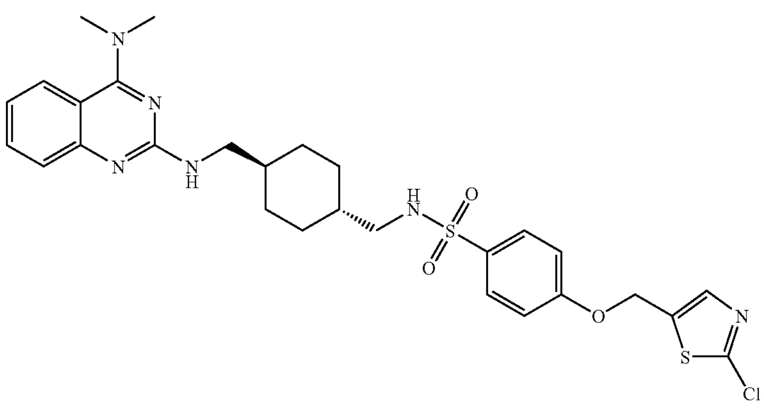 | 601 (M + H) |
| 223 | 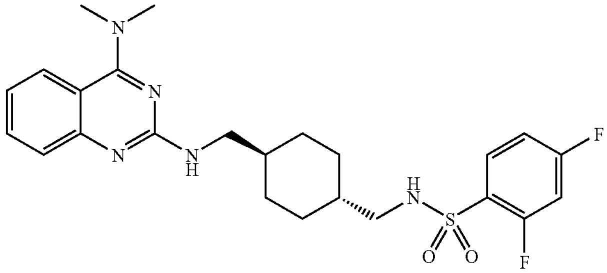 | 490 (M + H) |

-continued
| Example No. | Structure | APCI-MS |
|---|---|---|
| 224 | 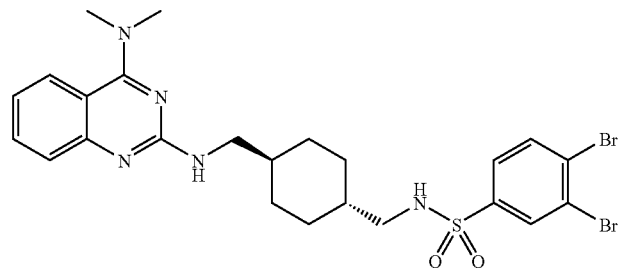 | 610 (M + H) |
| 225 | 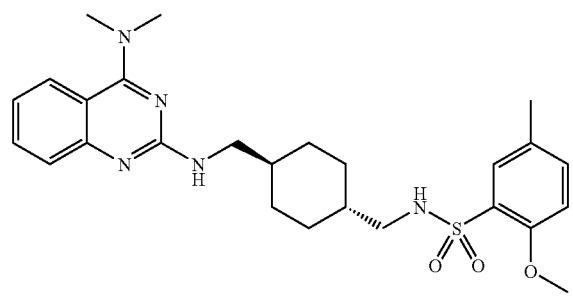 | 498 (M + H) |
| 226 | 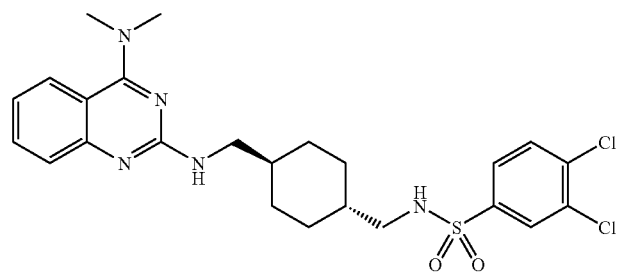 | 522 (M + H) |
| 227 | 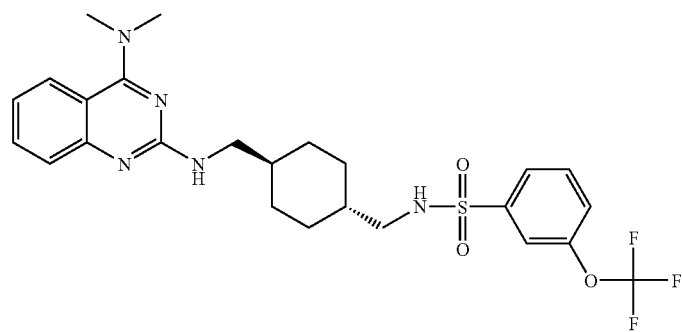 | 538 (M + H) |
| 228 | 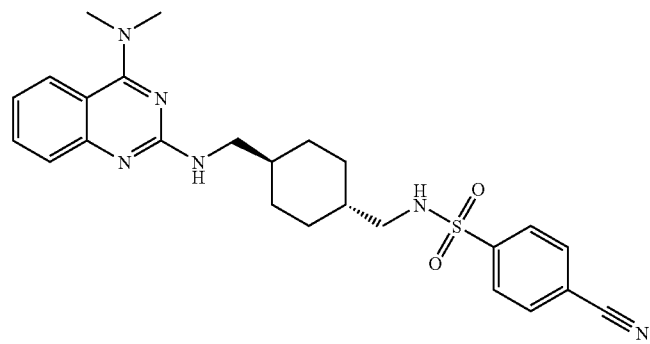 | 479 (M + H) |

-continued

| Example No. | Structure | APCI-MS |
|---|---|---|
| 229 | 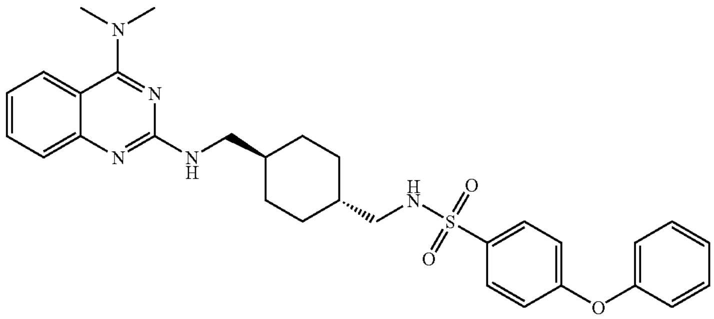 | 546 (M + H) |
| 230 | 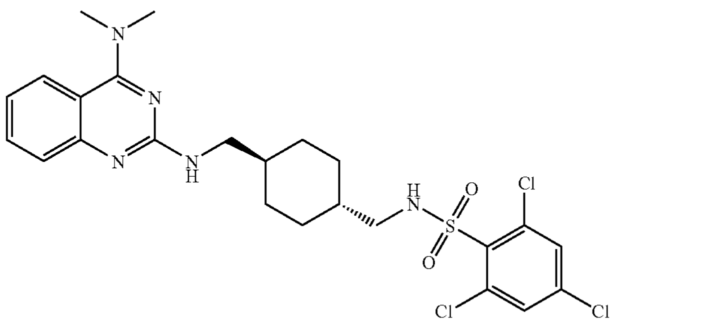 | 556 (M + H) |
| 231 | 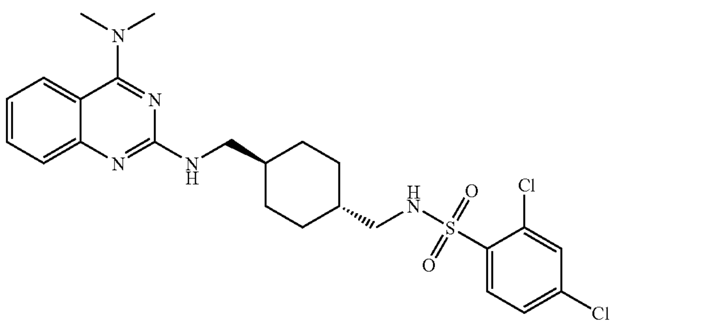 | 522 (M + H) |
| 232 | 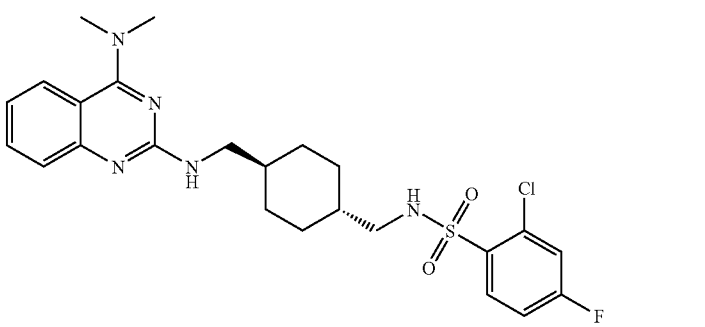 | 506 (M + H) |
| 233 | 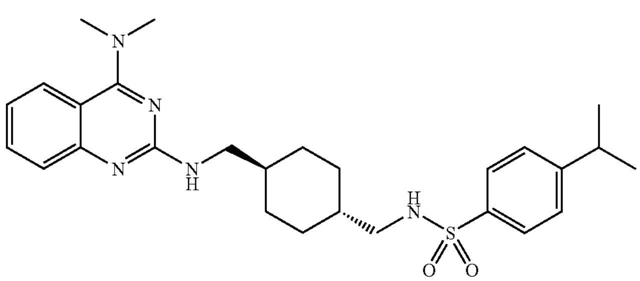 | 496 (M + H) |

| Example No. | Structure | APCI-MS |
|---|---|---|
| 234 | 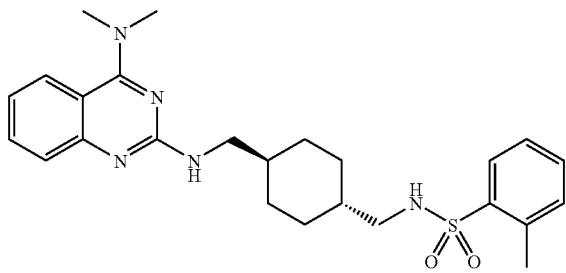 | 580 (M + H) |
| 235 | 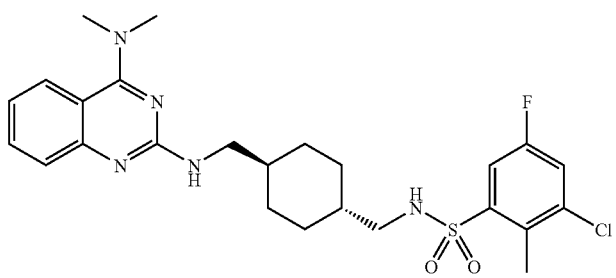 | 520 (M + H) |
| 236 | 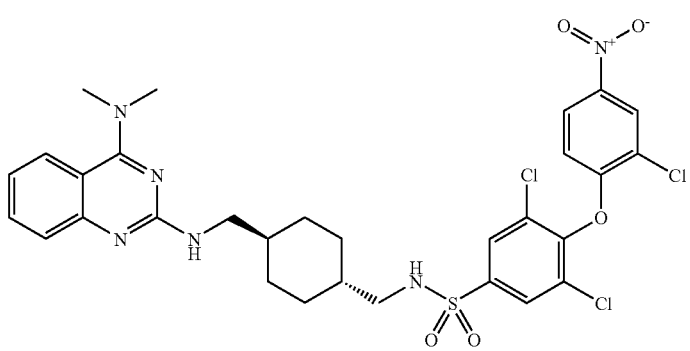 | 693 (M + H) |
| 237 | 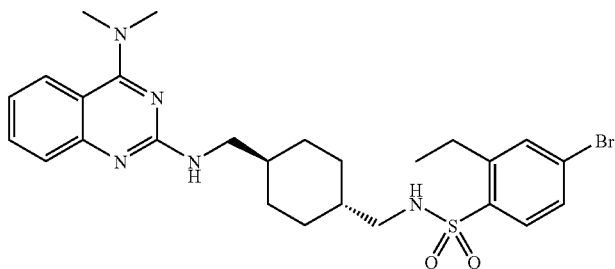 | 560 (M + H) |
| 238 | 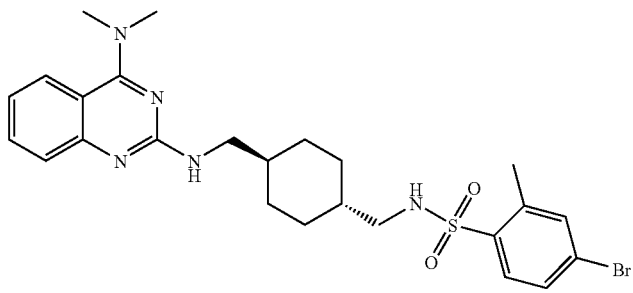 | 546 (M + H) |

-continued
| Example No. | Structure | APCI-MS |
|---|---|---|
| 239 | 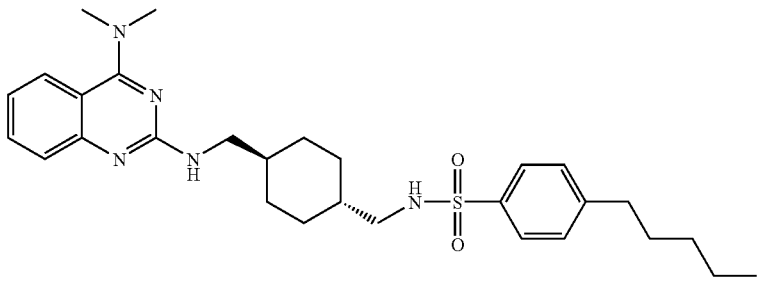 | 524 (M + H) |
| 240 | 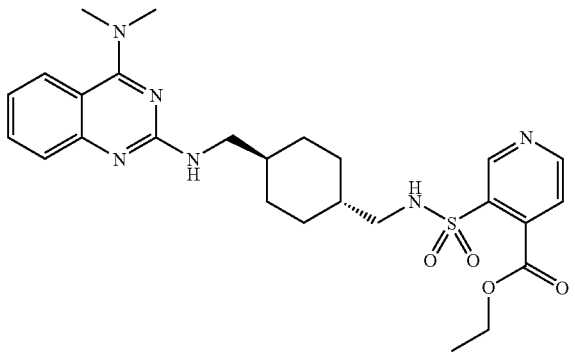 | 527 (M + H) |
| 241 | 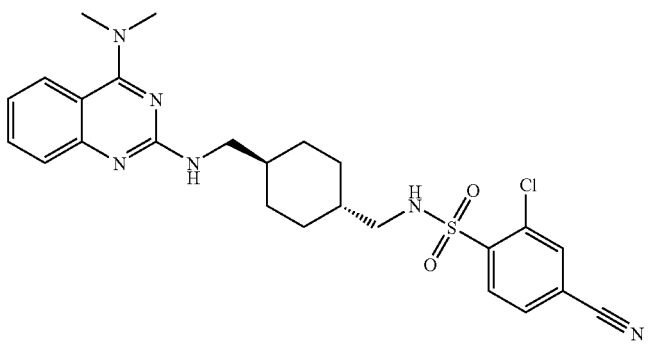 | 513 (M + H) |
| 242 | 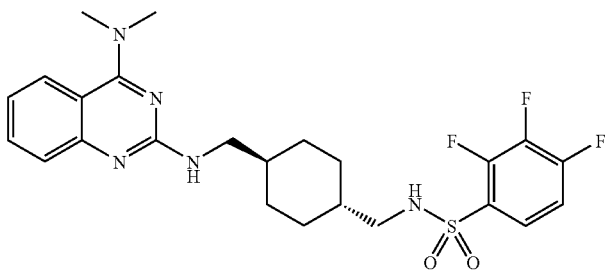 | 508 (M + H) |

| Example No. | Structure | APCI-MS |
|---|---|---|
| 243 | 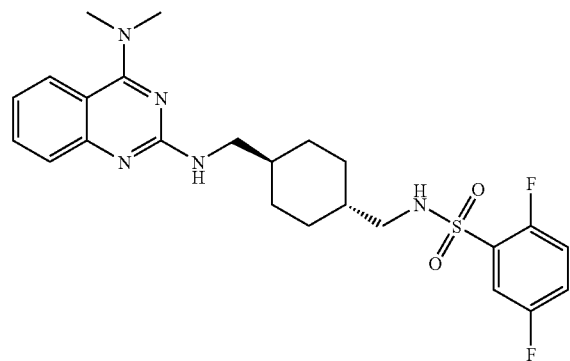 | 490 (M + H) |
| 244 | 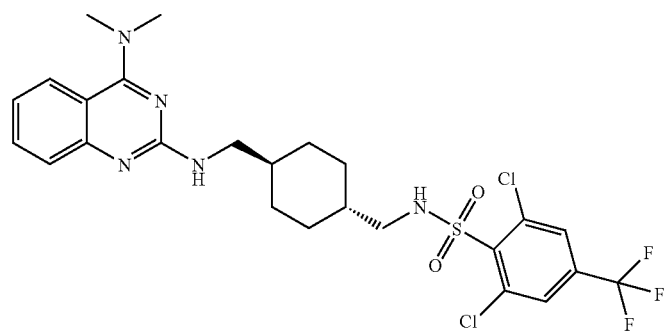 | 590 (M + H) |
| 245 | 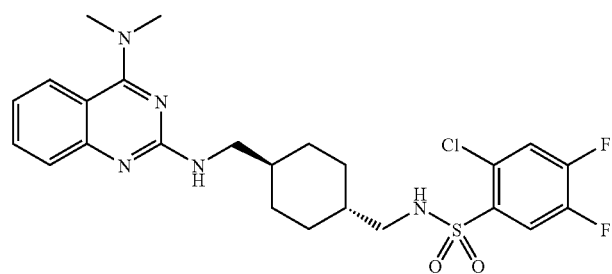 | 524 (M + H) |
| 246 | 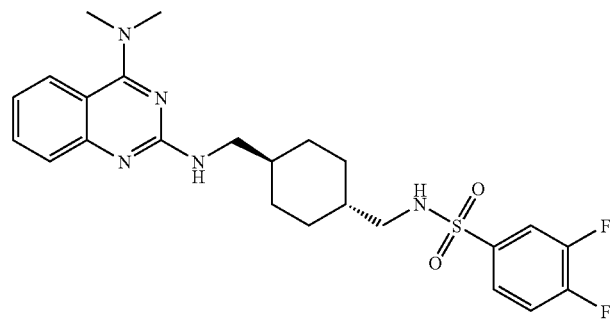 | 490 (M + H) |

-continued
| Example No. | Structure | APCI-MS |
|---|---|---|
| 247 | 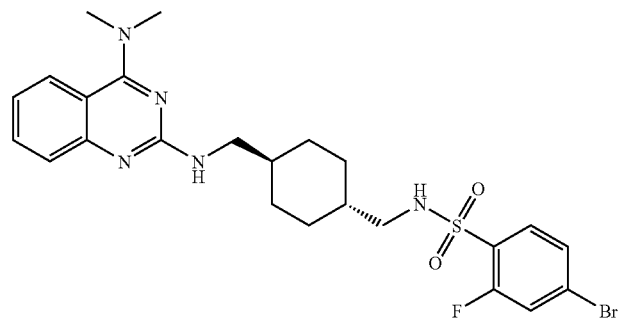 | 550 (M + H) |
| 248 | 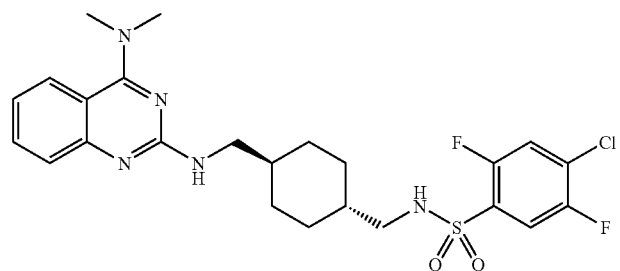 | 524 (M + H) |
| 249 | 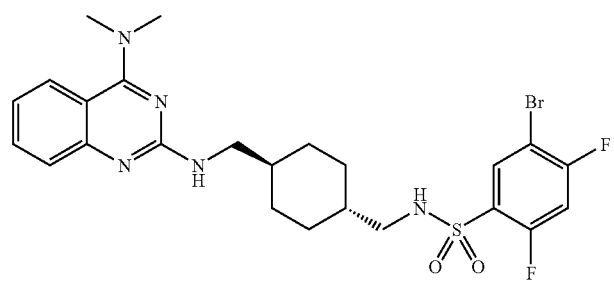 | 568 (M + H) |
| 250 | 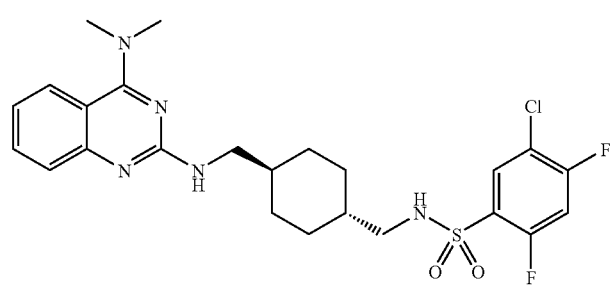 | 524 (M + H) |
| 251 | 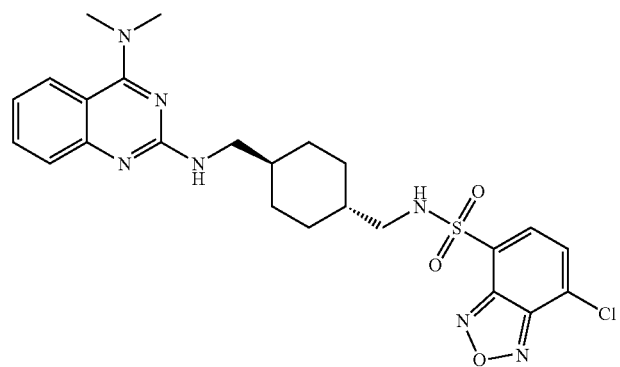 | 530 (M + H) |

-continued
| Example No. | Structure | APCI-MS |
|---|---|---|
| 252 | 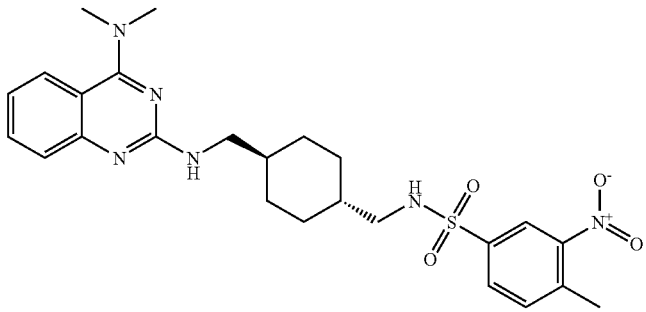 | 513 (M + H) |
| 253 | 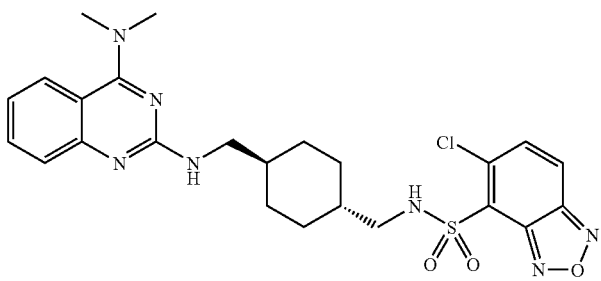 | 530 (M + H) |
| 254 | 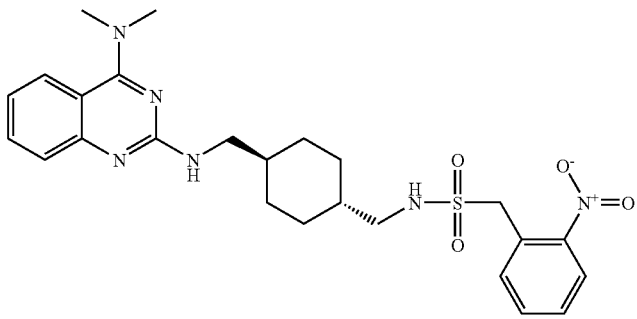 | 513 (M + H) |
| 255 | 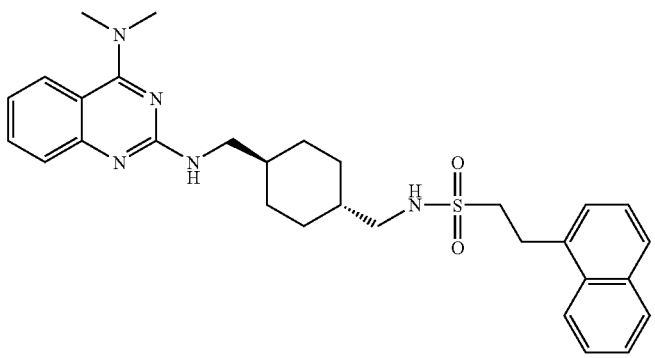 | 532 (M + H) |
| 256 | 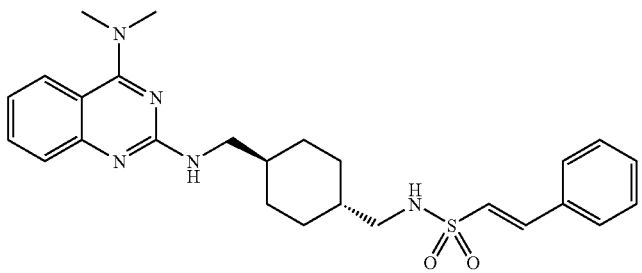 | 480 (M + H) |

-continued
| Example No. | Structure | APCI-MS |
|---|---|---|
| 257 | 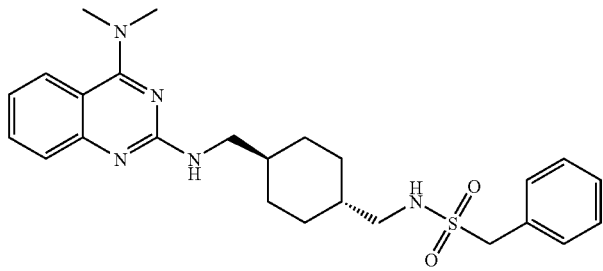 | 468 (M + H) |
| 258 | 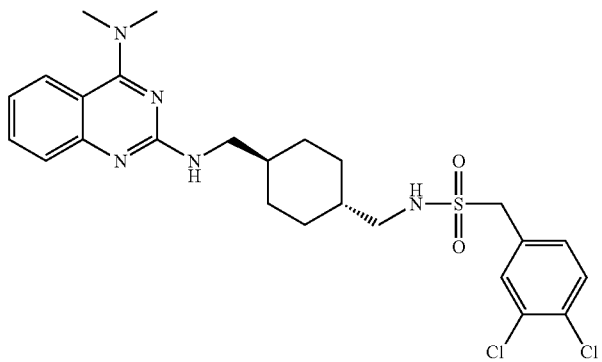 | 536 (M + H) |
| 259 | 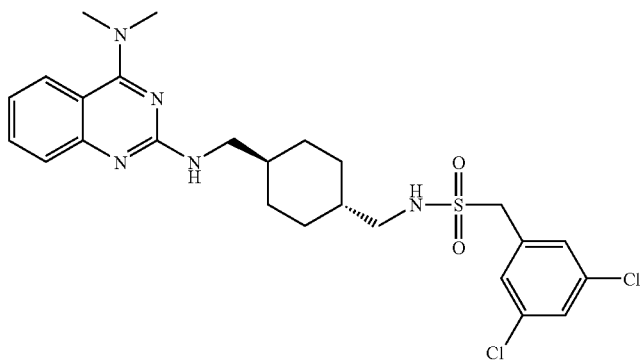 | 536 (M + H) |
| 260 | 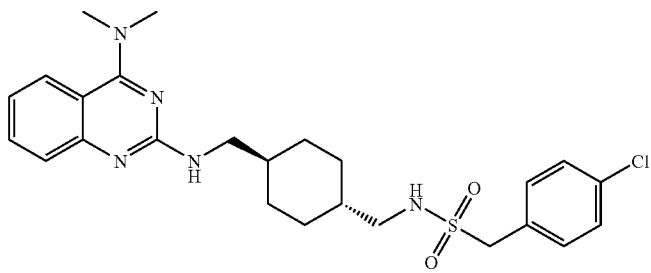 | 502 (M + H) |
| 261 | 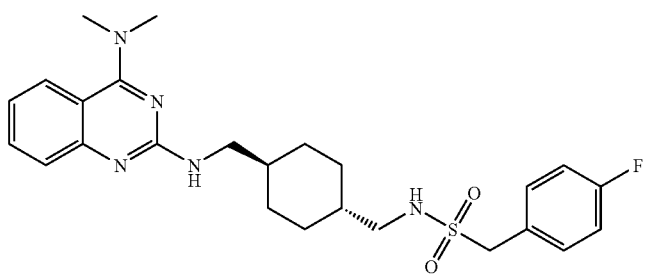 | 486 (M + H) |

-continued
| Example No. | Structure | APCI-MS |
| --- | --- | --- |
| 262 | 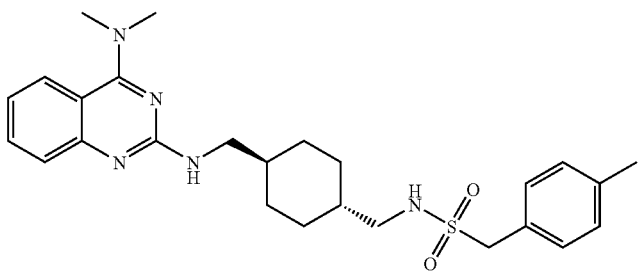 | 482 (M + H) |
| 263 | 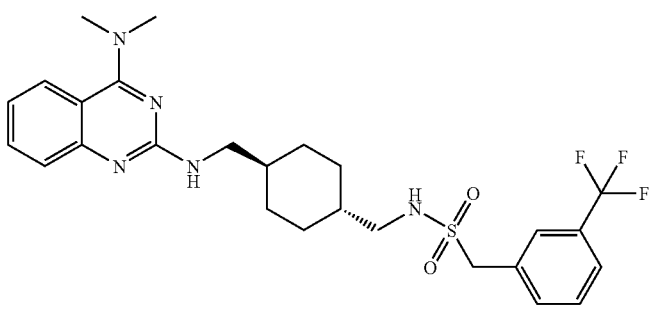 | 536 (M + H) |
| 264 | 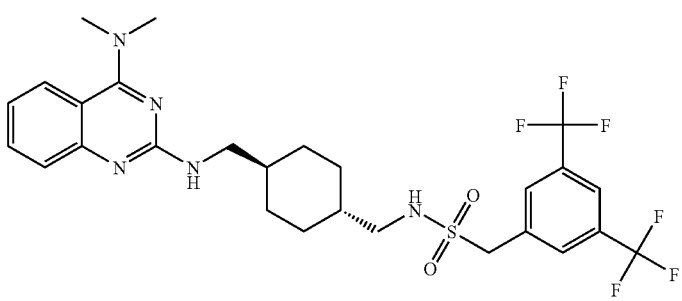 | 604 (M + H) |
| 265 | 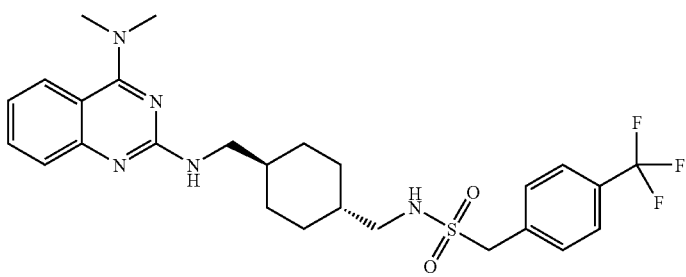 | 536 (M + H) |
| 266 | 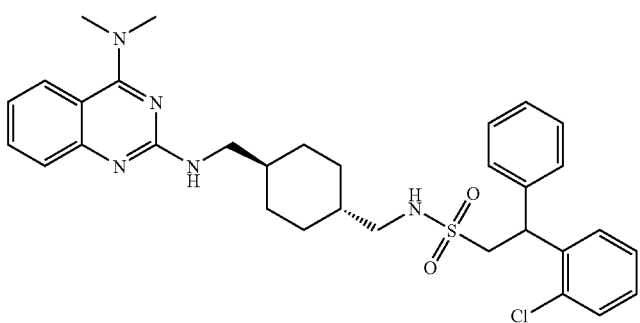 | 592 (M + H) |

-continued
| Example No. | Structure | APCI-MS |
|---|---|---|
| 267 | 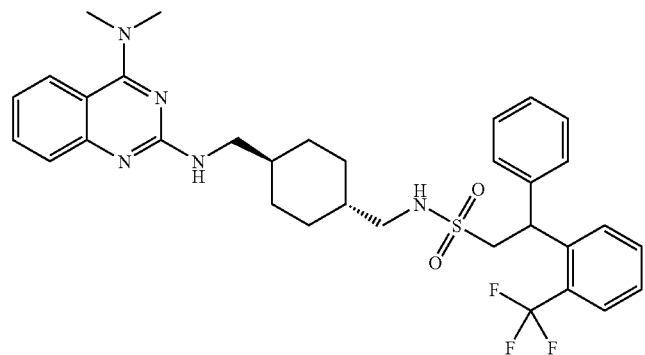 | 626 (M + H) |
| 268 | 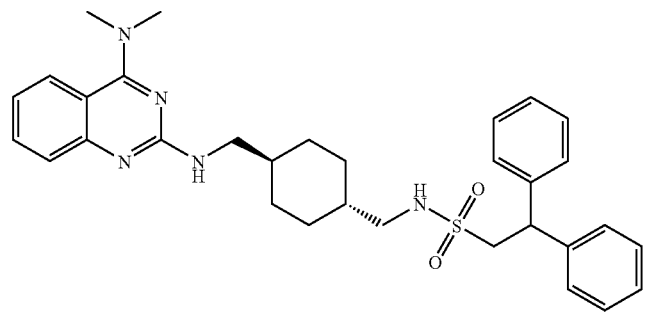 | 558 (M + H) |
| 269 | 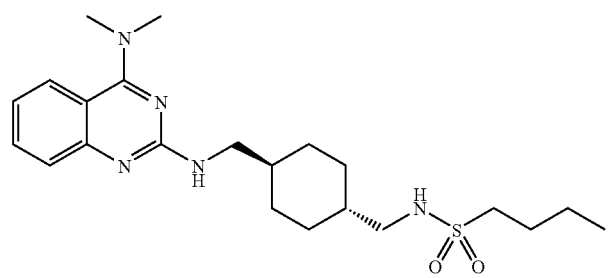 | 434 (M + H) |
| 270 | 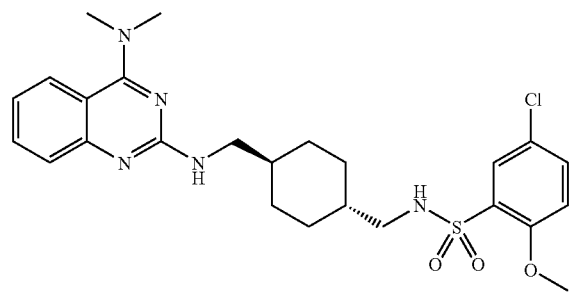 | 518 (M + H) |
| 271 | 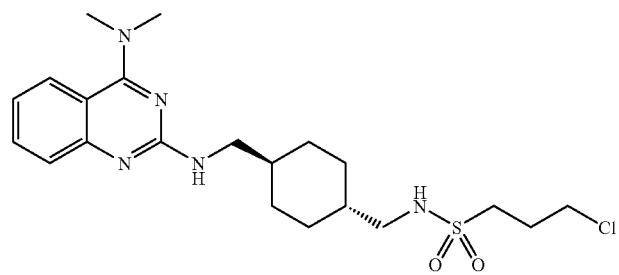 | 454 (M + H) |

-continued

| Example No. | Structure | APCI-MS |
|---|---|---|
| 272 | 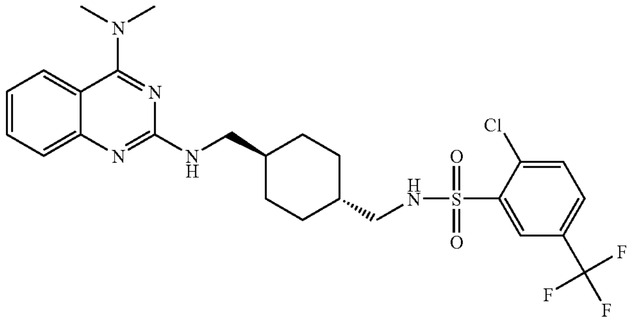 | 556 (M + H) |
| 273 | 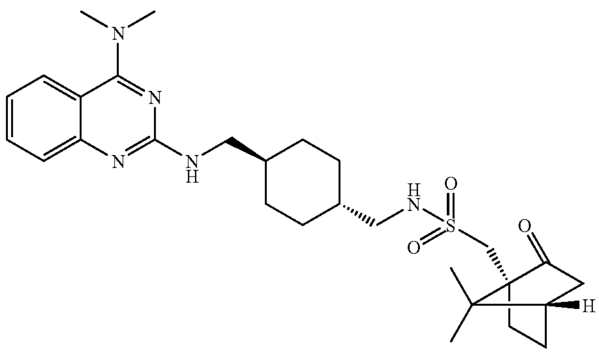 | 528 (M + H) |
| 274 | 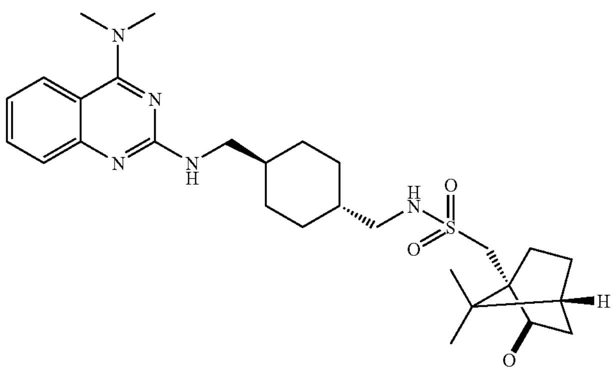 | 528 (M + H) |
| 275 | 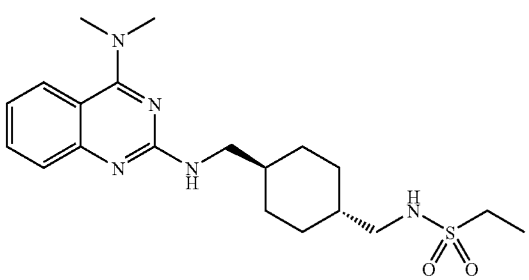 | 406 (M + H) |
| 276 | 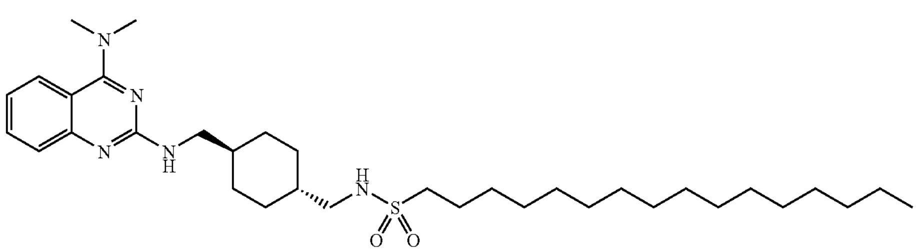 | 602 (M + H) |

-continued
| Example No. | Structure | APCI-MS |
|---|---|---|
| 277 | 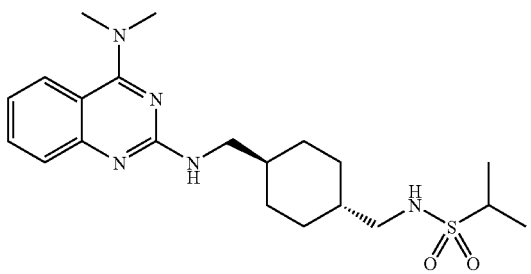 | 420 (M + H) |
| 278 | 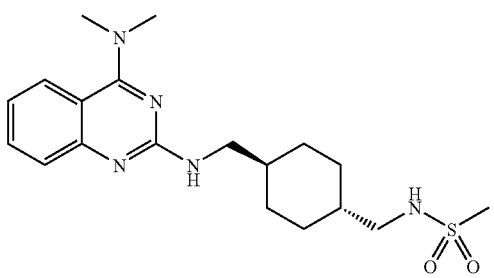 | 392 (M + H) |
| 279 | 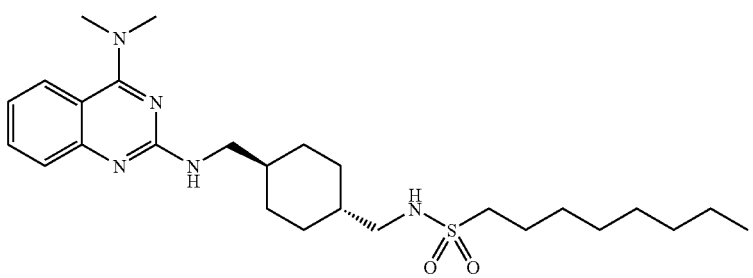 | 490 (M + H) |
| 280 | 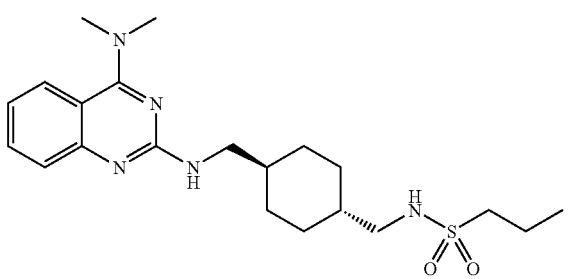 | 420 (M + H) |
| 281 | 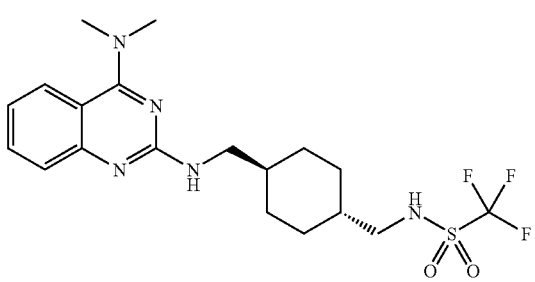 | 446 (M + H) |

-continued
| Example No. | Structure | APCI-MS |
|---|---|---|
| 282 | 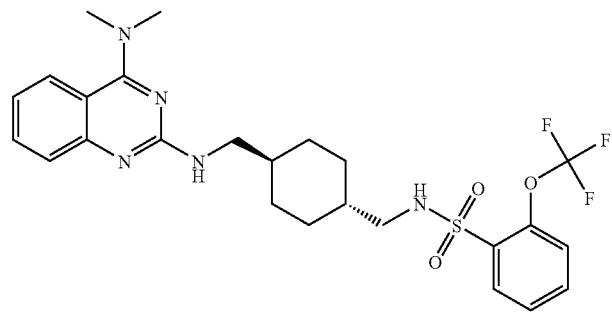 | 538 (M + H) |
| 283 | 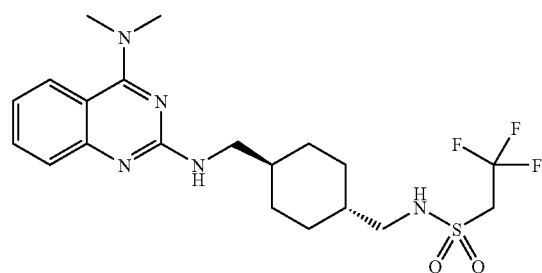 | 460 (M + H) |
| 284 | 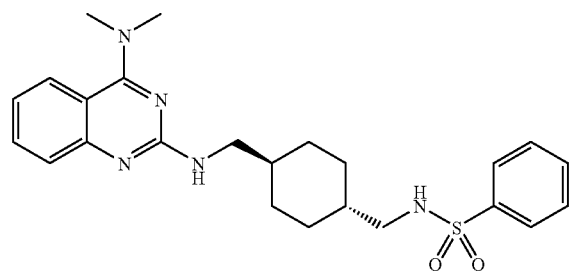 | 454 (M + H) |
| 285 | 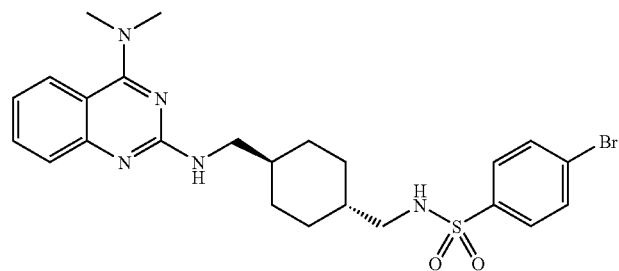 | 532 (M + H) |
| 286 | 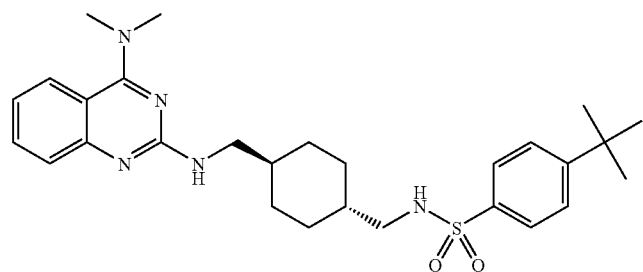 | 510 (M + H) |

-continued
| Example No. | Structure | APCI-MS |
|---|---|---|
| 287 | 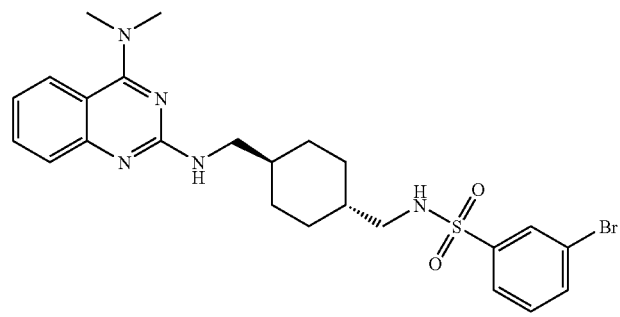 | 532 (M + H) |
| 288 | 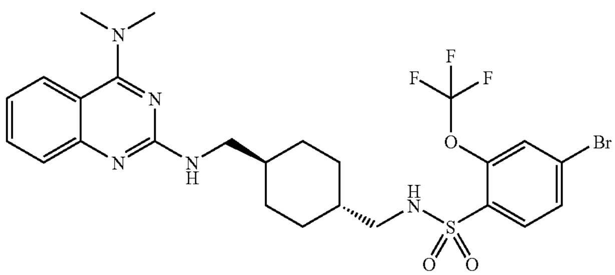 | 616 (M + H) |
| 289 | 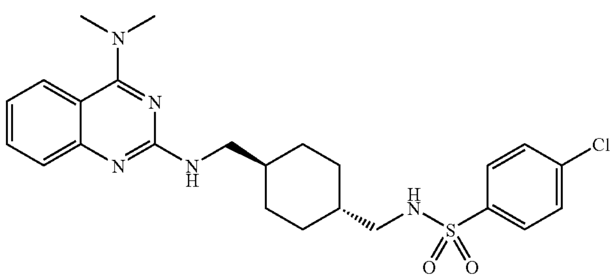 | 488 (M + H) |
| 290 | 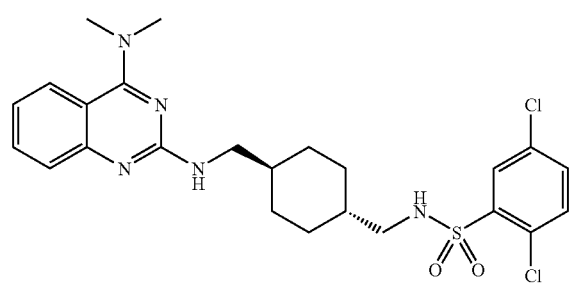 | 522 (M + H) |
| 291 | 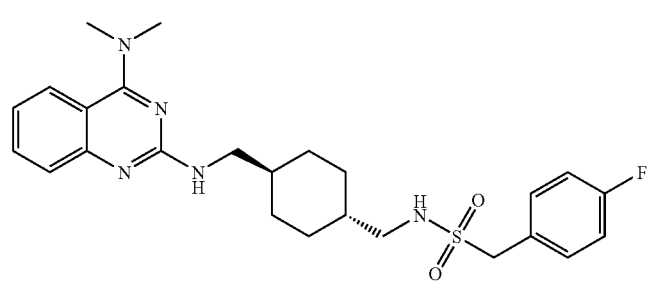 | 528 (M + H) |

| Example No. | Structure | APCI-MS |
|---|---|---|
| 292 | 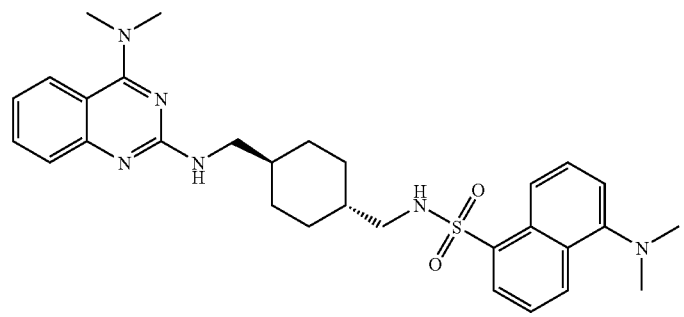 | 547 (M + H) |
| 293 | 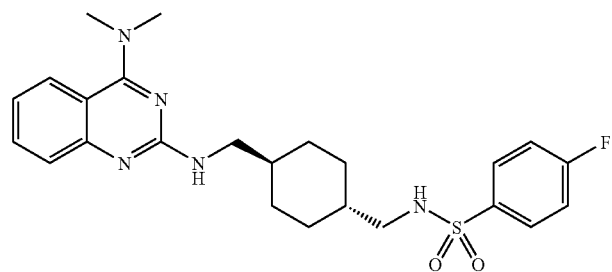 | 472 (M + H) |
| 294 | 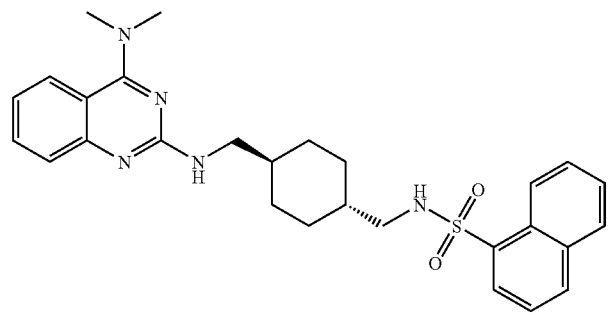 | 504 (M + H) |
| 295 | 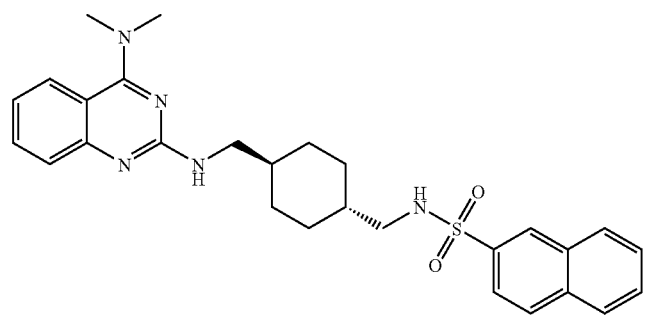 | 504 (M + H) |
| 296 | 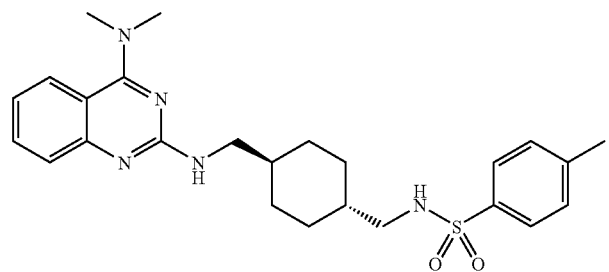 | 468 (M + H) |

-continued
| Example No. | Structure | APCI-MS |
|---|---|---|
| 297 | 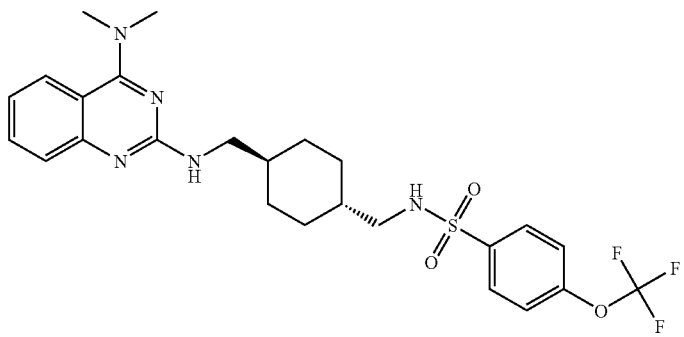 | 538 (M + H) |
| 298 | 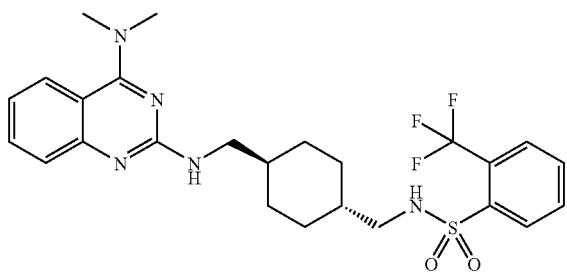 | 522 (M + H) |
| 299 | 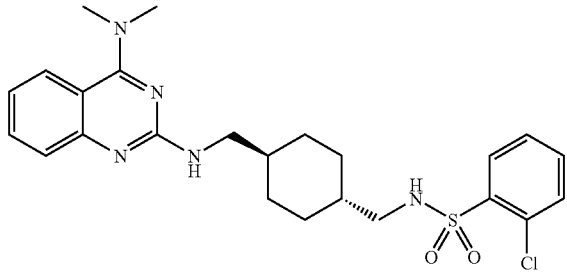 | 488 (M + H) |
| 300 | 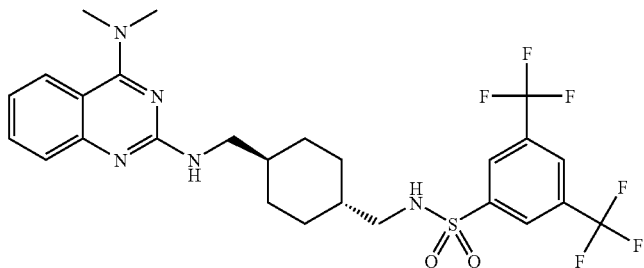 | 590 (M + H) |
| 301 | 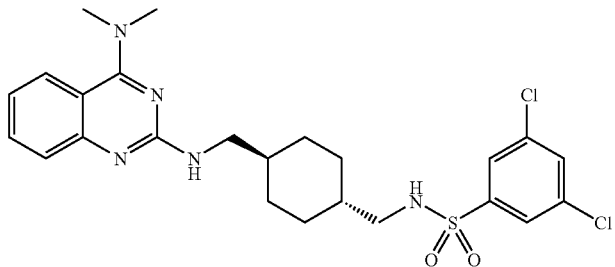 | 522 (M + H) |

-continued
| Example No. | Structure | APCI-MS |
|---|---|---|
| 302 | 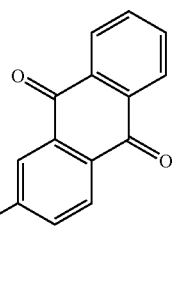 | 520 (M + H) |
| 303 | 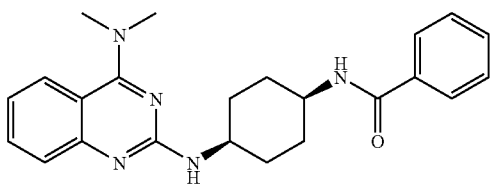 | 390 (M + H) |
| 304 | 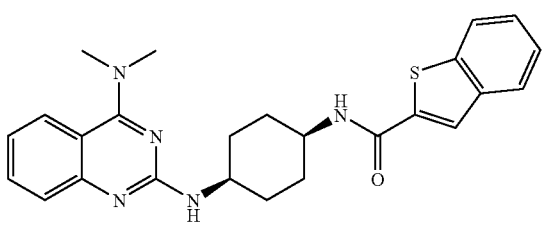 | 446 (M + H) |
| 305 | 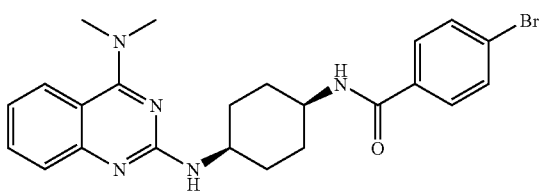 | 468 (M + H) |
| 306 | 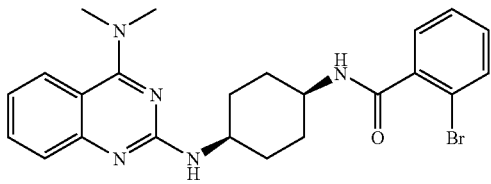 | 468 (M + H) |
| 307 | 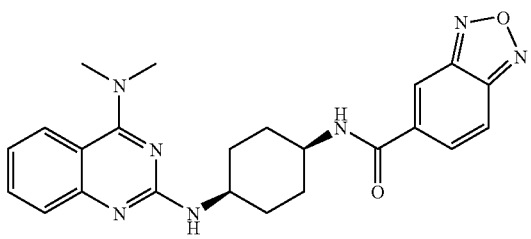 | 432 (M + H) |
| 308 | 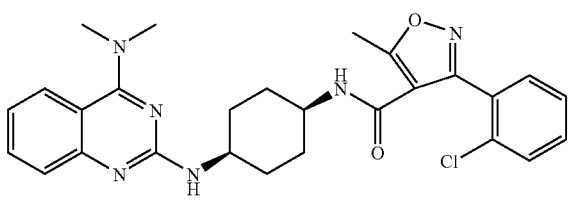 | 505 (M + H) |

-continued
| Example No. | Structure | APCI-MS |
|---|---|---|
| 309 | 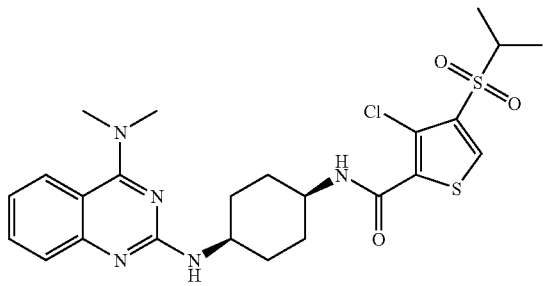 | 536 (M + H) |
| 310 | 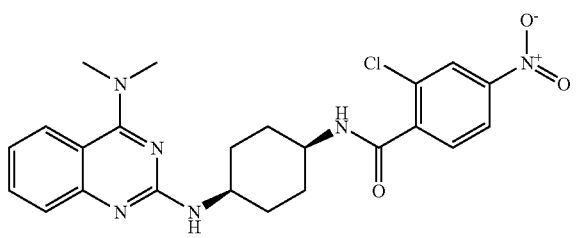 | 469 (M + H) |
| 311 | 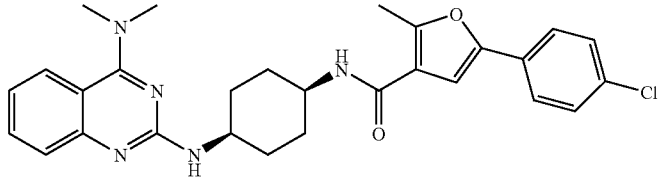 | 504 (M + H) |
| 312 | 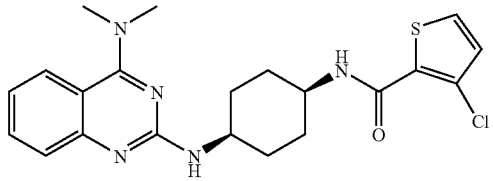 | 430 (M + H) |
| 313 | 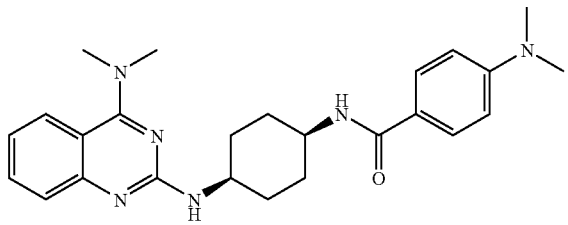 | 433 (M + H) |
| 314 | 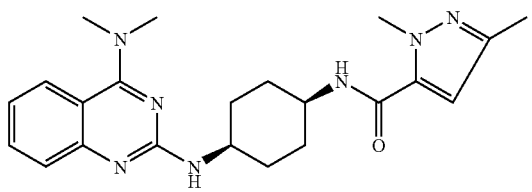 | 408 (M + H) |

-continued

| Example No. | Structure | APCI-MS |
|---|---|---|
| 315 | 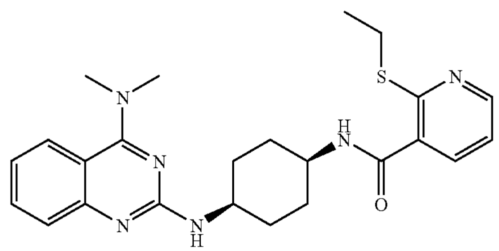 | 451 (M + H) |
| 316 | 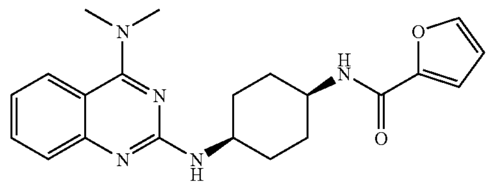 | 380 (M + H) |
| 317 | 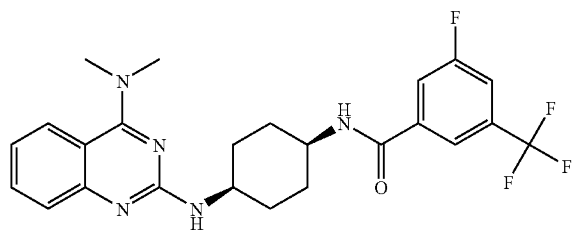 | 476 (M + H) |
| 318 | 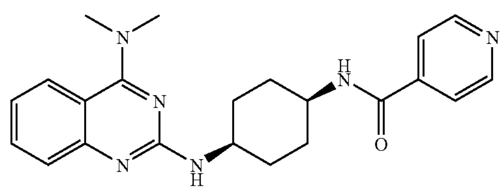 | 391 (M + H) |
| 319 | 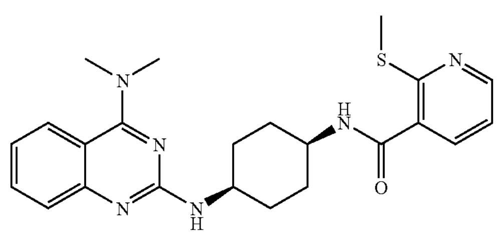 | 437 (M + H) |
| 320 | 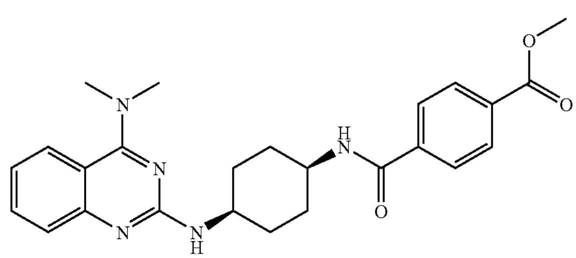 | 448 (M + H) |
| 321 | 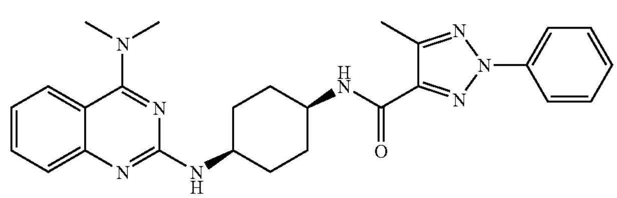 | 471 (M + H) |

-continued
| Example No. | Structure | APCI-MS |
|---|---|---|
| 322 | 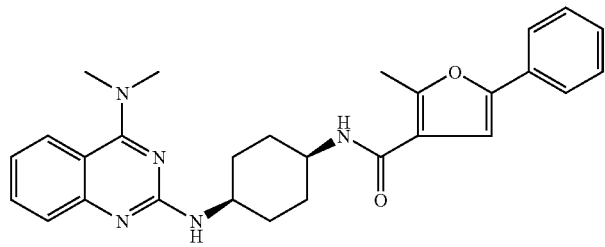 | 470 (M + H) |
| 323 | 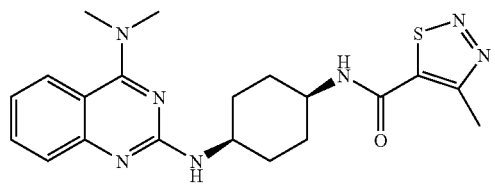 | 412 (M + H) |
| 324 | 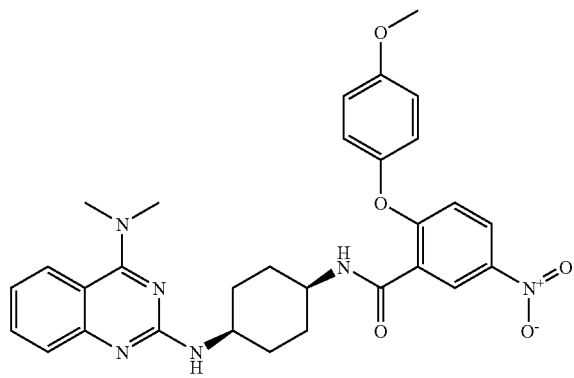 | 557 (M + H) |
| 325 | 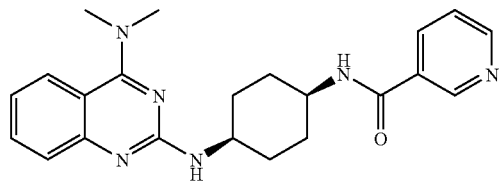 | 391 (M + H) |
| 326 | 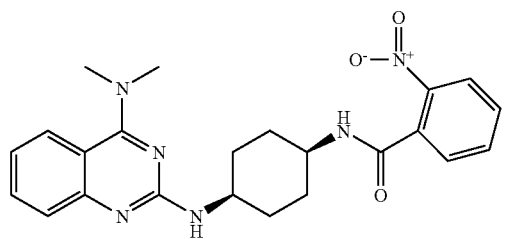 | 435 (M + H) |
| 327 | 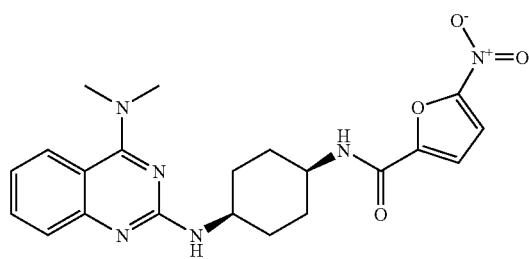 | 425 (M + H) |

-continued
| Example No. | Structure | APCI-MS |
|---|---|---|
| 328 | 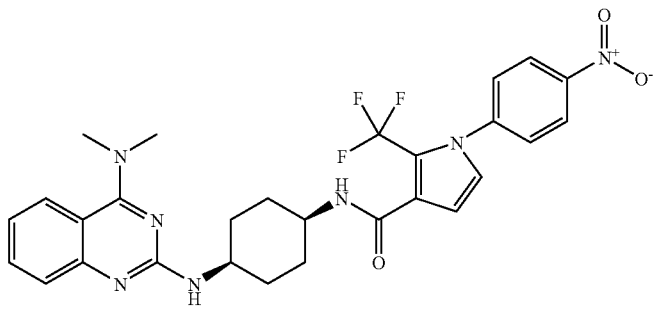 | 569 (M + H) |
| 329 | 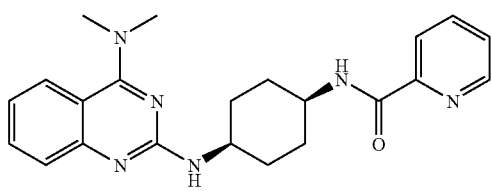 | 391 (M + H) |
| 330 | 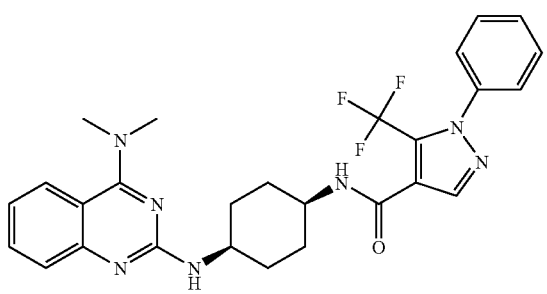 | 524 (M + H) |
| 331 | 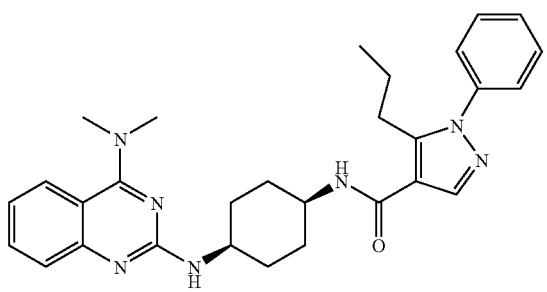 | 498 (M + H) |
| 332 | 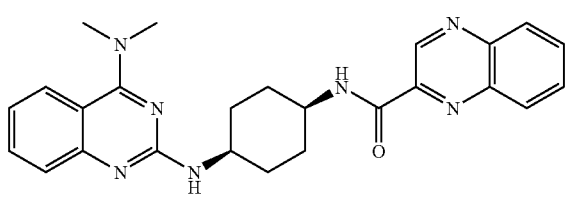 | 442 (M + H) |
| 333 | 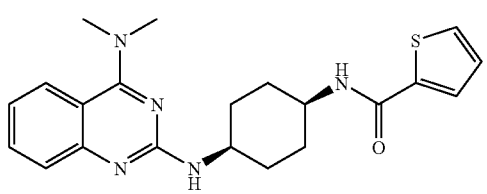 | 396 (M + H) |

-continued
| Example No. | Structure | APCI-MS |
|---|---|---|
| 334 | 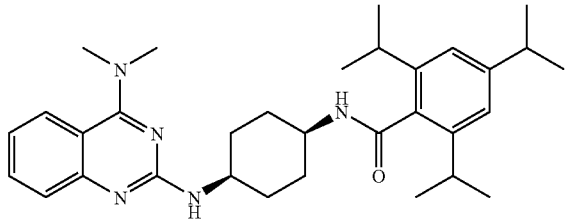 | 516 (M + H) |
| 335 | 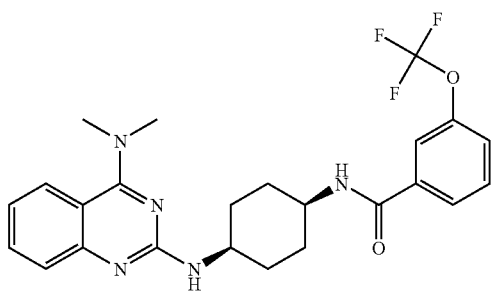 | 474 (M + H) |
| 336 | 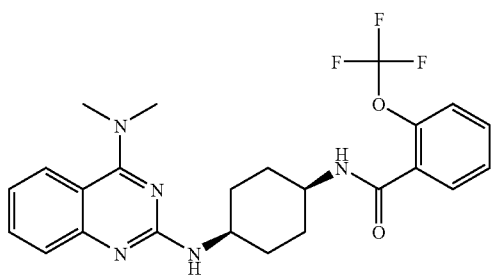 | 474 (M + H) |
| 337 | 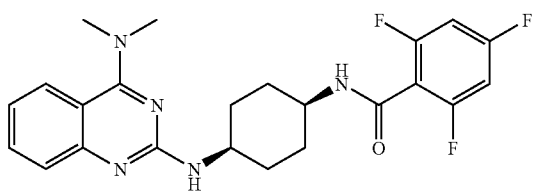 | 444 (M + H) |
| 338 | 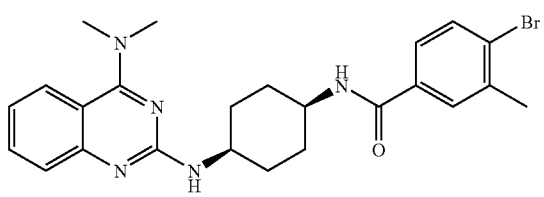 | 482 (M + H) |
| 339 | 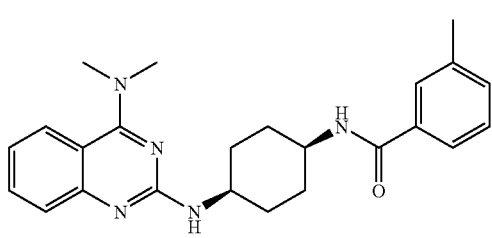 | 516 (M + H) |

-continued
| Example No. | Structure | APCI-MS |
|---|---|---|
| 340 | 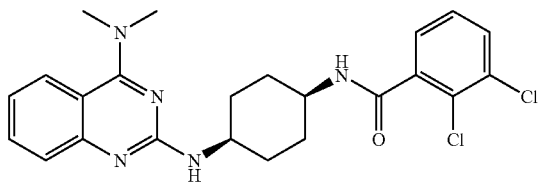 | 458 (M + H) |
| 341 | 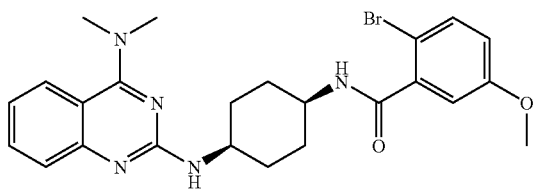 | 498 (M + H) |
| 342 | 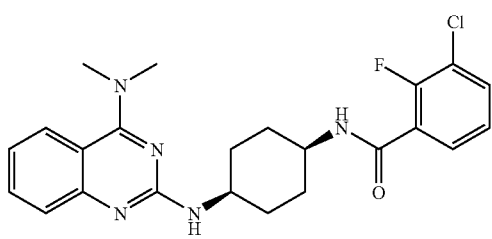 | 442 (M + H) |
| 343 | 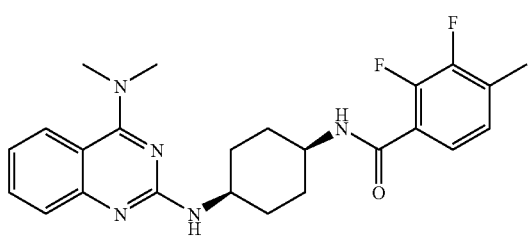 | 440 (M + H) |
| 344 | 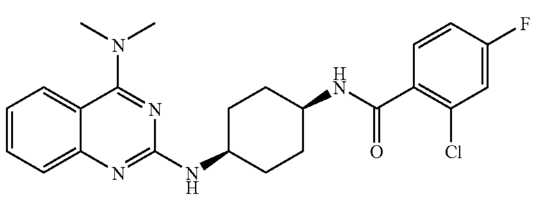 | 442 (M + H) |
| 345 | 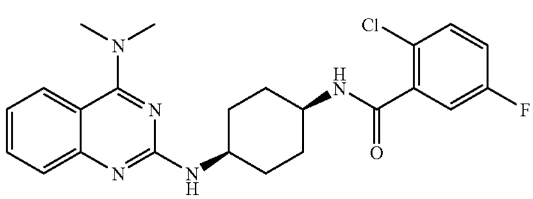 | 442 (M + H) |
| 346 | 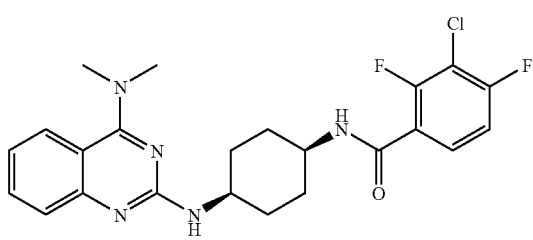 | 460 (M + H) |

-continued
| Example No. | Structure | APCI-MS |
|---|---|---|
| 347 | 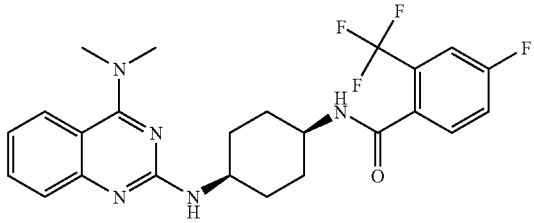 | 476 (M + H) |
| 348 | 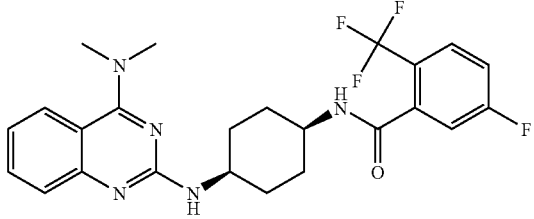 | 476 (M + H) |
| 349 | 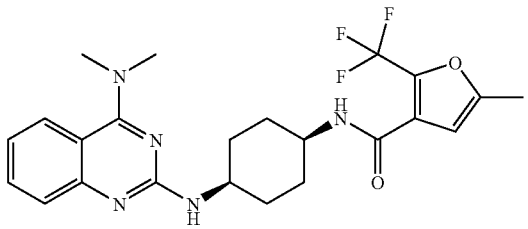 | 462 (M + H) |
| 350 | 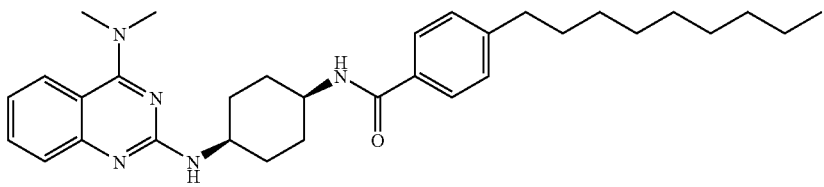 | 516 (M + H) |
| 351 | 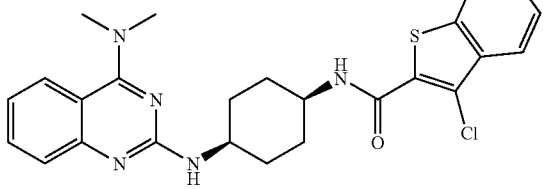 | 480 (M + H) |
| 352 | 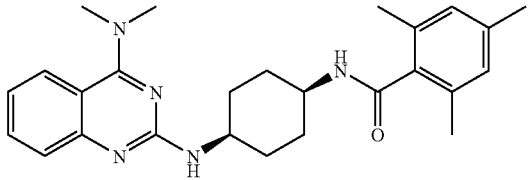 | 432 (M + H) |
| 353 | 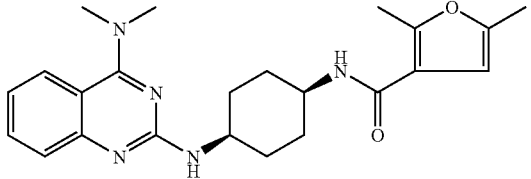 | 408 (M + H) |

| Example No. | Structure | APCI-MS |
|---|---|---|
| 354 | 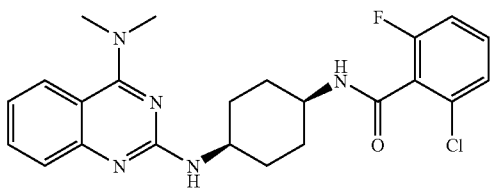 | 442 (M + H) |
| 355 | 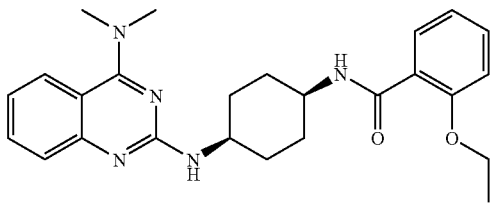 | 434 (M + H) |
| 356 | 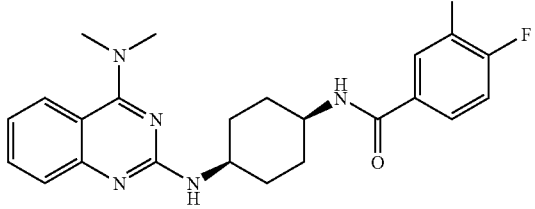 | 442 (M + H) |
| 357 | 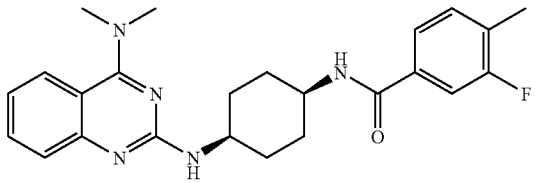 | 422 (M + H) |
| 358 | 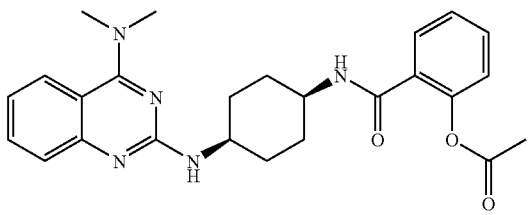 | 406 (M + H) |
| 359 | 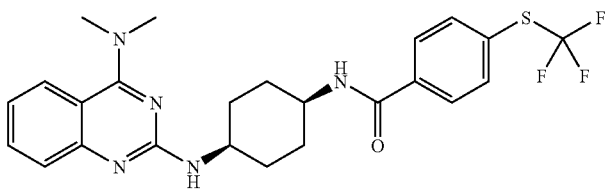 | 490 (M + H) |
| 360 | 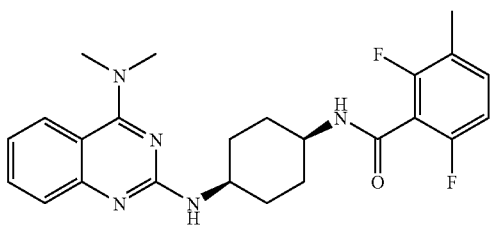 | 440 (M + H) |

-continued
| Example No. | Structure | APCI-MS |
|---|---|---|
| 361 | 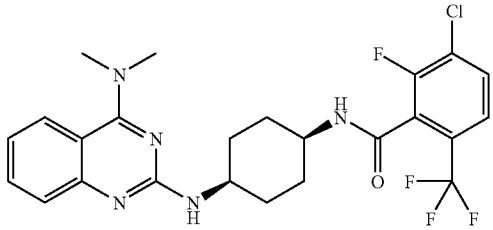 | 510 (M + H) |
| 362 | 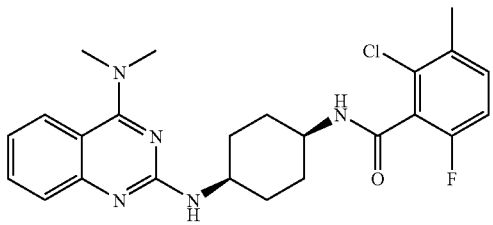 | 456 (M + H) |
| 363 | 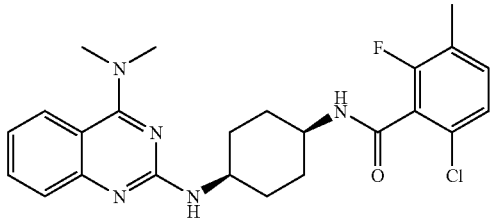 | 456 (M + H) |
| 364 | 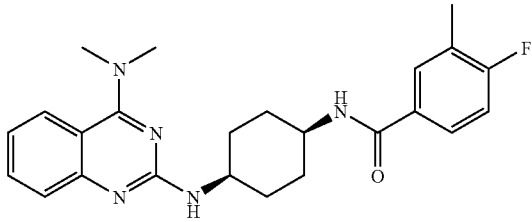 | 422 (M + H) |
| 365 | 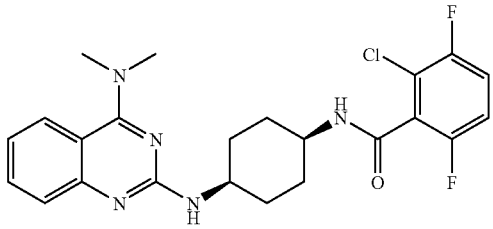 | 460 (M + H) |
| 366 | 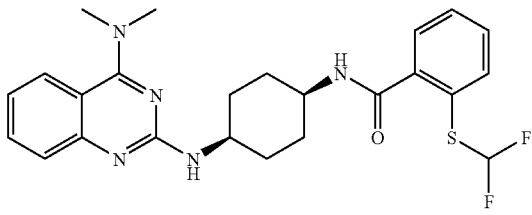 | 472 (M + H) |

-continued
| Example No. | Structure | APCI-MS |
|---|---|---|
| 367 | 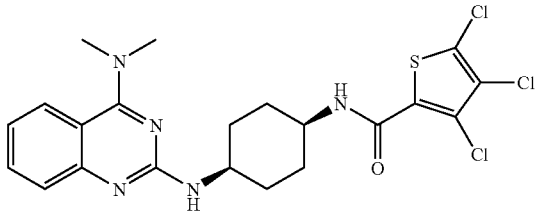 | 498 (M + H) |
| 368 | 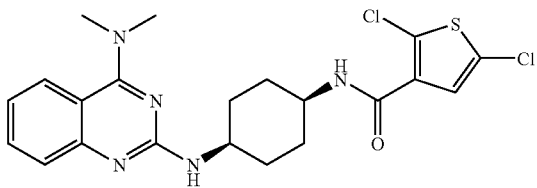 | 464 (M + H) |
| 369 | 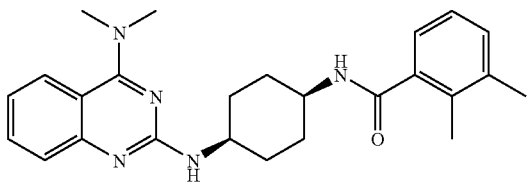 | 418 (M + H) |
| 370 | 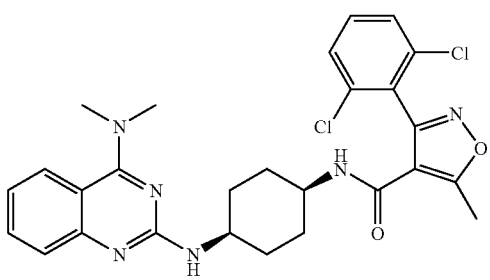 | 539 (M + H) |
| 371 | 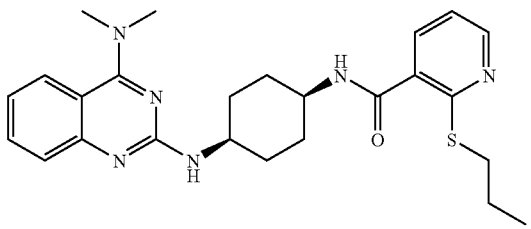 | 465 (M + H) |
| 372 | 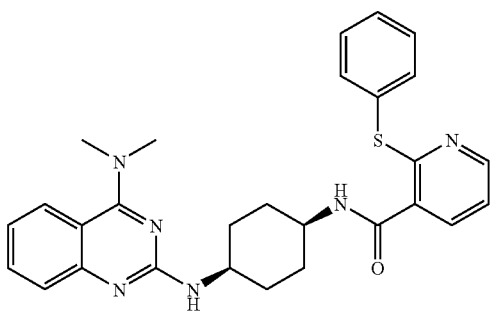 | 499 (M + H) |

| Example No. | Structure | APCI-MS |
|---|---|---|
| 373 | 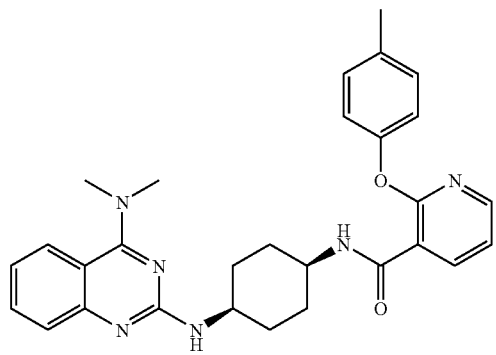 | 497 (M + H) |
| 374 | 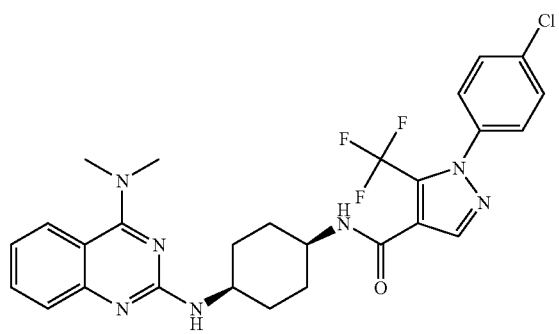 | 558 (M + H) |
| 375 | 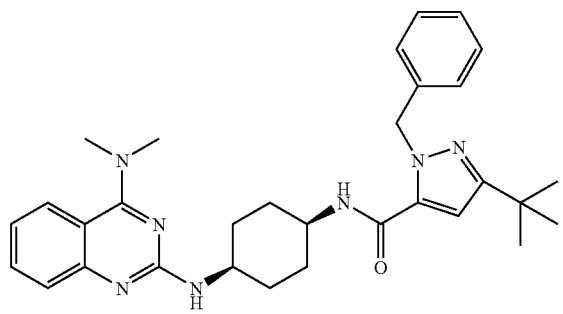 | 526 (M + H) |
| 376 | 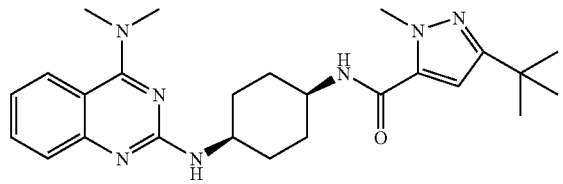 | 450 (M + H) |
| 377 | 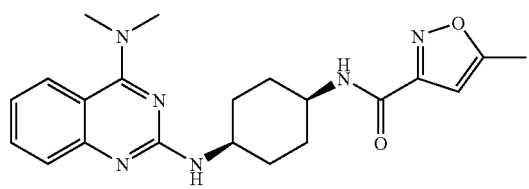 | 395 (M + H) |

-continued
| Example No. | Structure | APCI-MS |
|---|---|---|
| 378 | 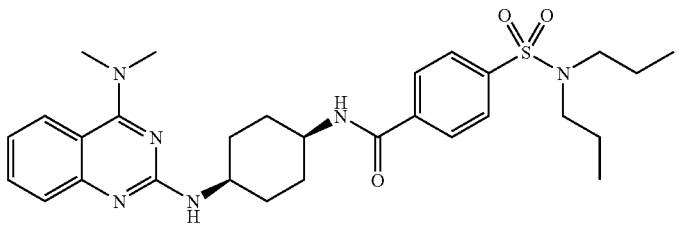 | 553 (M + H) |
| 379 | 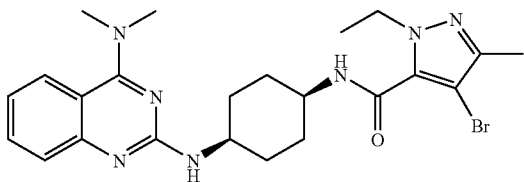 | 500 (M + H) |
| 380 | 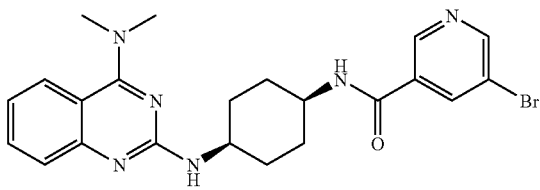 | 469 (M + H) |
| 381 | 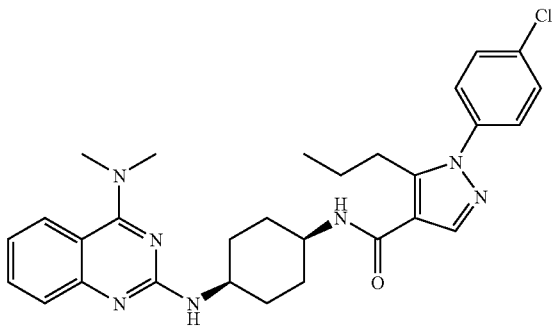 | 532 (M + H) |
| 382 | 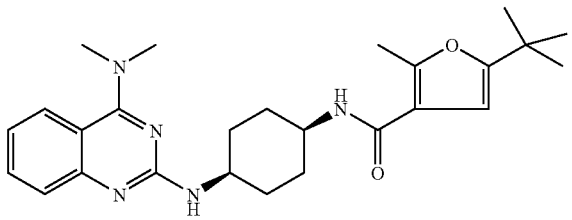 | 450 (M + H) |
| 383 | 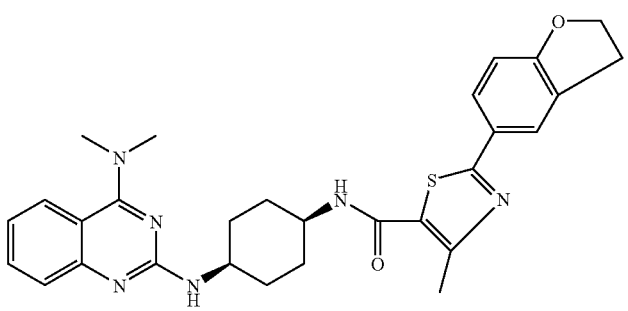 | 529 (M + H) |

-continued
| Example No. | Structure | APCI-MS |
|---|---|---|
| 384 | 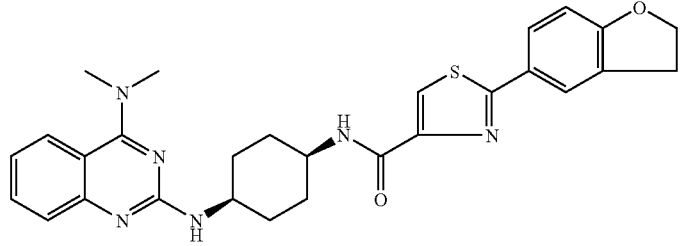 | 515 (M + H) |
| 385 | 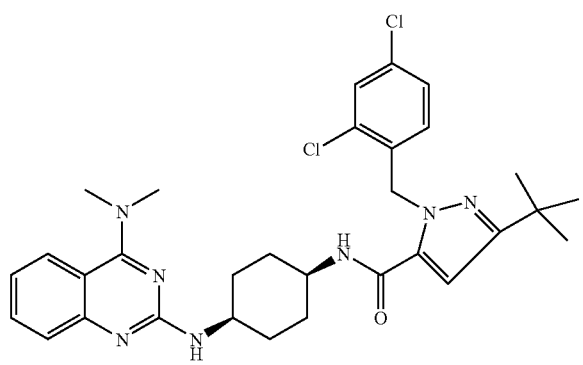 | 594 (M + H) |
| 386 | 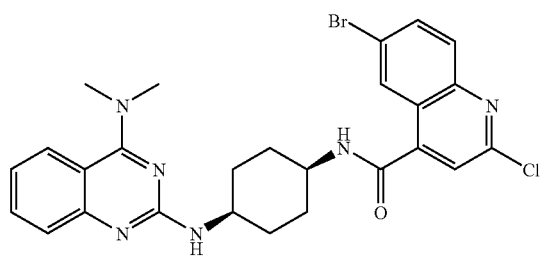 | 553 (M + H) |
| 387 | 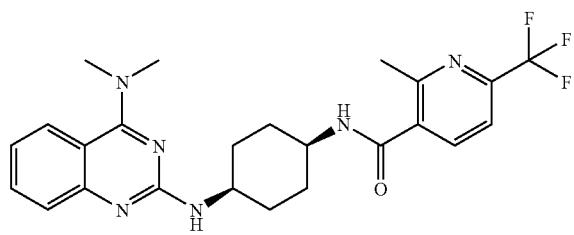 | 473 (M + H) |
| 388 | 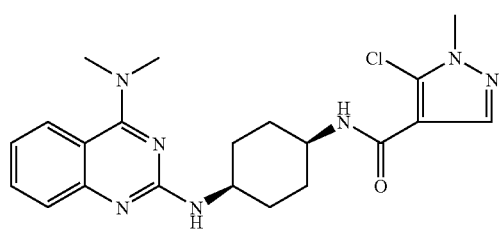 | 428 (M + H) |

-continued
| Example No. | Structure | APCI-MS |
|---|---|---|
| 389 | 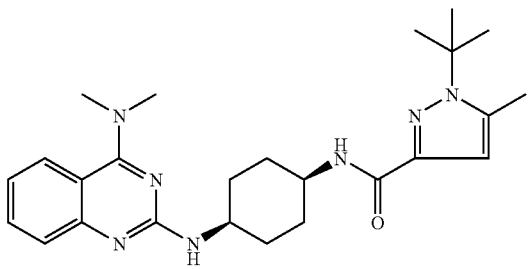 | 450 (M + H) |
| 390 | 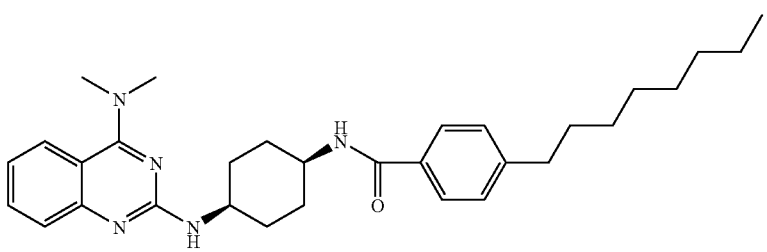 | 502 (M + H) |
| 391 | 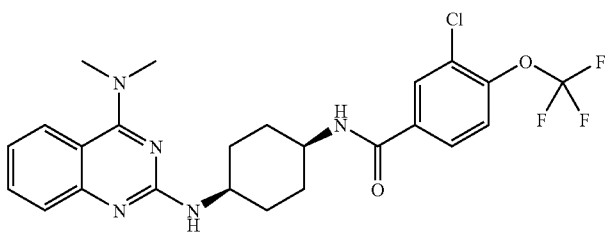 | 508 (M + H) |
| 392 | 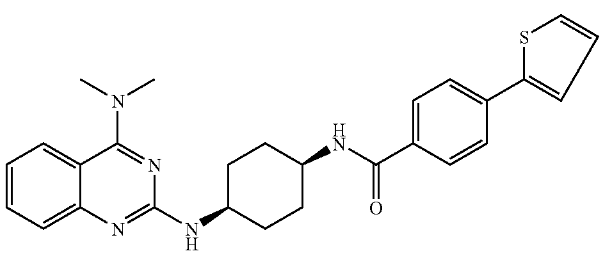 | 472 (M + H) |
| 393 | 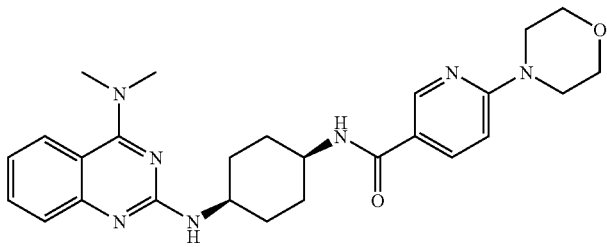 | 476 (M + H) |
| 394 | 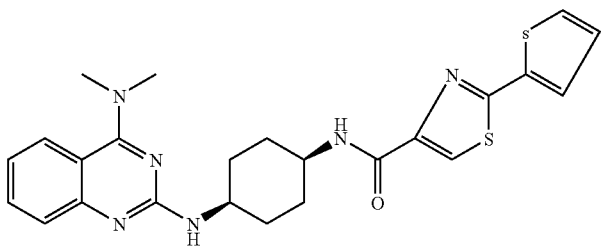 | 479 (M + H) |

| Example No. | Structure | APCI-MS |
|---|---|---|
| 395 | 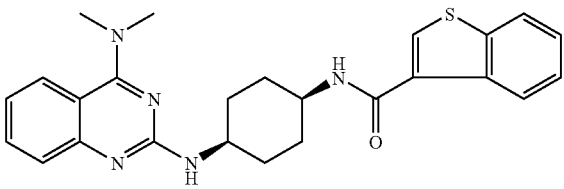 | 446 (M + H) |
| 396 | 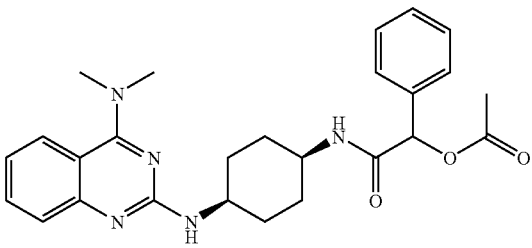 | 462 (M + H) |
| 397 | 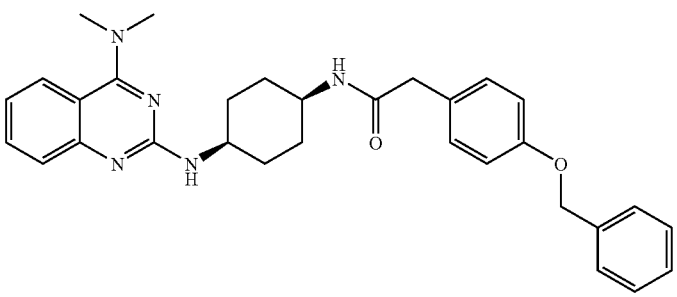 | 510 (M + H) |
| 398 | 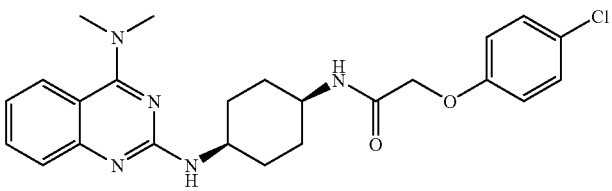 | 454 (M + H) |
| 399 | 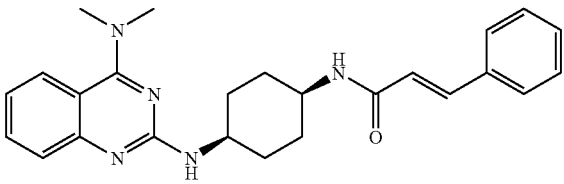 | 416 (M + H) |
| 400 | 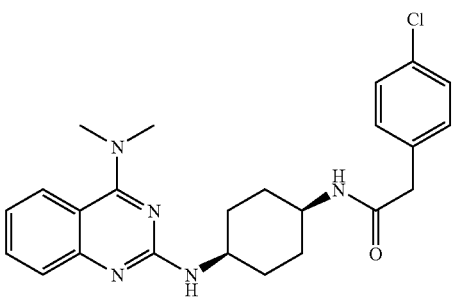 | 438 (M + H) |

-continued
| Example No. | Structure | APCI-MS |
|---|---|---|
| 401 | 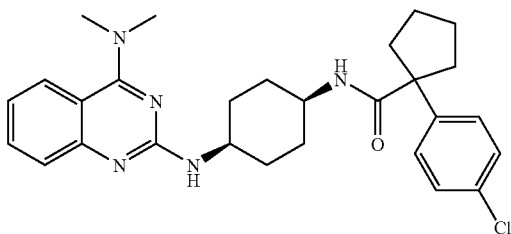 | 492 (M + H) |
| 402 | 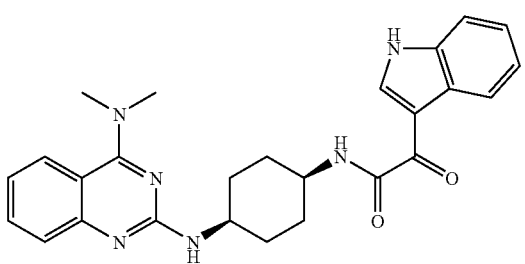 | 457 (M + H) |
| 403 | 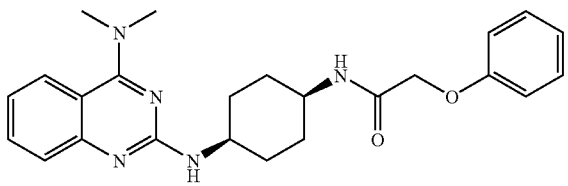 | 420 (M + H) |
| 404 | 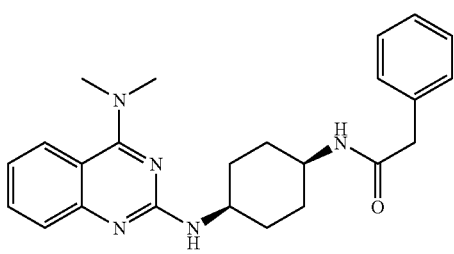 | 404 (M + H) |
| 405 | 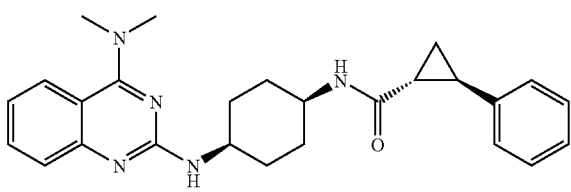 | 430 (M + H) |
| 406 | 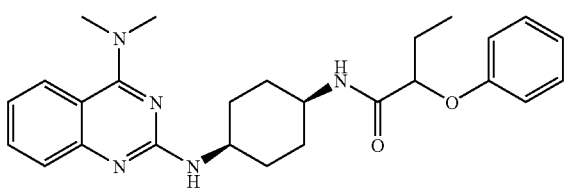 | 448 (M + H) |

-continued
| Example No. | Structure | APCI-MS |
|---|---|---|
| 407 | 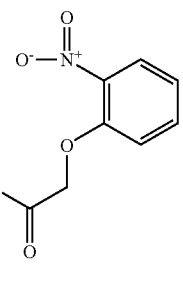 | 465 (M + H) |
| 408 | 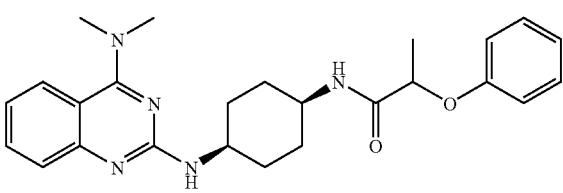 | 434 (M + H) |
| 409 | 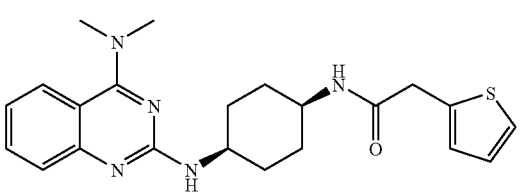 | 410 (M + H) |
| 410 | 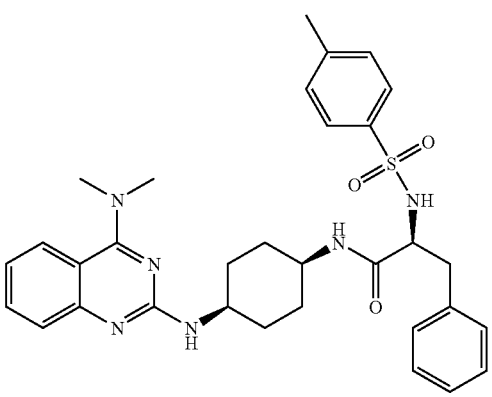 | 587 (M + H) |
| 411 | 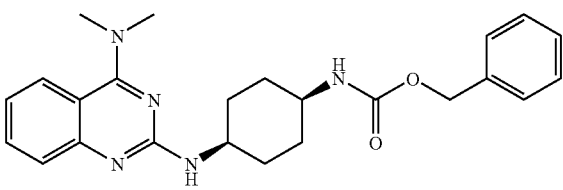 | 420 (M + H) |
| 412 | 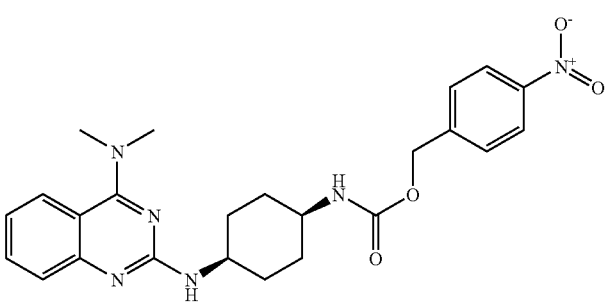 | 465 (M + H) |

-continued
| Example No. | Structure | APCI-MS |
|---|---|---|
| 413 | 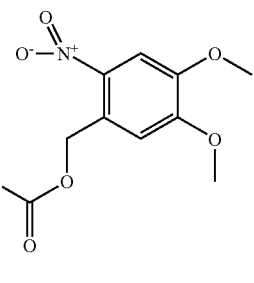 | 525 (M + H) |
| 414 | 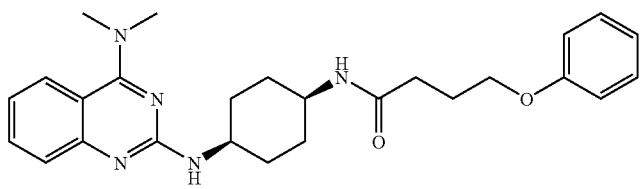 | 448 (M + H) |
| 415 | 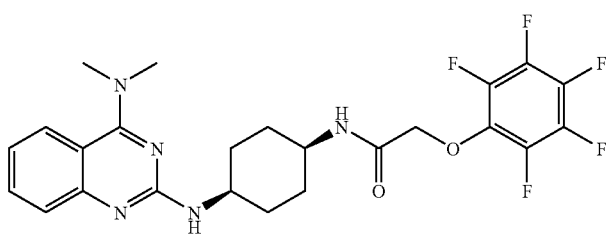 | 510 (M + H) |
| 416 | 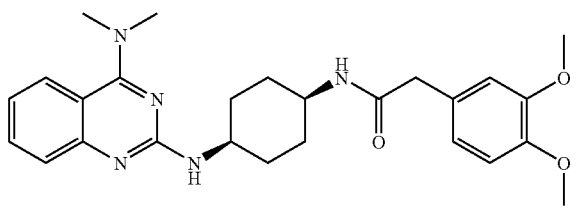 | 464 (M + H) |
| 417 | 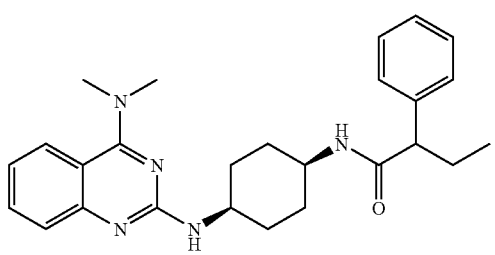 | 432 (M + H) |
| 418 | 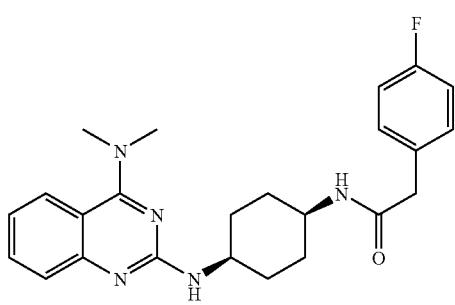 | 422 (M + H) |

| Example No. | Structure | APCI-MS |
|---|---|---|
| 419 | 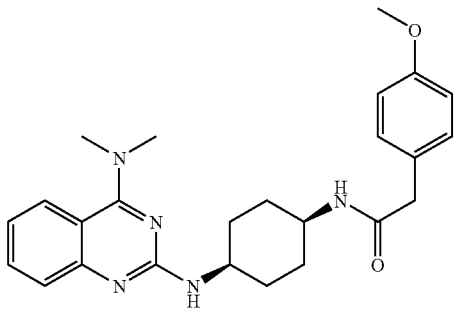 | 434 (M + H) |
| 420 | 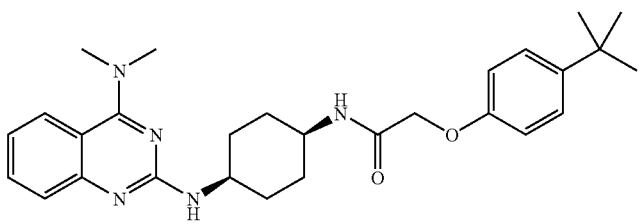 | 476 (M + H) |
| 421 | 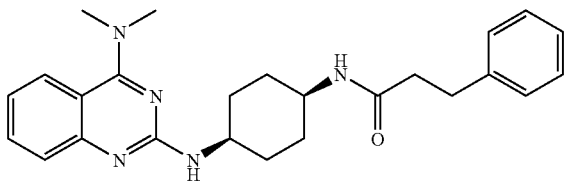 | 418 (M + H) |
| 422 | 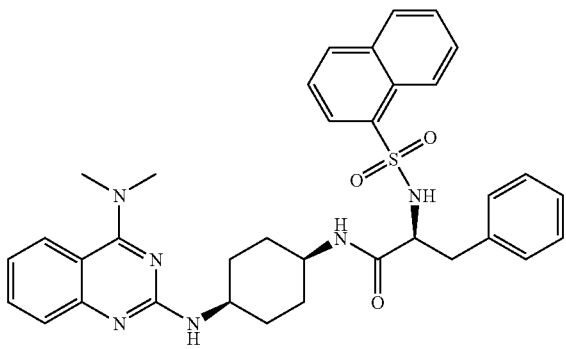 | 623 (M + H) |
| 423 | 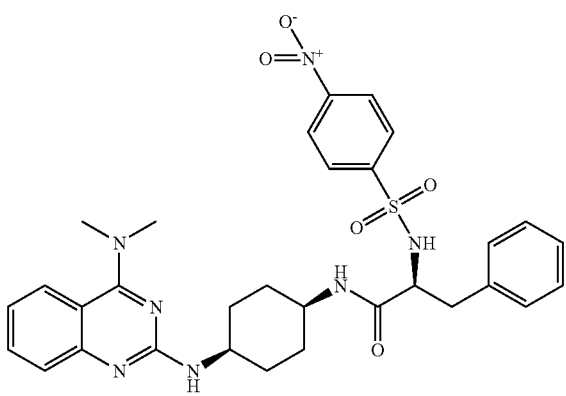 | 618 (M + H) |

-continued
| Example No. | Structure | APCI-MS |
|---|---|---|
| 424 | 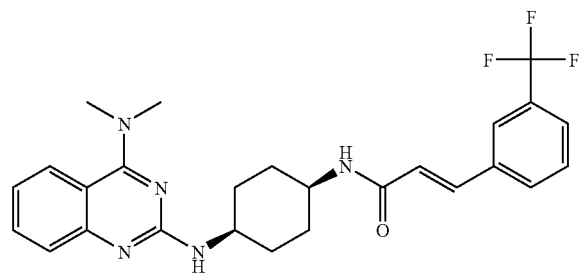 | 484 (M + H) |
| 425 | 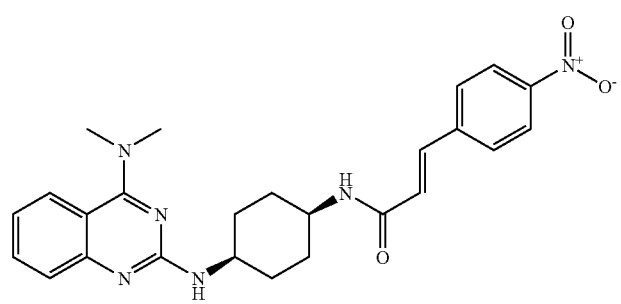 | 461 (M + H) |
| 426 | 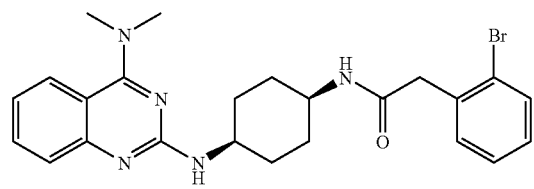 | 482 (M + H) |
| 427 | 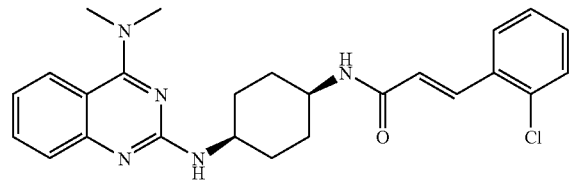 | 450 (M + H) |
| 428 | 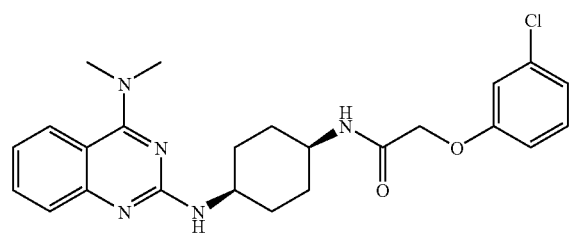 | 454 (M + H) |
| 429 | 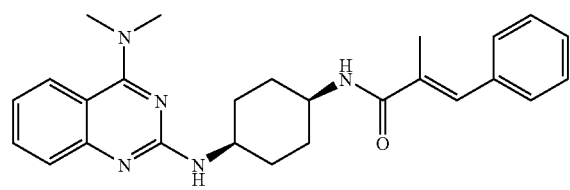 | 430 (M + H) |

-continued
| Example No. | Structure | APCI-MS |
|---|---|---|
| 430 | 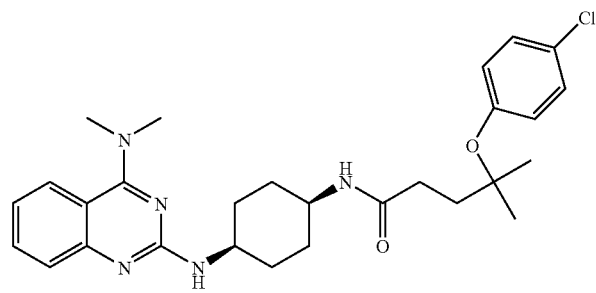 | 482 (M + H) |
| 431 | 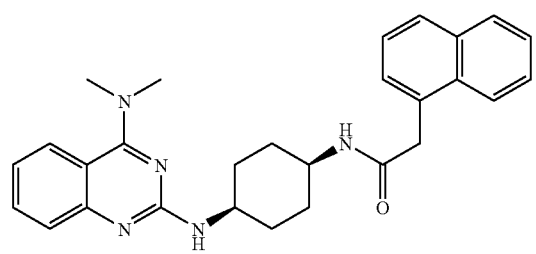 | 454 (M + H) |
| 432 | 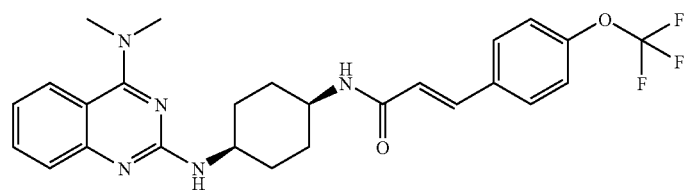 | 500 (M + H) |
| 433 | 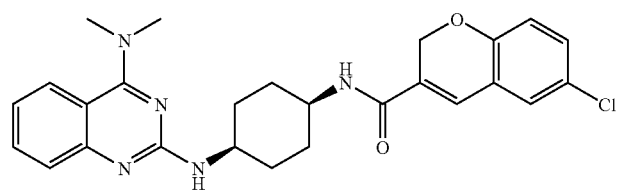 | 478 (M + H) |
| 434 | 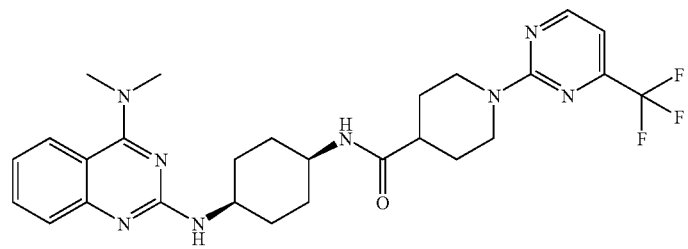 | 543 (M + H) |
| 435 | 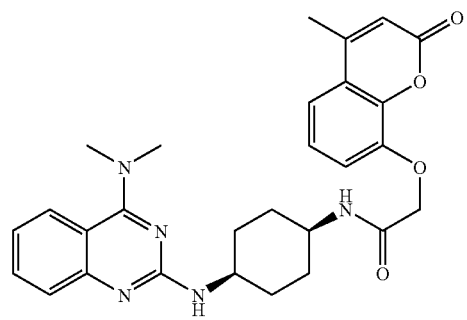 | 502 (M + H) |

-continued
| Example No. | Structure | APCI-MS |
|---|---|---|
| 436 | 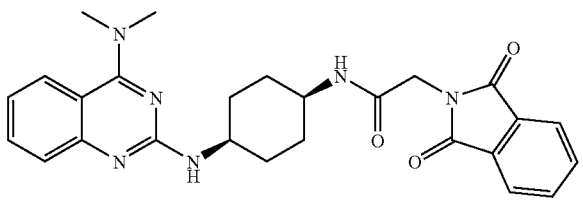 | 473 (M + H) |
| 437 | 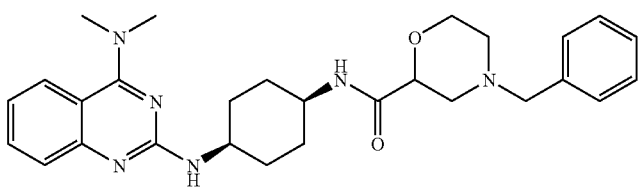 | 489 (M + H) |
| 438 | 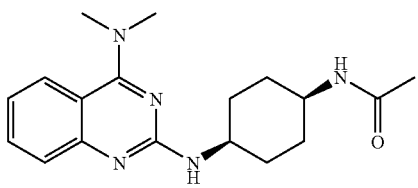 | 328 (M + H) |
| 439 | 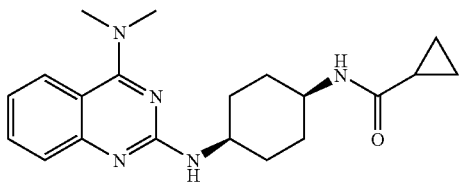 | 328 (M + H) |
| 440 | 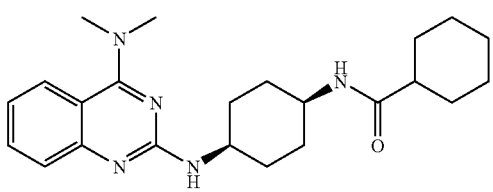 | 396 (M + H) |
| 441 | 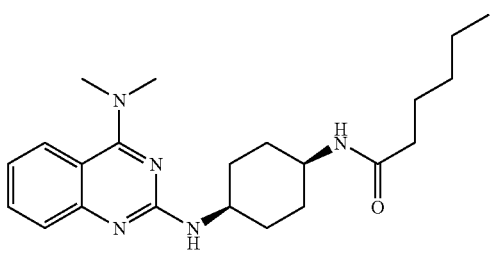 | 384 (M + H) |
| 442 | 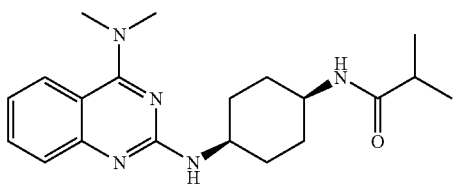 | 356 (M + H) |

-continued
| Example No. | Structure | APCI-MS |
|---|---|---|
| 443 | 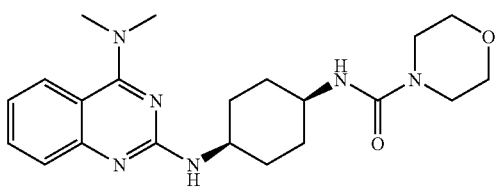 | 399 (M + H) |
| 444 | 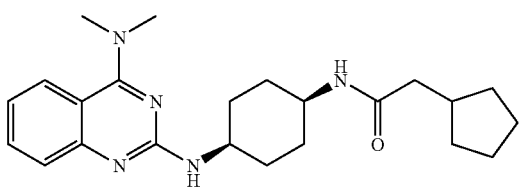 | 396 (M + H) |
| 445 | 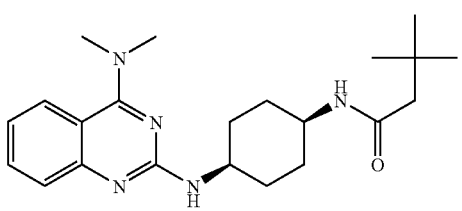 | 384 (M + H) |
| 446 | 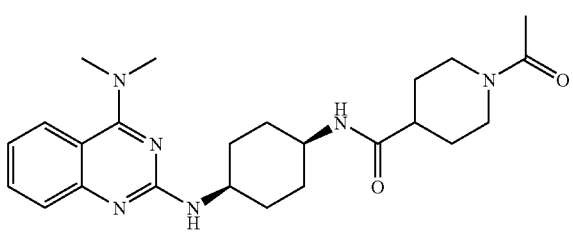 | 439 (M + H) |
| 447 | 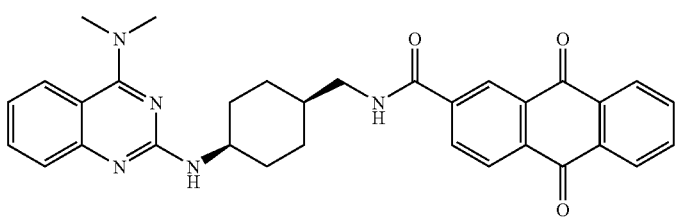 | 534 (M + H) |
| 448 | 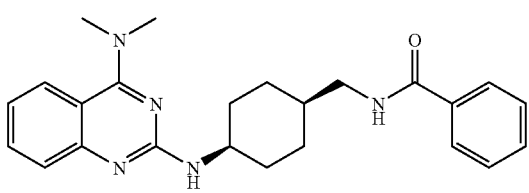 | 404 (M + H) |
| 449 | 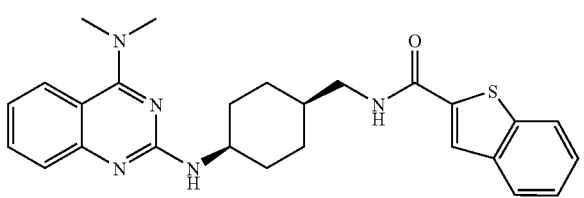 | 460 (M + H) |

| Example No. | Structure | APCI-MS |
|---|---|---|
| 450 | 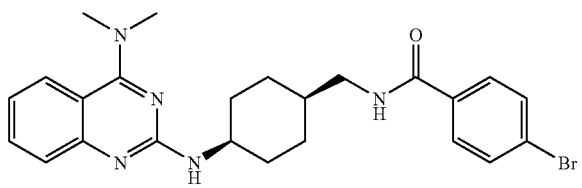 | 482 (M + H) |
| 451 | 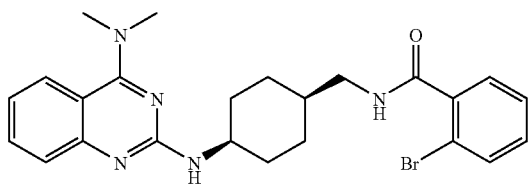 | 482 (M + H) |
| 452 | 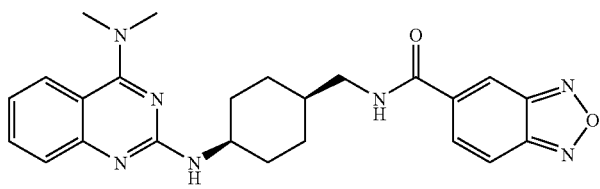 | 446 (M + H) |
| 453 | 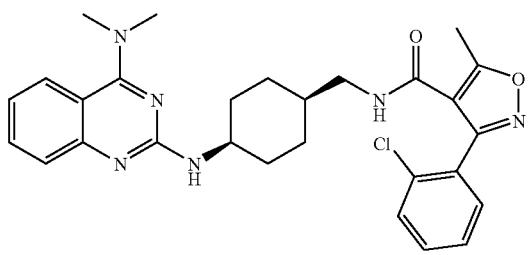 | 519 (M + H) |
| 454 | 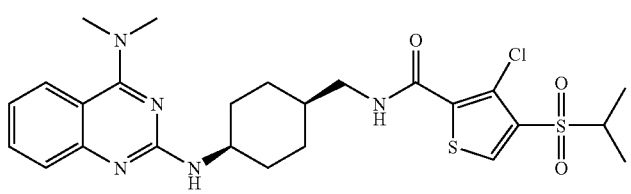 | 550 (M + H) |
| 455 | 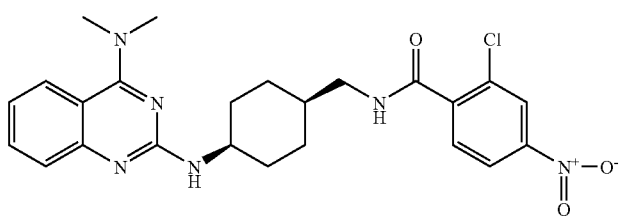 | 483 (M + H) |
| 456 | 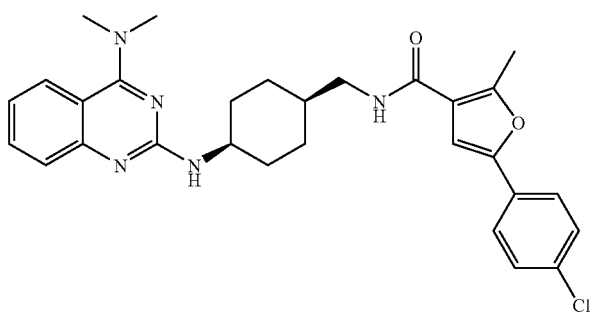 | 518 (M + H) |

-continued
| Example No. | Structure | APCI-MS |
|---|---|---|
| 457 | 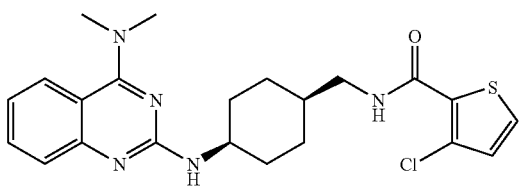 | 444 (M + H) |
| 458 | 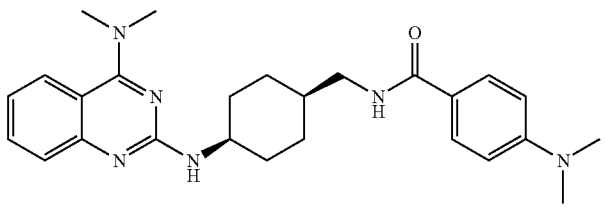 | 447 (M + H) |
| 459 | 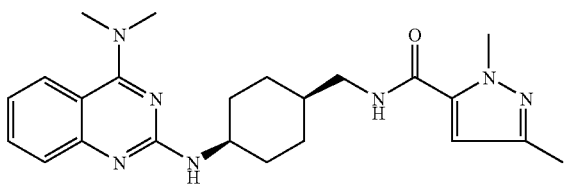 | 422 (M + H) |
| 460 | 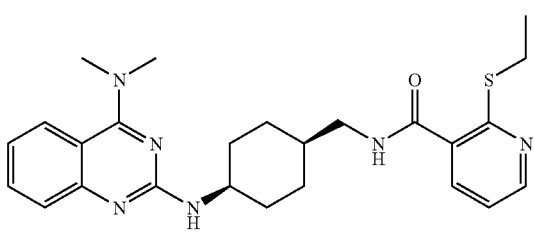 | 465 (M + H) |
| 461 | 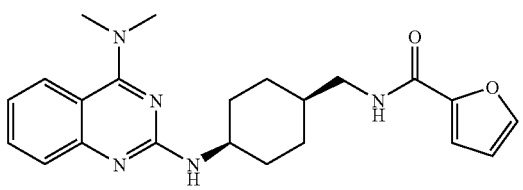 | 394 (M + H) |
| 462 | 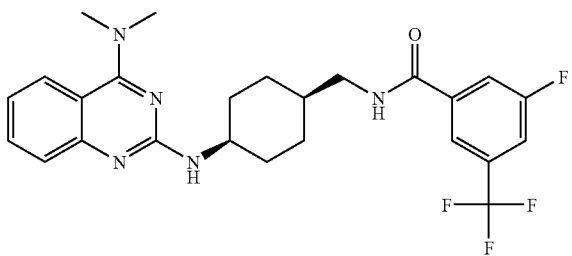 | 490 (M + H) |
| 463 | 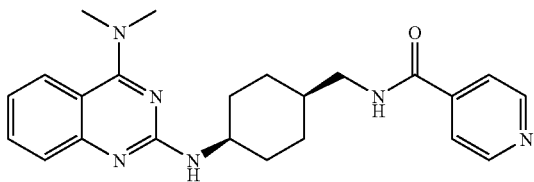 | 405 (M + H) |

-continued
| Example No. | Structure | APCI-MS |
|---|---|---|
| 464 | 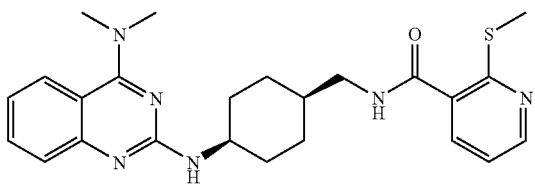 | 451 (M + H) |
| 465 | 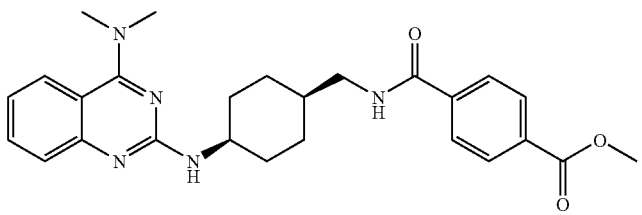 | 462 (M + H) |
| 466 | 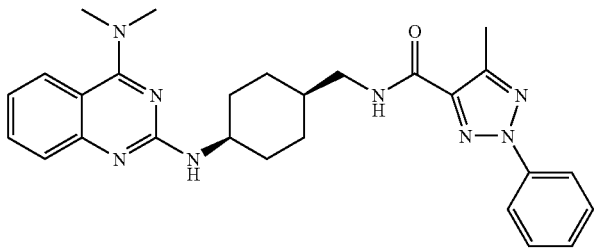 | 485 (M + H) |
| 467 | 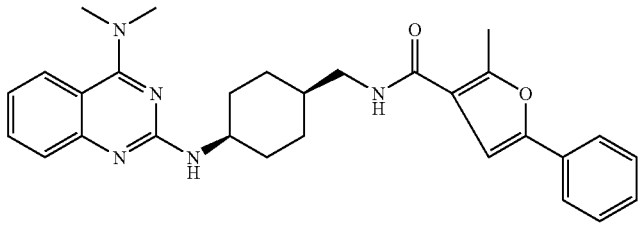 | 484 (M + H) |
| 468 | 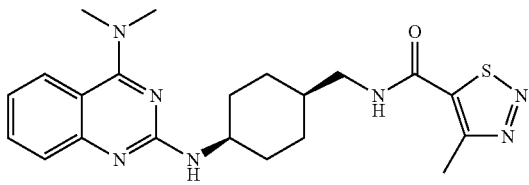 | 426 (M + H) |
| 469 | 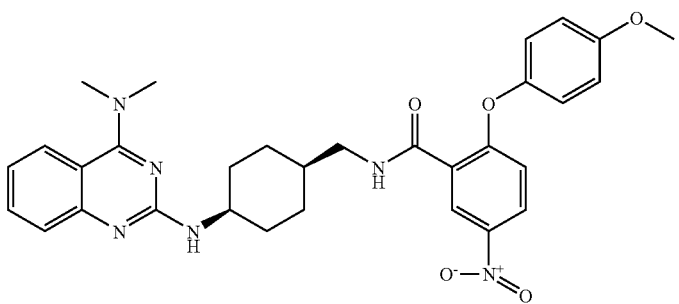 | 571 (M + H) |

-continued

| Example No. | Structure | APCI-MS |
|---|---|---|
| 470 | 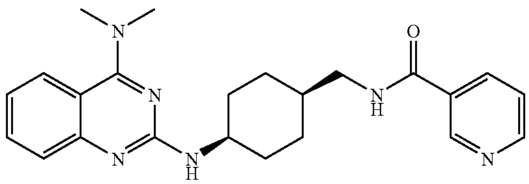 | 405 (M + H) |
| 471 | 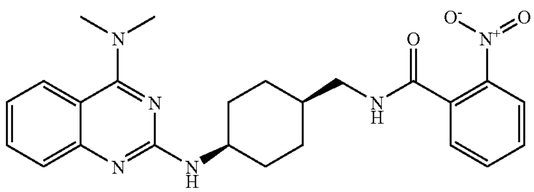 | 449 (M + H) |
| 472 | 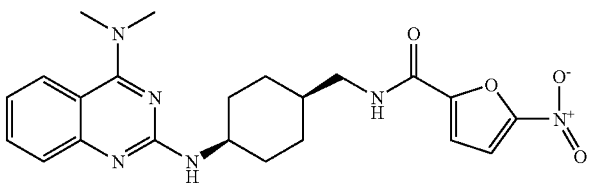 | 439 (M + H) |
| 473 | 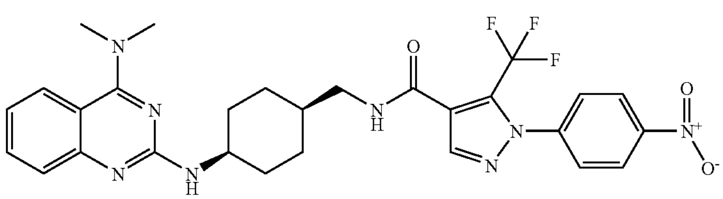 | 583 (M + H) |
| 474 | 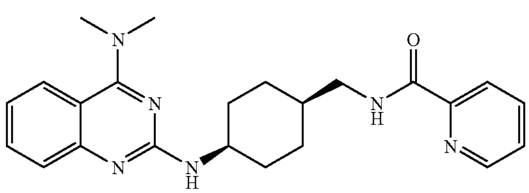 | 405 (M + H) |
| 475 | 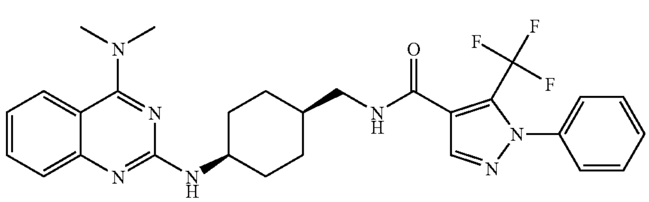 | 538 (M + H) |
| 476 | 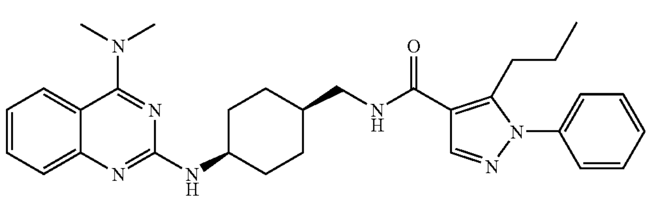 | 512 (M + H) |

-continued
| Example No. | Structure | APCI-MS |
|---|---|---|
| 477 | 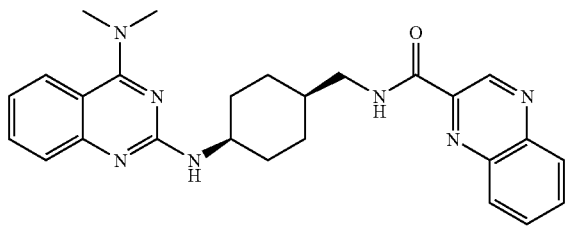 | 456 (M + H) |
| 478 | 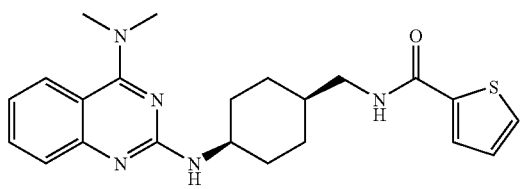 | 410 (M + H) |
| 479 | 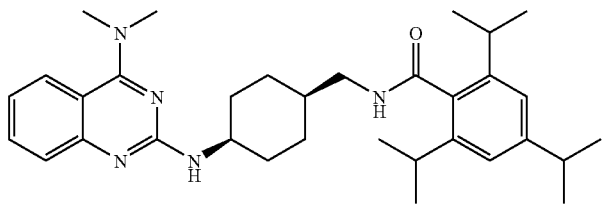 | 530 (M + H) |
| 480 | 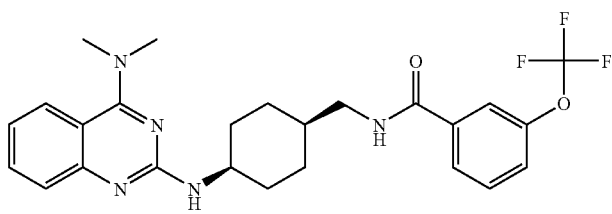 | 488 (M + H) |
| 481 | 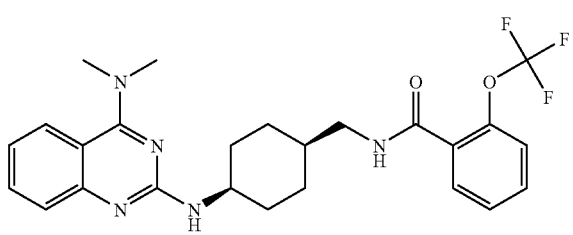 | 488 (M + H) |
| 482 | 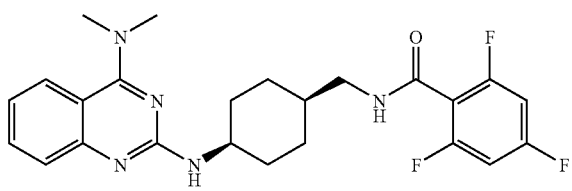 | 458 (M + H) |
| 483 | 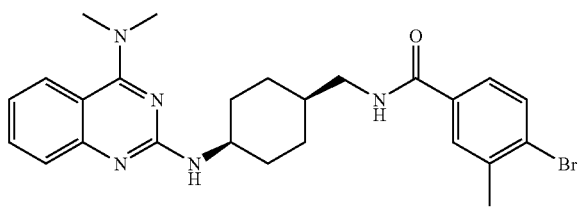 | 496 (M + H) |

-continued
| Example No. | Structure | APCI-MS |
|---|---|---|
| 484 | 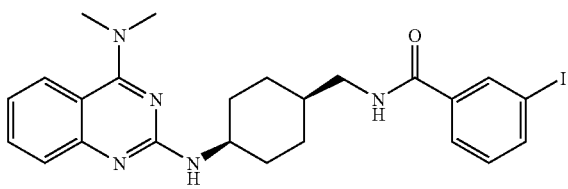 | 530 (M + H) |
| 485 | 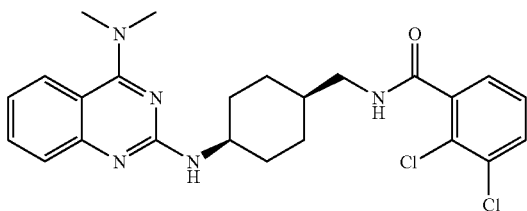 | 472 (M + H) |
| 486 | 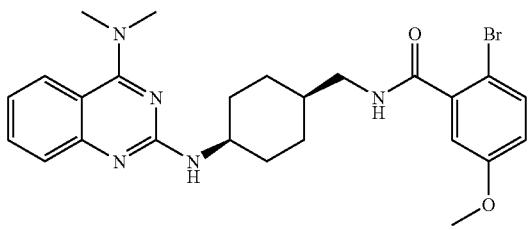 | 512 (M + H) |
| 487 | 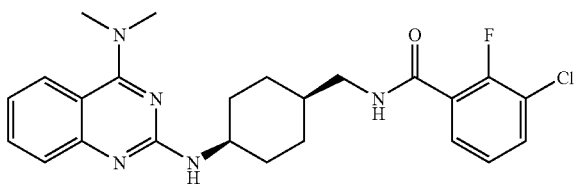 | 456 (M + H) |
| 488 | 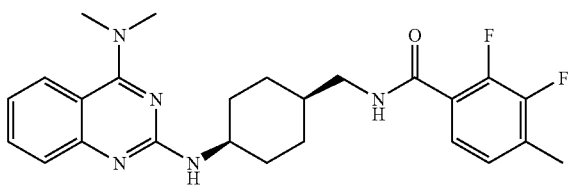 | 454 (M + H) |
| 489 | 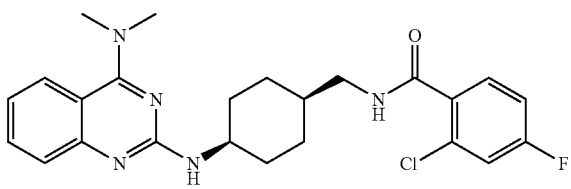 | 456 (M + H) |
| 490 | 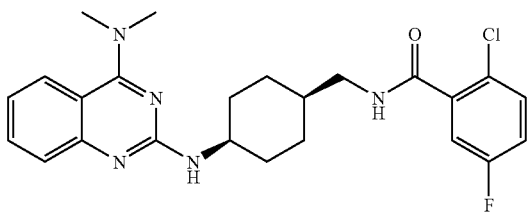 | 456 (M + H) |

-continued
| Example No. | Structure | APCI-MS |
|---|---|---|
| 491 | 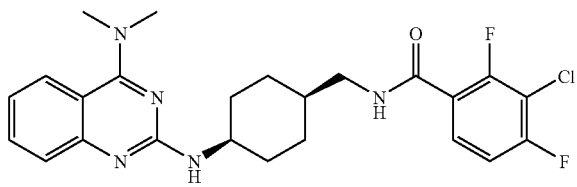 | 474 (M + H) |
| 492 | 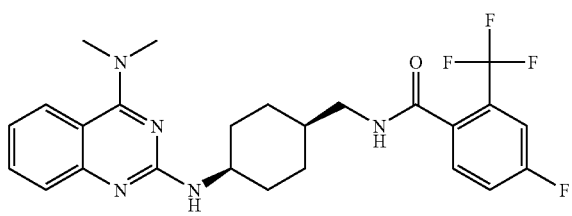 | 490 (M + H) |
| 493 | 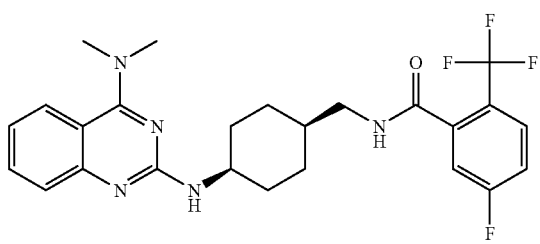 | 490 (M + H) |
| 494 | 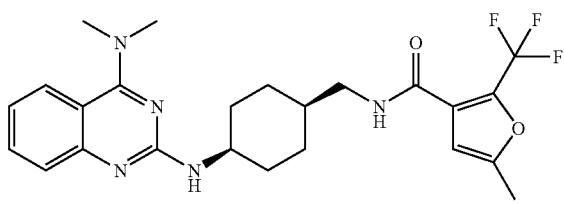 | 476 (M + H) |
| 495 | 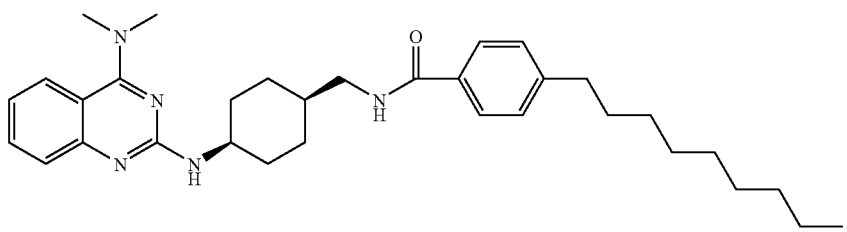 | 530 (M + H) |
| 496 | 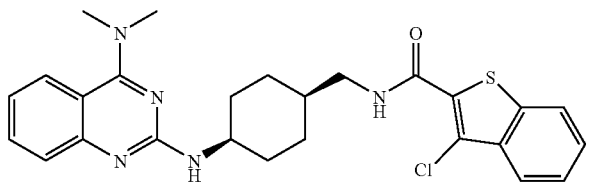 | 494 (M + H) |
| 497 | 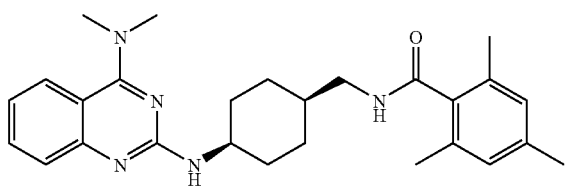 | 446 (M + H) |

-continued
| Example No. | Structure | APCI-MS |
|---|---|---|
| 498 | 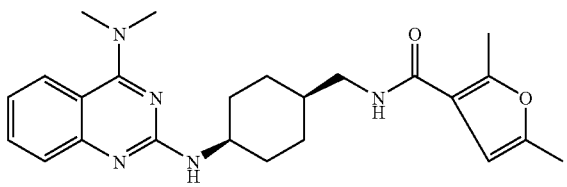 | 422 (M + H) |
| 499 | 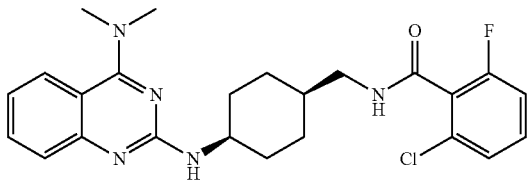 | 488 (M + H) |
| 500 | 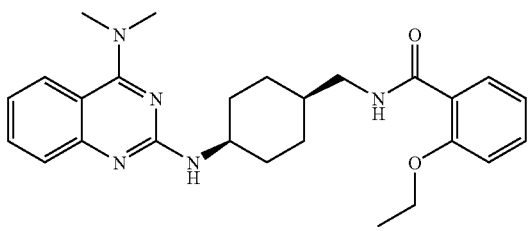 | 448 (M + H) |
| 501 | 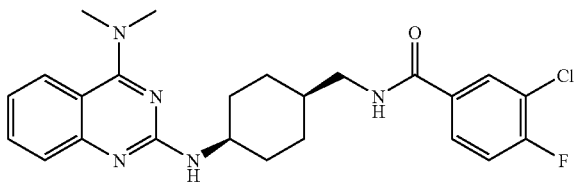 | 456 (M + H) |
| 502 | 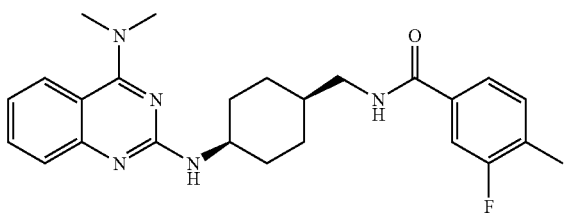 | 436 (M + H) |
| 503 | 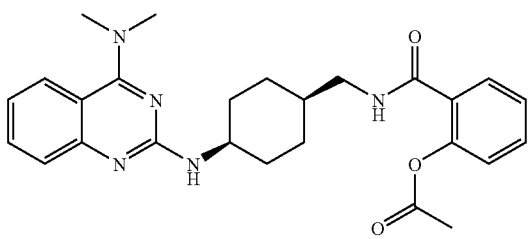 | 420 (M + H) |
| 504 | 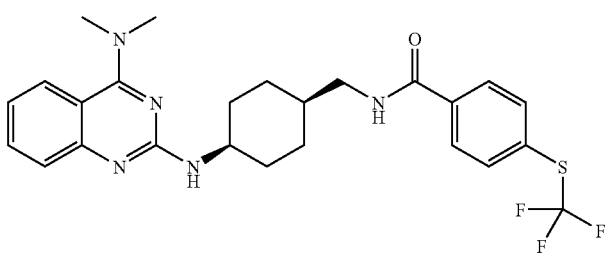 | 504 (M + H) |

-continued
| Example No. | Structure | APCI-MS |
|---|---|---|
| 505 | 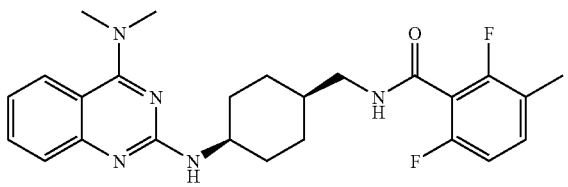 | 454 (M + H) |
| 506 | 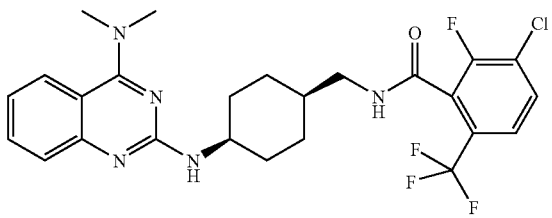 | 524 (M + H) |
| 507 | 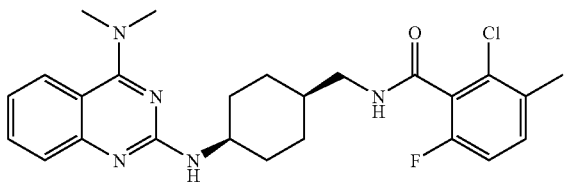 | 470 (M + H) |
| 508 | 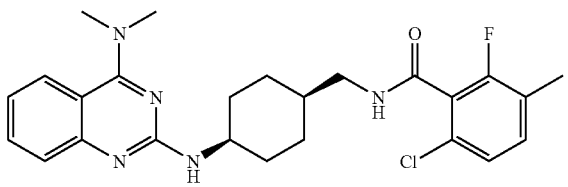 | 470 (M + H) |
| 509 | 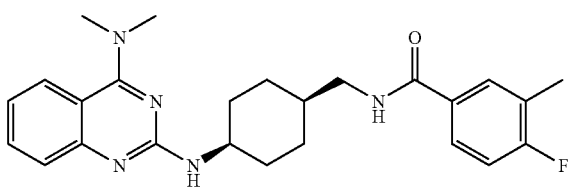 | 436 (M + H) |
| 510 | 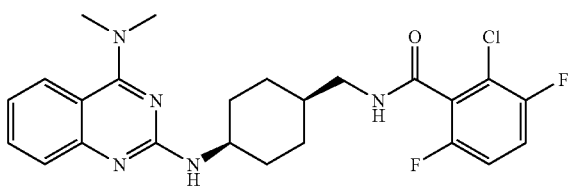 | 474 (M + H) |
| 511 | 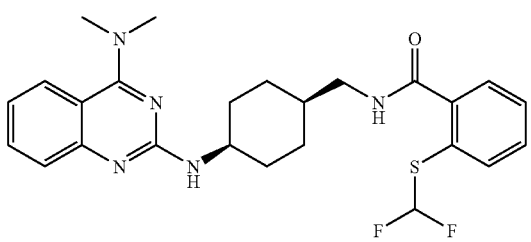 | 486 (M + H) |

-continued
| Example No. | Structure | APCI-MS |
|---|---|---|
| 512 | 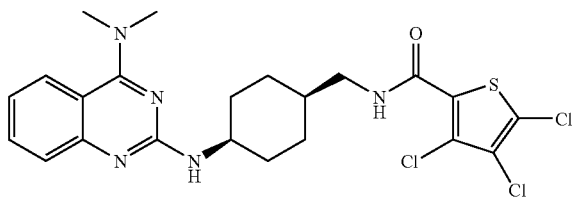 | 512 (M + H) |
| 513 | 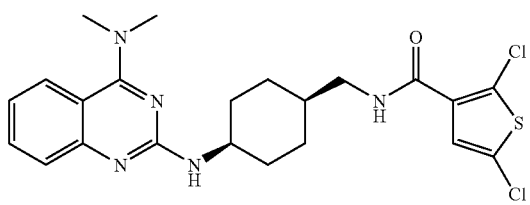 | 478 (M + H) |
| 514 | 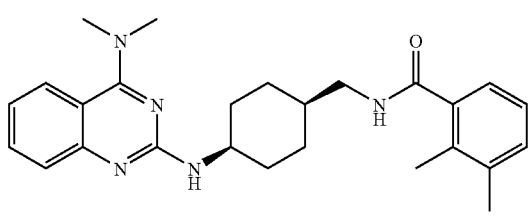 | 432 (M + H) |
| 515 | 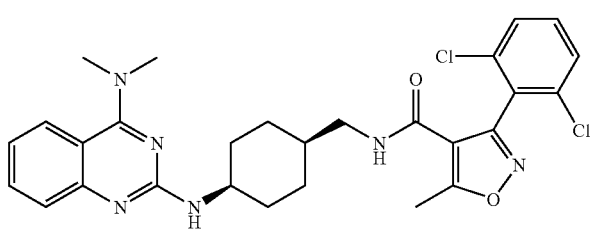 | 553 (M + H) |
| 516 | 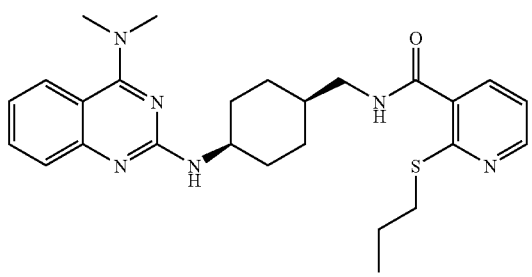 | 479 (M + H) |
| 517 | 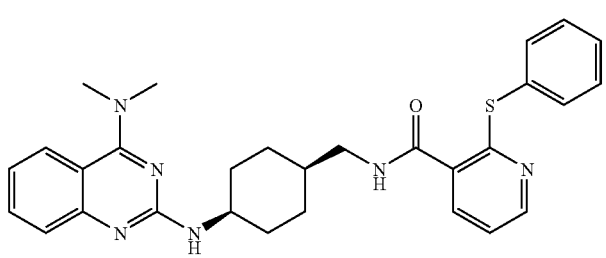 | 513 (M + H) |

| Example No. | Structure | APCI-MS |
|---|---|---|
| 518 | 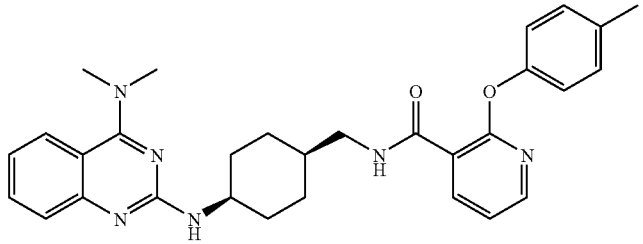 | 511 (M + H) |
| 519 | 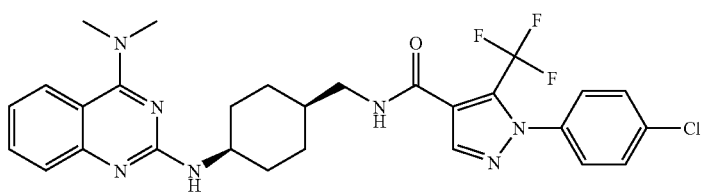 | 572 (M + H) |
| 520 | 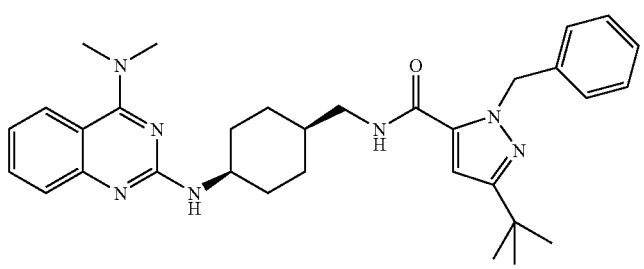 | 540 (M + H) |
| 521 | 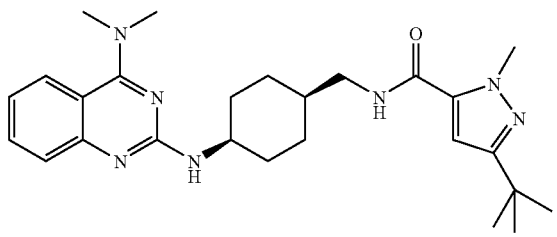 | 464 (M + H) |
| 522 | 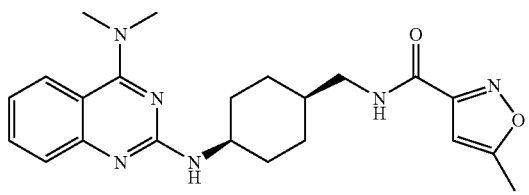 | 409 (M + H) |
| 523 | 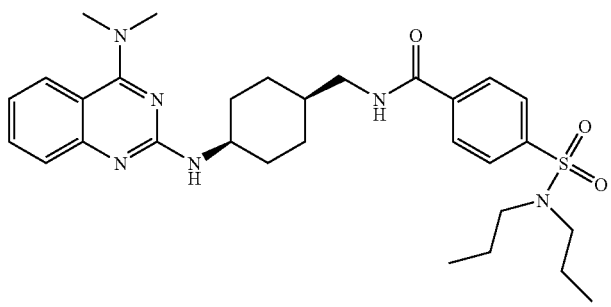 | 567 (M + H) |

-continued
| Example No. | Structure | APCI-MS |
|---|---|---|
| 524 | 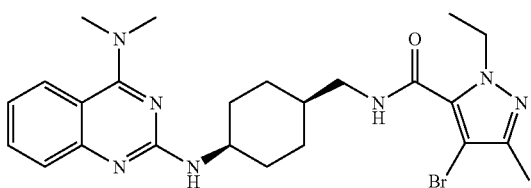 | 514 (M + H) |
| 525 | 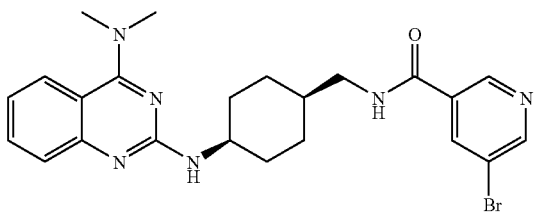 | 483 (M + H) |
| 526 | 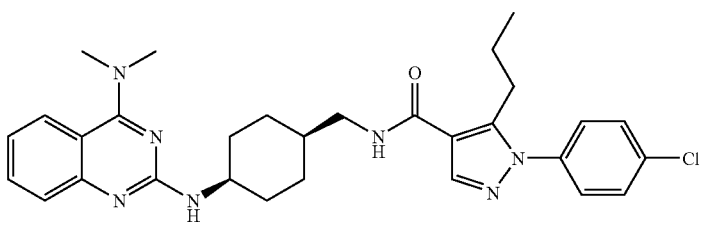 | 546 (M + H) |
| 527 | 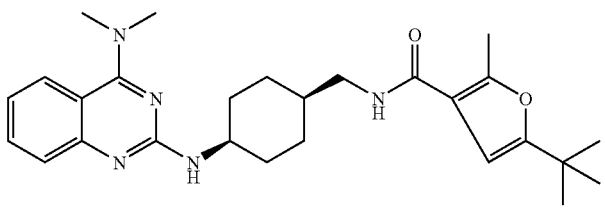 | 464 (M + H) |
| 528 | 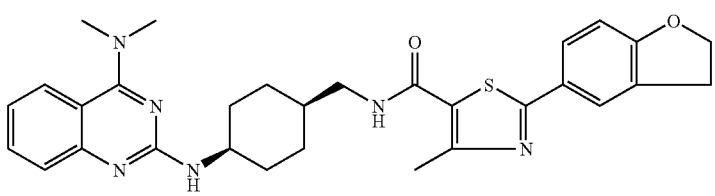 | 543 (M + H) |
| 529 | 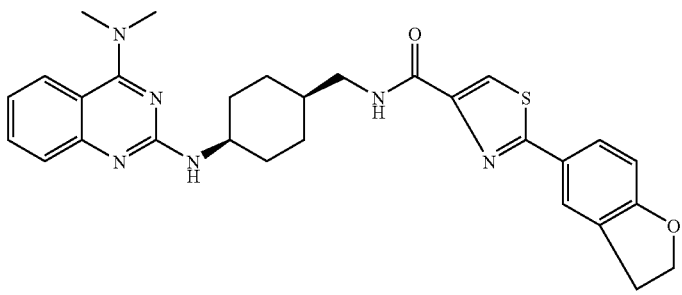 | 529 (M + H) |

-continued
| Example No. | Structure | APCI-MS |
|---|---|---|
| 530 | 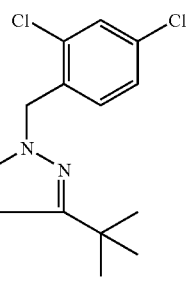 | 608 (M + H) |
| 531 | 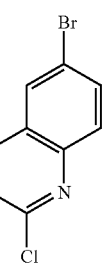 | 567 (M + H) |
| 532 | 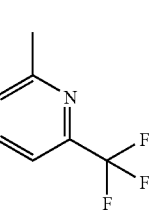 | 487 (M + H) |
| 533 | 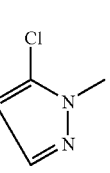 | 442 (M + H) |
| 534 | 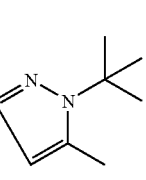 | 464 (M + H) |
| 535 | 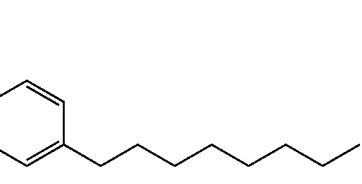 | 516 (M + H) |

-continued
| Example No. | Structure | APCI-MS |
|---|---|---|
| 536 | 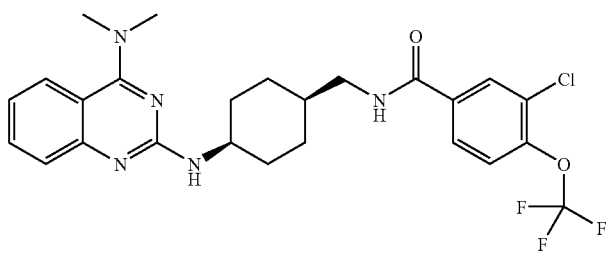 | 522 (M + H) |
| 537 | 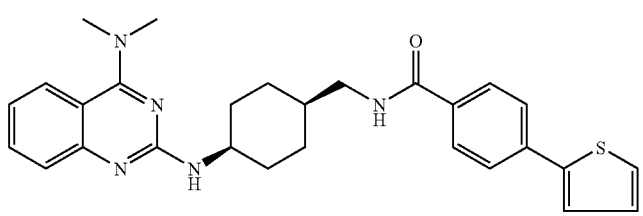 | 486 (M + H) |
| 538 | 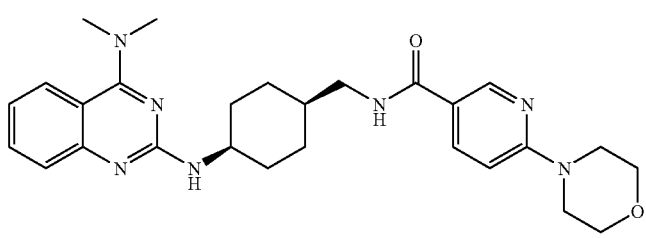 | 490 (M + H) |
| 539 | 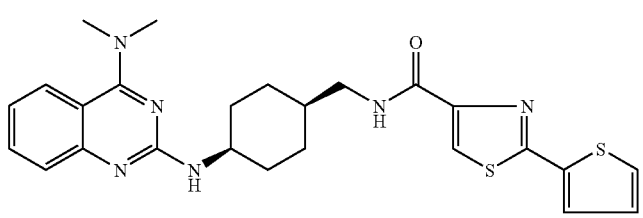 | 493 (M + H) |
| 540 | 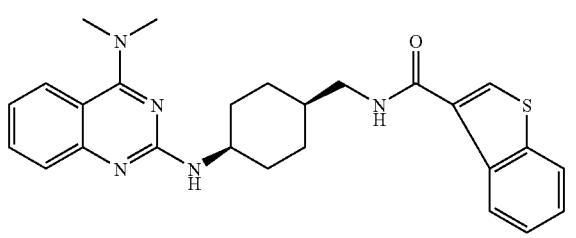 | 460 (M + H) |
| 541 | 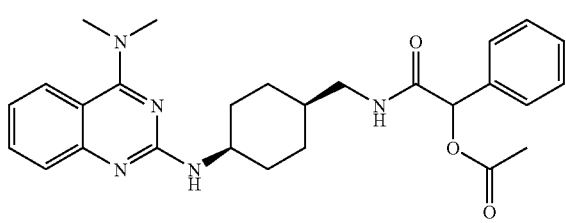 | 476 (M + H) |

-continued
| Example No. | Structure | APCI-MS |
|---|---|---|
| 542 | 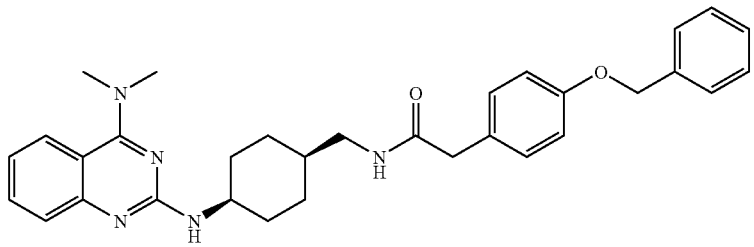 | 524 (M + H) |
| 543 | 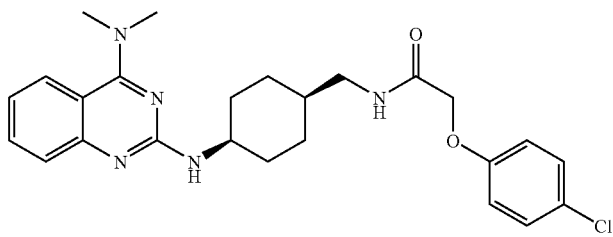 | 468 (M + H) |
| 544 | 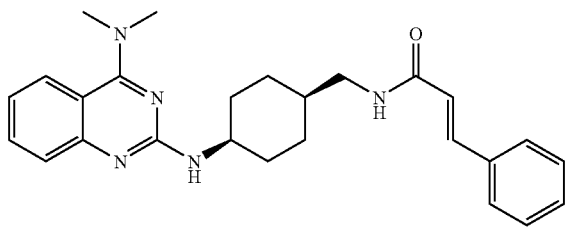 | 430 (M + H) |
| 545 | 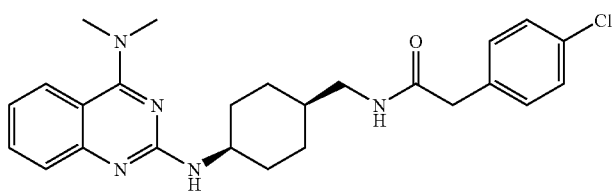 | 452 (M + H) |
| 546 | 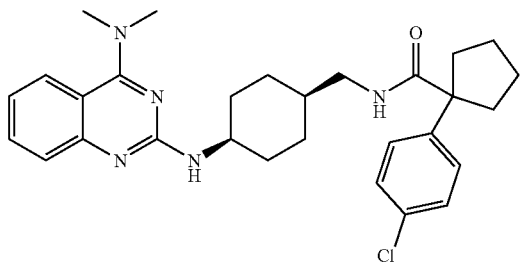 | 506 (M + H) |
| 547 | 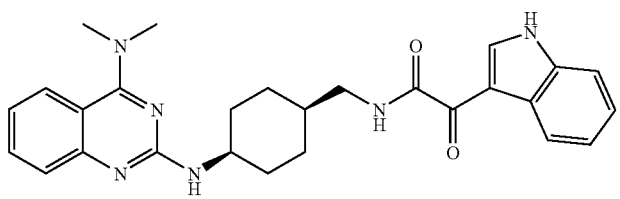 | 471 (M + H) |

| Example No. | Structure | APCI-MS |
|---|---|---|
| 548 | 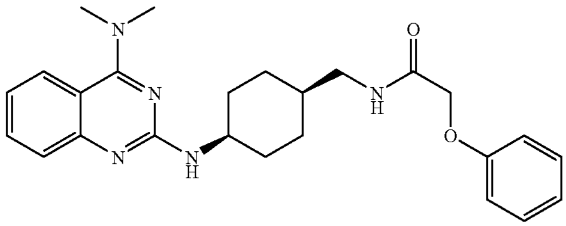 | 434 (M + H) |
| 549 | 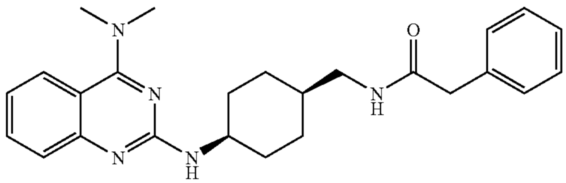 | 418 (M + H) |
| 550 | 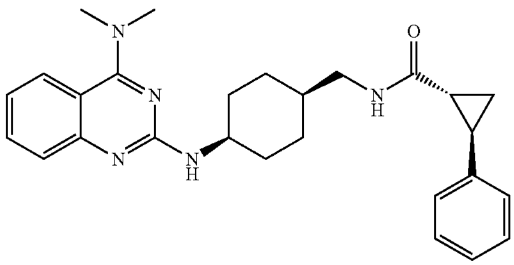 | 444 (M + H) |
| 551 | 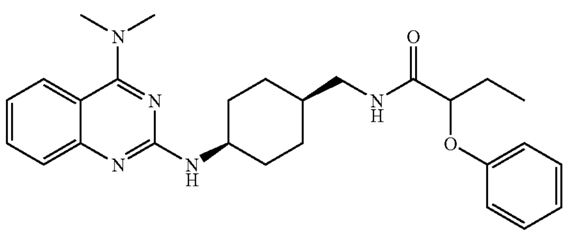 | 462 (M + H) |
| 552 | 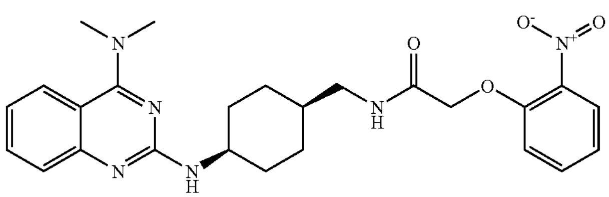 | 479 (M + H) |
| 553 | 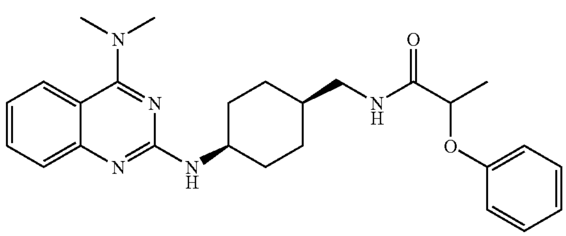 | 448 (M + H) |
| 554 | 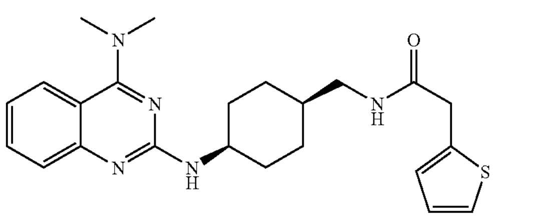 | 424 (M + H) |

-continued
| Example No. | Structure | APCI-MS |
|---|---|---|
| 555 | 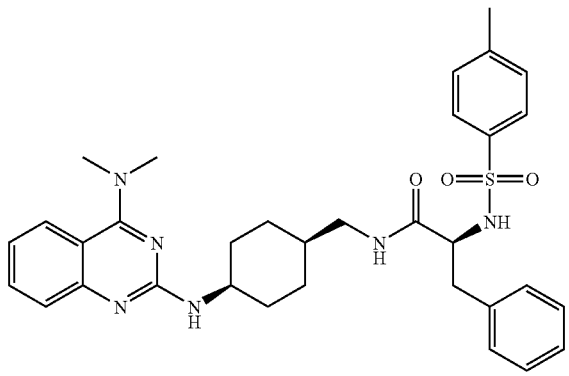 | 601 (M + H) |
| 556 | 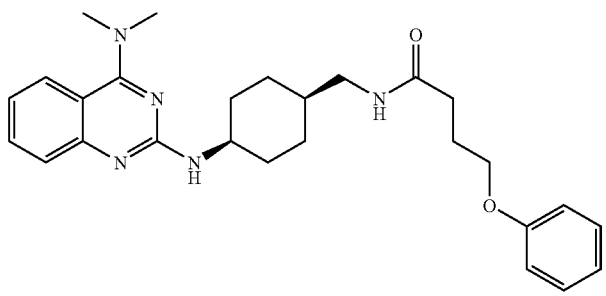 | 462 (M + H) |
| 557 | 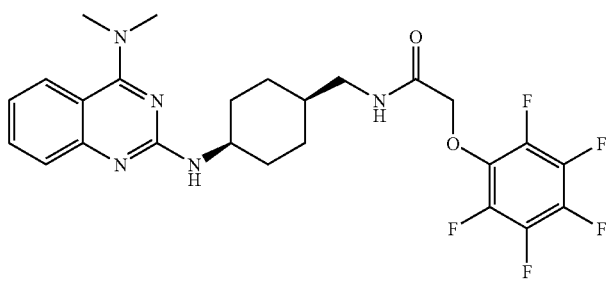 | 524 (M + H) |
| 558 | 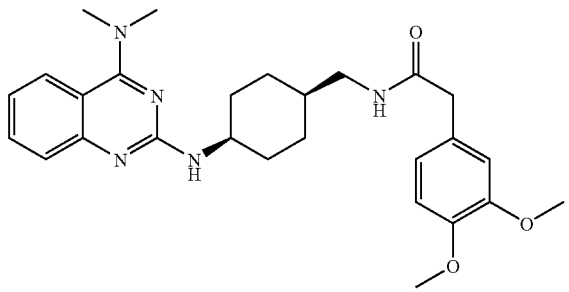 | 478 (M + H) |
| 559 | 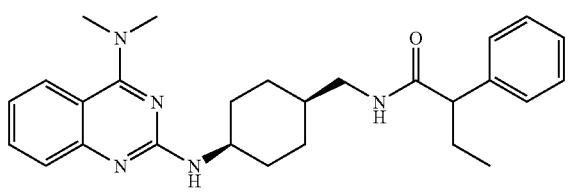 | 446 (M + H) |

-continued
| Example No. | Structure | APCI-MS |
|---|---|---|
| 560 | 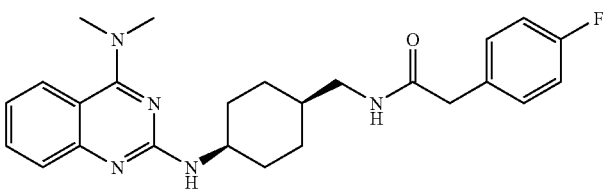 | 436 (M + H) |
| 561 | 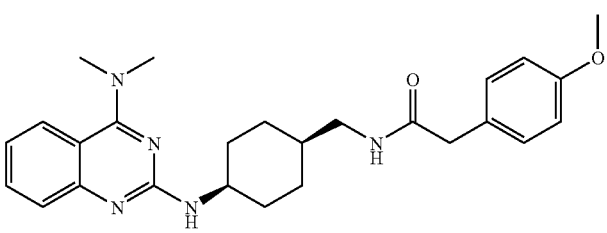 | 448 (M + H) |
| 562 | 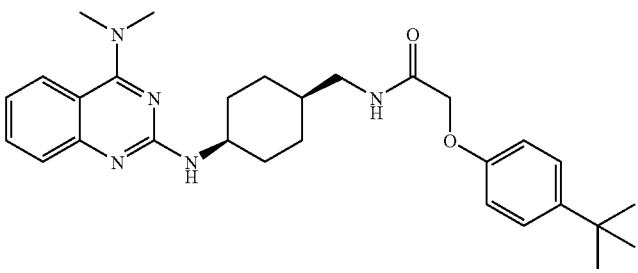 | 490 (M + H) |
| 563 | 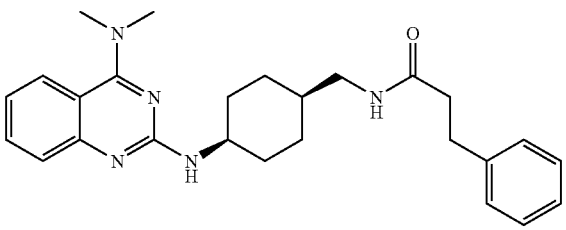 | 432 (M + H) |
| 564 | 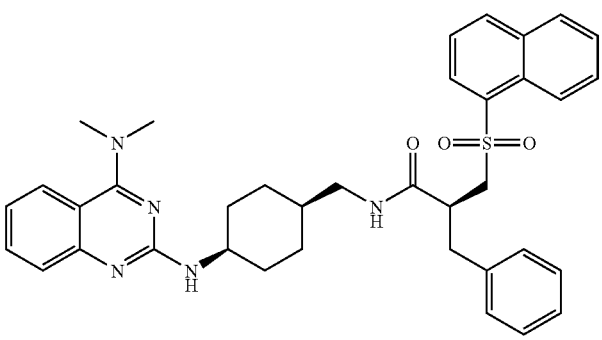 | 637 (M + H) |

-continued
| Example No. | Structure | APCI-MS |
|---|---|---|
| 565 | 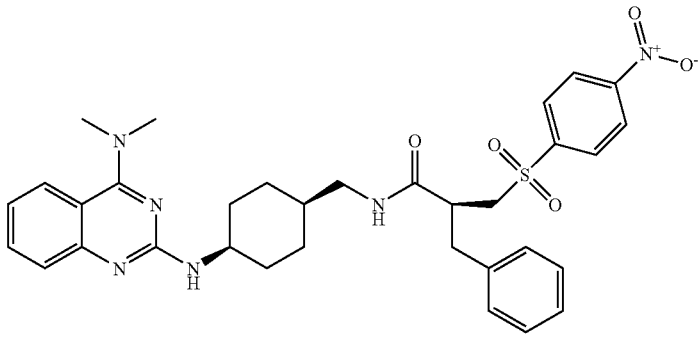 | 632 (M + H) |
| 566 | 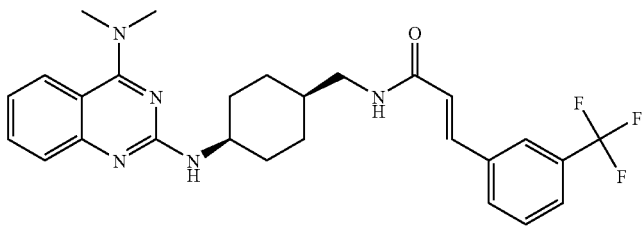 | 498 (M + H) |
| 567 | 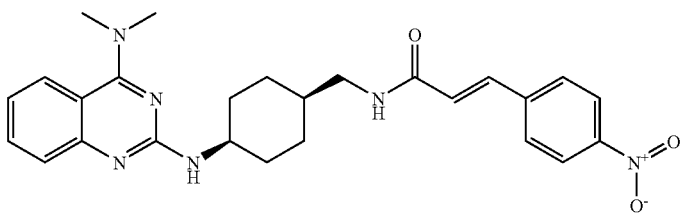 | 475 (M + H) |
| 568 | 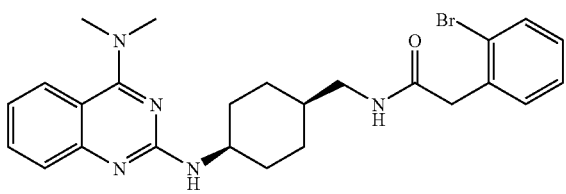 | 496 (M + H) |
| 569 | 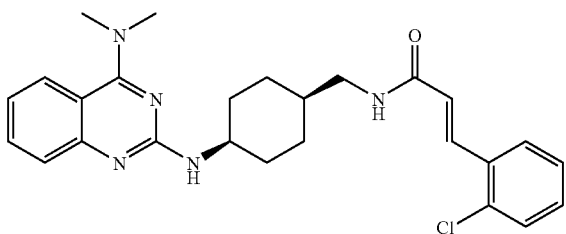 | 464 (M + H) |
| 570 | 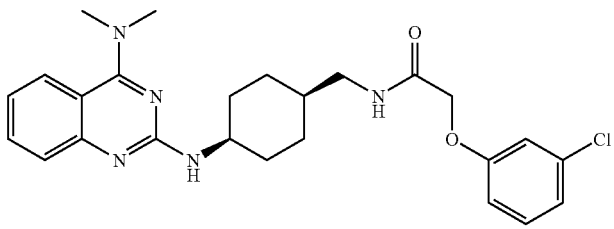 | 468 (M + H) |

-continued
| Example No. | Structure | APCI-MS |
|---|---|---|
| 571 | 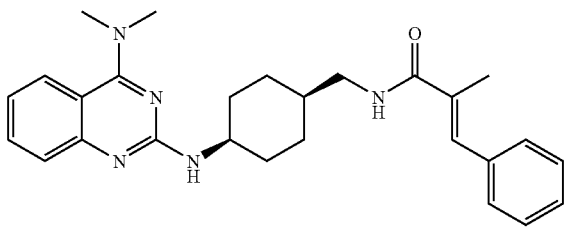 | 444 (M + H) |
| 572 | 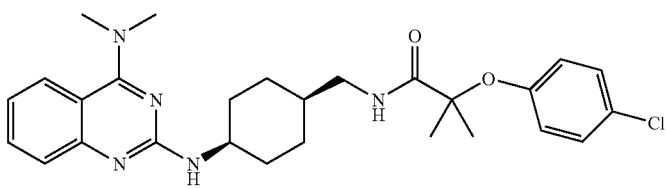 | 496 (M + H) |
| 573 | 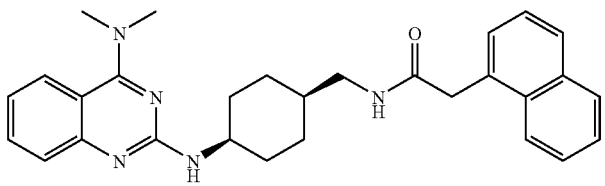 | 468 (M + H) |
| 574 | 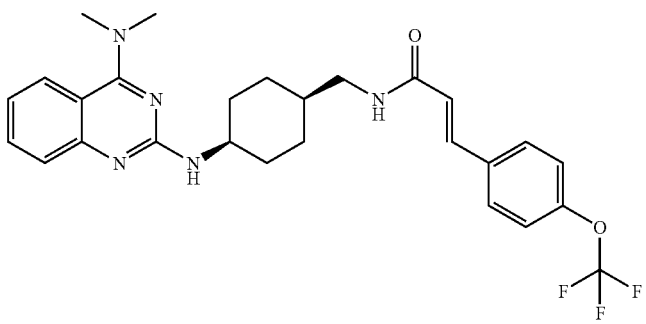 | 514 (M + H) |
| 575 | 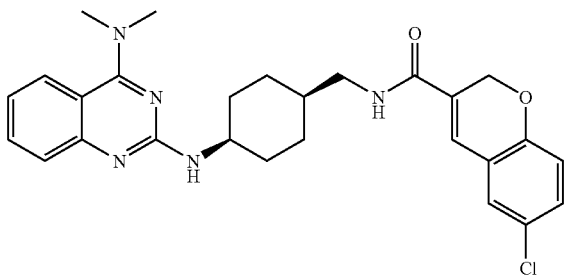 | 492 (M + H) |
| 576 | 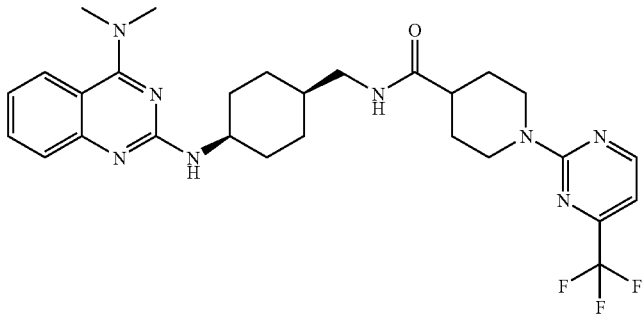 | 557 (M + H) |

-continued
| Example No. | Structure | APCI-MS |
| --- | --- | --- |
| 577 | 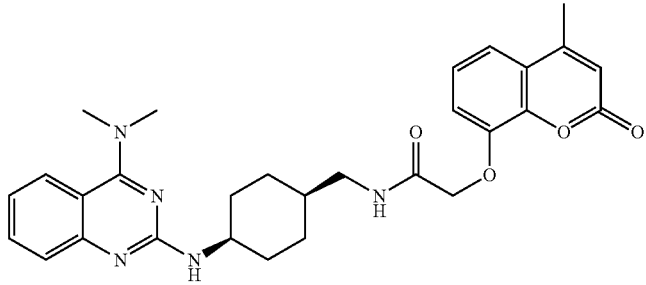 | 516 (M + H) |
| 578 | 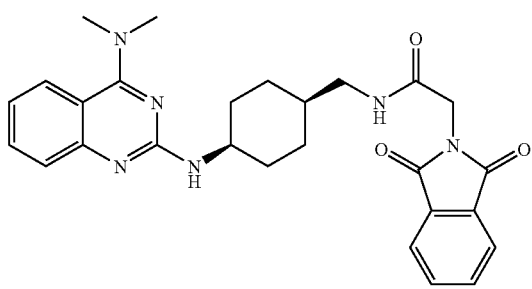 | 487 (M + H) |
| 579 | 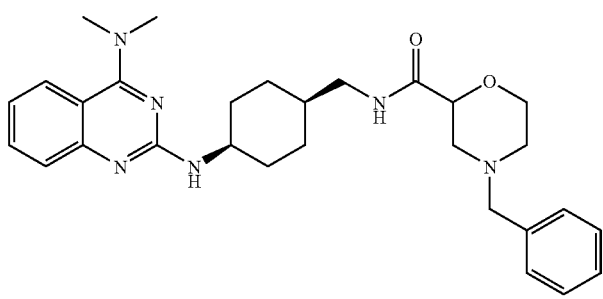 | 503 (M + H) |
| 580 | 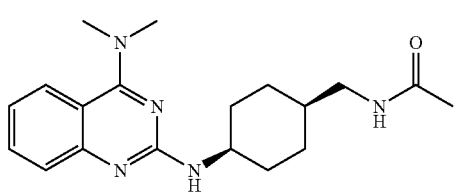 | 342 (M + H) |
| 581 | 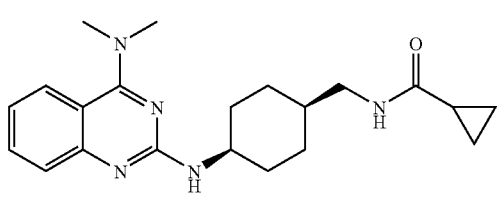 | 368 (M + H) |
| 582 | 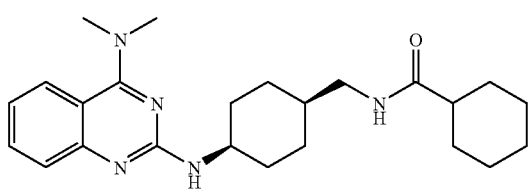 | 410 (M + H) |

-continued
| Example No. | Structure | APCI-MS |
|---|---|---|
| 583 | 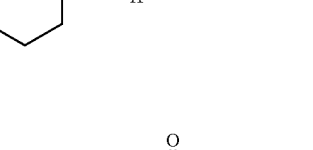 | 398 (M + H) |
| 584 | 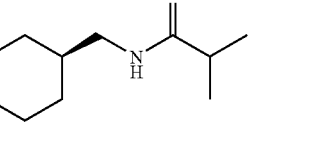 | 370 (M + H) |
| 585 | 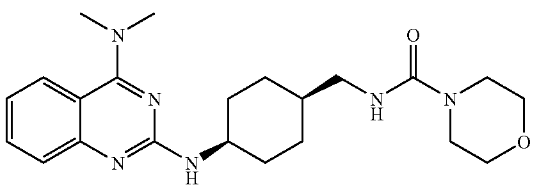 | 413 (M + H) |
| 586 | 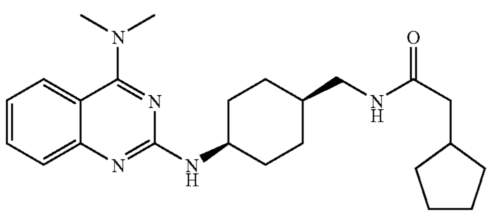 | 410 (M + H) |
| 587 | 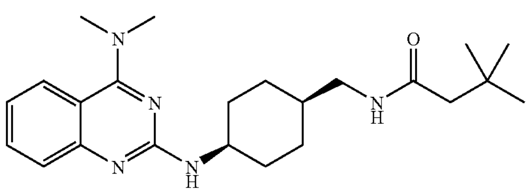 | 398 (M + H) |
| 588 | 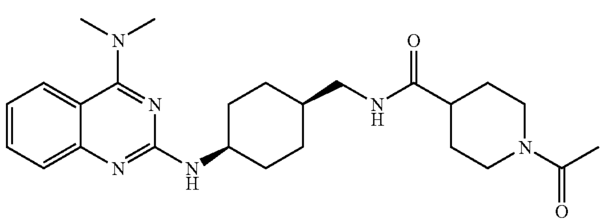 | 453 (M + H) |
| 589 | 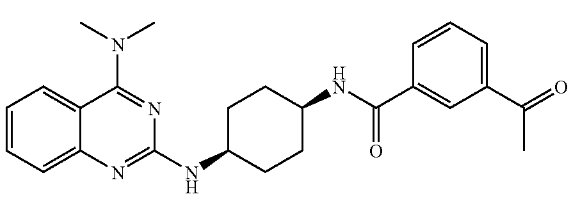 | 432 (M + H) |

-continued
| Example No. | Structure | APCI-MS |
|---|---|---|
| 590 | 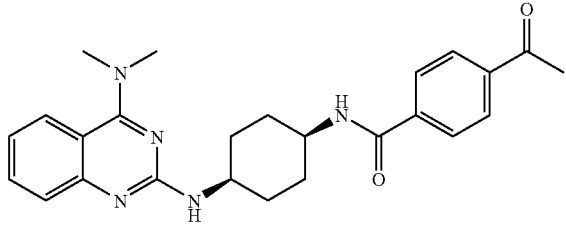 | 432 (M + H) |
| 591 | 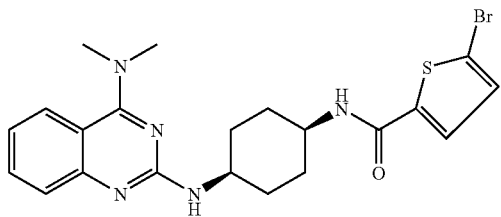 | 474 (M + H) |
| 592 | 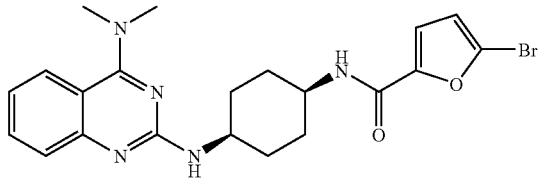 | 458 (M + H) |
| 593 | 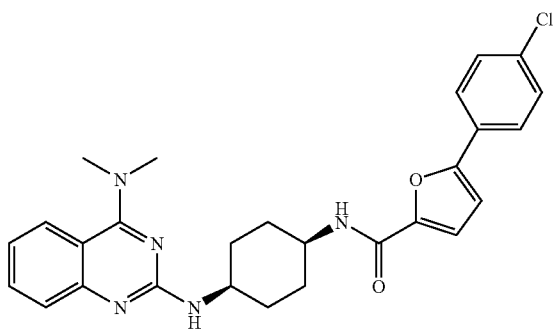 | 490 (M + H) |
| 594 | 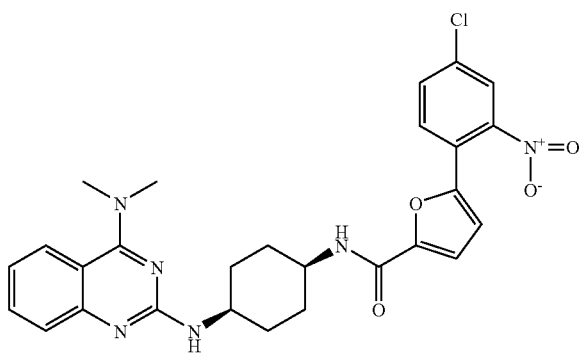 | 535 (M + H) |
| 595 | 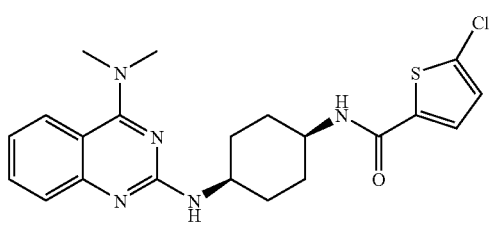 | 430 (M + H) |

-continued
| Example No. | Structure | APCI-MS |
|---|---|---|
| 596 | 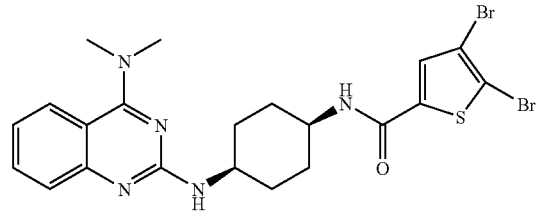 | 552 (M + H) |
| 597 | 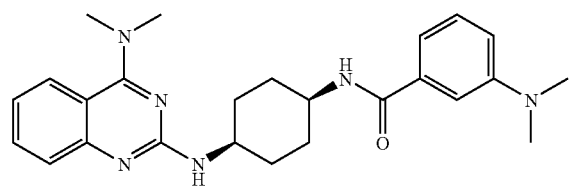 | 433 (M + H) |
| 598 | 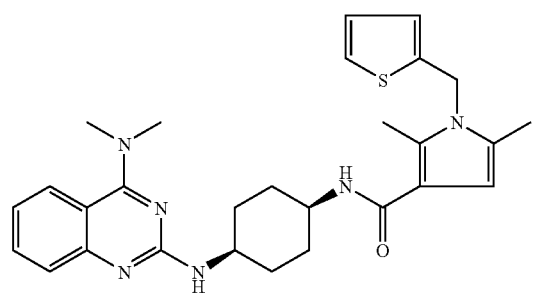 | 503 (M + H) |
| 599 | 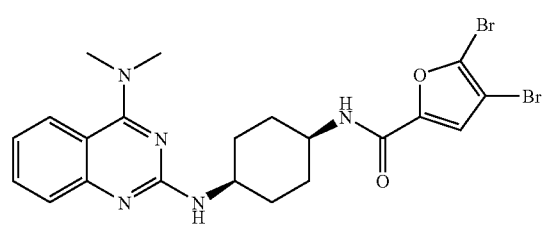 | 536 (M + H) |
| 600 | 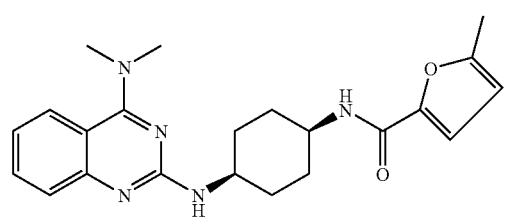 | 506 (M + H) |
| 601 | 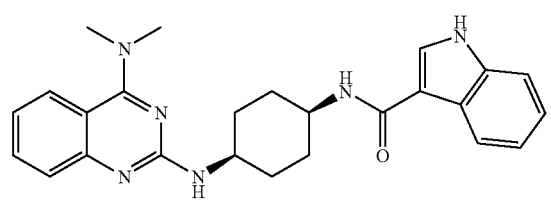 | 429 (M + H) |
| 602 | 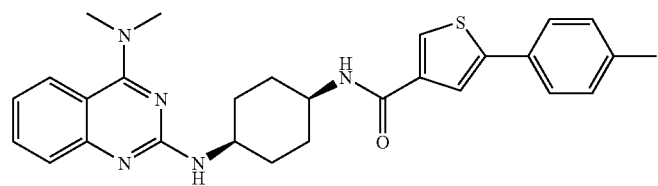 | 486 (M + H) |

-continued
| Example No. | Structure | APCI-MS |
|---|---|---|
| 603 | 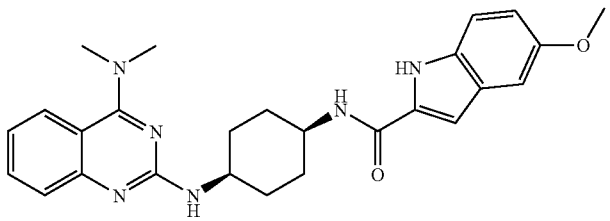 | 459 (M + H) |
| 604 | 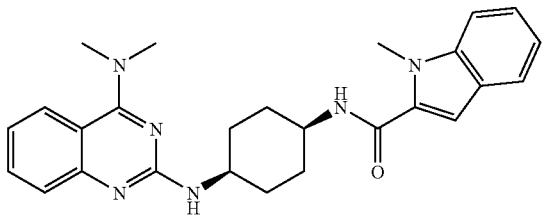 | 443 (M + H) |
| 605 | 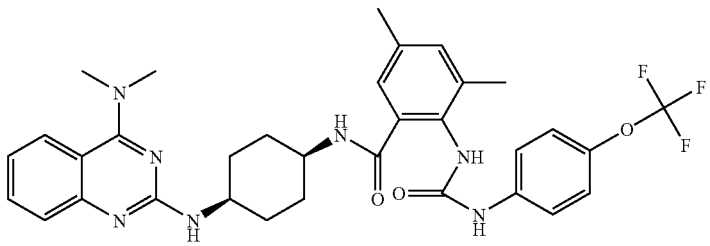 | 636 (M + H) |
| 606 | 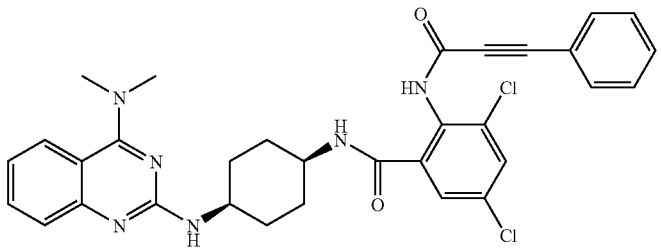 | 601 (M + H) |
| 607 | 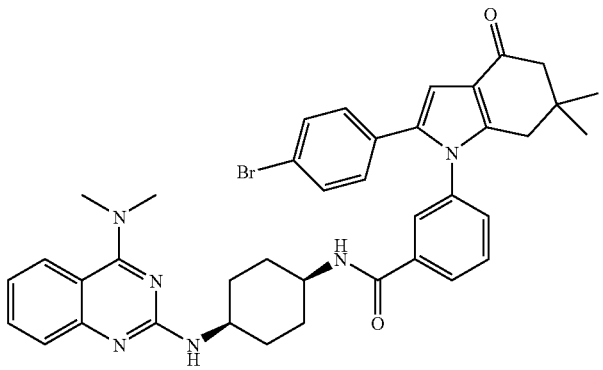 | 705 (M + H) |

-continued
| Example No. | Structure | APCI-MS |
|---|---|---|
| 608 | 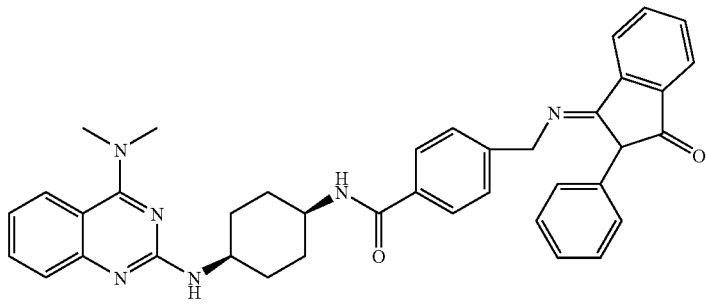 | 623 (M + H) |
| 609 | 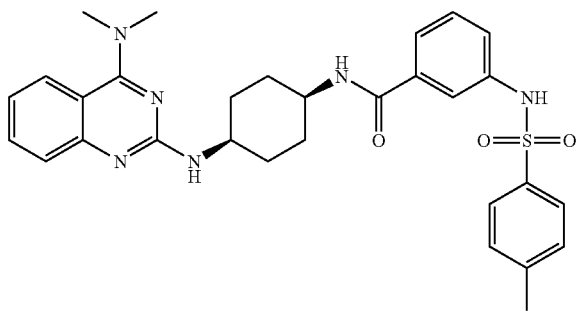 | 559 (M + H) |
| 610 | 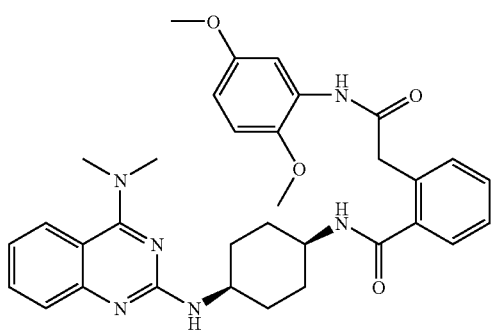 | 583 (M + H) |
| 611 | 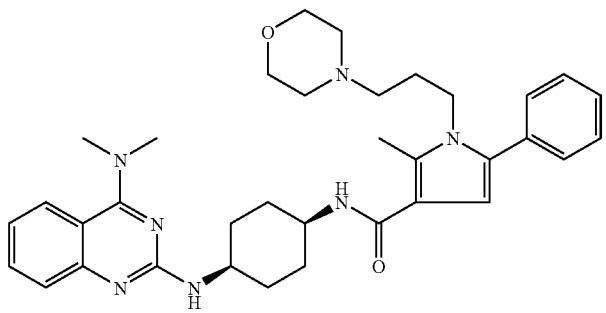 | 596 (M + H) |
| 612 | 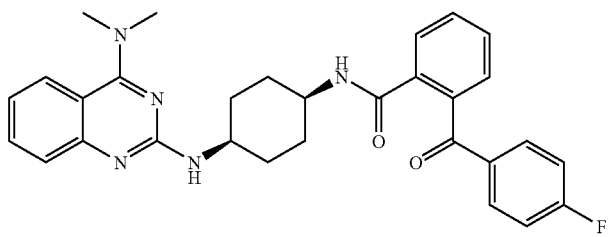 | 512 (M + H) |

-continued
| Example No. | Structure | APCI-MS |
|---|---|---|
| 613 | 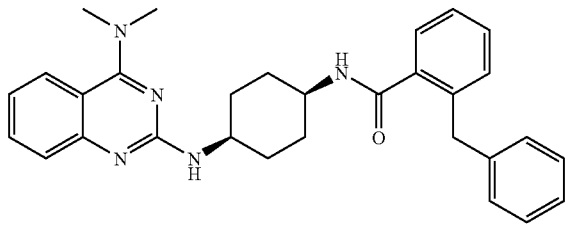 | 480 (M + H) |
| 614 | 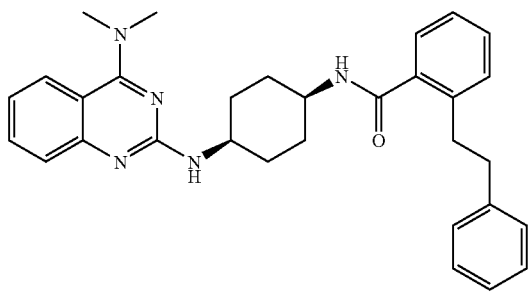 | 494 (M + H) |
| 615 | 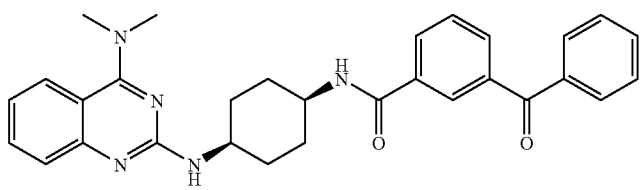 | 494 (M + H) |
| 616 | 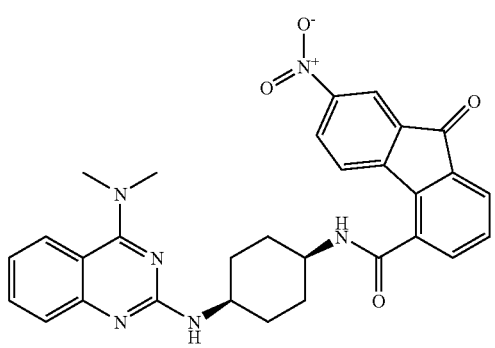 | 537 (M + H) |
| 617 | 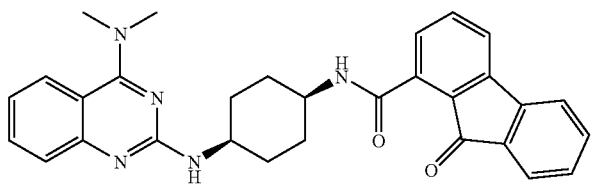 | 492 (M + H) |
| 618 | 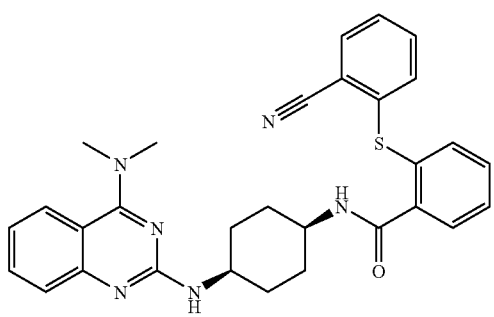 | 523 (M + H) |

-continued
| Example No. | Structure | APCI-MS |
|---|---|---|
| 619 | 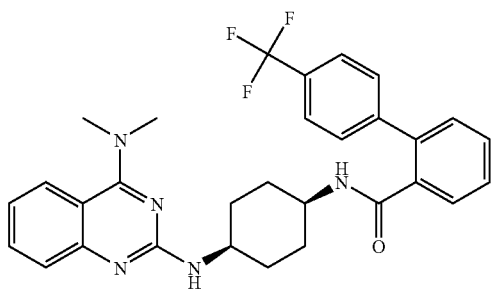 | 534 (M + H) |
| 620 | 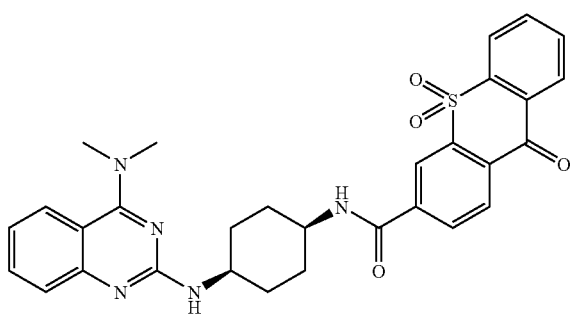 | 556 (M + H) |
| 621 | 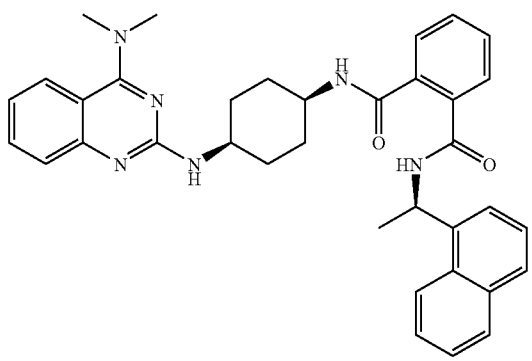 | 587 (M + H) |
| 622 | 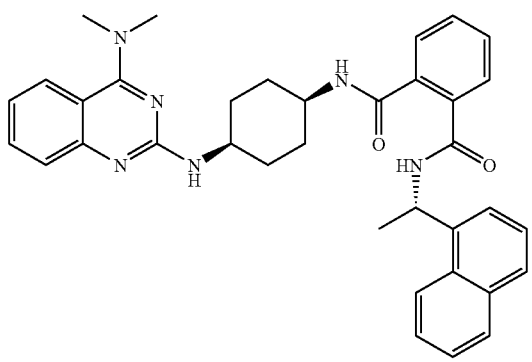 | 587 (M + H) |

-continued
| Example No. | Structure | APCI-MS |
|---|---|---|
| 623 | 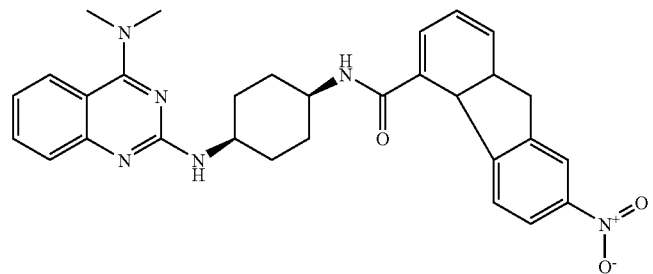 | 523 (M + H) |
| 624 | 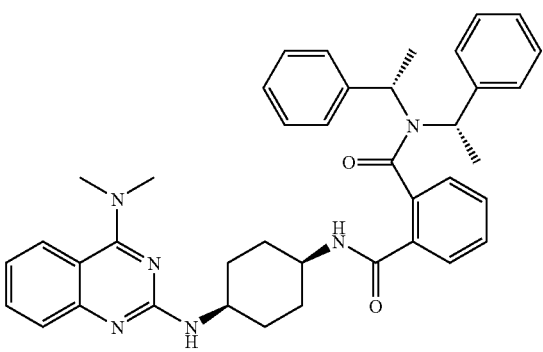 | 641 (M + H) |
| 625 | 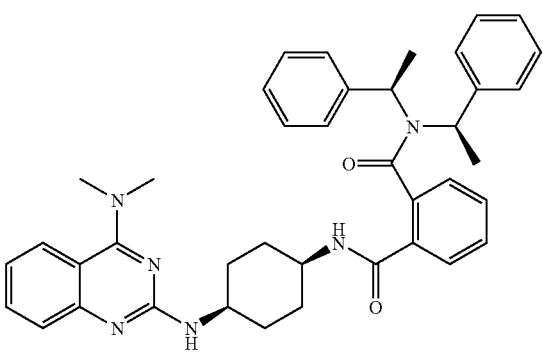 | 641 (M + H) |
| 626 | 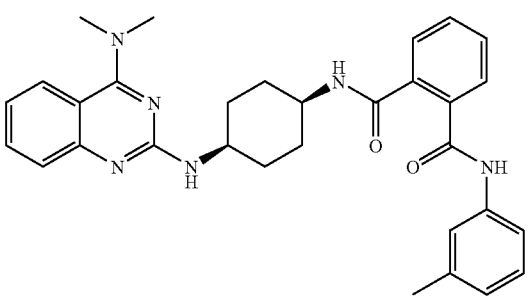 | 523 (M + H) |

| Example No. | Structure | APCI-MS |
|---|---|---|
| 627 | 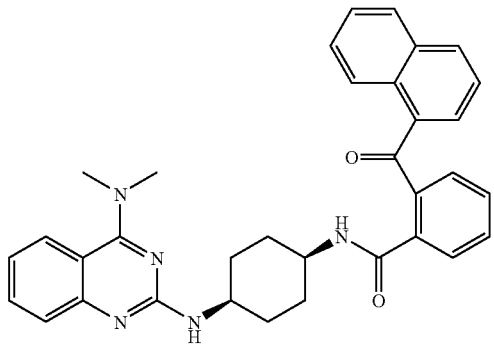 | 544 (M + H) |
| 628 | 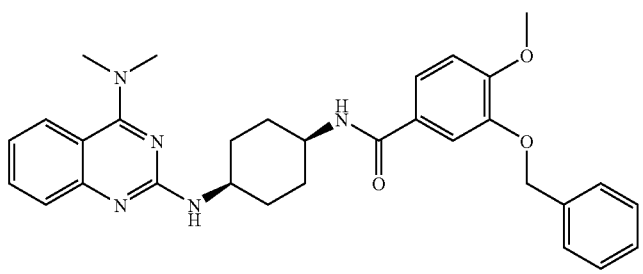 | 526 (M + H) |
| 629 | 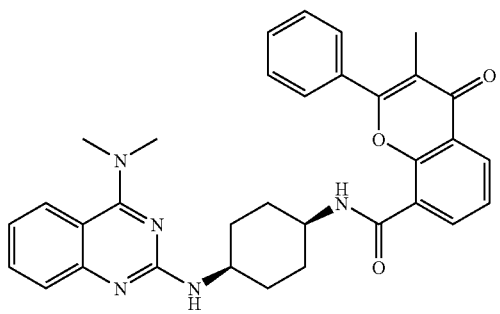 | 548 (M + H) |
| 630 | 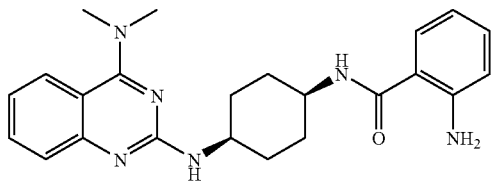 | 405 (M + H) |
| 631 | 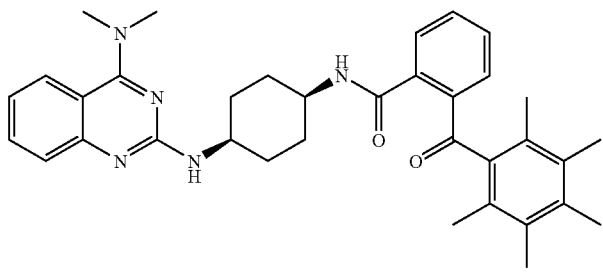 | 564 (M + H) |

-continued
| Example No. | Structure | APCI-MS |
|---|---|---|
| 632 | 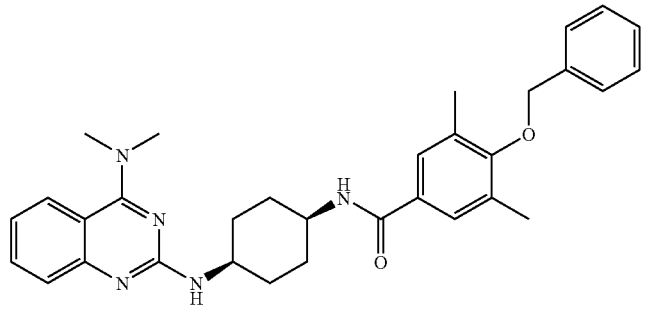 | 524 (M + H) |
| 633 | 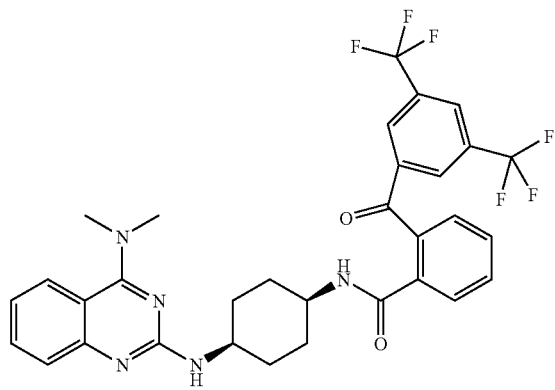 | 630 (M + H) |
| 634 | 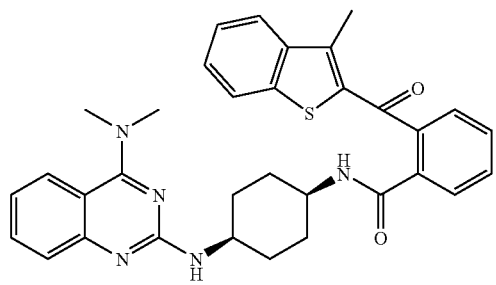 | 564 (M + H) |
| 635 | 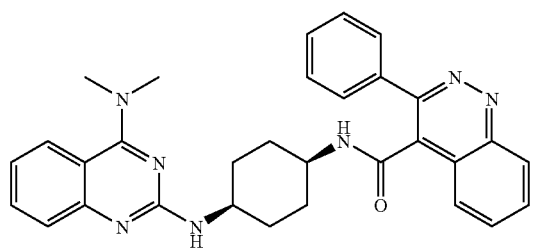 | 518 (M + H) |
| 636 | 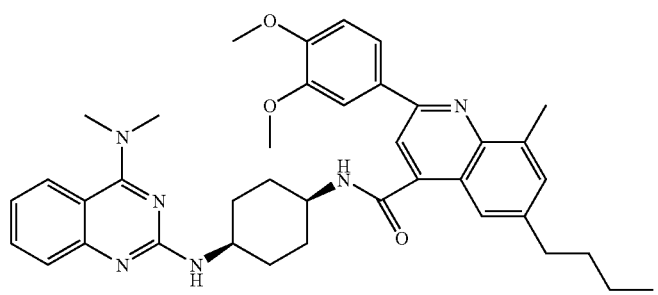 | 647 (M + H) |

-continued
| Example No. | Structure | APCI-MS |
|---|---|---|
| 637 | 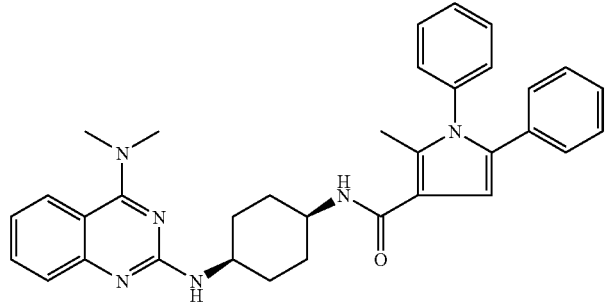 | 545 (M + H) |
| 638 | 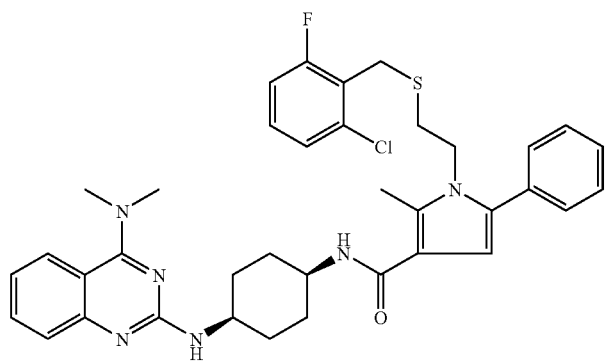 | 671 (M + H) |
| 639 | 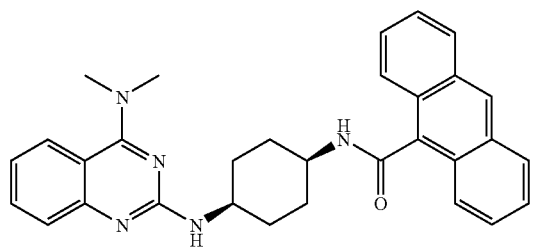 | 490 (M + H) |
| 640 | 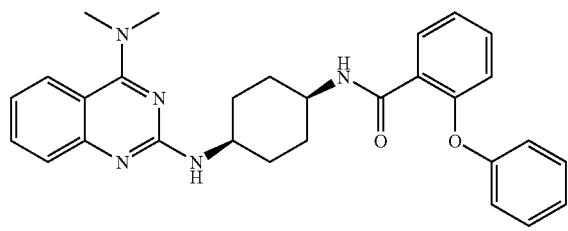 | 482 (M + H) |
| 641 | 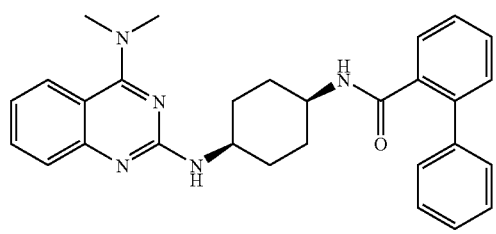 | 466 (M + H) |

-continued
| Example No. | Structure | APCI-MS |
|---|---|---|
| 642 | 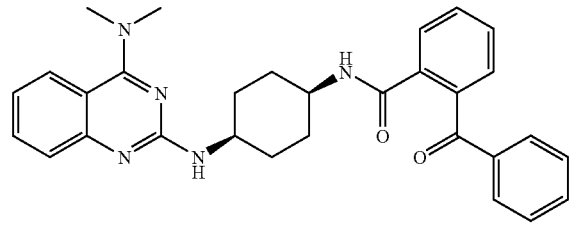 | 494 (M + H) |
| 643 | 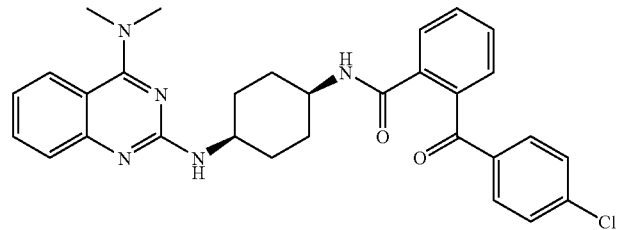 | 528 (M + H) |
| 644 | 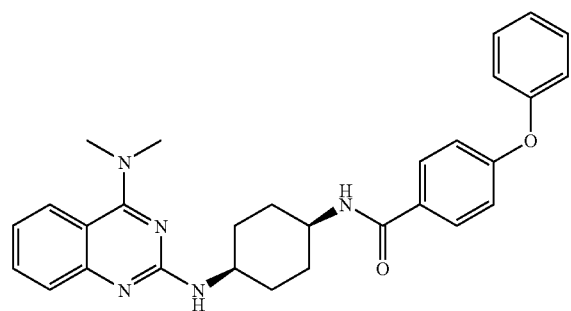 | 482 (M + H) |
| 645 | 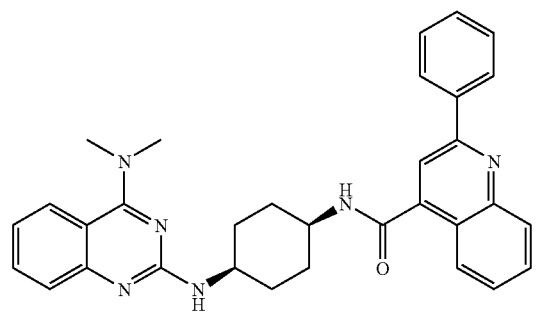 | 517 (M + H) |
| 646 | 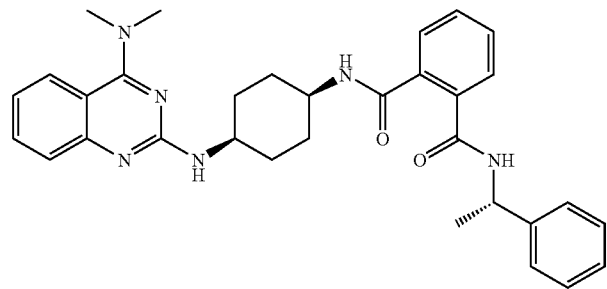 | 537 (M + H) |

-continued
| Example No. | Structure | APCI-MS |
|---|---|---|
| 647 | 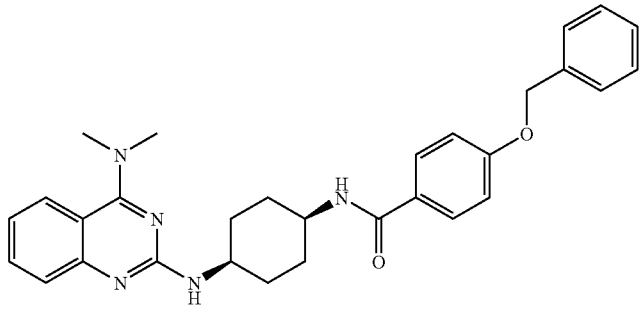 | 496 (M + H) |
| 648 | 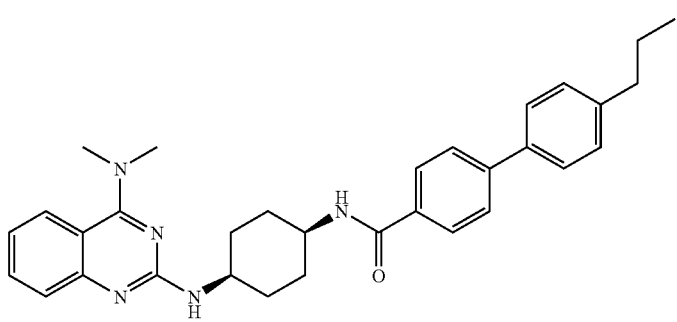 | 508 (M + H) |
| 649 | 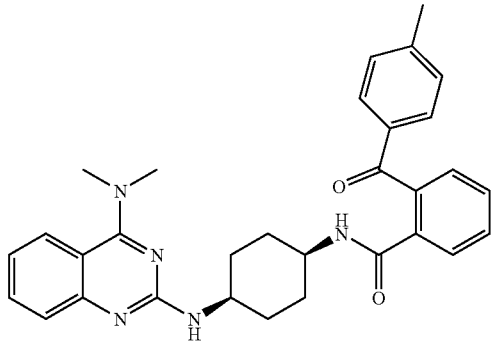 | 508 (M + H) |
| 650 | 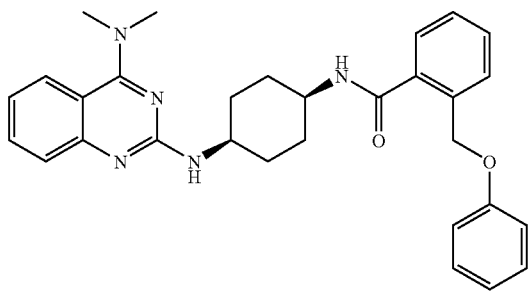 | 496 (M + H) |
| 651 | 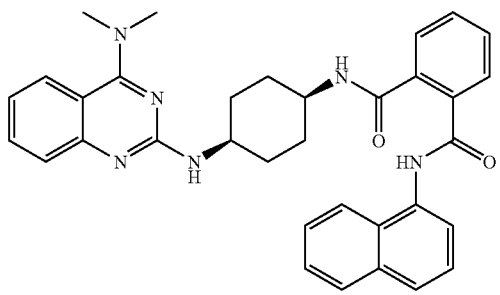 | 559 (M + H) |

| Example No. | Structure | APCI-MS |
|---|---|---|
| 652 | 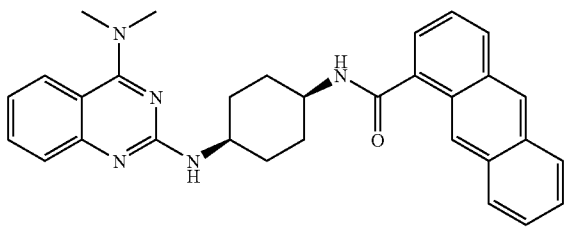 | 490 (M + H) |
| 653 | 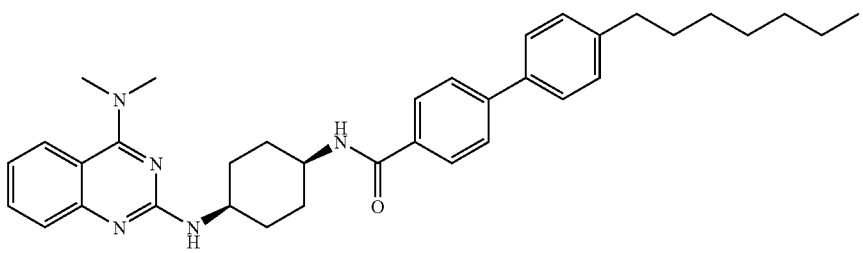 | 564 (M + H) |
| 654 | 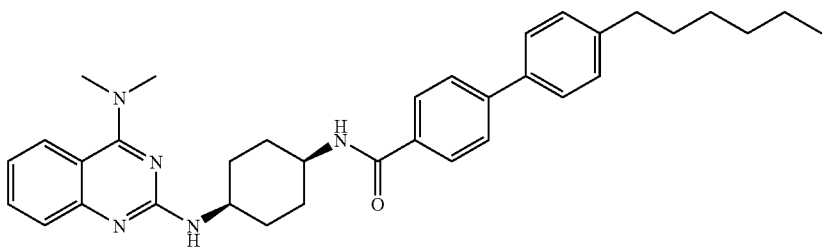 | 550 (M + H) |
| 655 | 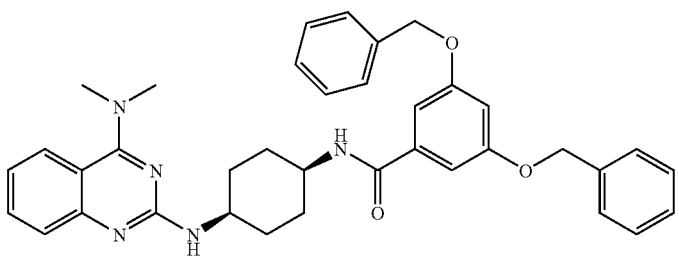 | 602 (M + H) |
| 656 | 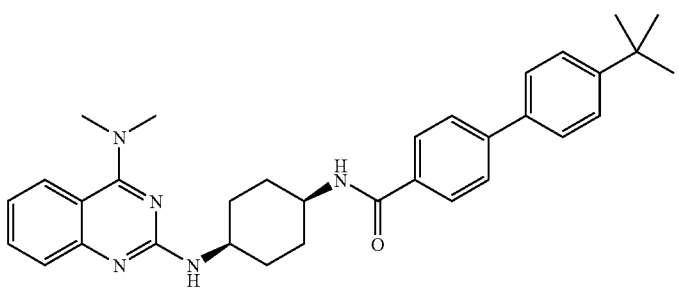 | 522 (M + H) |
| 657 | 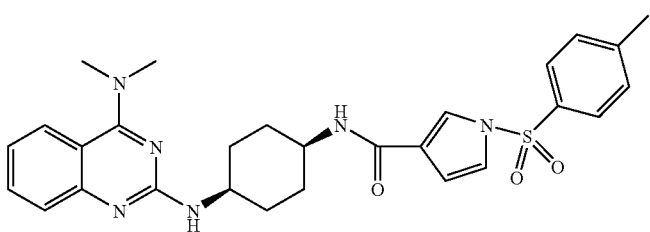 | 533 (M + H) |

-continued
| Example No. | Structure | APCI-MS |
|---|---|---|
| 658 | 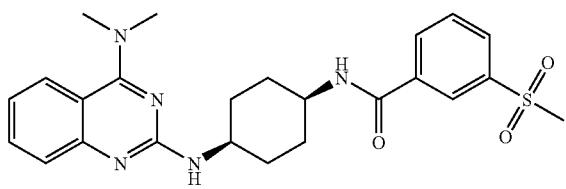 | 468 (M + H) |
| 659 | 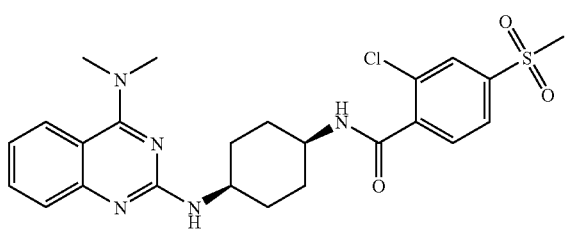 | 502 (M + H) |
| 660 | 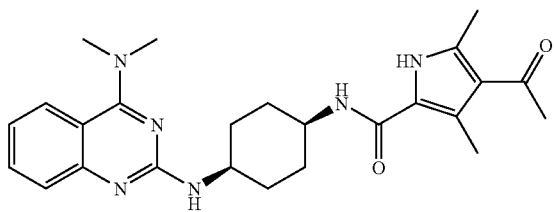 | 449 (M + H) |
| 661 | 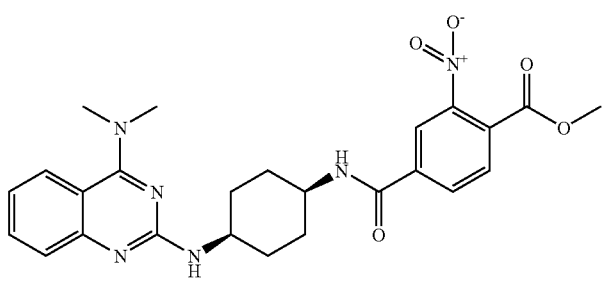 | 493 (M + H) |
| 662 | 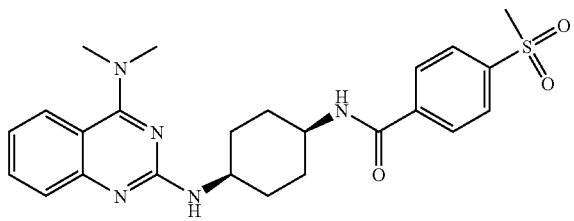 | 468 (M + H) |
| 663 | 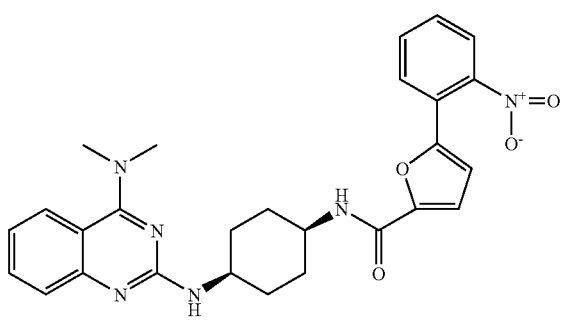 | 501 (M + H) |

-continued
| Example No. | Structure | APCI-MS |
|---|---|---|
| 664 | 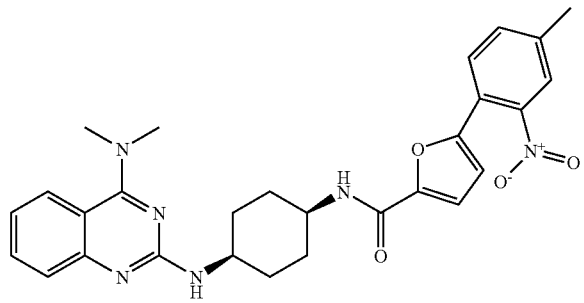 | 515 (M + H) |
| 665 | 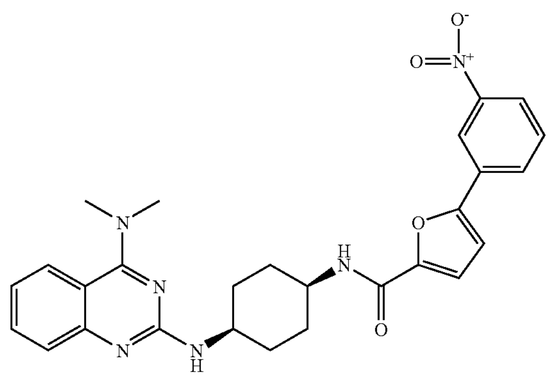 | 501 (M + H) |
| 666 | 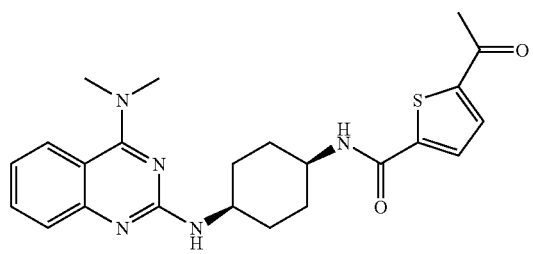 | 438 (M + H) |
| 667 | 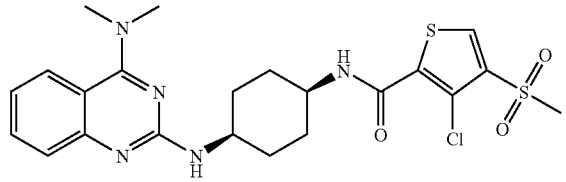 | 508 (M + H) |
| 668 | 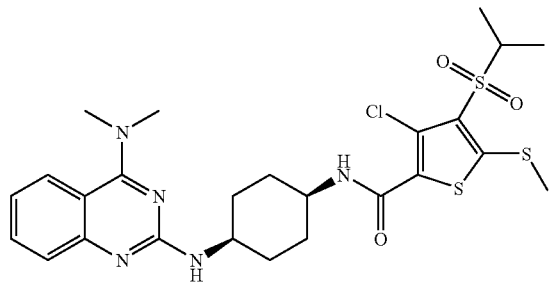 | 582 (M + H) |

-continued
| Example No. | Structure | APCI-MS |
|---|---|---|
| 669 | 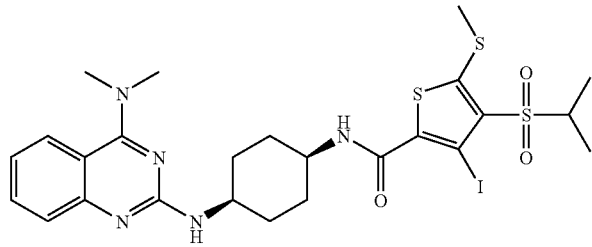 | 674 (M + H) |
| 670 | 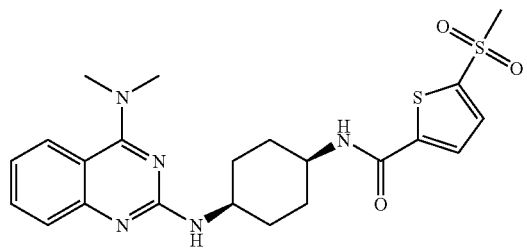 | 474 (M + H) |
| 671 | 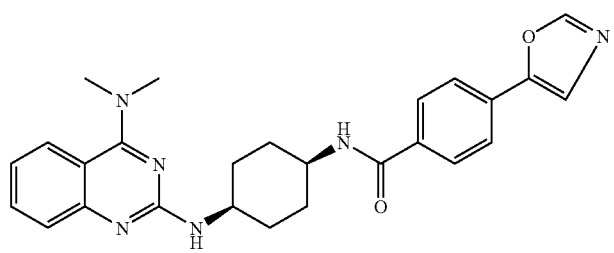 | 457 (M + H) |
| 672 | 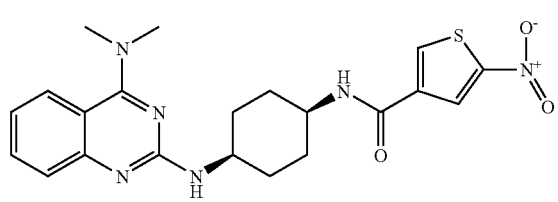 | 441 (M + H) |
| 673 | 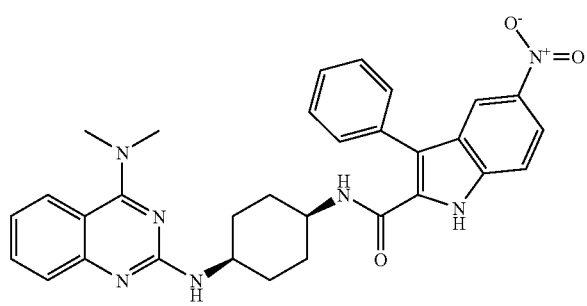 | 550 (M + H) |
| 674 | 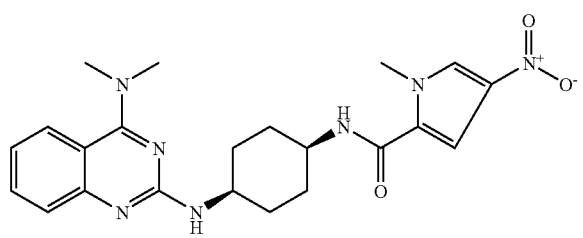 | 438 (M + H) |

-continued
| Example No. | Structure | APCI-MS |
|---|---|---|
| 675 | 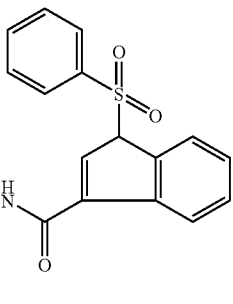 | 569 (M + H) |
| 676 | 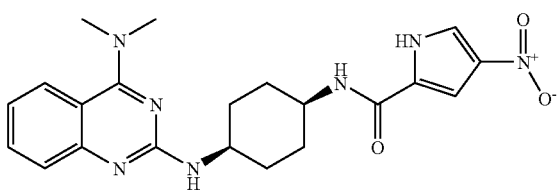 | 424 (M + H) |
| 677 | 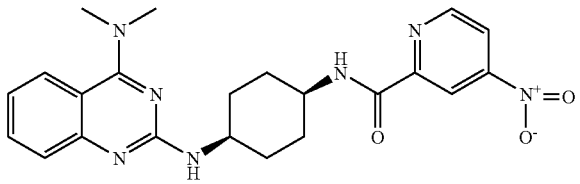 | 436 (M + H) |
| 678 | 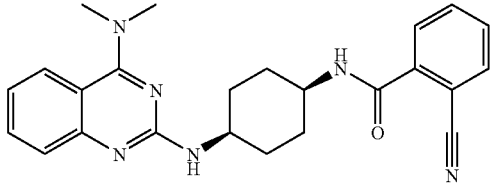 | 415 (M + H) |
| 679 | 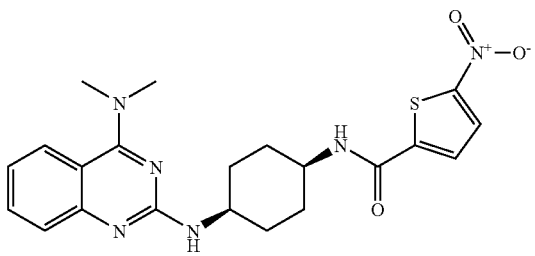 | 441 (M + H) |
| 680 | 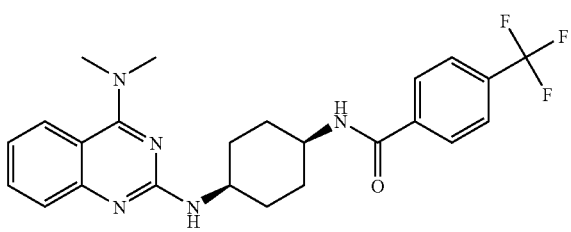 | 458 (M + H) |

-continued
| Example No. | Structure | APCI-MS |
|---|---|---|
| 681 | 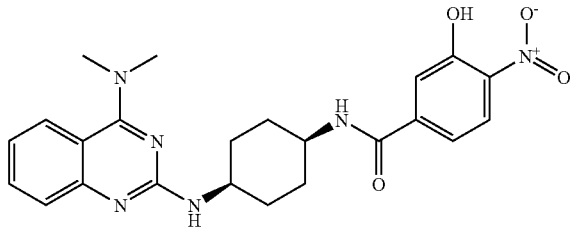 | 451 (M + H) |
| 682 | 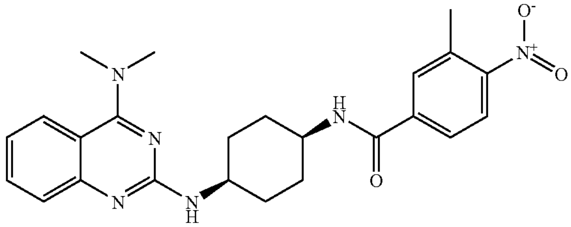 | 449 (M + H) |
| 683 | 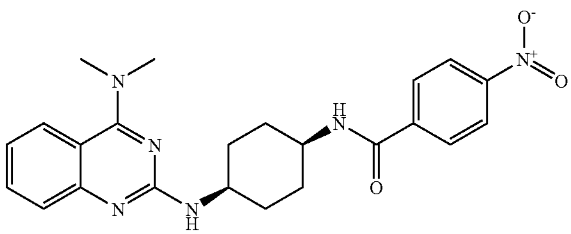 | 435 (M + H) |
| 684 | 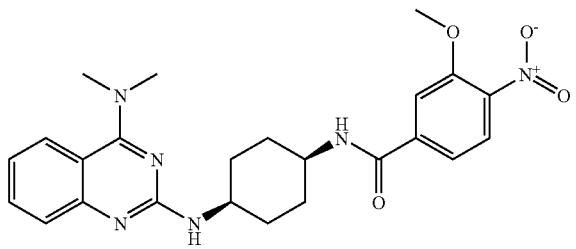 | 465 (M + H) |
| 685 | 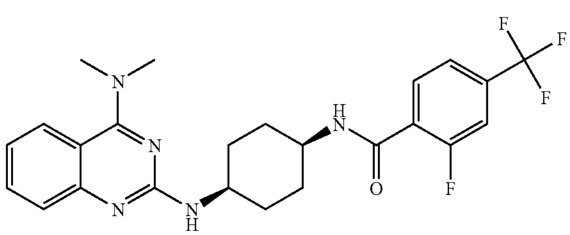 | 476 (M + H) |
| 686 | 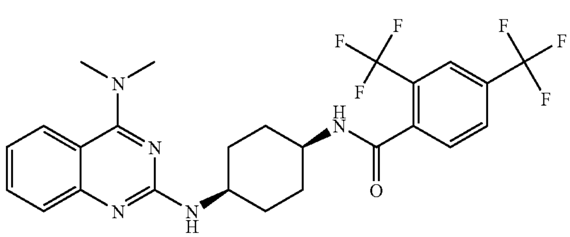 | 526 (M + H) |

-continued
| Example No. | Structure | APCI-MS |
|---|---|---|
| 687 | 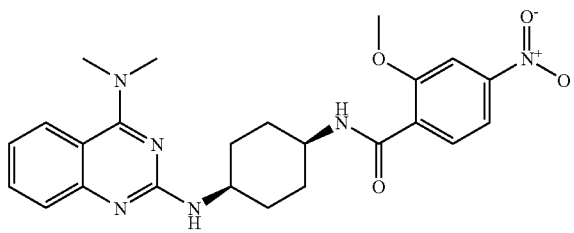 | 465 (M + H) |
| 688 | 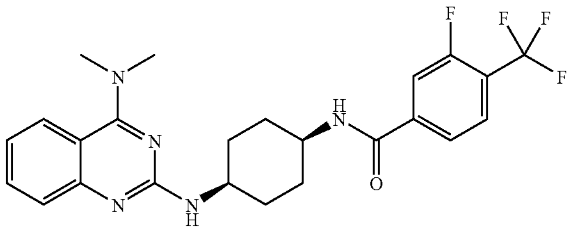 | 476 (M + H) |
| 689 | 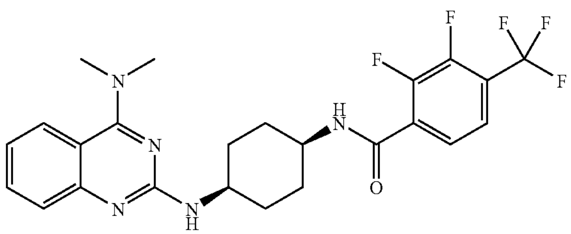 | 494 (M + H) |
| 690 | 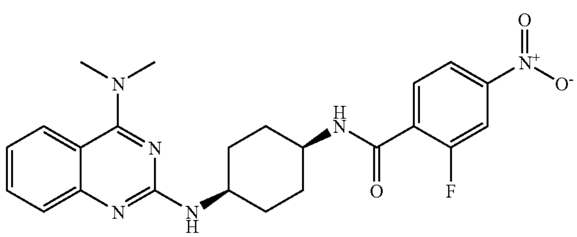 | 453 (M + H) |
| 691 | 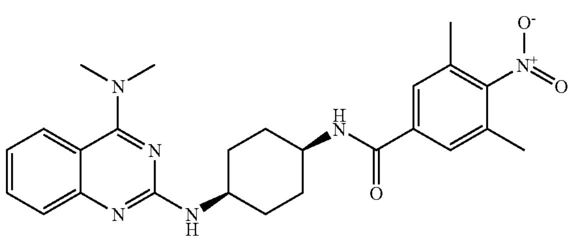 | 463 (M + H) |
| 692 | 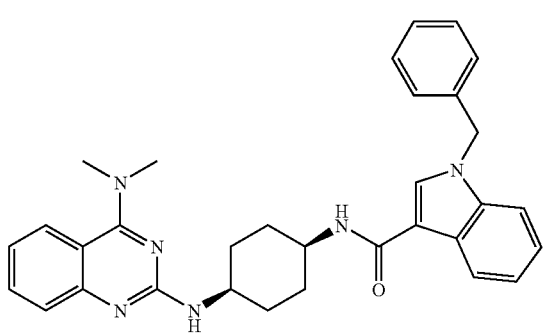 | 519 (M + H) |

-continued
| Example No. | Structure | APCI-MS |
|---|---|---|
| 693 | 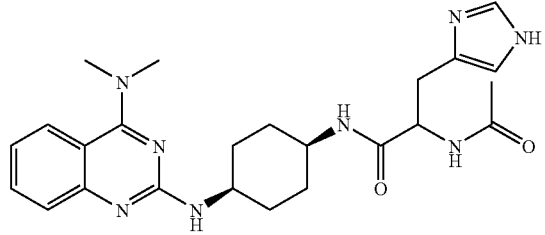 | 465 (M + H) |
| 694 | 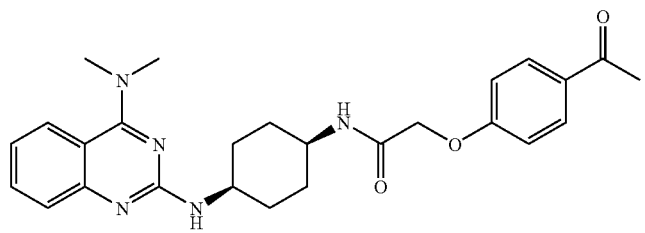 | 462 (M + H) |
| 695 | 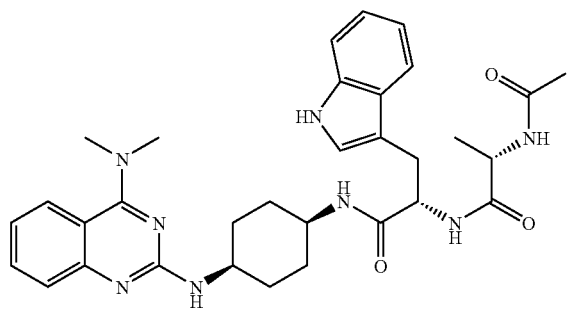 | 585 (M + H) |
| 696 | 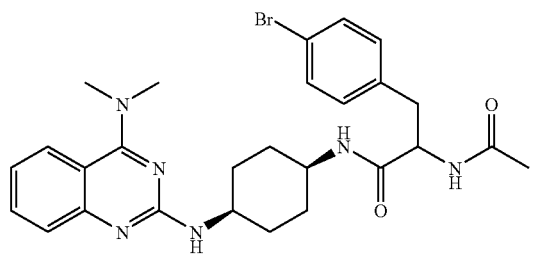 | 553 (M + H) |
| 697 | 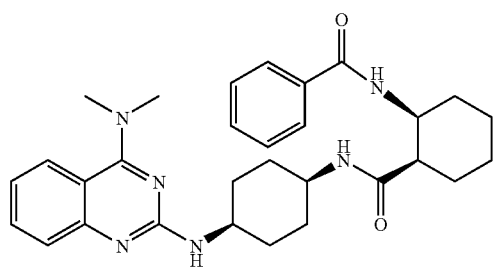 | 515 (M + H) |

-continued
| Example No. | Structure | APCI-MS |
|---|---|---|
| 698 | 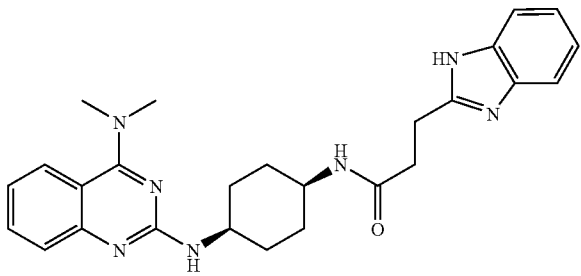 | 458 (M + H) |
| 699 | 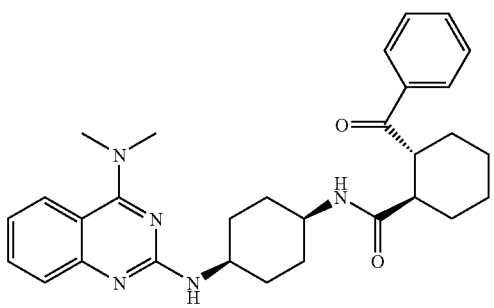 | 500 (M + H) |
| 700 | 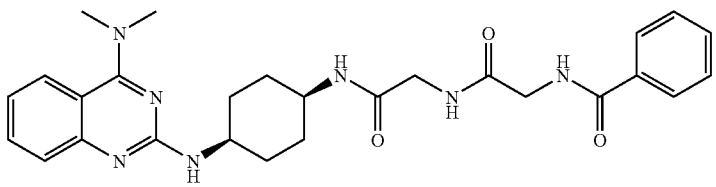 | 504 (M + H) |
| 701 | 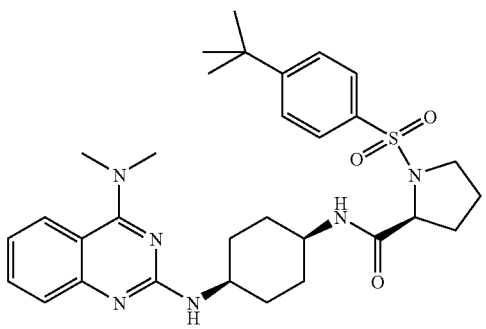 | 579 (M + H) |
| 702 | 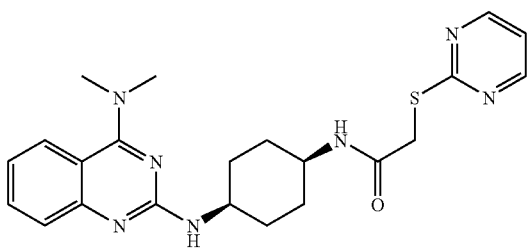 | 438 (M + H) |
| 703 | 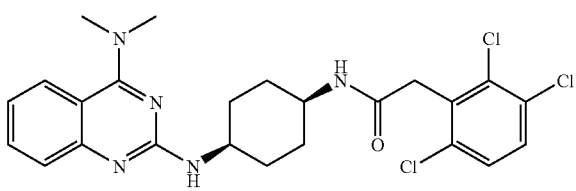 | 506 (M + H) |

-continued
| Example No. | Structure | APCI-MS |
|---|---|---|
| 704 | 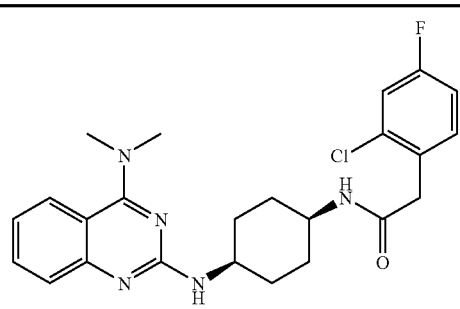 | 456 (M + H) |
| 705 | 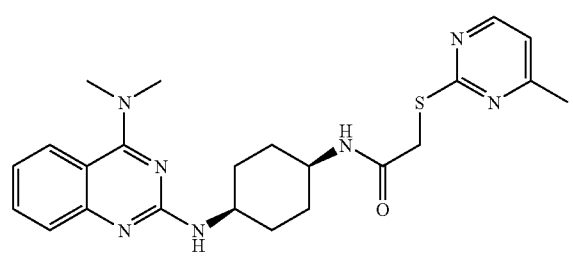 | 452 (M + H) |
| 706 | 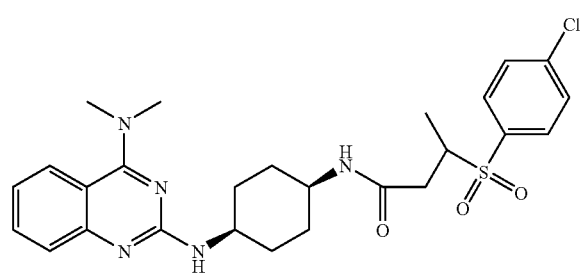 | 530 (M + H) |
| 707 | 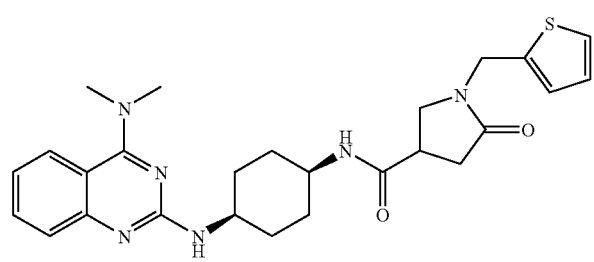 | 493 (M + H) |
| 708 | 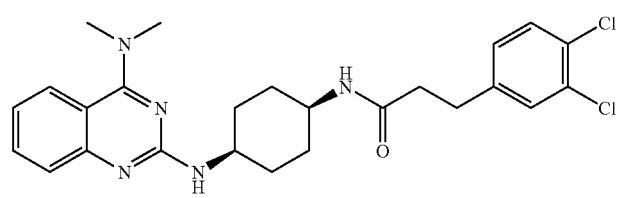 | 486 (M + H) |
| 709 | 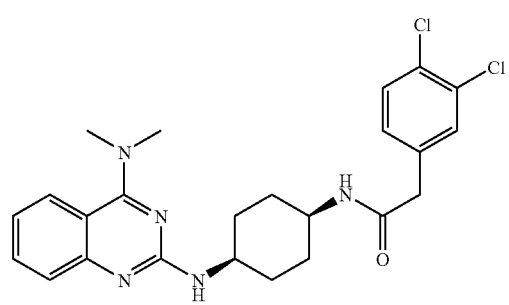 | 472 (M + H) |

-continued
| Example No. | Structure | APCI-MS |
|---|---|---|
| 710 | 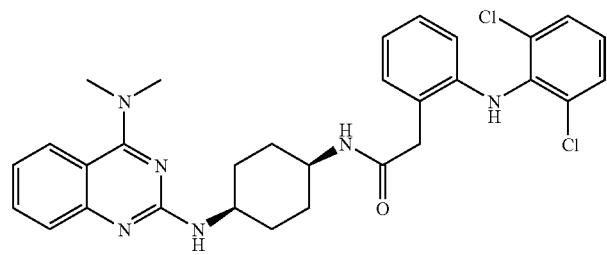 | 563 (M + H) |
| 711 | 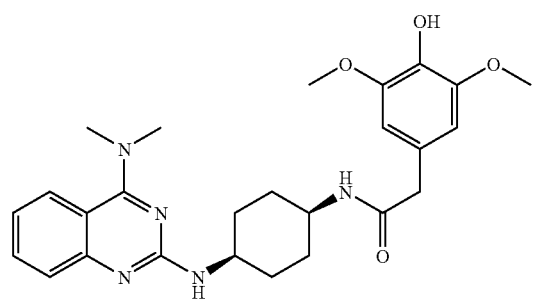 | 480 (M + H) |
| 712 | 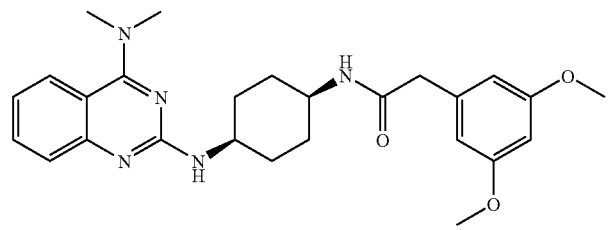 | 464 (M + H) |
| 713 | 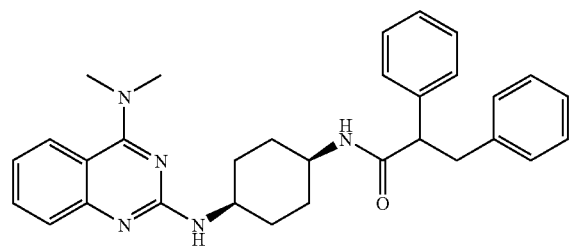 | 494 (M + H) |
| 714 | 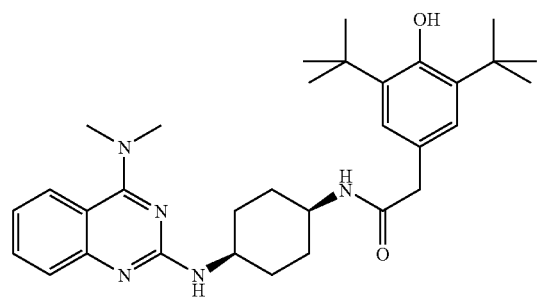 | 532 (M + H) |

-continued
| Example No. | Structure | APCI-MS |
|---|---|---|
| 715 | 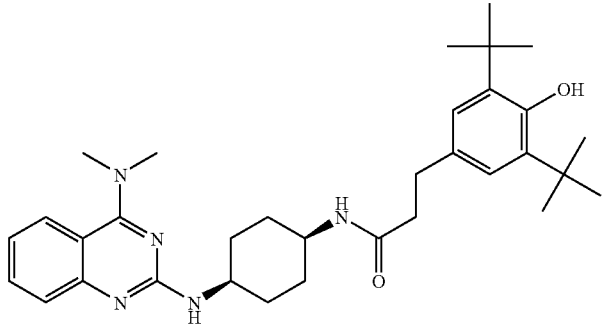 | 546 (M + H) |
| 716 | 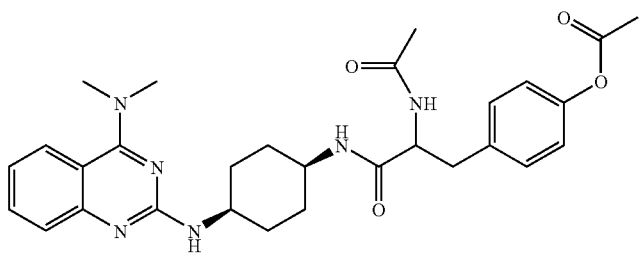 | 533 (M + H) |
| 717 | 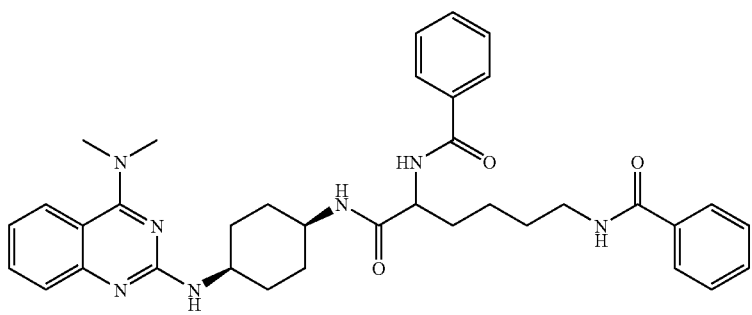 | 622 (M + H) |
| 718 | 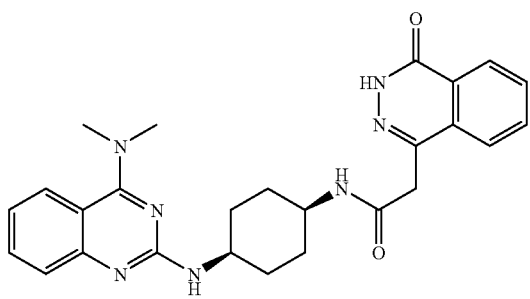 | 472 (M + H) |
| 719 | 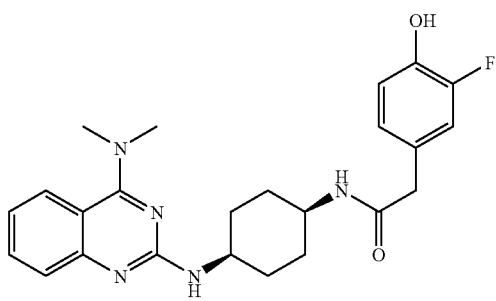 | 438 (M + H) |

-continued
| Example No. | Structure | APCI-MS |
|---|---|---|
| 720 | 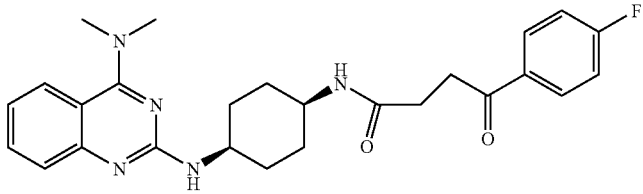 | 464 (M + H) |
| 721 | 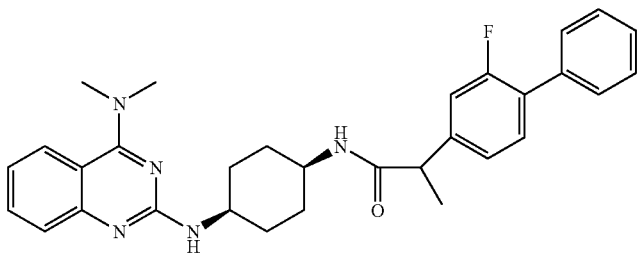 | 512 (M + H) |
| 722 | 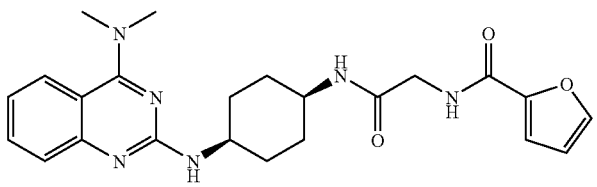 | 437 (M + H) |
| 723 | 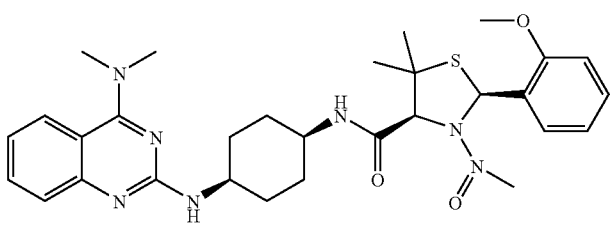 | 577 (M + H) |
| 724 | 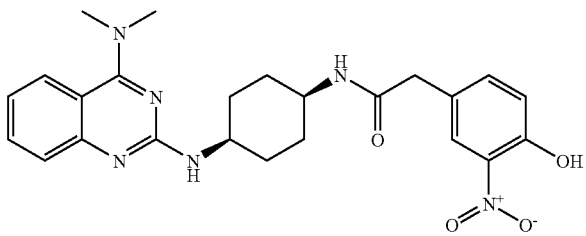 | 465 (M + H) |
| 725 | 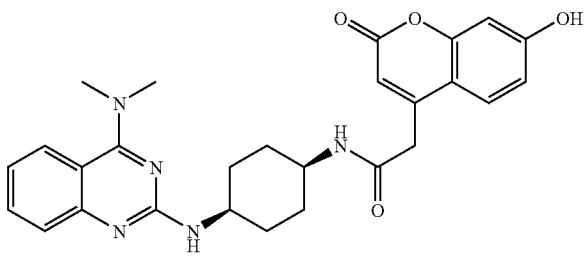 | 488 (M + H) |

-continued

| Example No. | Structure | APCI-MS |
|---|---|---|
| 726 | 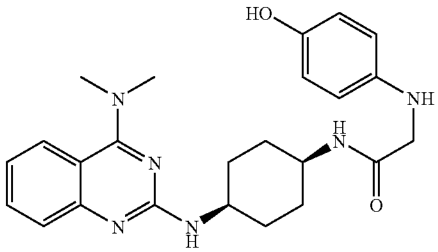 | 435 (M + H) |
| 727 | 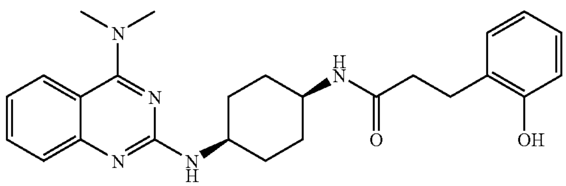 | 434 (M + H) |
| 728 | 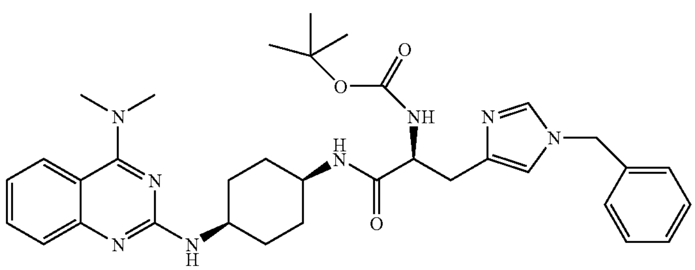 | 613 (M + H) |
| 729 | 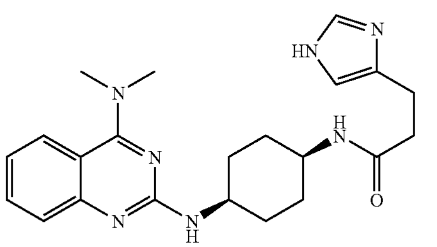 | 408 (M + H) |
| 730 | 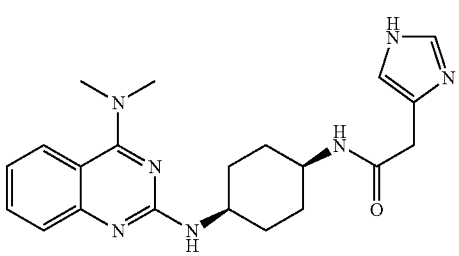 | 394 (M + H) |
| 731 | 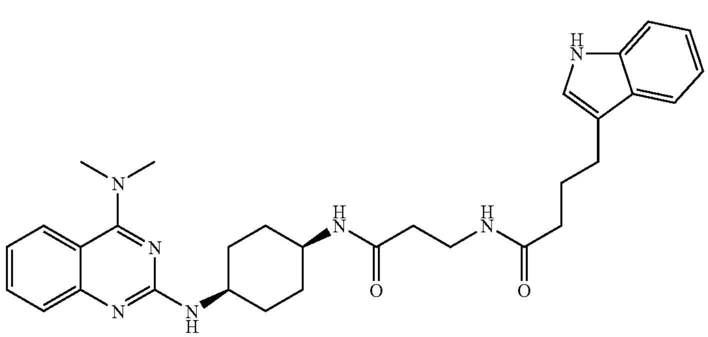 | 542 (M + H) |

-continued
| Example No. | Structure | APCI-MS |
|---|---|---|
| 732 | 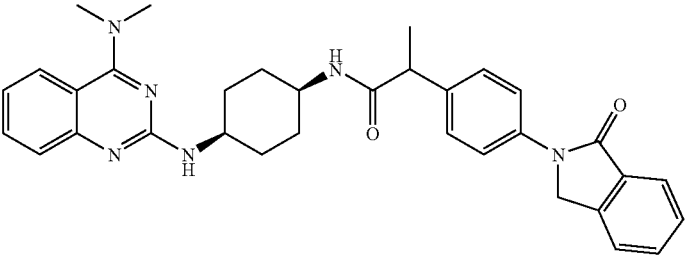 | 549 (M + H) |
| 733 | 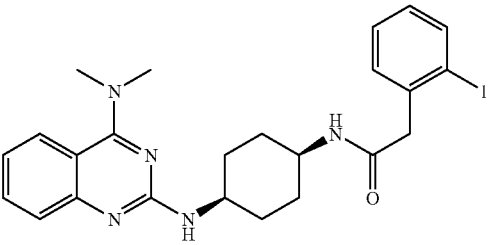 | 530 (M + H) |
| 734 | 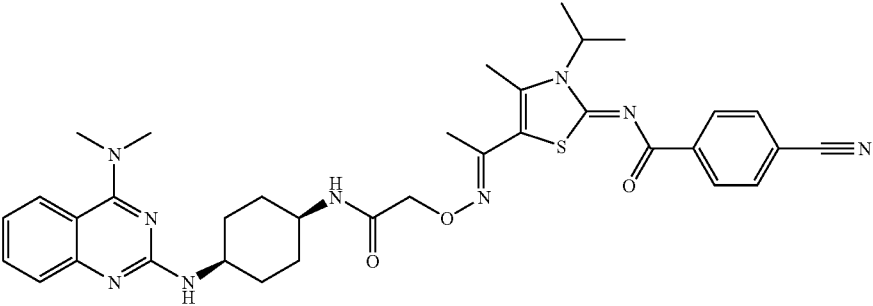 | 668 (M + H) |
| 735 | 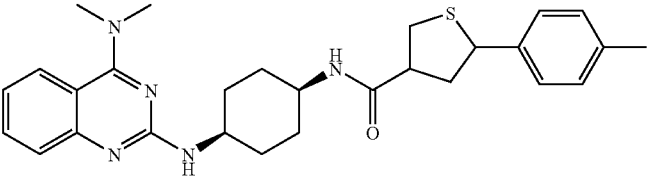 | 490 (M + H) |
| 736 | 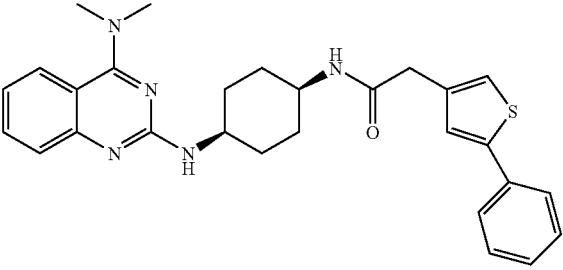 | 486 (M + H) |
| 737 | 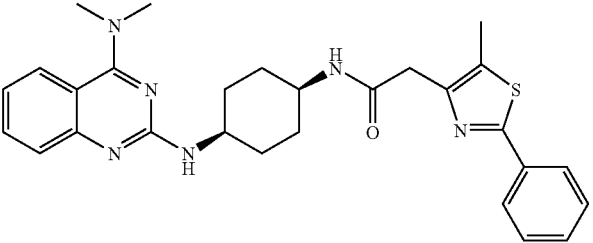 | 501 (M + H) |

| Example No. | Structure | APCI-MS |
|---|---|---|
| 738 | 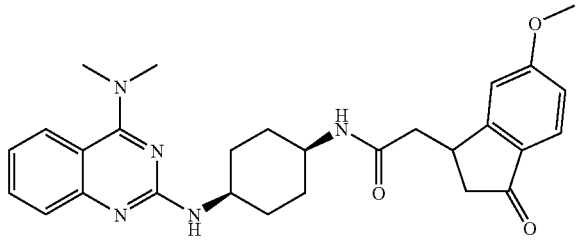 | 488 (M + H) |
| 739 | 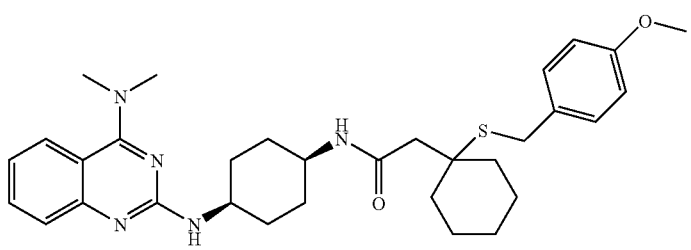 | 562 (M + H) |
| 740 | 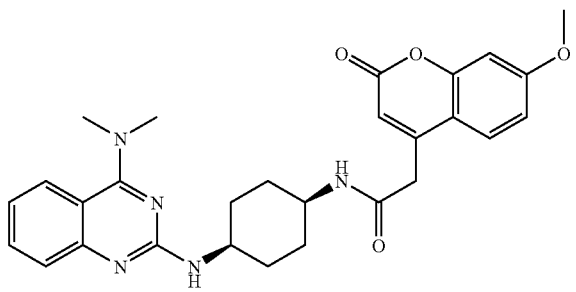 | 502 (M + H) |
| 741 | 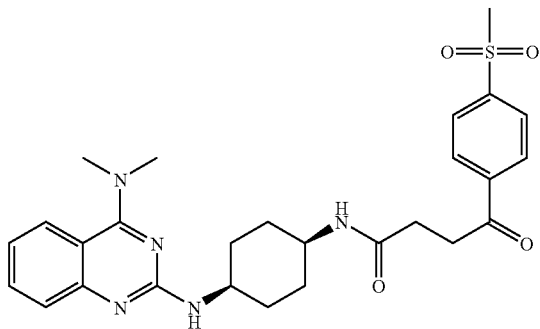 | 524 (M + H) |
| 742 | 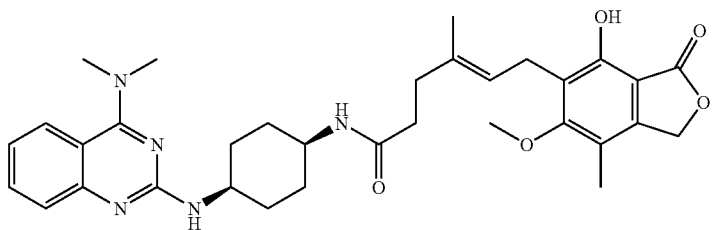 | 588 (M + H) |

-continued
| Example No. | Structure | APCI-MS |
|---|---|---|
| 743 | 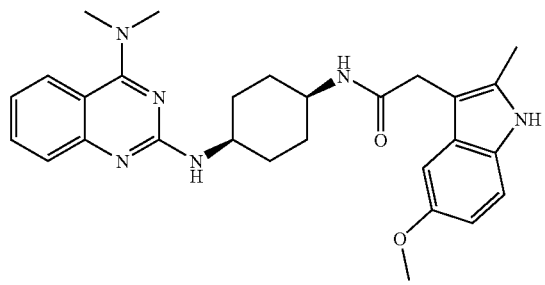 | 487 (M + H) |
| 744 | 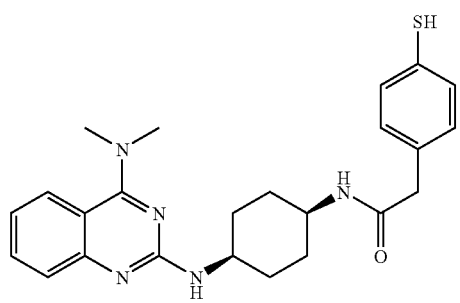 | 436 (M + H) |
| 745 | 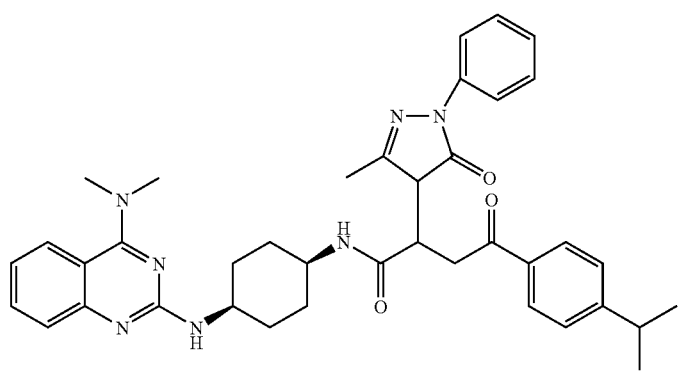 | 660 (M + H) |
| 746 | 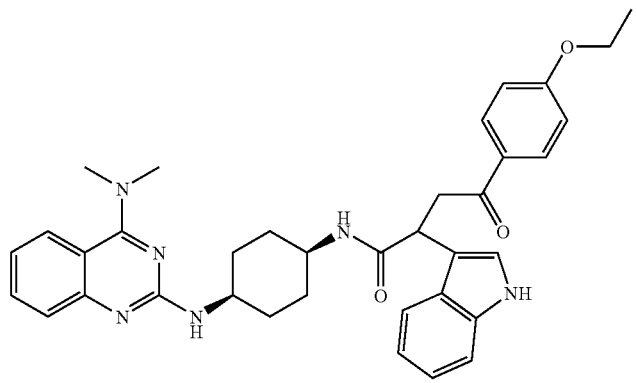 | 605 (M + H) |

-continued
| Example No. | Structure | APCI-MS |
|---|---|---|
| 747 | 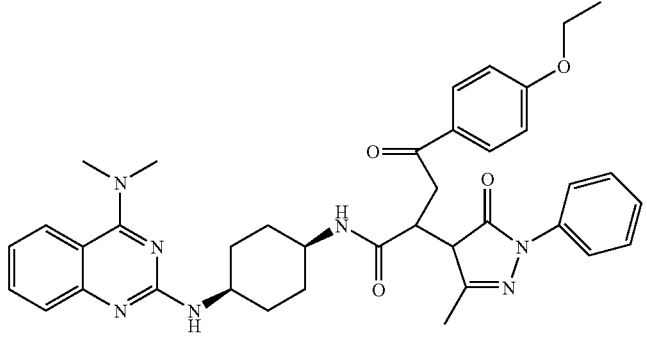 | 662 (M + H) |
| 748 | 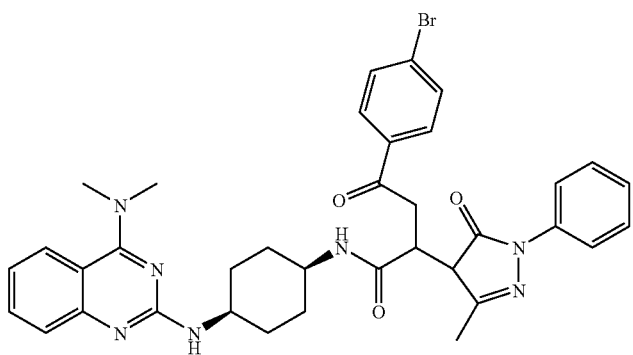 | 696 (M + H) |
| 749 | 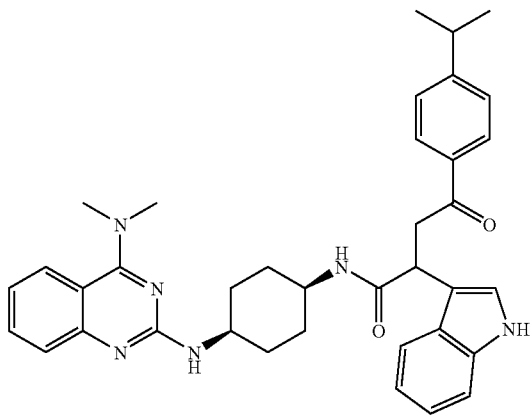 | 603 (M + H) |
| 750 | 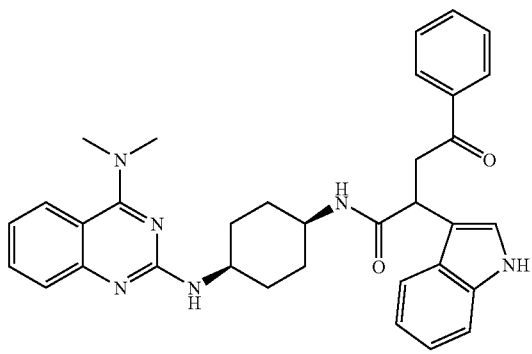 | 561 (M + H) |

-continued
| Example No. | Structure | APCI-MS |
|---|---|---|
| 751 | 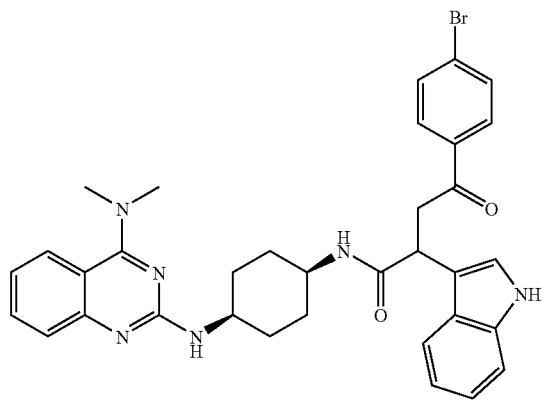 | 639 (M + H) |
| 752 | 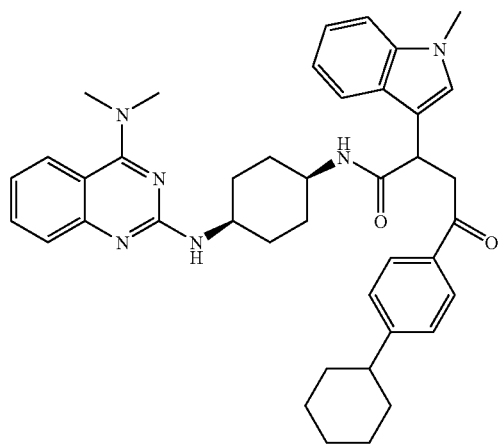 | 657 (M + H) |
| 753 | 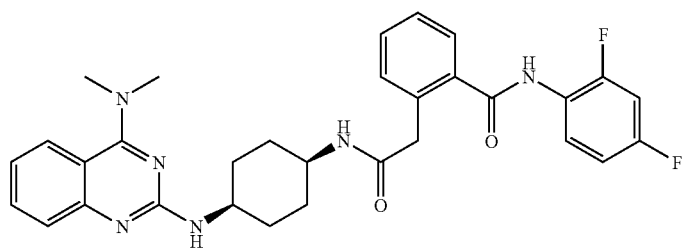 | 559 (M + H) |
| 754 | 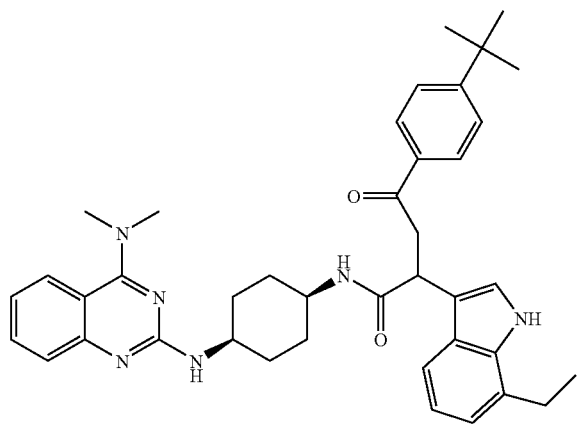 | 645 (M + H) |

-continued
| Example No. | Structure | APCI-MS |
|---|---|---|
| 755 | 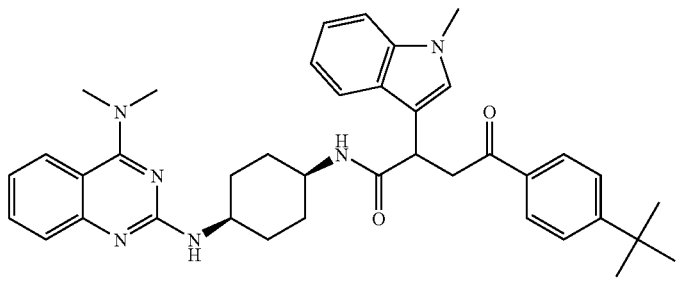 | 631 (M + H) |
| 756 | 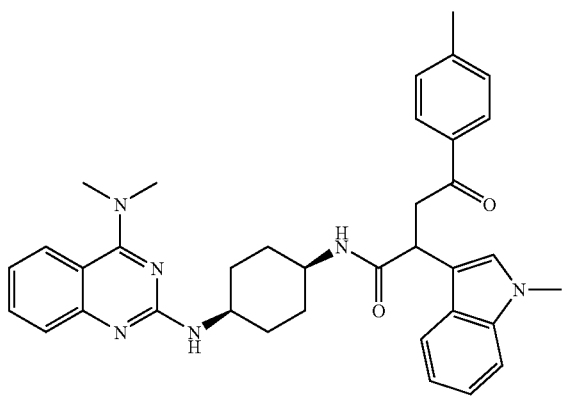 | 589 (M + H) |
| 757 | 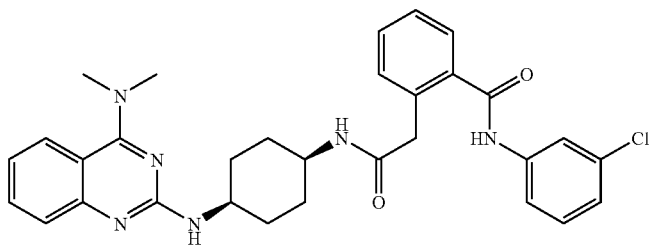 | 557 (M + H) |
| 758 | 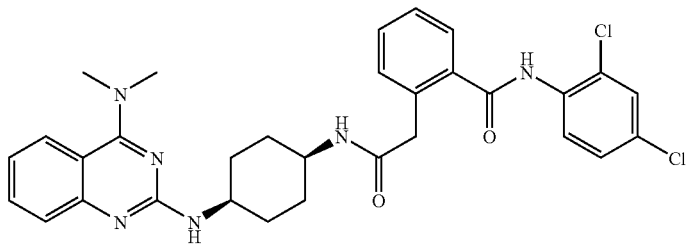 | 591 (M + H) |
| 759 | 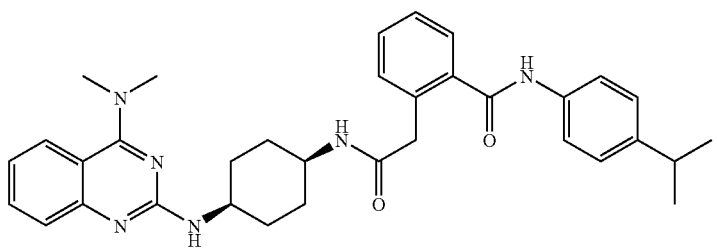 | 565 (M + H) |

-continued
| Example No. | Structure | APCI-MS |
|---|---|---|
| 760 | 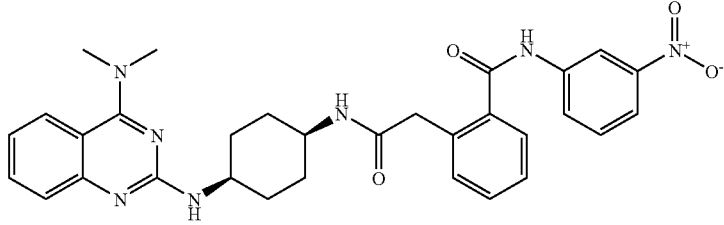 | 568 (M + H) |
| 761 | 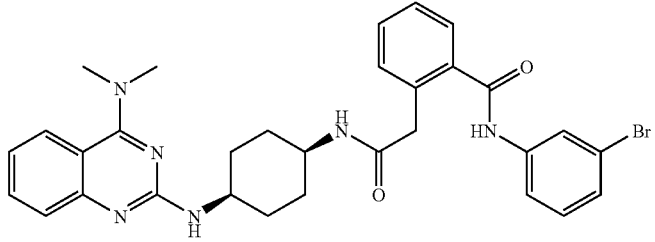 | 601 (M + H) |
| 762 | 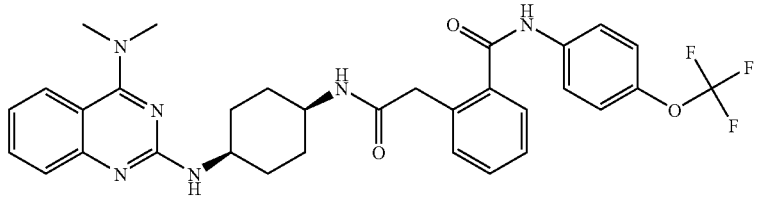 | 607 (M + H) |
| 763 | 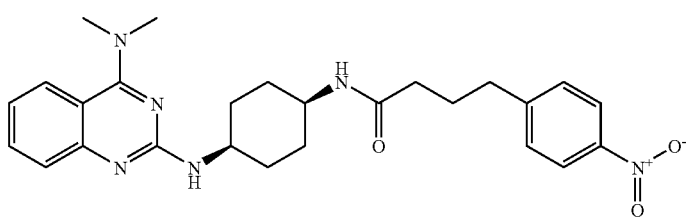 | 477 (M + H) |
| 764 | 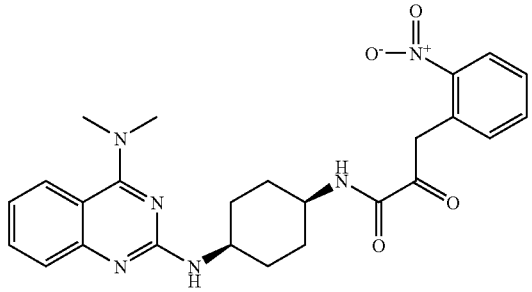 | 477 (M + H) |
| 765 | 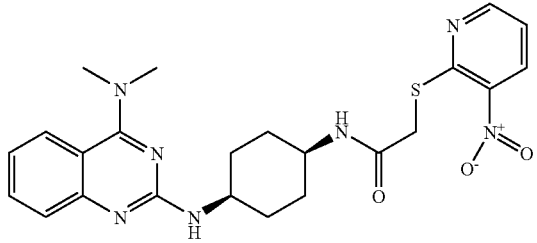 | 482 (M + H) |

-continued
| Example No. | Structure | APCI-MS |
|---|---|---|
| 766 | 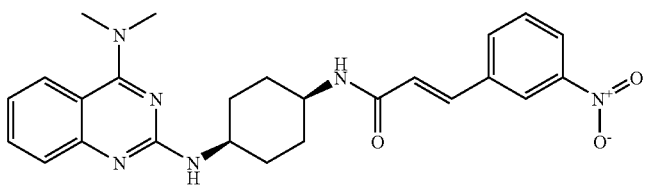 | 461 (M + H) |
| 767 | 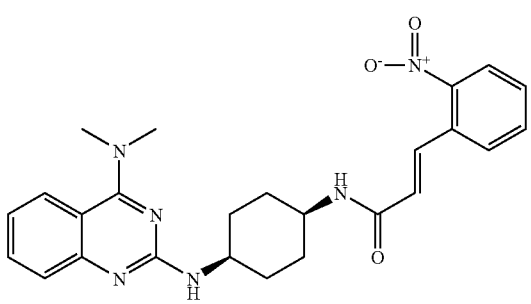 | 461 (M + H) |
| 768 | 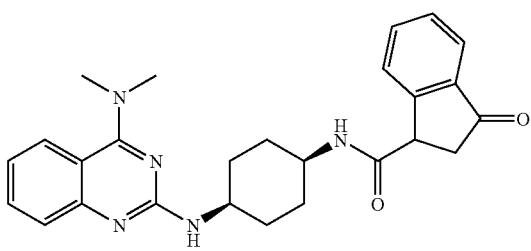 | 444 (M + H) |
| 769 | 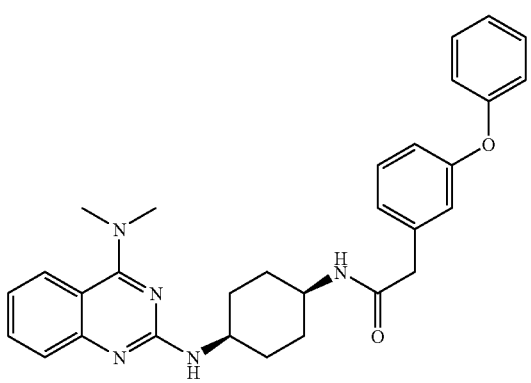 | 496 (M + H) |
| 770 | 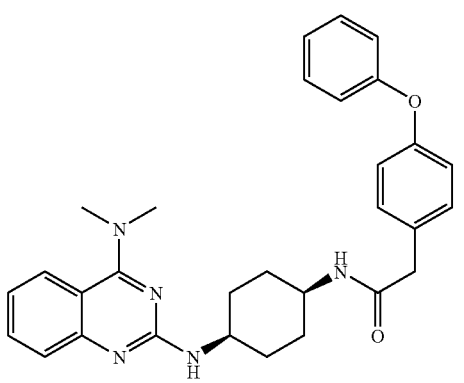 | 496 (M + H) |

-continued
| Example No. | Structure | APCI-MS |
|---|---|---|
| 771 | 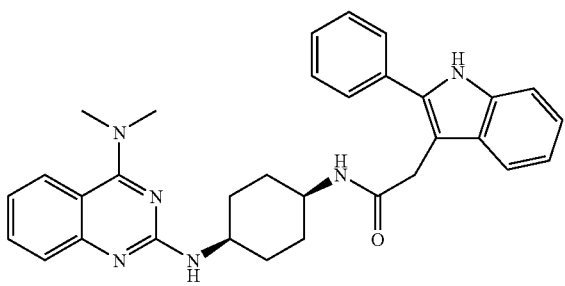 | 488 (M + H) |
| 772 | 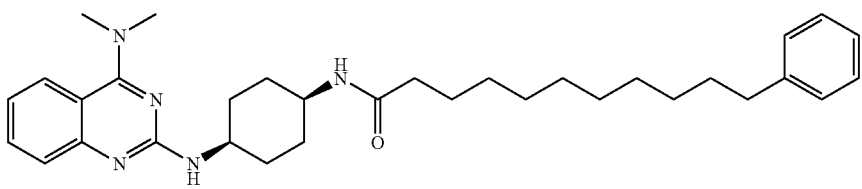 | 530 (M + H) |
| 773 | 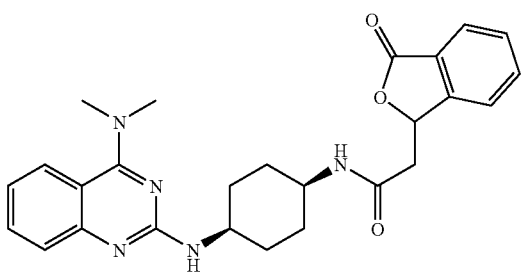 | 460 (M + H) |
| 774 | 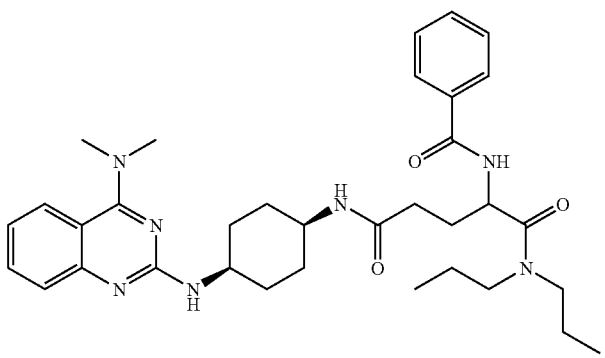 | 602 (M + H) |
| 775 | 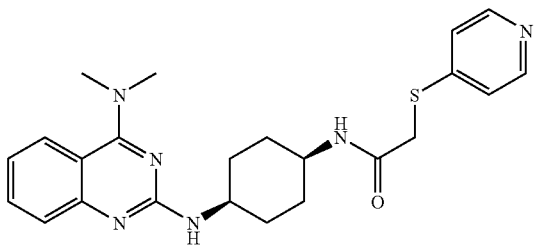 | 437 (M + H) |
| 776 | 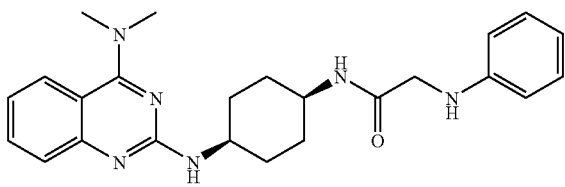 | 419 (M + H) |

-continued
| Example No. | Structure | APCI-MS |
|---|---|---|
| 777 | 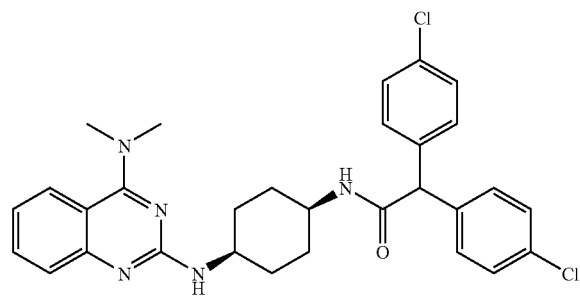 | 548 (M + H) |
| 778 | 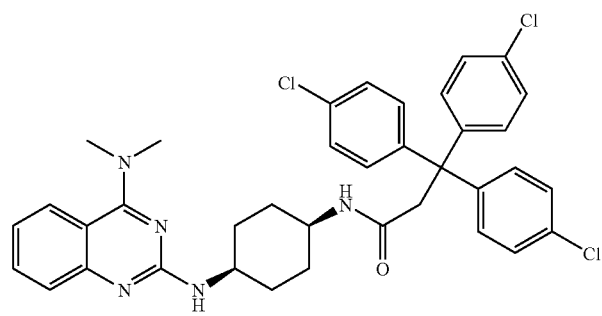 | 672 (M + H) |
| 779 | 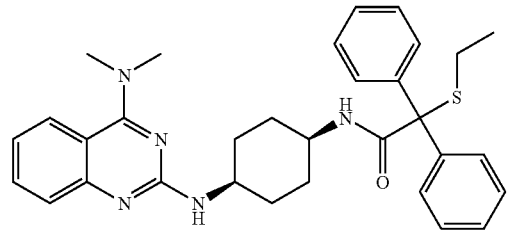 | 540 (M + H) |
| 780 | 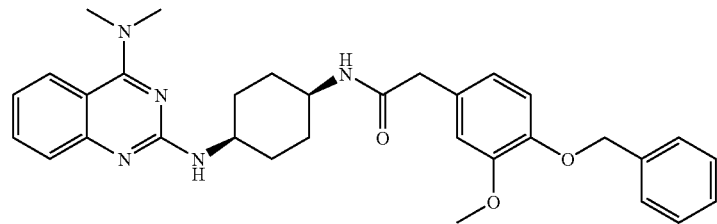 | 540 (M + H) |
| 781 | 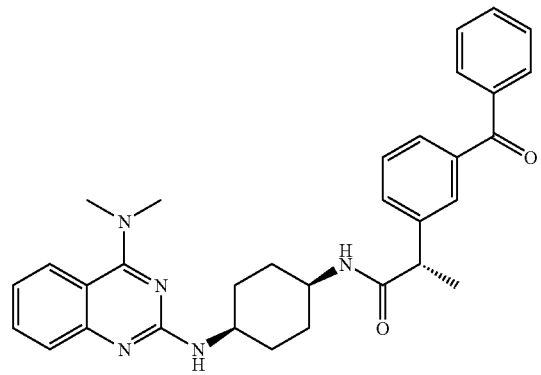 | 522 (M + H) |

| Example No. | Structure | APCI-MS |
|---|---|---|
| 782 | 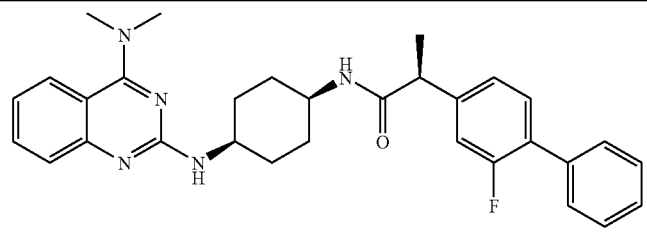 | 512 (M + H) |
| 783 | 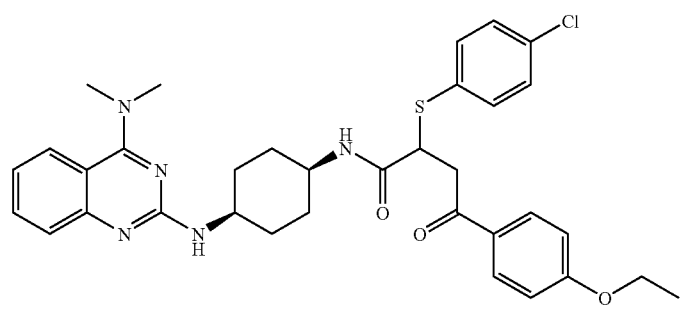 | 632 (M + H) |
| 784 | 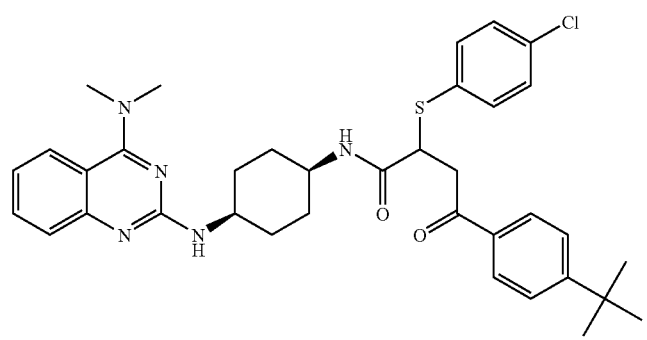 | 644 (M + H) |
| 785 | 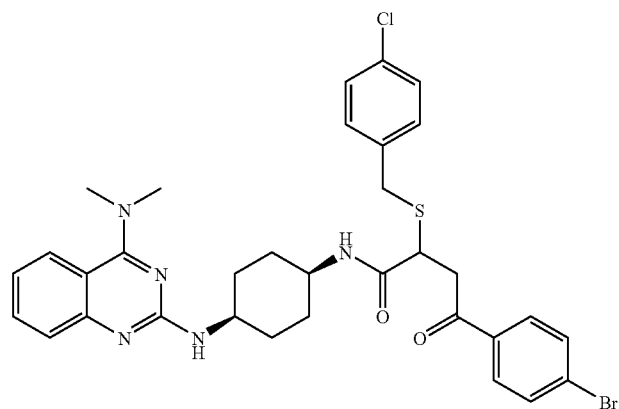 | 680 (M + H) |
| 786 | 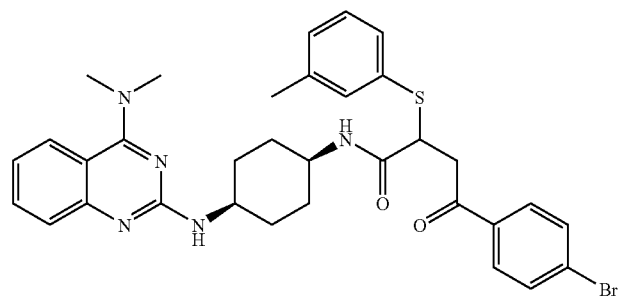 | 646 (M + H) |

-continued
| Example No. | Structure | APCI-MS |
|---|---|---|
| 787 | 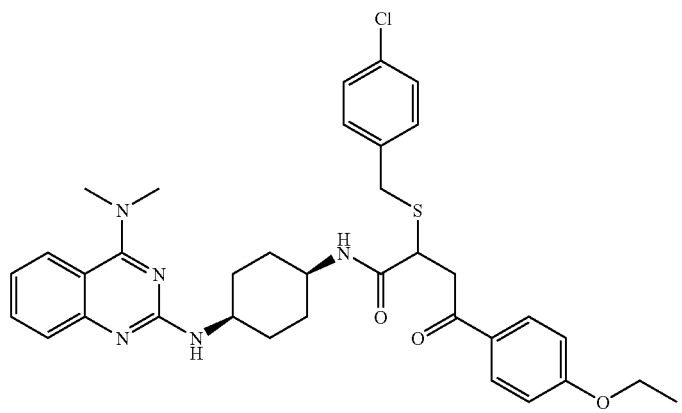 | 646 (M + H) |
| 788 | 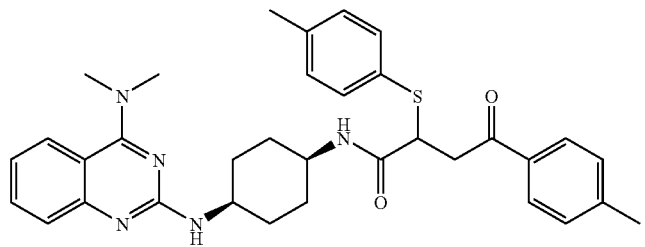 | 582 (M + H) |
| 789 | 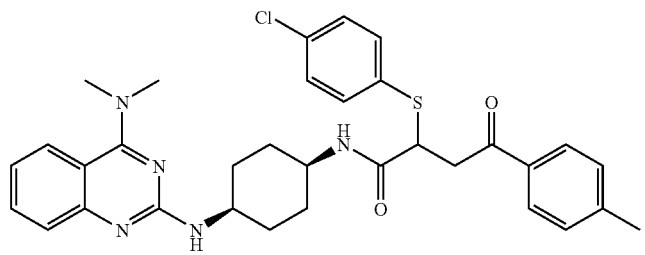 | 602 (M + H) |
| 790 | 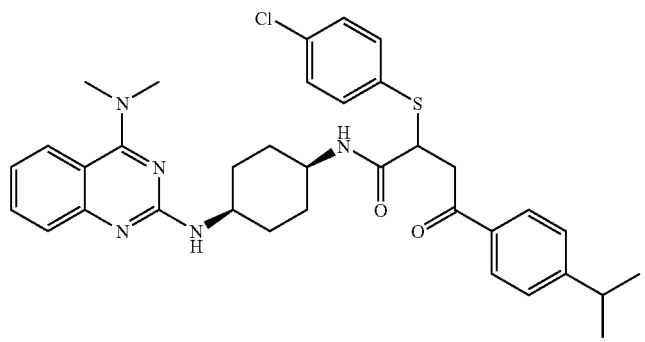 | 630 (M + H) |

-continued

| Example No. | Structure | APCI-MS |
|---|---|---|
| 791 | 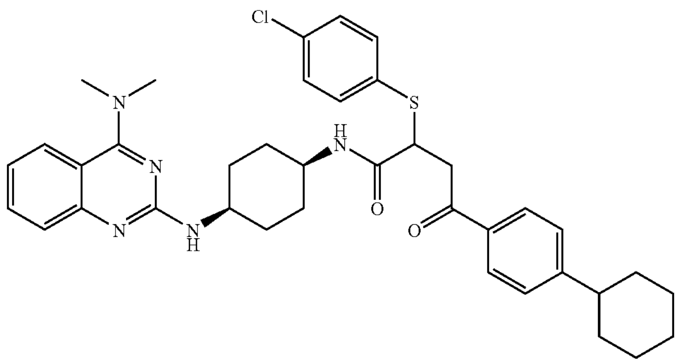 | 670 (M + H) |
| 792 | 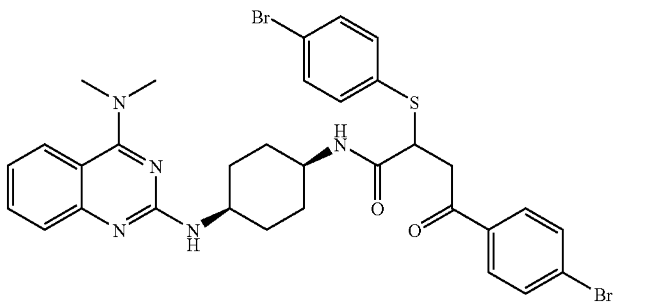 | 710 (M + H) |
| 793 | 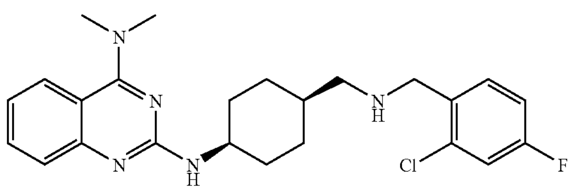 | 684 (M + H) |
| 794 | 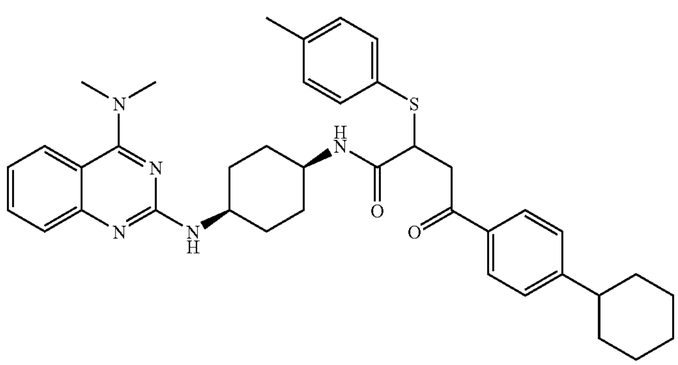 | 650 (M + H) |
| 795 | 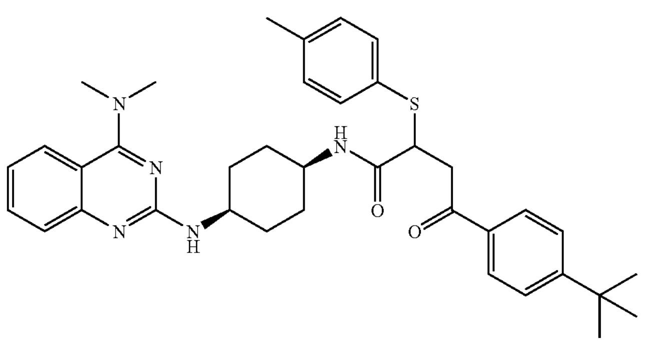 | 624 (M + H) |

-continued
| Example No. | Structure | APCI-MS |
|---|---|---|
| 796 | 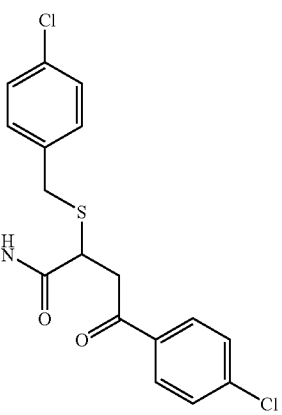 | 636 (M + H) |
| 797 | 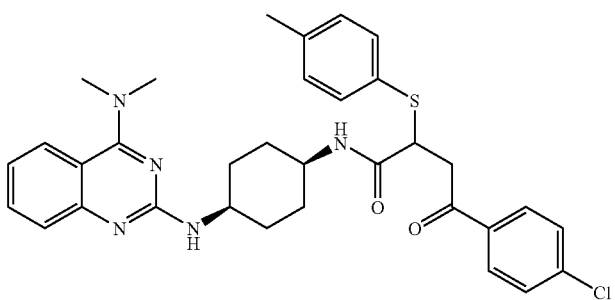 | 602 (M + H) |
| 798 | 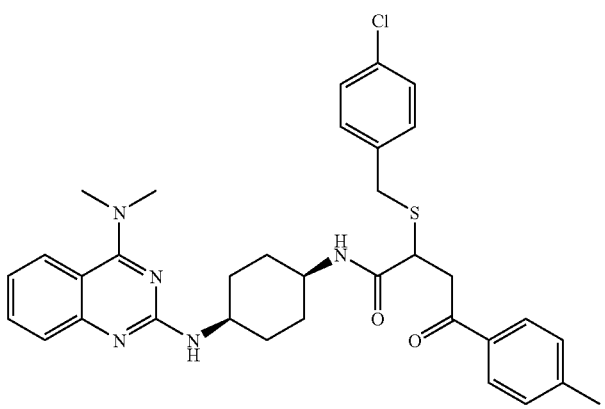 | 616 (M + H) |
| 799 | 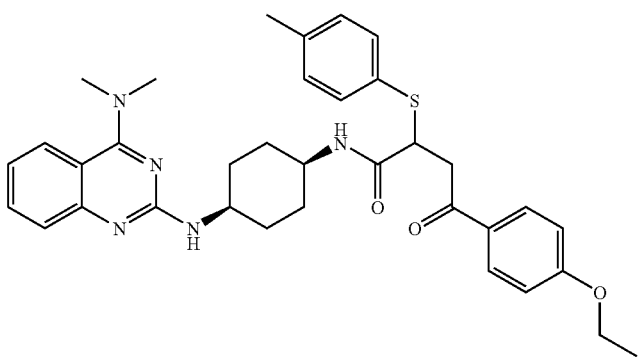 | 612 (M + H) |

-continued
| Example No. | Structure | APCI-MS |
|---|---|---|
| 800 | 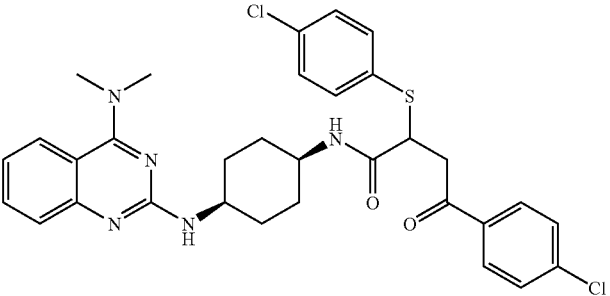 | 622 (M + H) |
| 801 | 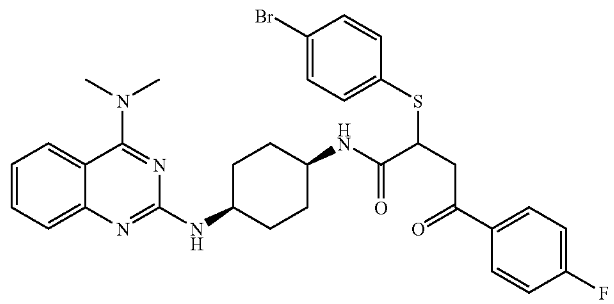 | 650 (M + H) |
| 802 | 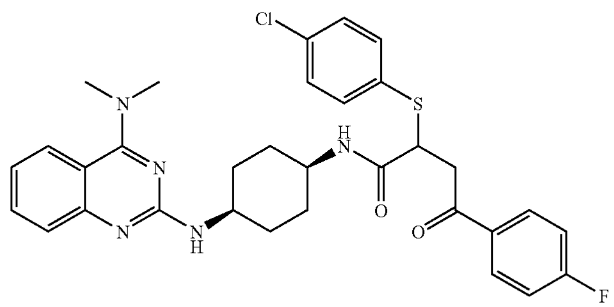 | 606 (M + H) |
| 803 | 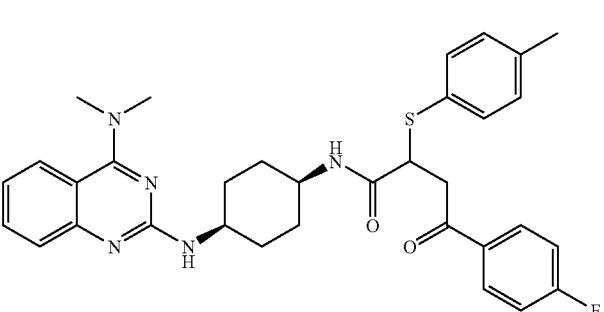 | 586 (M + H) |
| 804 | 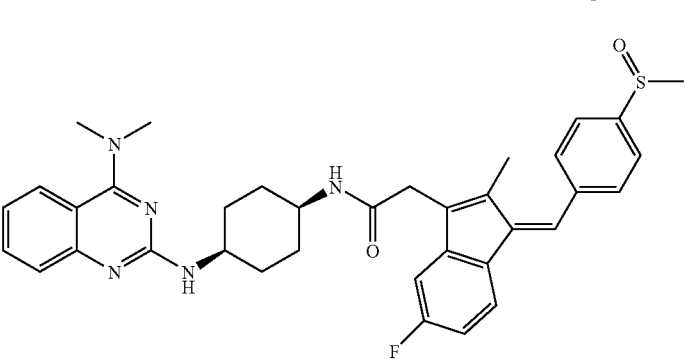 | 624 (M + H) |

-continued
| Example No. | Structure | APCI-MS |
|---|---|---|
| 805 | 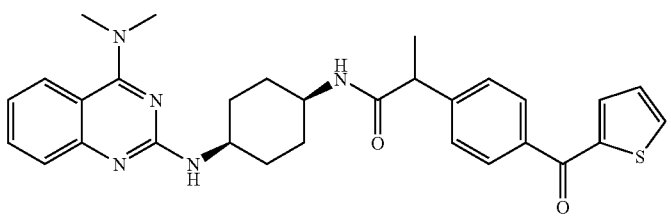 | 528 (M + H) |
| 806 | 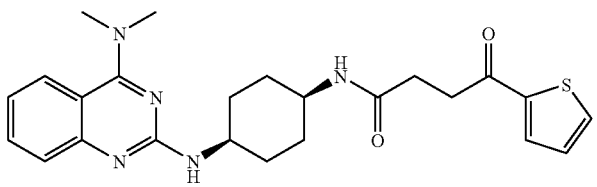 | 452 (M + H) |
| 807 | 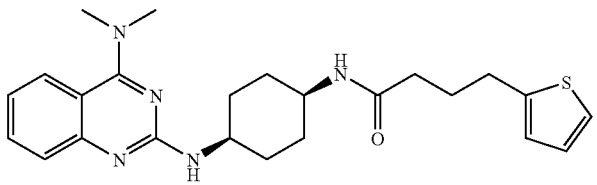 | 438 (M + H) |
| 808 | 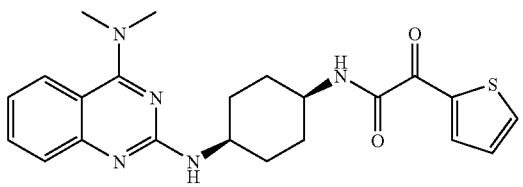 | 424 (M + H) |
| 809 | 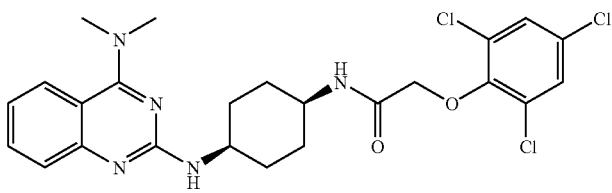 | 522 (M + H) |
| 810 | 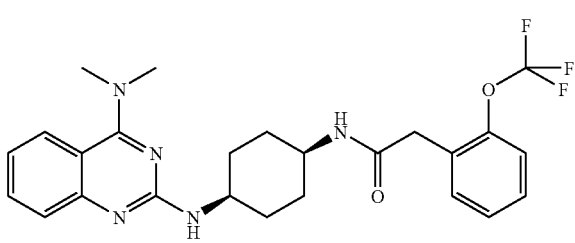 | 488 (M + H) |
| 811 | 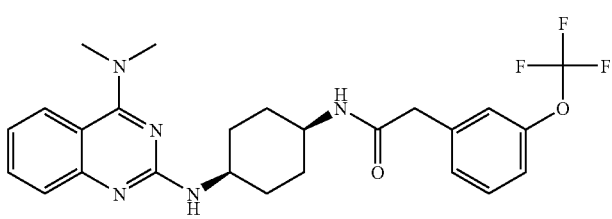 | 488 (M + H) |

-continued
| Example No. | Structure | APCI-MS |
|---|---|---|
| 812 | 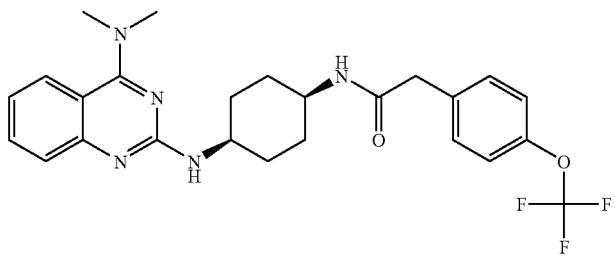 | 488 (M + H) |
| 813 | 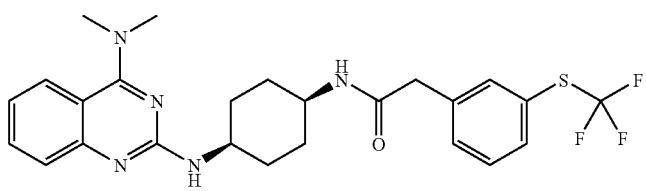 | 504 (M + H) |
| 814 | 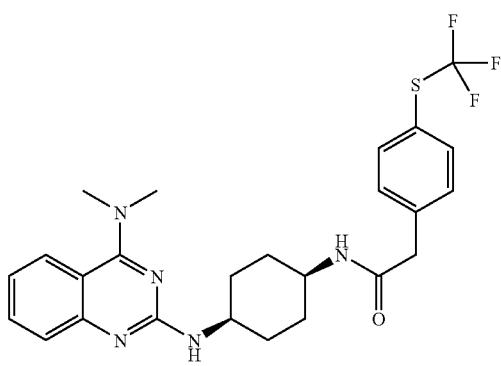 | 504 (M + H) |
| 815 | 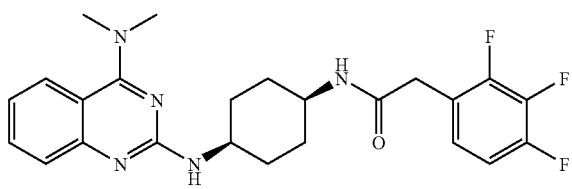 | 458 (M + H) |
| 816 | 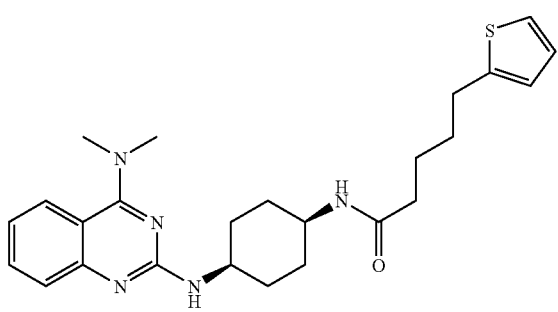 | 452 (M + H) |

-continued
| Example No. | Structure | APCI-MS |
|---|---|---|
| 817 | 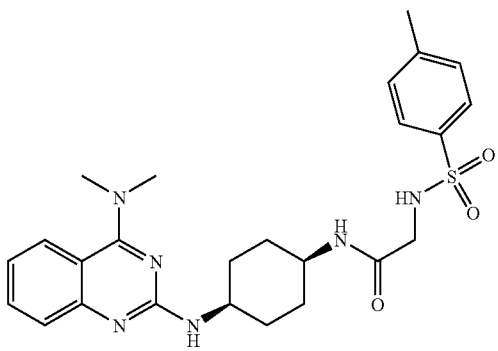 | 497 (M + H) |
| 818 | 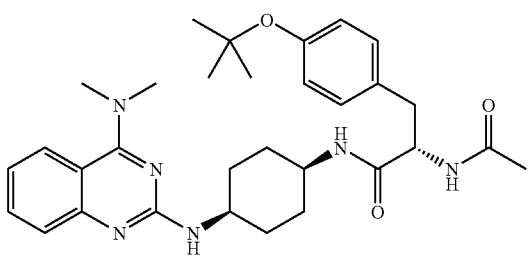 | 547 (M + H) |
| 819 | 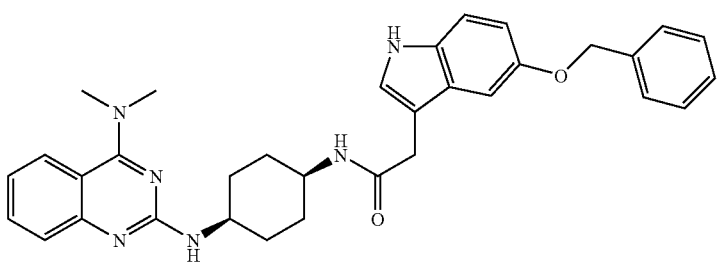 | 549 (M + H) |
| 820 | 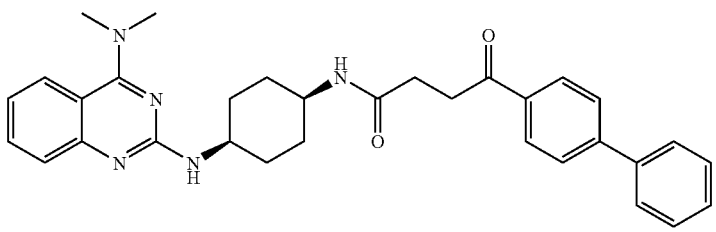 | 522 (M + H) |
| 821 | 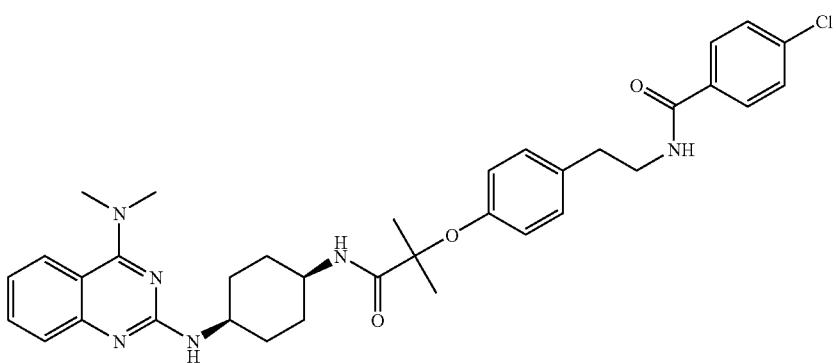 | 629 (M + H) |

-continued
| Example No. | Structure | APCI-MS |
|---|---|---|
| 822 | 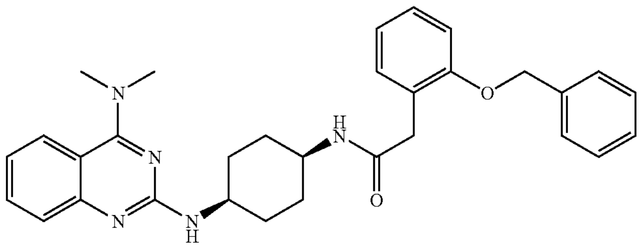 | 510 (M + H) |
| 823 | 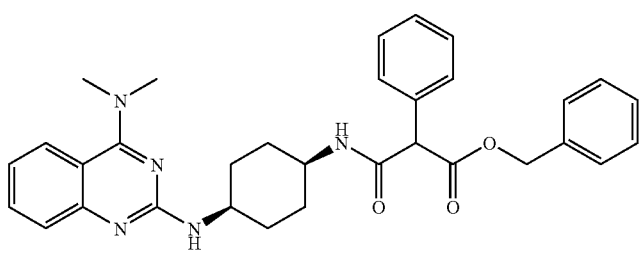 | 538 (M + H) |
| 824 | 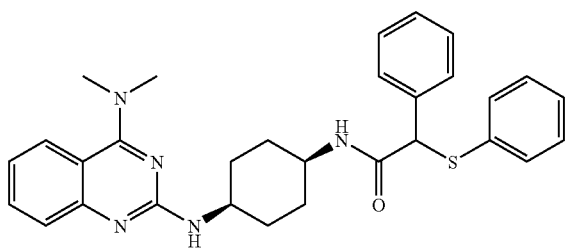 | 512 (M + H) |
| 825 | 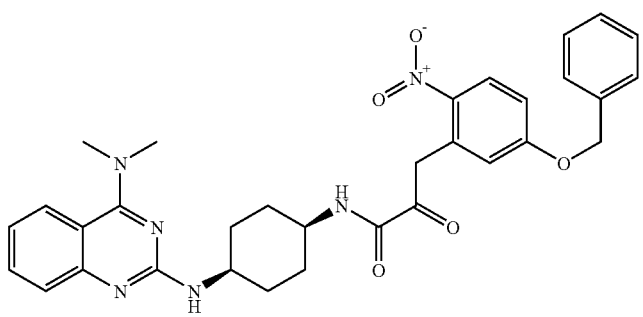 | 583 (M + H) |
| 826 | 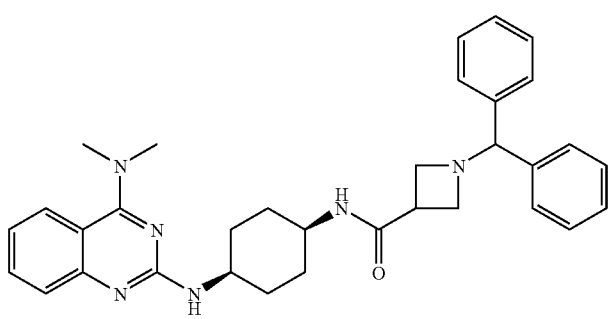 | 535 (M + H) |

-continued
| Example No. | Structure | APCI-MS |
|---|---|---|
| 827 | 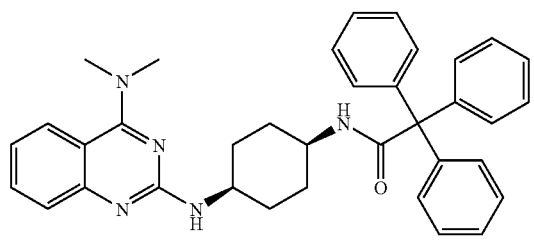 | 556 (M + H) |
| 828 | 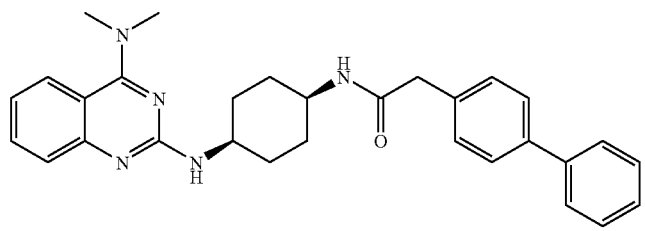 | 480 (M + H) |
| 829 | 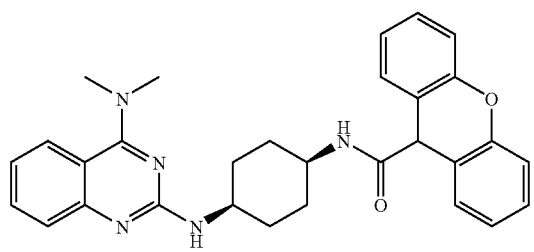 | 494 (M + H) |
| 830 | 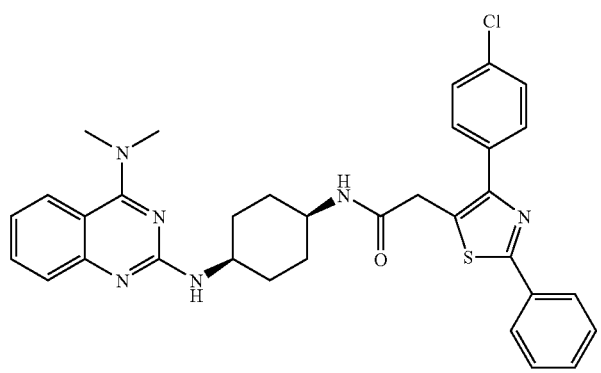 | 597 (M + H) |
| 831 | 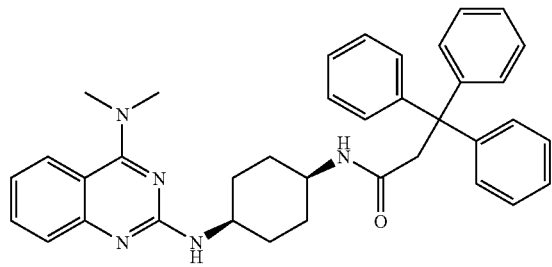 | 570 (M + H) |

-continued
| Example No. | Structure | APCI-MS |
|---|---|---|
| 832 | 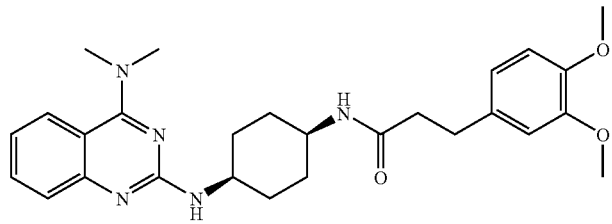 | 478 (M + H) |
| 833 | 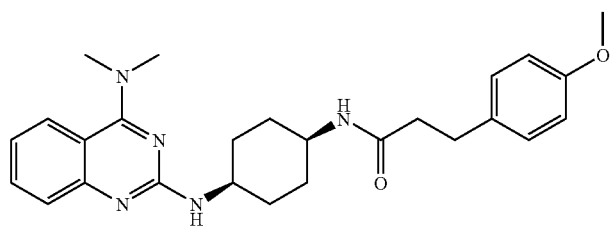 | 448 (M + H) |
| 834 | 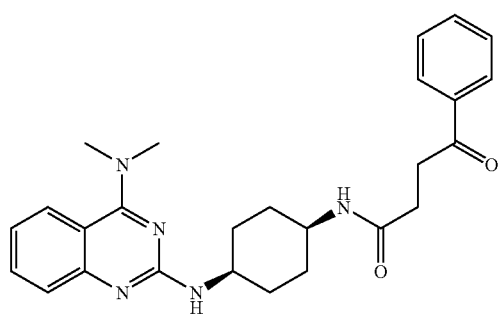 | 446 (M + H) |
| 835 | 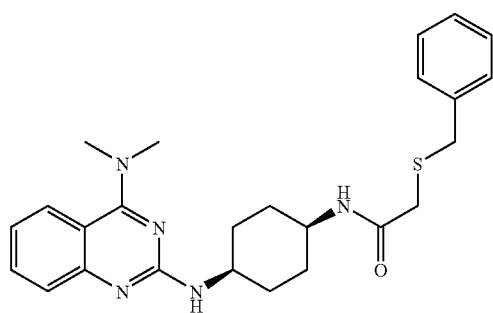 | 450 (M + H) |
| 836 | 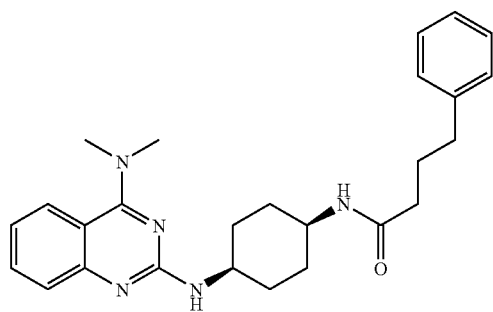 | 432 (M + H) |

| Example No. | Structure | APCI-MS |
|---|---|---|
| 837 | 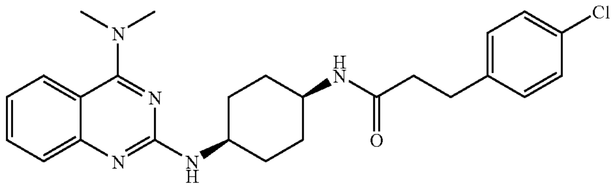 | 452 (M + H) |
| 838 | 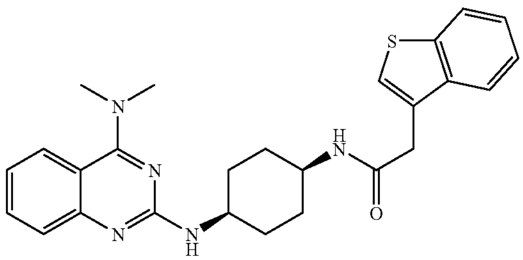 | 460 (M + H) |
| 839 | 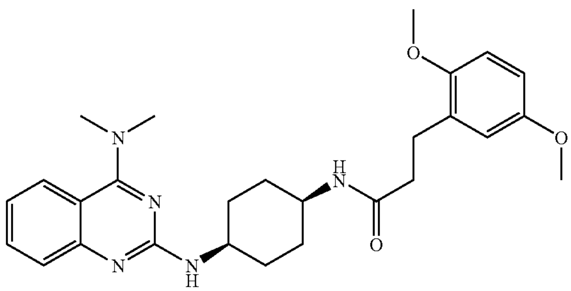 | 478 (M + H) |
| 840 | 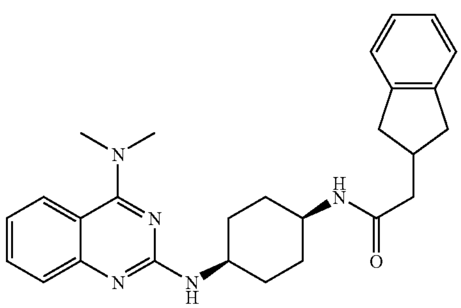 | 444 (M + H) |
| 841 | 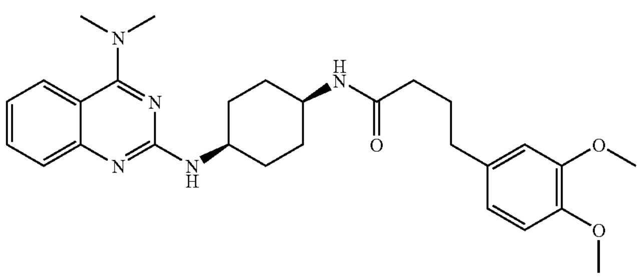 | 492 (M + H) |
| 842 | 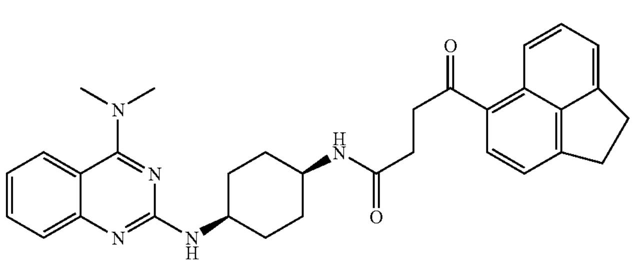 | 522 (M + H) |

-continued
| Example No. | Structure | APCI-MS |
|---|---|---|
| 843 | 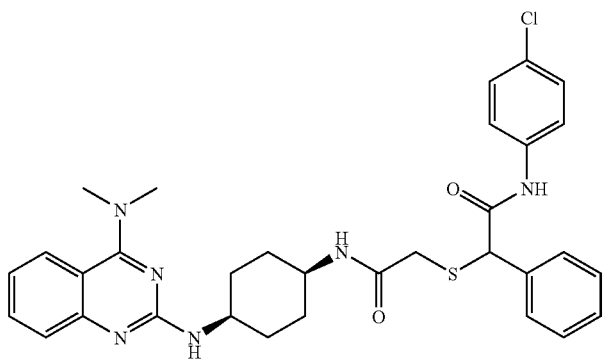 | 603 (M + H) |
| 844 | 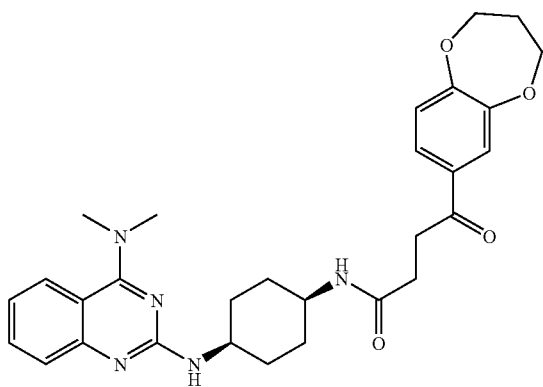 | 518 (M + H) |
| 845 | 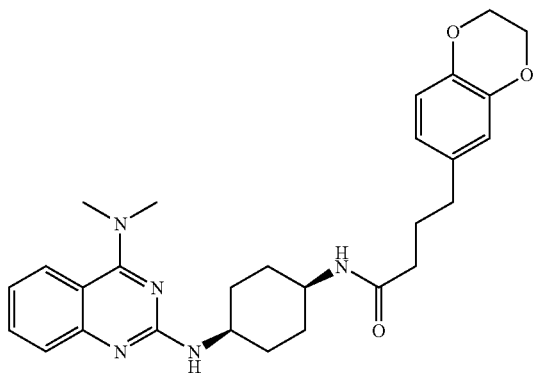 | 490 (M + H) |
| 846 | 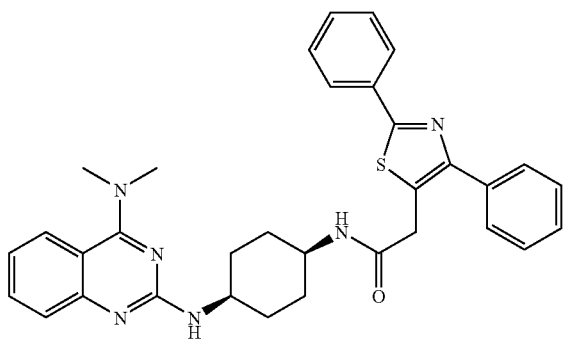 | 563 (M + H) |

-continued
| Example No. | Structure | APCI-MS |
|---|---|---|
| 847 | 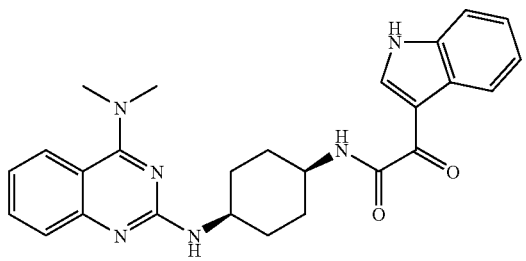 | 457 (M + H) |
| 848 | 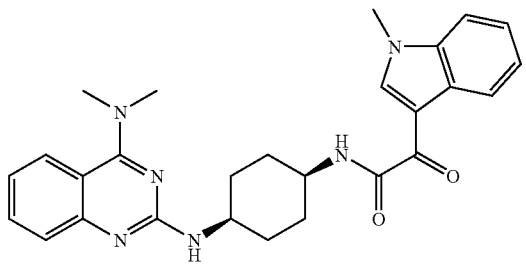 | 471 (M + H) |
| 849 | 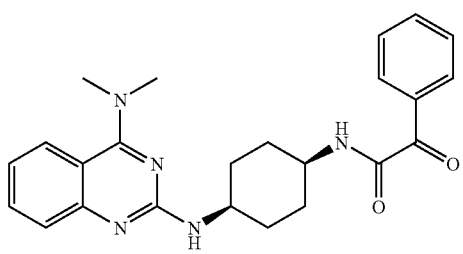 | 418 (M + H) |
| 850 | 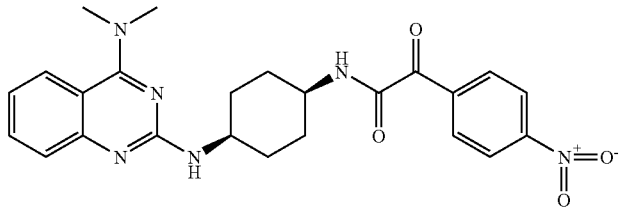 | 463 (M + H) |
| 851 | 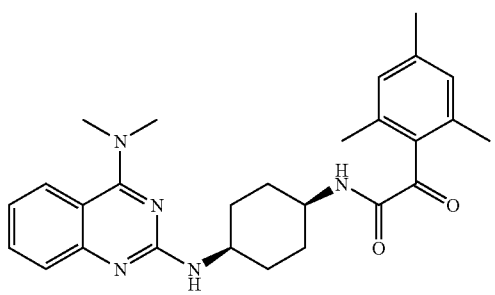 | 460 (M + H) |

-continued
| Example No. | Structure | APCI-MS |
|---|---|---|
| 852 | 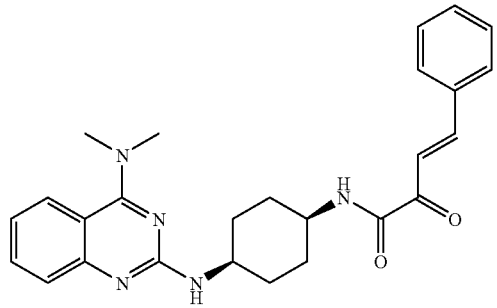 | 444 (M + H) |
| 853 | 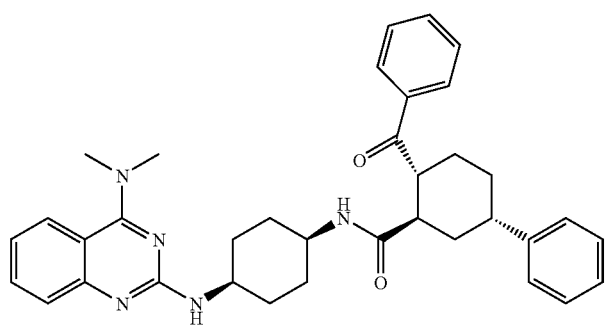 | 576 (M + H) |
| 854 | 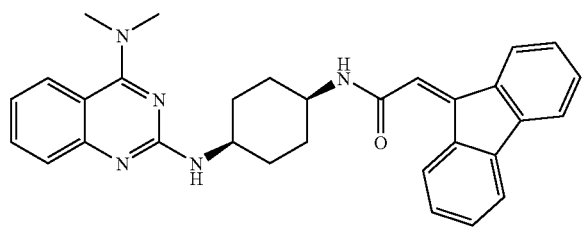 | 490 (M + H) |
| 855 | 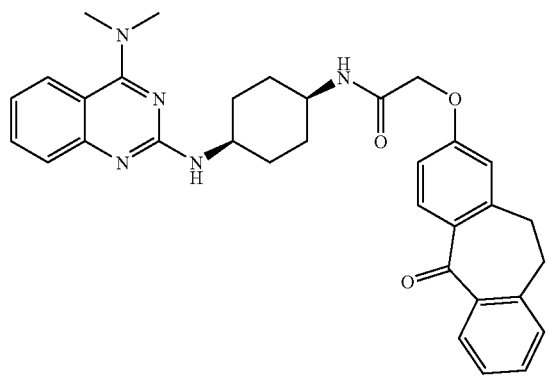 | 550 (M + H) |
| 856 | 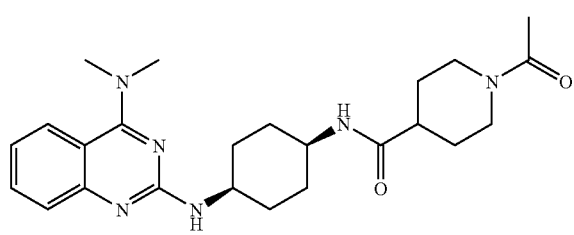 | 439 (M + H) |

-continued
| Example No. | Structure | APCI-MS |
|---|---|---|
| 857 | 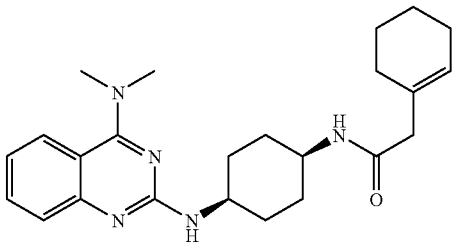 | 408 (M + H) |
| 858 | 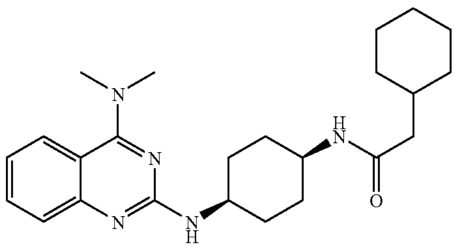 | 410 (M + H) |
| 859 | 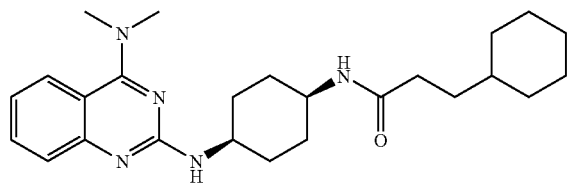 | 424 (M + H) |
| 860 | 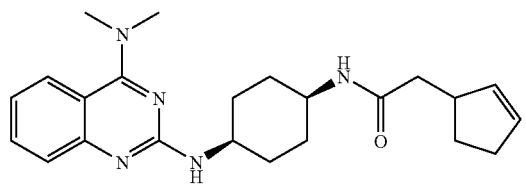 | 394 (M + H) |
| 861 | 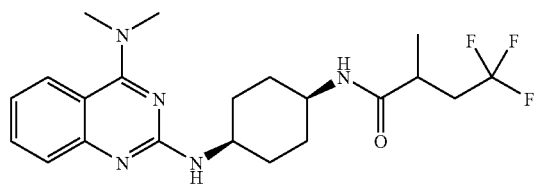 | 424 (M + H) |
| 862 | 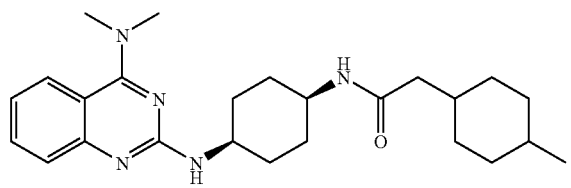 | 424 (M + H) |
| 863 | 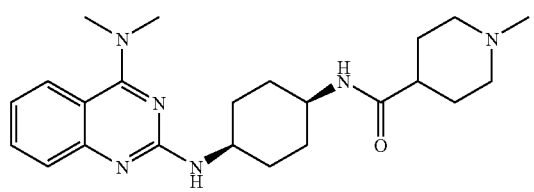 | 411 (M + H) |

-continued
| Example No. | Structure | APCI-MS |
|---|---|---|
| 864 | 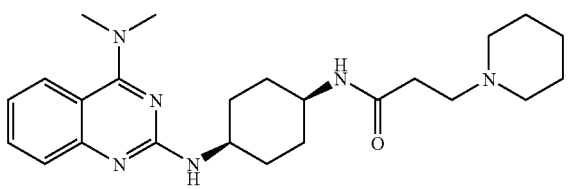 | 425 (M + H) |
| 865 | 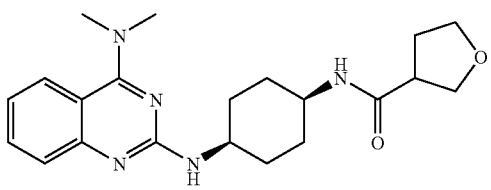 | 384 (M + H) |
| 866 | 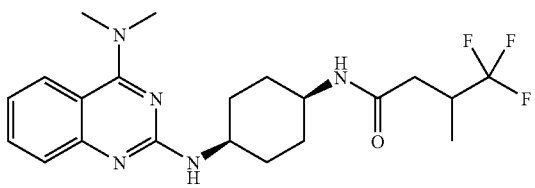 | 424 (M + H) |
| 867 | 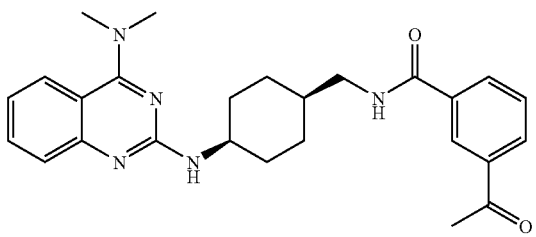 | 446 (M + H) |
| 868 | 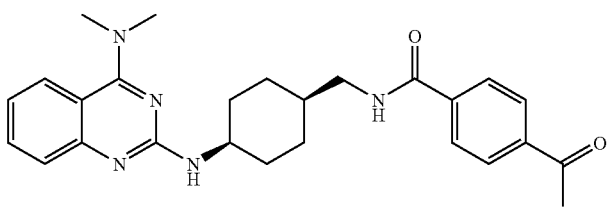 | 446 (M + H) |
| 869 | 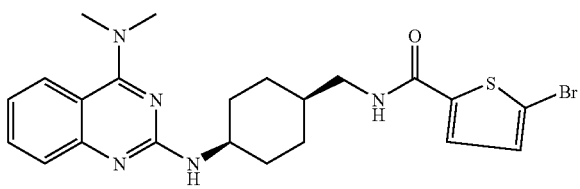 | 488 (M + H) |
| 870 | 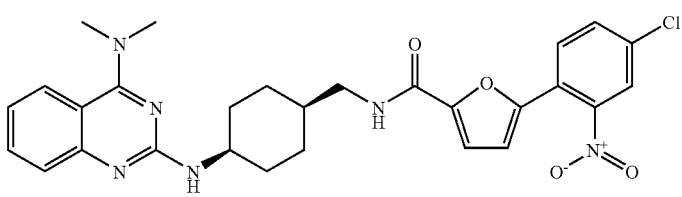 | 549 (M + H) |

-continued
| Example No. | Structure | APCI-MS |
|---|---|---|
| 871 | 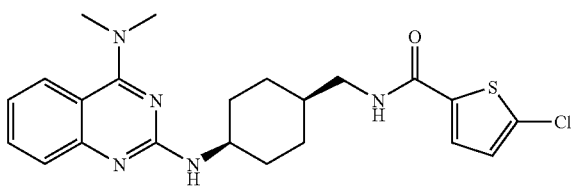 | 444 (M + H) |
| 872 | 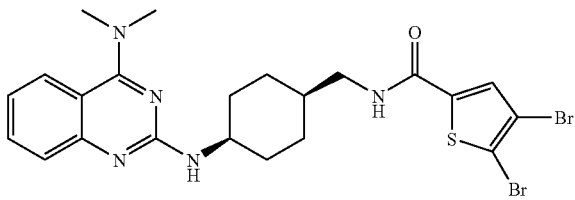 | 566 (M + H) |
| 873 | 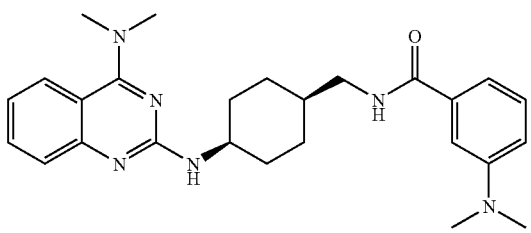 | 447 (M + H) |
| 874 | 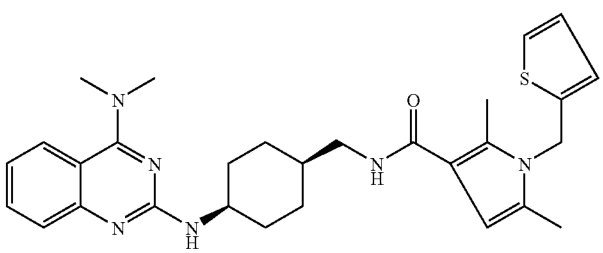 | 517 (M + H) |
| 875 | 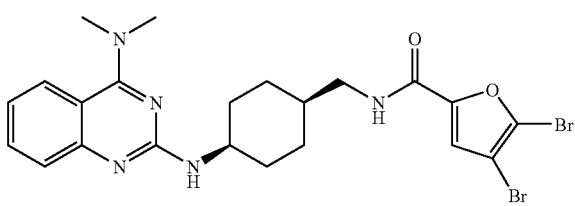 | 550 (M + H) |
| 876 | 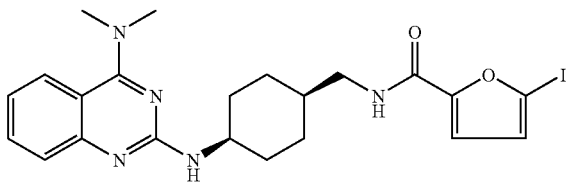 | 520 (M + H) |
| 877 | 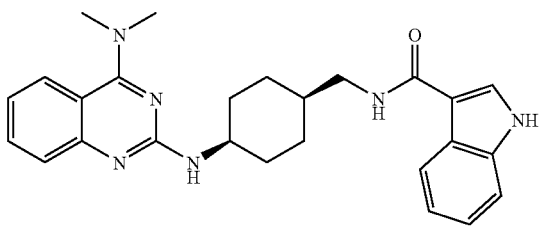 | 443 (M + H) |

| Example No. | Structure | APCI-MS |
|---|---|---|
| 878 | 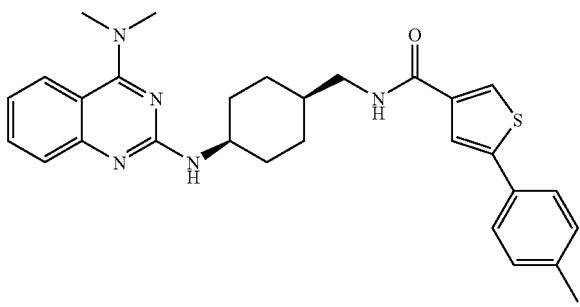 | 500 (M + H) |
| 879 | 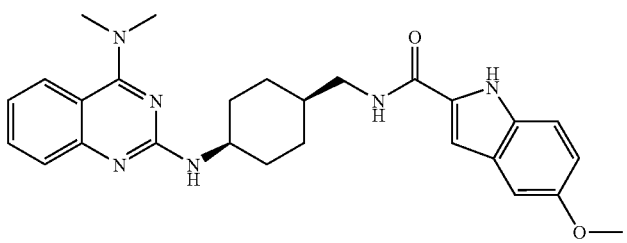 | 473 (M + H) |
| 880 | 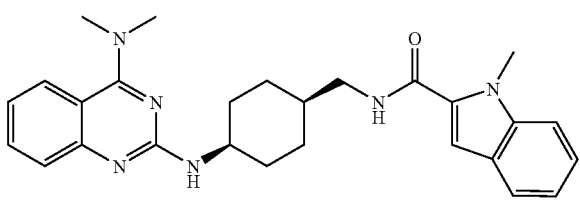 | 457 (M + H) |
| 881 | 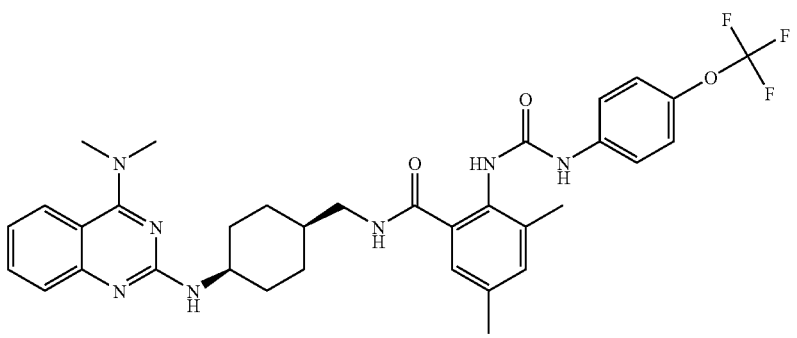 | 650 (M + H) |
| 882 | 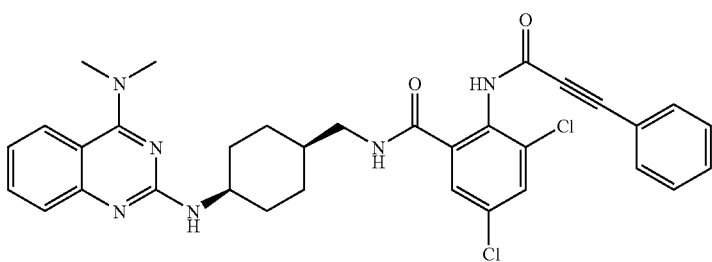 | 615 (M + H) |

-continued
| Example No. | Structure | APCI-MS |
|---|---|---|
| 883 | 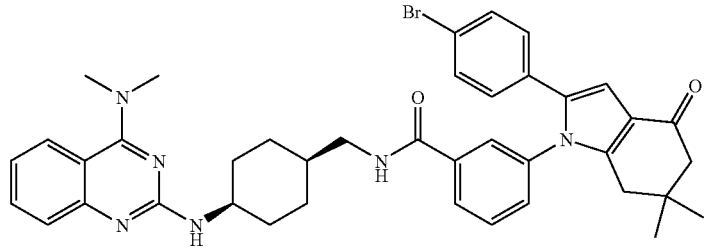 | 719 (M + H) |
| 884 | 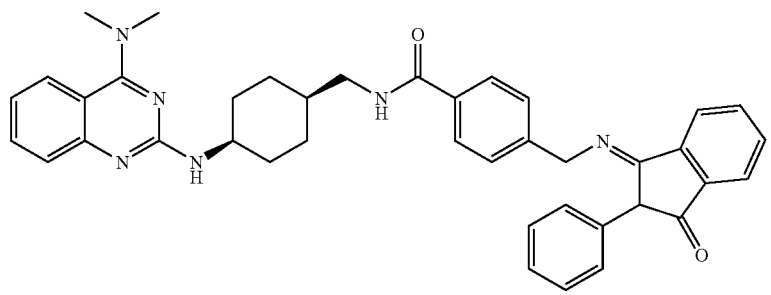 | 637 (M + H) |
| 885 | 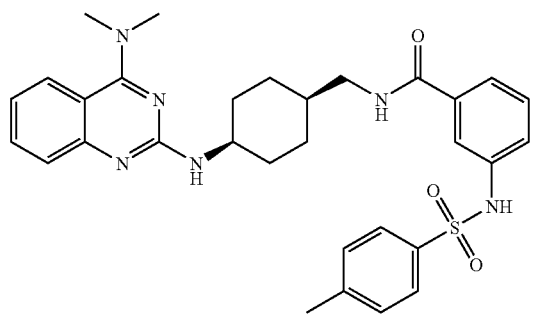 | 573 (M + H) |
| 886 | 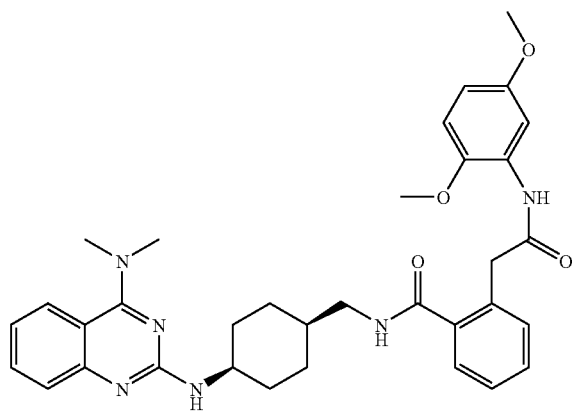 | 597 (M + H) |

| Example No. | Structure | APCI-MS |
|---|---|---|
| 887 | 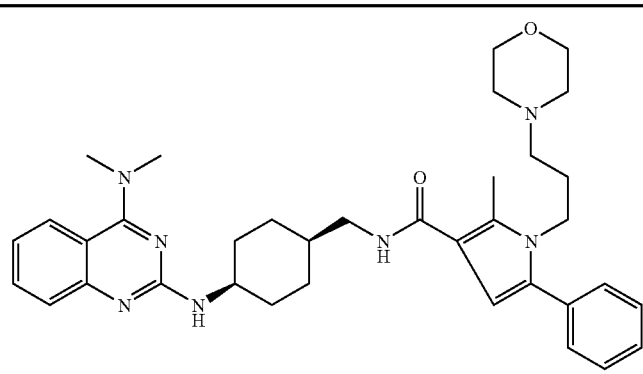 | 610 (M + H) |
| 888 | 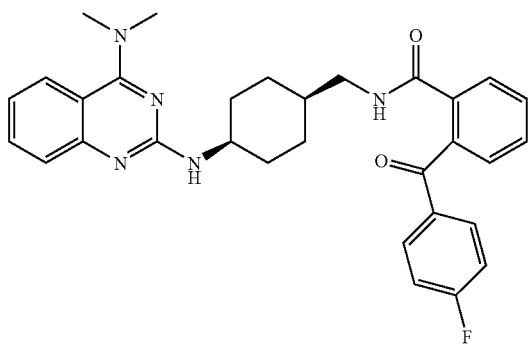 | 526 (M + H) |
| 889 | 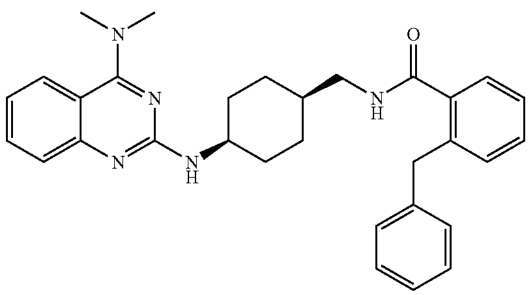 | 494 (M + H) |
| 890 | 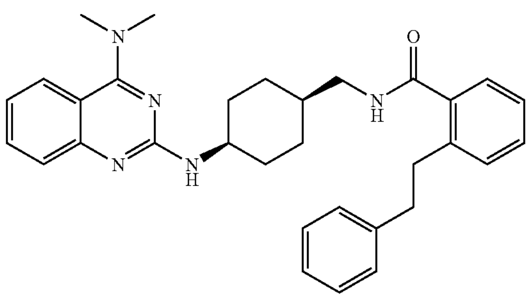 | 508 (M + H) |
| 891 | 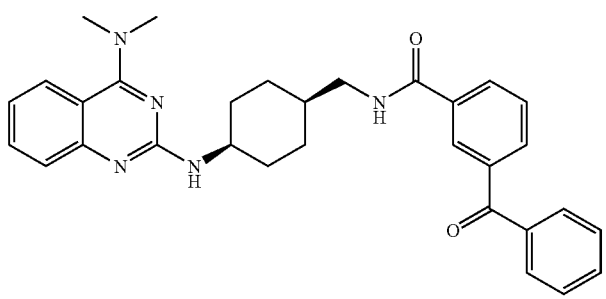 | 508 (M + H) |

-continued
| Example No. | Structure | APCI-MS |
|---|---|---|
| 892 | 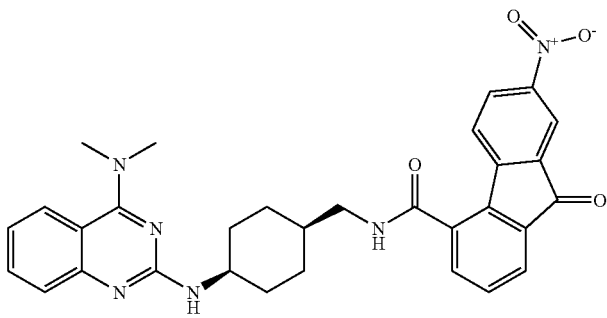 | 551 (M + H) |
| 893 | 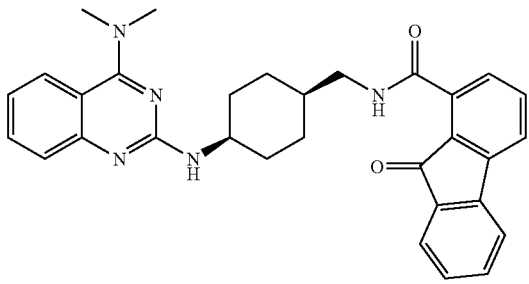 | 506 (M + H) |
| 894 | 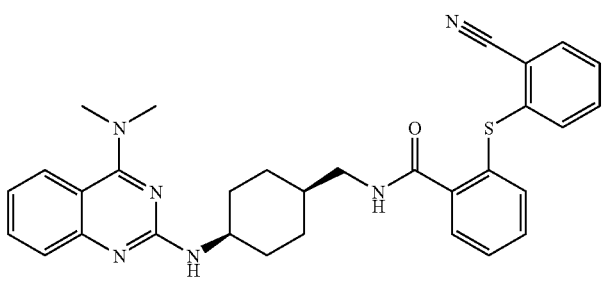 | 537 (M + H) |
| 895 | 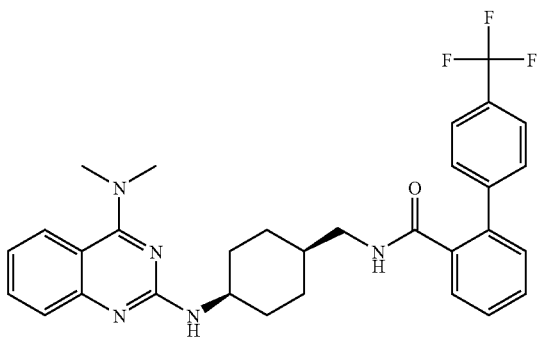 | 548 (M + H) |
| 896 | 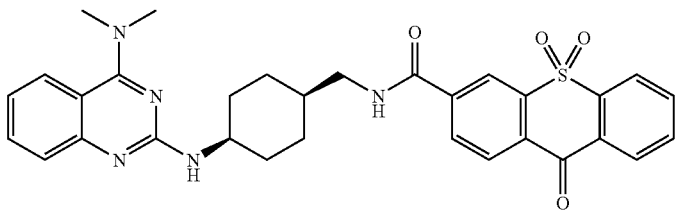 | 570 (M + H) |

-continued
| Example No. | Structure | APCI-MS |
|---|---|---|
| 897 | 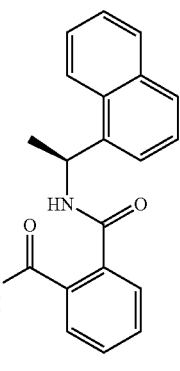 | 601 (M + H) |
| 898 | 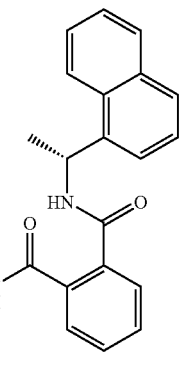 | 601 (M + H) |
| 899 | 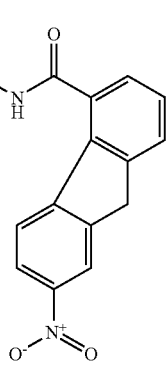 | 537 (M + H) |
| 900 | 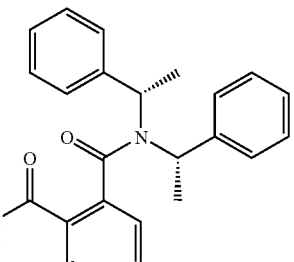 | 655 (M + H) |

-continued
| Example No. | Structure | APCI-MS |
|---|---|---|
| 901 | 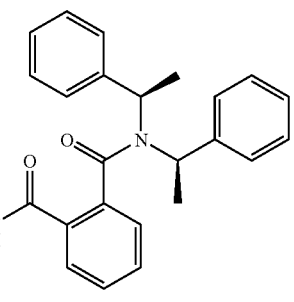 | 655 (M + H) |
| 902 | 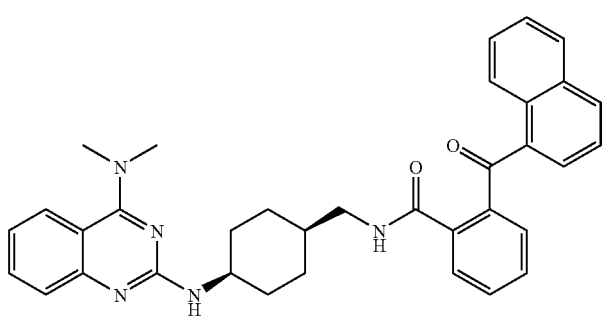 | 558 (M + H) |
| 903 | 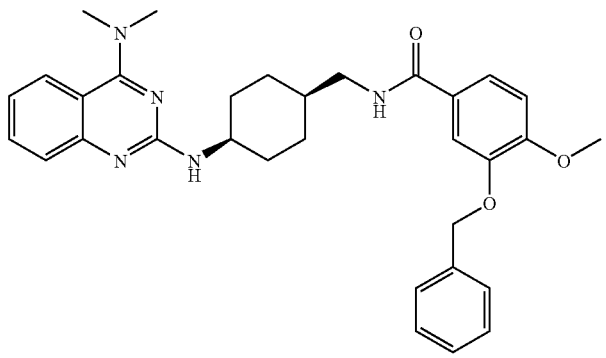 | 540 (M + H) |
| 904 | 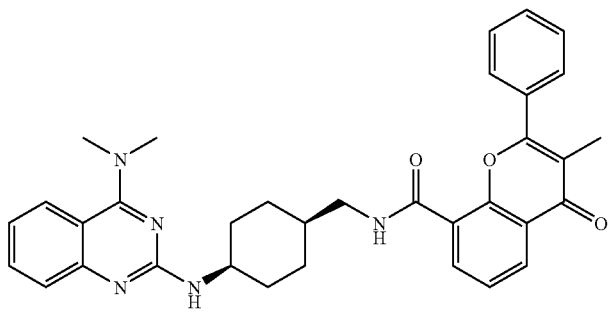 | 562 (M + H) |
| 905 | 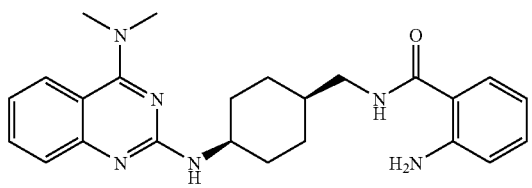 | 419 (M + H) |

-continued
| Example No. | Structure | APCI-MS |
|---|---|---|
| 906 | 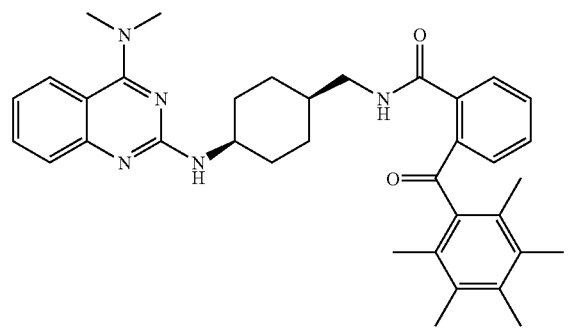 | 578 (M + H) |
| 907 | 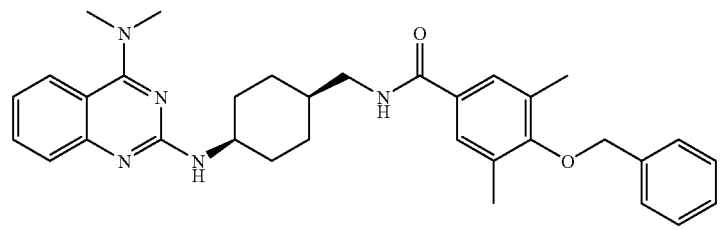 | 538 (M + H) |
| 908 | 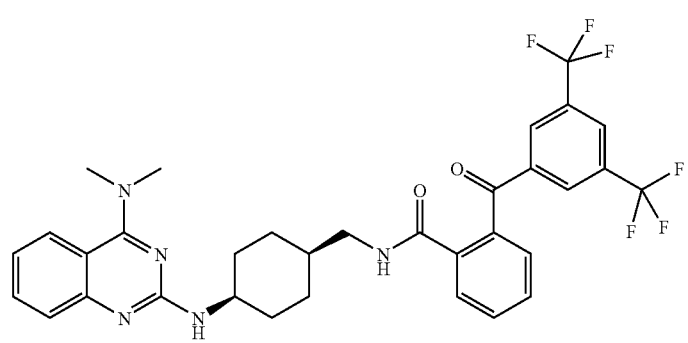 | 644 (M + H) |
| 909 | 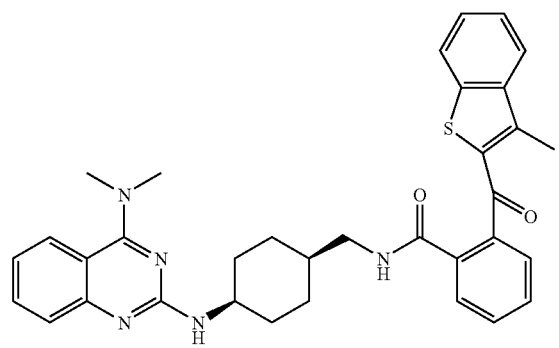 | 578 (M + H) |
| 910 | 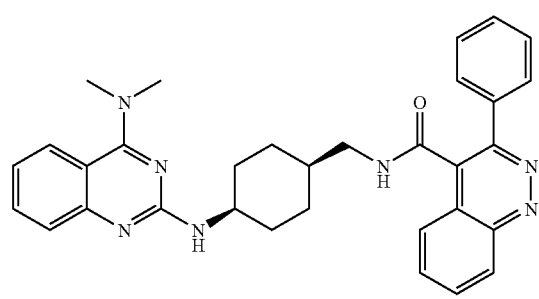 | 532 (M + H) |

| Example No. | Structure | APCI-MS |
|---|---|---|
| 911 | 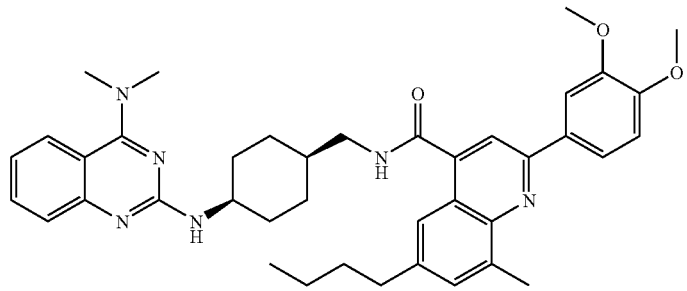 | 661 (M + H) |
| 912 | 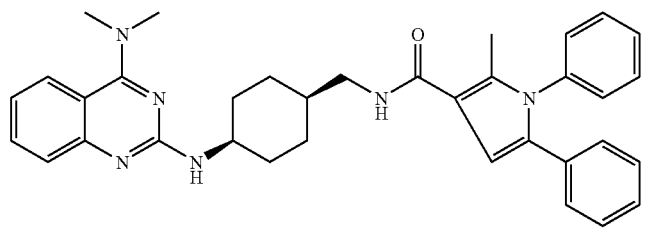 | 559 (M + H) |
| 913 | 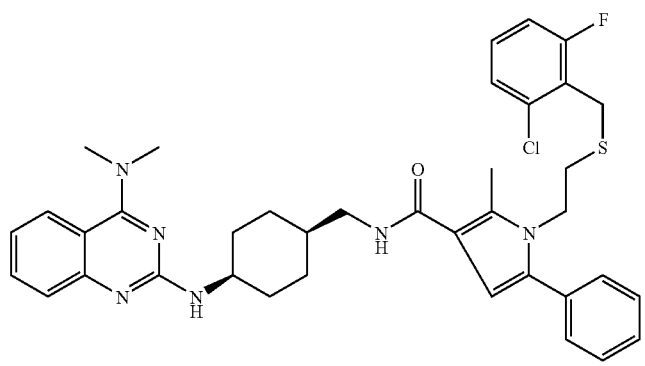 | 685 (M + H) |
| 914 | 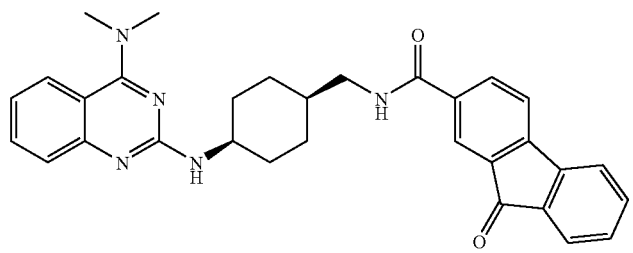 | 506 (M + H) |
| 915 | 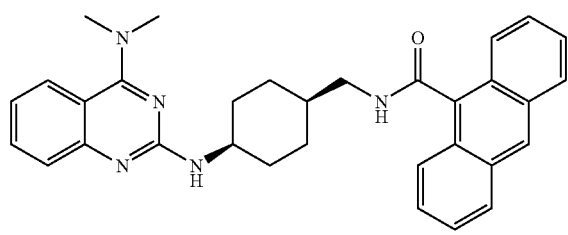 | 504 (M + H) |

-continued

| Example No. | Structure | APCI-MS |
|---|---|---|
| 916 | 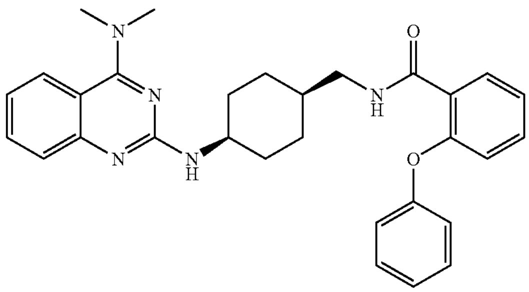 | 496 (M + H) |
| 917 | 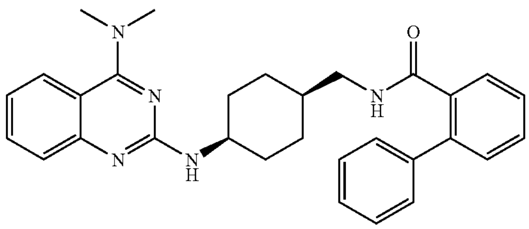 | 480 (M + H) |
| 918 | 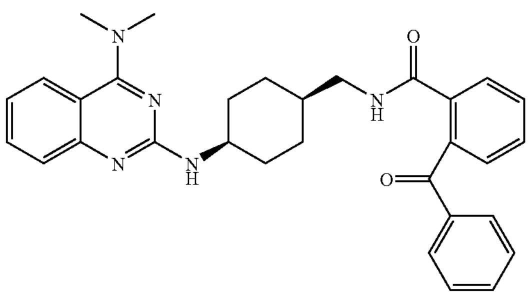 | 508 (M + H) |
| 919 | 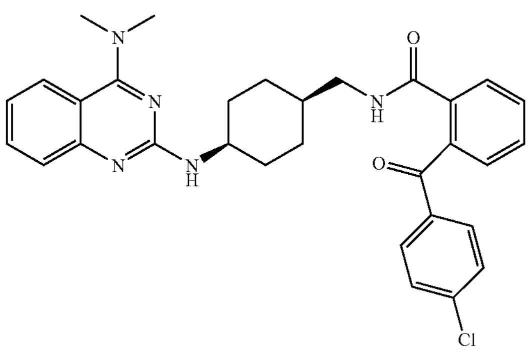 | 542 (M + H) |
| 920 | 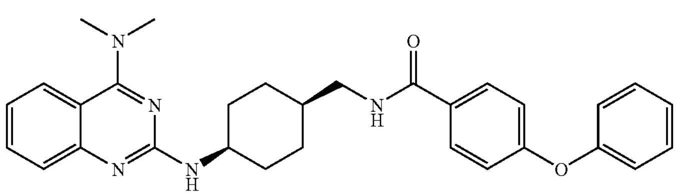 | 496 (M + H) |
| 921 | 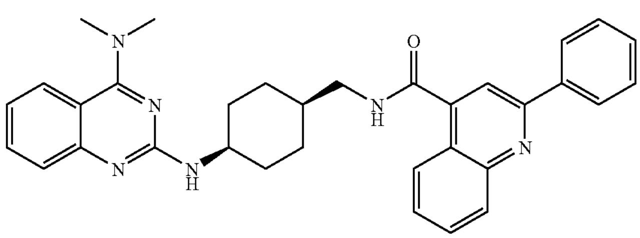 | 531 (M + H) |

-continued
| Example No. | Structure | APCI-MS |
|---|---|---|
| 922 | 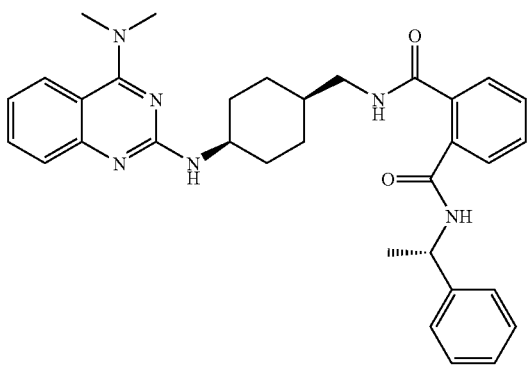 | 551 (M + H) |
| 923 | 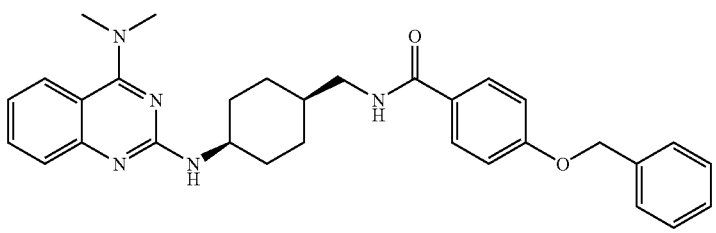 | 510 (M + H) |
| 924 | 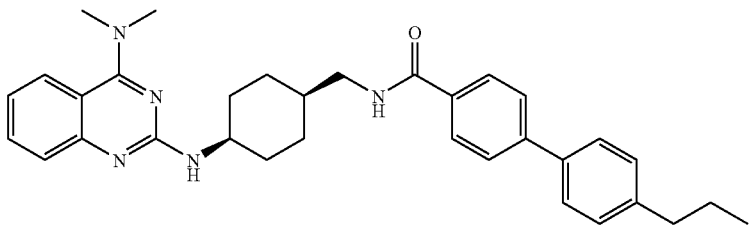 | 522 (M + H) |
| 925 | 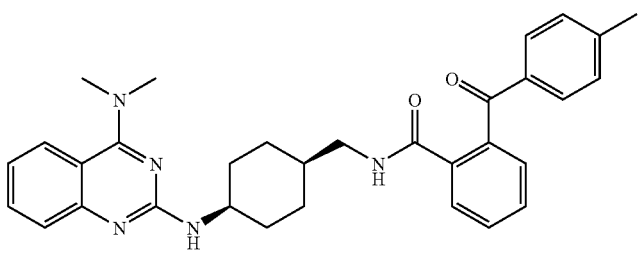 | 522 (M + H) |
| 926 | 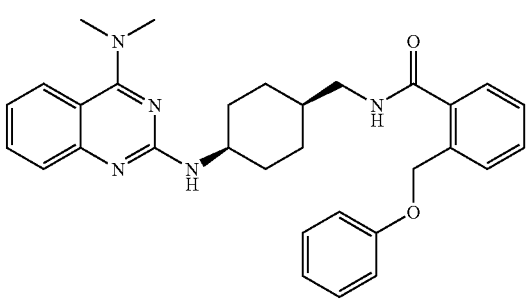 | 510 (M + H) |

-continued
| Example No. | Structure | APCI-MS |
|---|---|---|
| 927 | 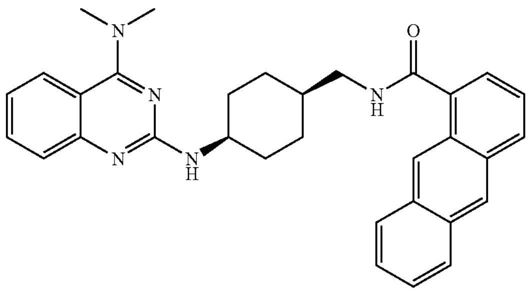 | 504 (M + H) |
| 928 | 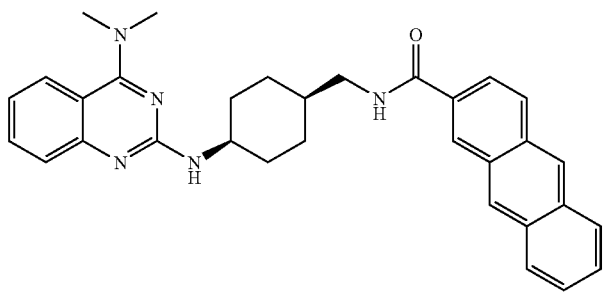 | 504 (M + H) |
| 929 | 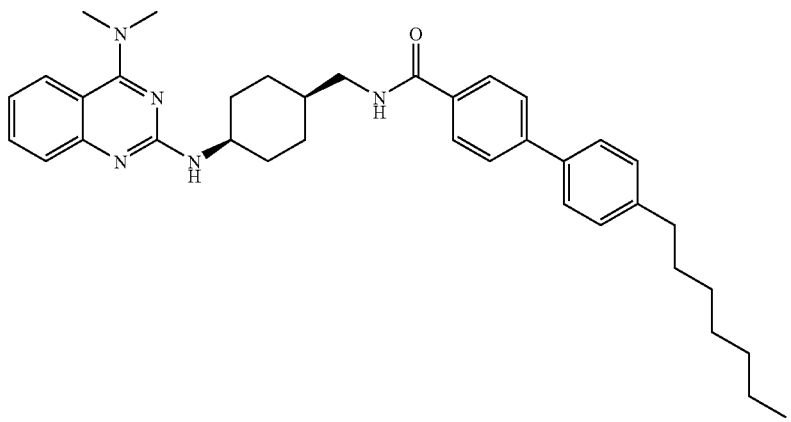 | 578 (M + H) |
| 930 | 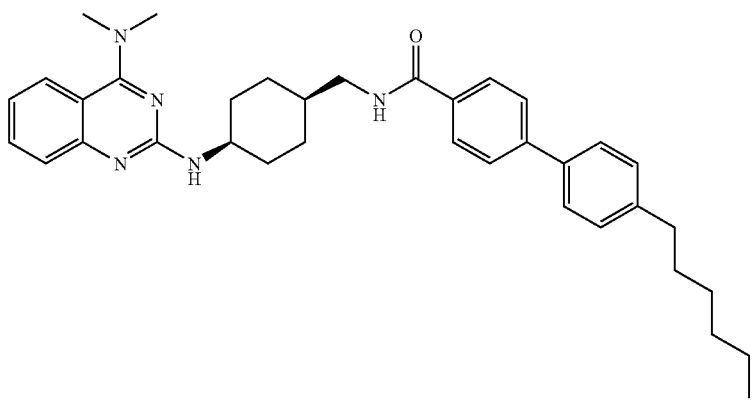 | 564 (M + H) |

-continued
| Example No. | Structure | APCI-MS |
|---|---|---|
| 931 | 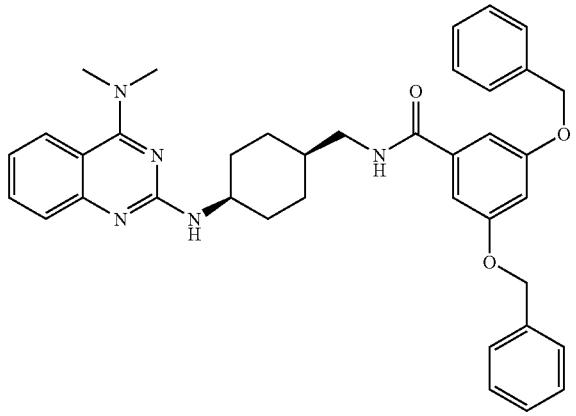 | 616 (M + H) |
| 932 | 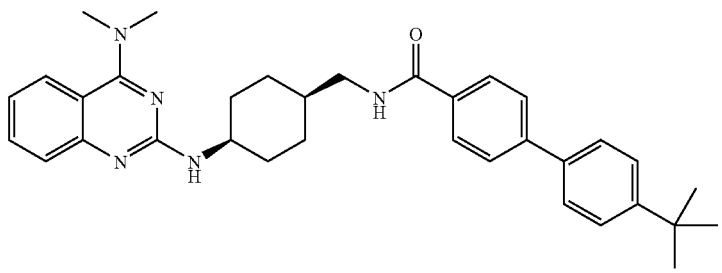 | 536 (M + H) |
| 933 | 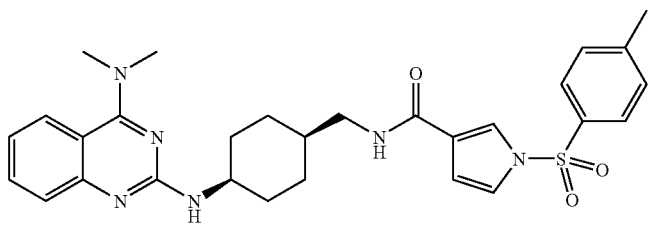 | 547 (M + H) |
| 934 | 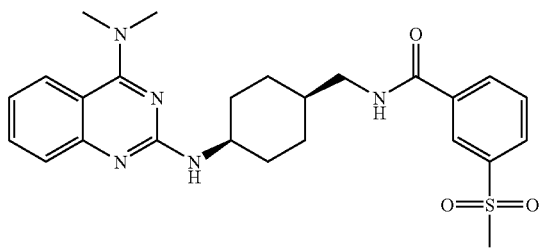 | 482 (M + H) |
| 935 | 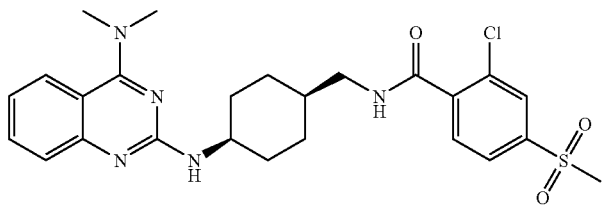 | 516 (M + H) |

-continued
| Example No. | Structure | APCI-MS |
|---|---|---|
| 936 | 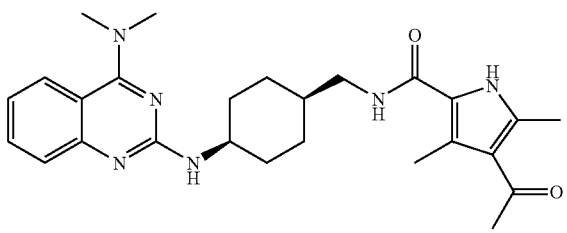 | 463 (M + H) |
| 937 | 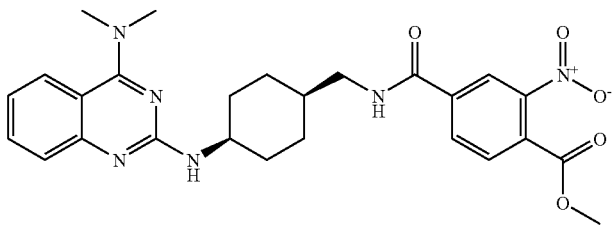 | 507 (M + H) |
| 938 | 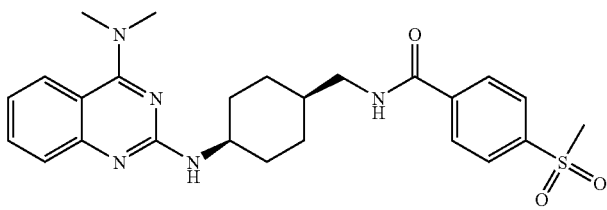 | 482 (M + H) |
| 939 | 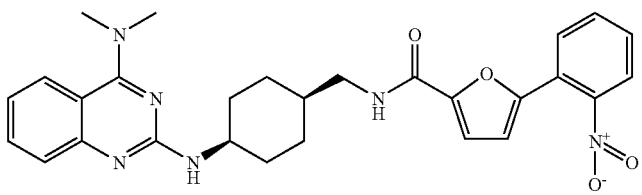 | 515 (M + H) |
| 940 | 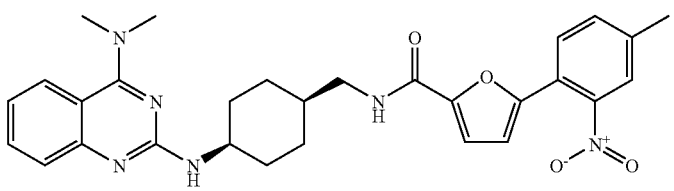 | 529 (M + H) |
| 941 | 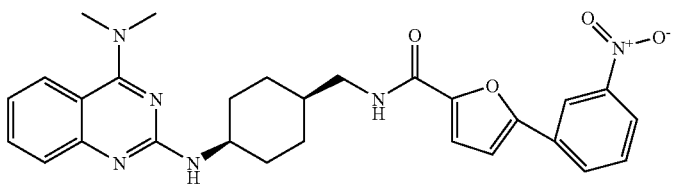 | 515 (M + H) |
| 942 | 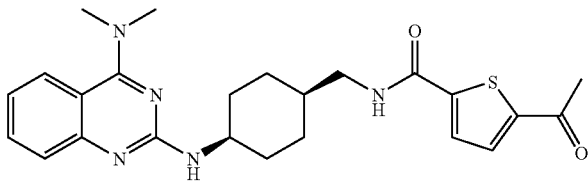 | 452 (M + H) |

-continued
| Example No. | Structure | APCI-MS |
|---|---|---|
| 943 | 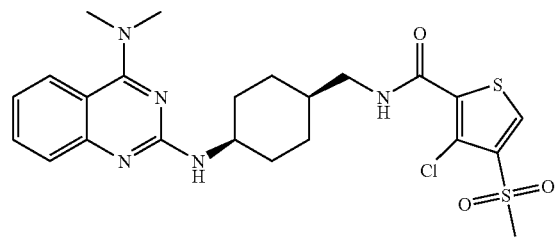 | 522 (M + H) |
| 944 | 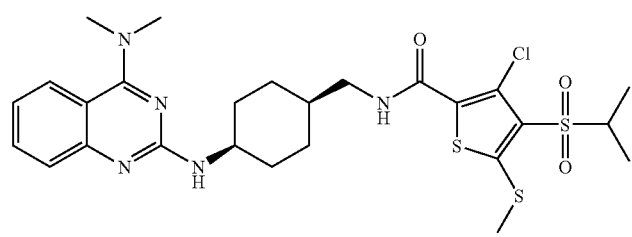 | 596 (M + H) |
| 945 | 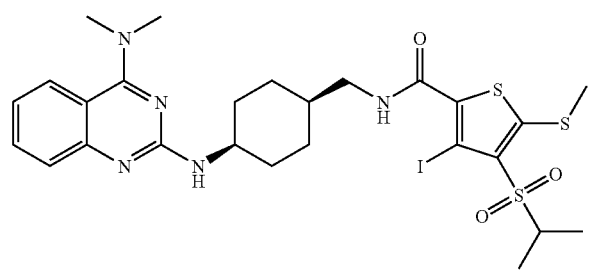 | 688 (M + H) |
| 946 | 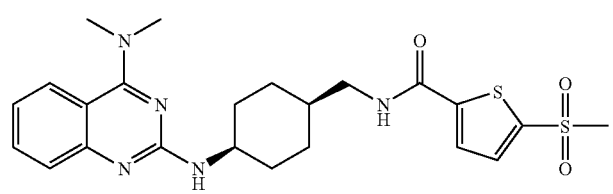 | 488 (M + H) |
| 947 | 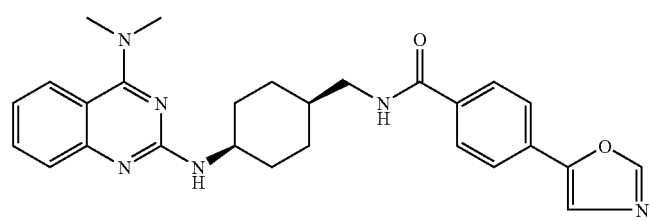 | 471 (M + H) |
| 948 | 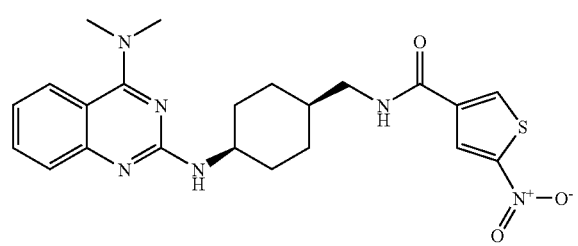 | 455 (M + H) |

| Example No. | Structure | APCI-MS |
|---|---|---|
| 949 | 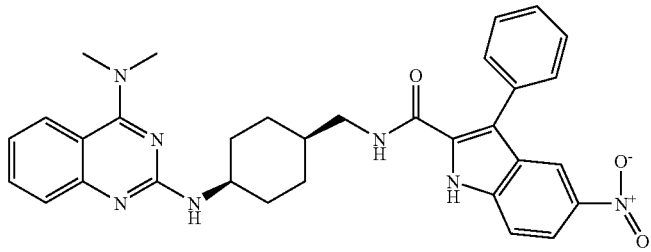 | 564 (M + H) |
| 950 | 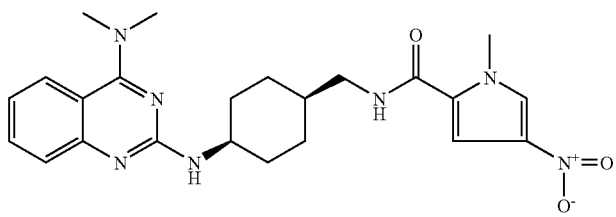 | 452 (M + H) |
| 951 | 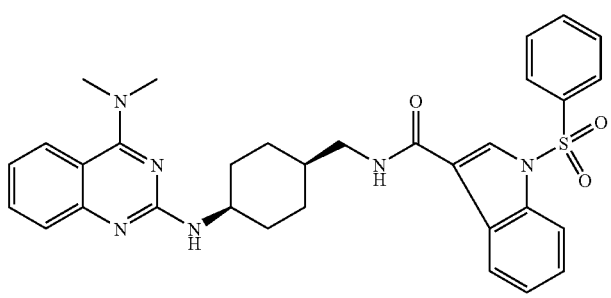 | 583 (M + H) |
| 952 | 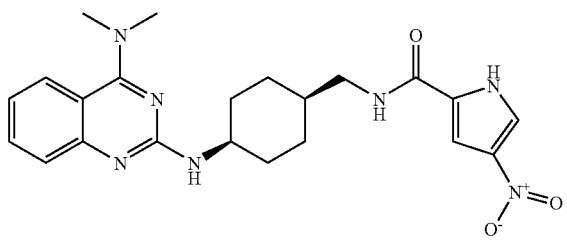 | 438 (M + H) |
| 953 | 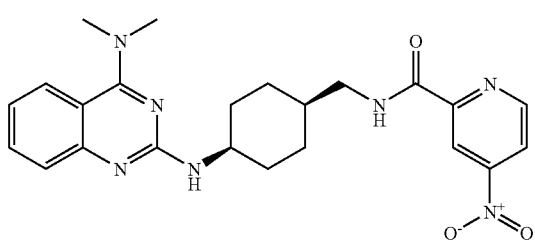 | 450 (M + H) |
| 954 | 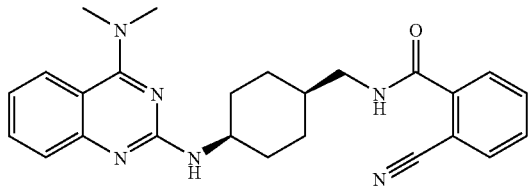 | 429 (M + H) |

-continued
| Example No. | Structure | APCI-MS |
|---|---|---|
| 955 | 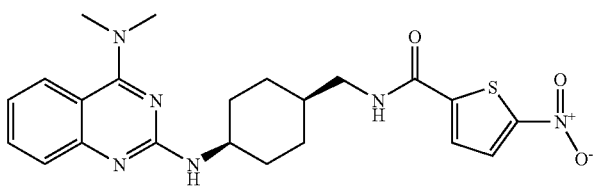 | 455 (M + H) |
| 956 | 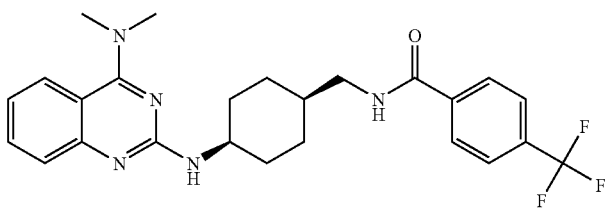 | 472 (M + H) |
| 957 | 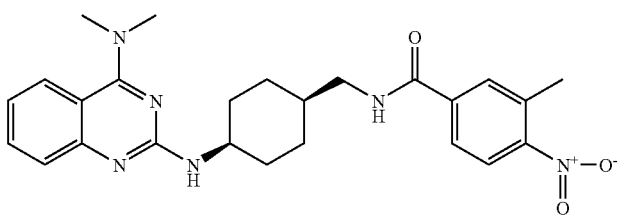 | 463 (M + H) |
| 958 | 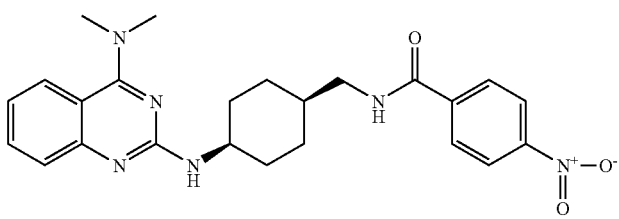 | 449 (M + H) |
| 959 | 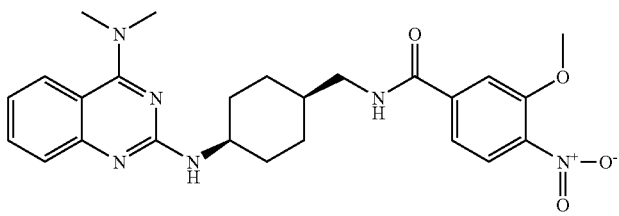 | 479 (M + H) |
| 960 | 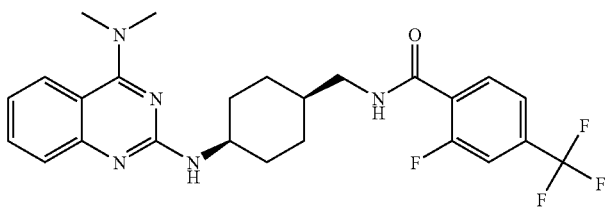 | 490 (M + H) |
| 961 | 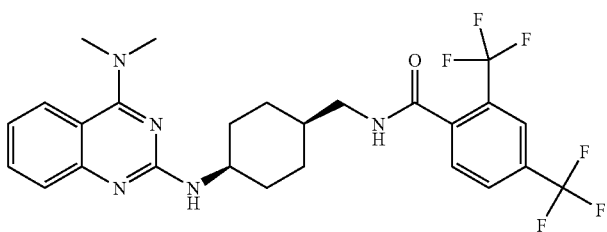 | 540 (M + H) |

-continued
| Example No. | Structure | APCI-MS |
|---|---|---|
| 962 | 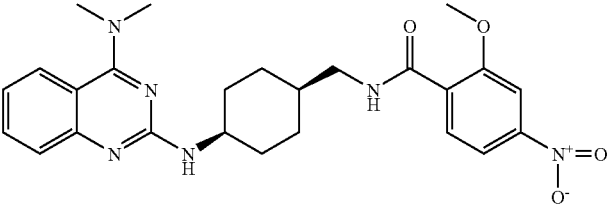 | 479 (M + H) |
| 963 | 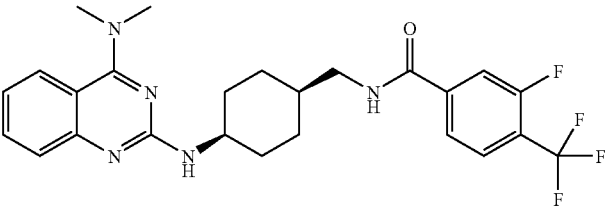 | 490 (M + H) |
| 964 | 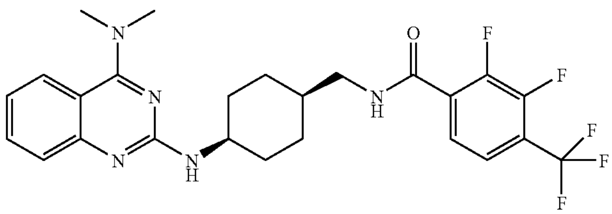 | 508 (M + H) |
| 965 | 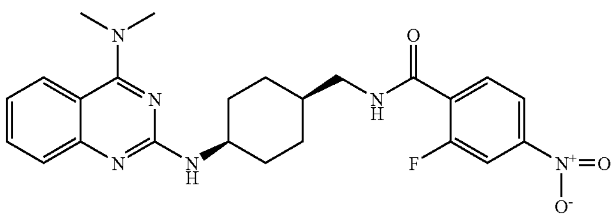 | 467 (M + H) |
| 966 | 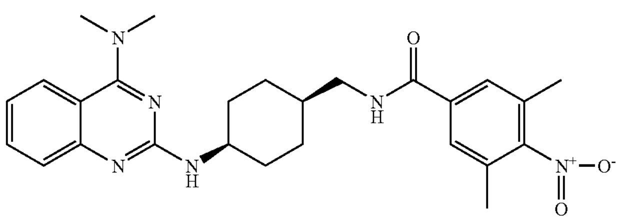 | 477 (M + H) |
| 967 | 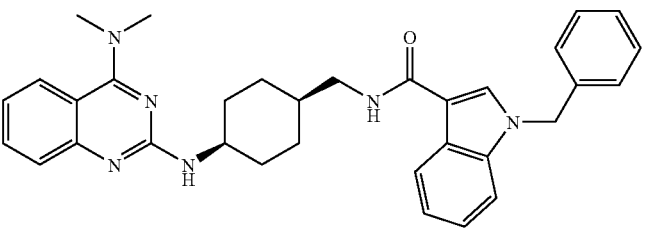 | 533 (M + H) |
| 968 | 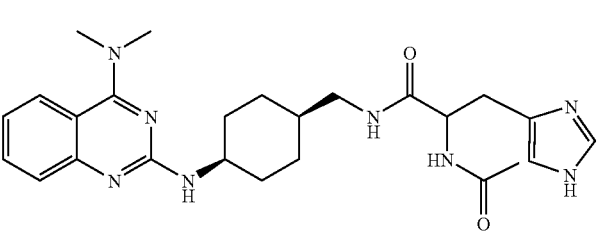 | 479 (M + H) |

-continued
| Example No. | Structure | APCI-MS |
|---|---|---|
| 969 | 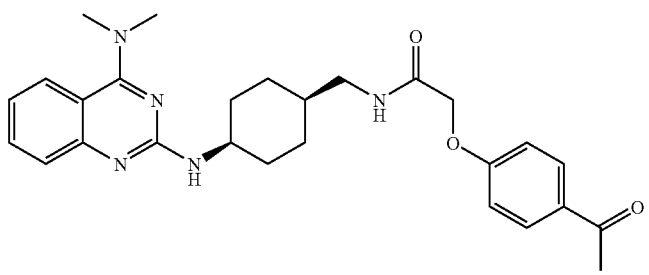 | 476 (M + H) |
| 970 | 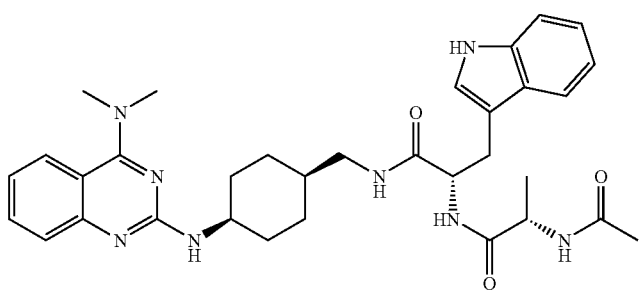 | 599 (M + H) |
| 971 | 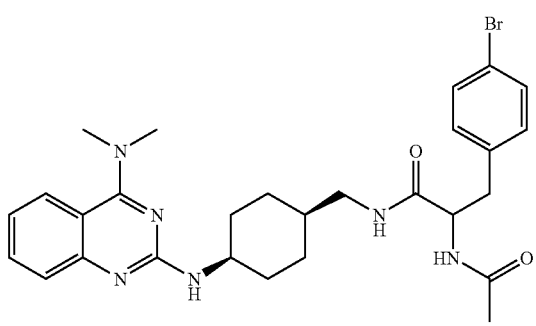 | 567 (M + H) |
| 972 | 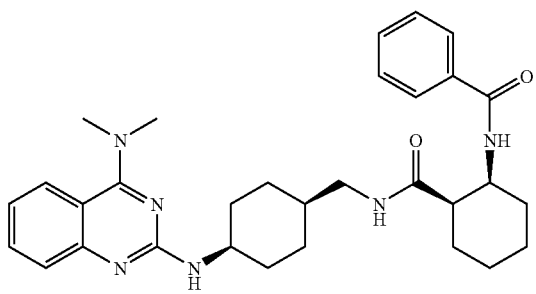 | 529 (M + H) |
| 973 | 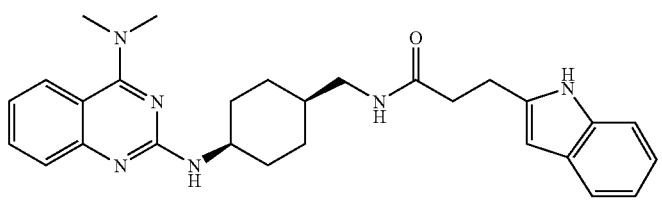 | 472 (M + H) |

-continued
| Example No. | Structure | APCI-MS |
|---|---|---|
| 974 | 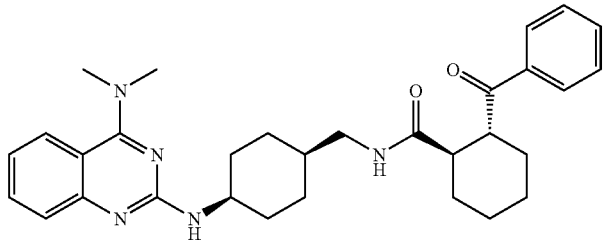 | 514 (M + H) |
| 975 | 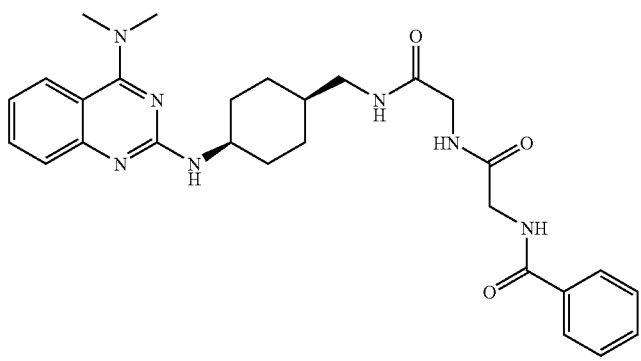 | 518 (M + H) |
| 976 | 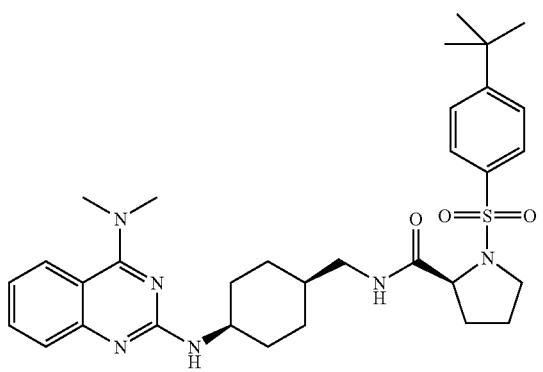 | 593 (M + H) |
| 977 | 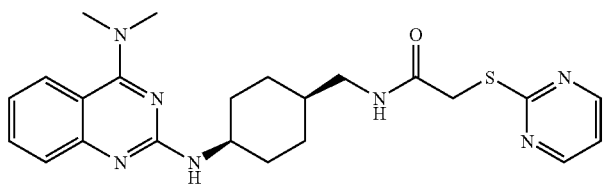 | 452 (M + H) |
| 978 | 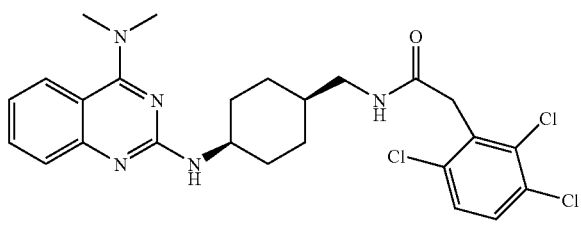 | 520 (M + H) |
| 979 | 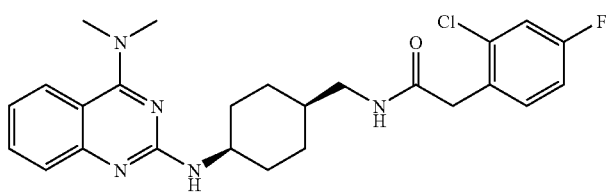 | 470 (M + H) |

-continued
| Example No. | Structure | APCI-MS |
|---|---|---|
| 980 | 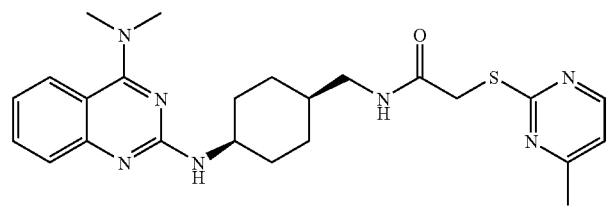 | 466 (M + H) |
| 981 | 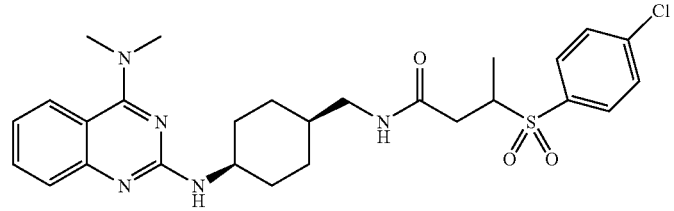 | 544 (M + H) |
| 982 | 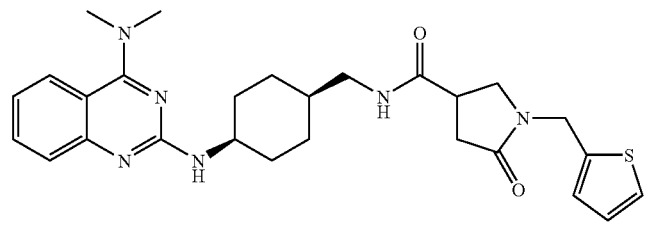 | 507 (M + H) |
| 983 | 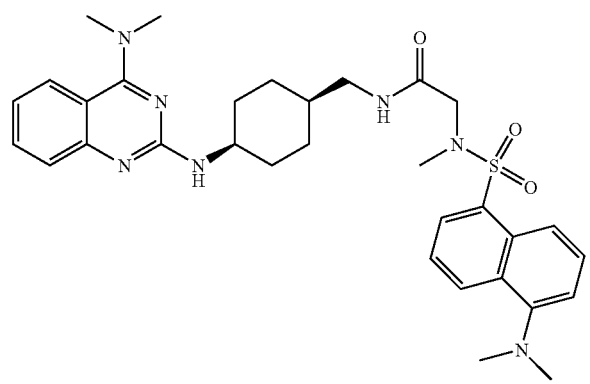 | 604 (M + H) |
| 984 | 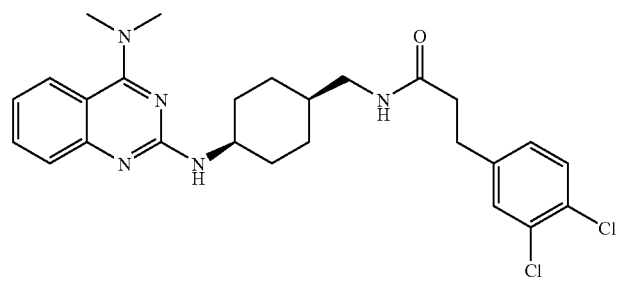 | 500 (M + H) |
| 985 | 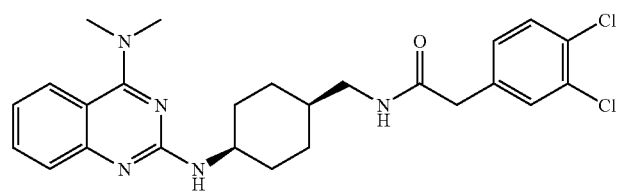 | 486 (M + H) |

-continued
| Example No. | Structure | APCI-MS |
|---|---|---|
| 986 | 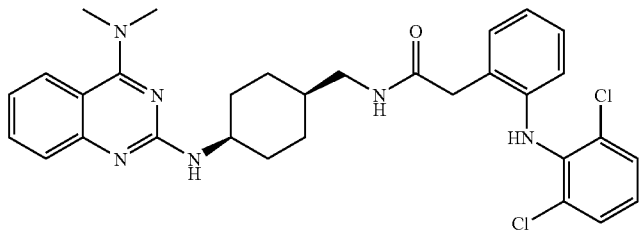 | 577 (M + H) |
| 987 | 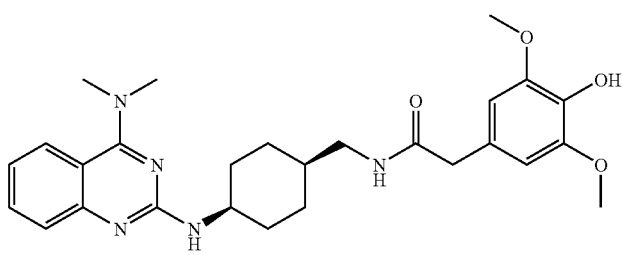 | 494 (M + H) |
| 988 | 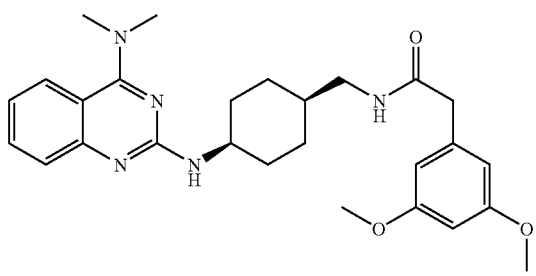 | 478 (M + H) |
| 989 | 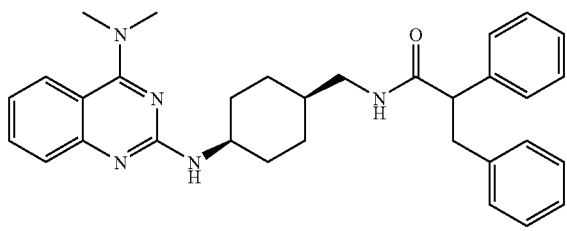 | 508 (M + H) |
| 990 | 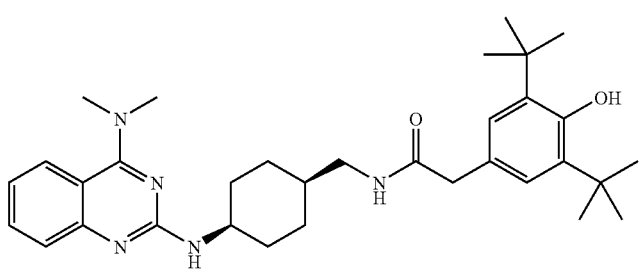 | 546 (M + H) |
| 991 | 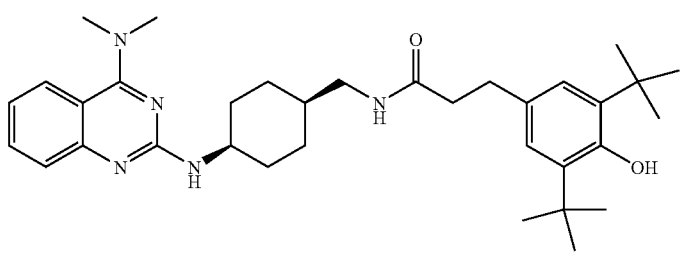 | 560 (M + H) |

-continued
| Example No. | Structure | APCI-MS |
|---|---|---|
| 992 | 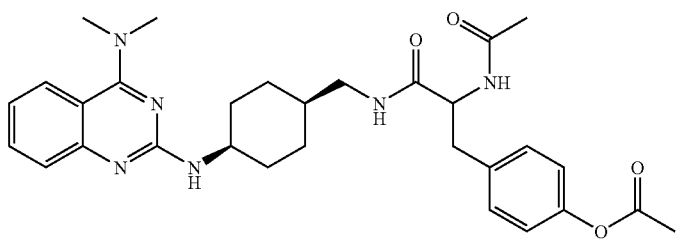 | 547 (M + H) |
| 993 | 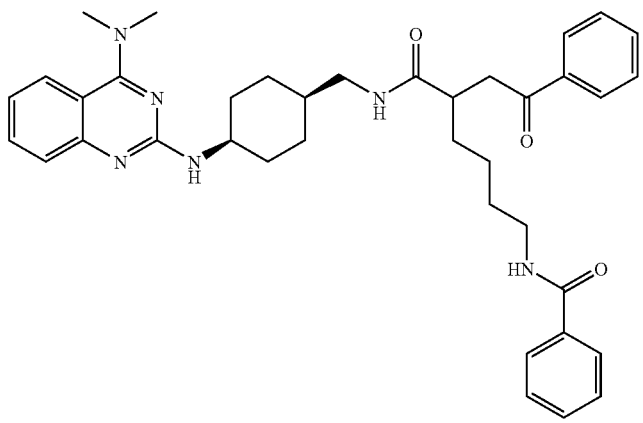 | 636 (M + H) |
| 994 | 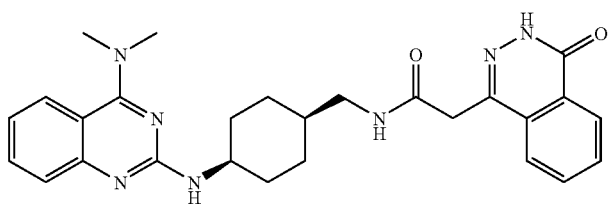 | 486 (M + H) |
| 995 | 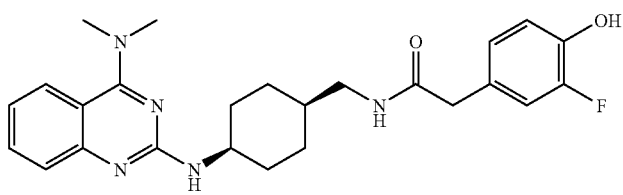 | 452 (M + H) |
| 996 | 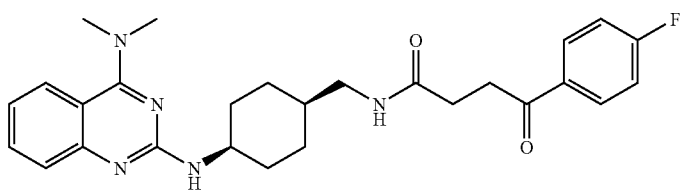 | 478 (M + H) |
| 997 | 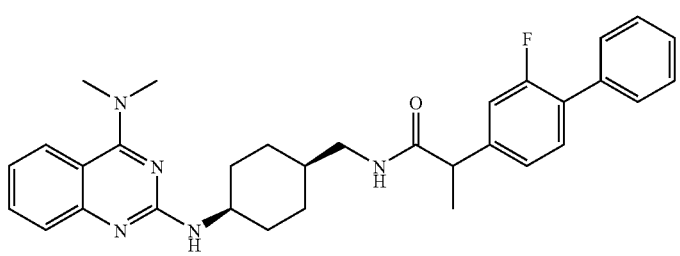 | 526 (M + H) |

| Example No. | Structure | APCI-MS |
|---|---|---|
| 998 | 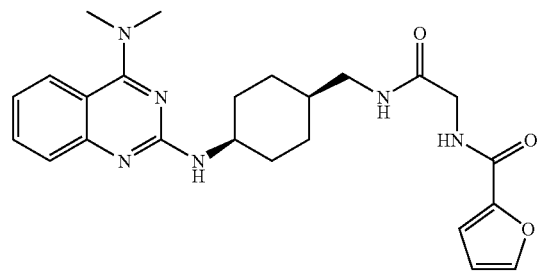 | 451 (M + H) |
| 999 | 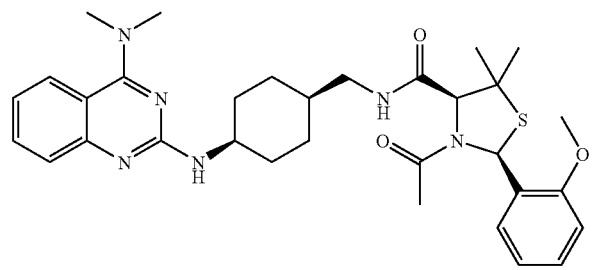 | 591 (M + H) |
| 1000 | 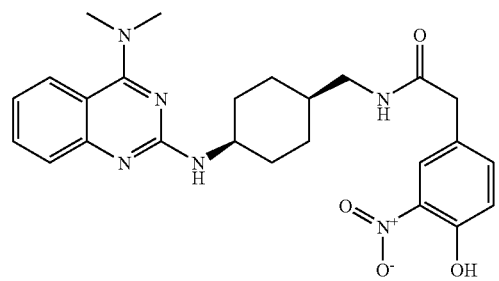 | 479 (M + H) |
| 1001 | 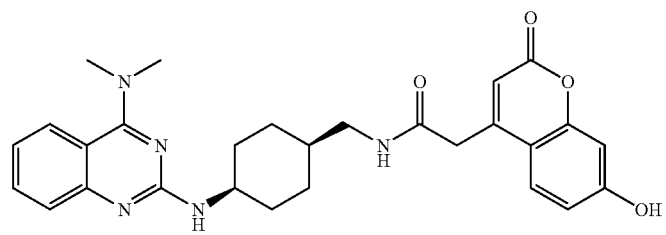 | 502 (M + H) |
| 1002 | 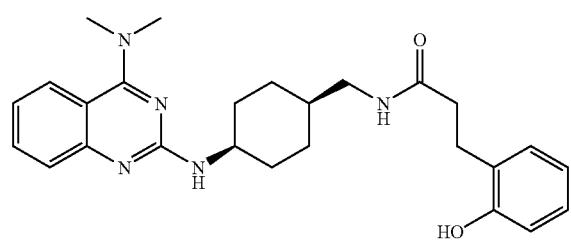 | 448 (M + H) |

-continued
| Example No. | Structure | APCI-MS |
|---|---|---|
| 1003 | 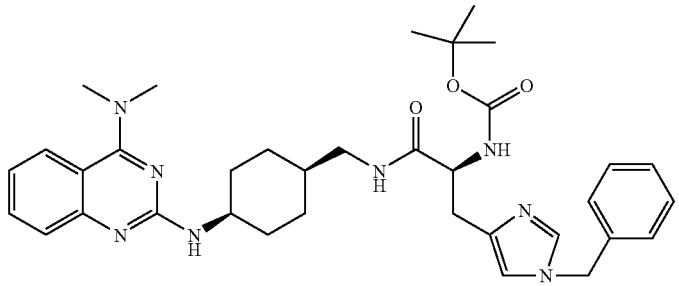 | 627 (M + H) |
| 1004 | 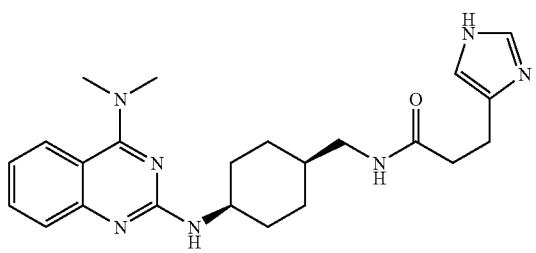 | 422 (M + H) |
| 1005 | 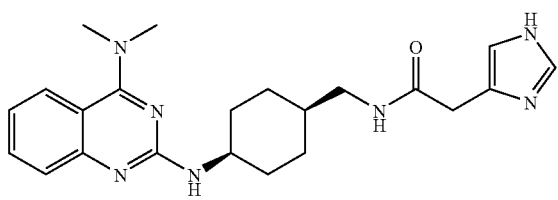 | 408 (M + H) |
| 1006 | 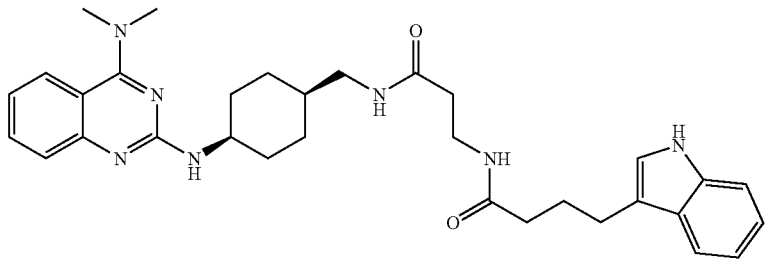 | 556 (M + H) |
| 1007 | 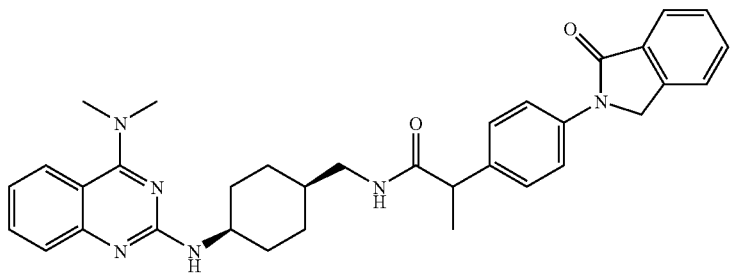 | 563 (M + H) |
| 1008 | 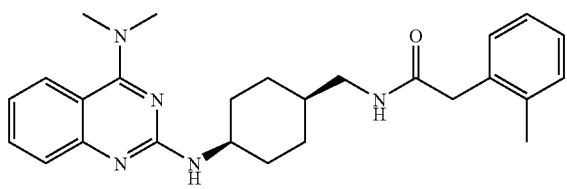 | 544 (M + H) |

-continued
| Example No. | Structure | APCI-MS |
|---|---|---|
| 1009 | 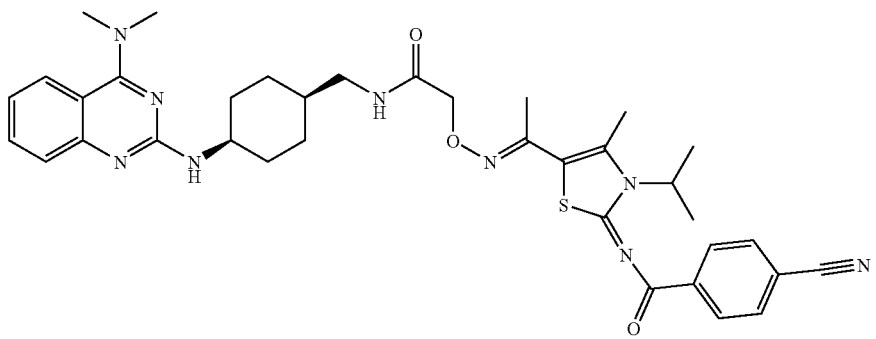 | 682 (M + H) |
| 1010 | 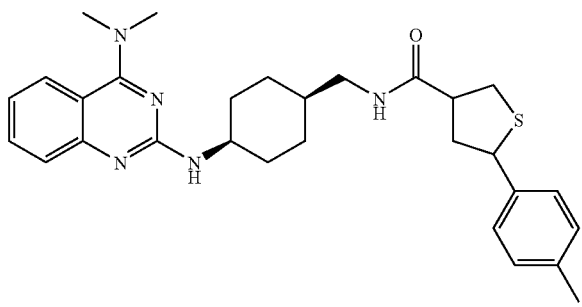 | 504 (M + H) |
| 1011 | 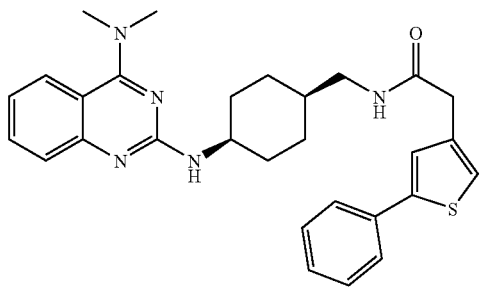 | 500 (M + H) |
| 1012 | 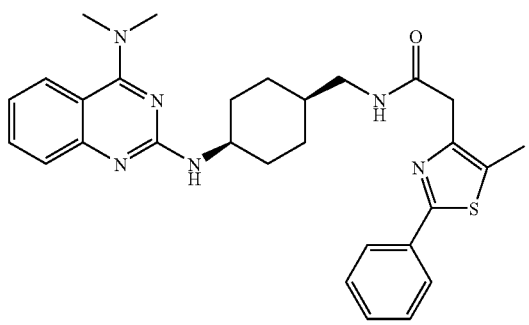 | 515 (M + H) |
| 1013 | 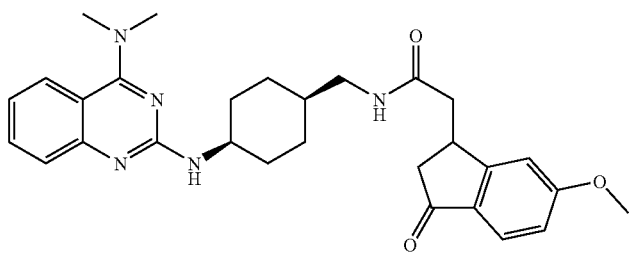 | 502 (M + H) |

-continued
| Example No. | Structure | APCI-MS |
|---|---|---|
| 1014 | 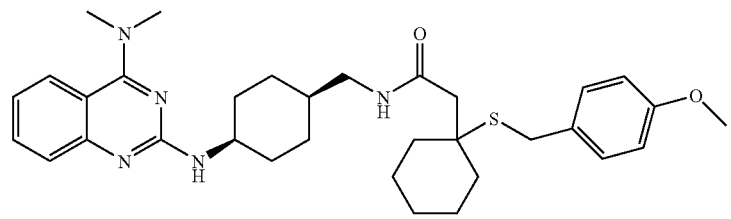 | 576 (M + H) |
| 1015 | 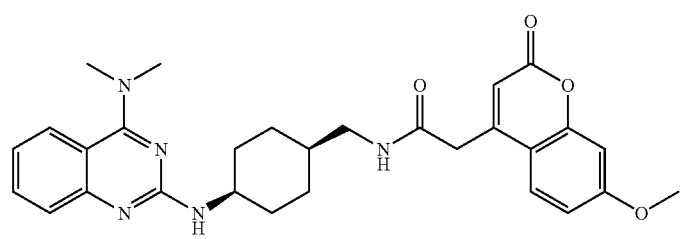 | 516 (M + H) |
| 1016 | 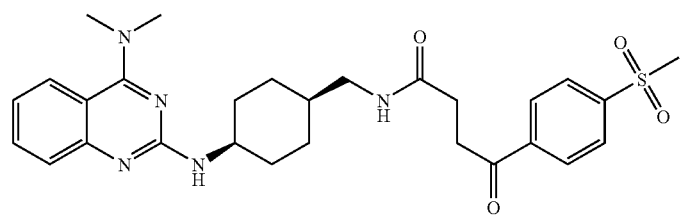 | 538 (M + H) |
| 1017 | 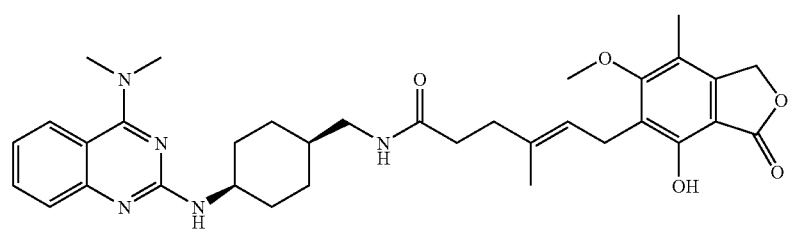 | 602 (M + H) |
| 1018 | 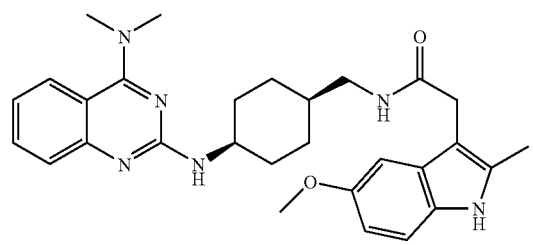 | 501 (M + H) |
| 1019 | 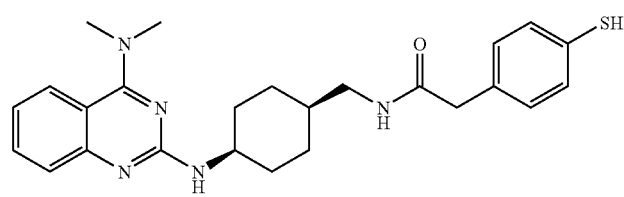 | 450 (M + H) |

-continued
| Example No. | Structure | APCI-MS |
|---|---|---|
| 1020 | 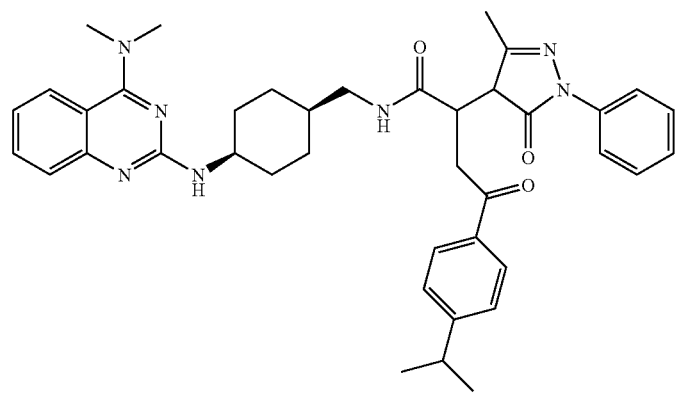 | 674 (M + H) |
| 1021 | 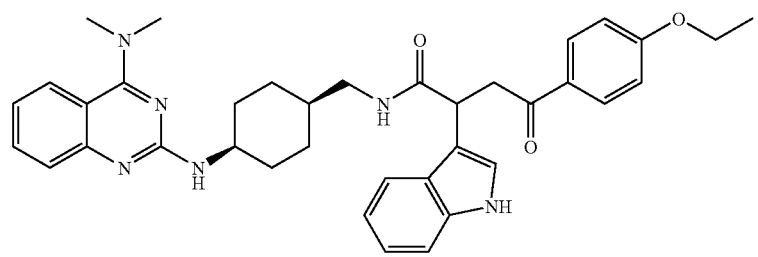 | 619 (M + H) |
| 1022 | 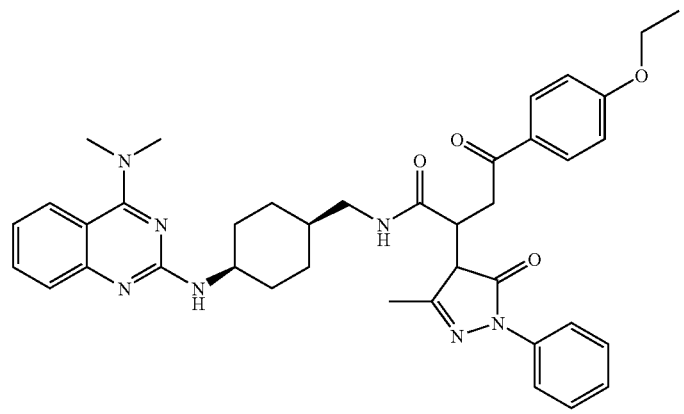 | 676 (M + H) |
| 1023 | 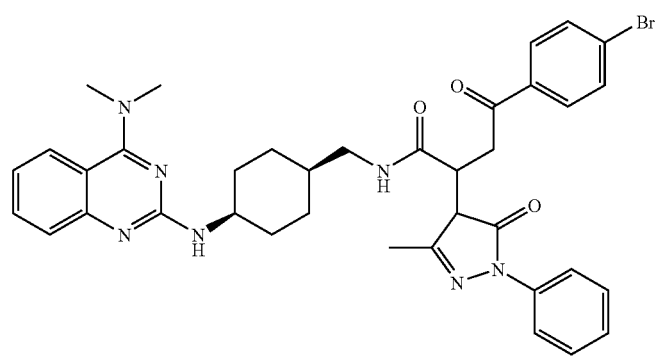 | 710 (M + H) |

-continued
| Example No. | Structure | APCI-MS |
|---|---|---|
| 1024 | 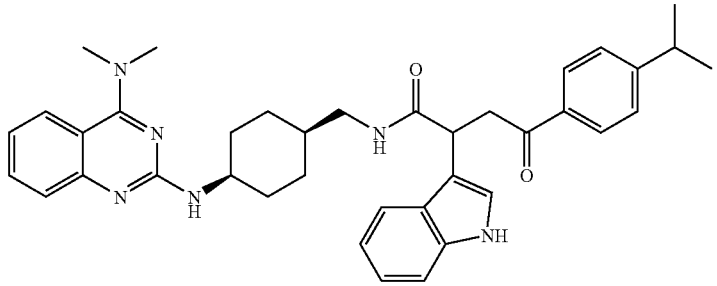 | 617 (M + H) |
| 1025 | 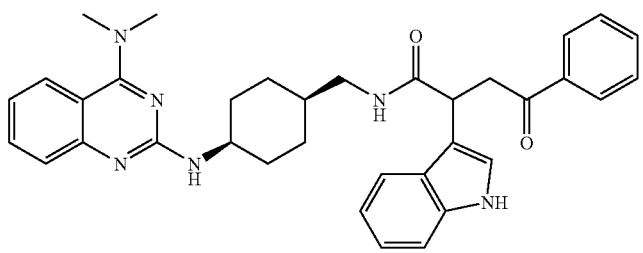 | 575 (M + H) |
| 1026 | 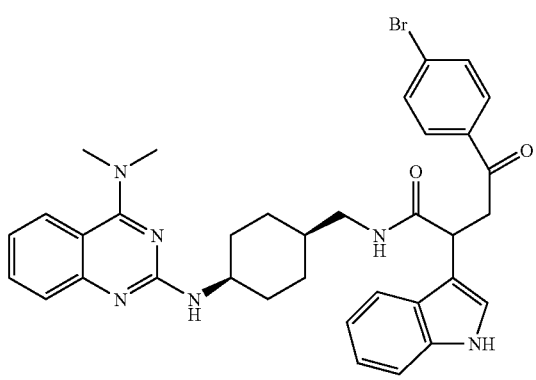 | 653 (M + H) |
| 1027 | 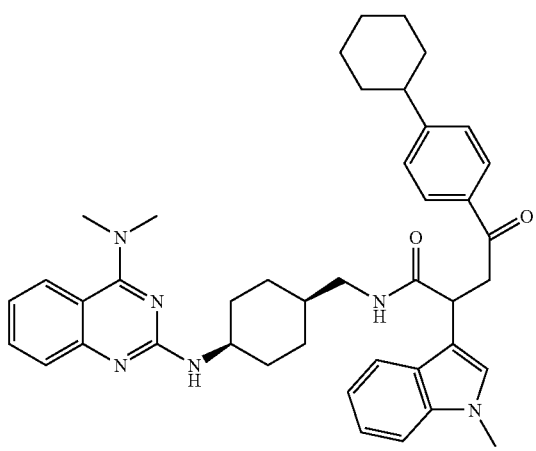 | 671 (M + H) |

-continued
| Example No. | Structure | APCI-MS |
|---|---|---|
| 1028 | 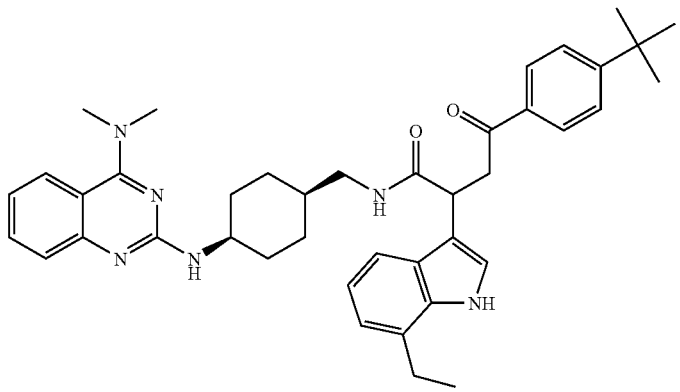 | 659 (M + H) |
| 1029 | 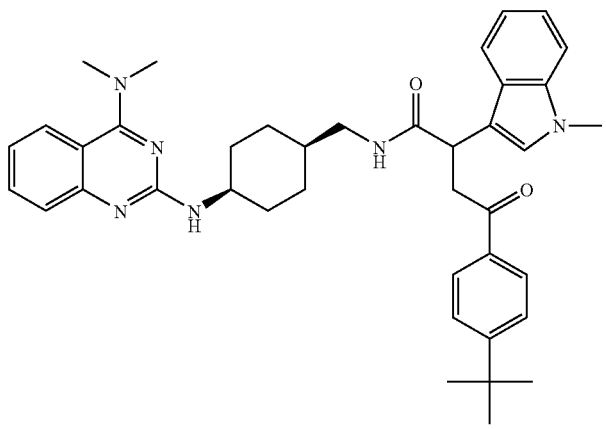 | 645 (M + H) |
| 1030 | 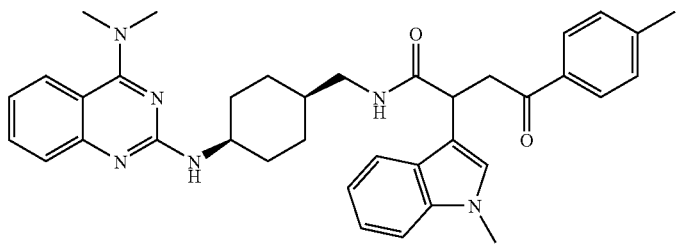 | 603 (M + H) |
| 1031 | 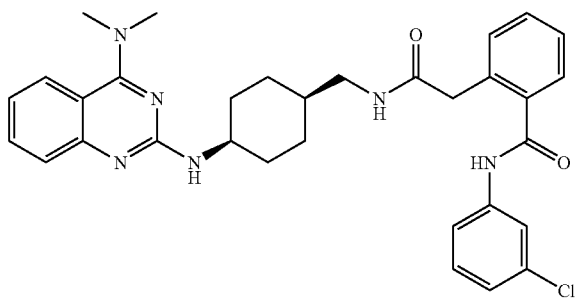 | 571 (M + H) |

-continued

| Example No. | Structure | APCI-MS |
|---|---|---|
| 1032 | 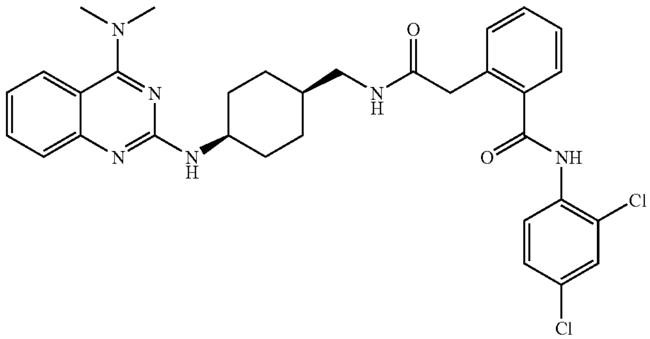 | 605 (M + H) |
| 1033 | 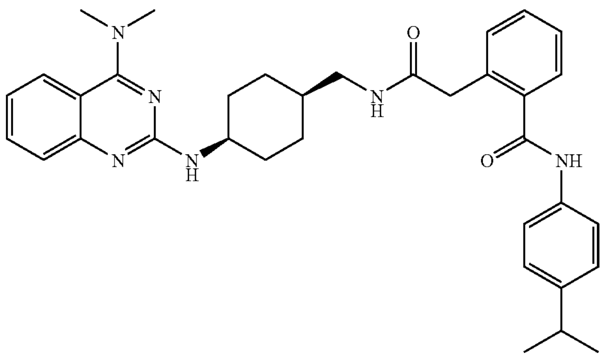 | 579 (M + H) |
| 1034 | 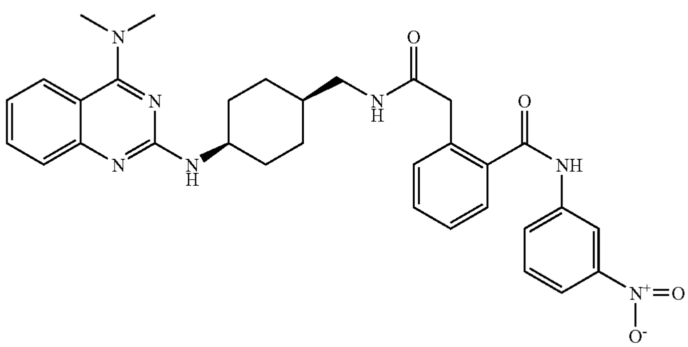 | 582 (M + H) |
| 1035 | 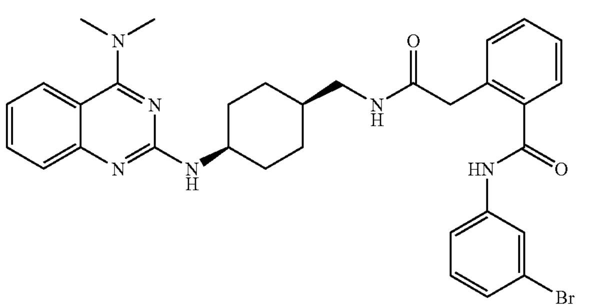 | 615 (M + H) |

| Example No. | Structure | APCI-MS |
|---|---|---|
| 1036 | 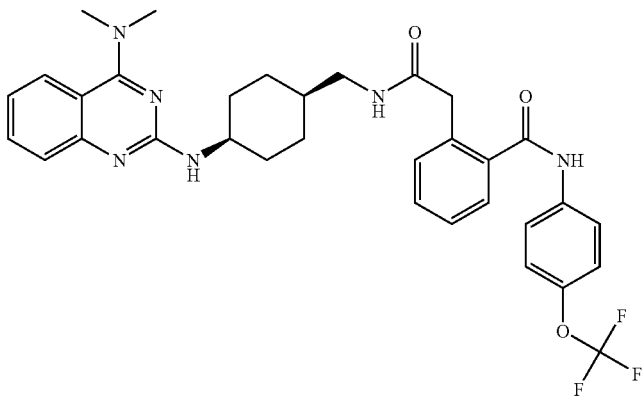 | 621 (M + H) |
| 1037 | 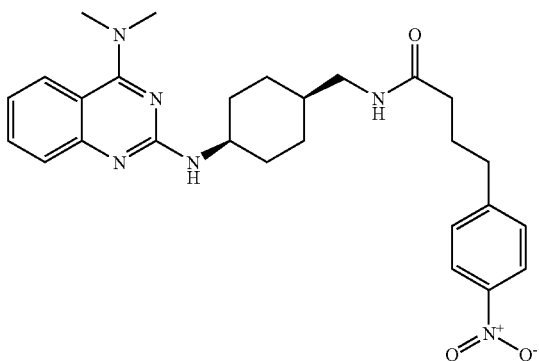 | 491 (M + H) |
| 1038 | 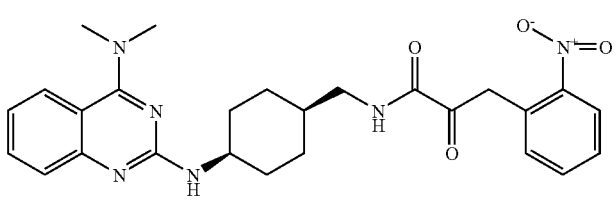 | 491 (M + H) |
| 1039 | 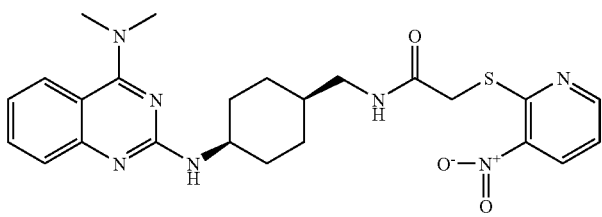 | 496 (M + H) |
| 1040 | 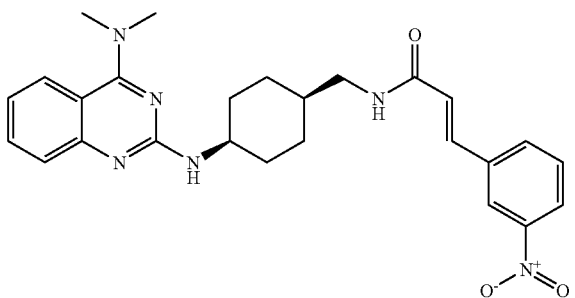 | 475 (M + H) |

-continued
| Example No. | Structure | APCI-MS |
|---|---|---|
| 1041 | 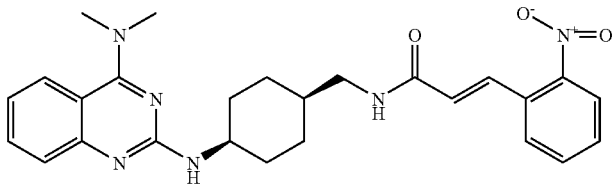 | 475 (M + H) |
| 1042 | 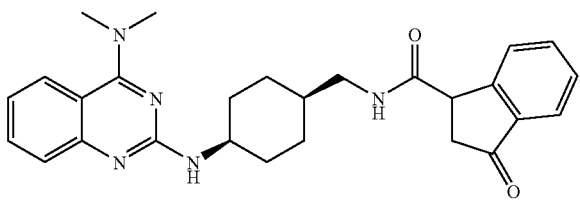 | 458 (M + H) |
| 1043 | 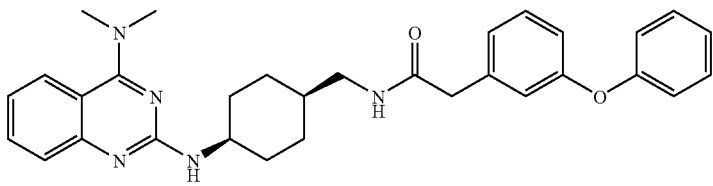 | 510 (M + H) |
| 1044 | 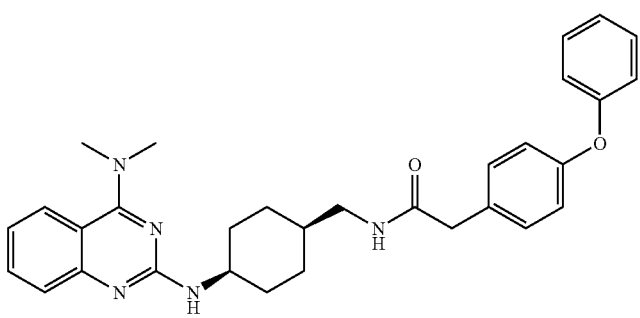 | 510 (M + H) |
| 1045 | 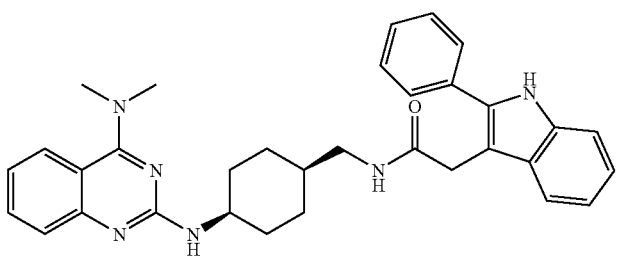 | 533 (M + H) |
| 1046 | 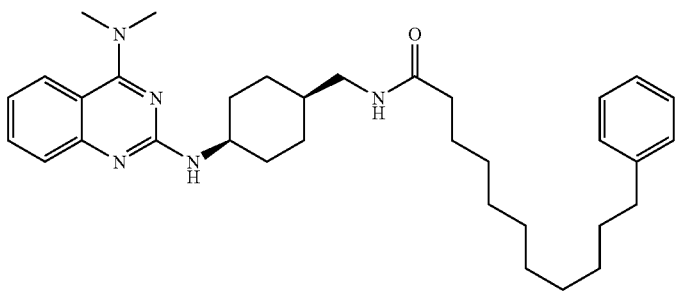 | 544 (M + H) |

-continued
| Example No. | Structure | APCI-MS |
|---|---|---|
| 1047 | 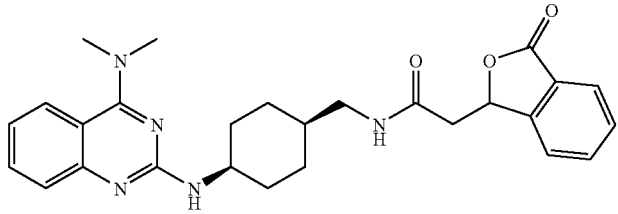 | 474 (M + H) |
| 1048 | 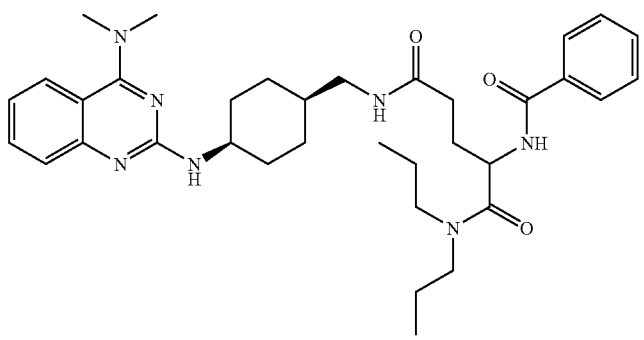 | 616 (M + H) |
| 1049 | 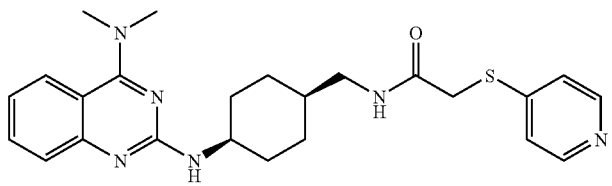 | 451 (M + H) |
| 1050 | 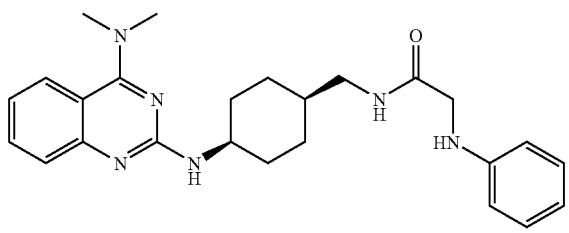 | 433 (M + H) |
| 1051 | 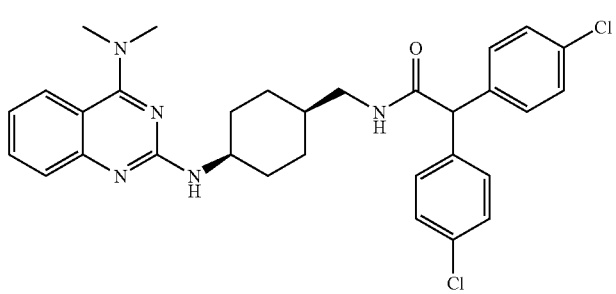 | 562 (M + H) |

-continued
| Example No. | Structure | APCI-MS |
|---|---|---|
| 1052 | 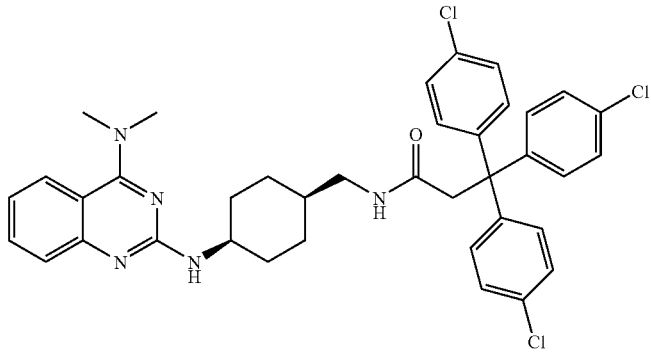 | 686 (M + H) |
| 1053 | 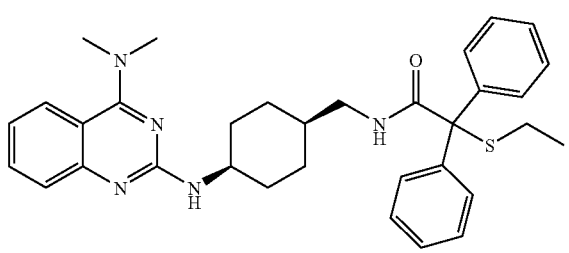 | 554 (M + H) |
| 1054 | 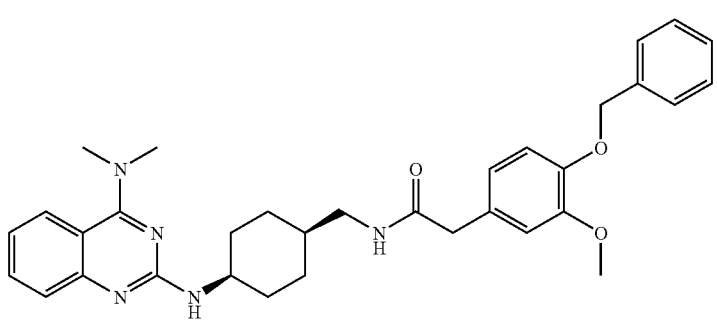 | 554 (M + H) |
| 1055 | 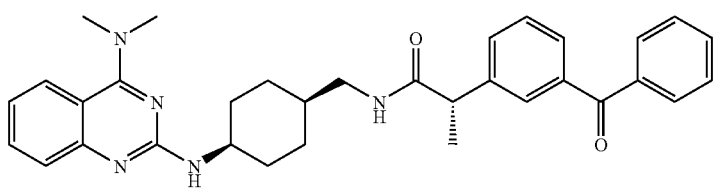 | 536 (M + H) |
| 1056 | 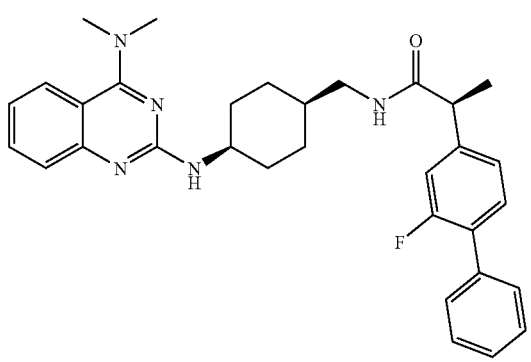 | 526 (M + H) |

-continued
| Example No. | Structure | APCI-MS |
|---|---|---|
| 1057 | 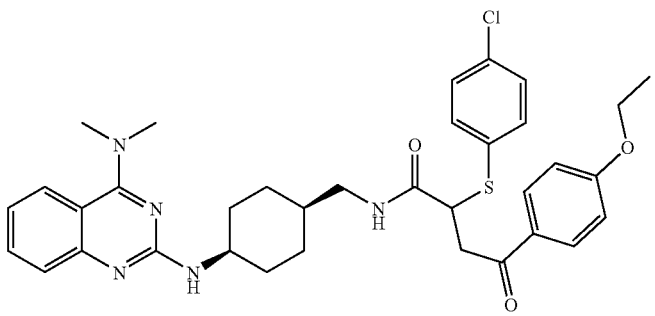 | 646 (M + H) |
| 1058 | 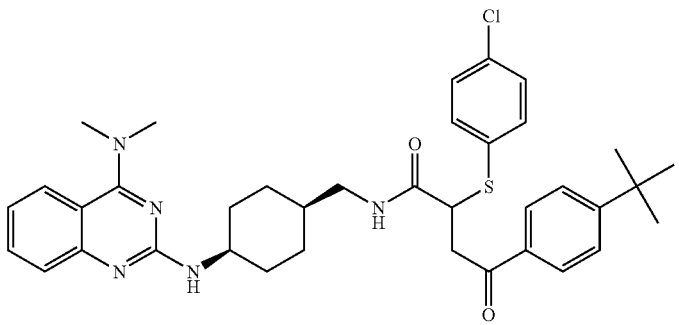 | 658 (M + H) |
| 1059 | 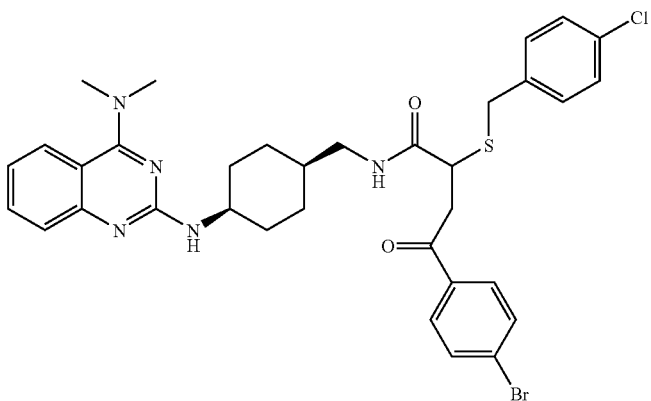 | 694 (M + H) |
| 1060 | 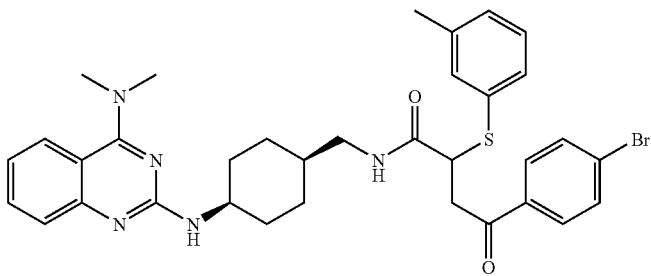 | 660 (M + H) |

-continued
| Example No. | Structure | APCI-MS |
|---|---|---|
| 1061 | 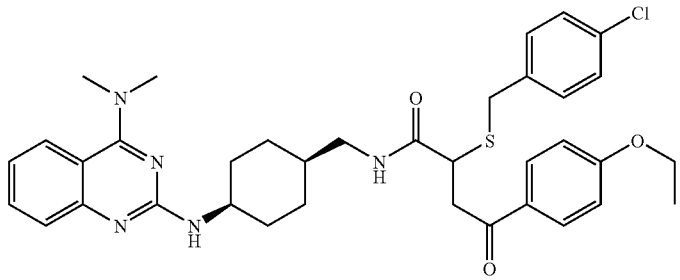 | 660 (M + H) |
| 1062 | 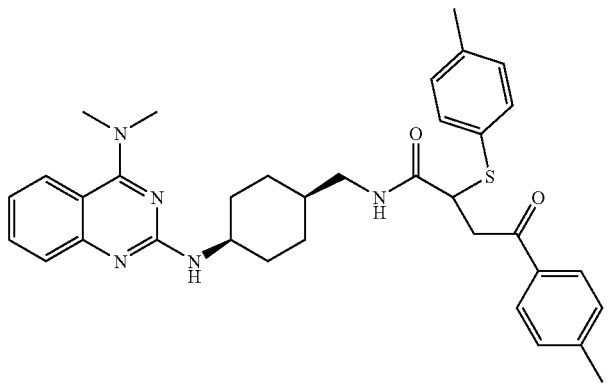 | 596 (M + H) |
| 1063 | 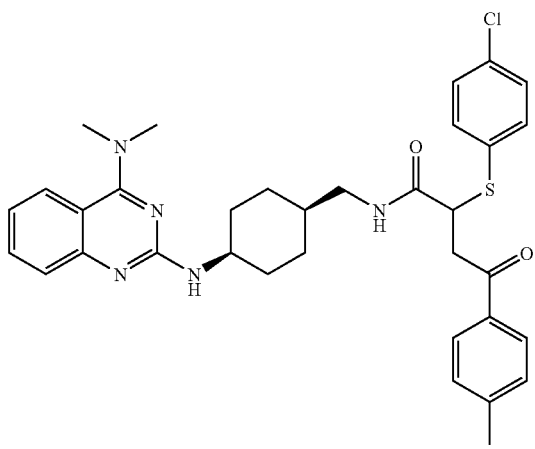 | 616 (M + H) |
| 1064 | 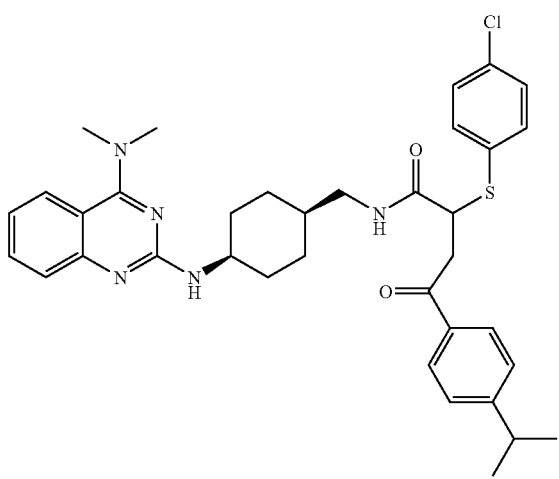 | 644 (M + H) |

-continued
| Example No. | Structure | APCI-MS |
|---|---|---|
| 1065 | 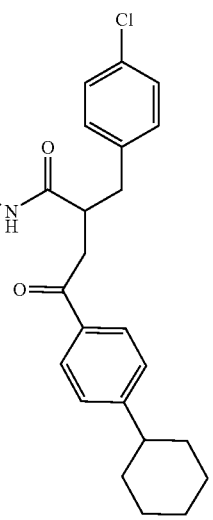 | 684 (M + H) |
| 1066 | 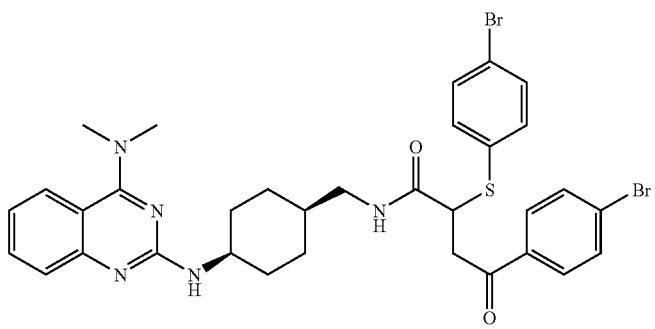 | 724 (M + H) |
| 1067 | 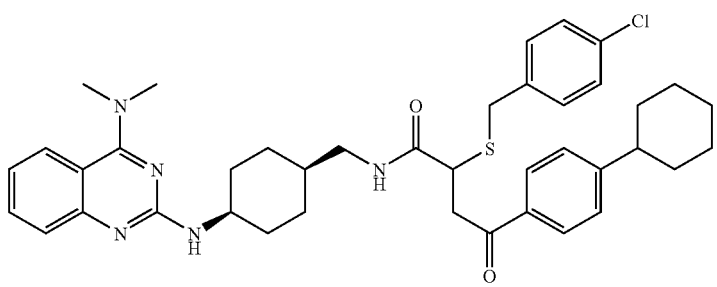 | 698 (M + H) |
| 1068 | 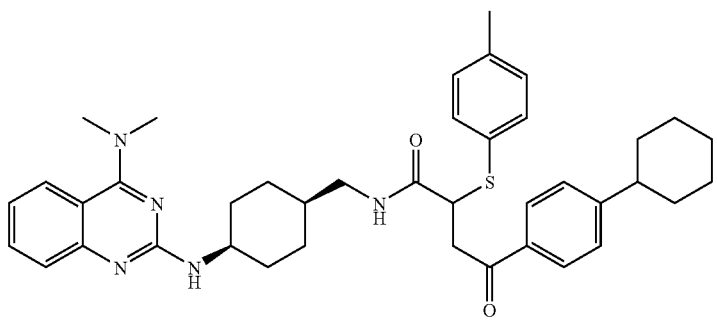 | 664 (M + H) |

| Example No. | Structure | APCI-MS |
|---|---|---|
| 1069 | 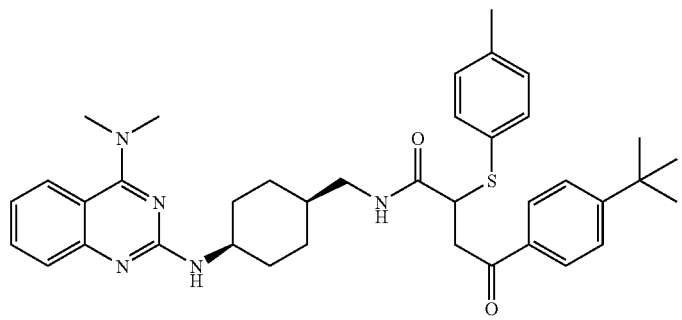 | 638 (M + H) |
| 1070 | 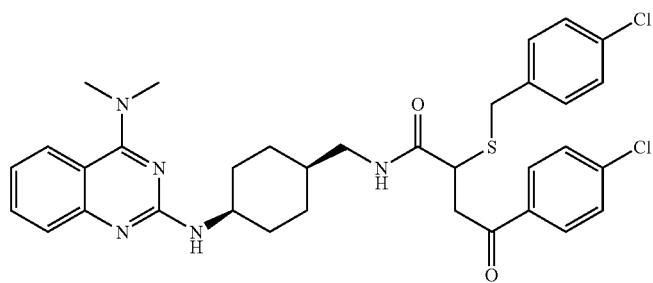 | 650 (M + H) |
| 1071 | 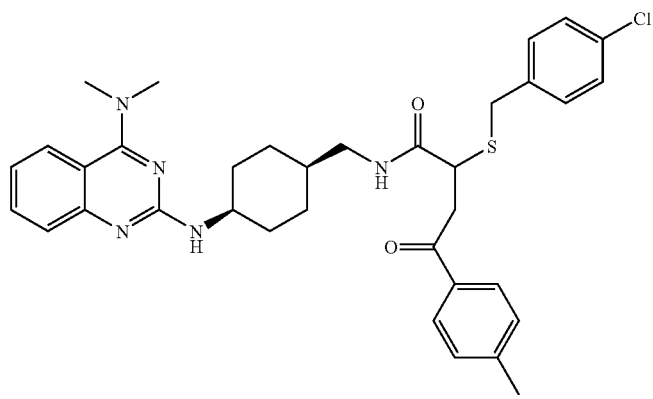 | 630 (M + H) |
| 1072 | 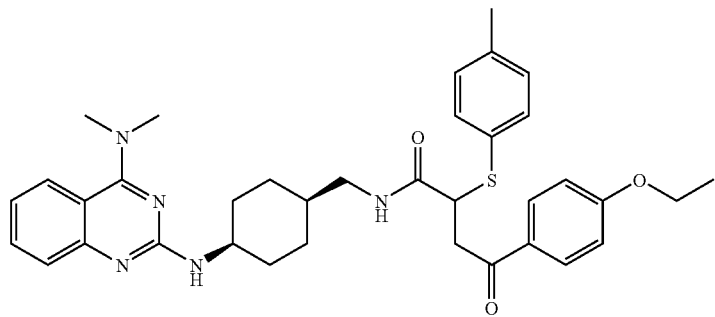 | 626 (M + H) |

-continued
| Example No. | Structure | APCI-MS |
|---|---|---|
| 1073 | 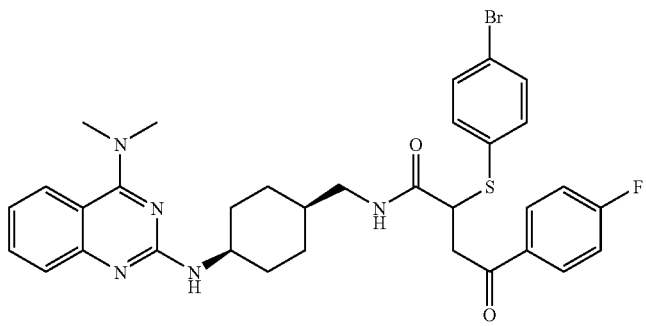 | 664 (M + H) |
| 1074 | 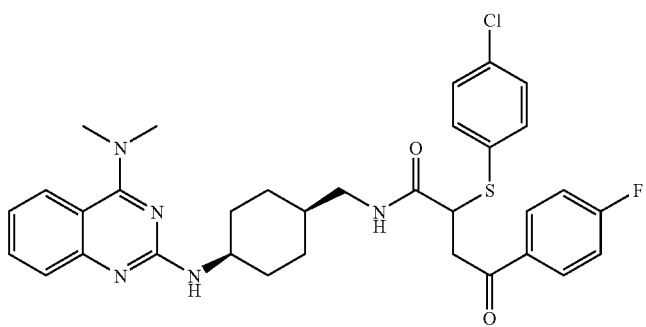 | 620 (M + H) |
| 1075 | 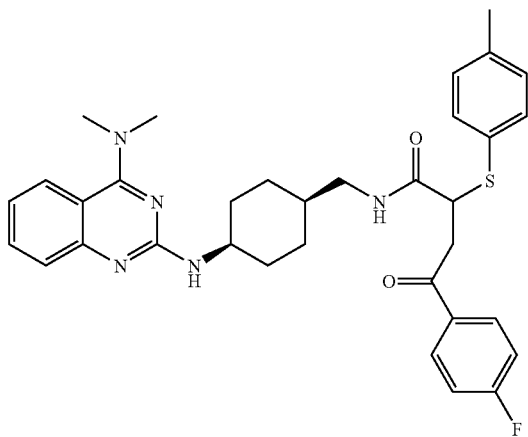 | 600 (M + H) |
| 1076 | 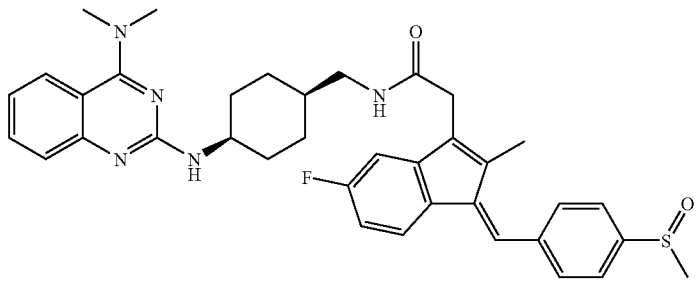 | 638 (M + H) |

-continued

| Example No. | Structure | APCI-MS |
|---|---|---|
| 1077 | 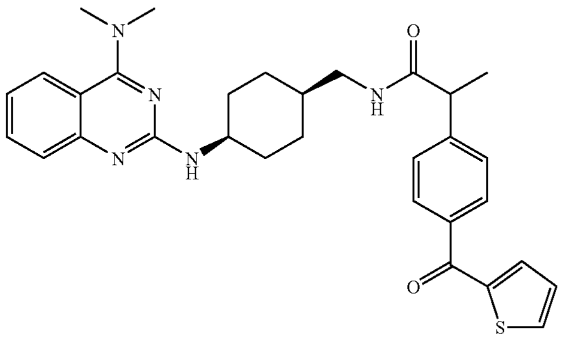 | 542 (M + H) |
| 1078 | 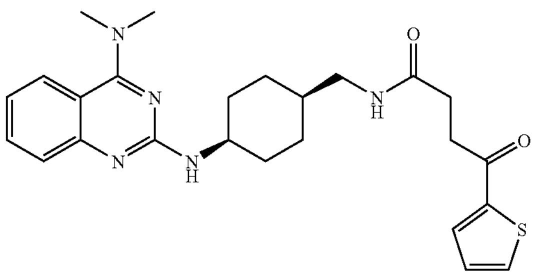 | 466 (M + H) |
| 1079 | 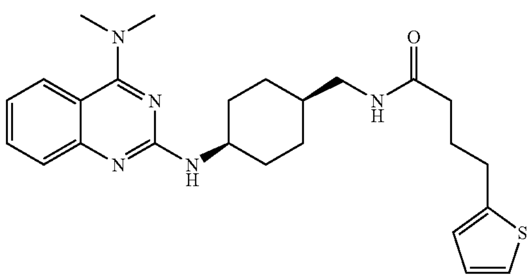 | 452 (M + H) |
| 1080 | 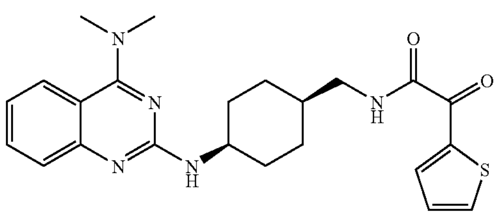 | 438 (M + H) |
| 1081 | 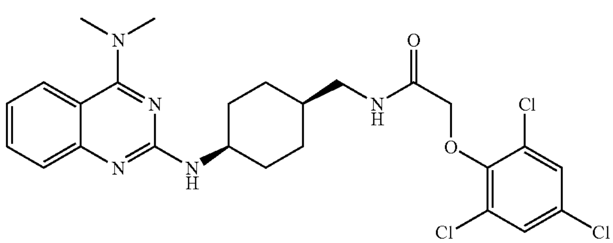 | 536 (M + H) |
| 1082 | 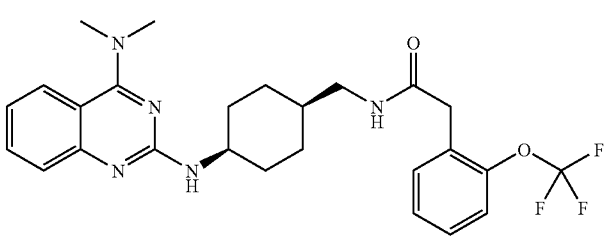 | 502 (M + H) |

-continued
| Example No. | Structure | APCI-MS |
|---|---|---|
| 1083 | 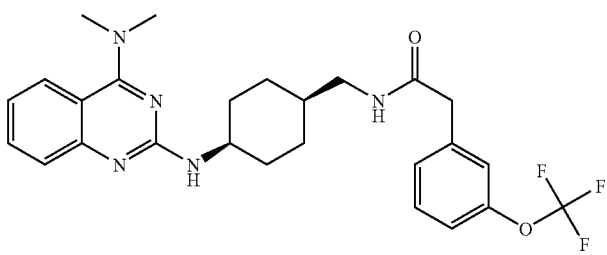 | 502 (M + H) |
| 1084 | 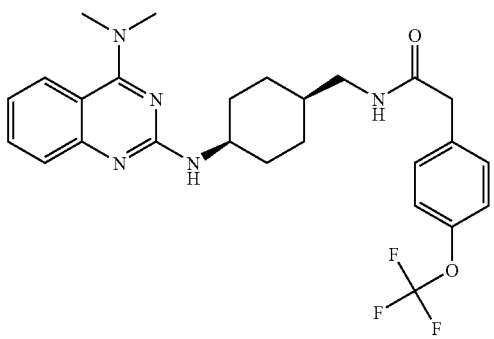 | 502 (M + H) |
| 1085 | 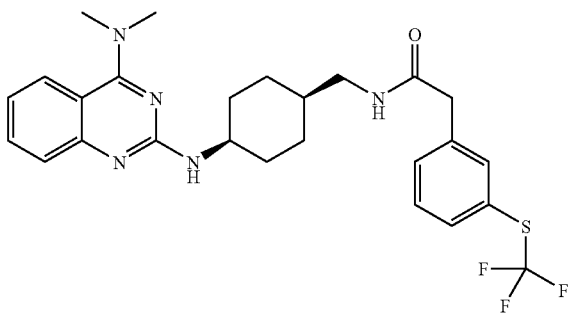 | 518 (M + H) |
| 1086 | 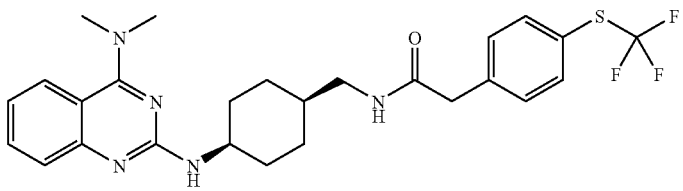 | 518 (M + H) |
| 1087 | 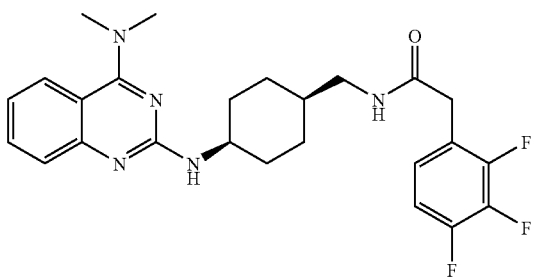 | 472 (M + H) |

-continued
| Example No. | Structure | APCI-MS |
|---|---|---|
| 1088 | 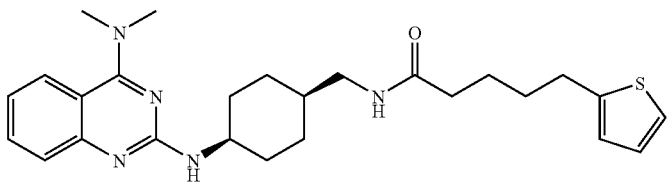 | 466 (M + H) |
| 1089 | 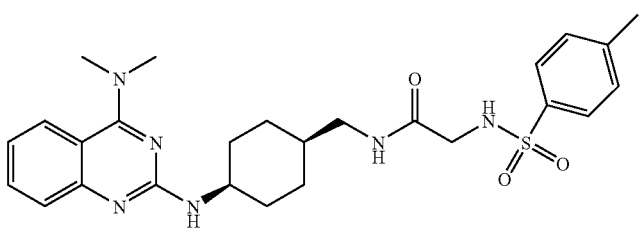 | 511 (M + H) |
| 1090 | 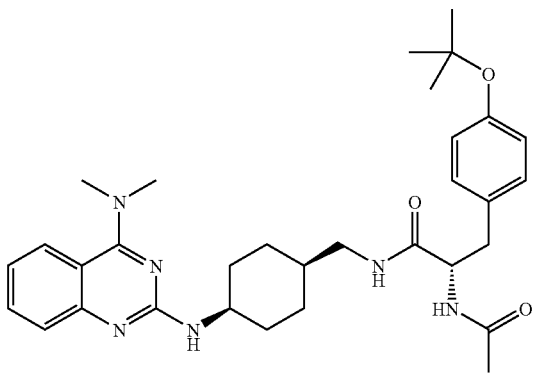 | 561 (M + H) |
| 1091 | 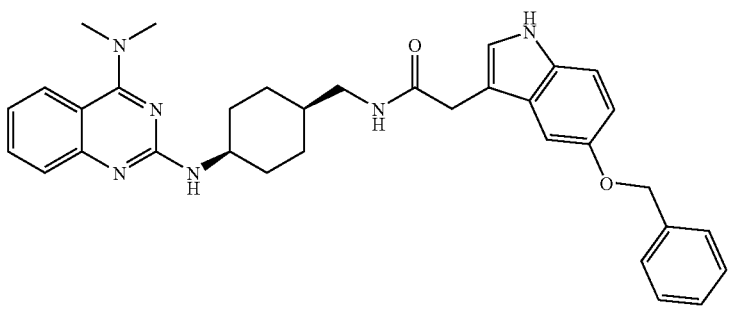 | 563 (M + H) |
| 1092 | 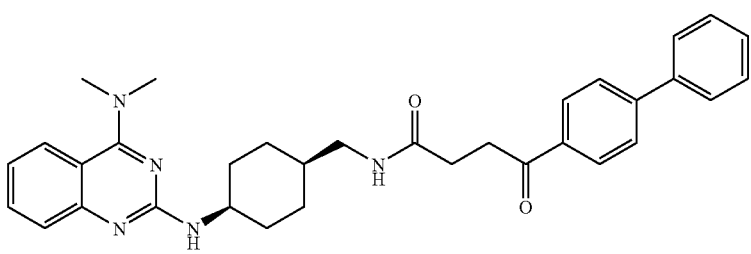 | 536 (M + H) |

-continued
| Example No. | Structure | APCI-MS |
|---|---|---|
| 1093 | 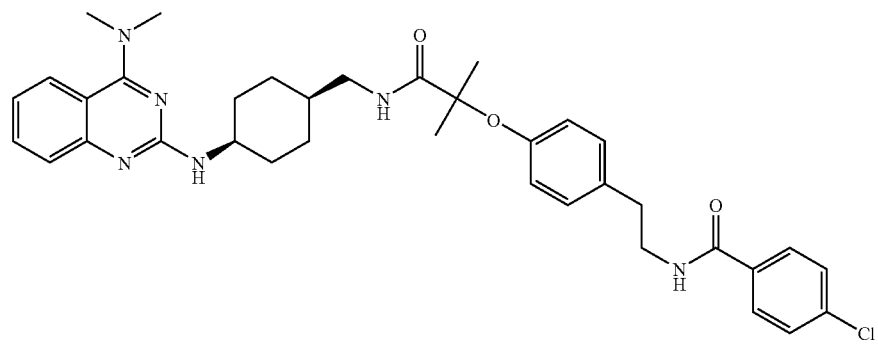 | 643 (M + H) |
| 1094 | 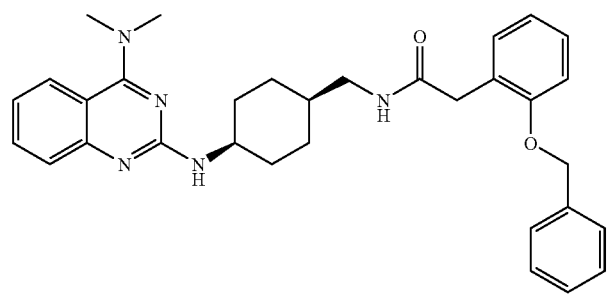 | 524 (M + H) |
| 1095 | 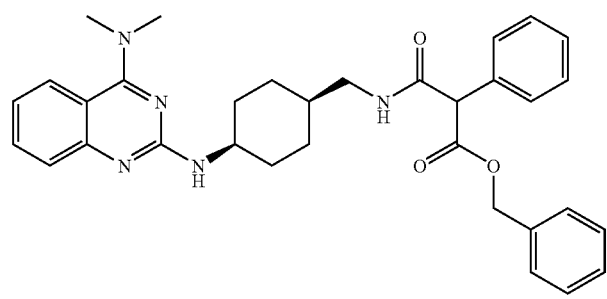 | 552 (M + H) |
| 1096 | 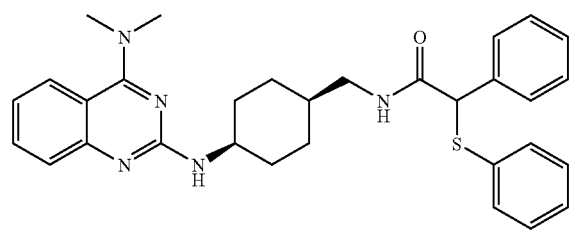 | 526 (M + H) |
| 1097 | 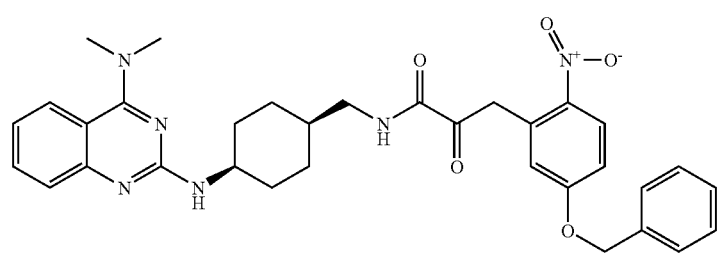 | 597 (M + H) |

-continued
| Example No. | Structure | APCI-MS |
|---|---|---|
| 1098 | 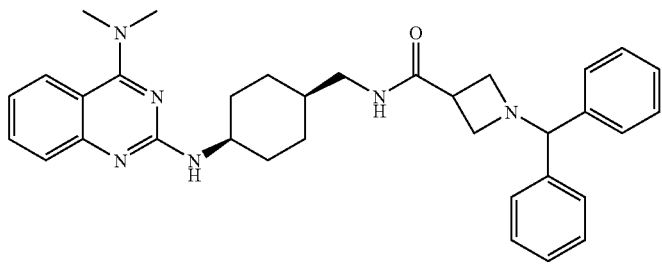 | 549 (M + H) |
| 1099 | 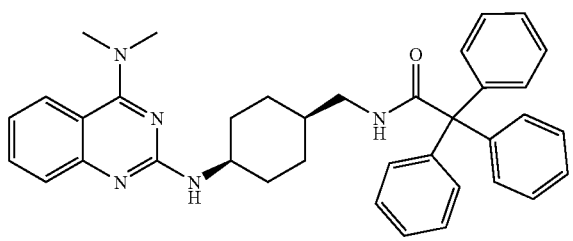 | 570 (M + H) |
| 1100 | 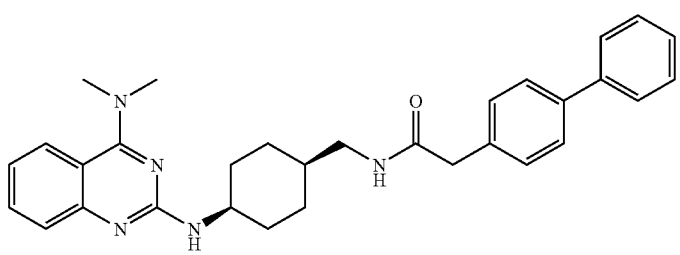 | 494 (M + H) |
| 1101 | 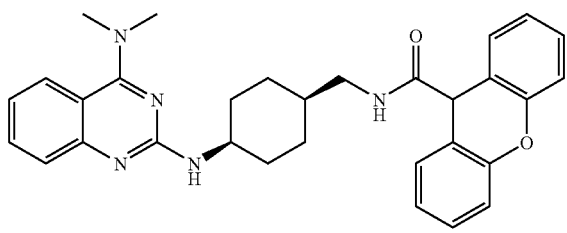 | 508 (M + H) |
| 1102 | 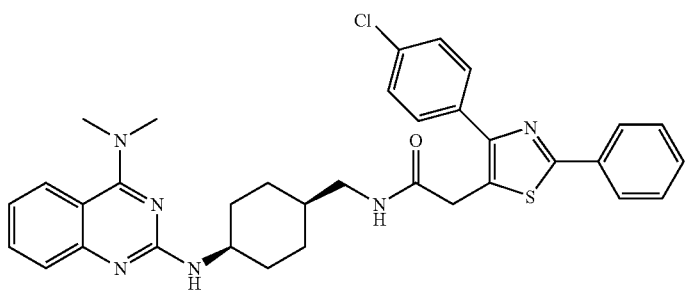 | 611 (M + H) |
| 1103 | 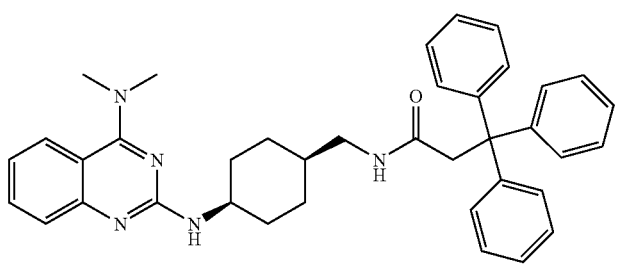 | 584 (M + H) |

-continued

| Example No. | Structure | APCI-MS |
|---|---|---|
| 1104 | 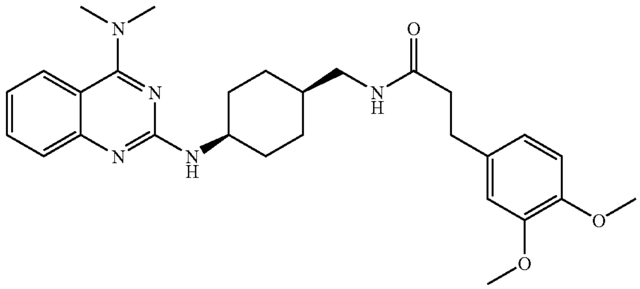 | 492 (M + H) |
| 1105 | 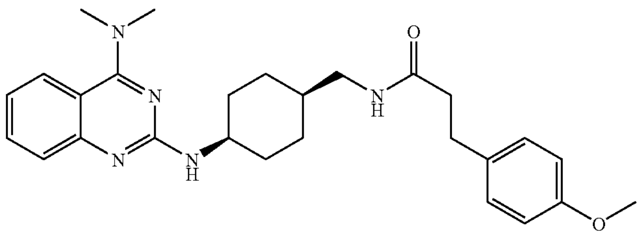 | 462 (M + H) |
| 1106 | 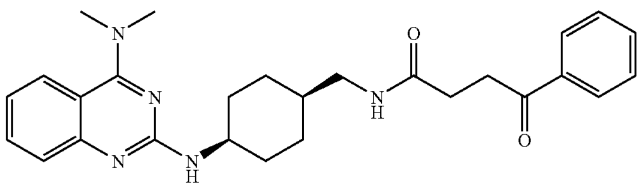 | 460 (M + H) |
| 1107 | 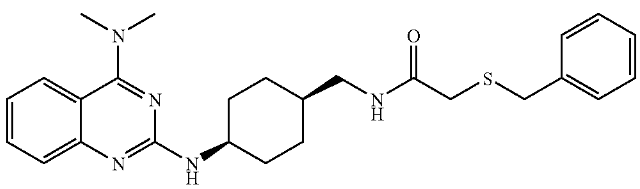 | 464 (M + H) |
| 1108 | 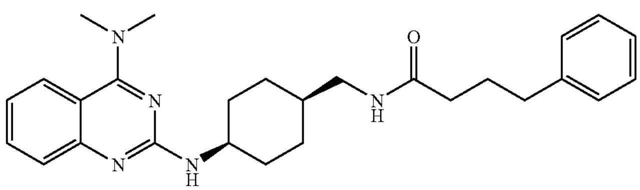 | 446 (M + H) |
| 1109 | 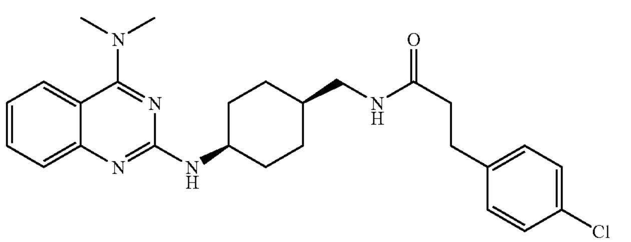 | 466 (M + H) |
| 1110 | 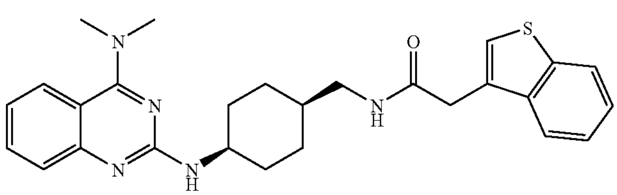 | 474 (M + H) |

-continued
| Example No. | Structure | APCI-MS |
|---|---|---|
| 1111 | 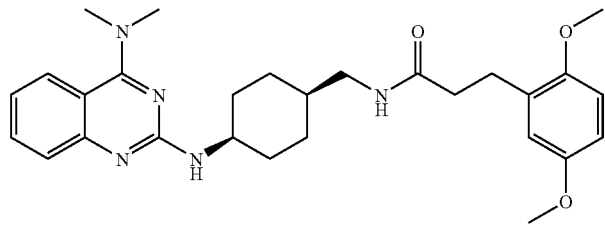 | 492 (M + H) |
| 1112 | 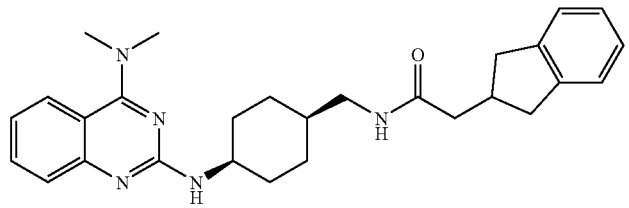 | 458 (M + H) |
| 1113 | 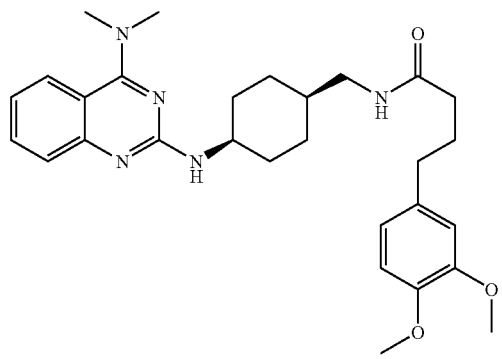 | 506 (M + H) |
| 1114 | 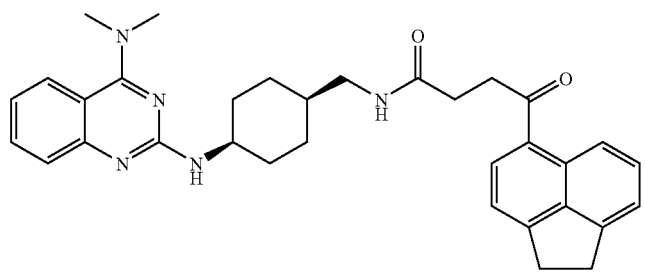 | 536 (M + H) |
| 1115 | 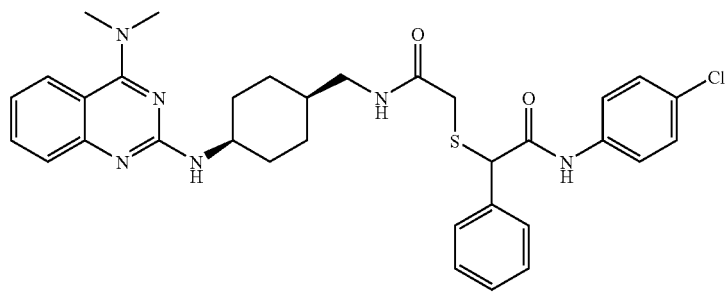 | 617 (M + H) |
| 1116 | 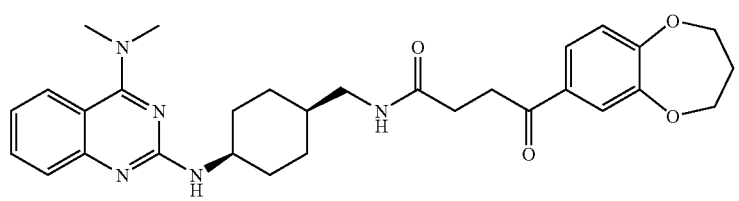 | 532 (M + H) |

-continued
| Example No. | Structure | APCI-MS |
|---|---|---|
| 1117 | 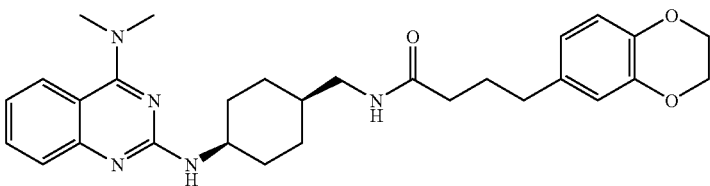 | 504 (M + H) |
| 1118 | 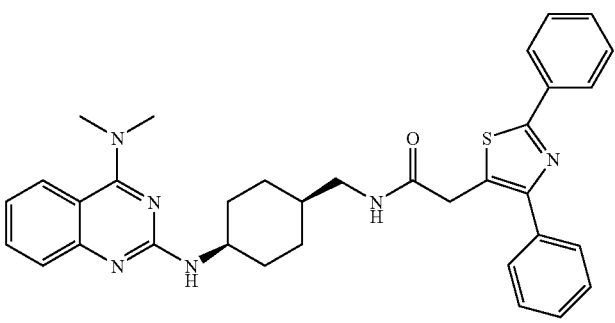 | 577 (M + H) |
| 1119 | 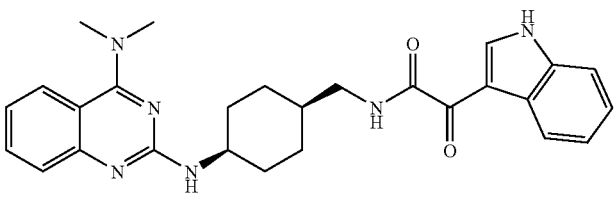 | 471 (M + H) |
| 1120 | 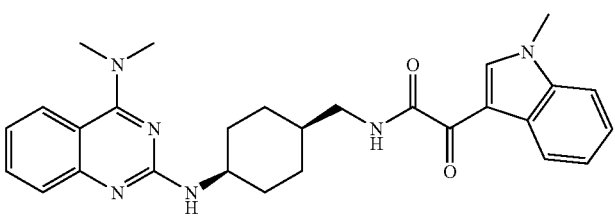 | 485 (M + H) |
| 1121 | 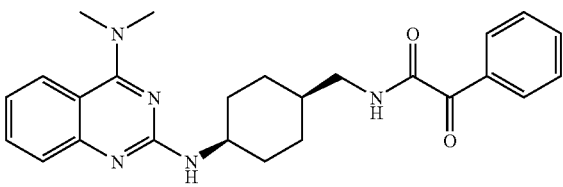 | 432 (M + H) |
| 1122 | 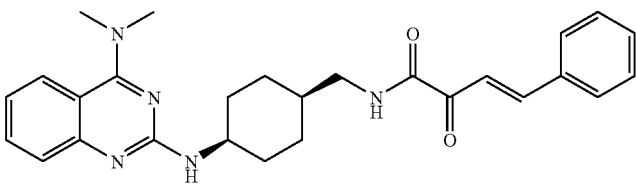 | 458 (M + H) |

-continued

| Example No. | Structure | APCI-MS |
|---|---|---|
| 1123 | 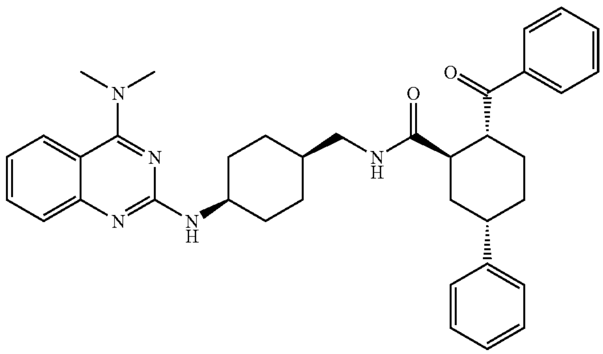 | 590 (M + H) |
| 1124 | 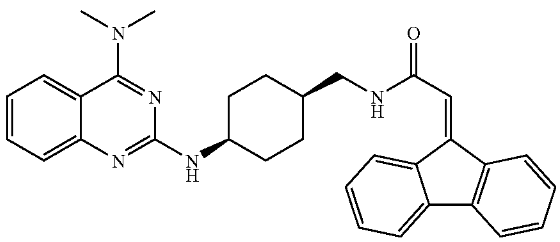 | 504 (M + H) |
| 1125 | 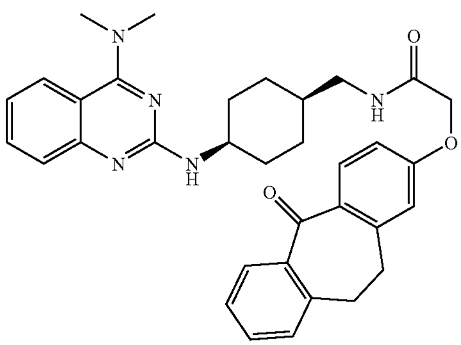 | 564 (M + H) |
| 1126 | 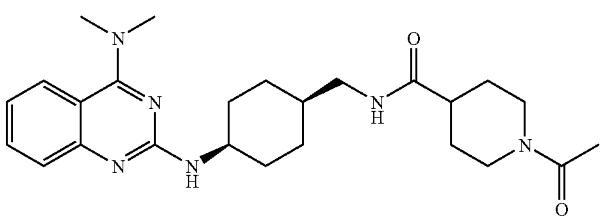 | 453 (M + H) |
| 1127 | 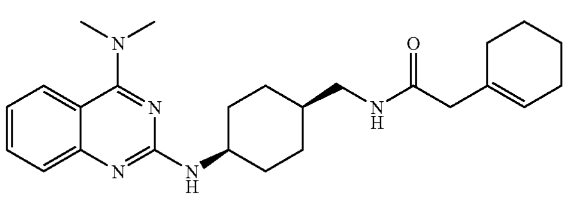 | 422 (M + H) |
| 1128 | 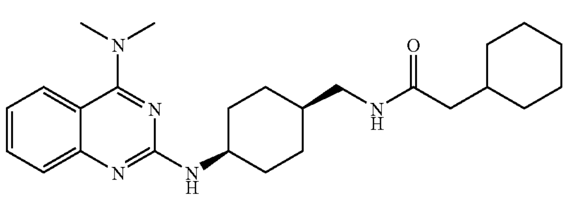 | 424 (M + H) |

-continued
| Example No. | Structure | APCI-MS |
|---|---|---|
| 1129 | 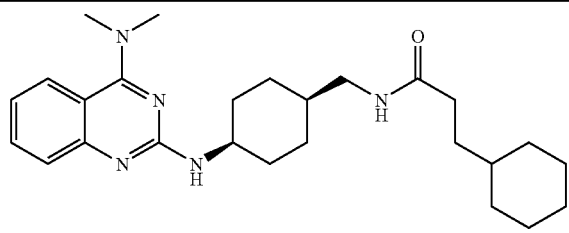 | 438 (M + H) |
| 1130 | 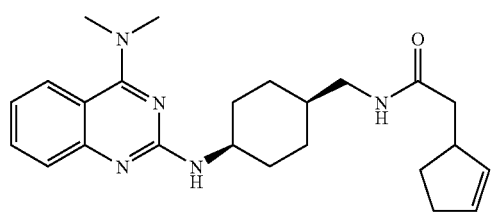 | 408 (M + H) |
| 1131 | 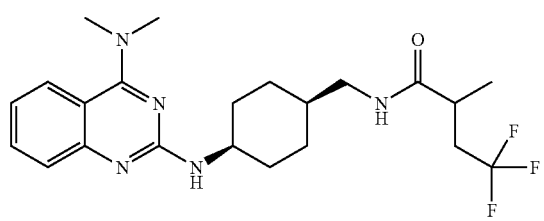 | 438 (M + H) |
| 1132 | 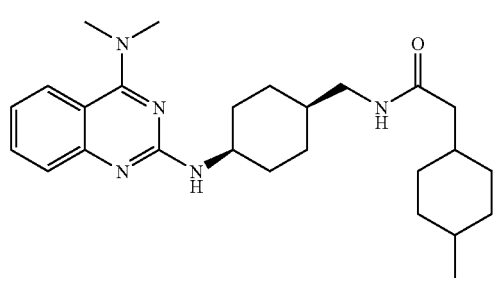 | 438 (M + H) |
| 1133 | 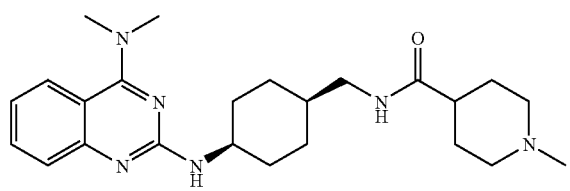 | 425 (M + H) |
| 1134 | 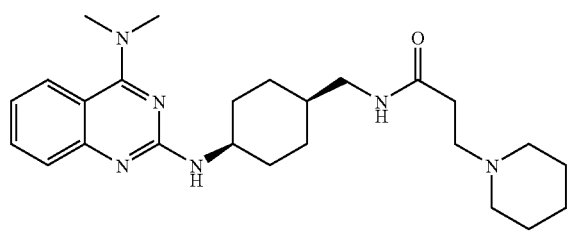 | 439 (M + H) |
| 1135 | 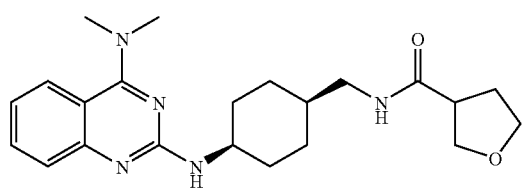 | 398 (M + H) |

| Example No. | Structure | APCI-MS |
|---|---|---|
| 1136 | 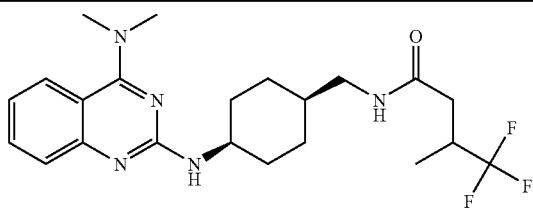 | 438 (M + H) |
| 1137 | 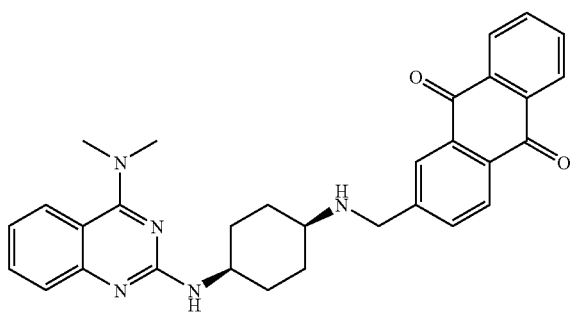 | 506 (M + H) |
| 1138 | 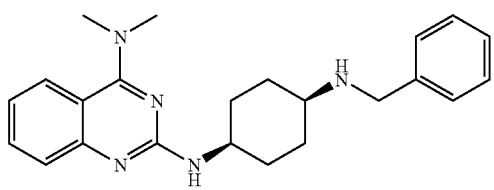 | 376 (M + H) |
| 1139 | 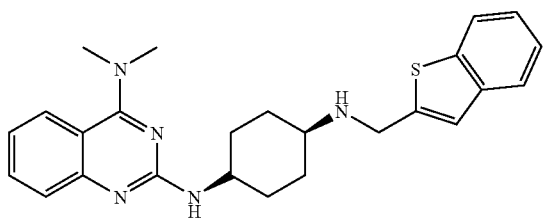 | 432 (M + H) |
| 1140 | 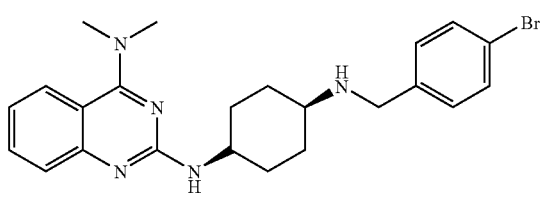 | 454 (M + H) |
| 1141 | 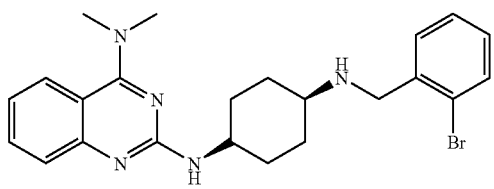 | 454 (M + H) |
| 1142 | 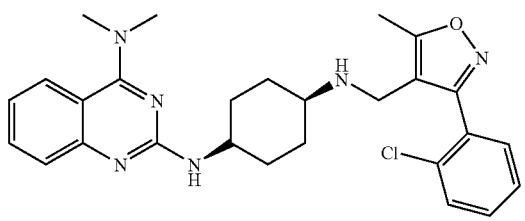 | 491 (M + H) |

-continued
| Example No. | Structure | APCI-MS |
|---|---|---|
| 1143 | 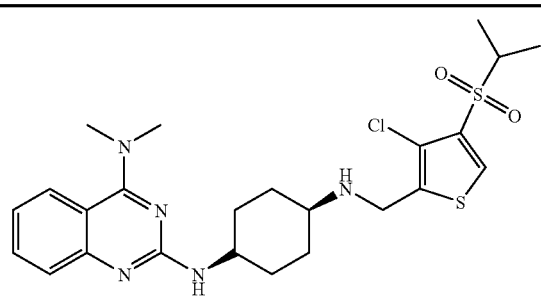 | 522 (M + H) |
| 1144 | 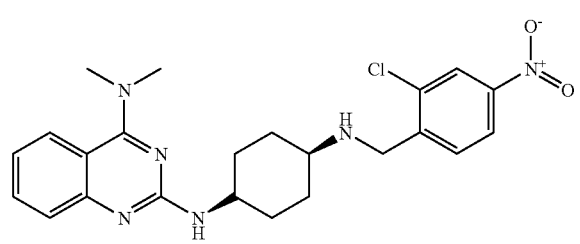 | 455 (M + H) |
| 1145 | 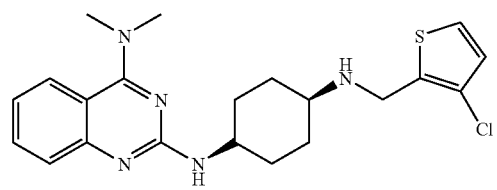 | 416 (M + H) |
| 1146 | 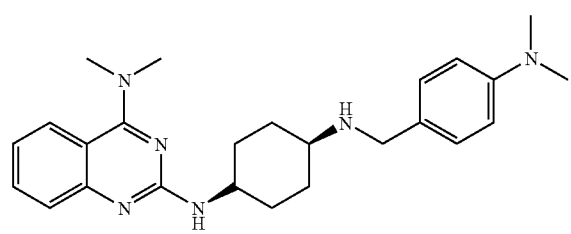 | 419 (M + H) |
| 1147 | 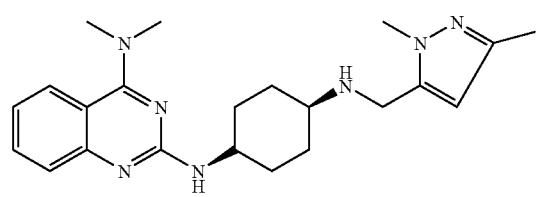 | 394 (M + H) |
| 1148 | 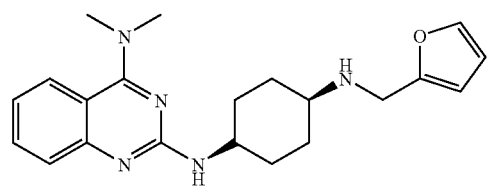 | 366 (M + H) |
| 1149 | 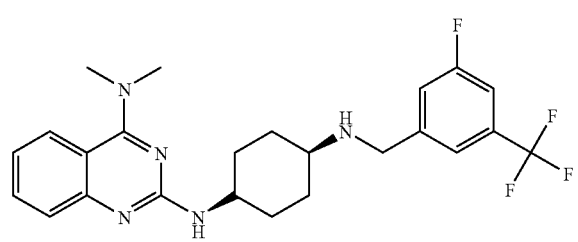 | 462 (M + H) |

-continued

| Example No. | Structure | APCI-MS |
|---|---|---|
| 1150 | 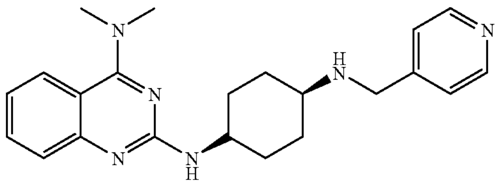 | 377 (M + H) |
| 1151 | 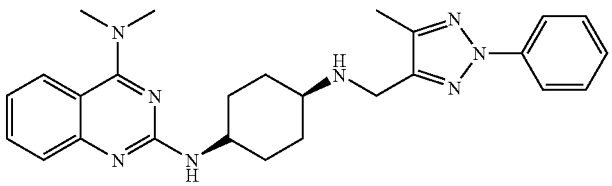 | 457 (M + H) |
| 1152 | 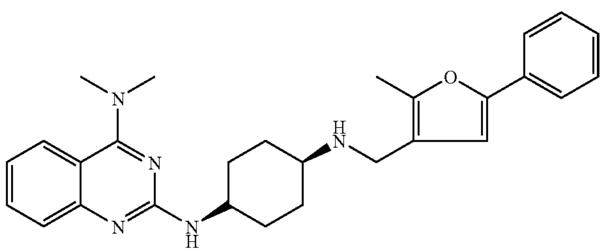 | 456 (M + H) |
| 1153 | 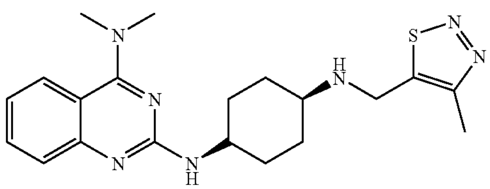 | 398 (M + H) |
| 1154 | 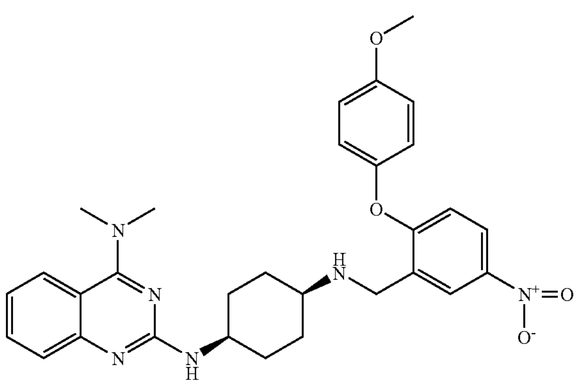 | 543 (M + H) |
| 1155 | 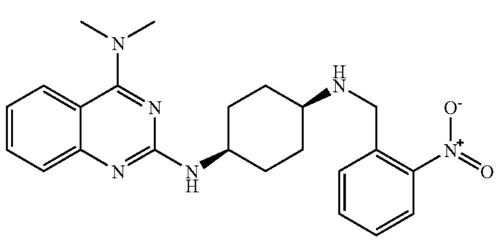 | 421 (M + H) |

-continued
| Example No. | Structure | APCI-MS |
|---|---|---|
| 1156 | 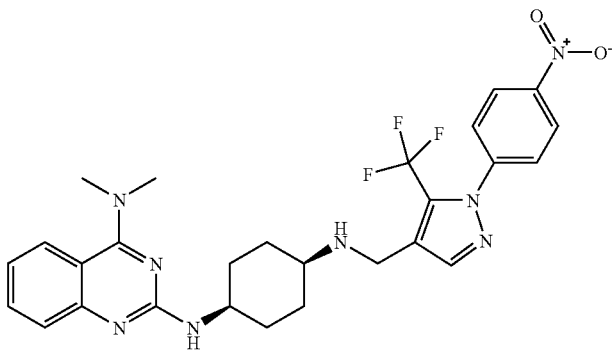 | 555 (M + H) |
| 1157 | 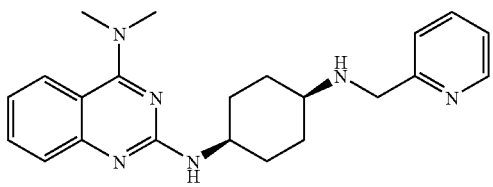 | 377 (M + H) |
| 1158 | 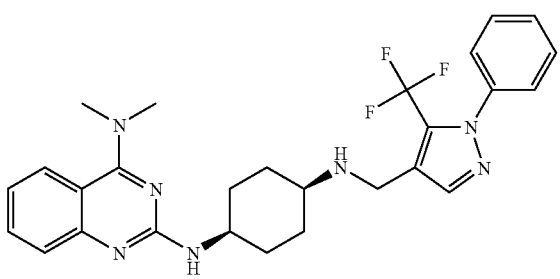 | 510 (M + H) |
| 1159 | 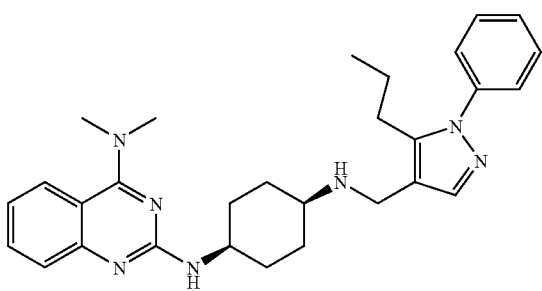 | 484 (M + H) |
| 1160 | 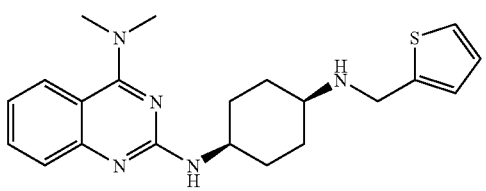 | 382 (M + H) |

-continued
| Example No. | Structure | APCI-MS |
|---|---|---|
| 1161 | 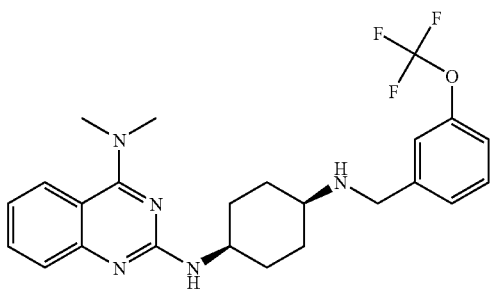 | 460 (M + H) |
| 1162 | 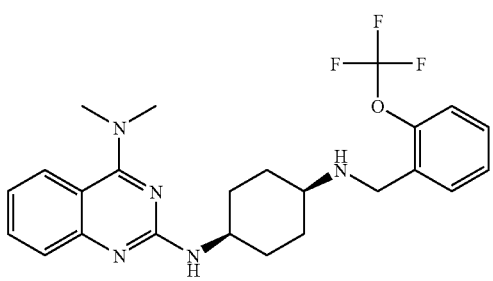 | 460 (M + H) |
| 1163 | 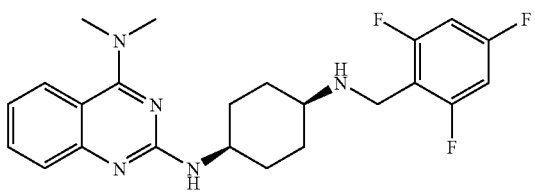 | 430 (M + H) |
| 1164 | 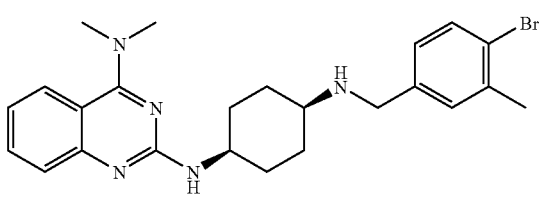 | 468 (M + H) |
| 1165 | 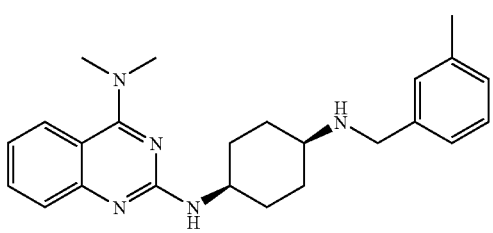 | 502 (M + H) |
| 1166 | 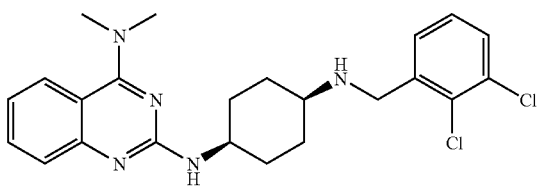 | 444 (M + H) |

-continued

| Example No. | Structure | APCI-MS |
|---|---|---|
| 1167 | 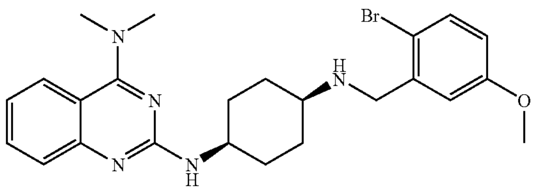 | 484 (M + H) |
| 1168 | 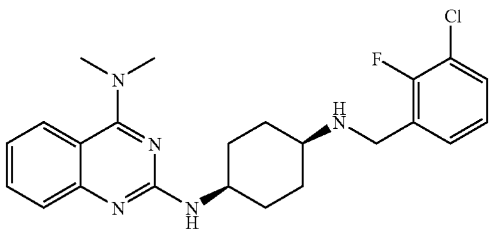 | 428 (M + H) |
| 1169 | 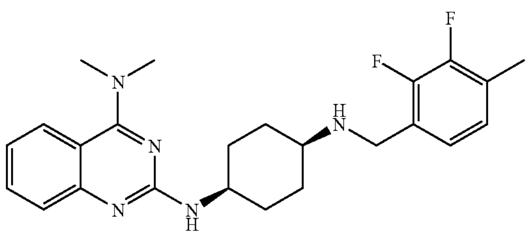 | 426 (M + H) |
| 1170 | 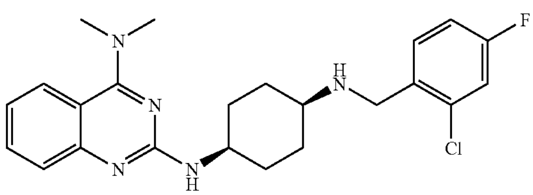 | 428 (M + H) |
| 1171 | 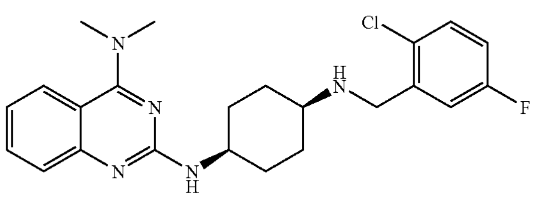 | 428 (M + H) |
| 1172 | 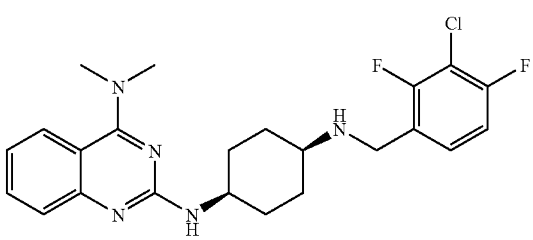 | 446 (M + H) |
| 1173 | 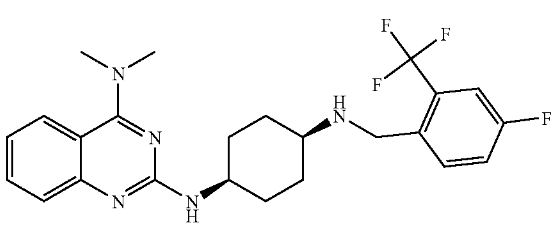 | 462 (M + H) |

-continued
| Example No. | Structure | APCI-MS |
|---|---|---|
| 1174 | 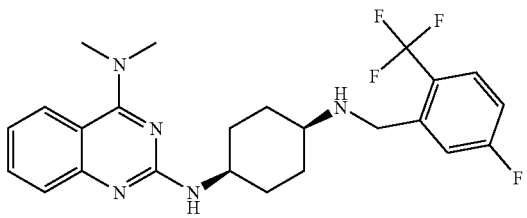 | 462 (M + H) |
| 1175 | 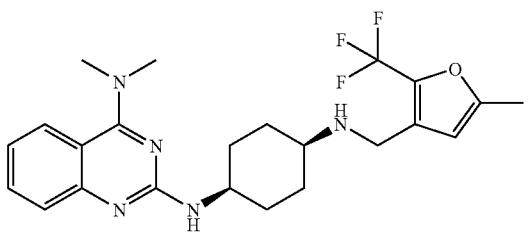 | 448 (M + H) |
| 1176 | 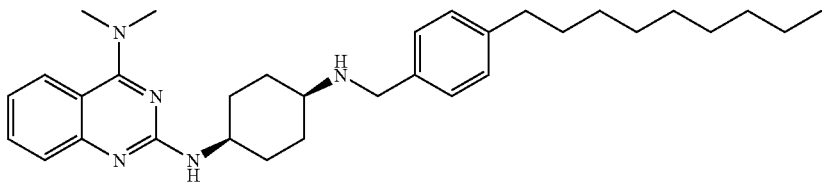 | 502 (M + H) |
| 1177 | 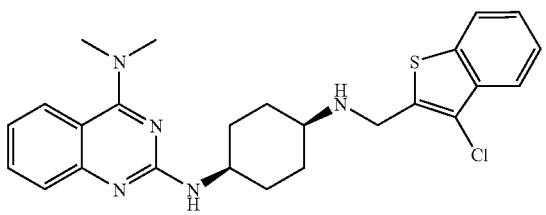 | 466 (M + H) |
| 1178 | 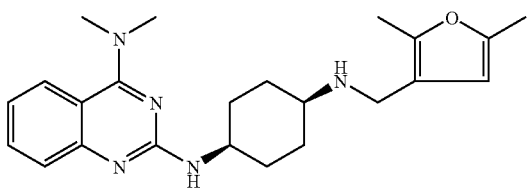 | 376 (M + H) |
| 1179 | 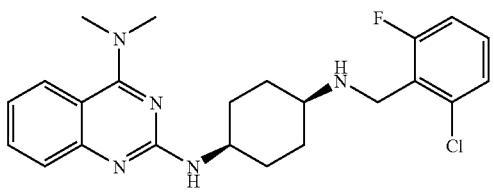 | 428 (M + H) |
| 1180 | 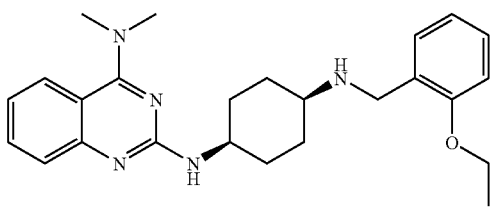 | 420 (M + H) |

-continued
| Example No. | Structure | APCI-MS |
|---|---|---|
| 1181 | 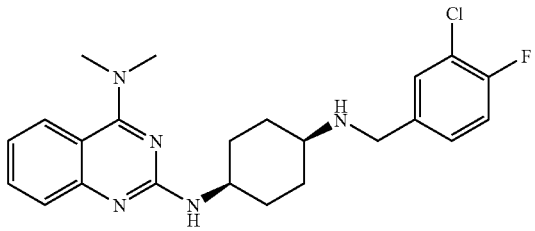 | 428 (M + H) |
| 1182 | 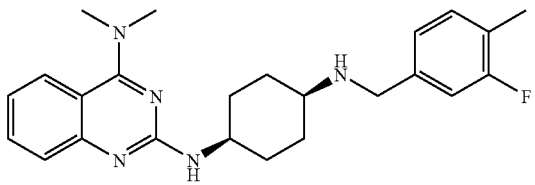 | 408 (M + H) |
| 1183 | 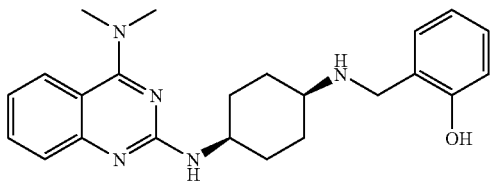 | 392 (M + H) |
| 1184 | 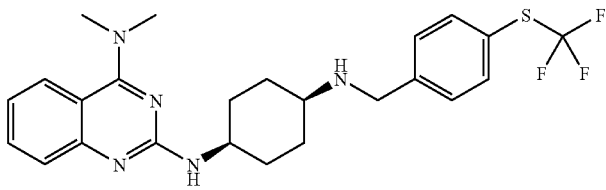 | 476 (M + H) |
| 1185 | 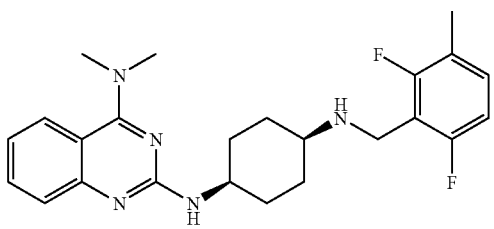 | 426 (M + H) |
| 1186 | 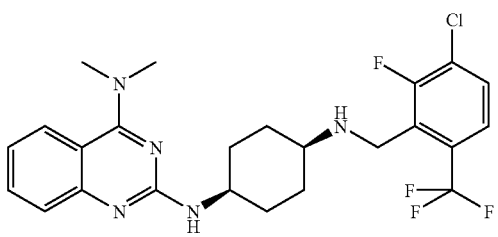 | 496 (M + H) |
| 1187 | 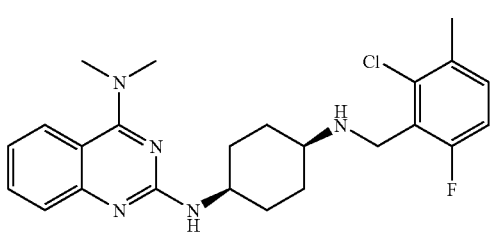 | 442 (M + H) |

|Example No.|Structure|APCI-MS|
|---|---|---|
|1188| 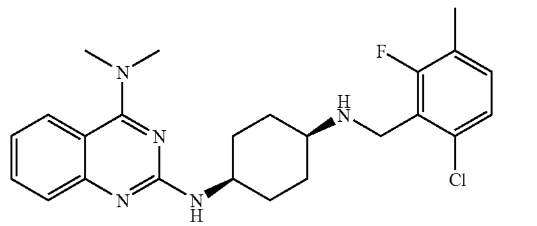 |442 (M + H)|
|1189| 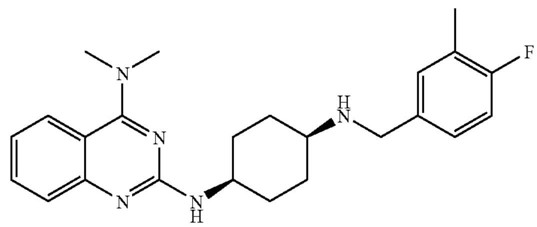 |408 (M + H)|
|1190| 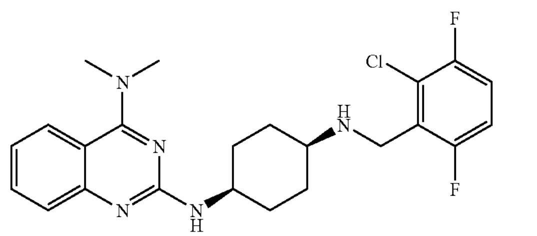 |446 (M + H)|
|1191| 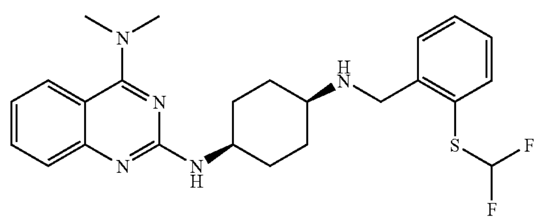 |458 (M + H)|
|1192| 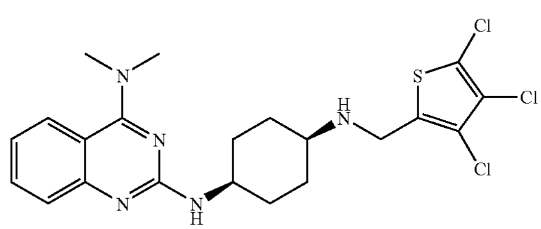 |484 (M + H)|
|1193| 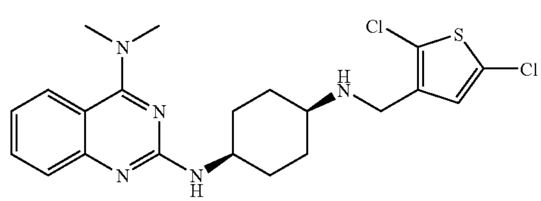 |450 (M + H)|
|1194| 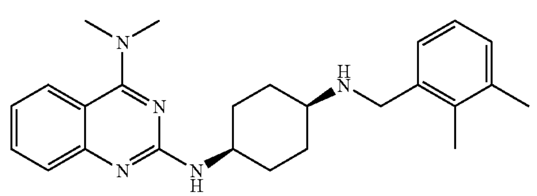 |404 (M + H)|

| Example No. | Structure | APCI-MS |
|---|---|---|
| 1195 | 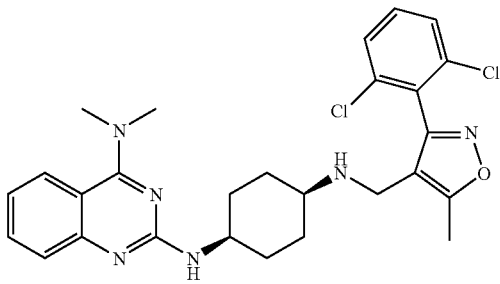 | 525 (M + H) |
| 1196 | 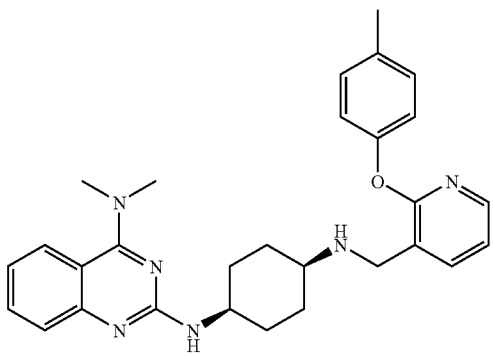 | 483 (M + H) |
| 1197 | 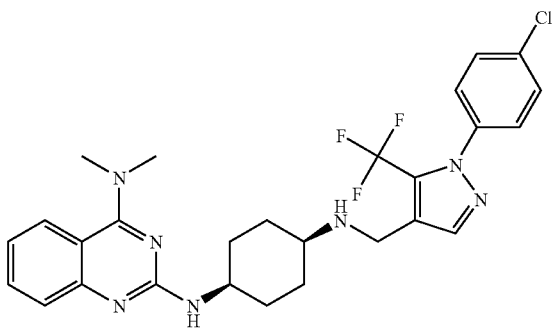 | 544 (M + H) |
| 1198 | 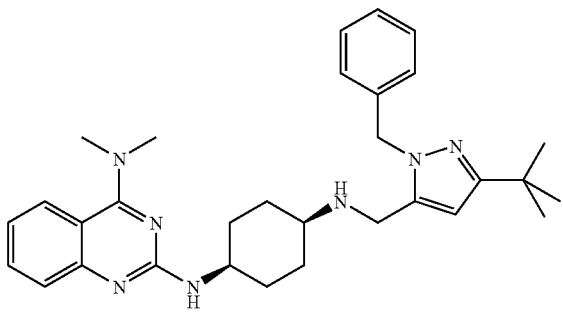 | 512 (M + H) |
| 1199 | 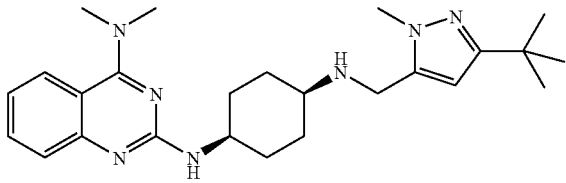 | 436 (M + H) |

-continued
| Example No. | Structure | APCI-MS |
|---|---|---|
| 1200 | 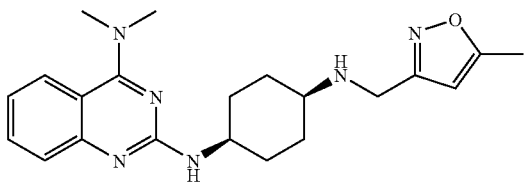 | 381 (M + H) |
| 1201 | 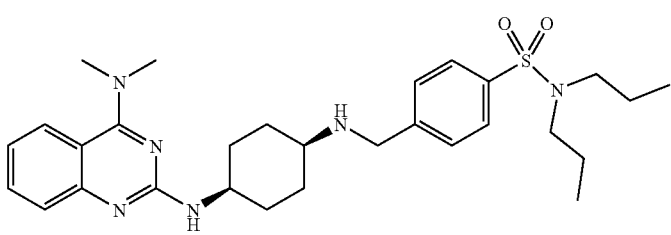 | 539 (M + H) |
| 1202 | 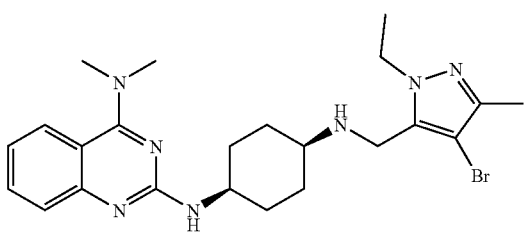 | 486 (M + H) |
| 1203 | 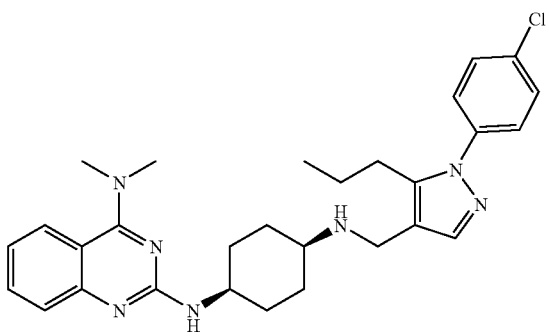 | 518 (M + H) |
| 1204 | 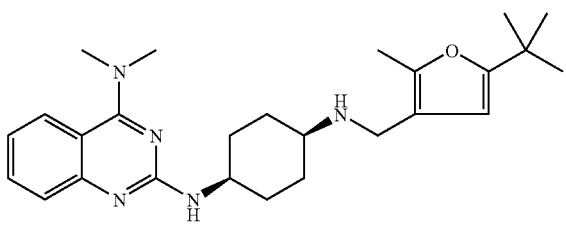 | 436 (M + H) |

-continued
| Example No. | Structure | APCI-MS |
|---|---|---|
| 1205 | 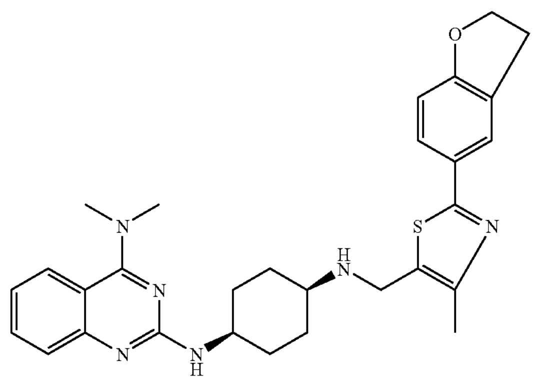 | 515 (M + H) |
| 1206 | 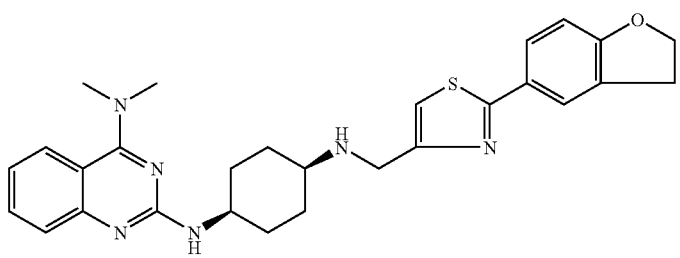 | 501 (M + H) |
| 1207 | 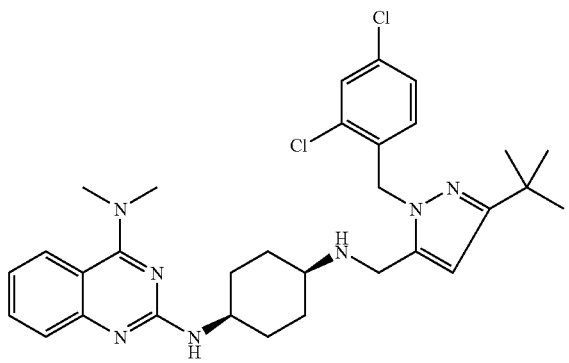 | 580 (M + H) |
| 1208 | 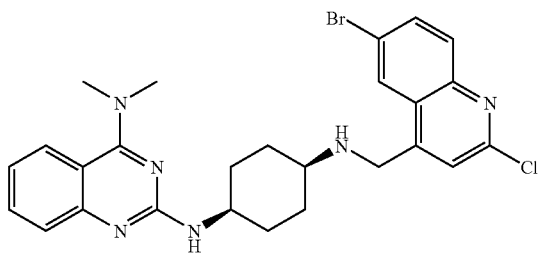 | 539 (M + H) |
| 1209 | 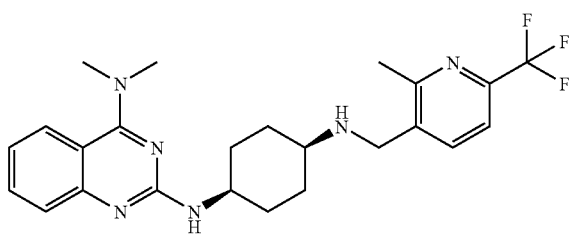 | 459 (M + H) |

-continued
| Example No. | Structure | APCI-MS |
|---|---|---|
| 1210 | 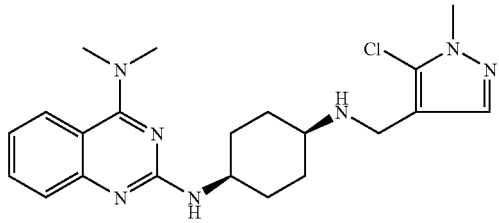 | 414 (M + H) |
| 1211 | 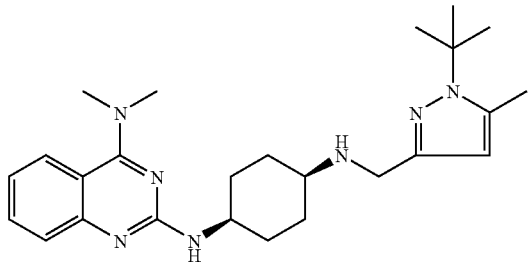 | 436 (M + H) |
| 1212 | 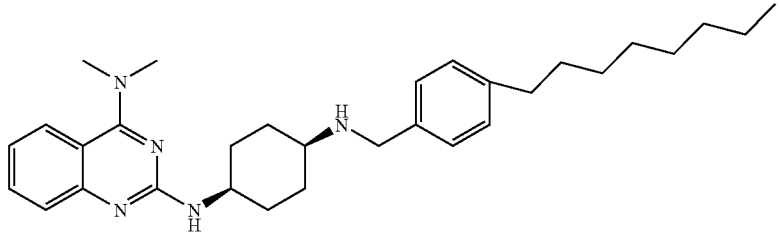 | 488 (M + H) |
| 1213 | 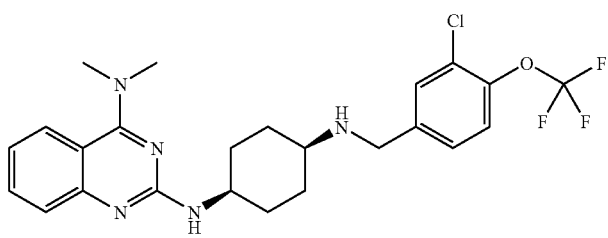 | 494 (M + H) |
| 1214 | 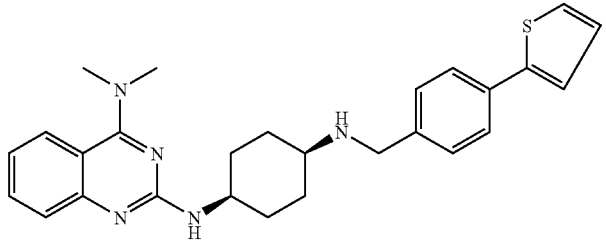 | 458 (M + H) |
| 1215 | 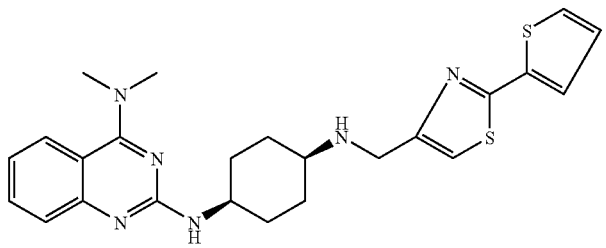 | 465 (M + H) |

-continued
| Example No. | Structure | APCI-MS |
|---|---|---|
| 1216 | 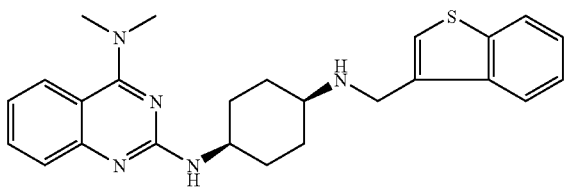 | 432 (M + H) |
| 1217 | 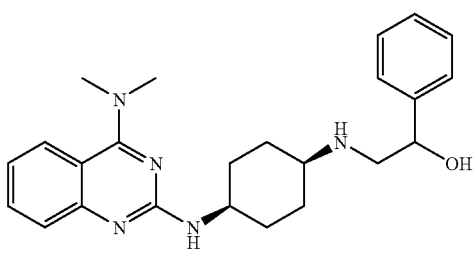 | 406 (M + H) |
| 1218 | 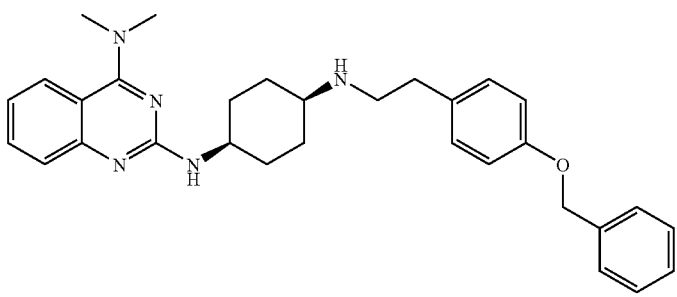 | 496 (M + H) |
| 1219 | 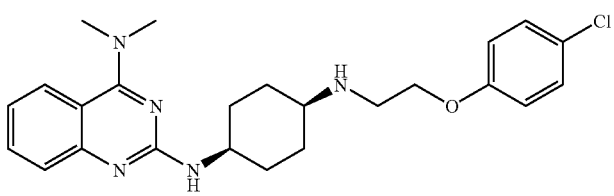 | 440 (M + H) |
| 1220 | 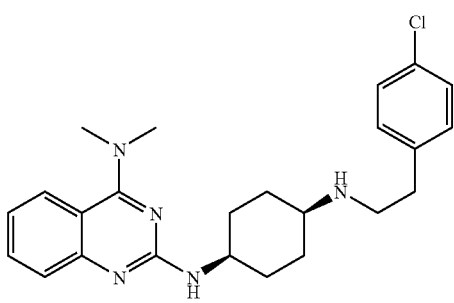 | 424 (M + H) |
| 1221 | 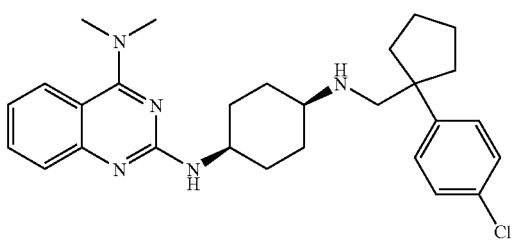 | 478 (M + H) |

-continued
| Example No. | Structure | APCI-MS |
|---|---|---|
| 1222 | 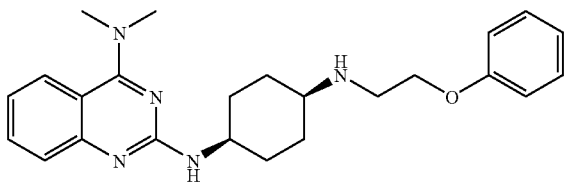 | 406 (M + H) |
| 1223 | 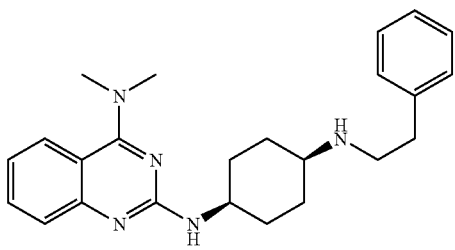 | 390 (M + H) |
| 1224 | 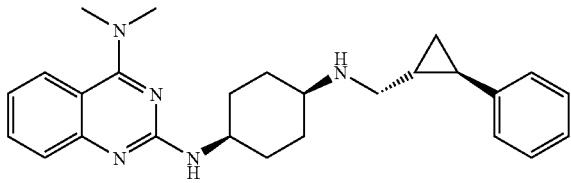 | 416 (M + H) |
| 1225 | 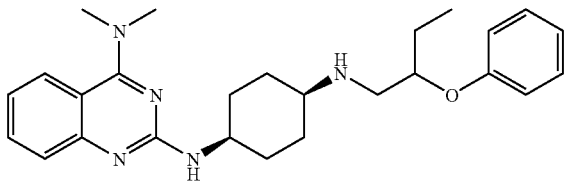 | 434 (M + H) |
| 1226 | 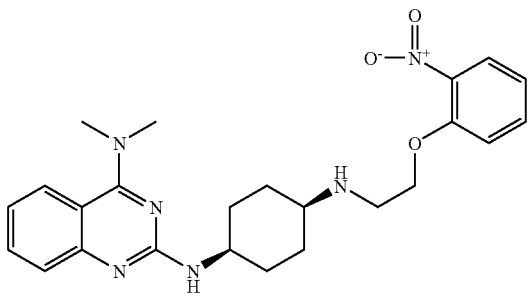 | 451 (M + H) |
| 1227 | 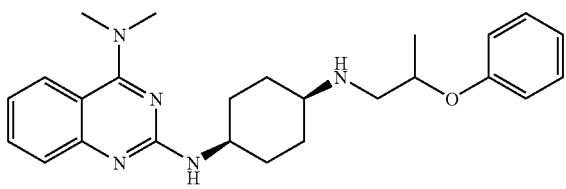 | 420 (M + H) |
| 1228 | 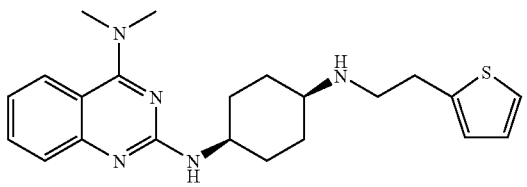 | 396 (M + H) |

-continued
| Example No. | Structure | APCI-MS |
|---|---|---|
| 1229 | 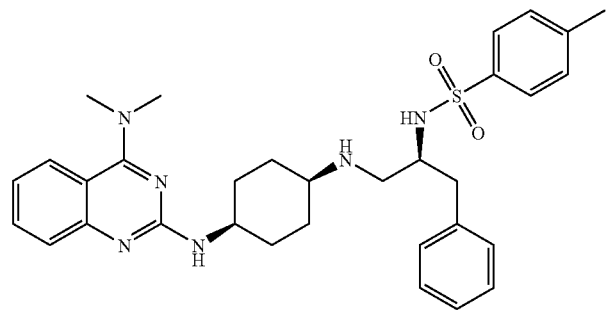 | 573 (M + H) |
| 1230 | 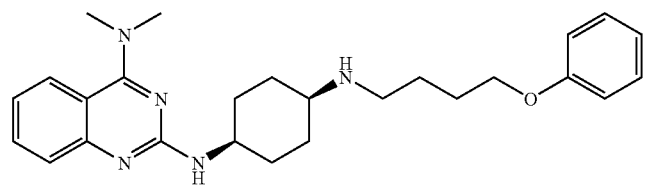 | 434 (M + H) |
| 1231 | 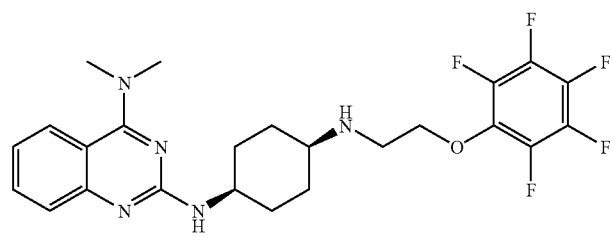 | 496 (M + H) |
| 1232 | 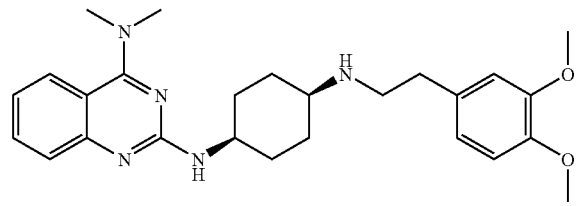 | 450 (M + H) |
| 1233 | 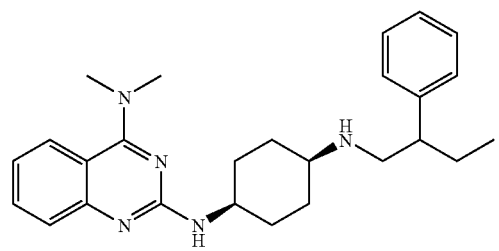 | 418 (M + H) |
| 1234 | 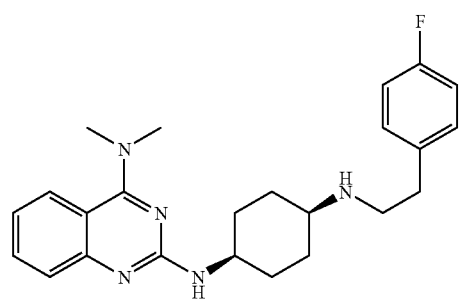 | 408 (M + H) |

-continued
| Example No. | Structure | APCI-MS |
|---|---|---|
| 1235 | 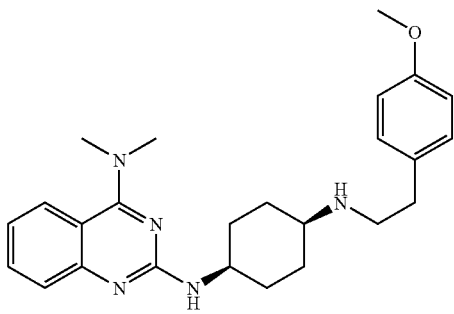 | 420 (M + H) |
| 1236 | 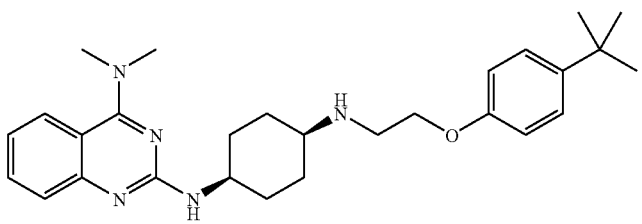 | 462 (M + H) |
| 1237 | 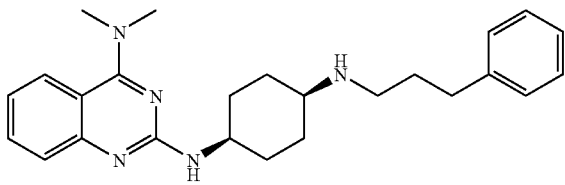 | 404 (M + H) |
| 1238 | 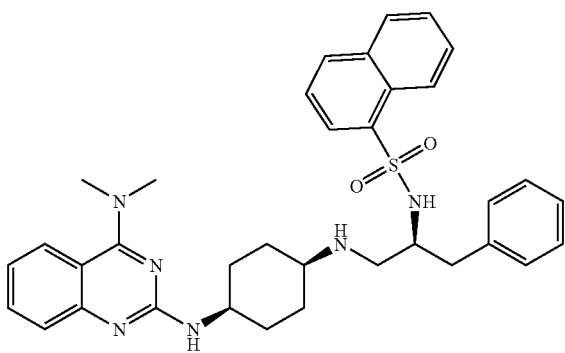 | 609 (M + H) |
| 1239 | 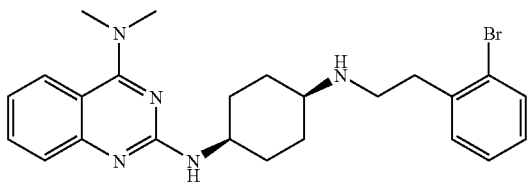 | 468 (M + H) |
| 1240 | 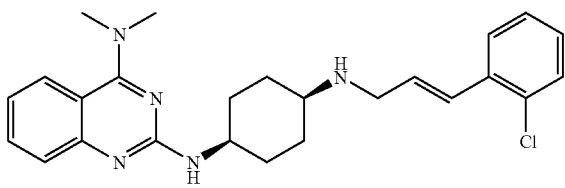 | 436 (M + H) |

-continued
| Example No. | Structure | APCI-MS |
|---|---|---|
| 1241 | 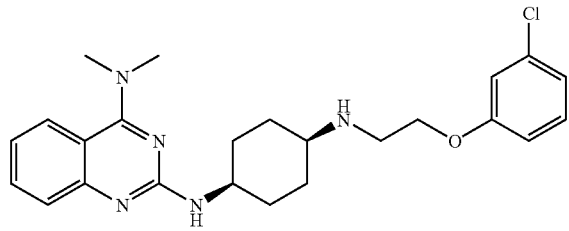 | 440 (M + H) |
| 1242 | 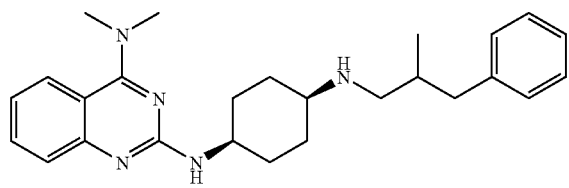 | 418 (M + H) |
| 1243 | 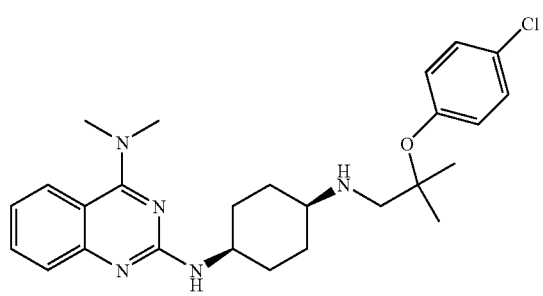 | 468 (M + H) |
| 1244 | 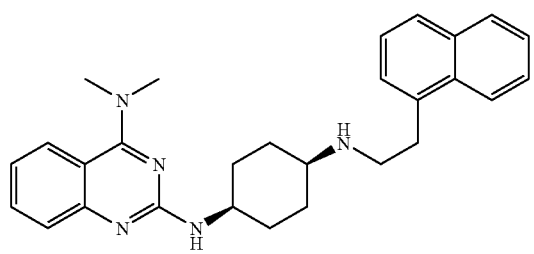 | 440 (M + H) |
| 1245 | 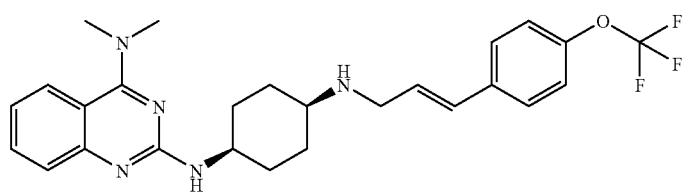 | 486 (M + H) |
| 1246 | 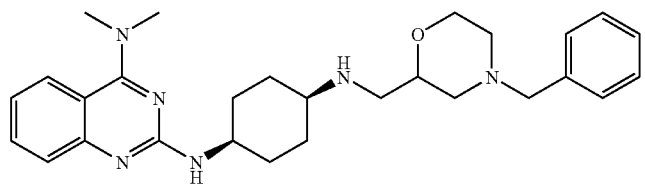 | 475 (M + H) |
| 1247 | 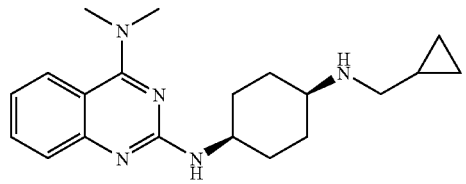 | 340 (M + H) |

-continued

| Example No. | Structure | APCI-MS |
|---|---|---|
| 1248 | 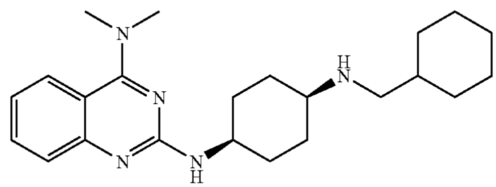 | 382 (M + H) |
| 1249 | 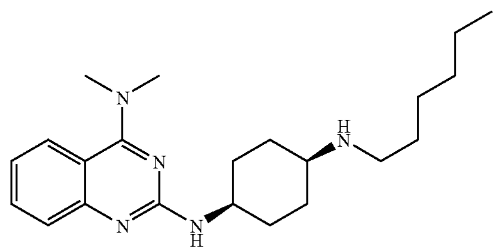 | 370 (M + H) |
| 1250 | 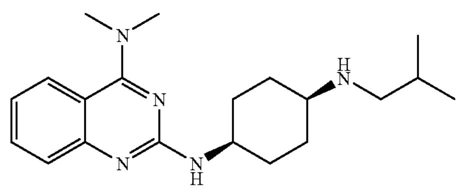 | 342 (M + H) |
| 1251 | 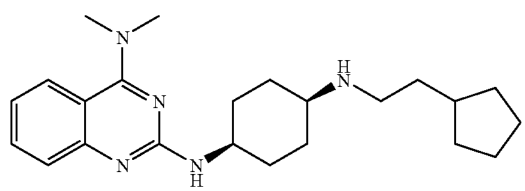 | 382 (M + H) |
| 1252 | 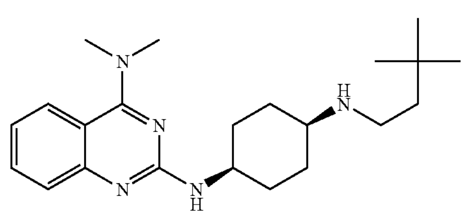 | 370 (M + H) |
| 1253 | 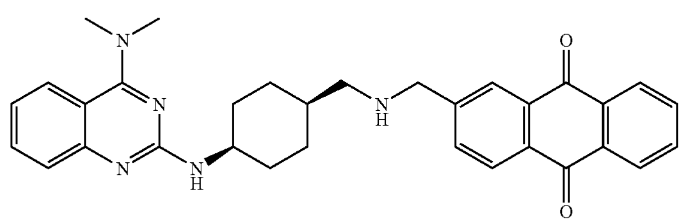 | 520 (M + H) |
| 1254 | 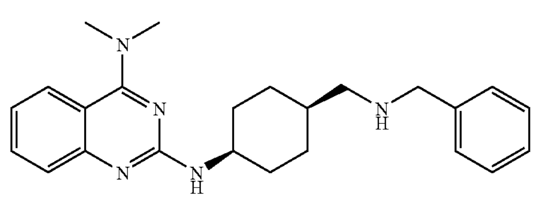 | 390 (M + H) |

-continued
| Example No. | Structure | APCI-MS |
|---|---|---|
| 1255 | 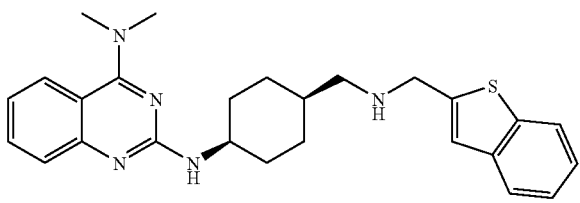 | 446 (M + H) |
| 1256 | 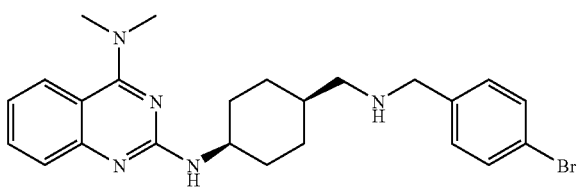 | 468 (M + H) |
| 1257 | 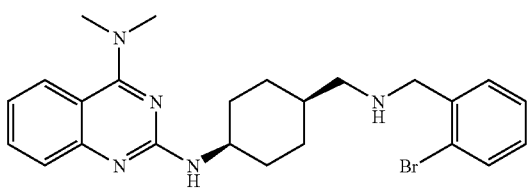 | 468 (M + H) |
| 1258 | 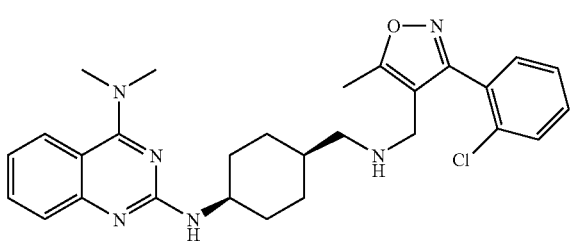 | 505 (M + H) |
| 1259 | 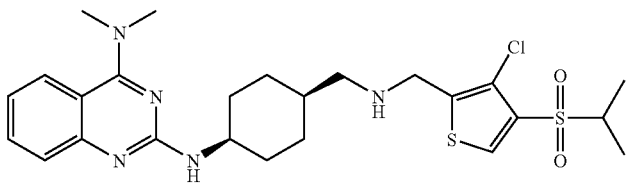 | 536 (M + H) |
| 1260 | 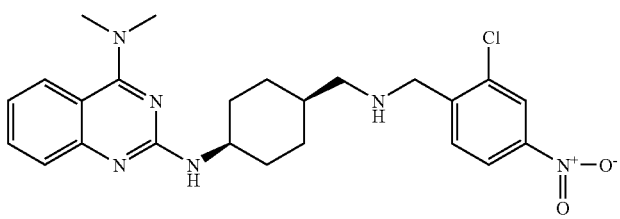 | 469 (M + H) |
| 1261 | 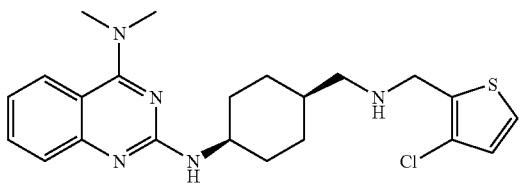 | 430 (M + H) |

-continued
| Example No. | Structure | APCI-MS |
|---|---|---|
| 1262 | 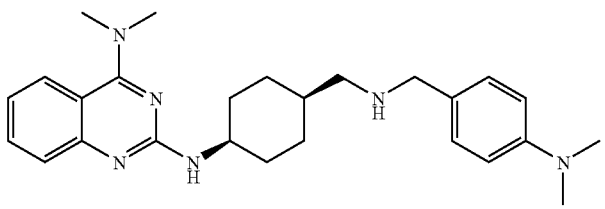 | 433 (M + H) |
| 1263 | 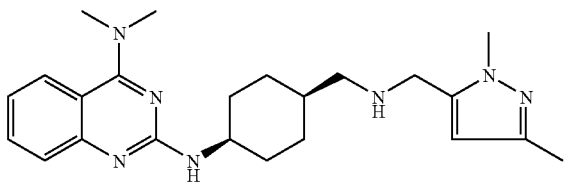 | 408 (M + H) |
| 1264 | 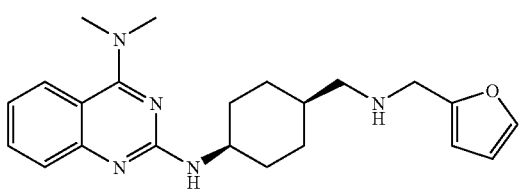 | 380 (M + H) |
| 1265 | 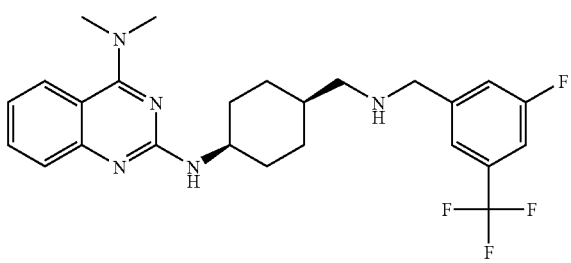 | 476 (M + H) |
| 1266 | 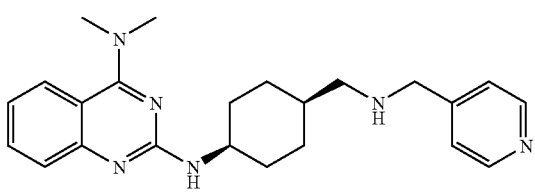 | 391 (M + H) |
| 1267 | 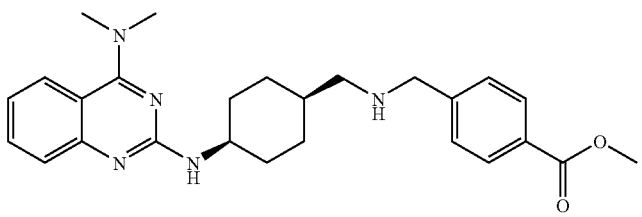 | 448 (M + H) |
| 1268 | 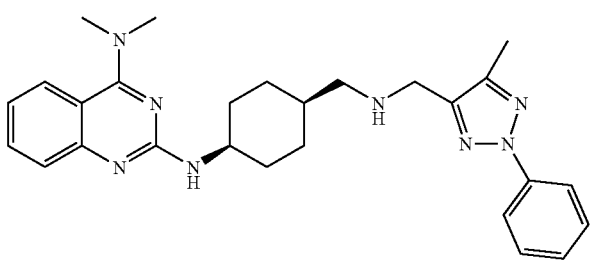 | 471 (M + H) |

-continued
| Example No. | Structure | APCI-MS |
|---|---|---|
| 1269 | 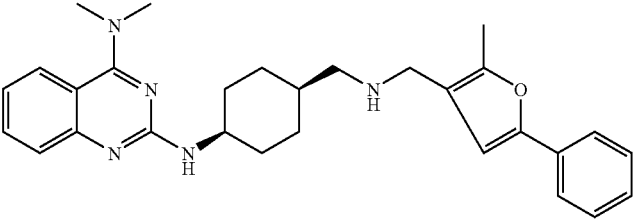 | 470 (M + H) |
| 1270 | 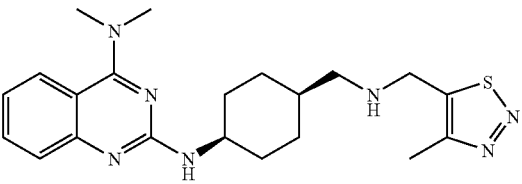 | 412 (M + H) |
| 1271 | 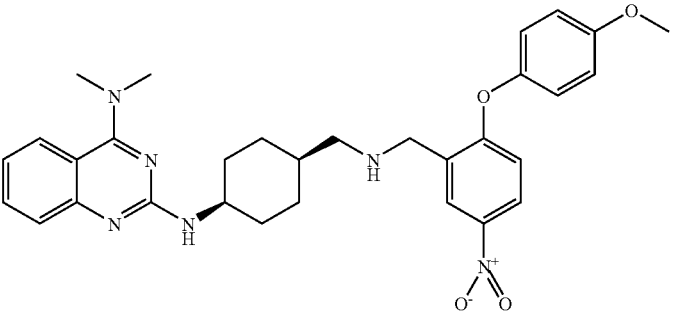 | 557 (M + H) |
| 1272 | 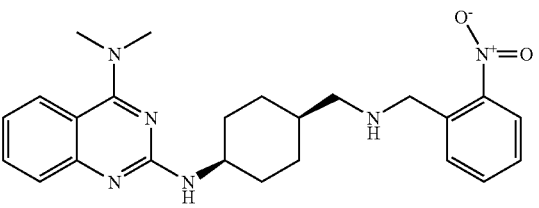 | 435 (M + H) |
| 1273 | 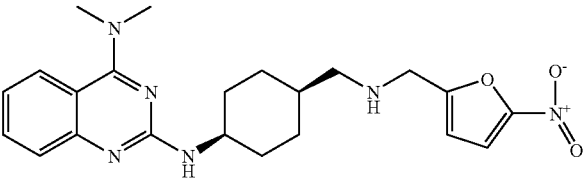 | 425 (M + H) |
| 1274 | 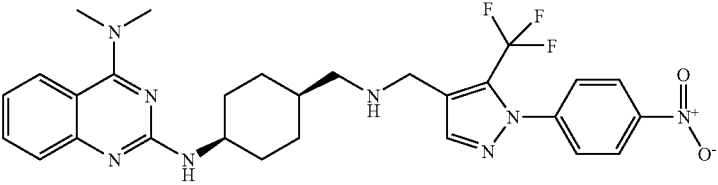 | 569 (M + H) |
| 1275 | 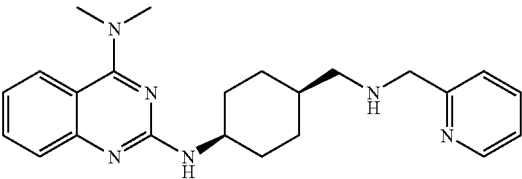 | 391 (M + H) |

-continued
| Example No. | Structure | APCI-MS |
|---|---|---|
| 1276 | 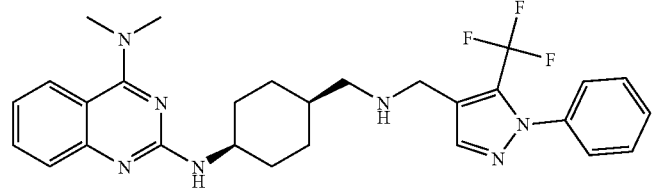 | 524 (M + H) |
| 1277 | 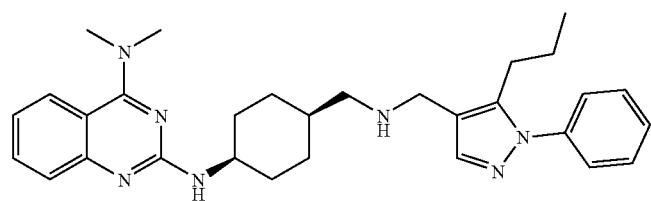 | 498 (M + H) |
| 1278 | 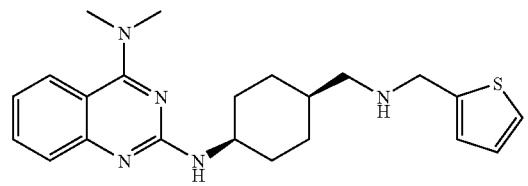 | 396 (M + H) |
| 1279 | 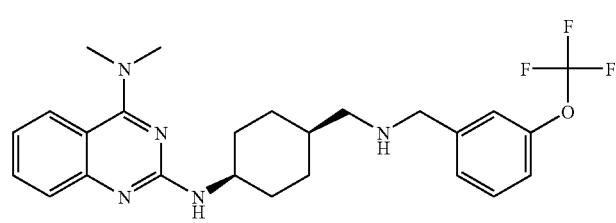 | 474 (M + H) |
| 1280 | 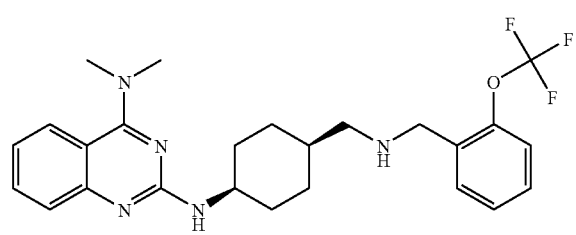 | 474 (M + H) |
| 1281 | 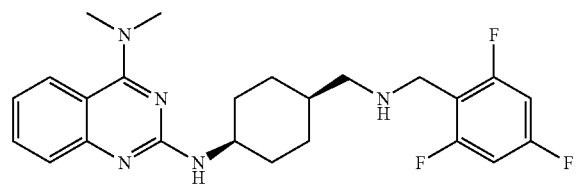 | 444 (M + H) |
| 1282 | 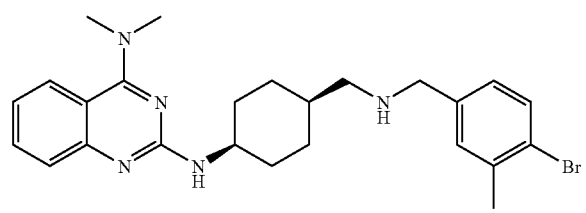 | 482 (M + H) |

-continued
| Example No. | Structure | APCI-MS |
|---|---|---|
| 1283 | 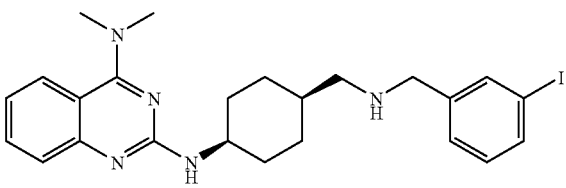 | 516 (M + H) |
| 1284 | 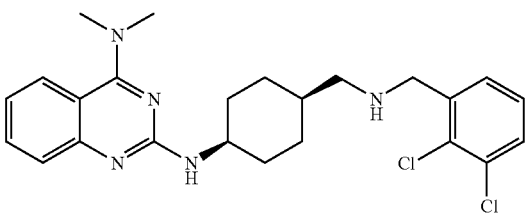 | 458 (M + H) |
| 1285 | 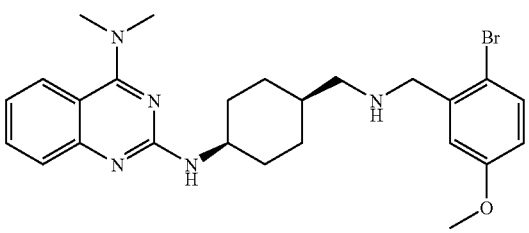 | 498 (M + H) |
| 1286 | 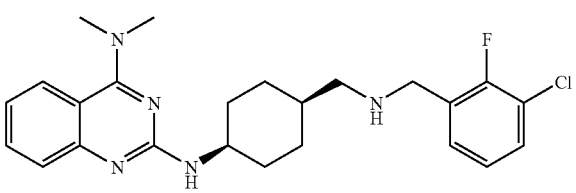 | 442 (M + H) |
| 1287 | 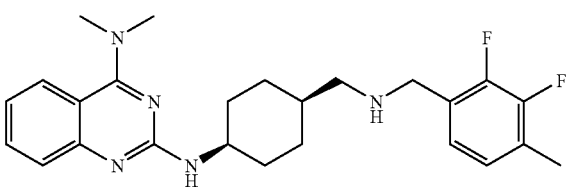 | 440 (M + H) |
| 1288 | 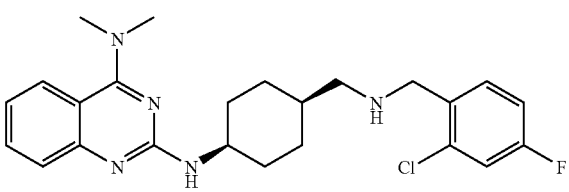 | 442 (M + H) |
| 1289 | 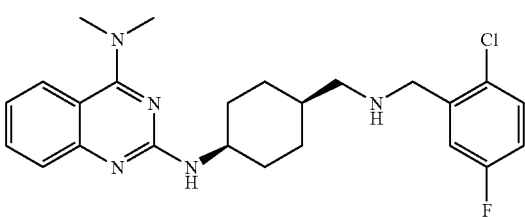 | 442 (M + H) |

-continued
| Example No. | Structure | APCI-MS |
|---|---|---|
| 1290 | 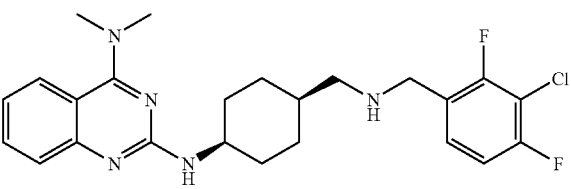 | 460 (M + H) |
| 1291 | 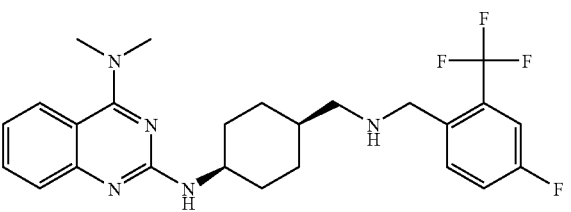 | 476 (M + H) |
| 1292 | 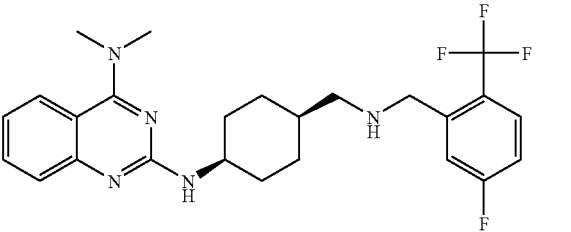 | 476 (M + H) |
| 1293 | 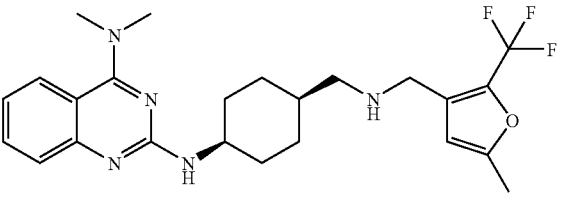 | 462 (M + H) |
| 1294 | 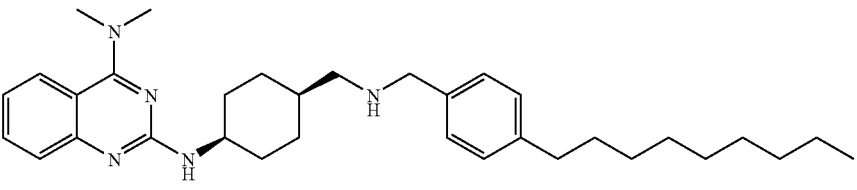 | 516 (M + H) |
| 1295 | 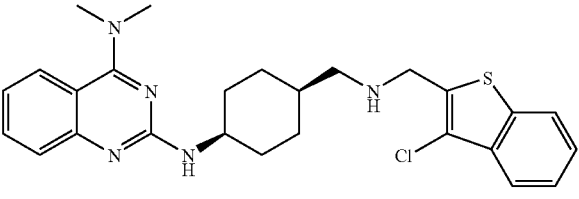 | 480 (M + H) |
| 1296 | 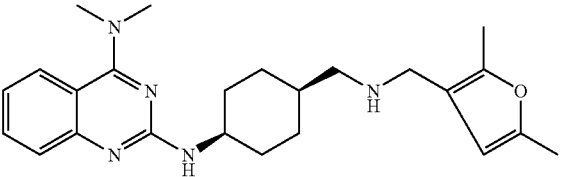 | 408 (M + H) |

-continued
| Example No. | Structure | APCI-MS |
|---|---|---|
| 1297 | 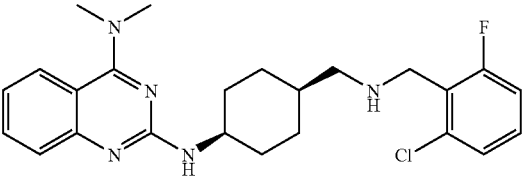 | 442 (M + H) |
| 1298 | 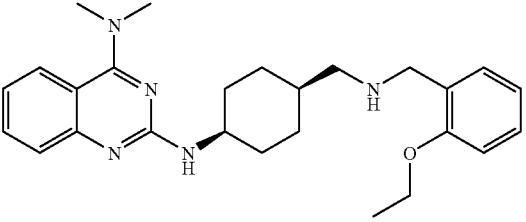 | 434 (M + H) |
| 1299 | 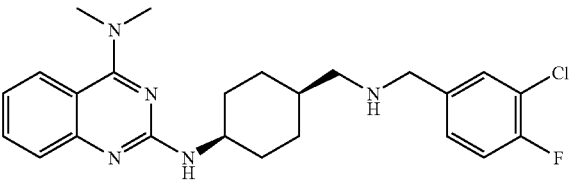 | 442 (M + H) |
| 1300 | 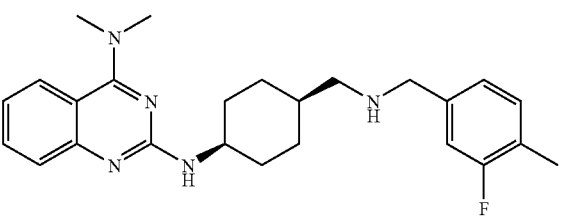 | 422 (M + H) |
| 1301 | 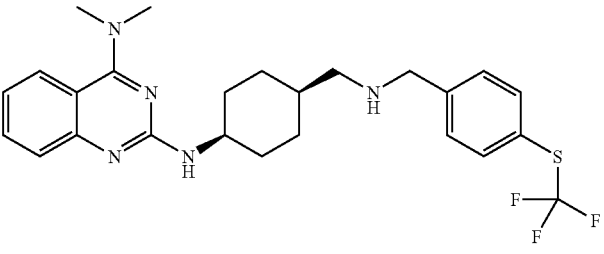 | 490 (M + H) |
| 1302 | 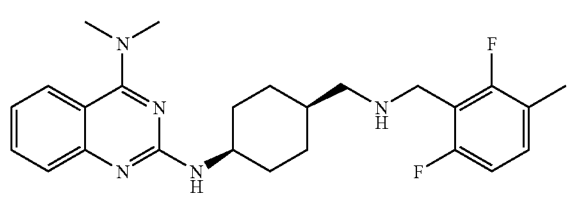 | 440 (M + H) |
| 1303 | 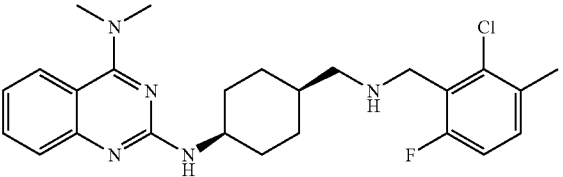 | 456 (M + H) |

-continued
| Example No. | Structure | APCI-MS |
|---|---|---|
| 1304 | 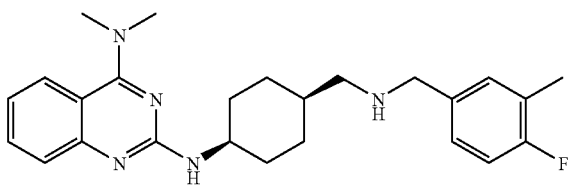 | 422 (M + H) |
| 1305 | 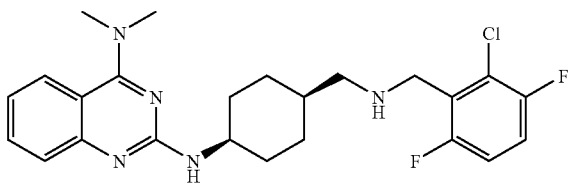 | 460 (M + H) |
| 1306 | 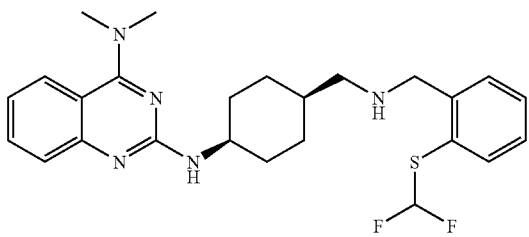 | 472 (M + H) |
| 1307 | 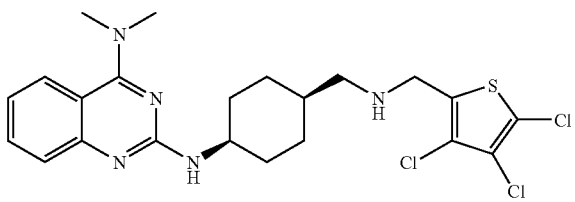 | 498 (M + H) |
| 1308 | 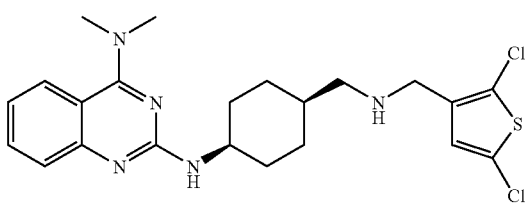 | 464 (M + H) |
| 1309 | 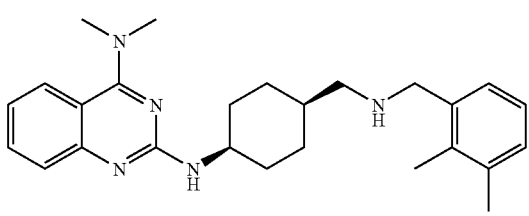 | 418 (M + H) |
| 1310 | 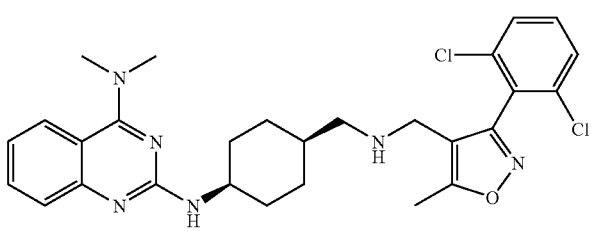 | 539 (M + H) |

-continued
| Example No. | Structure | APCI-MS |
|---|---|---|
| 1311 | 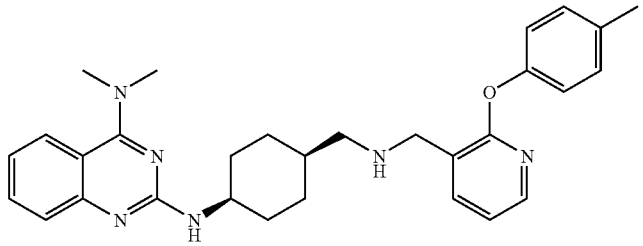 | 497 (M + H) |
| 1312 | 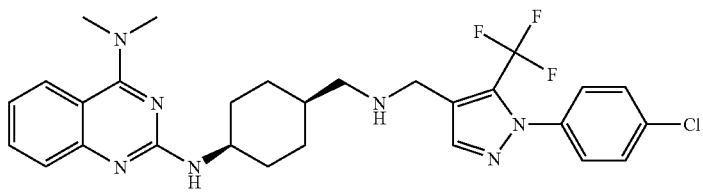 | 558 (M + H) |
| 1313 | 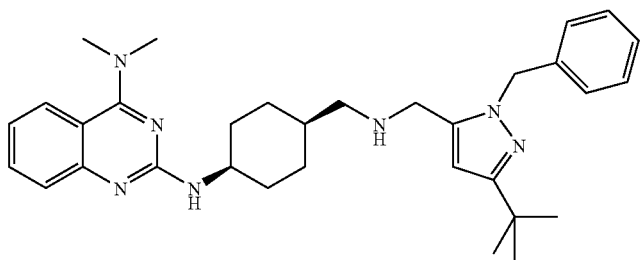 | 526 (M + H) |
| 1314 | 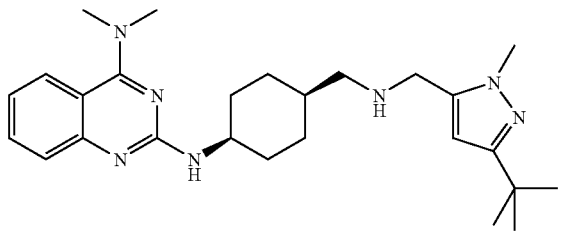 | 450 (M + H) |
| 1315 | 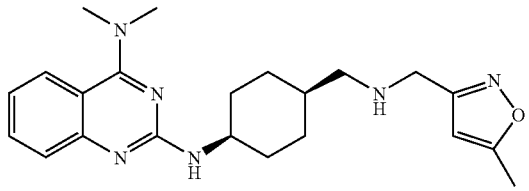 | 395 (M + H) |
| 1316 | 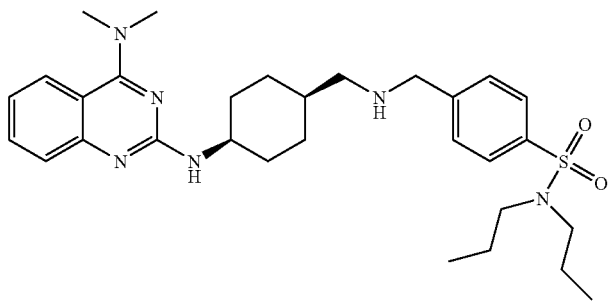 | 553 (M + H) |

-continued
| Example No. | Structure | APCI-MS |
|---|---|---|
| 1317 | 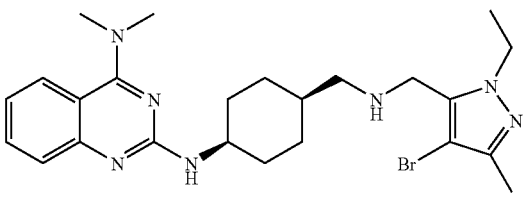 | 500 (M + H) |
| 1318 | 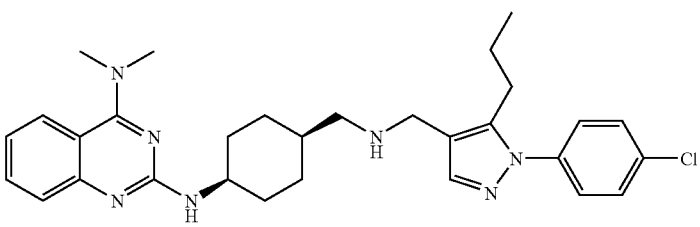 | 532 (M + H) |
| 1319 | 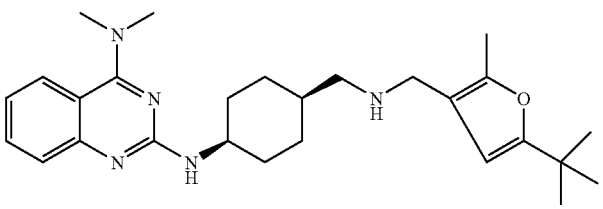 | 450 (M + H) |
| 1320 | 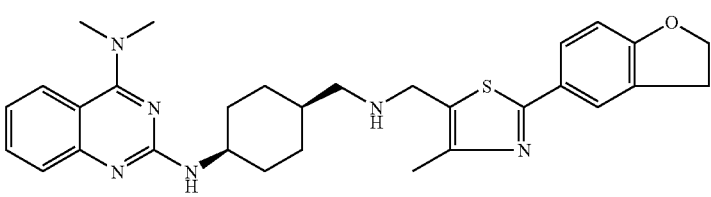 | 529 (M + H) |
| 1321 | 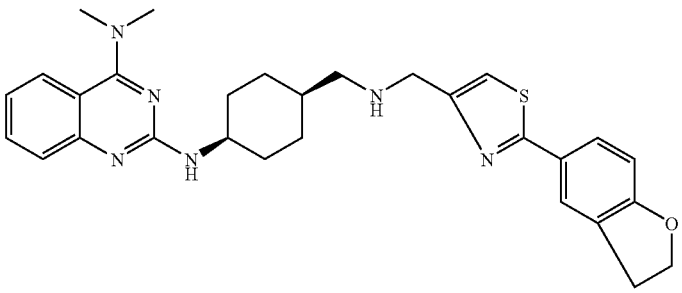 | 515 (M + H) |
| 1322 | 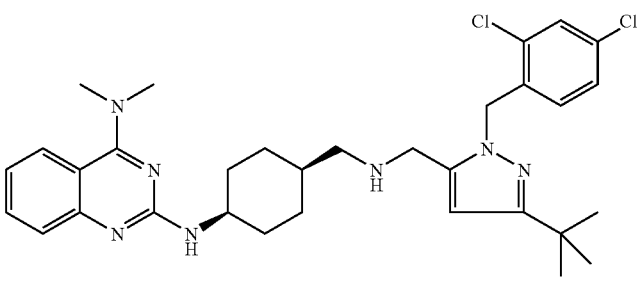 | 594 (M + H) |

-continued
| Example No. | Structure | APCI-MS |
|---|---|---|
| 1323 | 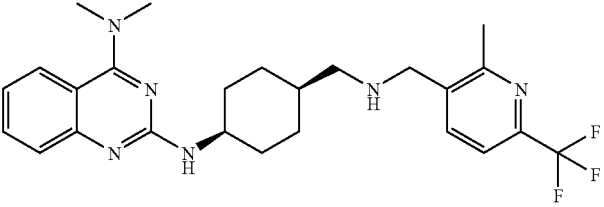 | 473 (M + H) |
| 1324 | 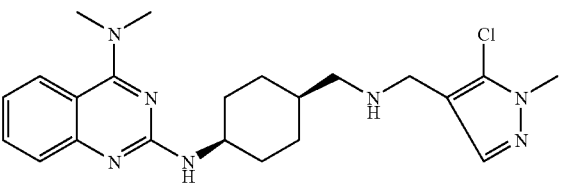 | 428 (M + H) |
| 1325 | 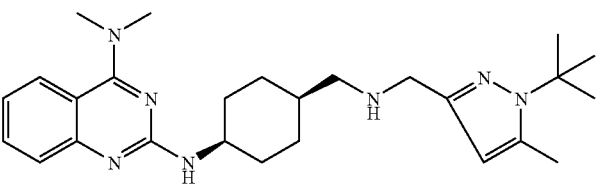 | 450 (M + H) |
| 1326 | 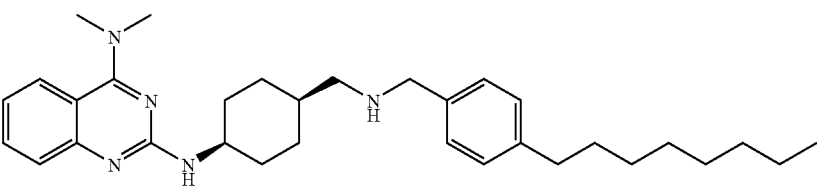 | 502 (M + H) |
| 1327 | 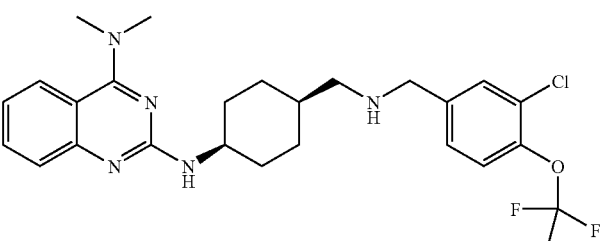 | 508 (M + H) |
| 1328 | 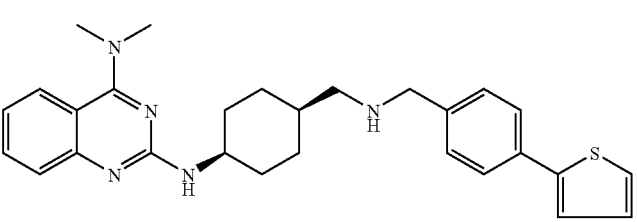 | 472 (M + H) |
| 1329 | 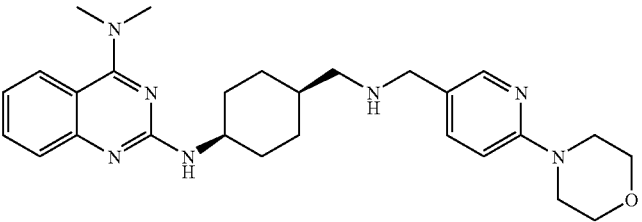 | 476 (M + H) |

-continued
| Example No. | Structure | APCI-MS |
|---|---|---|
| 1330 | 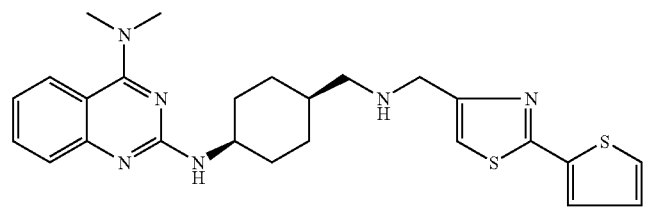 | 479 (M + H) |
| 1331 | 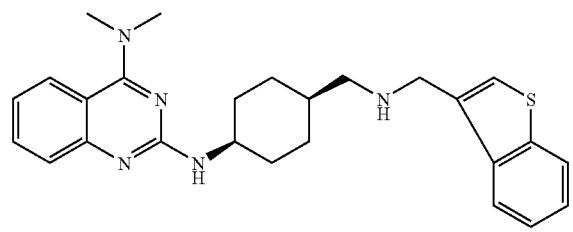 | 446 (M + H) |
| 1332 | 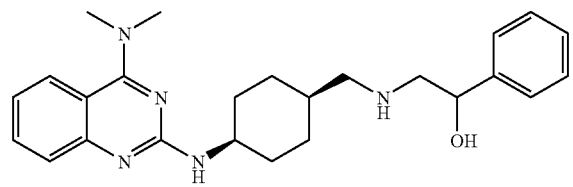 | 420 (M + H) |
| 1333 | 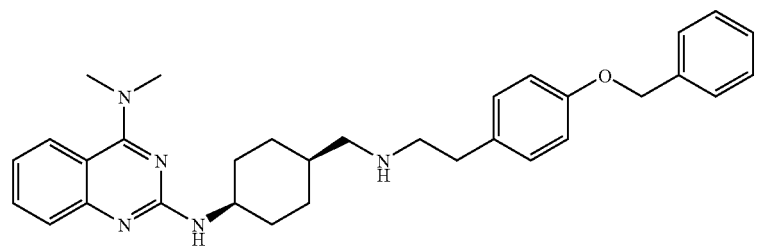 | 510 (M + H) |
| 1334 | 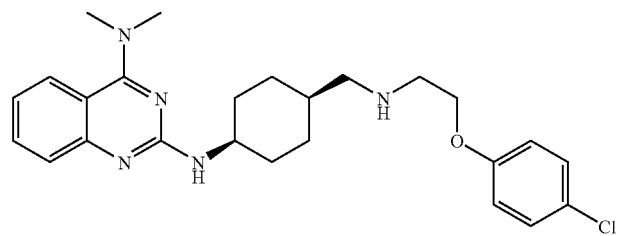 | 454 (M + H) |
| 1335 | 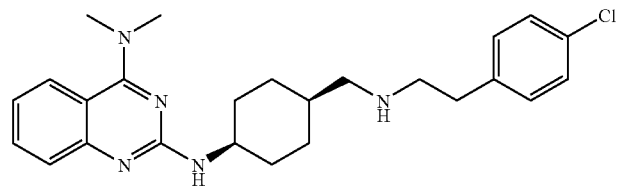 | 438 (M + H) |

-continued
| Example No. | Structure | APCI-MS |
|---|---|---|
| 1336 | 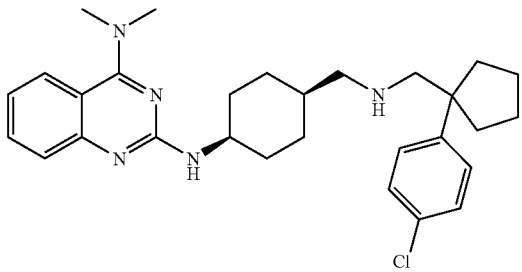 | 492 (M + H) |
| 1337 | 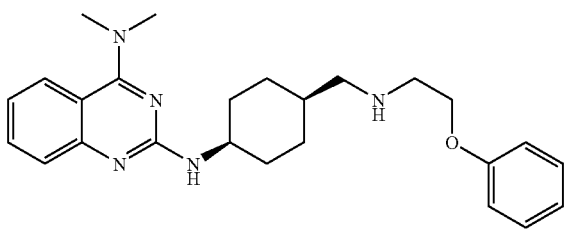 | 420 (M + H) |
| 1338 | 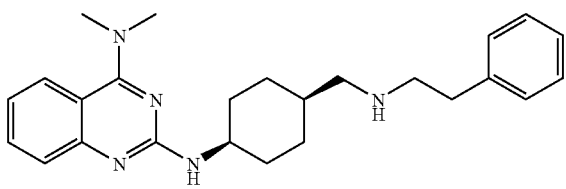 | 404 (M + H) |
| 1339 | 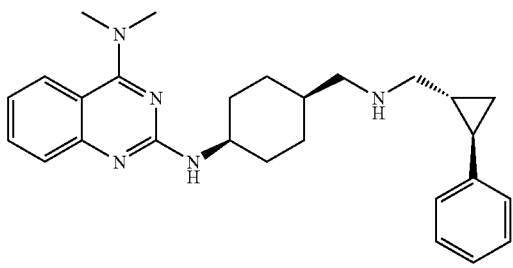 | 430 (M + H) |
| 1340 | 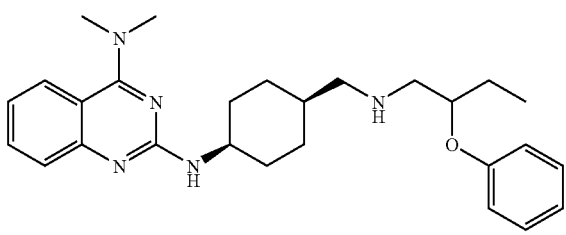 | 448 (M + H) |
| 1341 | 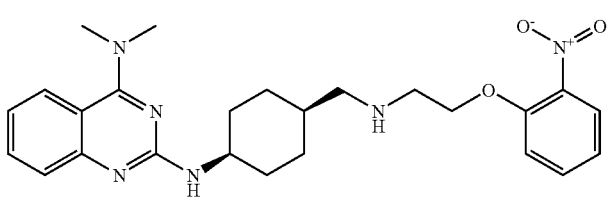 | 465 (M + H) |

-continued
| Example No. | Structure | APCI-MS |
|---|---|---|
| 1342 | 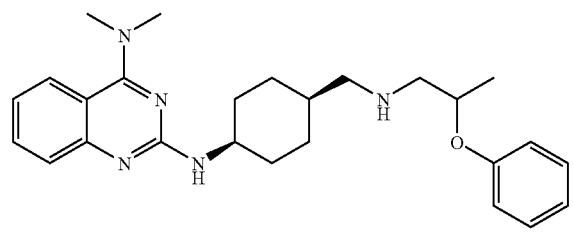 | 434 (M + H) |
| 1343 | 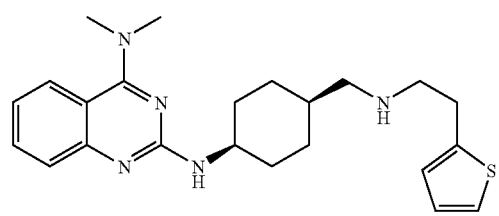 | 410 (M + H) |
| 1344 | 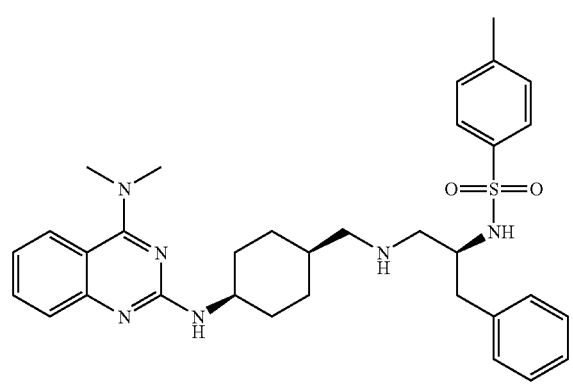 | 587 (M + H) |
| 1345 | 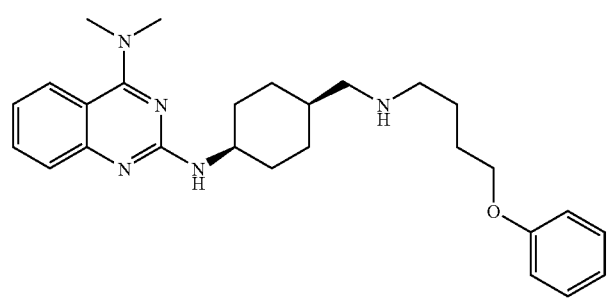 | 448 (M + H) |
| 1346 | 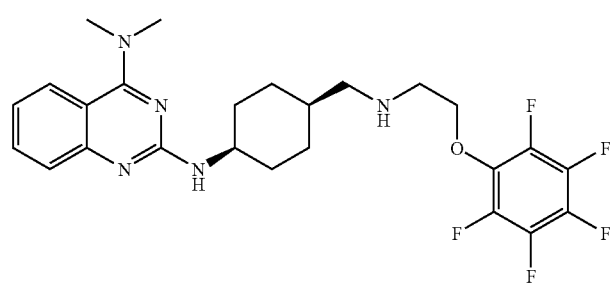 | 510 (M + H) |

| Example No. | Structure | APCI-MS |
|---|---|---|
| 1347 | 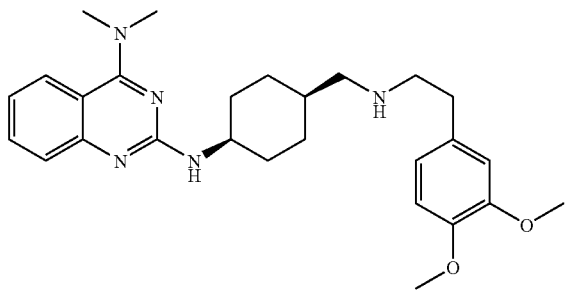 | 464 (M + H) |
| 1348 | 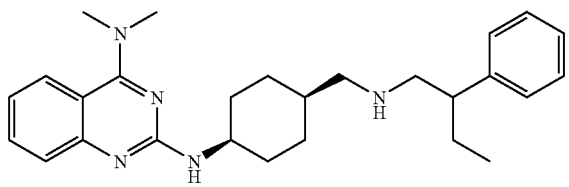 | 432 (M + H) |
| 1349 | 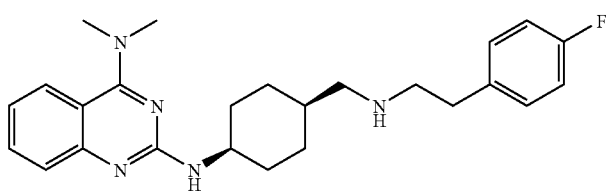 | 422 (M + H) |
| 1350 | 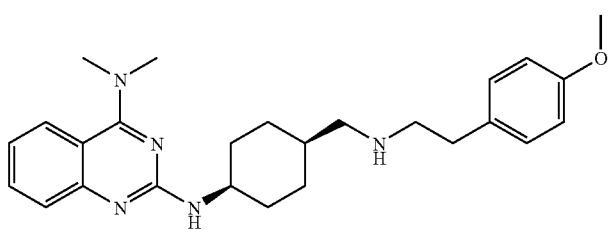 | 434 (M + H) |
| 1351 | 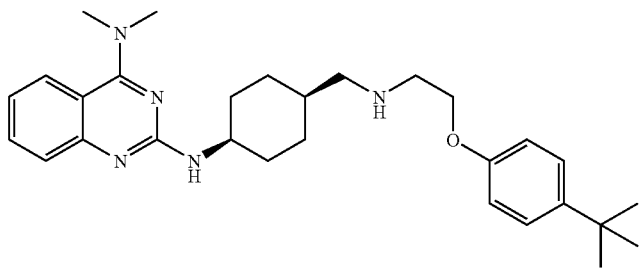 | 476 (M + H) |
| 1352 | 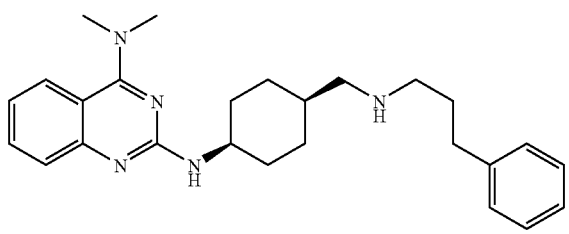 | 418 (M + H) |

| Example No. | Structure | APCI-MS |
|---|---|---|
| 1353 | 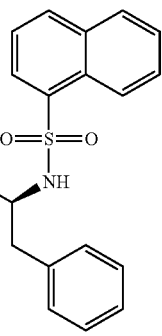 | 623 (M + H) |
| 1354 | 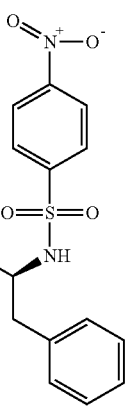 | 618 (M + H) |
| 1355 | 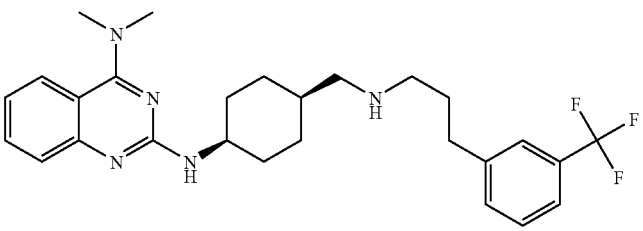 | 486 (M + H) |
| 1356 | 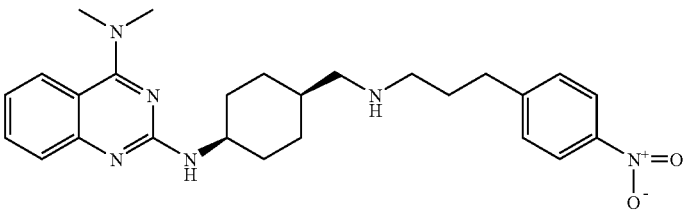 | 463 (M + H) |
| 1357 | 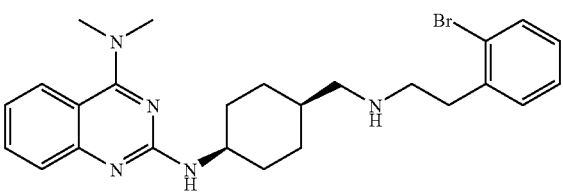 | 482 (M + H) |

-continued
| Example No. | Structure | APCI-MS |
|---|---|---|
| 1358 | 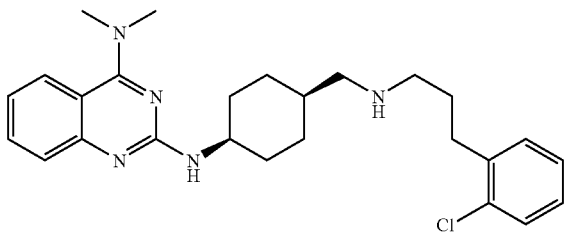 | 452 (M + H) |
| 1359 | 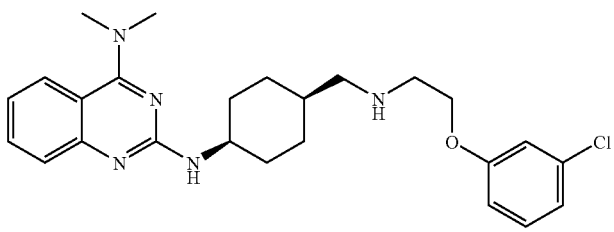 | 454 (M + H) |
| 1360 | 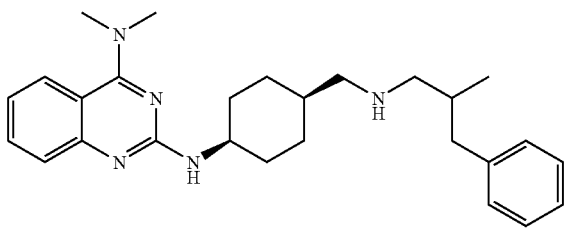 | 432 (M + H) |
| 1361 | 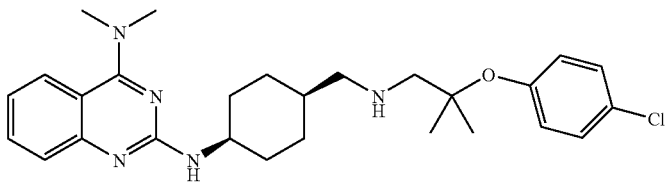 | 482 (M + H) |
| 1362 | 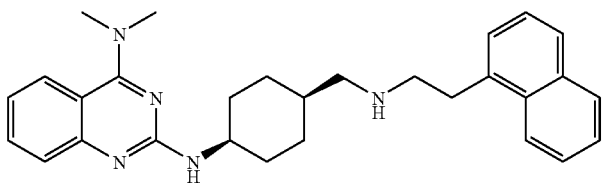 | 454 (M + H) |
| 1363 | 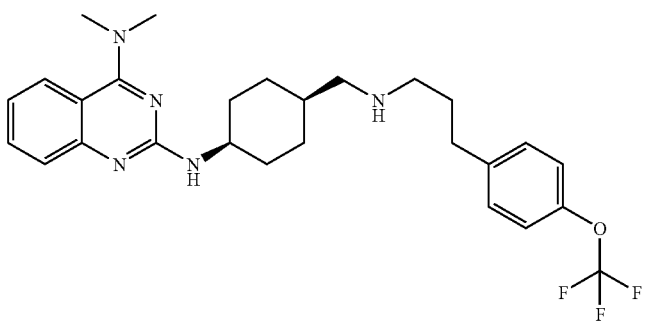 | 502 (M + H) |

-continued
| Example No. | Structure | APCI-MS |
|---|---|---|
| 1364 | 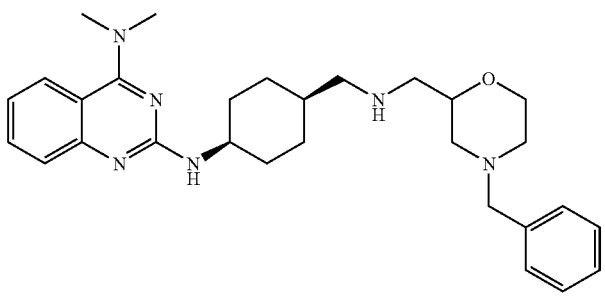 | 489 (M + H) |
| 1365 | 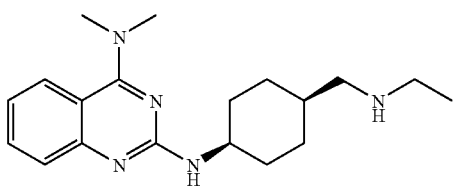 | 328 (M + H) |
| 1366 | 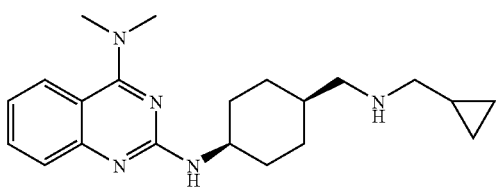 | 354 (M + H) |
| 1367 | 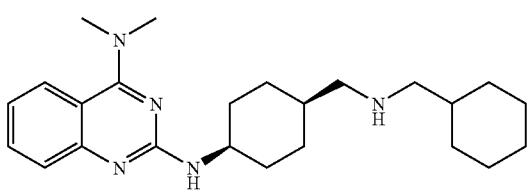 | 396 (M + H) |
| 1368 | 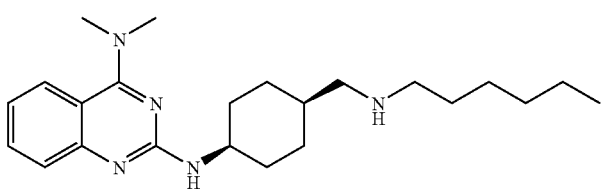 | 384 (M + H) |
| 1370 | 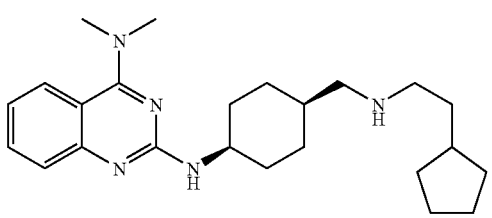 | 396 (M + H) |
| 1371 | 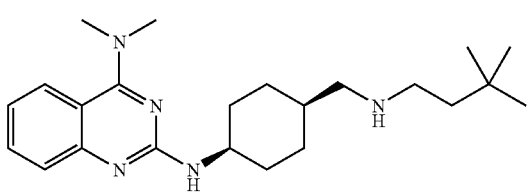 | 404 (M + H) |

-continued

| Example No. | Structure | APCI-MS |
|---|---|---|
| 1372 | 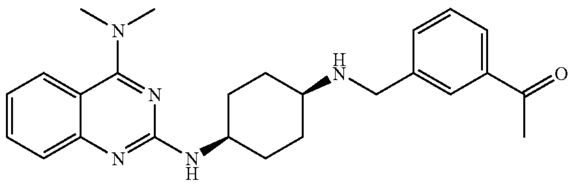 | 418 (M + H) |
| 1373 | 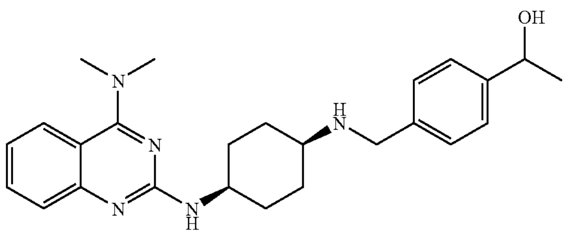 | 420 (M + H) |
| 1374 | 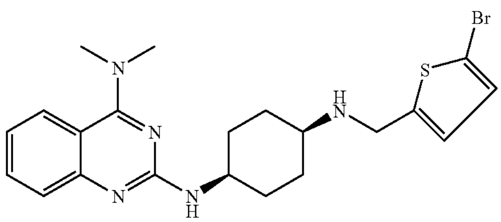 | 460 (M + H) |
| 1375 | 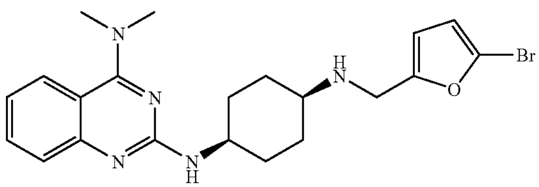 | 444 (M + H) |
| 1376 | 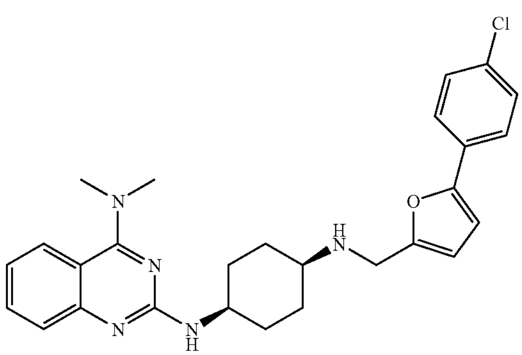 | 476 (M + H) |
| 1377 | 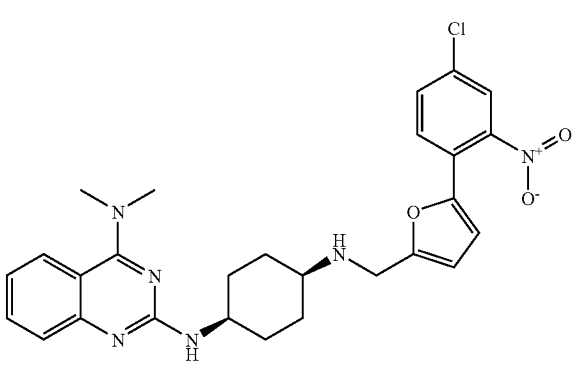 | 521 (M + H) |

-continued
| Example No. | Structure | APCI-MS |
|---|---|---|
| 1378 | 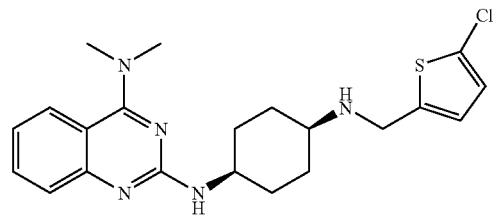 | 416 (M + H) |
| 1379 | 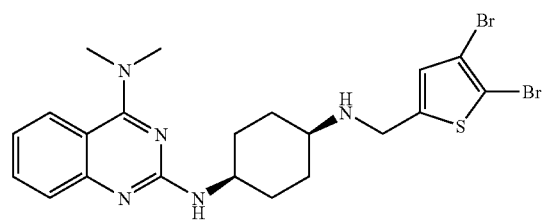 | 538 (M + H) |
| 1380 | 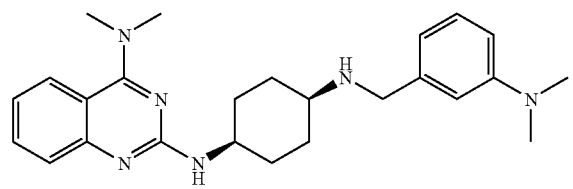 | 419 (M + H) |
| 1381 | 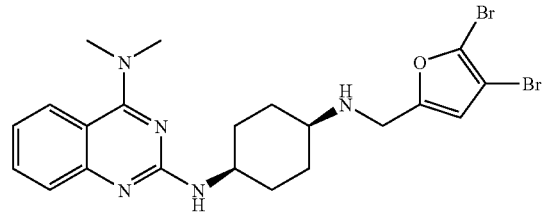 | 522 (M + H) |
| 1382 | 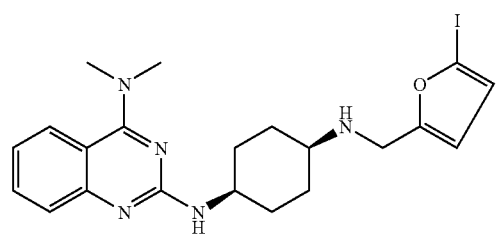 | 492 (M + H) |
| 1383 | 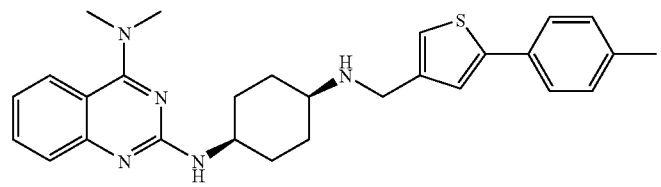 | 472 (M + H) |
| 1384 | 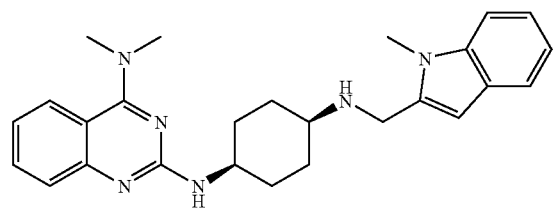 | 429 (M + H) |

-continued
| Example No. | Structure | APCI-MS |
|---|---|---|
| 1385 | 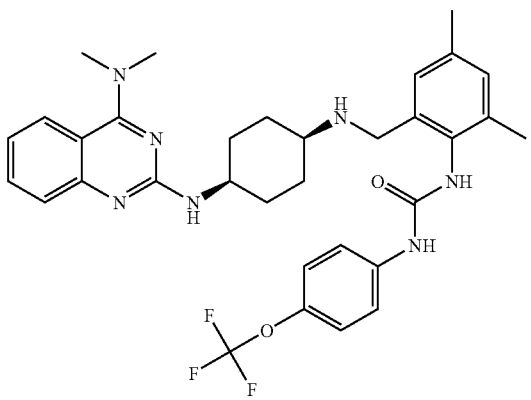 | 622 (M + H) |
| 1386 | 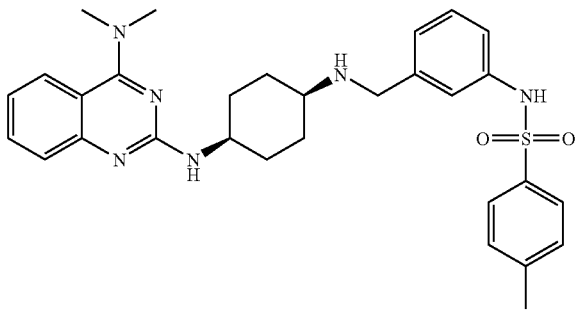 | 545 (M + H) |
| 1387 | 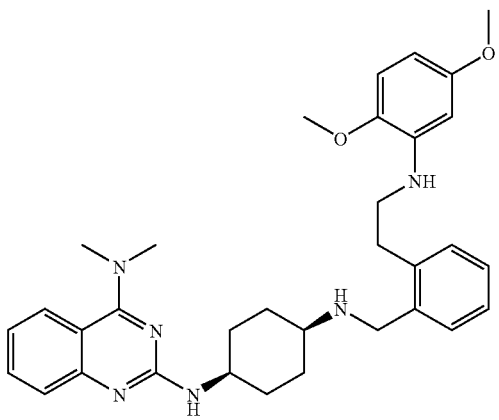 | 555 (M + H) |
| 1389 | 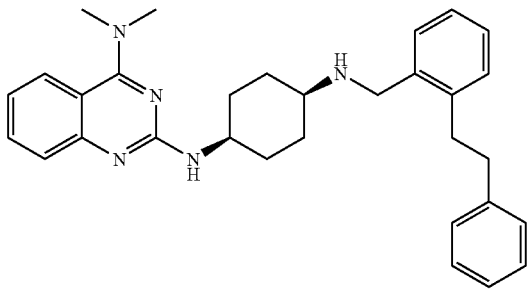 | 480 (M + H) |

-continued
| Example No. | Structure | APCI-MS |
|---|---|---|
| 1390 | 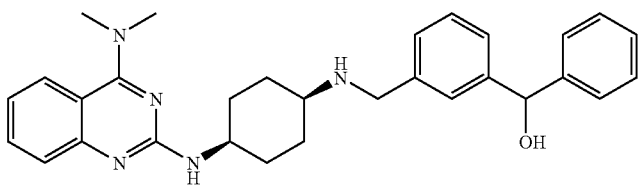 | 482 (M + H) |
| 1391 | 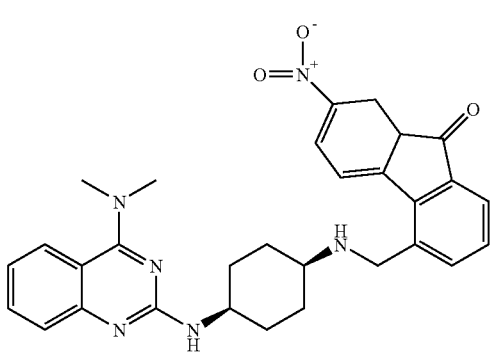 | 523 (M + H) |
| 1392 | 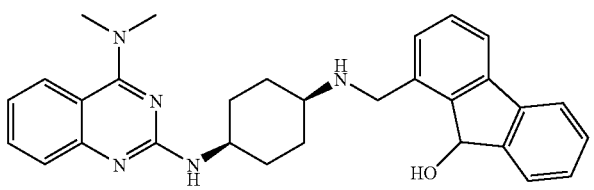 | 480 (M + H) |
| 1393 | 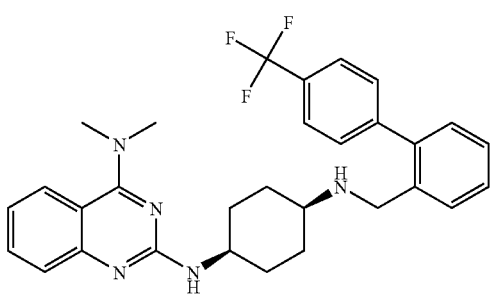 | 520 (M + H) |
| 1394 | 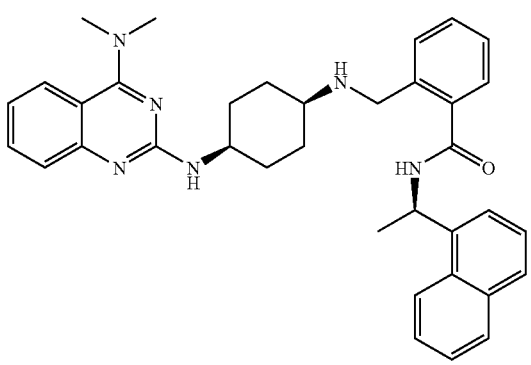 | 573 (M + H) |

-continued
| Example No. | Structure | APCI-MS |
|---|---|---|
| 1395 | 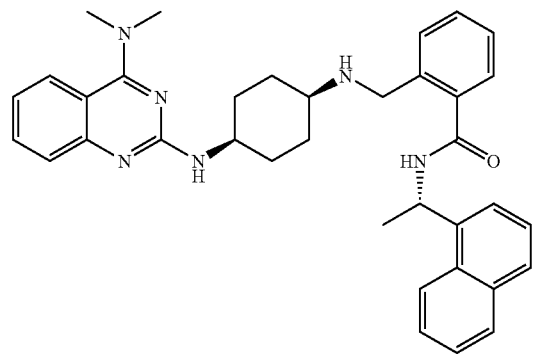 | 573 (M + H) |
| 1396 | 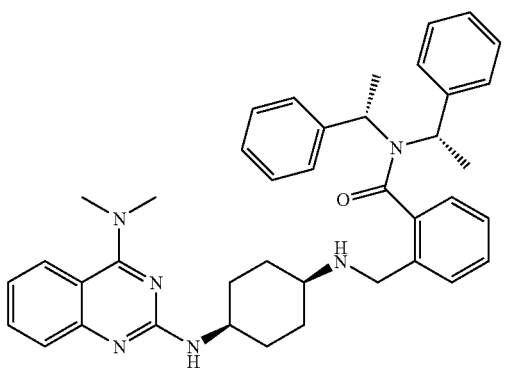 | 627 (M + H) |
| 1397 | 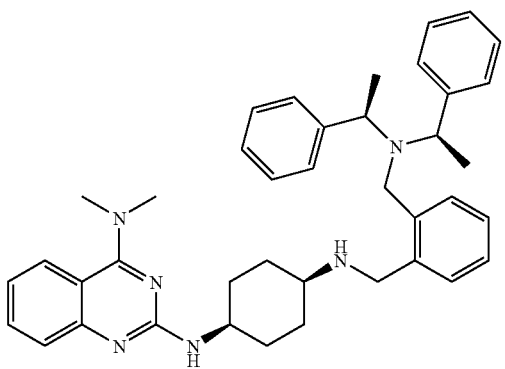 | 613 (M + H) |
| 1398 | 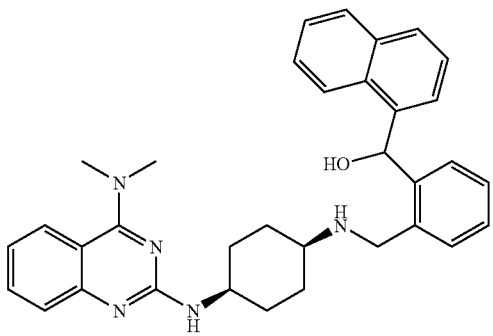 | 532 (M + H) |

-continued
| Example No. | Structure | APCI-MS |
|---|---|---|
| 1399 | 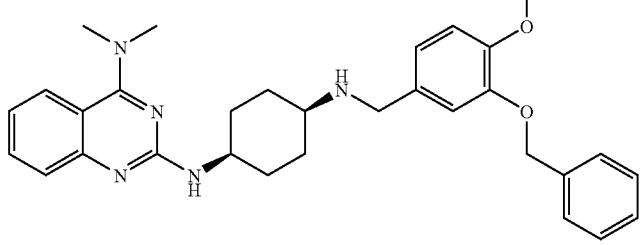 | 512 (M + H) |
| 1400 | 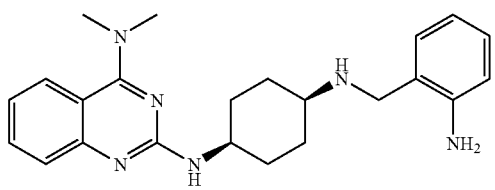 | 391 (M + H) |
| 1401 | 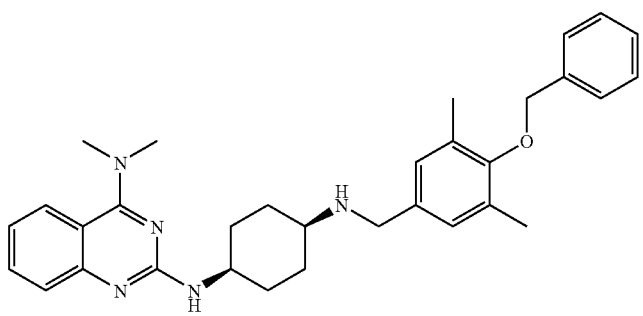 | 510 (M + H) |
| 1402 | 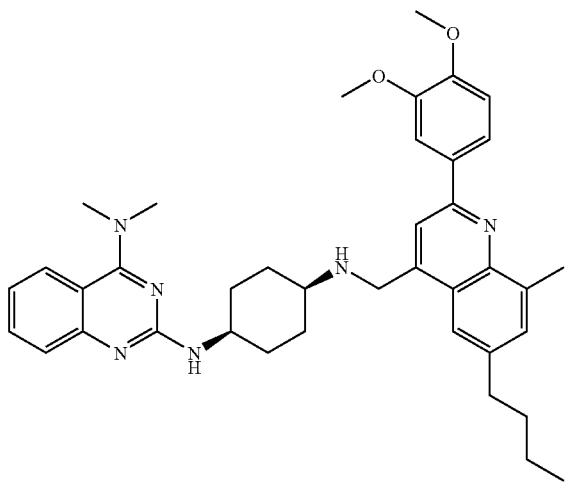 | 633 (M + H) |
| 1403 | 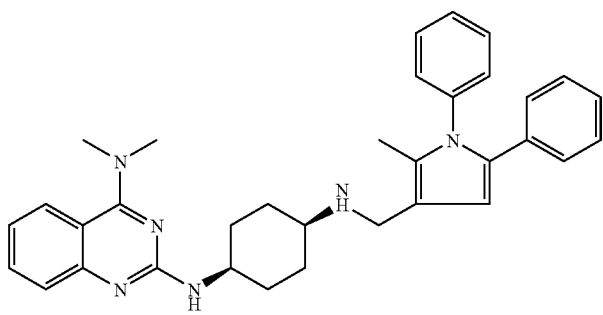 | 531 (M + H) |

-continued
| Example No. | Structure | APCI-MS |
|---|---|---|
| 1404 | 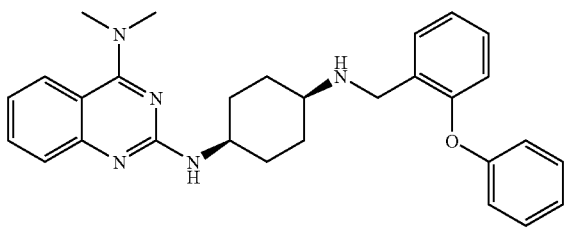 | 468 (M + H) |
| 1405 | 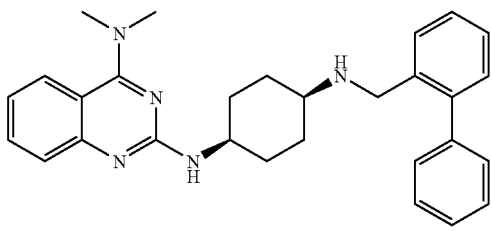 | 452 (M + H) |
| 1406 | 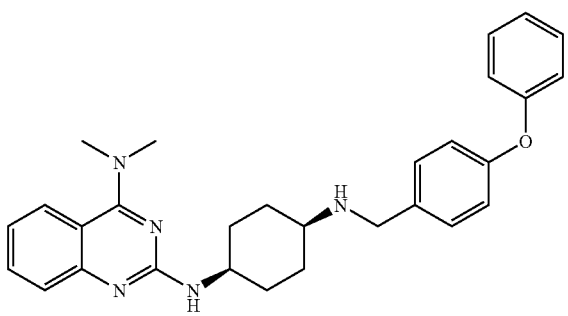 | 468 (M + H) |
| 1407 | 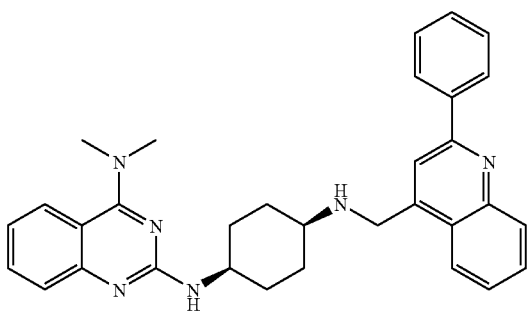 | 503 (M + H) |
| 1408 | 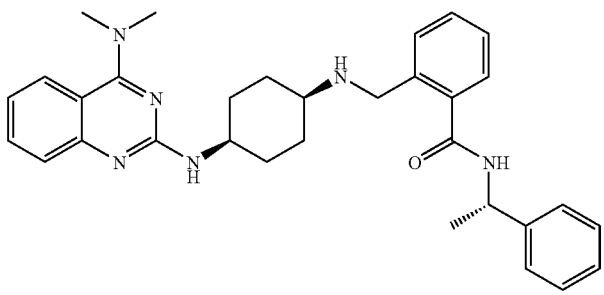 | 523 (M + H) |

-continued
| Example No. | Structure | APCI-MS |
|---|---|---|
| 1409 | 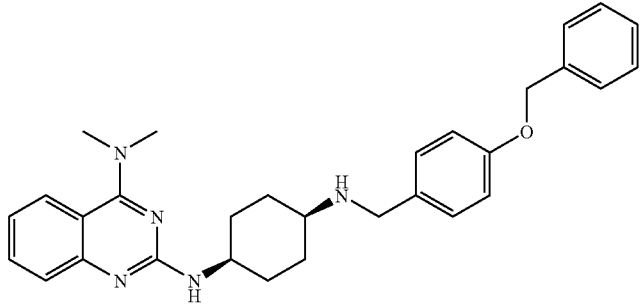 | 482 (M + H) |
| 1410 | 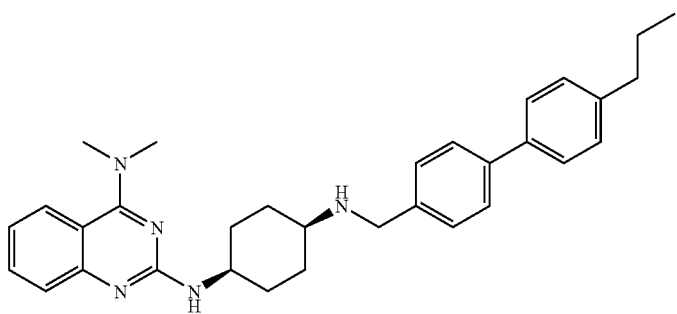 | 494 (M + H) |
| 1411 | 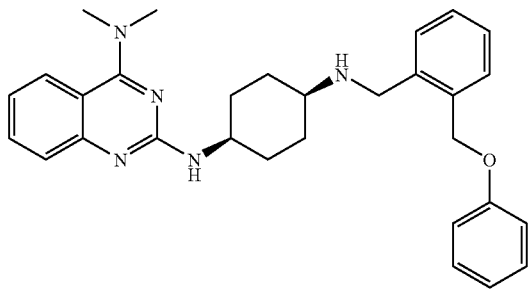 | 482 (M + H) |
| 1412 | 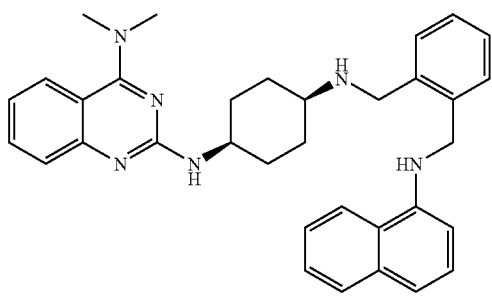 | 531 (M + H) |
| 1413 | 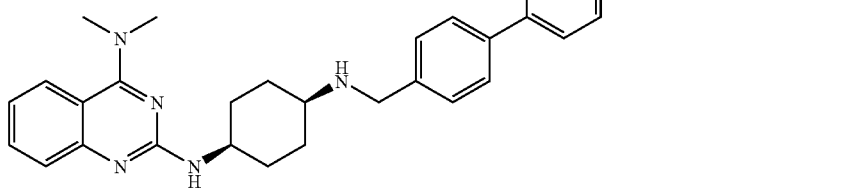 | 550 (M + H) |

-continued
| Example No. | Structure | APCI-MS |
|---|---|---|
| 1414 | 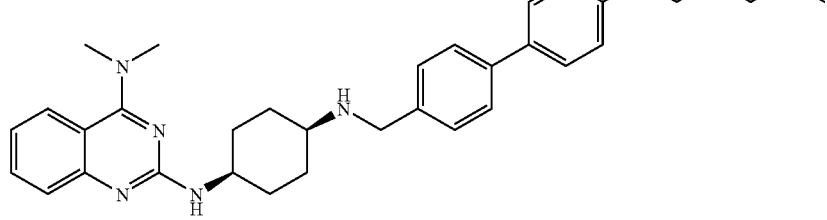 | 536 (M + H) |
| 1415 | 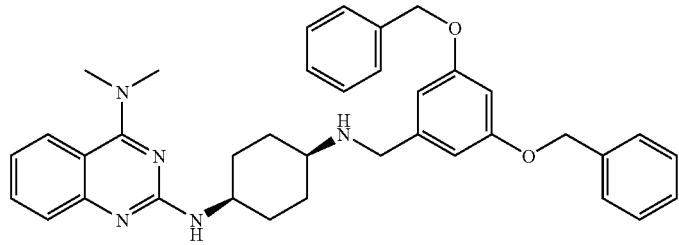 | 588 (M + H) |
| 1416 | 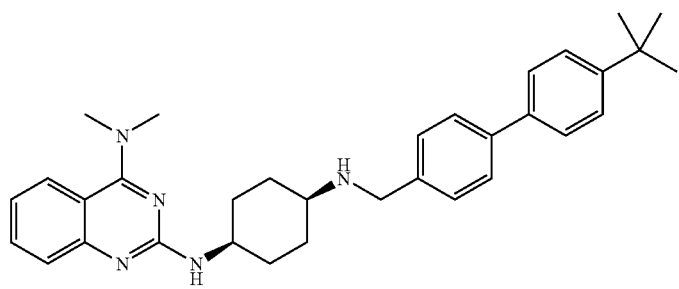 | 508 (M + H) |
| 1417 | 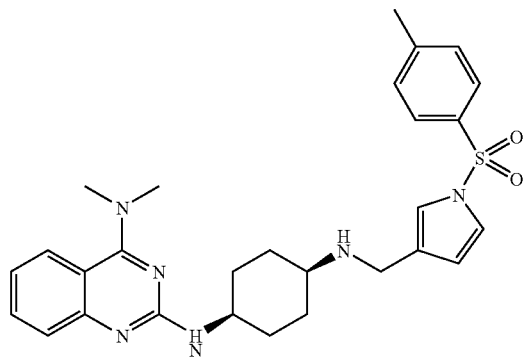 | 519 (M + H) |
| 1418 | 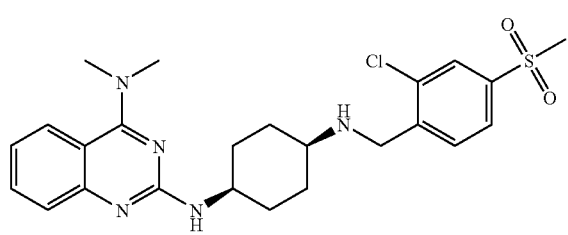 | 488 (M + H) |

| Example No. | Structure | APCI-MS |
|---|---|---|
| 1419 | 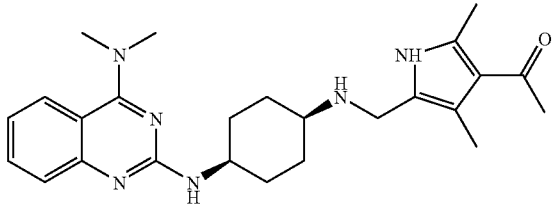 | 435 (M + H) |
| 1420 | 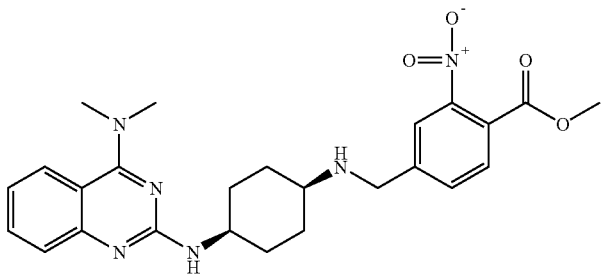 | 479 (M + H) |
| 1421 | 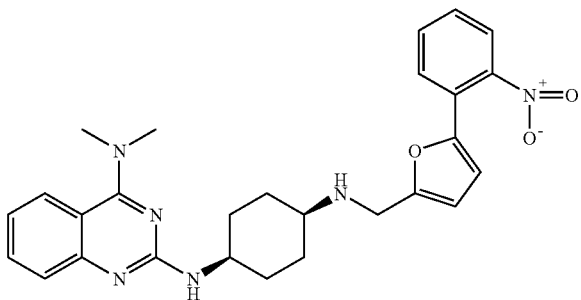 | 487 (M + H) |
| 1422 | 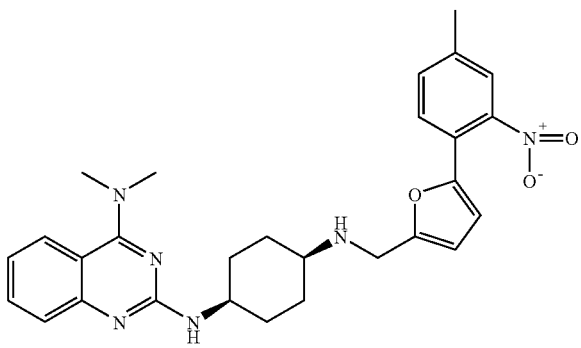 | 501 (M + H) |
| 1423 | 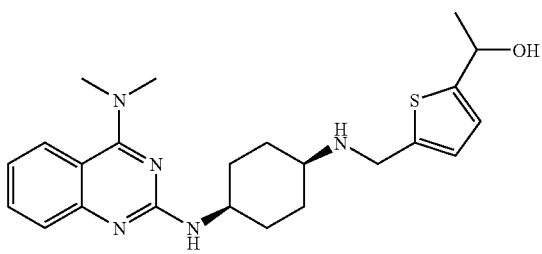 | 426 (M + H) |

-continued
| Example No. | Structure | APCI-MS |
|---|---|---|
| 1424 | 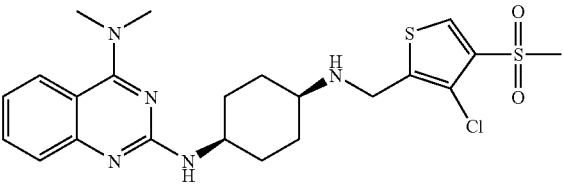 | 494 (M + H) |
| 1425 | 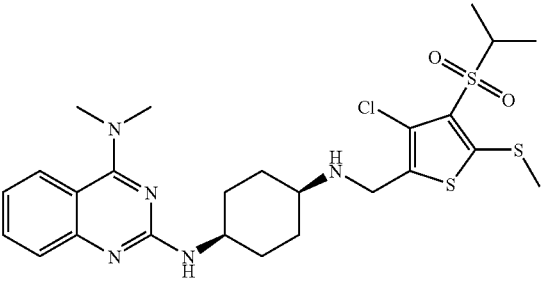 | 568 (M + H) |
| 1426 | 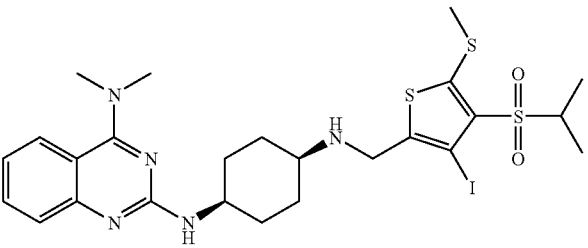 | 660 (M + H) |
| 1427 | 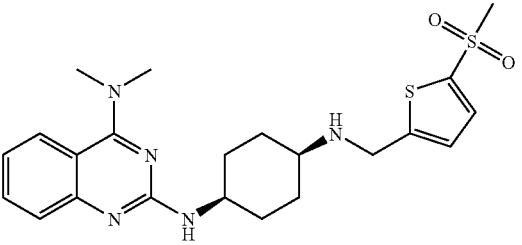 | 460 (M + H) |
| 1428 | 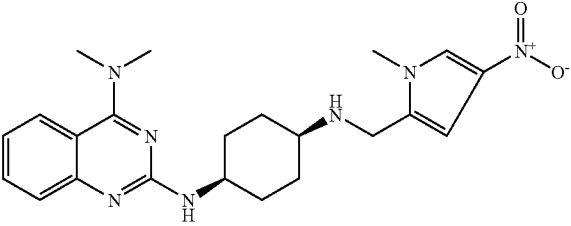 | 424 (M + H) |
| 1429 | 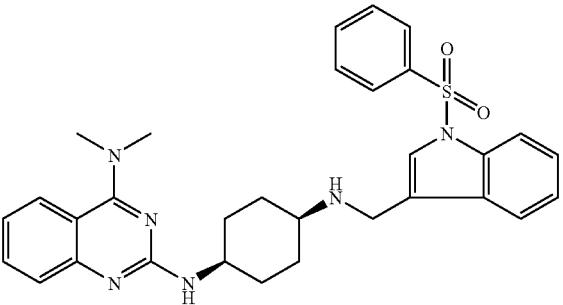 | 555 (M + H) |

| Example No. | Structure | APCI-MS |
|---|---|---|
| 1430 | 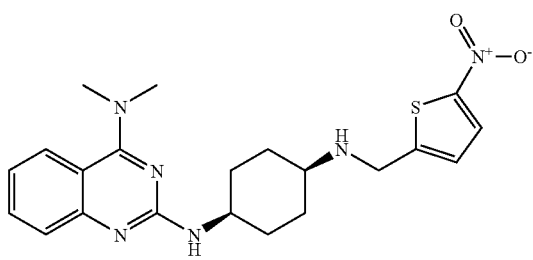 | 427 (M + H) |
| 1431 | 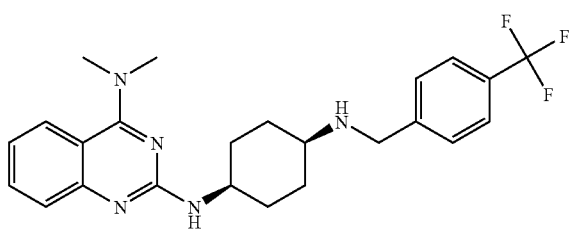 | 444 (M + H) |
| 1432 | 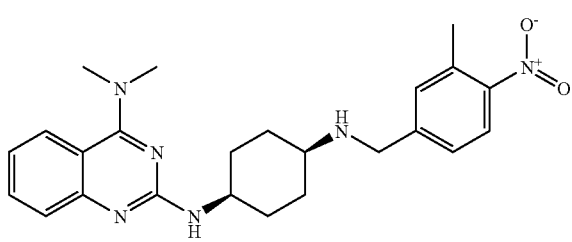 | 435 (M + H) |
| 1433 | 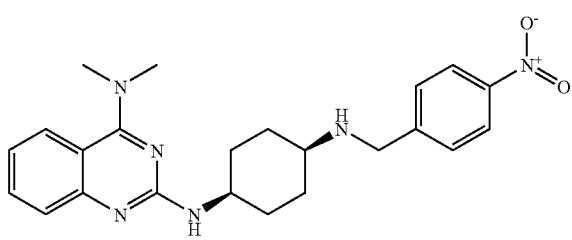 | 421 (M + H) |
| 1434 | 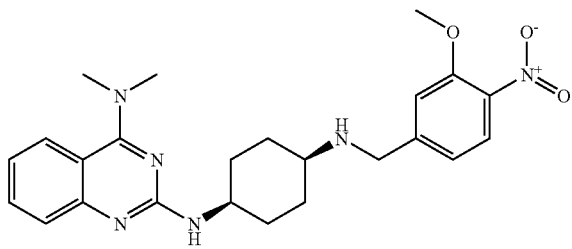 | 451 (M + H) |
| 1435 | 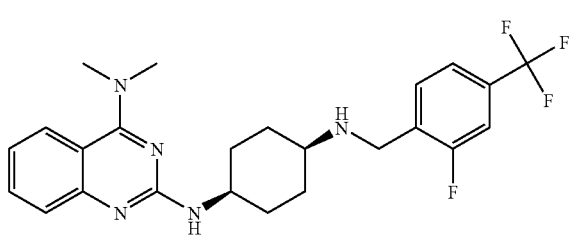 | 462 (M + H) |

-continued
| Example No. | Structure | APCI-MS |
|---|---|---|
| 1436 | 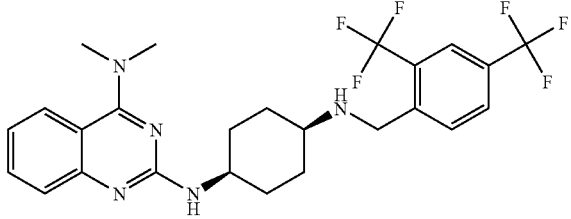 | 512 (M + H) |
| 1437 | 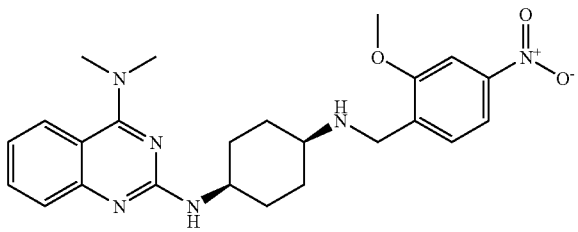 | 451 (M + H) |
| 1438 | 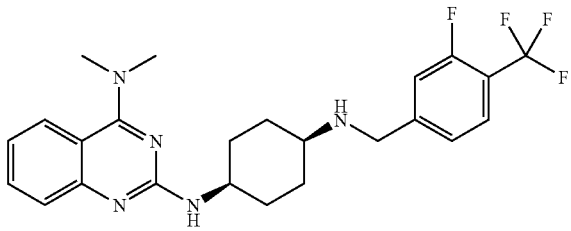 | 462 (M + H) |
| 1439 | 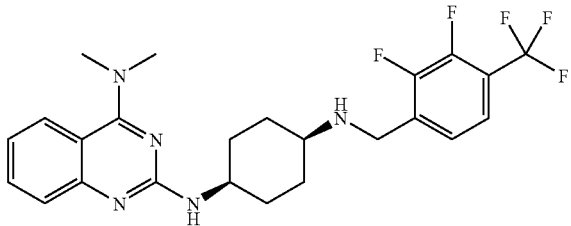 | 480 (M + H) |
| 1440 | 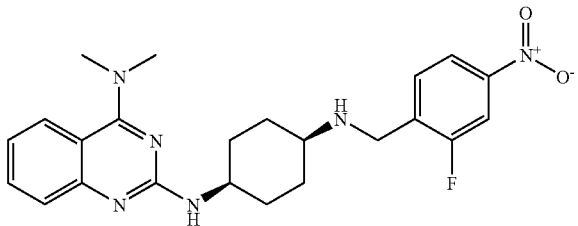 | 439 (M + H) |
| 1441 | 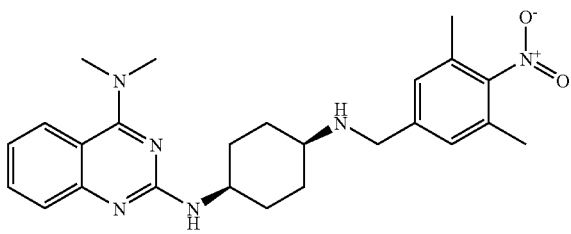 | 449 (M + H) |

-continued
| Example No. | Structure | APCI-MS |
|---|---|---|
| 1442 | 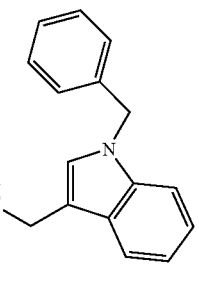 | 505 (M + H) |
| 1443 | 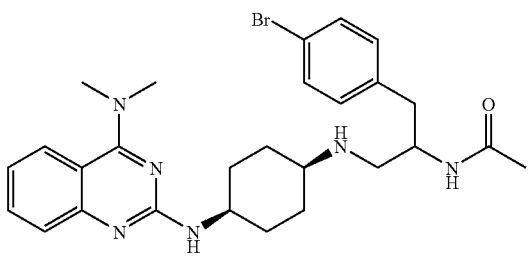 | 539 (M + H) |
| 1444 | 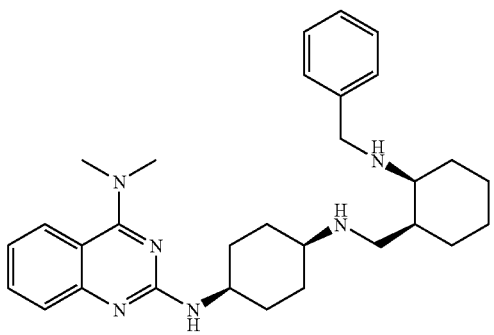 | 487 (M + H) |
| 1445 | 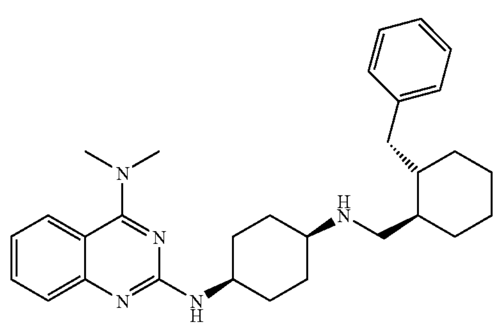 | 488 (M + H) |

-continued
| Example No. | Structure | APCI-MS |
|---|---|---|
| 1446 | 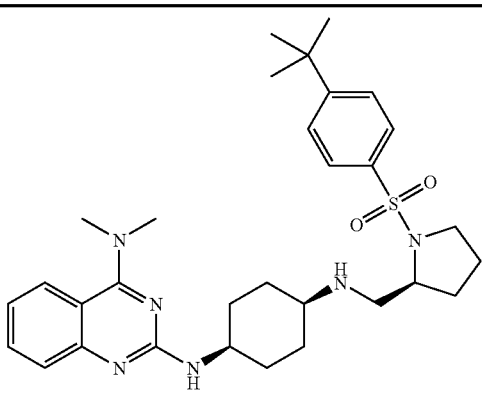 | 565 (M + H) |
| 1447 | 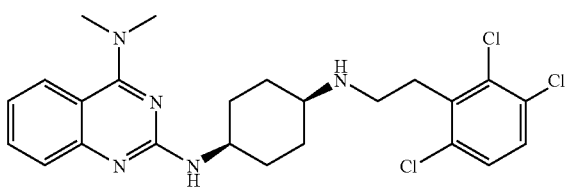 | 492 (M + H) |
| 1448 | 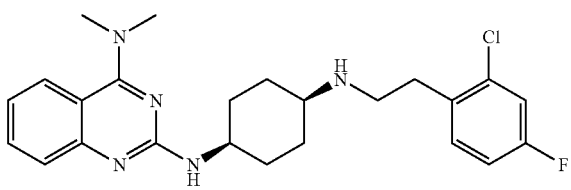 | 442 (M + H) |
| 1449 | 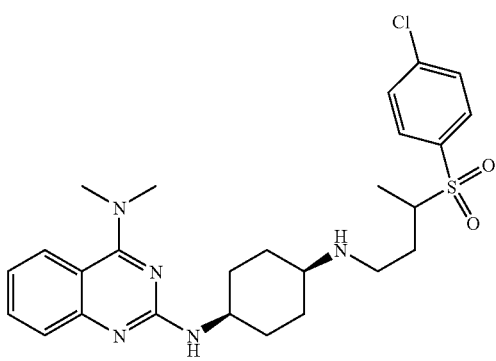 | 516 (M + H) |
| 1450 | 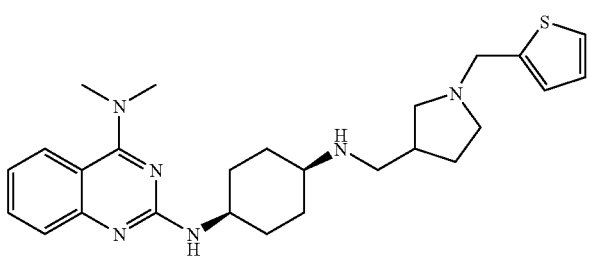 | 465 (M + H) |
| 1451 | 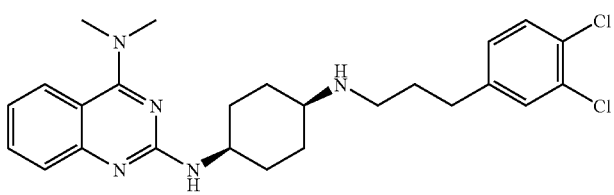 | 472 (M + H) |

-continued
| Example No. | Structure | APCI-MS |
|---|---|---|
| 1452 | 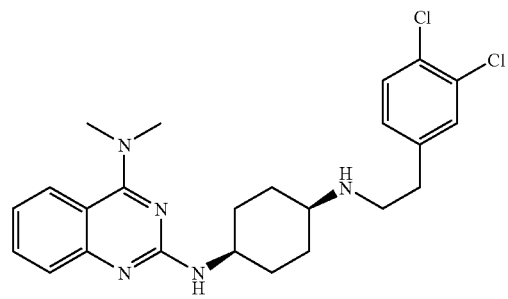 | 458 (M + H) |
| 1453 | 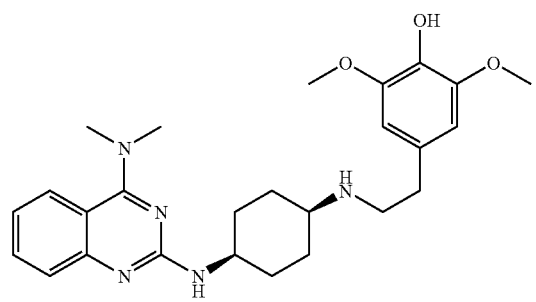 | 466 (M + H) |
| 1454 | 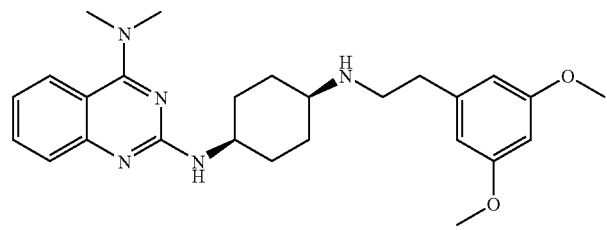 | 450 (M + H) |
| 1455 | 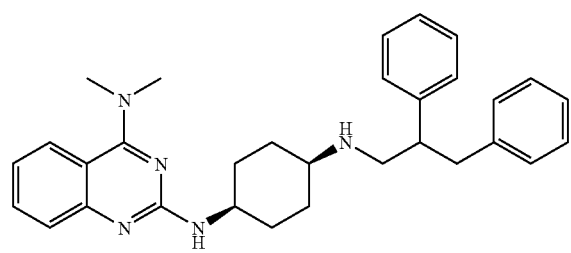 | 480 (M + H) |
| 1456 | 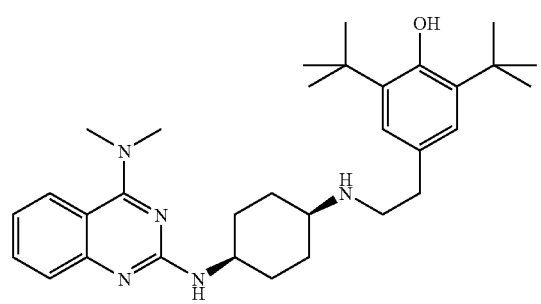 | 518 (M + H) |

| Example No. | Structure | APCI-MS |
|---|---|---|
| 1457 | 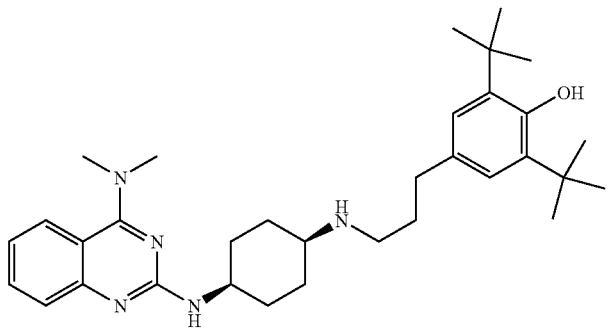 | 532 (M + H) |
| 1458 | 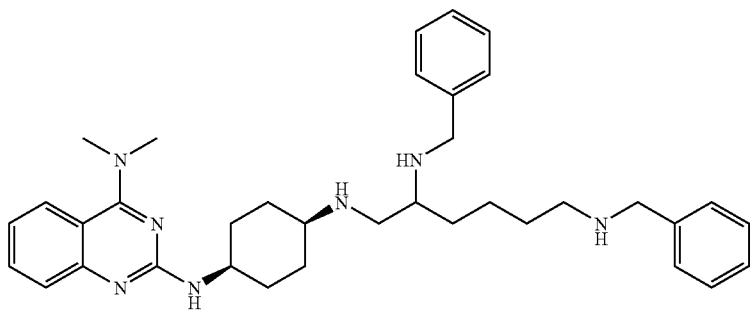 | 580 (M + H) |
| 1459 | 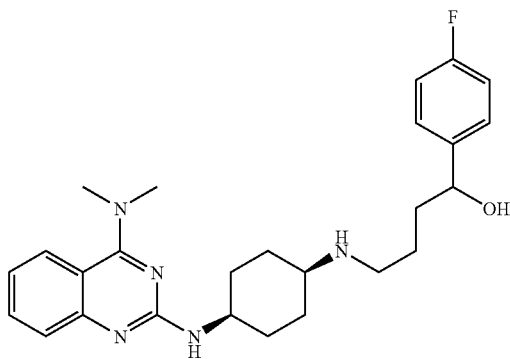 | 452 (M + H) |
| 1460 | 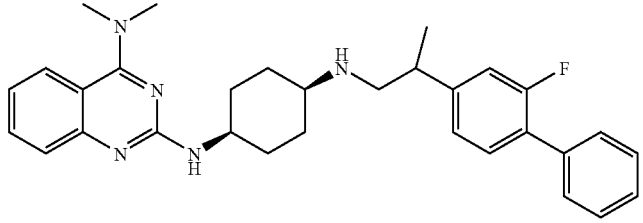 | 498 (M + H) |
| 1461 | 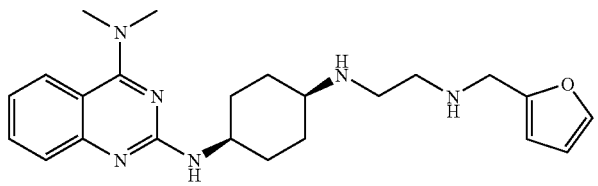 | 409 (M + H) |

-continued
| Example No. | Structure | APCI-MS |
|---|---|---|
| 1462 | 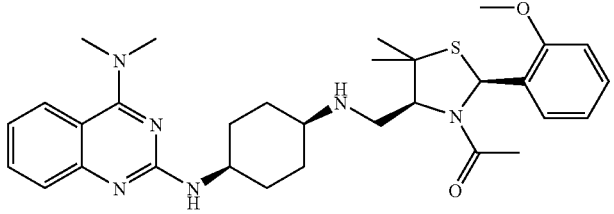 | 563 (M + H) |
| 1463 | 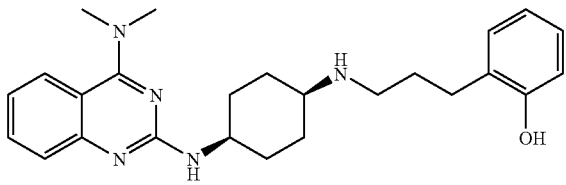 | 420 (M + H) |
| 1464 | 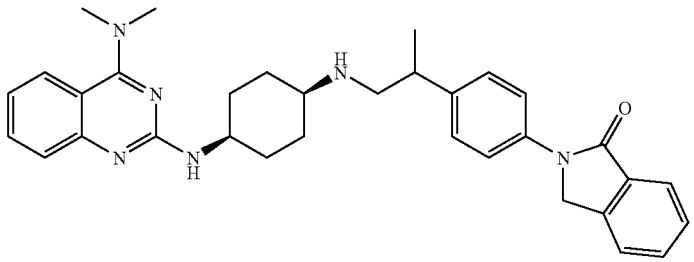 | 535 (M + H) |
| 1465 | 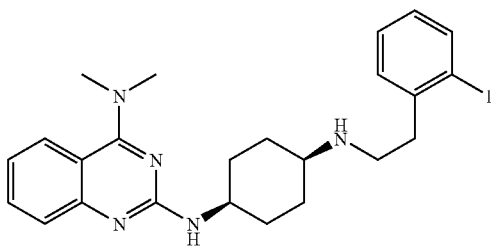 | 516 (M + H) |
| 1466 | 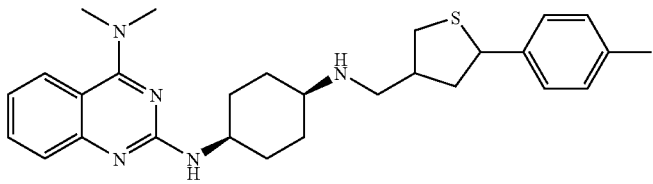 | 476 (M + H) |
| 1467 | 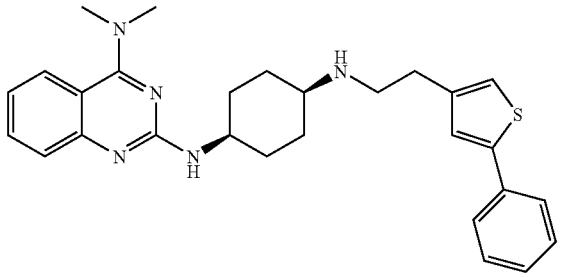 | 472 (M + H) |

-continued

| Example No. | Structure | APCI-MS |
|---|---|---|
| 1468 | 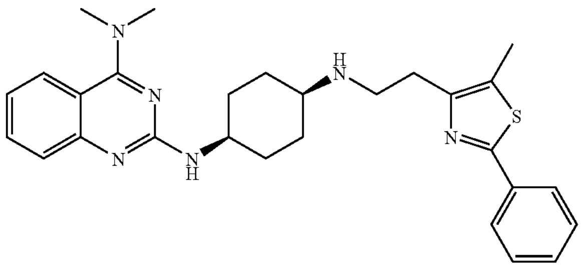 | 487 (M + H) |
| 1469 | 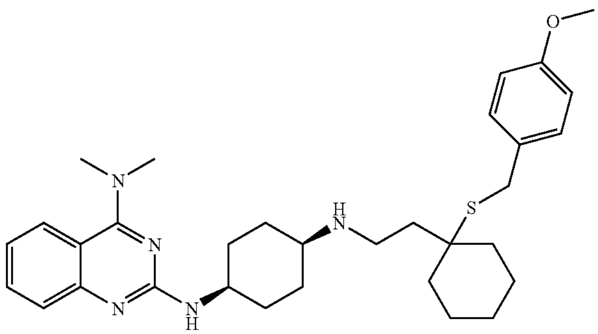 | 548 (M + H) |
| 1470 | 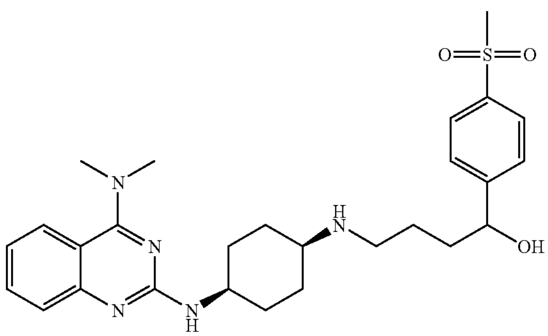 | 512 (M + H) |
| 1471 | 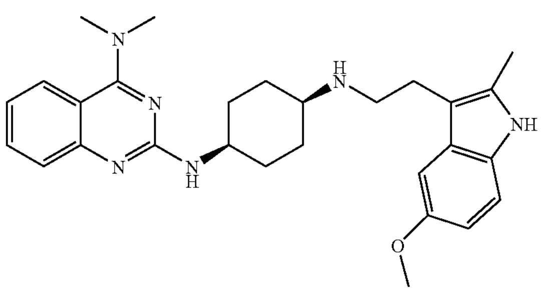 | 473 (M + H) |
| 1472 | 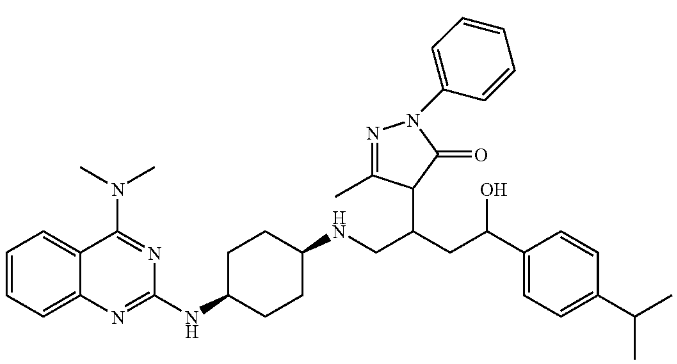 | 648 (M + H) |

-continued
| Example No. | Structure | APCI-MS |
|---|---|---|
| 1473 | 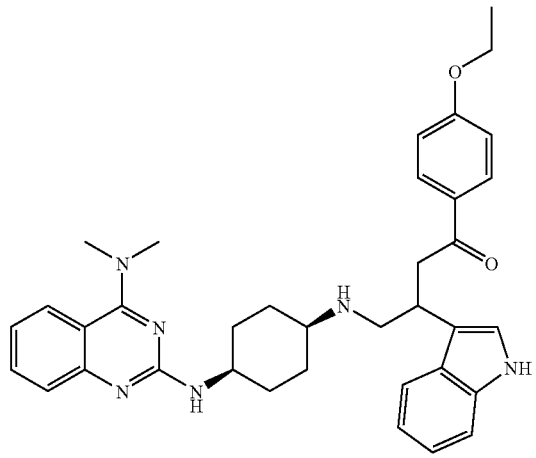 | 591 (M + H) |
| 1474 | 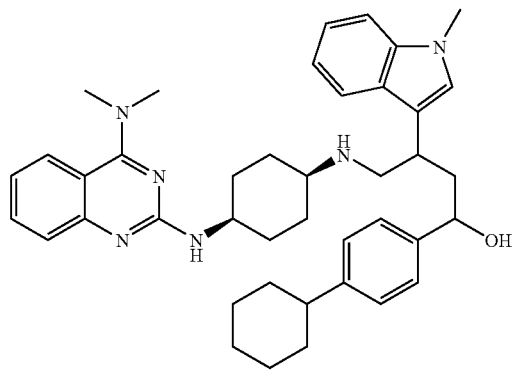 | 645 (M + H) |
| 1475 | 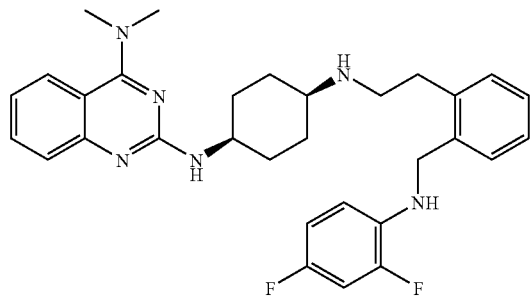 | 531 (M + H) |
| 1476 | 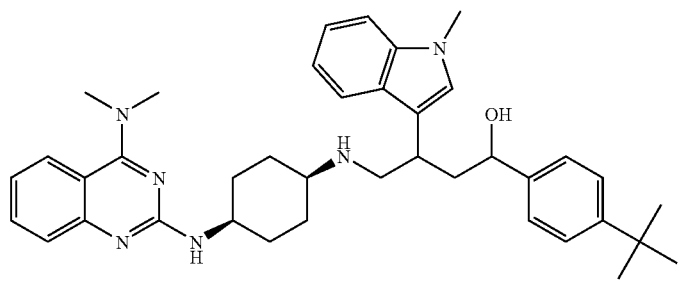 | 619 (M + H) |

| Example No. | Structure | APCI-MS |
|---|---|---|
| 1477 | 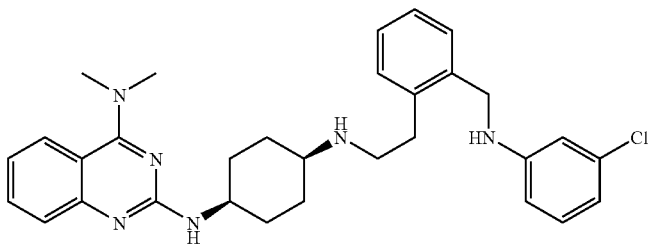 | 529 (M + H) |
| 1478 | 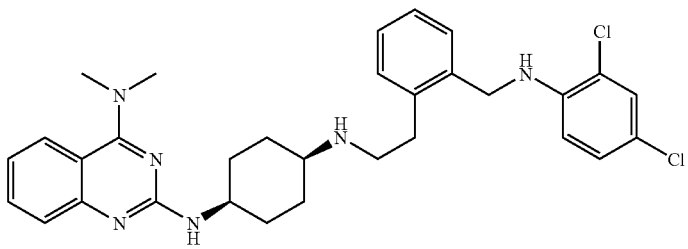 | 563 (M + H) |
| 1479 | 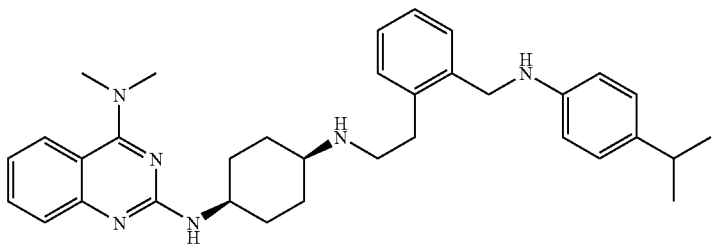 | 537 (M + H) |
| 1480 | 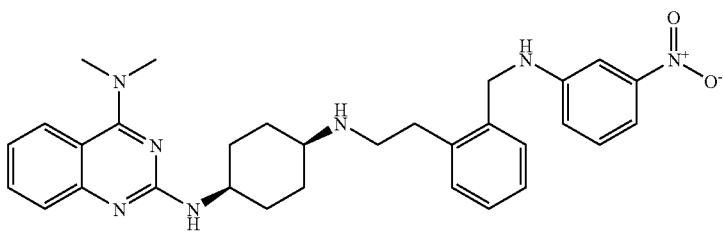 | 540 (M + H) |
| 1481 | 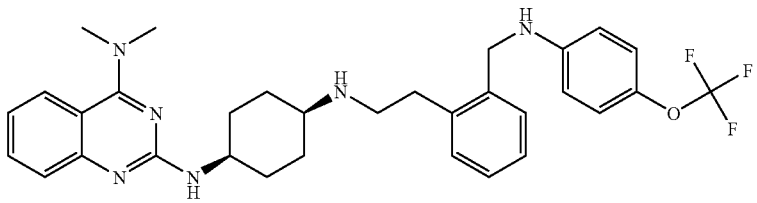 | 579 (M + H) |
| 1482 | 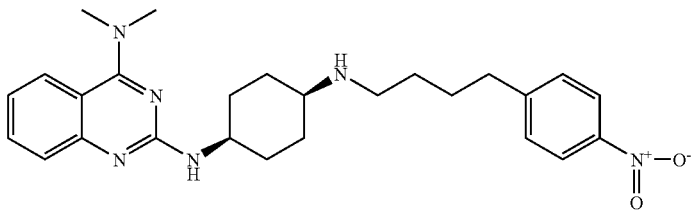 | 463 (M + H) |

-continued
| Example No. | Structure | APCI-MS |
|---|---|---|
| 1483 | 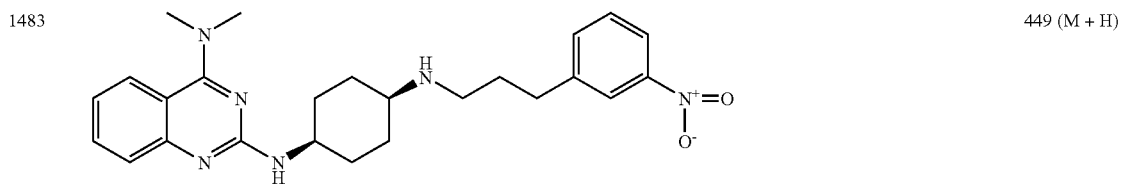 | 449 (M + H) |
| 1484 | 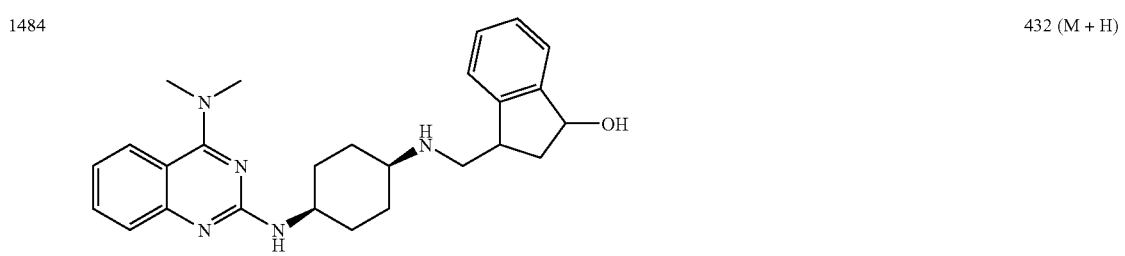 | 432 (M + H) |
| 1485 | 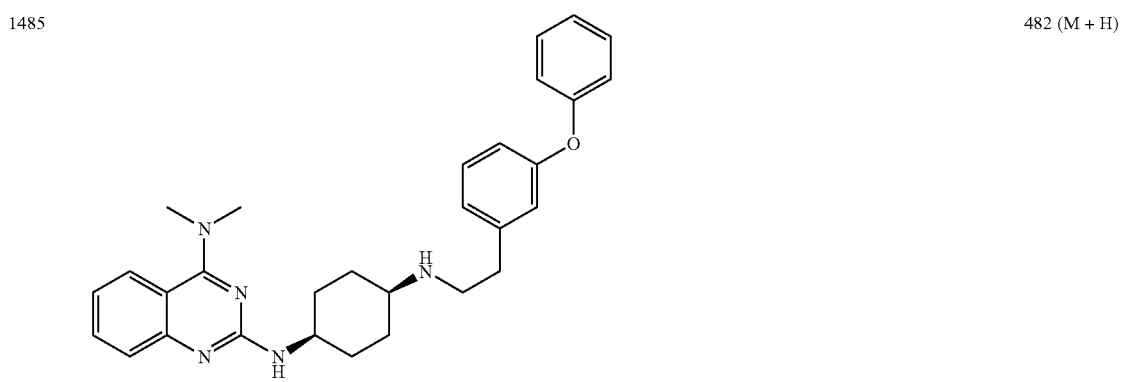 | 482 (M + H) |
| 1486 | 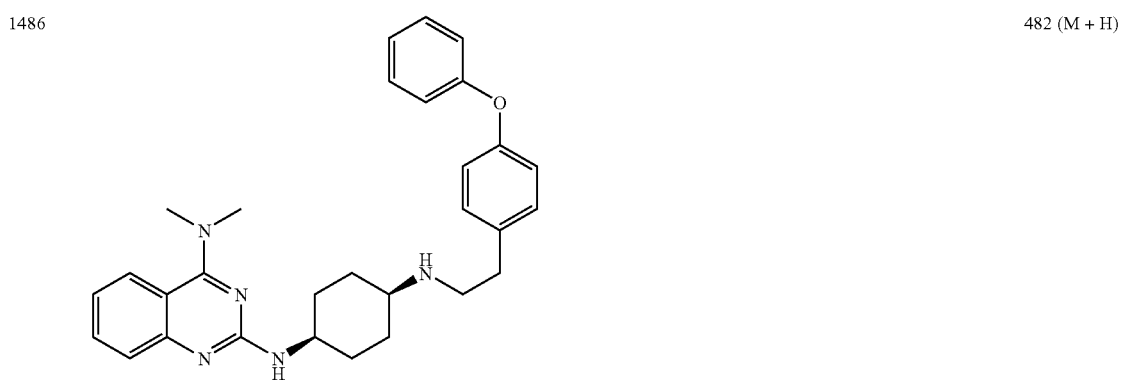 | 482 (M + H) |
| 1487 | 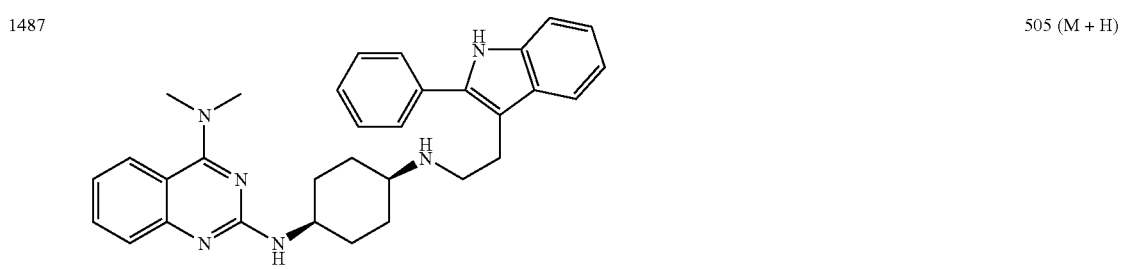 | 505 (M + H) |

-continued
| Example No. | Structure | APCI-MS |
|---|---|---|
| 1488 | 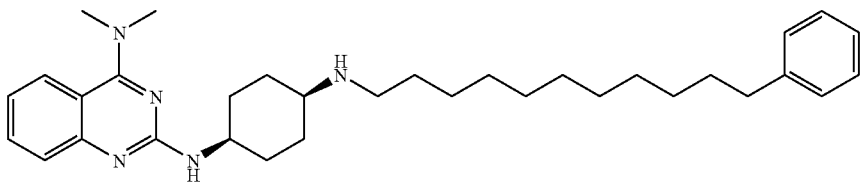 | 516 (M + H) |
| 1489 | 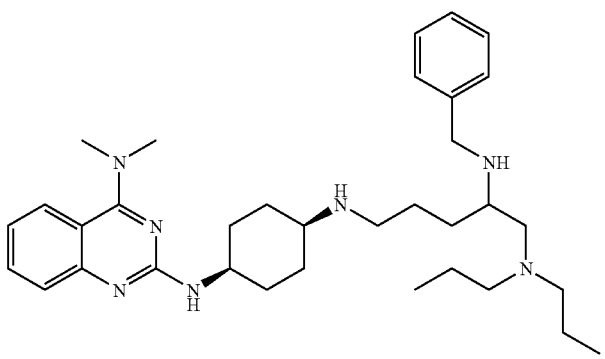 | 560 (M + H) |
| 1490 | 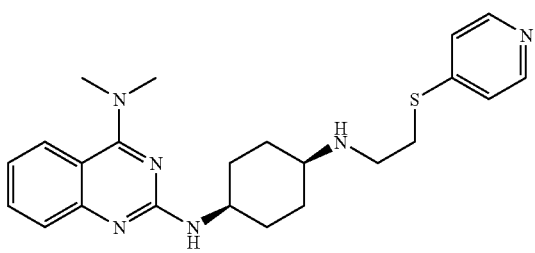 | 523 (M + H) |
| 1491 | 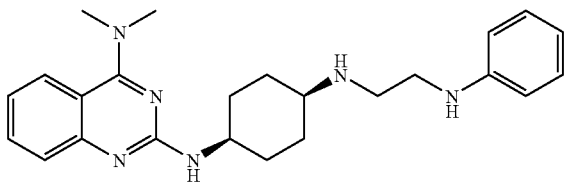 | 405 (M + H) |
| 1492 | 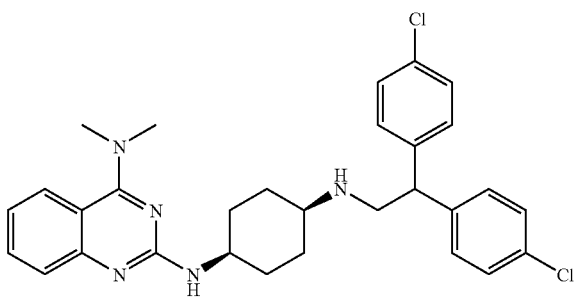 | 534 (M + H) |
| 1493 | 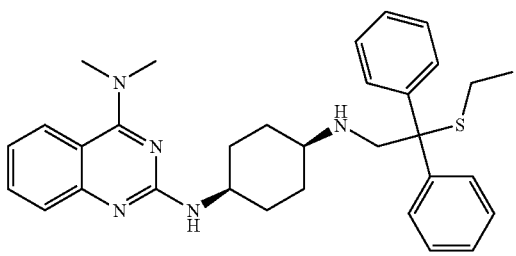 | 526 (M + H) |

-continued
| Example No. | Structure | APCI-MS |
|---|---|---|
| 1494 | 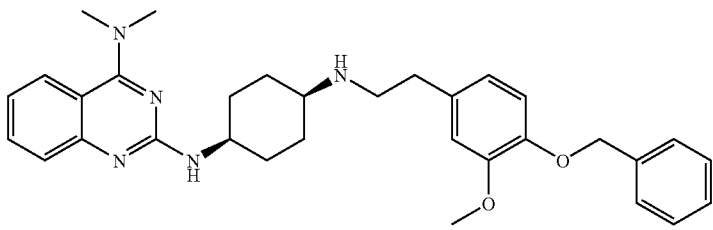 | 526 (M + H) |
| 1495 | 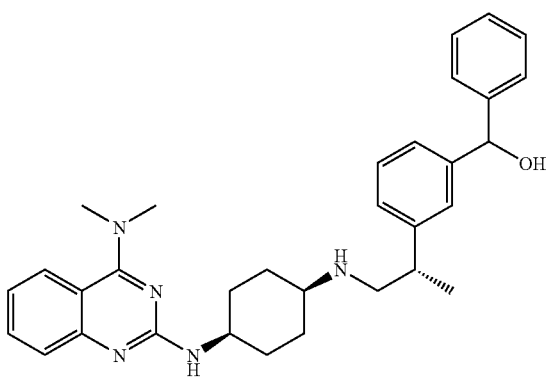 | 510 (M + H) |
| 1496 | 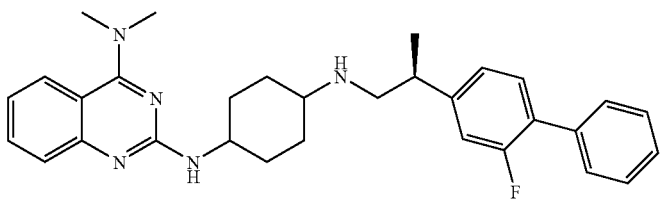 | 498 (M + H) |
| 1497 | 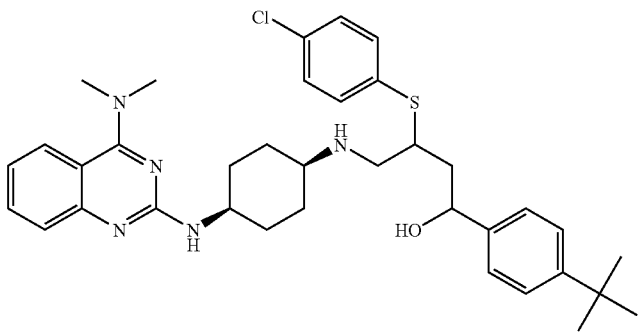 | 632 (M + H) |
| 1498 | 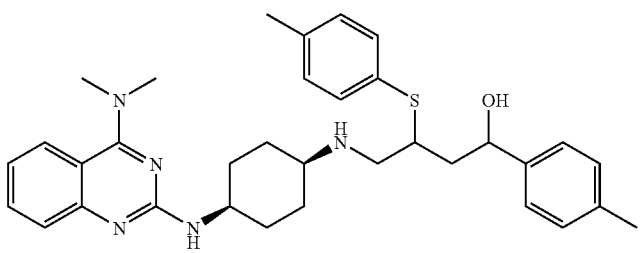 | 570 (M + H) |

-continued
| Example No. | Structure | APCI-MS |
|---|---|---|
| 1499 | 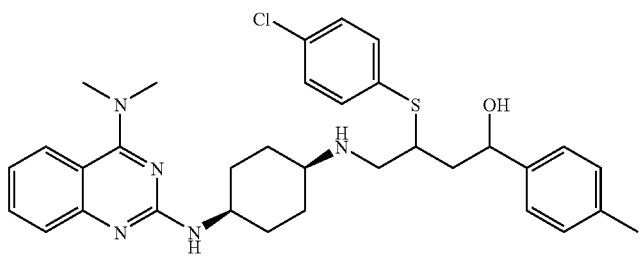 | 590 (M + H) |
| 1500 | 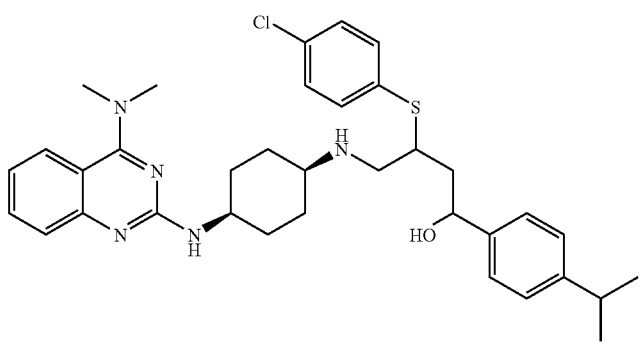 | 618 (M + H) |
| 1501 | 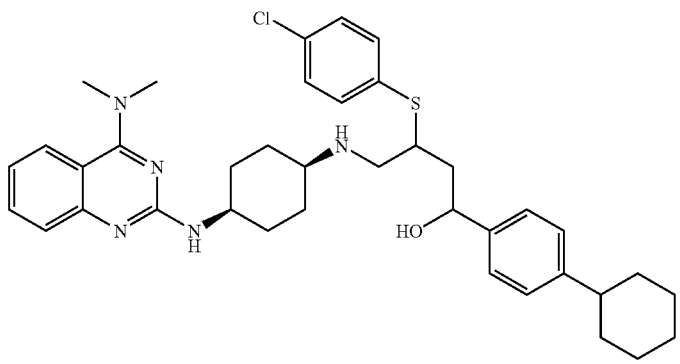 | 658 (M + H) |
| 1502 | 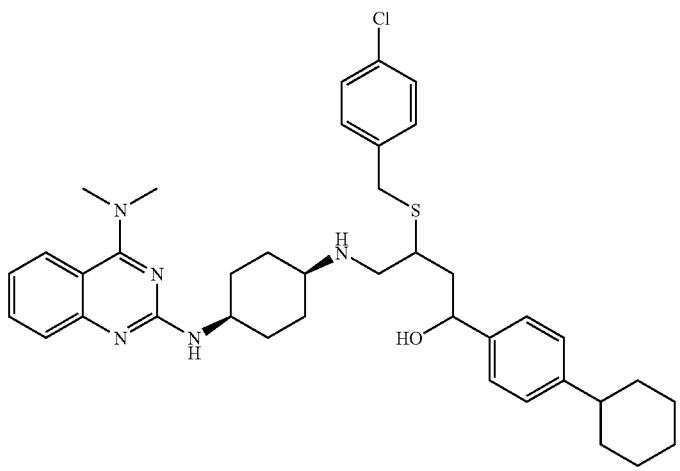 | 672 (M + H) |

-continued
| Example No. | Structure | APCI-MS |
|---|---|---|
| 1503 | 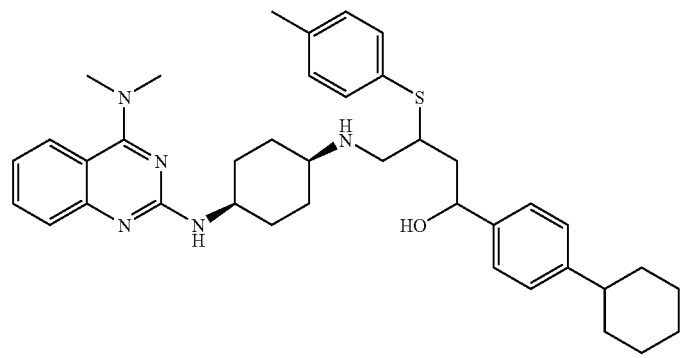 | 638 (M + H) |
| 1504 | 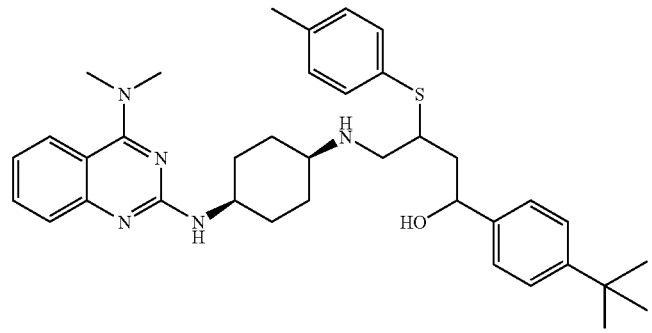 | 612 (M + H) |
| 1505 | 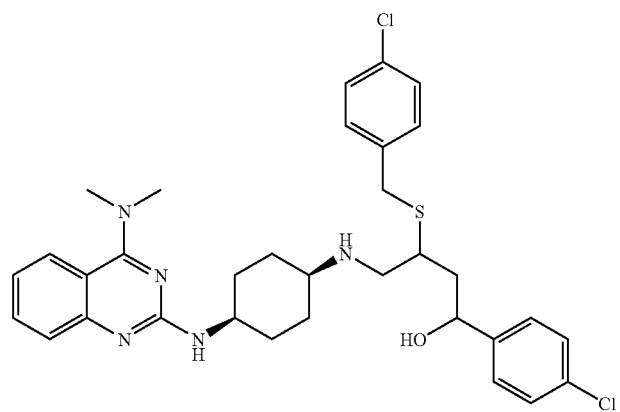 | 624 (M + H) |
| 1506 | 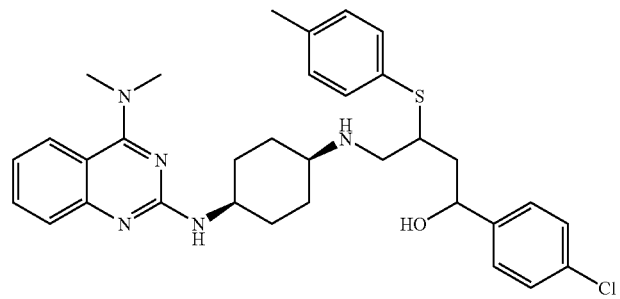 | 590 (M + H) |

| Example No. | Structure | APCI-MS |
|---|---|---|
| 1507 | 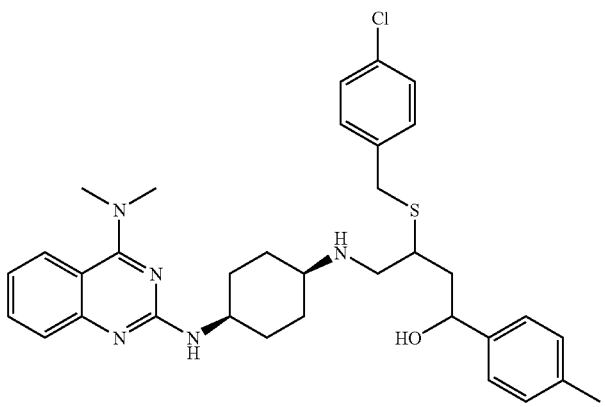 | 604 (M + H) |
| 1508 | 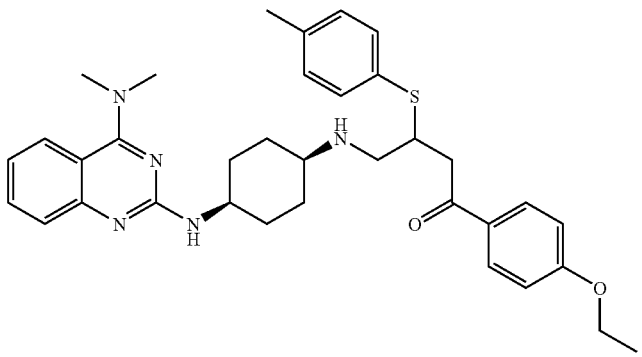 | 598 (M + H) |
| 1509 | 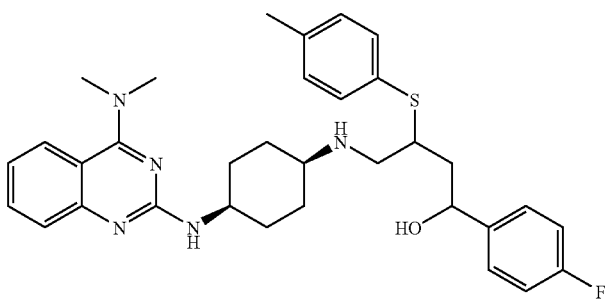 | 574 (M + H) |
| 1510 | 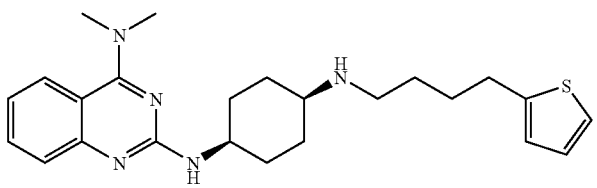 | 424 (M + H) |
| 1511 | 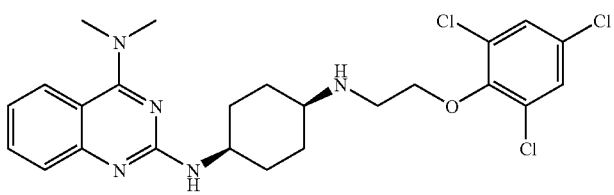 | 508 (M + H) |

-continued
| Example No. | Structure | APCI-MS |
|---|---|---|
| 1512 | 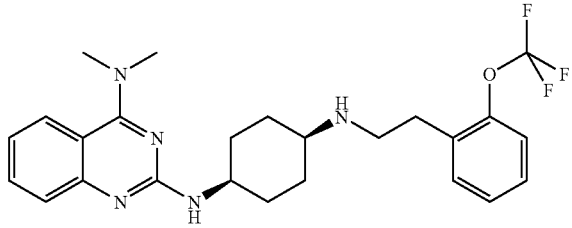 | 474 (M + H) |
| 1513 | 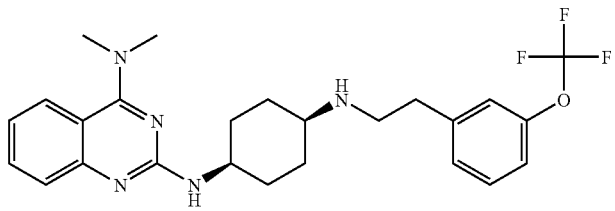 | 474 (M + H) |
| 1514 | 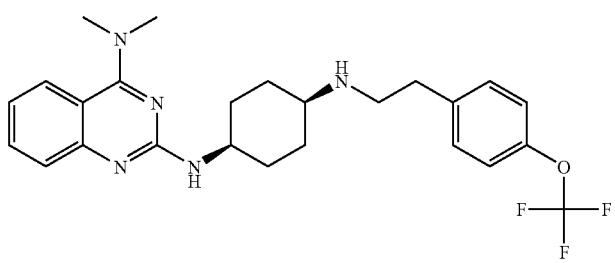 | 474 (M + H) |
| 1515 | 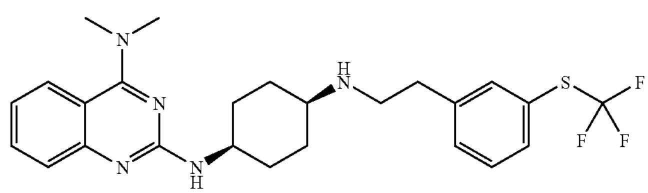 | 490 (M + H) |
| 1516 | 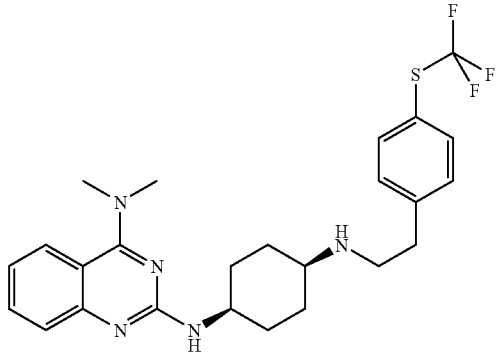 | 490 (M + H) |
| 1517 | 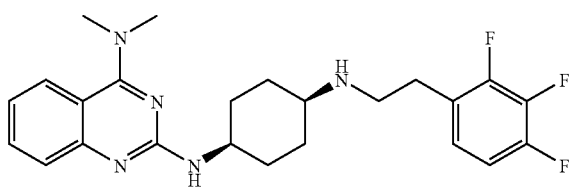 | 444 (M + H) |

-continued
| Example No. | Structure | APCI-MS |
|---|---|---|
| 1518 | 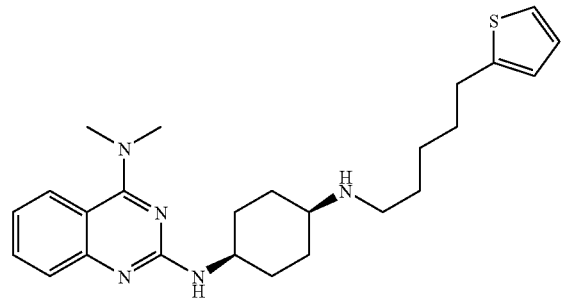 | 438 (M + H) |
| 1519 | 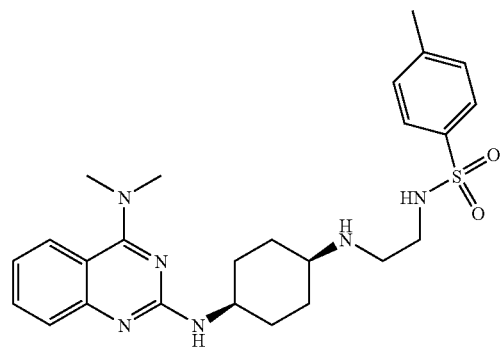 | 483 (M + H) |
| 1520 | 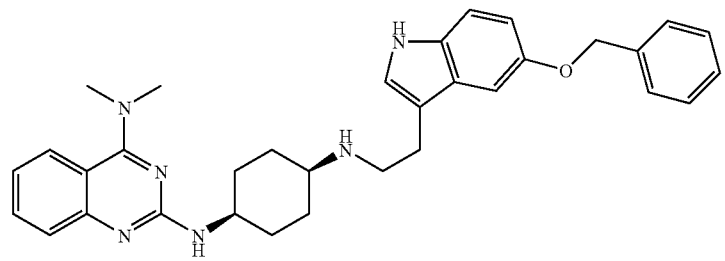 | 535 (M + H) |
| 1521 | 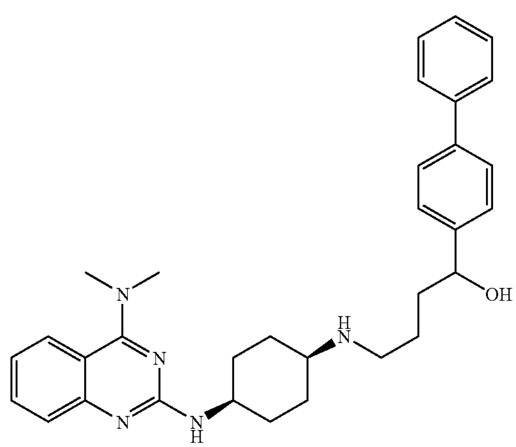 | 510 (M + H) |

-continued
| Example No. | Structure | APCI-MS |
|---|---|---|
| 1522 | 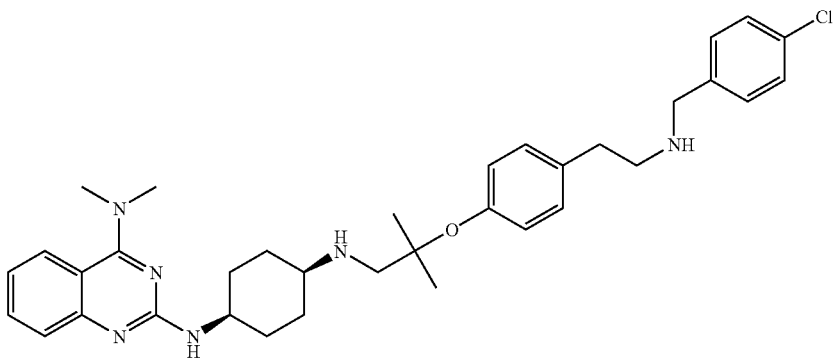 | 601 (M + H) |
| 1523 | 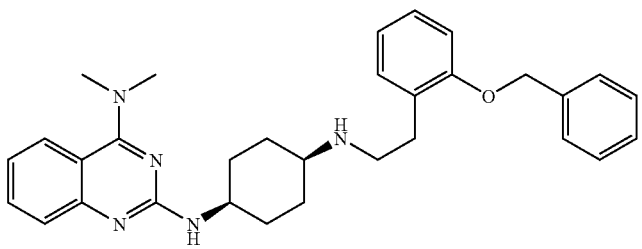 | 496 (M + H) |
| 1524 | 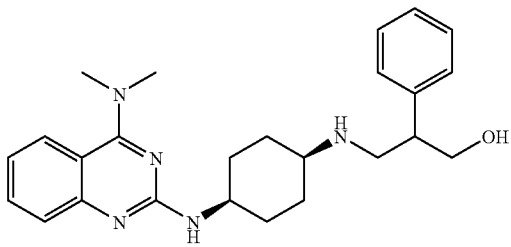 | 420 (M + H) |
| 1525 | 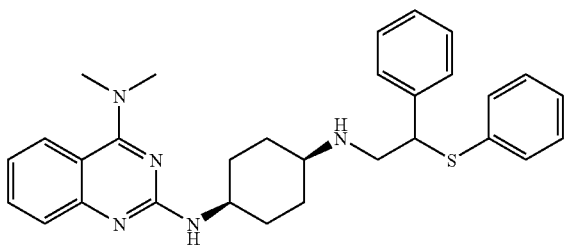 | 498 (M + H) |
| 1526 | 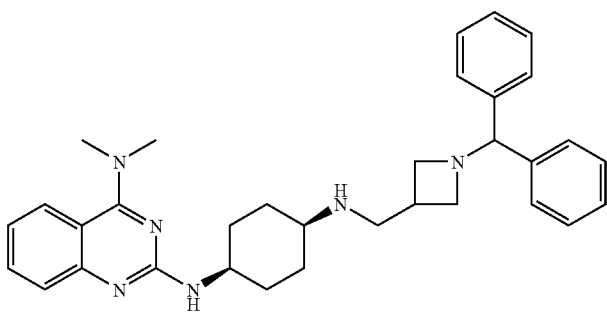 | 521 (M + H) |

-continued
| Example No. | Structure | APCI-MS |
|---|---|---|
| 1527 | 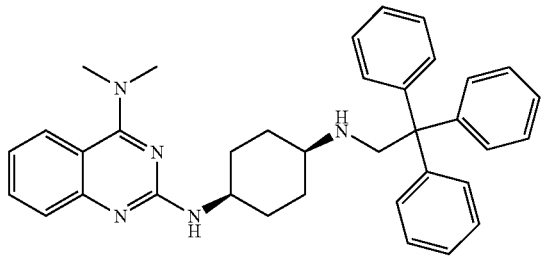 | 542 (M + H) |
| 1528 | 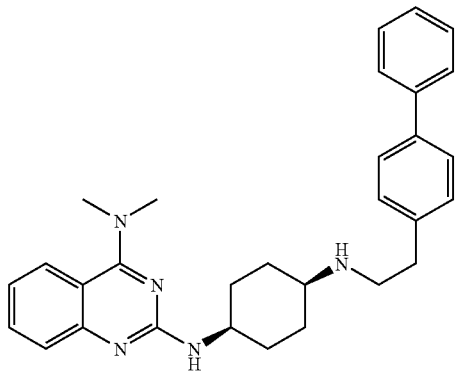 | 466 (M + H) |
| 1529 | 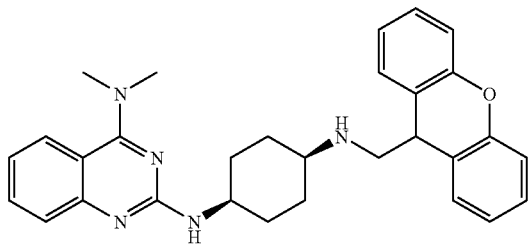 | 480 (M + H) |
| 1530 | 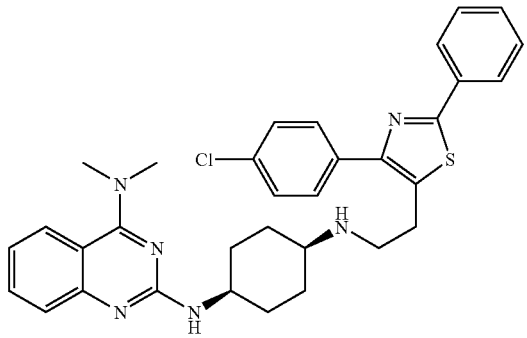 | 583 (M + H) |
| 1531 | 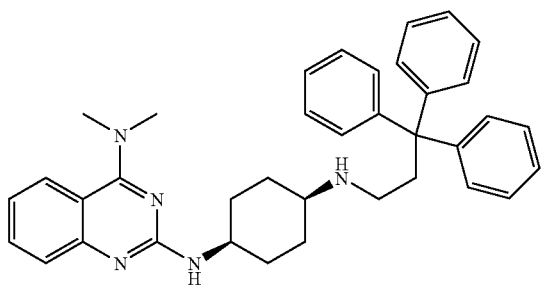 | 556 (M + H) |

-continued
| Example No. | Structure | APCI-MS |
|---|---|---|
| 1532 | 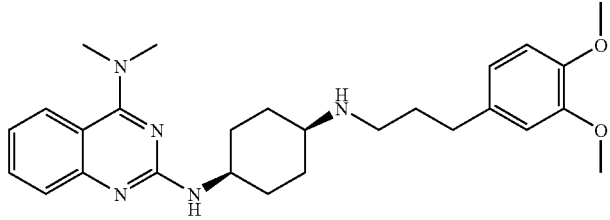 | 464 (M + H) |
| 1533 | 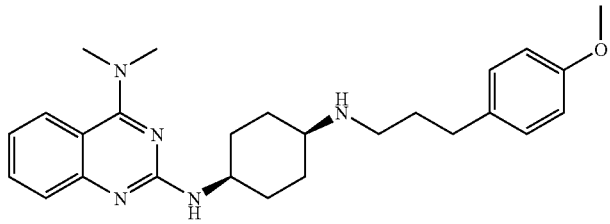 | 434 (M + H) |
| 1534 | 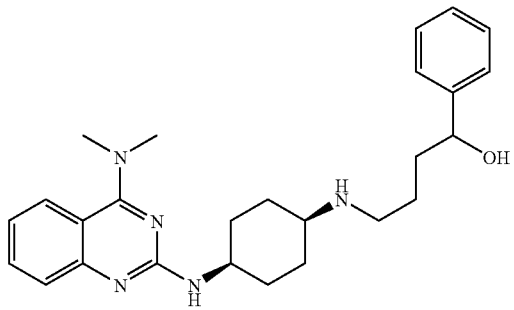 | 434 (M + H) |
| 1535 | 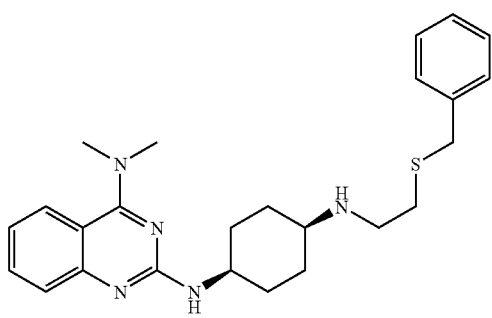 | 436 (M + H) |
| 1536 | 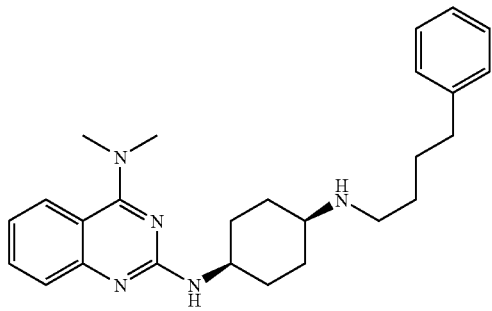 | 418 (M + H) |

-continued
| Example No. | Structure | APCI-MS |
|---|---|---|
| 1537 | 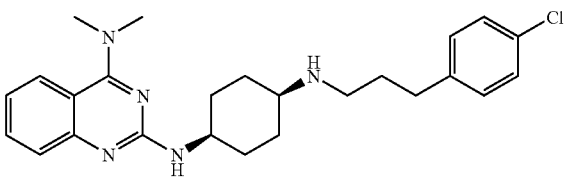 | 438 (M + H) |
| 1538 | 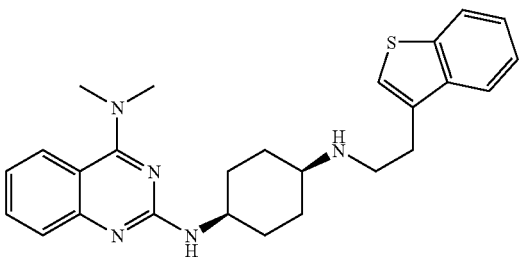 | 446 (M + H) |
| 1539 | 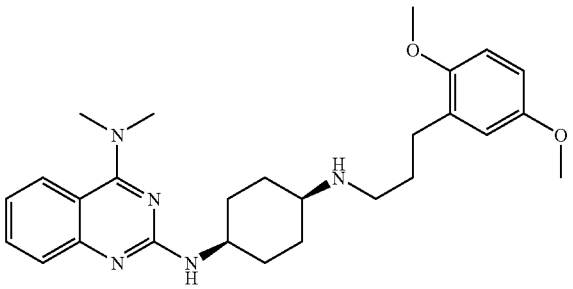 | 464 (M + H) |
| 1540 | 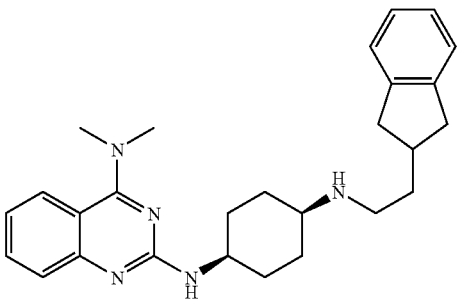 | 430 (M + H) |
| 1541 | 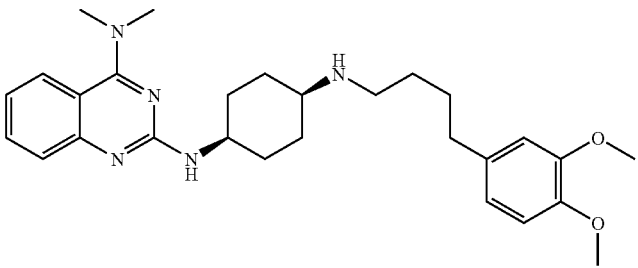 | 478 (M + H) |

-continued
| Example No. | Structure | APCI-MS |
|---|---|---|
| 1542 | 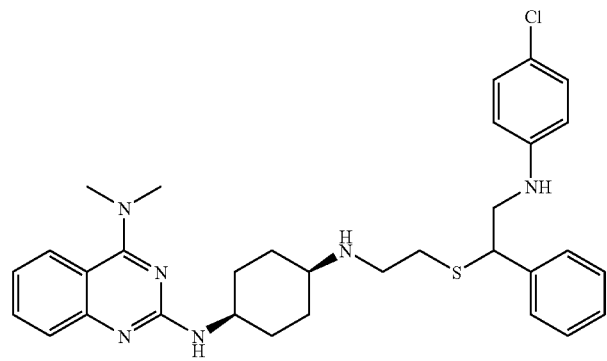 | 575 (M + H) |
| 1543 | 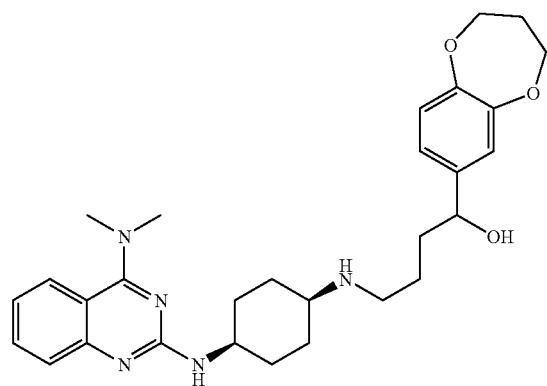 | 506 (M + H) |
| 1544 | 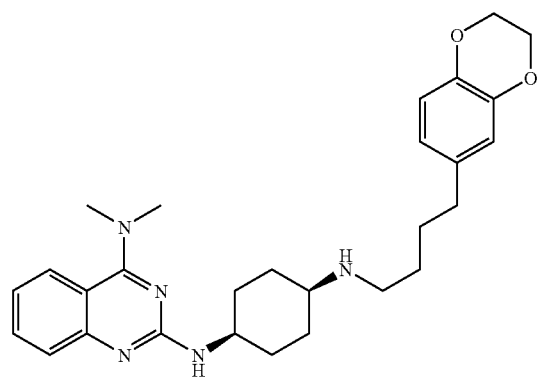 | 476 (M + H) |
| 1545 | 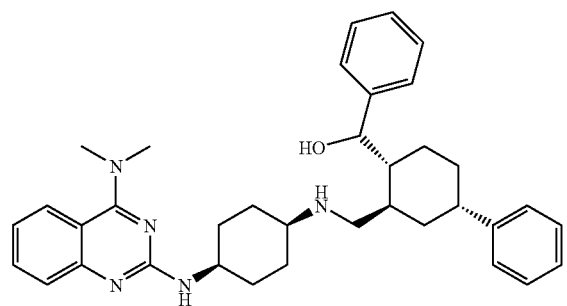 | 564 (M + H) |

-continued
| Example No. | Structure | APCI-MS |
|---|---|---|
| 1546 | 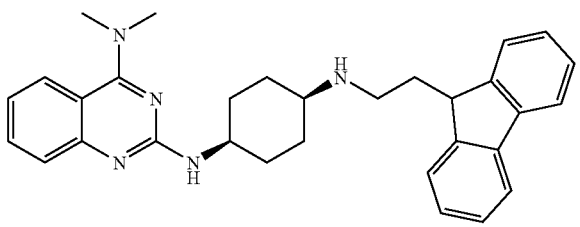 | 478 (M + H) |
| 1547 | 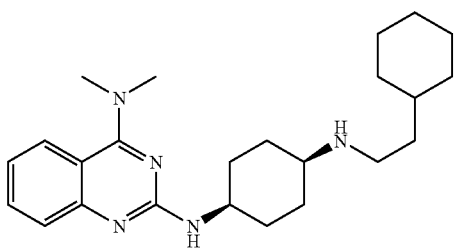 | 396 (M + H) |
| 1548 | 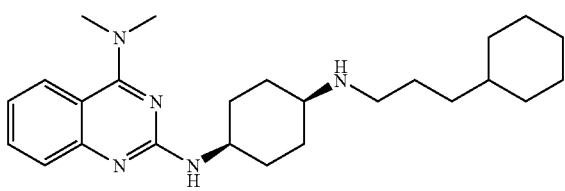 | 410 (M + H) |
| 1549 | 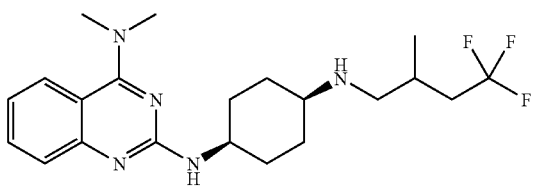 | 410 (M + H) |
| 1550 | 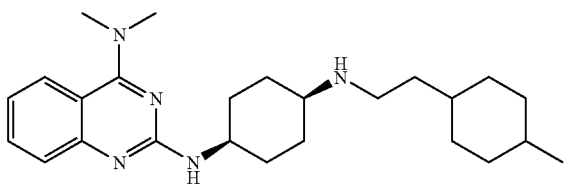 | 410 (M + H) |
| 1551 | 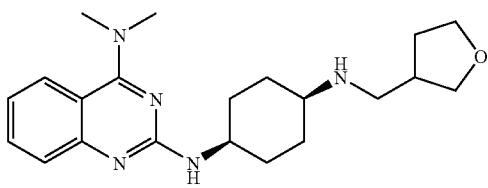 | 370 (M + H) |
| 1552 | 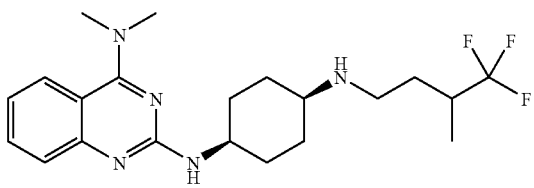 | 410 (M + H) |

-continued
| Example No. | Structure | APCI-MS |
|---|---|---|
| 1553 | 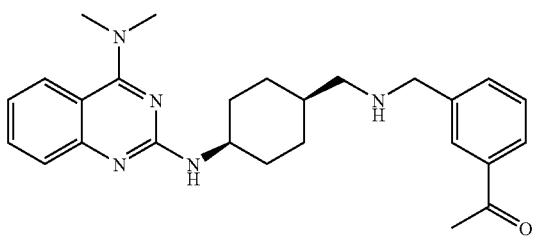 | 432 (M + H) |
| 1554 | 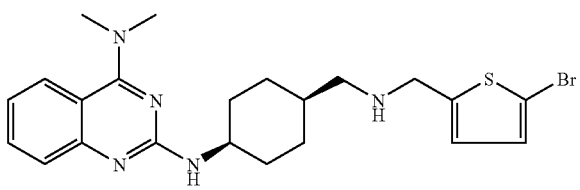 | 474 (M + H) |
| 1555 | 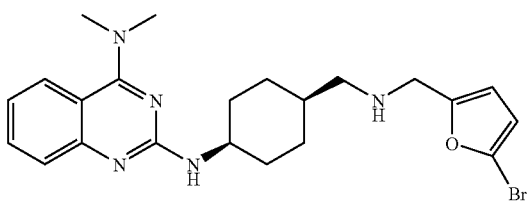 | 458 (M + H) |
| 1556 | 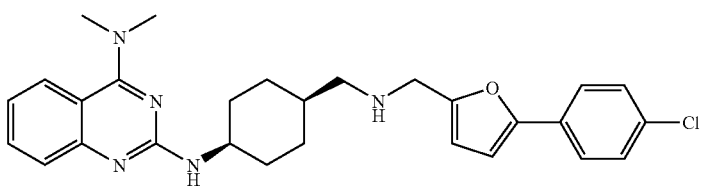 | 490 (M + H) |
| 1557 | 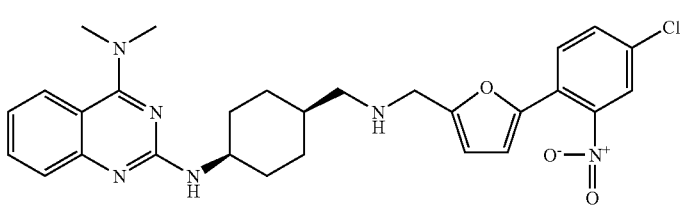 | 535 (M + H) |
| 1558 | 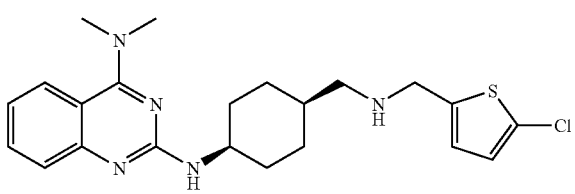 | 430 (M + H) |
| 1559 | 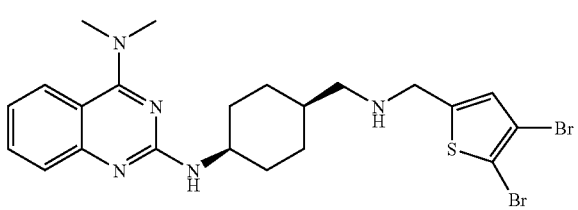 | 552 (M + H) |

-continued
| Example No. | Structure | APCI-MS |
|---|---|---|
| 1560 | 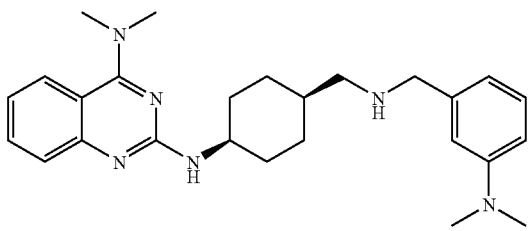 | 433 (M + H) |
| 1561 | 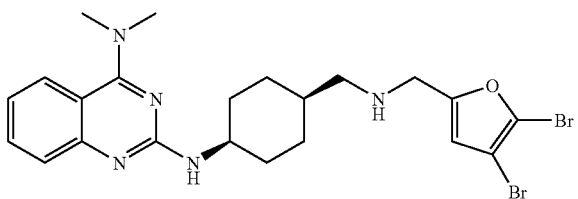 | 536 (M + H) |
| 1562 | 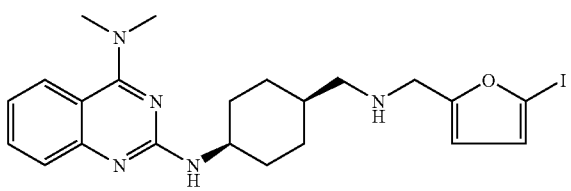 | 506 (M + H) |
| 1563 | 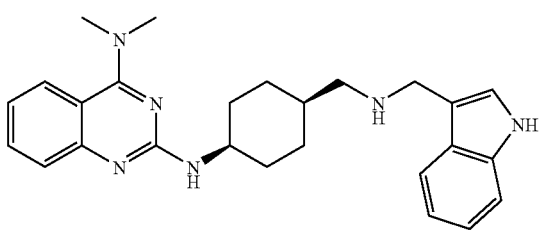 | 429 (M + H) |
| 1564 | 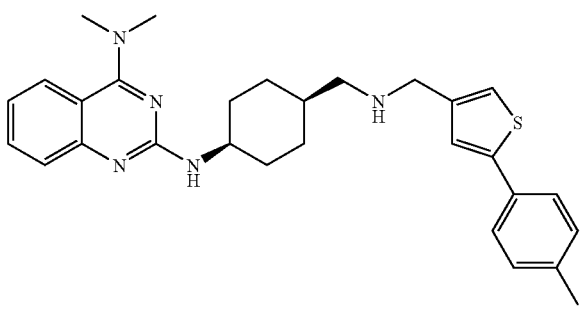 | 486 (M + H) |
| 1565 | 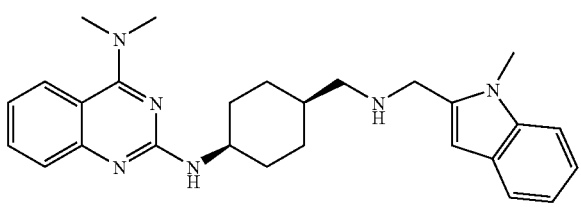 | 443 (M + H) |

-continued
| Example No. | Structure | APCI-MS |
|---|---|---|
| 1566 | 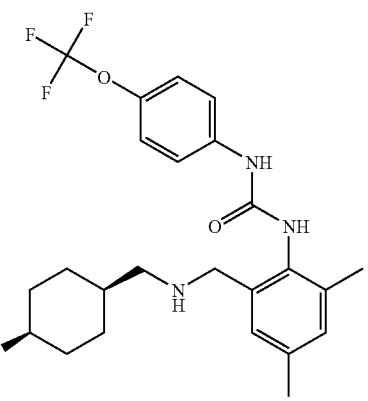 | 636 (M + H) |
| 1567 | 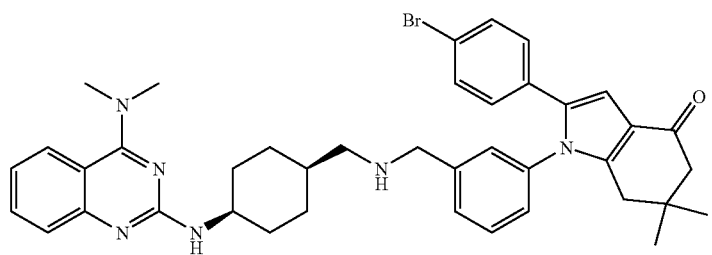 | 705 (M + H) |
| 1568 | 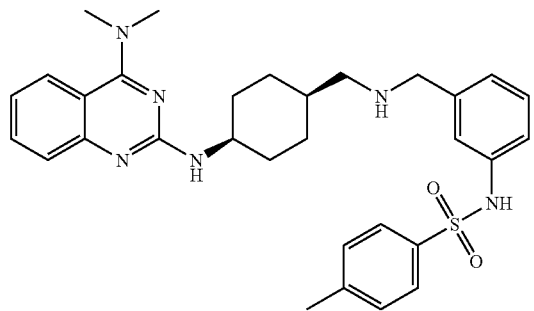 | 559 (M + H) |
| 1569 | 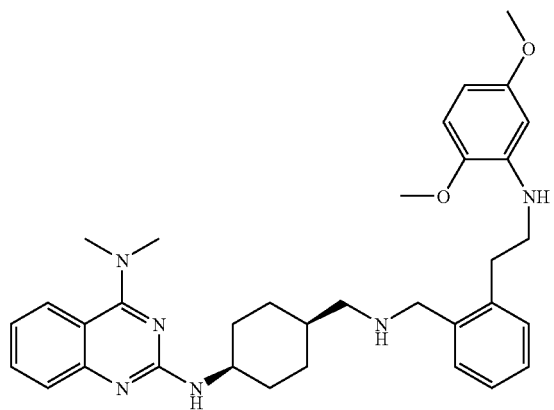 | 569 (M + H) |

-continued
| Example No. | Structure | APCI-MS |
|---|---|---|
| 1570 | 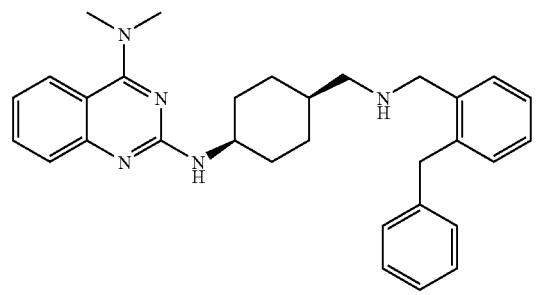 | 480 (M + H) |
| 1571 | 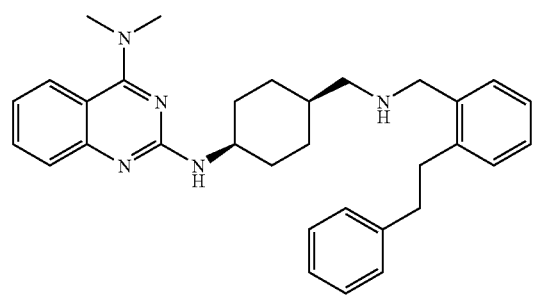 | 494 (M + H) |
| 1572 | 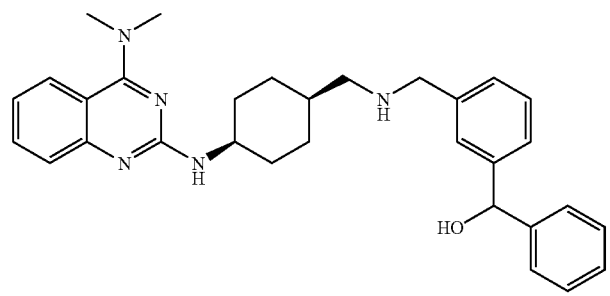 | 496 (M + H) |
| 1573 | 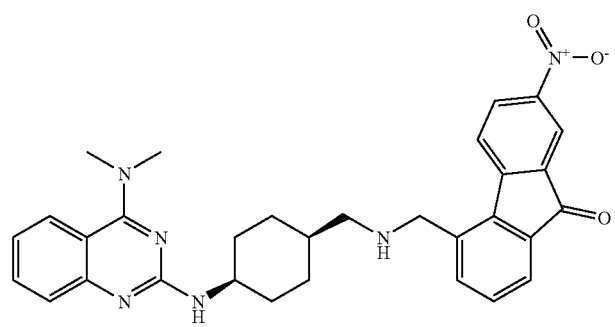 | 537 (M + H) |
| 1574 | 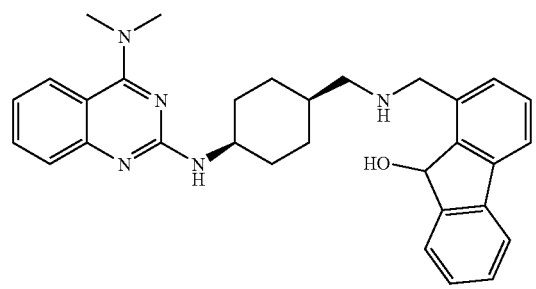 | 494 (M + H) |

-continued
| Example No. | Structure | APCI-MS |
|---|---|---|
| 1575 | 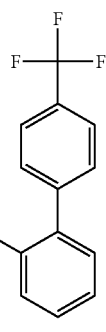 | 534 (M + H) |
| 1576 | 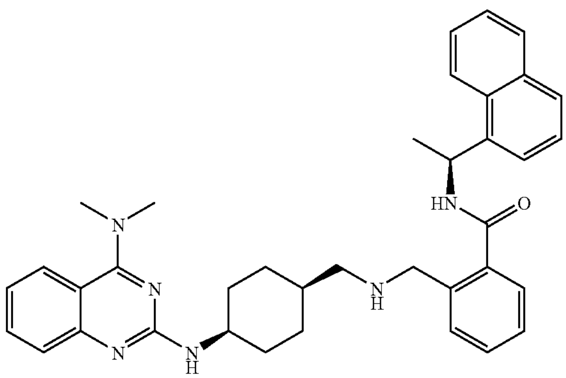 | 587 (M + H) |
| 1577 | 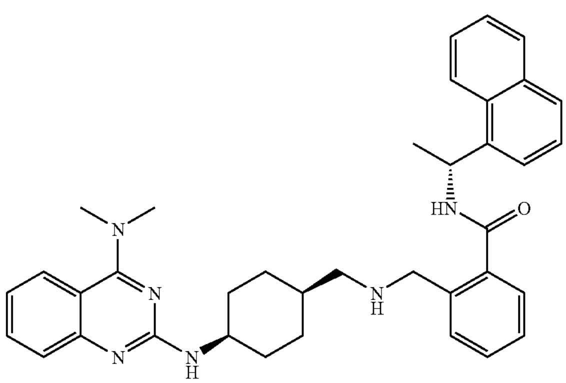 | 587 (M + H) |
| 1578 | 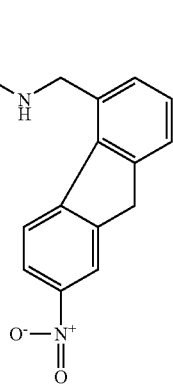 | 523 (M + H) |

-continued
| Example No. | Structure | APCI-MS |
|---|---|---|
| 1579 | 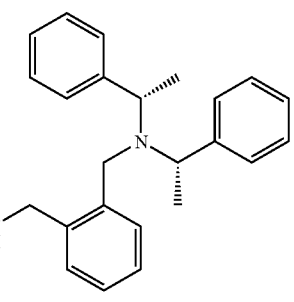 | 627 (M + H) |
| 1580 | 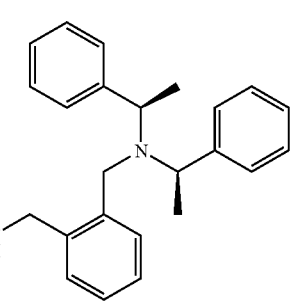 | 627 (M + H) |
| 1581 | 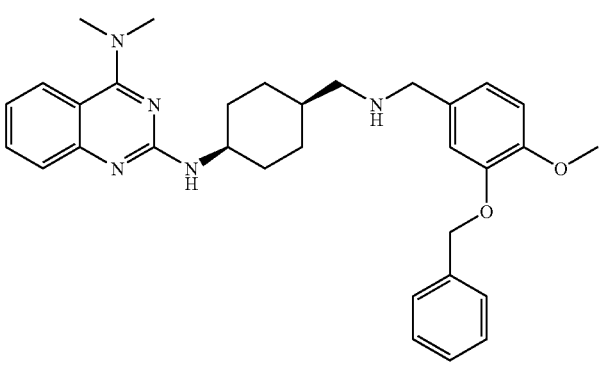 | 526 (M + H) |
| 1582 | 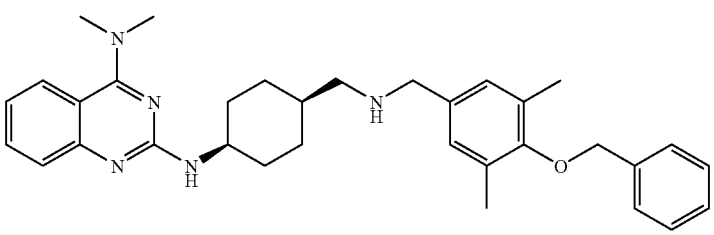 | 524 (M + H) |
| 1583 | 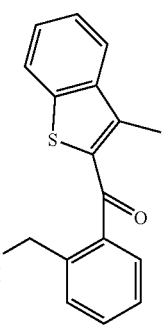 | 564 (M + H) |

-continued
| Example No. | Structure | APCI-MS |
|---|---|---|
| 1584 | 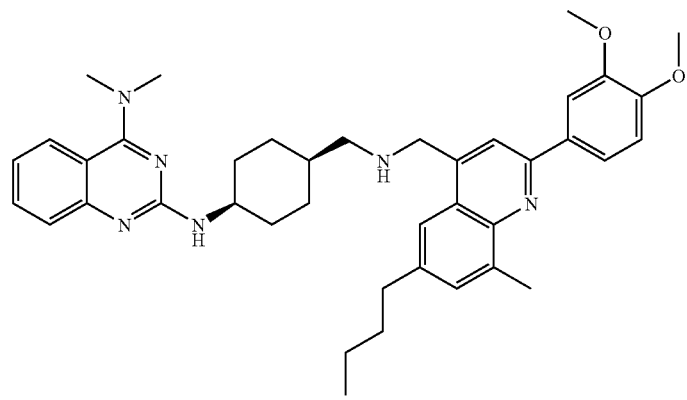 | 647 (M + H) |
| 1585 | 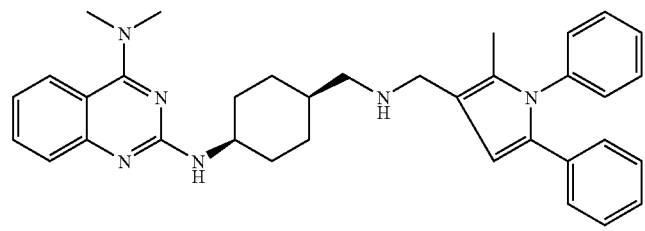 | 545 (M + H) |
| 1586 | 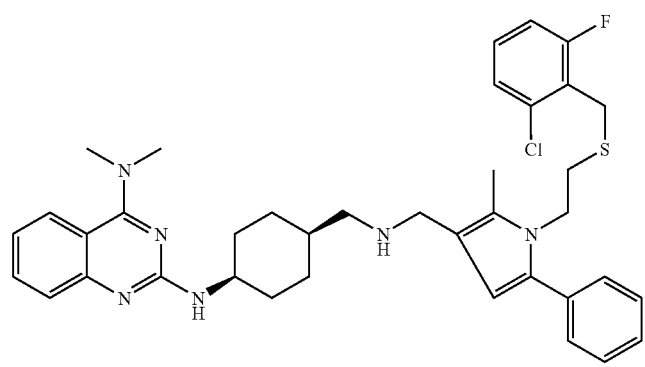 | 671 (M + H) |
| 1587 | 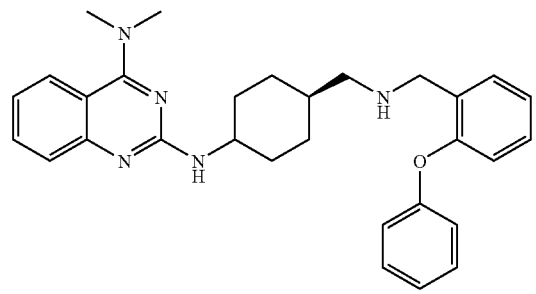 | 482 (M + H) |
| 1588 | 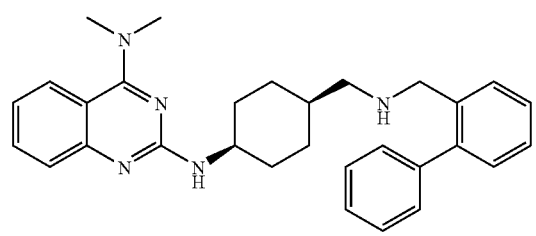 | 466 (M + H) |

-continued
| Example No. | Structure | APCI-MS |
|---|---|---|
| 1589 | 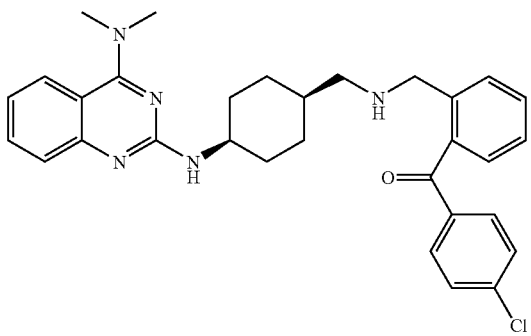 | 528 (M + H) |
| 1590 | 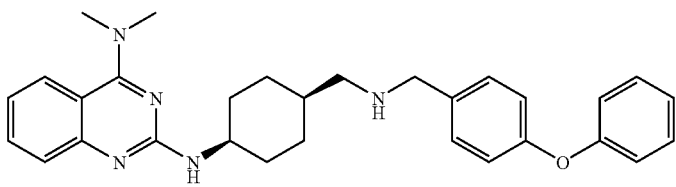 | 482 (M + H) |
| 1591 | 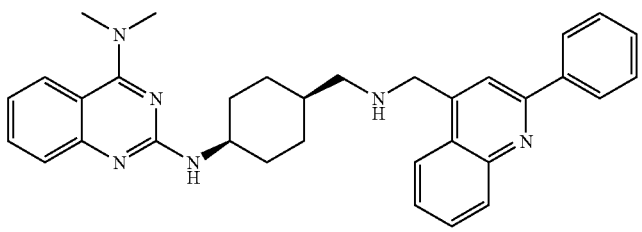 | 517 (M + H) |
| 1592 | 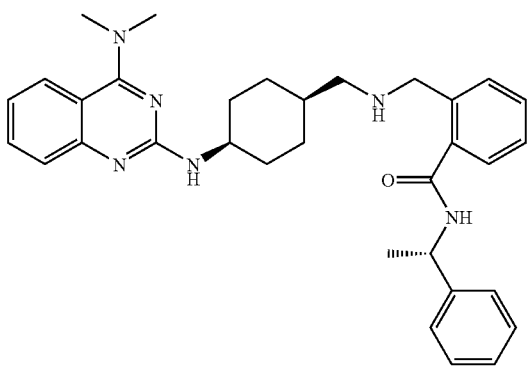 | 537 (M + H) |
| 1593 | 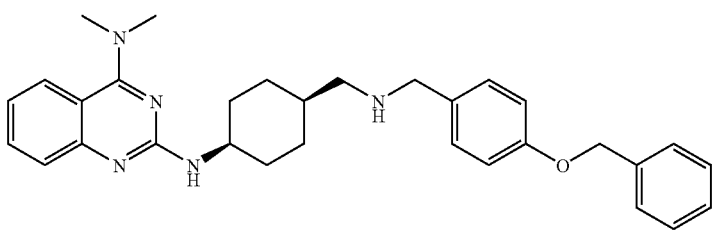 | 496 (M + H) |

-continued

| Example No. | Structure | APCI-MS |
|---|---|---|
| 1594 | 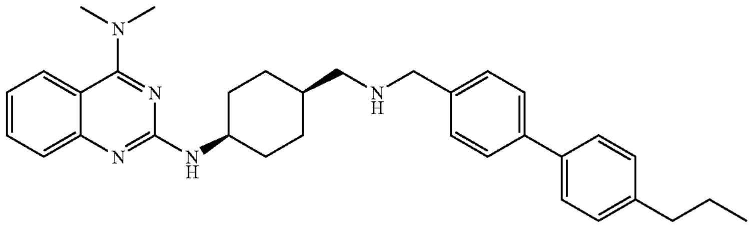 | 508 (M + H) |
| 1595 | 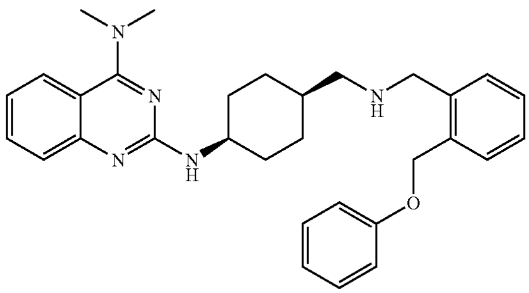 | 496 (M + H) |
| 1596 | 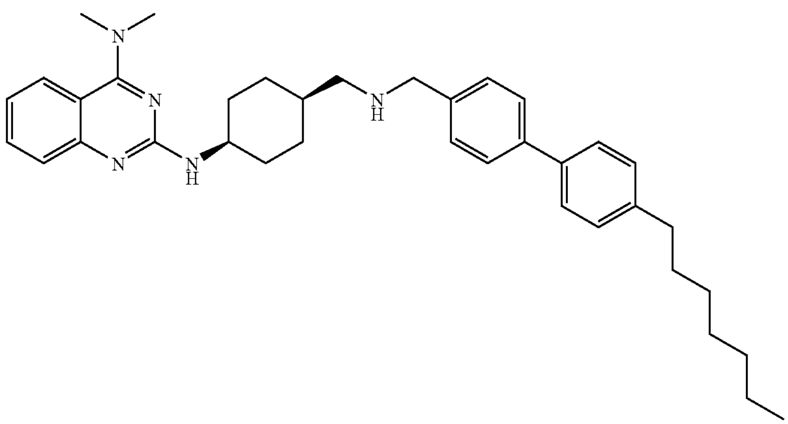 | 564 (M + H) |
| 1597 | 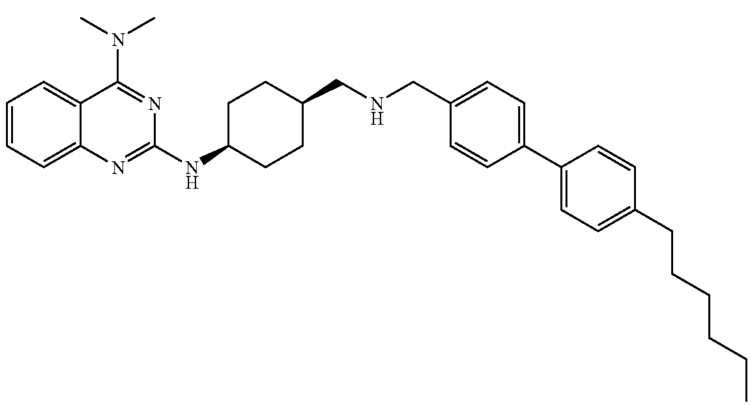 | 550 (M + H) |

-continued
| Example No. | Structure | APCI-MS |
|---|---|---|
| 1598 | 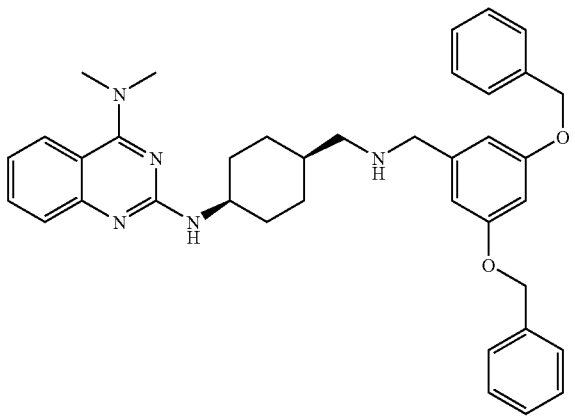 | 602 (M + H) |
| 1599 | 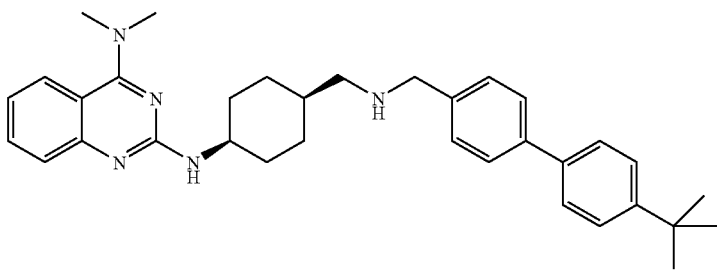 | 522 (M + H) |
| 1600 | 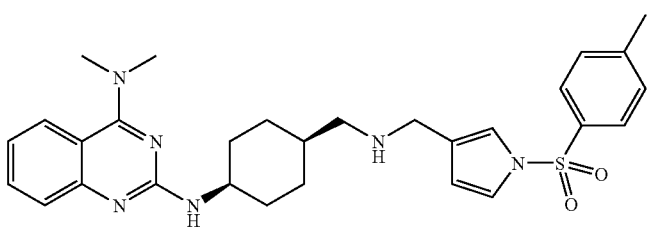 | 533 (M + H) |
| 1601 | 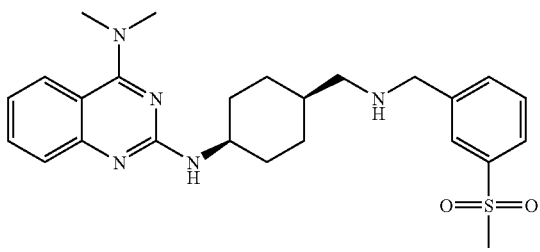 | 468 (M + H) |
| 1602 | 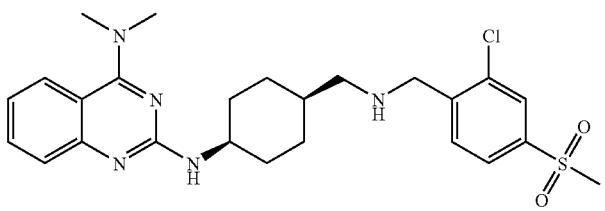 | 502 (M + H) |

-continued
| Example No. | Structure | APCI-MS |
|---|---|---|
| 1603 | 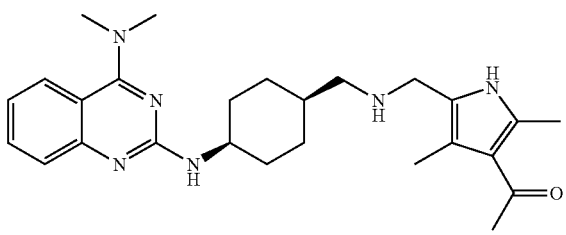 | 449 (M + H) |
| 1604 | 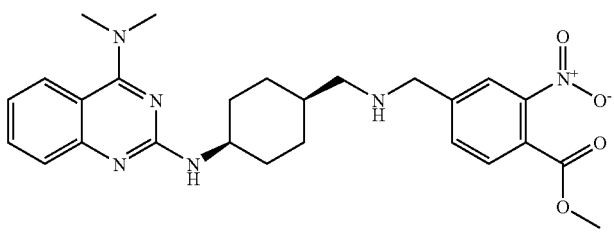 | 493 (M + H) |
| 1605 | 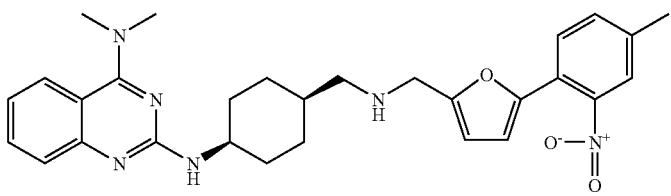 | 515 (M + H) |
| 1606 | 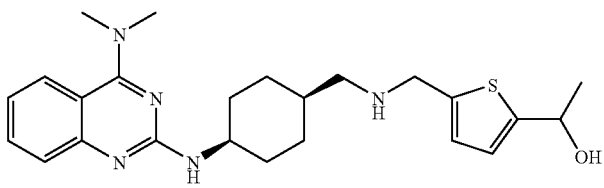 | 440 (M + H) |
| 1607 | 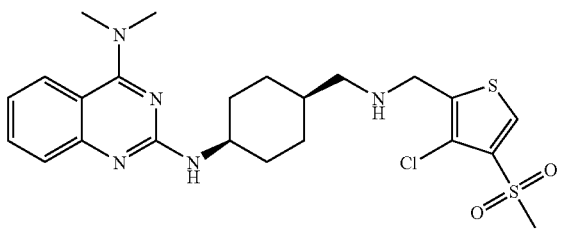 | 508 (M + H) |
| 1608 | 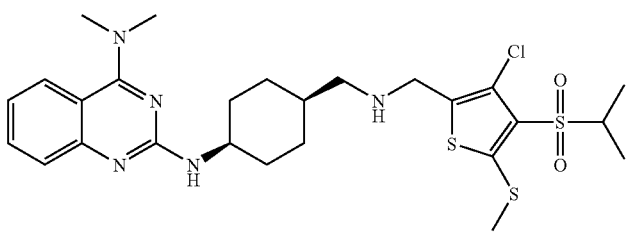 | 582 (M + H) |

-continued
| Example No. | Structure | APCI-MS |
|---|---|---|
| 1609 | 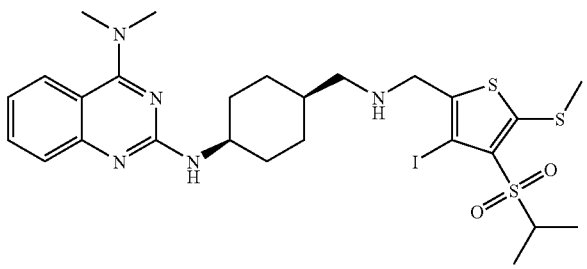 | 674 (M + H) |
| 1610 | 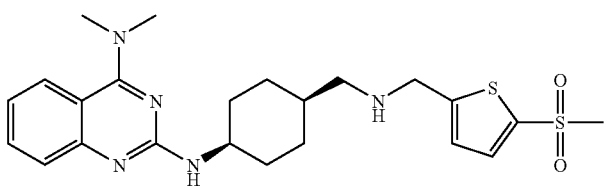 | 474 (M + H) |
| 1611 | 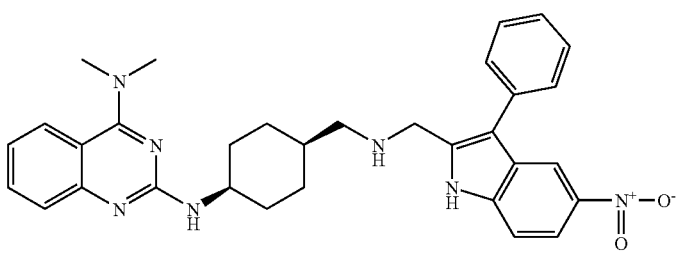 | 548 (M + H) |
| 1612 | 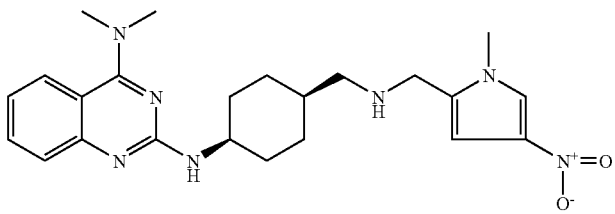 | 438 (M + H) |
| 1613 | 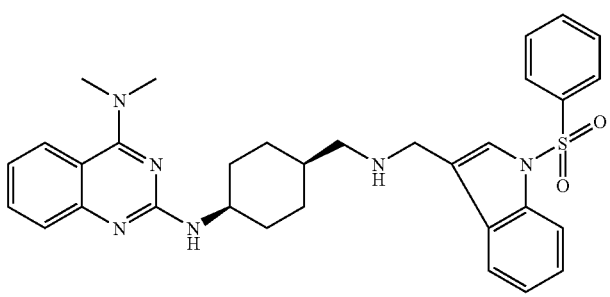 | 569 (M + H) |
| 1614 | 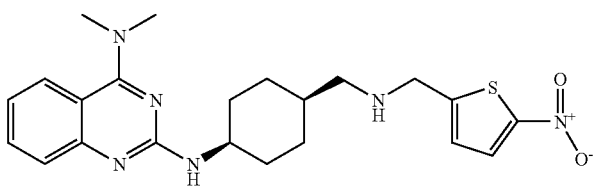 | 441 (M + H) |

-continued

| Example No. | Structure | APCI-MS |
|---|---|---|
| 1615 | 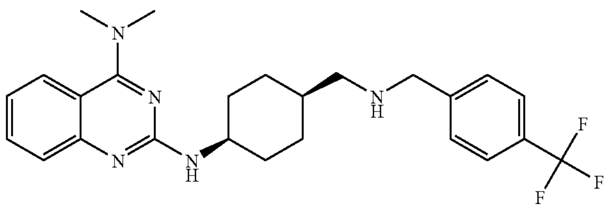 | 458 (M + H) |
| 1616 | 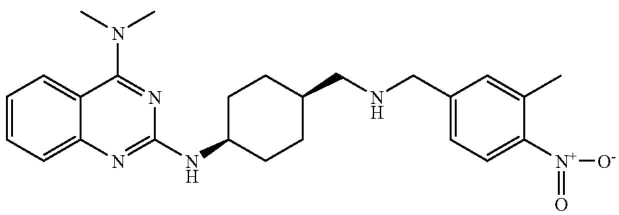 | 449 (M + H) |
| 1617 | 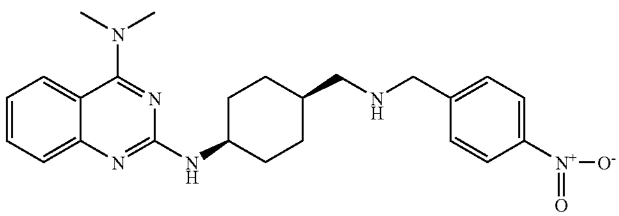 | 435 (M + H) |
| 1618 | 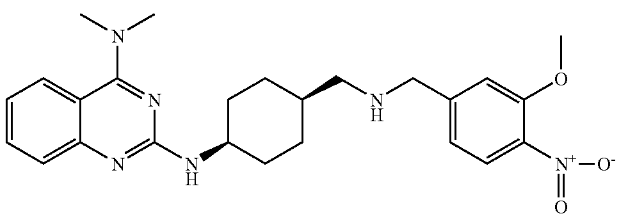 | 465 (M + H) |
| 1619 | 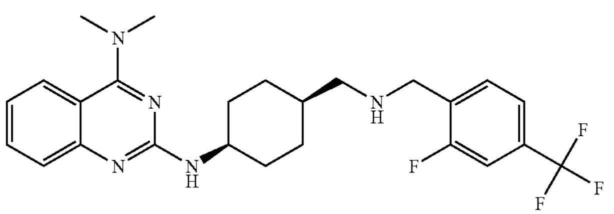 | 476 (M + H) |
| 1620 | 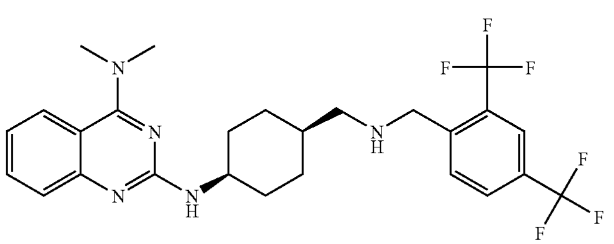 | 526 (M + H) |
| 1621 | 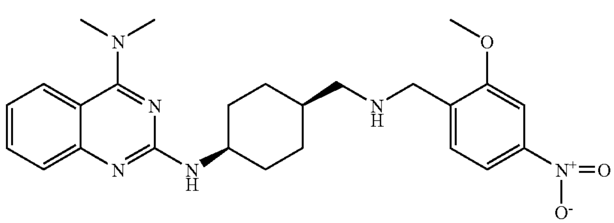 | 465 (M + H) |

-continued
| Example No. | Structure | APCI-MS |
|---|---|---|
| 1622 | 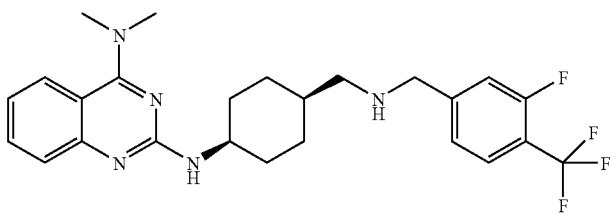 | 476 (M + H) |
| 1623 | 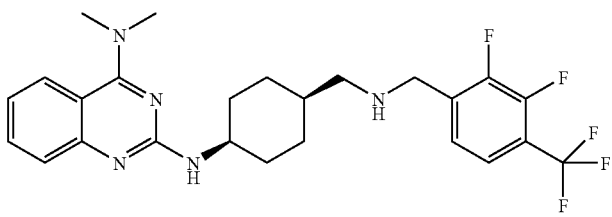 | 494 (M + H) |
| 1624 | 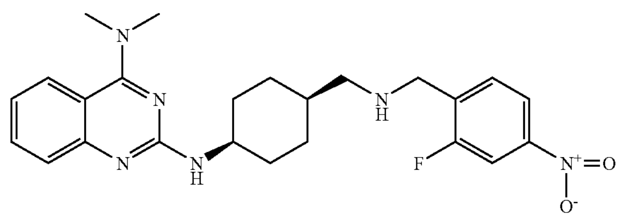 | 453 (M + H) |
| 1625 | 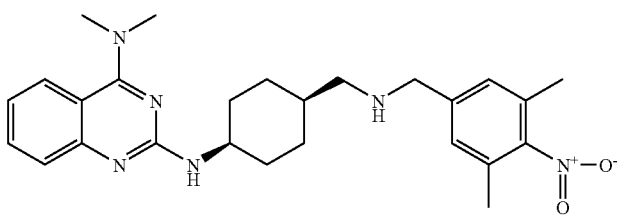 | 463 (M + H) |
| 1626 | 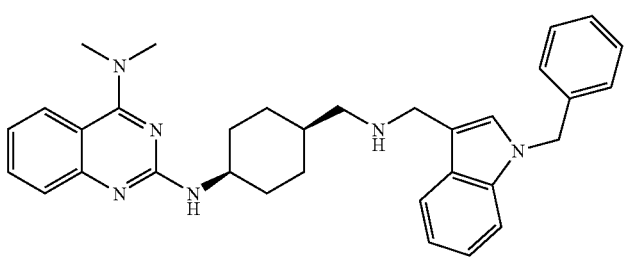 | 519 (M + H) |
| 1627 | 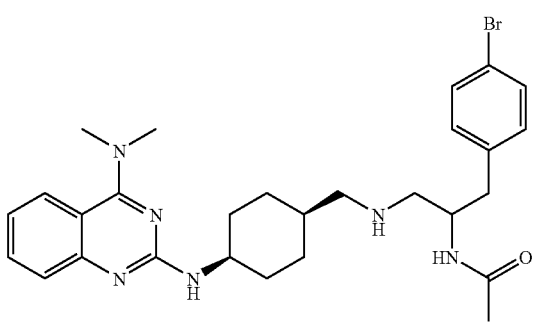 | 553 (M + H) |

-continued
| Example No. | Structure | APCI-MS |
|---|---|---|
| 1628 | 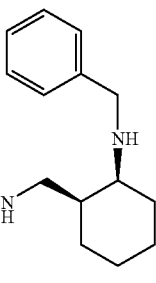 | 501 (M + H) |
| 1629 | 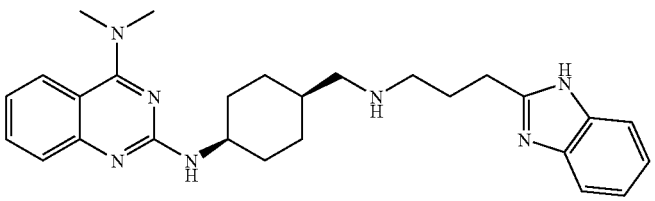 | 458 (M + H) |
| 1630 | 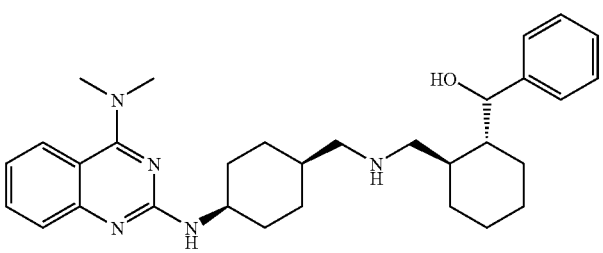 | 502 (M + H) |
| 1631 | 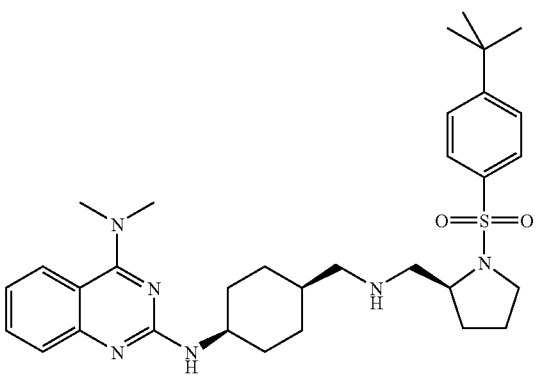 | 579 (M + H) |
| 1632 | 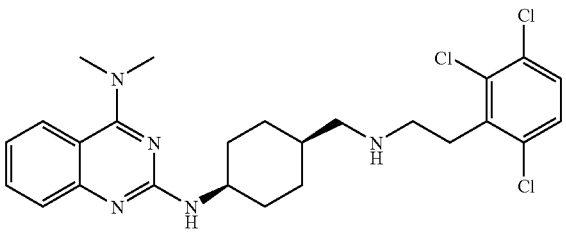 | 506 (M + H) |
| 1633 | 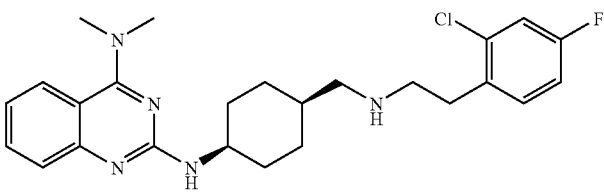 | 456 (M + H) |

-continued
| Example No. | Structure | APCI-MS |
|---|---|---|
| 1634 | 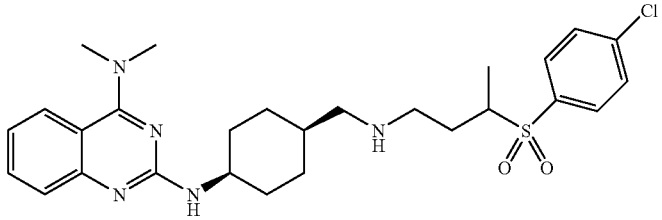 | 530 (M + H) |
| 1635 | 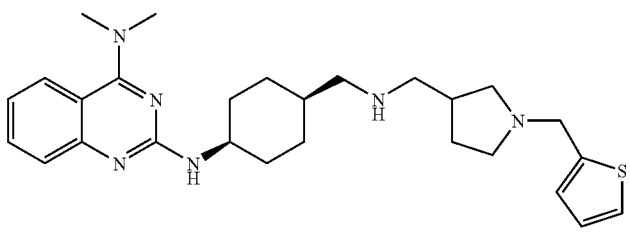 | 479 (M + H) |
| 1636 | 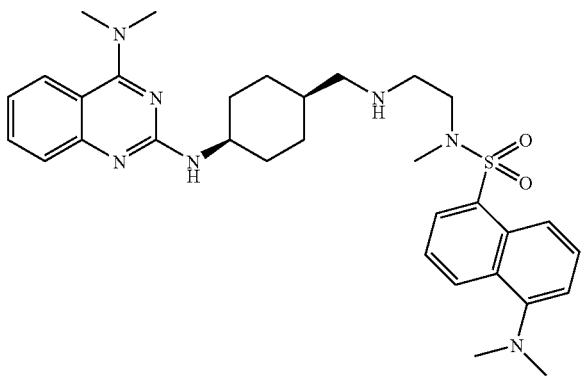 | 590 (M + H) |
| 1637 | 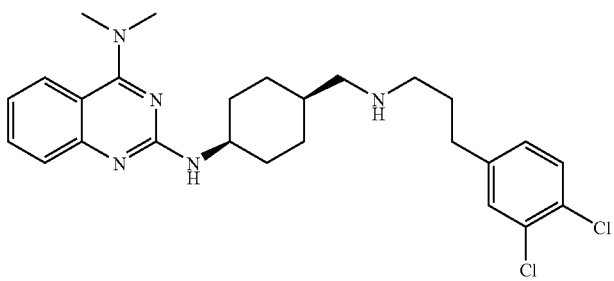 | 486 (M + H) |
| 1638 | 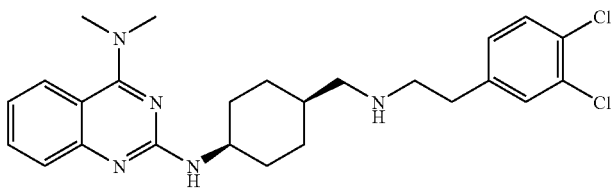 | 472 (M + H) |
| 1639 | 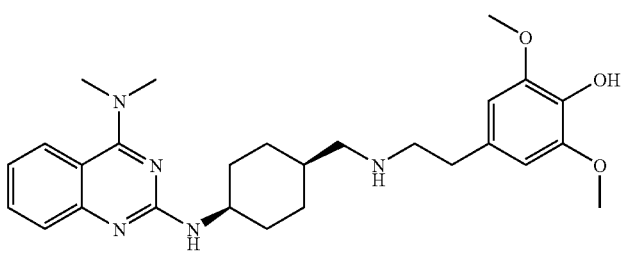 | 480 (M + H) |

-continued
| Example No. | Structure | APCI-MS |
|---|---|---|
| 1640 | 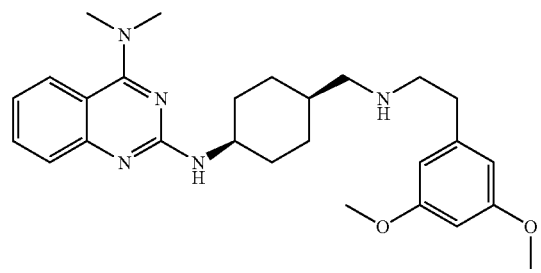 | 464 (M + H) |
| 1641 | 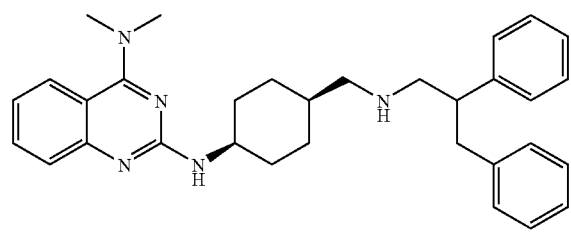 | 494 (M + H) |
| 1642 | 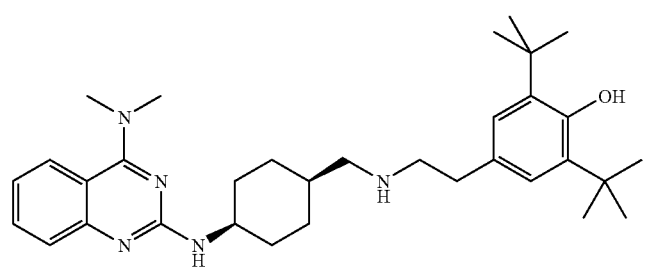 | 532 (M + H) |
| 1643 | 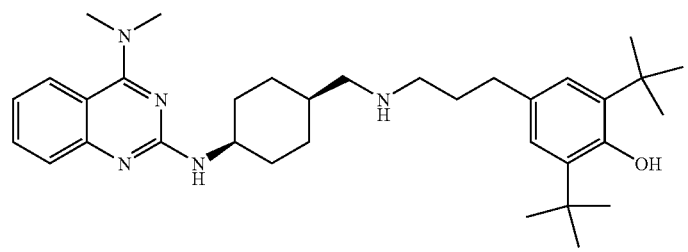 | 546 (M + H) |
| 1644 | 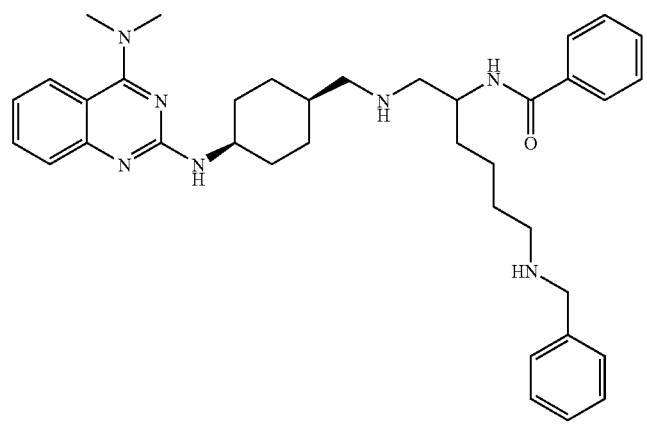 | 608 (M + H) |

-continued
| Example No. | Structure | APCI-MS |
|---|---|---|
| 1645 | 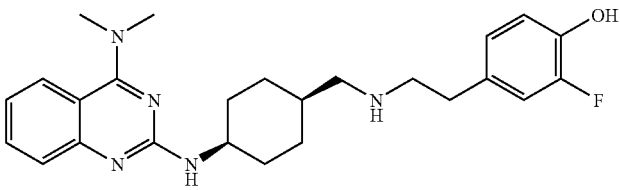 | 438 (M + H) |
| 1646 | 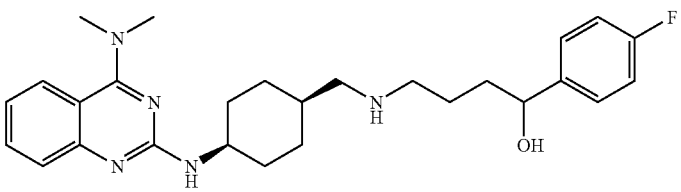 | 466 (M + H) |
| 1647 | 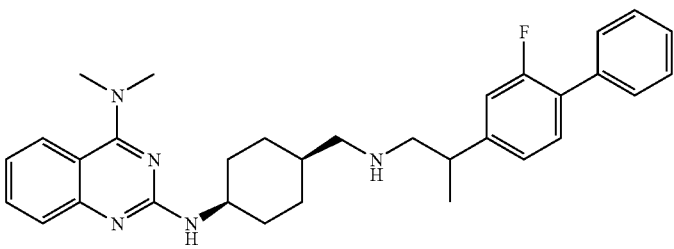 | 512 (M + H) |
| 1648 | 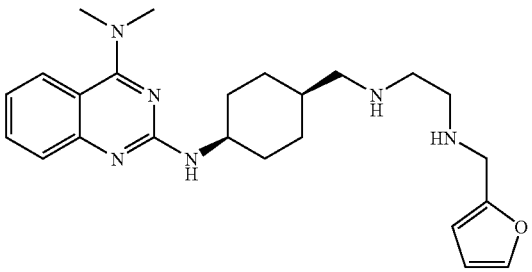 | 423 (M + H) |
| 1649 | 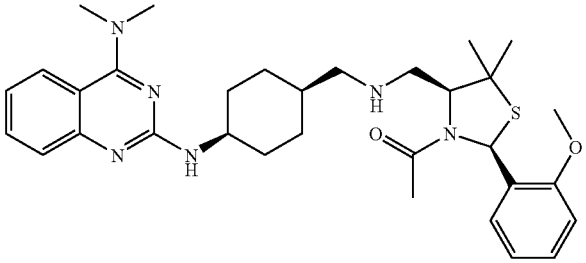 | 577 (M + H) |
| 1650 | 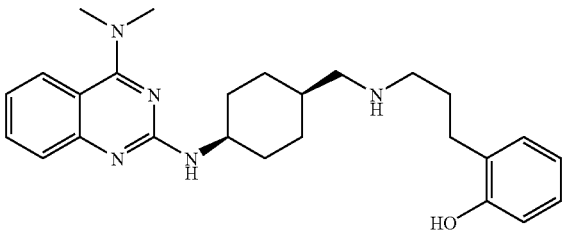 | 434 (M + H) |

-continued
| Example No. | Structure | APCI-MS |
|---|---|---|
| 1651 | 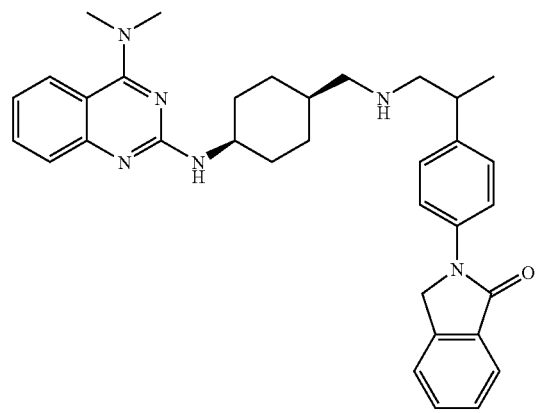 | 549 (M + H) |
| 1652 | 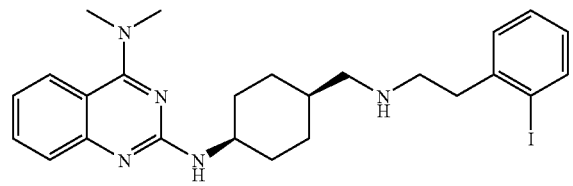 | 530 (M + H) |
| 1653 | 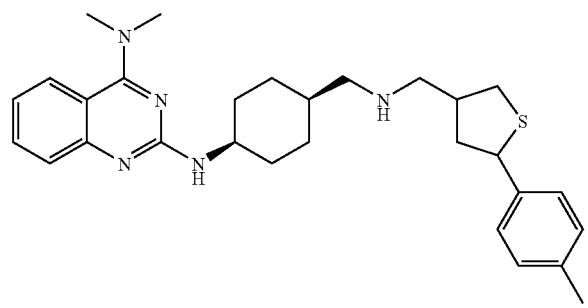 | 490 (M + H) |
| 1654 | 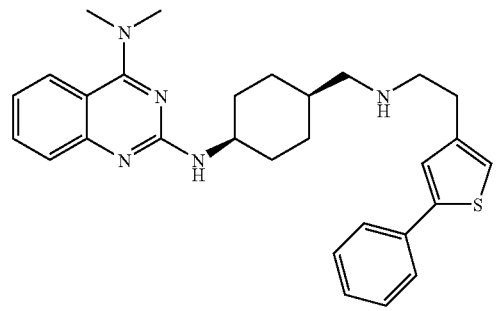 | 486 (M + H) |
| 1655 | 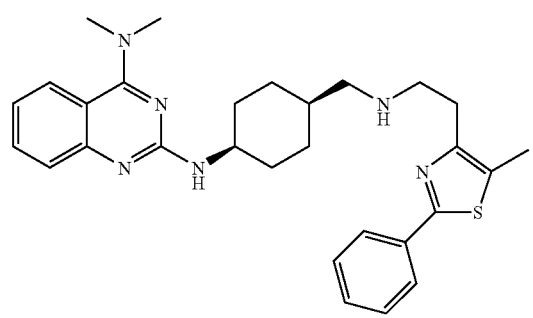 | 501 (M + H) |

| Example No. | Structure | APCI-MS |
|---|---|---|
| 1656 | 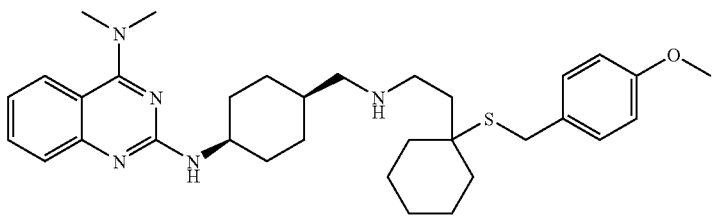 | 562 (M + H) |
| 1657 | 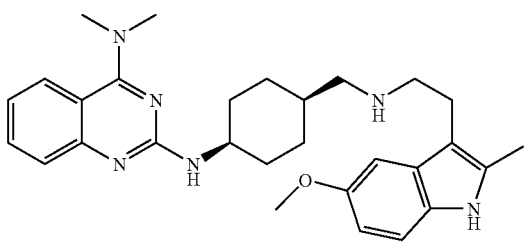 | 487 (M + H) |
| 1658 | 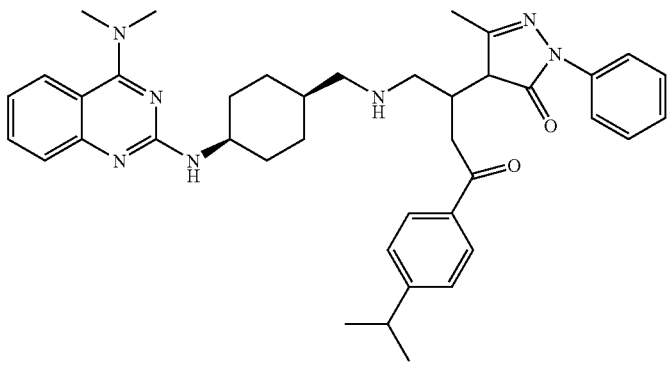 | 660 (M + H) |
| 1659 | 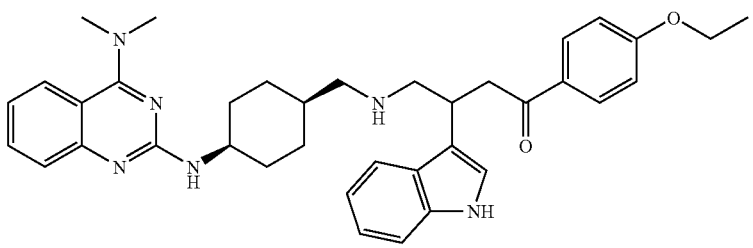 | 605 (M + H) |
| 1660 | 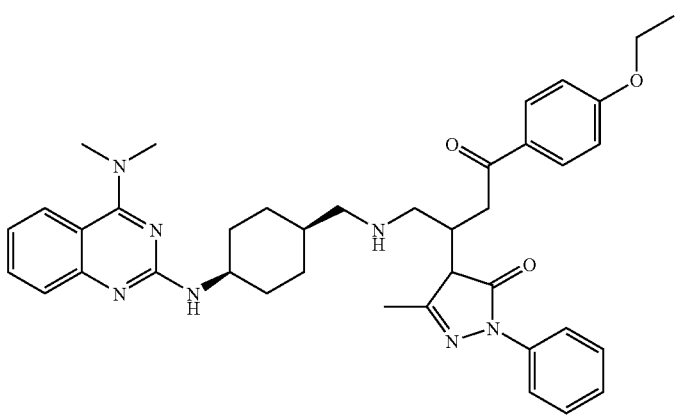 | 662 (M + H) |

-continued
| Example No. | Structure | APCI-MS |
|---|---|---|
| 1661 | 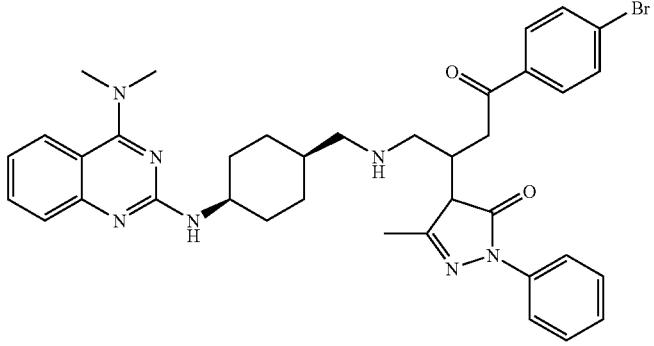 | 696 (M + H) |
| 1662 | 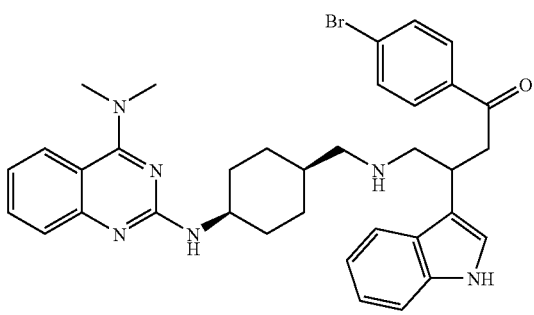 | 639 (M + H) |
| 1663 | 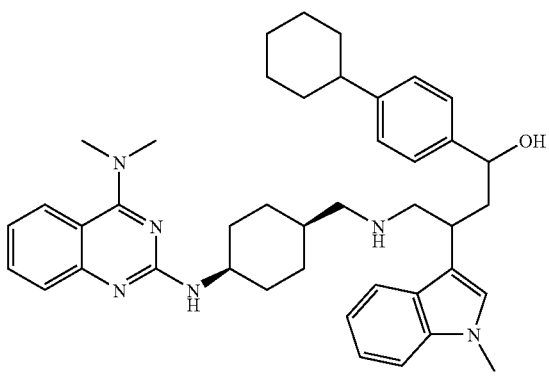 | 659 (M + H) |
| 1664 | 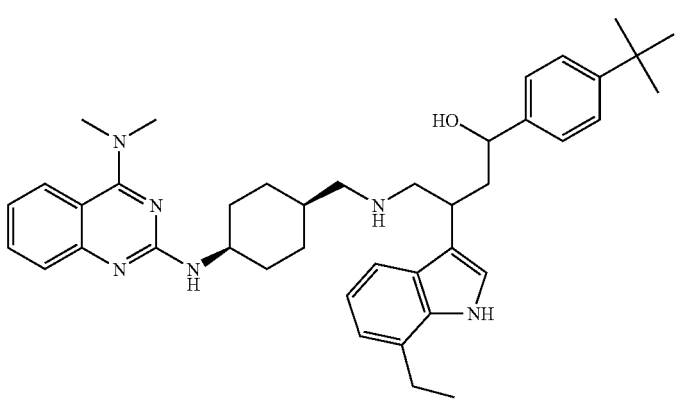 | 647 (M + H) |

-continued
| Example No. | Structure | APCI-MS |
|---|---|---|
| 1665 | 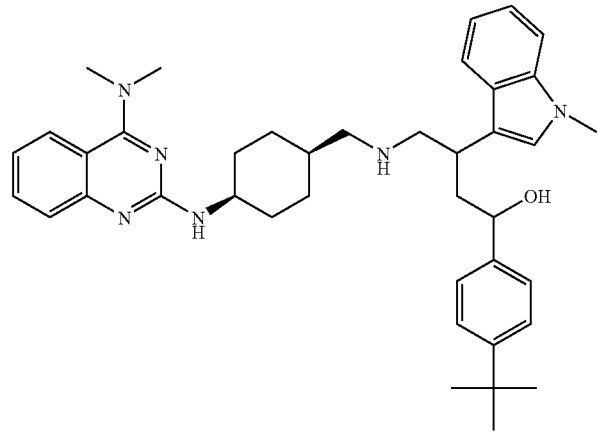 | 633 (M + H) |
| 1666 | 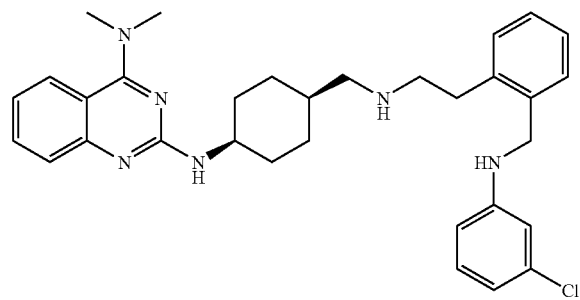 | 543 (M + H) |
| 1667 | 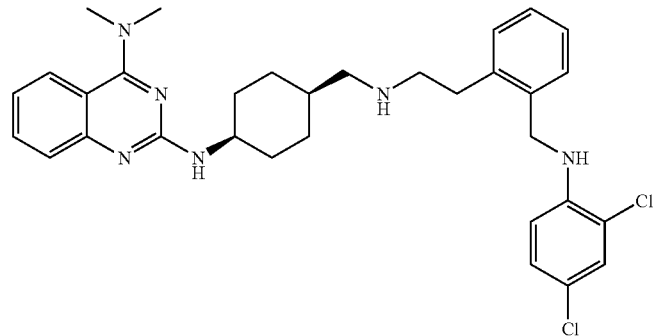 | 577 (M + H) |
| 1668 | 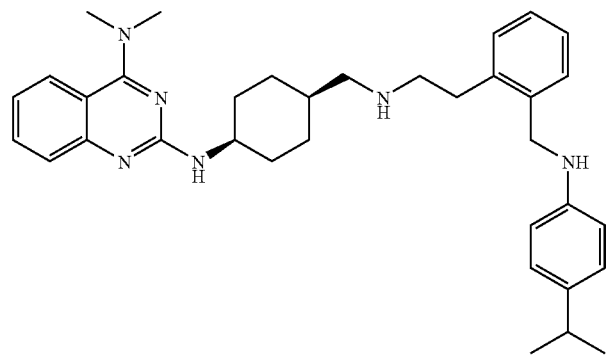 | 551 (M + H) |

-continued

| Example No. | Structure | APCI-MS |
|---|---|---|
| 1669 | 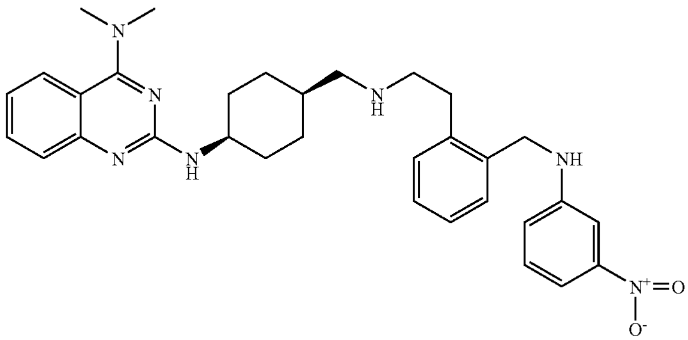 | 554 (M + H) |
| 1670 | 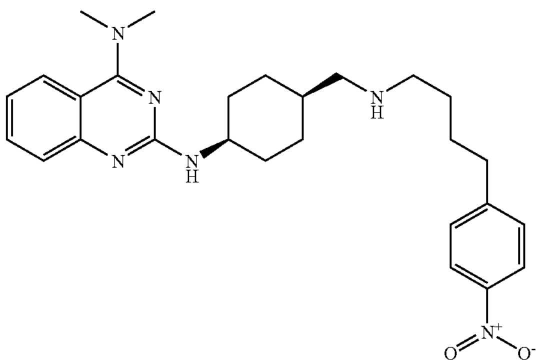 | 477 (M + H) |
| 1671 | 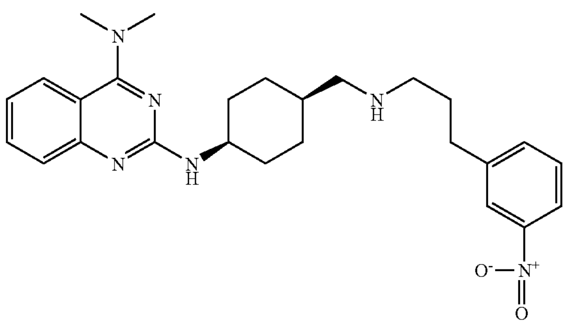 | 463 (M + H) |
| 1672 | 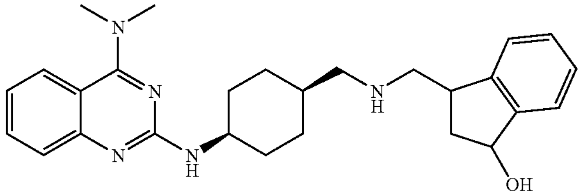 | 446 (M + H) |
| 1673 | 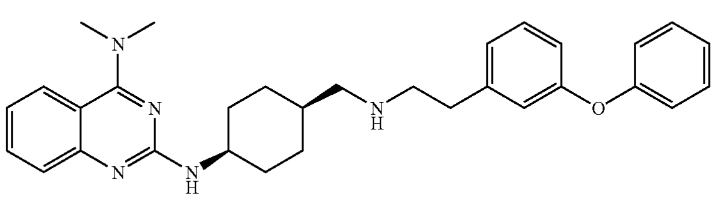 | 496 (M + H) |

-continued
| Example No. | Structure | APCI-MS |
|---|---|---|
| 1674 | 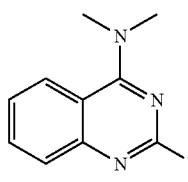  | 496 (M + H) |
| 1675 | 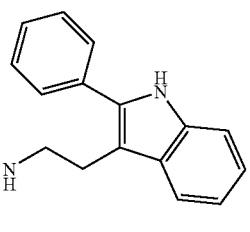 | 519 (M + H) |
| 1676 | 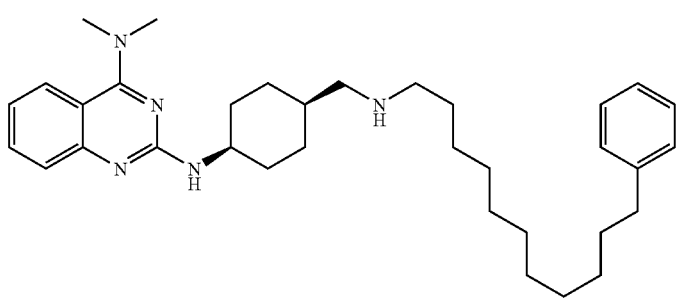 | 530 (M + H) |
| 1677 | 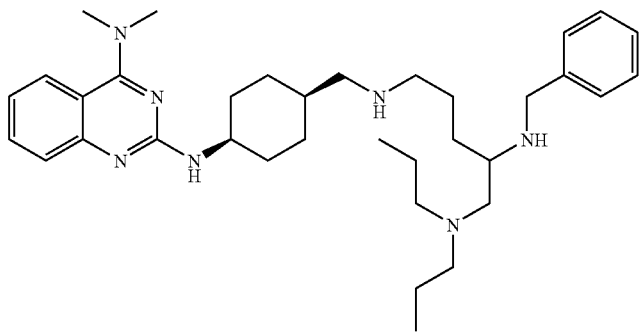 | 574 (M + H) |
| 1678 | 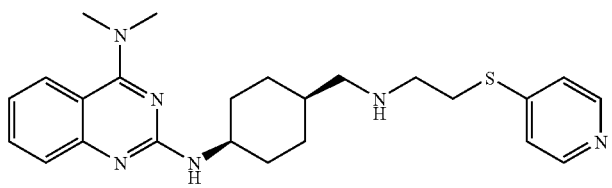 | 437 (M + H) |

| Example No. | Structure | APCI-MS |
|---|---|---|
| 1679 | 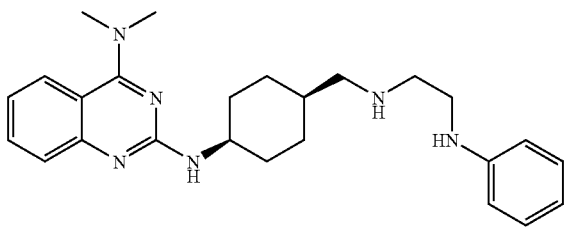 | 419 (M + H) |
| 1680 | 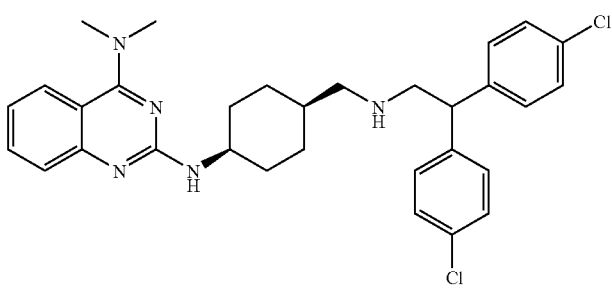 | 548 (M + H) |
| 1681 | 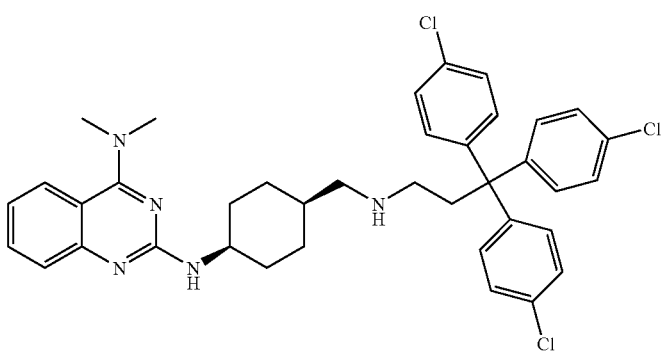 | 672 (M + H) |
| 1682 | 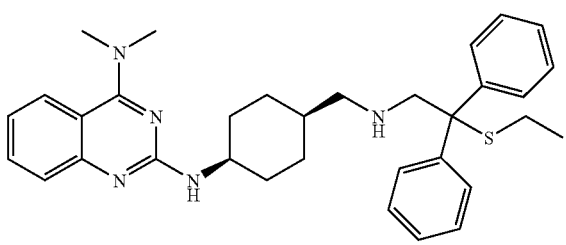 | 540 (M + H) |
| 1683 | 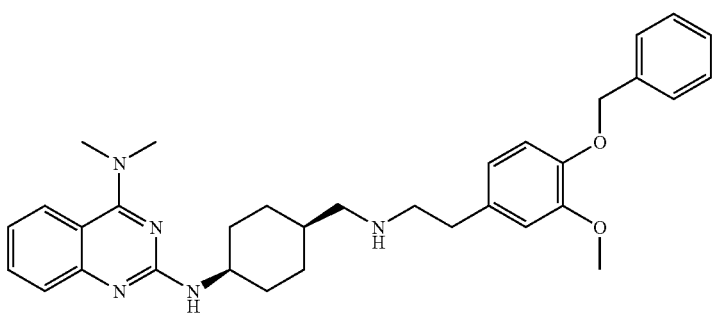 | 540 (M + H) |

-continued
| Example No. | Structure | APCI-MS |
|---|---|---|
| 1684 | 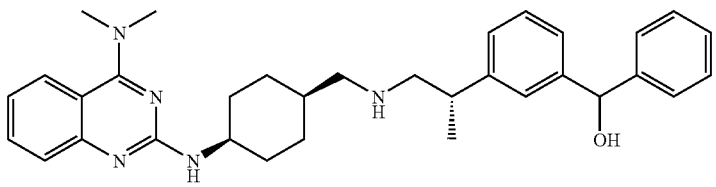 | 524 (M + H) |
| 1685 | 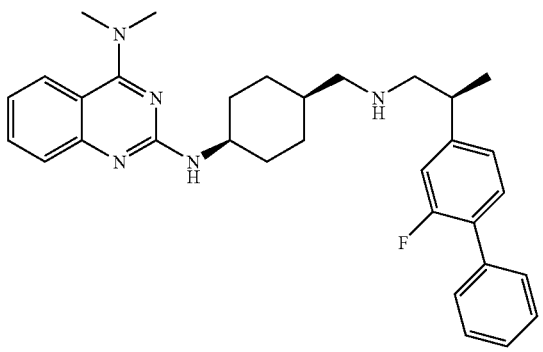 | 512 (M + H) |
| 1686 | 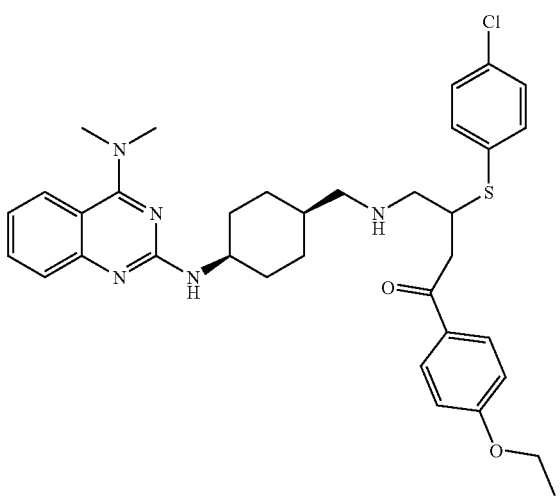 | 632 (M + H) |
| 1687 | 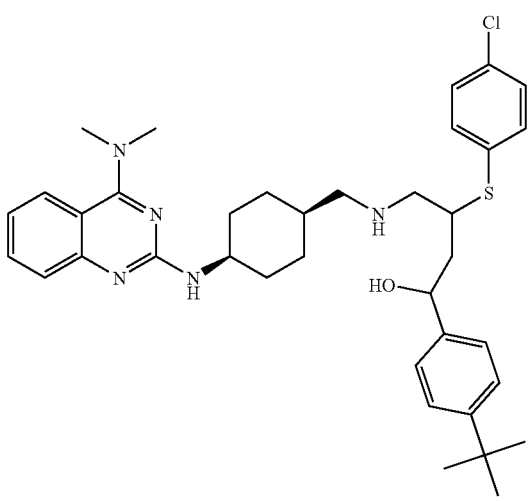 | 646 (M + H) |

-continued
| Example No. | Structure | APCI-MS |
|---|---|---|
| 1688 | 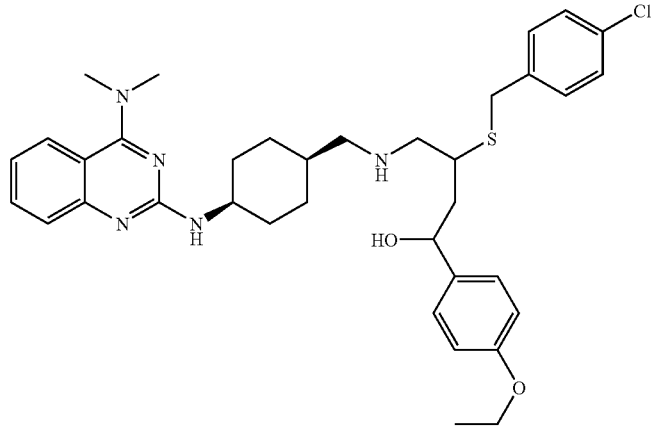 | 648 (M + H) |
| 1689 | 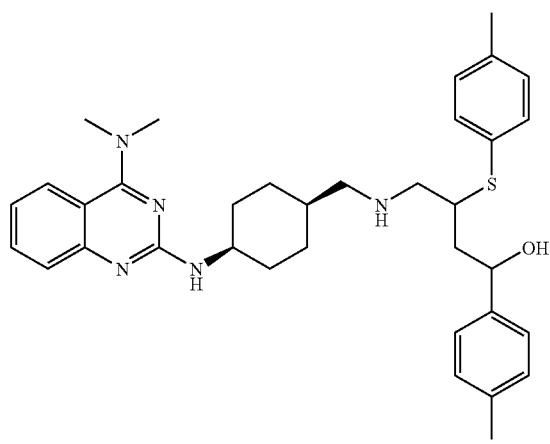 | 584 (M + H) |
| 1690 | 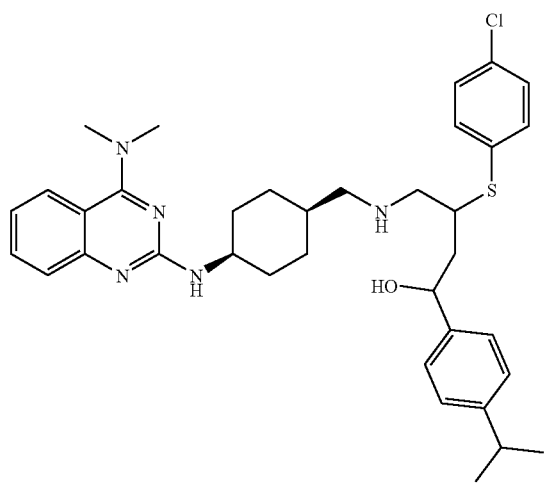 | 632 (M + H) |

-continued
| Example No. | Structure | APCI-MS |
|---|---|---|
| 1691 | 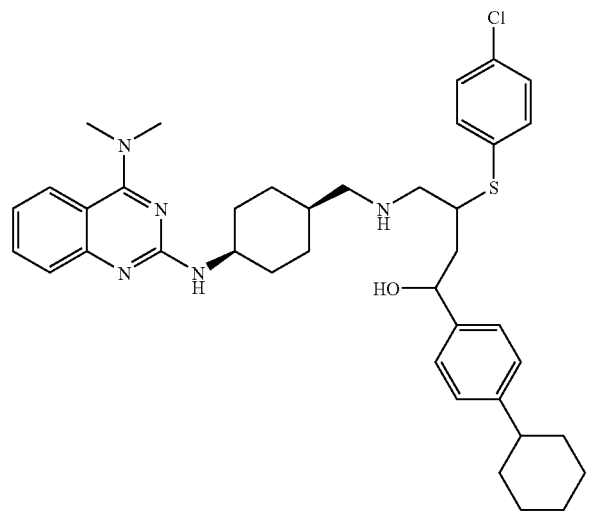 | 672 (M + H) |
| 1692 | 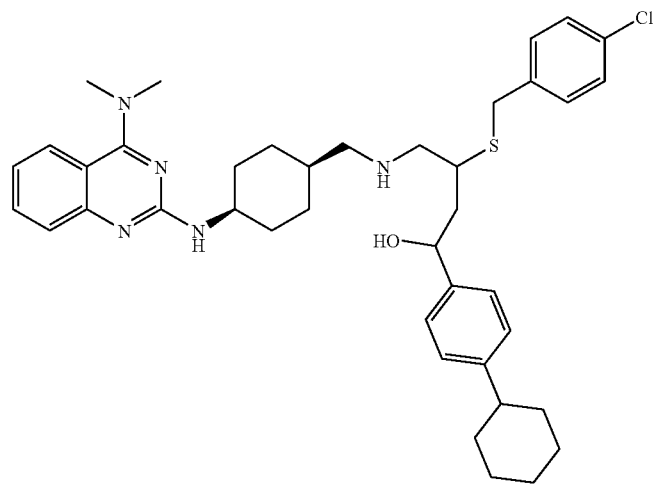 | 686 (M + H) |
| 1693 | 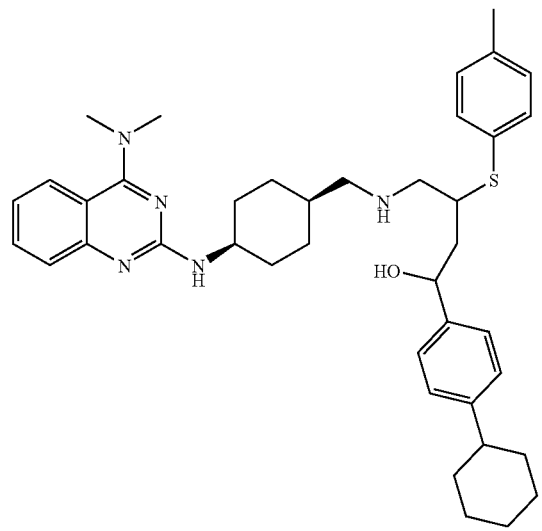 | 652 (M + H) |

-continued
| Example No. | Structure | APCI-MS |
|---|---|---|
| 1694 | 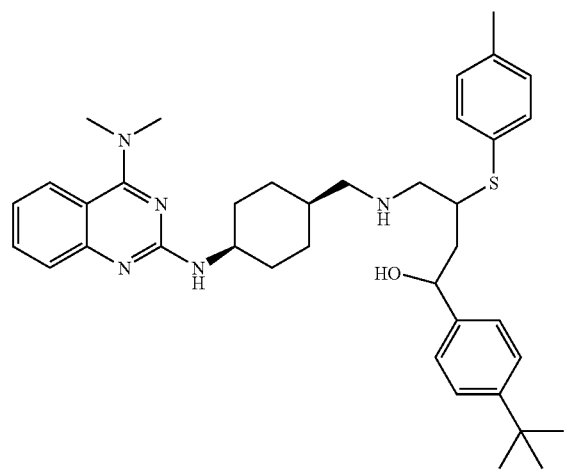 | 626 (M + H) |
| 1695 | 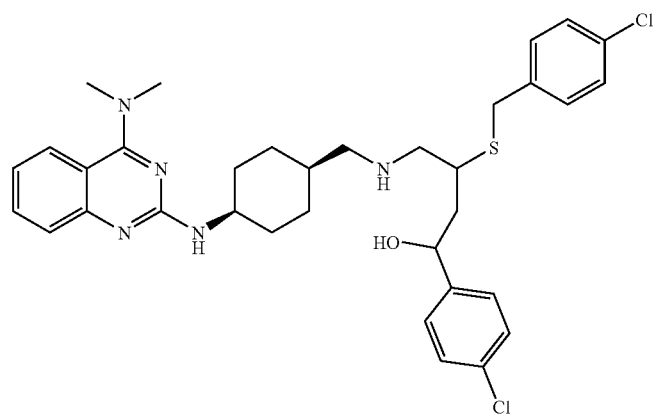 | 638 (M + H) |
| 1696 | 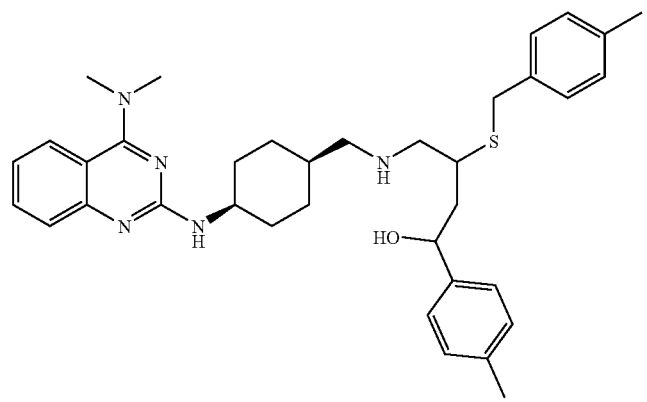 | 618 (M + H) |

-continued
| Example No. | Structure | APCI-MS |
|---|---|---|
| 1697 | 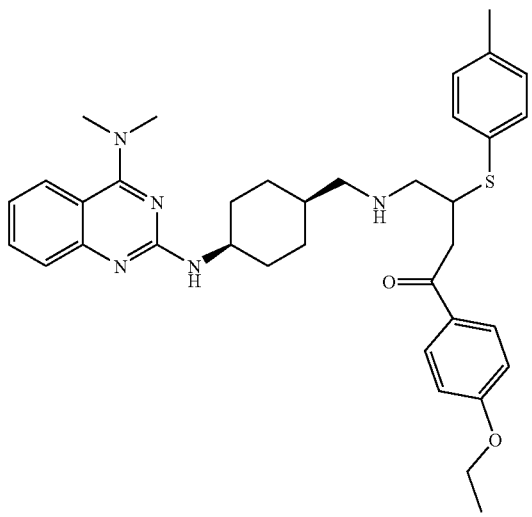 | 612 (M + H) |
| 1698 | 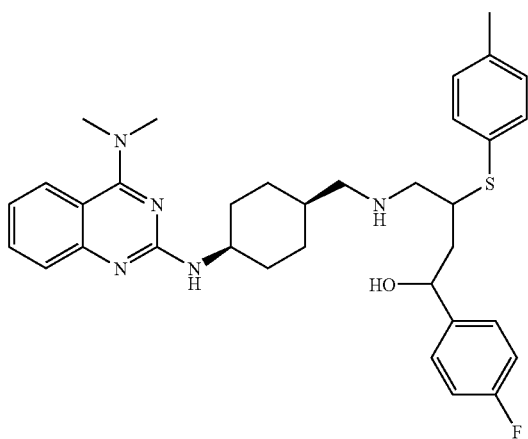 | 588 (M + H) |
| 1699 | 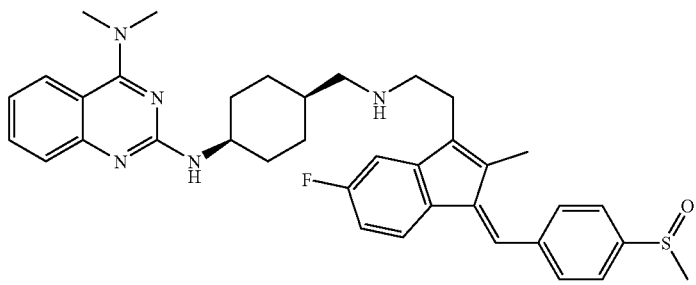 | 624 (M + H) |
| 1700 | 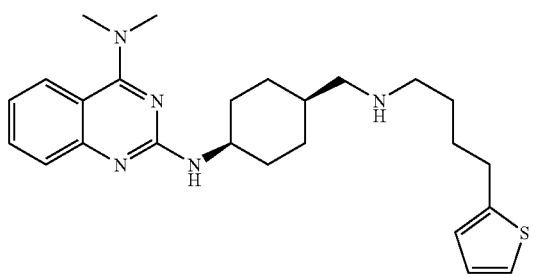 | 438 (M + H) |

-continued
| Example No. | Structure | APCI-MS |
|---|---|---|
| 1701 | 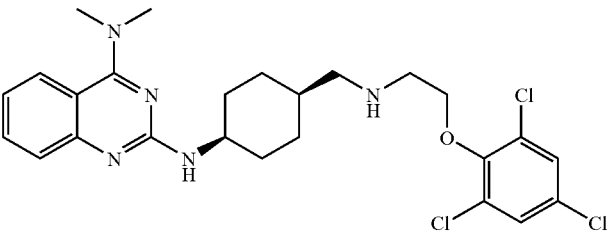 | 522 (M + H) |
| 1702 | 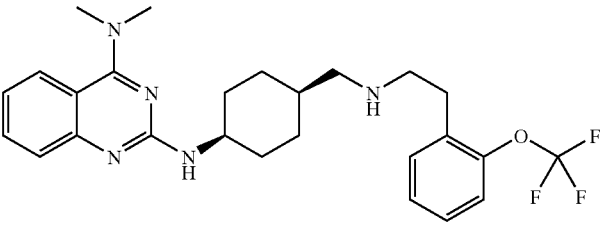 | 488 (M + H) |
| 1703 | 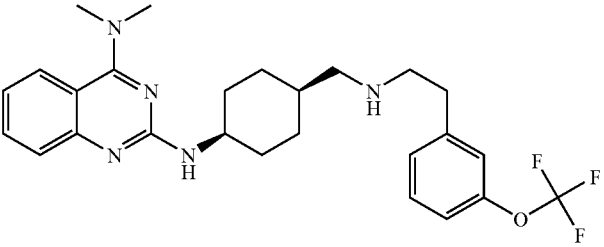 | 488 (M + H) |
| 1704 | 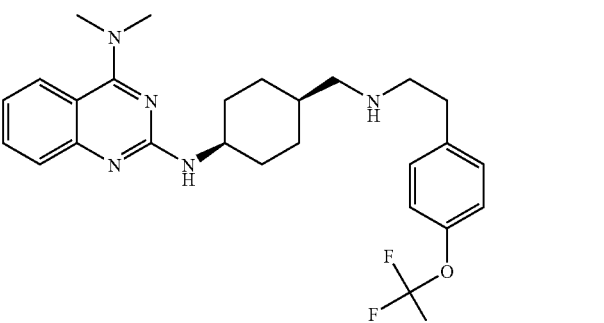 | 488 (M + H) |
| 1705 | 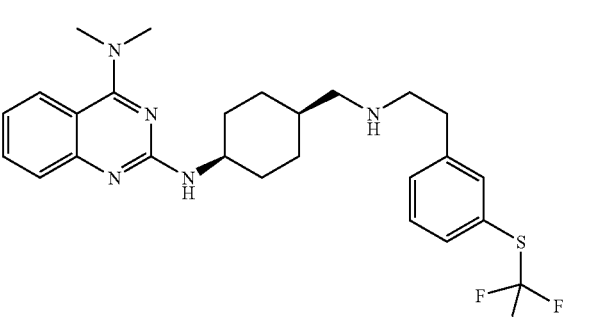 | 504 (M + H) |
| 1706 | 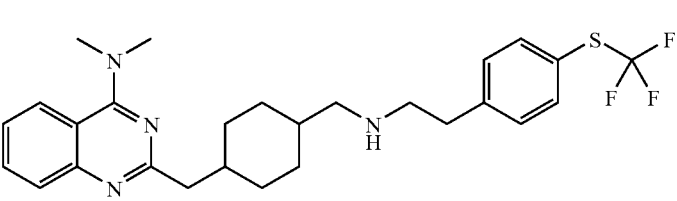 | 504 (M + H) |

-continued

| Example No. | Structure | APCI-MS |
|---|---|---|
| 1707 | 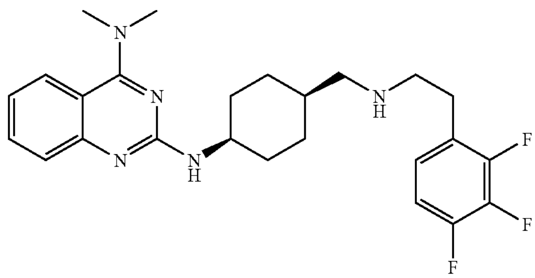 | 458 (M + H) |
| 1708 | 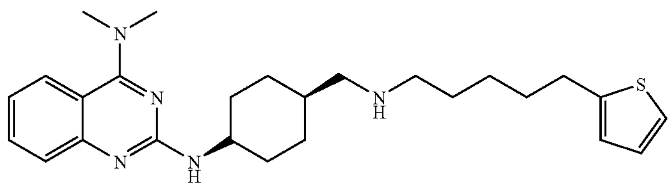 | 452 (M + H) |
| 1709 | 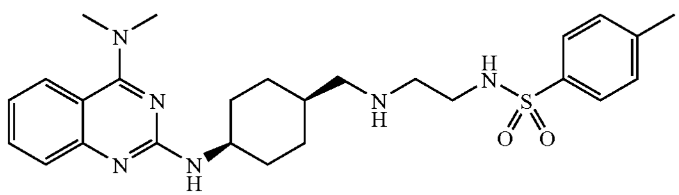 | 497 (M + H) |
| 1710 | 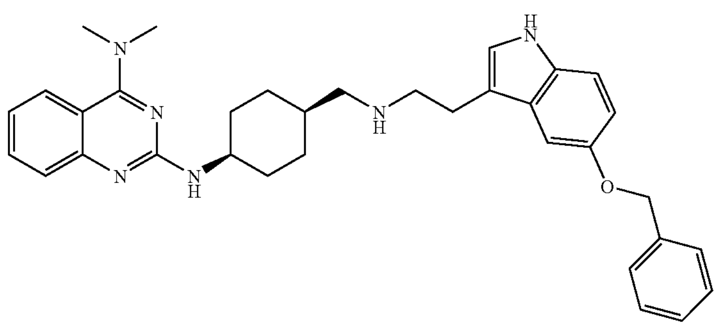 | 549 (M + H) |
| 1711 | 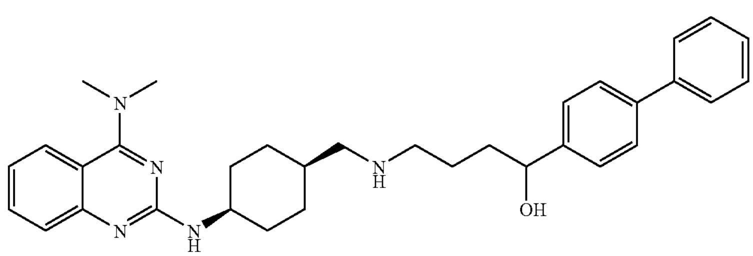 | 524 (M + H) |
| 1712 | 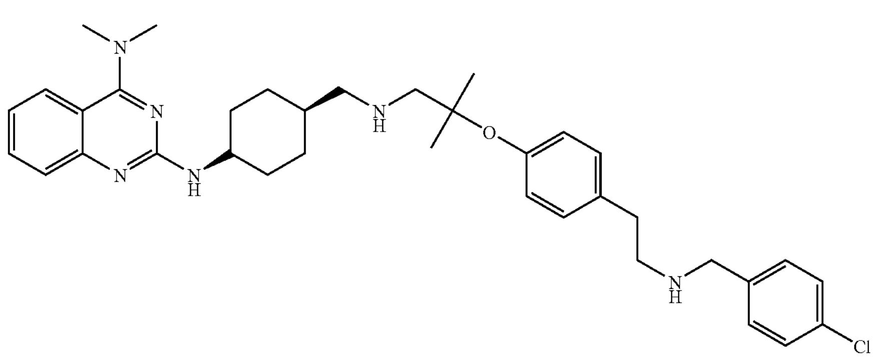 | 615 (M + H) |

-continued
| Example No. | Structure | APCI-MS |
|---|---|---|
| 1713 | 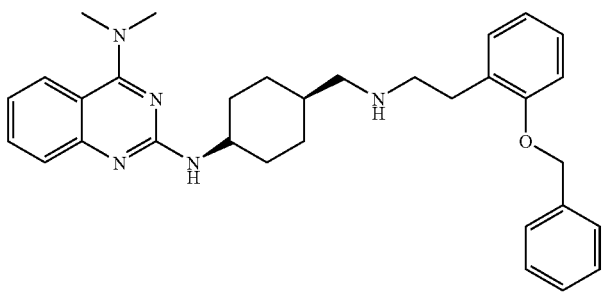 | 510 (M + H) |
| 1714 | 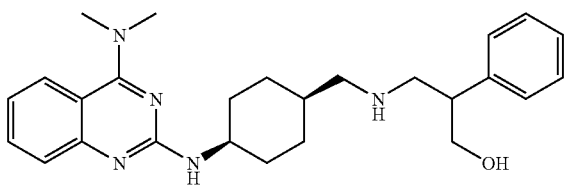 | 434 (M + H) |
| 1715 | 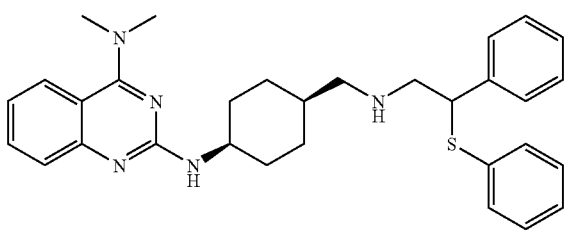 | 512 (M + H) |
| 1716 | 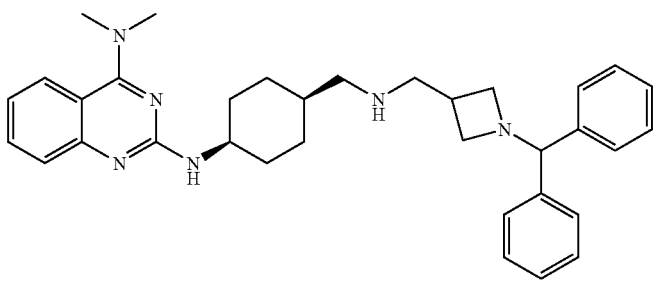 | 535 (M + H) |
| 1717 | 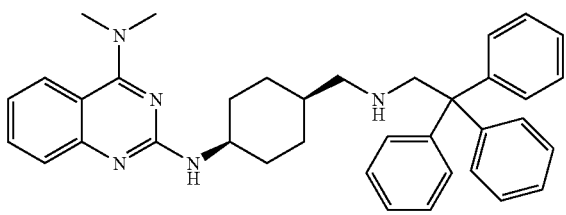 | 556 (M + H) |
| 1718 | 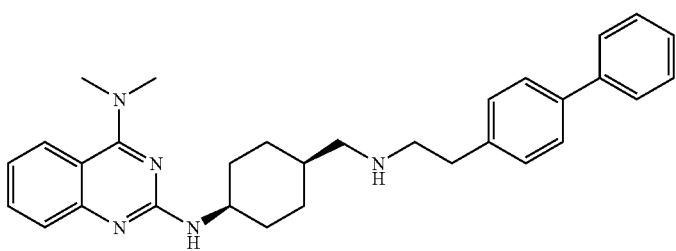 | 480 (M + H) |

-continued
| Example No. | Structure | APCI-MS |
|---|---|---|
| 1719 | 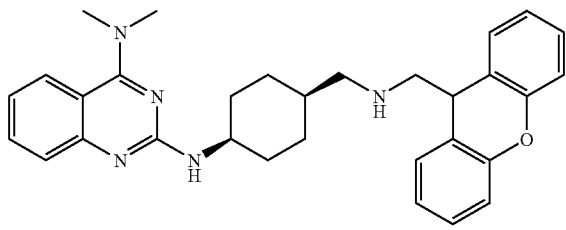 | 494 (M + H) |
| 1720 | 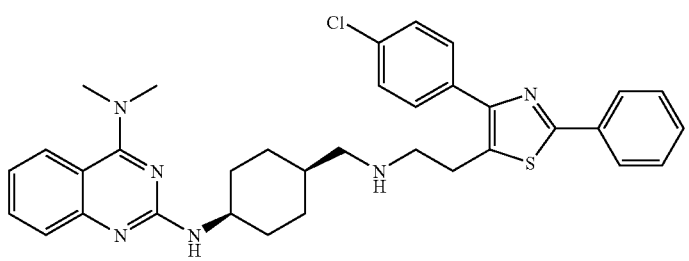 | 597 (M + H) |
| 1721 | 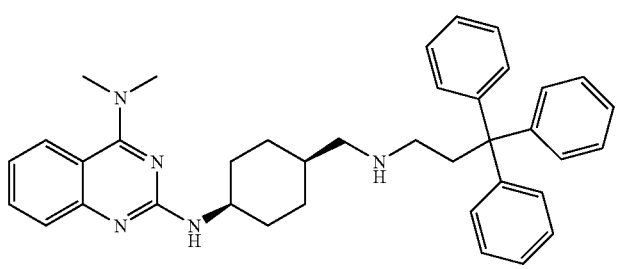 | 570 (M + H) |
| 1722 | 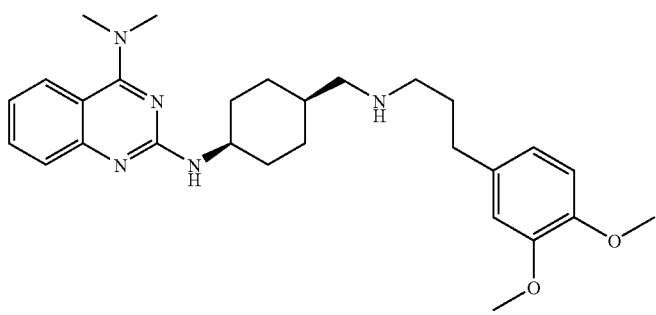 | 478 (M + H) |
| 1723 | 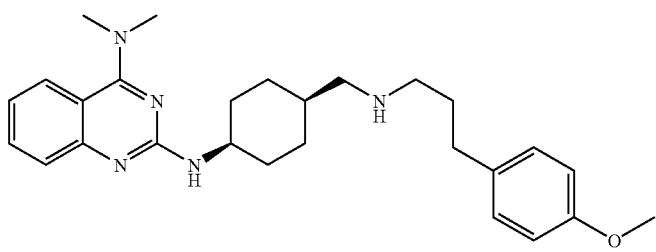 | 448 (M + H) |
| 1724 | 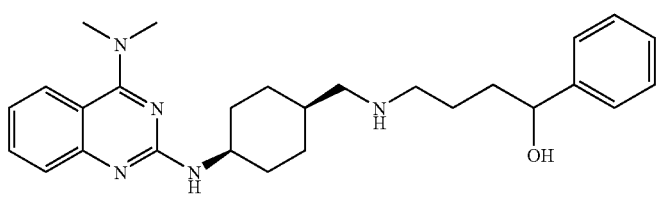 | 448 (M + H) |

-continued
| Example No. | Structure | APCI-MS |
|---|---|---|
| 1725 | 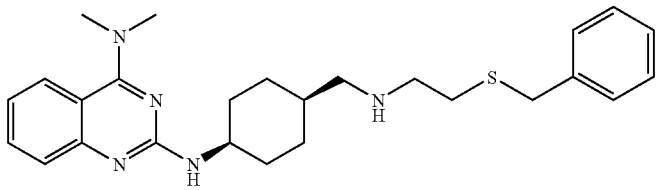 | 450 (M + H) |
| 1726 | 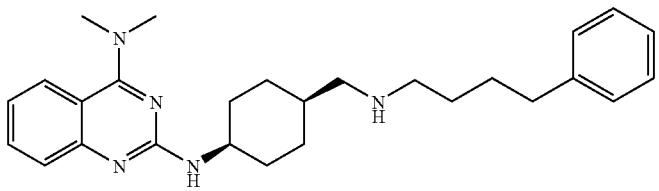 | 432 (M + H) |
| 1727 | 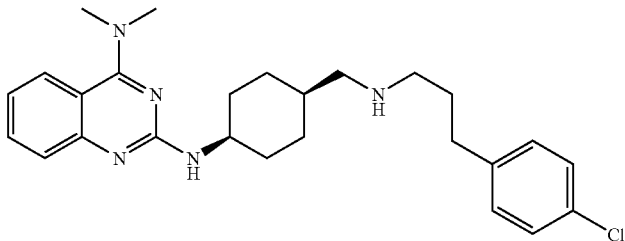 | 452 (M + H) |
| 1728 | 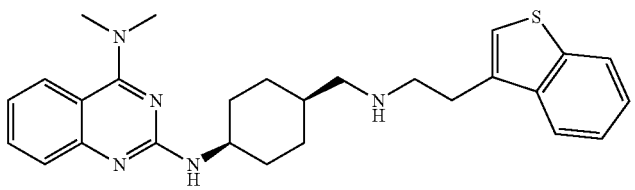 | 460 (M + H) |
| 1729 | 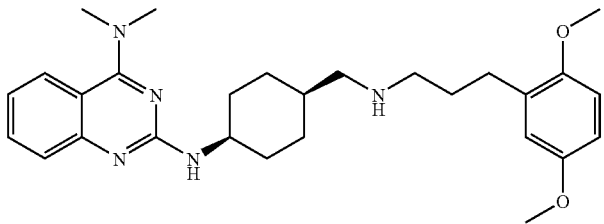 | 478 (M + H) |
| 1730 | 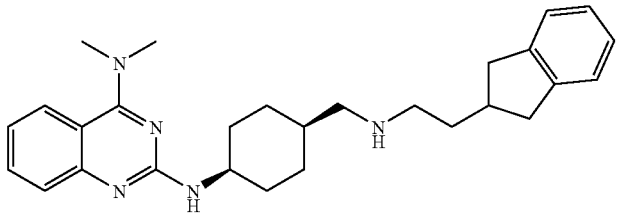 | 444 (M + H) |

-continued
| Example No. | Structure | APCI-MS |
|---|---|---|
| 1731 | 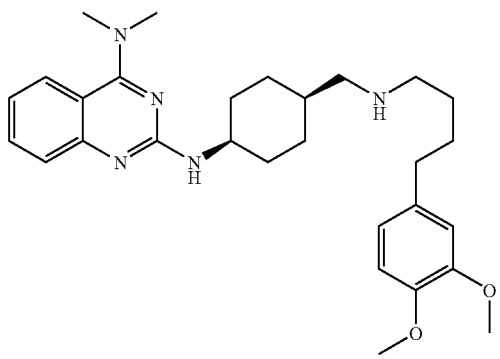 | 492 (M + H) |
| 1732 | 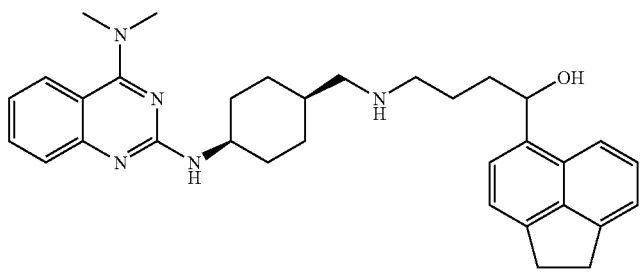 | 524 (M + H) |
| 1733 | 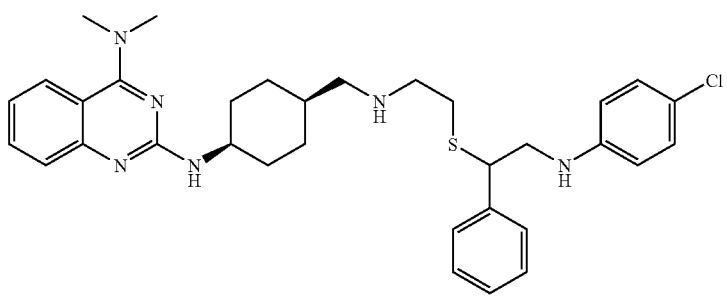 | 589 (M + H) |
| 1734 | 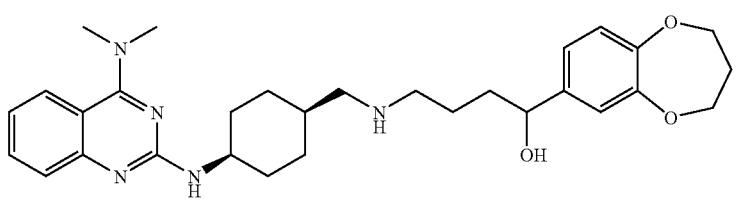 | 490 (M + H) |
| 1735 | 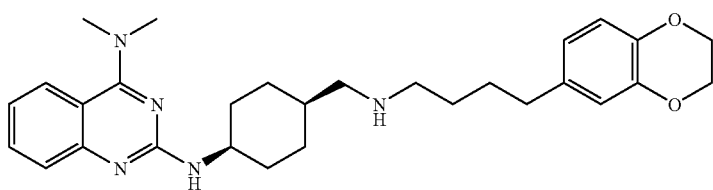 | 490 (M + H) |

-continued
| Example No. | Structure | APCI-MS |
|---|---|---|
| 1736 | 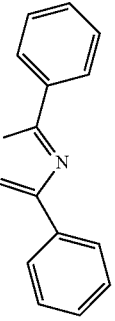 | 563 (M + H) |
| 1737 | 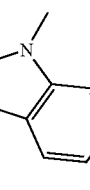 | 471 (M + H) |
| 1738 | 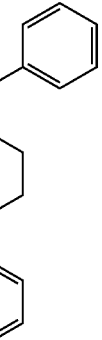 | 578 (M + H) |
| 1739 | 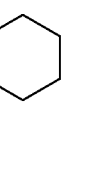 | 410 (M + H) |
| 1740 | 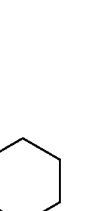 | 424 (M + H) |
| 1741 | 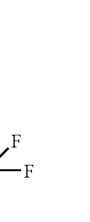 | 424 (M + H) |

-continued
| Example No. | Structure | APCI-MS |
|---|---|---|
| 1742 | 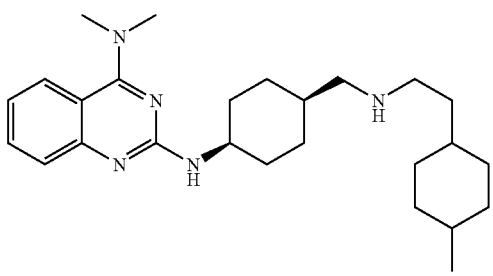 | 424 (M + H) |
| 1743 | 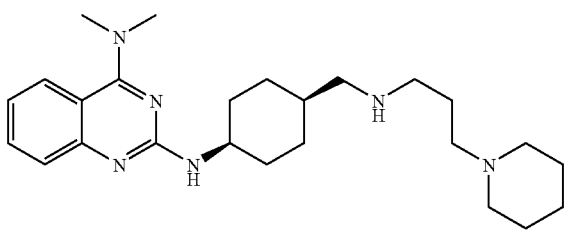 | 447 (M + H) |
| 1744 | 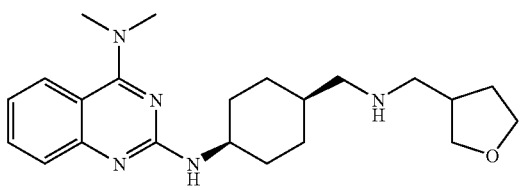 | 384 (M + H) |
| 1745 | 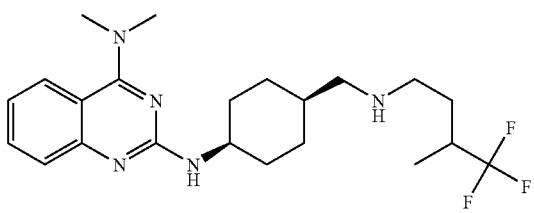 | 424 (M + H) |
| 1746 | 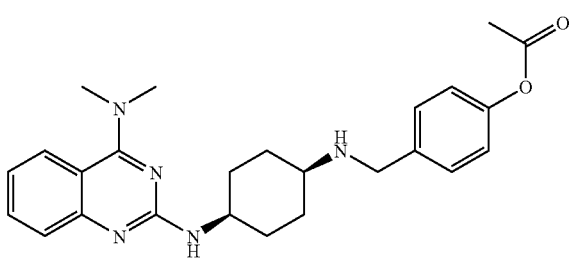 | 434 (M + H) |
| 1747 | 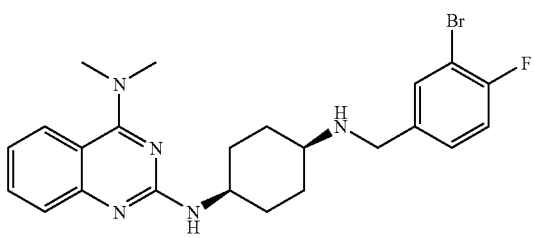 | 472 (M + H) |

-continued
| Example No. | Structure | APCI-MS |
|---|---|---|
| 1748 | 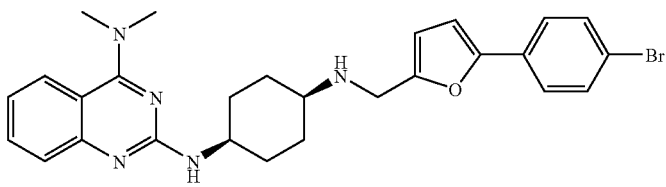 | 520 (M + H) |
| 1749 | 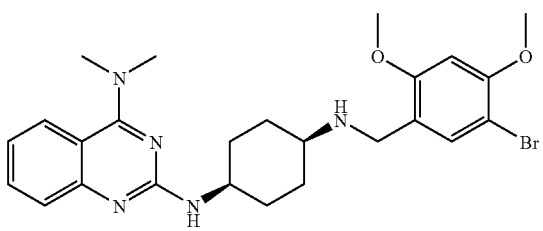 | 514 (M + H) |
| 1750 | 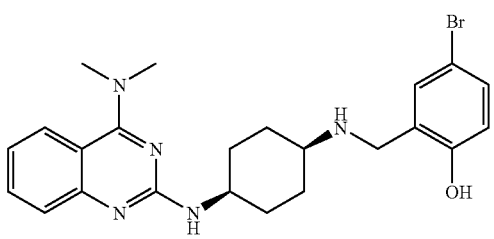 | 470 (M + H) |
| 1751 | 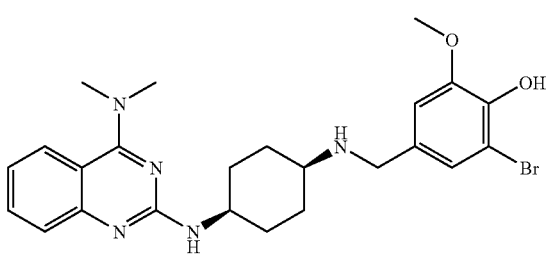 | 500 (M + H) |
| 1752 | 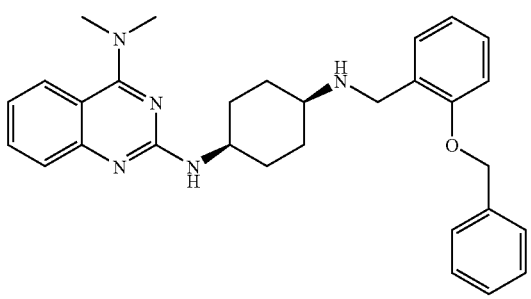 | 482 (M + H) |
| 1753 | 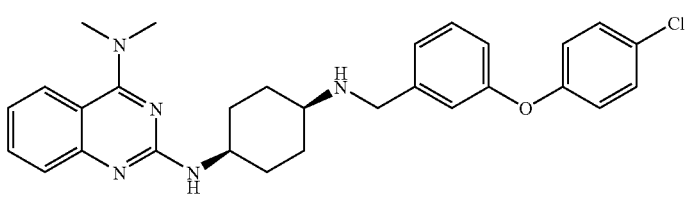 | 502 (M + H) |

-continued
| Example No. | Structure | APCI-MS |
|---|---|---|
| 1754 | 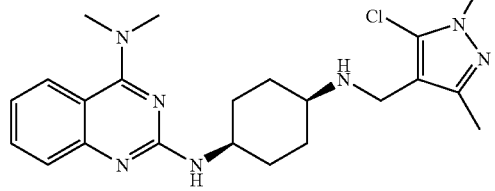 | 490 (M + H) |
| 1755 | 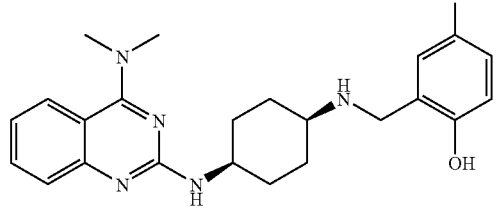 | 426 (M + H) |
| 1756 | 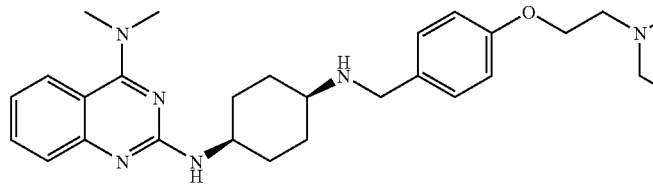 | 683 (M + H) |
| 1757 | 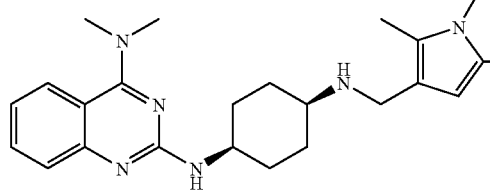 | 537 (M + H) |
| 1758 | 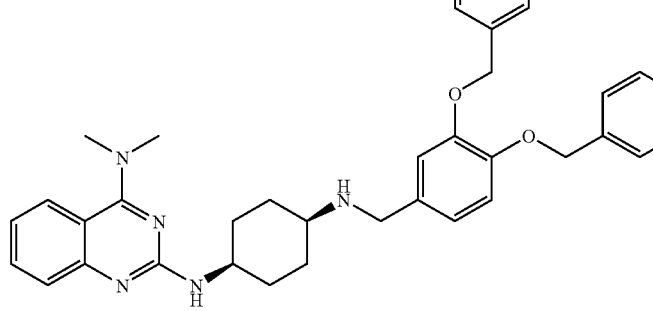 | 588 (M + H) |

-continued
| Example No. | Structure | APCI-MS |
|---|---|---|
| 1759 | 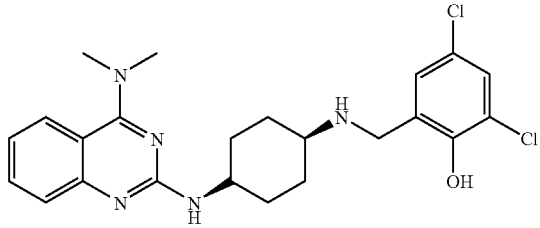 | 460 (M + H) |
| 1760 | 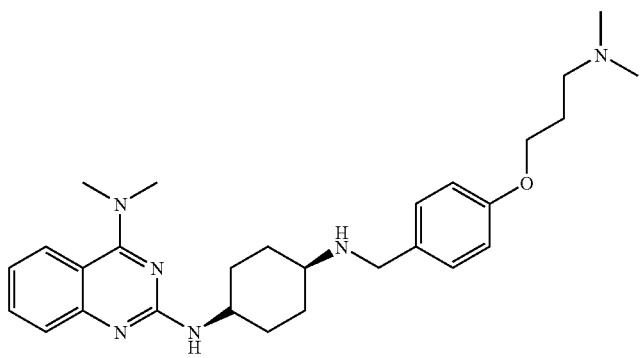 | 477 (M + H) |
| 1761 | 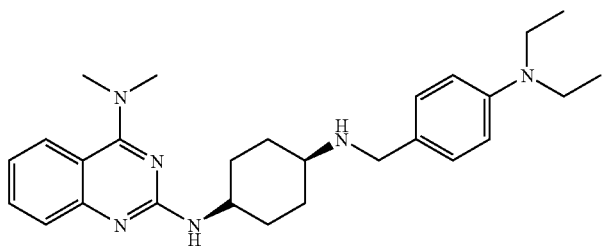 | 447 (M + H) |
| 1762 | 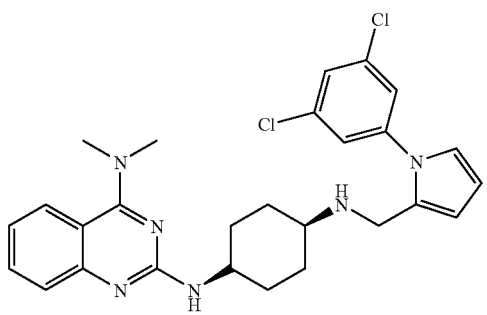 | 509 (M + H) |
| 1763 | 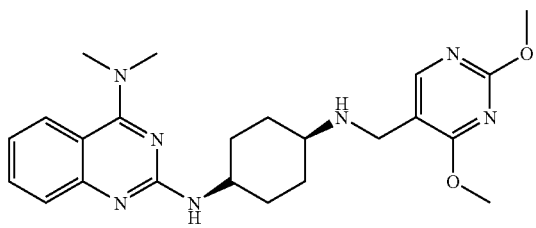 | 438 (M + H) |

-continued
| Example No. | Structure | APCI-MS |
|---|---|---|
| 1764 | 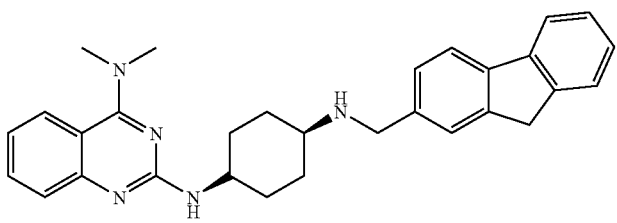 | 464 (M + H) |
| 1765 | 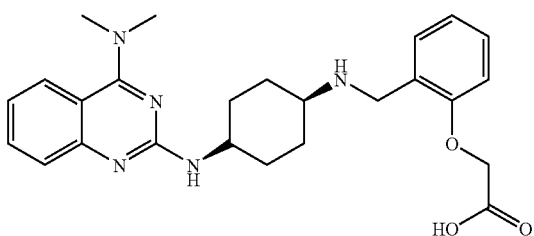 | 450 (M + H) |
| 1766 | 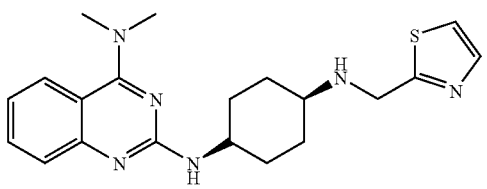 | 383 (M + H) |
| 1767 | 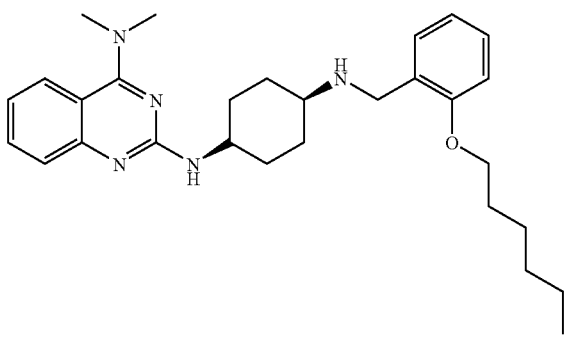 | 476 (M + H) |
| 1768 | 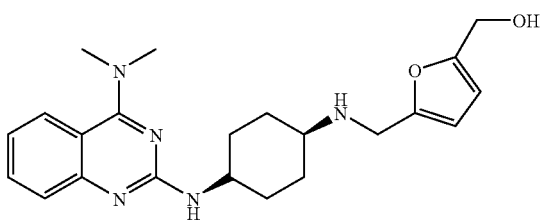 | 396 (M + H) |
| 1769 | 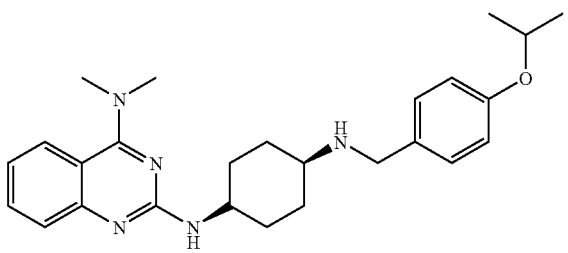 | 434 (M + H) |

-continued
| Example No. | Structure | APCI-MS |
|---|---|---|
| 1770 | 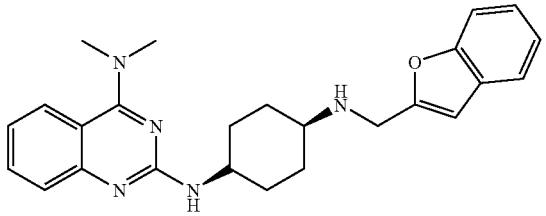 | 416 (M + H) |
| 1771 | 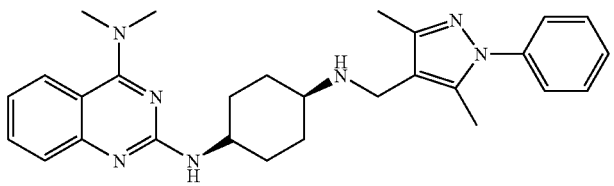 | 470 (M + H) |
| 1772 | 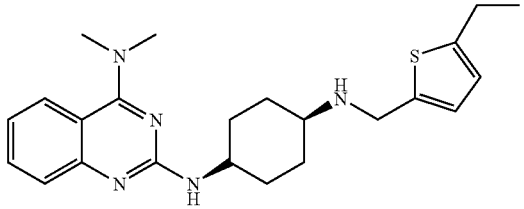 | 410 (M + H) |
| 1773 | 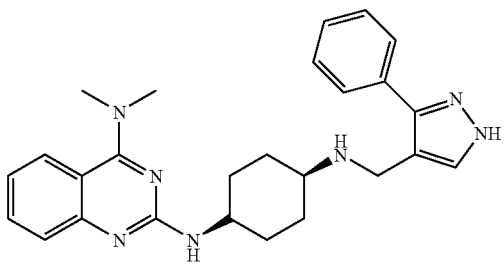 | 442 (M + H) |
| 1774 | 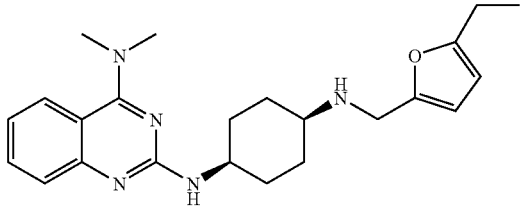 | 394 (M + H) |
| 1775 | 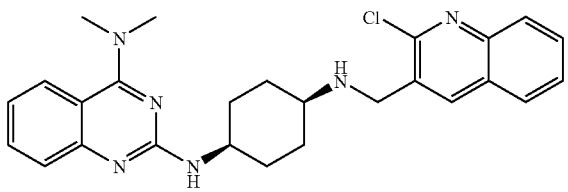 | 461 (M + H) |

-continued
| Example No. | Structure | APCI-MS |
|---|---|---|
| 1776 | 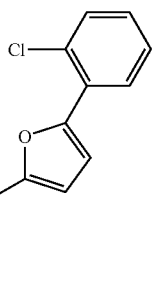 | 476 (M + H) |
| 1777 | 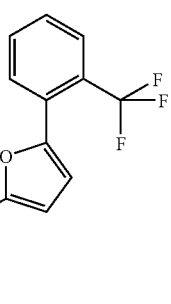 | 510 (M + H) |
| 1778 | 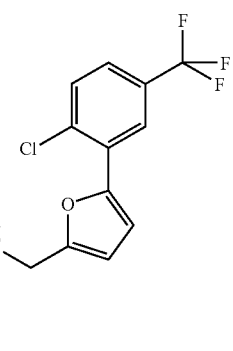 | 544 (M + H) |
| 1779 | 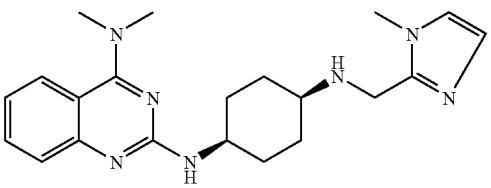 | 380 (M + H) |
| 1780 | 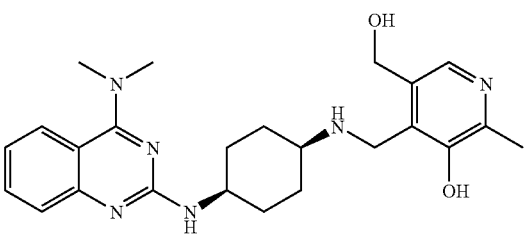 | 437 (M + H) |
| 1781 | 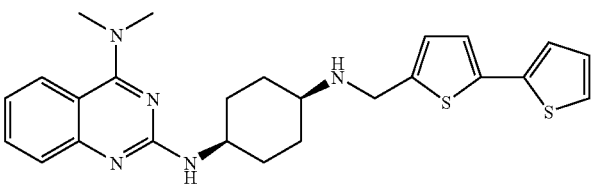 | 464 (M + H) |

| Example No. | Structure | APCI-MS |
|---|---|---|
| 1782 | 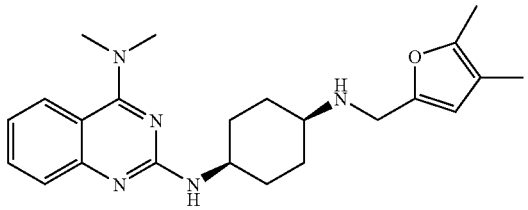 | 394 (M + H) |
| 1783 | 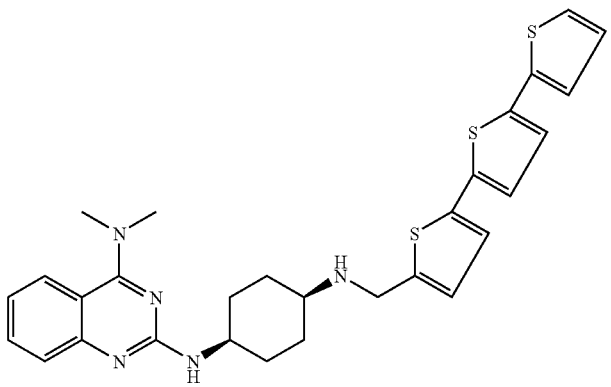 | 546 (M + H) |
| 1784 | 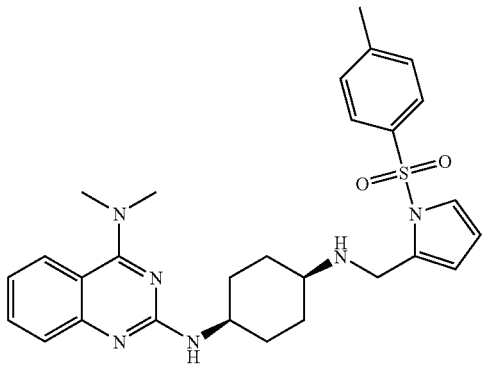 | 519 (M + H) |
| 1785 | 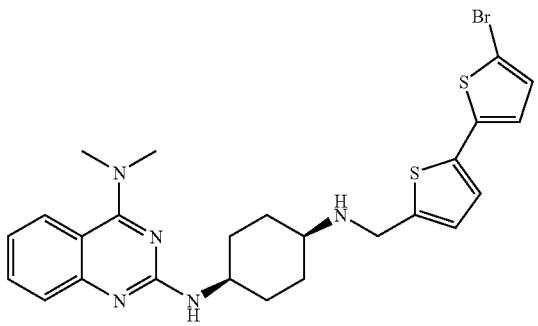 | 542 (M + H) |
| 1786 | 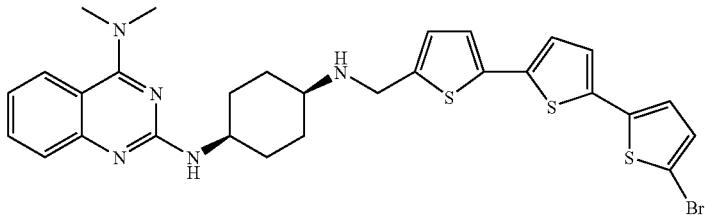 | 624 (M + H) |

-continued
| Example No. | Structure | APCI-MS |
|---|---|---|
| 1787 | 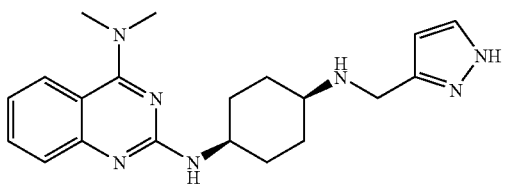 | 366 (M + H) |
| 1788 | 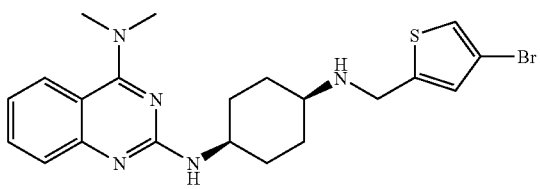 | 460 (M + H) |
| 1789 | 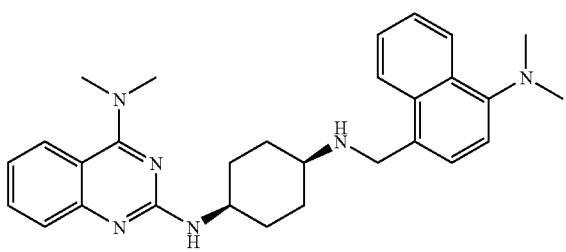 | 469 (M + H) |
| 1790 | 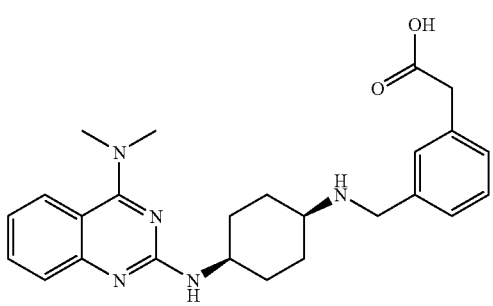 | 450 (M + H) |
| 1791 | 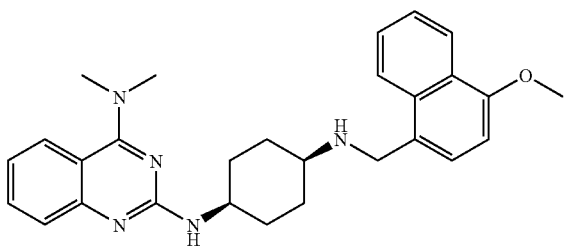 | 456 (M + H) |
| 1792 | 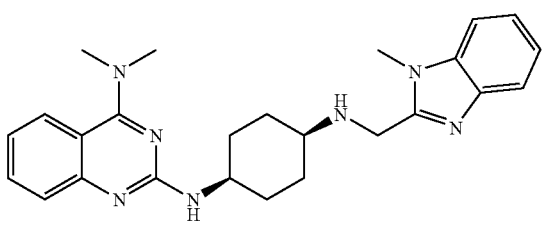 | 430 (M + H) |

-continued
| Example No. | Structure | APCI-MS |
|---|---|---|
| 1793 | 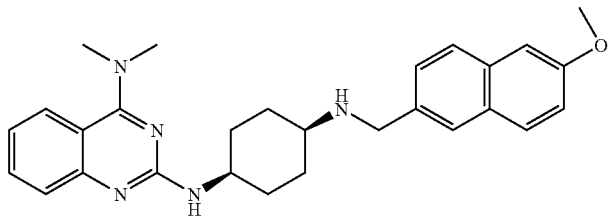 | 456 (M + H) |
| 1794 | 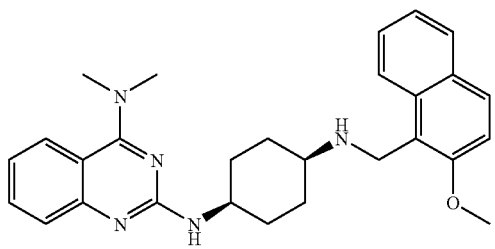 | 456 (M + H) |
| 1795 | 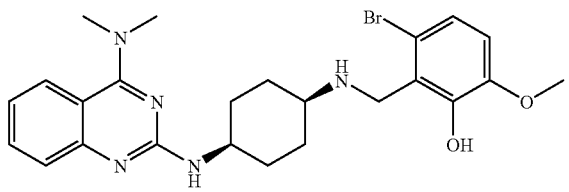 | 500 (M + H) |
| 1796 | 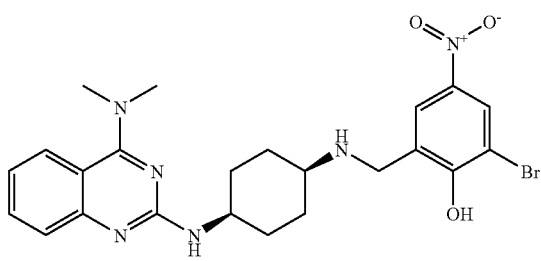 | 537 (M + H) |
| 1797 | 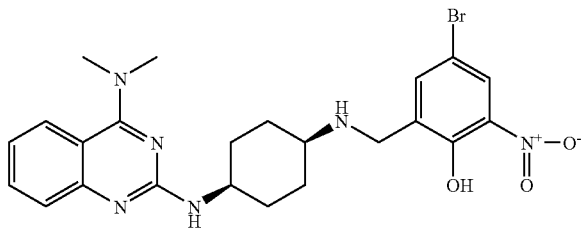 | 537 (M + H) |
| 1798 | 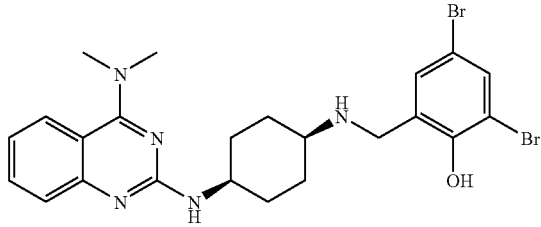 | 548 (M + H) |

-continued
| Example No. | Structure | APCI-MS |
|---|---|---|
| 1799 | 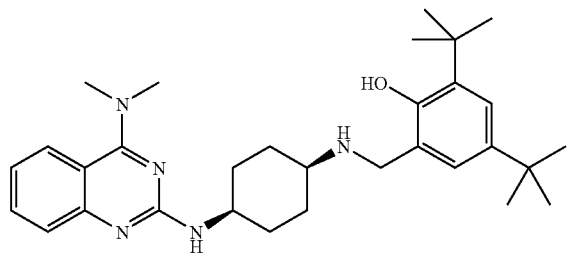 | 504 (M + H) |
| 1800 | 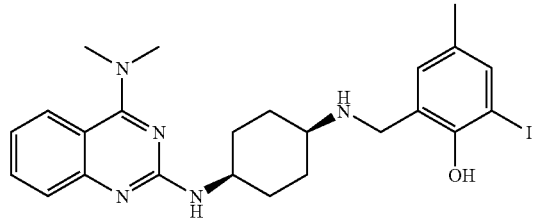 | 644 (M + H) |
| 1801 | 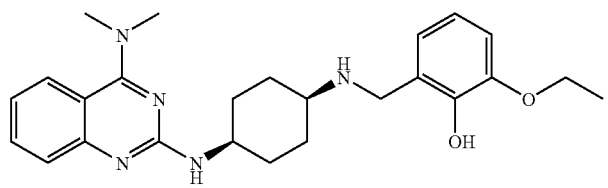 | 436 (M + H) |
| 1802 | 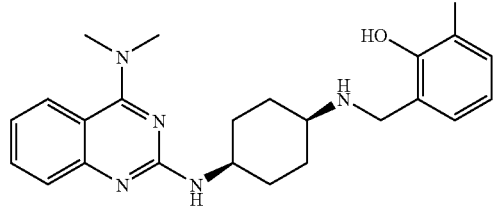 | 410 (M + H) |
| 1803 | 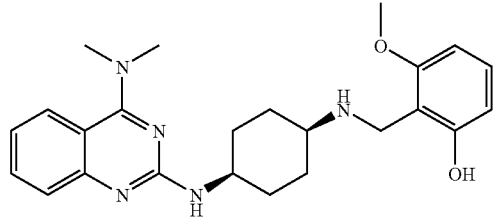 | 422 (M + H) |
| 1804 | 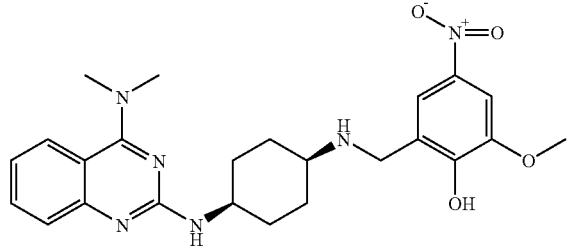 | 467 (M + H) |

-continued
| Example No. | Structure | APCI-MS |
|---|---|---|
| 1805 | 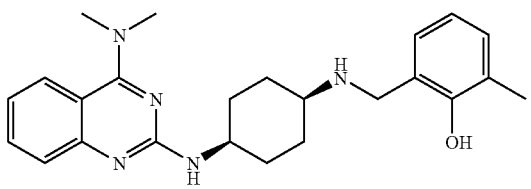 | 406 (M + H) |
| 1806 | 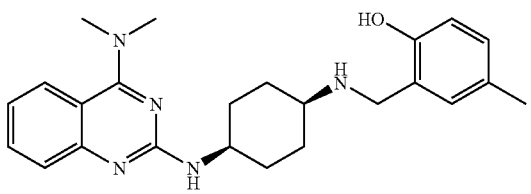 | 406 (M + H) |
| 1807 | 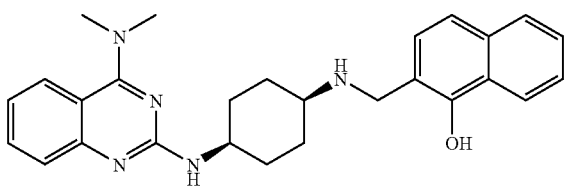 | 440 (M + H) |
| 1808 | 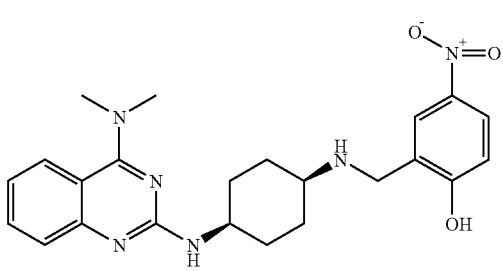 | 437 (M + H) |
| 1809 | 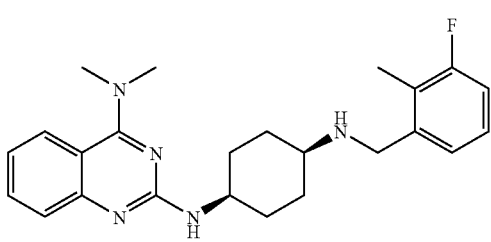 | 408 (M + H) |
| 1810 | 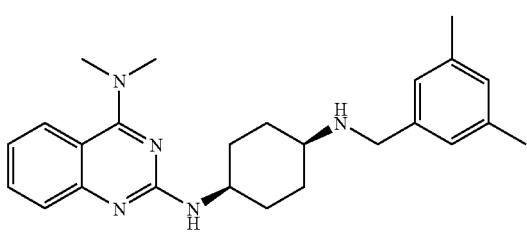 | 404 (M + H) |
| 1811 | 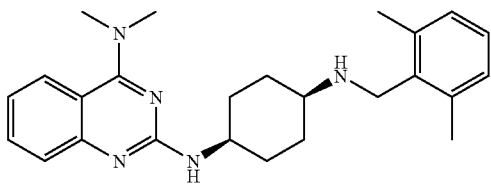 | 404 (M + H) |

-continued
| Example No. | Structure | APCI-MS |
|---|---|---|
| 1812 | 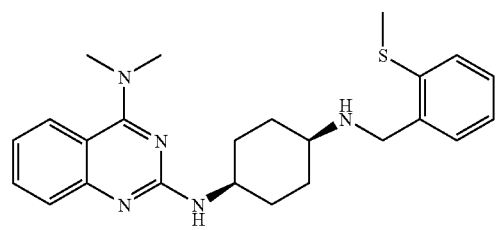 | 422 (M + H) |
| 1813 | 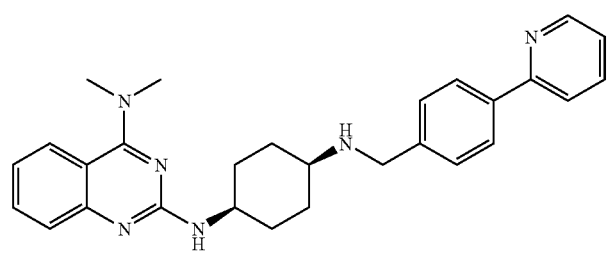 | 453 (M + H) |
| 1814 | 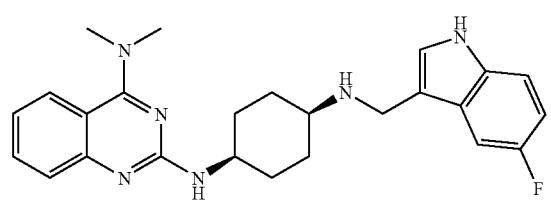 | 433 (M + H) |
| 1815 | 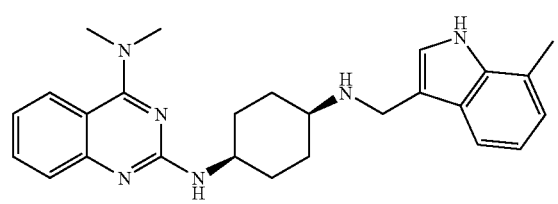 | 429 (M + H) |
| 1816 | 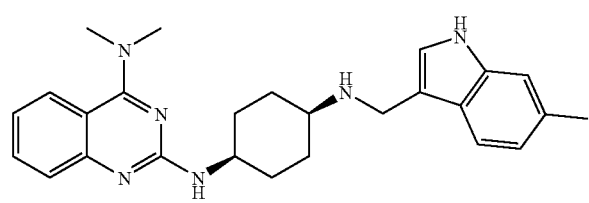 | 429 (M + H) |
| 1817 | 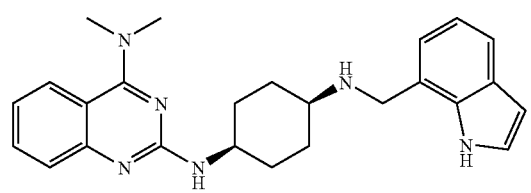 | 415 (M + H) |
| 1818 | 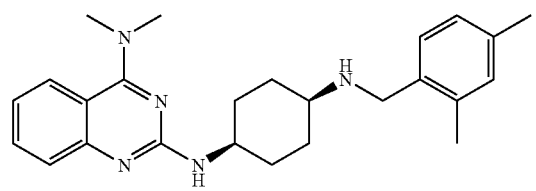 | 404 (M + H) |

-continued
| Example No. | Structure | APCI-MS |
|---|---|---|
| 1819 | 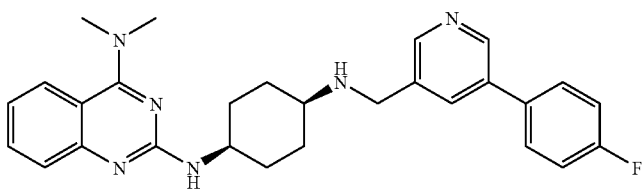 | 471 (M + H) |
| 1820 | 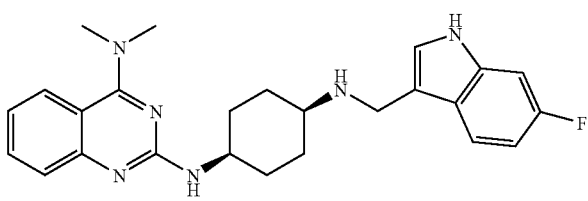 | 433 (M + H) |
| 1821 | 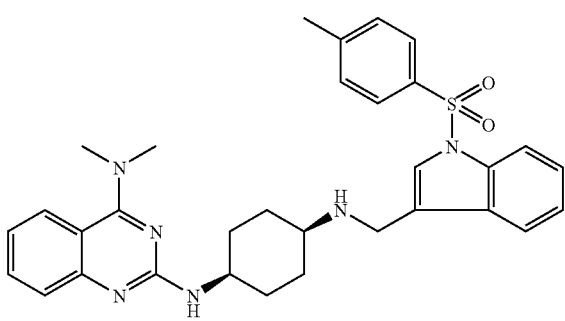 | 569 (M + H) |
| 1822 | 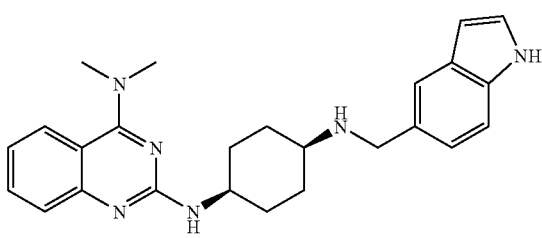 | 415 (M + H) |
| 1823 | 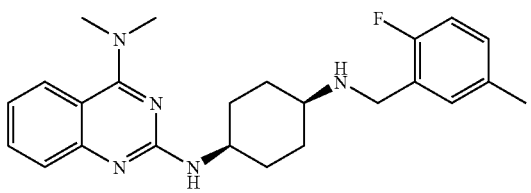 | 408 (M + H) |
| 1824 | 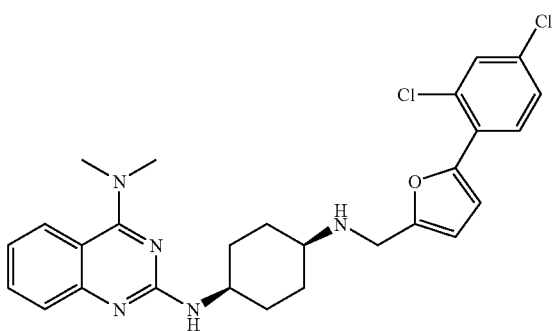 | 510 (M + H) |

-continued
| Example No. | Structure | APCI-MS |
|---|---|---|
| 1825 | 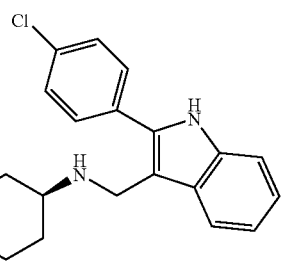 | 525 (M + H) |
| 1826 | 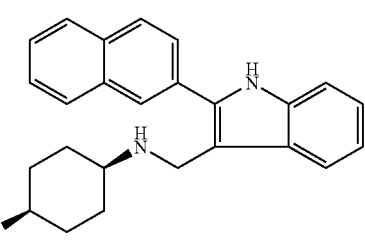 | 541 (M + H) |
| 1827 | 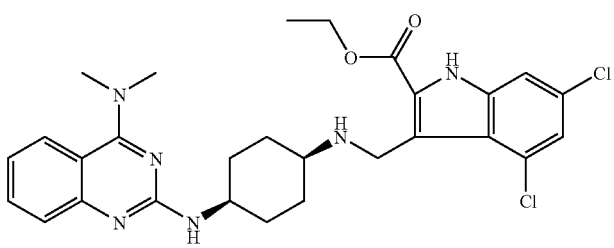 | 555 (M + H) |
| 1828 | 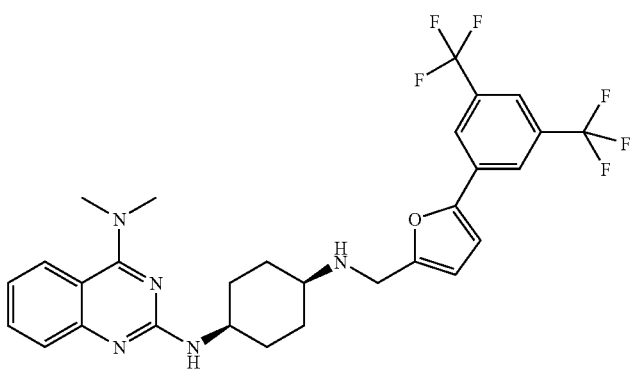 | 578 (M + H) |
| 1829 | 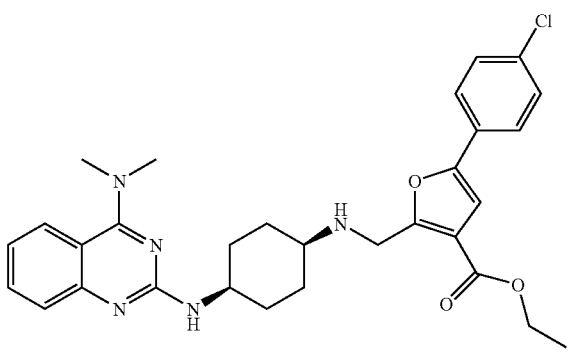 | 548 (M + H) |

-continued
| Example No. | Structure | APCI-MS |
|---|---|---|
| 1830 | 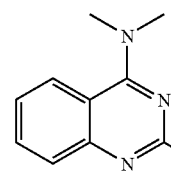 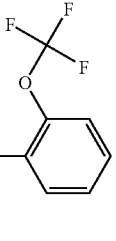 | 526 (M + H) |
| 1831 | 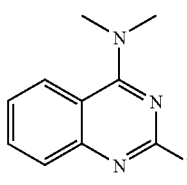 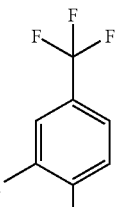 | 544 (M + H) |
| 1832 | 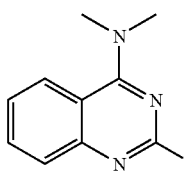 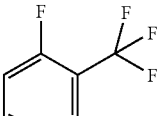 | 528 (M + H) |
| 1833 | 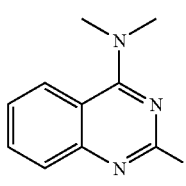  | 476 (M + H) |

-continued
| Example No. | Structure | APCI-MS |
|---|---|---|
| 1834 | 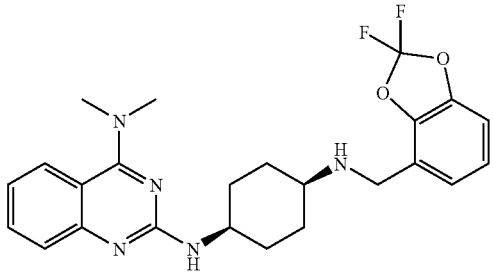 | 456 (M + H) |
| 1835 | 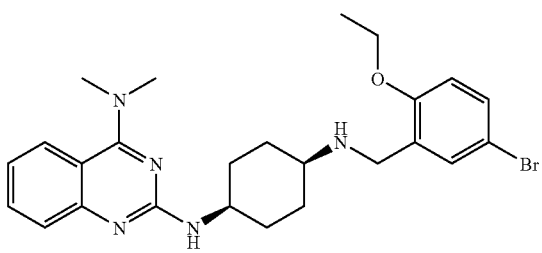 | 498 (M + H) |
| 1836 | 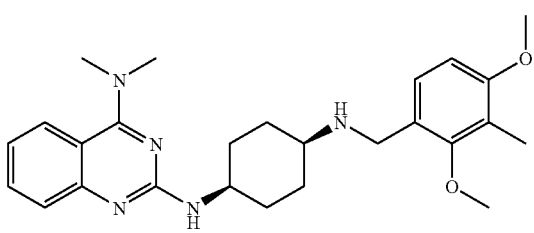 | 450 (M + H) |
| 1837 | 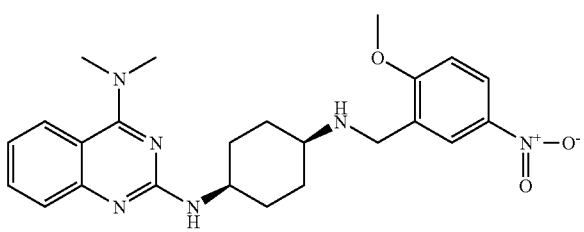 | 451 (M + H) |
| 1838 | 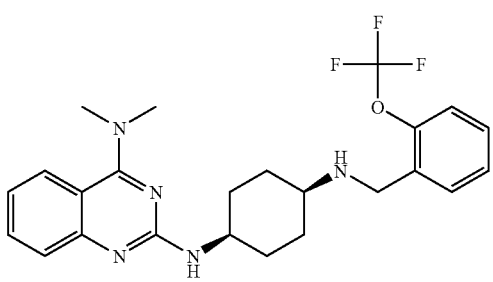 | 460 (M + H) |
| 1839 | 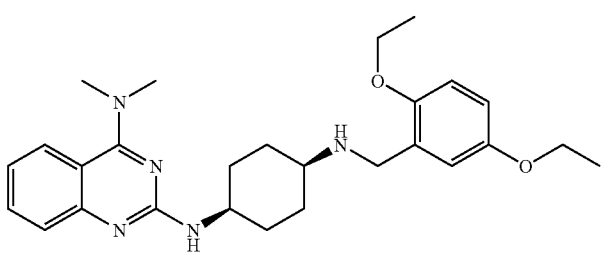 | 464 (M + H) |

-continued
| Example No. | Structure | APCI-MS |
|---|---|---|
| 1840 | 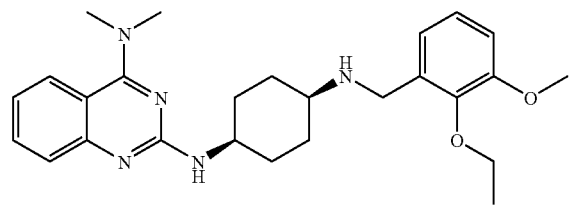 | 450 (M + H) |
| 1842 | 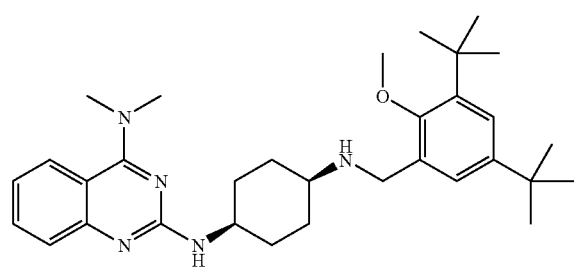 | 518 (M + H) |
| 1843 | 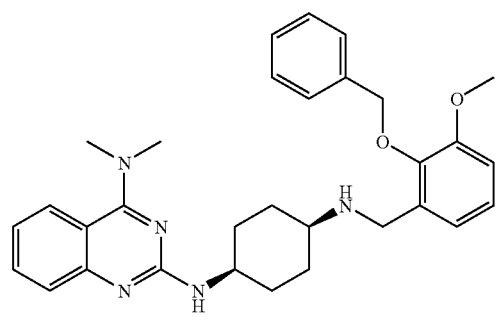 | 512 (M + H) |
| 1844 | 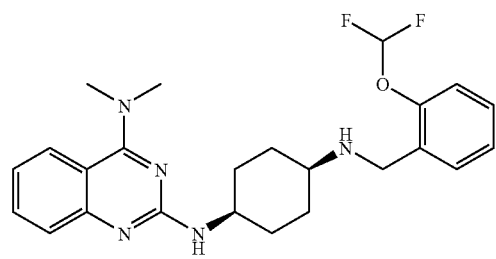 | 442 (M + H) |
| 1845 | 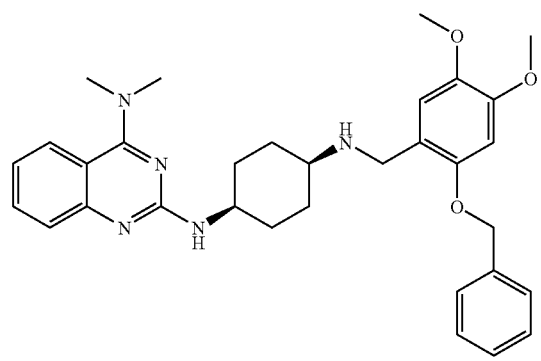 | 542 (M + H) |

-continued
| Example No. | Structure | APCI-MS |
|---|---|---|
| 1846 | 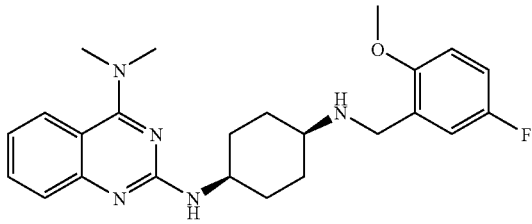 | 424 (M + H) |
| 1847 | 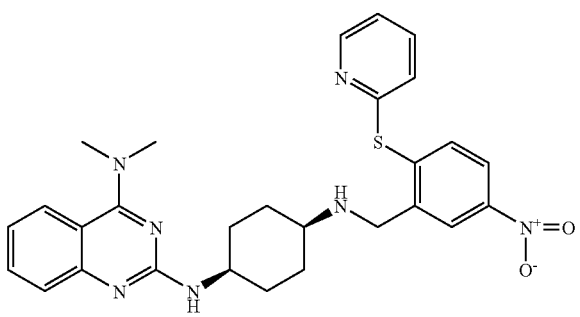 | 530 (M + H) |
| 1848 | 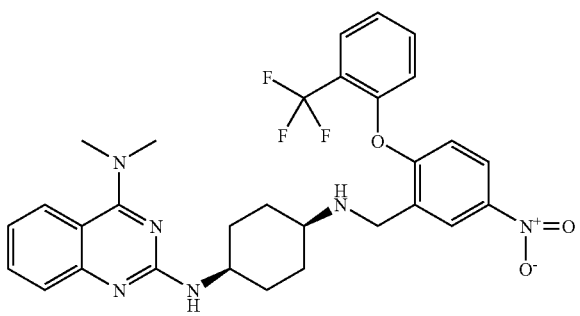 | 581 (M + H) |
| 1849 | 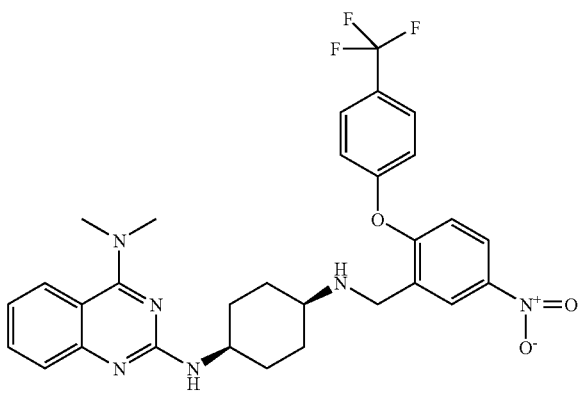 | 581 (M + H) |
| 1850 | 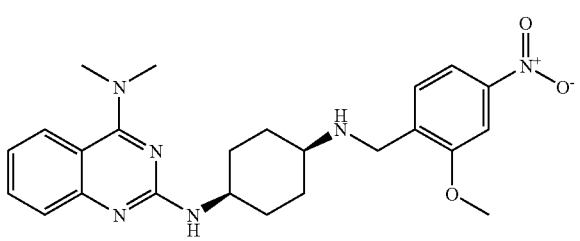 | 451 (M + H) |

-continued
| Example No. | Structure | APCI-MS |
|---|---|---|
| 1851 | 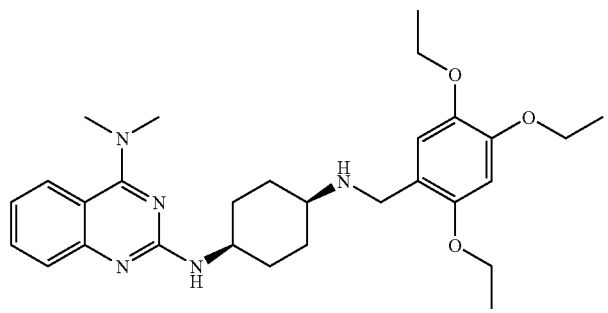 | 508 (M + H) |
| 1852 | 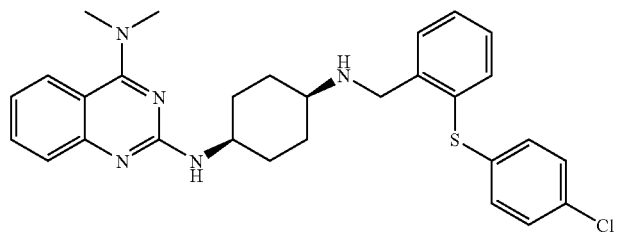 | 518 (M + H) |
| 1853 | 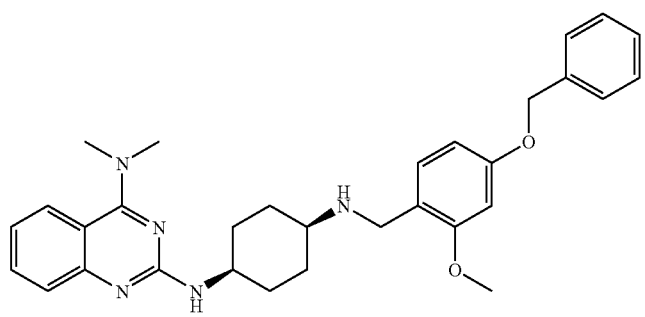 | 512 (M + H) |
| 1854 | 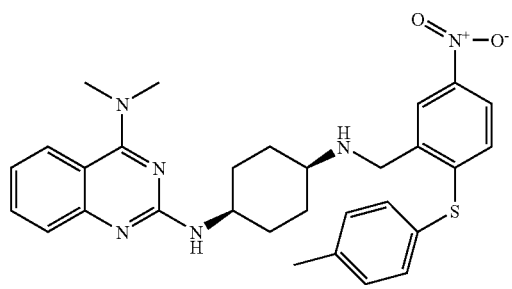 | 543 (M + H) |
| 1855 | 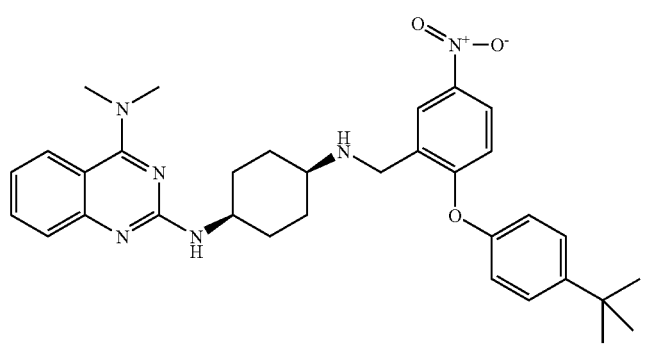 | 569 (M + H) |

-continued
| Example No. | Structure | APCI-MS |
|---|---|---|
| 1856 | 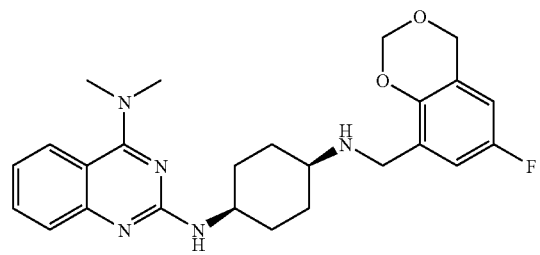 | 452 (M + H) |
| 1857 | 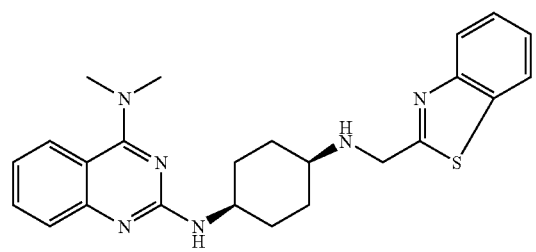 | 433 (M + H) |
| 1858 | 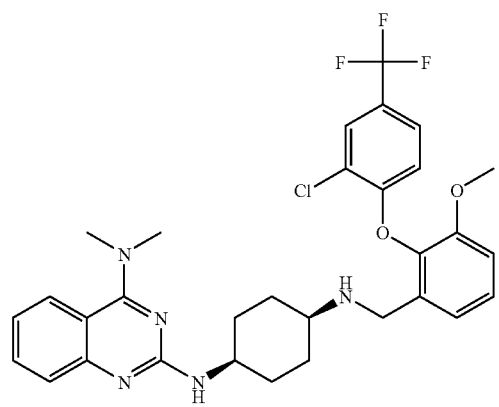 | 601 (M + H) |
| 1859 | 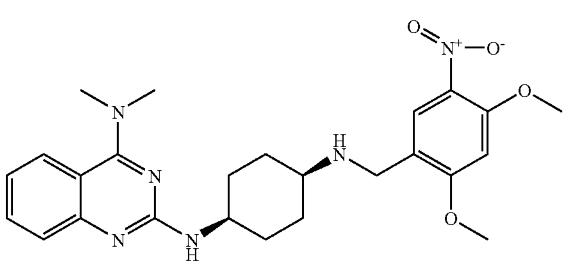 | 481 (M + H) |
| 1860 | 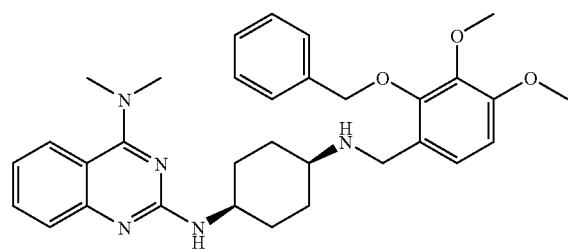 | 542 (M + H) |

-continued

| Example No. | Structure | APCI-MS |
|---|---|---|
| 1861 | 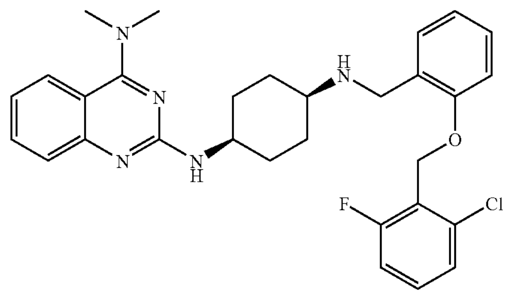 | 534 (M + H) |
| 1862 | 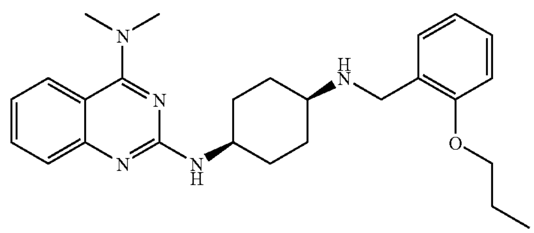 | 434 (M + H) |
| 1863 | 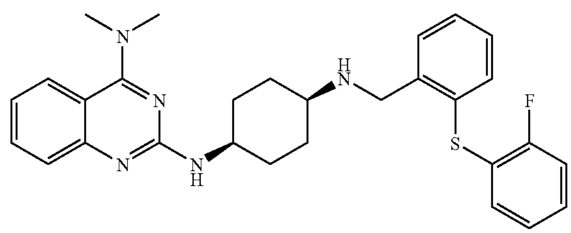 | 502 (M + H) |
| 1864 | 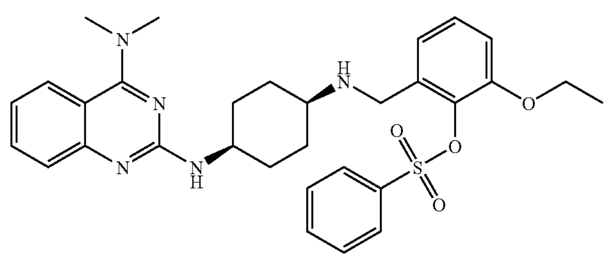 | 576 (M + H) |
| 1865 | 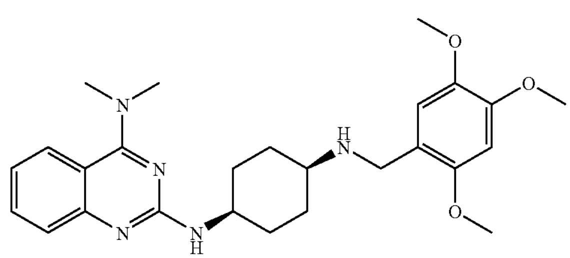 | 466 (M + H) |
| 1866 | 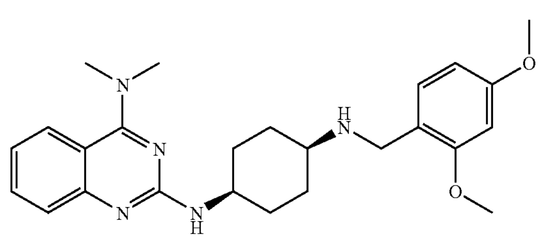 | 436 (M + H) |

-continued

| Example No. | Structure | APCI-MS |
|---|---|---|
| 1867 | 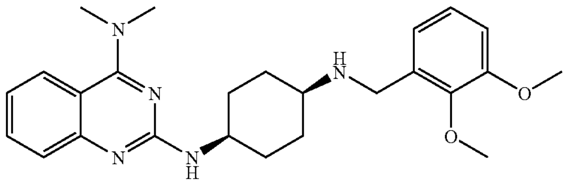 | 436 (M + H) |
| 1868 | 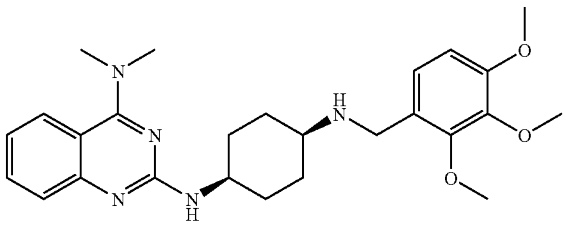 | 466 (M + H) |
| 1869 | 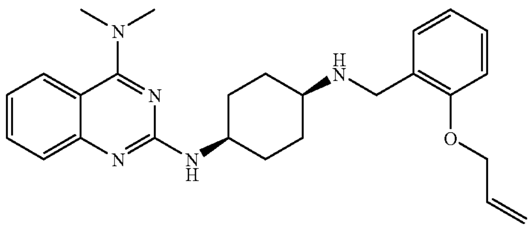 | 432 (M + H) |
| 1870 | 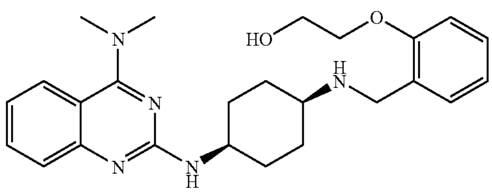 | 436 (M + H) |
| 1871 | 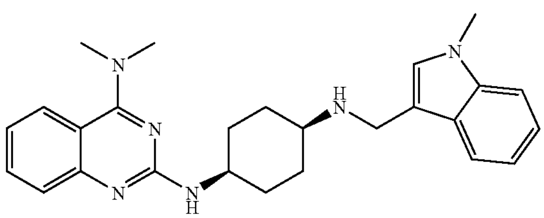 | 429 (M + H) |
| 1872 | 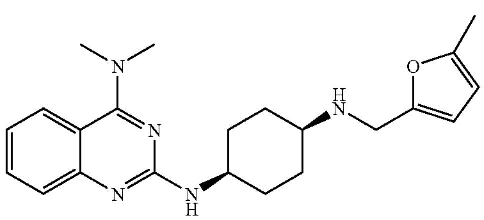 | 380 (M + H) |
| 1873 | 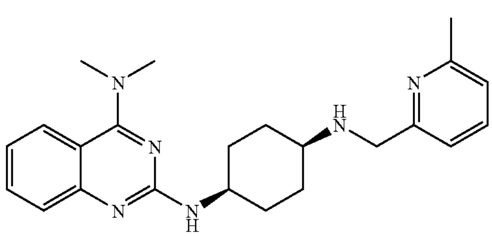 | 391 (M + H) |

-continued
| Example No. | Structure | APCI-MS |
|---|---|---|
| 1874 | 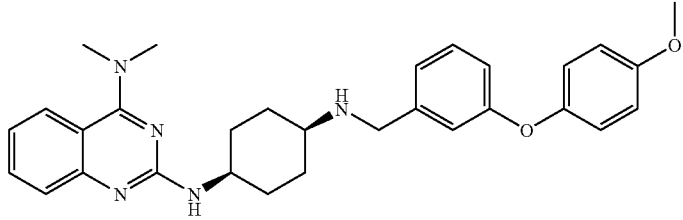 | 498 (M + H) |
| 1875 | 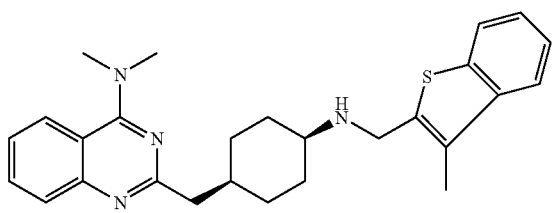 | 446 (M + H) |
| 1876 | 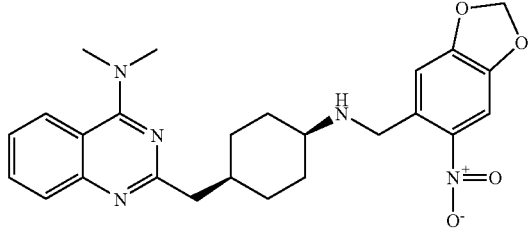 | 465 (M + H) |
| 1877 | 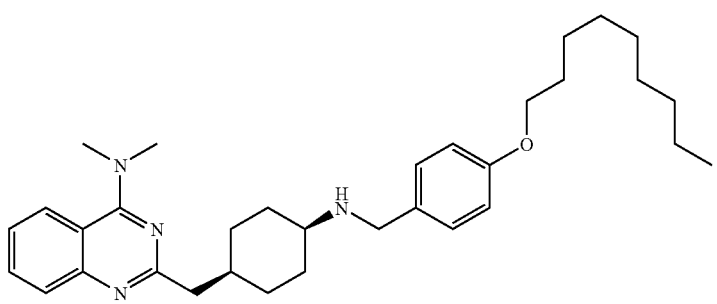 | 518 (M + H) |
| 1878 | 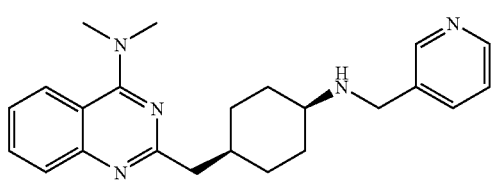 | 377 (M + H) |
| 1879 | 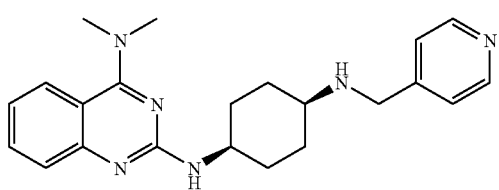 | 377 (M + H) |

-continued
| Example No. | Structure | APCI-MS |
|---|---|---|
| 1880 | 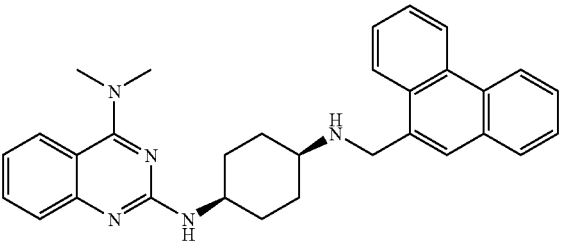 | 476 (M + H) |
| 1881 | 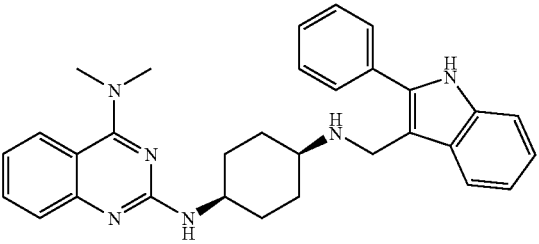 | 491 (M + H) |
| 1882 | 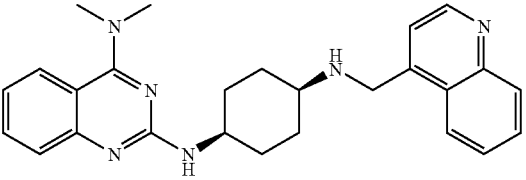 | 427 (M + H) |
| 1883 | 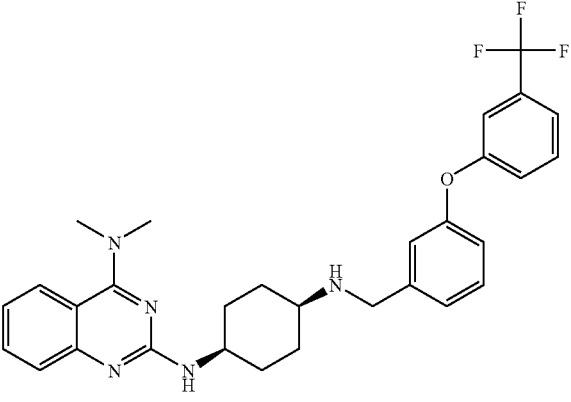 | 536 (M + H) |
| 1884 | 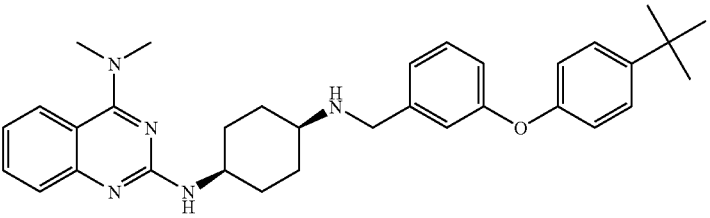 | 524 (M + H) |
| 1885 | 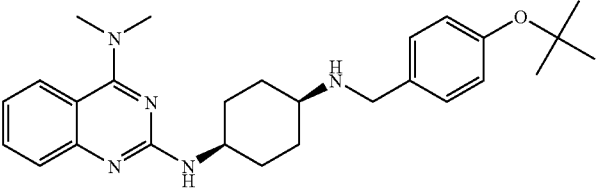 | 448 (M + H) |

-continued
| Example No. | Structure | APCI-MS |
|---|---|---|
| 1886 | 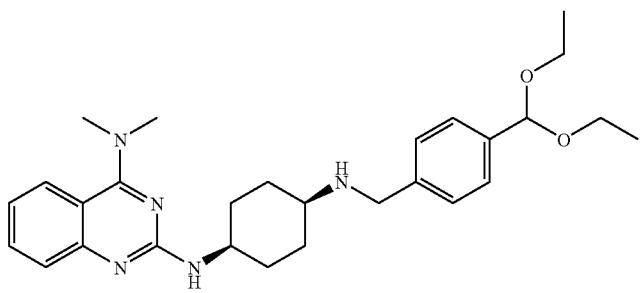 | 478 (M + H) |
| 1887 | 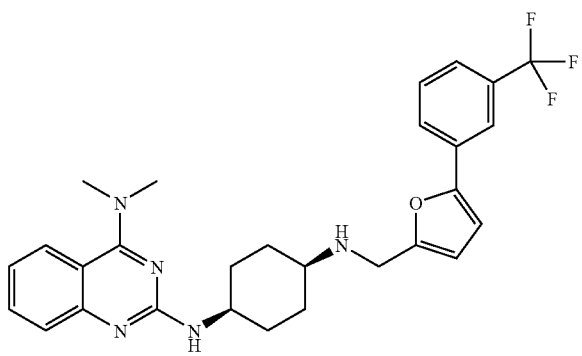 | 510 (M + H) |
| 1888 | 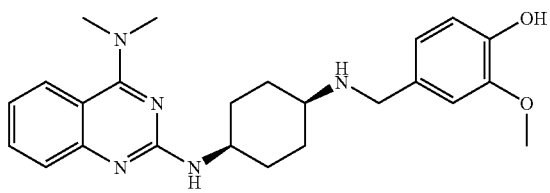 | 422 (M + H) |
| 1889 | 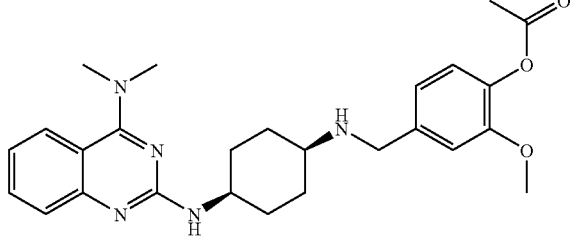 | 464 (M + H) |
| 1890 | 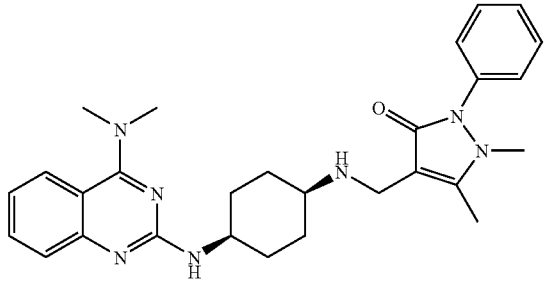 | 486 (M + H) |
| 1891 | 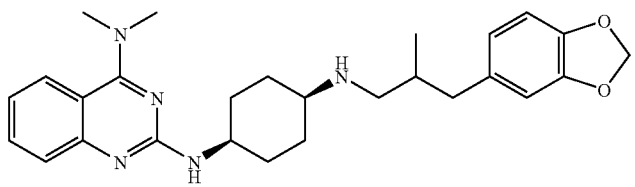 | 462 (M + H) |

-continued
| Example No. | Structure | APCI-MS |
|---|---|---|
| 1892 | 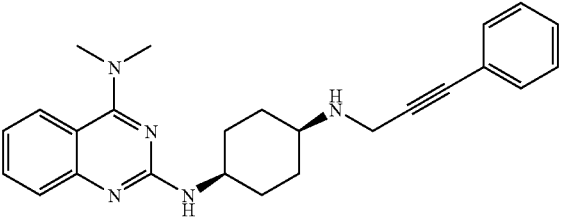 | 400 (M + H) |
| 1893 | 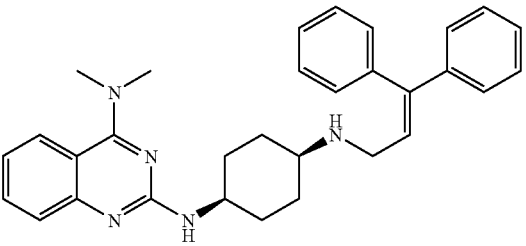 | 478 (M + H) |
| 1894 | 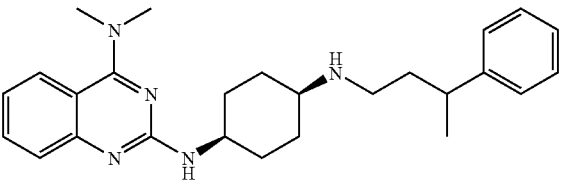 | 418 (M + H) |
| 1895 | 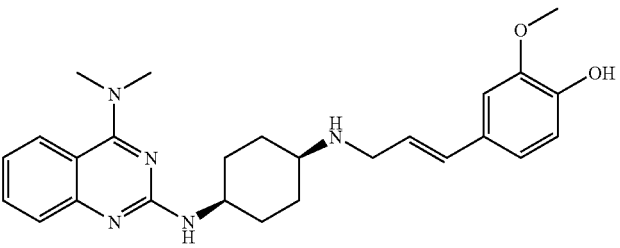 | 448 (M + H) |
| 1896 | 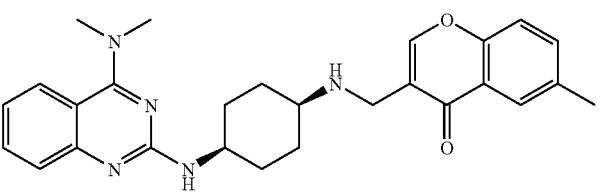 | 458 (M + H) |
| 1897 | 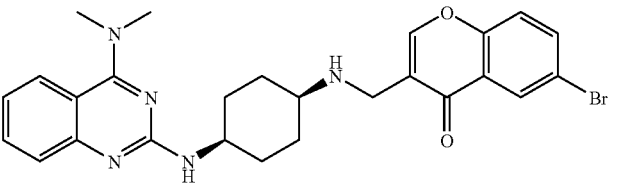 | 522 (M + H) |
| 1898 | 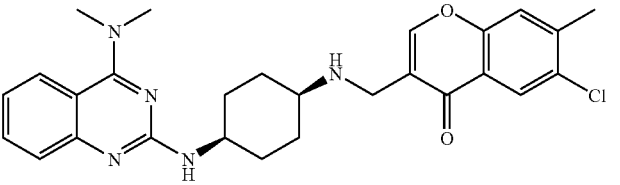 | 492 (M + H) |

-continued
| Example No. | Structure | APCI-MS |
|---|---|---|
| 1899 | 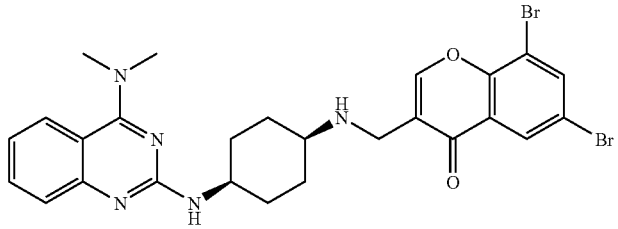 | 600 (M + H) |
| 1900 | 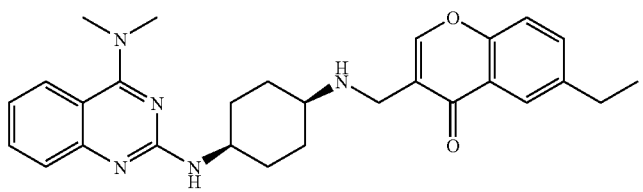 | 472 (M + H) |
| 1901 | 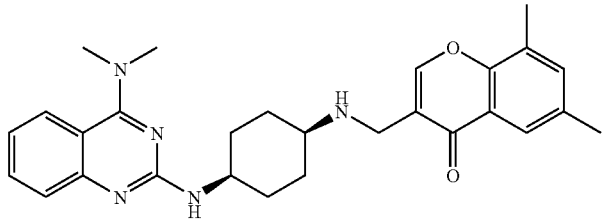 | 472 (M + H) |
| 1902 | 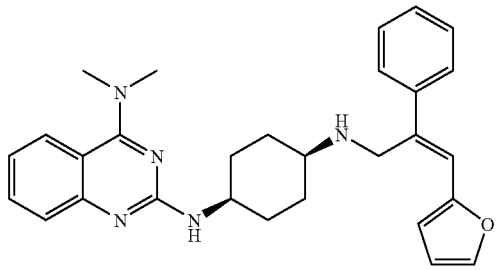 | 468 (M + H) |
| 1903 | 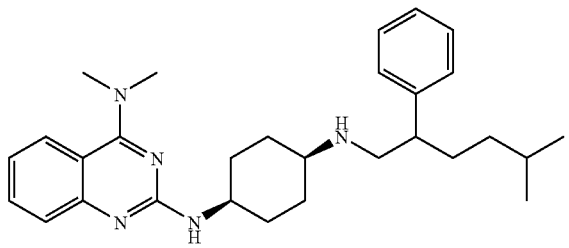 | 460 (M + H) |
| 1904 | 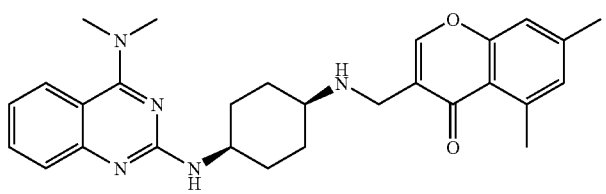 | 472 (M + H) |

-continued
| Example No. | Structure | APCI-MS |
|---|---|---|
| 1905 | 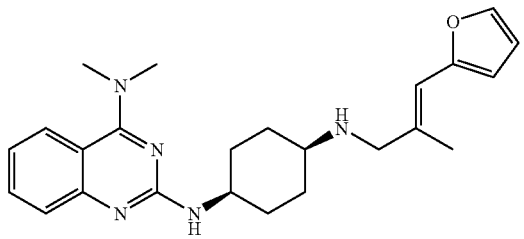 | 406 (M + H) |
| 1906 | 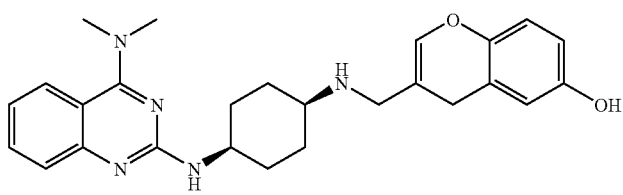 | 446 (M + H) |
| 1907 | 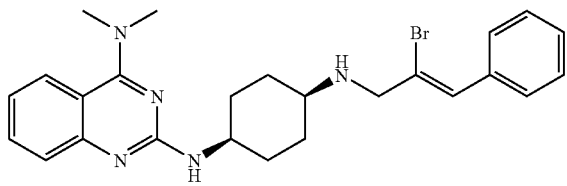 | 480 (M + H) |
| 1908 | 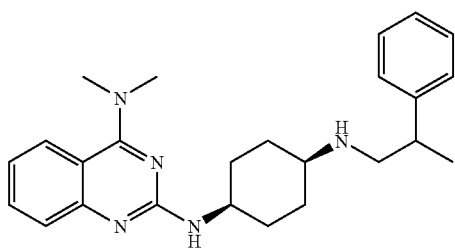 | 404 (M + H) |
| 1909 | 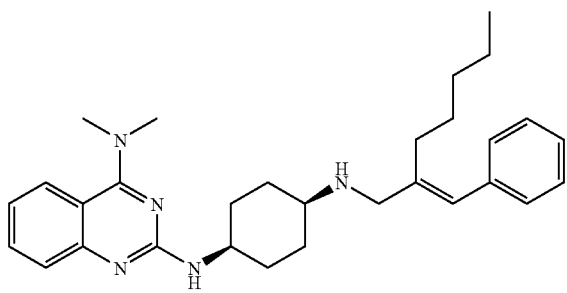 | 472 (M + H) |
| 1910 | 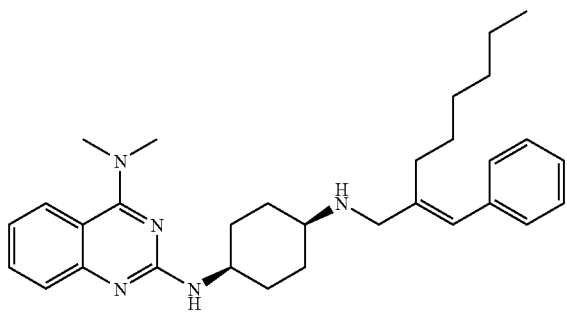 | 486 (M + H) |

-continued
| Example No. | Structure | APCI-MS |
|---|---|---|
| 1911 | 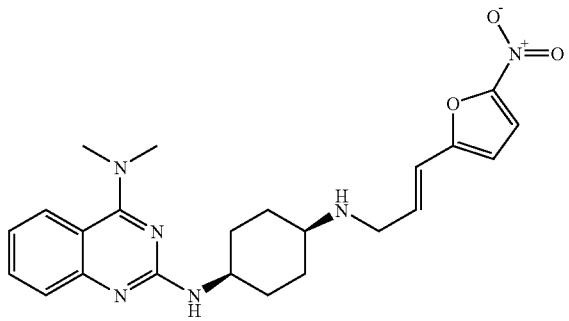 | 437 (M + H) |
| 1912 | 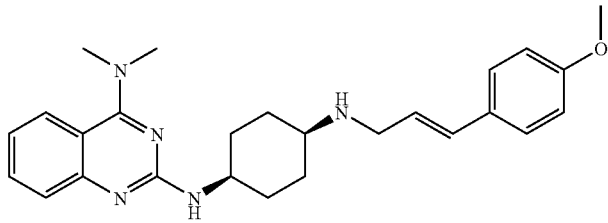 | 432 (M + H) |
| 1913 | 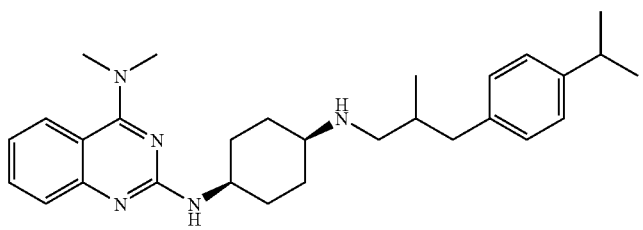 | 460 (M + H) |
| 1914 | 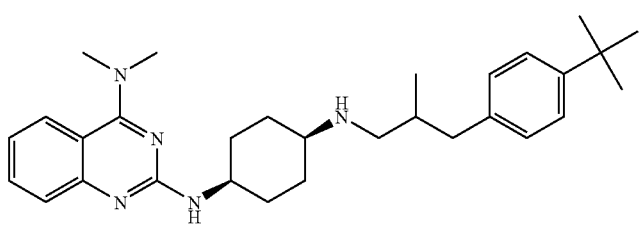 | 474 (M + H) |
| 1915 | 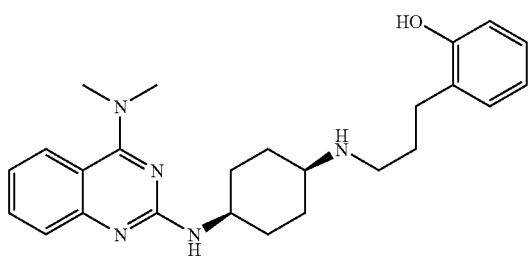 | 420 (M + H) |
| 1916 | 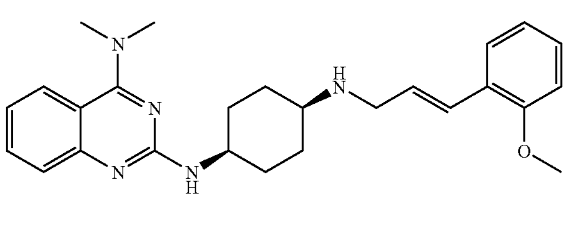 | 432 (M + H) |

-continued
| Example No. | Structure | APCI-MS |
|---|---|---|
| 1917 | 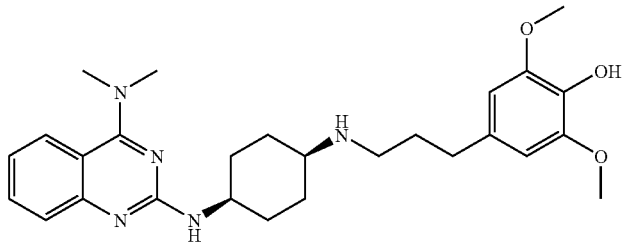 | 480 (M + H) |
| 1918 | 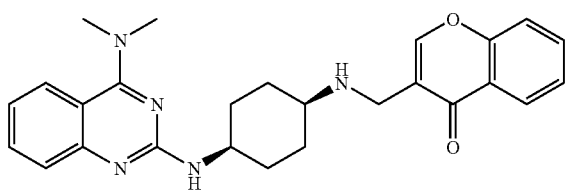 | 444 (M + H) |
| 1919 | 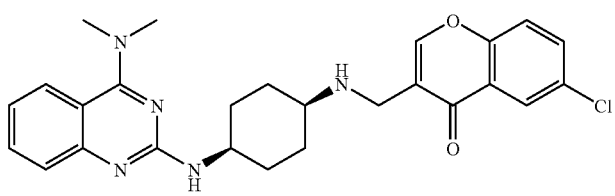 | 478 (M + H) |
| 1920 | 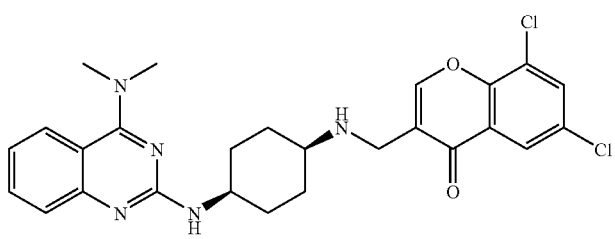 | 512 (M + H) |
| 1921 | 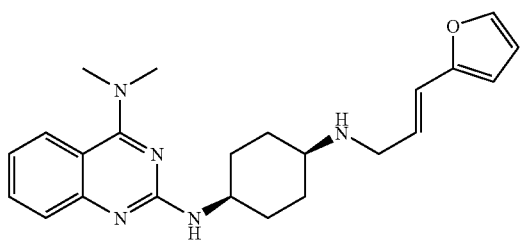 | 392 (M + H) |
| 1922 | 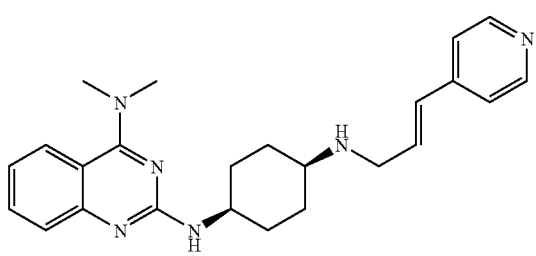 | 403 (M + H) |

-continued
| Example No. | Structure | APCI-MS |
|---|---|---|
| 1923 | 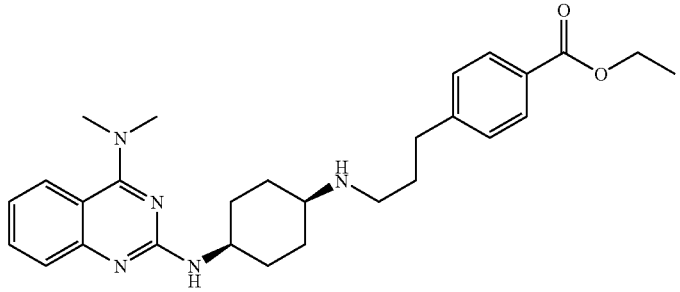 | 476 (M + H) |
| 1924 | 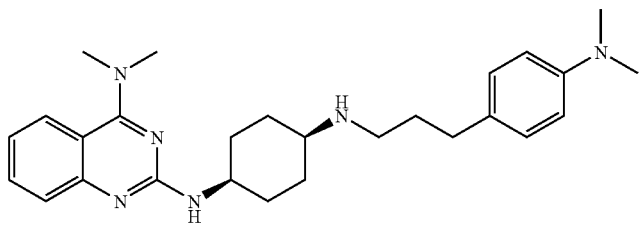 | 447 (M + H) |
| 1925 | 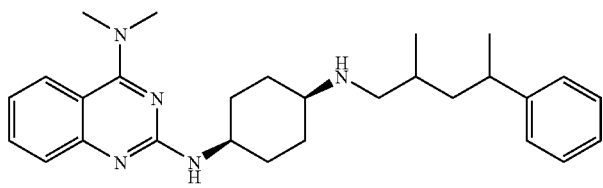 | 446 (M + H) |
| 1926 | 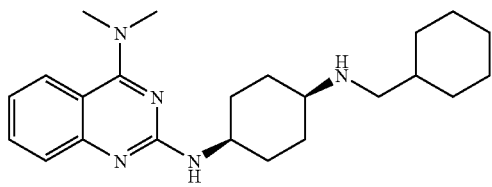 | 382 (M + H) |
| 1927 | 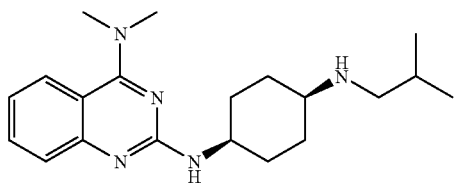 | 342 (M + H) |
| 1928 | 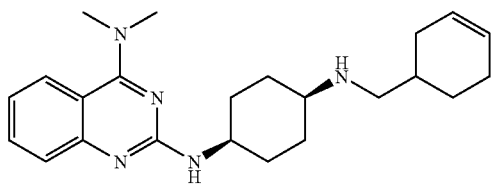 | 380 (M + H) |
| 1929 | 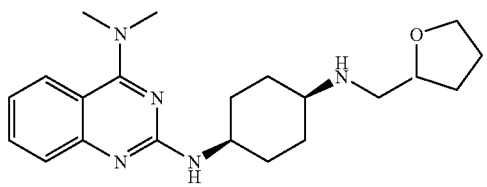 | 370 (M + H) |

-continued
| Example No. | Structure | APCI-MS |
|---|---|---|
| 1930 | 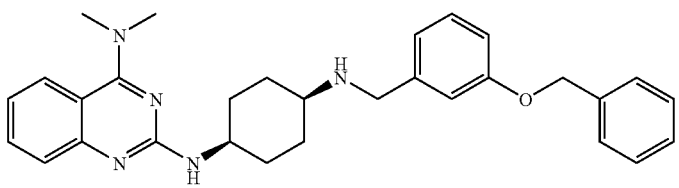 | 482 (M + H) |
| 1931 | 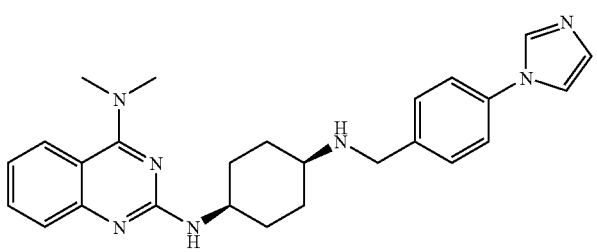 | 442 (M + H) |
| 1932 | 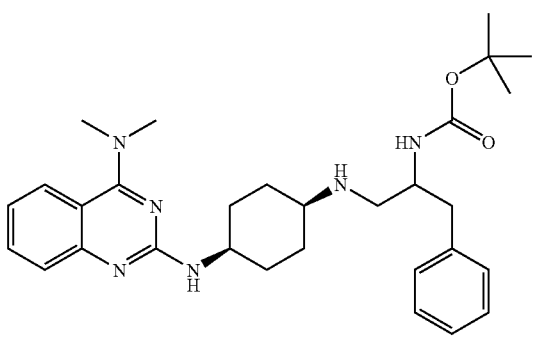 | 519 (M + H) |
| 1933 | 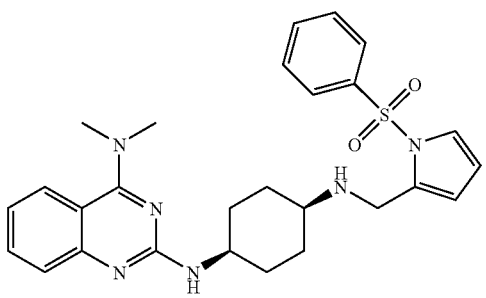 | 505 (M + H) |
| 1934 | 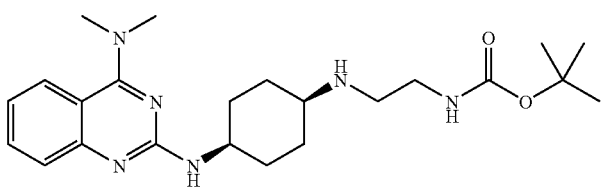 | 429 (M + H) |
| 1935 | 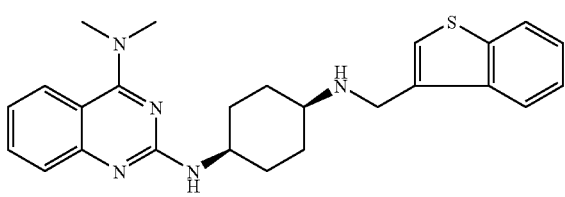 | 432 (M + H) |

-continued
| Example No. | Structure | APCI-MS |
|---|---|---|
| 1936 | 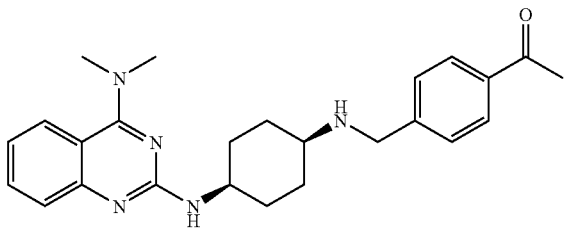 | 418 (M + H) |
| 1937 | 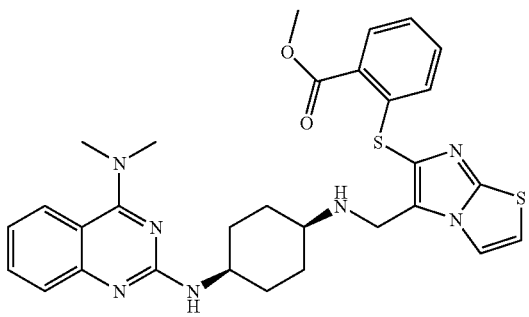 | 588 (M + H) |
| 1938 | 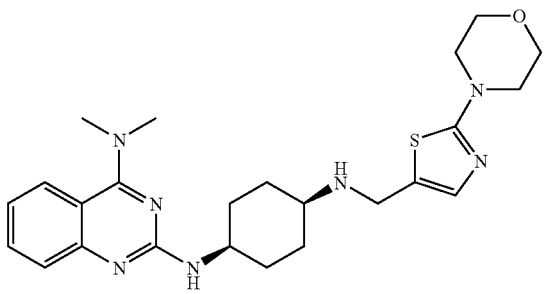 | 468 (M + H) |
| 1939 | 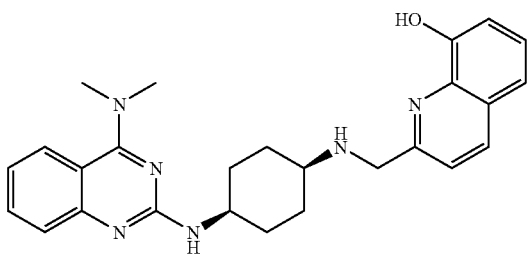 | 443 (M + H) |
| 1940 | 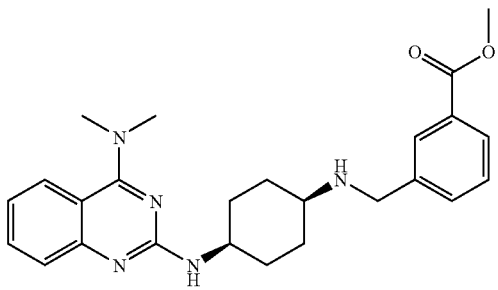 | 434 (M + H) |

-continued
| Example No. | Structure | APCI-MS |
|---|---|---|
| 1941 | 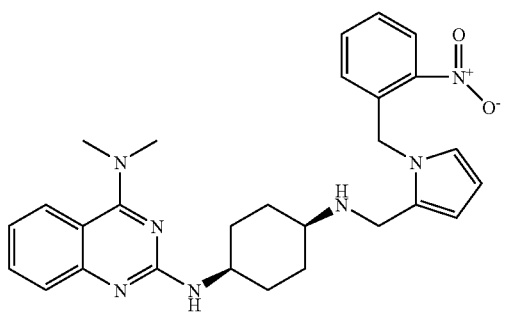 | 500 (M + H) |
| 1942 | 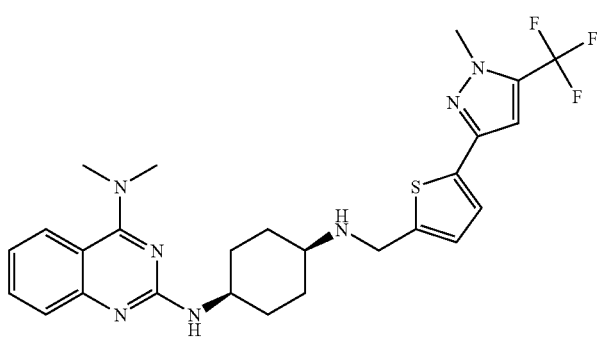 | 530 (M + H) |
| 1943 | 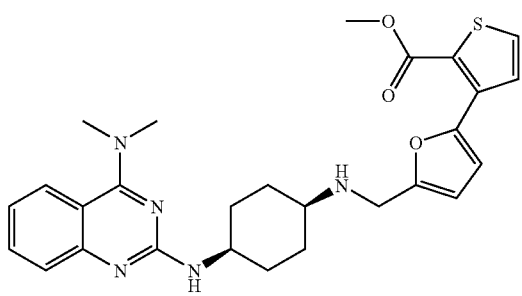 | 506 (M + H) |
| 1944 | 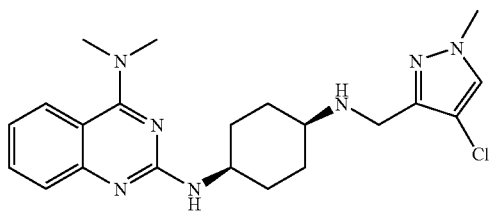 | 414 (M + H) |
| 1945 | 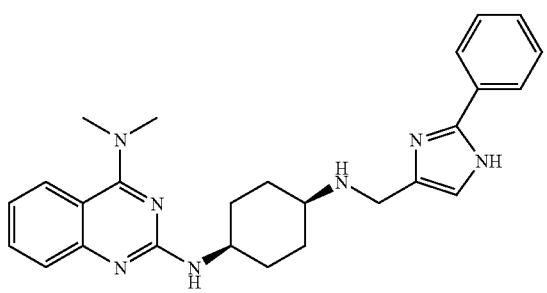 | 442 (M + H) |

-continued
| Example No. | Structure | APCI-MS |
|---|---|---|
| 1946 | 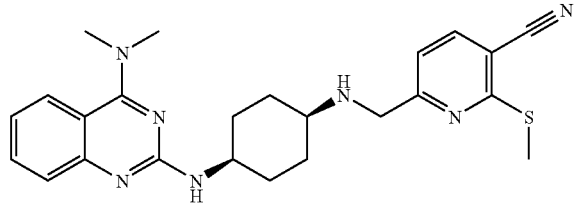 | 448 (M + H) |
| 1947 | 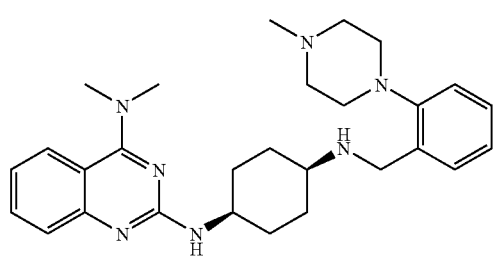 | 474 (M + H) |
| 1948 | 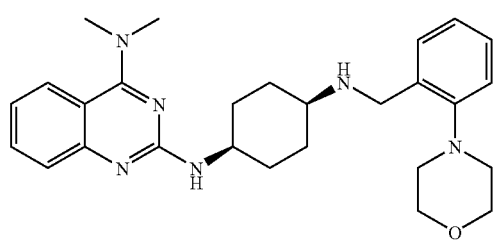 | 461 (M + H) |
| 1949 | 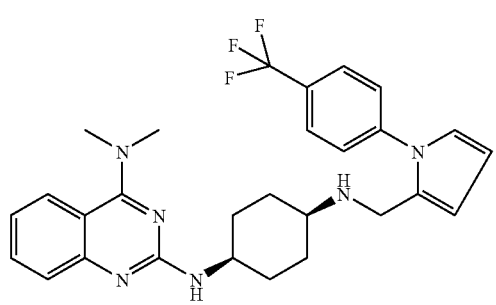 | 509 (M + H) |
| 1950 | 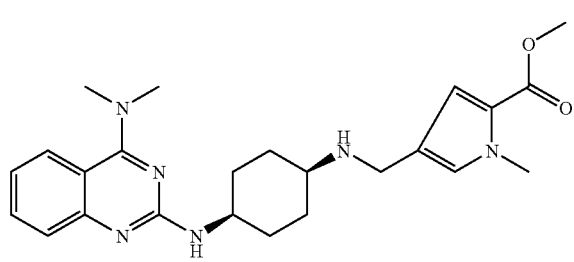 | 437 (M + H) |
| 1951 | 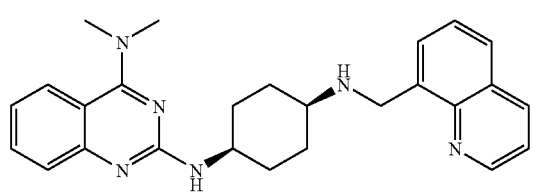 | 427 (M + H) |

-continued
| Example No. | Structure | APCI-MS |
|---|---|---|
| 1952 | 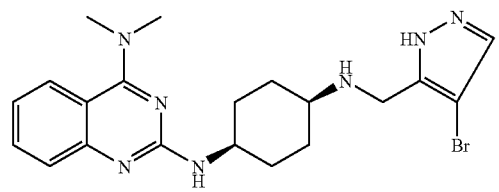 | 444 (M + H) |
| 1953 | 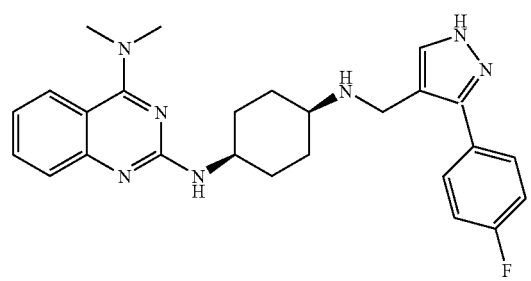 | 460 (M + H) |
| 1954 | 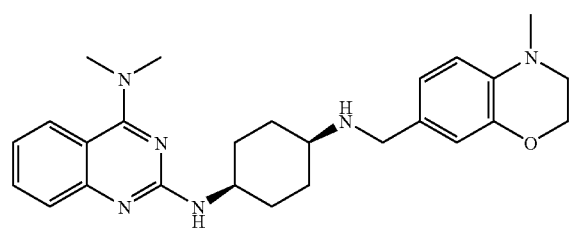 | 447 (M + H) |
| 1955 | 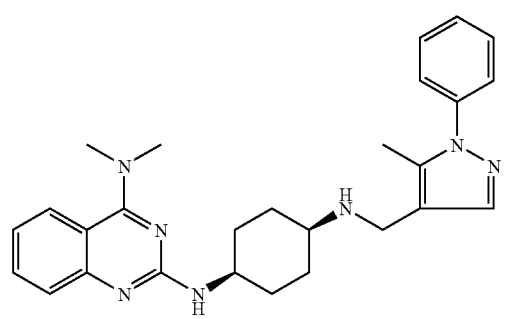 | 456 (M + H) |
| 1956 | 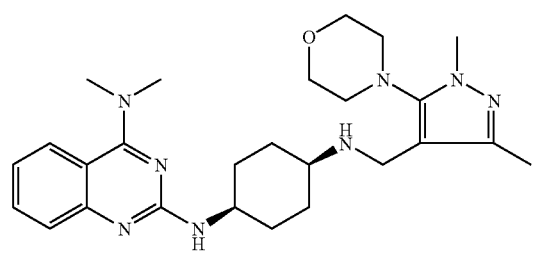 | 479 (M + H) |
| 1957 | 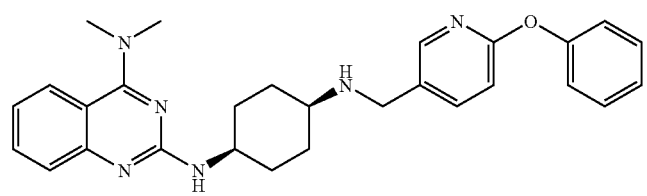 | 469 (M + H) |

-continued
| Example No. | Structure | APCI-MS |
|---|---|---|
| 1958 | 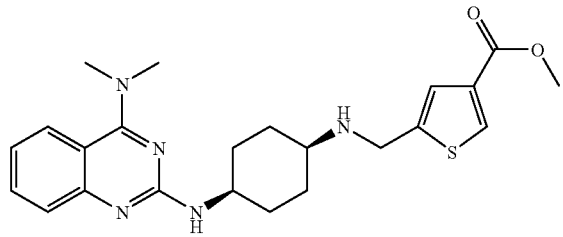 | 440 (M + H) |
| 1959 | 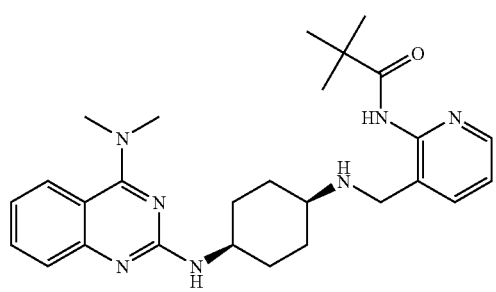 | 476 (M + H) |
| 1960 | 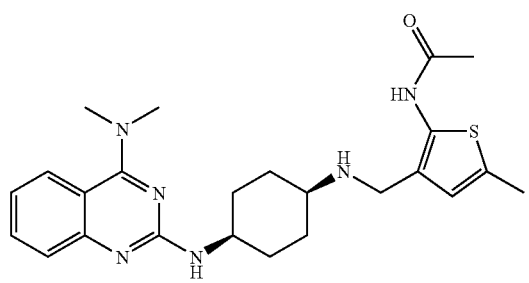 | 453 (M + H) |
| 1961 | 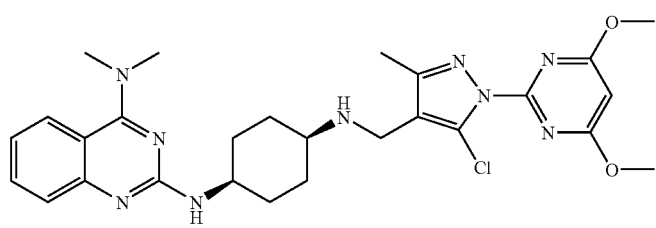 | 552 (M + H) |
| 1962 | 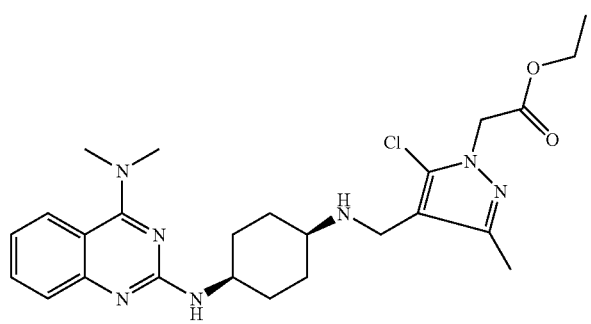 | 500 (M + H) |

-continued
| Example No. | Structure | APCI-MS |
|---|---|---|
| 1963 | 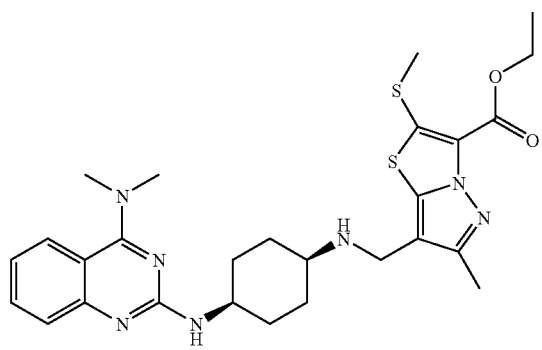 | 554 (M + H) |
| 1964 | 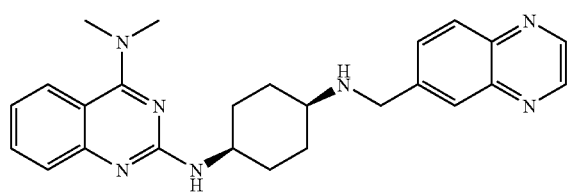 | 428 (M + H) |
| 1965 | 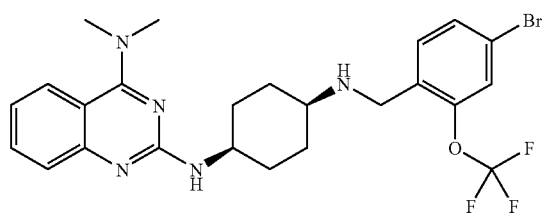 | 538 (M + H) |
| 1966 | 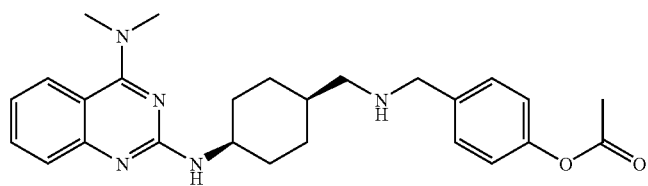 | 448 (M + H) |
| 1967 | 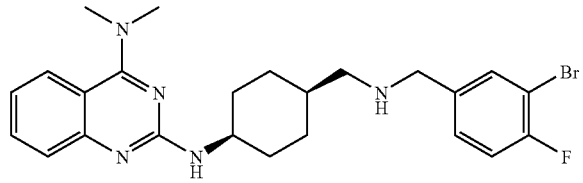 | 486 (M + H) |
| 1968 | 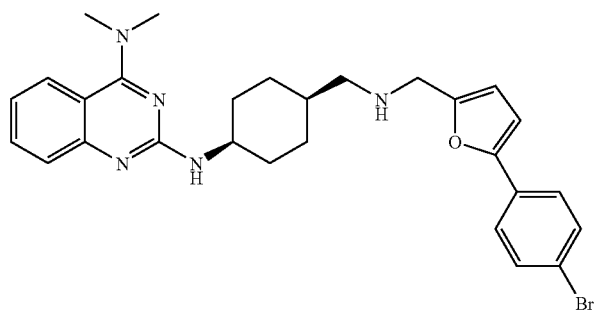 | 534 (M + H) |

-continued
| Example No. | Structure | APCI-MS |
|---|---|---|
| 1969 | 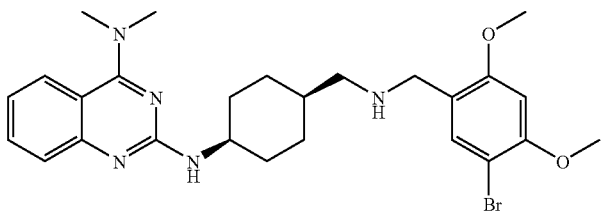 | 528 (M + H) |
| 1970 | 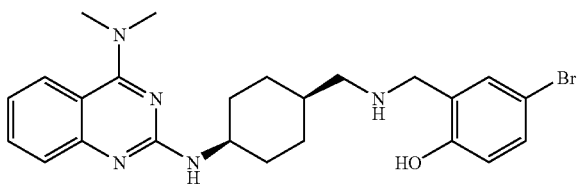 | 484 (M + H) |
| 1971 | 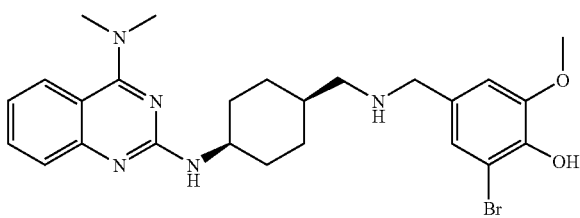 | 514 (M + H) |
| 1972 | 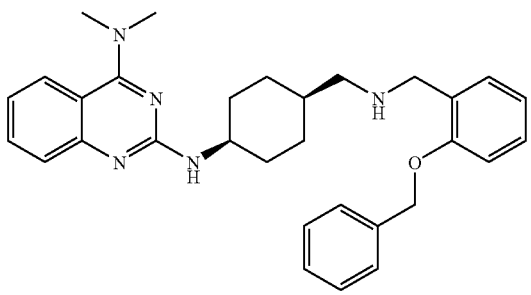 | 496 (M + H) |
| 1973 | 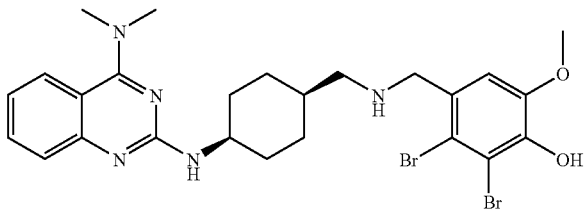 | 592 (M + H) |
| 1974 | 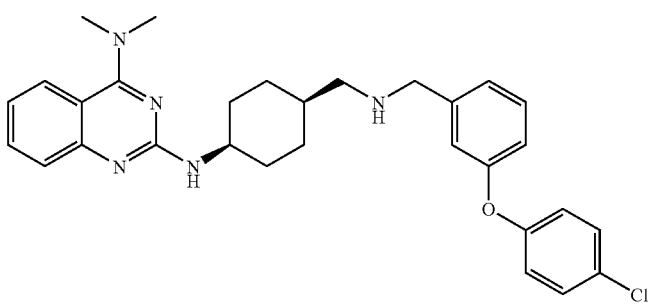 | 516 (M + H) |

-continued
| Example No. | Structure | APCI-MS |
|---|---|---|
| 1975 | 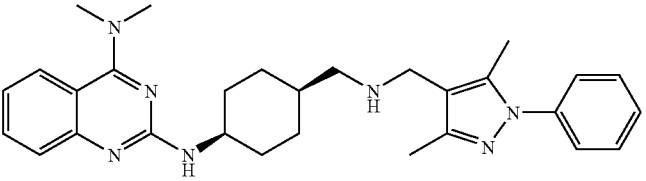 | 504 (M + H) |
| 1976 | 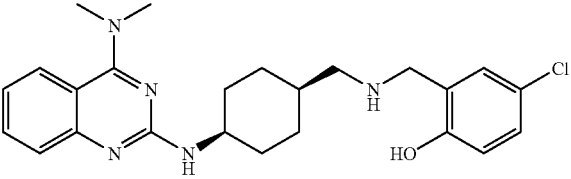 | 440 (M + H) |
| 1977 | 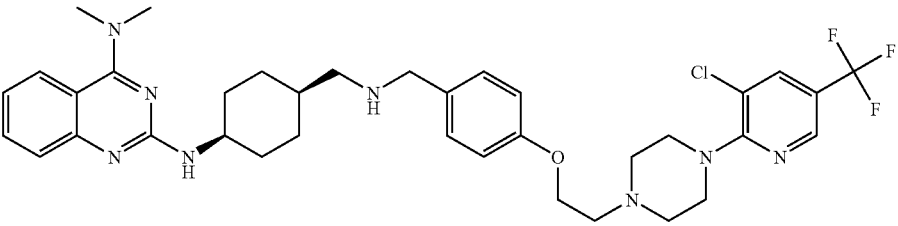 | 697 (M + H) |
| 1978 | 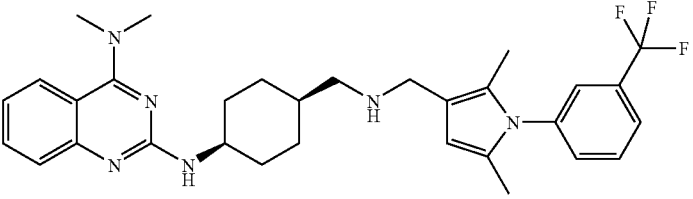 | 551 (M + H) |
| 1979 | 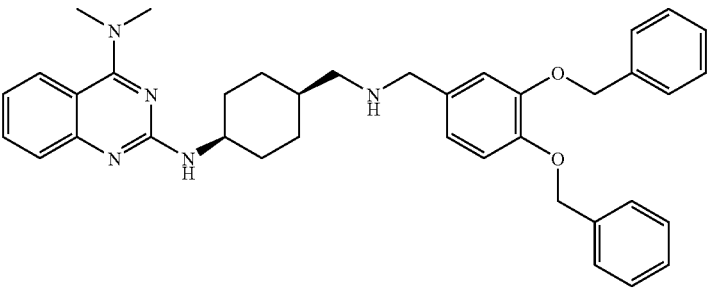 | 602 (M + H) |
| 1980 | 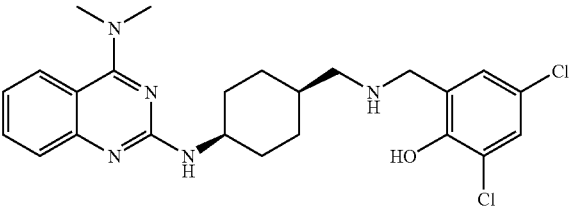 | 474 (M + H) |
| 1981 | 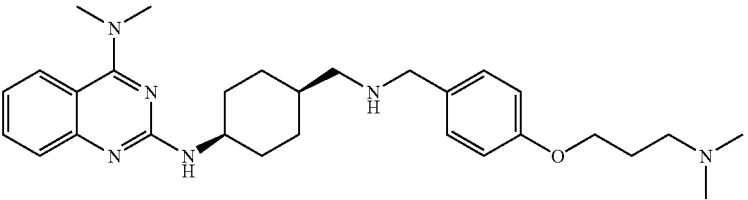 | 491 (M + H) |

-continued
| Example No. | Structure | APCI-MS |
|---|---|---|
| 1982 | 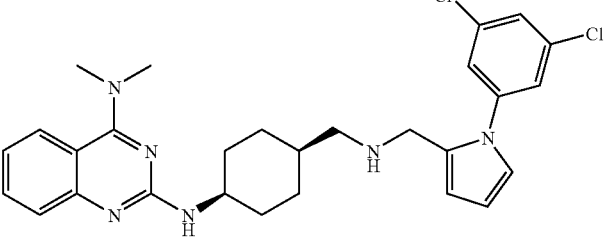 | 523 (M + H) |
| 1983 | 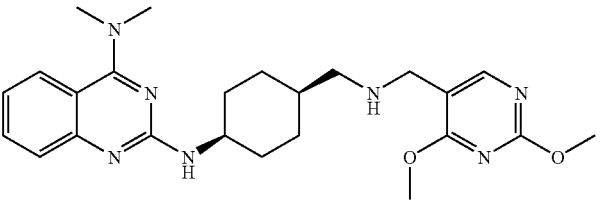 | 452 (M + H) |
| 1984 | 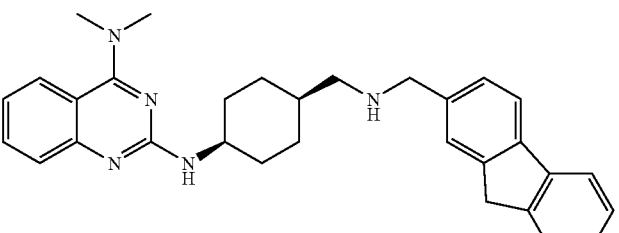 | 478 (M + H) |
| 1985 | 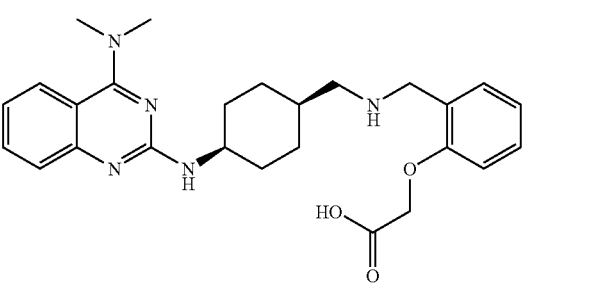 | 464 (M + H) |
| 1986 | 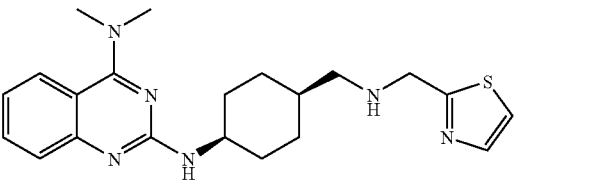 | 397 (M + H) |
| 1987 | 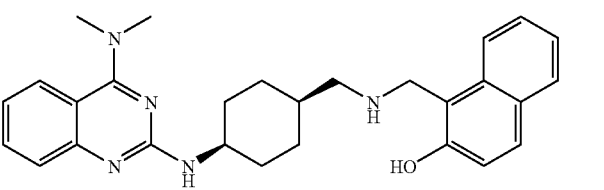 | 454 (M + H) |

-continued
| Example No. | Structure | APCI-MS |
|---|---|---|
| 1988 | 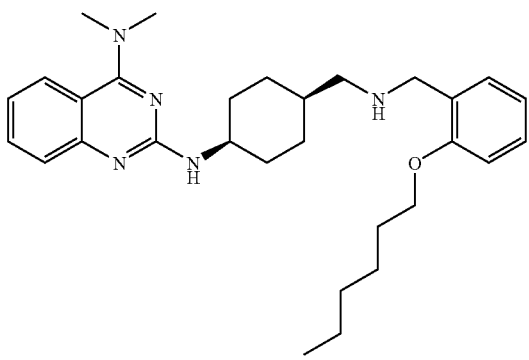 | 490 (M + H) |
| 1989 | 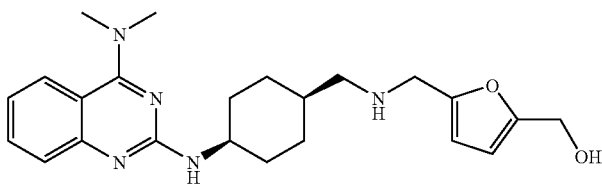 | 410 (M + H) |
| 1990 | 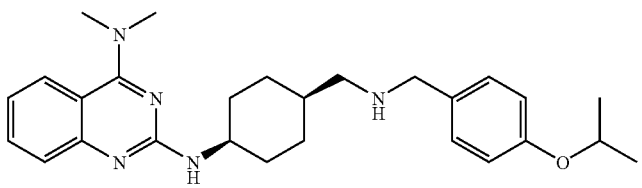 | 448 (M + H) |
| 1991 | 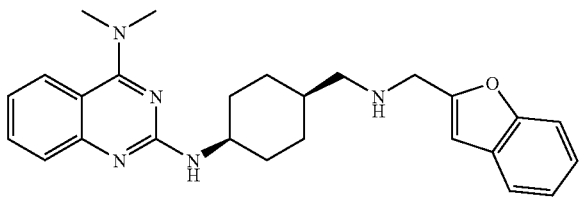 | 430 (M + H) |
| 1992 | 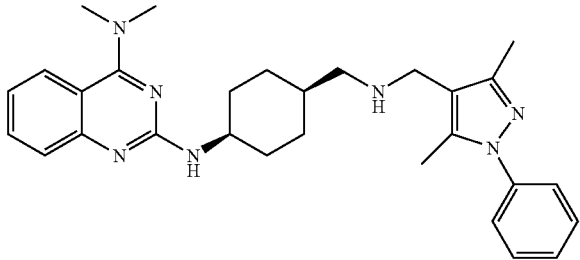 | 484 (M + H) |
| 1993 | 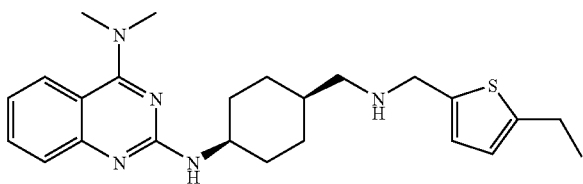 | 424 (M + H) |

-continued
| Example No. | Structure | APCI-MS |
|---|---|---|
| 1994 | 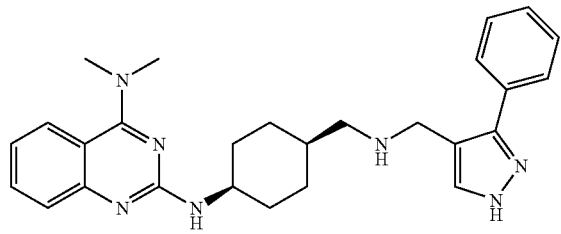 | 456 (M + H) |
| 1995 | 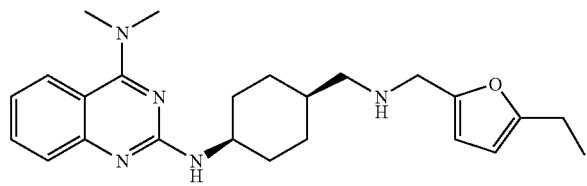 | 408 (M + H) |
| 1996 | 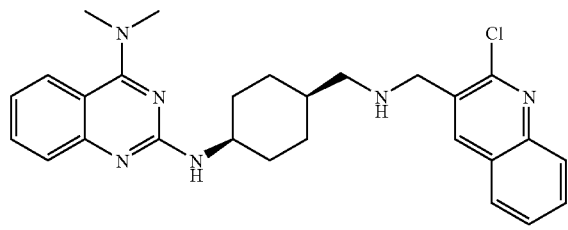 | 475 (M + H) |
| 1997 | 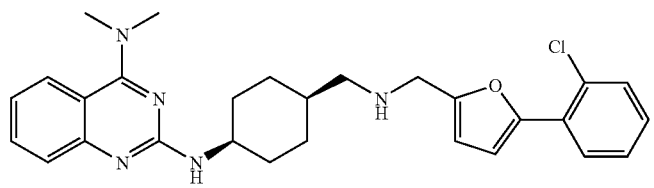 | 490 (M + H) |
| 1998 | 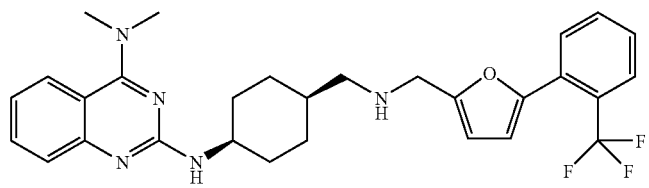 | 524 (M + H) |
| 1999 | 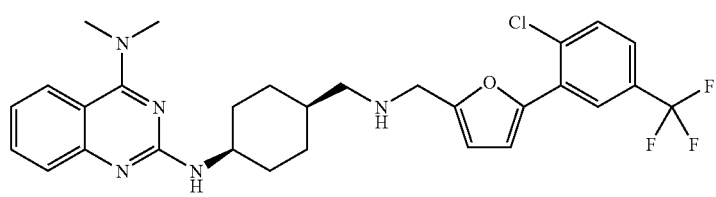 | 558 (M + H) |
| 2000 | 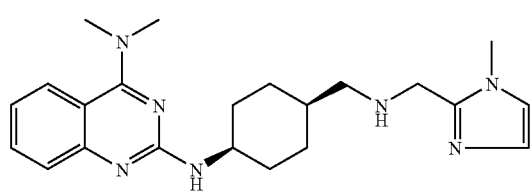 | 394 (M + H) |

-continued
| Example No. | Structure | APCI-MS |
|---|---|---|
| 2001 | 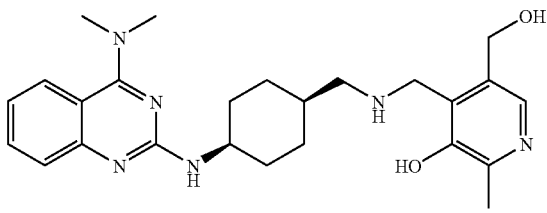 | 451 (M + H) |
| 2002 | 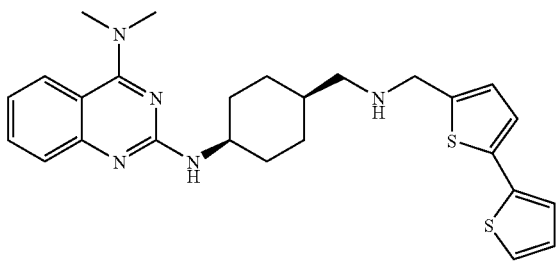 | 478 (M + H) |
| 2003 | 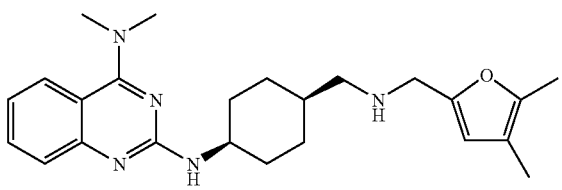 | 408 (M + H) |
| 2004 | 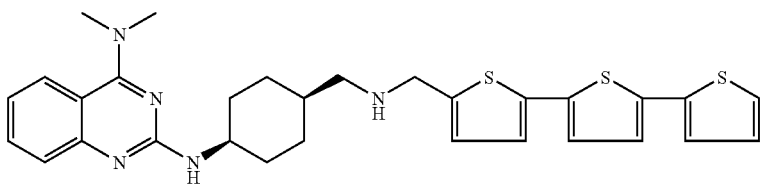 | 560 (M + H) |
| 2005 | 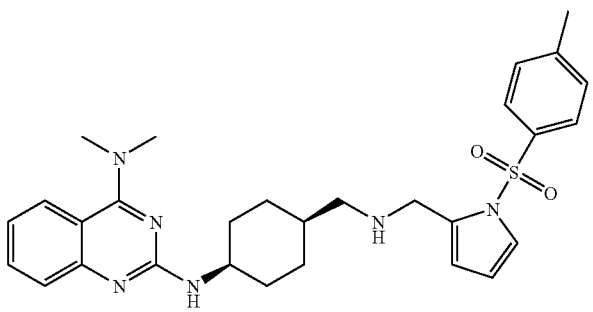 | 533 (M + H) |
| 2006 | 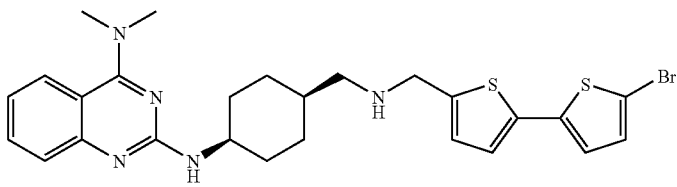 | 556 (M + H) |

-continued
| Example No. | Structure | APCI-MS |
|---|---|---|
| 2007 | 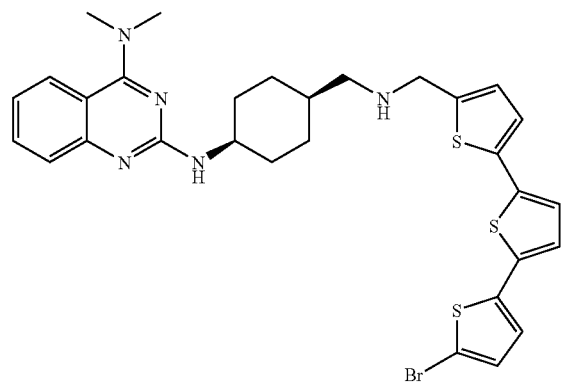 | 638 (M + H) |
| 2008 | 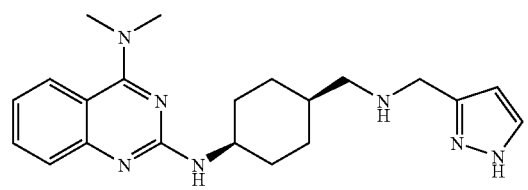 | 380 (M + H) |
| 2009 | 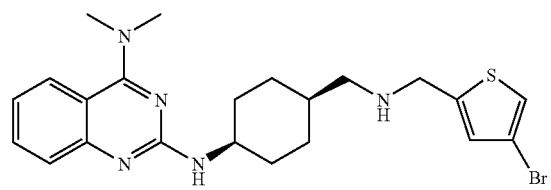 | 474 (M + H) |
| 2010 | 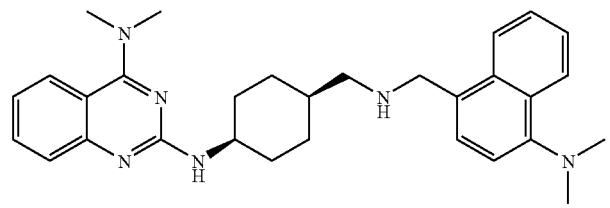 | 483 (M + H) |
| 2011 | 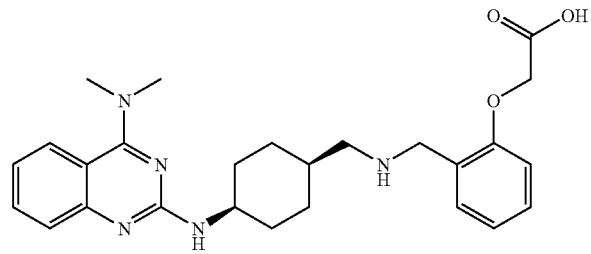 | 464 (M + H) |
| 2012 | 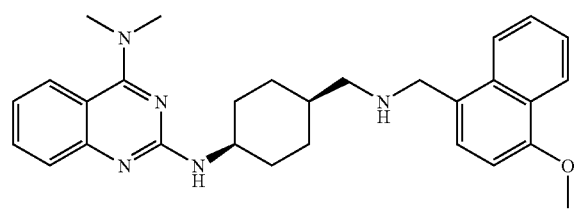 | 470 (M + H) |

-continued
| Example No. | Structure | APCI-MS |
|---|---|---|
| 2013 | 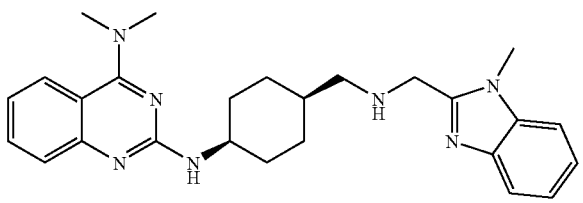 | 444 (M + H) |
| 2014 | 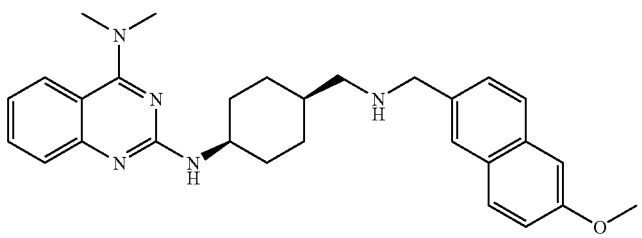 | 470 (M + H) |
| 2015 | 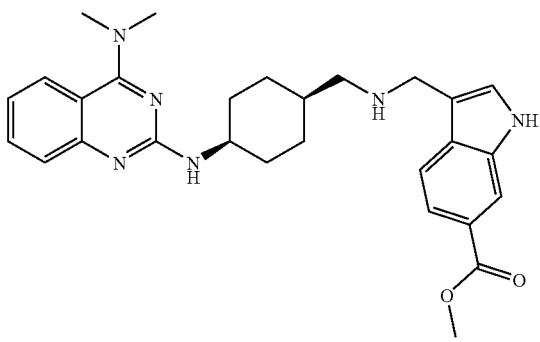 | 487 (M + H) |
| 2016 | 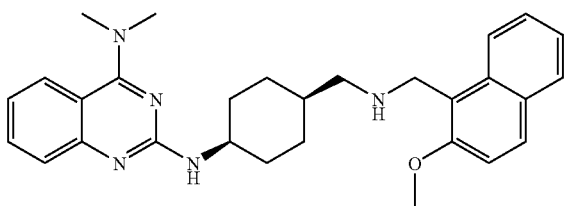 | 470 (M + H) |
| 2017 | 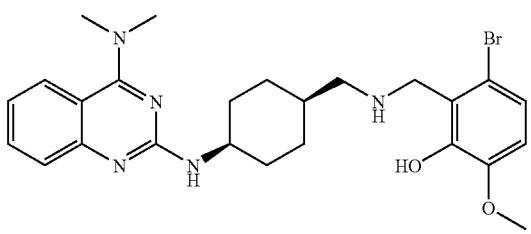 | 514 (M + H) |
| 2018 | 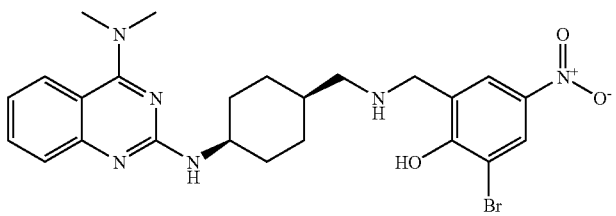 | 527 (M + H) |

-continued
| Example No. | Structure | APCI-MS |
|---|---|---|
| 2019 | 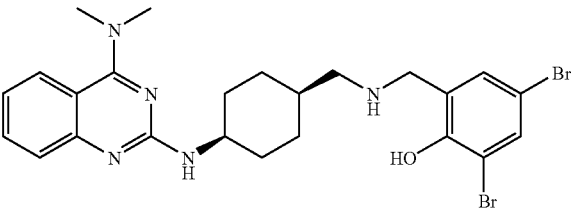 | 562 (M + H) |
| 2020 | 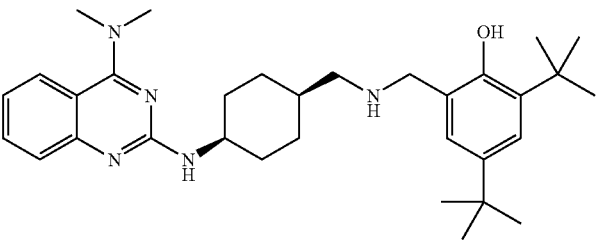 | 518 (M + H) |
| 2021 | 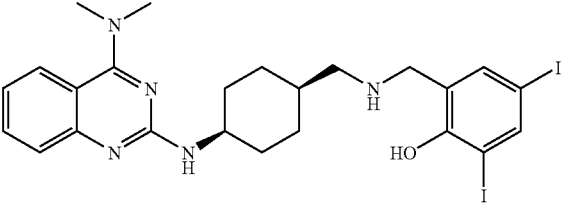 | 658 (M + H) |
| 2022 | 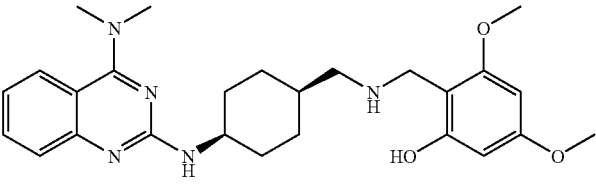 | 466 (M + H) |
| 2023 | 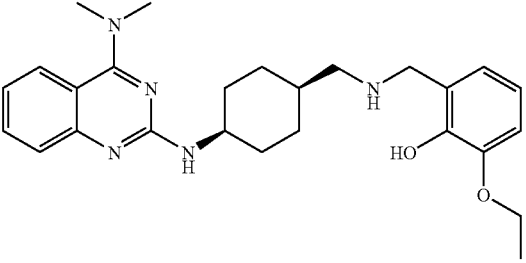 | 450 (M + H) |
| 2024 | 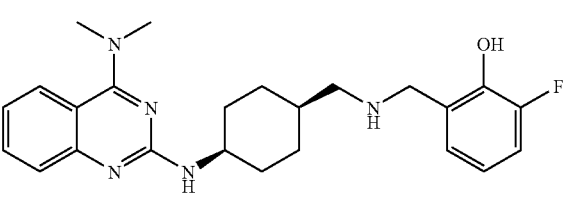 | 424 (M + H) |
| 2025 | 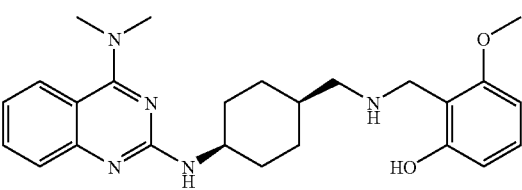 | 436 (M + H) |

-continued
| Example No. | Structure | APCI-MS |
|---|---|---|
| 2026 | 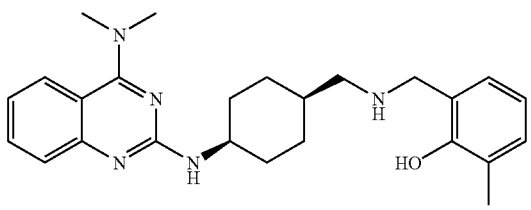 | 420 (M + H) |
| 2027 | 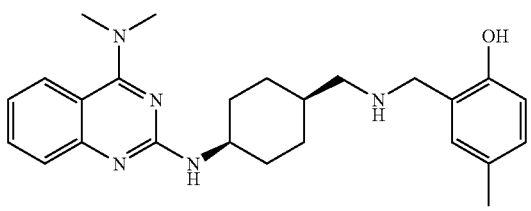 | 420 (M + H) |
| 2028 | 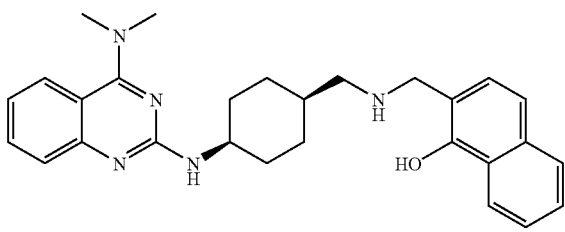 | 456 (M + H) |
| 2029 | 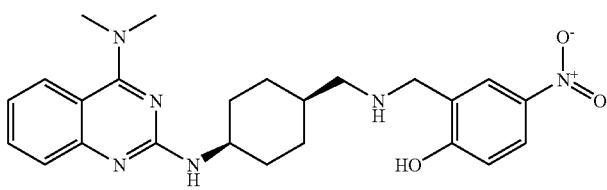 | 451 (M + H) |
| 2030 | 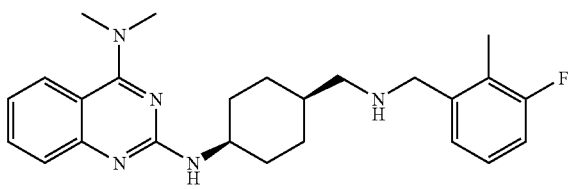 | 422 (M + H) |
| 2031 | 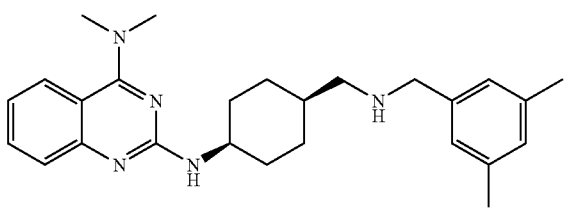 | 418 (M + H) |
| 2032 | 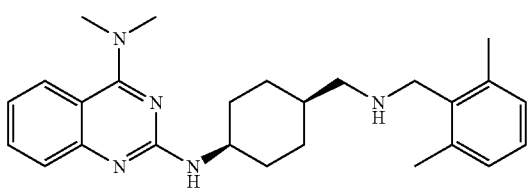 | 418 (M + H) |

-continued
| Example No. | Structure | APCI-MS |
|---|---|---|
| 2033 | 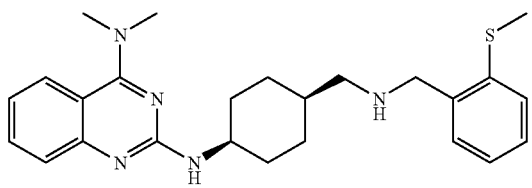 | 436 (M + H) |
| 2034 | 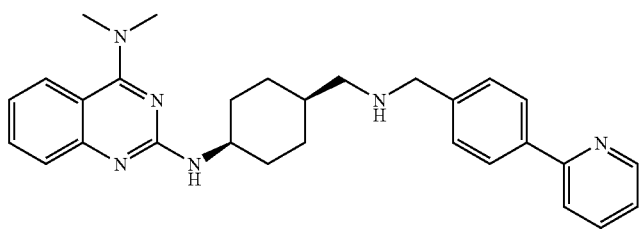 | 467 (M + H) |
| 2035 | 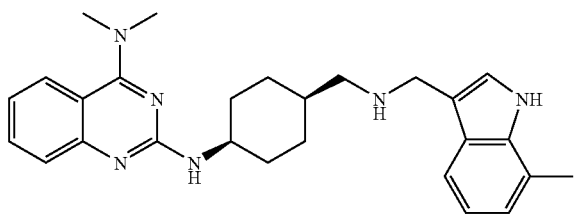 | 443 (M + H) |
| 2036 | 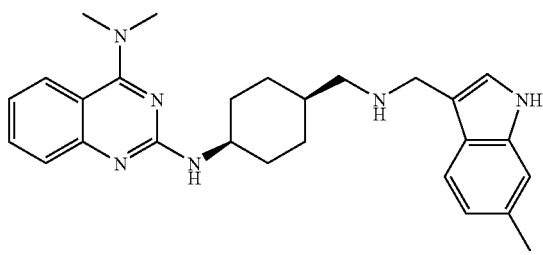 | 443 (M + H) |
| 2037 | 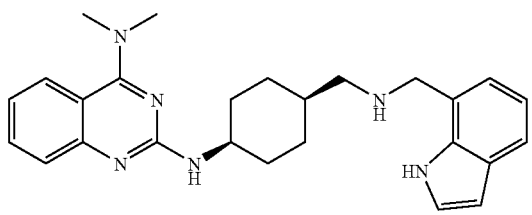 | 429 (M + H) |
| 2038 | 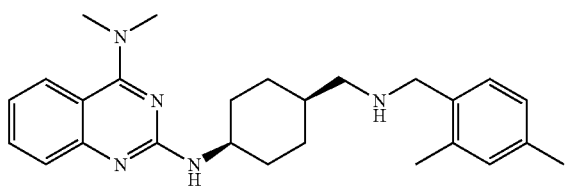 | 418 (M + H) |

-continued
| Example No. | Structure | APCI-MS |
|---|---|---|
| 2039 | 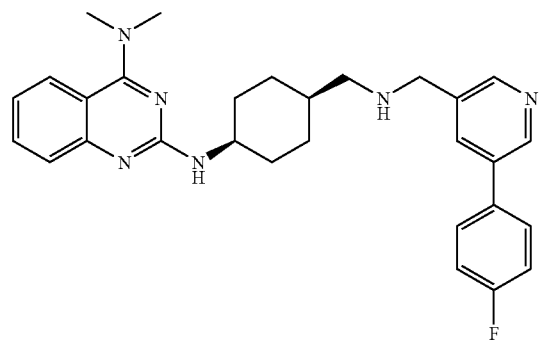 | 485 (M + H) |
| 2040 | 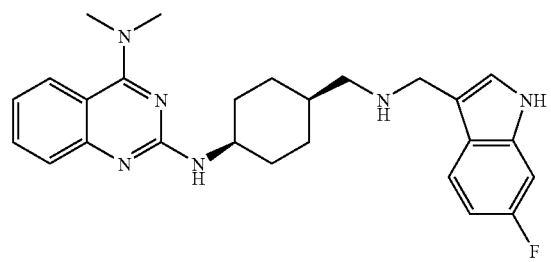 | 447 (M + H) |
| 2041 | 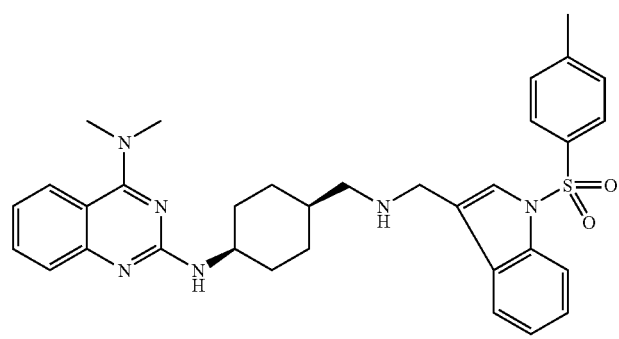 | 583 (M + H) |
| 2042 | 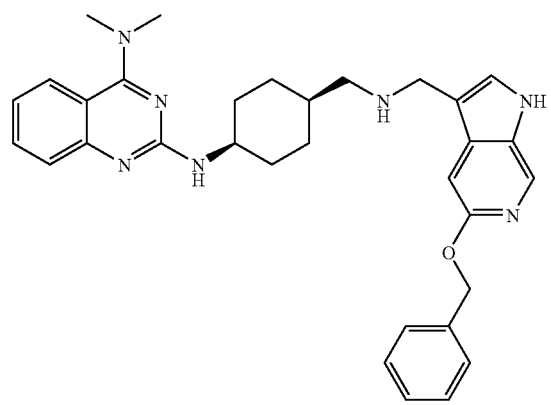 | 536 (M + H) |
| 2043 | 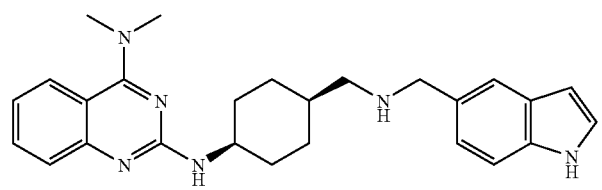 | 429 (M + H) |

-continued
| Example No. | Structure | APCI-MS |
|---|---|---|
| 2044 | 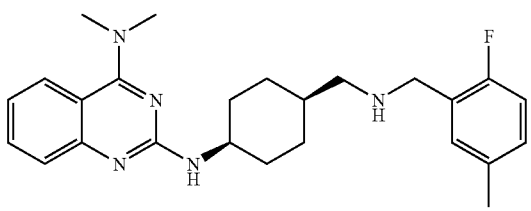 | 422 (M + H) |
| 2045 | 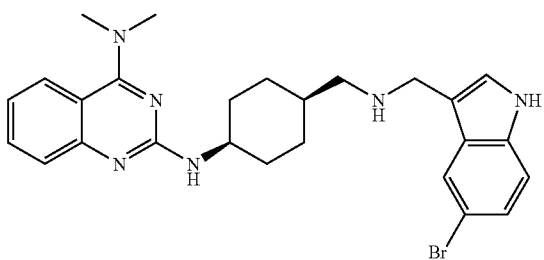 | 507 (M + H) |
| 2046 | 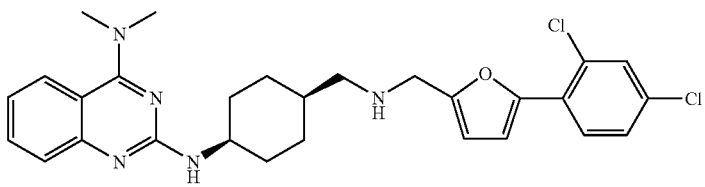 | 524 (M + H) |
| 2047 | 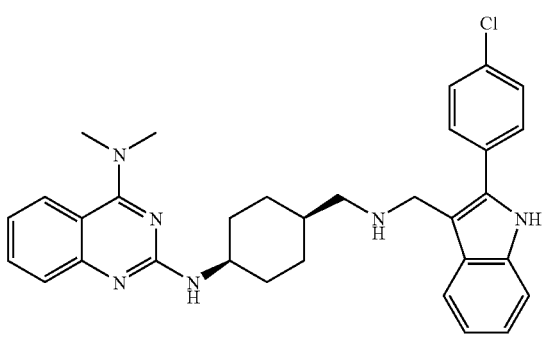 | 539 (M + H) |
| 2048 | 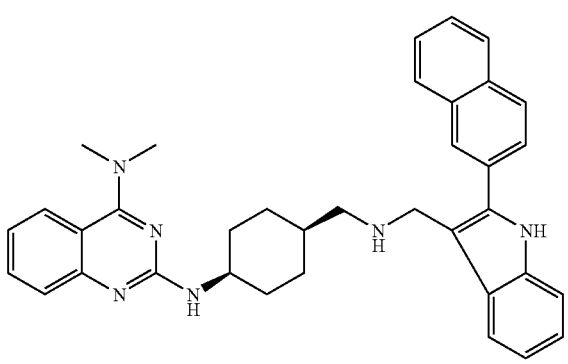 | 555 (M + H) |

-continued
| Example No. | Structure | APCI-MS |
|---|---|---|
| 2049 | 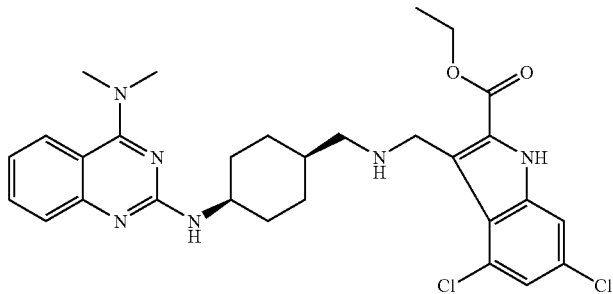 | 569 (M + H) |
| 2050 | 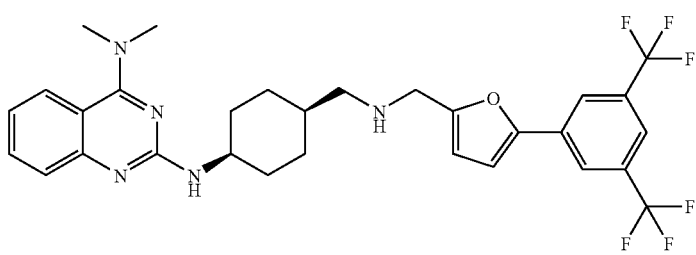 | 592 (M + H) |
| 2051 | 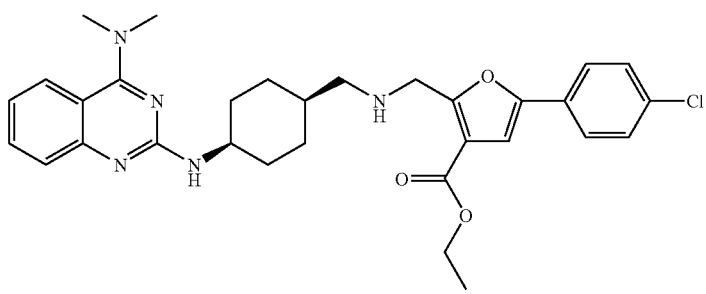 | 562 (M + H) |
| 2052 | 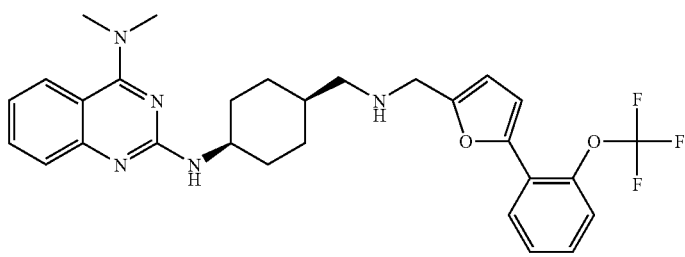 | 540 (M + H) |
| 2053 | 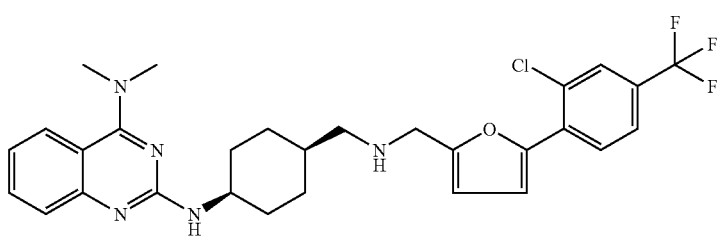 | 558 (M + H) |
| 2054 | 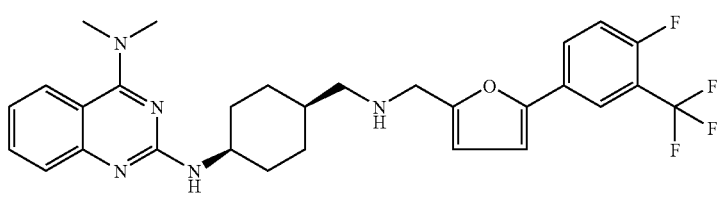 | 542 (M + H) |

-continued
| Example No. | Structure | APCI-MS |
|---|---|---|
| 2055 | 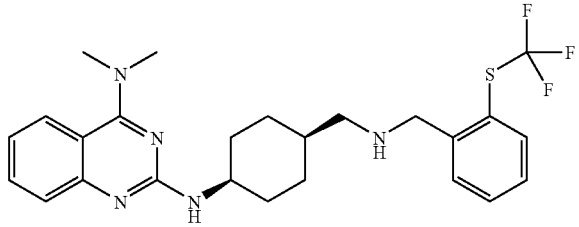 | 490 (M + H) |
| 2056 | 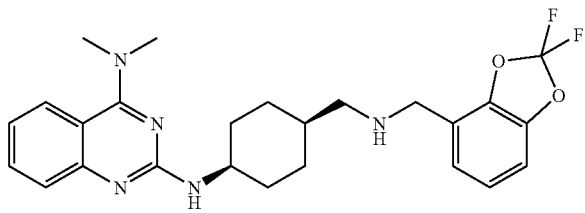 | 470 (M + H) |
| 2057 | 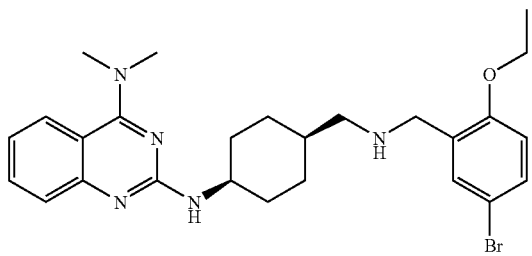 | 512 (M + H) |
| 2058 | 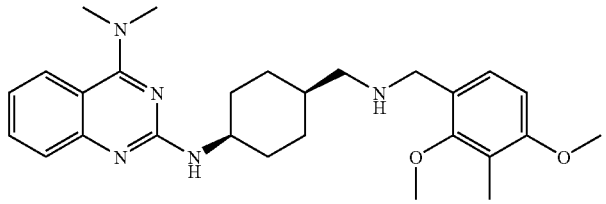 | 464 (M + H) |
| 2059 | 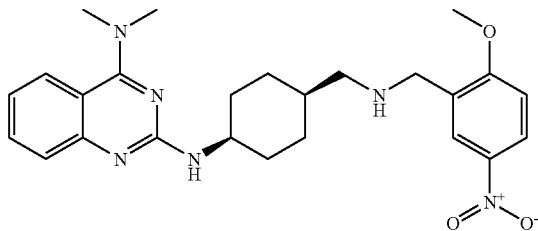 | 465 (M + H) |
| 2060 | 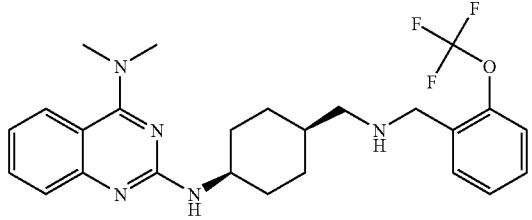 | 474 (M + H) |

-continued
| Example No. | Structure | APCI-MS |
|---|---|---|
| 2061 | 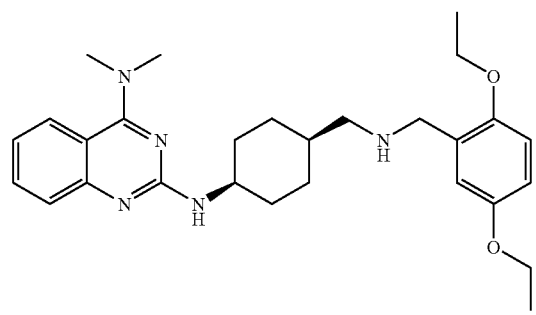 | 478 (M + H) |
| 2062 | 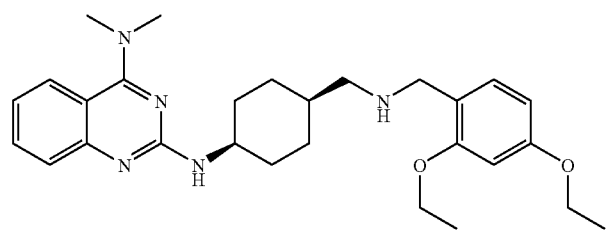 | 478 (M + H) |
| 2063 | 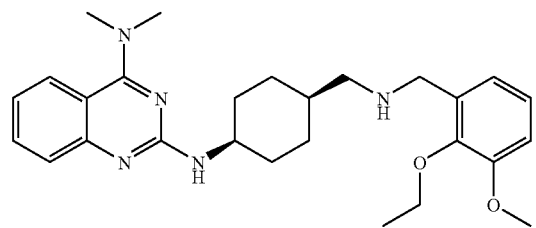 | 464 (M + H) |
| 2064 | 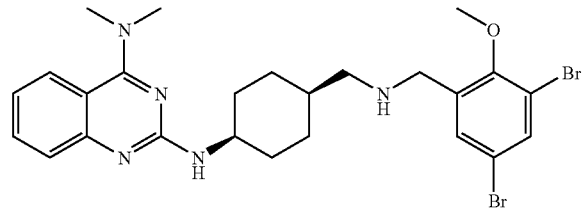 | 576 (M + H) |
| 2065 | 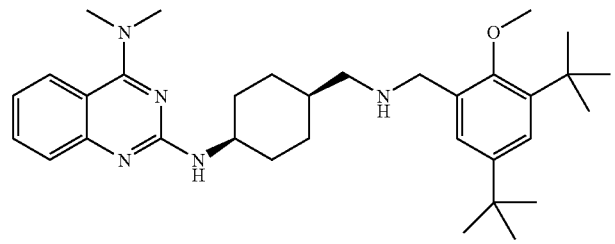 | 532 (M + H) |
| 2066 | 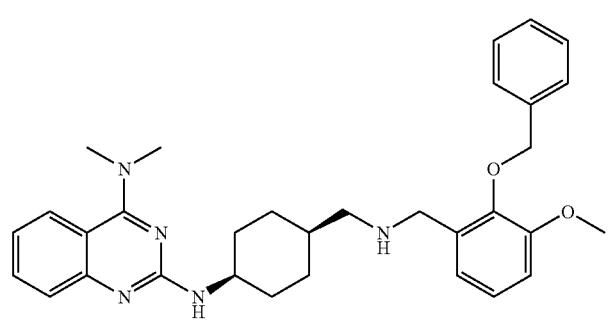 | 526 (M + H) |

-continued
| Example No. | Structure | APCI-MS |
|---|---|---|
| 2067 | 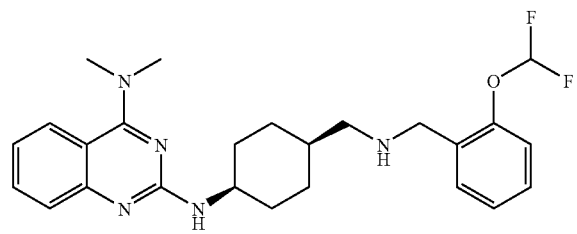 | 456 (M + H) |
| 2068 | 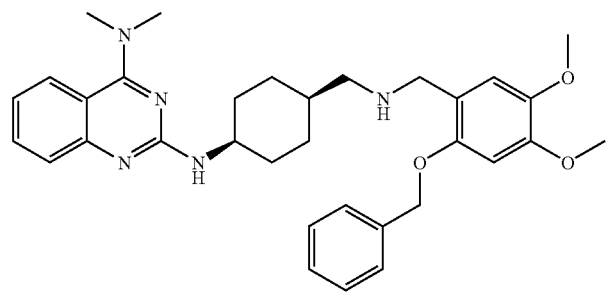 | 556 (M + H) |
| 2069 | 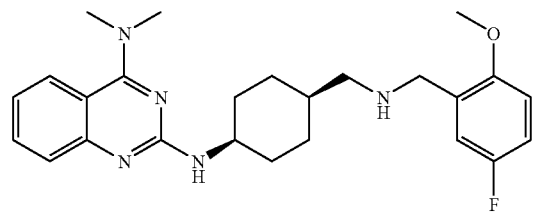 | 438 (M + H) |
| 2070 | 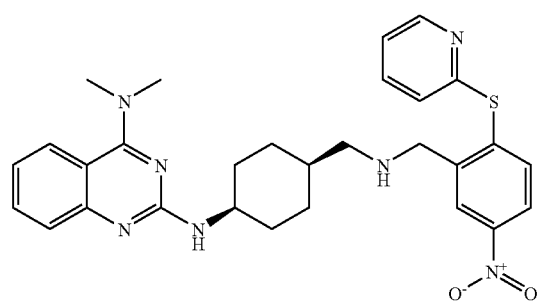 | 544 (M + H) |
| 2071 | 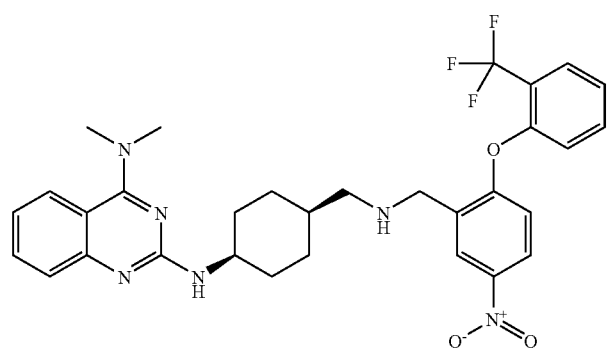 | 595 (M + H) |

| Example No. | Structure | APCI-MS |
|---|---|---|
| 2072 | 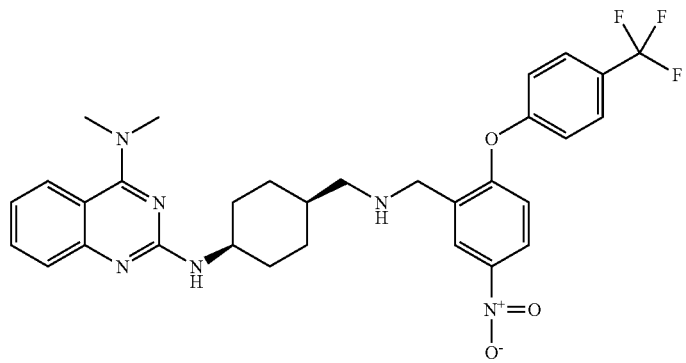 | 595 (M + H) |
| 2073 | 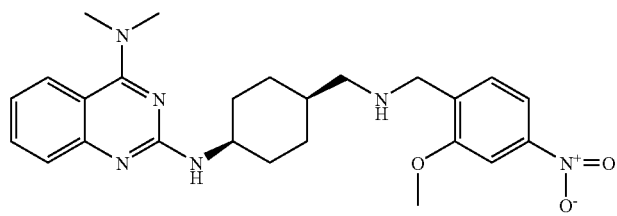 | 465 (M + H) |
| 2074 | 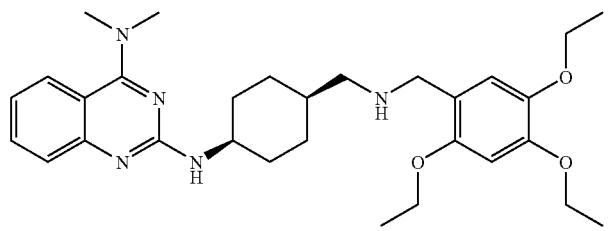 | 522 (M + H) |
| 2075 | 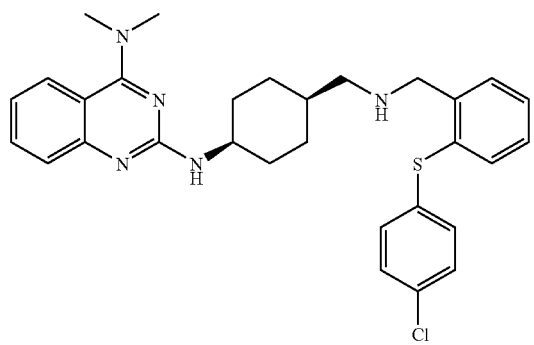 | 532 (M + H) |
| 2076 | 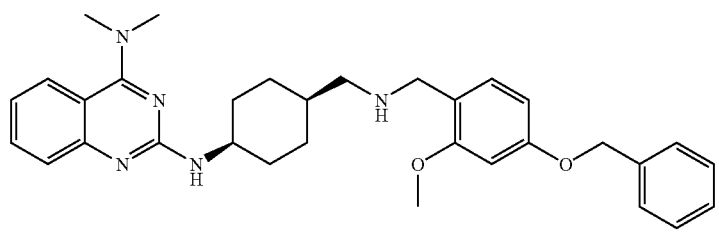 | 526 (M + H) |

-continued
| Example No. | Structure | APCI-MS |
|---|---|---|
| 2077 | 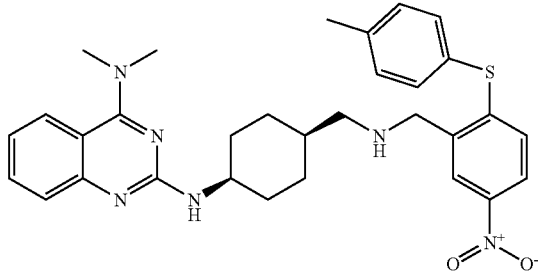 | 557 (M + H) |
| 2078 | 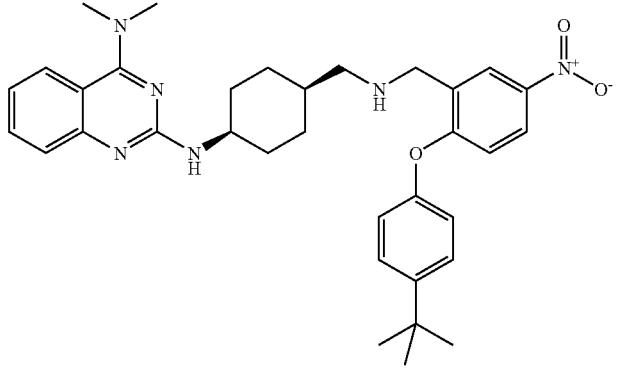 | 583 (M + H) |
| 2079 | 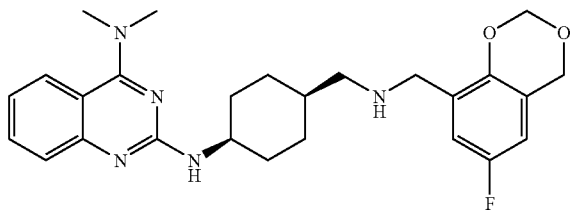 | 466 (M + H) |
| 2080 | 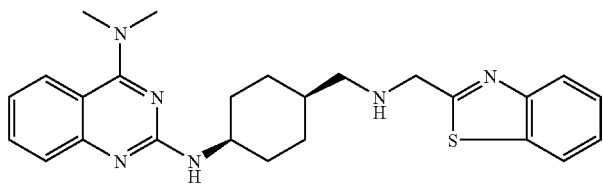 | 447 (M + H) |
| 2081 | 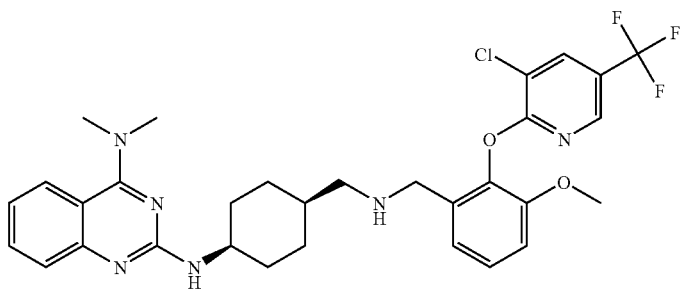 | 615 (M + H) |
| 2082 | 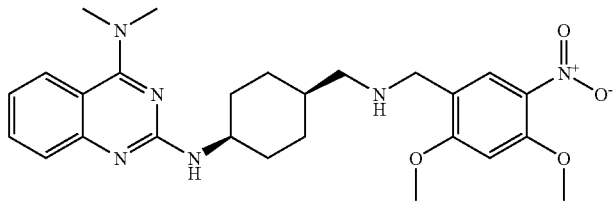 | 495 (M + H) |

-continued
| Example No. | Structure | APCI-MS |
|---|---|---|
| 2083 | 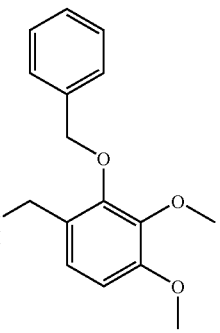 | 556 (M + H) |
| 2084 | 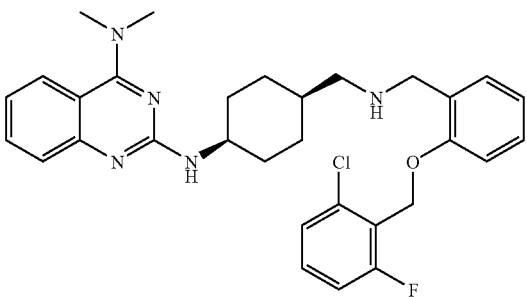 | 548 (M + H) |
| 2085 | 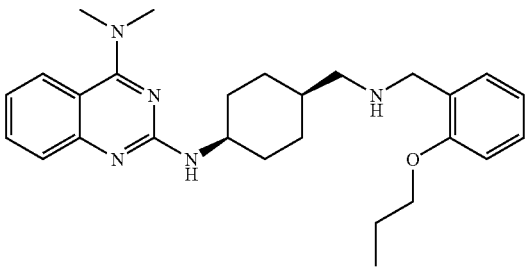 | 448 (M + H) |
| 2086 | 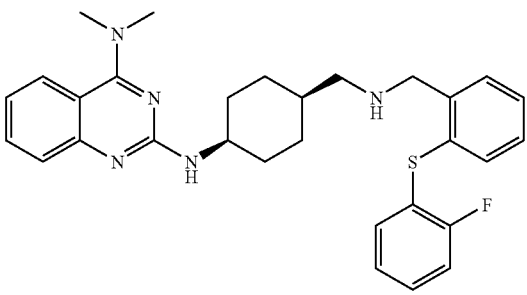 | 516 (M + H) |
| 2087 | 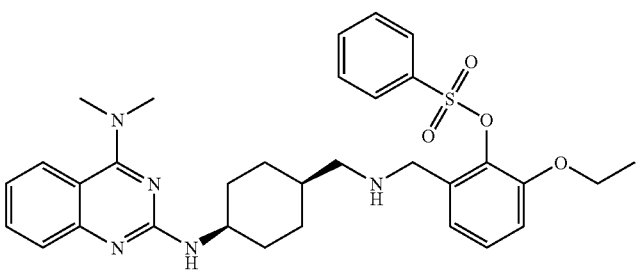 | 590 (M + H) |

-continued
| Example No. | Structure | APCI-MS |
|---|---|---|
| 2088 | 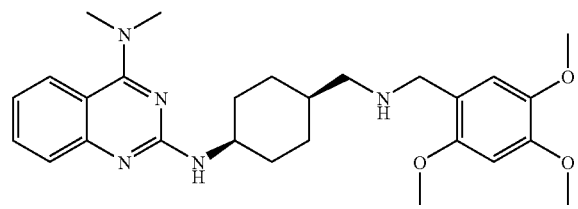 | 480 (M + H) |
| 2089 | 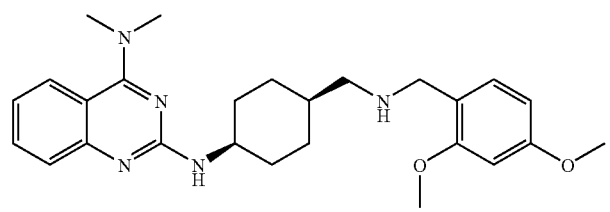 | 450 (M + H) |
| 2090 | 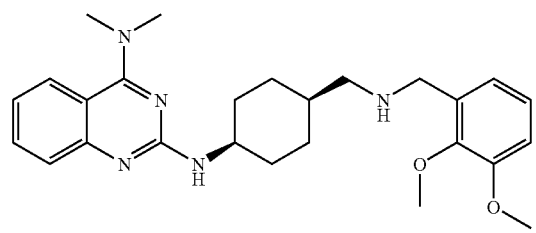 | 450 (M + H) |
| 2091 | 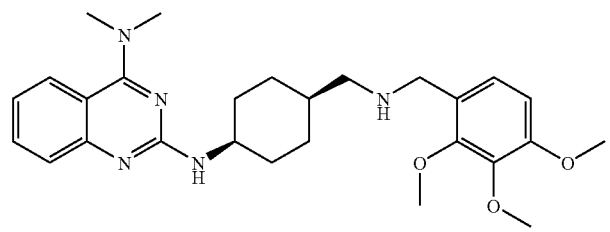 | 480 (M + H) |
| 2092 | 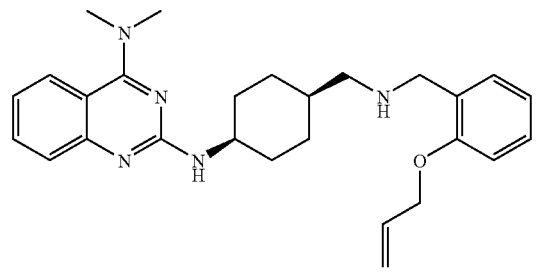 | 446 (M + H) |
| 2093 | 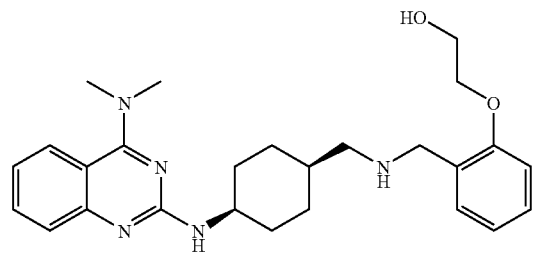 | 450 (M + H) |

-continued

| Example No. | Structure | APCI-MS |
|---|---|---|
| 2094 | 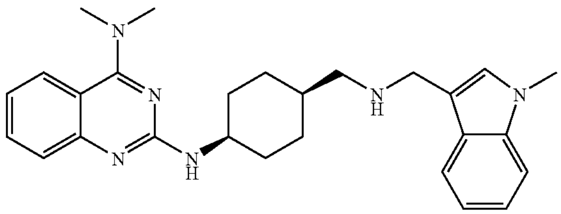 | 443 (M + H) |
| 2095 | 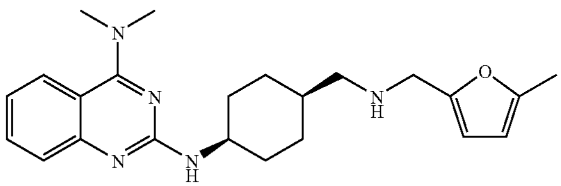 | 394 (M + H) |
| 2096 | 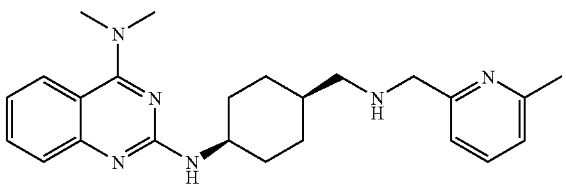 | 405 (M + H) |
| 2097 | 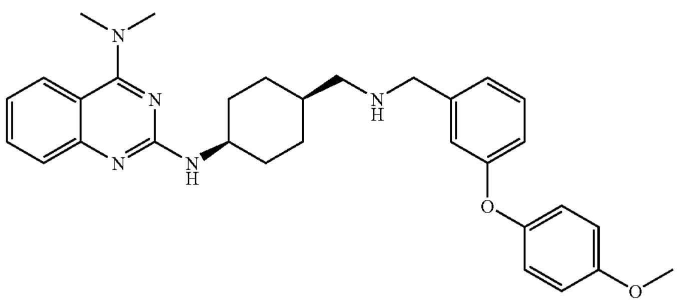 | 512 (M + H) |
| 2098 | 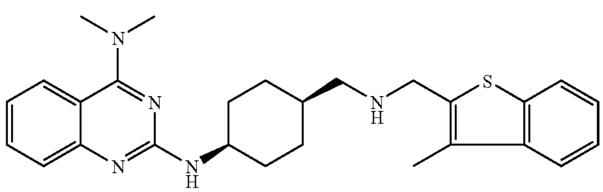 | 460 (M + H) |
| 2099 | 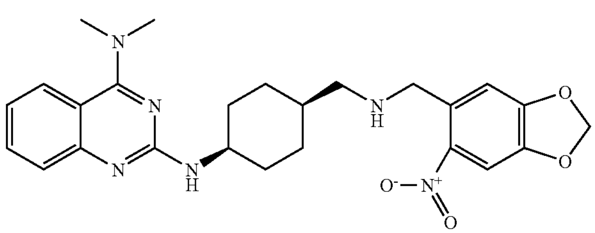 | 479 (M + H) |
| 2100 | 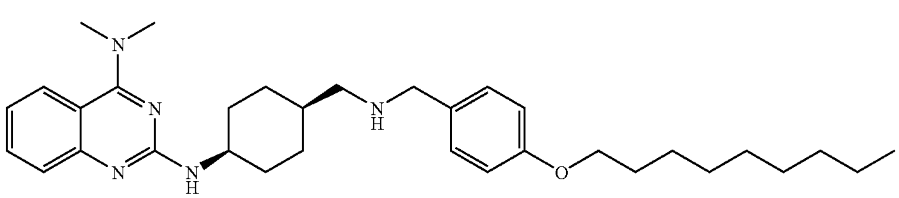 | 532 (M + H) |

-continued
| Example No. | Structure | APCI-MS |
|---|---|---|
| 2101 | 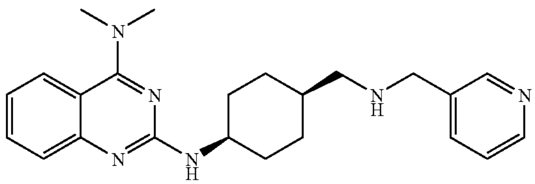 | 391 (M + H) |
| 2102 | 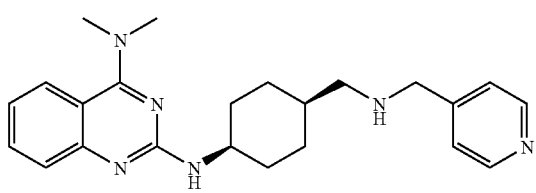 | 391 (M + H) |
| 2103 | 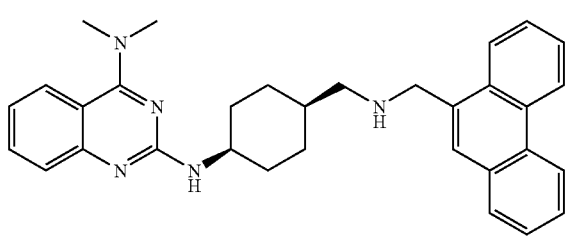 | 490 (M + H) |
| 2104 | 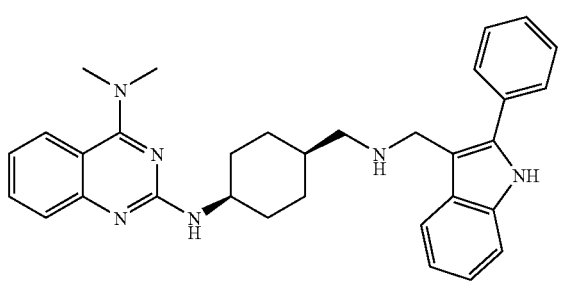 | 505 (M + H) |
| 2105 | 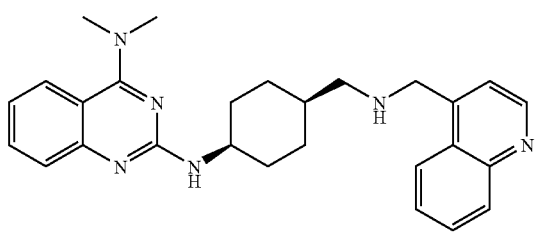 | 441 (M + H) |
| 2106 | 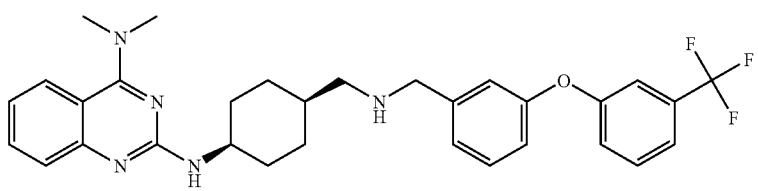 | 550 (M + H) |

-continued
| Example No. | Structure | APCI-MS |
|---|---|---|
| 2107 | 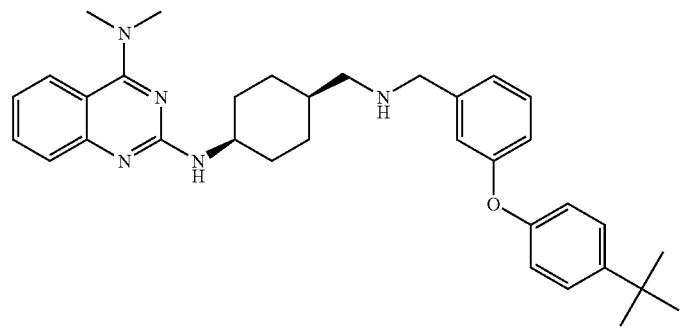 | 538 (M + H) |
| 2108 | 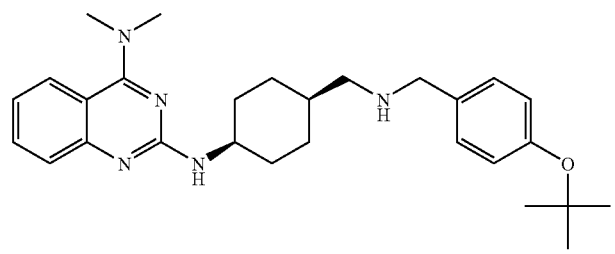 | 462 (M + H) |
| 2109 | 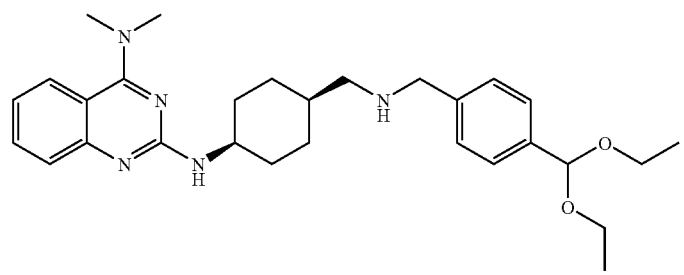 | 492 (M + H) |
| 2110 | 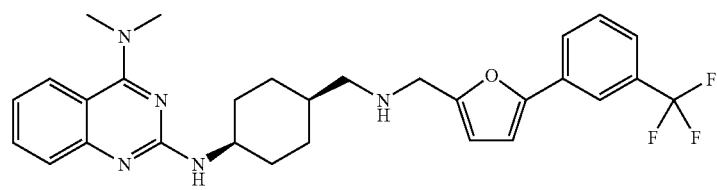 | 524 (M + H) |
| 2111 | 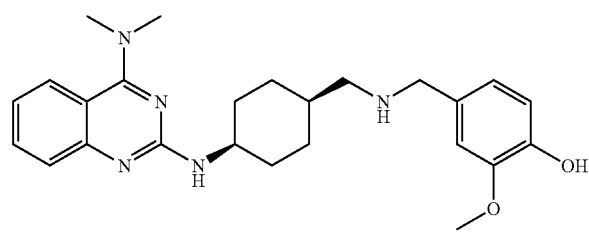 | 436 (M + H) |
| 2112 | 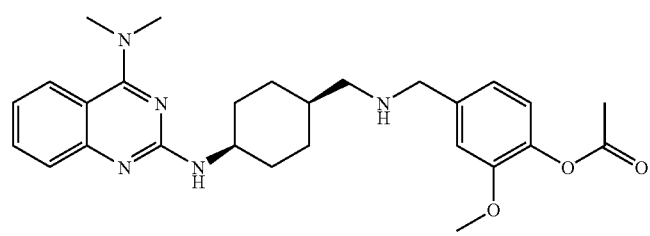 | 478 (M + H) |

-continued
| Example No. | Structure | APCI-MS |
|---|---|---|
| 2113 | 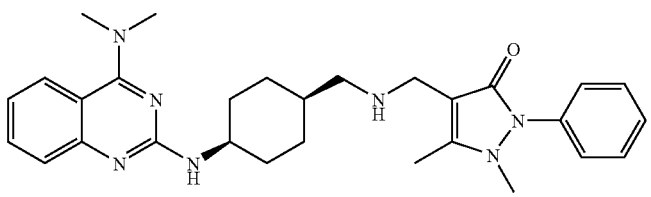 | 500 (M + H) |
| 2114 | 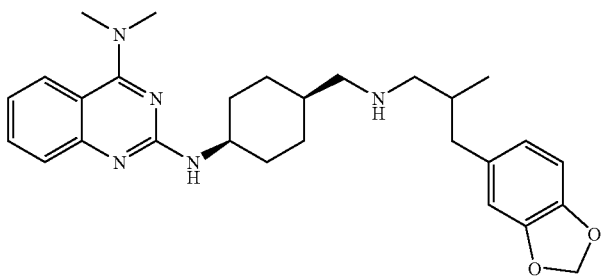 | 476 (M + H) |
| 2115 | 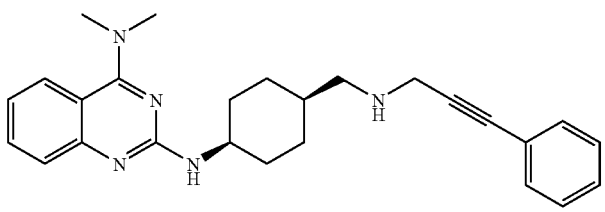 | 414 (M + H) |
| 2116 | 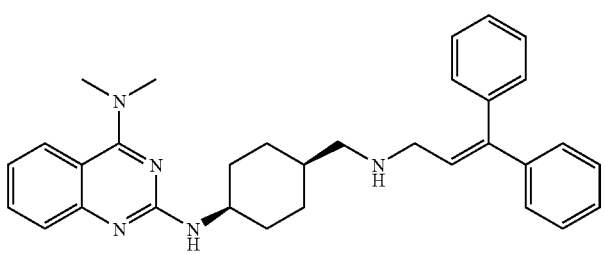 | 492 (M + H) |
| 2117 | 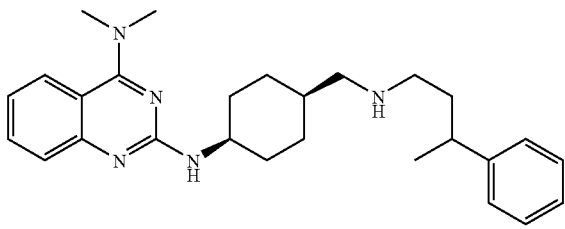 | 432 (M + H) |
| 2118 | 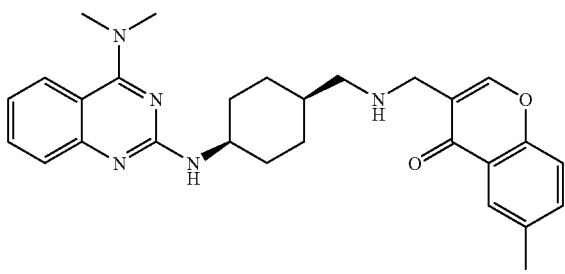 | 472 (M + H) |

-continued
| Example No. | Structure | APCI-MS |
|---|---|---|
| 2119 | 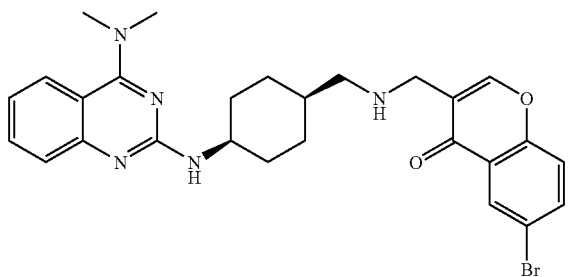 | 536 (M + H) |
| 2120 | 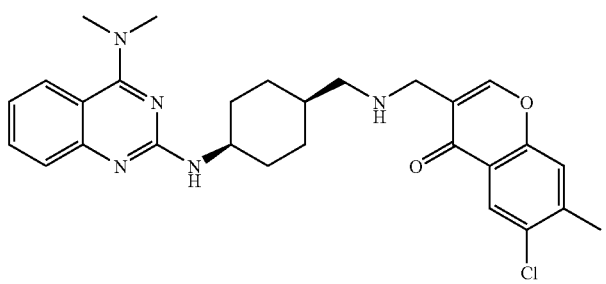 | 506 (M + H) |
| 2121 | 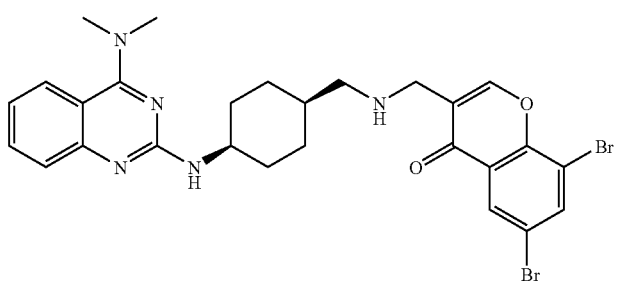 | 614 (M + H) |
| 2122 | 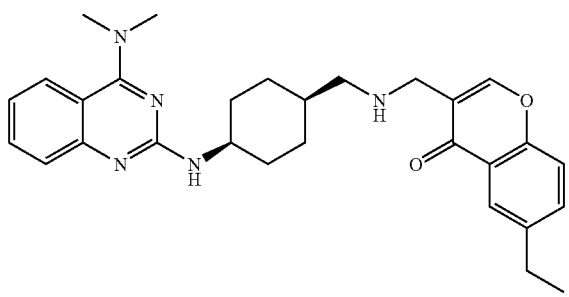 | 486 (M + H) |
| 2123 | 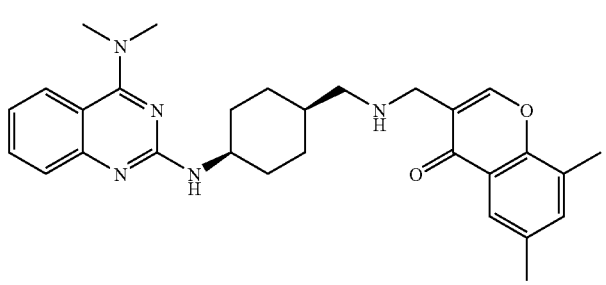 | 486 (M + H) |

-continued

| Example No. | Structure | APCI-MS |
|---|---|---|
| 2124 | 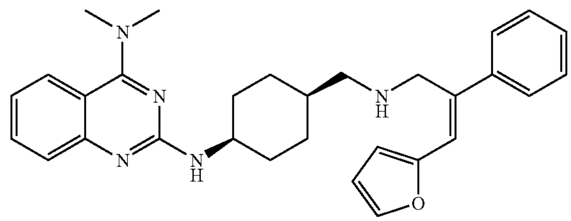 | 482 (M + H) |
| 2125 | 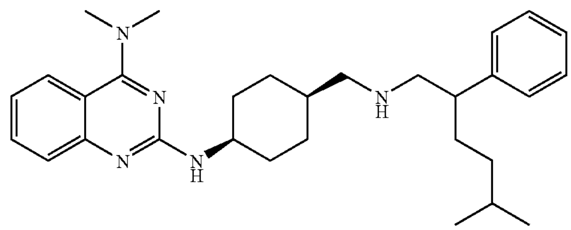 | 474 (M + H) |
| 2126 | 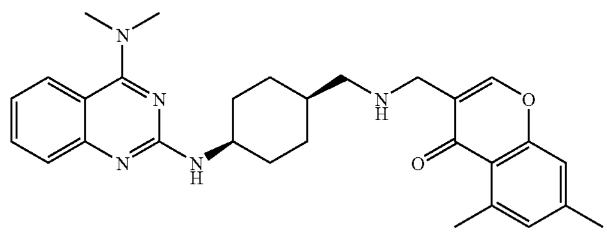 | 486 (M + H) |
| 2127 | 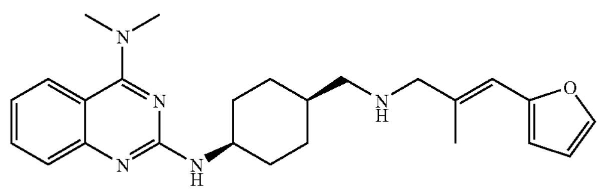 | 420 (M + H) |
| 2128 | 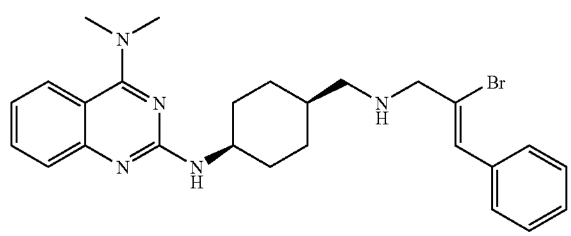 | 494 (M + H) |
| 2129 | 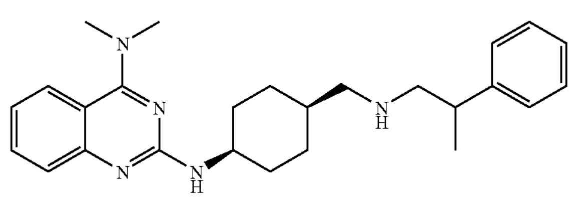 | 418 (M + H) |
| 2130 | 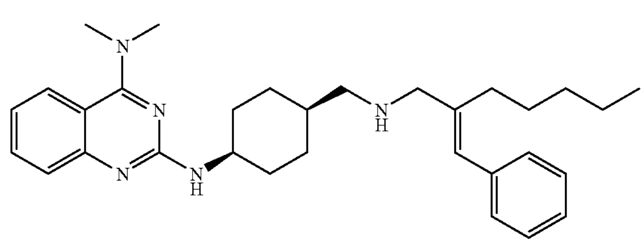 | 486 (M + H) |

-continued
| Example No. | Structure | APCI-MS |
|---|---|---|
| 2131 | 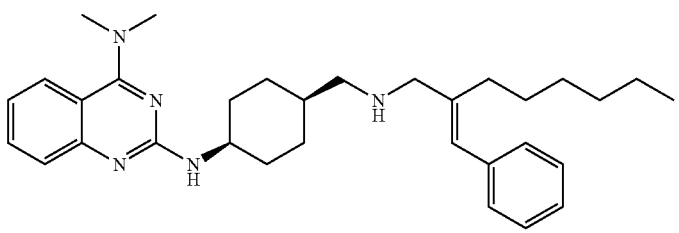 | 500 (M + H) |
| 2132 | 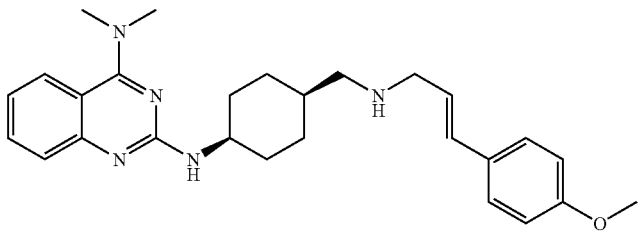 | 446 (M + H) |
| 2133 | 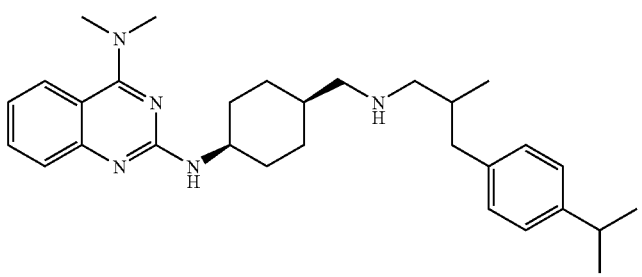 | 474 (M + H) |
| 2134 | 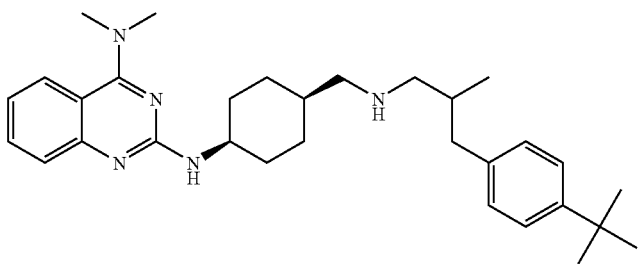 | 488 (M + H) |
| 2135 | 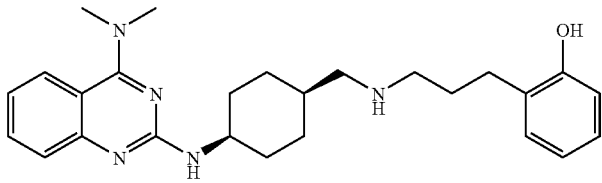 | 434 (M + H) |
| 2136 | 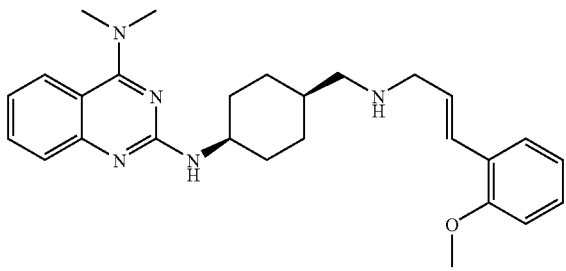 | 446 (M + H) |

-continued
| Example No. | Structure | APCI-MS |
|---|---|---|
| 2137 | 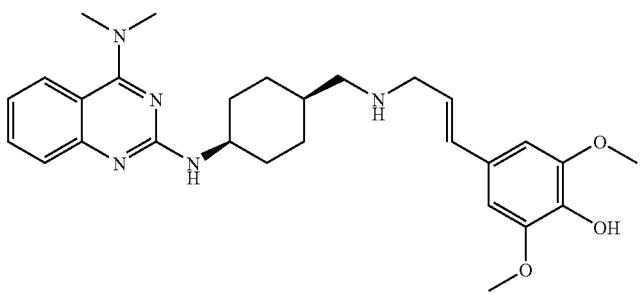 | 492 (M + H) |
| 2138 | 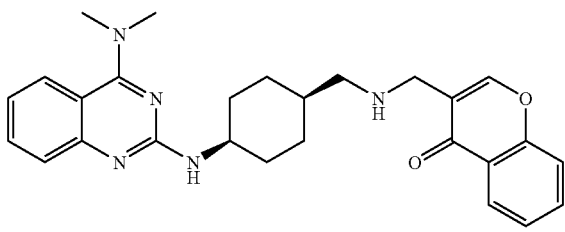 | 458 (M + H) |
| 2139 | 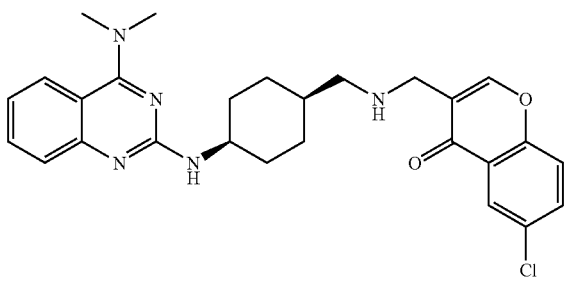 | 492 (M + H) |
| 2140 | 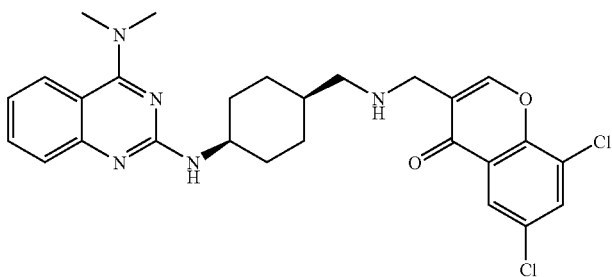 | 526 (M + H) |
| 2141 | 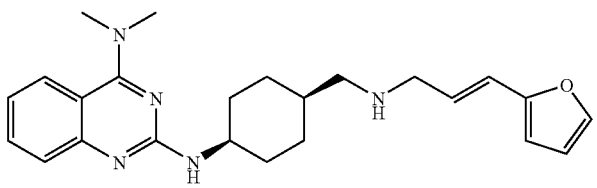 | 406 (M + H) |
| 2142 | 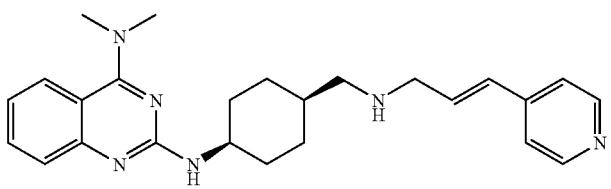 | 417 (M + H) |

-continued
| Example No. | Structure | APCI-MS |
|---|---|---|
| 2143 | 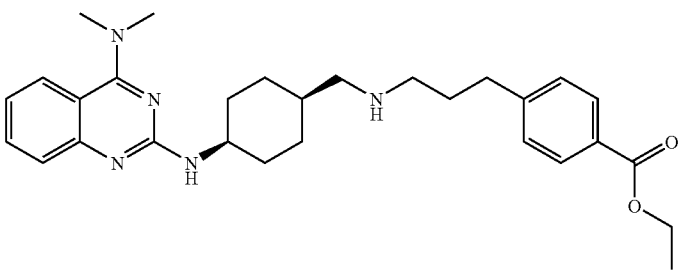 | 490 (M + H) |
| 2144 | 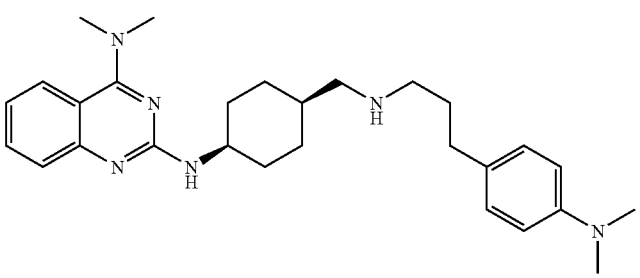 | 461 (M + H) |
| 2145 | 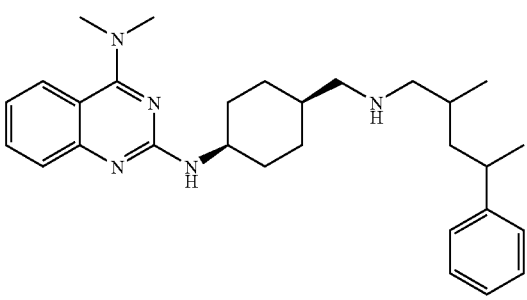 | 460 (M + H) |
| 2146 | 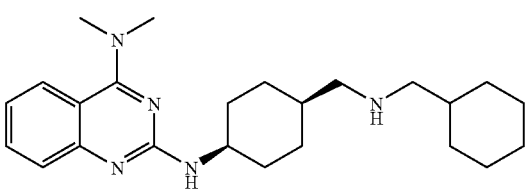 | 396 (M + H) |
| 2147 | 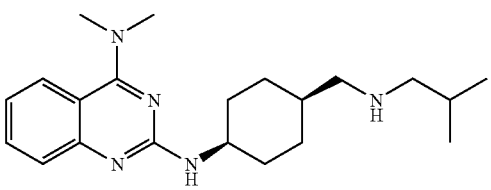 | 356 (M + H) |
| 2148 | 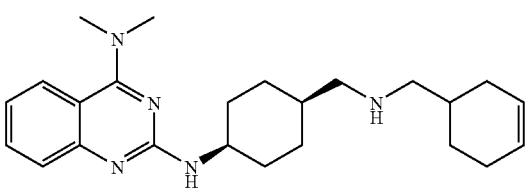 | 394 (M + H) |

-continued

| Example No. | Structure | APCI-MS |
|---|---|---|
| 2149 | 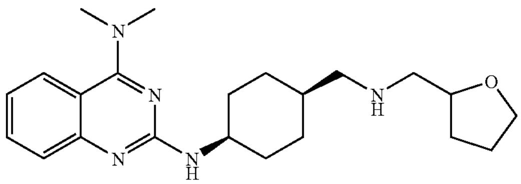 | 384 (M + H) |
| 2150 | 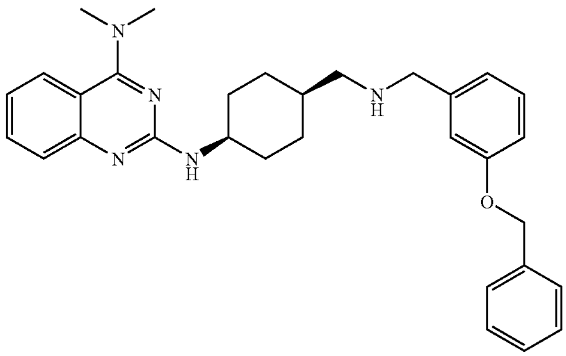 | 496 (M + H) |
| 2151 | 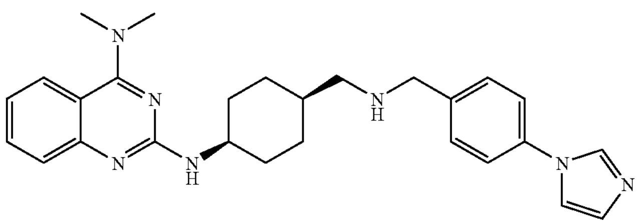 | 456 (M + H) |
| 2152 | 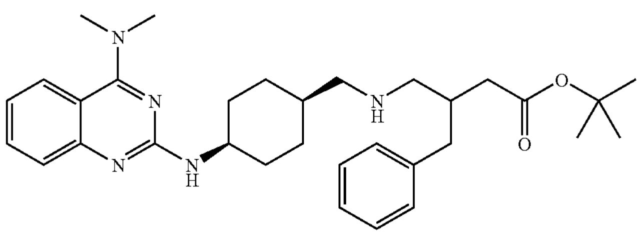 | 533 (M + H) |
| 2153 | 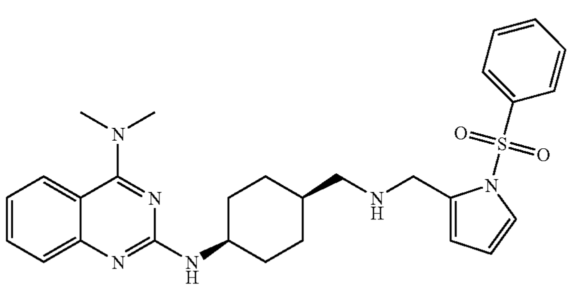 | 519 (M + H) |
| 2154 | 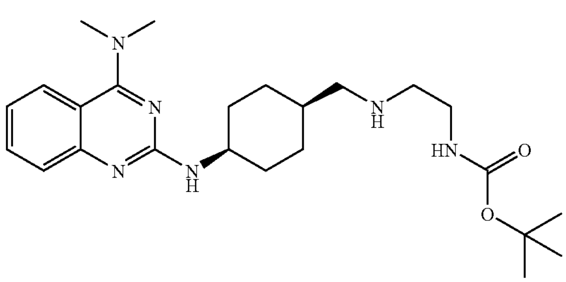 | 443 (M + H) |

| Example No. | Structure | APCI-MS |
|---|---|---|
| 2155 | 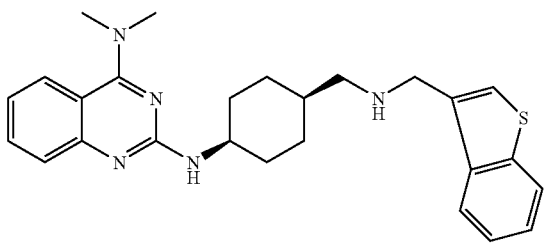 | 446 (M + H) |
| 2156 | 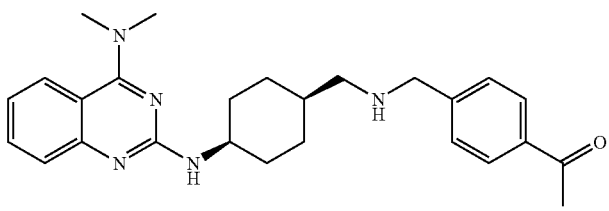 | 432 (M + H) |
| 2157 | 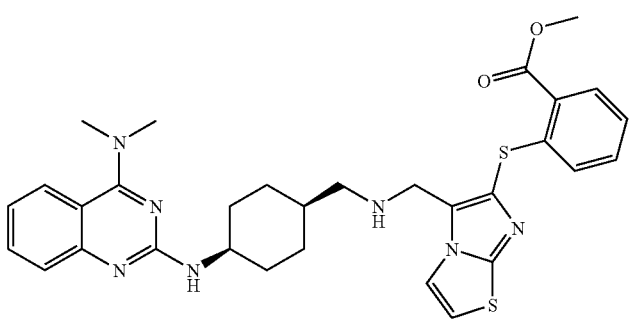 | 602 (M + H) |
| 2158 | 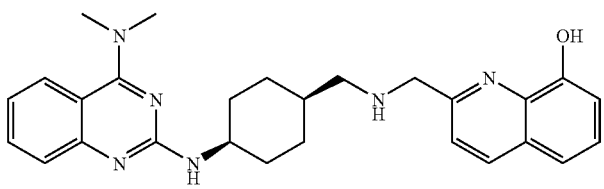 | 457 (M + H) |
| 2159 | 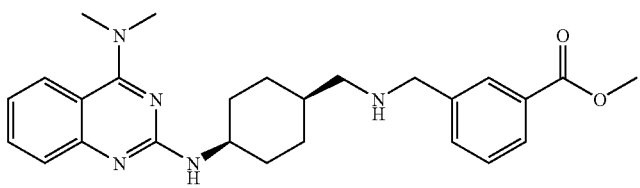 | 448 (M + H) |
| 2160 | 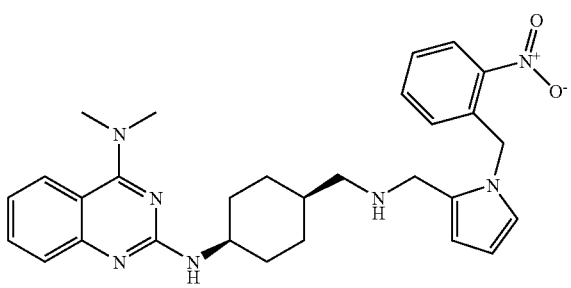 | 514 (M + H) |

-continued
| Example No. | Structure | APCI-MS |
|---|---|---|
| 2161 | 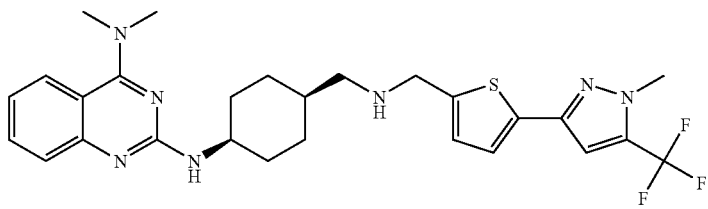 | 544 (M + H) |
| 2162 | 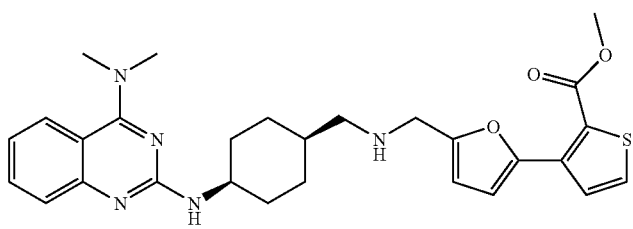 | 520 (M + H) |
| 2163 | 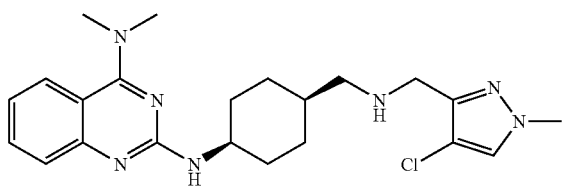 | 428 (M + H) |
| 2164 | 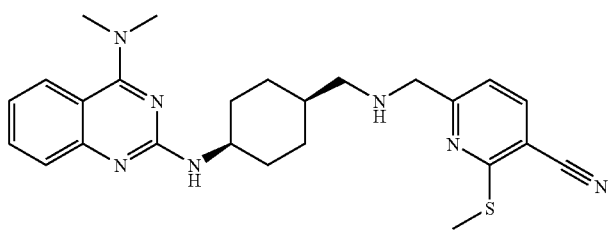 | 462 (M + H) |
| 2165 | 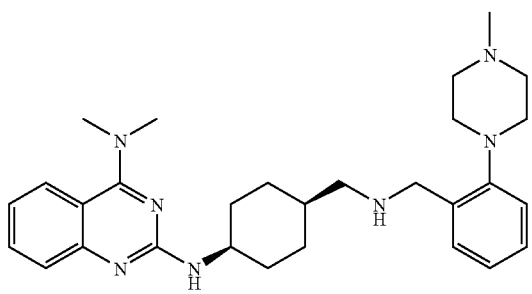 | 488 (M + H) |
| 2166 | 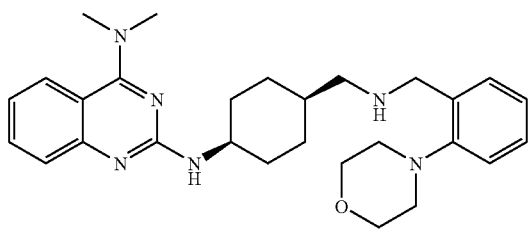 | 475 (M + H) |

-continued
| Example No. | Structure | APCI-MS |
|---|---|---|
| 2167 | 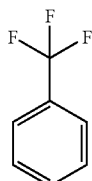 | 523 (M + H) |
| 2168 | 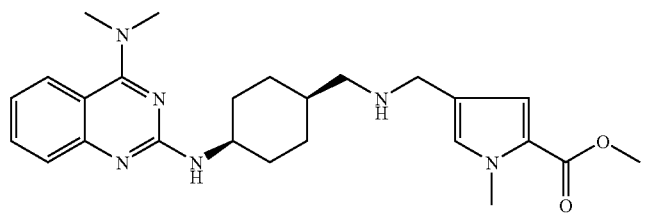 | 451 (M + H) |
| 2169 | 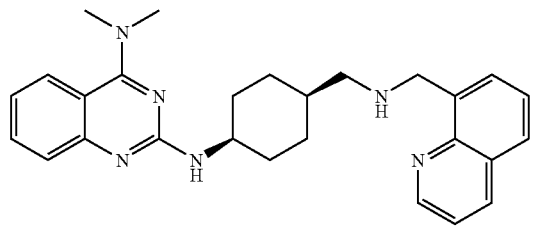 | 441 (M + H) |
| 2170 | 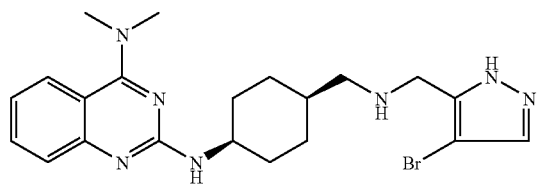 | 458 (M + H) |
| 2171 | 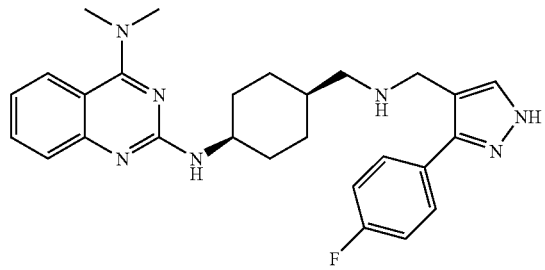 | 474 (M + H) |
| 2172 | 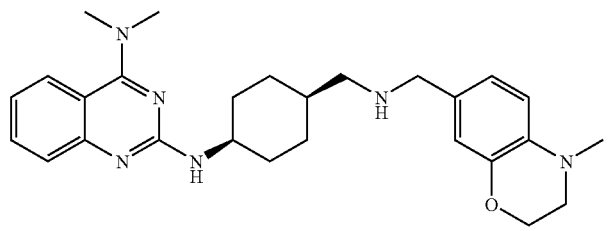 | 461 (M + H) |

-continued
| Example No. | Structure | APCI-MS |
|---|---|---|
| 2173 | 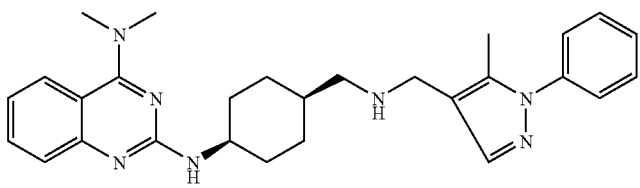 | 470 (M + H) |
| 2174 | 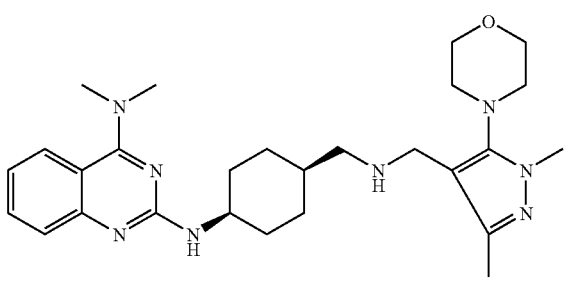 | 493 (M + H) |
| 2175 | 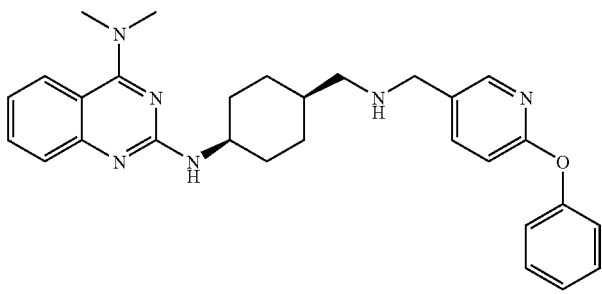 | 483 (M + H) |
| 2176 | 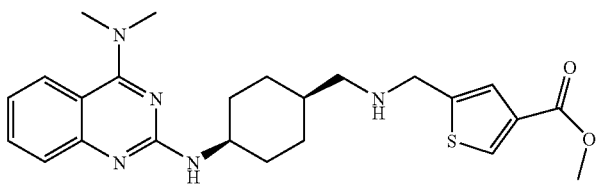 | 454 (M + H) |
| 2177 | 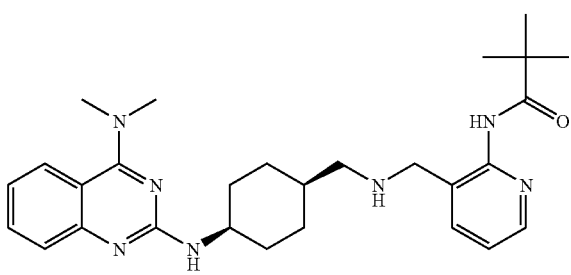 | 490 (M + H) |
| 2178 | 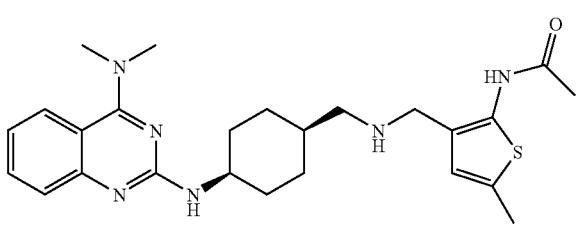 | 467 (M + H) |

-continued

| Example No. | Structure | APCI-MS |
|---|---|---|
| 2179 | 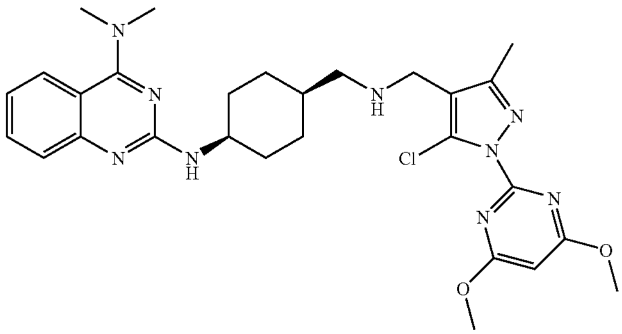 | 566 (M + H) |
| 2180 | 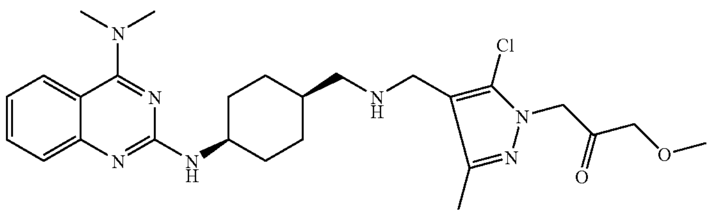 | 514 (M + H) |
| 2181 | 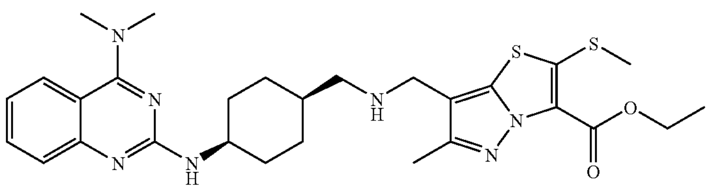 | 568 (M + H) |
| 2182 | 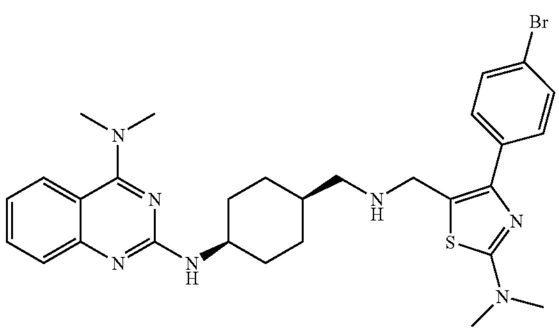 | 594 (M + H) |
| 2183 | 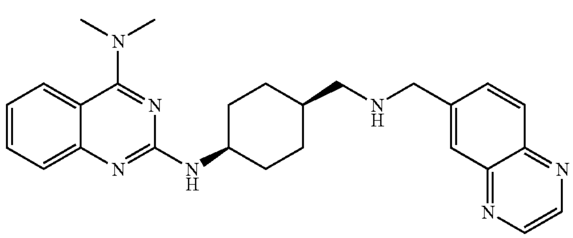 | 442 (M + H) |
| 2184 | 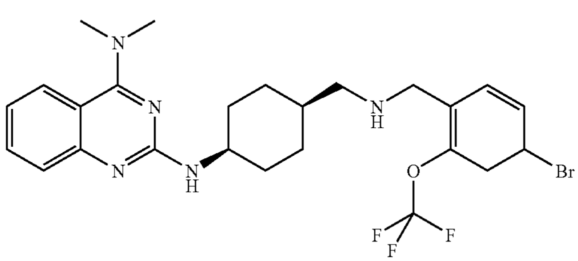 | 552 (M + H) |

-continued
| Example No. | Structure | APCI-MS |
|---|---|---|
| 2185 | 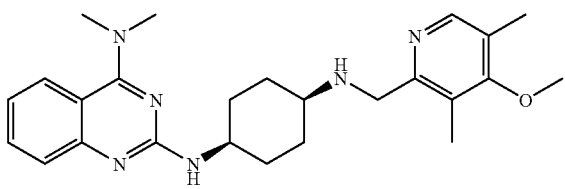 | 435 (M + H) |
| 2186 | 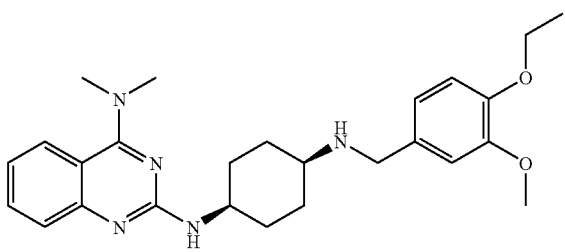 | 450 (M + H) |
| 2187 | 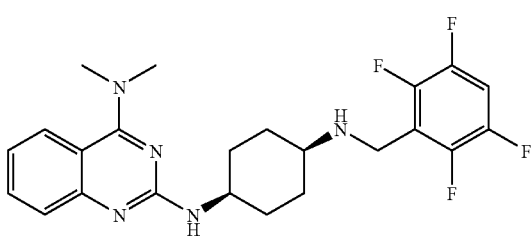 | 448 (M + H) |
| 2188 | 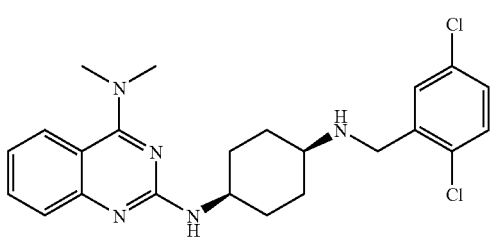 | 444 (M + H) |
| 2189 | 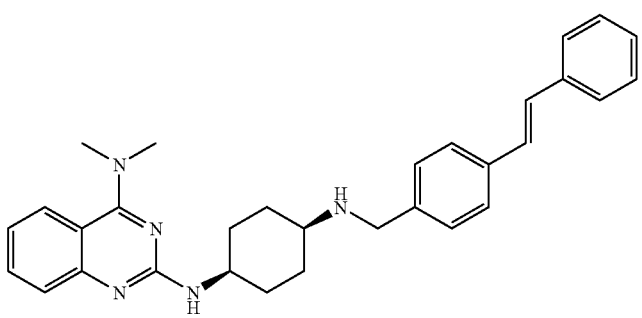 | 478 (M + H) |
| 2190 | 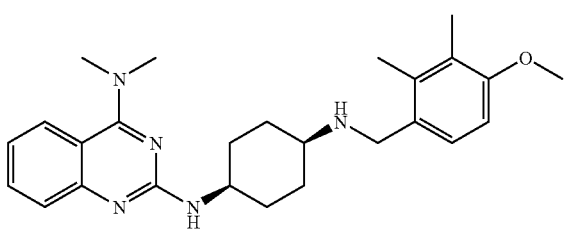 | 434 (M + H) |

-continued
| Example No. | Structure | APCI-MS |
|---|---|---|
| 2191 | 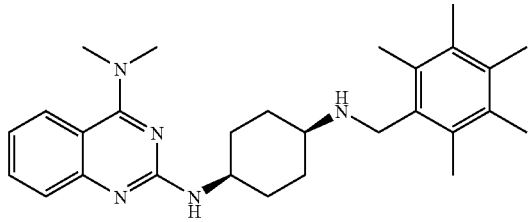 | 446 (M + H) |
| 2192 | 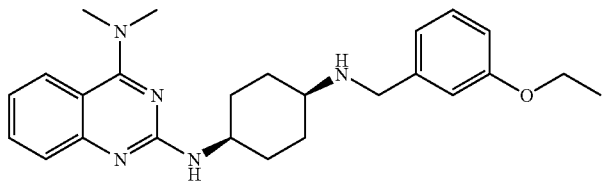 | 420 (M + H) |
| 2193 | 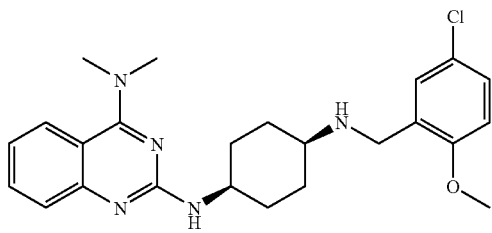 | 440 (M + H) |
| 2194 | 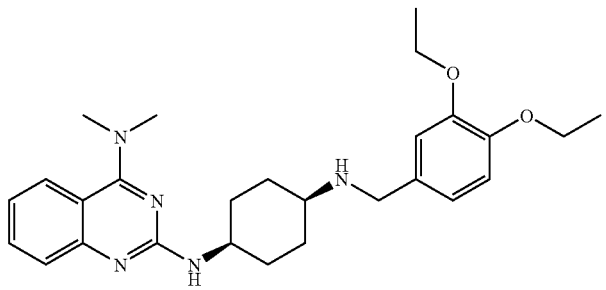 | 464 (M + H) |
| 2195 | 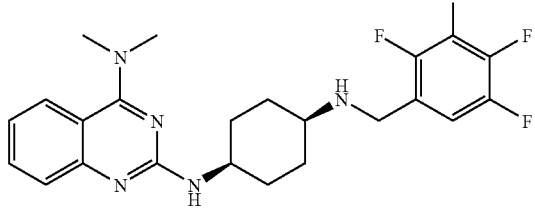 | 448 (M + H) |
| 2196 | 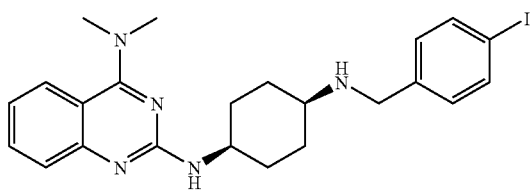 | 502 (M + H) |

-continued
| Example No. | Structure | APCI-MS |
|---|---|---|
| 2197 | 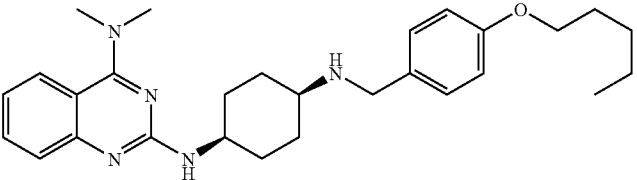 | 462 (M + H) |
| 2198 | 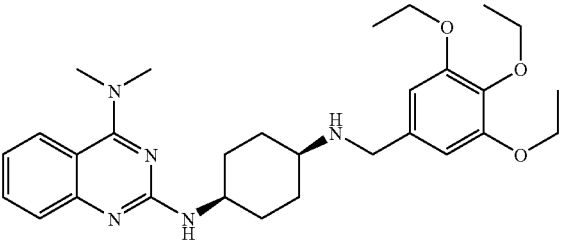 | 508 (M + H) |
| 2199 | 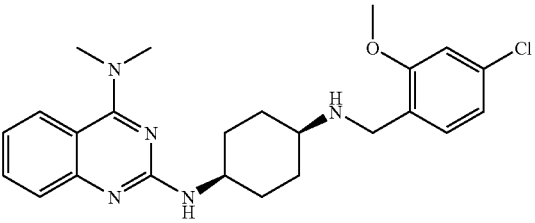 | 440 (M + H) |
| 2200 | 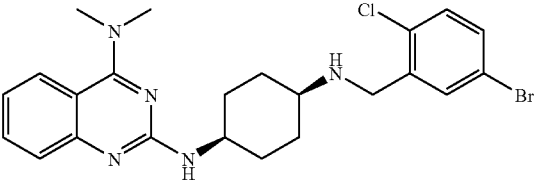 | 488 (M + H) |
| 2201 | 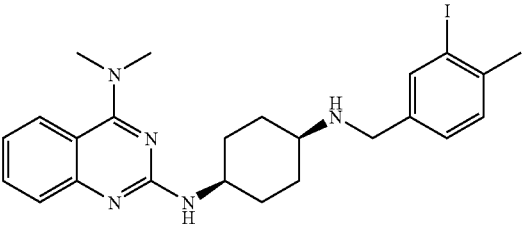 | 516 (M + H) |
| 2202 | 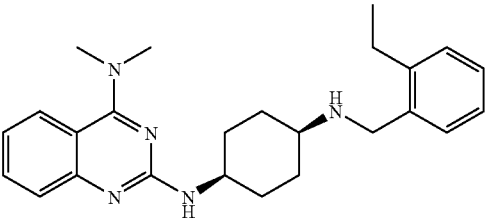 | 404 (M + H) |
| 2203 | 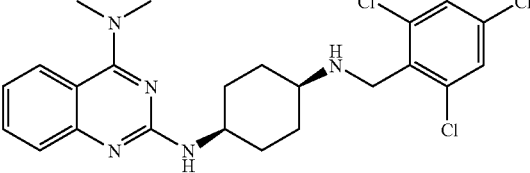 | 478 (M + H) |

-continued
| Example No. | Structure | APCI-MS |
|---|---|---|
| 2204 | 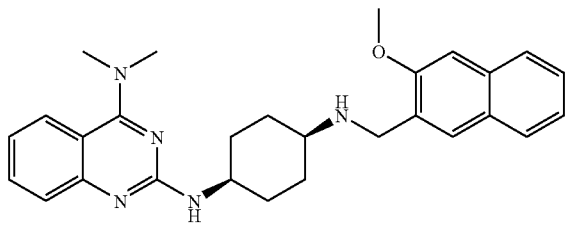 | 456 (M + H) |
| 2205 | 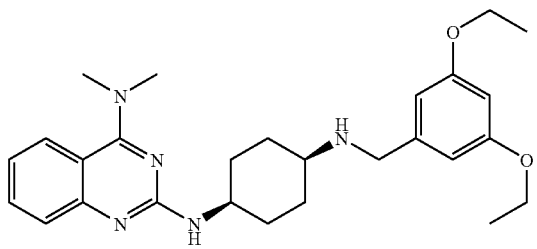 | 464 (M + H) |
| 2206 | 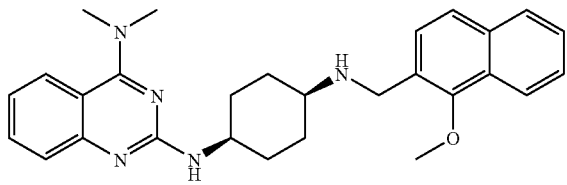 | 456 (M + H) |
| 2207 | 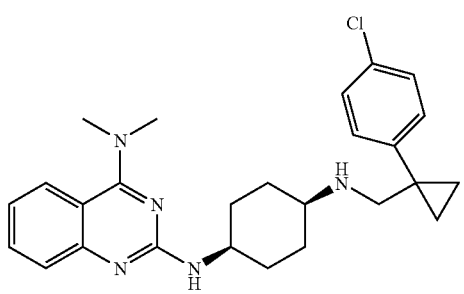 | 450 (M + H) |
| 2208 | 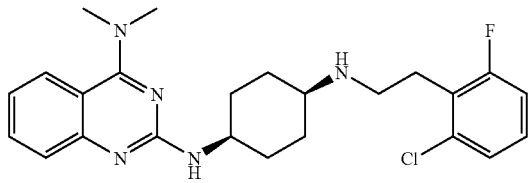 | 442 (M + H) |
| 2209 | 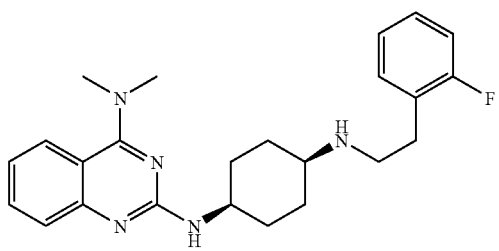 | 408 (M + H) |

-continued

| Example No. | Structure | APCI-MS |
|---|---|---|
| 2210 | 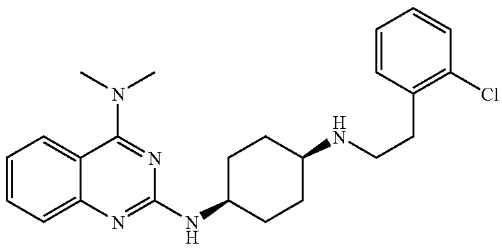 | 424 (M + H) |
| 2211 | 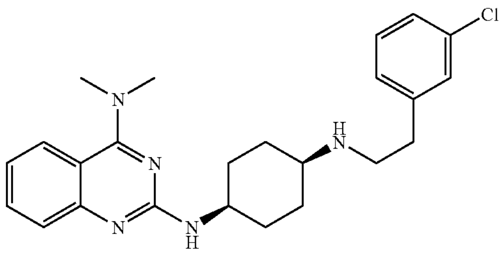 | 424 (M + H) |
| 2212 | 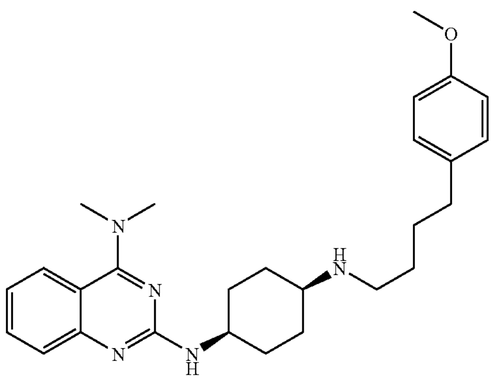 | 448 (M + H) |
| 2213 | 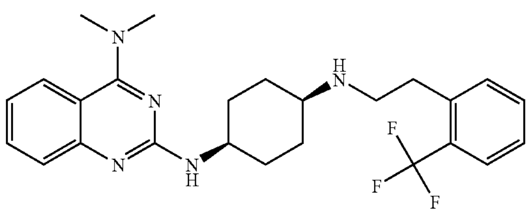 | 458 (M + H) |
| 2214 | 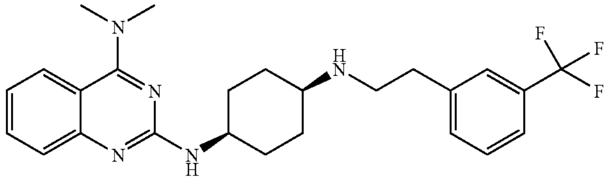 | 458 (M + H) |
| 2215 | 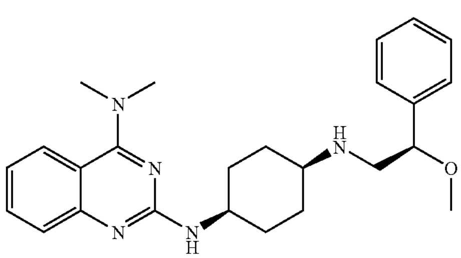 | 420 (M + H) |

-continued
| Example No. | Structure | APCI-MS |
|---|---|---|
| 2216 | 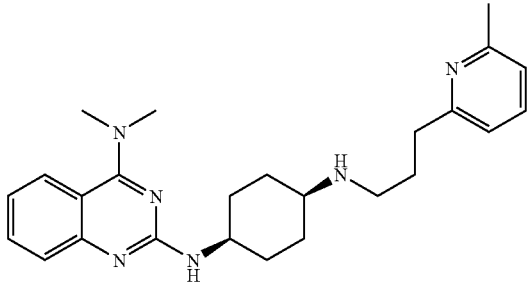 | 419 (M + H) |
| 2217 | 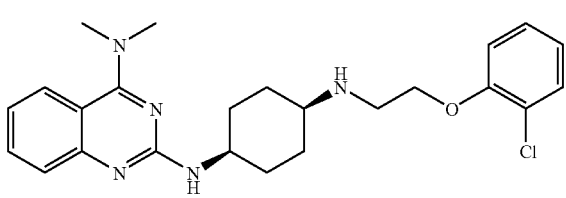 | 440 (M + H) |
| 2218 | 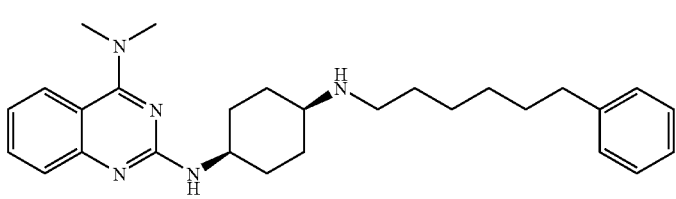 | 446 (M + H) |
| 2219 | 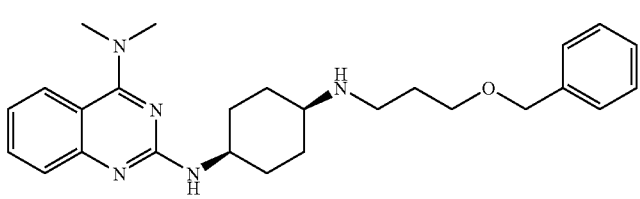 | 434 (M + H) |
| 2220 | 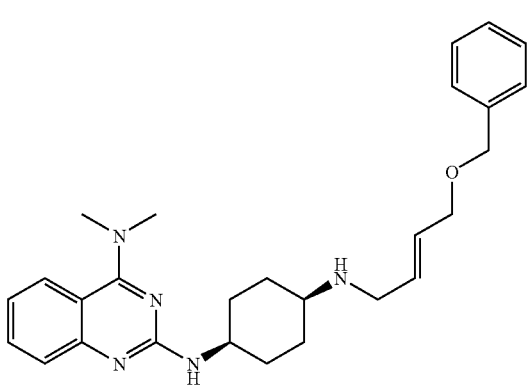 | 446 (M + H) |
| 2221 | 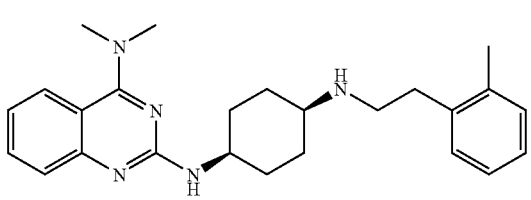 | 404 (M + H) |

-continued
| Example No. | Structure | APCI-MS |
|---|---|---|
| 2222 | 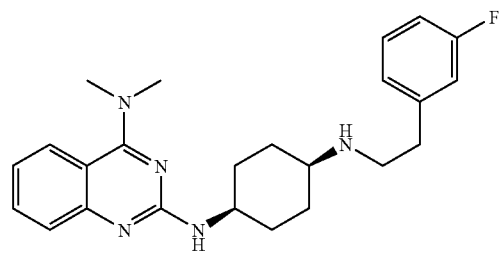 | 408 (M + H) |
| 2223 | 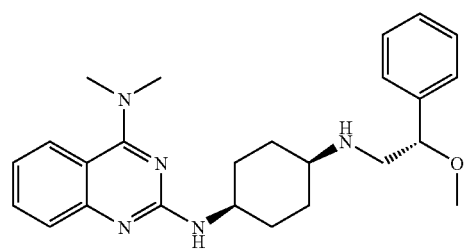 | 420 (M + H) |
| 2224 | 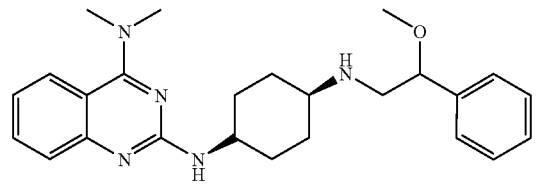 | 420 (M + H) |
| 2225 | 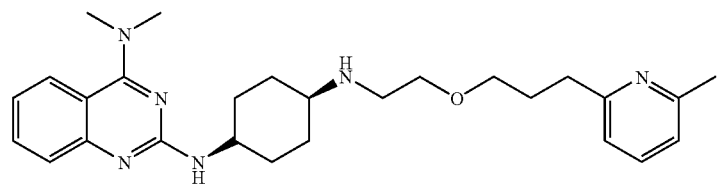 | 463 (M + H) |
| 2226 | 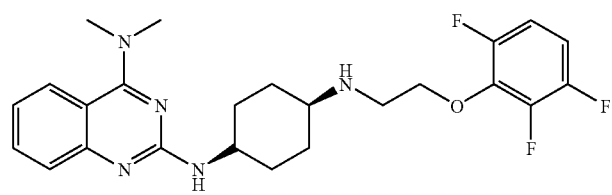 | 460 (M + H) |
| 2227 | 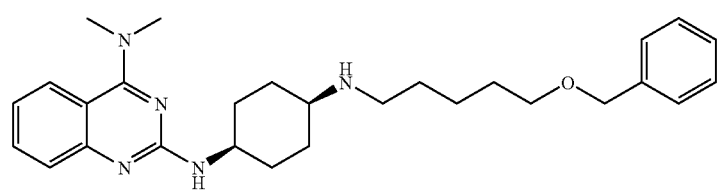 | 462 (M + H) |
| 2228 | 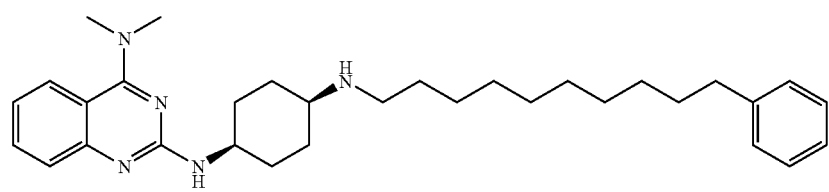 | 502 (M + H) |

-continued
| Example No. | Structure | APCI-MS |
|---|---|---|
| 2229 | 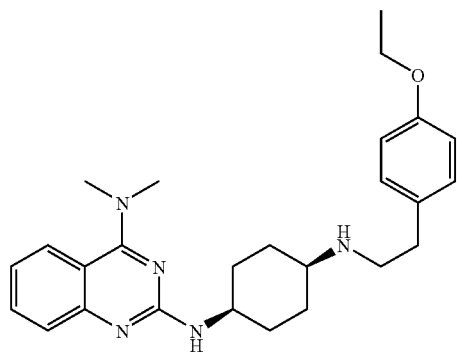 | 434 (M + H) |
| 2230 | 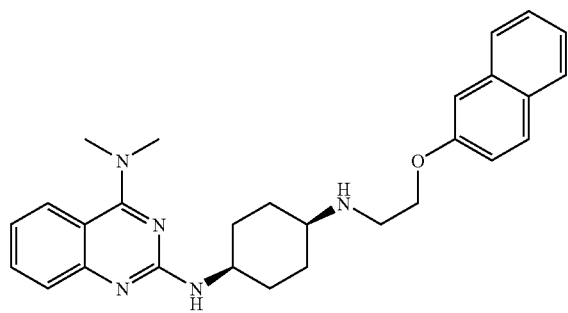 | 456 (M + H) |
| 2231 | 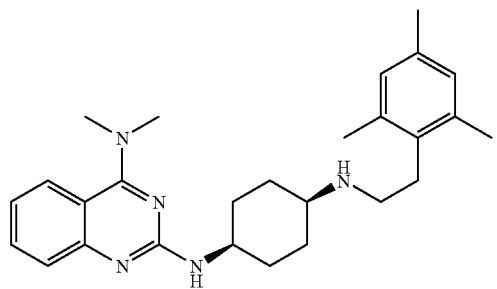 | 432 (M + H) |
| 2232 | 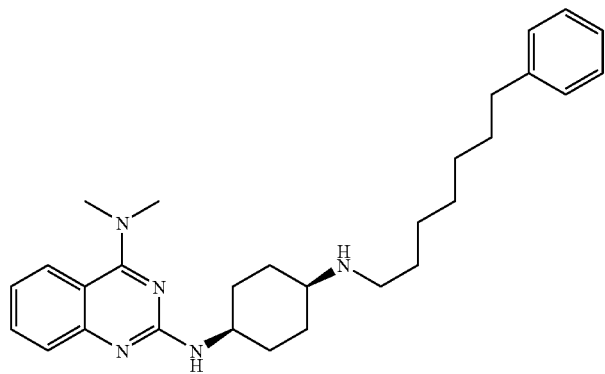 | 460 (M + H) |

-continued
| Example No. | Structure | APCI-MS |
|---|---|---|
| 2233 | 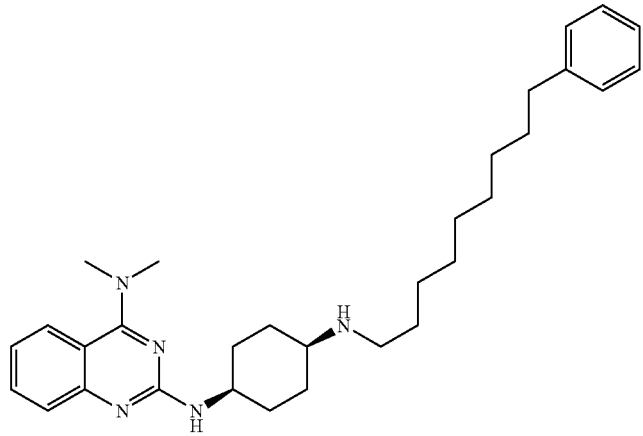 | 488 (M + H) |
| 2234 | 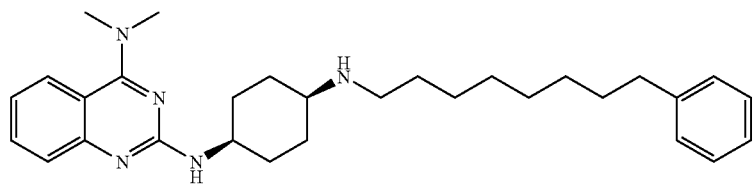 | 474 (M + H) |
| 2235 | 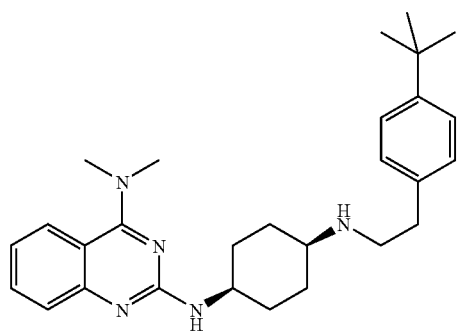 | 446 (M + H) |
| 2236 | 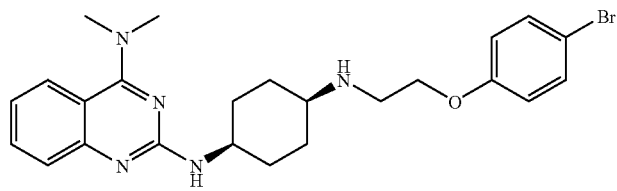 | 484 (M + H) |
| 2237 | 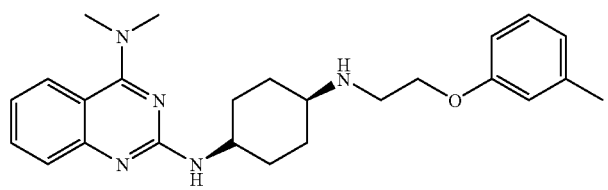 | 420 (M + H) |

-continued
| Example No. | Structure | APCI-MS |
|---|---|---|
| 2238 | 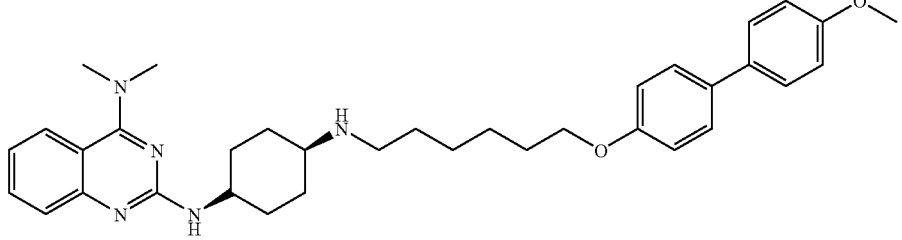 | 568 (M + H) |
| 2239 | 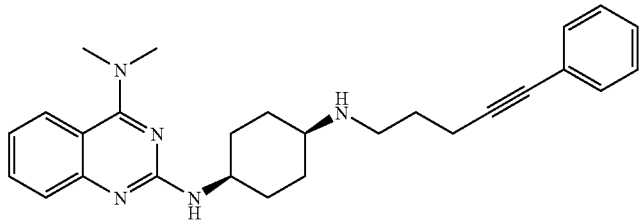 | 428 (M + H) |
| 2240 | 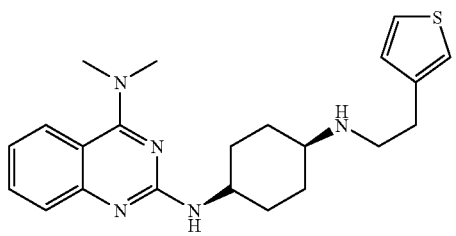 | 396 (M + H) |
| 2241 | 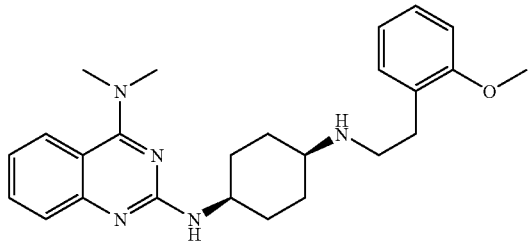 | 420 (M + H) |
| 2242 | 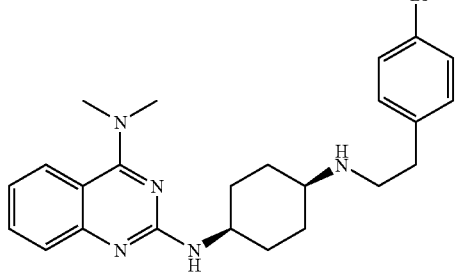 | 468 (M + H) |
| 2243 | 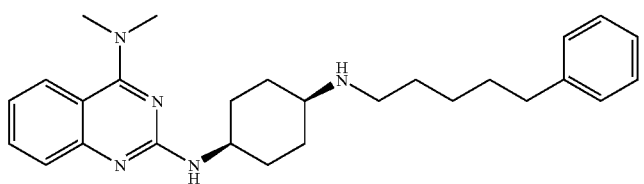 | 432 (M + H) |

-continued
| Example No. | Structure | APCI-MS |
|---|---|---|
| 2244 | 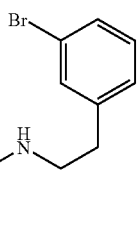 | 468 (M + H) |
| 2245 | 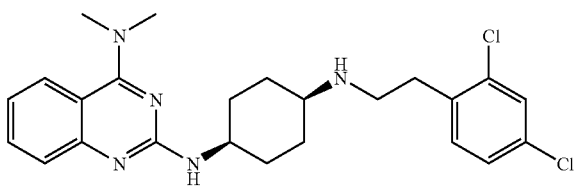 | 458 (M + H) |
| 2246 | 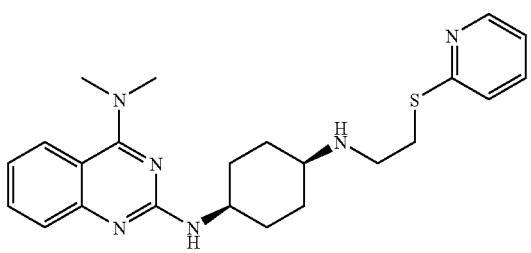 | 423 (M + H) |
| 2247 | 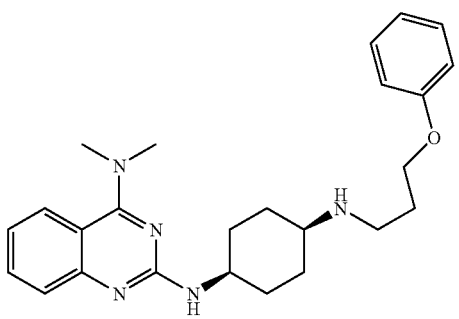 | 420 (M + H) |
| 2248 | 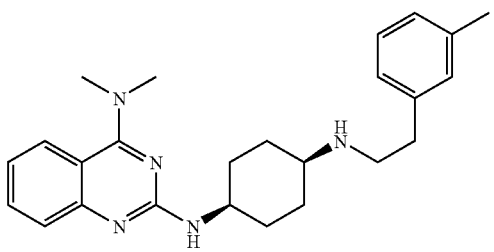 | 404 (M + H) |
| 2249 | 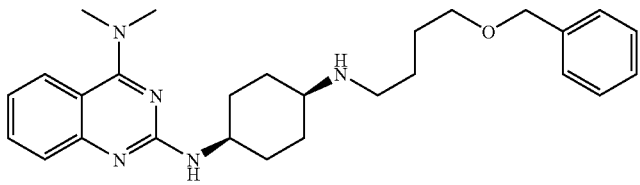 | 448 (M + H) |

-continued
| Example No. | Structure | APCI-MS |
|---|---|---|
| 2250 | 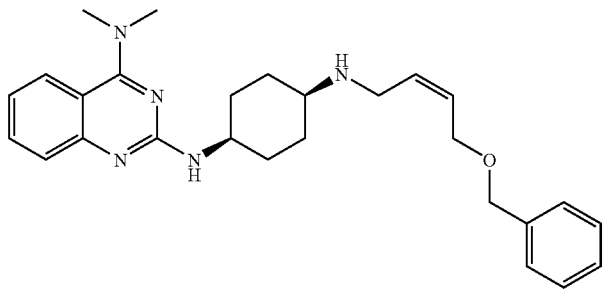 | 446 (M + H) |
| 2251 | 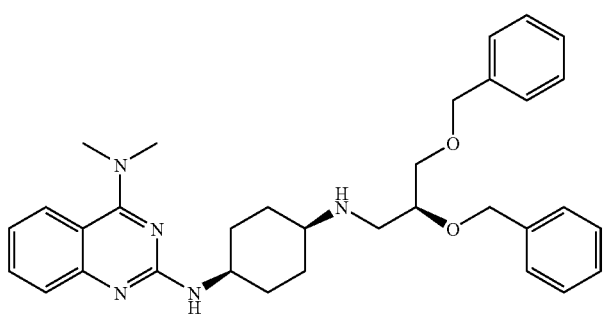 | 540 (M + H) |
| 2252 | 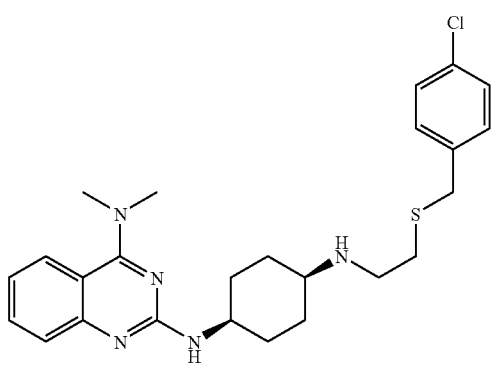 | 470 (M + H) |
| 2253 | 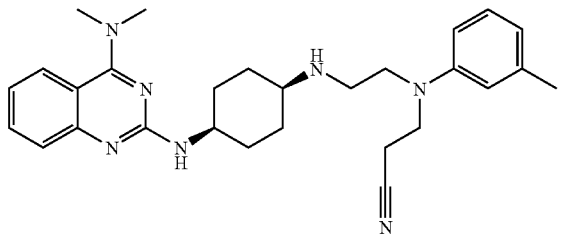 | 472 (M + H) |
| 2254 | 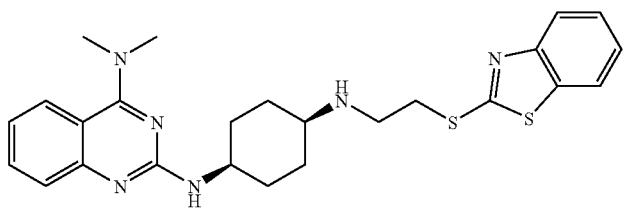 | 479 (M + H) |

-continued
| Example No. | Structure | APCI-MS |
|---|---|---|
| 2255 | 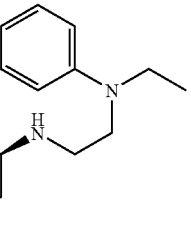 | 433 (M + H) |
| 2256 | 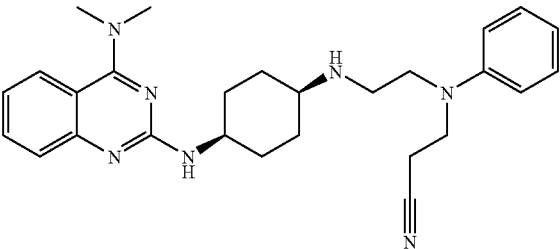 | 458 (M + H) |
| 2257 | 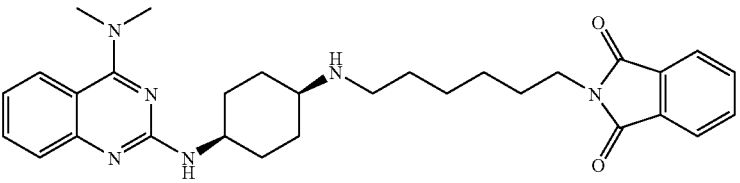 | 515 (M + H) |
| 2258 | 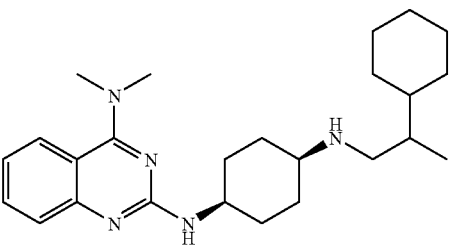 | 410 (M + H) |
| 2259 | 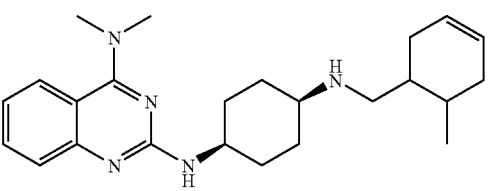 | 394 (M + H) |
| 2260 | 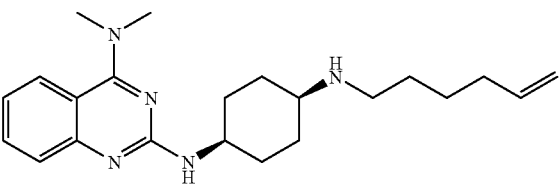 | 368 (M + H) |
| 2261 | 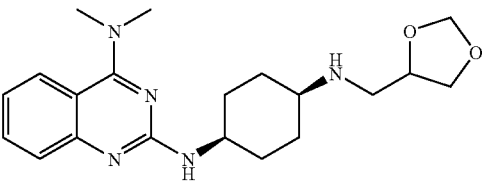 | 372 (M + H) |

-continued

| Example No. | Structure | APCI-MS |
|---|---|---|
| 2262 | 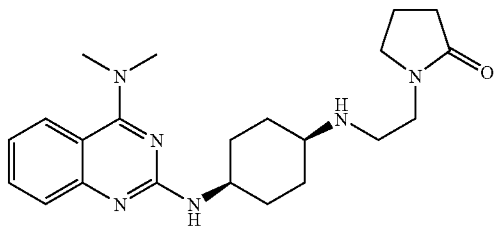 | 397 (M + H) |
| 2263 | 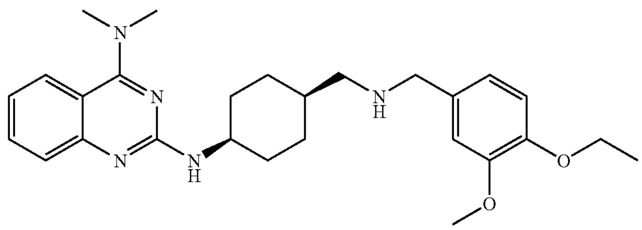 | 464 (M + H) |
| 2264 | 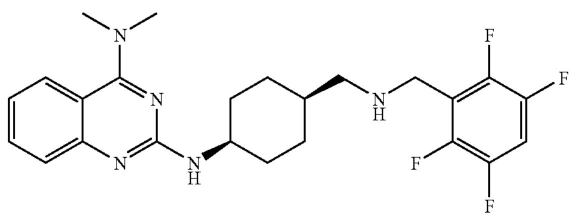 | 462 (M + H) |
| 2265 | 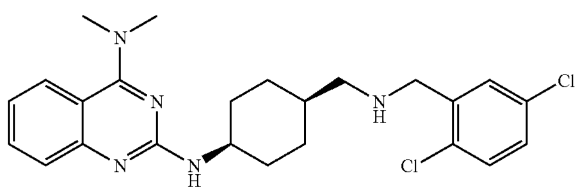 | 458 (M + H) |
| 2266 | 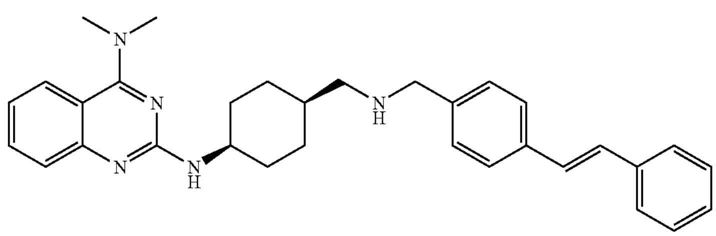 | 492 (M + H) |
| 2267 | 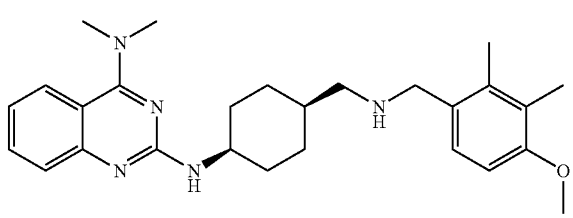 | 448 (M + H) |
| 2268 | 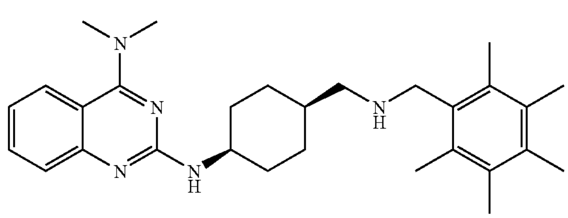 | 460 (M + H) |

| Example No. | Structure | APCI-MS |
|---|---|---|
| 2269 | 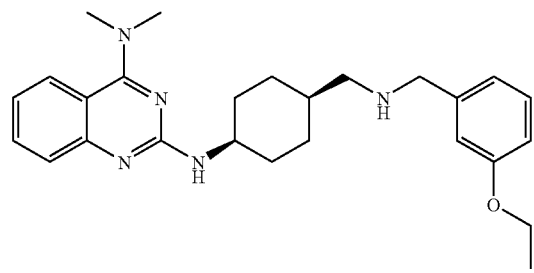 | 434 (M + H) |
| 2270 | 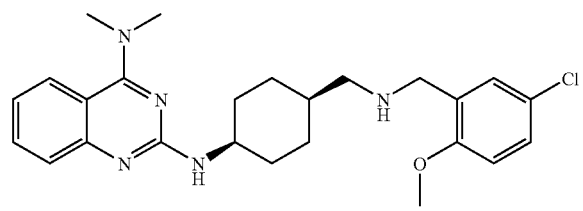 | 454 (M + H) |
| 2271 | 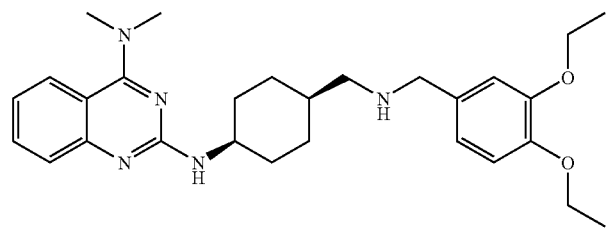 | 478 (M + H) |
| 2272 | 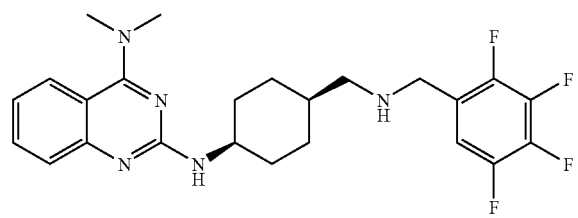 | 462 (M + H) |
| 2273 | 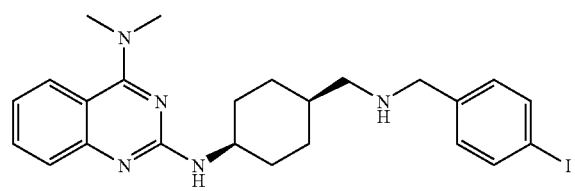 | 516 (M + H) |
| 2274 | 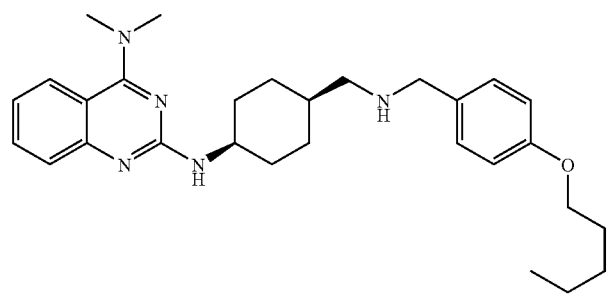 | 476 (M + H) |

-continued
| Example No. | Structure | APCI-MS |
|---|---|---|
| 2275 | 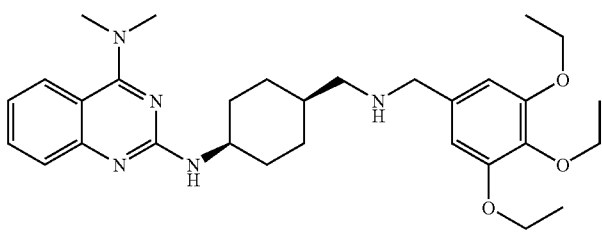 | 522 (M + H) |
| 2276 | 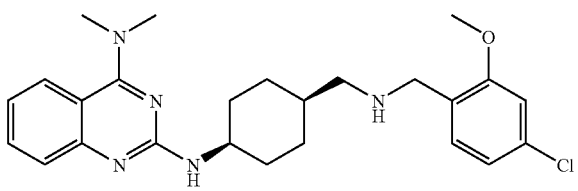 | 454 (M + H) |
| 2277 | 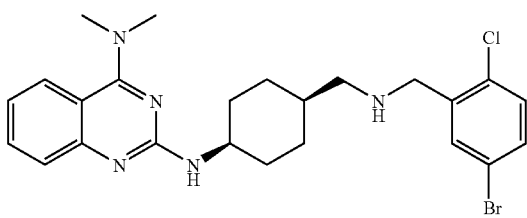 | 502 (M + H) |
| 2278 | 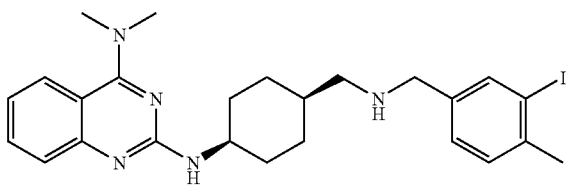 | 530 (M + H) |
| 2279 | 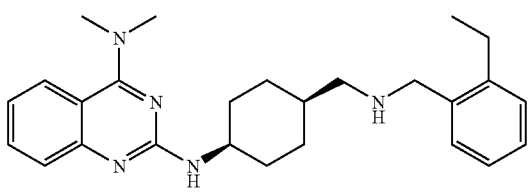 | 418 (M + H) |
| 2280 | 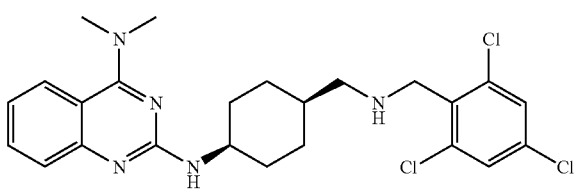 | 492 (M + H) |
| 2281 | 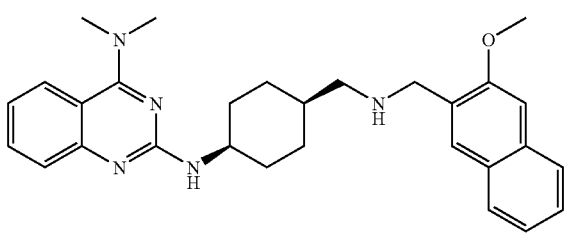 | 470 (M + H) |

-continued

| Example No. | Structure | APCI-MS |
|---|---|---|
| 2282 | 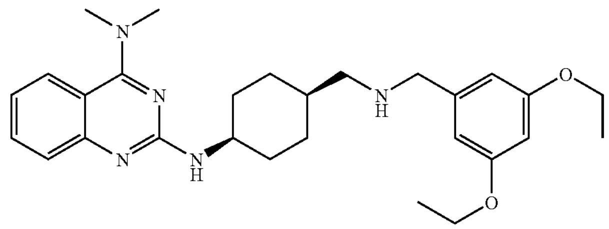 | 478 (M + H) |
| 2283 | 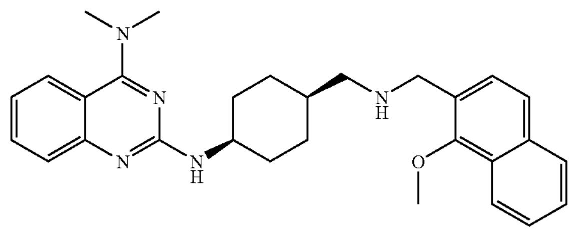 | 470 (M + H) |
| 2284 | 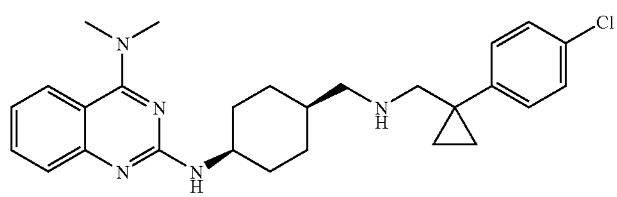 | 464 (M + H) |
| 2285 | 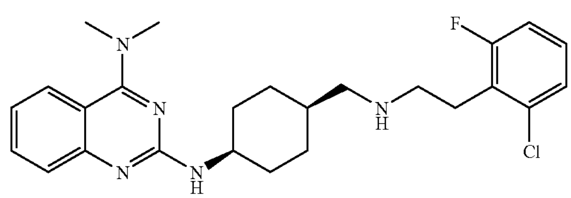 | 456 (M + H) |
| 2286 | 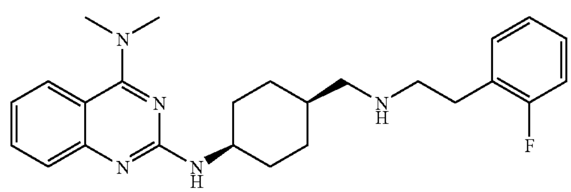 | 422 (M + H) |
| 2287 | 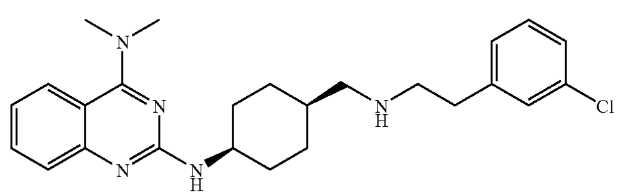 | 438 (M + H) |
| 2288 | 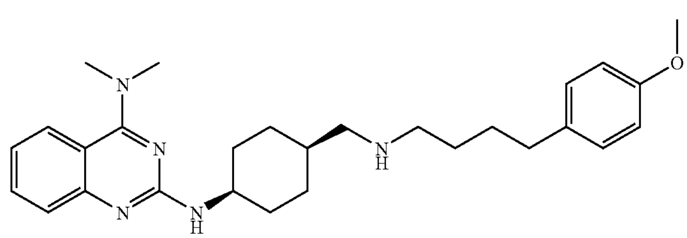 | 462 (M + H) |

-continued
| Example No. | Structure | APCI-MS |
|---|---|---|
| 2289 | 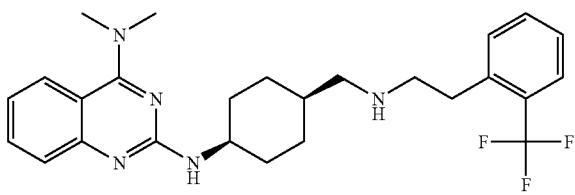 | 472 (M + H) |
| 2290 | 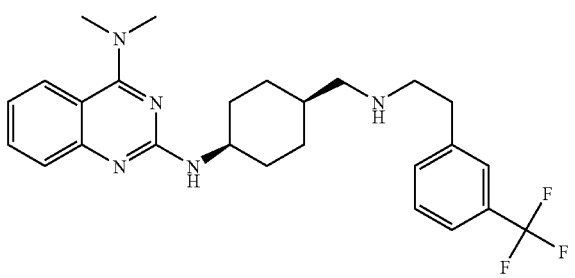 | 472 (M + H) |
| 2291 | 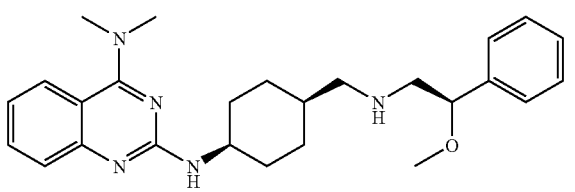 | 434 (M + H) |
| 2292 | 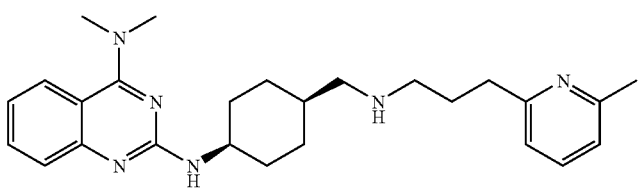 | 433 (M + H) |
| 2293 | 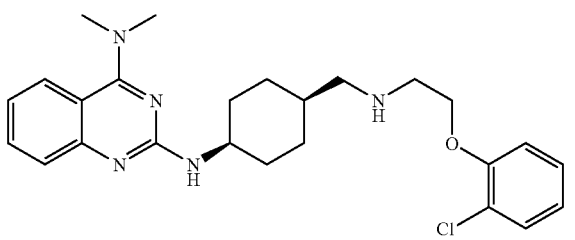 | 454 (M + H) |
| 2294 | 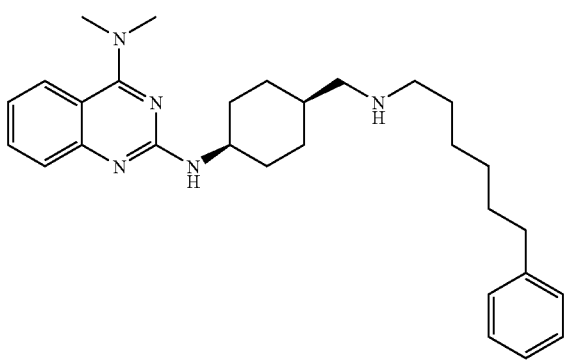 | 460 (M + H) |

-continued

| Example No. | Structure | APCI-MS |
| --- | --- | --- |
| 2295 | 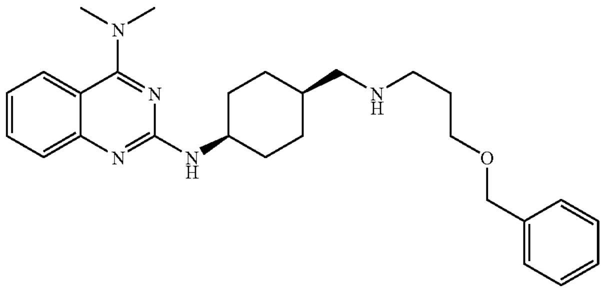 | 448 (M + H) |
| 2296 | 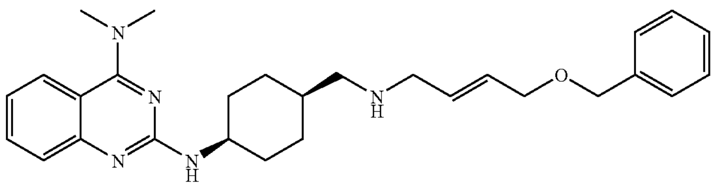 | 460 (M + H) |
| 2297 | 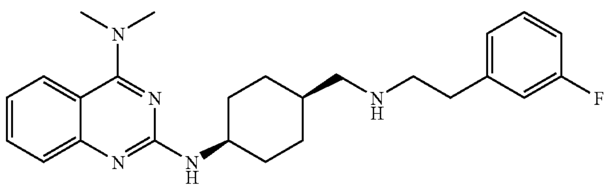 | 422 (M + H) |
| 2298 | 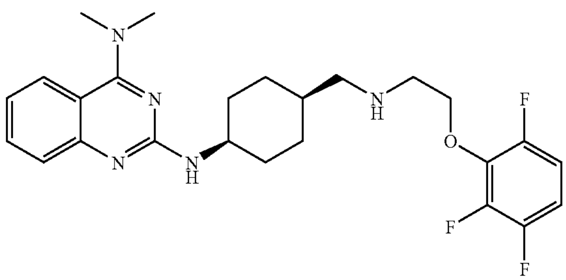 | 474 (M + H) |
| 2299 | 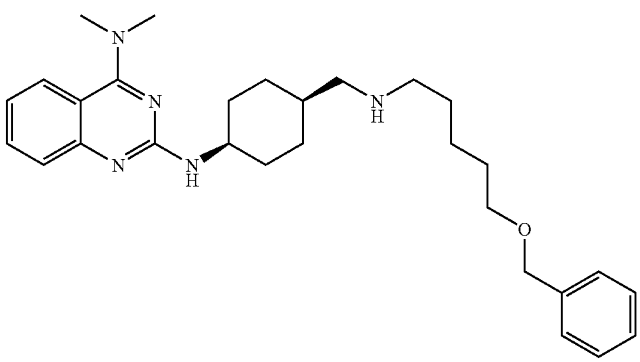 | 476 (M + H) |
| 2300 | 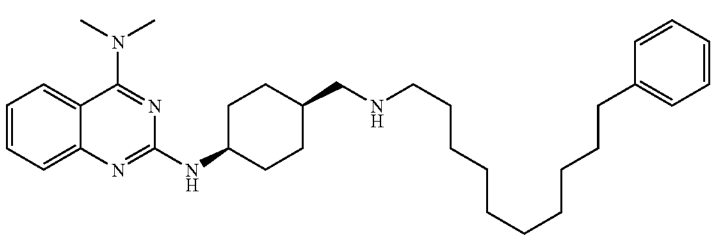 | 516 (M + H) |

-continued
| Example No. | Structure | APCI-MS |
|---|---|---|
| 2301 | 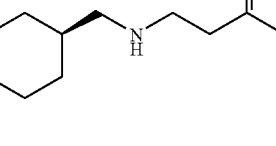 | 448 (M + H) |
| 2302 | 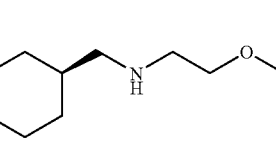 | 470 (M + H) |
| 2303 | 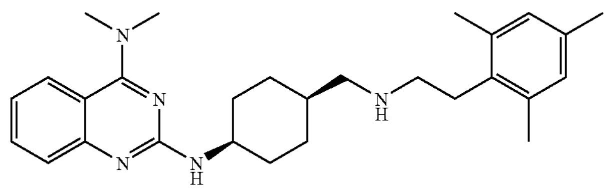 | 446 (M + H) |
| 2304 | 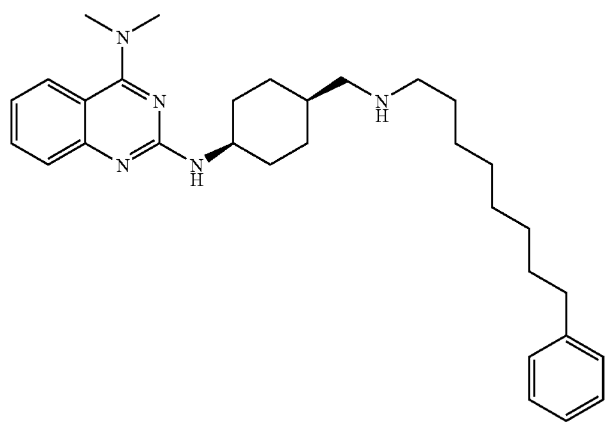 | 488 (M + H) |
| 2305 | 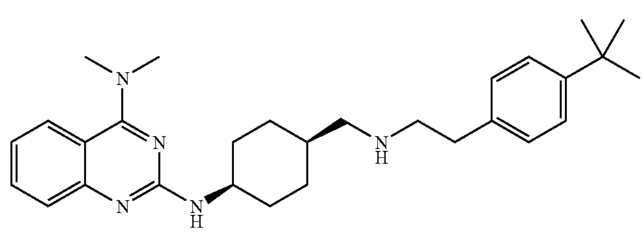 | 460 (M + H) |
| 2306 | 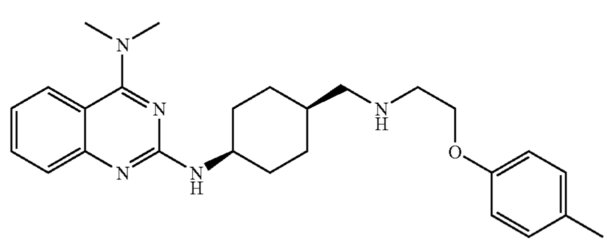 | 434 (M + H) |

-continued

| Example No. | Structure | APCI-MS |
|---|---|---|
| 2307 | 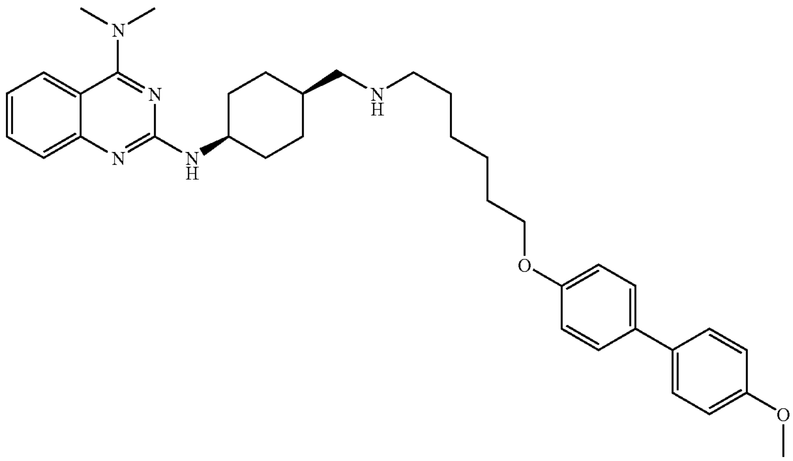 | 582 (M + H) |
| 2308 | 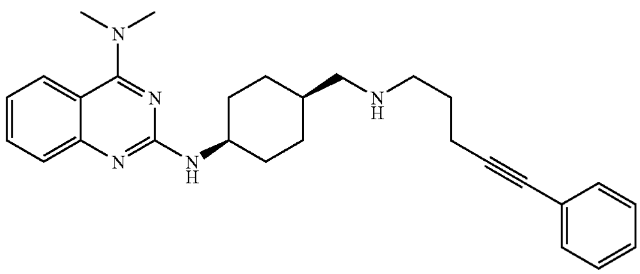 | 442 (M + H) |
| 2309 | 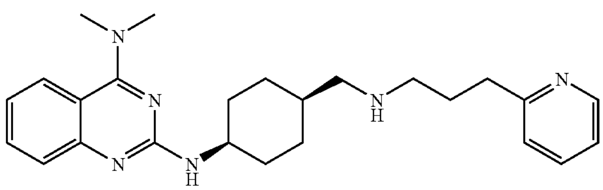 | 419 (M + H) |
| 2310 | 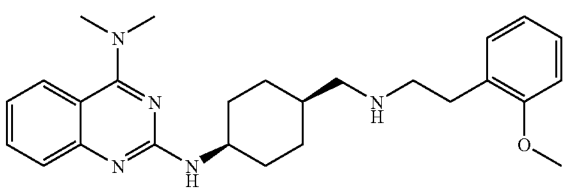 | 434 (M + H) |
| 2311 | 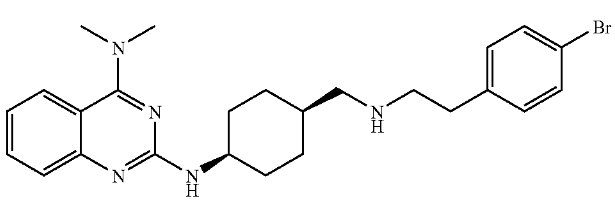 | 482 (M + H) |
| 2312 | 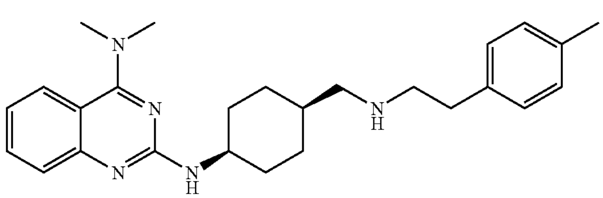 | 418 (M + H) |

-continued
| Example No. | Structure | APCI-MS |
|---|---|---|
| 2313 | 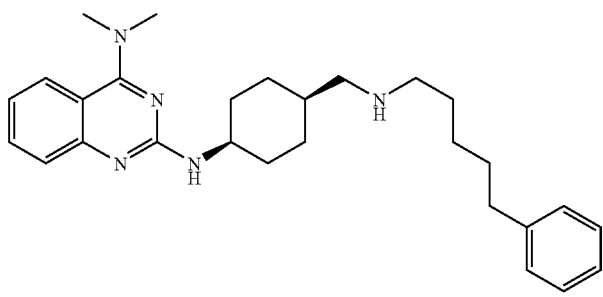 | 446 (M + H) |
| 2314 | 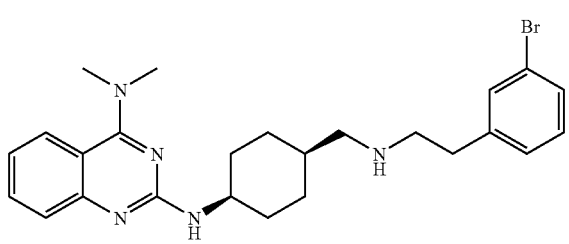 | 482 (M + H) |
| 2315 | 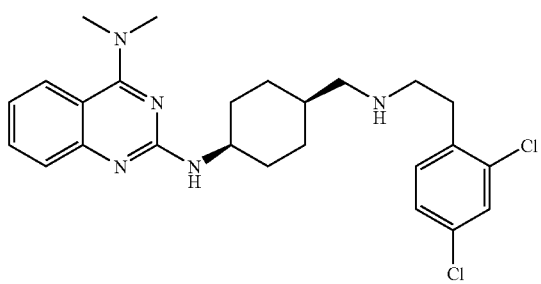 | 472 (M + H) |
| 2316 | 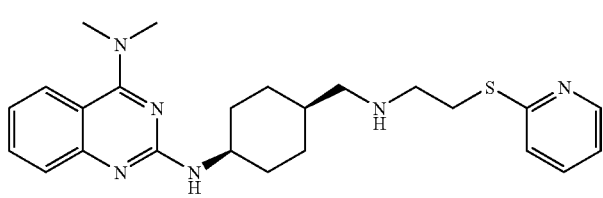 | 437 (M + H) |
| 2317 | 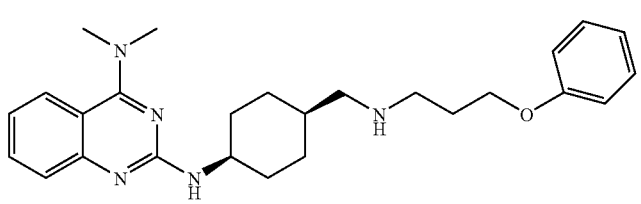 | 434 (M + H) |
| 2318 | 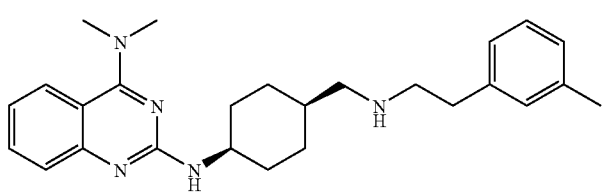 | 418 (M + H) |

| Example No. | Structure | APCI-MS |
|---|---|---|
| 2319 | 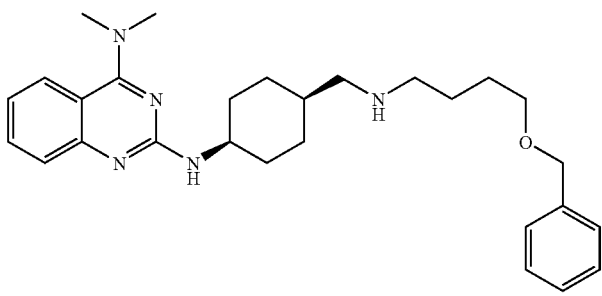 | 462 (M + H) |
| 2320 | 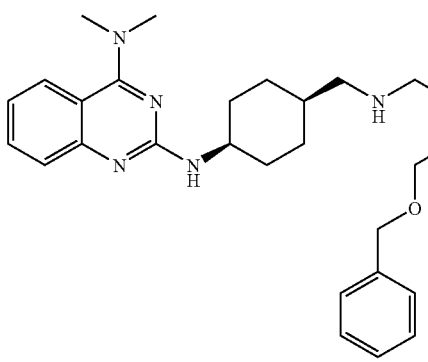 | 460 (M + H) |
| 2321 | 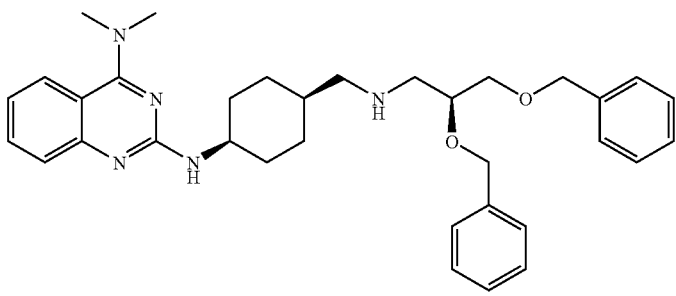 | 554 (M + H) |
| 2322 | 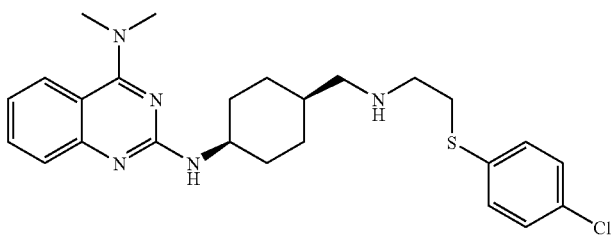 | 470 (M + H) |
| 2323 | 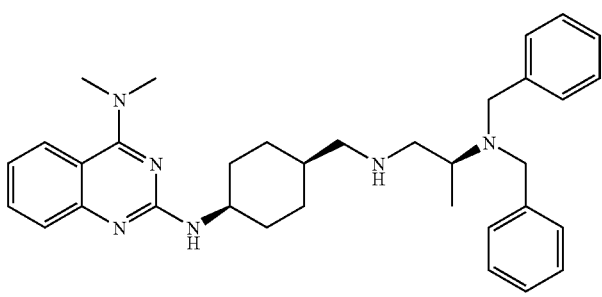 | 537 (M + H) |

-continued
| Example No. | Structure | APCI-MS |
|---|---|---|
| 2324 | 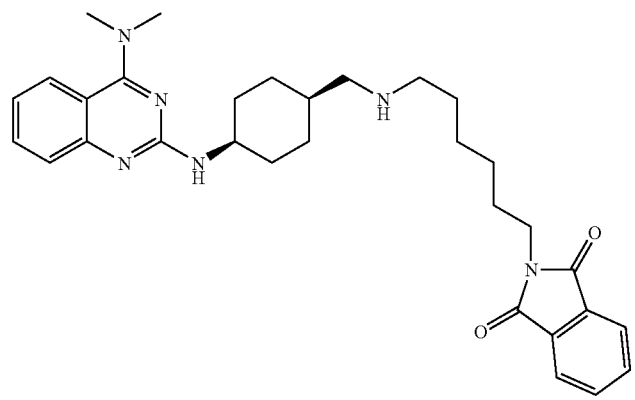 | 529 (M + H) |
| 2325 | 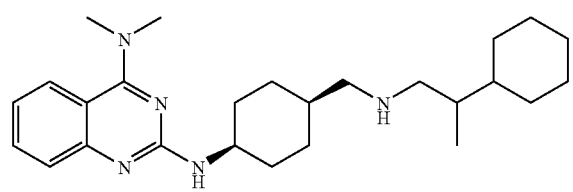 | 424 (M + H) |
| 2326 | 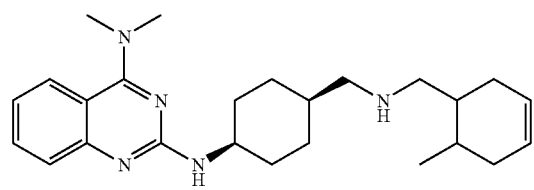 | 408 (M + H) |
| 2327 | 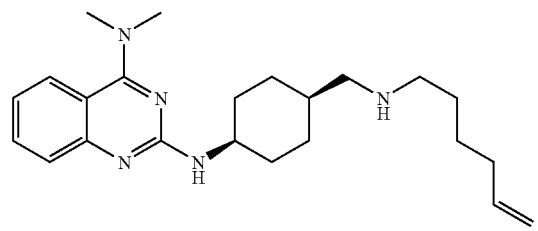 | 382 (M + H) |
| 2328 | 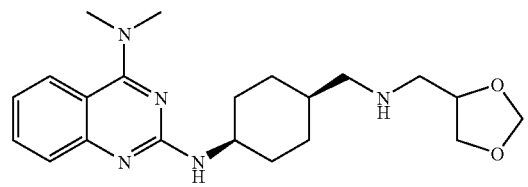 | 386 (M + H) |

Example 2329

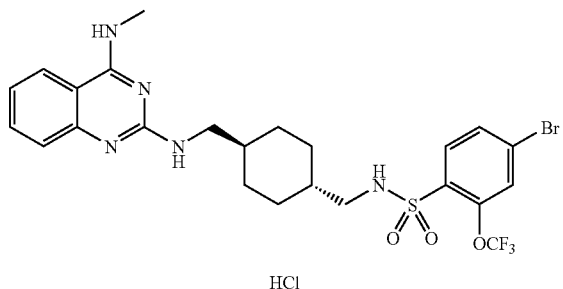

HCl trans-4-Bromo-N-{4-[(4-methylamino-quinazolin-2-ylamino)-methyl]-cyclohexylmethyl}-2-trifluoromethoxy-benzenesulfonamide hydrochloride Step A: Synthesis of trans-4-[(4-bromo-2-trifluoromethoxy-benzenesulfonylamino)-methyl]-cyclohexanecarboxylic acid.

To a solution of trans-4-aminomethyl-cyclohexanecarboxylic acid (3.14 g, 20 mmol) in THF (20 mL) and 1 M aqueous sodium hydroxide (42 mL) was added a solution of 4-bromo-2-trifluoromethoxy benzenesulfonyl chloride (6.9 g, 20.4 mmol) in THF (20 mL) and the mixture was stirred for 2 hr at ambient temperature. The resulting mixture was concentrated and 1 M aqueous HCl (45 mL) was added. The resulting precipitate was filtered, washed with water and hexanes to give trans-4-[(4-bromo-2-trifluoromethoxy-benzenesulfonylamino)-methyl]-cyclohexanecarboxylic acid (7.18 g, 78%) as a white powder.

ESI MS m/e 460/462 M+H$^+$; $^1$H NMR (500 MHz, DMSO-d$_6$) δ 12.00 (brs, 1 H), 7.99 (brs, 1 H), 7.84-7.80 (m, 3 H), 2.72 (d, J=6.3 Hz, 2 H), 2.10 (m, 1 H), 1.86 (m, 2 H), 1.71 (m, 2 H), 1.31 (m, 1 H), 1.23 (m, 2 H), 0.87 (m, 2 H).

Step B: Synthesis of trans-4-[(4-bromo-2-trifluoromethoxy-benzenesulfonylamino)-methyl]-cyclohexanecarboxylic acid amide.

A solution of trans-4-[(4-bromo-2-trifluoromethoxy-benzenesulfonylamino)-methyl]-cyclohexanecarboxylic acid (7.14 g, 15.5 mmol) and triethylamine (2.35 mL, 16.9 mmol) in THF (25 mL) was cooled to 0° C. To the mixture was added ethyl chloroformate (1.62 mL, 17 mmol) in THF (5 mL) over 10 min. After stirring at 0° C. for 15 min, aqueous ammonia (27 mL) was added dropwise and the mixture was stirred at ambient temperature for 2 hr. The mixture was concentrated under reduced pressure and the concentrate was treated with water to give a solid. The solid was filtered and washed with water and hexanes to give trans-4-[(4-bromo-2-trifluoromethoxy-benzenesulfonylamino)-methyl]-cyclohexanecarboxylic acid amide as a white solid (4.2 g, 59%).

ESI MS m/e 459/461 M+H$^+$; $^1$H NMR (500 MHz, DMSO-d$_6$) δ 7.98 (brs, 1 H), 7.84-7.80 (m, 3 H), 7.13 (s, 1 H), 6.62 (s, 1 H), 2.72 (d, J=6.5 Hz, 2 H), 1.98 (m, 1 H), 1.70 (m, 4 H), 1.29 (m, 1 H), 1.23 (m, 2 H), 0.83 (m, 2 H).

Step C: Synthesis of trans-N-(4-aminomethyl-cyclohexylmethyl)-4-bromo-2-trifluoromethoxy-benzenesulfonamide.

To a solution of trans-4-[(4-bromo-2-trifluoromethoxy-benzenesulfonylamino)-methyl]-cyclohexanecarboxylic acid amide (4.2 g, 9.2 mmol) in THF (40 mL) was added a solution of 1 M BH$_3$ in THF (32 mL, 32 mmol) over 40 min. The mixture was refluxed for 2 hr. After cooling to 0° C., the mixture was quenched with water (7 mL). To the resulting mixture were added 4 M HCl in EtOAc (28 mL) and MeOH (28 mL) and the mixture was concentrated. To the residue was added MeOH (28 mL) and the mixture was once again concentrated. The resulting HCl-salt was recrystallized from Et$_2$O and subsequently neutralized with 1 M aqueous sodium hydroxide. The aqueous layer was extracted with CH$_2$Cl$_2$ (twice), the organic layers combined, dried over sodium sulfate, and concentrated under reduced pressure to give trans-N-(4-aminomethyl-cyclohexylmethyl)-4-bromo-2-trifluoromethoxy-benzenesulfonamide as a white solid (3.0 g, 74%).

ESI MS m/e 445/447 M+H$^+$; $^1$H NMR (500 MHz, DMSO-d$_6$) δ 7.84-7.79 (m, 3 H), 3.42 (brs, 2 H), 2.72 (d, J=6.8 Hz, 2 H), 2.33 (d, J=6.5 Hz, 2 H), 1.73 (m, 4 H), 1.27 (m, 1 H), 1.09 (m, 1 H), 0.80 (m, 4 H).

Step D: Synthesis of trans-4-Bromo-N-{4-[(4-methylamino-quinazolin-2-ylamino)-methyl]-cyclohexylmethyl}-2-trifluoromethoxy-benzenesulfonamide hydrochloride.

A mixture of (2-chloro-quinazolin-4-yl)-methylamine obtained in step A of example 50 (58 mg, 0.3 mmol) and trans-N-(4-aminomethyl-cyclohexylmethyl)-4-bromo-2-trifluoromethoxy-benzenesulfonamide amide (133 mg, 0.3 mmol) in 2-propanol (0.5 mL) was stirred at reflux for 24 hr. The mixture was cooled and the resulting white solid was collected by filtration and washed with 2-propanol to give trans-4-Bromo-N-{4-[(4-methylamino-quinazolin-2-ylamino)-methyl]-cyclohexylmethyl}-2-trifluoromethoxy-benzenesulfonamide hydrochloride as a white solid (121 mg, 67%).

ESI MS m/e 602/604 M+H$^+$; $^1$H NMR (500 MHz, DMSO-d$_6$) δ 12.61 (brs, 1 H), 9.70 (brs, 1 H), 8.26 (d, J=8.1 Hz, 1 H), 8.15 (brs, 1 H), 8.02 (t, J=5.7 Hz, 1 H), 7.84-7.74 (m, 4 H), 7.41 (m, 1 H), 3.32 (m, 2 H), 3.07 (d, J=3.5 Hz, 3 H), 2.73 (t, J=6.2 Hz, 2 H), 1.77 (m, 4 H), 1.53 (m, 1 H), 1.32 (m, 1 H), 0.96 (m, 2 H), 0.82 (m, 2 H).

Example 2330

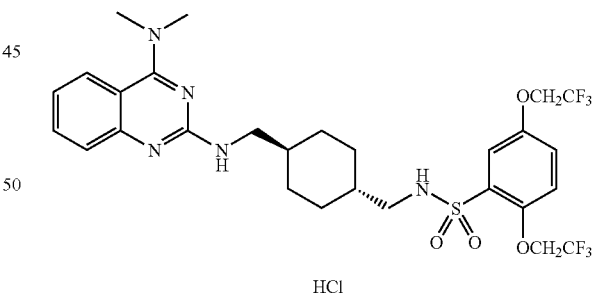

HCl trans-N-{4-[(4-Dimethylamino-quinazolin-2-ylamino)-methyl]-cyclohexylmethyl}-2,5-bis-(2,2,2-trifluoro-ethoxy)-benzenesulfonamide hydrochloride Step A: Synthesis of trans-4-{[2,5-bis-(2,2,2-trifluoroethoxy)-benzenesulfonylamino]-methyl}-cyclohexanecarboxylic acid.

To a solution of trans-4-aminomethyl-cyclohexanecarboxylic acid (1.5 g, 10 mmol) in THF (10 mL) and 1 M aqueous sodium hydroxide (27 mL) was added a solution of 2,5-bis(2,2,2-trifluoroethoxy)benzenesulfonyl chloride (3.8 g, 10.25 mmol) in THF (10 mL) dropwise and the mixture was stirred at ambient temperature for 2 hr. The resulting mixture was concentrated and 1 M aqueous HCl (22.5 mL) was added. The resulting precipitate was filtered, washed with water and hexanes to give trans-4-{[2,5-bis-(2,2,2-trifluoro-ethoxy)-benzenesulfonylamino]-methyl}-cyclohexanecarboxylic acid as a white powder (2.8 g, 57%).

ESI MS m/e 494 M+H$^+$; $^1$H NMR (500 MHz, DMSO-d$_6$) δ 7.36 (m, 3 H), 7.23 (brs, 1 H), 4.88 (m, 4 H), 2.73 (m, 2 H), 2.10 (m, 1 H), 1.87 (m, 2 H), 1.72 (m, 2 H), 1.30 (m, 1 H), 1.23 (m, 2 H), 0.87 (m, 2 H).

Step B: Synthesis of trans-4-{[2,5-bis-(2,2,2-trifluoro-ethoxy)-benzenesulfonylamino]-methyl}-cyclohexanecarboxylic acid amide.

A solution of trans-4-{[2,5-bis-(2,2,2-trifluoro-ethoxy)-benzenesulfonylamino]-methyl}-cyclohexanecarboxylic acid (2.78 g, 5.63 mmol) and triethylamine (1.9 mL, 13.6 mmol) in THF (25 mL) was cooled to 0° C. To the mixture was added ethyl chloroformate (0.586 mL, 6.2 mmol) in THF (5 mL) over 10 min. After stirring at 0° C. for 15 min, 25% aqueous ammonia (10 mL) was added dropwise. The mixture was stirred at ambient temperature for 2 hr. The resulting mixture was concentrated under reduced pressure and the concentrate was diluted with water to give a solid. The solid was filtered and washed with water and hexanes to give trans-4-{[2,5-bis-(2,2,2-trifluoro-ethoxy)-benzenesulfonylamino]-methyl}-cyclohexanecarboxylic acid amide as a white solid (2.7 g, 98%).

ESI MS m/e 493 M+H$^+$; $^1$H NMR (500 MHz, DMSO-d$_6$) δ 7.36 (m, 3 H), 7.23 (t, J=6.1 Hz, 1 H), 7.13 (s, 1 H), 6.62 (s, 1 H), 4.88 (m, 4 H), 2.74 (t, J=6.4 Hz, 2 H), 1.99 (m, 1 H), 1.75 (m, 4 H), 1.28 (m, 1 H), 1.23 (m, 2 H), 0.83 (m, 2 H).

Step C: Synthesis of trans-N-(4-aminomethyl-cyclohexylmethyl)-2,5-bis-(2,2,2-trifluoro-ethoxy)-benzenesulfonamide.

To a solution of trans-4-{[2,5-bis-(2,2,2-trifluoro-ethoxy)-benzenesulfonylamino]-methyl}-cyclohexanecarboxylic acid amide (2.7 g, 5.5 mmol) in THF (20 mL) was added a solution of 1 M BH$_3$ in THF (20 mL, 20 mmol) over 40 min. The mixture was stirred at reflux for 2 hr. After cooling to 0° C., the mixture was quenched with water (7 mL). To the mixture were added 4 M HCl in EtOAc (28 mL) and MeOH (50 mL) and the mixture was concentrated. To the residue was added MeOH (50 mL) and the mixture was once again concentrated. The resulting HCl-salt was recrystallized from Et$_2$O and subsequently neutralized with 1 M aqueous sodium hydroxide. The aqueous layer was extracted with CH$_2$Cl$_2$ (twice), the combined organic layers were dried over sodium sulfate, and concentrated under reduced pressure to give trans-N-(4-aminomethyl-cyclohexylmethyl)-2,5-bis-(2,2,2-trifluoro-ethoxy)-benzenesulfonamide as a white solid (1.5 g, 57%).

ESI MS m/e 479 M+H$^+$; $^1$H NMR (500 MHz, DMSO-d$_6$) δ 7.36-7.32 (m, 3 H), 6.62 (brs, 1 H), 4.88-4.78 (m, 4 H), 3.42 (b, 2 H), 2.73 (d, J=6.6 Hz, 2 H), 2.34 (d, J=6.3 Hz, 2 H), 1.73 (m, 4 H), 1.27 (m, 1 H), 1.10 (m, 1 H), 0.77 (m, 4 H).

Step D: Synthesis of trans-N-{4-[(4-Dimethylamino-quinazolin-2-ylamino)-methyl]-cyclohexylmethyl}-2,5-bis-(2,2,2-trifluoro-ethoxy)-benzenesulfonamide hydrochloride.

A mixture of (2-chloro-quinazoline-4-yl)-dimethyl-amine obtained in step B of example 1 (41.4 mg, 0.2 mmol) and trans-AT-(4-aminomethyl-cyclohexylmethyl)-2,5-bis-(2,2,2-trifluoro-ethoxy)-benzenesulfonamide (95.6 mg, 0.2 mmol) in 2-propanol was stirred at reflux for 24 hr. The reaction mixture was concentrated and the residue was purified by column chromatography (silica gel) to give the product as a white foam. The product was dissolved in CH$_2$Cl$_2$ and treated with 1 M HCl in Et$_2$O. The mixture was concentrated to give trans-N-{4-[(4-Dimethylamino-quinazolin-2-ylamino)-methyl]-cyclohexylmethyl}-2,5-bis-(2,2,2-trifluoro-ethoxy)-benzenesulfonamide hydrochloride as a white foam (101 mg, 78%).

ESI MS m/e 650 M+H$^+$; $^1$H NMR (500 MHz, DMSO-d$_6$) δ 8.16 (d, J=8.2 Hz, 1 H), 8.00 (brs, 1 H), 7.78 (t, J=7.9, 1 H), 7.44 (brs, 1 H), 7.34 (m, 4H), 7.24 (t, J=5.9 Hz, 1 H), 4.88 (m, 4 H), 3.32 (s, 6 H), 3.29 (m, 2 H), 2.75 (t, J=6.2 Hz, 2 H), 1.74 (m, 4 H), 1.52 (m, 1 H), 1.32 (m, 1 H), 0.94 (m, 2 H), 0.83 (m, 2 H).

Example 2331

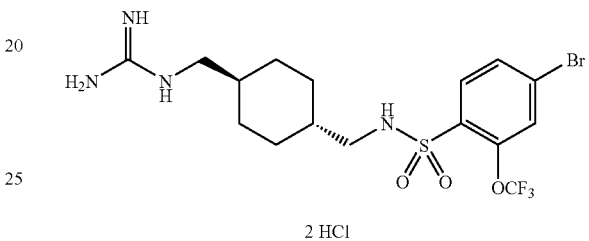

2 HCl trans-4-Bromo-N-(4-guanidinomethyl-cyclohexylmethyl)-2-trifluoromethoxy-benzenesulfonamide dihydrochloride Step A: Synthesis of trans-[({4-[(4-bromo-2-trifluoromethoxy-benzenesulfonylamino)-methyl]-cyclohexylmethyl}-amino)-tert-butoxycarbonylamino-methyl]-carbamic acid tert-butyl ester.

To a solution of trans-N-(4-aminomethyl-cyclohexylmethyl)-4-bromo-2-trifluoromethoxy-benzenesulfonamide obtain in step C of example 2329 (45 mg, 0.1 mmol) and triethylamine (14 µL, 0.1 mmol) in CH$_2$Cl$_2$ (5 mL) was added (tert-butoxycarbonylamino-trifluoromethanesulfonylimino-methyl)-carbamic acid tert-butyl ester (39.1 mg, 0.1 mmol). The reaction mixture was stirred at ambient temperature for 2 hr and concentrated. The residue was purified by column chromatography (silica gel, CH$_2$Cl$_2$ to 10% MeOH in CH$_2$Cl$_2$) to give trans-[({4-[(4-bromo-2-trifluoromethoxy-benzenesulfonylamino)-methyl]-cyclohexylmethyl}-amino)-tert-butoxycarbonylamino-methyl]-carbamic acid tert-butyl ester as a white solid (63 mg, 92%).

ESI MS m/e 687/689 M+H$^+$; $^1$H NMR (400 MHz, DMSO-d$_6$) δ 11.45 (s, 1 H), 8.22 (t, J=5.6 Hz, 1 H), 7.97 (t, J=5.6 Hz, 1 H), 7.99-7.79 (m, 3 H), 3.13 (t, J=6.4 Hz, 2 H), 2.72 (t, J=6 Hz, 2 H), 1.70 (m, 4 H), 1.46 (s, 9 H), 1.38 (s, 9 H), 1.31 (m, 2 H), 0.83 (m, 4 H).

Step B: Synthesis of trans-4-bromo-N-(4-guanidinomethyl-cyclohexylmethyl)-2-trifluoromethoxy-benzenesulfonamide dihydrochloride.

A solution of trans-[({4-[(4-bromo-2-trifluoromethoxy-benzenesulfonylamino)-methyl]-cyclohexylmethyl}-amino)-tert-butoxycarbonylamino-methyl]-carbamic acid tert-butyl ester (53 mg, 0.077 mmol) in 50% TFA in CH$_2$Cl$_2$ (2 mL) was stirred at ambient temperature for 3 hr and the reaction mixture was concentrated. To the residue was added a solution of 1 M HCl in Et$_2$O (0.5 mL) and the mixture was concentrated to give trans-4-Bromo-N-(4-guanidinomethyl-cyclohexylmethyl)-2-trifluoromethoxy-benzenesulfonamide dihydrochloride as a white solid (29 mg, 68%).

ESI MS m/e 487/489 M+H+; 1H NMR (500 MHz, DMSO-d6) δ 8.01 (t, J=5.5 Hz, 1 H), 7.84 (m, 3 H), 7.68 (m, 1 H), 7.30 (m, 2 H), 6.85 (m, 2 H), 2.94 (t, J=6.1 Hz, 2 H), 2.74 (t, J=6.1 Hz, 2 H), 1.71 (m, 2 H), 1.31 (m, 4 H), 0.86 (m, 4 H).

Example 2332

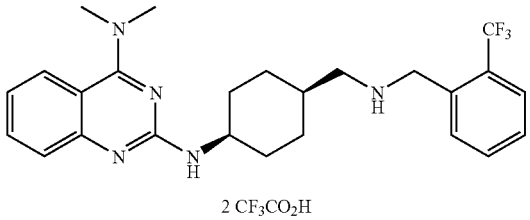

2 CF3CO2H cis-N4,N4-Dimethyl-N2-{4-[(2-trifluoromethyl-benzylamino)-methyl]-cyclohexyl}-quinazoline-2,4-diamine ditrifluoro-acetic acid Step A: Synthesis of cis-4-tert-butoxycarbonylamino-cyclohexanecarboxylic acid.

To a solution of cis-4-amino-cyclohexanecarboxylic acid (50 g, 350 mmol) in THF (200 mL) and 1 M aqueous sodium hydroxide (380 mL, 380 mmol) was added (Boc)2O (83.5 g, 360 mmol). The reaction mixture was stirred at ambient temperature for 2 hr and concentrated. The residue was cooled to 0° C. followed by acidification with 1 M HCl (pH=3). The resulting white solid was filtered, washed with water and hexanes to give cis-4-tert-butoxycarbonylamino-cyclohexanecarboxylic acid (71 g, 83%) as a white solid.

ESI MS m/e 244 M+H+; 1H NMR (400 MHz, DMSO-d6) δ 12.00 (brs, 1 H), 6.74 (d, J=4.25, 1 H), 3.30 (brs, 1 H), 2.35 (m, 1 H), 1.87 (m, 2 H), 1.55-1.37 (m, 15 H).

Step B: Synthesis of cis-(4-carbamoyl-cyclohexyl)-carbamic acid tert-butyl ester.

To a solution cooled at 0° C. of cis-4-tert-butoxycarbonylamino-cyclohexanecarboxylic acid (68.0 g, 280 mmol) and triethylamine (31.1 g, 307 mmol) in THF (300 mL) was added ethyl chloroformate (29.3 mL, 308 mmol) dropwise. After stirring at 0° C. for 30 min, 25% aqueous ammonia (168 mL) was added dropwise. The reaction mixture was stirred at ambient temperature for 2 hr and concentrated. The residue was extracted with EtOAc (three times). The combined organic layer was washed with saturated aqueous NaHCO3, 1 M HCl, brine, and water, dried over Na2SO4, filtered, and concentrated to give cis-(4-carbamoyl-cyclohexyl)-carbamic acid tert-butyl ester (62.0 g, 88%) as a white solid.

ESI MS m/e 243 M+H+; 1H NMR (400 MHz, DMSO-d6) δ 7.10 (brs, 1 H), 6.69 (b, 2 H), 3.41 (brs, 1 H), 2.14 (m, 1 H), 1.79 (m, 2 H), 1.59 (m, 2 H), 1.45-1.37 (m, 13 H).

Step C: Synthesis of cis-4-amino-cyclohexanecarboxylic acid amide hydrochloride.

To a solution of cis-(4-carbamoyl-cyclohexyl)-carbamic acid tert-butyl ester (62 g, 256 mmol) in CH2Cl2 (250 mL) was added TFA (250 mL) and the mixture was stirred at ambient temperature for 1 hr. The mixture was concentrated and 2 M HCl in Et2O (150 mL) was added to give a white precipitate. The mixture was concentrated to give cis-4-amino-cyclohexanecarboxylic acid amide hydrochloride (45 g, 98%) as a white solid.

ESI MS m/e 143 M+H+; 1H NMR (400 MHz, DMSO-d6) δ 8.08 (m, 3 H), 7.28 (s, 1 H), 6.78 (s, 1 H), 3.10 (m, 1 H), 2.24 (m, 1 H), 1.90 (m, 2 H), 1.66 (m, 4 H), 1.50 (m, 2 H).

Step D: Synthesis of cis-4-(4-dimethylamino-quinazolin-2-ylamino)-cyclohexanecarboxylic acid amide.

A solution of (2-chloro-quinazolin-4-yl)-dimethyl-amine obtained in step B of example 1 (31.05 g, 150 mmol) and cis-4-amino-cyclohexanecarboxylic acid amide hydrochloride (26.7 g, 150 mmol) in pyridine (150 mL) was stirred at reflux for overnight. The reaction mixture was concentrated and residue was dissolve in CH2Cl2. The organic layer was washed with saturated aqueous NaHCO3 and the aqueous layer was extracted with CH2Cl2. The organic layer was dried over Na2SO4, filtered and concentrated. The residue was purified by column chromatography (silica gel, 2% to 10% 2 M NH3/MeOH in CH2Cl2) to give a slightly brown solid and the solid was recrystallized from CH2Cl2 to give cis-4-(4-dimethylamino-quinazolin-2-ylamino)-cyclohexanecarboxylic acid amide (20.6 g, 44%) as yellow crystals.

ESI MS m/e 314 M+H+; 1H NMR (400 MHz, DMSO-d6) δ 8.19 (brs, 1 H), 8.15 (d, J=8.4 Hz, 1 H), 7.77 (t, J=8.0 Hz, 1 H), 7.42 (d, J=7.2 Hz, 1 H), 7.35 (t, J=8.4 Hz, 1 H), 7.21 (s, 1 H), 6.74 (s, 1 H), 4.12 (m, 1 H), 3.46 (m, 6 H), 2.24 (m, 1 H), 1.79-1.61 (m, 8 H).

Step E: Synthesis of cis-N2-(4-aminomethyl-cyclohexyl)-N4,N4-dimethyl-quinazoline-2,4-diamine.

To a solution of cis-4-(4-dimethylamino-quinazolin-2-ylamino)-cyclohexanecarboxylic acid amide (18.78 g, 60 mmol) in THF (200 mL) was added a solution of 1 M BH3 in THF (300 mL, 300 mmol). The mixture was stirred at reflux for 2 hr. After cooling the reaction mixture to 0° C., 4 M HCl in EtOAc (100 mL) and MeOH (200 mL) were added. The mixture was concentrated. The mixture was treated with 1 M aqueous sodium hydroxide and the aqueous layer was extracted with CH2Cl2. The organic layer was dried over sodium sulfate, concentrated, and purified by column chromatography (silica gel, 10% 2 M NH3/MeOH in CH2Cl2) to give cis-N2-(4-aminomethyl-cyclohexyl)-N4,N4-dimethyl-quinazoline-2,4-diamine as a white solid (10.6 g, 59%).

ESI MS m/e 300 M+H+; 1H NMR (400 MHz, DMSO-d6) δ 7.84 (d, J=8.4 Hz, 1 H), 7.46 (t, J=6.8 Hz, 1 H), 7.26 (d, J=8.4 Hz, 1 H), 6.99 (t, J=6.8 Hz, 1 H), 6.28 (brs, 1 H), 4.02 (m, 1 H), 3.19 (m, 6 H), 2.47 (d, J=6.8 Hz, 2 H), 2.73 (m 2 H), 1.68-1.33 (m, 9 H).

Step F: Synthesis of cis-N4,N4-dimethyl-N2-{4-[(2-trifluoromethyl-benzylamino)-methyl]-cyclohexyl}-quinazoline-2,4-diamine ditrifluoro-acetic acid.

A solution of cis-N2-(4-aminomethyl-cyclohexyl)-N4,N4-dimethyl-quinazoline-2,4-diamine (33 mg, 0.11 mmol) and 2-trifluoromethyl benzaldehyde (17.41 mg, 0.11 mmol) in MeOH (1 mL) was stirred at ambient temperature for 3 hr. To the mixture was added NaBH(OAc)3 (85 mg, 0.4 mmol) and the mixture was stirred at ambient temperature for overnight. This resulting mixture was quenched with 50% DMSO in water (2 mL) and the solution was purified by preparative HPLC. The pure fractions were combined and lyophilized to give cis-N4,N4-dimethyl-N2-{4-[(2-trifluoromethyl-benzylamino)-methyl]-cyclohexyl}-quinazoline-2,4-diamine ditrifluoro-acetic acid (41.4 mg, 60%) as a white solid.

ESI MS m/e 458 M+H+; 1H NMR (400 MHz, DMSO-d6) δ 13.12 (brs, 1 H), 8.94 (b, 2 H), 8.65 (d, J=6.8 Hz, 1 H), 8.16 (d, J=8.8 Hz, 1 H), 7.77-7.66 (m, 5 H), 7.41 (d, J=8.4 Hz, 1 H), 7.35 (t, J=8 Hz, 1 H), 4.22 (s, 2 H), 4.17 (m, 1 H), 3.46 (b, 6 H), 2.94 (m, 2 H), 1.87-1.44 (m, 9 H).

Example 2333

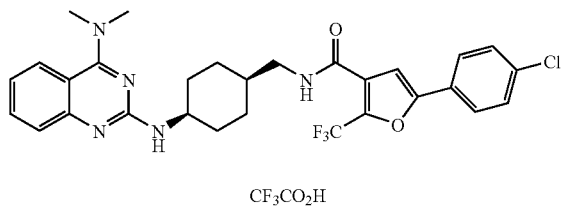

CF$_3$CO$_2$H cis-5-(4-Chloro-phenyl)-2-trifluoromethyl-furan-3-carboxylic acid [4-(4-dimethylamino-quinazolin-2-ylamino)-cyclohexylmethyl]-amide trifluoro-acetic acid Step A: Synthesis of cis-5-(4-chloro-phenyl)-2-trifluoromethyl-furan-3-carboxylic acid [4-(4-dimethylamino-quinazolin-2-ylamino)-cyclohexylmethyl]-amide trifluoro-acetic acid.

A solution of cis-N$^2$-(4-aminomethyl-cyclohexyl)-N$^4$,N$^4$-dimethyl-quinazoline-2,4-diamine obtained in step E of example 2332 (30 mg, 0.1 mmol), 5-(4-chloro-phenyl)-2-trifluoromethyl-furan-3-acid chloride (37 mg, 0.12 mmol), and pyridine (12 µL, 0.15 mmol) in DMF (0.5 mL) was stirred at ambient temperature for overnight. The resulting mixture was diluted with DMSO (0.8 mL) and the mixture was purified by preparative HPLC. The pure fractions were combined and lyophilized to give cis-5-(4-chloro-phenyl)-2-trifluoromethyl-furan-3-carboxylic acid [4-(4-dimethylamino-quinazolin-2-ylamino)-cyclohexylmethyl]-amide trifluoro-acetic acid (17.5 mg, 26%) as a white solid.

ESI MS m/e 572 M+H$^+$; $^1$H NMR (400 MHz, DMSO-d$_6$) δ 12.30 (brs, 1 H), 8.65 (t, J=6.8 Hz, 1 H), 8.19 (brs, 1 H), 8.14 (d, J=8.0 Hz, 1 H), 7.83-7.30 (m, 8 H), 4.1 (m, 1 H), 3.46 (b, 6 H), 3.09 (m, 2 H), 1.77-1.38 (m, 9 H).

Example 2334

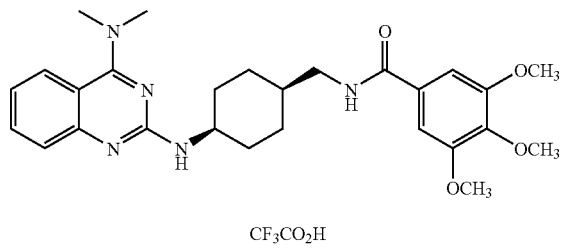

CF$_3$CO$_2$H cis-N-[4-(4-Dimethylamino-quinazolin-2-ylamino)-cyclohexylmethyl]-3,4,5-trimethoxy-benzamide trifluoro-acetic acid Step A: Synthesis of cis-N-[4-(4-dimethylamino-quinazolin-2-ylamino)-cyclohexylmethyl]-3,4,5-trimethoxy-benzamide trifluoro-acetic acid.

To HOBt-6-carboxaamidomethyl polystyrene 200-400 mesh (77 mg, 0.1 mmol) were added a solution of 0.3 M PyBroP in DMF (1 mL, 0.3 mmol), 3,4,5-trimethoxybenzoic acid (63 mg, 0.3 mmol), and diisopropylethylamine (85 µL, 0.5 mmol). The mixture was stirred at ambient temperature for 5 hr. The resin was washed with DMF (3 times), CH$_2$Cl$_2$ (3 times), MeOH (3 times), CH$_2$Cl$_2$ (2 times), and DMF (2 times). To the resin was added cis-N$^2$-(4-aminomethyl-cyclohexyl)-N$^4$,N$^4$-dimethyl-quinazoline-2,4-diamine obtained in step E of example 2332 (28 mg, 0.09 mmol) in DMF (0.5 mL) and the mixture was stirred at ambient temperature for overnight. The resin was filtered and washed with 0.5 mL DMSO (2 times). The combined filtrates were purified by preparative HPLC. The pure fractions were combined and lyophilized to give cis N-[4-(4-dimethylamino-quinazolin-2-ylamino)-cyclohexylmethyl]-3,4,5-trimethoxy-benzamide trifluoro-acetic acid (7.4 mg, 12%) as a white solid.

ESI MS m/e 494 M+H$^+$; $^1$H NMR (400 MHz, DMSO-d$_6$) δ 12.25 (brs, 1 H), 8.45 (t, J=5.6 Hz, 1 H), 8.17 (brs, 1 H), 8.14 (d, J=8.0 Hz, 1 H), 7.76 (t, J=8.4 Hz, 1 H), 7.42 (d, J=7.2 Hz, 1 H), 7.34 (t, J=7.6 Hz, 1 H), 7.15 (s, 2 H), 4.13 (m, 1 H), 3.44 (s, 3 H), 3.39 (s, 3 H), 3.20 (m, 2 H), 1.77-1.37 (m, 9 H).

Example 2335

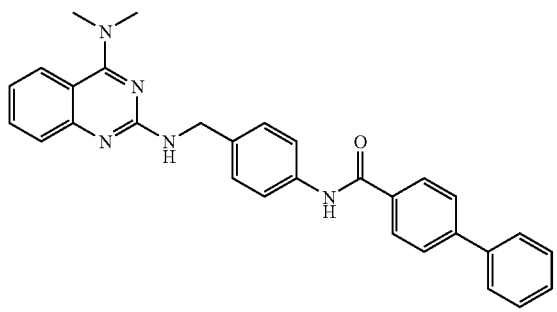

Biphenyl-4-carboxylic acid {4-[(4-dimethylamino-quinazolin-2-ylamino)-methyl]-phenyl}-amide Step A: Synthesis of (4-amino-benzyl)-carbamic acid tert-butyl ester.

A solution of 4-aminomethyl-phenylamine (12.2 g, 100 mmol) and (Boc)$_2$O (21.8 g, 100 mmol) in CH$_2$Cl$_2$ (100 mL) was stirred at ambient temperature for overnight. The mixture was concentrated and the residue was purified by column chromatography (silica gel, CH$_2$Cl$_2$ to 10% MeOH in CH$_2$Cl$_2$) to give (4-amino-benzyl)-carbamic acid tert-butyl ester (11.6 g, 52%) as a slightly yellow solid.

ESI MS m/e 223 M+H$^+$; $^1$H NMR (400 MHz, DMSO-d$_6$) δ 7.27 (t, J=6.0 Hz, 1 H), 6.86 (d, J=8.0 Hz, 2 H), 6.47 (d, J=6.4 Hz, 2 H), 4.89 (s, 2 H), 3.91 (d, J=6.0 Hz, 2 H), 1.39 (s, 9 H).

Step B: Synthesis of biphenyl-4-carboxylic acid (4-aminomethyl-phenyl)-amide hydrochloride.

To a solution of (4-amino-benzyl)-carbamic acid tert-butyl ester (1.11 g, 5 mmol), biphenyl carboxylic acid (0.99 g, 5 mmol), EDC (1.2 g, 6.25 mmol), and HOAt (0.82 g, 6 mmol) in CH$_2$CG$_2$ (10 mL) was added triethylamine (pH=10) and the mixture was stirred at ambient temperature for overnight. The organic layer was washed with saturated aqueous NaHCO$_3$, 1 M aqueous HCl, water, dried over Na$_2$SO$_4$, filtered, and concentrated. The residue was dissolved in 50% TFA in CH$_2$Cl$_2$ (10 mL) and the mixture was stirred at ambient temperature. After 30 minutes, the mixture was concentrated and diluted with 1 M HCl in Et$_2$O (5 mL). The mixture was concentrated to give biphenyl-4-carboxylic acid (4-aminomethyl-phenyl)-amide hydrochloride (828 mg, 49%).

ESI MS m/e 303 M+H$^+$; $^1$H NMR (400 MHz, DMSO-d$_6$) δ 10.40 (s, 1 H), 8.34 (b, 3 H), 8.07 (d, J=8.0 Hz, 2 H), 7.83-7.73 (m, 6 H), 7.51-7.38 (m, 5 H), 4.0 (q, J=5.6 Hz, 2 H).

Step C: Synthesis of biphenyl-4-carboxylic acid {4-[(4-dimethylamino-quinazolin-2-ylamino)-methyl]-phenyl}-amide.

A mixture of (2-chloro-quinazolin-4-yl)-dimethyl-amine obtained in step B of example 1 (42 mg, 0.2 mmol) and biphenyl-4-carboxylic acid (4-aminomethyl-phenyl)-amide hydrochloride (49 mg, 0.14 mmol) in 2-propanol (1 mL) and triethylamine (200 μL) was stirred at reflux for 2 days. The resulting mixture was concentrated and purified by column chromatography (silica gel, CH$_2$Cl$_2$ to 10% 2 M NH$_3$/MeOH in CH$_2$Cl$_2$) to give biphenyl-4-carboxylic acid {4-[(4-dimethylamino-quinazolin-2-ylamino)-methyl]-phenyl}-amide (10 mg, 15%) as a white solid.

ESI MS m/e 474 M+H$^+$; $^1$H NMR (400 MHz, DMSO-d$_6$) δ 10.19 (s, 1 H), 8.02 (d, J=7.2 Hz, 2 H), 7.86 (d, J=8.4 Hz, 1 H), 7.80 (d, J=8.4 Hz, 2 H), 7.73 (d, J=7.2 Hz, 2 H), 7.68 (d, J=7.6 Hz, 2 H), 7.50-7.15 (m, 8 H), 7.01 (t, J=8.4 Hz, 1 H), 4.51 (d, J=6.4 Hz, 2 H), 3.30(s, 3 H), 3.2(s, 3 H).

Example 2336

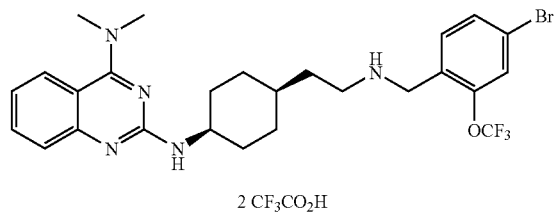

2 CF$_3$CO$_2$H cis-N$^2$-{4-[2-(4-Bromo-2-trifluoromethoxy-benzylamino)-ethyl]-cyclohexyl}-N$^4$,N$^4$-dimethyl-quinazoline-2,4-diamine ditrifluoro-acetic acid Step A: Synthesis of cis-[4-(2-benzyloxycarbonylamino-ethyl)-cyclohexyl]-carbamic acid tert-butyl ester.

To a solution of cis-[4-(2-amino-ethyl)-cyclohexyl]-carbamic acid tert-butyl ester (4.84 g, 20 mmol) in CH$_2$Cl$_2$ (50 mL) and triethylamine (3.06 mL, 22 mmol) was added benzyl chloroformate (3.13 mL, 22 mmol) and the mixture was stirred for 4 hr. The resulting mixture was washed with water, 1 M aqueous HCl, dried over Na$_2$SO$_4$, filtered and concentrated. The residue was purified by column chromatography (silica gel, CH$_2$Cl$_2$ to 10% MeOH in CH$_2$Cl$_2$) to give cis-[4-(2-benzyloxycarbonylamino-ethyl)-cyclohexyl]-carbamic acid tert-butyl ester (5.46 g, 73%) as a colorless oil.

ESI MS m/e 377 M+H$^+$; $^1$H NMR (400 MHz, DMSO-d$_6$) δ 7.36-7.24 (m, 5 H), 7.19 (t, J=5.6 Hz, 1 H), 6.76 (d, J=6.8. Hz, 1 H), 4.91 (s, 2 H), 3.40 (m, 1 H), 2.99 (m, 2 H), 1.44-1.33 (m, 20H).

Step B: Synthesis of cis-[2-(4-amino-cyclohexyl)-ethyl]-carbamic acid benzyl ester.

A solution of cis-[4-(2-benzyloxycarbonylamino-ethyl)-cyclohexyl]-carbamic acid tert-butyl ester (5.26 g, 14 mmol) in 50% TFA in CH$_2$Cl$_2$ (60 mL) was stirred at ambient temperature for 1 hr. The mixture was concentrated and the residue was diluted with saturated aqueous NaHCO$_3$. The aqueous layer was extracted with CH$_2$Cl$_2$ (therr times). The organic layer was dried over Na$_2$SO$_4$ and concentrated to give cis-[2-(4-amino-cyclohexyl)-ethyl]-carbamic acid benzyl ester (3.5 g, 91%) as a colorless oil.

ESI MS m/e 277 M+H$^+$; $^1$H NMR (400 MHz, DMSO-d$_6$) δ 7.72 (b, 2 H), 7.34-7.27 (m, 5 H), 7.21 (t, J=5.2 Hz, 1 H), 4.97 (s, 2 H), 3.14 (m, 1 H), 2.99 (q, J=6.4 Hz, 2 H), 1.58-1.34 (m, 11 H).

Step C: Synthesis of cis{2-[4-(4-dimethylamino-quinazolin-2-ylamino)-cyclohexyl]-ethyl}-carbamic acid benzyl ester.

A mixture of (2-chloro-quinazolin-4-yl)-dimethyl-amine obtained in step B of example 1 (2.45 g, 10.2 mmol) and cis-[2-(4-amino-cyclohexyl)-ethyl]-carbamic acid benzyl ester (3.3 g, 10.2 mmol) and triethylamine (1.65 mL, 10.2 mmol) in 2-propanol (15 mL) was heated at 170° C. for 45 min using a Smith Microwave Synthesizer. The mixture was concentrated and the residue was purified by column chromatography (silica gel, CH$_2$Cl$_2$ to 10% 2 M NH$_3$/MeOH in CH$_2$Cl$_2$) to give cis{2-[4-(4-dimethylamino-quinazolin-2-ylamino)-cyclohexyl]-ethyl}-carbamic acid benzyl ester (4.48 g, 85%) as a yellow oil.

ESI MS m/e 448 M+H$^+$; $^1$H NMR (400 MHz, DMSO-d$_6$) δ 8.07-7.20 (m, 11 H), 4.98 (s, 2 H), 4.08 (m, 1 H), 3.39 (b, 6 H), 3.04 (m, 2 H), 1.7-1.3 (m, 11 H).

Step D: Synthesis of cis-N$^2$-[4-(2-amino-ethyl)-cyclohexyl]-N$^4$,N$^4$-dimethyl-quinazoline-2,4-diamine.

To a solution of cis-{2-[4-(4-dimethylamino-quinazolin-2-ylamino)-cyclohexyl]-ethyl}-carbamic acid benzyl ester (4.47 g, 10 mmol) in EtOH (20 mL) was added 1,4-cyclohexadiene (20 mL) and 200 mg of 10% Pd/C. The reaction mixture was stirred at ambient temperature for 18 hr, filtered through pad of celite, and concentrated. The residue was purified by column chromatography (silica gel, 5% to 15% 2 M NH$_3$/MeOH in CH$_2$Cl$_2$) to give cis-N$^2$-[4-(2-amino-ethyl)-cyclohexyl]-N$^4$,N$^4$-dimethyl-quinazoline-2,4-diamine (2.41 g, 77%) as a yellow oil.

ESI MS m/e 314 M+H$^+$; $^1$H NMR (400 MHz, DMSO-d$_6$) δ 7.82 (d, J=8.0 Hz, 1 H), 7.44 (t, J=6.8 Hz, 1 H), 7.27 (d, J=8.0 Hz, 1 H), 6.97 (t, J=6.8 Hz, 1 H), 6.31 (brs, 1 H), 3.97 (m, 1 H), 3.37 (b, 2 H), 3.17 (s, 3 H), 3.14 (s, 3 H), 2.62 (t, J=7.6 Hz, 2 H), 1.68-1.31 (m, 11 H).

Step E: Synthesis of cis-N$^2$-{4-[2-(4-bromo-2-trifluoromethoxy-benzylamino)-ethyl]-cyclohexyl}-N$^4$,N$^4$-dimethyl-quinazoline-2,4-diamine ditrifluoro-acetic acid.

A solution of cis-N$^2$-{4-(2-amino-ethyl)-cyclohexyl]-N$^4$,N$^4$-dimethyl-quinazoline-2,4-diamine (31.4 mg, 0.1 mmol) and 4-bromo-2-trifluoromethoxy benzaldehyde (26.9 mg, 0.1 mmol) in MeOH (1 mL) was stirred at ambient temperature. After 3 hr, NaBH(OAc)$_3$ (85 mg, 0.4 mmol) was added and the resulting mixture was stirred at ambient temperature for overnight. The reaction mixture was quenched with 50% DMSO in water (2 mL). The mixture was concentrated and purified by preparative HPLC. The pure fractions were combined and lyophilized to give cis-N$^2$-{4-[2-(4-bromo-2-trifluoromethoxy-benzylamino)-ethyl]-cyclohexyl}-N$^4$,N$^4$-dimethyl-quinazoline-2,4-diamine ditrifluoro-acetic acid (32.2 mg, 41%) as a white solid.

ESI MS m/e 566/568 M+H$^+$; $^1$H NMR (400 MHz, DMSO-d$_6$) δ 12.76 (brs, 1 H), 8.81 (b, 2 H), 8.43 (m, 1 H), 8.09 (d, J=8.4 Hz, 1 H), 7.71-7.56 (m, 4 H), 7.35 (d, J=8.0 Hz, 1 H), 7.29 (t, J=8.0 Hz, 1 H), 4.15 (m, 3 H), 3.39 (m, 6 H), 2.97 (m, 2 H), 1.67-1.30 (m, 11 H).

Example 2337

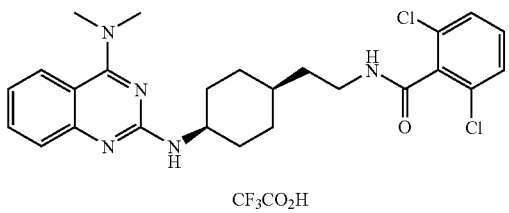

CF₃CO₂H cis-2,6-Dichloro-N-{2-[4-(4-dimethylamino-quinazolin-2-ylamino)-cyclohexyl]-ethyl}-benzamide trifluoro-acetic acid Step A: Synthesis of cis-2,6-dichloro-N-{2-[4-(4-dimethylamino-quinazolin-2-ylamino)-cyclohexyl]-ethyl}-benzamide trifluoro-acetic acid.

To a solution of cis-$N^2$-[4-(2-amino-ethyl)-cyclohexyl]-$N^4$,$N^4$-dimethyl-quinazoline-2,4-diamine (31.4 mg, 0.1 mmol) and 2,6-dichlorobenzoyl chloride (20.7 mg, 0.1 mmol) in DMF (0.5 mL) was added triethylamine (20 uL, 0.14 mmol). After stirring the mixture at ambient temperature for 6 hr, DMSO (0.5 mL) was added and the mixture was purified by preparative HPLC. The pure fractions were combined and lyophilized to give cis-2,6-dichloro-N-{2-[4-(4-dimethylamino-quinazolin-2-ylamino)-cyclohexyl]-ethyl}-benzamide trifluoro-acetic acid (17.6 mg, 29%) as a white solid.

ESI MS m/e 486 M+H⁺; ¹H NMR (400 MHz, DMSO-d) δ 11.93 (brs, 1 H), 8.26 (t, J=5.2 Hz, 1 H), 8.14 (d, J=8.0 Hz, 1 H), 7.95 (brs, 1 H), 7.76 (t, J=8.4 Hz, 1 H), 7.52-7.31 (m, 5 H), 4.15 (m, 1 H), 3.45 (b, 6 H), 3.29 (m, 2 H), 1.76-1.31 (m, 11 H).

Example 2338

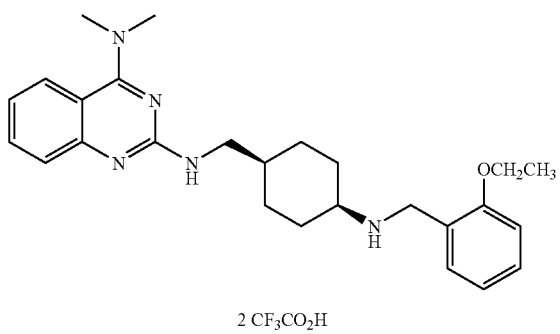

2 CF₃CO₂H cis-$N^2$-[4-(2-Ethoxy-benzylamino)-cyclohexylmethyl]-$N^4$,$N^4$-dimethyl-quinazoline-2,4-diamine ditrifluoro-acetic acid Step A: Synthesis of cis-(4-aminomethyl-cyclohexyl)-carbamic acid tert-butyl ester.

To a solution of cis-(4-carbamoyl-cyclohexyl)-carbamic acid tert-butyl ester obtained in step B of example 2332 (9.68 g, 40 mmol) in THF (100 mL) was added a solution of 1 M BH₃ in THF (80 mL, 80 mmol) over 30 min. The mixture was stirred at reflux for 2 hr. After cooling the reaction mixture to ambient temperature, 1 M aqueous sodium hydroxide was carefully added. The solvents were removed under reduced pressure and the aqueous layer was extracted with CH₂Cl₂ (twice). The organic layer was dried over sodium sulfate and concentrated under reduced pressure to give cis-(4-aminomethyl-cyclohexyl)-carbamic acid tert-butyl ester as colorless oil (5.16 g, 57%).

ESI MS m/e 229 M+H⁺; ¹H NMR (400 MHz, DMSO-d₆) δ 6.67 (d, J=6.8 Hz, 1 H), 3.43 (m, 1 H), 2.41 (d, J=6.4 Hz, 2 H) 1.49-1.22 (m, 18 H).

Step B: Synthesis of cis-{4-[(4-dimethylamino-quinazolin-2-ylamino)-methyl]-cyclohexyl}-carbamic acid tert-butyl ester.

A mixture of cis-(4-aminomethyl-cyclohexyl)-carbamic acid tert-butyl ester (1.14 g, 5 mmol), (2-chloro-quinazoline-4-yl)-dimethyl-amine obtained in step B of example 1 (1.035 g, 5 mmol), and triethylamine (1.5 mL, 11 mmol) in 2-propanol (2.5 mL) was heated at 170° C. for 35 min using a Smith Microwave Synthesizer. The mixture was concentrated and the residue was purified by column chromatography (silica gel, CH₂Cl₂ to 10% 2 M NH₃/MeOH in CH₂Cl₂) to give cis-{4-[(4-dimethylamino-quinazolin-2-ylamino)-methyl]-cyclohexyl}-carbamic acid tert-butyl ester (1.28 g, 80%) as a white solid.

ESI MS m/e 400 M+H⁺; ¹H NMR (400 MHz, DMSO-d₆) δ 8.04-7.06 (m, 4 H), 6.77 (d, J=6.0 Hz, 1 H), 3.40-3.16 (m, 9 H), 1.70-1.37 (m, 18 H).

Step C: Synthesis of cis-IV-(4-amino-cyclohexylmethyl)-$N^4$,$N^4$-dimethyl-quinazoline-2,4-diamine.

A solution of cis-{4-[(4-dimethylamino-quinazolin-2-ylamino)-methyl]-cyclohexyl}-carbamic acid tert-butyl ester (1.2 g, 3 mmol) in 50% TFA in CH₂Cl₂ (20 mL) was stirred at ambient temperature. After 30 minutes, the mixture was concentrated and the residue was diluted with 1 M aqueous sodium hydroxide. The aqueous layer was extracted with CH₂Cl₂ (twice). The combined organic layer was dried over Na₂SO₄, filtered and concentrated to give cis-$N^2$-(4-amino-cyclohexylmethyl)-$N^4$,$N^4$-dimethyl-quinazoline-2,4-diamine (0.88 g, 98%) as a white solid.

ESI MS m/e 300 M+H⁺; ¹H NMR (400 MHz, DMSO-d₆) δ 7.85 (d, J=7.6 Hz, 1 H), 7.47 (t, J=6.8 Hz, 1 H), 7.27 (brs, 1 H), 7.0 (t, J=7.2 Hz, 1 H), 6.66 (brs, 1 H), 3.33-3.14 (m, 9 H), 1.69-1.48 (m, 9 H).

Step D: Synthesis of cis-$N^2$-[4-(2-ethoxy-benzylamino)-cyclohexylmethyl]-$N^4$,$N^4$-dimethyl-quinazoline-2,4-diamine ditrifluoro-acetic acid.

A solution of cis-$N^2$-(4-amino-cyclohexylmethyl)-$N^4$,$N^4$-dimethyl-quinazoline-2,4-diamine (30 mg, 0.1 mmol) and 2-ethoxy benzaldehyde (15 mg, 0.1 mmol) in MeOH (1 mL) was stirred at ambient temperature. After 3 hr, NaBH(OAc)₃ (85 mg, 0.4 mmol) was added and the mixture was stirred at ambient temperature for overnight. The resulting mixture was quenched with 50% DMSO in water (2 mL) and the solution was purified by preparative HPLC. The pure fractions were combined and lyophilized to give cis-$N^2$-[4-(2-ethoxy-benzylamino)-cyclohexylmethyl]-$N^4$,$N^4$-dimethyl-quinazoline-2,4-diamine ditrifluoro-acetic acid (33 mg, 50%) as a white solid.

ESI MS m/e 434 M+H⁺; ¹H NMR (400 MHz, DMSO-d₆) δ 13.03 (brs, 1 H), 8.79 (brs, 1 H), 8.49 (m, 2 H), 8.15 (d, J=8.4 Hz, 1 H), 7.77 (t, J=7.6 Hz, 1 H), 7.40-7.33 (m, 4 H), 7.07 (d, J=7.6 Hz, 1 H), 6.99 (t, J=7.2 Hz, 1 H), 4.11-4.06 (m, 4 H), 3.47-3.41 (m, 8 H), 3.15 (m, 1 H), 1.90-1.60 (m, 9 H), 1.37 (t, J=7.2 Hz, 3 H).

Example 2339

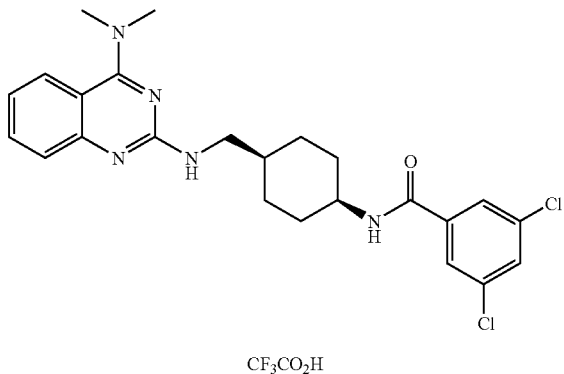

CF$_3$CO$_2$H cis-3,5-Dichloro-N-{4-[(4-dimethylamino-quinazolin-2-ylamino)-methyl]-cyclohexyl}-benzamide trifluoro-acetic acid Step A: Synthesis of cis-3,5-dichloro-N-{4-[(4-dimethylamino-quinazolin-2-ylamino)-methyl]-cyclohexyl}-benzamide trifluoro-acetic acid.

A solution of cis-N$^2$-(4-amino-cyclohexylmethyl)-N$^4$,N$^4$-dimethyl-quinazoline-2,4-diamine (30 mg, 0.1 mmol) and 3,5-dichlorobenzoylchloride (20.9 mg, 0.1 mmol) and pyridine (12 µL, 0.25 mmol) in DMSO (1 mL) was stirred at ambient temperature for overnight. The mixture was purified by preparative HPLC. The pure fractions were combined and lyophilized to give cis-3,5-dichloro-N-{4-[(4-dimethylamino-quinazolin-2-ylamino)-methyl]-cyclohexyl}-benzamide trifluoro-acetic acid. (18 mg, 31%) as a white solid.

ESI MS m/e 472 M+H$^+$; $^1$H NMR (400 MHz, DMSO-d$_6$) δ 12.13 (brs, 1 H), 8.34 (d, J=7.2 Hz, 1 H), 8.15 (d, J=8.8 Hz, 1 H), 8.06 (brs, 1 H), 7.82-7.73 (m, 4 H), 7.45 (d, J=7.6 Hz, 1 H), 7.36 (t, J=7.6 Hz, 1 H), 3.9 (m, 1 H), 3.47-3.25 (m, 8 H), 1.83-1.56 (m, 9 H).

Example 2340

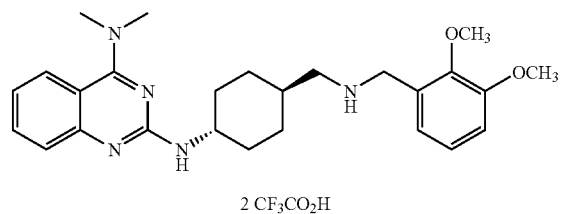

2 CF$_3$CO$_2$H trans-N$^2$-{4-[(2,3-Dimethoxy-benzylamino)-methyl]-cyclohexyl}-N$^4$,N$^4$-dimethyl-quinazoline-2,4-diamine ditrifluoro-acetic acid Step A: Synthesis of trans-4-(tert-butoxycarbonylamino-methyl)-cyclohexanecarboxylic acid.

To a solution of trans-4-amino-cyclohexanecarboxylic acid (37.7 g, 0.24 mol) in a mixture of dioxane (250 ml) and water (200 ml) cooled in an ice bath were added 1 M aqueous sodium hydroxide (10.07 g, 0.25 mol) and (Boc)$_2$O (57.6 g, 0.26 mol). The reaction mixture was stirred at ambient temperature. After 3 hr, the mixture was concentrated and the residue was dissolved in water. The aqueous layer was washed with Et$_2$O (3 times). The aqueous layer was cooled in an ice bath and acidified with 1 M aqueous HCl (pH=2) and the resulting white precipitate was dried to give trans-4-(tert-butoxycarbonylamino-methyl)-cyclohexanecarboxylic acid (47.4 g, 76.8%) as a white solid.

ESI MS m/e 258 M+H$^+$; $^1$H NMR (400 MHz, CDCl$_3$) δ 11.95 (brs, 1 H), 6.79 (t, J=6.0 Hz, 1 H), 2.76 (t, J=6.0 Hz, 2 H), 2.11 (m, 1 H), 1.87 (m, 2 H), 1.69 (m, 2 H), 1.36 (s, 9 H), 1.27(m, 3 H), 0.9 (m, 2 H).

Step B: Synthesis of trans-[4-(tert-butoxycarbonylamino-methyl)-cyclohexyl]-carbamic acid benzyl ester.

To a solution of trans-4-(tert-butoxycarbonylamino-methyl)-cyclohexanecarboxylic acid (46.9 g, 0.18 mol) in benzene (300 mL) were added triethylamine (24.2 g, 0.24 mol) and diphenylphosphoryl azide (55.9 g, 0.20 mol). The reaction mixture was stirred at 80° C. for 1 hr. To the mixture was added benzyl alcohol (25.9 g, 0.24 mol) and stirred at 100° C. for 4 hr. The mixture was subsequently cooled to ambient temperature for overnight, concentrated, and the resulting pale orange solid dissolved in EtOAc. The organic layer was washed with water (three times), concentrated, and the residue was purified by column chromatography (silica gel, 50% EtOAc in hexane) to give trans-[4-(tert-butoxycarbonylamino-methyl)-cyclohexyl]-carbamic acid benzyl ester (66.7 g, 100%) as a white solid.

ESI MS m/e 363 M+H$^+$; $^1$H NMR (400 MHz, CDCl$_3$) δ 7.24-7.23 (m, 5 H), 5.06 (s, 2 H), 4.57 (m, 2 H), 3.44 (brs, 1 H), 2.97 (t, J=6.4 Hz, 2 H), 2.04 (m, 2 H), 1.79 (m, 2 H), 1.43 (s, 9 H), 1.08-0.76 (m, 5 H).

Step C: Synthesis of trans-(4-amino-cyclohexylmethyl)-carbamic acid tert-butyl ester.

To a solution of trans-[4-(tert-butoxycarbonylamino-methyl)-cyclohexyl]-carbamic acid benzyl ester (5.32 g, 0.015 mol) in EtOH (200 mL) was added 10% Pd/C (50 mg). The mixture was stirred at ambient temperature under hydrogen atmosphere for 4 hr. The resulting mixture was filtered through a pad of celite and concentrated. The residue was purified by column chromatography (silica gel, 3% 2 M NH$_3$/MeOH in CH$_2$Cl$_2$) to give trans-(4-amino-cyclohexylmethyl)-carbamic acid tert-butyl ester as a colorless solid (3.197 g, 95.4%).

ESI MS m/e 229 M+H$^+$; $^1$H NMR (400 MHz, CDCl$_3$) δ 8.44 (brs, 1 H), 4.59 (b, 1 H), 2.96 (m, 2 H), 2.08 (m, 2 H), 1.83 (m, 2 H), 1.43 (s, 9 H), 1.08 (m, 5 H).

Step D: Synthesis of trans-N$^2$-(4-aminomethyl-cyclohexyl)-N$^4$,N$^4$-dimethyl-quinazoline-2,4-diamine ditrifluoro-acetic acid.

A mixture of trans-(4-amino-cyclohexylmethyl)-carbamic acid tert-butyl ester (0.24 g, 1 mmol) and (2-chloro-quinazolin-4-yl)-dimethyl-amine obtained in step B of example 1 (0.32 g, 1.4 mmol) in 2-propanol (5 mL) was heated to 170° C. for 30 min using a Smith Microwave Synthesizer. This procedure was repeated 19 times. The reaction mixtures were combined and purified by column chromatography (silica gel) to give 1.13 g of a yellow solid. The yellow solid was dissolved in 50% TFA in CH$_2$Cl$_2$ (20 mL) and the mixture was stirred at ambient temperature. After 10 hours, the mixture was concentrated and the residue was purified by preparative HPLC. The pure fractions were combined and lyophilized to give trans-N$^2$-(4-aminomethyl-cyclohexyl)-N$^4$,N$^4$-dimethyl-quinazoline-2,4-diamine ditrifluoro-acetic acid (0.49 g, 5%) as a white solid.

ESI MS m/e 300 M+H+; 1H NMR (400 MHz, CDCl3) δ 9.16 (d, J=5.6 Hz, 1 H), 8.11 (m, 2 H), 7.86 (d, J=8.0 Hz, 1 H), 7.51 (t, J=7.6 Hz, 1 H), 7.41 (d, J=8.0 Hz, 1 H), 7.18 (t, J=6.8 Hz, 1 H), 3.8 (brs, 1 H), 3.47 (s, 6 H), 2.10 (m, 2 H), 1.92 (m, 2 H), 1.42-1.12 (m, 5 H).

Step E: Synthesis of trans-N2-{4-[(2,3-dimethoxy-benzylamino)-methyl]-cyclohexyl}-N4,N4-dimethyl-quinazoline-2,4-diamine ditrifluoro-acetic acid.

A mixture of 2,3-dimethoxy benzaldehyde (15 mg, 0.09 mmol), trans-N2-(4-aminomethyl-cyclohexyl)-N4,N4-dimethyl-quinazoline-2,4-diamine ditrifluoro-acetic acid (28 mg, 0.053 mmol), NaBH(OAc)3 (76 mg, 0.36 mmol), and MeOH (2 mL) was heated at 100° C. for 40 seconds using a Smith Microwave Synthesizer. The resulting mixture was purified by preparative HPLC. The pure fractions were combined and lyophilized to give trans-N2-{4-[(2,3-dimethoxy-benzylamino)-methyl]-cyclohexyl}-N4,N4-dimethyl-quinazoline-2,4-diamine ditrifluoro-acetic acid (10.2 mg, 28%).

ESI MS m/e 450 M+H+; 1H NMR (400 MHz, CDCl3) δ 9.68 (d, J=6.0 Hz, 1 H), 9.41 (brs, 1 H), 7.85 (d, J=7.6 Hz, 1 H), 7.52 (t, J=7.2 Hz, 1 H), 7.46 (d, J=8.0 Hz, 1 H), 7.19 (t, J=7.2 Hz, 1 H), 7.09 (t, J=8.0 Hz, 1 H), 6.98 (d, J=7.2 Hz, 1 H), 6.90 (d, J=7.6 Hz, 1 H), 4.16 (s, 2 H), 3.96 (s, 3 H), 3.87 (s, 3 H), 3.75 (m, 1 H), 3.47 (m, 6 H), 2.80 (m, 2 H), 2.11 (m, 2 H), 1.86 (m, 2 H), 1.48-1.50 (m, 5 H).

Example 2341

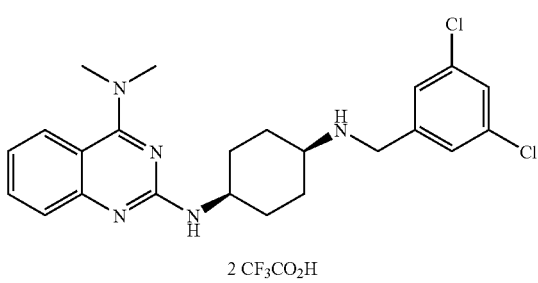

2 CF3CO2H cis-N2-[4-(3,5-Dichloro-benzylamino)-cyclohexyl]-N4,N4-dimethyl-quinazoline-2,4-diamine ditrifluoro-acetic acid Step A: Synthesis of cis-(4-tert-butoxycarbonylamino-cyclohexyl)-carbamic acid benzyl ester.

To a suspension of cis-4-tert-butoxycarbonylamino-cyclohexanecarboxylic acid (50.0 g, 206 mmol) in benzene were added triethylamine (26.9 g, 266 mmol) and phosphorazidic acid diphenyl ester (62.2 g, 226 mmol). The reaction mixture was stirred at 80° C. for 1 hr. Benzyl alcohol (31.4 g, 290 mmol) was added and the mixture was stirred at reflux for 24 hr. The reaction mixture was concentrated and the residue was dissolved in EtOAc and H2O. The organic layer was separated and the aqueous layer was extracted with EtOAc (twice). The combined organic layer was dried over MgSO4, filtered, concentrated, and purified by flash chromatography (silica gel, 30% EtOAc in hexane) to give cis-(4-tert-butoxycarbonylamino-cyclohexyl)-carbamic acid benzyl ester (54.1 g, 76%) as a colorless oil.

ESI MS m/e 349 M+H+; 1H NMR (400 MHz, DMSO-d6) δ 7.34-7.28 (m, 5 H), 7.12 (d, J=5.6 Hz, 1 H), 6.62 (brs, 1 H), 4.98 (s, 2 H), 3.39-3.37 (m, 2 H), 1.60-1.45 (m, 8 H), 1.37 (s, 9 H).

Step B: Synthesis of cis-(4-amino-cyclohexyl)-carbamic acid tert-butyl ester.

Using the procedure for the step C of example 2340, the title compound was obtained ESI MS m/e 215 M+H+; 1H NMR (400 MHz, DMSO-d6) δ 6.60 (d, J=6.0 Hz, 1 H), 3.30-3.28 (m, 1 H), 2.74 (s, 1 H), 1.59-1.51 (m, 2 H), 1.45-1.37 (m, 15 H).

Step C: Synthesis of cis-[4-(4-dimethlyamino-quinazolin-2-ylamino)-cyclohexyl]-carbamic acid tert-butyl ester.

A solution of cis-(4-amino-cyclohexyl)-carbamic acid tert-butyl ester (0.5 g, 2.3 mmol), (2-chloro-quinazolin-4-yl)-dimethly-amine obtained in step B in example 1 (0.53, 2.6 mmol), diisopropylethylamine (1.22 mL, 7.0 mmol) and 2-propanol (1.0 mL) was heated using a Smith Microwave Synthesizer at 170° C. for 1 hour. This reaction procedure was repeated 39 more times and the resulting reaction mixtures were combined. The mixture was concentrated and the residue was purified by column chromatography (silica gel, 2% to 4% 2 M NH3/MeOH in CH2Cl2) to give cis-[4-(4-dimethlyamino-quinazolin-2-ylamino)-cyclohexyl]-carbamic acid tert-butyl ester (22.1 g, 0.057 mol, 61%) as a colorless oil.

ESI MS m/e 386 M+H+; 1H NMR (400 MHz, DMSO-d6) δ 7.85 (d, J=8.0 Hz, 1 H), 7.47 (t, J=8.4 Hz, 1 H), 7.27 (d, J=8.0 Hz, 1 H), 7.00 (t, J=7.6 Hz, 1 H), 6.60 (brs, 1 H), 6.18 (brs, 1 H), 3.89-3.88 (m, 1 H), 3.39 (brs, 1 H), 3.19 (s, 6 H), 1.77-1.71 (m, 2 H), 1.68-1.52(m, 6 H), 1.38(s, 9 H).

Step D: Synthesis of cis-N2-(4-amino-cyclohexyl)-N4,N4-dimethyl-quinazolin-2,4-diamine.

Using the procedure for the step C of example 2338, the title compound was obtained.

ESI MS m/e 286 M+H+; 1H NMR (400 MHz, DMSO-d6) δ 7.84 (d, J=8.4 Hz, 1 H), 7.45 (t, J=6.8 Hz, 1 H), 7.26 (d, J=8.4 Hz, 1 H), 6.99 (t, J=7.6 Hz, 1 H), 6.20 (brs, 1 H), 3.90-3.89 (m, 1 H), 3.18 (s, 6 H), 2.79 (s, 1 H), 1.74-1.71 (m, 2 H), 1.57-1.41 (m, 8 H).

Step E: Synthesis of cis-N2-[4-(3,5-dichloro-benzylamino)-cyclohexyl]-N4,N4-dimethyl-quinazoline-2,4-diamine ditrifluoro-acetic acid.

To a solution of cis-N2-(4-amino-cyclohexyl)-N4,N4-dimethyl-quinazolin-2,4-diamine (31.4 mg, 0.11 mmol) in MeOH (0.5 mL) was added 3,5-dichlorobenzaldehyde (17.5 mg, 0.10 mmol). The mixture was stirred at ambient temperature for 0.5 hr and sodium triacetoxyborohydride (85 mg, 0.40 mmol) was added. The mixture was stirred for overnight and the reaction was quenched with 50% DMSO in water (1.0 mL). The mixture was purified by preparative HPLC. The pure fractions were combined and lyophilized to give cis-M2-[4-(3,5-dichloro-benzylamino)-cyclohexyl]-N4,N4-dimethyl-quinazolide-2,4-diamine ditrifluoro-acetic acid (23 mg, 0.041 mmol, 37%) as a white solid.

ESI MS m/e 444 M+H+, 1H NMR (400 MHz, DMSO-d6) δ 13.55 (s, 1 H), 8.90 (brs, 3 H), 8.17 (d, J=8.0 Hz, 1 H), 7.79 (t, 7.6 Hz, 1 H), 7.68 (s, 1 H), 7.61 (s, 2 H), 7.41 (d, J=7.6 Hz, 1 H), 7.36 (t, J=7.6 Hz, 1 H), 4.23 (s, 2 H), 4.07 (s, 1 H), 3.48 (s, 6 H), 2.00-1.92 (m, 4 H), 1.82-1.74 (m, 4 H).

Example 2342

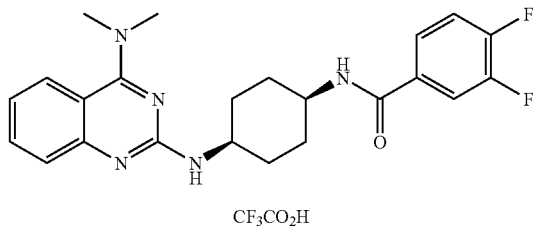

CF₃CO₂H cis-N-[4-(4-Dimethylamino-quinazolin-2-ylamino)-cyclohexyl]-3,4-difluoro-benzamide trifluoro-acetic acid Step A: Synthesis of cis-N-[4-(4-dimethylamino-quinazolin-2-ylamino)-cyclohexyl]-3,4-difluoro-benzamide trifluoro-acetic acid.

Using the procedure for the step A of example 2333, the title compound was obtained.

ESI MS m/e 426 M+H⁺; ¹H NMR (400 MHz, DMSO-d₆) δ 12.46 (brs, 1 H), 8.36 (s, 1 H), 8.15 (d, J=8.0 Hz, 1 H), 7.97 (brs, 1 H), 7.94-7.89 (m, 1 H), 7.77-7.73 (m, 2 H), 7.56-7.49 (m, 1 H), 7.41 (brs, 1 H), 7.36 (t, J=7.6 Hz, 1 H), 4.07 (m, 1 H), 3.87 (m, 1 H), 3.47 (brs, 6 H), 1.89 (m, 2 H), 1.74 (m, 6 H).

Example 2343

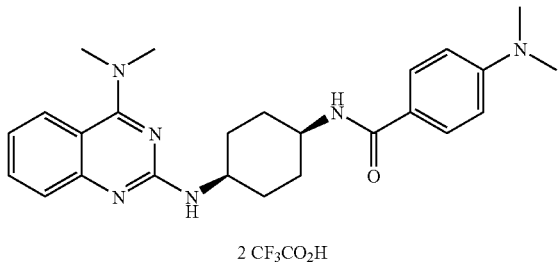

2 CF₃CO₂H cis-4-Dimethlyamino-N-[4-(4-dimethlyamino-quinazolin-2-ylamino)-cyclohexyl]-benzamide ditrifluoro-acetic acid Step A: Synthesis of cis-4-dimethlyamino-N-[4-(4-dimethlyamino-quinazolin-2-ylamino)-cyclohexyl]-benzamide ditrifluoro-acetic acid To a solution of 4-dimethylaminobenzoic acid (16.5 mg, 0.10 mmol) in DMF (0.5 mL) were added HATU (45.6 mg, 0.12 mmol), diisopropylethylamine (34.8 uL, 0.20 mmol), and cis-N²-(4-amino-cyclohexyl)-N⁴,N⁴-dimethyl-quinazolin-2,4-diamine obtained in step D of example 2341 (28.5 mg, 0.10 mmol) and stirred at ambient temperature for overnight. The resulting mixture was diluted with DMSO (0.5 mL) and purified by preparative HPLC. The pure fractions combined and lyophilized to give cis-4-dimethlyamino-N-[4-(4-dimethlyamino-quinazolin-2-ylamino)-cyclohexyl]-benzamide ditrifluoro-acetic acid (34.1 mg, 0.052 mmol, 52%) as a white solid.

ESI MS m/e 433 M+H⁺; ¹H NMR (400 MHz, DMSO-d₆) δ 12.73 (s, 1 H), 8.34 (s, 1 H), 8.16 (d, J=8.0 Hz, 1 H), 7.78-7.70 (m, 4 H), 7.43 (d, J=7.6 Hz, 1 H), 7.35 (t, J=8.0 Hz, 1 H), 6.67 (d, J=8.8 Hz, 2 H), 4.05 (m, 1 H), 3.86 (m, 1 H), 3.47 (s, 6 H), 2.95 (s, 3 H), 2.53 (s, 3 H), 1.91 (m, 2 H), 1.75-1.72 (m, 6 H).

Example 2344

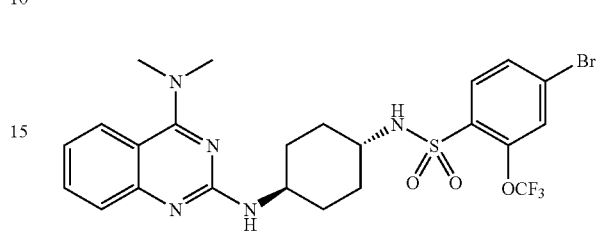

trans-4-Bromo-N-[4-(4-dimethlyamino-quinazolin-2-ylamino)-cyclohexyl]-2-trifluoromethoxy-benzenesulfonamide Step A: Synthesis of trans-(4-amino-cyclohexyl)-carbamic acid tert-butyl ester.

To a solution of trans-1,4-diamino-cyclohexane (10 g, 0.088 mol) in 1,4-dioxane (400 mL) was added a solution of (Boc)₂O (4.78 g, 0.022 mol) in 1,4-dioxane (100 ml) over 30 min. The mixture was stirred at ambient temperature for overnight and then the dioxane was removed in vacuo. The resulting precipitate was dissolved in H₂O (500 mL) and left to sit for 1 hour. During this time, the di-Boc-protected diamino-cyclohexane fell out as a white crystalline precipitate. This was subsequently filtered from the aqueous solvent. The aqueous layer was extracted with EtOAc (three times). The organic layers were combined and washed with H₂O. The organic layer was dried over MgSO₄ and concentrated to give trans-(4-amino-cyclohexyl)-carbamic acid tert-butyl ester (4 g, 0.019 mol, 85%).

ESI MS m/e 215 M+H⁺; ¹H NMR (400 MHz, DMSO-d₆) 66.63 (d, J=8.0 Hz, 1 H), 3.11-3.09 (m, 1 H), 2.44-2.37 (m, 1 H), 1.70-1.67 (m, 4 H), 1.41-1.31 (m, 11 H), 1.20-0.95 (m, 4 H).

Step B: Synthesis of trans-[4-(4-bromo-2-trifluoromethoxy-benzenesulfonylamino)-cyclohexyl]-carbamic acid tert-butyl ester.

To a solution of trans-(4-amino-cyclohexyl)-carbamic acid tert-butyl ester (1 g, 0.0047 mol) in CH₂Cl₂ were added diisopropylethylamine (1.63 mL, 0.0093 mol) and 4-bromo-2-trifluoromethoxy-benzenesulfonyl chloride (1.03 mL, 0.0051 mol). The reaction mixture was stirred at ambient temperature for 1 hr and then washed with water. The aqueous layer was extracted with CH₂Cl₂ (twice), the organic layers were combined, dried over MgSO₄, and concentrated. The resulting precipitate was recrystallized with CH₂Cl₂ and hexanes to give trans-[4-(4-bromo-2-trifluoromethoxy-benzenesulfonylamino)-cyclohexyl]-carbamic acid tert-butyl ester (2.39 g, 0.0046 mol, 99%).

ESI MS m/e 517 M+H⁺; ¹H NMR (400 MHz, DMSO-d₆) δ 7.99 (d, J=7.6 Hz, 1 H), 7.85 (d, J=8.0 Hz, 1 H), 7.79-7.77 (m, 1 H), 6.67 (d, J=8.0 Hz, 1 H), 3.14-2.94 (m, 2 H), 1.70-1.60 (m, 4 H), 1.34 (s, 9 H), 1.30-1.18 (m, 2 H), 1.14-1.03 (m, 2 H).

Step C: Synthesis of trans-N-(4-amino-cyclohexyl)-4-bromo-2-trifluoromethoxy-benzenesulfonamide.

Using the procedure for the step C of example 2338, the title compound was obtained.

ESI MS m/e 417/419 M+H⁺; ¹H NMR (400 MHz, DMSO-d₆) δ 7.85 (d, J=8.4 Hz, 1 H), 7.79-7.76 (m, 3 H), 3.32 (brs, 2 H), 3.03-2.95 (m, 1 H), 2.41-2.36 (m, 1 H), 1.67-1.57 (m, 4 H), 1.28-1.18 (m, 2 H), 0.99-0.89 (m, 2 H).

Step D: Synthesis of trans-4-bromo-N-[4-(4-dimethlyamino-quinazolin-2-ylamino)-cyclohexyl]-2-trifluoromethoxy-benzenesulfonamide.

To a solution of trans-N-(4-amino-cyclohexyl)-4-bromo-2-trifluoromethoxy-benzenesulfonamide (100 mg, 0.24 mmol) in 2-propanol (0.5 mL) was added (2-chloro-quinazolin-4-yl)-dimethly-amine obtained in step B of example 1 (54.7 mg, 0.26 mmol). The mixture was heated using a Smith Microwave Synthesizer at 170° C. for 15 min. The mixture was concentrated and the residue was purified by chromatography (2% to 4% 2 M NH₃/MeOH in CH₂Cl₂) to give trans-4-bromo-N-[4-(4-dimethlyamino-quinazolin-2-ylamino)-cyclohexyl]-2-trifluoromethoxy-benzenesulfonamide (42 mg, 0.71 mmol, 30%) as a white solid.

ESI MS m/e 588/590 M+H⁺; ¹H NMR (400 MHz, DMSO-d₆) δ 8.02 (d, J=7.6 Hz, 1 H), 7.88 (d, J=8.4 Hz, 1 H), 7.82-7.77 (m, 3 H), 7.45-7.41 (m, 1 H), 7.25-7.41 (m, 1 H), 6.99 (t, J=7.2 Hz, 1 H), 6.37 (brs, 1 H), 3.68-3.67 (m, 1 H), 3.16 (s, 6 H), 3.09-3.02 (m, 1 H), 1.89-1.86 (m, 2 H), 1.69-1.67 (m, 2 H), 1.40-1.17 (m, 4 H).

Example 2345

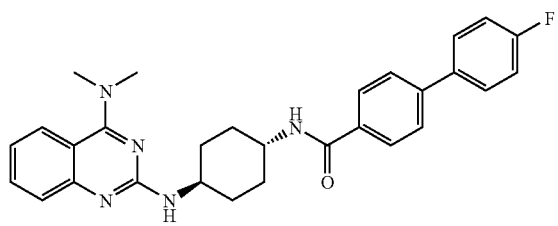

trans-4'-Fluoro-biphenyl-4-carboxylic acid [4-(4-dimethlyamino-quinazolin-2-ylamino)-cyclohexyl]-amide Step A: Synthesis of 4'-fluoro-biphenyl-4-carboxylic acid.

To a solution of 4-bromobenzoic acid (5 g, 0.025 mol) in THF (150 mL) under an atmosphere of argon were added tetrakis(triphenylphosphine) palladium(0) (862 mg, 0.75 mmol), 2 M aqueous Na₂CO₃ (30 mL), and a solution 4-fluorophenyboronic acid (3.48 g, 0.025 mol) in a minimal amount of ethanol (~10 mL). The resulting reaction mixture was stirred at reflux under an argon atmosphere for overnight. The reaction mixture was cooled to ambient temperature and acidified with addition of 1 M HCl aqueous. The aqueous layer was extracted with Et₂O (three times). The organic layers were combined, dried over MgSO₄, filtered and concentrated. The resulting precipitate was crystallized in Et₂O and hexane to give 4'-fluoro-biphenyl-4-carboxylic acid (4.4 g, 0.020 mol, 82%) as a white solid.

¹H NMR (400 MHz, DMSO-d₆) δ 12.96 (s, 1 H), 8.00-7.98 (m, 2 H), 7.78-7.75 (m, 4 H), 7.34-7.31 (m, 2 H).

Step B: Synthesis of trans-[4-(4-dimethlyamino-quinazolin-2-ylamino)-cyclohexyl]-carbamic acid tert-butyl ester.

Using the procedure for the step D of example 2344, the title compound was obtained.

ESI MS m/e 386 M+H⁺; ¹H NMR (400 MHz, DMSO-d₆) δ 7.83 (d, J=8.0 Hz, 1 H), 7.46 (t, J=6.8 Hz, 1 H), 7.27-7.25 (m, 1 H), 6.99 (t, J=7.2 Hz, 1 H), 6.71 (d, J=8.4 Hz, 1 H), 6.38 (brs, 1 H), 3.72 (m, 1 H), 3.17 (s, 6 H), 1.92-1.90 (m, 2 H), 1.79-1.76 (m, 2 H), 1.37 (s, 9 H), 1.34-1.23 (m, 4 H).

Step C: Synthesis of trans-4'-fluoro-biphenyl-4-carboxylic acid [4-(4-dimethlyamino-quinazolin-2-ylamino)-cyclohexyl]-amide.

To a solution of trans-[4-(4-dimethlyamino-quinazolin-2-ylamino)-cyclohexyl]-carbamic acid tert-butyl ester (0.76 g, 0.20 mmol) in CH₂Cl₂ (20 mL) was added TFA (304 μL, 0.39 mmol). The solution was stirred at ambient temperature for 4 hr. The resulting mixture was concentrated and the residue was dissolved in CH₂Cl₂. The organic layer was washed with a dilute aqueous NaOH and aqueous NaHCO₃ solution. The aqueous layer was extracted with CH₂Cl₂ (twice) and the organic layers combined, dried over MgSO₄, and concentrated. To a solution of the residue (0.1 g) and 4-fluoro-biphenyl-4-carboxylic acid (76 mg, 0.35 mmol) in CH₂Cl₂ were added HOAt (62 mg, 0.46 mmol), WSC—HCl (87 mg, 0.46 mmol), and diisopropylethylamine (31 uL, 0.18 mmol). The mixture was stirred for 1 hr at ambient temperature and the reaction was quenched with water. The aqueous layer was extracted with CH₂Cl₂ (twice). The organic layers were combined, dried over MgSO₄, concentrated and the residue purified by column chromatography (silica gel, 2% to 4% 2 M NH₃/MeOH in CH₂Cl₂) to give trans-4'-fluoro-biphenyl-4-carboxylic acid [4-(4-dimethlyamino-quinazolin-2-ylamino)-cyclohexyl]-amide (35 mg, 0.072, 21%) as a white solid.

ESI MS m/e 484 M+H⁺; ¹H NMR (400 MHz, DMSO-d₆) δ 8.30 (brs, 1 H), 8.12 (brs, 2 H), 7.92 (d, J=8.4 Hz, 2 H), 7.77-7.72 (m, 5 H), 7.44 (brs, 1 H), 7.34-7.28 (m, 3 H), 3.82 (brs, 2 H), 3.47 (brs, 6 H), 2.04 (m, 2 H), 1.94 (m, 2 H), 1.54-1.48 (m, 4 H).

Example 2346

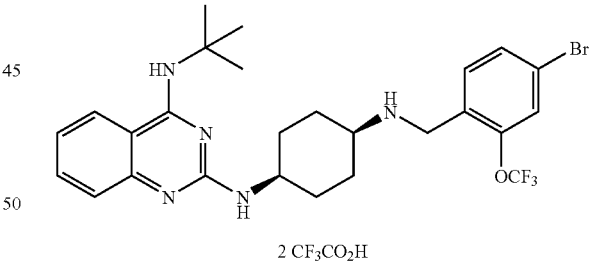

2 CF₃CO₂H cis-N²-[4-(4-Bromo-2-trifluoromethoxy-benzylamino)-cyclohexyl]-N⁴-tert-butyl-quinazoline-2,4-diamine ditrifluoro-acetic acid Step A: Synthesis of tert-butyl-(2-chloro-quinazolin-4-yl)-amine.

To a solution of 2,4-dichloro-quinazoline obtained in step B of example 1 (4 g, 20 mmol) in THF (50 mL) were added tert-butyl amine (2.15 mL, 20.5 mmol) and diisopropylethylamine (3.5 mL, 21 mmol). The mixture was stirred at ambient temperature for 2 hr. The mixture was concentrated and the residue was dissolved in EtOAc. The organic layer was washed with water, dried over Na₂SO₄, and filtered. The mixture was concentrated to give tert-butyl-(2-chloro-quinazolin-4-yl)-amine as a white solid (3 g, 64%).

ESI MS m/e 236 M+H$^+$; $^1$H NMR (400 MHz, DMSO-d$_6$) δ 8.40 (d, J=8.4 Hz, 1 H), 7.75-7.36 (m, 2 H), 7.58 (d, J=8.4 Hz, 1 H), 7.48 (t, J=7.2 Hz, 1 H), 1.52 (s, 9 H).

Step B: Synthesis of cis-N$^2$-(4-amino-cyclohexyl)-N$^2$-tert-butyl-quinazoline-2,4-diamine.

To a suspension of cis-(4-amino-cyclohexyl)-carbamic acid tert-butyl ester (122 mg, 0.57 mmol) in 2-propanol (2 mL) were added tert-butyl-(2-chloro-quinazolin-4-yl)-amine (100 mg, 0.42 mmol) and diisopropylethylamine (180 μL, 1 mmol) and the mixture was heated at 170° C. for 1 hr using a Smith Microwave Synthesizer. The resulting solution was concentrated and purified by column chromatography (silica gel, 3% MeOH in CH$_2$Cl$_2$) to give [4-(4-tert-butylamino-quinazolin-2-ylamino)-cyclohexyl]-carbamic acid tert-butyl ester (112 mg, 65%) as a yellow solid. To a suspension of cis-[4-(4-tert-butylamino-quinazolin-2-ylamino)-cyclohexyl]-carbamic acid tert-butyl ester (95 mg, 0.23 mmol) in CH$_2$Cl$_2$ (3 mL) was added trifluoroacetic acid (2 mL) dropwise. The reaction mixture was stirred at ambient temperature for 2 hr. The solution was concentrated, alkalized with saturated aqueous NaHCO$_3$ and 1 M aqueous sodium hydroxide (pH=9), and the aqueous layer was extracted with CH$_2$Cl$_2$ (three times). The combined organic layer was dried over MgSO$_4$, filtered, and concentrated. The solid was collected by filtration to give cis-N$^2$-(4-amino-cyclohexyl)-N-tert-butyl-quinazoline-2,4-diamine (44.6 mg, 53%) as a yellow solid.

ESI MS m/e 314 M+H$^+$; $^1$H NMR (400 MHz, CDCl$_3$) δ 7.48 (t, J=6.8 Hz, 1 H), 7.38 (m, 2 H), 7.04 (t, J=8.0 Hz, 1 H), 5.42 (brs, 1 H), 4.15 (m, 1 H), 2.85 (m, 1 H), 1.2-1.9 (m, 17 H).

Step C: Synthesis of cis-N$^2$-[4-(4-bromo-2-trifluoromethoxy-benzylamino)-cyclohexyl]-N$^4$-tert-butyl-quinazoline-2,4-diamine ditrifluoro-acetic acid.

Using the procedure for the step C of example 2341, the title compound was obtained.

ESI MS m/e 566 M+H$^+$; $^1$H NMR (400 MHz, CDCl$_3$) δ 9.36 (d, J=8.0 Hz, 1 H), 7.67-7.64 (m, 2 H), 7.53-7.48 (m, 3 H), 7.43 (s, 1 H), 7.33 (m, 1 H), 6.17 (s, 1 H), 4.45 (m, 1 H), 4.28 (s, 2 H), 3.35 (m, 1 H), 2.14-1.6 (m, 17 H).

Example 2347

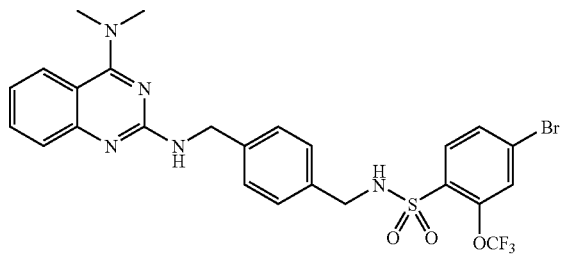

4-Bromo-N-{4-[(4-dimethylamino-quinazolin-2-ylamino)-methyl]-benzyl}-2-trifluoromethoxy-benzenesulfonamide Step A: Synthesis of {4-[(4-dimethylamino-quinazolin-2-ylamino)-methyl]-benzyl}-carbamic acid tert-butyl ester.

Using the procedure for the step D of example 2330, the title compound was obtained.

ESI MS m/e 377 M+H$^+$; $^1$H NMR (400 MHz, DMSO-d$_6$) δ 8.38 (brs, 1 H), 8.08 (brs, 1 H), 7.70 (brs, 1 H), 7.47 (brs, 1 H), 7.36 (t, J=6.2 Hz, 1 H), 7.30 (d, J=8.0 Hz, 3 H), 7.16 (d, J=7.6 Hz, 2 H), 4.60 (d, J=6.4 Hz, 2 H), 4.07 (d, J=6.0 Hz, 2 H), 3.39 (s, 6 H), 1.37 (s, 9 H).

Step B: Synthesis of N$^2$-(4-aminomethyl-benzyl)-N$^4$,N$^4$-dimethyl-quinazoline-2,4-diamine hydrochloride.

To a cooled solution of {4-[(4-dimethylamino-quinazolin-2-ylamino)-methyl]-benzyl}-carbamic acid tert-butyl ester (3.90 g, 9.57 mmol) in MeOH was added 1 M HCl in Et$_2$O (67.0 ml, 67.0 mmol) and the solution was stirred for overnight. The resulting mixture was concentrated to give N$^2$-(4-aminomethyl-benzyl)-N$^4$,N$^4$-dimethyl-quinazoline-2,4-diamine hydrochloride as a white crystalline solid (3.48 g, 95.6%).

ESI MS m/e 308.2 M+H$^+$; $^1$H NMR (400 MHz, CD$_3$OD) δ 8.16 (d, J=7.2 Hz, 1 H), 7.75 (brs, 1 H), 7.48 (m, 5 H), 7.39 (brs, 1 H), 4.76 (s, 2 H), 4.12 (s, 2 H), 3.51 (m, 6 H).

Step C: Synthesis of 4-bromo-N-{4-[(4-dimethylamino-quinazolin-2-ylamino)-methyl]-benzyl}-2-trifluoromethoxy-benzenesulfonamide.

A solution of N$^2$-(4-aminomethyl-benzyl)-N$^4$,N$^4$-dimethyl-quinazoline-2,4-diamine hydrochloride (50.0 mg, 0.131 mmol), 4-bromo-2-trifluoromethoxy-benzenesulfonyl chloride (53.3 mg, 0.157 mmol) and diisopropylethylamine (91 μl, 0.524 mmol) in 2-propanol (1.5 mL) was stirred at ambient temperature for 2 hr. The resulting mixture was concentrated, and the residue was purified by column chromatography (silica gel, 10% MeOH in CH$_2$Cl$_2$) to give 4-bromo-N-{4-[(4-dimethylamino-quinazolin-2-ylamino)-methyl]-benzyl}-2-trifluoromethoxy-benzenesulfonamide as a white crystalline compound (40 mg, 50%).

ESI MS m/e 612 M+H$^+$; $^1$H NMR (400 MHz, DMSO-d$_6$) δ 8.51 (t, J=6.4 Hz, 1 H), 8.06 (brs, 1 H), 7.76-7.67 (m, 4 H), 7.54-7.41 (m, 2 H), 7.24 (d, J=7.6 Hz, 3 H), 7.14 (d, J=8.0 Hz, 2 H), 4.56 (d, J=6.0 Hz, 2 H), 4.08 (d, J=6.0 Hz, 2 H), 3.36 (s, 6 H).

Example 2348

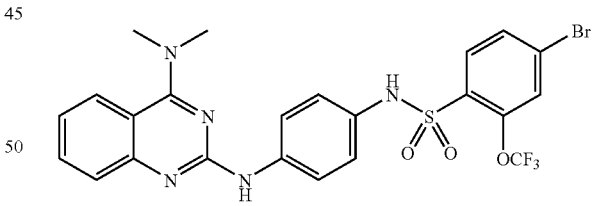

4-bromo-N-[4-(4-dimethylamino-quinazolin-2-ylamino)-phenyl]-2-trifluoromethoxy-benzene-sulfonamide Step A: Synthesis of (4-amino-phenyl)-carbamic acid tert-butyl ester.

Using the procedure for the step A of example 2344, the title compound was obtained ESI MS m/e 209 M+H$^+$; $^1$H NMR (400 MHz, DMSO-d$_6$) δ 8.75 (s, 1 H), 7.03 (d, J=7.6 Hz, 2 H), 6.43 (dt, J=9.5, 2.7 Hz, 2 H), 4.71 (s, 2 H), 1.43 (s, 9 H).

Step B: Synthesis of $N^2$-(4-amino-phenyl)-$N^4$,$N^4$-dimethyl-quinazoline-2,4-diamine hydrochloride.

A mixture of (2-chloro-quinazolin-4-yl)-dimethyl-amine obtained in step B of example 1 (0.5 g, 2.6 mmol) and (4-amino-phenyl)-carbamic acid tert-butyl ester (0.5 g, 2.6 mmol) in $CH_2Cl_2$ (2 mL) was heated by Smith Synthesizer at 130° C. for 20 min. The mixture was concentrated to give [4-(4-dimethylamino-quinazolin-2-ylamino)-phenyl]-carbamic acid tert-butyl ester as a pale yellow solid (0.86 g, 87%). The reaction was repeated six times, and the total product combined was 8.5 g. To a solution of above product (8.5 g, 22.4 mmol) in MeOH (250 mL) was added 4 M HCl in dioxane (8.4 ml, 33.6 mmol) dropwise, and the mixture was stirred at ambient temperature for overnight. The mixture was concentrated to give $N^2$-(4-amino-phenyl)-$N^4$,$N^4$-dimethyl-quinazoline-2,4-diamine hydrochloride as a pale pink solid (6.2 g, 87.5%).

ESI MS m/e 280 M+H$^+$; $^1$H NMR (400 MHz, $D_2O$) δ 7.84 (d, J=8.8 Hz, 1 H), 7.54 (td, J=7.8, 1.2 Hz, 1 H), 7.46 (dt, J=9.5, 2.7 Hz, 2 H), 7.27-7.16 (m, 4 H), 3.35 (b, 3 H), 3.12 (b, 3 H).

Step C: Synthesis of 4-bromo-N-[4-(4-dimethylamino-quinazolin-2-ylamino)-phenyl]-2-trifluoromethoxy-benzenesulfonamide.

Using the procedure for the step C of example 2347, the title compound was obtained.

ESI MS m/e 584 M+H$^+$; $^1$H NMR (400 MHz, DMSO-$d_6$) δ 10.27 (brs, 1 H), 9.14 (brs, 1 H), 7.98 (d, J=8.4 Hz, 1 H), 7.80-7.71 (m, 5 H), 7.60-7.56 (m, 1 H), 7.44 (d, J=8.4 Hz, 1 H), 7.15 (t, J=7.4 Hz, 1 H), 6.95 (d, J=16.8 Hz, 2 H), 9.29 (s, 6 H).

Example 2349

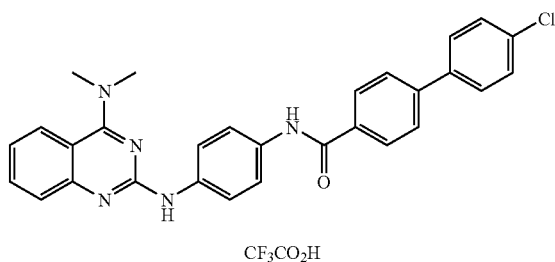

CF$_3$CO$_2$H

4'-Chloro-biphenyl-4-carboxylic acid [4-(4-dimethylamino-quinazolin-2-ylamino)-phenyl]-amide trifluoro-acetic acid Synthesis of 4'-chloro-biphenyl-4-carboxylic acid [4-(4-dimethylamino-quinazolin-2-ylamino)-phenyl]-amide trifluoro-acetic acid.

A solution of $N^2$-(4-amino-phenyl)-$N^4$,$N^4$-dimethyl-quinazoline-2,4-diamine hydrochloride obtained in step B of example 2348 (81.6 mg, 0.258 mmol), 4'-chloro-biphenyl-4-carboxylic acid (50.0 mg, 0.215 mmol), HATU (106 mg, 0.280 mmol), and diisopropylethylamine (150 μL, 0.860 mmol), in $CH_2Cl_2$ (2 mL) was stirred at ambient temperature for overnight, and the mixture was concentrated. The residue was purified by HPLC to give 4'-chloro-biphenyl-4-carboxylic acid [4-(4-dimethylamino-quinazolin-2-ylamino)-phenyl]-amide trifluoro-acetic acid as a white solid (10 mg, 9%).

ESI MS m/e 494 M+H$^+$; $^1$H NMR (400 MHz, DMSO-$d_6$) δ 10.33 (s, 1 H), 8.17 (d, J=8.0 Hz, 1 H), 8.80 (d, J=8.8 Hz, 2 H), 7.85-7.75 (m, 7 H), 7.63-7.53 (m, 6 H), 7.36 (t, J=7.6 Hz, 1 H), 3.46 (s, 6 H).

Example 2350

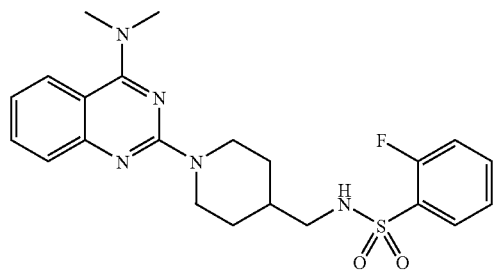

N-[1-(4-Dimethylamino-quinazolin-2-yl)-piperidin-4-ylmethyl]-2-fluoro-benzenesulfonamide Step A: Synthesis of N-[1-(4-dimethylamino-quinazolin-2-yl)-piperidin-4-ylmethyl]-2-fluoro-benzenesulfonamide.

To a solution of 4-aminomethyl-piperidine-1-carboxylic acid tert-butyl ester (60 mg, 0.28 mmol) and diisopropylethylamine (49 mL, 0.28 mmol) in $CH_2Cl_2$ (2 mL) was added 2-fluorobenzenesulfonyl chloride (54 mg, 0.28 mmol) and the mixture was stirred at ambient temperature for 18 hr. To the resulting mixture was added trifluoroacetic acid (0.70 mL) and stirred at ambient temperature for 18 hr. The reaction mixture was concentrated and neutralized with saturated aqueous NaHCO$_3$. The aqueous layer was extracted with EtOAc, and the organic layer was concentrated to give 2-fluoro-N-piperidin-4-ylmethyl-benzenesulfonamide as a pale yellow solid. To a solution of above solid (0.076 g, 0.28 mmol) and diisopropylethylamine (0.072 mL, 0.42 mmol) in 2-propanol (3 mL) was added (2-chloro-quinazolin-4-yl)-dimethyl-amine obtained in step B of example 1 (0.044 g, 0.21 mmol) and the resulting mixture was stirred at 100° C. for 18 hr. The mixture was concentrated, and the residue was purified by column chromatography (silica gel, 5% MeOH in $CH_2Cl_2$) to give N-[1-(4-dimethylamino-quinazolin-2-yl)-piperidin-4-ylmethyl]-2-fluoro-benzenesulfonamide as a pale yellow solid (0.024 g, 26%).

ESI MS m/e 444 M+H$^+$; $^1$H NMR (400 MHz, DMSO-$d_6$) δ 7.98 (m, 1 H), 7.86 (m, 1 H), 7.77 (m 1 H), 7.67 (m, 1 H), 7.47-7.29 (m, 4 H), 7.02 (m, 1 H), 4.69 (m, 2 H), 3.21 (s, 6 H), 2.76 (m, 4 H), 1.66 (m, 3 H), 1.00 (m, 2 H).

Using the procedure for example 2329 and purification by preparative HPLC, the compounds of example 2351-2819 were obtained.

Using the procedure for example 2331 and purification by preparative HPLC, the compounds of example 2820-2842 were obtained.

Using the procedure for example 2332, the compounds of example 2843-3003 were obtained.

Using the procedure for example 2333, the compounds of example 3004-3090 were obtained.

Using the procedure for example 2334, the compounds of example 3091-3161 were obtained.

Using the procedure for example 2335 and purification by preparative HPLC, the compounds of example 3162-3178 were obtained.

Using the procedure for example 2336, the compounds of example 3179-3208 were obtained.

Using the procedure for example 2337, the compounds of example 3209 was obtained.

Using the procedure for example 2338, the compounds of example 3210-3225 were obtained.

Using the procedure for example 2339, the compounds of example 3226-3228 were obtained.

Using the procedure for example 2340, the compounds of example 3229-3231 were obtained.

Using the procedure for example 2341, the compounds of example 3232-3393 were obtained.

Using the procedure for example 2342, the compounds of example 3394-3472 were obtained.

Using the procedure for example 2343, the compounds of example 3473-3527 were obtained.

Using the procedure for example 2346, the compounds of example 3528-3535 were obtained.

Using the procedure for example 2347 and purification by preparative HPLC, the compounds of example 3536-3545 were obtained.

Using the procedure for example 2348 and purification by preparative HPLC, the compounds of example 3546-3548 were obtained.

Using the procedure for example 2349, the compounds of example 3549-3567 were obtained.

Using the procedure for example 2350 and purification by preparative HPLC, the compounds of example 3568-3579 were obtained.

| Example No. | Structure | ESI-MS | Retention Time (min) |
|---|---|---|---|
| 2351 | 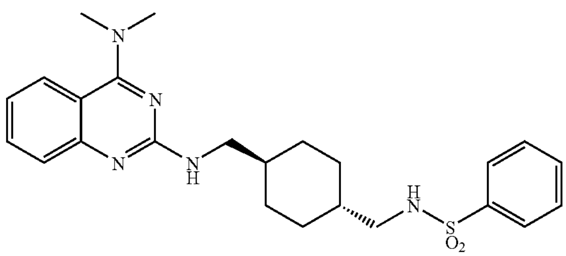 | 454.0 (M + H) | 3.60 |
| 2352 | 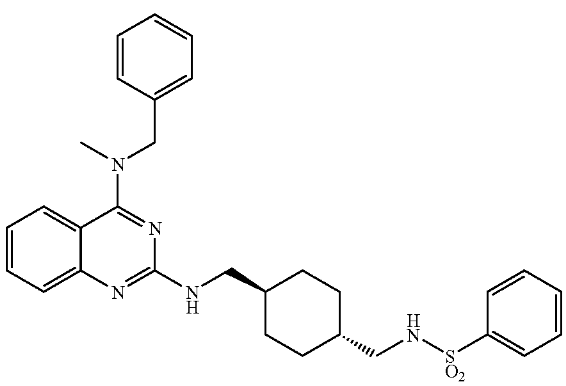 | 530.2 (M + H) | 4.02 |
| 2353 | 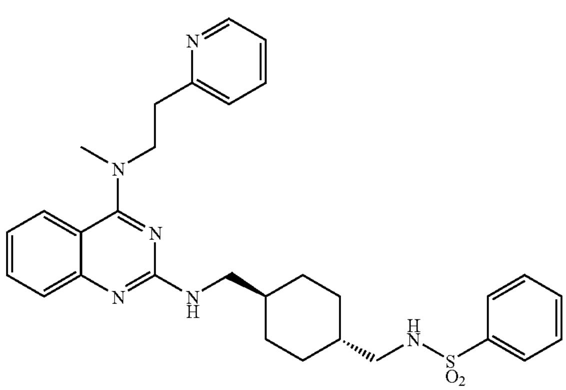 | 545.4 (M + H) | 3.05 |

-continued
| Example No. | Structure | ESI-MS | Retention Time (min) |
|---|---|---|---|
| 2354 | 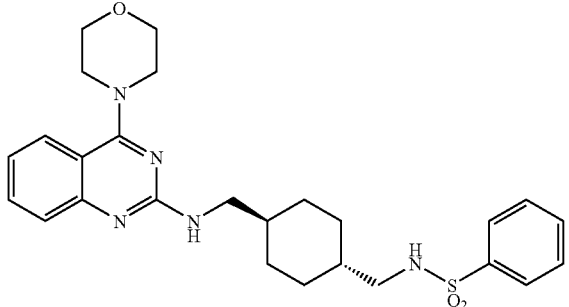 CF$_3$CO$_2$H | 496.4 (M + H) | 3.49 |
| 2355 | 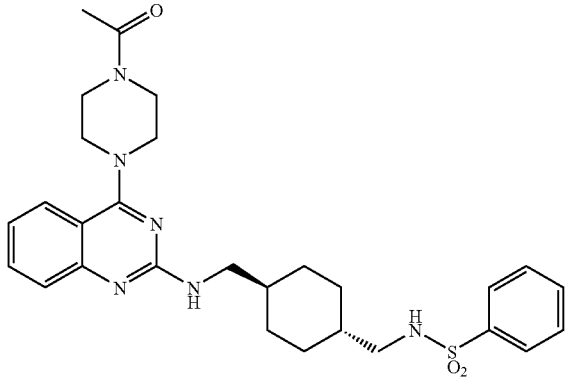 CF$_3$CO$_2$H | 537.4 (M + H) | 3.24 |
| 2356 | 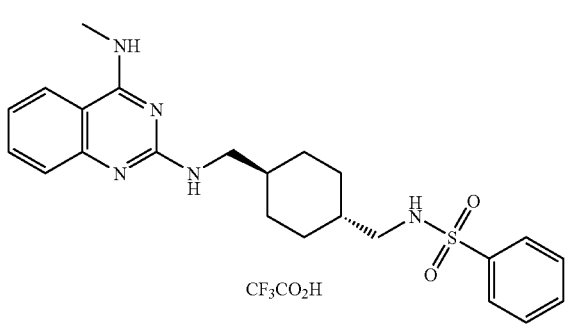 CF$_3$CO$_2$H | 440.0 (M + H) | 3.47 |
| 2357 | 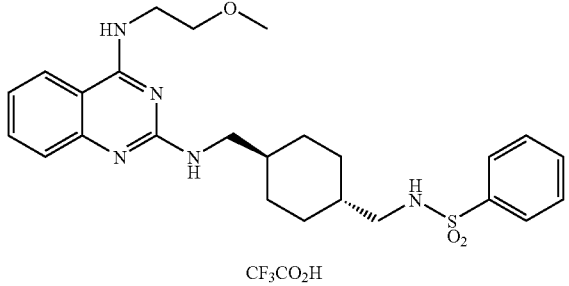 CF$_3$CO$_2$H | 484.4 (M + H) | 3.49 |

-continued
| Example No. | Structure | ESI-MS | Retention Time (min) |
|---|---|---|---|
| 2358 | 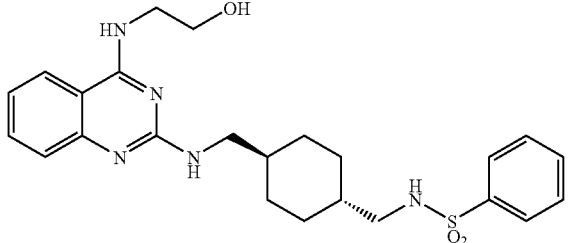 CF₃CO₂H | 470.2 (M + H) | 3.20 |
| 2359 | 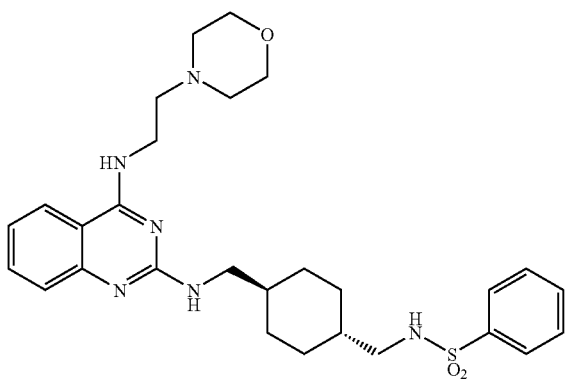 2CF₃CO₂H | 539.4 (M + H) | 3.12 |
| 2360 | 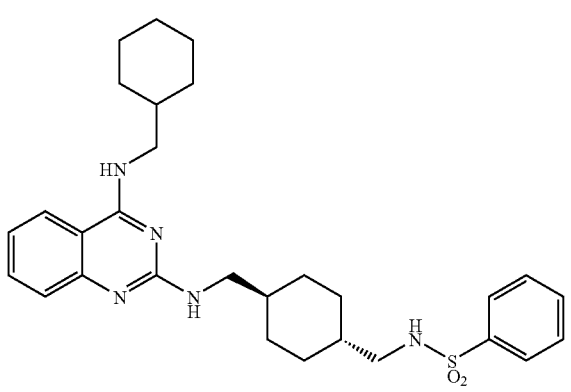 CF₃CO₂H | 522.2 (M + H) | 4.22 |
| 2361 | 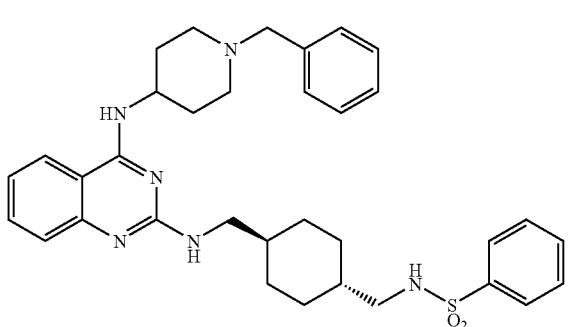 2CF₃CO₂H | 599.0 (M + H) | 3.48 |

-continued
| Example No. | Structure | ESI-MS | Retention Time (min) |
|---|---|---|---|
| 2362 | 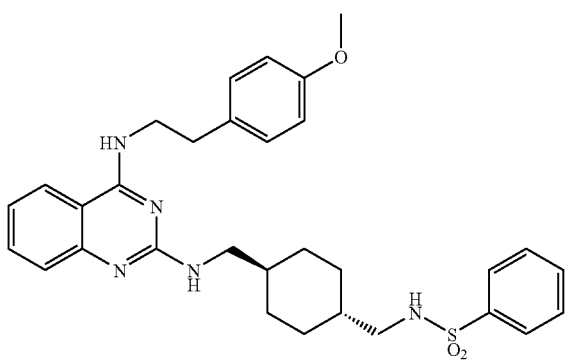 CF$_3$CO$_2$H | 560.2 (M + H) | 3.99 |
| 2363 | 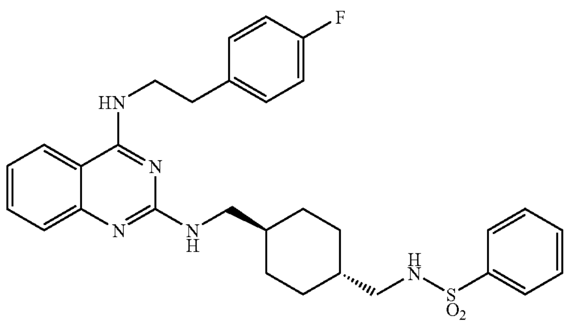 | 584.4 (M + H) | 4.06 |
| 2364 |  2CF$_3$CO$_2$H | 534.0 (M + H) | 3.11 |
| 2365 | 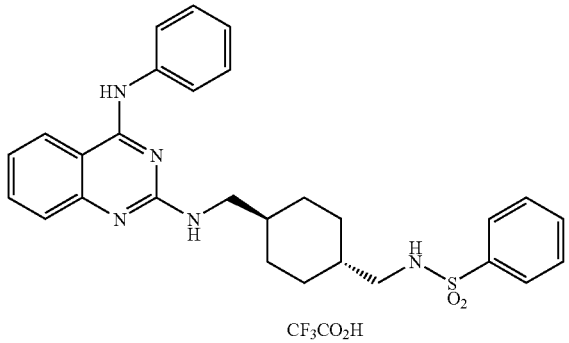 CF$_3$CO$_2$H | 502.4 (M + H) | 3.81 |

-continued

| Example No. | Structure | ESI-MS | Retention Time (min) |
|---|---|---|---|
| 2366 | 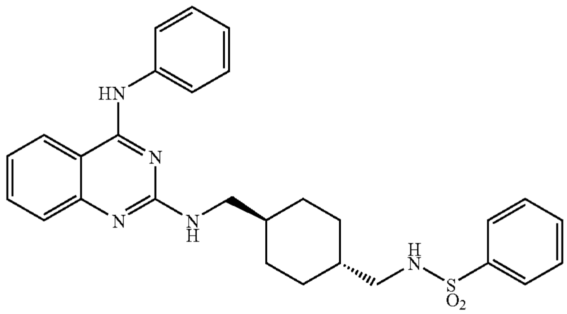 | 530.2 (M + H) | 4.04 |
| 2367 | 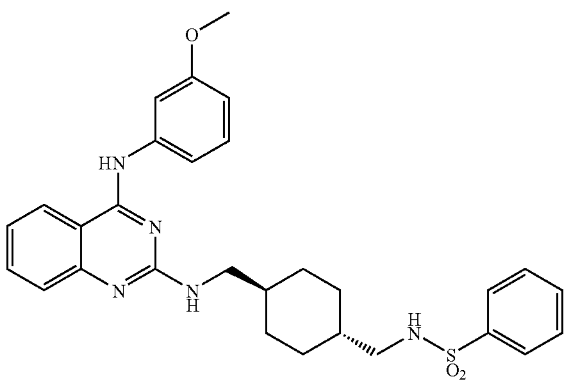 | 532.4 (M + H) | 3.85 |
| 2368 | 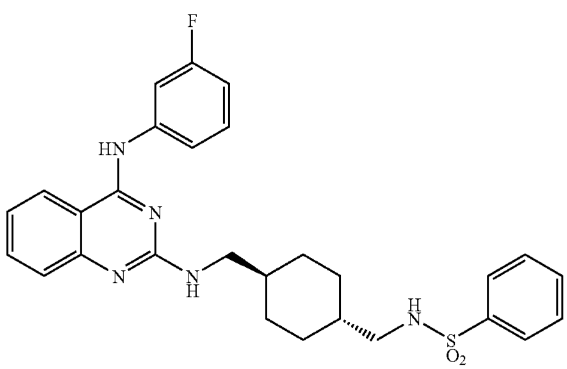 | 520.2 (M + H) | 3.86 |
| 2369 | 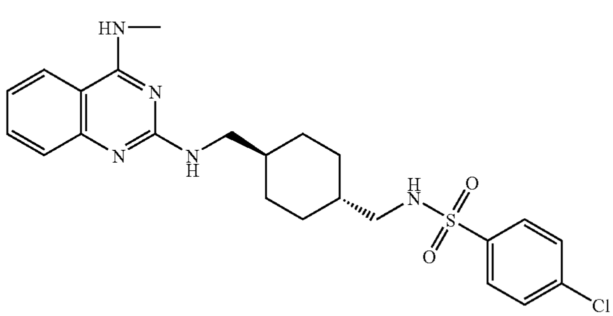 | 474.2 (M + H) | 3.72 |

-continued

| Example No. | Structure | ESI-MS | Retention Time (min) |
|---|---|---|---|
| 2370 | CF₃CO₂H | 518.2 (M + H) | 3.71 |
| 2371 | 2CF₃CO₂H | 573.2 (M + H) | 3.15 |
| 2372 | CF₃CO₂H | 556.2 (M + H) | 4.38 |
| 2373 | 2CF₃CO₂H | 633.4 (M + H) | 3.48 |

-continued

| Example No. | Structure | ESI-MS | Retention Time (min) |
|---|---|---|---|
| 2374 | 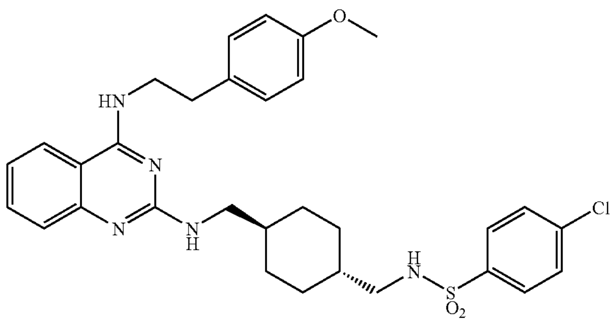 | 594.2 (M + H) | 4.23 |
| 2375 | 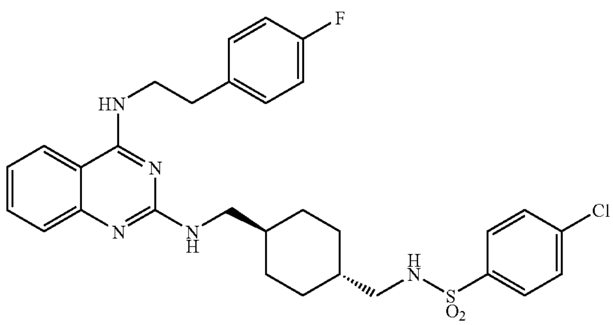 | 582.4 (M + H) | 4.26 |
| 2376 | 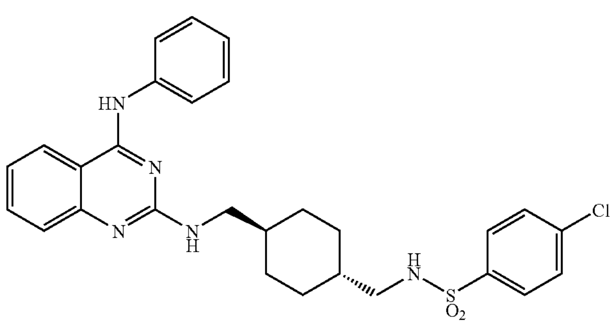 | 536.2 (M + H) | 4.06 |
| 2377 | 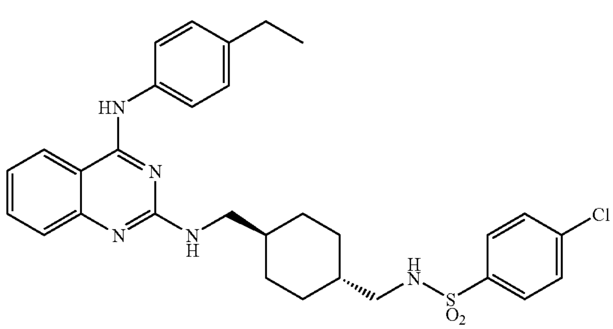 | 564.2 (M + H) | 4.32 |

-continued
| Example No. | Structure | ESI-MS | Retention Time (min) |
|---|---|---|---|
| 2378 | 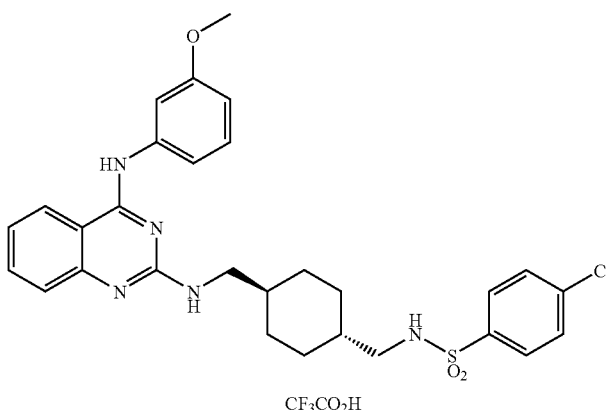 CF₃CO₂H | 566.4 (M + H) | 4.11 |
| 2379 | 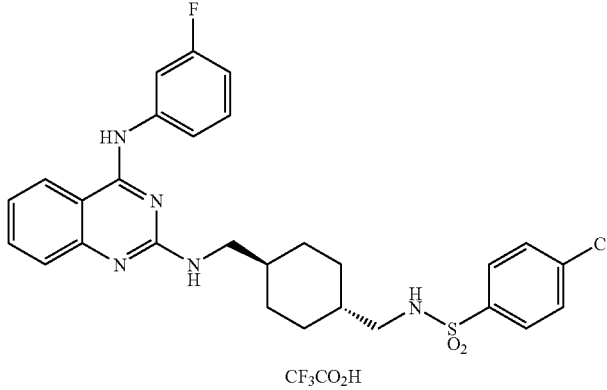 CF₃CO₂H | 554.2 (M + H) | 4.10 |
| 2380 | 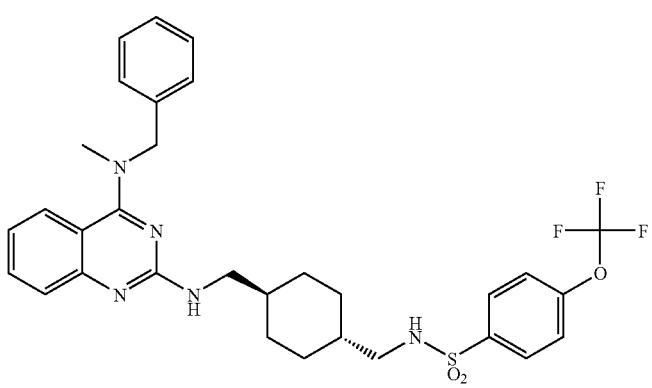 CF₃CO₂H | 614.2 (M + H) | 4.26 |

-continued

| Example No. | Structure | ESI-MS | Retention Time (min) |
|---|---|---|---|
| 2381 | *[structure with CF₃CO₂H]* | 524.4 (M + H) | 3.87 |
| 2382 | *[structure with CF₃CO₂H]* | 568.2 (M + H) | 3.87 |
| 2383 | *[structure with CF₃CO₂H]* | 586.2 (M + H) | 4.18 |
| 2384 | *[structure with CF₃CO₂H]* | 614.2 (M + H) | 4.45 |

-continued
| Example No. | Structure | ESI-MS | Retention Time (min) |
|---|---|---|---|
| 2385 | 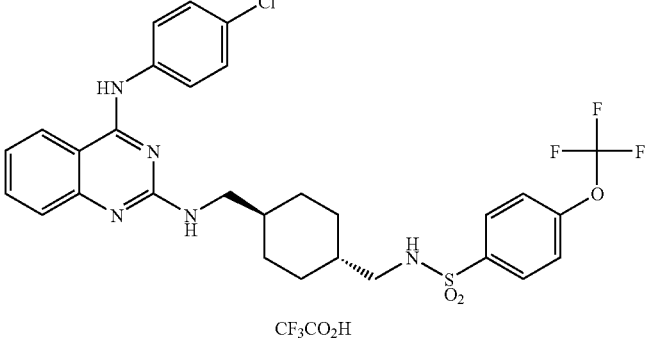 CF₃CO₂H | 620.4 (M + H) | 4.32 |
| 2386 | 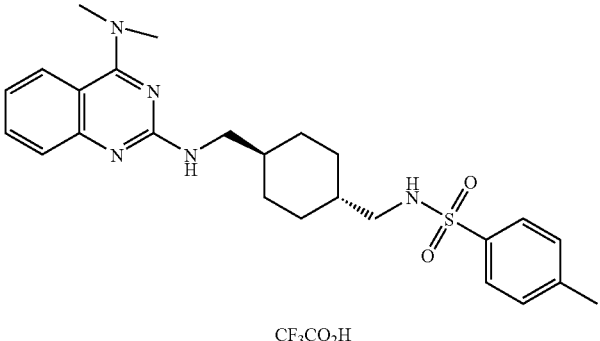 CF₃CO₂H | 468.2 (M + H) | 3.20 |
| 2387 | 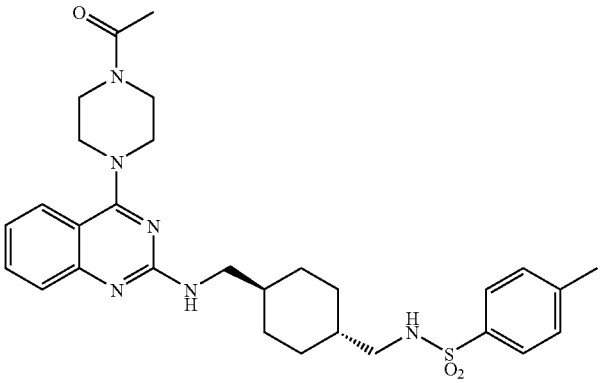 CF₃CO₂H | 551.6 (M + H) | 2.82 |
| 2388 | 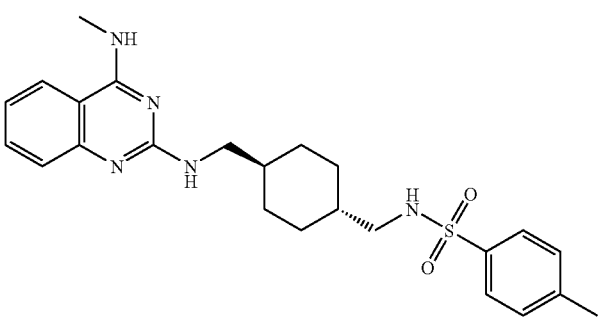 CF₃CO₂H | 454.0 (M + H) | 3.06 |

-continued
| Example No. | Structure | ESI-MS | Retention Time (min) |
|---|---|---|---|
| 2389 | 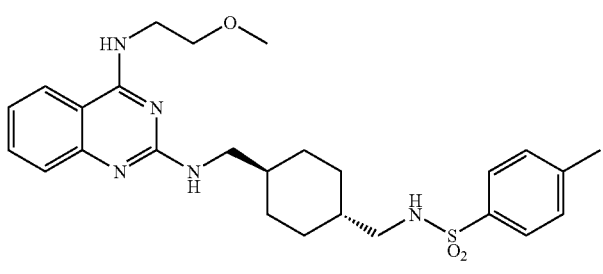 CF$_3$CO$_2$H | 498.6 (M + H) | 3.10 |
| 2390 | 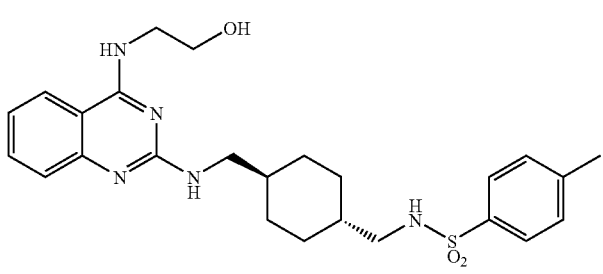 CF$_3$CO$_2$H | 484.2 (M + H) | 2.76 |
| 2391 | 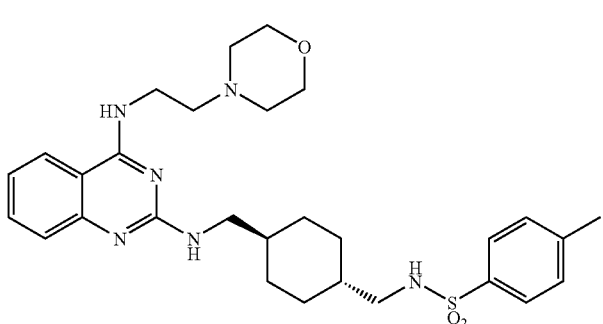 2CF$_3$CO$_2$H | 553.6 (M + H) | 2.40 |
| 2392 | 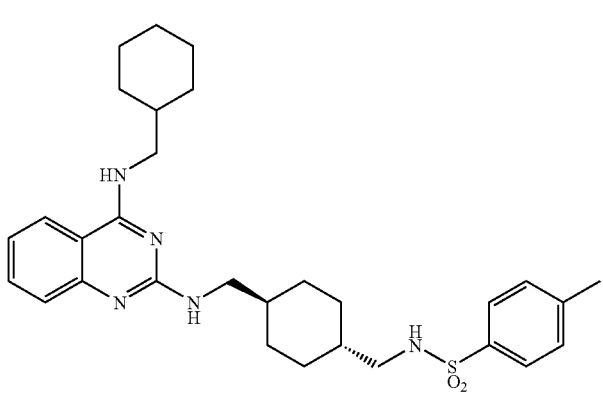 CF$_3$CO$_2$H | 536.4 (M + H) | 3.77 |

-continued

| Example No. | Structure | ESI-MS | Retention Time (min) |
|---|---|---|---|
| 2393 | 2CF₃CO₂H | 613.4 (M + H) | 2.74 |
| 2394 | CF₃CO₂H | 623.4 (M + H) | 3.06 |
| 2395 | CF₃CO₂H | 574.4 (M + H) | 3.51 |
| 2396 | CF₃CO₂H | 562.2 (M + H) | 3.59 |

-continued

| Example No. | Structure | ESI-MS | Retention Time (min) |
|---|---|---|---|
| 2397 | 2CF₃CO₂H | 548.6 (M + H) | 2.48 |
| 2398 | CF₃CO₂H | 516.4 (M + H) | 3.39 |
| 2399 | CF₃CO₂H | 550.4 (M + H) | 3.56 |
| 2400 | CF₃CO₂H | 546.2 (M + H) | 3.38 |

-continued
| Example No. | Structure | ESI-MS | Retention Time (min) |
|---|---|---|---|
| 2401 |  CF₃CO₂H | 534.0 (M + H) | 3.43 |
| 2402 | 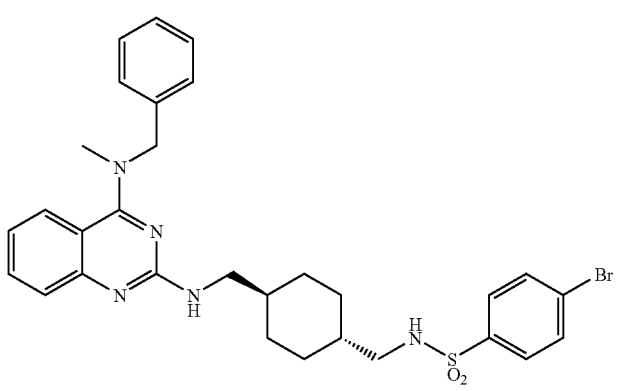 CF₃CO₂H | 608.2 (M + H) | 3.75 |
| 2403 | 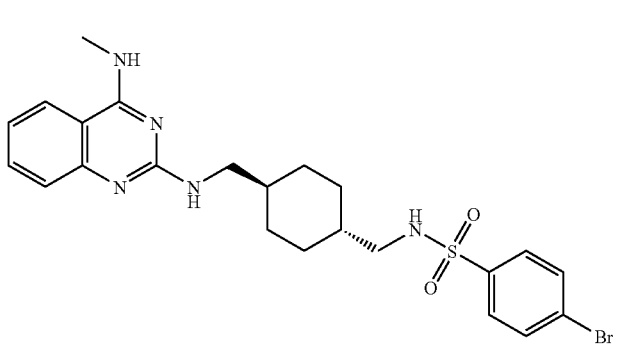 CF₃CO₂H | 518 (M + H) | 3.22 |
| 2404 | 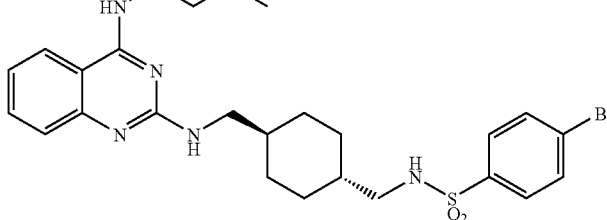 CF₃CO₂H | 562.2 (M + H) | 3.20 |

-continued

| Example No. | Structure | ESI-MS | Retention Time (min) |
|---|---|---|---|
| 2405 | 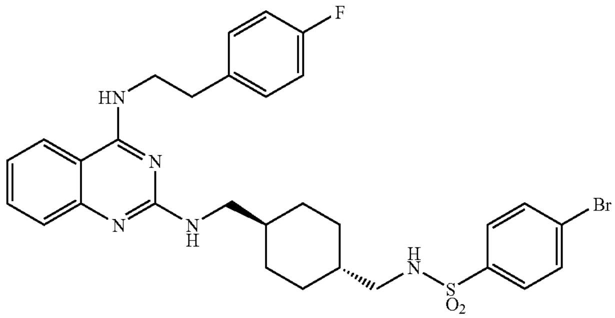 | 626.0 (M + H) | 3.76 |
| 2406 | 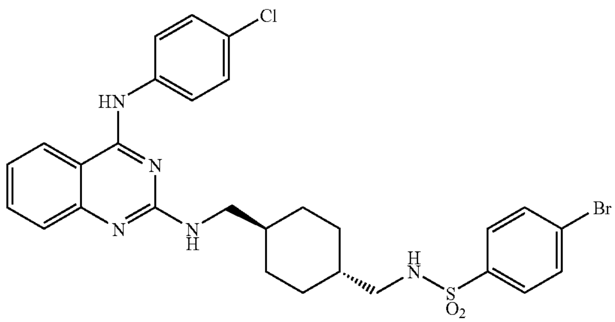 | 614.0 (M + H) | 3.72 |
| 2407 | 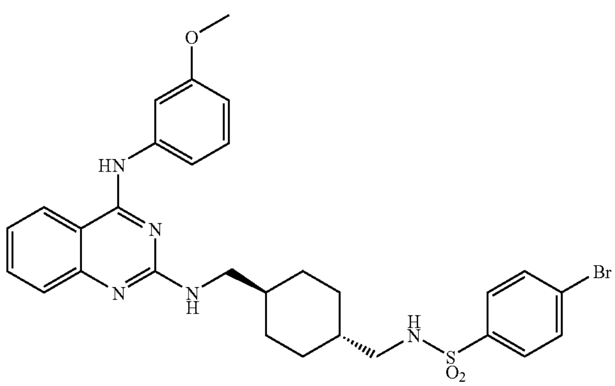 | 610.0 (M + H) | 3.57 |
| 2408 | 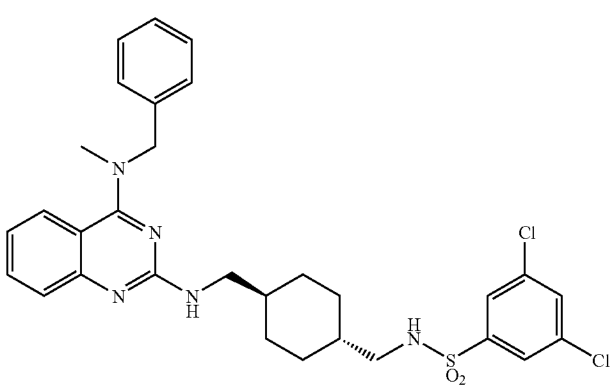 | 598.2 (M + H) | 3.97 |

-continued
| Example No. | Structure | ESI-MS | Retention Time (min) |
|---|---|---|---|
| 2409 | 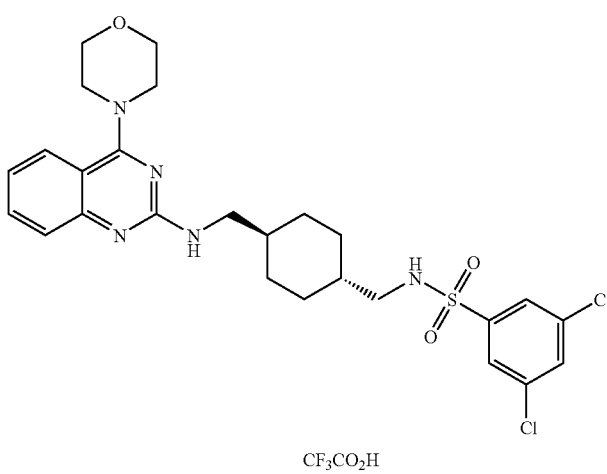 CF₃CO₂H | 564.2 (M + H) | 3.46 |
| 2410 | 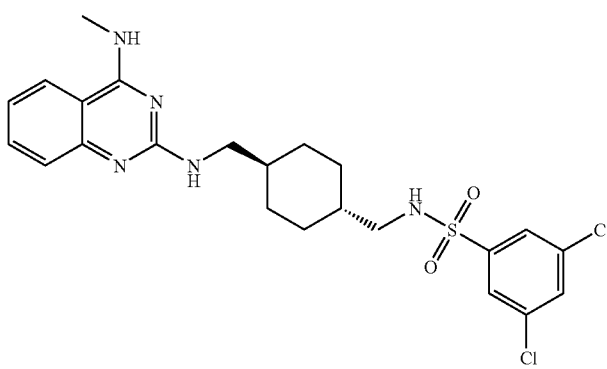 CF₃CO₂H | 508.0 (M + H) | 3.44 |
| 2411 | 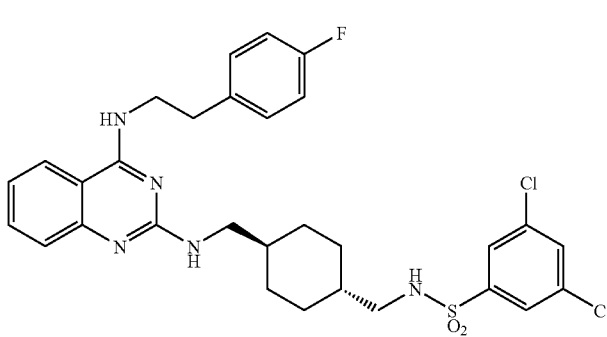 CF₃CO₂H | 616.2 (M + H) | 3.94 |

-continued
| Example No. | Structure | ESI-MS | Retention Time (min) |
|---|---|---|---|
| 2412 | 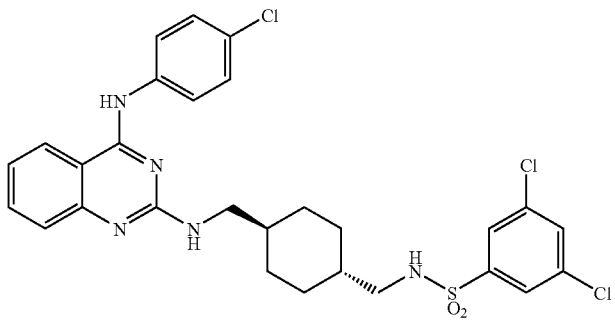 CF₃CO₂H | 604.2 (M + H) | 4.51 |
| 2413 |  CF₃CO₂H | 600.2 (M + H) | 4.32 |
| 2414 | 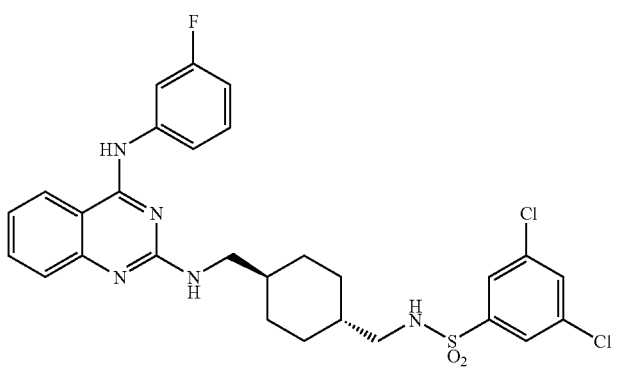 CF₃CO₂H | 588.0 (M + H) | 4.38 |

-continued

| Example No. | Structure | ESI-MS | Retention Time (min) |
|---|---|---|---|
| 2415 | *(structure shown)* CF₃CO₂H | 650.2 (M + H) | 4.20 |
| 2416 | *(structure shown)* CF₃CO₂H | 726.4 (M + H) | 4.52 |
| 2417 | *(structure shown)* 2CF₃CO₂H | 741.6 (M + H) | 3.59 |

| Example No. | Structure | ESI-MS | Retention Time (min) |
|---|---|---|---|
| 2418 | 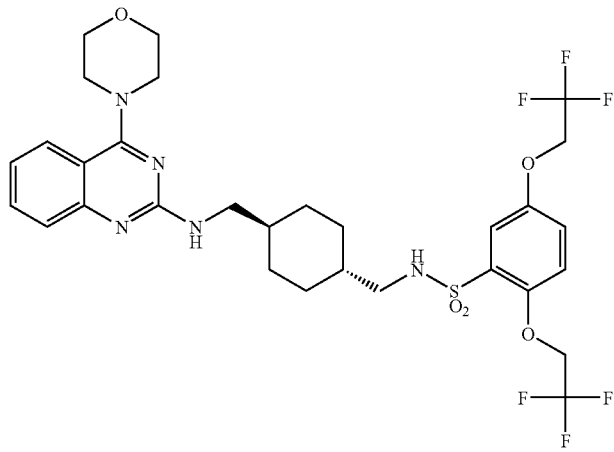 CF$_3$CO$_2$H | 692.2 (M + H) | 4.12 |
| 2419 | 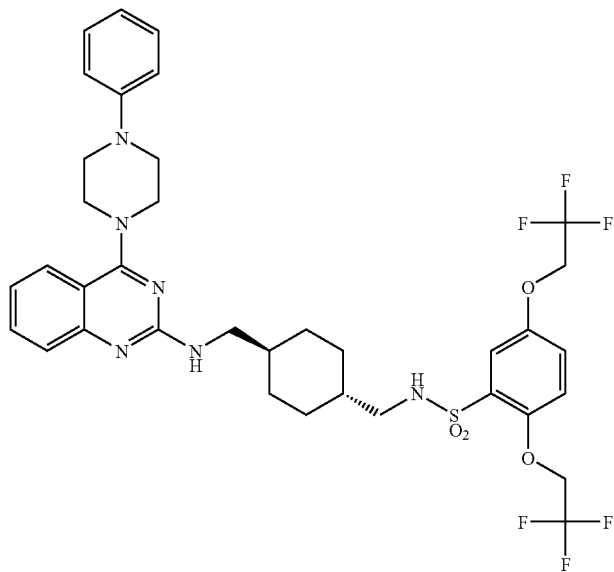 2CF$_3$CO$_2$H | 767.6 (M + H) | 4.59 |

-continued
| Example No. | Structure | ESI-MS | Retention Time (min) |
|---|---|---|---|
| 2420 | 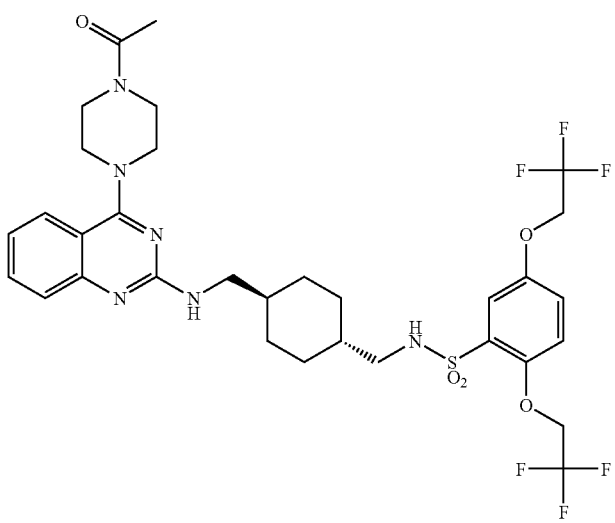 CF₃CO₂H | 733.4 (M + H) | 3.87 |
| 2421 | 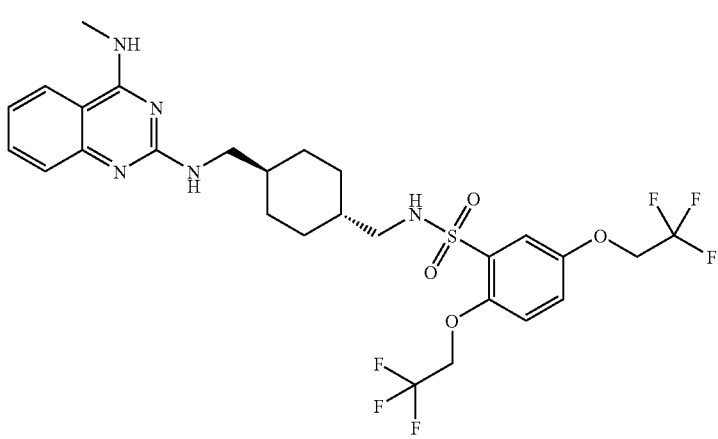 CF₃CO₂H | 636.2 (M + H) | 4.08 |
| 2422 | 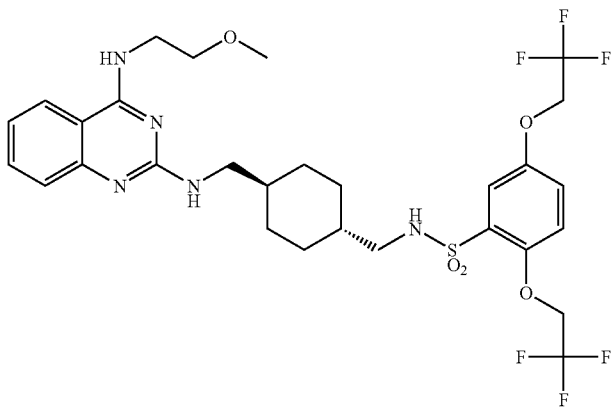 CF₃CO₂H | 680.2 (M + H) | 4.07 |

-continued
| Example No. | Structure | ESI-MS | Retention Time (min) |
|---|---|---|---|
| 2423 | 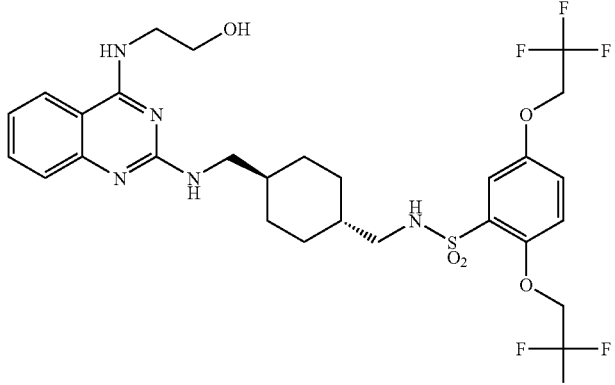 CF₃CO₂H | 666.0 (M + H) | 3.86 |
| 2424 | 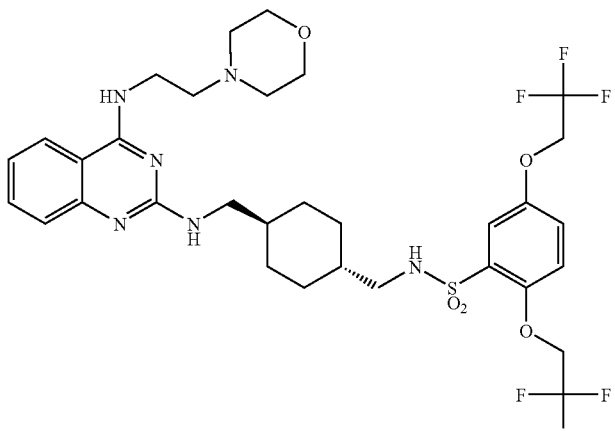 2CF₃CO₂H | 735.4 (M + H) | 3.50 |
| 2425 | 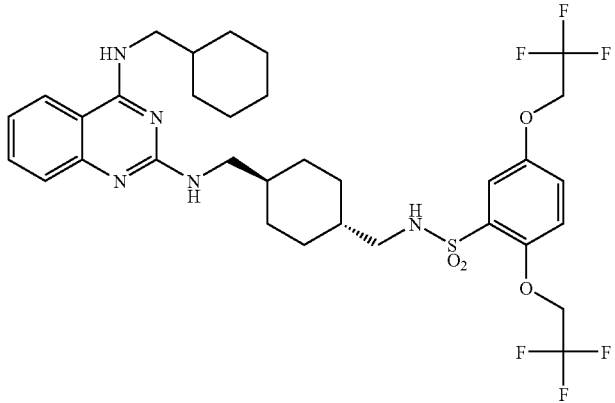 CF₃CO₂H | 718.4 (M + H) | 4.64 |

-continued

| Example No. | Structure | ESI-MS | Retention Time (min) |
|---|---|---|---|
| 2426 | 2CF₃CO₂H | 795.6 (M + H) | 3.70 |
| 2427 | CF₃CO₂H | 744.2 (M + H) | 4.43 |
| 2428 | CF₃CO₂H | 698.0 (M + H) | 4.26 |

-continued
| Example No. | Structure | ESI-MS | Retention Time (min) |
|---|---|---|---|
| 2429 | 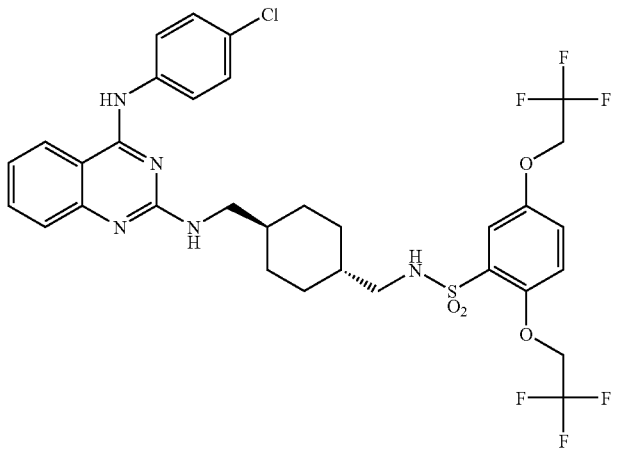 CF$_3$CO$_2$H | 732.4 (M + H) | 4.37 |
| 2430 | 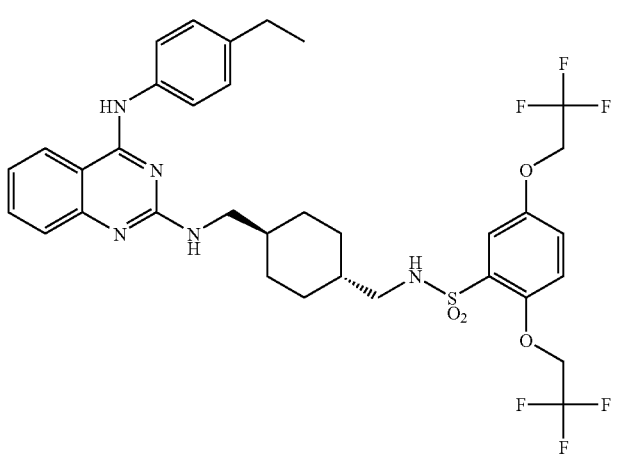 CF$_3$CO$_2$H | 726.4 (M + H) | 4.52 |
| 2431 | 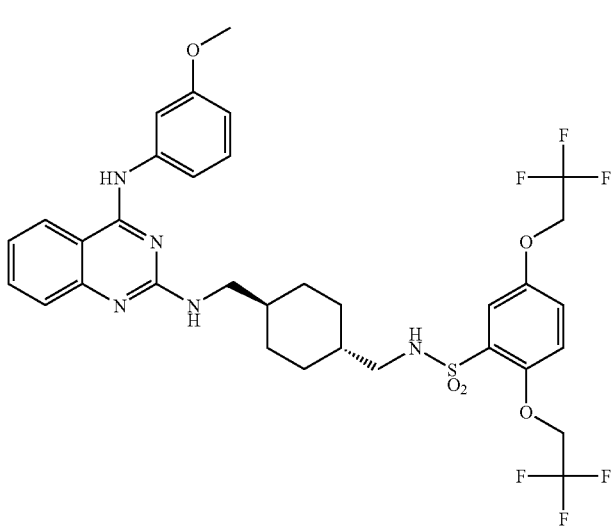 CF$_3$CO$_2$H | 728.4 (M + H) | 4.36 |

-continued
| Example No. | Structure | ESI-MS | Retention Time (min) |
|---|---|---|---|
| 2432 | 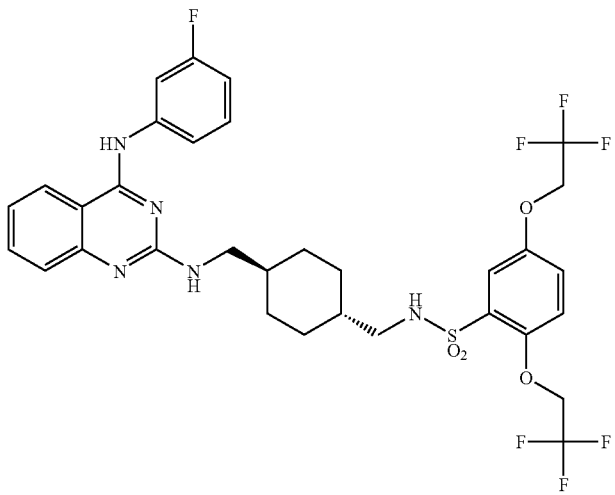 CF₃CO₂H | 716.4 (M + H) | 4.32 |
| 2433 | 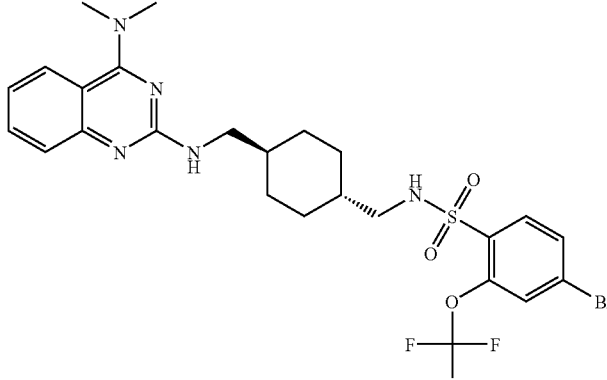 CF₃CO₂H | 616.0 (M + H) | 4.22 |
| 2434 | 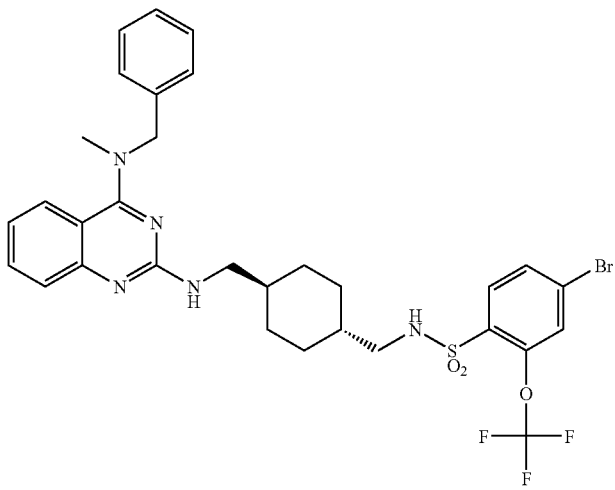 CF₃CO₂H | 692.0 (M + H) | 4.57 |

-continued
| Example No. | Structure | ESI-MS | Retention Time (min) |
|---|---|---|---|
| 2435 | 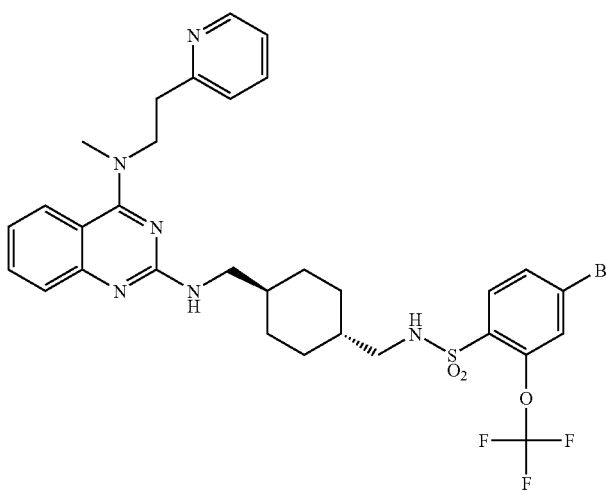 2CF$_3$CO$_2$H | 707.2 (M + H) | 3.64 |
| 2436 | 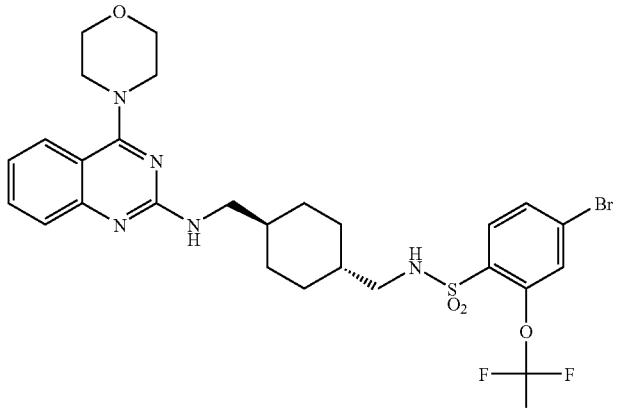 CF$_3$CO$_2$H | 658.2 (M + H) | 4.15 |

-continued

| Example No. | Structure | ESI-MS | Retention Time (min) |
|---|---|---|---|
| 2437 | 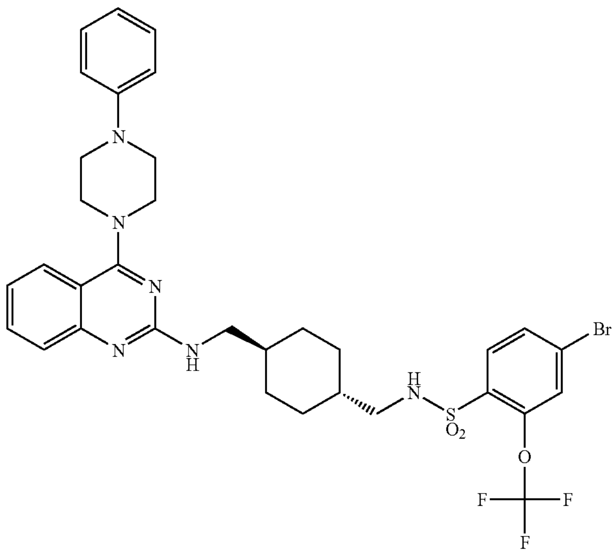 | 733.2 (M + H) | 4.68 |
| 2438 | 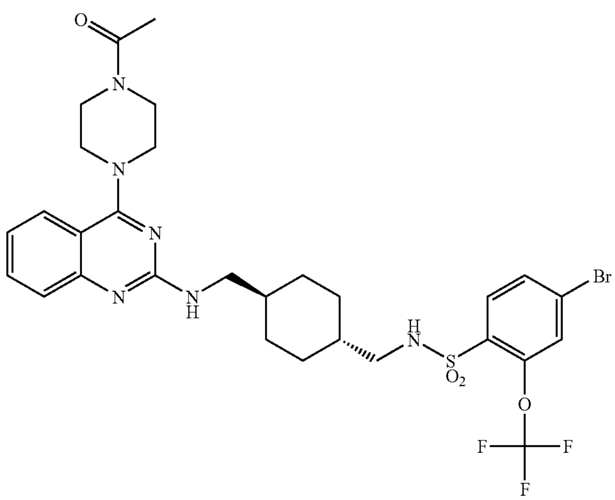 | 699.2 (M + H) | 3.88 |
| 2439 | 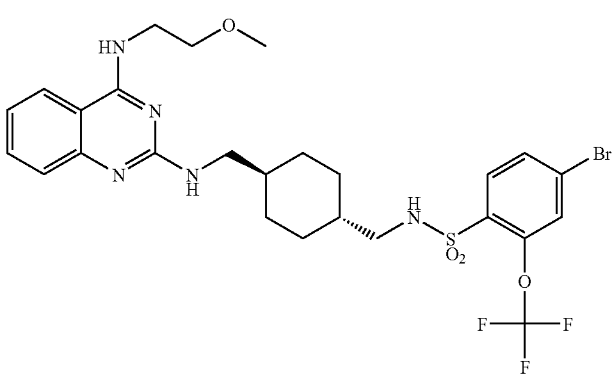 | 646.4 (M + H) | 4.08 |

-continued
| Example No. | Structure | ESI-MS | Retention Time (min) |
|---|---|---|---|
| 2440 | 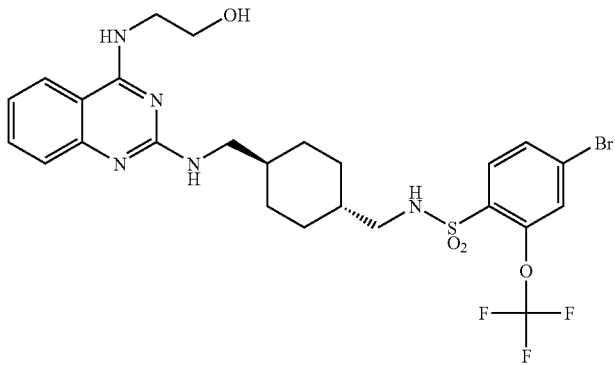 CF$_3$CO$_2$H | 632.4 (M + H) | 3.86 |
| 2441 | 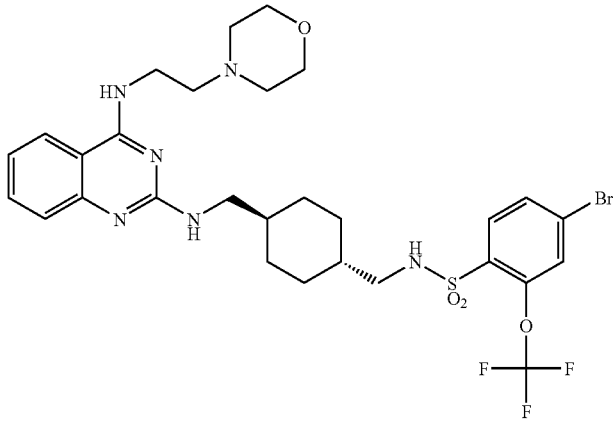 2CF$_3$CO$_2$H | 701.4 (M + H) | 3.51 |
| 2442 | 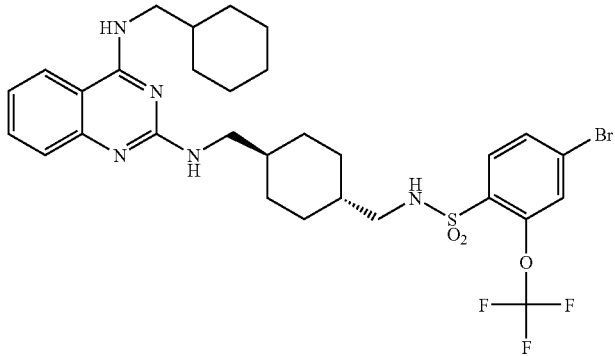 CF$_3$CO$_2$H | 684.2 (M + H) | 4.75 |

-continued
| Example No. | Structure | ESI-MS | Retention Time (min) |
|---|---|---|---|
| 2443 | 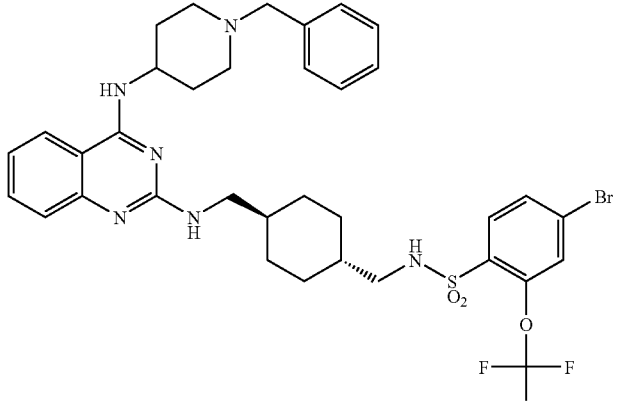 2CF$_3$CO$_2$H | 761.2 (M + H) | 3.74 |
| 2444 | 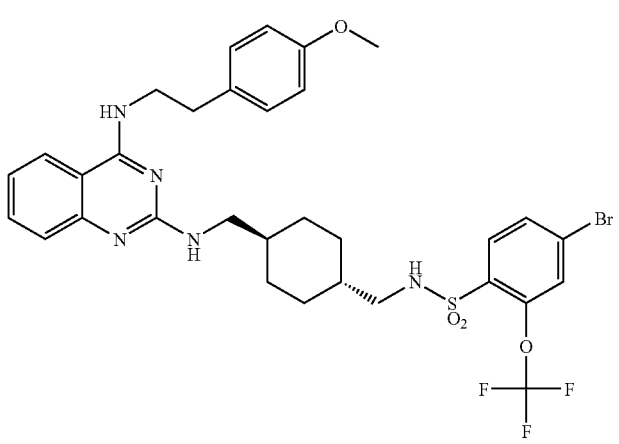 CF$_3$CO$_2$H | 722.2 (M + H) | 4.59 |
| 2445 |  CF$_3$CO$_2$H | 710.2 (M + H) | 4.60 |

US 7,544,690 B2
-continued
| Example No. | Structure | ESI-MS | Retention Time (min) |
|---|---|---|---|
| 2446 | 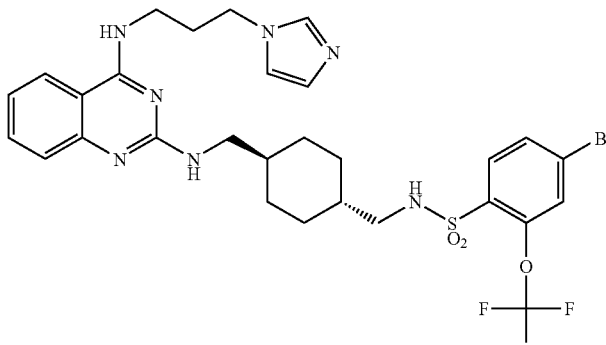<br>2CF$_3$CO$_2$H | 696.2 (M + H) | 3.53 |
| 2447 | 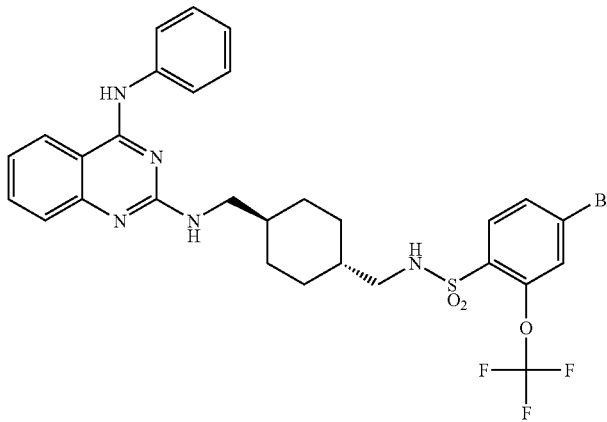<br>CF$_3$CO$_2$H | 664.2 (M + H) | 4.39 |
| 2448 | 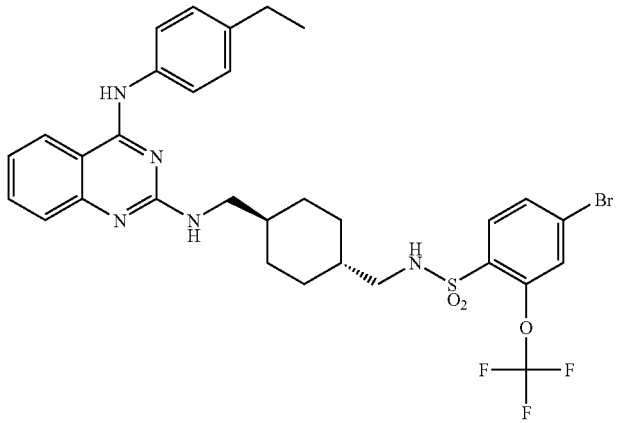<br>CF$_3$CO$_2$H | 692.0 (M + H) | 4.65 |

-continued

| Example No. | Structure | ESI-MS | Retention Time (min) |
|---|---|---|---|
| 2449 | 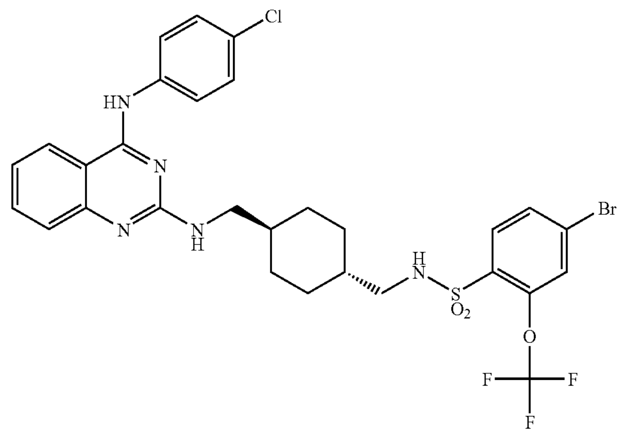 | 698.0 (M + H) | 4.59 |
| 2450 | 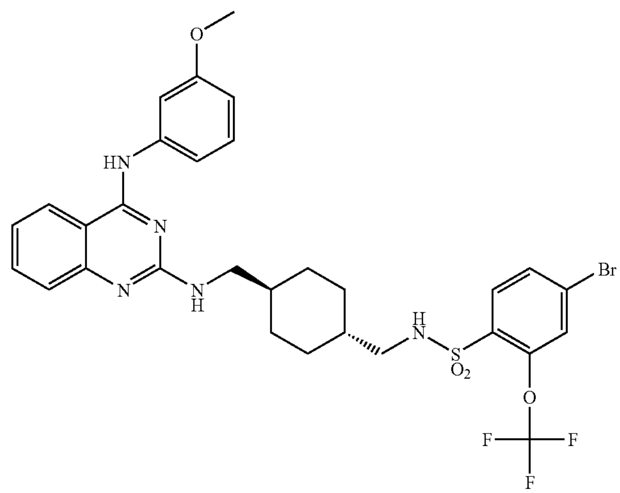 | 694.2 (M + H) | 4.42 |
| 2451 | 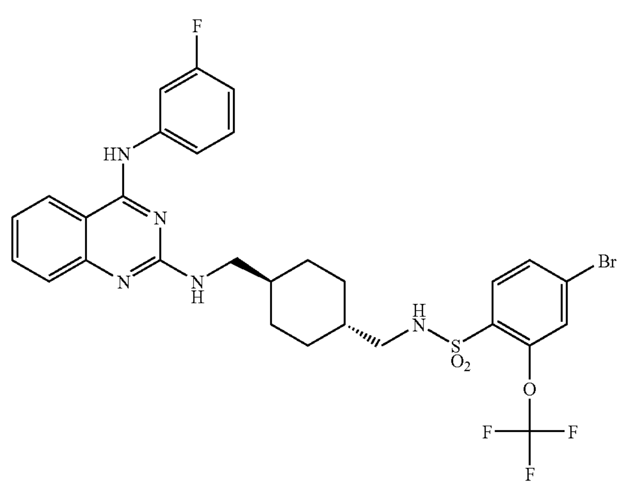 | 682.2 (M + H) | 4.42 |

-continued

| Example No. | Structure | ESI-MS | Retention Time (min) |
|---|---|---|---|
| 2452 | 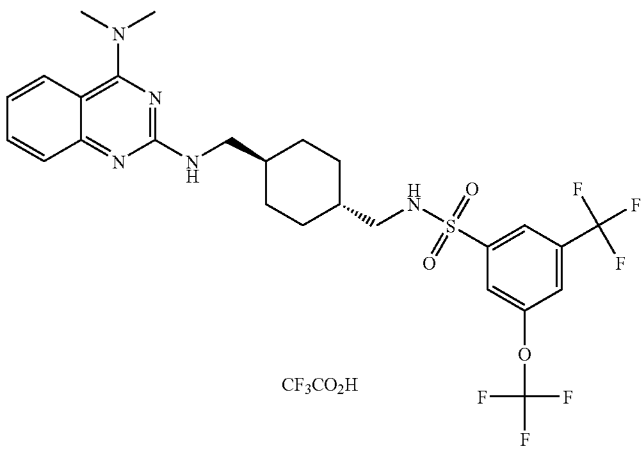 | 590.2 (M + H) | 4.28 |
| 2453 | 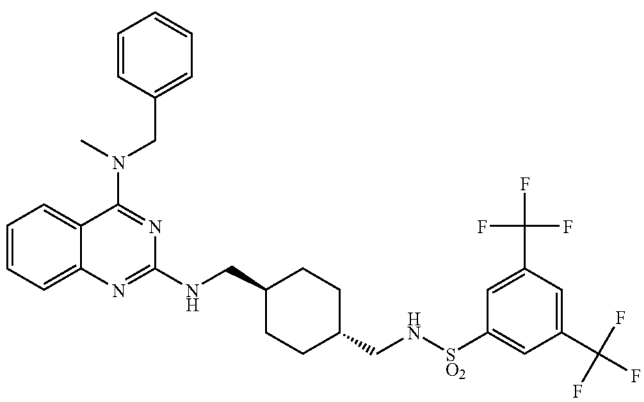 | 666.2 (M + H) | 4.61 |
| 2454 | 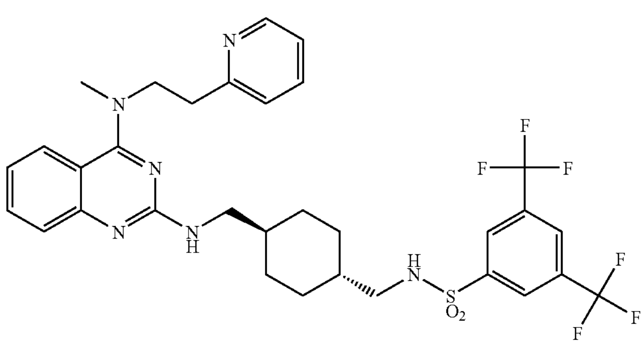 | 681.2 (M + H) | 3.72 |

-continued
| Example No. | Structure | ESI-MS | Retention Time (min) |
|---|---|---|---|
| 2455 | 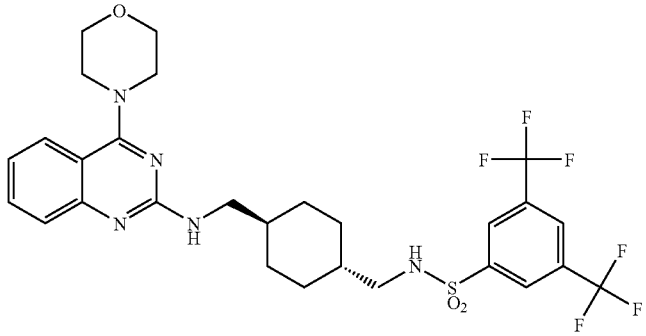 CF₃CO₂H | 632.4 (M + H) | 4.21 |
| 2456 | 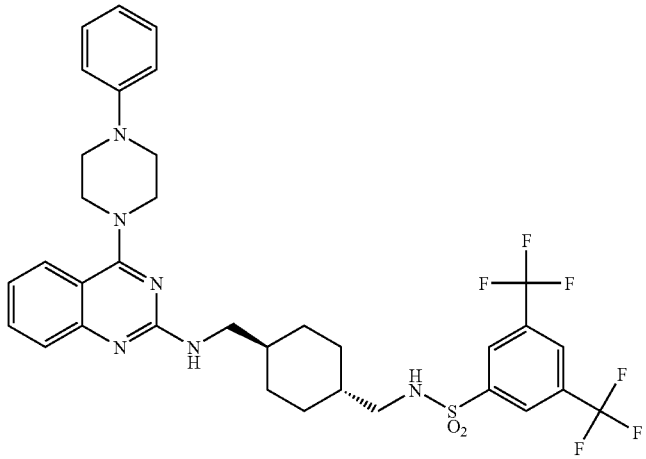 2CF₃CO₂H | 707.2 (M + H) | 4.70 |
| 2457 | 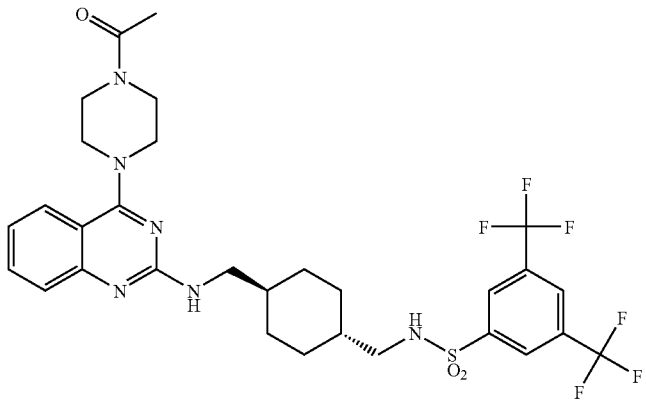 CF₃CO₂H | 673.2 (M + H) | 3.94 |

-continued
| Example No. | Structure | ESI-MS | Retention Time (min) |
|---|---|---|---|
| 2458 | 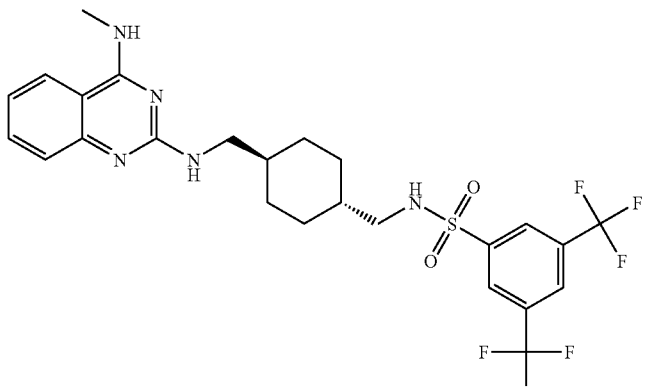 CF$_3$CO$_2$H | 576.2 (M + H) | 4.16 |
| 2459 | 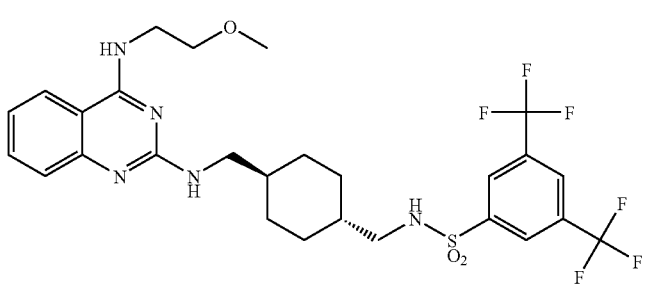 CF$_3$CO$_2$H | 620.4 (M + H) | 4.19 |
| 2460 | 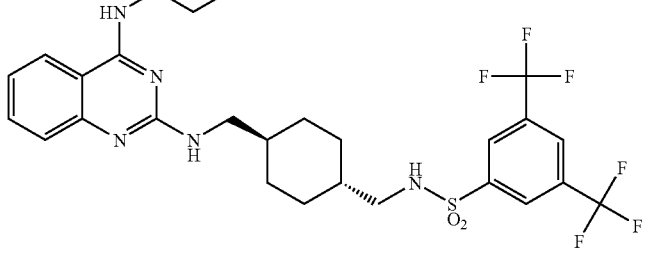 CF$_3$CO$_2$H | 606.6 (M + H) | 3.94 |
| 2461 | 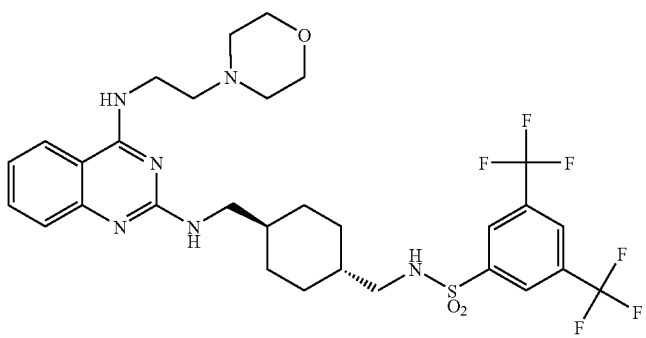 2CF$_3$CO$_2$H | 675.4 (M + H) | 3.59 |

-continued

| Example No. | Structure | ESI-MS | Retention Time (min) |
|---|---|---|---|
| 2462 | (structure) CF₃CO₂H | 658.6 (M + H) | 4.82 |
| 2463 | (structure) 2CF₃CO₂H | 735.4 (M + H) | 3.82 |
| 2464 | (structure) CF₃CO₂H | 696.0 (M + H) | 4.56 |
| 2465 | (structure) CF₃CO₂H | 684.4 (M + H) | 4.61 |

-continued

| Example No. | Structure | ESI-MS | Retention Time (min) |
|---|---|---|---|
| 2466 | 2CF₃CO₂H | 670.2 (M + H) | 3.56 |
| 2467 | CF₃CO₂H | 638.2 (M + H) | 4.43 |
| 2468 | CF₃CO₂H | 666.2 (M + H) | 4.68 |
| 2469 | CF₃CO₂H | 672.2 (M + H) | 4.60 |

-continued
| Example No. | Structure | ESI-MS | Retention Time (min) |
|---|---|---|---|
| 2470 | 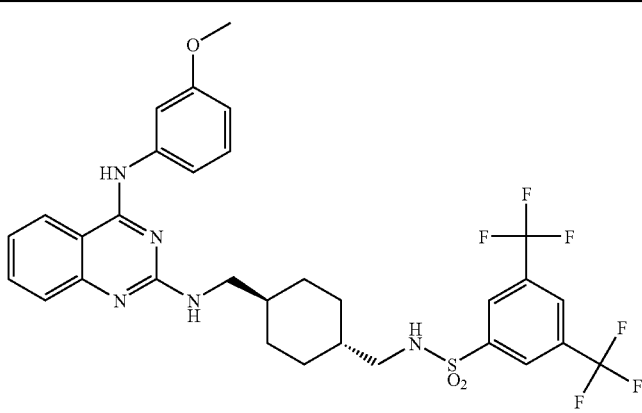 CF₃CO₂H | 668.2 (M + H) | 4.44 |
| 2471 | 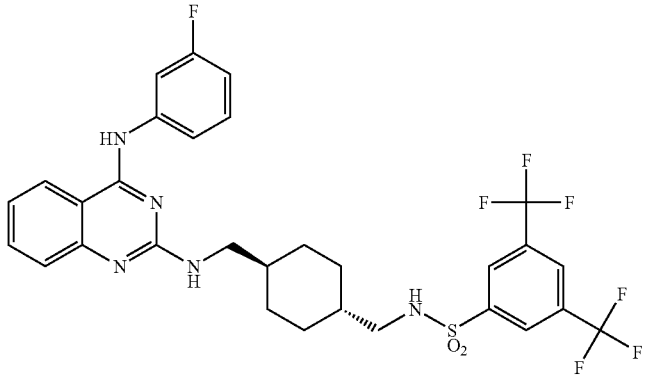 CF₃CO₂H | 656.4 (M + H) | 4.47 |
| 2472 | 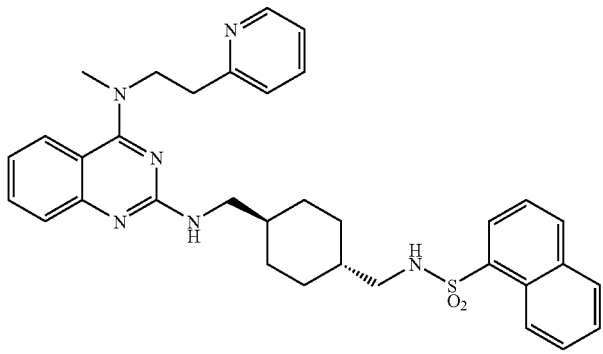 2CF₃CO₂H | 585.4 (M + H) | 3.32 |

-continued
| Example No. | Structure | ESI-MS | Retention Time (min) |
|---|---|---|---|
| 2473 | 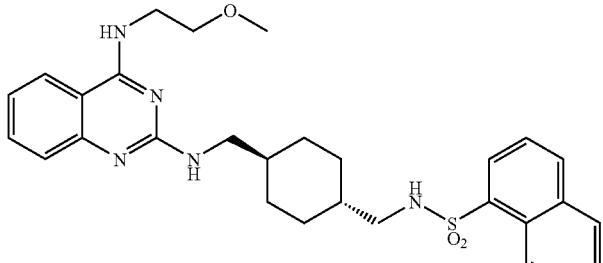 CF₃CO₂H | 534.0 (M + H) | 3.81 |
| 2474 | 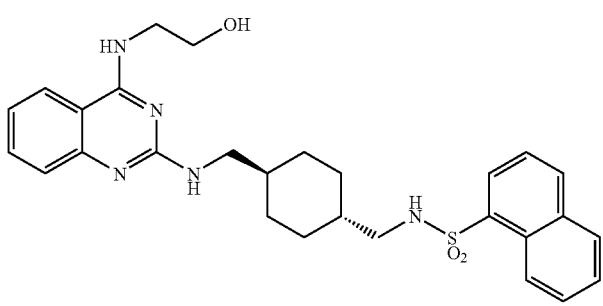 CF₃CO₂H | 520.4 (M + H) | 3.56 |
| 2475 | 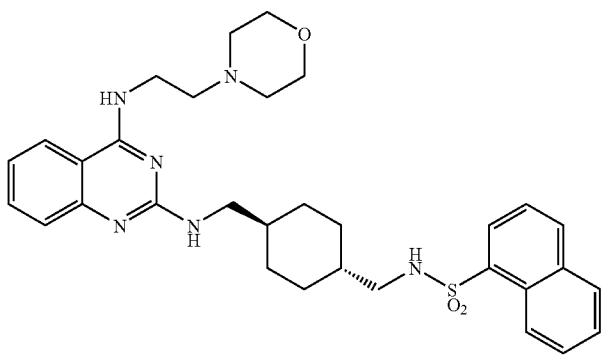 2CF₃CO₂H | 589.2 (M + H) | 3.25 |
| 2476 | 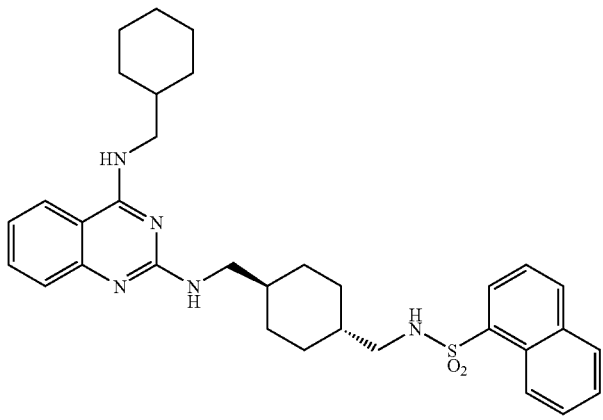 CF₃CO₂H | 572.4 (M + H) | 4.47 |

-continued
| Example No. | Structure | ESI-MS | Retention Time (min) |
|---|---|---|---|
| 2477 | 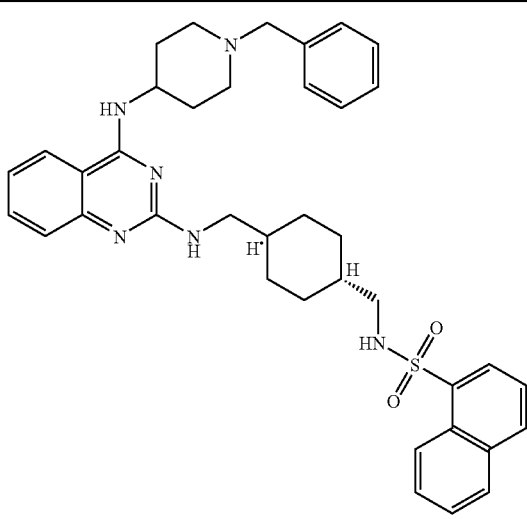 2CF₃CO₂H | 649.4 (M + H) | 3.50 |
| 2478 | 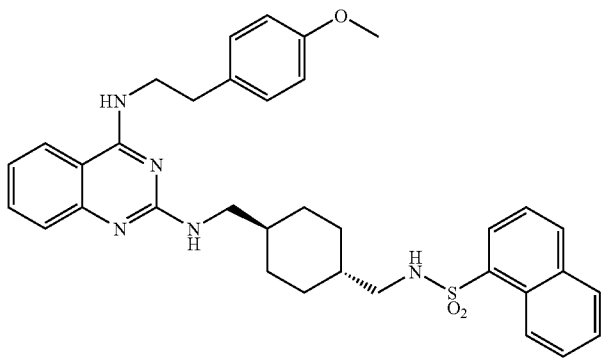 CF₃CO₂H | 610.4 (M + H) | 4.26 |
| 2479 | 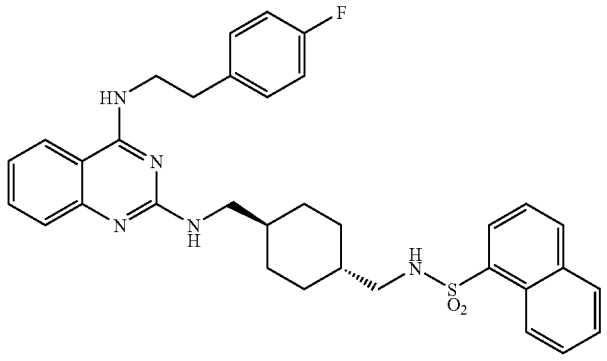 CF₃CO₂H | 598.2 (M + H) | 4.30 |

-continued

| Example No. | Structure | ESI-MS | Retention Time (min) |
|---|---|---|---|
| 2480 | 2CF$_3$CO$_2$H | 584.4 (M + H) | 3.29 |
| 2481 | CF$_3$CO$_2$H | 552.6 (M + H) | 4.11 |
| 2482 | CF$_3$CO$_2$H | 580.6 (M + H) | 4.40 |
| 2483 | CF$_3$CO$_2$H | 586.2 (M + H) | 4.30 |

-continued
| Example No. | Structure | ESI-MS | Retention Time (min) |
|---|---|---|---|
| 2484 | 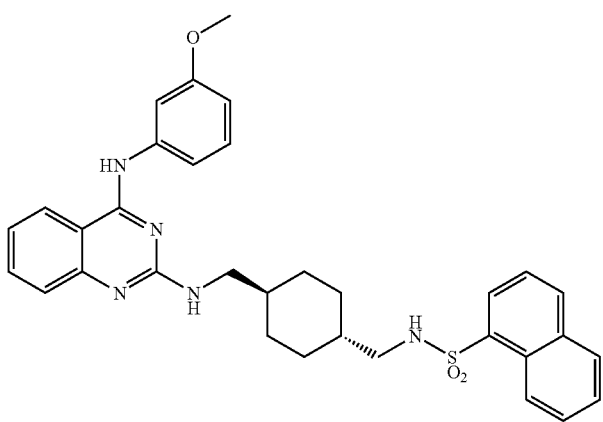 CF₃CO₂H | 582.4 (M + H) | 4.14 |
| 2485 | 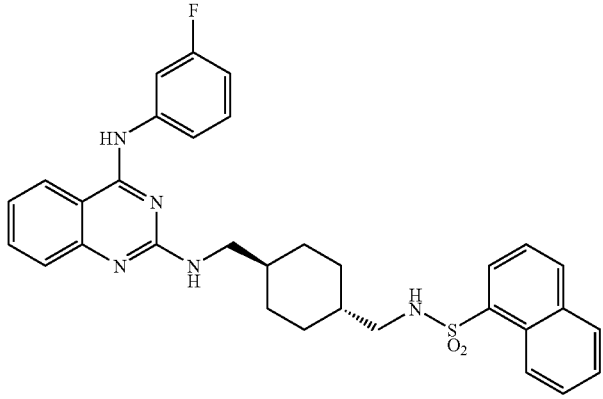 CF₃CO₂H | 570.2 (M + H) | 4.14 |
| 2486 | 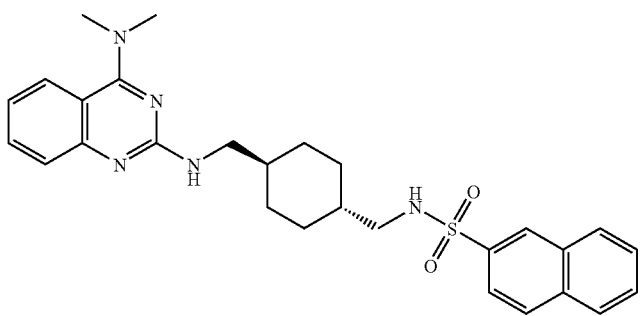 CF₃CO₂H | 504.2 (M + H) | 3.94 |

-continued

| Example No. | Structure | ESI-MS | Retention Time (min) |
|---|---|---|---|
| 2487 | 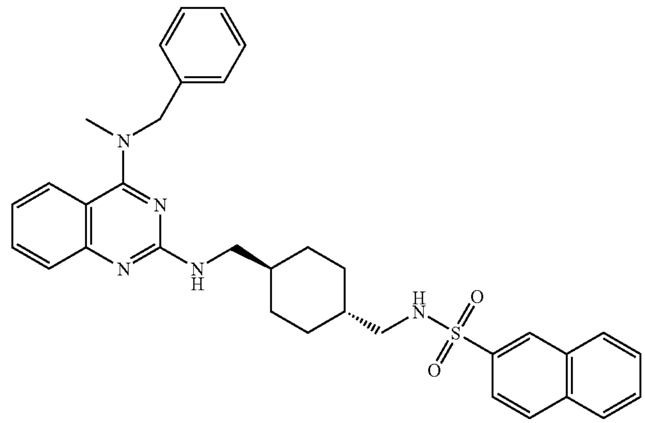 | 580.6 (M + H) | 4.34 |
| 2488 | 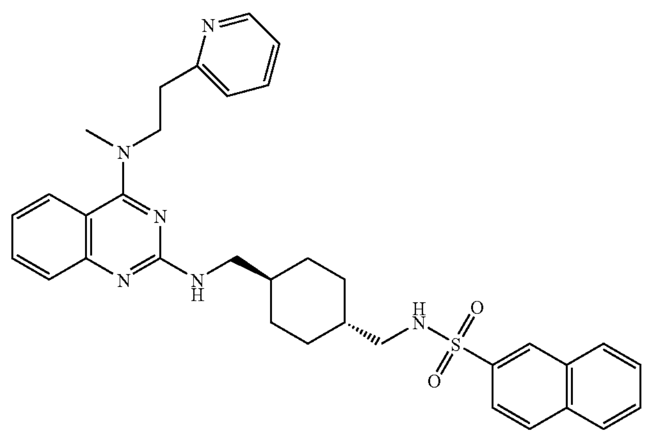 | 595.2 (M + H) | 3.41 |
| 2489 | 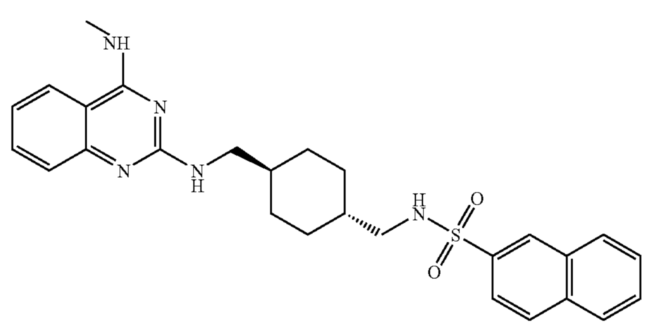 | 490.2 (M + H) | 3.84 |

-continued
| Example No. | Structure | ESI-MS | Retention Time (min) |
|---|---|---|---|
| 2490 | 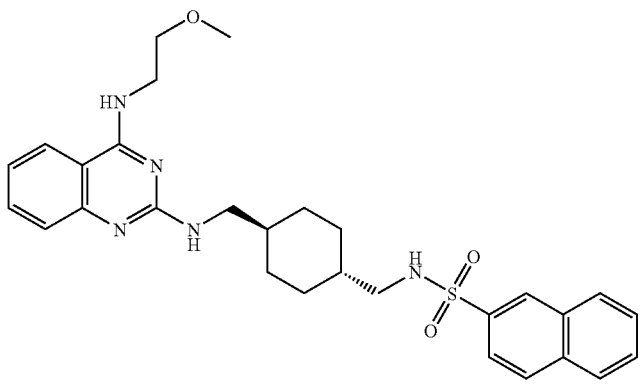 CF₃CO₂H | 534.2 (M + H) | 3.84 |
| 2491 | 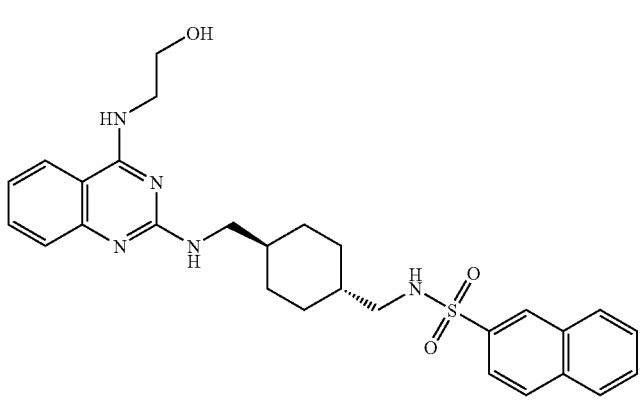 CF₃CO₂H | 520.4 (M + H) | 3.60 |
| 2492 | 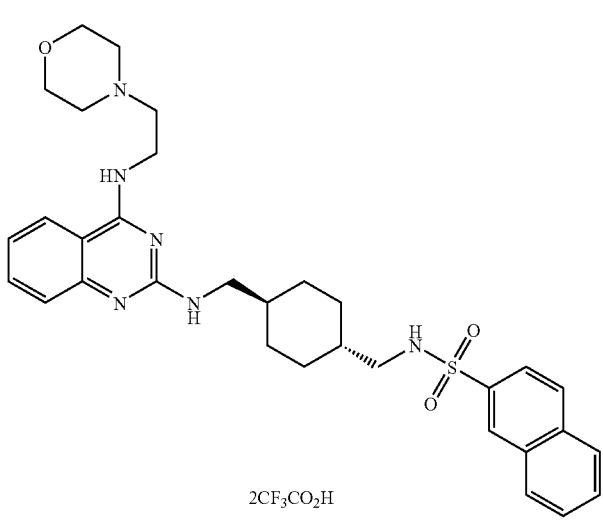 2CF₃CO₂H | 589.2 (M + H) | 3.29 |

-continued

| Example No. | Structure | ESI-MS | Retention Time (min) |
|---|---|---|---|
| 2493 | CF₃CO₂H | 572.4 (M + H) | 4.51 |
| 2494 | 2CF₃CO₂H | 649.4 (M + H) | 3.52 |
| 2495 | CF₃CO₂H | 610.2 (M + H) | 4.29 |

-continued

| Example No. | Structure | ESI-MS | Retention Time (min) |
|---|---|---|---|
| 2496 | *structure with 4-fluorophenethylamino-quinazoline, cyclohexyl, naphthalenesulfonamide; CF₃CO₂H* | 598.2 (M + H) | 4.34 |
| 2497 | *structure with phenylamino-quinazoline, cyclohexyl, naphthalenesulfonamide; CF₃CO₂H* | 552.6 (M + H) | 4.13 |
| 2498 | *structure with 4-ethylphenylamino-quinazoline, cyclohexyl, naphthalenesulfonamide; CF₃CO₂H* | 580.6 (M + H) | 4.37 |

-continued
| Example No. | Structure | ESI-MS | Retention Time (min) |
|---|---|---|---|
| 2499 | 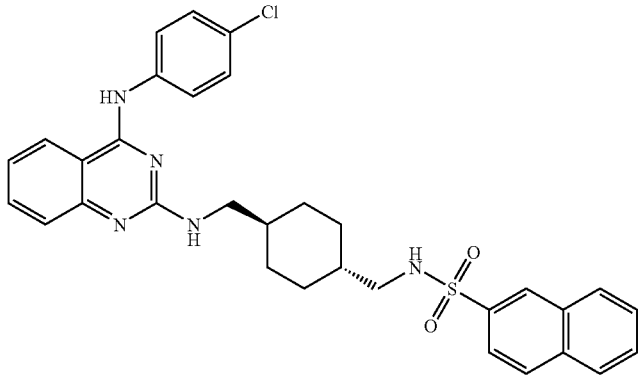 CF₃CO₂H | 586.2 (M + H) | 4.30 |
| 2500 | 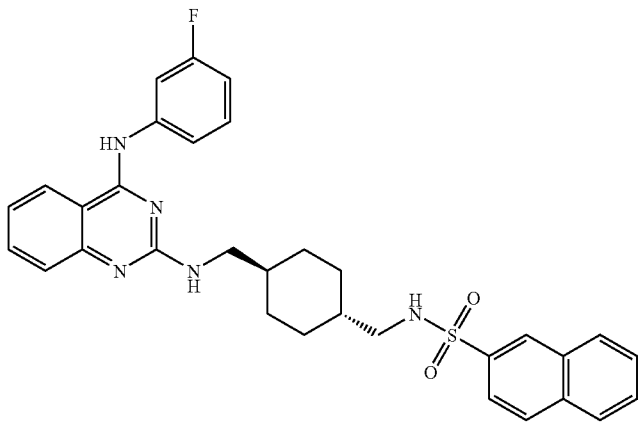 CF₃CO₂H | 570.2 (M + H) | 4.18 |
| 2501 | 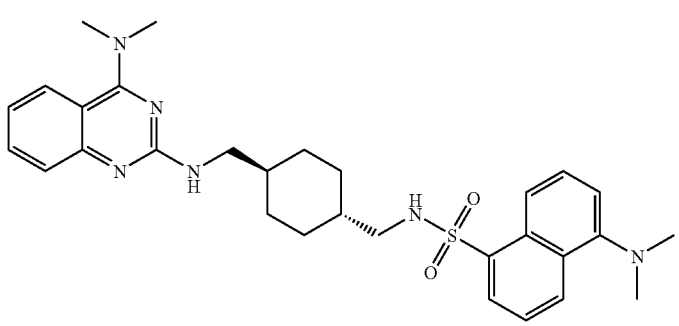 2CF₃CO₂H | 547.4 (M + H) | 3.69 |

-continued
| Example No. | Structure | ESI-MS | Retention Time (min) |
|---|---|---|---|
| 2502 | 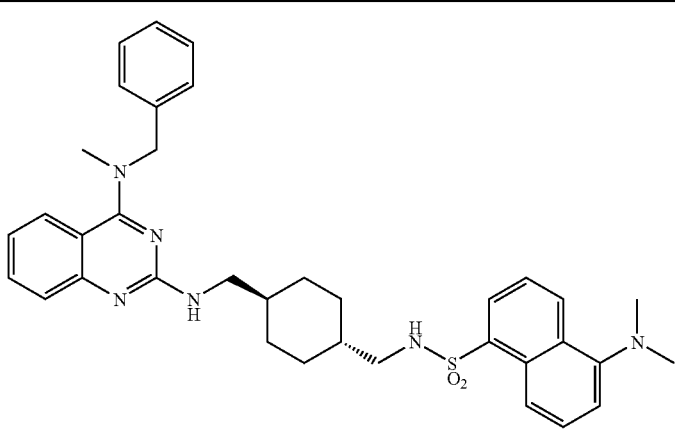 2CF₃CO₂H | 623.4 (M + H) | 4.10 |
| 2503 |  3CF₃CO₂H | 638.2 (M + H) | 3.20 |
| 2504 |  2CF₃CO₂H | 589.2 (M + H) | 3.62 |

-continued
| Example No. | Structure | ESI-MS | Retention Time (min) |
|---|---|---|---|
| 2505 | 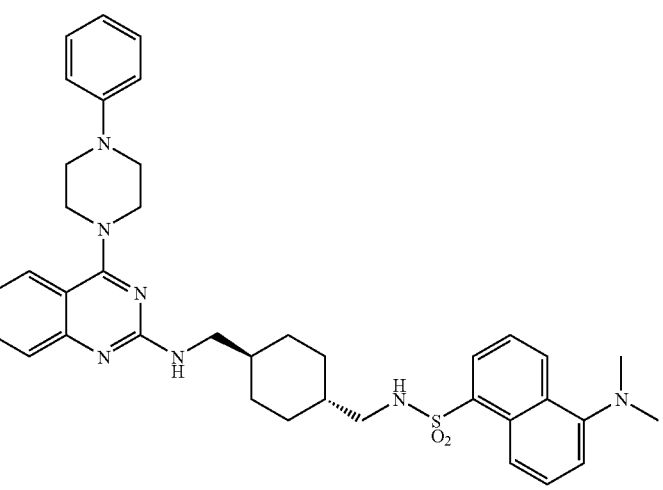 3CF$_3$CO$_2$H | 664.4 (M + H) | 4.25 |
| 2506 | 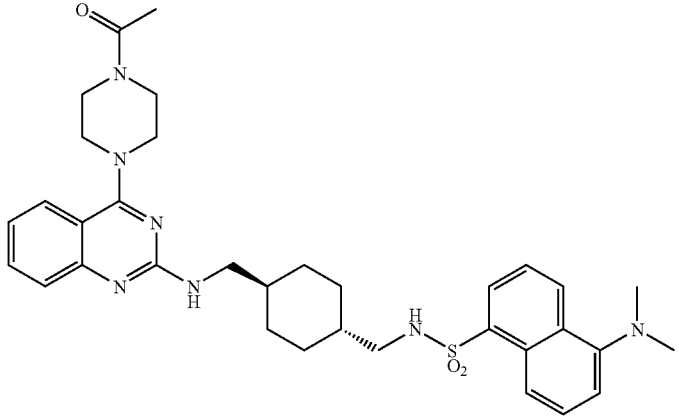 2CF$_3$CO$_2$H | 630.4 (M + H) | 3.35 |
| 2507 | 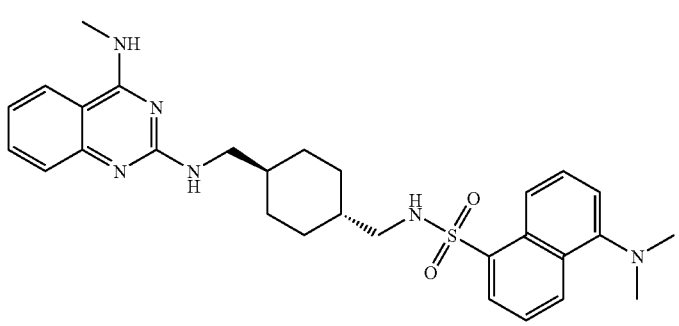 2CF$_3$CO$_2$H | 533.2 (M + H) | 3.57 |

-continued

| Example No. | Structure | ESI-MS | Retention Time (min) |
|---|---|---|---|
| 2508 | 2CF₃CO₂H | 577.6 (M + H) | 3.58 |
| 2509 | 2CF₃CO₂H | 563.2 (M + H) | 3.28 |
| 2510 | 3CF₃CO₂H | 632.6 (M + H) | 3.06 |
| 2511 | 2CF₃CO₂H | 615.4 (M + H) | 4.30 |

-continued
| Example No. | Structure | ESI-MS | Retention Time (min) |
|---|---|---|---|
| 2512 |  3CF3CO2H | 692.2 (M + H) | 3.38 |
| 2513 | 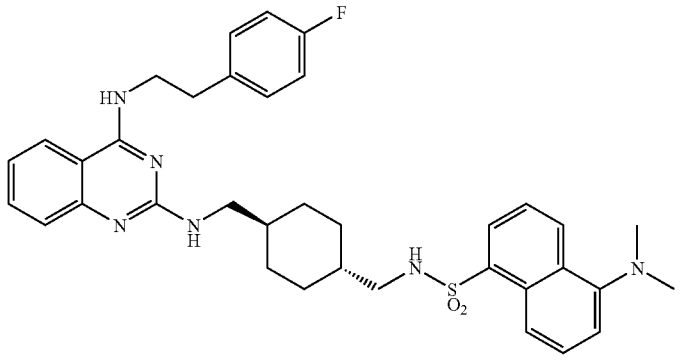 2CF3CO2H | 641.4 (M + H) | 4.13 |
| 2514 | 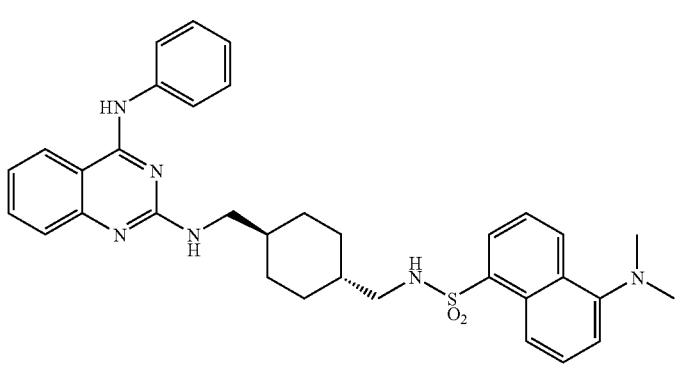 2CF3CO2H | 595.4 (M + H) | 3.89 |

-continued
| Example No. | Structure | ESI-MS | Retention Time (min) |
|---|---|---|---|
| 2515 | 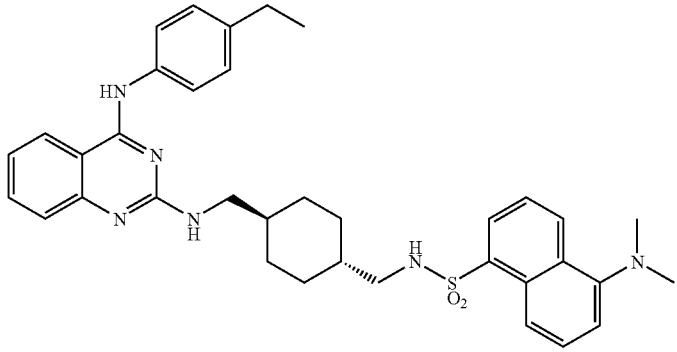 2CF₃CO₂H | 623.4 (M + H) | 4.20 |
| 2516 | 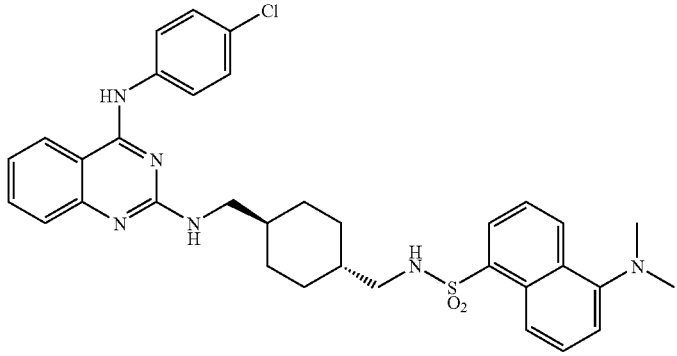 2CF3CO2H | 629.2 (M + H) | 4.15 |
| 2517 | 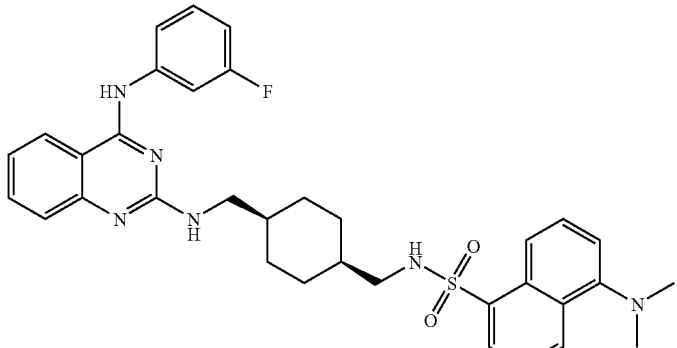 2CF₃CO₂H | 613.2 (M + H) | 4.02 |

-continued

| Example No. | Structure | ESI-MS | Retention Time (min) |
|---|---|---|---|
| 2518 | CF₃CO₂H | 528.2 (M + H) | 4.03 |
| 2519 | CF₃CO₂H | 570.2 (M + H) | 3.96 |
| 2520 | CF₃CO₂H | 611.0 (M + H) | 3.69 |

-continued

| Example No. | Structure | ESI-MS | Retention Time (min) |
|---|---|---|---|
| 2521 | 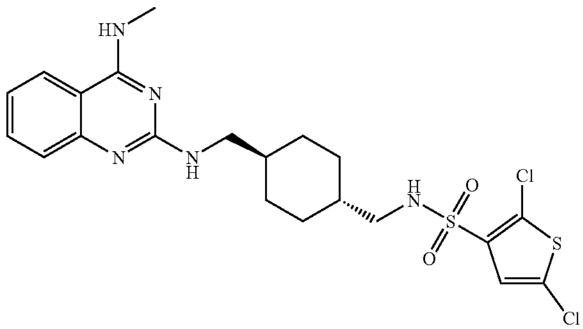 | 514.2 (M + H) | 3.94 |
| 2522 | 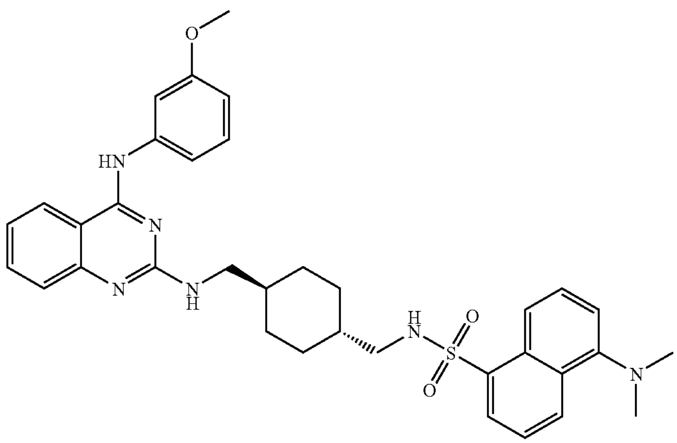 | 625.4 (M + H) | 3.94 |
| 2523 | 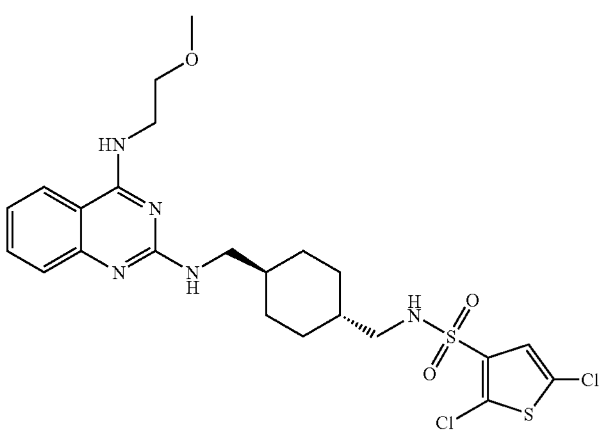 | 558.2 (M + H) | 3.96 |

-continued
| Example No. | Structure | ESI-MS | Retention Time (min) |
|---|---|---|---|
| 2524 | 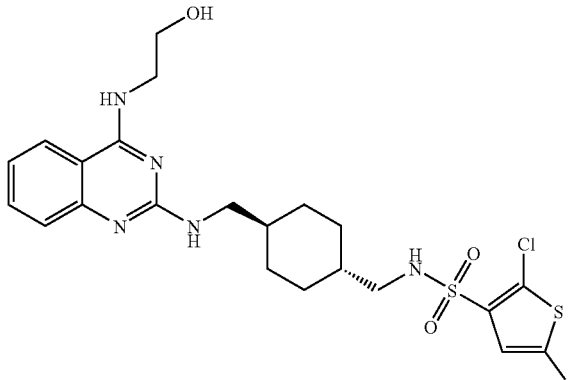 CF₃CO₂H | 544.2 (M + H) | 3.67 |
| 2525 | 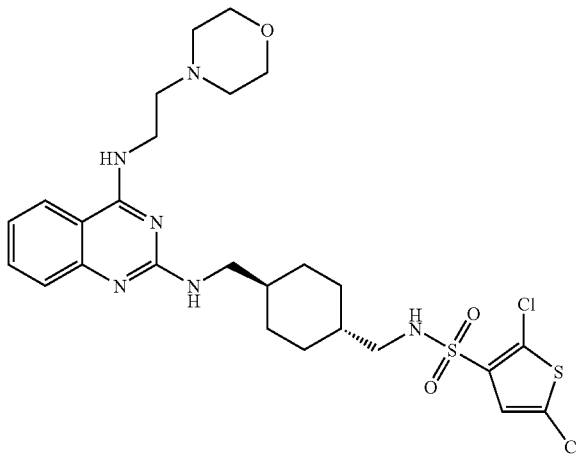 2CF₃CO₂H | 613.2 (M + H) | 3.31 |
| 2526 | 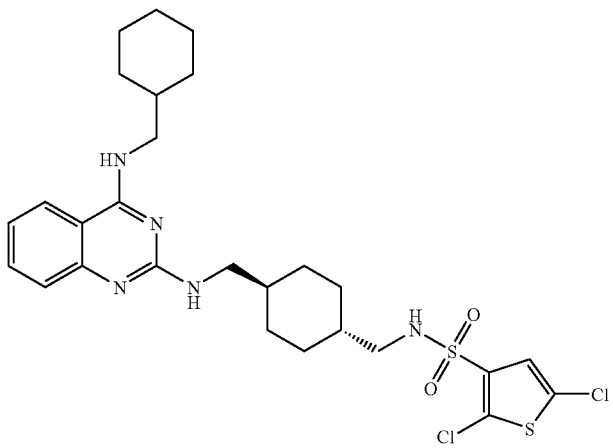 CF₃CO₂H | 596.2 (M + H) | 4.69 |

-continued
| Example No. | Structure | ESI-MS | Retention Time (min) |
|---|---|---|---|
| 2527 | 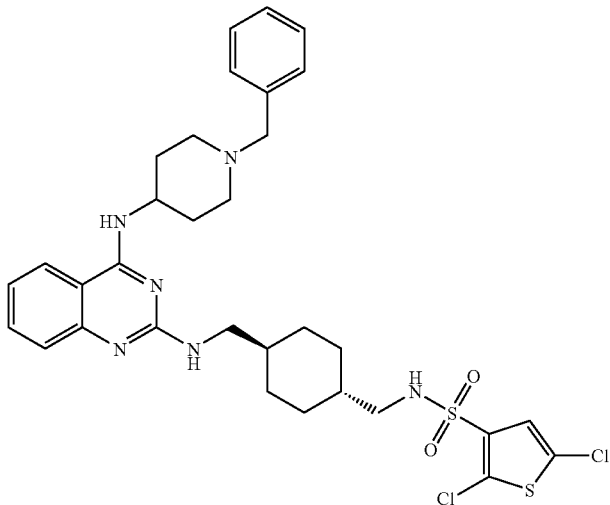 2CF₃CO₂H | 673.4 (M + H) | 3.57 |
| 2528 | 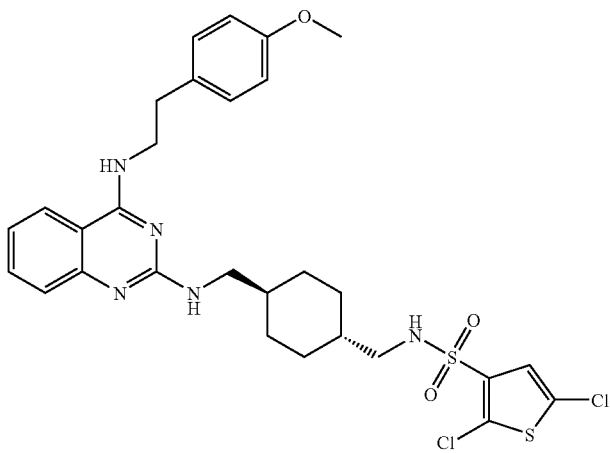 CF₃CO₂H | 634.4 (M + H) | 4.41 |

-continued

| Example No. | Structure | ESI-MS | Retention Time (min) |
|---|---|---|---|
| 2529 | 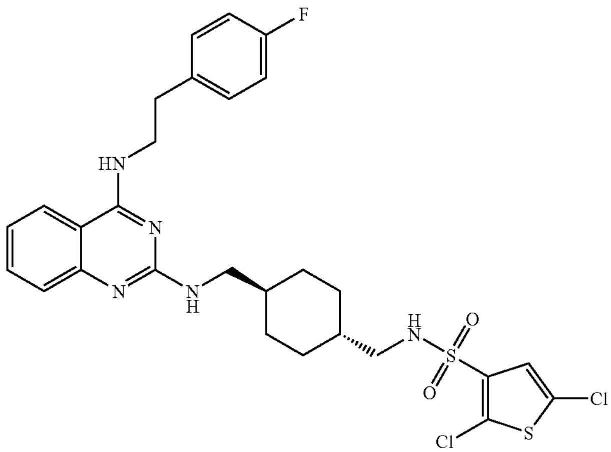 | 622.2 (M + H) | 4.45 |
| 2530 | 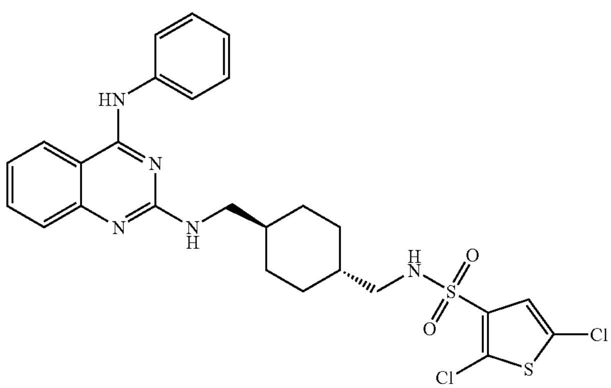 | 576 (M + H) | 4.25 |
| 2531 | 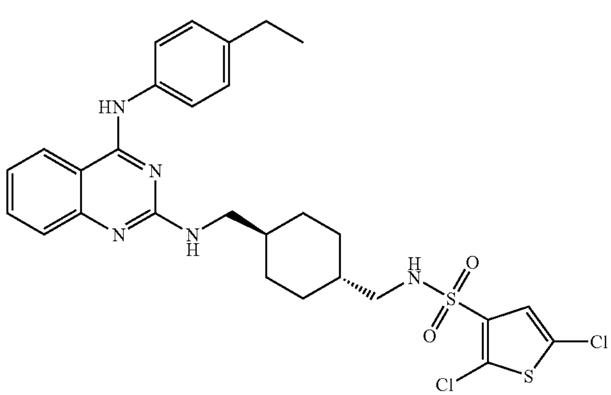 | 604.4 (M + H) | 4.52 |

-continued

| Example No. | Structure | ESI-MS | Retention Time (min) |
|---|---|---|---|
| 2532 | 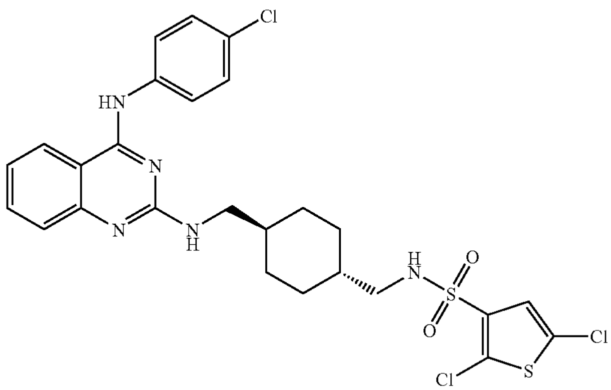 | 610.2 (M + H) | 4.40 |
| 2533 | 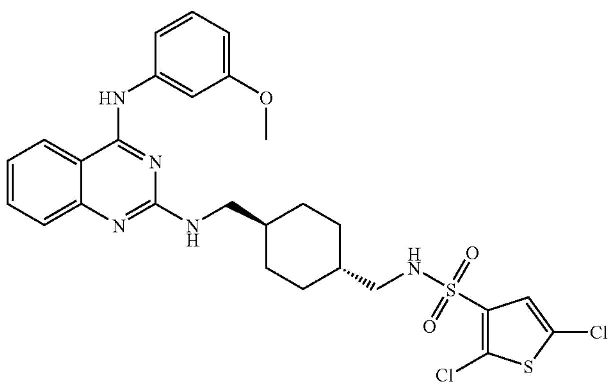 | 606.4 (M + H) | 4.29 |
| 2534 | 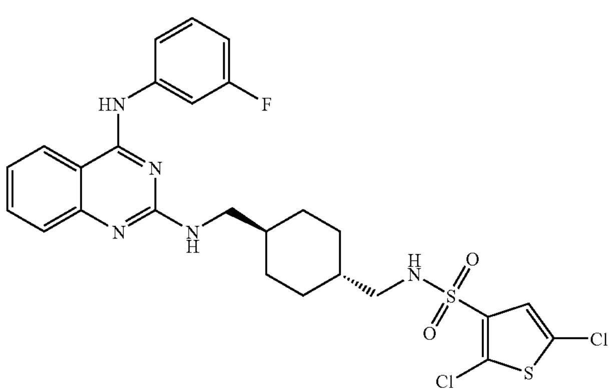 | 594.2 (M + H) | 4.27 |

-continued

| Example No. | Structure | ESI-MS | Retention Time (min) |
|---|---|---|---|
| 2535 | (4-phenylpiperazin-1-yl)quinazoline with trans-cyclohexylmethyl-NH-SO2-phenyl; 2CF3CO2H | 571.8 (M + H) | 4.99 |
| 2536 | 4-(4-sulfamoylphenethylamino)quinazoline with trans-cyclohexylmethyl-NH-SO2-phenyl; CF3CO2H | 609.8 (M + H) | 4.43 |
| 2537 | 4-(4-chlorophenylamino)quinazoline with trans-cyclohexylmethyl-NH-SO2-phenyl; CF3CO2H | 536.4 (M + H) | 4.86 |

-continued
| Example No. | Structure | ESI-MS | Retention Time (min) |
|---|---|---|---|
| 2538 | 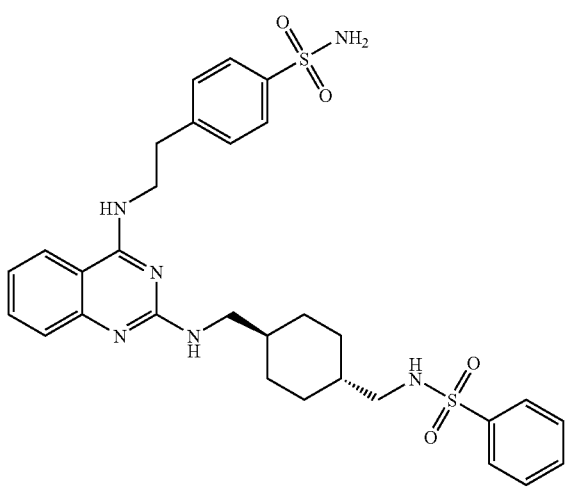<br>CF3CO2H | 564.6 (M + H) | 5.13 |
| 2539 | 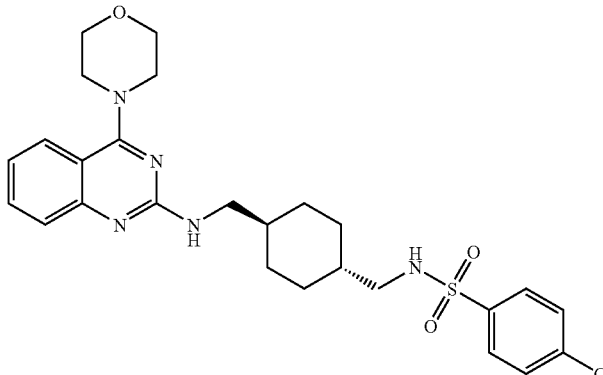<br>CF3CO2H | 530.6 (M + H) | 4.65 |
| 2540 | 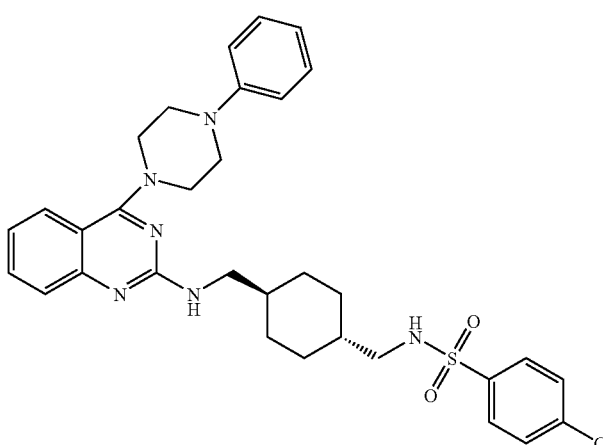<br>2CF3CO2H | 605.6 (M + H) | 5.21 |

-continued
| Example No. | Structure | ESI-MS | Retention Time (min) |
|---|---|---|---|
| 2541 | 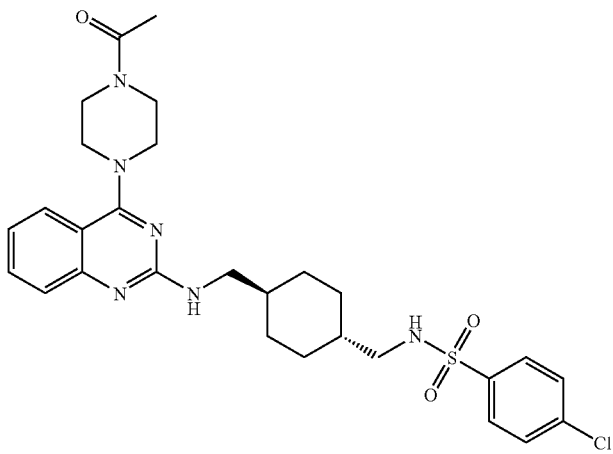 CF₃CO₂H | 571.6 (M + H) | 4.45 |
| 2542 | 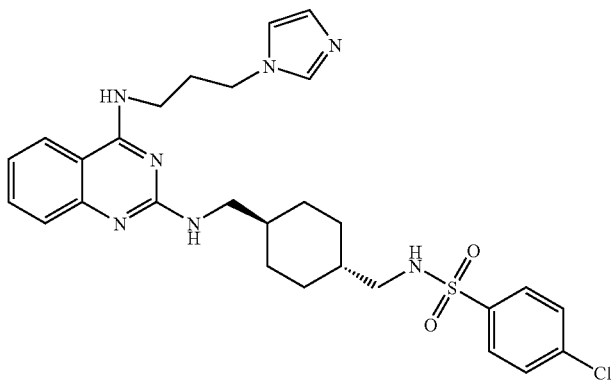 2CF₃CO₂H | 568.8 (M + H) | 4.09 |
| 2543 | 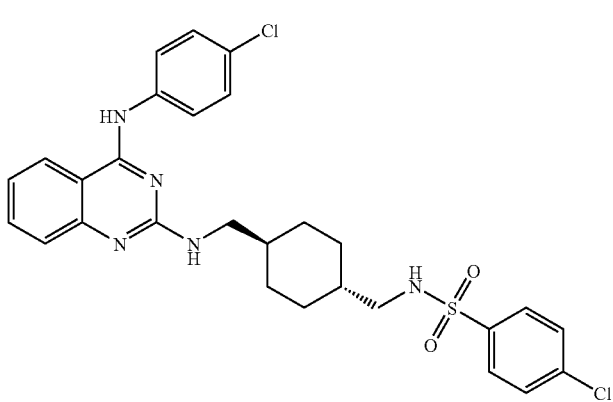 CF₃CO₂H | 570.6 (M + H) | 5.11 |

-continued

| Example No. | Structure | ESI-MS | Retention Time (min) |
|---|---|---|---|
| 2544 | 2CF₃CO₂H | 629.6 (M + H) | 4.37 |
| 2545 | 2CF₃CO₂H | 655.6 (M + H) | 5.35 |
| 2546 | CF₃CO₂H | 621.8 (M + H) | 4.63 |

-continued

| Example No. | Structure | ESI-MS | Retention Time (min) |
|---|---|---|---|
| 2547 | 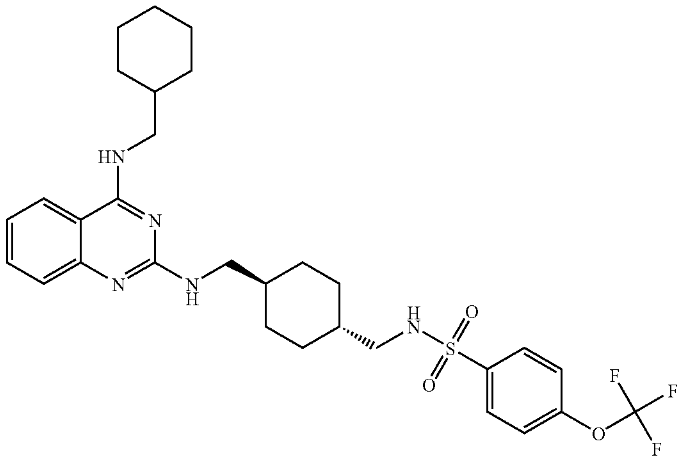 | 606.8 (M + H) | 5.45 |
| 2548 | 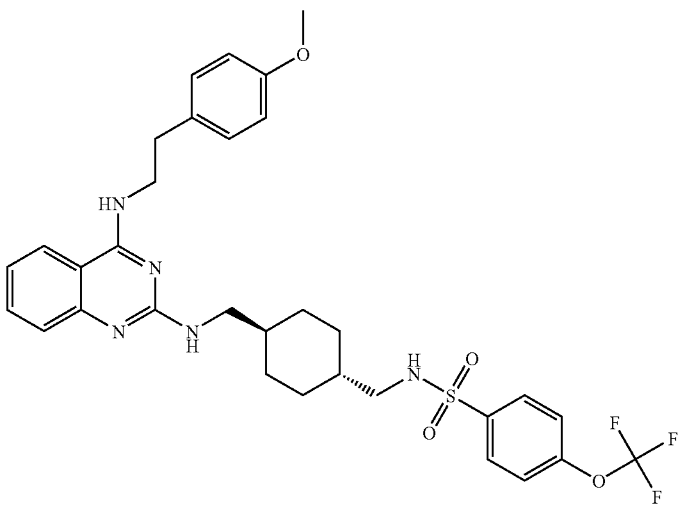 | 644.6 (M + H) | 5.21 |
| 2549 | 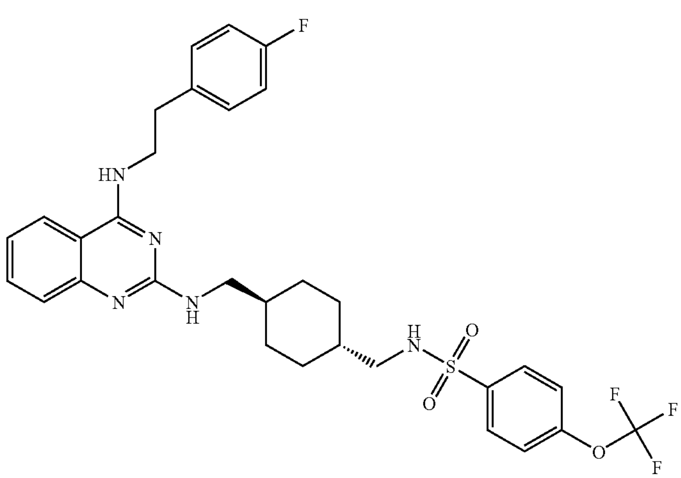 | 632.6 (M + H) | 5.25 |

-continued
| Example No. | Structure | ESI-MS | Retention Time (min) |
|---|---|---|---|
| 2550 | 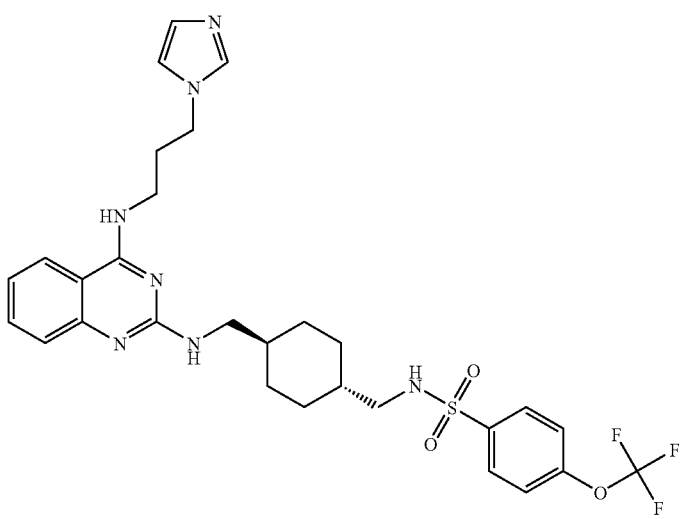 2CF₃CO₂H | 618.6 (M + H) | 4.29 |
| 2551 | 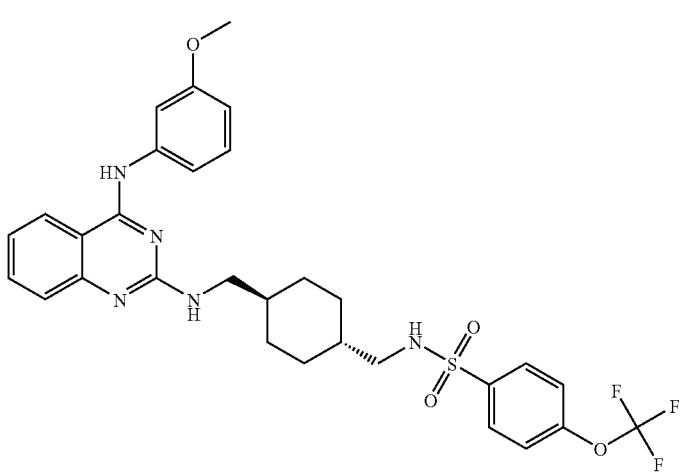 CF₃CO₂H | 616.6 (M + H) | 5.14 |

-continued
| Example No. | Structure | ESI-MS | Retention Time (min) |
|---|---|---|---|
| 2552 | 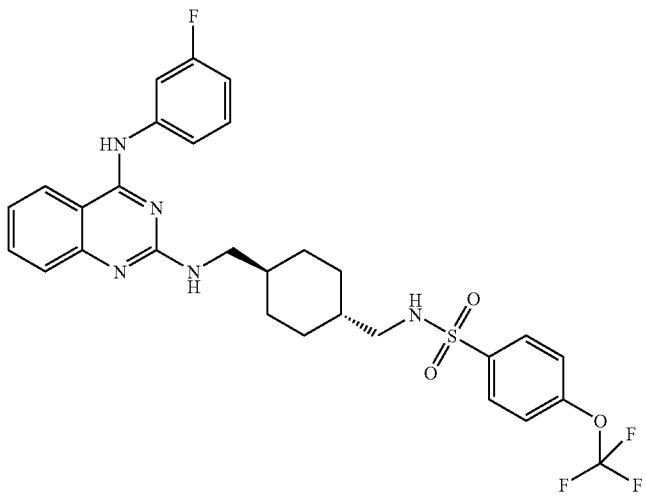 CF₃CO₂H | 604.6 (M + H) | 5.13 |
| 2553 | 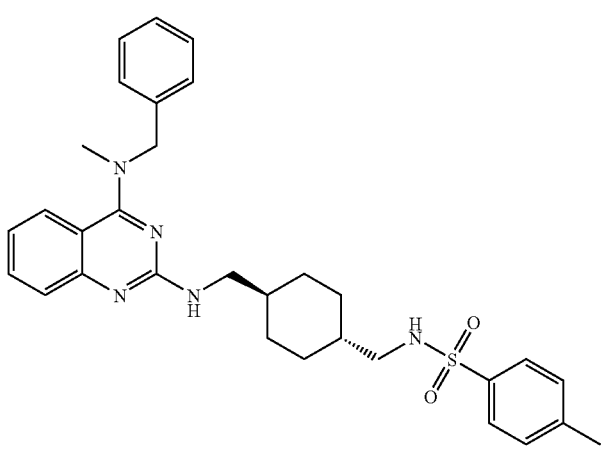 CF₃CO₂H | 544.6 (M + H) | 5.03 |
| 2554 | 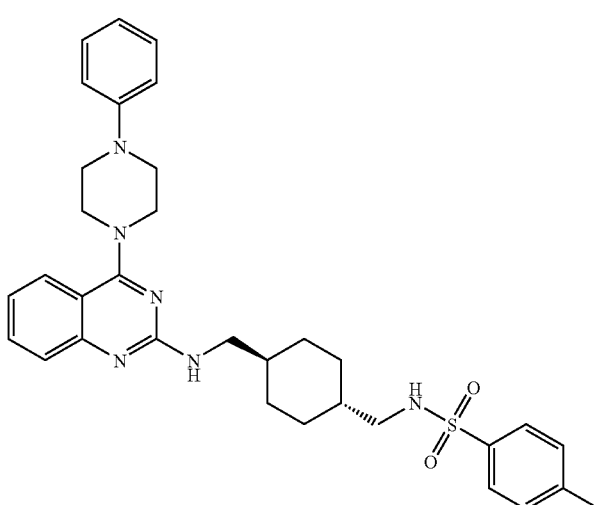 2CF₃CO₂H | 585.6 (M + H) | 5.13 |

-continued

| Example No. | Structure | ESI-MS | Retention Time (min) |
|---|---|---|---|
| 2555 | 2CF₃CO₂H | 623.6 (M + H) | 4.25 |
| 2556 | CF₃CO₂H | 574.6 (M + H) | 4.73 |
| 2557 | 2CF₃CO₂H | 649.0 (M + H) | 5.25 |

-continued
| Example No. | Structure | ESI-MS | Retention Time (min) |
|---|---|---|---|
| 2558 | 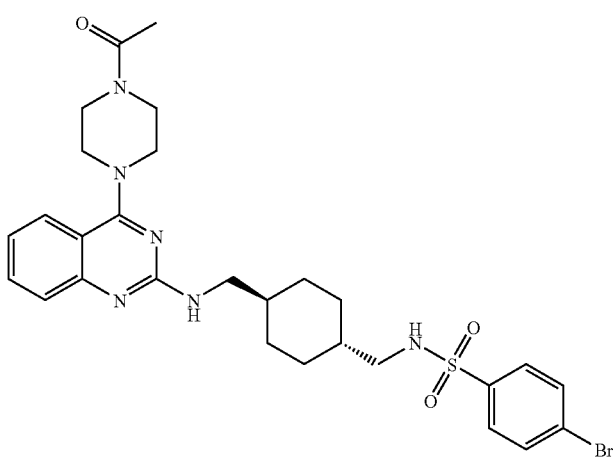 CF₃CO₂H | 615.0 (M + H) | 4.51 |
| 2559 | 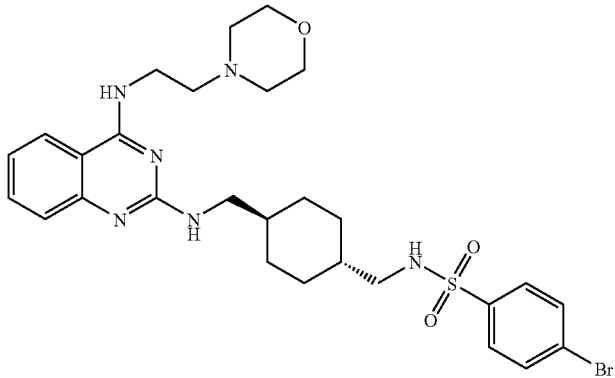 2CF₃CO₂H | 617.4 (M + H) | 4.15 |
| 2560 | 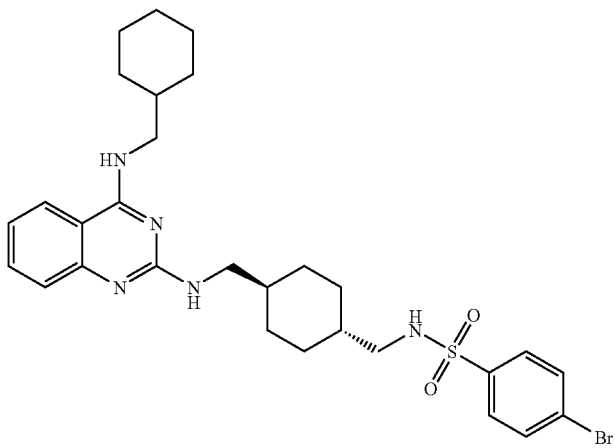 CF₃CO₂H | 600.6 (M + H) | 5.37 |

-continued
| Example No. | Structure | ESI-MS | Retention Time (min) |
|---|---|---|---|
| 2561 | 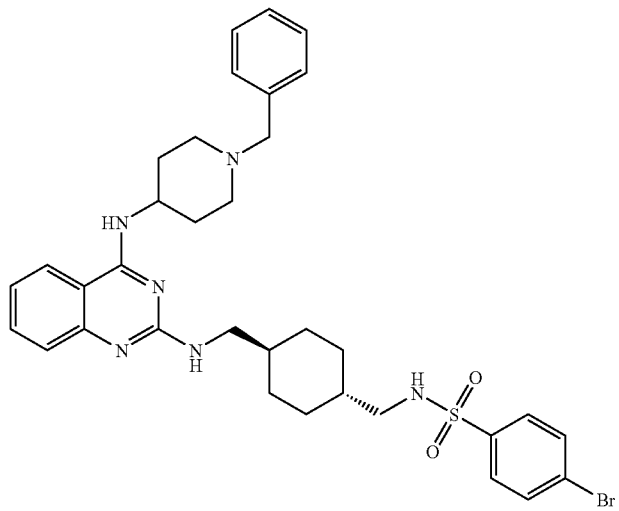 2CF$_3$CO$_2$H | 677.0 (M + H) | 4.45 |
| 2562 | 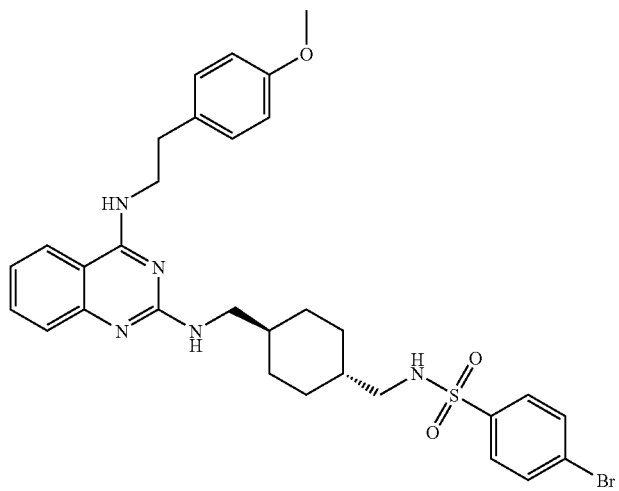 CF$_3$CO$_2$H | 638.6 (M + H) | 5.18 |

-continued
| Example No. | Structure | ESI-MS | Retention Time (min) |
|---|---|---|---|
| 2563 | 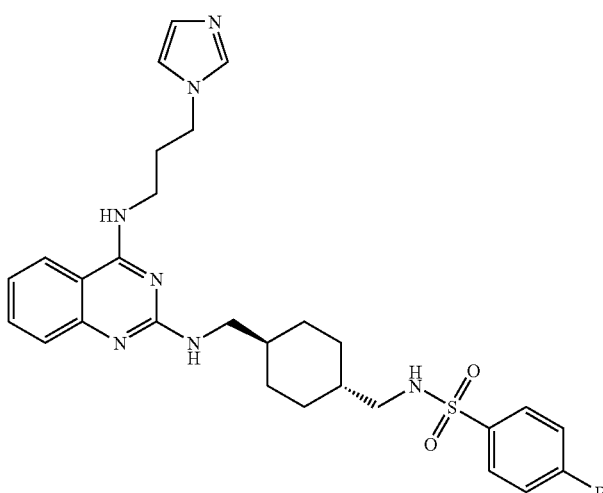 2CF₃CO₂H | 612.6 (M + H) | 4.16 |
| 2564 | 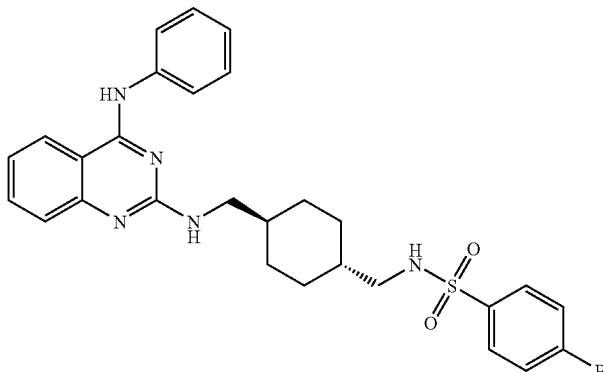 CF₃CO₂H | 580.0 (M + H) | 5.01 |
| 2565 | 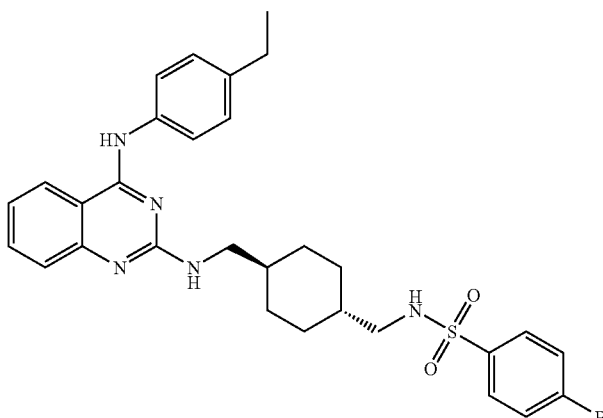 CF₃CO₂H | 608.0 (M + H) | 5.26 |

-continued
| Example No. | Structure | ESI-MS | Retention Time (min) |
|---|---|---|---|
| 2566 | 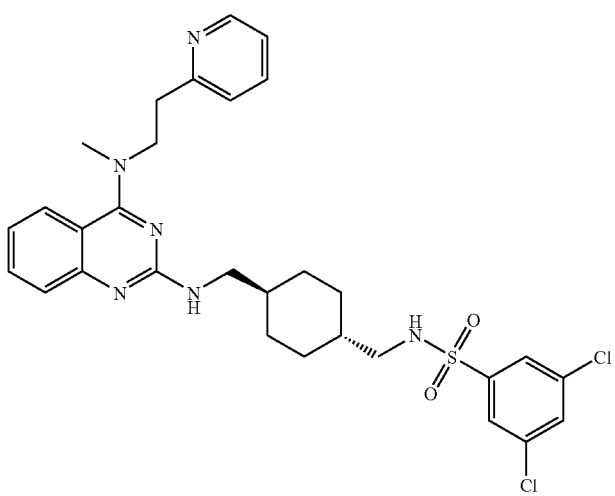<br>2CF₃CO₂H | 613.6 (M + H) | 4.44 |
| 2567 | 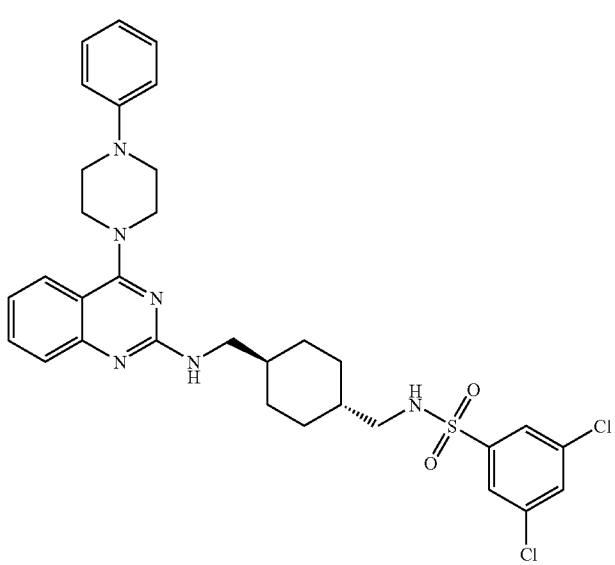<br>2CF₃CO₂H | 639.6 (M + H) | 5.48 |

-continued
| Example No. | Structure | ESI-MS | Retention Time (min) |
|---|---|---|---|
| 2568 | 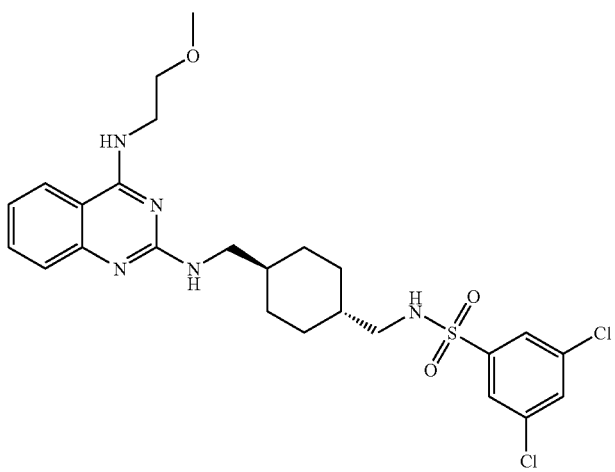 CF₃CO₂H | 552.6 (M + H) | 4.92 |
| 2569 | 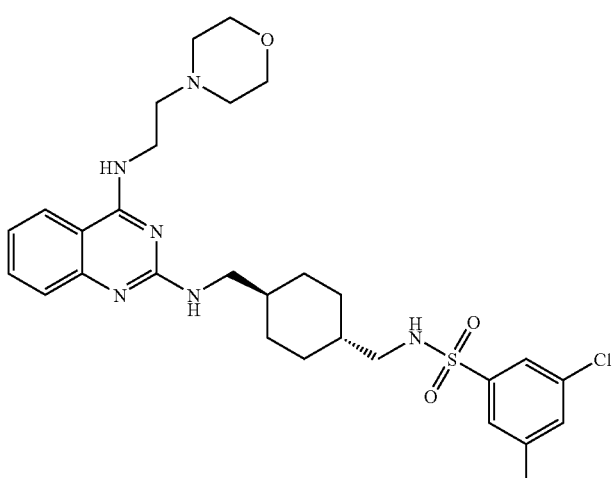 2CF₃CO₂H | 607.8 (M + H) | 4.33 |

| Example No. | Structure | ESI-MS | Retention Time (min) |
|---|---|---|---|
| 2570 | 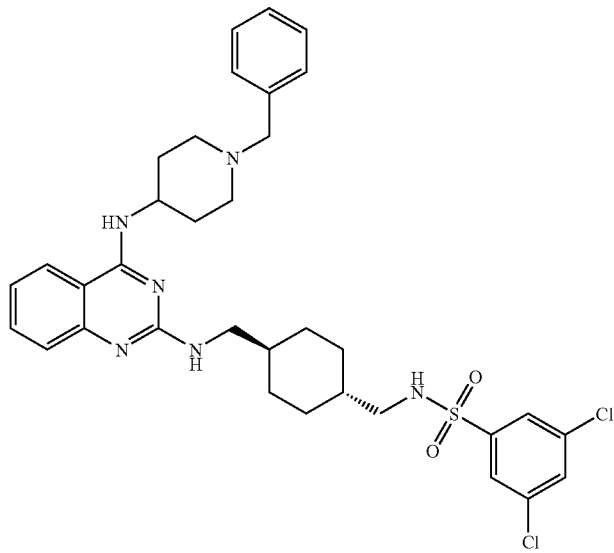  2CF₃CO₂H | 667.4 (M + H) | 4.67 |
| 2571 | 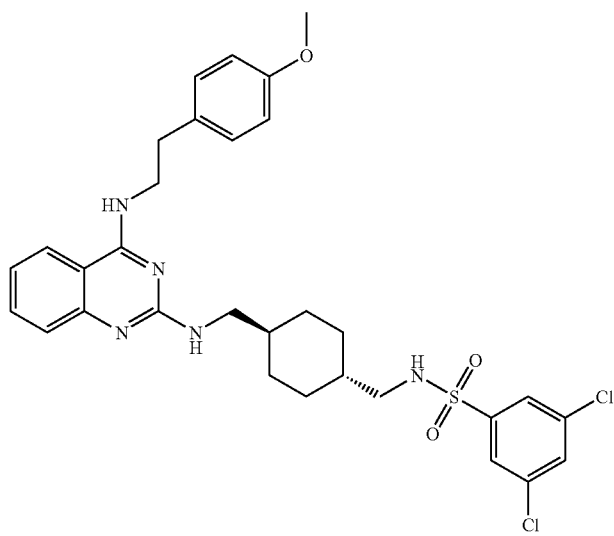  CF₃CO₂H | 628.6 (M + H) | 5.29 |

-continued
| Example No. | Structure | ESI-MS | Retention Time (min) |
|---|---|---|---|
| 2572 | 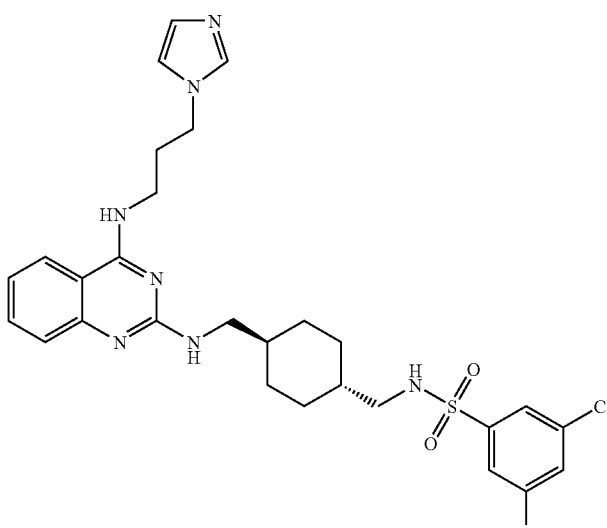 2CF₃CO₂H | 602.6 (M + H) | 4.35 |
| 2573 | 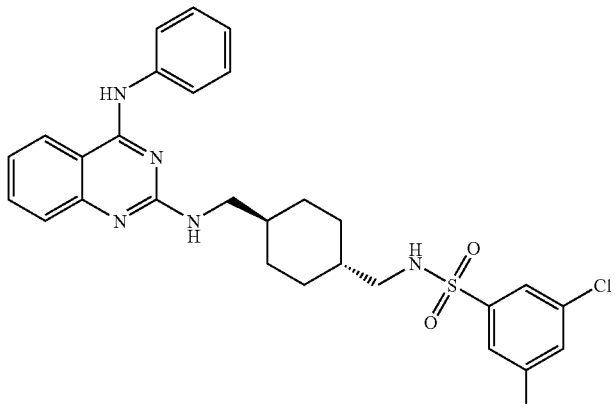 CF₃CO₂H | 570.6 (M + H) | 5.23 |

-continued
| Example No. | Structure | ESI-MS | Retention Time (min) |
|---|---|---|---|
| 2574 | 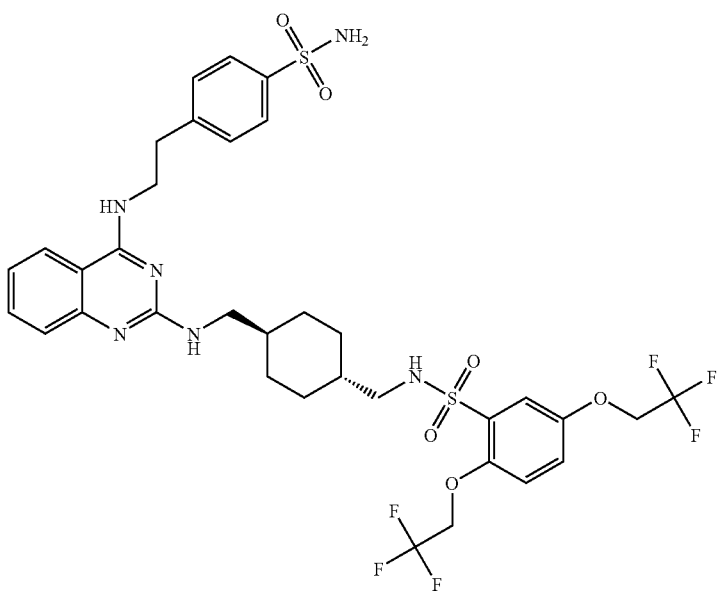 CF₃CO₂H | 805.4 (M + H) | 4.91 |
| 2575 |  2CF₃CO₂H | 730.8 (M + H) | 4.47 |

-continued
| Example No. | Structure | ESI-MS | Retention Time (min) |
|---|---|---|---|
| 2576 | 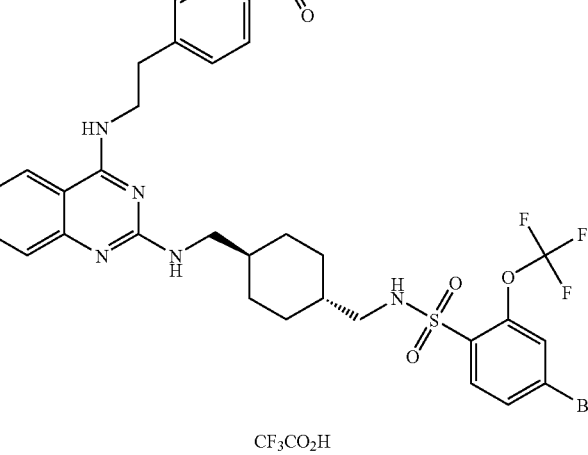 CF₃CO₂H | 771.6 (M + H) | 4.93 |
| 2577 | 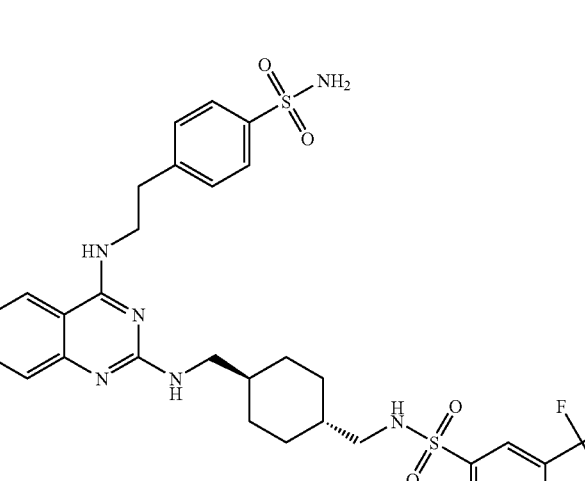 CF₃CO₂H | 745.6 (M + H) | 5.01 |

-continued

| Example No. | Structure | ESI-MS | Retention Time (min) |
|---|---|---|---|
| 2578 | CF₃CO₂H | 580.8 (M + H) | 5.18 |
| 2579 | 2CF₃CO₂H | 621.8 (M + H) | 5.27 |
| 2580 | CF₃CO₂H | 587.6 (M + H) | 4.51 |

-continued
| Example No. | Structure | ESI-MS | Retention Time (min) |
|---|---|---|---|
| 2581 | 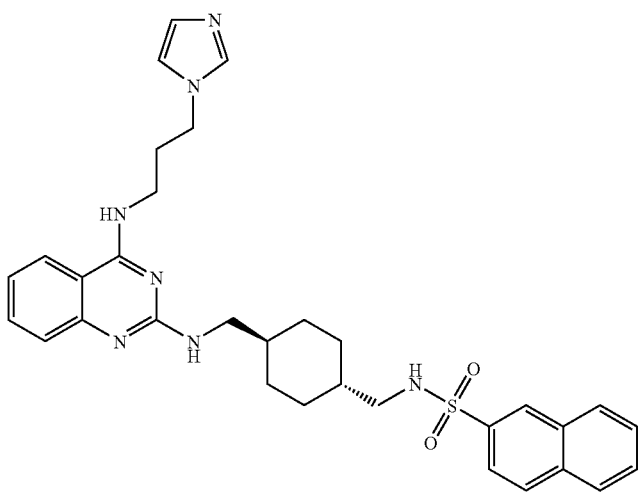 2CF₃CO₂H | 584.6 (M + H) | 4.21 |
| 2582 | 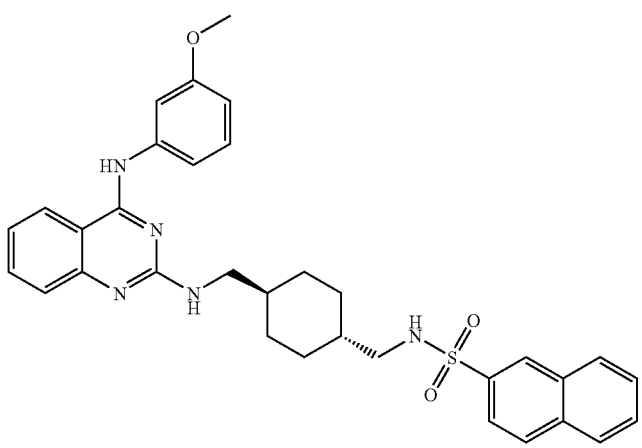 CF₃CO₂H | 582.8 (M + H) | 5.03 |

-continued
| Example No. | Structure | ESI-MS | Retention Time (min) |
|---|---|---|---|
| 2583 | 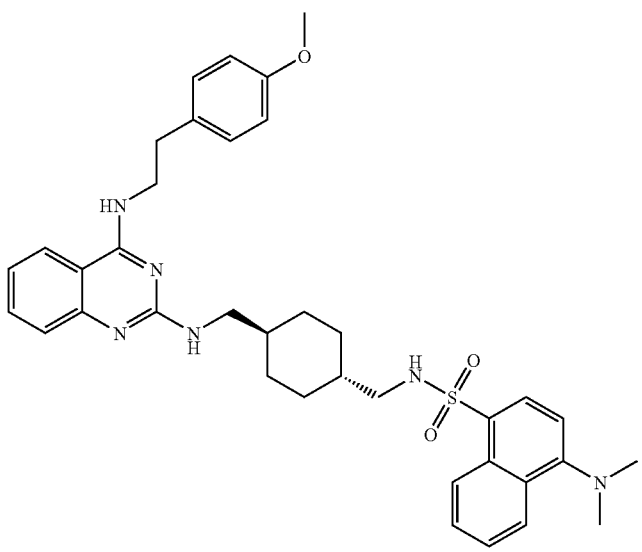 CF₃CO₂H | 653.8 (M + H) | 4.92 |
| 2584 | 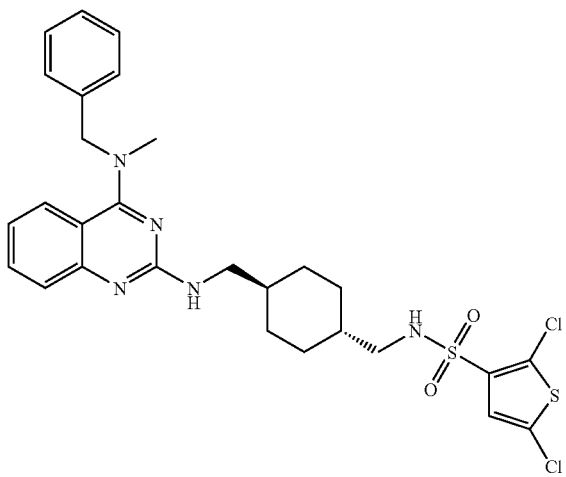 CF₃CO₂H | 604.6 (M + H) | 5.33 |

-continued
| Example No. | Structure | ESI-MS | Retention Time (min) |
|---|---|---|---|
| 2585 | 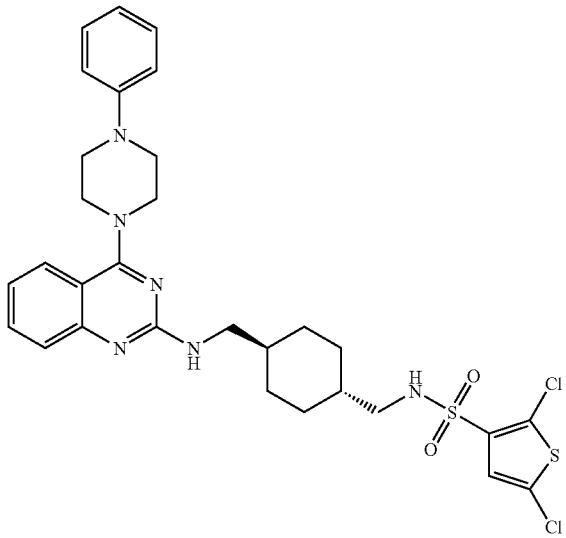 2CF₃CO₂H | 645.6 (M + H) | 5.41 |
| 2586 | 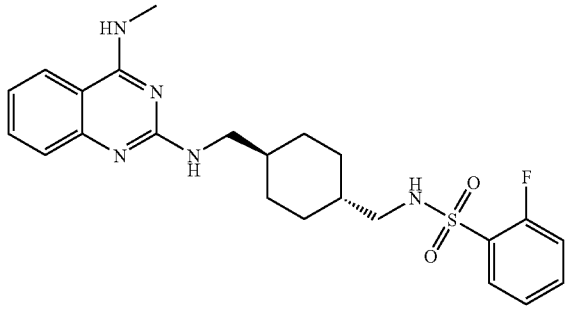 CF₃CO₂H | 458.6 (M + H) | 4.39 |
| 2587 | 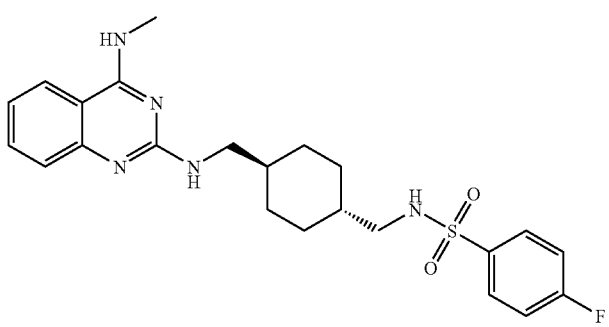 CF₃CO₂H | 458.6 (M + H) | 4.40 |

-continued

| Example No. | Structure | ESI-MS | Retention Time (min) |
|---|---|---|---|
| 2588 | *structure*; CF$_3$CO$_2$H | 474.6 (M + H) | 4.39 |
| 2589 | *structure*; CF$_3$CO$_2$H | 474.6 (M + H) | 4.58 |
| 2590 | *structure*; CF$_3$CO$_2$H | 542.6 (M + H) | 4.79 |
| 2591 | *structure*; CF$_3$CO$_2$H | 518.6 (M + H) | 4.51 |

-continued
| Example No. | Structure | ESI-MS | Retention Time (min) |
|---|---|---|---|
| 2592 | 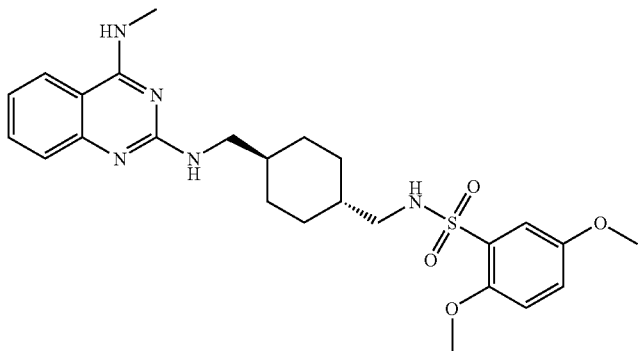 CF₃CO₂H | 500.8 (M + H) | 4.33 |
| 2593 | 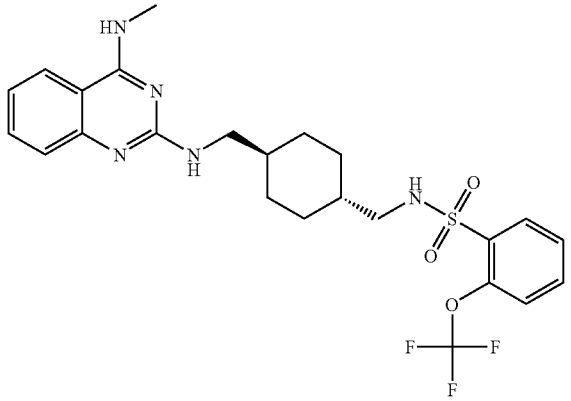 CF₃CO₂H | 524.6 (M + H) | 4.61 |
| 2594 | 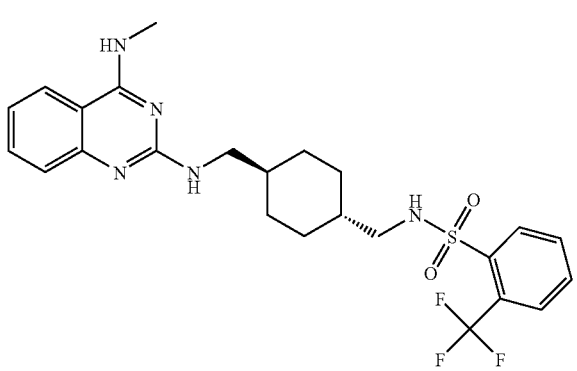 CF₃CO₂H | 508.6 (M + H) | 4.57 |

-continued

| Example No. | Structure | ESI-MS | Retention Time (min) |
|---|---|---|---|
| 2595 | (4-methylamino-quinazolin-2-yl)aminomethyl-cyclohexyl-methyl-N-(4-tert-butylbenzenesulfonyl)amide · $CF_3CO_2H$ | 496.8 (M + H) | 4.87 |
| 2596 | (4-methylamino-quinazolin-2-yl)aminomethyl-cyclohexyl-methyl-N-(thiophene-2-sulfonyl)amide · $CF_3CO_2H$ | 446.8 (M + H) | 4.29 |
| 2597 | (4-dimethylamino-quinazolin-2-yl)aminomethyl-cyclohexyl-methyl-N-(2-fluorobenzenesulfonyl)amide · $CF_3CO_2H$ | 472.8 (M + H) | 4.47 |
| 2598 | (4-dimethylamino-quinazolin-2-yl)aminomethyl-cyclohexyl-methyl-N-(4-fluorobenzenesulfonyl)amide · $CF_3CO_2H$ | 472.8 (M + H) | 4.53 |

-continued

| Example No. | Structure | ESI-MS | Retention Time (min) |
|---|---|---|---|
| 2599 | CF₃CO₂H | 488.6 (M + H) | 4.55 |
| 2600 | CF₃CO₂H | 487.6 (M + H) | 4.65 |
| 2601 | CF₃CO₂H | 556.6 (M + H) | 4.91 |
| 2602 | CF₃CO₂H | 523.4 (M + H) | 4.61 |

-continued
| Example No. | Structure | ESI-MS | Retention Time (min) |
|---|---|---|---|
| 2603 | 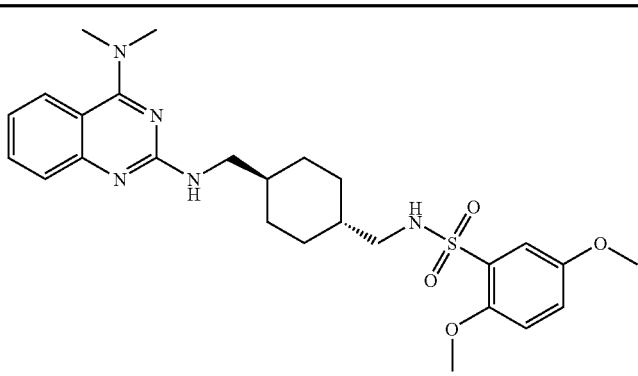 CF₃CO₂H | 514.8 (M + H) | 4.43 |
| 2604 | 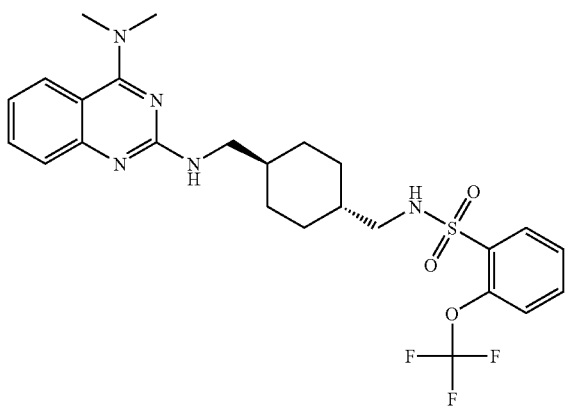 CF₃CO₂H | 538.6 (M + H) | 4.80 |
| 2605 | 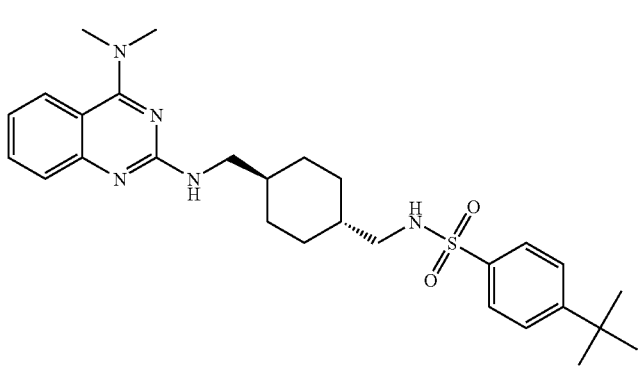 CF₃CO₂H | 510.6 (M + H) | 5.00 |

-continued
| Example No. | Structure | ESI-MS | Retention Time (min) |
|---|---|---|---|
| 2606 | 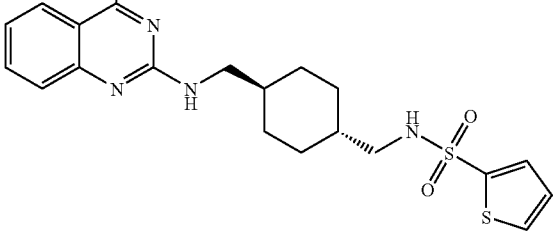<br>CF$_3$CO$_2$H | 460.6 (M + H) | 4.40 |
| 2607 | 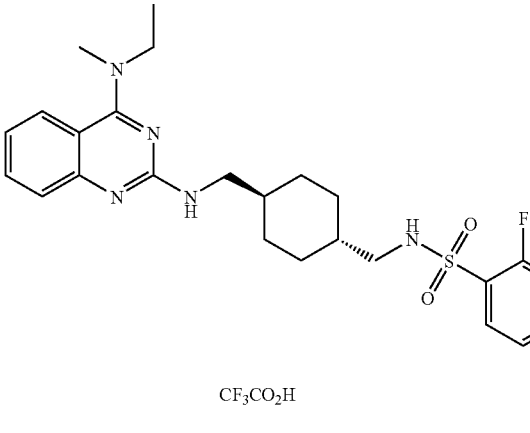<br>CF$_3$CO$_2$H | 486.6 (M + H) | 4.60 |
| 2608 | 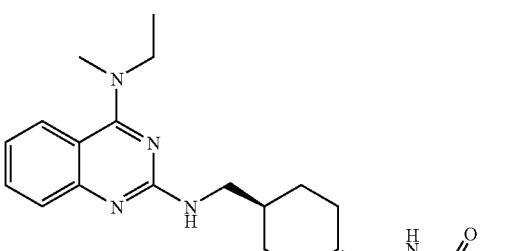<br>CF$_3$CO$_2$H | 484.6 (M + H) | 4.64 |

-continued

| Example No. | Structure | ESI-MS | Retention Time (min) |
|---|---|---|---|
| 2609 | CF₃CO₂H | 503.6 (M + H) | 4.74 |
| 2610 | CF₃CO₂H | 502.6 (M + H) | 4.86 |
| 2611 | CF₃CO₂H | 570.8 (M + H) | 5.00 |

-continued
| Example No. | Structure | ESI-MS | Retention Time (min) |
|---|---|---|---|
| 2612 | 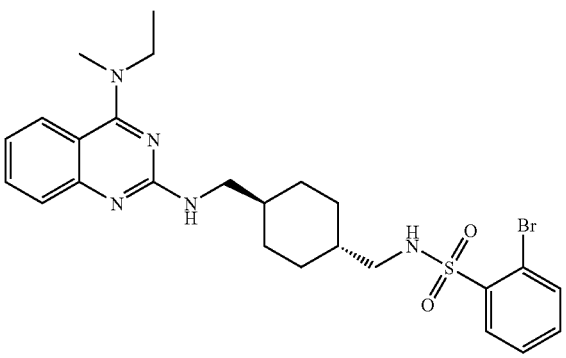 CF₃CO₂H | 546.0 (M + H) | 4.80 |
| 2613 | 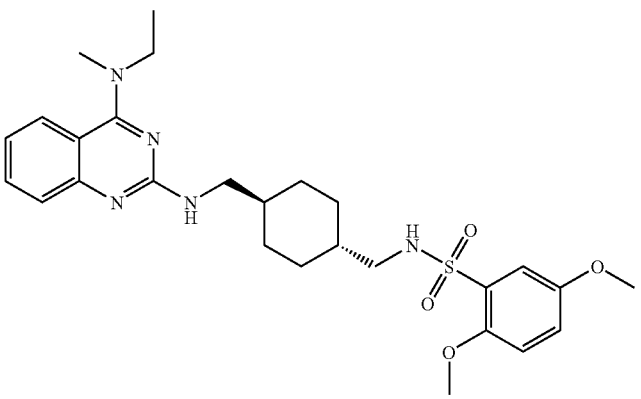 CF₃CO₂H | 528.8 (M + H) | 4.63 |
| 2614 | 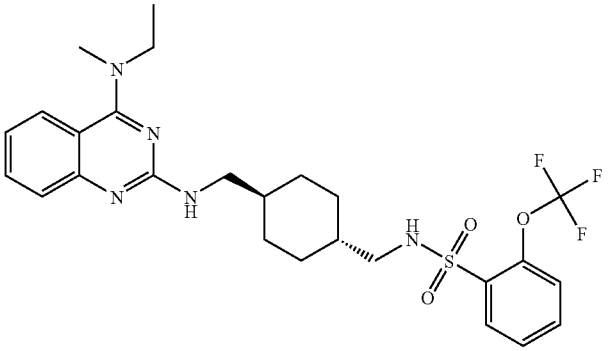 CF₃CO₂H | 552.8 (M + H) | 4.90 |

-continued

| Example No. | Structure | ESI-MS | Retention Time (min) |
|---|---|---|---|
| 2615 | CF₃CO₂H | 536.6 (M + H) | 4.82 |
| 2616 | CF₃CO₂H | 524.8 (M + H) | 5.07 |
| 2617 | CF₃CO₂H | 474.6 (M + H) | 4.55 |

-continued

| Example No. | Structure | ESI-MS | Retention Time (min) |
|---|---|---|---|
| 2618 | CF$_3$CO$_2$H | 486.4 (M + H) | 4.59 |
| 2619 | CF$_3$CO$_2$H | 502.6 (M + H) | 4.81 |
| 2620 | CF$_3$CO$_2$H | 552.8 (M + H) | 4.94 |

-continued
| Example No. | Structure | ESI-MS | Retention Time (min) |
|---|---|---|---|
| 2621 |  CF₃CO₂H | 482.6 (M + H) | 4.73 |
| 2622 | 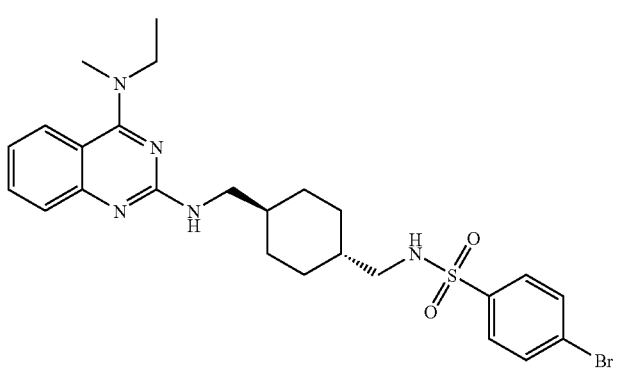 CF₃CO₂H | 546.6 (M + H) | 4.85 |
| 2623 | 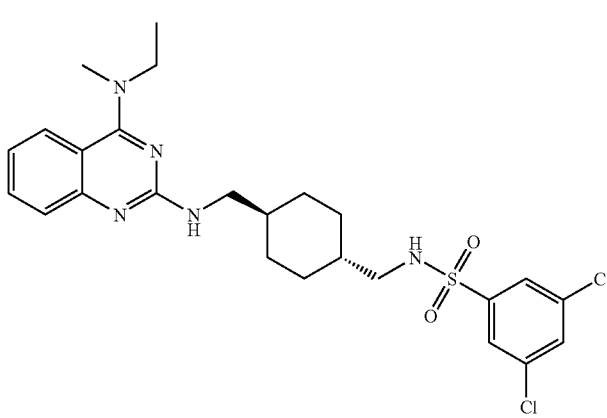 CF₃CO₂H | 536.4 (M + H) | 5.08 |

| Example No. | Structure | ESI-MS | Retention Time (min) |
|---|---|---|---|
| 2624 | *structure with CF₃CO₂H* | 630.4 (M + H) | 5.11 |
| 2625 | *structure with CF₃CO₂H* | 604.6 (M + H) | 5.16 |
| 2626 | *structure with CF₃CO₂H* | 518.6 (M + H) | 4.75 |

-continued
| Example No. | Structure | ESI-MS | Retention Time (min) |
|---|---|---|---|
| 2627 | 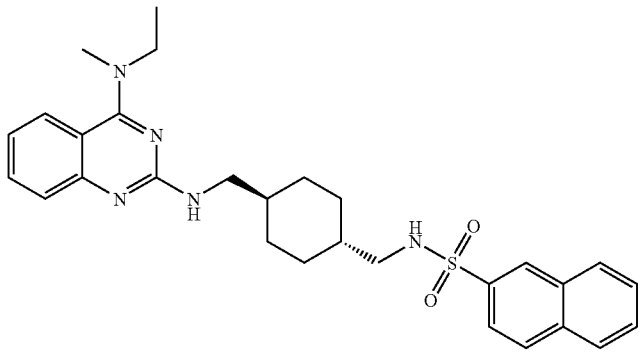 CF$_3$CO$_2$H | 518.6 (M + H) | 4.91 |
| 2628 | 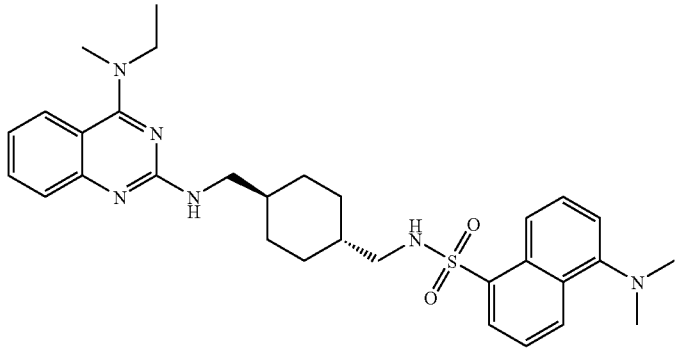 CF$_3$CO$_2$H | 561.6 (M + H) | 4.61 |
| 2629 | 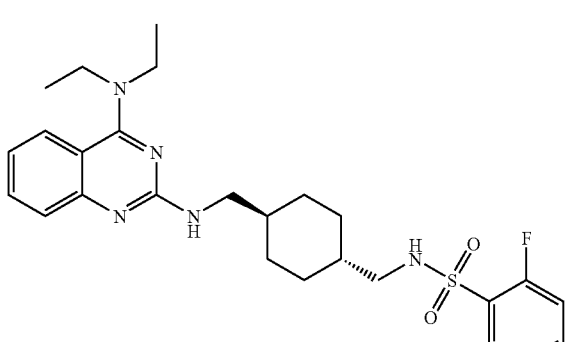 CF$_3$CO$_2$H | 500.8 (M + H) | 4.75 |

-continued
| Example No. | Structure | ESI-MS | Retention Time (min) |
|---|---|---|---|
| 2630 | 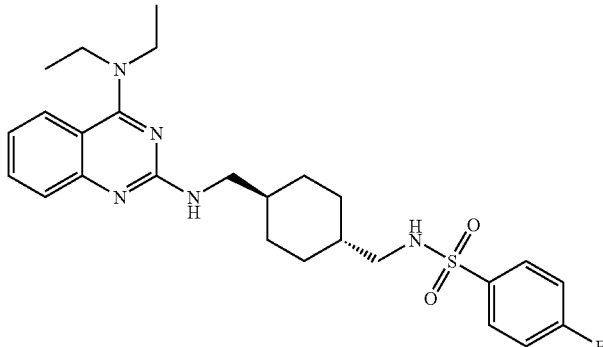 CF$_3$CO$_2$H | 500.2 (M + H) | 4.85 |
| 2631 | 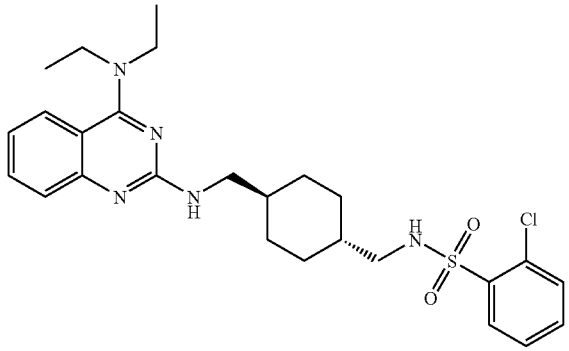 CF$_3$CO$_2$H | 516.6 (M + H) | 4.81 |
| 2632 | 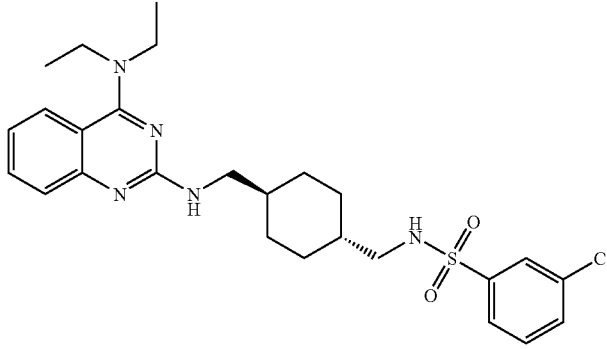 CF$_3$CO$_2$H | 516.6 (M + H) | 4.95 |

| Example No. | Structure | ESI-MS | Retention Time (min) |
|---|---|---|---|
| 2633 | 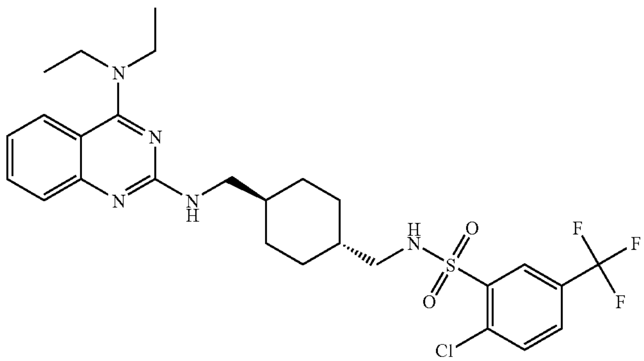 | 584.6 (M + H) | 5.18 |
| 2634 | 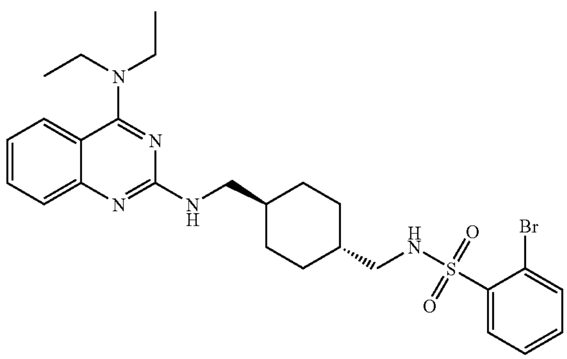 | 560.6 (M + H) | 4.87 |
| 2635 | 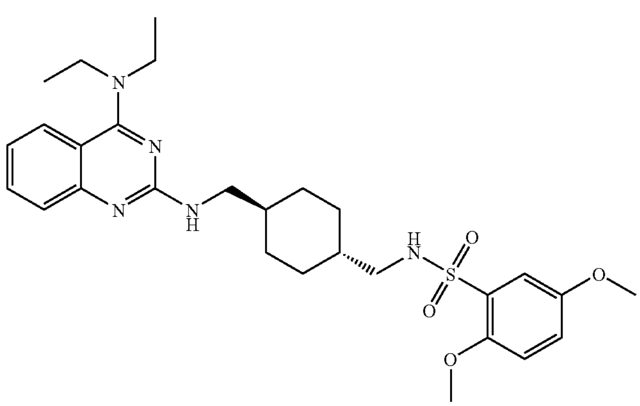 | 542.8 (M + H) | 4.80 |

-continued

| Example No. | Structure | ESI-MS | Retention Time (min) |
|---|---|---|---|
| 2636 | 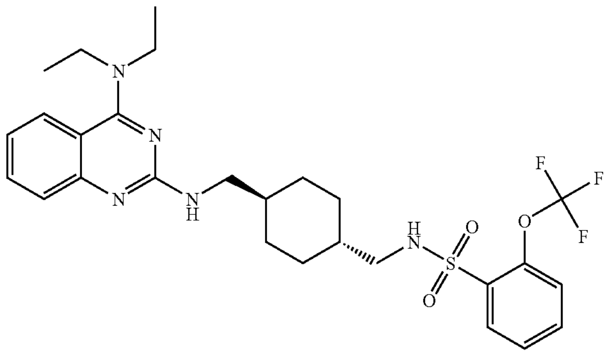 | 566.6 (M + H) | 5.01 |
| 2637 | 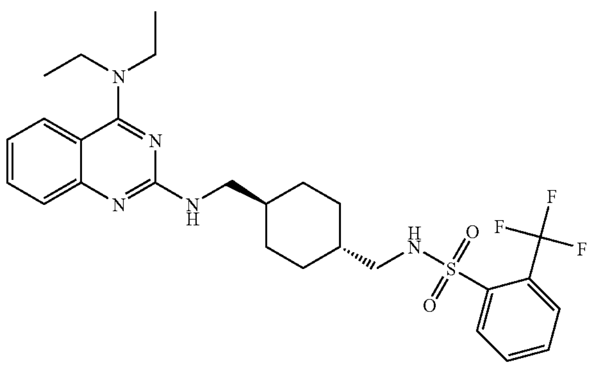 | 550.8 (M + H) | 4.95 |
| 2638 | 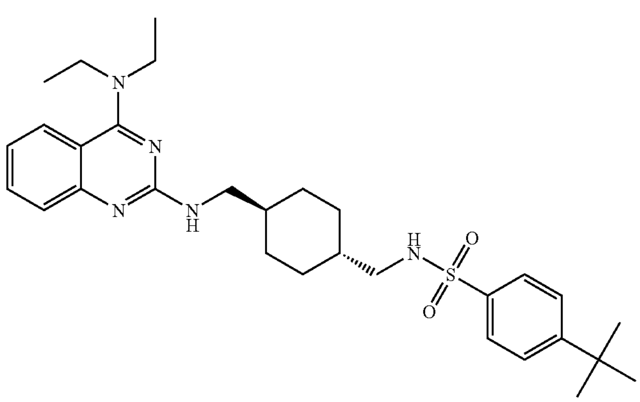 | 538.6 (M + H) | 5.20 |

-continued
| Example No. | Structure | ESI-MS | Retention Time (min) |
|---|---|---|---|
| 2639 | 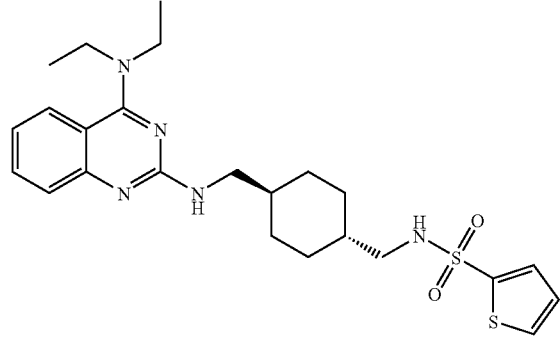 CF₃CO₂H | 488.6 (M + H) | 4.65 |
| 2640 | 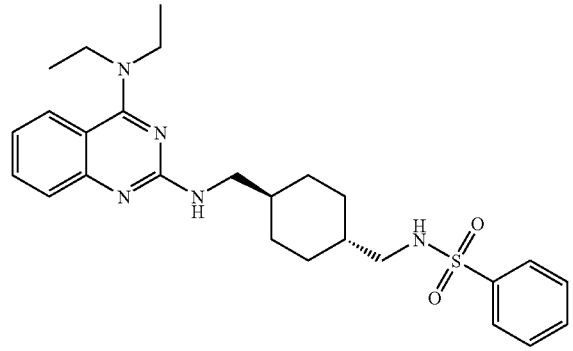 CF₃CO₂H | 482.6 (M + H) | 4.73 |
| 2641 | 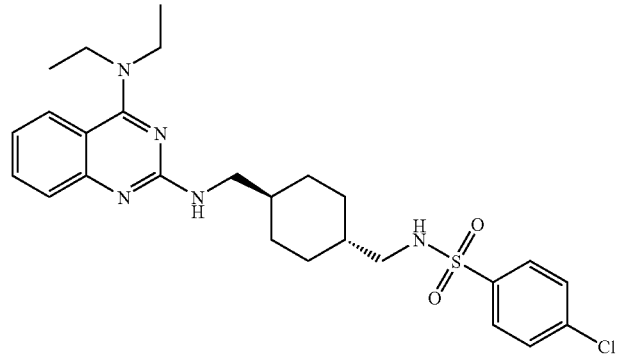 CF₃CO₂H | 516.8 (M + H) | 4.97 |
| 2642 | 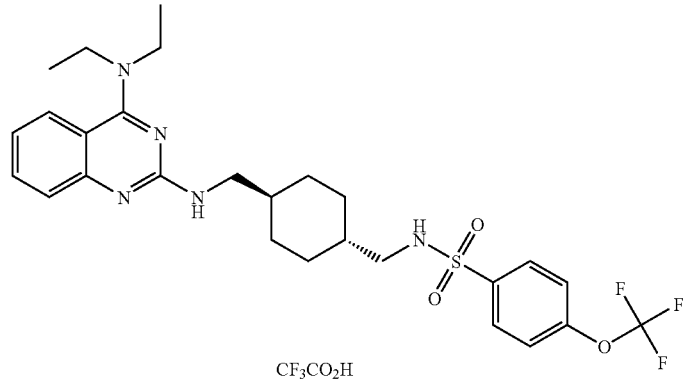 CF₃CO₂H | 566.6 (M + H) | 5.12 |

-continued
| Example No. | Structure | ESI-MS | Retention Time (min) |
|---|---|---|---|
| 2643 | 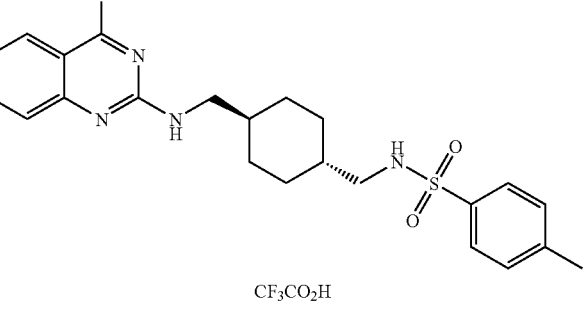 CF$_3$CO$_2$H | 496.8 (M + H) | 4.89 |
| 2644 | 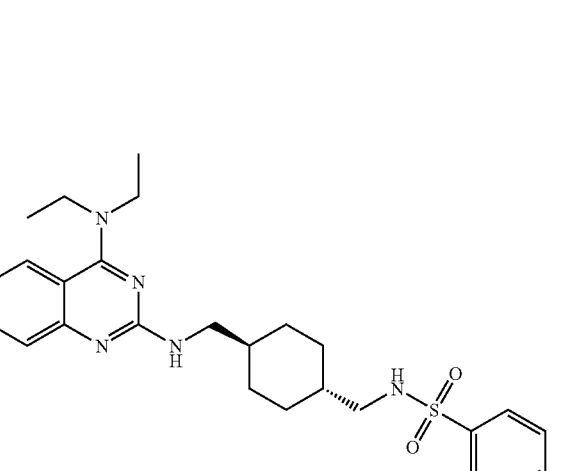 CF$_3$CO$_2$H | 560.0 (M + H) | 4.98 |
| 2645 | 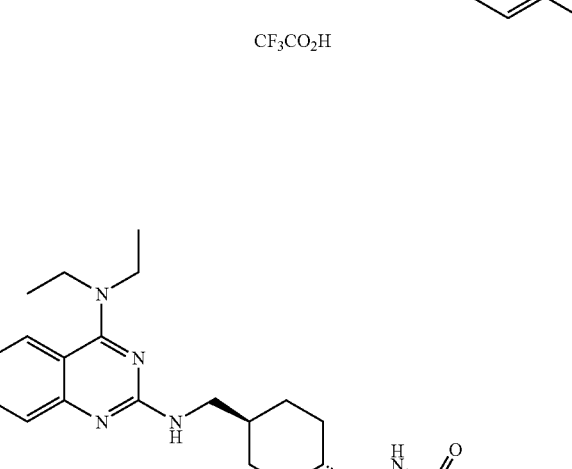 CF$_3$CO$_2$H | 550.6 (M + H) | 5.21 |

-continued
| Example No. | Structure | ESI-MS | Retention Time (min) |
|---|---|---|---|
| 2646 | 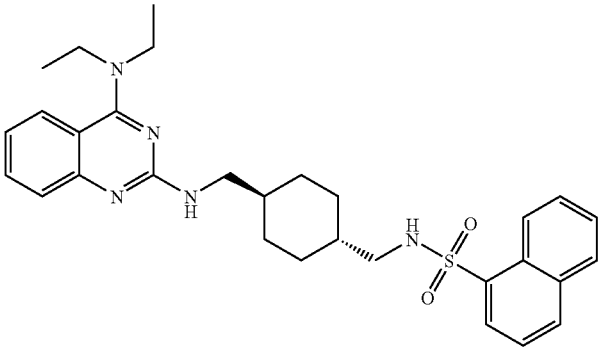 CF₃CO₂H | 532.6 (M + H) | 4.99 |
| 2647 | 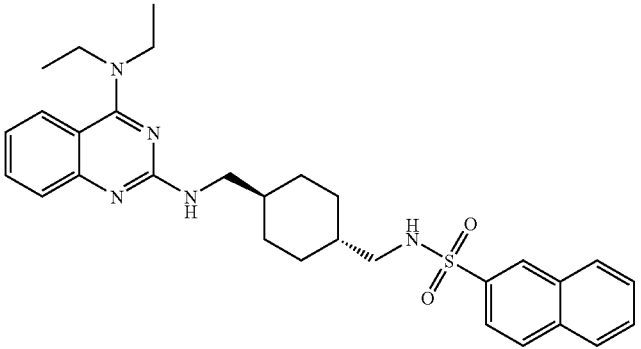 CF₃CO₂H | 532.6 (M + H) | 5.03 |
| 2648 | 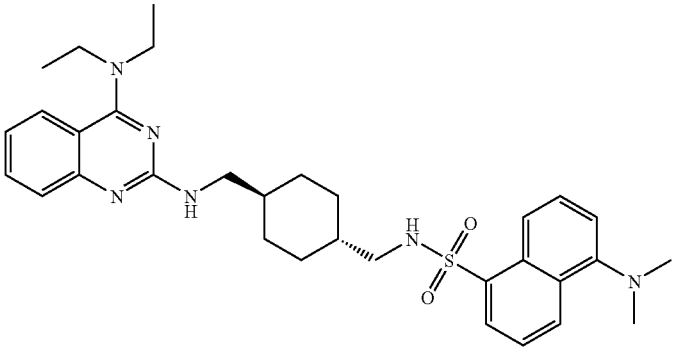 2CF₃CO₂H | 575.8 (M + H) | 4.80 |

-continued
| Example No. | Structure | ESI-MS | Retention Time (min) |
|---|---|---|---|
| 2649 | 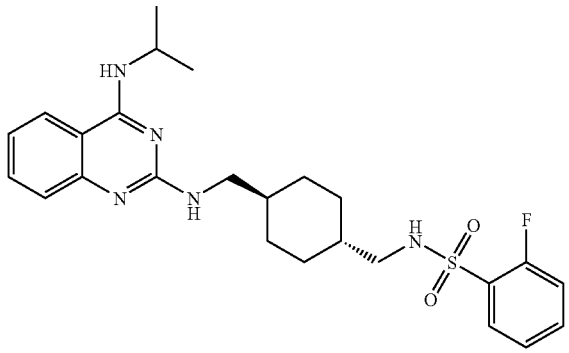 CF$_3$CO$_2$H | 486.6 (M + H) | 4.64 |
| 2650 | 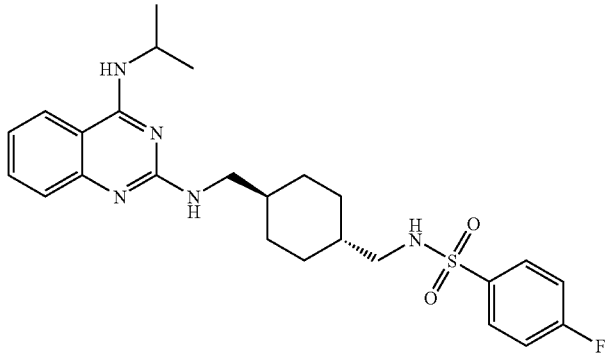 CF$_3$CO$_2$H | 486.6 (M + H) | 4.66 |
| 2651 | 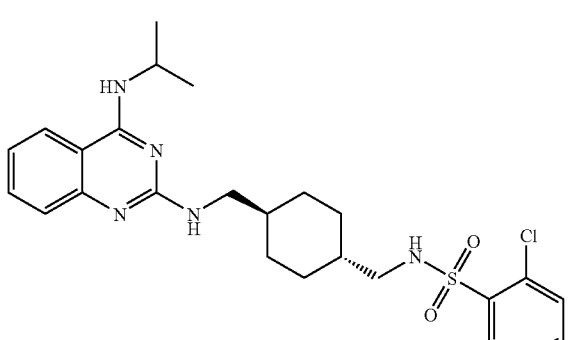 CF$_3$CO$_2$H | 502.6 (M + H) | 4.72 |

-continued

| Example No. | Structure | ESI-MS | Retention Time (min) |
|---|---|---|---|
| 2652 | CF₃CO₂H | 502.6 (M + H) | 4.87 |
| 2653 | CF₃CO₂H | 570.6 (M + H) | 5.03 |
| 2654 | CF₃CO₂H | 546.6 (M + H) | 4.77 |

-continued
| Example No. | Structure | ESI-MS | Retention Time (min) |
|---|---|---|---|
| 2655 | 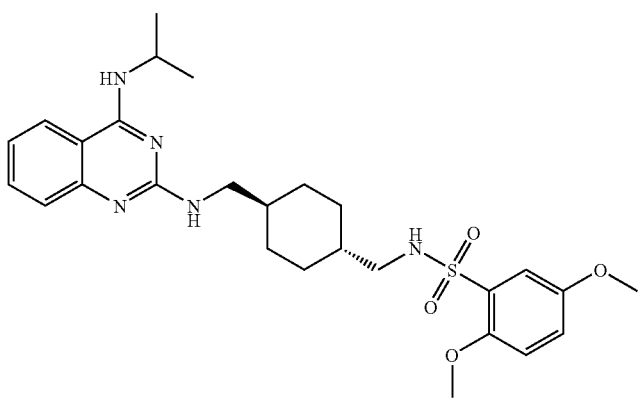<br>CF$_3$CO$_2$H | 528.8 (M + H) | 4.68 |
| 2656 | 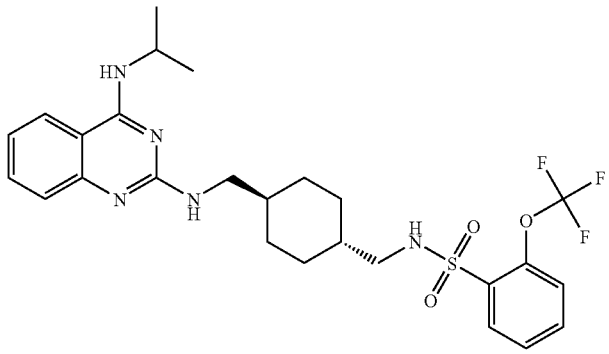<br>CF$_3$CO$_2$H | 552.8 (M + H) | 4.89 |
| 2657 | 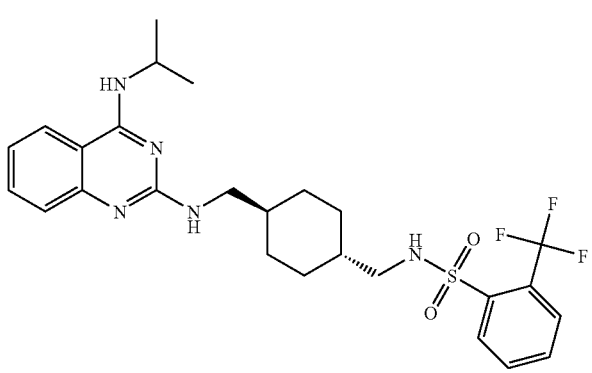<br>CF$_3$CO$_2$H | 536.6 (M + H) | 4.85 |

-continued
| Example No. | Structure | ESI-MS | Retention Time (min) |
|---|---|---|---|
| 2658 | 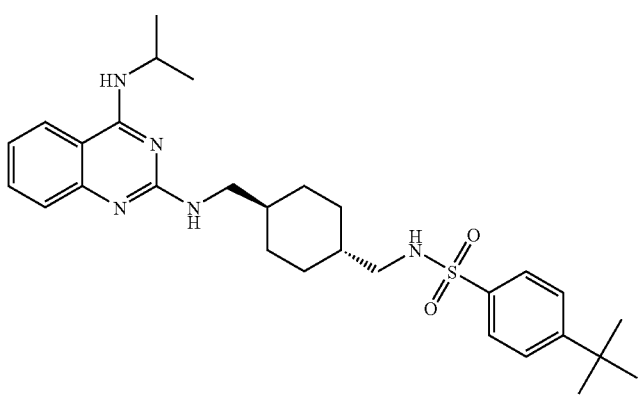 CF₃CO₂H | 524.8 (M + H) | 5.15 |
| 2659 | 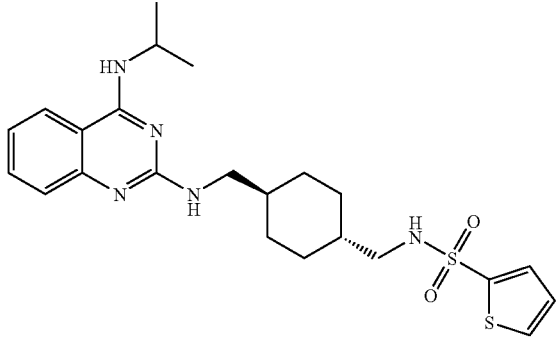 CF₃CO₂H | 474.8 (M + H) | 4.63 |
| 2660 | 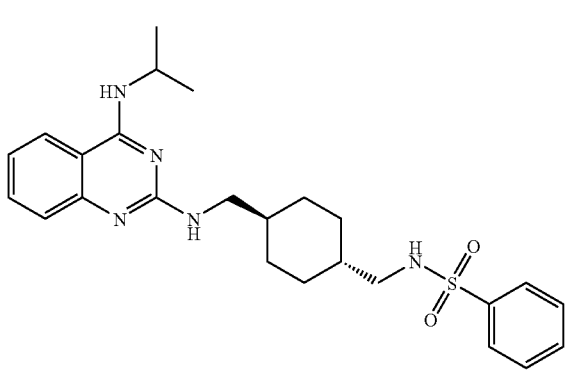 CF₃CO₂H | 468.4 (M + H) | 4.61 |

-continued
| Example No. | Structure | ESI-MS | Retention Time (min) |
|---|---|---|---|
| 2661 | 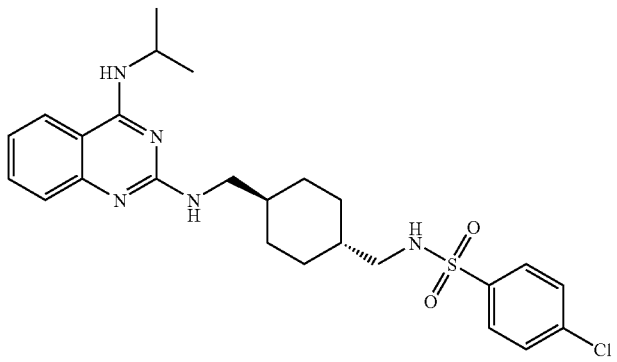 CF₃CO₂H | 502.6 (M + H) | 4.86 |
| 2662 | 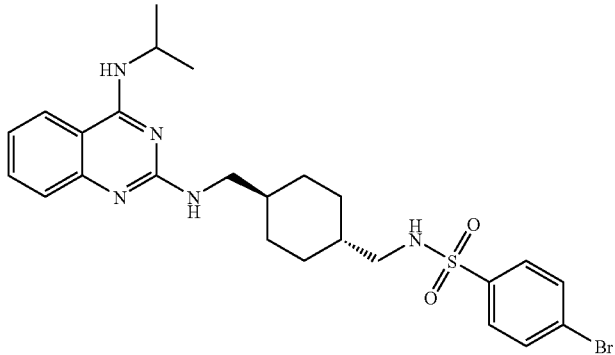 CF₃CO₂H | 546.6 (M + H) | 4.64 |
| 2663 | 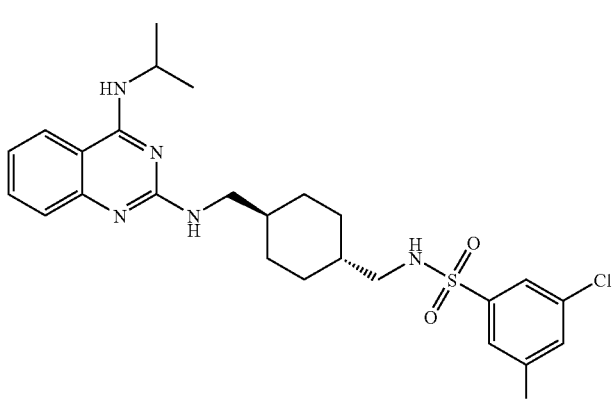 CF₃CO₂H | 536.4 (M + H) | 4.81 |

| Example No. | Structure | ESI-MS | Retention Time (min) |
|---|---|---|---|
| 2664 | 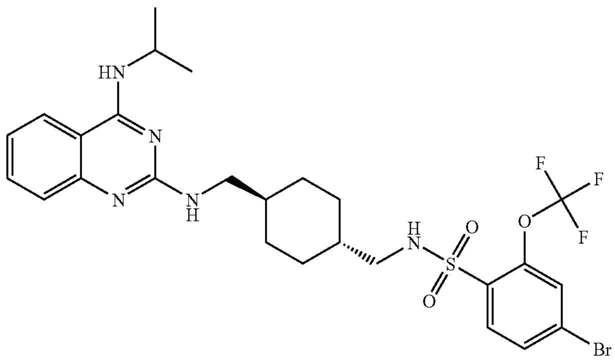 | 630.4 (M + H) | 4.85 |
| 2665 | 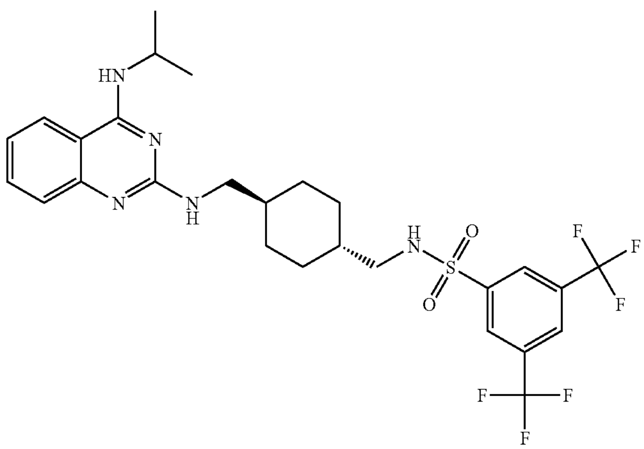 | 604.6 (M + H) | 4.87 |
| 2666 | 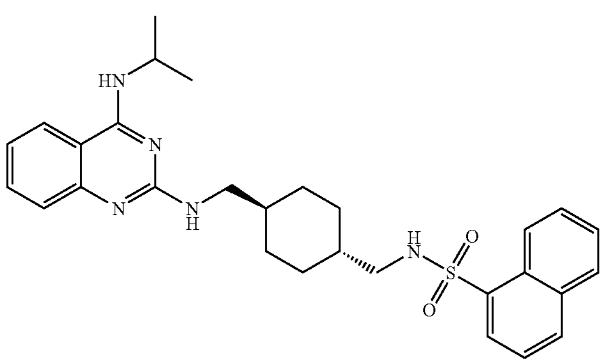 | 518.6 (M + H) | 4.67 |

-continued
| Example No. | Structure | ESI-MS | Retention Time (min) |
|---|---|---|---|
| 2667 | 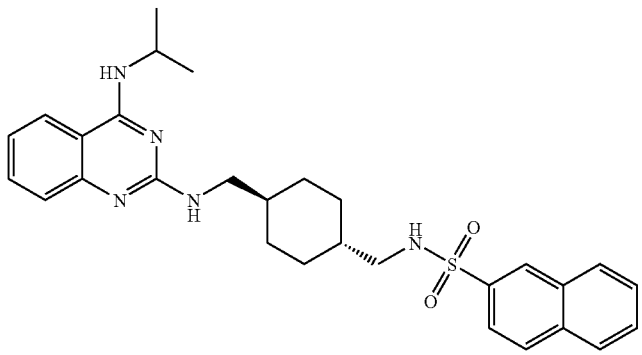<br>CF₃CO₂H | 518.6 (M + H) | 4.90 |
| 2668 | 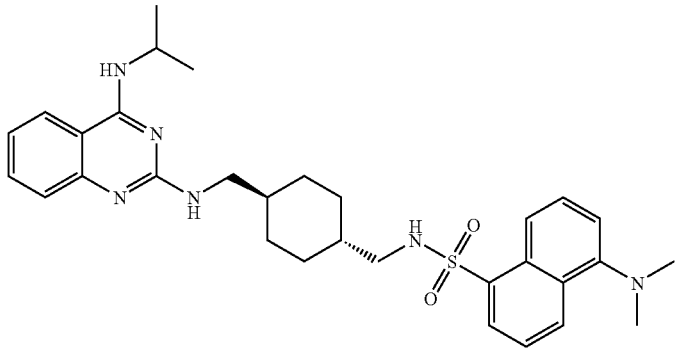<br>2CF₃CO₂H | 561.6 (M + H) | 4.64 |
| 2669 | 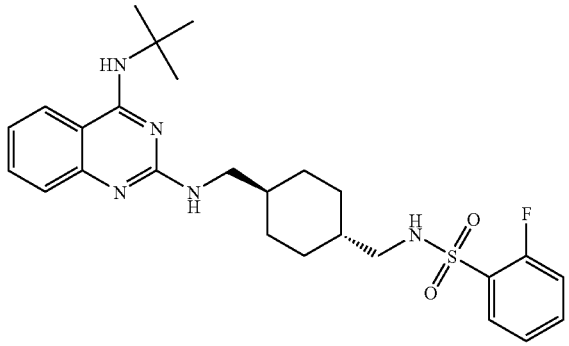<br>CF₃CO₂H | 500.8 (M + H) | 4.73 |

-continued
| Example No. | Structure | ESI-MS | Retention Time (min) |
|---|---|---|---|
| 2670 | 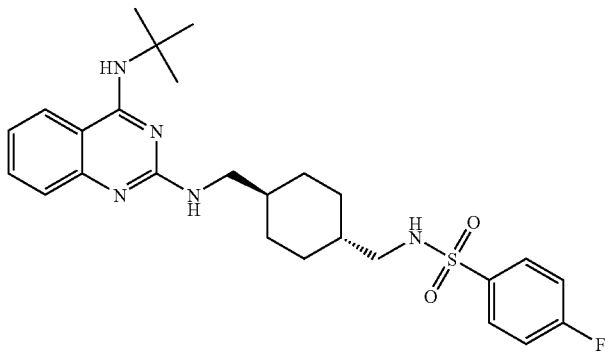 CF₃CO₂H | 500.8 (M + H) | 4.74 |
| 2671 | 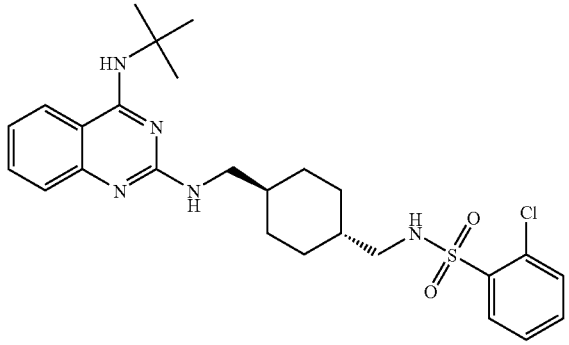 CF₃CO₂H | 516.6 (M + H) | 4.89 |
| 2672 | 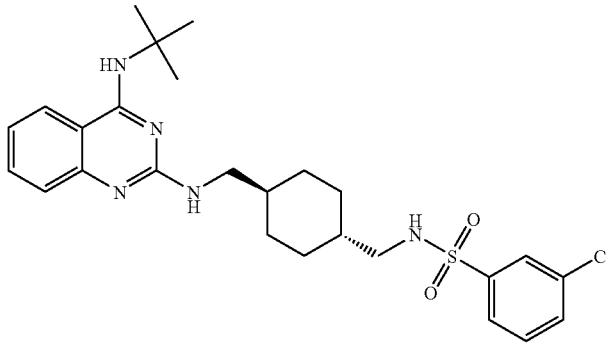 CF₃CO₂H | 516.6 (M + H) | 4.93 |

-continued
| Example No. | Structure | ESI-MS | Retention Time (min) |
|---|---|---|---|
| 2673 | 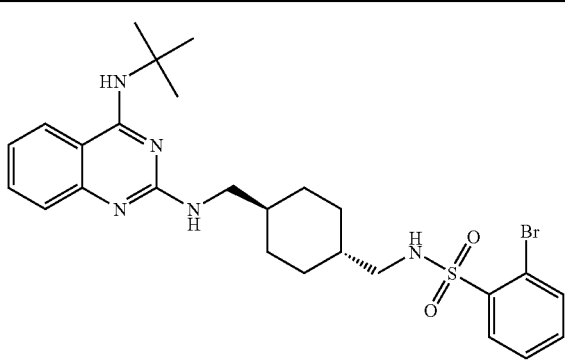 CF₃CO₂H | 560.0 (M + H) | 4.89 |
| 2674 | 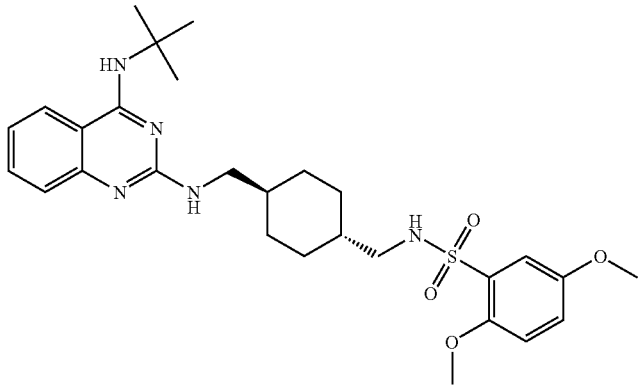 CF₃CO₂H | 542.8 (M + H) | 4.76 |
| 2675 | 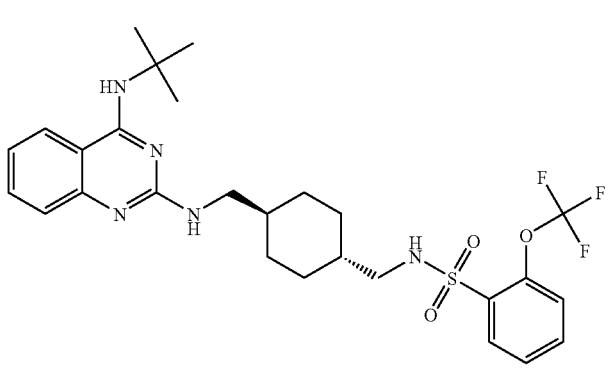 CF₃CO₂H | 566.6 (M + H) | 5.03 |

-continued
| Example No. | Structure | ESI-MS | Retention Time (min) |
|---|---|---|---|
| 2676 | 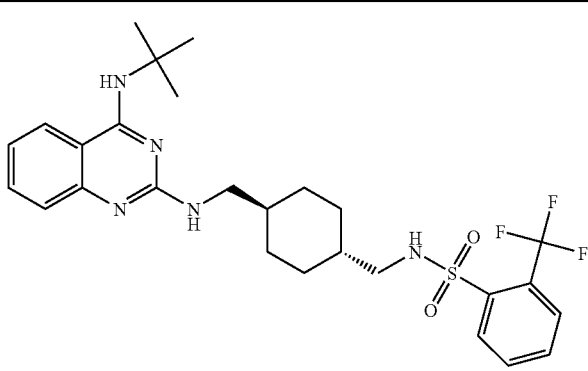 CF₃CO₂H | 550.8 (M + H) | 4.96 |
| 2677 | 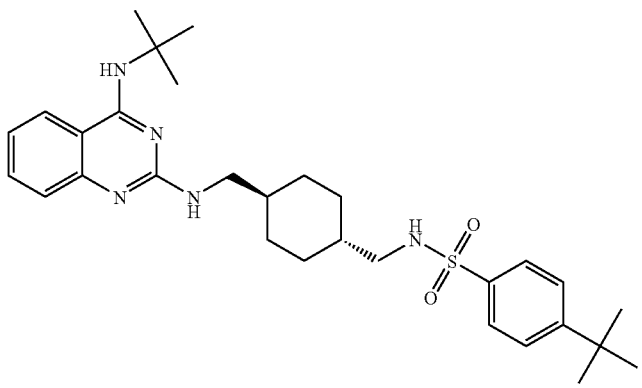 CF₃CO₂H | 538.8 (M + H) | 5.25 |
| 2678 | 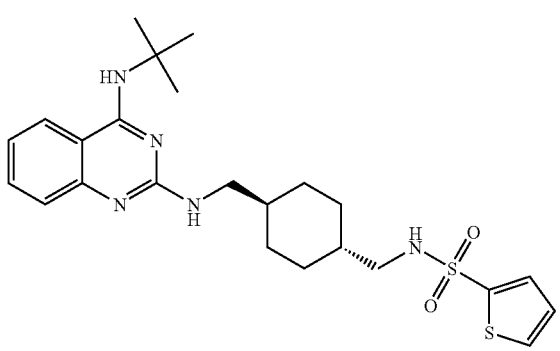 CF₃CO₂H | 488.6 (M + H) | 4.67 |

-continued

| Example No. | Structure | ESI-MS | Retention Time (min) |
|---|---|---|---|
| 2679 | (structure) CF₃CO₂H | 482.4 (M + H) | 4.71 |
| 2680 | (structure) CF₃CO₂H | 516.6 (M + H) | 4.95 |
| 2681 | (structure) CF₃CO₂H | 566.8 (M + H) | 5.07 |
| 2682 | (structure) CF₃CO₂H | 496.8 (M + H) | 4.83 |

-continued
| Example No. | Structure | ESI-MS | Retention Time (min) |
|---|---|---|---|
| 2683 |  CF₃CO₂H | 560.6 (M + H) | 5.01 |
| 2684 | 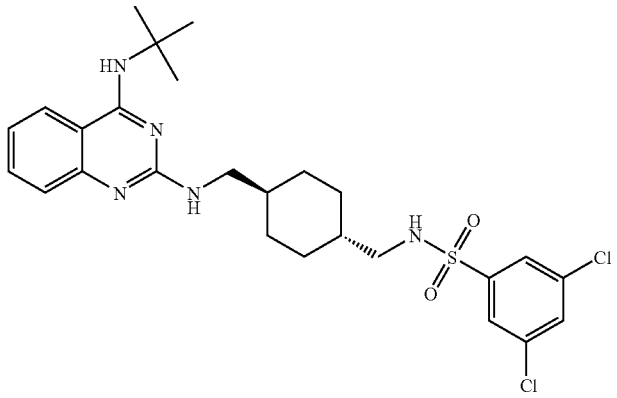 CF₃CO₂H | 550.6 (M + H) | 5.07 |
| 2685 | 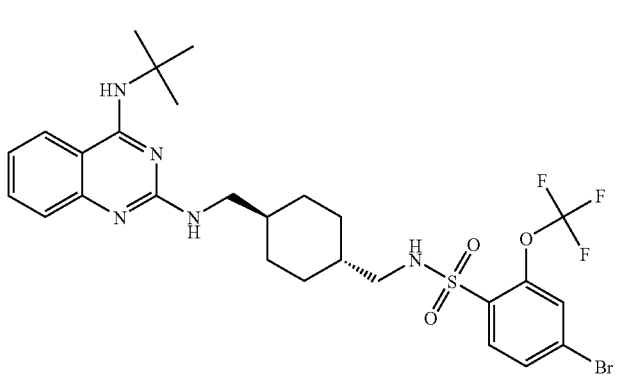 CF₃CO₂H | 644.6 (M + H) | 5.29 |

-continued

| Example No. | Structure | ESI-MS | Retention Time (min) |
|---|---|---|---|
| 2686 | CF₃CO₂H | 618.6 (M + H) | 5.25 |
| 2687 | CF₃CO₂H | 532.6 (M + H) | 5.01 |
| 2688 | CF₃CO₂H | 532.6 (M + H) | 5.04 |

-continued

| Example No. | Structure | ESI-MS | Retention Time (min) |
|---|---|---|---|
| 2689 | CF₃CO₂H | 575.8 (M + H) | 4.75 |
| 2690 | CF₃CO₂H | 484.6 (M + H) | 4.51 |
| 2691 | CF₃CO₂H | 500.8 (M + H) | 4.59 |
| 2692 | CF₃CO₂H | 500.8 (M + H) | 4.71 |

-continued

| Example No. | Structure | ESI-MS | Retention Time (min) |
|---|---|---|---|
| 2693 | 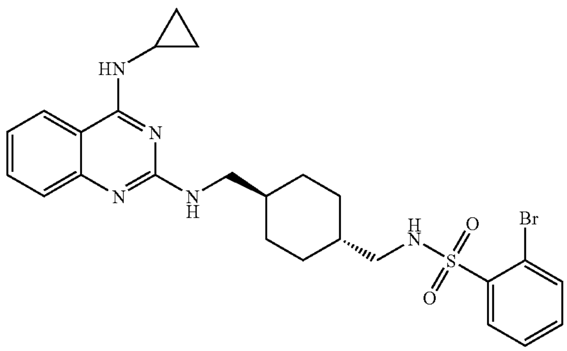 | 544.6 (M + H) | 4.63 |
| 2694 | 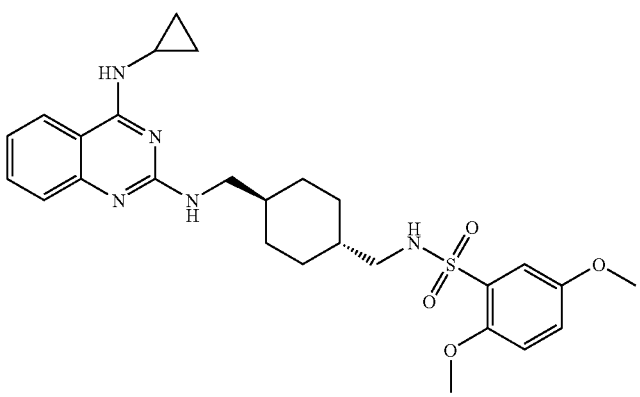 | 526.8 (M + H) | 4.55 |
| 2695 | 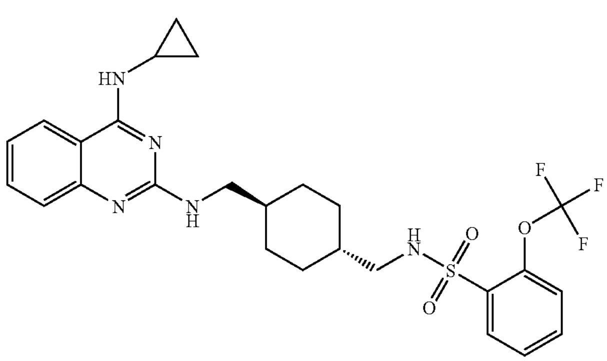 | 550.6 (M + H) | 4.79 |

-continued
| Example No. | Structure | ESI-MS | Retention Time (min) |
|---|---|---|---|
| 2696 | 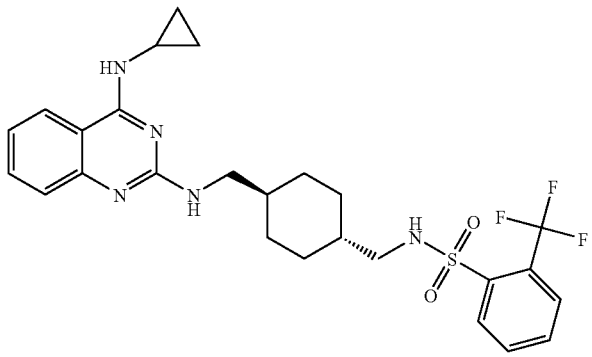 CF$_3$CO$_2$H | 534.6 (M + H) | 4.69 |
| 2697 | 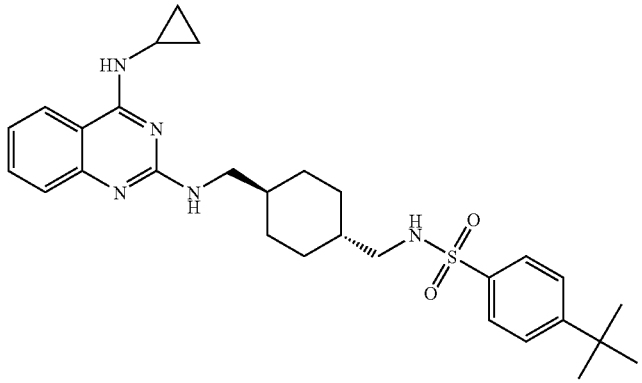 CF$_3$CO$_2$H | 522.4 (M + H) | 5.03 |
| 2698 | 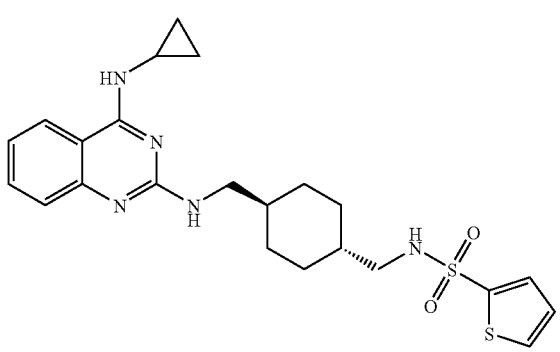 CF$_3$CO$_2$H | 472.8 (M + H) | 4.43 |

-continued

| Example No. | Structure | ESI-MS | Retention Time (min) |
|---|---|---|---|
| 2699 | CF$_3$CO$_2$H | 466.6 (M + H) | 4.50 |
| 2700 | CF$_3$CO$_2$H | 550.6 (M + H) | 4.87 |
| 2701 | CF$_3$CO$_2$H | 480.6 (M + H) | 4.65 |

-continued
| Example No. | Structure | ESI-MS | Retention Time (min) |
|---|---|---|---|
| 2702 | 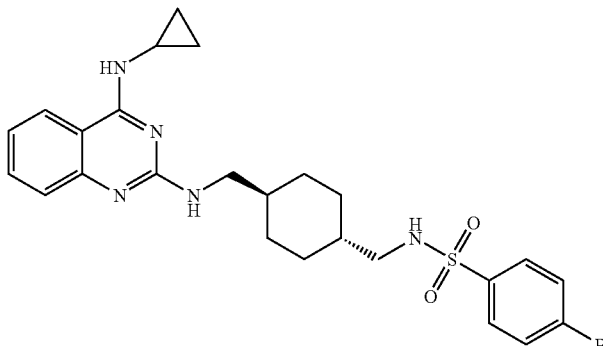 CF$_3$CO$_2$H | 544.6 (M + H) | 4.75 |
| 2703 | 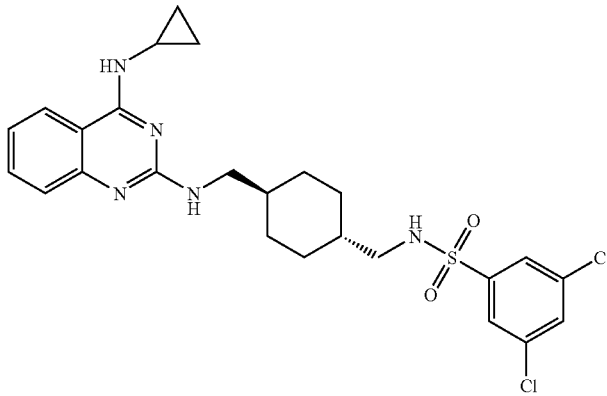 CF$_3$CO$_2$H | 534.6 (M + H) | 4.90 |
| 2704 | 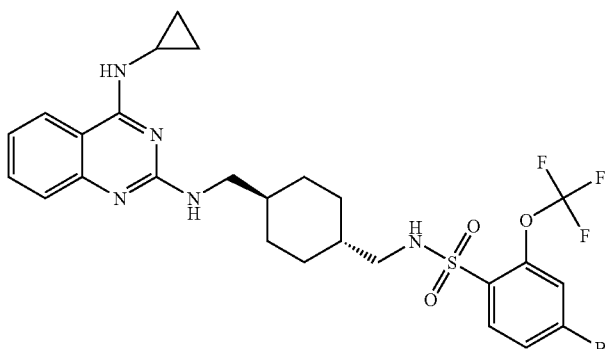 CF$_3$CO$_2$H | 628.6 (M + H) | 5.08 |

| Example No. | Structure | ESI-MS | Retention Time (min) |
|---|---|---|---|
| 2705 | 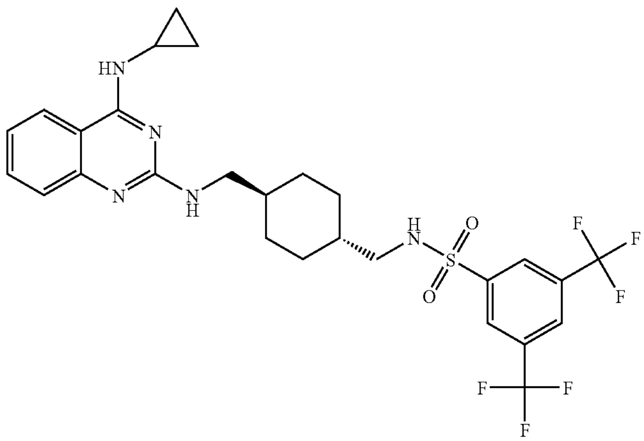 | 602.6 (M + H) | 5.10 |
| 2706 | 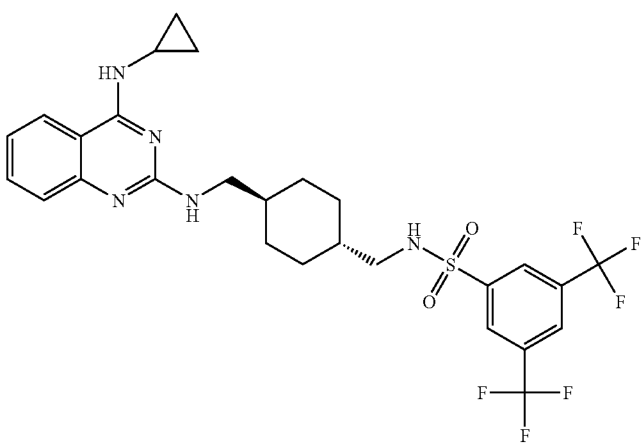 | 516.8 (M + H) | 4.71 |
| 2707 | 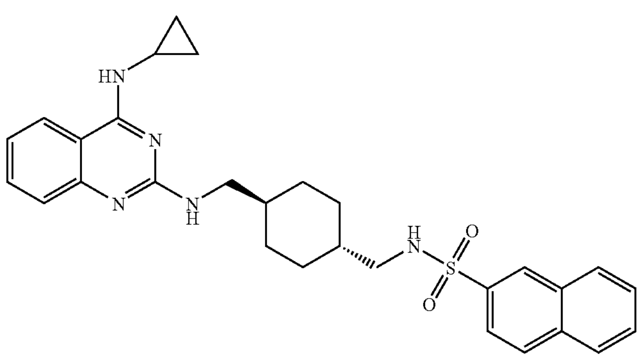 | 516.8 (M + H) | 4.81 |

-continued
| Example No. | Structure | ESI-MS | Retention Time (min) |
|---|---|---|---|
| 2708 | 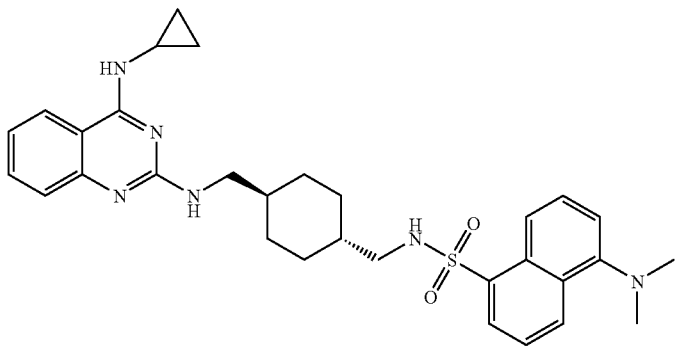 2CF₃CO₂H | 559.6 (M + H) | 4.50 |
| 2709 | 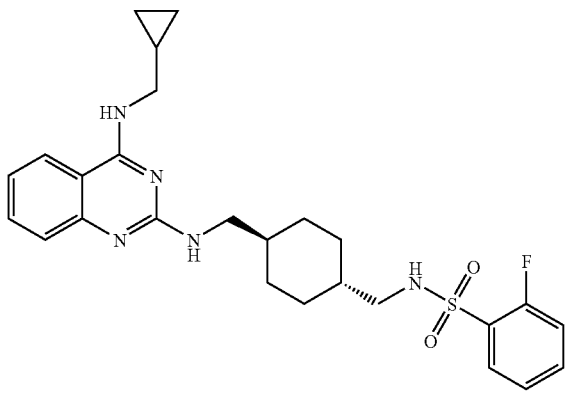 CF₃CO₂H | 498.8 (M + H) | 4.64 |
| 2710 | 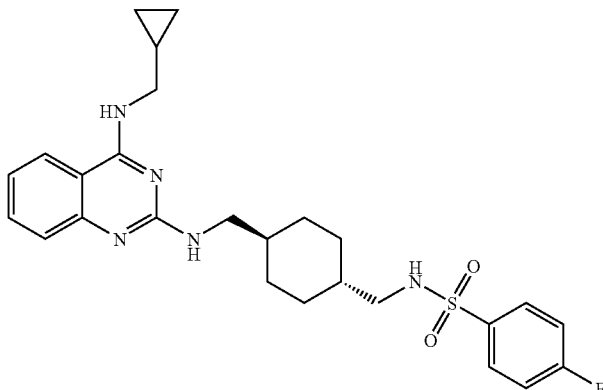 CF₃CO₂H | 498.8 (M + H) | 4.73 |

-continued
| Example No. | Structure | ESI-MS | Retention Time (min) |
|---|---|---|---|
| 2711 | 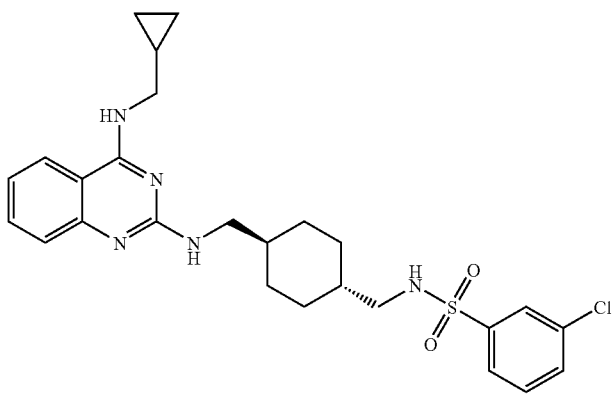 CF₃CO₂H | 514.8 (M + H) | 4.87 |
| 2712 | 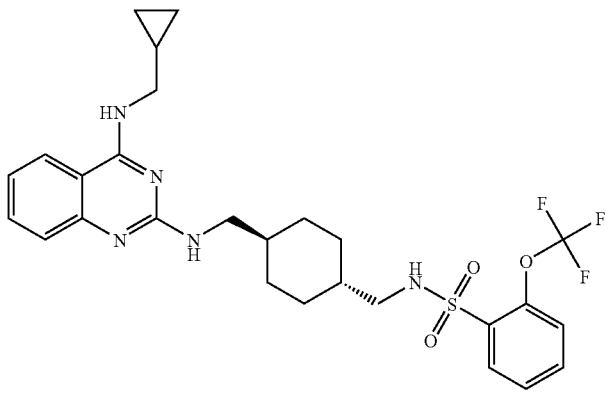 CF₃CO₂H | 564.6 (M + H) | 4.93 |
| 2713 | 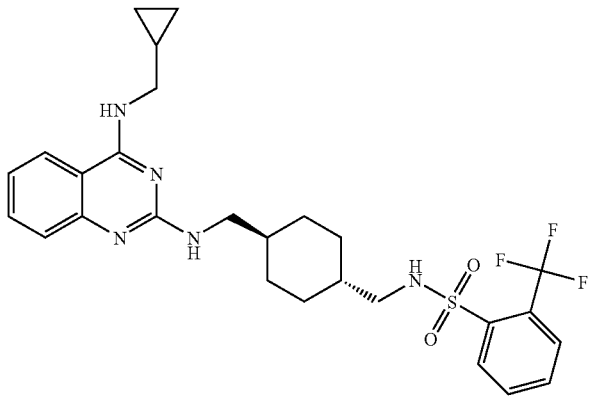 CF₃CO₂H | 548.6 (M + H) | 4.87 |

-continued

| Example No. | Structure | ESI-MS | Retention Time (min) |
|---|---|---|---|
| 2714 | CF$_3$CO$_2$H | 536.6 (M + H) | 5.19 |
| 2715 | CF$_3$CO$_2$H | 603.8 (M + H) | 4.76 |
| 2716 | CF$_3$CO$_2$H | 603.4 (M + H) | 4.87 |

-continued
| Example No. | Structure | ESI-MS | Retention Time (min) |
|---|---|---|---|
| 2717 | 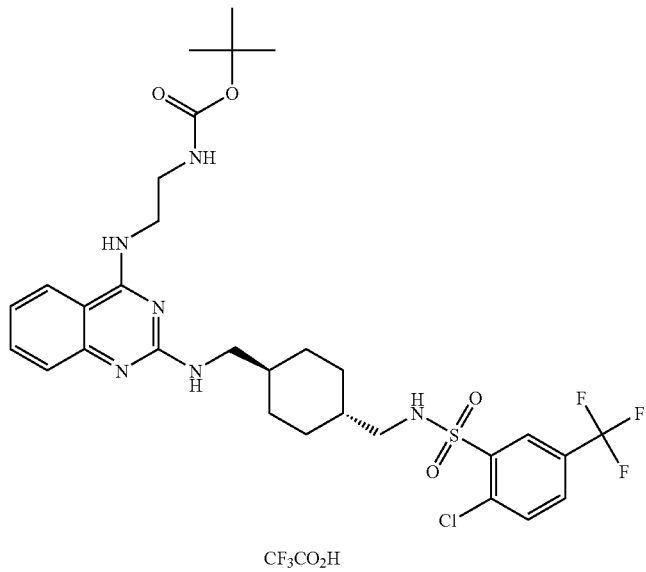 CF₃CO₂H | 671.6 (M + H) | 5.05 |
| 2718 | 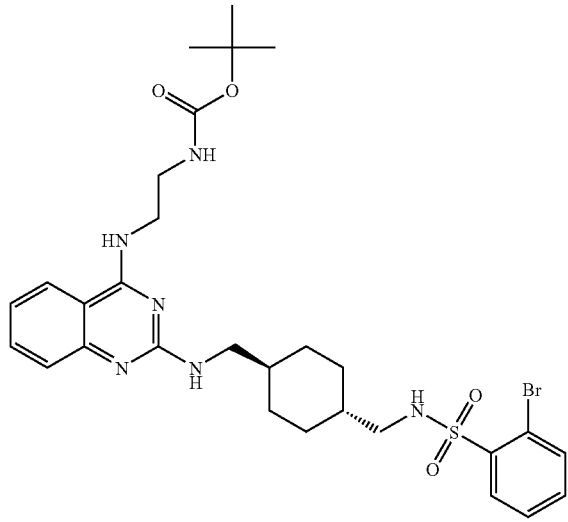 CF₃CO₂H | 647.6 (M + H) | 4.79 |

-continued
| Example No. | Structure | ESI-MS | Retention Time (min) |
|---|---|---|---|
| 2719 | 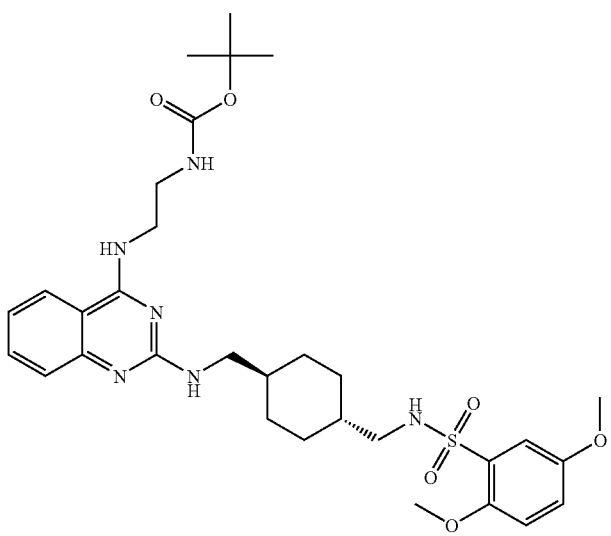 CF₃CO₂H | 629.8 (M + H) | 4.67 |
| 2720 | 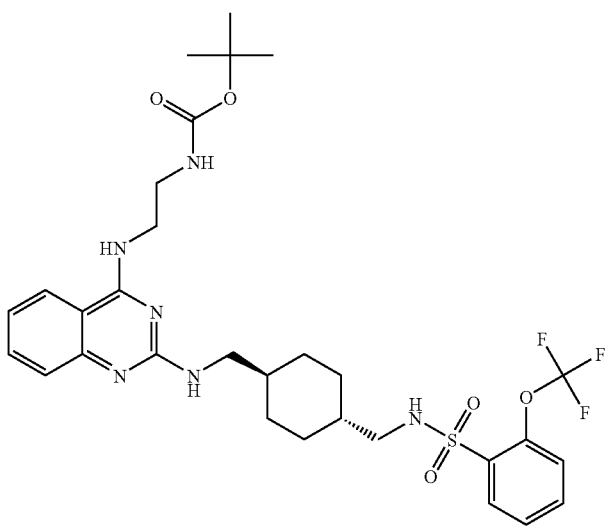 CF₃CO₂H | 653.8 (M + H) | 4.91 |

-continued
| Example No. | Structure | ESI-MS | Retention Time (min) |
|---|---|---|---|
| 2721 | 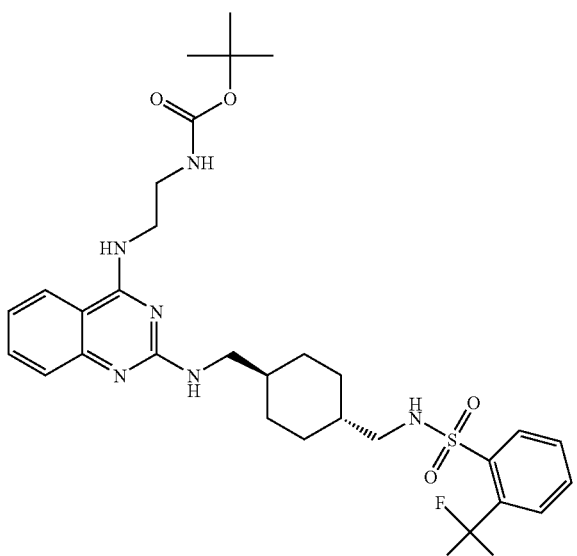<br>CF$_3$CO$_2$H | 637.8 (M + H) | 4.85 |
| 2722 | 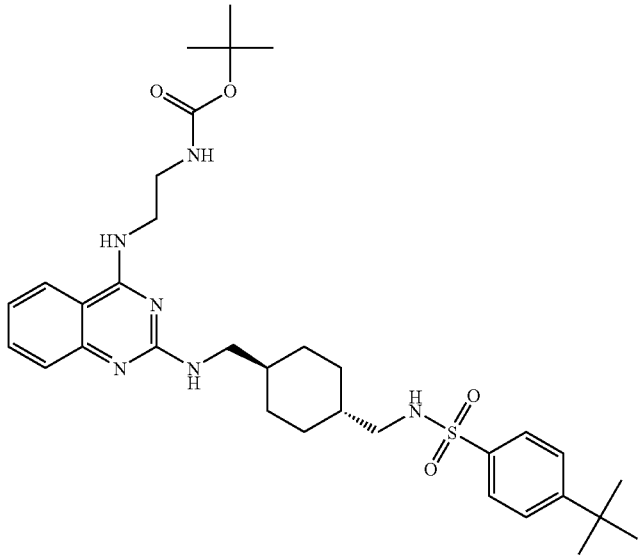<br>CF$_3$CO$_2$H | 625.8 (M + H) | 5.14 |

-continued
| Example No. | Structure | ESI-MS | Retention Time (min) |
|---|---|---|---|
| 2723 | 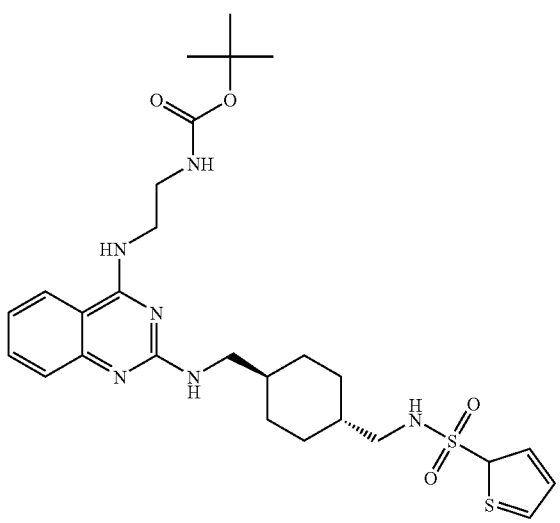 CF₃CO₂H | 575.6 (M + H) | 4.63 |
| 2724 | 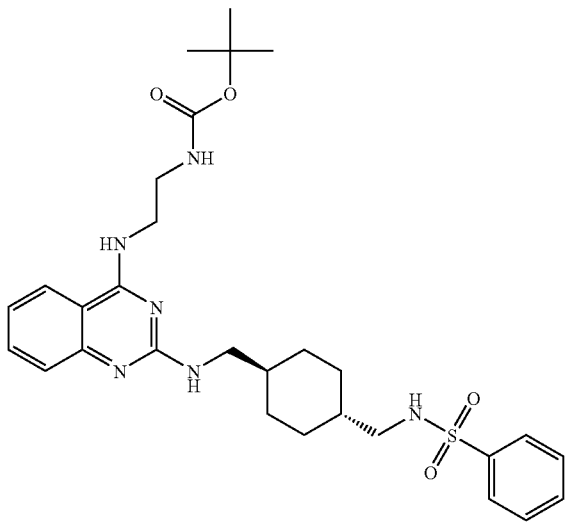 CF₃CO₂H | 569.8 (M + H) | 4.66 |

-continued
| Example No. | Structure | ESI-MS | Retention Time (min) |
|---|---|---|---|
| 2725 | 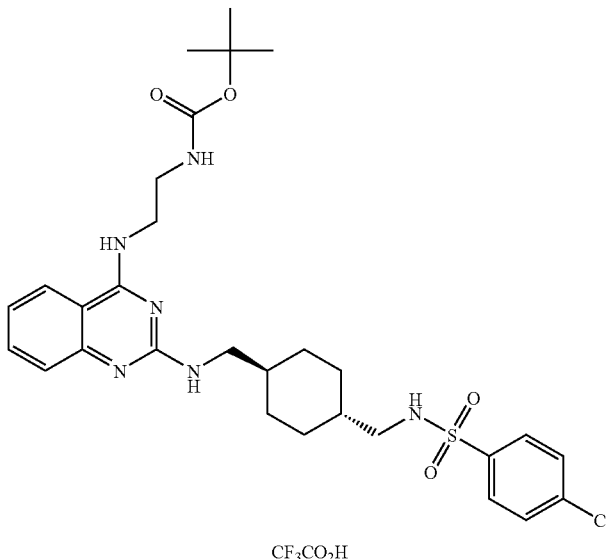 | 603.8 (M + H) | 4.88 |
| 2726 | 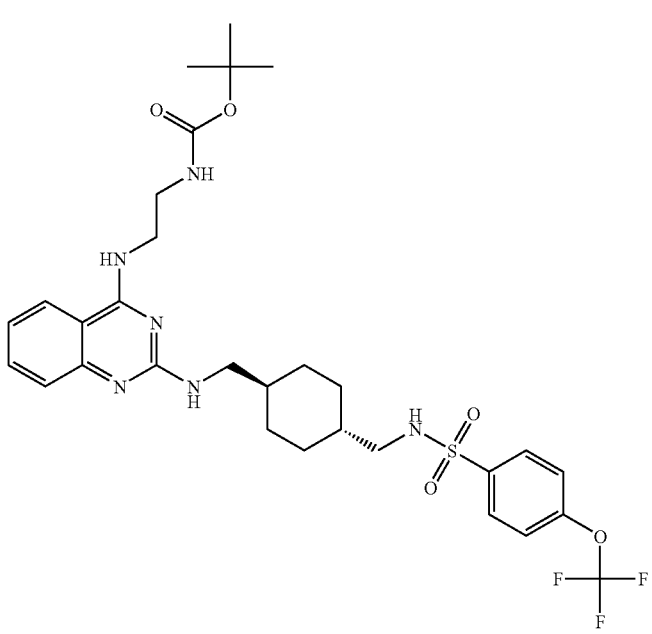 | 653.8 (M + H) | 5.01 |

| Example No. | Structure | ESI-MS | Retention Time (min) |
|---|---|---|---|
| 2727 | 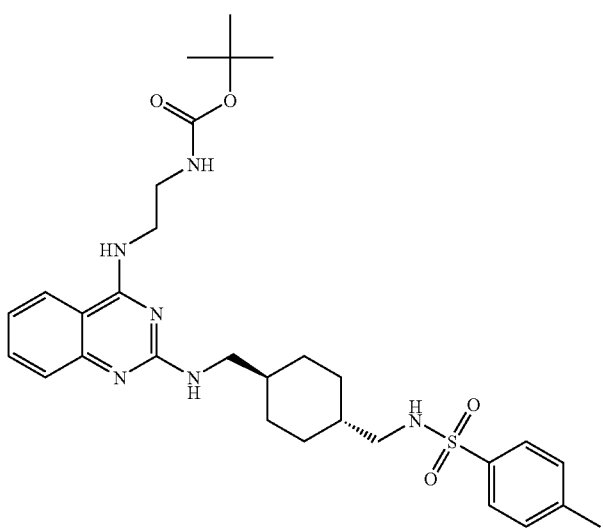 | 583.8 (M + H) | 4.77 |
| 2728 | 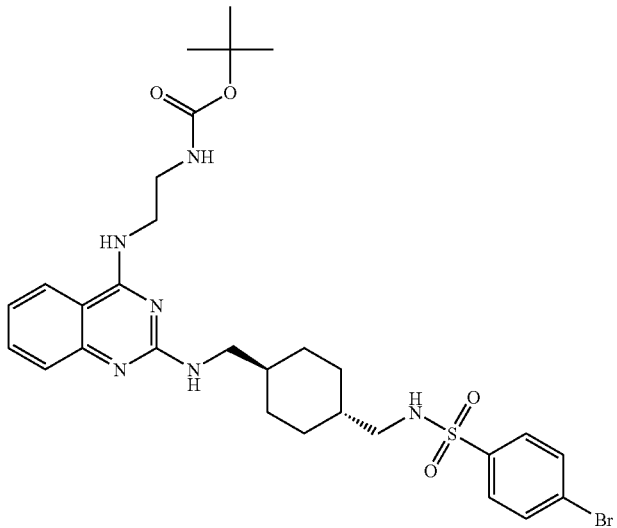 | 647 (M + H) | 4.92 |

| Example No. | Structure | ESI-MS | Retention Time (min) |
|---|---|---|---|
| 2729 | 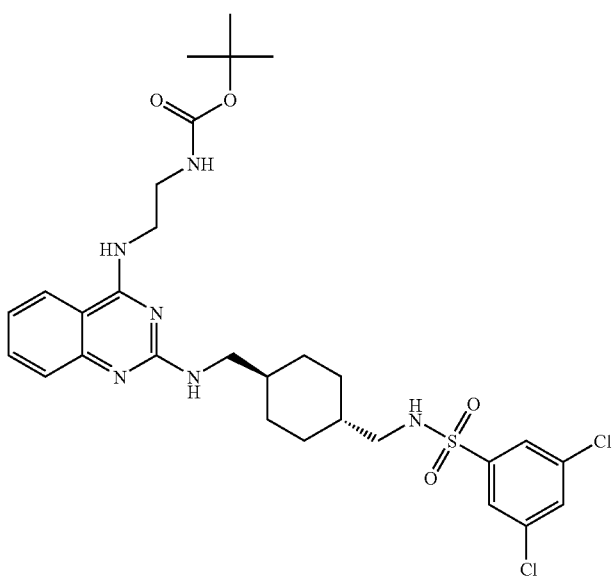 CF₃CO₂H | 637.8 (M + H) | 5.13 |
| 2730 | 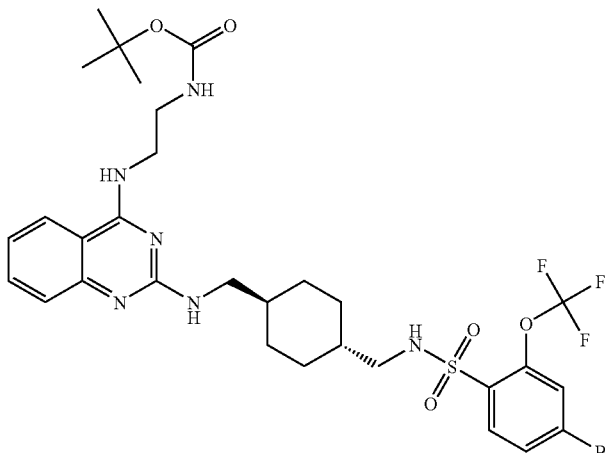 CF₃CO₂H | 731.6 (M + H) | 5.19 |

-continued
| Example No. | Structure | ESI-MS | Retention Time (min) |
|---|---|---|---|
| 2731 | 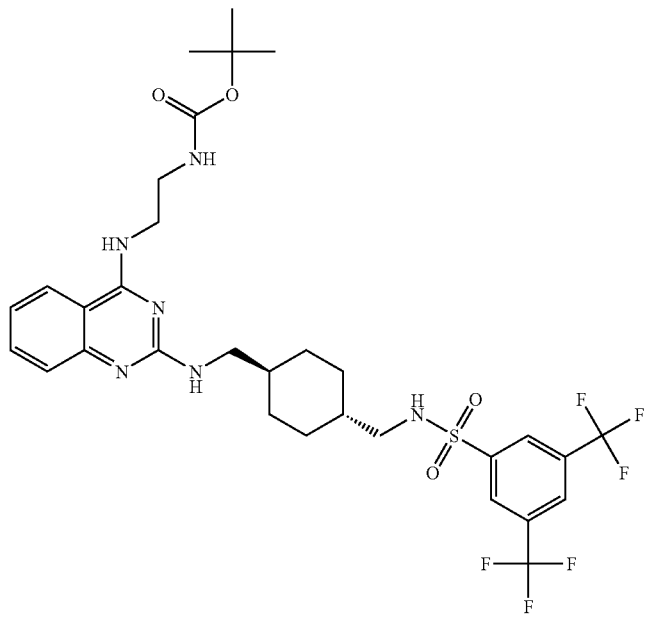 CF3CO2H | 705.8 (M + H) | 5.22 |
| 2732 | 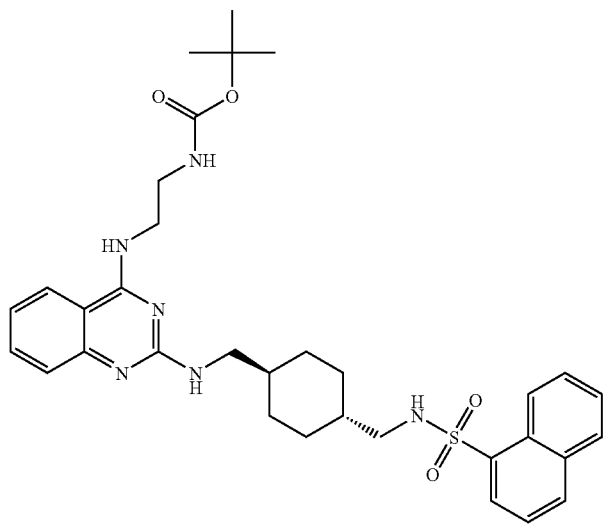 CF3CO2H | 619.8 (M + H) | 4.91 |

-continued

| Example No. | Structure | ESI-MS | Retention Time (min) |
|---|---|---|---|
| 2733 | 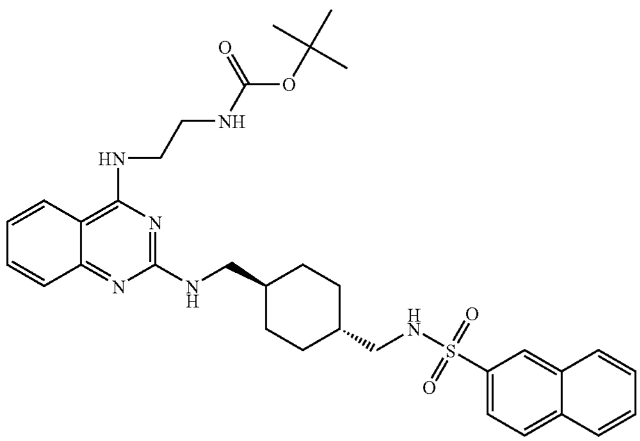 | 619.8 (M + H) | 4.93 |
| 2734 | 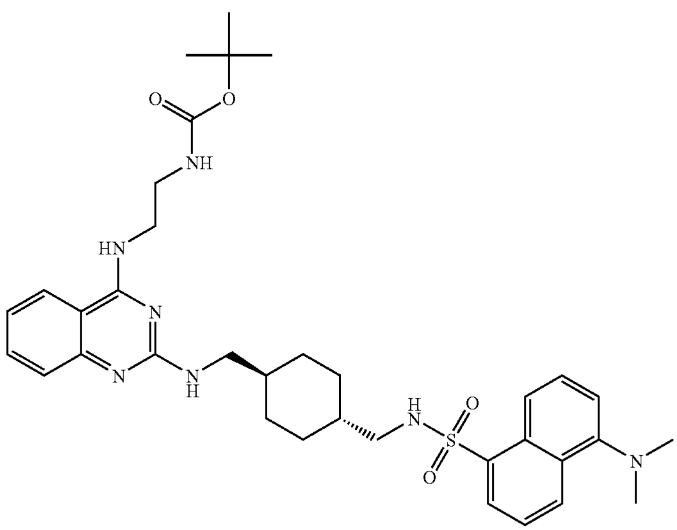 | 663.0 (M + H) | 4.67 |
| 2735 | 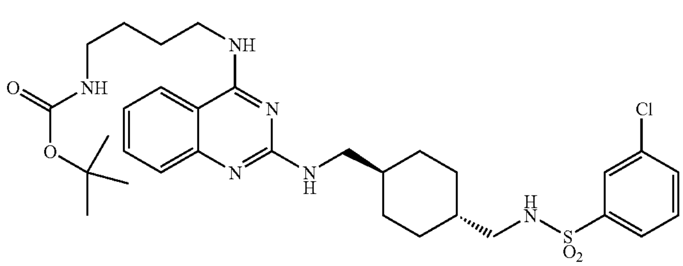 | 631.8 (M + H) | 5.01 |

-continued
| Example No. | Structure | ESI-MS | Retention Time (min) |
|---|---|---|---|
| 2736 | <br>CF$_3$CO$_2$H | 699.0 (M + H) | 5.19 |
| 2737 | 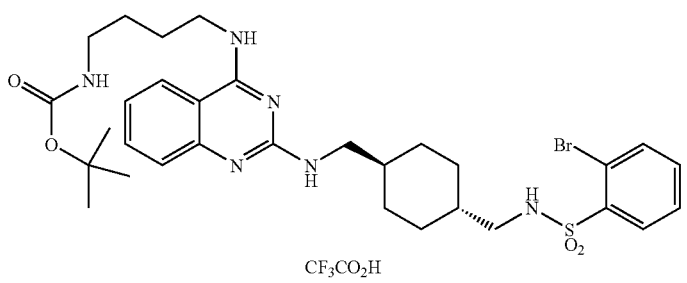<br>CF$_3$CO$_2$H | 675.8 (M + H) | 4.95 |
| 2738 | <br>CF$_3$CO$_2$H | 657.8 (M + H) | 4.81 |
| 2739 | 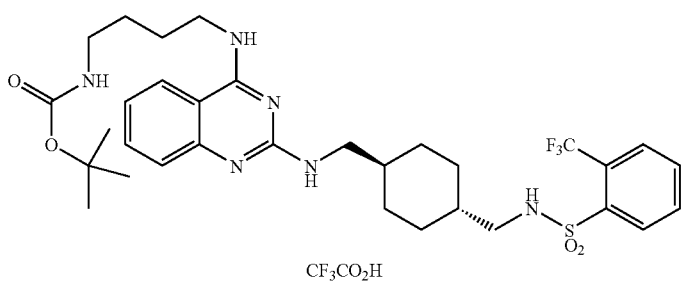<br>CF$_3$CO$_2$H | 665.8 (M + H) | 4.97 |
| 2740 | 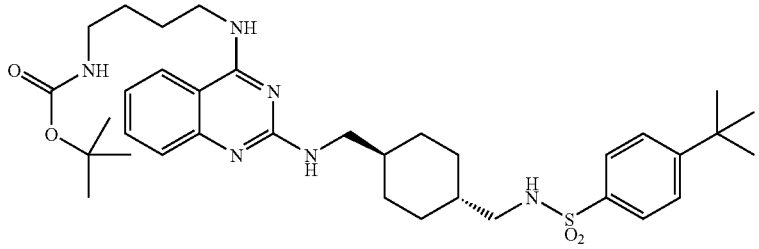<br>CF$_3$CO$_2$H | 653.8 (M + H) | 5.27 |

| Example No. | Structure | ESI-MS | Retention Time (min) |
|---|---|---|---|
| 2741 | (structure) CF$_3$CO$_2$H | 603.4 (M + H) | 4.77 |
| 2742 | (structure) CF$_3$CO$_2$H | 597.8 (M + H) | 4.79 |
| 2743 | (structure) CF$_3$CO$_2$H | 631.8 (M + H) | 5.02 |
| 2744 | (structure) CF$_3$CO$_2$H | 681.8 (M + H) | 5.14 |
| 2745 | (structure) CF$_3$CO$_2$H | 611.8 (M + H) | 4.93 |

-continued

| Example No. | Structure | ESI-MS | Retention Time (min) |
|---|---|---|---|
| 2746 | 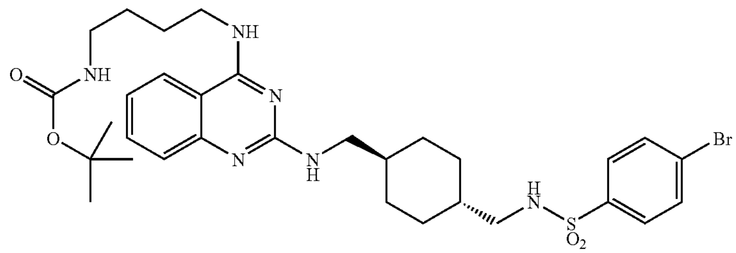 | 675.0 (M + H) | 5.05 |
| 2747 | 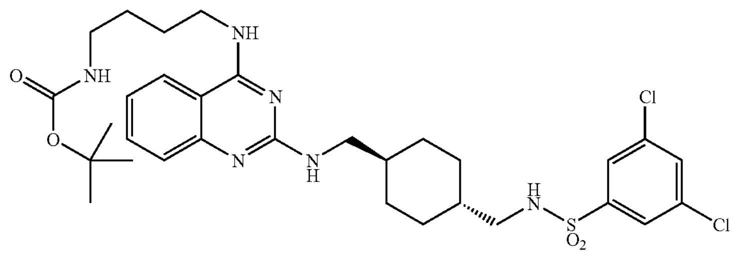 | 655.8 (M + H) | 5.29 |
| 2748 | 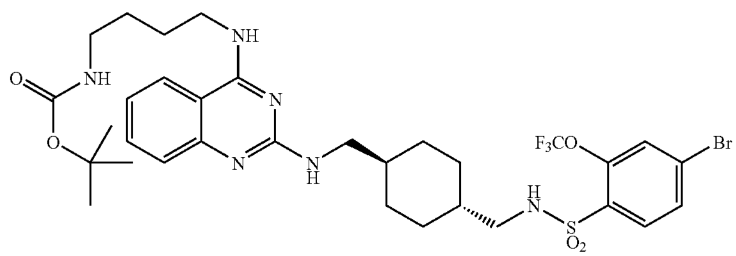 | 759.6 (M + H) | 5.31 |
| 2749 | 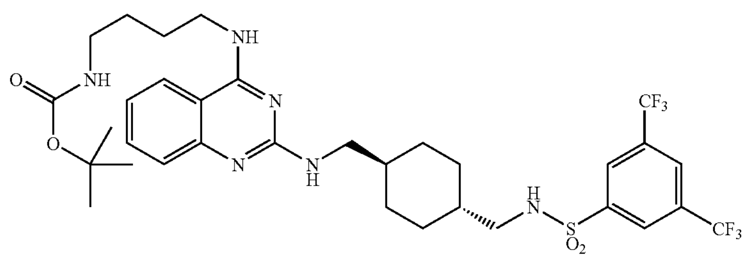 | 733.8 (M + H) | 5.36 |
| 2750 | 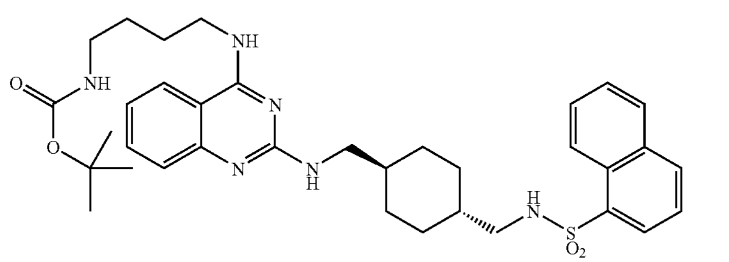 | 647.8 (M + H) | 5.05 |

-continued
| Example No. | Structure | ESI-MS | Retention Time (min) |
|---|---|---|---|
| 2751 | 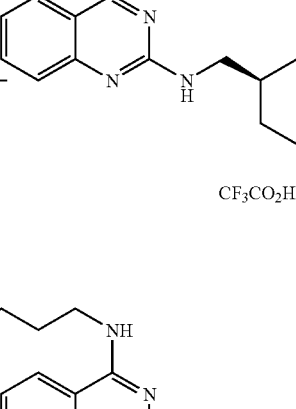 CF₃CO₂H | 647.8 (M + H) | 5.08 |
| 2752 | 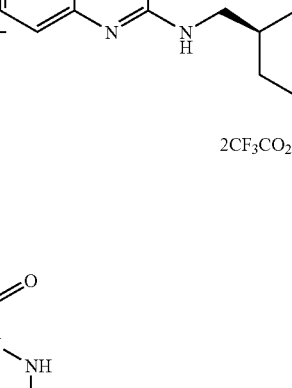 2CF₃CO₂H | 691.0 (M + H) | 4.89 |
| 2753 | 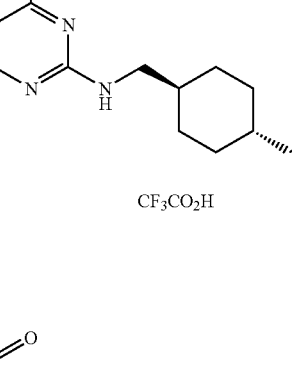 CF₃CO₂H | 559.6 (M + H) | 4.51 |
| 2754 | 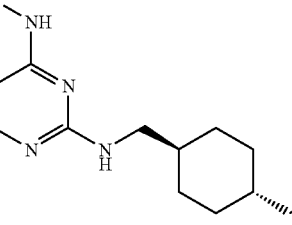 CF₃CO₂H | 575.6 (M + H) | 4.57 |

-continued
| Example No. | Structure | ESI-MS | Retention Time (min) |
|---|---|---|---|
| 2755 | 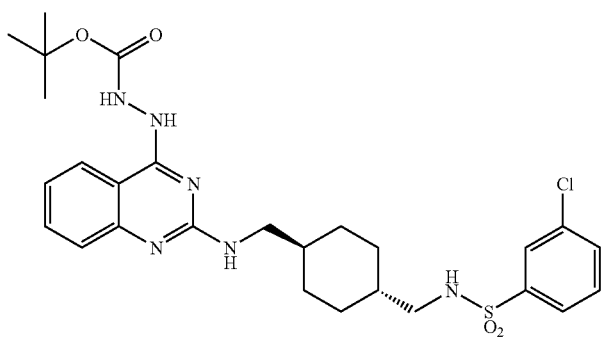 CF$_3$CO$_2$H | 575.6 (M + H) | 4.69 |
| 2756 | 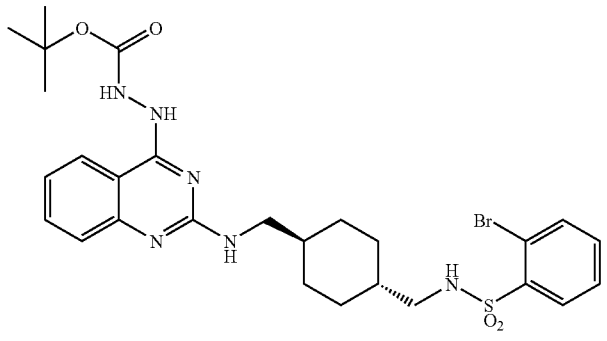 CF$_3$CO$_2$H | 619.6 (M + H) | 4.63 |
| 2757 |  CF$_3$CO$_2$H | 625.8 (M + H) | 4.72 |

-continued
| Example No. | Structure | ESI-MS | Retention Time (min) |
|---|---|---|---|
| 2758 | 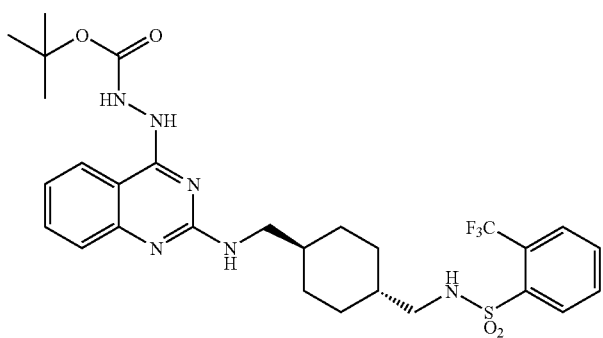 CF₃CO₂H | 609.8 (M + H) | 4.67 |
| 2759 | 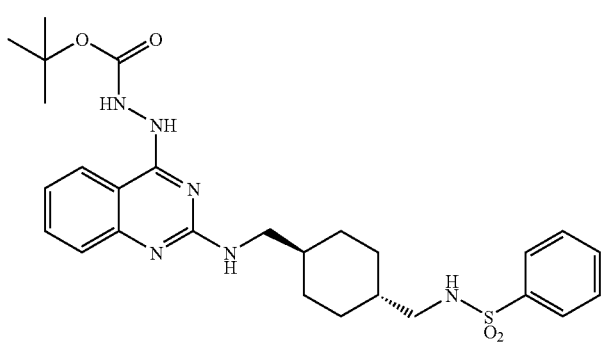 CF₃CO₂H | 514.8 (M + H) | 4.45 |
| 2760 | 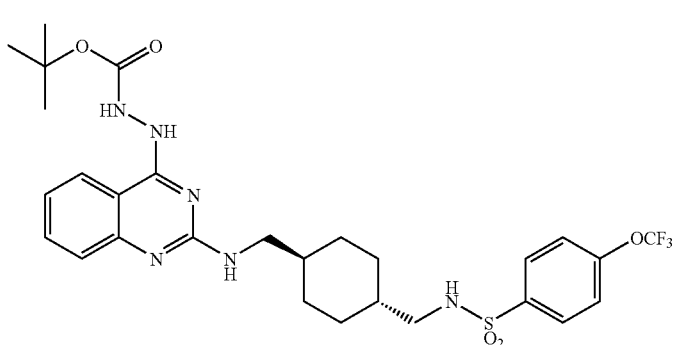 CF₃CO₂H | 625.8 (M + H) | 4.38 |

-continued
| Example No. | Structure | ESI-MS | Retention Time (min) |
|---|---|---|---|
| 2761 | 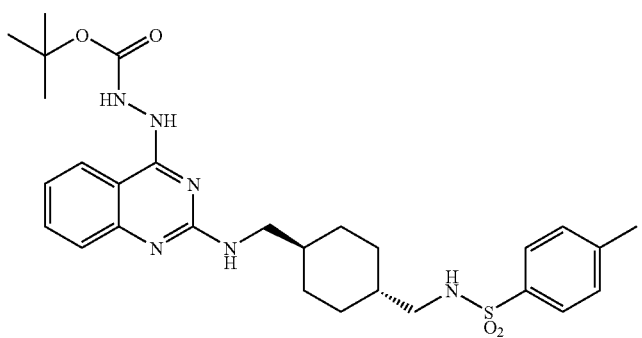 CF₃CO₂H | 555.8 (M + H) | 4.57 |
| 2762 | 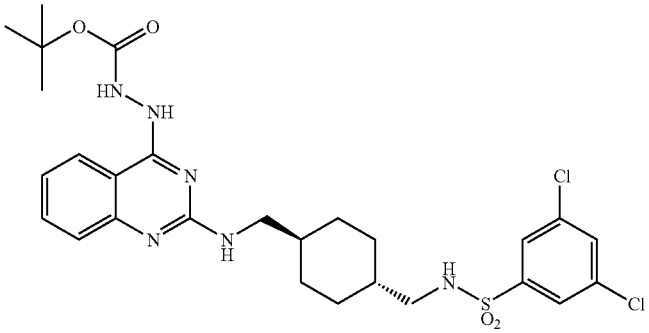 CF₃CO₂H | 609.8 (M + H) | 4.94 |
| 2763 | 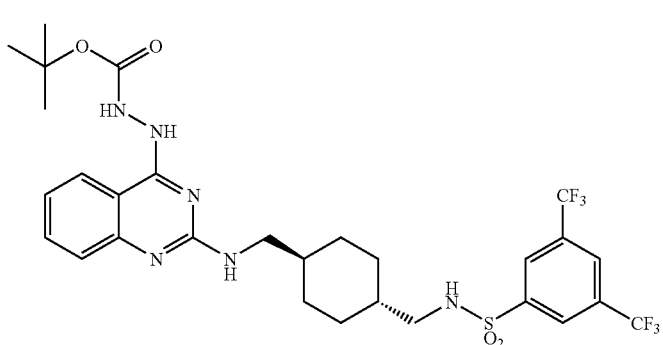 CF₃CO₂H | 677.8 (M + H) | 5.05 |

-continued

| Example No. | Structure | ESI-MS | Retention Time (min) |
|---|---|---|---|
| 2764 | CF₃CO₂H | 591.6 (M + H) | 4.73 |
| 2765 | CF₃CO₂H | 591.6 (M + H) | 4.75 |
| 2766 | 2CF₃CO₂H | 635.0 (M + H) | 4.47 |

-continued

| Example No. | Structure | ESI-MS | Retention Time (min) |
|---|---|---|---|
| 2767 | 2CF$_3$CO$_2$H | 503.6 (M + H) | 3.83 |
| 2768 | 2CF$_3$CO$_2$H | 503.6 (M + H) | 3.99 |
| 2769 | 2CF$_3$CO$_2$H | 571.6 (M + H) | 4.16 |

-continued

| Example No. | Structure | ESI-MS | Retention Time (min) |
|---|---|---|---|
| 2770 | 2CF₃CO₂H | 547.6 (M + H) | 3.85 |
| 2771 | 2CF₃CO₂H | 529.6 (M + H) | 3.75 |
| 2772 | 2CF₃CO₂H | 553.8 (M + H) | 3.99 |

-continued

| Example No. | Structure | ESI-MS | Retention Time (min) |
|---|---|---|---|
| 2773 | 2CF₃CO₂H | 537.6 (M + H) | 3.93 |
| 2774 | 2CF₃CO₂H | 525.8 (M + H) | 4.22 |
| 2775 | 2CF₃CO₂H | 475.6 (M + H) | 3.64 |

-continued

| Example No. | Structure | ESI-MS | Retention Time (min) |
|---|---|---|---|
| 2776 | 2CF₃CO₂H | 469.6 (M + H) | 3.71 |
| 2777 | 2CF₃CO₂H | 503.6 (M + H) | 3.97 |
| 2778 | 2CF₃CO₂H | 553.8 (M + H) | 4.17 |

-continued

| Example No. | Structure | ESI-MS | Retention Time (min) |
|---|---|---|---|
| 2779 | (structure) 2CF₃CO₂H | 483.4 (M + H) | 3.87 |
| 2780 | (structure) 2CF₃CO₂H | 547.6 (M + H) | 4.04 |
| 2781 | (structure) 2CF₃CO₂H | 537.4 (M + H) | 4.23 |

-continued

| Example No. | Structure | ESI-MS | Retention Time (min) |
|---|---|---|---|
| 2782 | 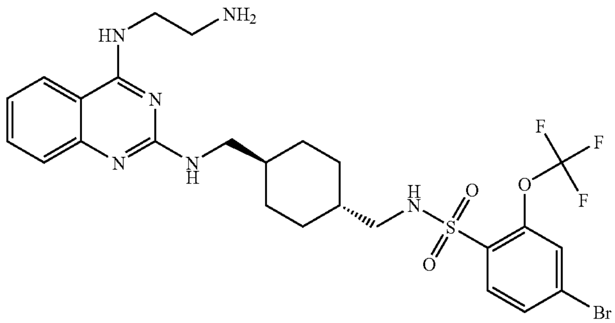 | 631.6 (M + H) | 4.23 |
| 2783 | 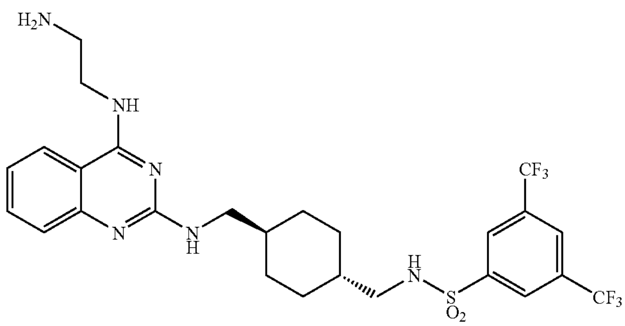 | 605.8 (M + H) | 4.41 |
| 2784 | 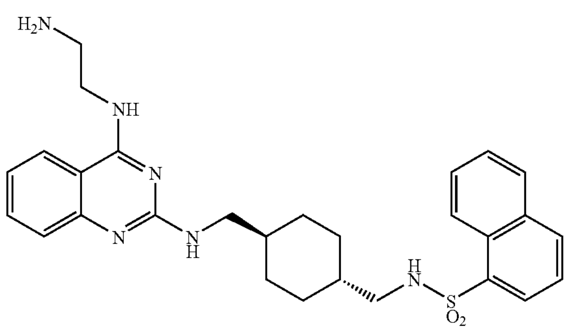 | 519.6 (M + H) | 4.01 |
| 2785 | 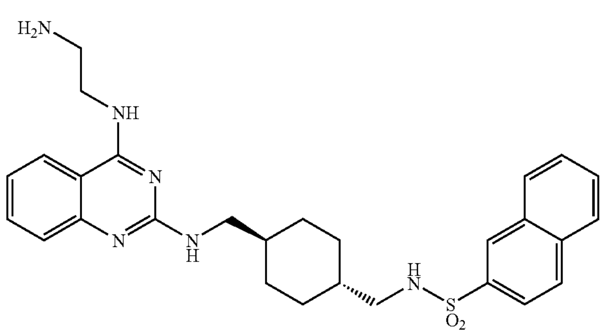 | 519.6 (M + H) | 4.07 |

-continued
| Example No. | Structure | ESI-MS | Retention Time (min) |
|---|---|---|---|
| 2786 | 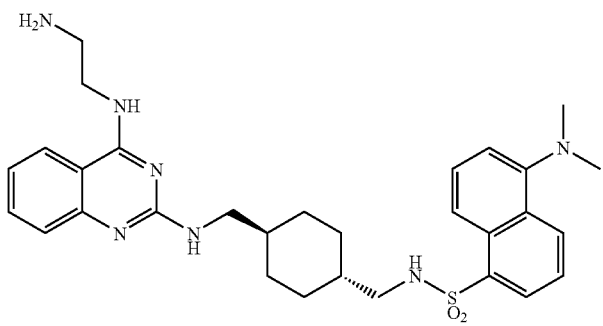 3CF$_3$CO$_2$H | 562.6 (M + H) | 3.77 |
| 2787 | 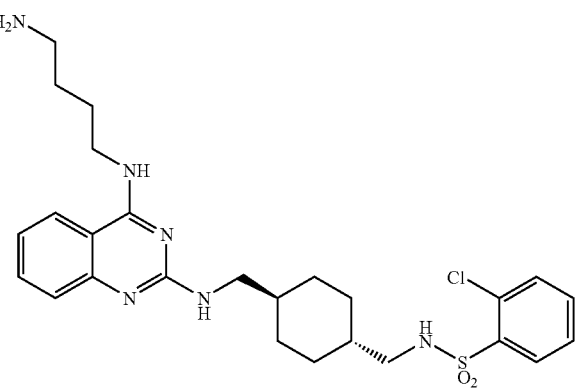 2CF$_3$CO$_2$H | 531.6 (M + H) | 3.90 |
| 2788 | 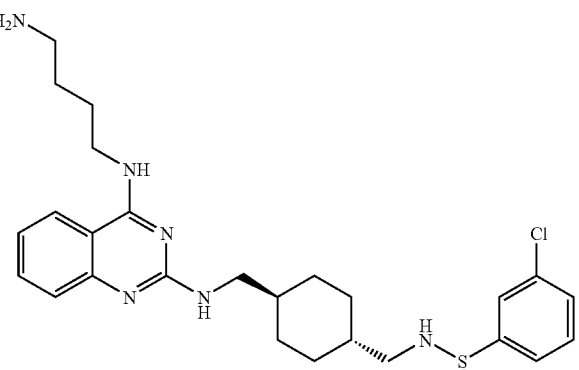 2CF$_3$CO$_2$H | 531.6 (M + H) | 4.04 |

-continued
| Example No. | Structure | ESI-MS | Retention Time (min) |
|---|---|---|---|
| 2789 | 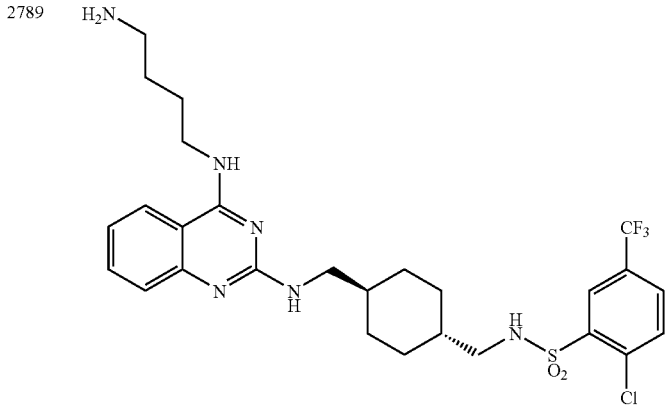 2CF$_3$CO$_2$H | 599.6 (M + H) | 4.24 |
| 2790 | 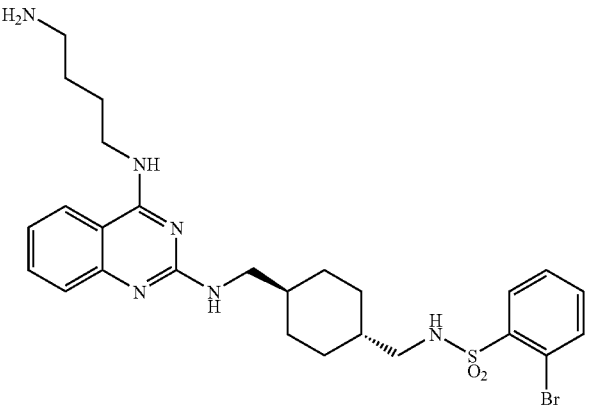 2CF$_3$CO$_2$H | 575.0 (M + H) | 3.95 |
| 2791 | 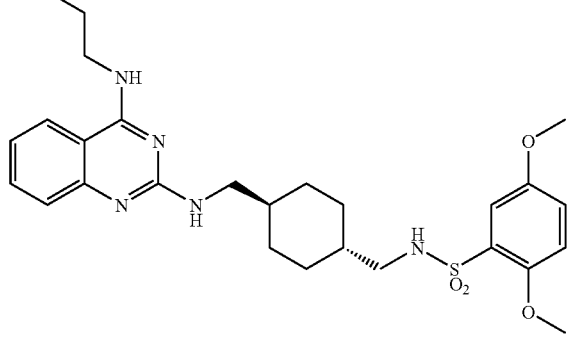 2CF$_3$CO$_2$H | 557.6 (M + H) | 3.86 |

-continued
| Example No. | Structure | ESI-MS | Retention Time (min) |
|---|---|---|---|
| 2792 | 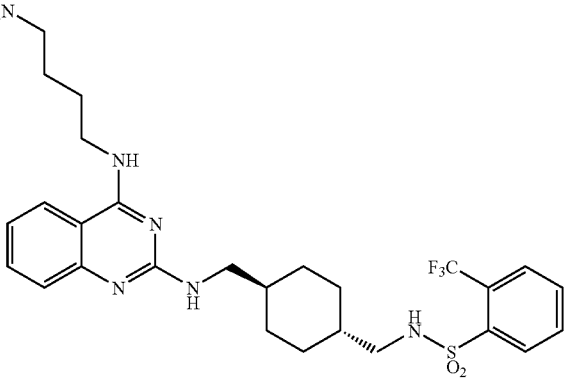 2CF₃CO₂H | 565.6 (M + H) | 4.03 |
| 2793 | 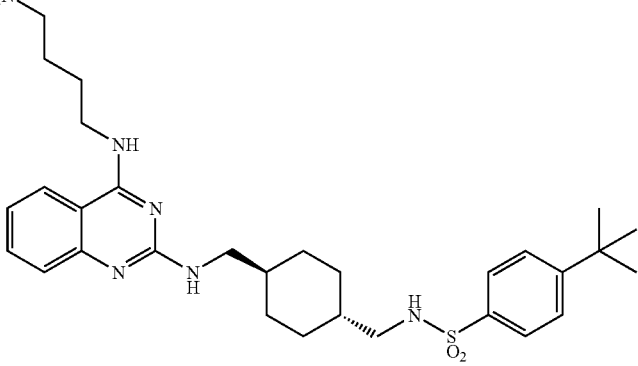 2CF₃CO₂H | 554 (M + H) | 4.29 |
| 2794 | 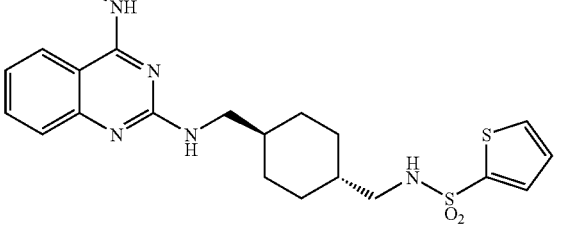 2CF₃CO₂H | 503.6 (M + H) | 3.78 |

-continued
| Example No. | Structure | ESI-MS | Retention Time (min) |
|---|---|---|---|
| 2795 | 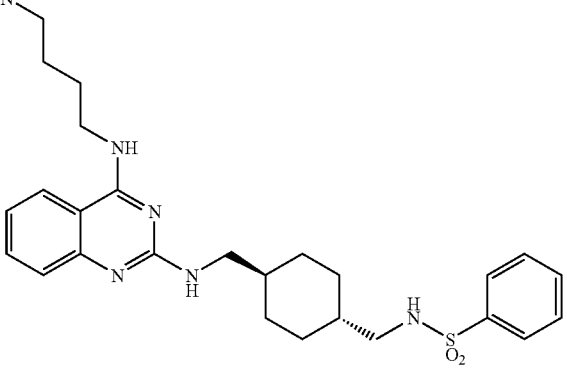 2CF₃CO₂H | 497.6 (M + H) | 3.83 |
| 2796 | 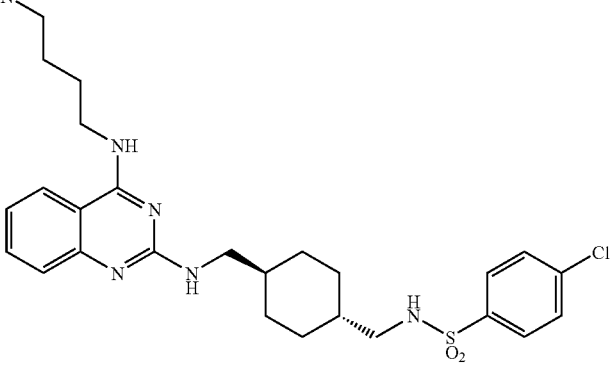 2CF₃CO₂H | 531.6 (M + H) | 4.05 |
| 2797 | 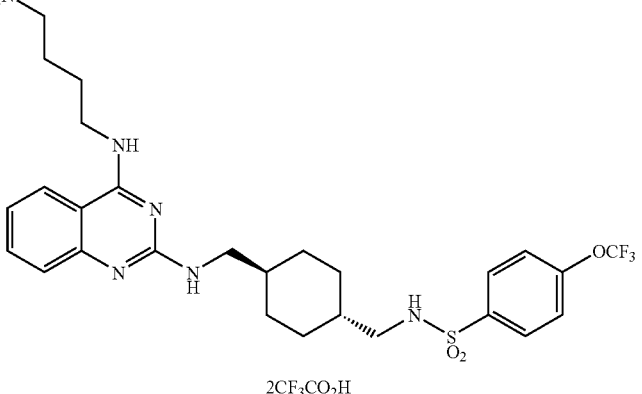 2CF₃CO₂H | 582.0 (M + H) | 4.23 |

-continued

| Example No. | Structure | ESI-MS | Retention Time (min) |
|---|---|---|---|
| 2798 | (structure) 2CF₃CO₂H | 511 (M + H) | 3.95 |
| 2799 | (structure) 2CF₃CO₂H | 575.6 (M + H) | 4.10 |
| 2800 | (structure) 2CF₃CO₂H | 565.0 (M + H) | 4.32 |

-continued
| Example No. | Structure | ESI-MS | Retention Time (min) |
|---|---|---|---|
| 2801 | 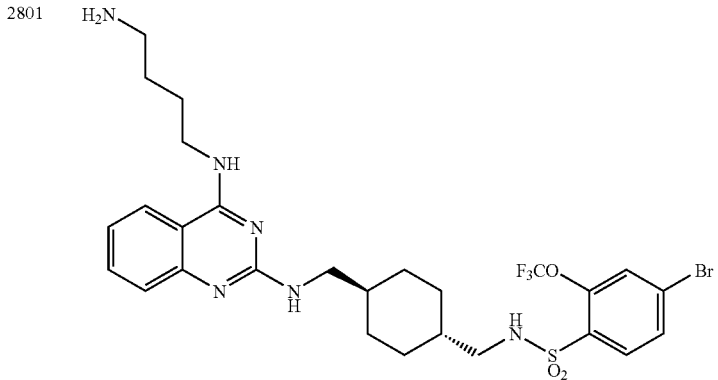 2CF₃CO₂H | 659.6 (M + H) | 4.35 |
| 2802 | 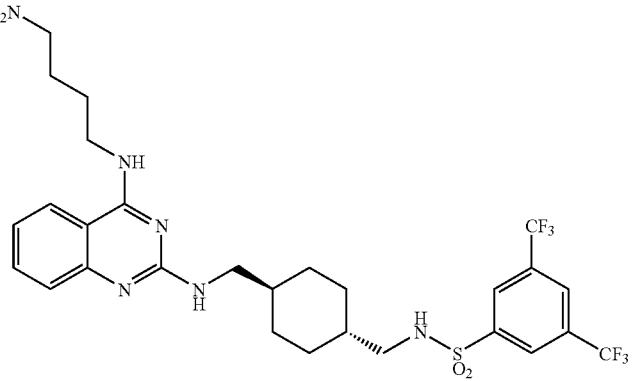 2CF₃CO₂H | 634.0 (M + H) | 4.43 |
| 2803 | 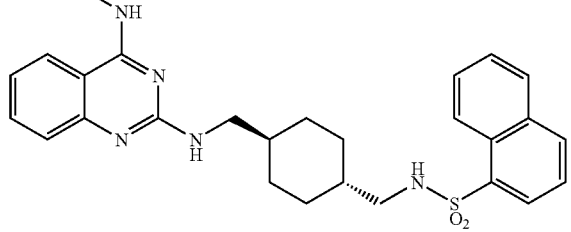 2CF₃CO₂H | 547.6 (M + H) | 4.09 |

-continued
| Example No. | Structure | ESI-MS | Retention Time (min) |
|---|---|---|---|
| 2804 | 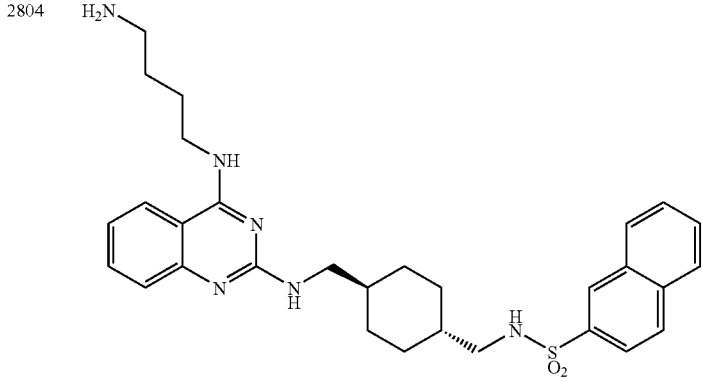 2CF₃CO₂H | 547.6 (M + H) | 4.15 |
| 2805 | 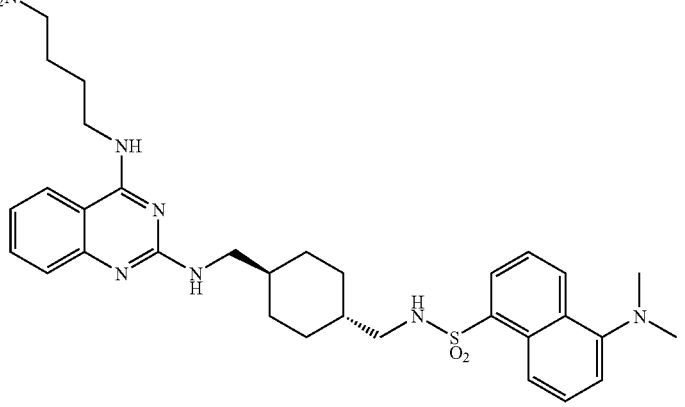 2CF₃CO₂H | 590.6 (M + H) | 3.93 |
| 2806 | 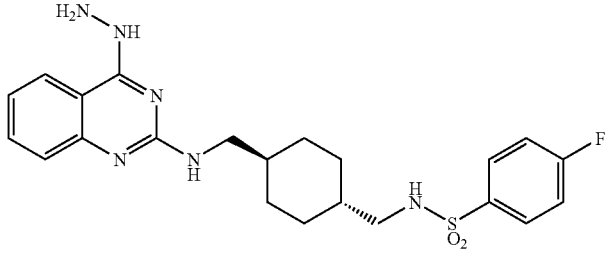 2CF₃CO₂H | 495.6 (M + H) | 4.07 |

-continued
| Example No. | Structure | ESI-MS | Retention Time (min) |
|---|---|---|---|
| 2807 | <br>2CF$_3$CO$_2$H | 477.6 (M + H) | 4.07 |
| 2808 | 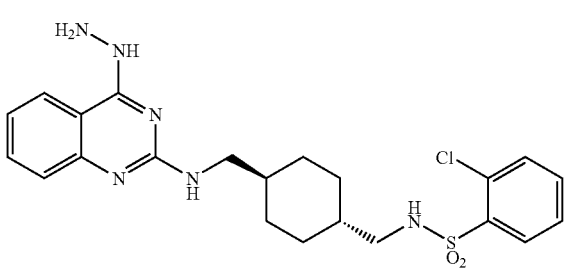<br>2CF$_3$CO$_2$H | 475.6 (M + H) | 4.07 |
| 2809 | <br>2CF$_3$CO$_2$H | 475.6 (M + H) | 4.23 |
| 2810 | <br>2CF$_3$CO$_2$H | 501.8 (M + H) | 4.15 |

-continued

| Example No. | Structure | ESI-MS | Retention Time (min) |
|---|---|---|---|
| 2811 | 2CF₃CO₂H | 509.4 (M + H) | 4.27 |
| 2812 | 2CF₃CO₂H | 525.6 (M + H) | 4.37 |
| 2813 | 2CF₃CO₂H | 519.6 (M + H) | 4.25 |
| 2814 | 2CF₃CO₂H | 509.4 (M + H) | 4.49 |

-continued

| Example No. | Structure | ESI-MS | Retention Time (min) |
|---|---|---|---|
| 2815 | 2CF₃CO₂H | 603.0 (M + H) | 4.60 |
| 2816 | 2CF₃CO₂H | 577.6 (M + H) | 4.72 |
| 2817 | 2CF₃CO₂H | 491 (M + H) | 4.31 |
| 2818 | 2CF₃CO₂H | 491.6 (M + H) | 4.33 |
| 2819 | 3CF₃CO₂H | 534.6 (M + H) | 4.01 |

-continued

| Example No. | Structure | ESI-MS | Retention Time (min) |
|---|---|---|---|
| 2820 | 2HCl | 325.4 (M + H) | 3.91 |
| 2821 | 2HCl | 359.4 (M + H) | 4.24 |
| 2822 | 2HCl | 409.4 (M + H) | 4.51 |
| 2823 | 2HCl | 339.6 (M + H) | 4.09 |
| 2824 | 2HCl | 403.4 (M + H) | 4.28 |

-continued
| Example No. | Structure | ESI-MS | Retention Time (min) |
|---|---|---|---|
| 2825 | 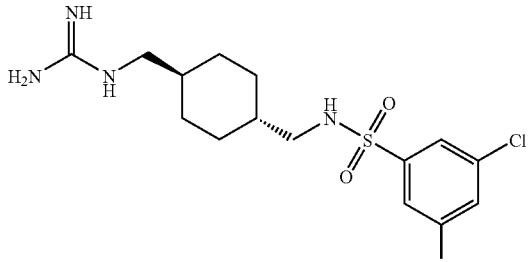 2HCl | 393.0 (M + H) | 4.57 |
| 2826 | 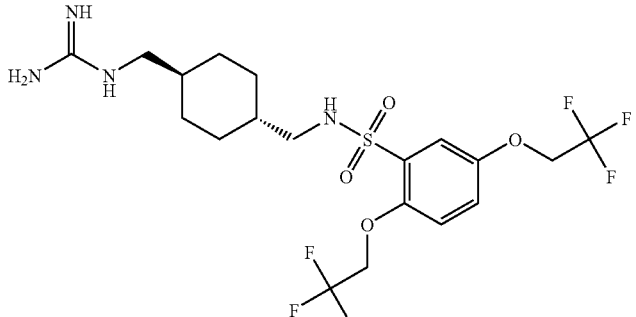 2HCl | 521.6 (M + H) | 4.69 |
| 2827 | 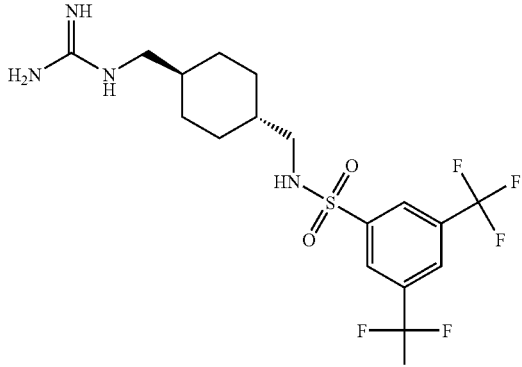 2HCl | 491.6 (M + H) | 4.77 |
| 2828 | 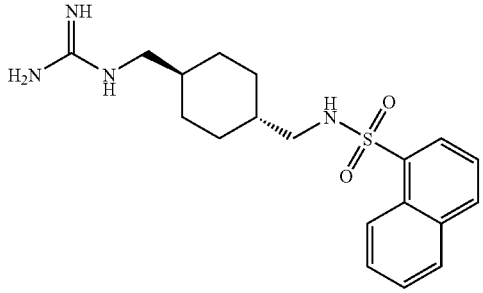 2HCl | 375.4 (M + H) | 4.33 |

-continued

| Example No. | Structure | ESI-MS | Retention Time (min) |
|---|---|---|---|
| 2829 | 2HCl | 375.4 (M + H) | 4.39 |
| 2830 | 2HCl | 418.8 (M + H) | 4.33 |
| 2831 | 2HCl | 343.4 (M + H) | 3.96 |
| 2832 | 2HCl | 343.4 (M + H) | 4.03 |
| 2833 | 2HCl | 359.4 (M + H) | 4.05 |

-continued

| Example No. | Structure | ESI-MS | Retention Time (min) |
|---|---|---|---|
| 2834 | 2HCl | 359.4 (M + H) | 4.24 |
| 2835 | 2HCl | 403.4 (M + H) | 4.07 |
| 2836 | 2HCl | 385.4 (M + H) | 4.00 |
| 2837 | 2HCl | 409.4 (M + H) | 4.32 |
| 2838 | 2HCl | 393.6 (M + H) | 4.23 |

-continued

| Example No. | Structure | ESI-MS | Retention Time (min) |
|---|---|---|---|
| 2839 | 2HCl | 381.6 (M + H) | 4.62 |
| 2840 | 2HCl | 330.8 (M + H) | 3.83 |
| 2841 | 2HCl | 361.4 (M + H) | 4.05 |
| 2842 | 2HCl | 427.4 (M + H) | 4.51 |
| 2843 | 2CF$_3$CO$_2$H | 458.4 (M + H) | 3.22 |

-continued

| Example No. | Structure | ESI-MS | Retention Time (min) |
|---|---|---|---|
| 2844 | 2CF₃CO₂H | 415.4 (M + H) | 3.01 |
| 2845 | 2CF₃CO₂H | 432.6 (M + H) | 3.26 |
| 2846 | 2CF₃CO₂H | 396.2 (M + H) | 2.81 |
| 2847 | 2CF₃CO₂H | 450.0 (M + H) | 3.09 |
| 2848 | 2CF₃CO₂H | 408.4 (M + H) | 2.85 |
| 2849 | 2CF₃CO₂H | 434.4 (M + H) | 2.89 |

-continued

| Example No. | Structure | ESI-MS | Retention Time (min) |
|---|---|---|---|
| 2850 | 2CF₃CO₂H | 440.0 (M + H) | 3.20 |
| 2851 | 2CF₃CO₂H | 482.4 (M + H) | 3.43 |
| 2852 | 2CF₃CO₂H | 466.4 (M + H) | 2.71 |
| 2853 | 2CF₃CO₂H | 380.2 (M + H) | 2.72 |
| 2854 | 2CF₃CO₂H | 429.2 (M + H) | 2.91 |

-continued

| Example No. | Structure | ESI-MS | Retention Time (min) |
|---|---|---|---|
| 2855 | 2CF$_3$CO$_2$H | 450.0 (M + H) | 2.82 |
| 2856 | 2CF$_3$CO$_2$H | 434.4 (M + H) | 2.69 |
| 2857 | 2CF$_3$CO$_2$H | 440.0 (M + H) | 2.85 |
| 2858 | 2CF$_3$CO$_2$H | 550.6 (M + H) | 3.80 |
| 2859 | 3CF$_3$CO$_2$H | 441.4 (M + H) | 3.03 |
| 2860 | 2CF$_3$CO$_2$H | 446.6 (M + H) | 3.41 |

-continued

| Example No. | Structure | ESI-MS | Retention Time (min) |
|---|---|---|---|
| 2861 | 2CF₃CO₂H | 448.4 (M + H) | 2.91 |
| 2862 | 2CF₃CO₂H | 424.2 (M + H) | 3.05 |
| 2863 | 3CF₃CO₂H | 441.4 (M + H) | 2.68 |
| 2864 | 3CF₃CO₂H | 463.4 (M + H) | 2.76 |
| 2865 | 2CF₃CO₂H | 408.4 (M + H) | 2.91 |
| 2866 | 2CF₃CO₂H | 492.2 (M + H) | 3.30 |

-continued

| Example No. | Structure | ESI-MS | Retention Time (min) |
|---|---|---|---|
| 2867 | 2CF₃CO₂H | 464.2 (M + H) | 2.93 |
| 2868 | 2CF₃CO₂H | 474.4 (M + H) | 3.27 |
| 2869 | 2CF₃CO₂H | 390.6 (M + H) | 2.88 |
| 2870 | 2CF₃CO₂H | 482.2 (M + H) | 3.43 |
| 2871 | 2CF₃CO₂H | 408.4 (M + H) | 2.91 |

-continued
| Example No. | Structure | ESI-MS | Retention Time (min) |
|---|---|---|---|
| 2872 | 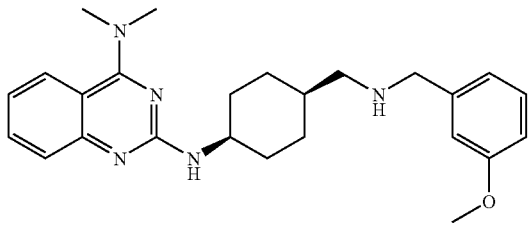 2CF₃CO₂H | 420.4 (M + H) | 2.91 |
| 2873 | 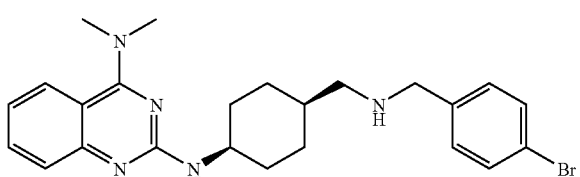 2CF₃CO₂H | 468.2 (M + H) | 3.09 |
| 2874 | 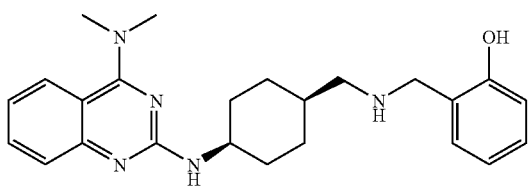 2CF₃CO₂H | 406.4 (M + H) | 2.80 |
| 2875 | 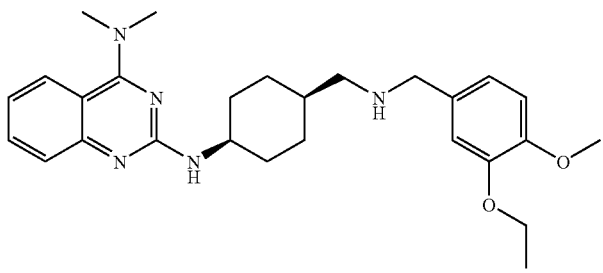 2CF₃CO₂H | 464.2 (M + H) | 2.97 |
| 2876 | 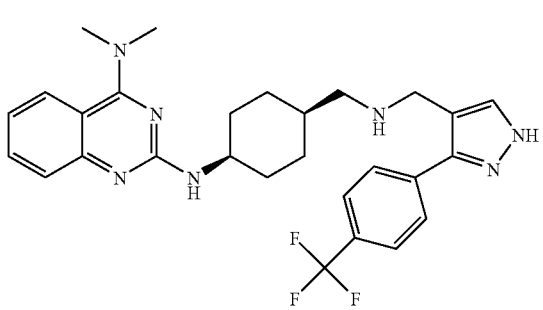 3CF₃CO₂H | 524.6 (M + H) | 3.12 |

-continued

| Example No. | Structure | ESI-MS | Retention Time (min) |
|---|---|---|---|
| 2877 | 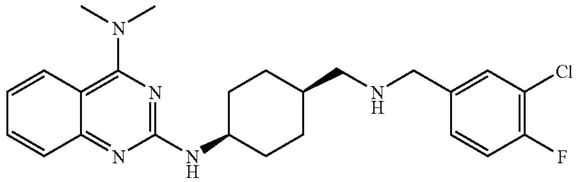 | 442.4 (M + H) | 3.10 |
| 2878 | 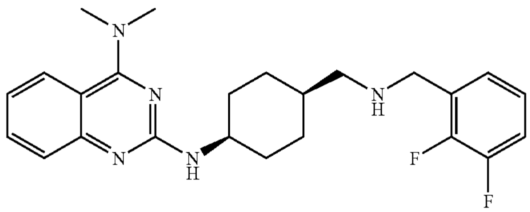 | 426.2 (M + H) | 2.90 |
| 2879 | 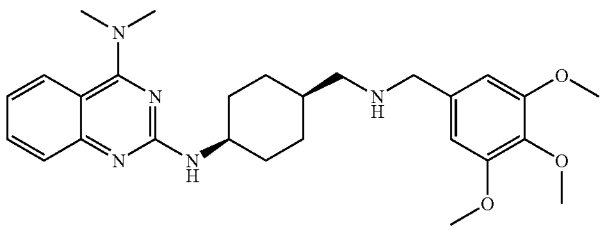 | 480.2 (M + H) | 2.89 |
| 2880 | 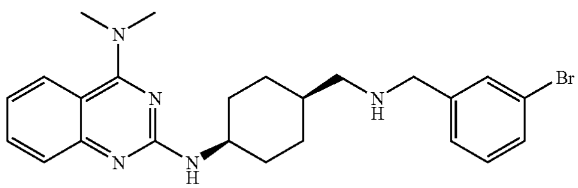 | 468.2 (M + H) | 3.07 |
| 2881 | 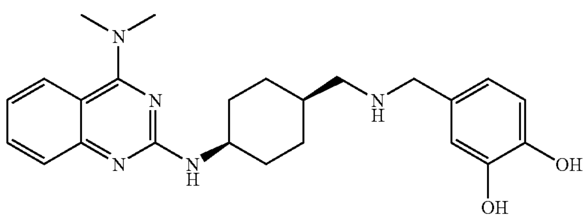 | 422.4 (M + H) | 2.61 |
| 2882 | 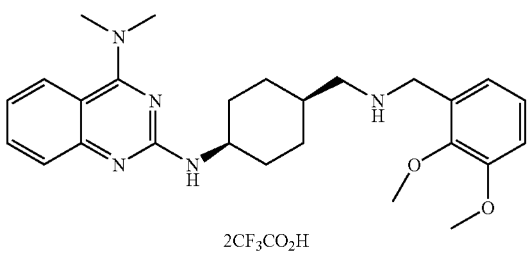 | 450.0 (M + H) | 2.93 |

-continued

| Example No. | Structure | ESI-MS | Retention Time (min) |
|---|---|---|---|
| 2883 | 2CF$_3$CO$_2$H | 404.6 (M + H) | 3.01 |
| 2884 | 2CF$_3$CO$_2$H | 436.4 (M + H) | 3.08 |
| 2885 | 2CF$_3$CO$_2$H | 440.0 (M + H) | 3.18 |
| 2886 | 2CF$_3$CO$_2$H | 470.4 (M + H) | 3.25 |
| 2887 | 2CF$_3$CO$_2$H | 450.0 (M + H) | 3.01 |
| 2888 | 2CF$_3$CO$_2$H | 466.4 (M + H) | 3.40 |

-continued

| Example No. | Structure | ESI-MS | Retention Time (min) |
|---|---|---|---|
| 2889 | (structure) 2CF₃CO₂H | 415.4 (M + H) | 2.83 |
| 2890 | (structure) 2CF₃CO₂H | 458.4 (M + H) | 3.25 |
| 2891 | (structure) 2CF₃CO₂H | 468.2 (M + H) | 3.00 |
| 2892 | (structure) 2CF₃CO₂H | 406.4 (M + H) | 2.66 |
| 2893 | (structure) 2CF₃CO₂H | 420.4 (M + H) | 2.92 |
| 2894 | (structure) 3CF₃CO₂H | 379.4 (M + H) | 2.71 |

-continued
| Example No. | Structure | ESI-MS | Retention Time (min) |
|---|---|---|---|
| 2895 | 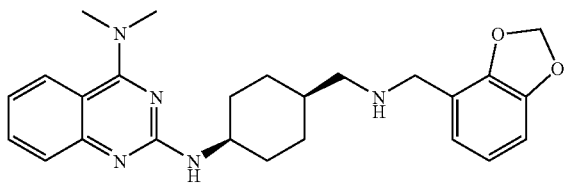 2CF$_3$CO$_2$H | 434.4 (M + H) | 2.87 |
| 2896 | 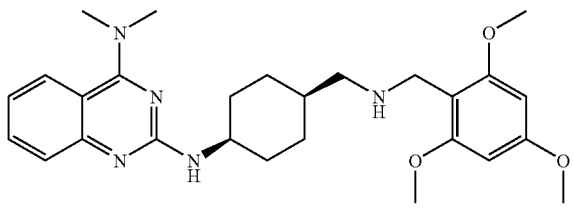 2CF$_3$CO$_2$H | 480.2 (M + H)\ | 3.17 |
| 2897 | 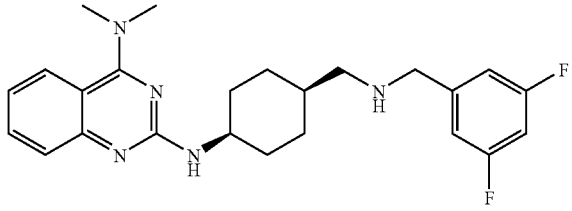 2CF$_3$CO$_2$H | 426.2 (M + H) | 2.98 |
| 2898 | 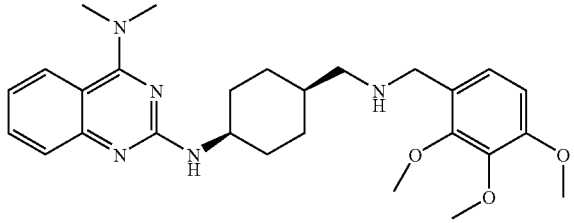 2CF$_3$CO$_2$H | 480.2 (M + H) | 2.99 |
| 2899 | 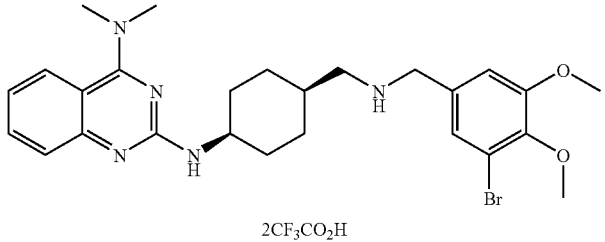 2CF$_3$CO$_2$H | 528.4 (M + H) | 3.15 |
| 2900 | 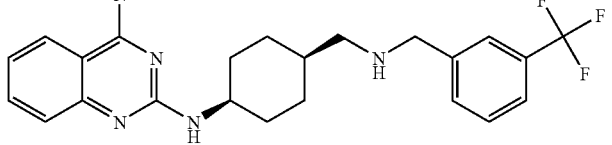 2CF$_3$CO$_2$H | 458.4 (M + H) | 3.19 |

-continued

| Example No. | Structure | ESI-MS | Retention Time (min) |
|---|---|---|---|
| 2901 | 2CF₃CO₂H | 480.2 (M + H) | 2.92 |
| 2902 | 2CF₃CO₂H | 470.4 (M + H) | 3.27 |
| 2903 | 2CF₃CO₂H | 404.6 (M + H) | 2.87 |
| 2904 | 2CF₃CO₂H | 460.4 (M + H) | 3.48 |
| 2905 | 2CF₃CO₂H | 410.4 (M + H) | 2.96 |
| 2906 | 2CF₃CO₂H | 450.0 (M + H) | 3.03 |

-continued

| Example No. | Structure | ESI-MS | Retention Time (min) |
|---|---|---|---|
| 2907 | (4-dimethylamino-quinazolin-2-yl)-amino-cyclohexyl-methyl-NH-CH2-(4-methoxy-3-methylphenyl); 2CF3CO2H | 434.4 (M + H) | 3.08 |
| 2908 | (4-dimethylamino-quinazolin-2-yl)-amino-cyclohexyl-methyl-NH-CH2-(5-acetoxymethyl-furan-2-yl); 2CF3CO2H | 452.2 (M + H) | 2.79 |
| 2909 | (4-dimethylamino-quinazolin-2-yl)-amino-cyclohexyl-methyl-NH-CH2-(thiophen-3-yl); 2CF3CO2H | 396.2 (M + H) | 2.81 |
| 2910 | (4-dimethylamino-quinazolin-2-yl)-amino-cyclohexyl-methyl-NH-CH2-(4-pyrrolidin-1-yl-phenyl); 3CF3CO2H | 459.4 (M + H) | 3.21 |
| 2911 | (4-dimethylamino-quinazolin-2-yl)-amino-cyclohexyl-methyl-NH-CH2-(2,3-dichlorophenyl); 2CF3CO2H | 458.2 (M + H) | 3.08 |

-continued

| Example No. | Structure | ESI-MS | Retention Time (min) |
|---|---|---|---|
| 2912 | (structure) 2CF₃CO₂H | 410.4 (M + H) | 2.88 |
| 2913 | (structure) 2CF₃CO₂H | 426.2 (M + H) | 3.01 |
| 2914 | (structure) 3CF₃CO₂H | 429.4 (M + H) | 2.97 |
| 2915 | (structure) 3CF₃CO₂H | 507.2 (M + H) | 3.53 |
| 2916 | (structure) 2CF₃CO₂H | 522.4 (M + H) | 3.56 |

| Example No. | Structure | ESI-MS | Retention Time (min) |
|---|---|---|---|
| 2917 | (structure) 3CF$_3$CO$_2$H | 483.2 (M + H) | 2.80 |
| 2918 | (structure) 3CF$_3$CO$_2$H | 507.2 (M + H) | 3.27 |
| 2919 | (structure) 2CF$_3$CO$_2$H | 474.2 (M + H) | 3.10 |
| 2920 | (structure) 2CF$_3$CO$_2$H | 450.0 (M + H) | 3.00 |
| 2921 | (structure) 2CF$_3$CO$_2$H | 498.4 (M + H) | 3.15 |

-continued
| Example No. | Structure | ESI-MS | Retention Time (min) |
|---|---|---|---|
| 2922 | 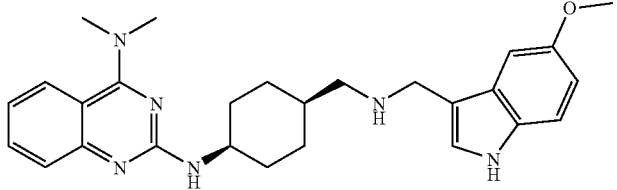 3CF$_3$CO$_2$H | 459.4 (M + H) | 2.99 |
| 2923 | 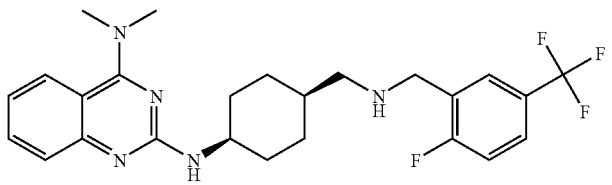 2CF$_3$CO$_2$H | 476.0 (M + H) | 3.10 |
| 2924 | 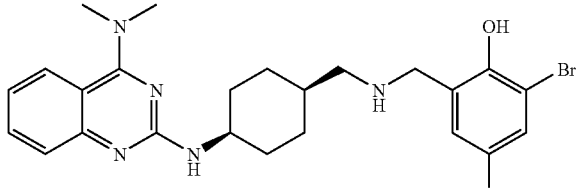 2CF$_3$CO$_2$H | 518.2 (M + H) | 3.10 |
| 2925 | 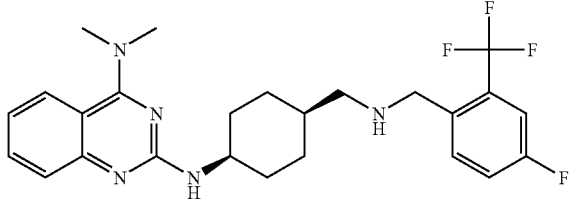 2CF$_3$CO$_2$H | 476.2 (M + H) | 3.12 |
| 2926 | 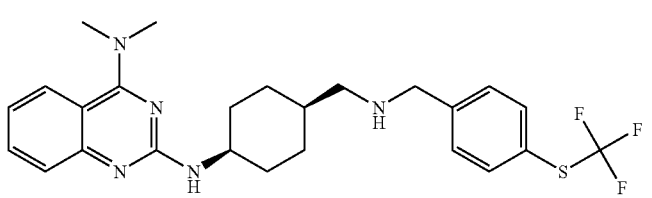 2CF$_3$CO$_2$H | 490.4 (M + H) | 3.35 |
| 2927 | 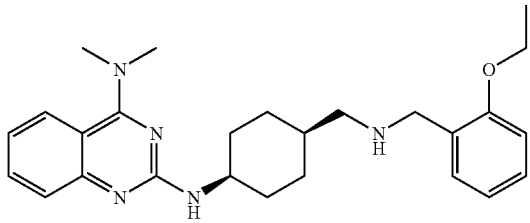 2CF$_3$CO$_2$H | 434.4 (M + H) | 3.11 |

-continued
| Example No. | Structure | ESI-MS | Retention Time (min) |
|---|---|---|---|
| 2928 | 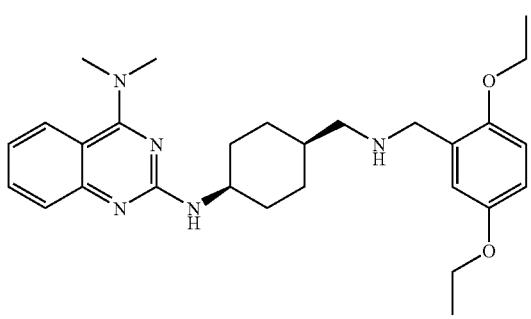 2CF$_3$CO$_2$H | 478.4 (M + H) | 3.29 |
| 2929 | 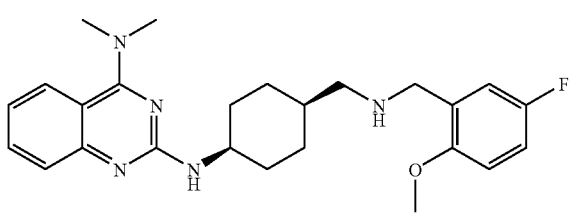 2CF$_3$CO$_2$H | 438.2 (M + H) | 3.01 |
| 2930 | 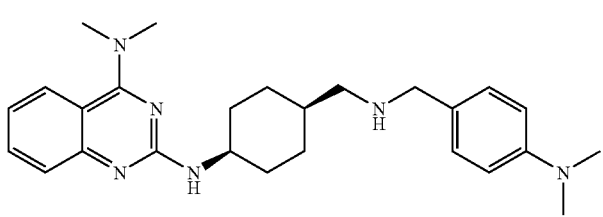 2CF$_3$CO$_2$H | 433.4 (M + H) | 2.59 |
| 2931 | 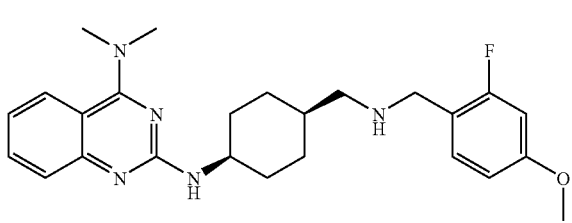 2CF$_3$CO$_2$H | 438.2 (M + H) | 2.90 |
| 2932 | 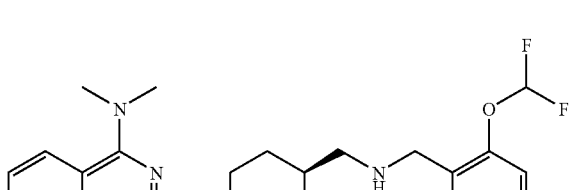 2CF$_3$CO$_2$H | 456.2 (M + H) | 3.10 |

-continued
| Example No. | Structure | ESI-MS | Retention Time (min) |
|---|---|---|---|
| 2933 | 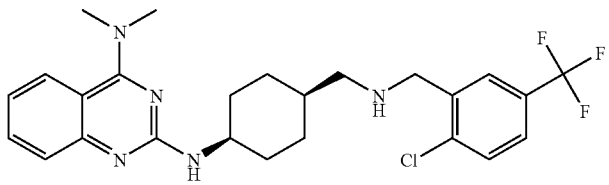 2CF$_3$CO$_2$H | 492.2 (M + H) | 3.25 |
| 2934 | 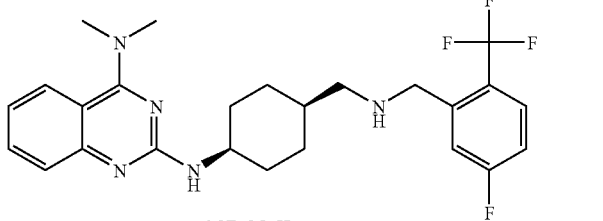 2CF$_3$CO$_2$H | 476.2 (M + H) | 3.11 |
| 2935 | 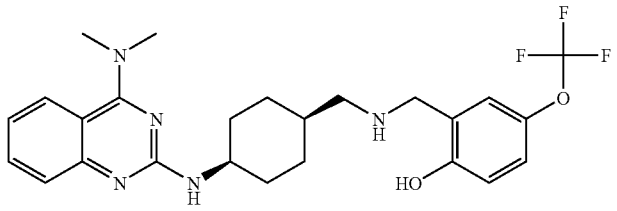 2CF$_3$CO$_2$H | 490.4 (M + H) | 3.20 |
| 2936 | 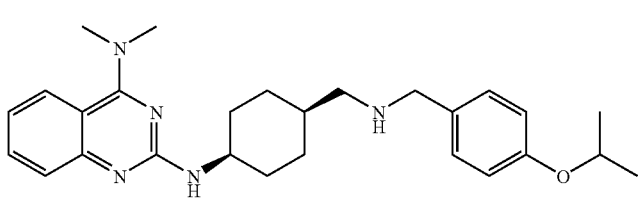 2CF$_3$CO$_2$H | 448.4 (M + H) | 3.17 |
| 2937 | 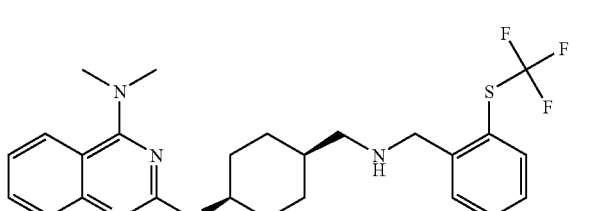 2CF$_3$CO$_2$H | 489.6 (M + H) | 3.31 |
| 2938 | 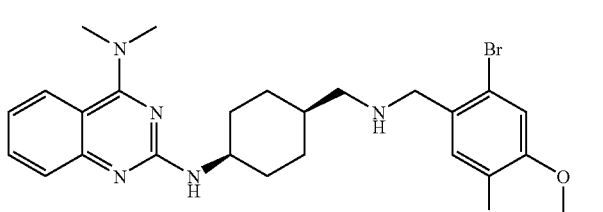 2CF$_3$CO$_2$H | 528.2 (M + H) | 3.03 |

-continued
| Example No. | Structure | ESI-MS | Retention Time (min) |
|---|---|---|---|
| 2939 | 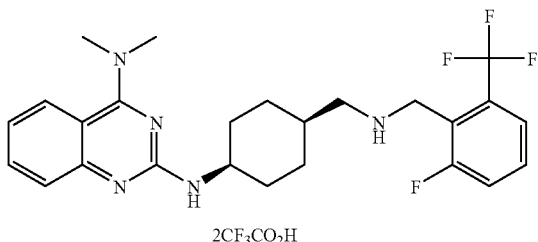 2CF₃CO₂H | 476.2 (M + H) | 2.99 |
| 2940 | 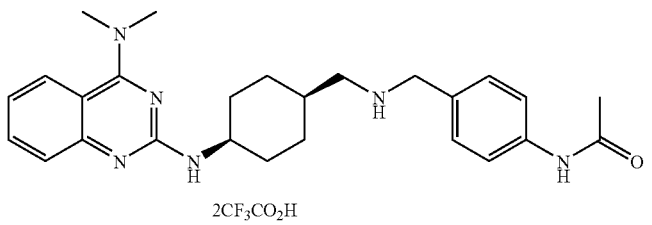 2CF₃CO₂H | 447.4 (M + H) | 2.66 |
| 2941 | 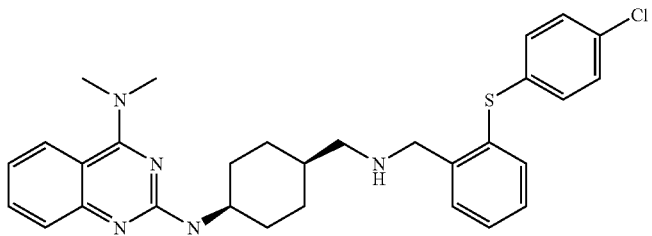 2CF₃CO₂H | 532.4 (M + H) | 3.66 |
| 2942 | 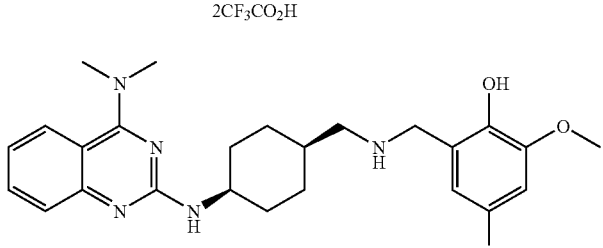 2CF₃CO₂H | 514.4 (M + H) | 3.08 |
| 2943 | 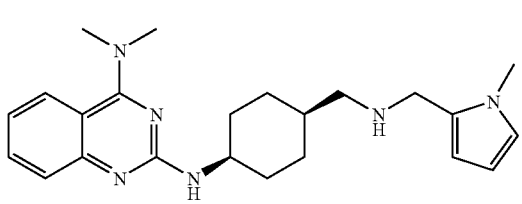 3CF₃CO₂H | 393.4 (M + H) | 2.79 |
| 2944 | 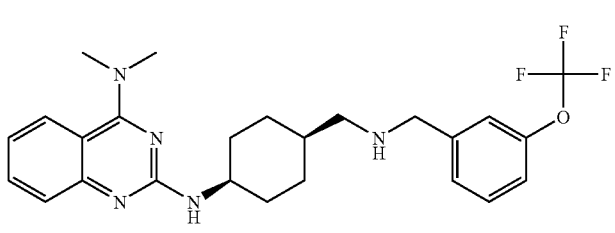 2CF₃CO₂H | 474.4 (M + H) | 3.24 |

-continued
| Example No. | Structure | ESI-MS | Retention Time (min) |
|---|---|---|---|
| 2945 | 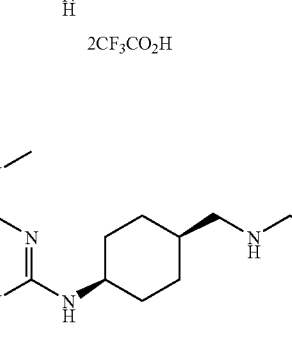 2CF$_3$CO$_2$H | 526.6 (M + H) | 3.44 |
| 2946 | 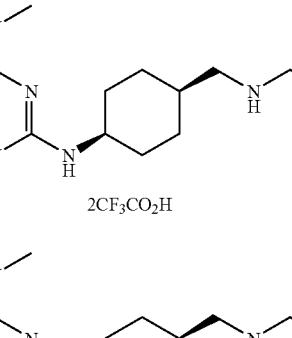 2CF$_3$CO$_2$H | 526.6 (M + H) | 3.42 |
| 2947 | 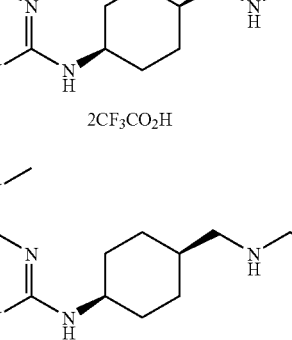 2CF$_3$CO$_2$H | 490.4 (M + H) | 3.35 |
| 2948 | 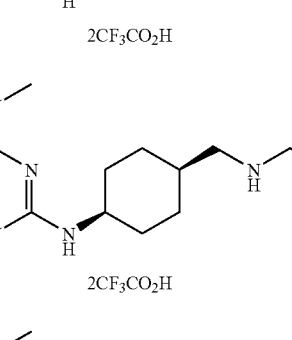 2CF$_3$CO$_2$H | 462.2 (M + H) | 3.43 |
| 2949 | 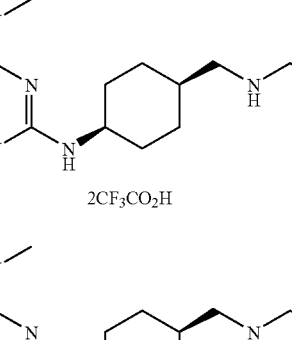 2CF$_3$CO$_2$H | 418.6 (M + H) | 3.13 |
| 2950 | 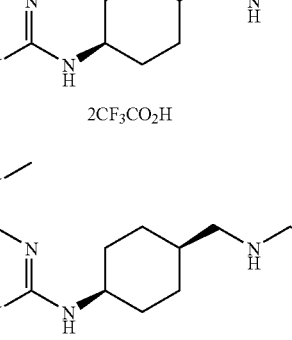 2CF$_3$CO$_2$H | 458.4 (M + H) | 3.10 |

-continued
| Example No. | Structure | ESI-MS | Retention Time (min) |
|---|---|---|---|
| 2951 | 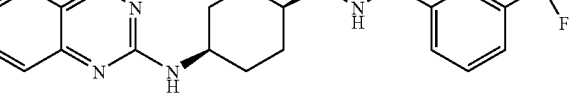<br>2CF₃CO₂H | 476.4 (M + H) | 3.19 |
| 2952 | <br>2CF₃CO₂H | 438.2 (M + H) | 2.95 |
| 2953 | <br>2CF₃CO₂H | 422.4 (M + H) | 2.61 |
| 2954 | <br>2CF₃CO₂H | 458.2 (M + H) | 3.07 |
| 2955 | <br>2CF₃CO₂H | 470.4 (M + H) | 3.45 |
| 2956 | 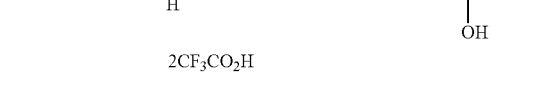<br>2CF₃CO₂H | 471.6 (M + H) | 2.88 |

-continued
| Example No. | Structure | ESI-MS | Retention Time (min) |
|---|---|---|---|
| 2957 | 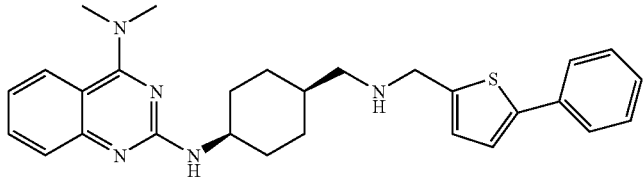 2CF₃CO₂H | 472.4 (M + H) | 3.36 |
| 2958 | 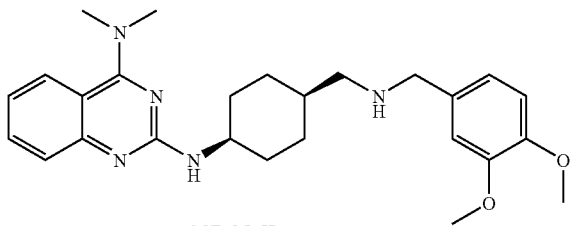 2CF₃CO₂H | 450 (M + H) | 2.75 |
| 2959 | 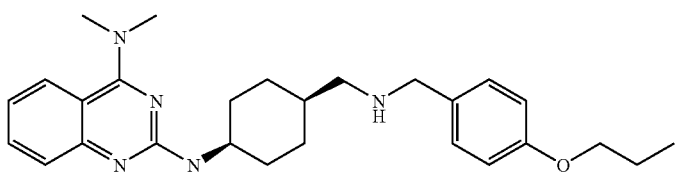 2CF₃CO₂H | 448.4 (M + H) | 3.20 |
| 2960 | 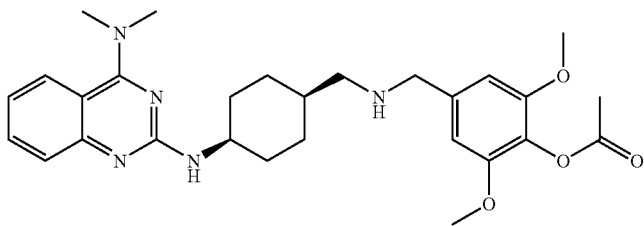 2CF₃CO₂H | 508.4 (M + H) | 3.00 |
| 2961 | 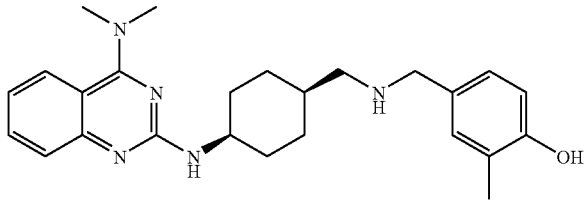 2CF₃CO₂H | 420.4 (M + H) | 2.80 |
| 2962 | 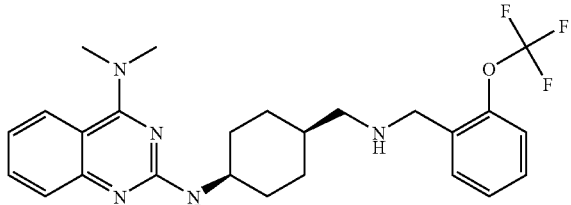 2CF₃CO₂H | 474.4 (M + H) | 3.20 |

-continued
| Example No. | Structure | ESI-MS | Retention Time (min) |
|---|---|---|---|
| 2963 | 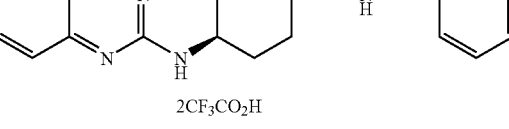 2CF₃CO₂H | 404.4 (M + H) | 2.87 |
| 2964 | 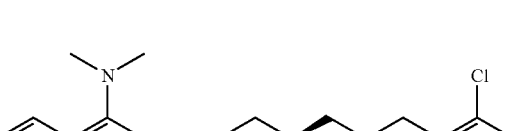 2CF₃CO₂H | 458.2 (M + H) | 3.00 |
| 2965 | 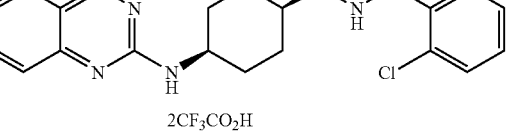 3CF₃CO₂H | 394.4 (M + H) | 2.30 |
| 2966 | 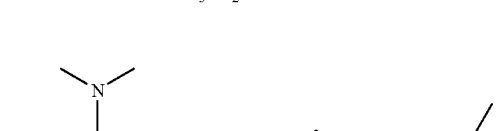 2CF₃CO₂H | 505.4 (M + H) | 2.60 |
| 2967 | 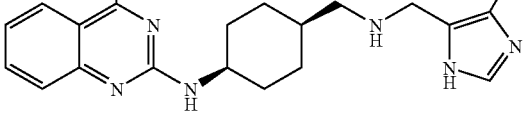 2CF₃CO₂H | 424.2 (M + H) | 3.00 |
| 2968 | 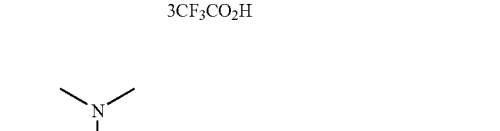 2CF₃CO₂H | 436.4 (M + H) | 2.71 |

-continued
| Example No. | Structure | ESI-MS | Retention Time (min) |
|---|---|---|---|
| 2969 | 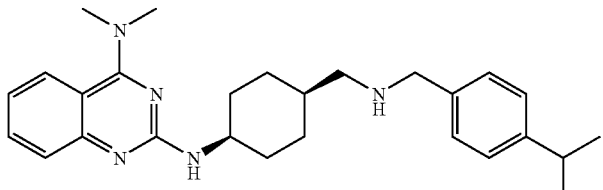 2CF$_3$CO$_2$H | 432.4 (M + H) | 3.30 |
| 2970 | 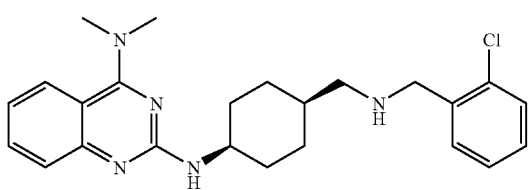 2CF$_3$CO$_2$H | 424.2 (M + H) | 2.95 |
| 2971 | 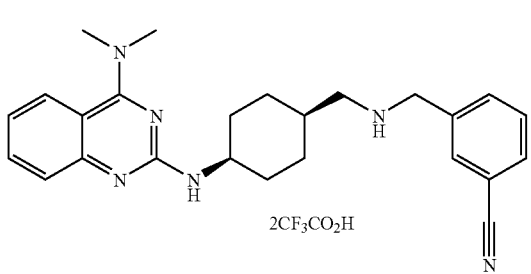 2CF$_3$CO$_2$H | 415.4 (M + H) | 2.79 |
| 2972 | 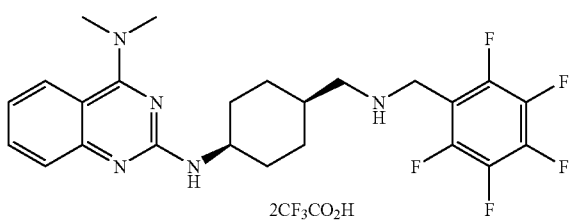 2CF$_3$CO$_2$H | 480.2 (M + H) | 3.00 |
| 2973 | 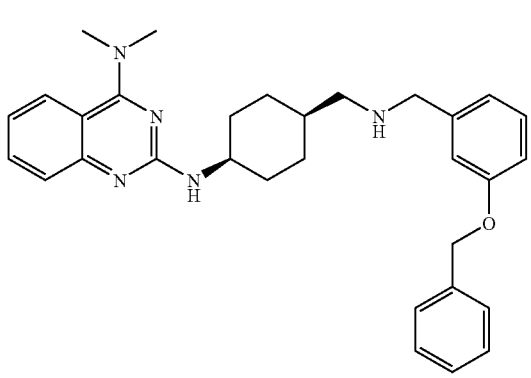 2CF$_3$CO$_2$H | 496.2 (M + H) | 3.46 |

-continued
| Example No. | Structure | ESI-MS | Retention Time (min) |
|---|---|---|---|
| 2974 | 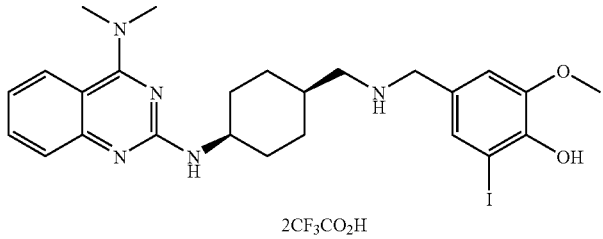 2CF₃CO₂H | 562.2 (M + H) | 2.99 |
| 2975 | 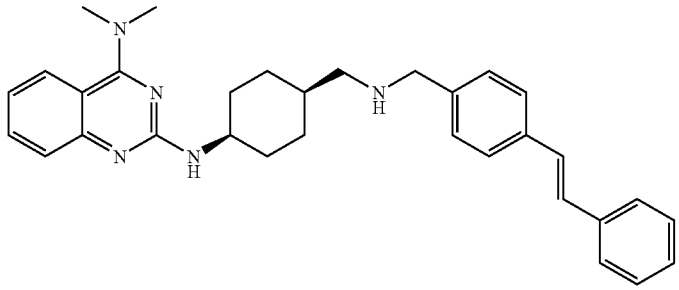 2CF₃CO₂H | 492.4 (M + H) | 3.64 |
| 2976 | 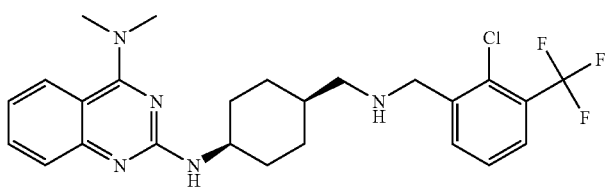 2CF₃CO₂H | 492.2 (M + H) | 3.25 |
| 2977 | 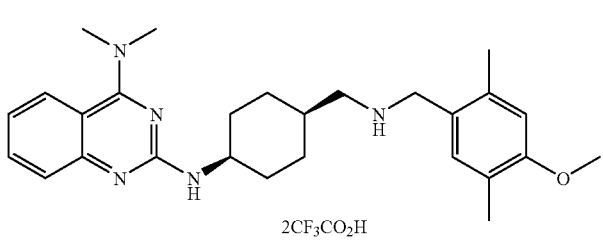 2CF₃CO₂H | 448.4 (M + H) | 3.22 |
| 2978 | 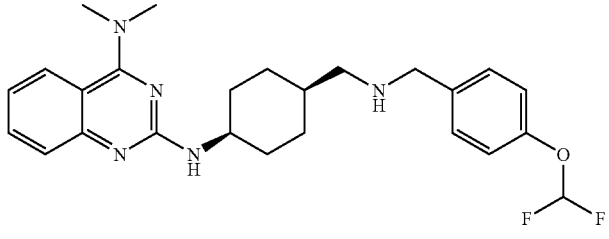 2CF₃CO₂H | 456.2 (M + H) | 3.09 |
| 2979 | 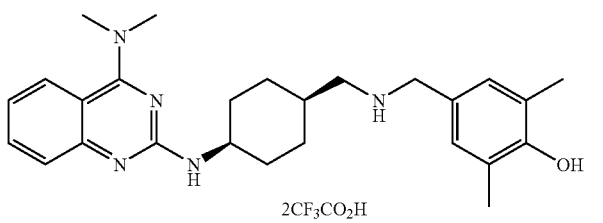 2CF₃CO₂H | 434.4 (M + H) | 2.89 |

-continued
| Example No. | Structure | ESI-MS | Retention Time (min) |
|---|---|---|---|
| 2980 | 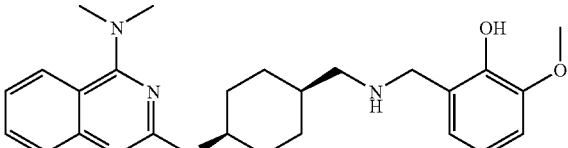 2CF₃CO₂H | 436.4 (M + H) | 2.79 |
| 2981 | 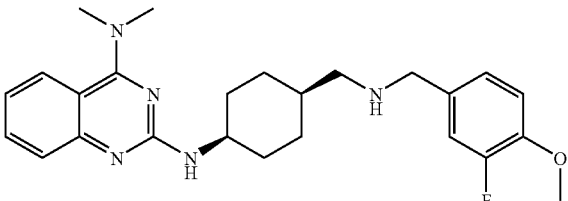 2CF₃CO₂H | 438.2 (M + H) | 2.91 |
| 2982 | 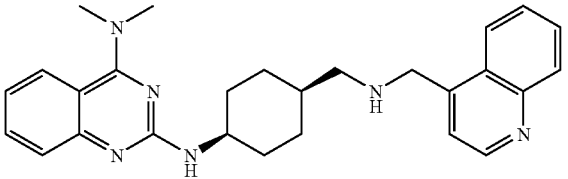 3CF₃CO₂H | 441.4 (M + H) | 2.55 |
| 2983 | 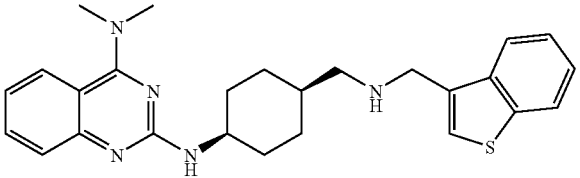 2CF₃CO₂H | 446.4 (M + H) | 3.13 |
| 2984 | 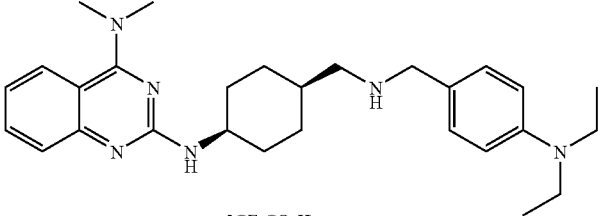 3CF₃CO₂H | 461.4 (M + H) | 2.46 |
| 2985 | 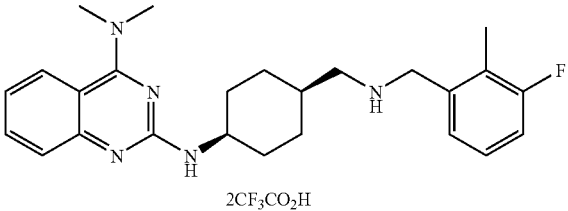 2CF₃CO₂H | 422.2 (M + H) | 3.01 |

-continued
| Example No. | Structure | ESI-MS | Retention Time (min) |
|---|---|---|---|
| 2986 | 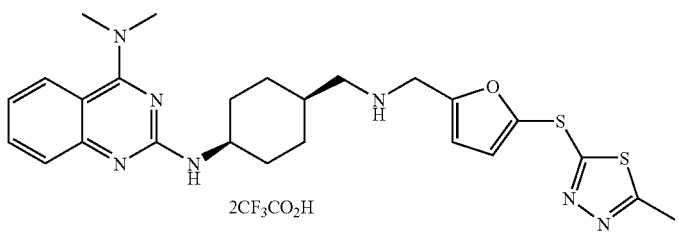 2CF₃CO₂H | 510.2 (M + H) | 2.85 |
| 2987 | 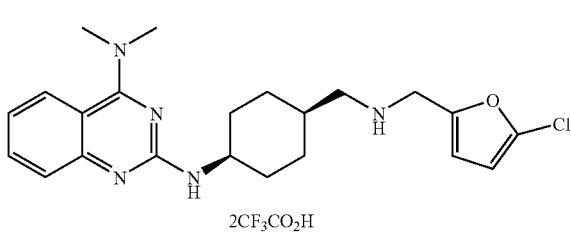 2CF₃CO₂H | 414.4 (M + H) | 2.86 |
| 2988 | 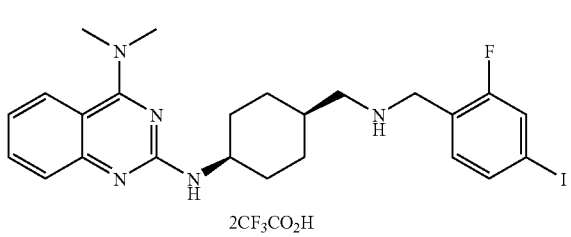 2CF₃CO₂H | 534.2 (M + H) | 3.13 |
| 2989 | 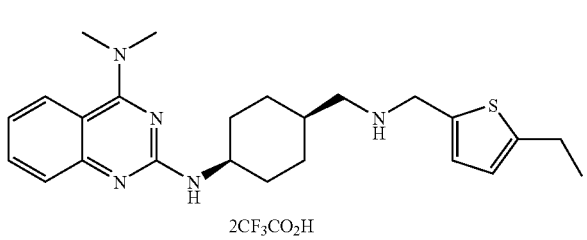 2CF₃CO₂H | 424.2 (M + H) | 3.08 |
| 2990 | 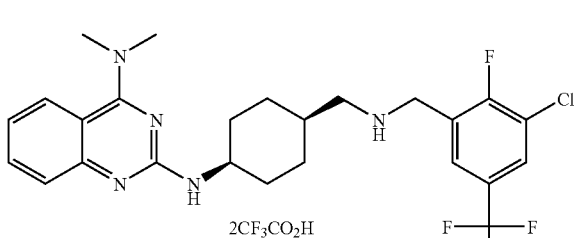 2CF₃CO₂H | 510.4 (M + H) | 3.32 |
| 2991 | 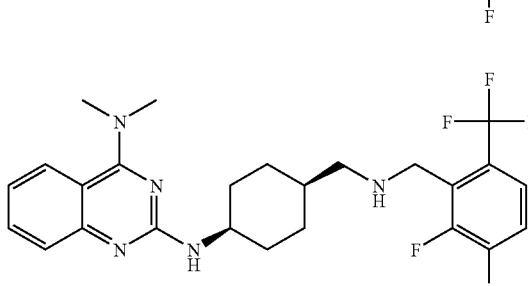 2CF₃CO₂H | 510.4 (M + H) | 3.17 |

-continued
| Example No. | Structure | ESI-MS | Retention Time (min) |
|---|---|---|---|
| 2992 | 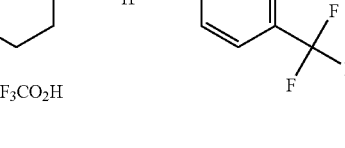 2CF₃CO₂H | 476.4 (M + H) | 3.17 |
| 2993 | 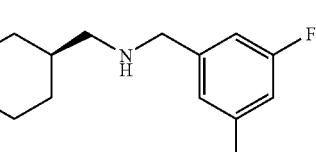 2CF₃CO₂H | 476.2 (M + H) | 3.21 |
| 2994 | 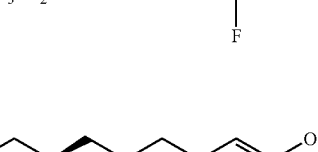 2CF₃CO₂H | 454.2 (M + H) | 2.77 |
| 2995 | 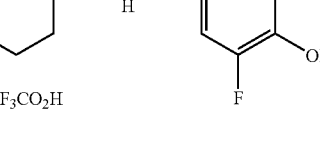 2CF₃CO₂H | 468.4 (M + H) | 2.89 |
| 2996 | 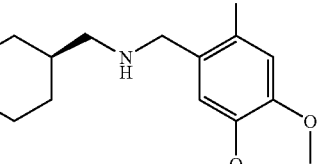 2CF₃CO₂H | 418.6 (M + H) | 3.12 |
| 2997 | 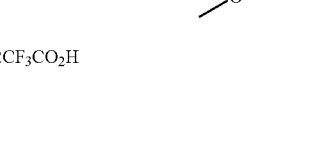 2CF₃CO₂H | 496.4 (M + H) | 3.29 |

-continued

| Example No. | Structure | ESI-MS | Retention Time (min) |
|---|---|---|---|
| 2998 | 3CF₃CO₂H | 472.6 (M + H) | 2.99 |
| 2999 | 2CF₃CO₂H | 466.4 (M + H) | 3.37 |
| 3000 | 2CF₃CO₂H | 574.2 (M + H) | 3.64 |
| 3001 | 2CF₃CO₂H | 430.4 (M + H) | 3.05 |
| 3002 | 2CF₃CO₂H | 532.4 (M + H) | 4.05 |

-continued

| Example No. | Structure | ESI-MS | Retention Time (min) |
|---|---|---|---|
| 3003 | 2CF₃CO₂H | 552.0 (M + H) | 3.37 |
| 3004 | CF₃CO₂H | 448.4 (M + H) | 3.51 |
| 3005 | CF₃CO₂H | 454.2 (M + H) | 3.91 |
| 3006 | CF₃CO₂H | 472.4 (M + H) | 4.02 |
| 3007 | CF₃CO₂H | 494.4 (M + H) | 4.01 |

-continued

| Example No. | Structure | ESI-MS | Retention Time (min) |
|---|---|---|---|
| 3008 | CF$_3$CO$_2$H | 537.4 (M + H) | 3.77 |
| 3009 | CF$_3$CO$_2$H | 418.6 (M + H) | 3.63 |
| 3010 | CF$_3$CO$_2$H | 418.6 (M + H) | 3.51 |
| 3011 | CF$_3$CO$_2$H | 396.2 (M + H) | 3.47 |
| 3012 | CF$_3$CO$_2$H | 434.4 (M + H) | 3.52 |
| 3013 | CF$_3$CO$_2$H | 395.4 (M + H) | 3.15 |

-continued

| Example No. | Structure | ESI-MS | Retention Time (min) |
|---|---|---|---|
| 3014 | CF$_3$CO$_2$H | 460.2 (M + H) | 4.03 |
| 3015 | CF$_3$CO$_2$H | 418.6 (M + H) | 3.65 |
| 3016 | CF$_3$CO$_2$H | 462.2 (M + H) | 4.09 |
| 3017 | CF$_3$CO$_2$H | 482.2 (M + H) | 3.79 |
| 3018 | CF$_3$CO$_2$H | 498.6 (M + H) | 3.88 |
| 3019 | CF$_3$CO$_2$H | 483.2 (M + H) | 3.80 |

-continued
| Example No. | Structure | ESI-MS | Retention Time (min) |
|---|---|---|---|
| 3020 | 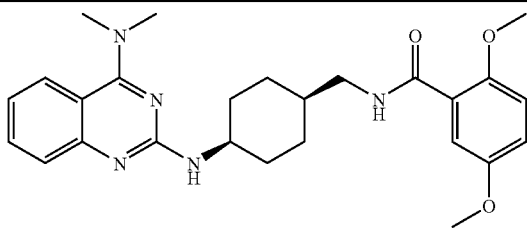 CF₃CO₂H | 478.2 (M + H) | 3.49 |
| 3021 | 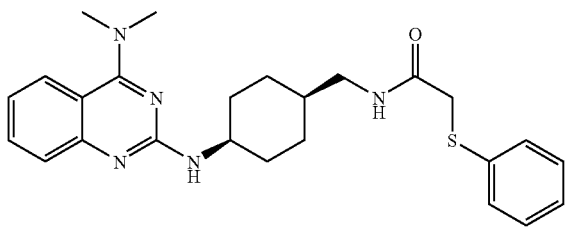 CF₃CO₂H | 450.0 (M + H) | 3.61 |
| 3022 | 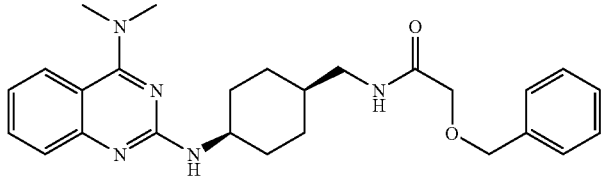 CF₃CO₂H | 448.2 (M + H) | 3.70 |
| 3023 | 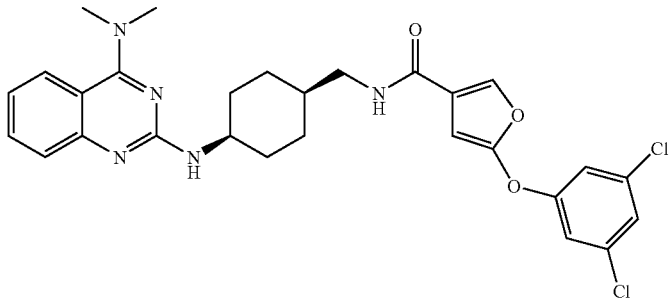 CF₃CO₂H | 554.4 (M + H) | 4.41 |
| 3024 | 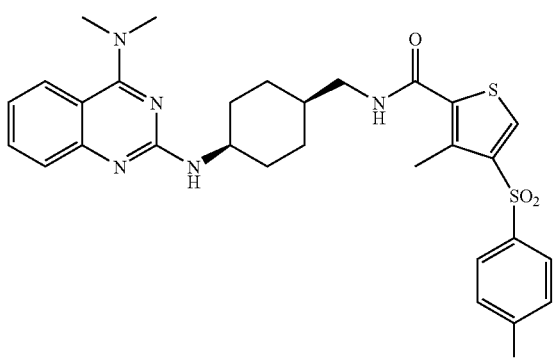 CF₃CO₃H | 598.2 (M + H) | 4.03 |

-continued

| Example No. | Structure | ESI-MS | Retention Time (min) |
|---|---|---|---|
| 3025 | (structure) CF₃CO₂H | 499.2 (M + H) | 3.59 |
| 3026 | (structure) CF₃CO₂H | 524.6 (M + H) | 3.84 |
| 3027 | (structure) 2CF₃CO₂H | 497.4 (M + H) | 3.80 |
| 3028 | (structure) CF₃CO₂H | 410.2 (M + H) | 3.43 |
| 3029 | (structure) CF₃CO₂H | 468.2 (M + H) | 3.77 |

-continued

| Example No. | Structure | ESI-MS | Retention Time (min) |
|---|---|---|---|
| 3030 | 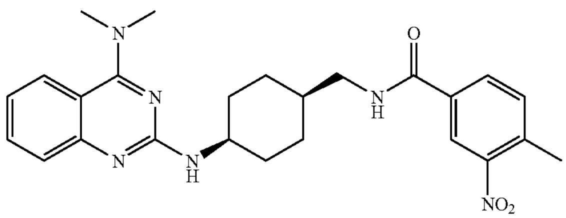 | 463.2 (M + H) | 3.73 |
| 3031 | 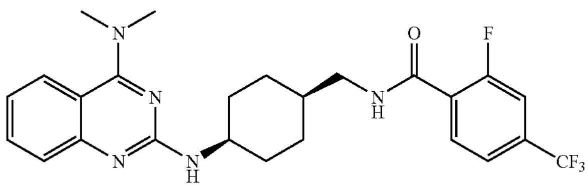 | 490.4 (M + H) | 3.91 |
| 3032 | 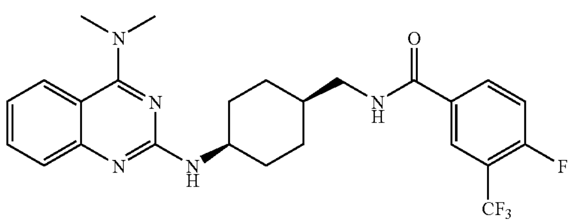 | 490.4 (M + H) | 3.94 |
| 3033 | 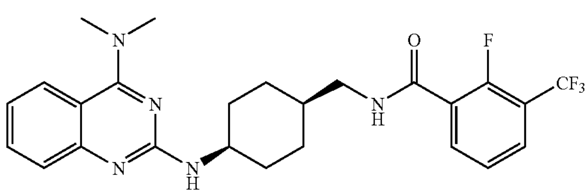 | 490.4 (M + H) | 3.85 |
| 3034 | 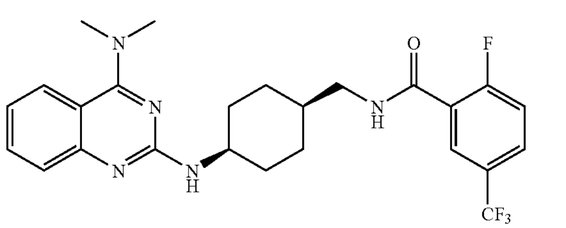 | 490.4 (M + H) | 3.87 |

-continued

| Example No. | Structure | ESI-MS | Retention Time (min) |
|---|---|---|---|
| 3035 | CF₃CO₂H | 490.4 (M + H) | 3.63 |
| 3036 | CF₃CO₂H | 490.2 (M + H) | 3.54 |
| 3037 | CF₃CO₂H | 540.4 (M + H) | 3.95 |
| 3038 | CF₃CO₂H | 440.4 (M + H) | 3.58 |
| 3039 | CF₃CO₂H | 458.4 (M + H) | 3.56 |
| 3040 | CF₃CO₂H | 476.4 (M + H) | 3.83 |

-continued

| Example No. | Structure | ESI-MS | Retention Time (min) |
|---|---|---|---|
| 3041 | CF₃CO₂H | 490.4 (M + H) | 3.82 |
| 3042 | CF₃CO₂H | 508.0 (M + H) | 3.85 |
| 3043 | CF₃CO₂H | 438.2 (M + H) | 3.71 |
| 3044 | CF₃CO₂H | 464.2 (M + H) | 3.65 |
| 3045 | CF₃CO₂H | 448.4 (M + H) | 3.47 |
| 3046 | CF₃CO₂H | 440.4 (M + H) | 3.59 |

-continued
| Example No. | Structure | ESI-MS | Retention Time (min) |
|---|---|---|---|
| 3047 | 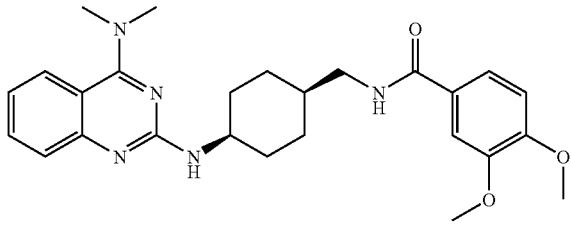 CF$_3$CO$_2$H | 464.2 (M + H) | 3.36 |
| 3048 | 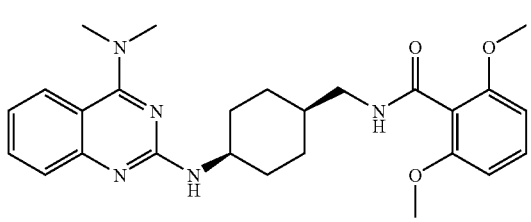 CF$_3$CO$_2$H | 464.4 (M + H) | 3.39 |
| 3049 | 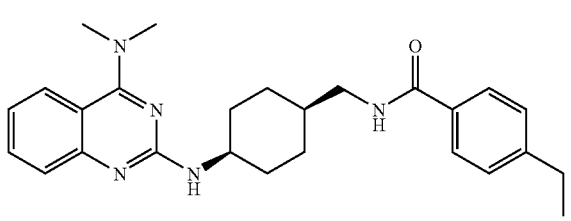 CF$_3$CO$_2$H | 432.4 (M + H) | 3.81 |
| 3050 | 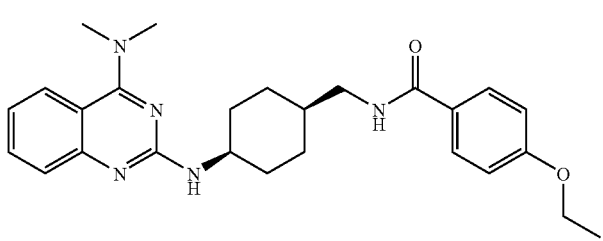 CF$_3$CO$_2$H | 448.4 (M + H) | 3.69 |
| 3051 | 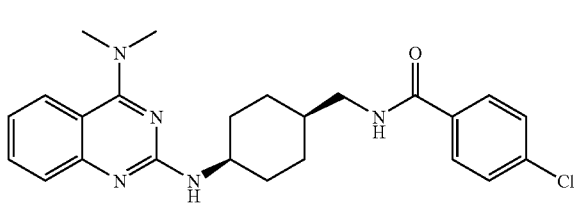 CF$_3$CO$_2$H | 438.2 (M + H) | 3.69 |

-continued

| Example No. | Structure | ESI-MS | Retention Time (min) |
|---|---|---|---|
| 3052 | 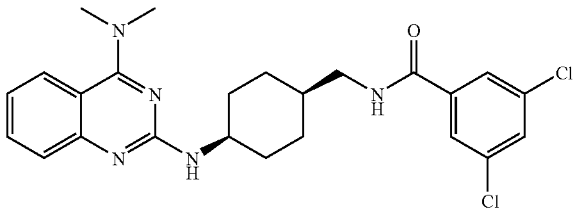 | 472.4 (M + H) | 4.03 |
| 3053 | 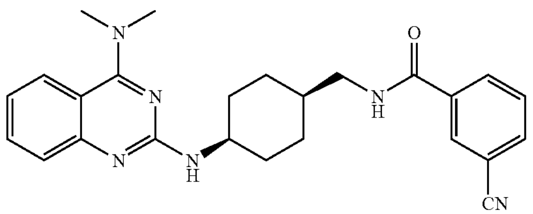 | 429.2 (M + H) | 3.47 |
| 3054 | 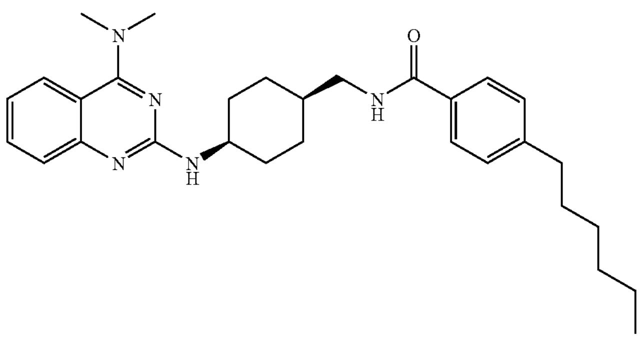 | 488.4 (M + H) | 4.60 |
| 3055 | 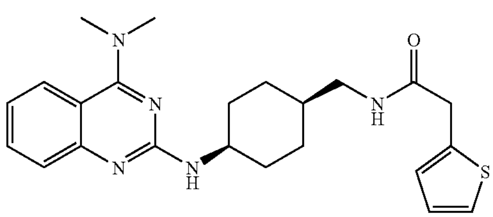 | 424.2 (M + H) | 3.41 |
| 3056 | 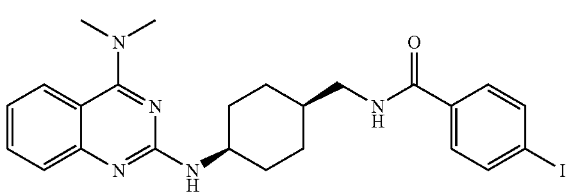 | 530.2 (M + H) | 3.83 |

-continued
| Example No. | Structure | ESI-MS | Retention Time (min) |
|---|---|---|---|
| 3057 | 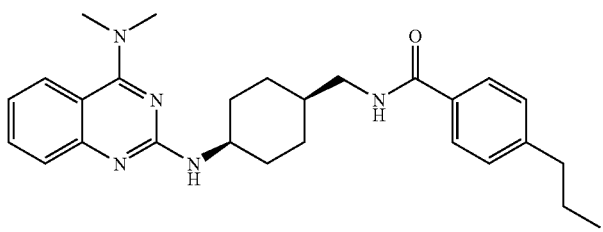 CF$_3$CO$_2$H | 446.4 (M + H) | 4.02 |
| 3058 | 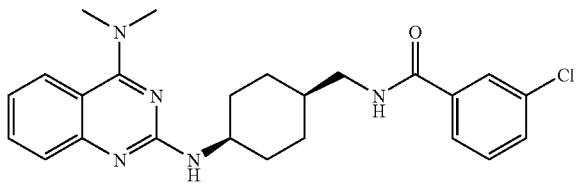 CF$_3$CO$_2$H | 438.2 (M + H) | 3.70 |
| 3059 | 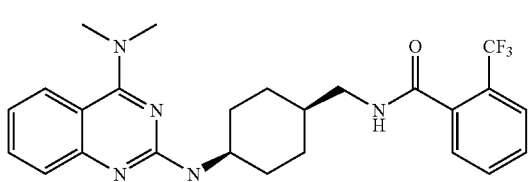 CF$_3$CO$_2$H | 472.4 (M + H) | 3.55 |
| 3060 | 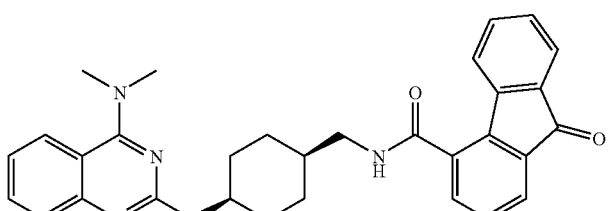 CF$_3$CO$_2$H | 506.4 (M + H) | 3.71 |
| 3061 | 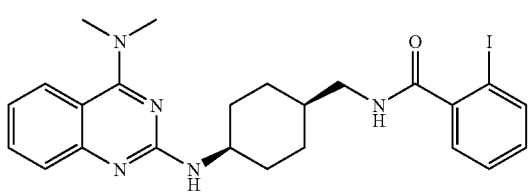 CF$_3$CO$_2$H | 530.2 (M + H) | 3.61 |

-continued
| Example No. | Structure | ESI-MS | Retention Time (min) |
|---|---|---|---|
| 3062 | 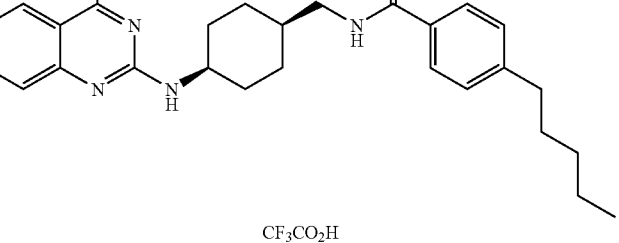 CF$_3$CO$_2$H | 474.4 (M + H) | 4.41 |
| 3063 | 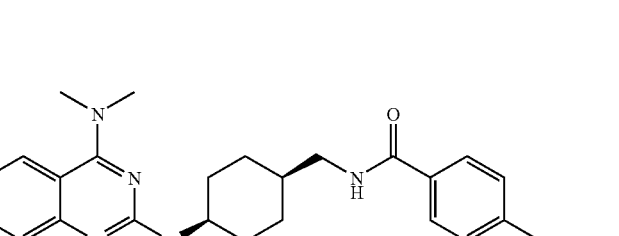 CF$_3$CO$_2$H | 476.4 (M + H) | 4.14 |
| 3064 | 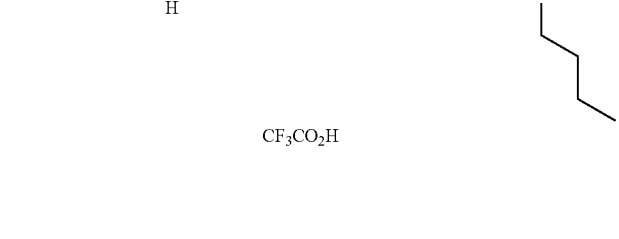 CF$_3$CO$_2$H | 502.4 (M + H) | 4.83 |
| 3065 | 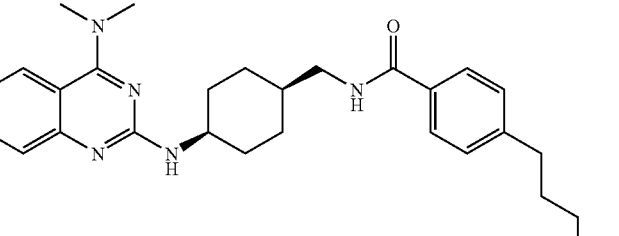 CF$_3$CO$_2$H | 480.4 (M + H) | 4.09 |

-continued
| Example No. | Structure | ESI-MS | Retention Time (min) |
|---|---|---|---|
| 3066 | 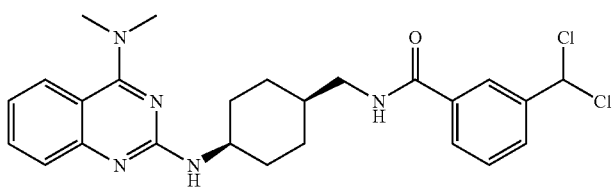 CF₃CO₂H | 486.4 (M + H) | 3.84 |
| 3067 | 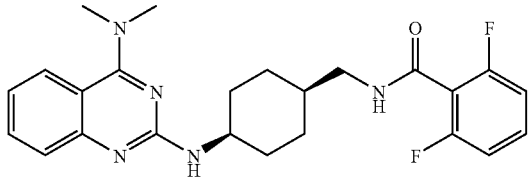 CF₃CO₂H | 440.4 (M + H) | 3.46 |
| 3068 | 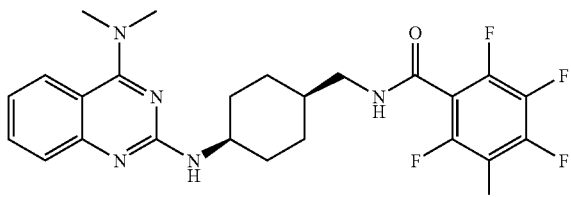 CF₃CO₂H | 494.4 (M + H) | 3.79 |
| 3069 | 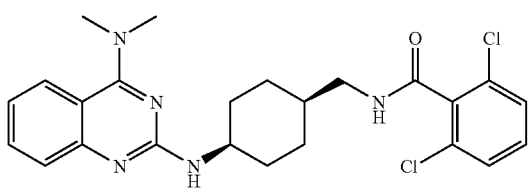 CF₃CO₂H | 472.4 (M + H) | 3.55 |
| 3070 | 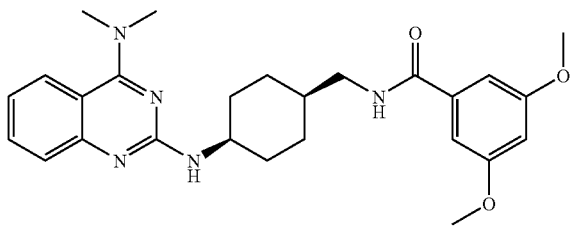 CF₃CO₂H | 464.4 (M + H) | 3.63 |

-continued

| Example No. | Structure | ESI-MS | Retention Time (min) |
|---|---|---|---|
| 3071 | (structure) CF₃CO₂H | 458.2 (M + H) | 3.69 |
| 3072 | (structure) CF₃CO₂H | 440.4 (M + H) | 3.69 |
| 3073 | (structure) CF₃CO₂H | 440.4 (M + H) | 3.66 |
| 3074 | (structure) CF₃CO₂H | 422.4 (M + H) | 3.55 |
| 3075 | (structure) CF₃CO₂H | 460.4 (M + H) | 4.24 |

-continued

| Example No. | Structure | ESI-MS | Retention Time (min) |
|---|---|---|---|
| 3076 | 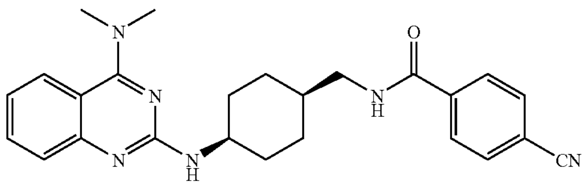 | 429.2 (M + H) | 3.42 |
| 3077 | 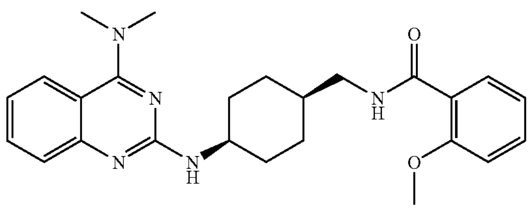 | 434.4 (M + H) | 3.61 |
| 3078 | 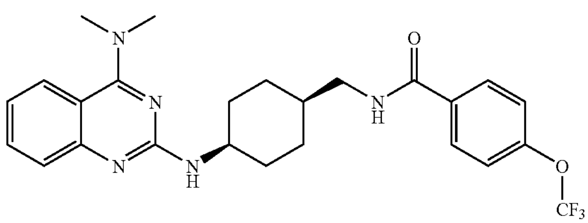 | 488.4 (M + H) | 3.86 |
| 3079 | 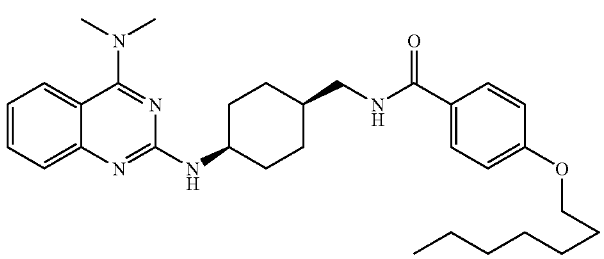 | 518.6 (M + H) | 4.74 |
| 3080 | 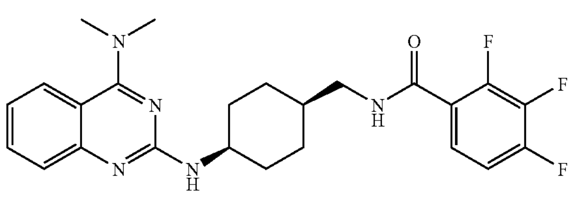 | 458.2 (M + H) | 3.68 |

-continued
| Example No. | Structure | ESI-MS | Retention Time (min) |
|---|---|---|---|
| 3081 | 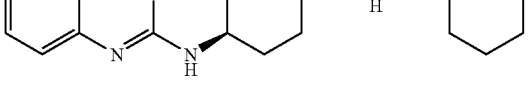 CF₃CO₂H | 410.4 (M + H) | 3.58 |
| 3082 | 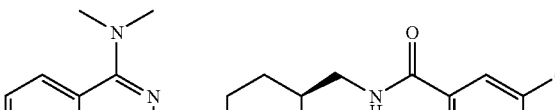 CF₃CO₂H | 540.4 (M + H) | 4.19 |
| 3083 | 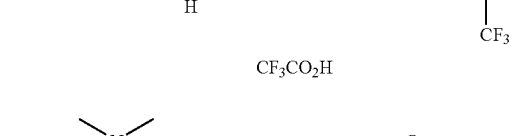 CF₃CO₂H | 422.2 (M + H) | 3.50 |
| 3084 | 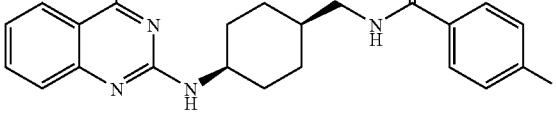 CF₃CO₂H | 494.4 (M + H) | 3.39 |
| 3085 | 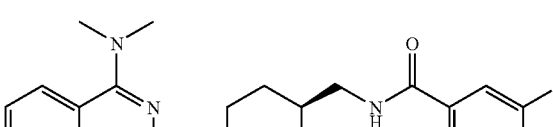 CF₃CO₂H | 440.0 (M + H) | 3.55 |
| 3086 | 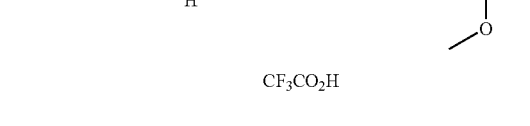 CF₃CO₂H | 438.2 (M + H) | 3.48 |

-continued

| Example No. | Structure | ESI-MS | Retention Time (min) |
|---|---|---|---|
| 3087 | CF$_3$CO$_2$H | 454.2 (M + H) | 3.75 |
| 3088 | CF$_3$CO$_2$H | 472.4 (M + H) | 3.83 |
| 3089 | CF$_3$CO$_2$H | 422.2 (M + H) | 3.51 |
| 3090 | CF$_3$CO$_2$H | 472.4 (M + H) | 3.87 |
| 3091 | CF$_3$CO$_2$H | 500.4 (M + H) | 3.03 |
| 3092 | 2CF$_3$CO$_2$H | 447.4 (M + H) | 2.59 |

| Example No. | Structure | ESI-MS | Retention Time (min) |
|---|---|---|---|
| 3093 | (structure) CF₃CO₂H | 486.4 (M + H) | 3.25 |
| 3094 | (structure) CF₃CO₂H | 488.4 (M + H) | 2.81 |
| 3095 | (structure) CF₃CO₂H | 452.4 (M + H) | 2.98 |
| 3096 | (structure) CF₃CO₂H | 496.4 (M + H) | 3.29 |
| 3097 | (structure) CF₃CO₂H | 448.4 (M + H) | 2.77 |

-continued
| Example No. | Structure | ESI-MS | Retention Time (min) |
|---|---|---|---|
| 3098 | 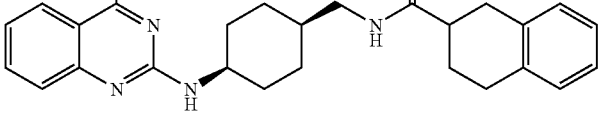 CF₃CO₂H | 458.4 (M + H) | 3.06 |
| 3099 | 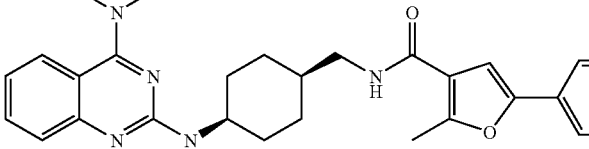 CF₃CO₂H | 484.4 (M + H) | 3.40 |
| 3100 | 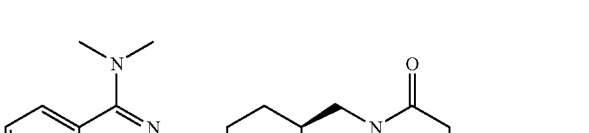 CF₃CO₂H | 418.6 (M + H) | 2.69 |
| 3101 | 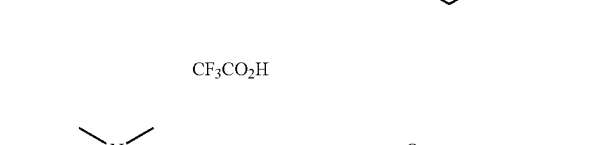 2CF₃CO₂H | 496.6 (M + H) | 3.01 |
| 3102 | 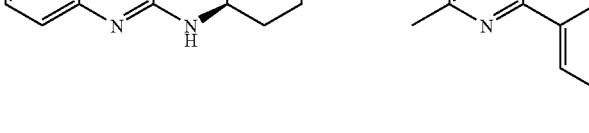 CF₃CO₂H | 483.4 (M + H) | 2.79 |

-continued

| Example No. | Structure | ESI-MS | Retention Time (min) |
|---|---|---|---|
| 3103 | CF$_3$CO$_2$H | 420.4 (M + H) | 2.76 |
| 3104 | CF$_3$CO$_2$H | 516.2 (M + H) | 3.03 |
| 3105 | CF$_3$CO$_2$H | 480.4 (M + H) | 2.41 |
| 3106 | CF$_3$CO$_2$H | 483.2 (M + H) | 2.84 |
| 3107 | 2CF$_3$CO$_2$H | 455 (M + H) | 2.45 |

-continued

| Example No. | Structure | ESI-MS | Retention Time (min) |
|---|---|---|---|
| 3108 | 2CF$_3$CO$_2$H | 455.2 (M + H) | 3.19 |
| 3109 | CF$_3$CO$_2$H | 461.4 (M + H) | 2.60 |
| 3110 | CF$_3$CO$_2$H | 447.4 (M + H) | 2.74 |
| 3111 | CF$_3$CO$_2$H | 466.6 (M + H) | 2.61 |
| 3112 | CF$_3$CO$_2$H | 464.4 (M + H) | 2.35 |

-continued
| Example No. | Structure | ESI-MS | Retention Time (min) |
|---|---|---|---|
| 3113 | 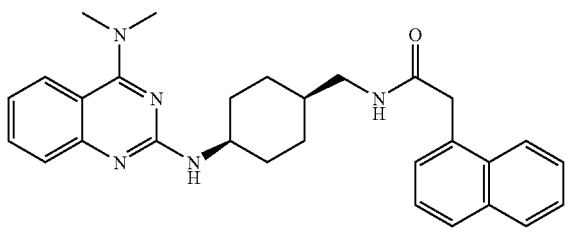 CF$_3$CO$_2$H | 468.4 (M + H) | 3.04 |
| 3114 | 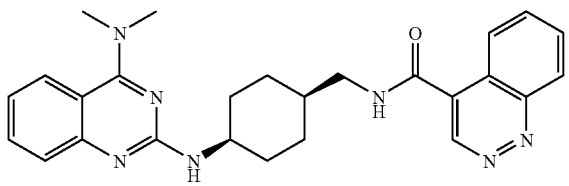 2CF$_3$CO$_2$H | 456.2 (M + H) | 2.44 |
| 3115 | 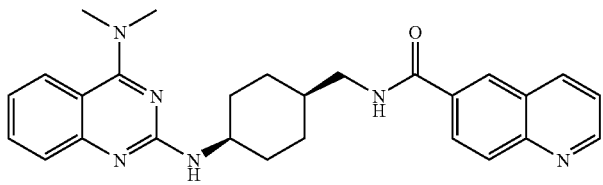 2CF$_3$CO$_2$H | 455.2 (M + H) | 2.11 |
| 3116 | 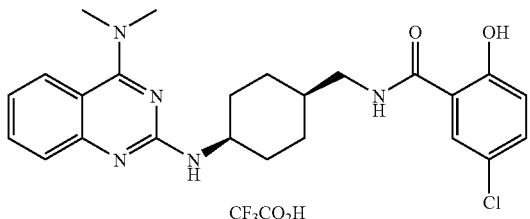 CF$_3$CO$_2$H | 454.2 (M + H) | 3.21 |
| 3117 | 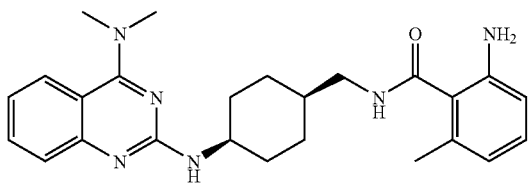 2CF$_3$CO$_2$H | 433.6 (M + H) | 2.34 |
| 3118 | 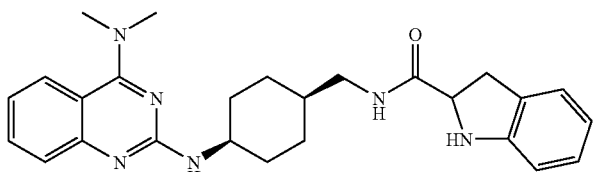 2CF$_3$CO$_2$H | 444.6 (M + H) | 2.93 |

-continued
| Example No. | Structure | ESI-MS | Retention Time (min) |
|---|---|---|---|
| 3119 | 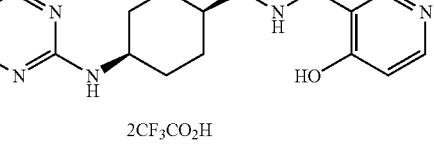<br>2CF$_3$CO$_2$H | 421.4 (M + H) | 2.23 |
| 3120 | 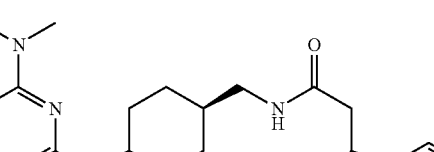<br>CF$_3$CO$_2$H | 506.4 (M + H) | 3.31 |
| 3121 | 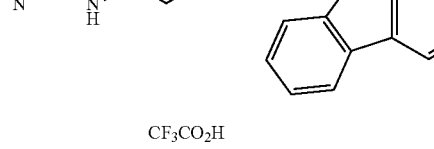<br>2CF$_3$CO$_2$H | 511.6 (M + H) | 3.21 |
| 3122 | 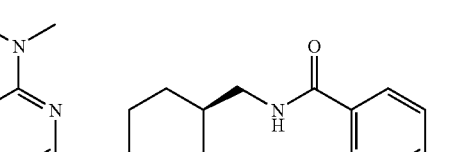<br>CF$_3$CO$_2$H | 479.4 (M + H) | 3.60 |
| 3123 | <br>CF$_3$CO$_2$H | 434.4 (M + H) | 2.37 |

-continued
| Example No. | Structure | ESI-MS | Retention Time (min) |
|---|---|---|---|
| 3124 | 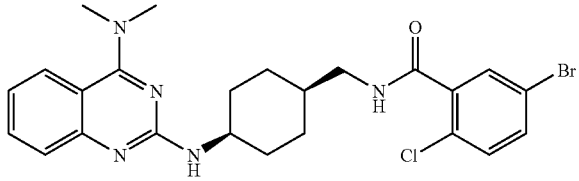<br>CF₃CO₂H | 516.4 (M + H) | 3.02 |
| 3125 | 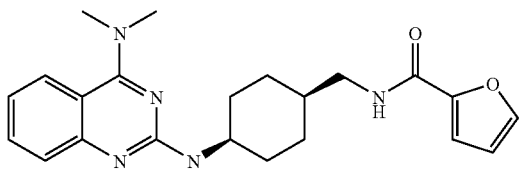<br>CF₃CO₂H | 394.4 (M + H) | 2.45 |
| 3126 | 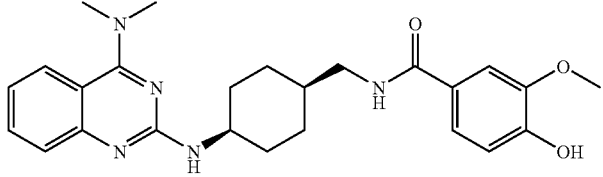<br>CF₃CO₂H | 450.2 (M + H) | 2.41 |
| 3127 | 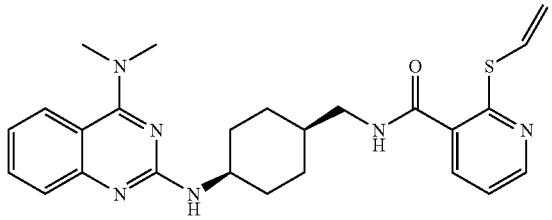<br>2CF₃CO₂H | 477.0 (M + H) | 2.88 |
| 3128 | 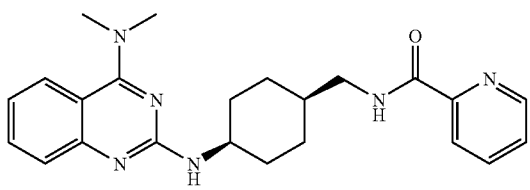<br>2CF₃CO₂H | 405.6 (M + H) | 2.61 |
| 3129 | 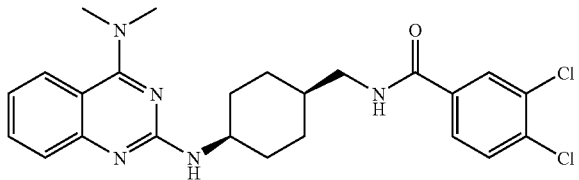<br>CF₃CO₂H | 472.6 (M + H) | 3.17 |

-continued

| Example No. | Structure | ESI-MS | Retention Time (min) |
|---|---|---|---|
| 3130 | CF$_3$CO$_2$H | 464.4 (M + H) | 2.59 |
| 3131 | CF$_3$CO$_2$H | 484.2 (M + H) | 2.99 |
| 3132 | CF$_3$CO$_2$H | 453.0 (M + H) | 2.45 |
| 3133 | CF$_3$CO$_2$H | 488.4 (M + H) | 3.59 |
| 3134 | CF$_3$CO$_2$H | 454.2 (M + H) | 2.81 |
| 3135 | 2CF$_3$CO$_2$H | 421.4 (M + H) | 2.89 |

-continued
| Example No. | Structure | ESI-MS | Retention Time (min) |
|---|---|---|---|
| 3136 | 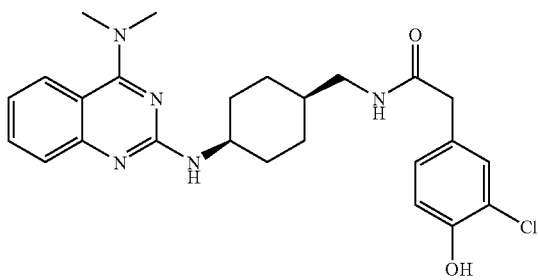<br>CF₃CO₂H | 468.4 (M + H) | 2.53 |
| 3137 | 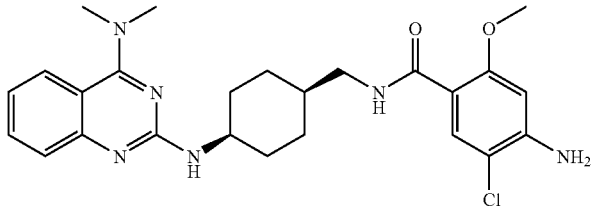<br>2CF₃CO₂H | 483.2 (M + H) | 2.83 |
| 3138 | 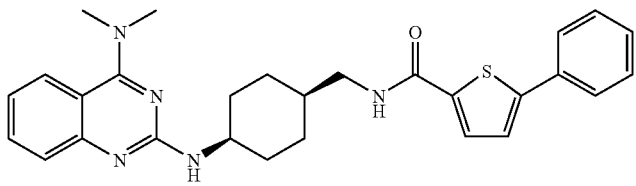<br>CF₃CO₂H | 487.4 (M + 2H+) | 3.40 |
| 3139 | 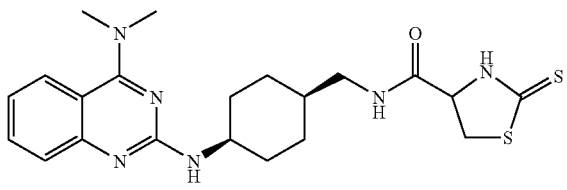<br>CF₃CO₂H | 445.6 (M + H) | 2.36 |
| 3140 | 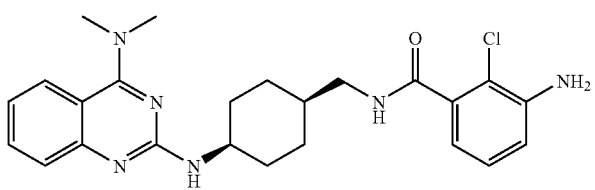<br>2CF₃CO₂H | 453.2 (M + H) | 2.46 |

-continued

| Example No. | Structure | ESI-MS | Retention Time (min) |
|---|---|---|---|
| 3141 | CF₃CO₂H | 478.4 (M + H) | 2.77 |
| 3142 | CF₃CO₂H | 672.2 (M + H) | 3.92 |
| 3143 | CF₃CO₂H | 576.2 (M + H) | 3.71 |
| 3144 | 2CF₃CO₂H | 421.2 (M + H) | 2.01 |
| 3145 | CF₃CO₂H | 494.4 (M + H) | 2.77 |
| 3146 | 2CF₃CO₂H | 405.6 (M + H) | 1.99 |

-continued
| Example No. | Structure | ESI-MS | Retention Time (min) |
|---|---|---|---|
| 3147 | 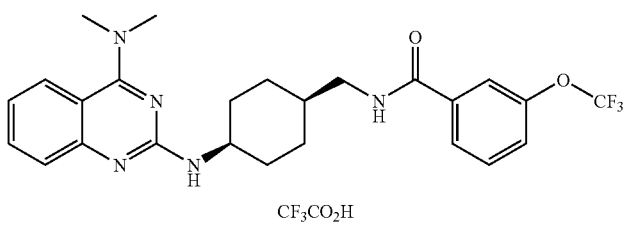<br>CF$_3$CO$_2$H | 488.4 (M + H) | 3.13 |
| 3148 | 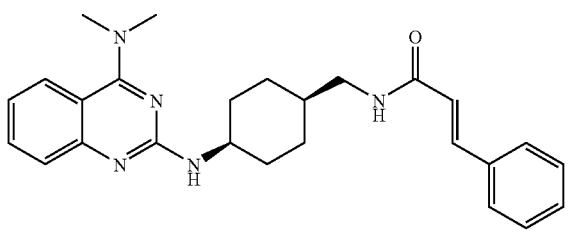<br>CF$_3$CO$_2$H | 430.4 (M + H) | 2.91 |
| 3149 | 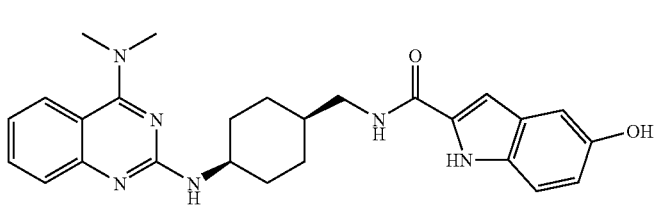<br>2CF$_3$CO$_2$H | 459.4 (M + H) | 2.47 |
| 3150 | 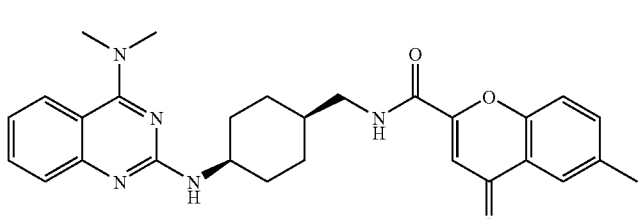<br>CF$_3$CO$_2$H | 486.6 (M + H) | 2.93 |
| 3151 | 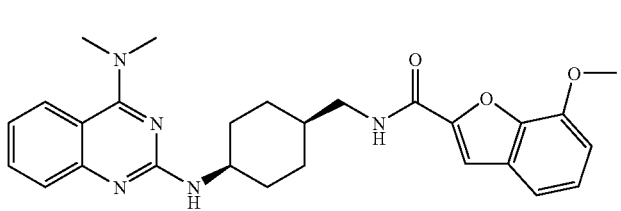<br>CF$_3$CO$_2$H | 474.4 (M + H) | 3.03 |
| 3152 | 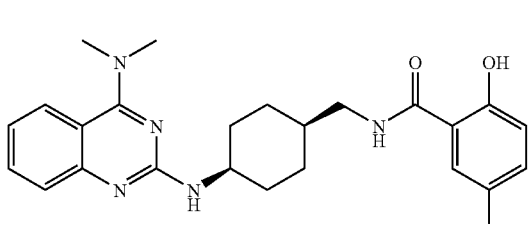<br>CF$_3$CO$_2$H | 464.2 (M + H) | 3.13 |

-continued

| Example No. | Structure | ESI-MS | Retention Time (min) |
|---|---|---|---|
| 3153 | 2CF₃CO₂H | 483.4 (M + H) | 2.67 |
| 3154 | CF₃CO₂H | 556.4 (M + H) | 2.84 |
| 3155 | 2CF₃CO₂H | 443.4 (M + H) | 2.94 |
| 3156 | CF₃CO₂H | 508.2 (M + H) | 3.20 |
| 3157 | CF₃CO₂H | 440.0 (M + H) | 2.72 |

-continued

| Example No. | Structure | ESI-MS | Retention Time (min) |
|---|---|---|---|
| 3158 | (structure) CF₃CO₂H | 532.4 (M + H) | 3.58 |
| 3159 | (structure) CF₃CO₂H | 535.4 (M + H) | 3.51 |
| 3160 | (structure) CF₃CO₂H | 504.4 (M + H) | 3.49 |
| 3161 | (structure) CF₃CO₂H | 572.4 (M + H) | 3.71 |

-continued

| Example No. | Structure | ESI-MS | Retention Time (min) |
|---|---|---|---|
| 3162 | CF₃CO₂H | 460.2 (M + H) | 3.80 |
| 3163 | CF₃CO₂H | 589.2 (M + H) | 4.00 |
| 3164 | CF₃CO₂H | 492.2 (M + H) | 3.90 |
| 3165 | CF₃CO₂H | 478.2 (M + H) | 3.80 |

-continued

| Example No. | Structure | ESI-MS | Retention Time (min) |
|---|---|---|---|
| 3166 | CF₃CO₂H | 607.6 (M + H) | 4.00 |
| 3167 | CF₃CO₂H | 504.2 (M + H) | 3.40 |
| 3168 | CF₃CO₂H | 506.2 (M + H) | 3.90 |

-continued

| Example No. | Structure | ESI-MS | Retention Time (min) |
|---|---|---|---|
| 3169 | CF$_3$CO$_2$H | 480.2 (M + H) | 3.80 |
| 3170 | CF$_3$CO$_2$H | 466.2 (M + H) | 3.70 |
| 3171 | CF$_3$CO$_2$H | 515.2 (M + H) | 3.90 |

-continued
| Example No. | Structure | ESI-MS | Retention Time (min) |
|---|---|---|---|
| 3172 | 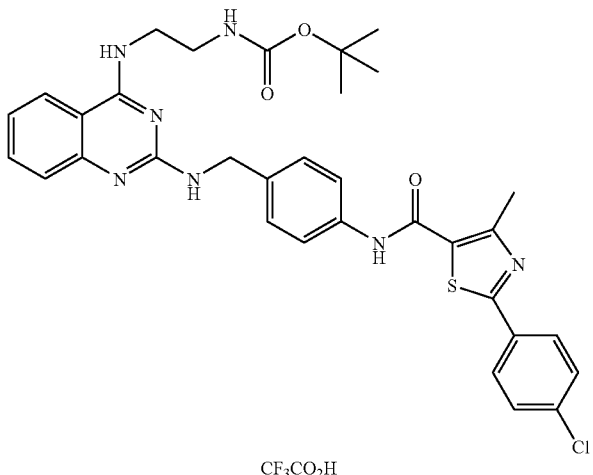 CF$_3$CO$_2$H | 644.2 (M + H) | 4.10 |
| 3173 | 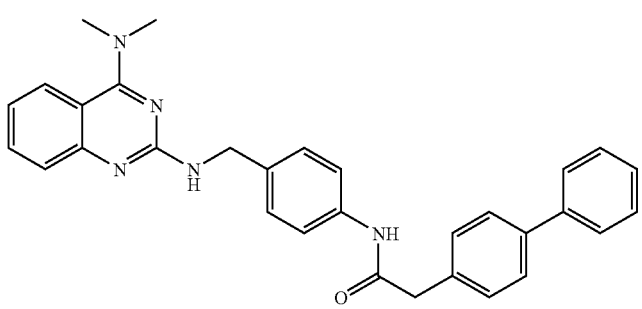 CF$_3$CO$_2$H | 488.2 (M + H) | 3.90 |
| 3174 | 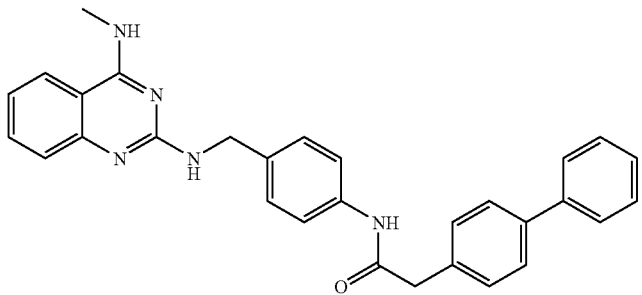 CF$_3$CO$_2$H | 474.4 (M + H) | 3.80 |

-continued

| Example No. | Structure | ESI-MS | Retention Time (min) |
|---|---|---|---|
| 3175 | 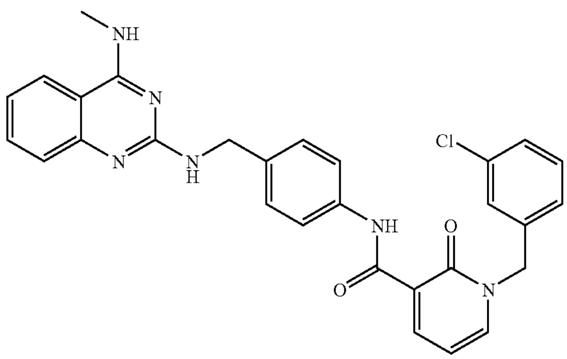 | 525.4 (M + H) | 3.70 |
| 3176 | 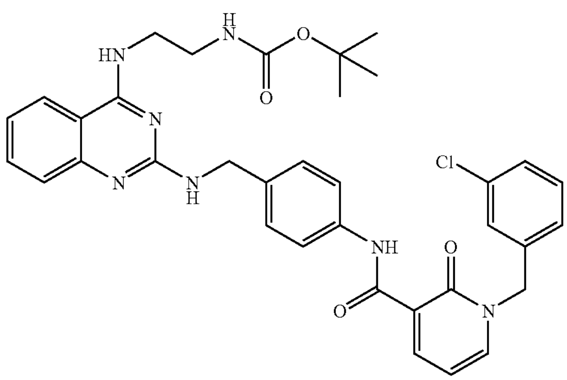 | 654.2 (M + H) | 3.90 |
| 3177 | 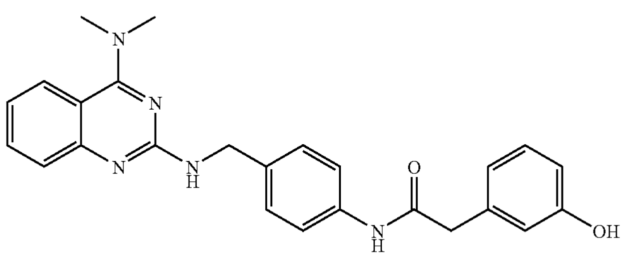 | 428.2 (M + H) | 3.10 |
| 3178 | 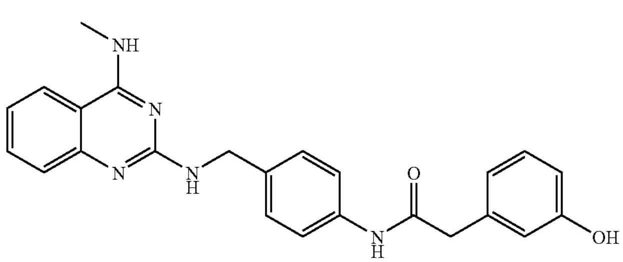 | 414.4 (M + H) | 2.90 |

-continued

| Example No. | Structure | ESI-MS | Retention Time (min) |
|---|---|---|---|
| 3179 | 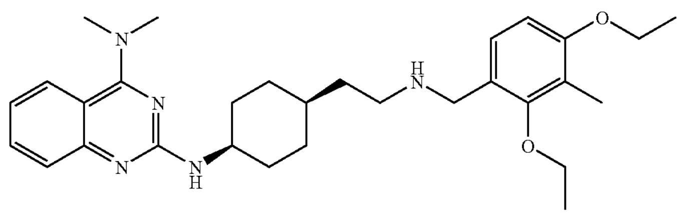 | 506.4 (M + H) | 3.04 |
| 3180 | 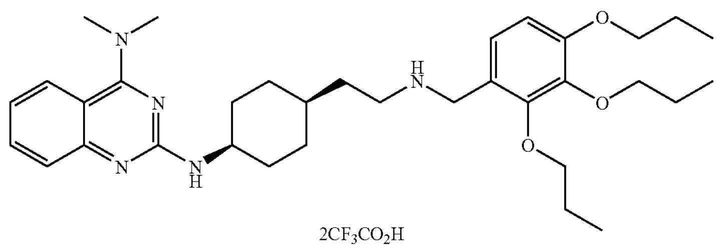 | 578.8 (M + H) | 3.50 |
| 3181 | 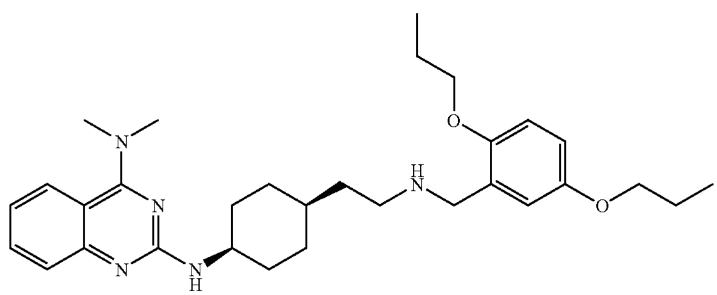 | 520.6 (M + H) | 3.19 |
| 3182 | 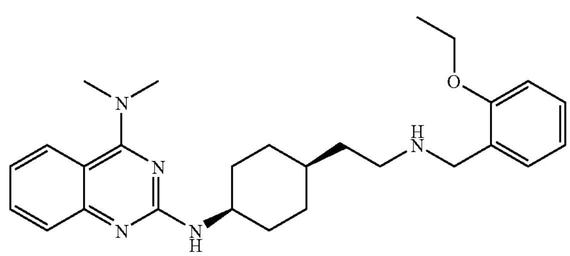 | 448.4 (M + H) | 2.80 |
| 3183 | 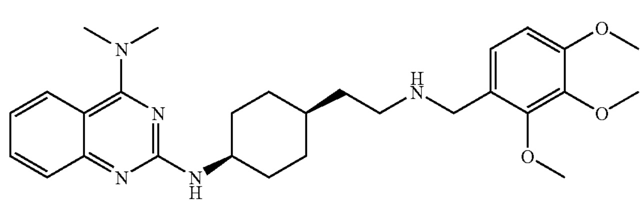 | 494.6 (M + H) | 2.66 |

-continued

| Example No. | Structure | ESI-MS | Retention Time (min) |
|---|---|---|---|
| 3184 | 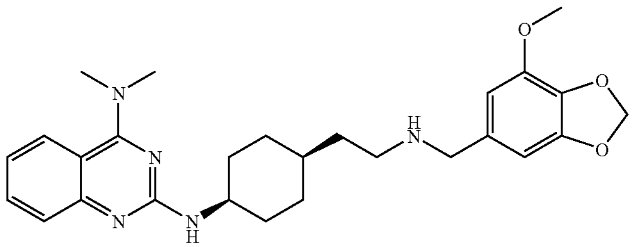 | 478.4 (M + H) | 2.66 |
| 3185 | 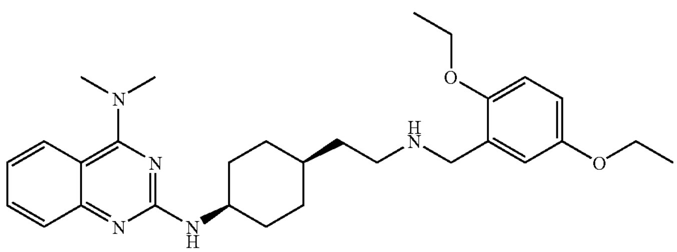 | 492.6 (M + H) | 2.94 |
| 3186 | 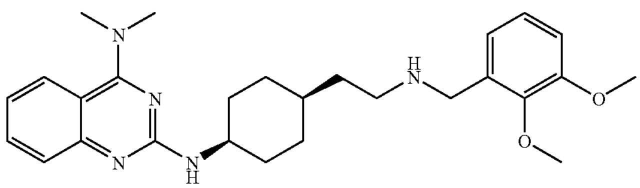 | 464.4 (M + H) | 2.65 |
| 3187 | 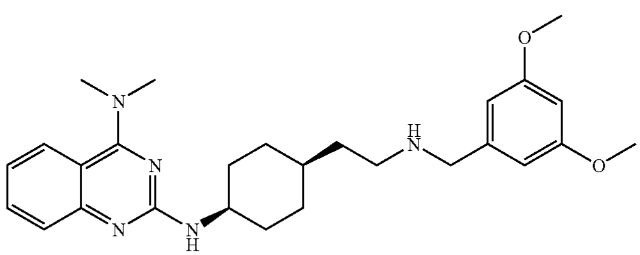 | 464.4 (M + H) | 2.68 |
| 3188 | 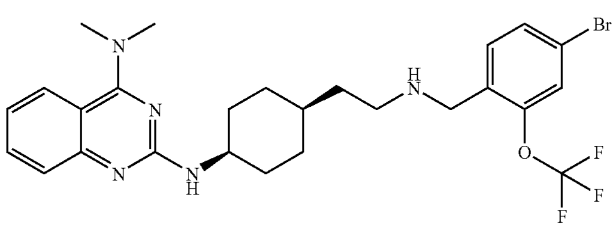 | 566.4 (M + H) | 3.03 |

-continued

| Example No. | Structure | ESI-MS | Retention Time (min) |
|---|---|---|---|
| 3189 | 2CF$_3$CO$_2$H | 512.6 (M + H) | 2.85 |
| 3190 | 2CF$_3$CO$_2$H | 474.4 (M + H) | 3.09 |
| 3191 | 3CF$_3$CO$_2$H | 477.4 (M + H) | 2.51 |
| 3192 | 2CF$_3$CO$_2$H | 464.4 (M + H) | 2.67 |
| 3193 | 2CF$_3$CO$_2$H | 494.6 (M + H) | 2.78 |

-continued
| Example No. | Structure | ESI-MS | Retention Time (min) |
|---|---|---|---|
| 3194 | 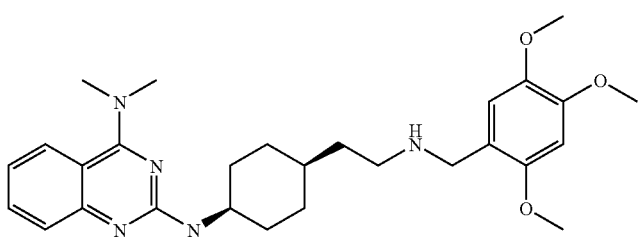 2CF$_3$CO$_2$H | 494.6 (M + H) | 2.60 |
| 3195 | 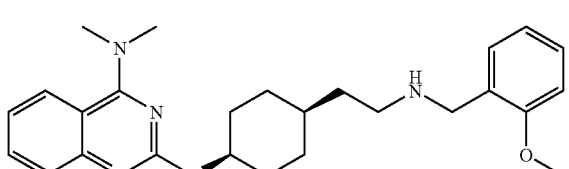 2CF$_3$CO$_2$H | 434.6 (M + H) | 2.67 |
| 3196 | 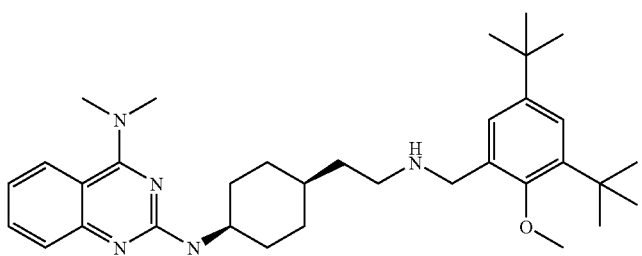 2CF$_3$CO$_2$H | 546.4 (M + H) | 4.30 |
| 3197 | 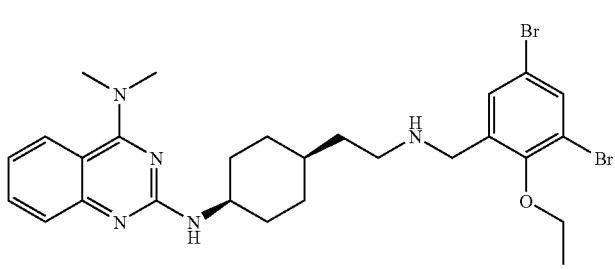 2CF$_3$CO$_2$H | 606.6 (M + H) | 3.95 |
| 3198 | 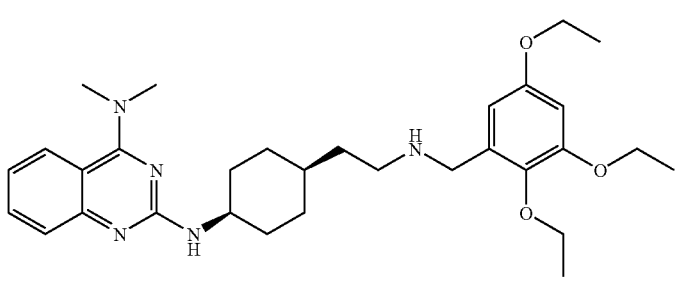 2CF$_3$CO$_2$H | 536.6 (M + H) | 3.83 |

-continued

| Example No. | Structure | ESI-MS | Retention Time (min) |
|---|---|---|---|
| 3199 | 2CF₃CO₂H | 492.4 (M + H) | 2.97 |
| 3200 | 2CF₃CO₂H | 478.4 (M + H) | 2.79 |
| 3201 | 2CF₃CO₂H | 542.0 (M + H) | 2.85 |
| 3202 | 2CF₃CO₂H | 492.6 (M + H) | 2.81 |
| 3203 | 2CF₃CO₂H | 590.4 (M + H) | 3.02 |

-continued

| Example No. | Structure | ESI-MS | Retention Time (min) |
|---|---|---|---|
| 3204 | 2CF₃CO₂H | 502.2 (M + H) | 2.91 |
| 3205 | 2CF₃CO₂H | 480.4 (M + H) | 2.51 |
| 3206 | 2CF₃CO₂H | 536.4 (M + H) | 3.21 |
| 3207 | 3CF₃CO₂H | 443.6 (M + H) | 2.66 |
| 3208 | 2CF₃CO₂H | 536.4 (M + H) | 3.08 |

-continued
| Example No. | Structure | ESI-MS | Retention Time (min) |
|---|---|---|---|
| 3209 | 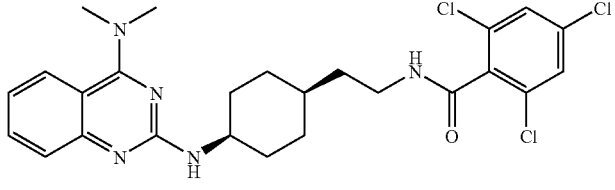<br>2CF$_3$CO$_2$H | 520.0 (M + H) | 3.51 |
| 3210 | 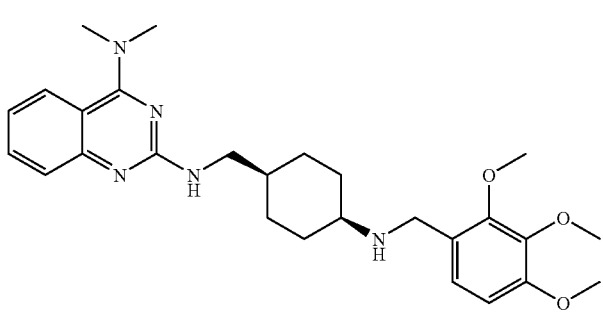<br>2CF$_3$CO$_2$H | 480.4 (M + H) | 2.58 |
| 3211 | 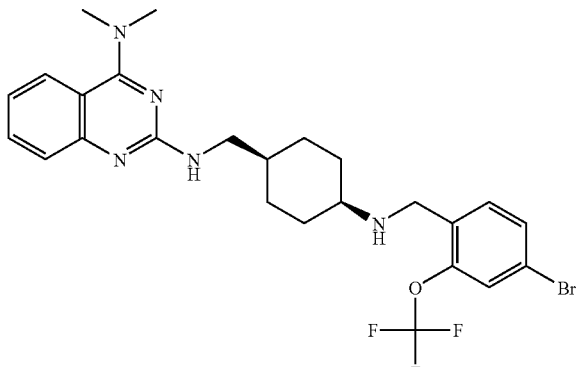<br>2CF$_3$CO$_2$H | 552.0 (M + H) | 3.11 |
| 3212 | 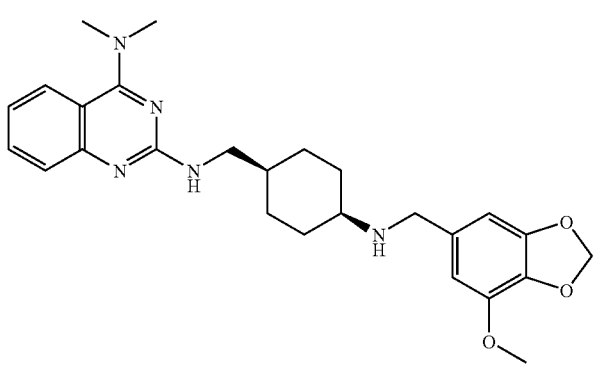<br>2CF$_3$CO$_2$H | 464.4 (M + H) | 3.22 |

-continued

| Example No. | Structure | ESI-MS | Retention Time (min) |
|---|---|---|---|
| 3213 | 2CF₃CO₂H | 450.4 (M + H) | 2.70 |
| 3214 | 2CF₃CO₂H | 450.4 (M + H) | 2.58 |
| 3215 | 2CF₃CO₂H | 480.4 (M + H) | 2.73 |
| 3216 | 3CF₃CO₂H | 429.4 (M + H) | 3.29 |

-continued
| Example No. | Structure | ESI-MS | Retention Time (min) |
|---|---|---|---|
| 3217 | 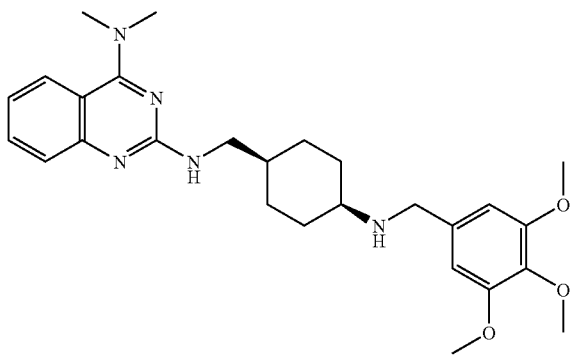 2CF$_3$CO$_2$H | 480.2 (M + H) | 2.78 |
| 3218 | 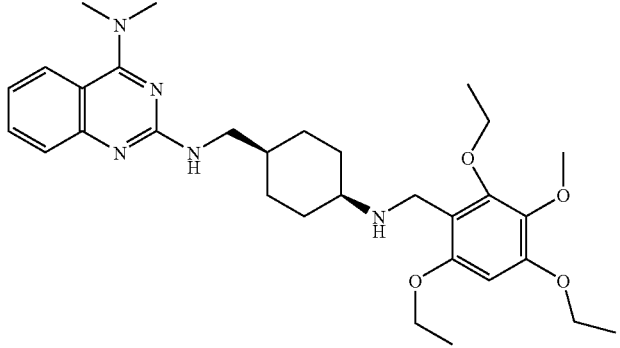 2CF$_3$CO$_2$H | 522.4 (M + H) | 3.77 |
| 3219 | 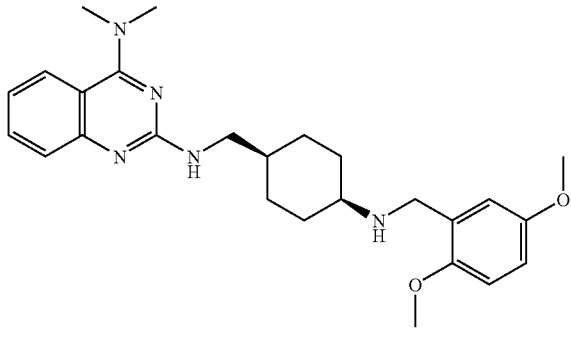 2CF$_3$CO$_2$H | 450.2 (M + H) | 2.57 |
| 3220 | 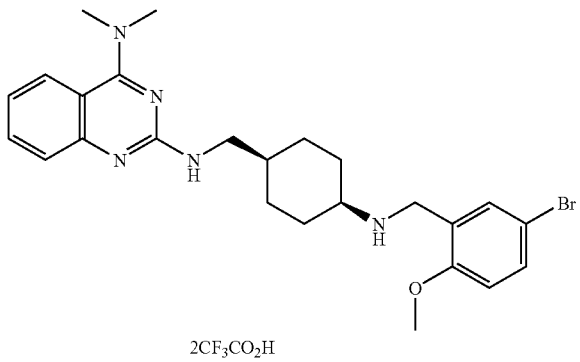 2CF$_3$CO$_2$H | 480.0 (M + H) | 2.97 |

-continued
| Example No. | Structure | ESI-MS | Retention Time (min) |
|---|---|---|---|
| 3221 | 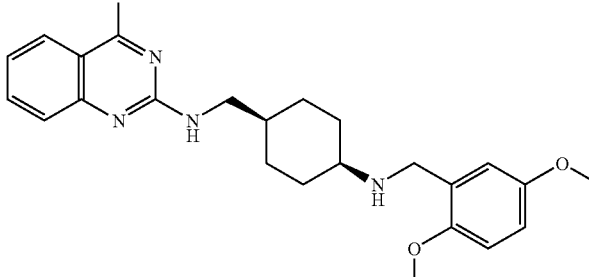<br>2CF₃CO₂H | 478.4 (M + H) | 3.17 |
| 3222 | 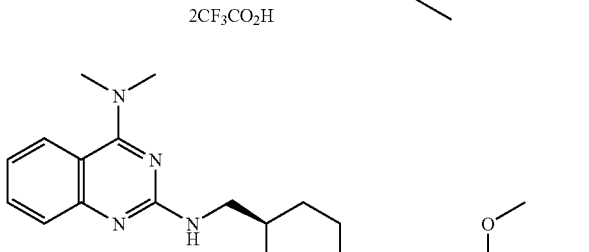<br>2CF₃CO₂H | 480.0 (M + H) | 3.08 |
| 3223 | 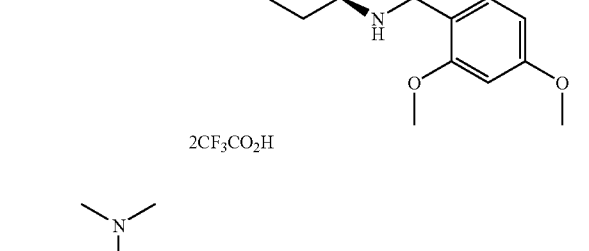<br>2CF₃CO₂H | 590.2 (M + H) | 4.20 |
| 3224 | 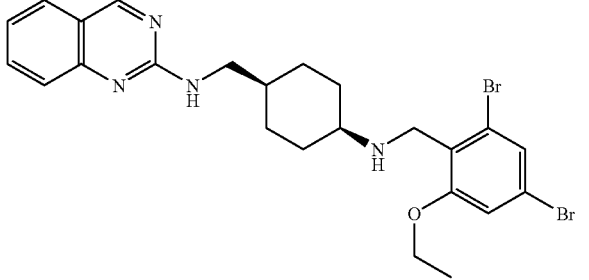<br>2CF₃CO₂H | 576.4 (M + H) | 3.95 |

-continued

| Example No. | Structure | ESI-MS | Retention Time (min) |
|---|---|---|---|
| 3225 | 2CF₃CO₂H | 512.4 (M + H) | 3.86 |
| 3226 | CF₃CO₂H | 472.4 (M + H) | 3.07 |
| 3227 | CF₃CO₂H | 540.6 (M + H) | 3.75 |
| 3228 | CF₃CO₂H | 464.4 (M + H) | 3.07 |

-continued

| Example No. | Structure | ESI-MS | Retention Time (min) |
|---|---|---|---|
| 3229 | 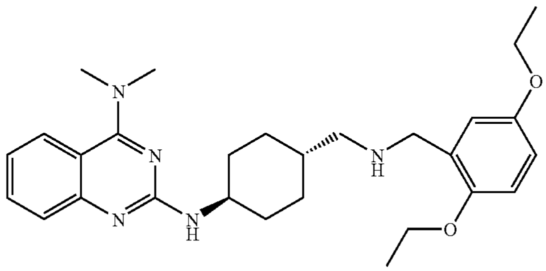 | 478.4 (M + H) | 3.40 |
| 3230 | 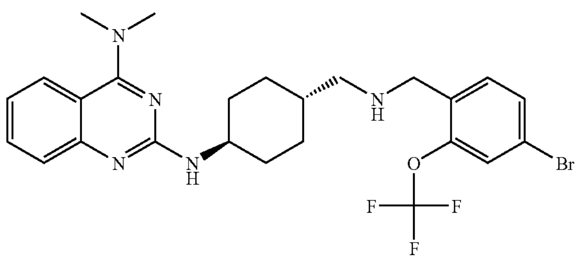 | 552.6 (M + H) | 3.50 |
| 3231 | 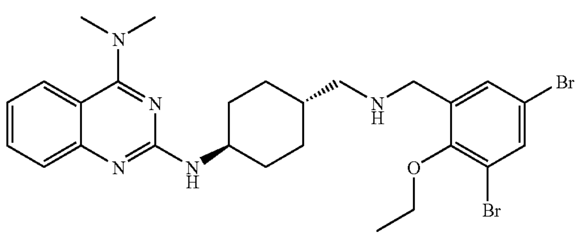 | 590.2 (M + H) | 3.60 |
| 3232 | 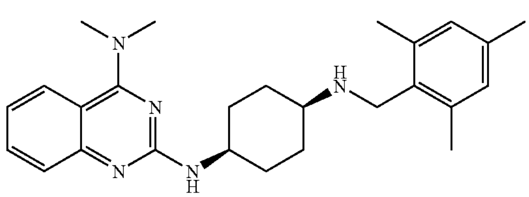 | 418.6 (M + H) | 3.25 |
| 3233 | 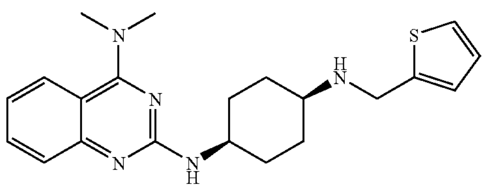 | 382.2 (M + H) | 2.67 |

-continued
| Example No. | Structure | ESI-MS | Retention Time (min) |
|---|---|---|---|
| 3234 | 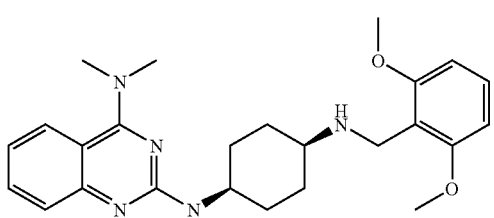 2CF$_3$CO$_2$H | 436.4 (M + H) | 3.05 |
| 3235 | 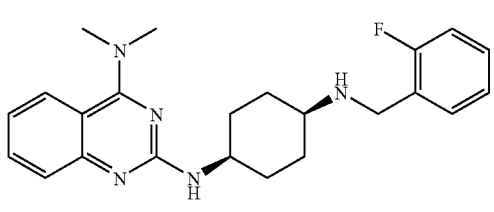 2CF$_3$CO$_2$H | 394.4 (M + H) | 2.75 |
| 3236 | 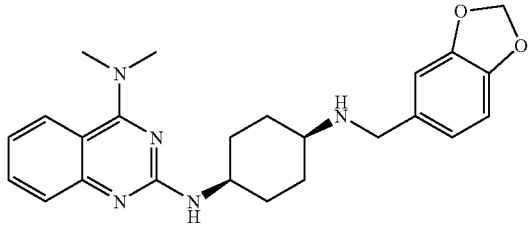 2CF$_3$CO$_2$H | 420.4 (M + H) | 2.82 |
| 3237 | 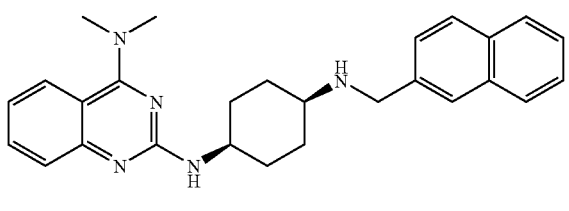 2CF$_3$CO$_2$H | 426.4 (M + H) | 3.17 |
| 3238 | 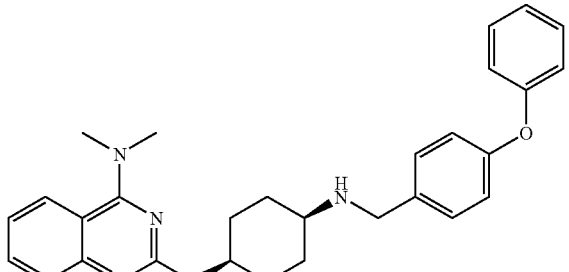 2CF$_3$CO$_2$H | 468.4 (M + H) | 3.44 |

-continued

| Example No. | Structure | ESI-MS | Retention Time (min) |
|---|---|---|---|
| 3239 | 2CF₃CO₂H | 452.2 (M + H) | 2.69 |
| 3240 | 2CF₃CO₂H | 436.4 (M + H) | 2.80 |
| 3241 | 2CF₃CO₂H | 426.2 (M + H) | 2.79 |
| 3242 | 2CF₃CO₂H | 536.4 (M + H) | 3.75 |
| 3243 | 3CF₃CO₂H | 427.2 (M + H) | 2.95 |

-continued

| Example No. | Structure | ESI-MS | Retention Time (min) |
|---|---|---|---|
| 3244 | 2CF$_3$CO$_2$H | 432.4 (M + H) | 3.41 |
| 3245 | 2CF$_3$CO$_2$H | 434.2 (M + H) | 2.84 |
| 3246 | 2CF$_3$CO$_2$H | 410.2 (M + H) | 3.02 |
| 3247 | 3CF$_3$CO$_2$H | 427.4 (M + H) | 2.61 |
| 3248 | 2CF$_3$CO$_2$H | 450.4 (M + H) | 2.91 |

-continued
| Example No. | Structure | ESI-MS | Retention Time (min) |
|---|---|---|---|
| 3249 | 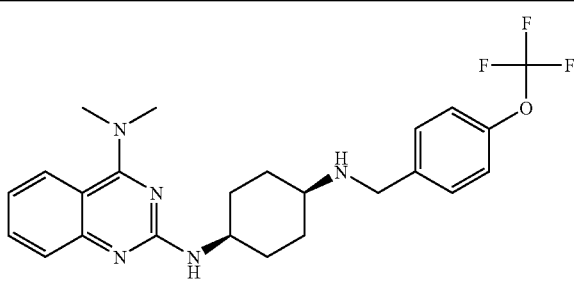<br>2CF₃CO₂H | 460.4 (M + H) | 3.19 |
| 3250 | 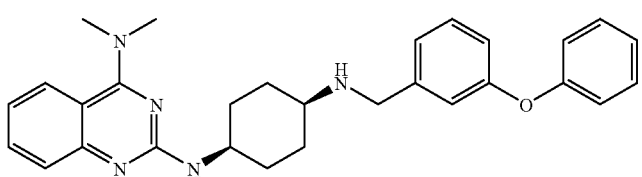<br>2CF₃CO₂H | 468.4 (M + H) | 2.79 |
| 3251 | 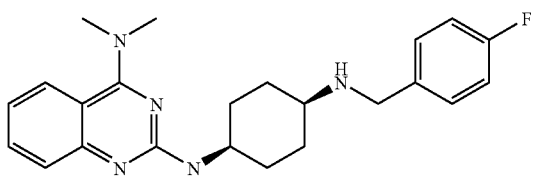<br>2CF₃CO₂H | 394.4 (M + H) | 2.83 |
| 3252 | 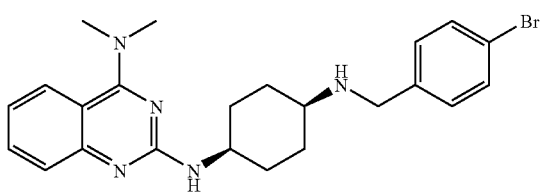<br>2CF₃CO₂H | 454.2 (M + H) | 3.08 |
| 3253 | 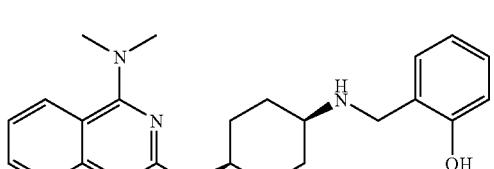<br>2CF₃CO₂H | 392.4 (M + H) | 2.73 |
| 3254 | 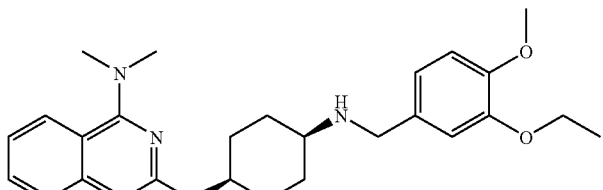<br>2CF₃CO₂H | 450.4 (M + H) | 2.92 |

-continued
| Example No. | Structure | ESI-MS | Retention Time (min) |
|---|---|---|---|
| 3255 | 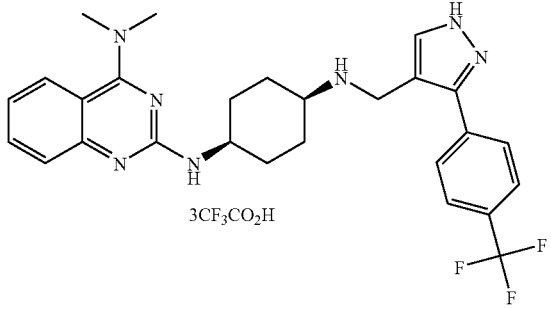<br>3CF₃CO₂H | 510.4 (M + H) | 3.17 |
| 3256 | 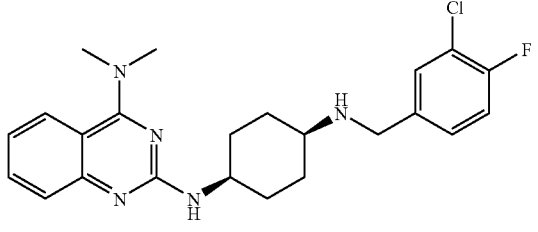<br>2CF₃CO₂H | 428.2 (M + H) | 3.08 |
| 3257 | 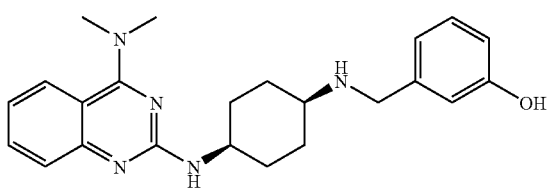<br>2CF₃CO₂H | 392.4 (M + H) | 2.63 |
| 3258 | 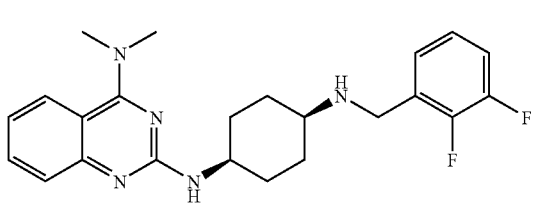<br>2CF₃CO₂H | 412.2 (M + H) | 2.83 |
| 3259 | 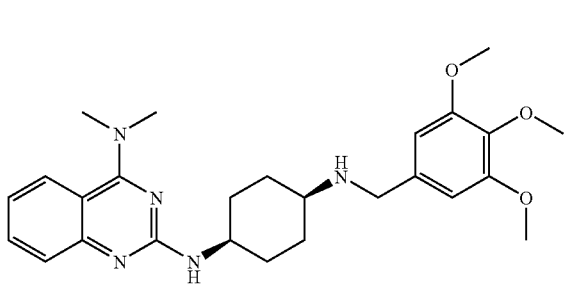<br>2CF₃CO₂H | 466.4 (M + H) | 2.89 |

-continued
| Example No. | Structure | ESI-MS | Retention Time (min) |
|---|---|---|---|
| 3260 | 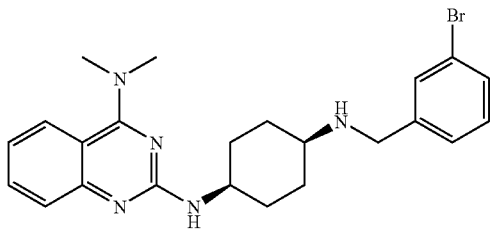<br>2CF₃CO₂H | 454.0 (M + H) | 3.05 |
| 3261 | 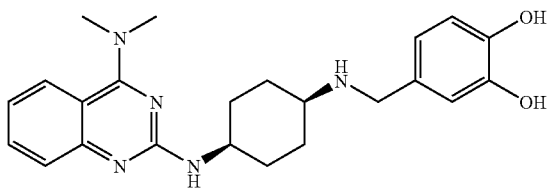<br>2CF₃CO₂H | 408.2 (M + H) | 2.53 |
| 3262 | 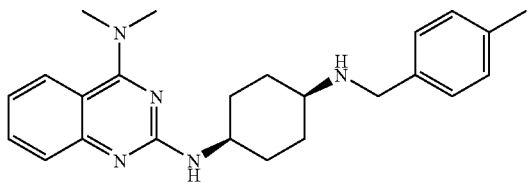<br>2CF₃CO₂H | 390.4 (M + H) | 2.92 |
| 3263 | 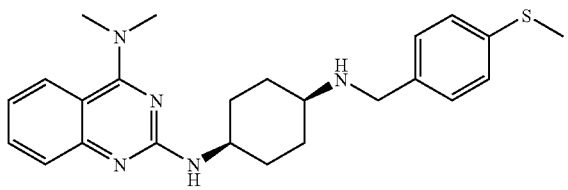<br>2CF₃CO₂H | 422.2 (M + H) | 3.05 |
| 3264 | 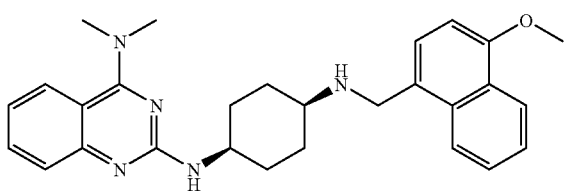<br>2CF₃CO₂H | 456.4 (M + H) | 3.25 |
| 3265 | 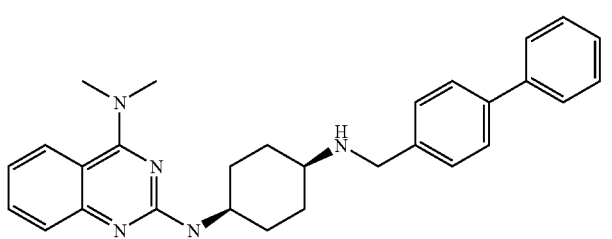<br>2CF₃CO₂H | 452.2 (M + H) | 3.37 |

-continued
| Example No. | Structure | ESI-MS | Retention Time (min) |
|---|---|---|---|
| 3266 | 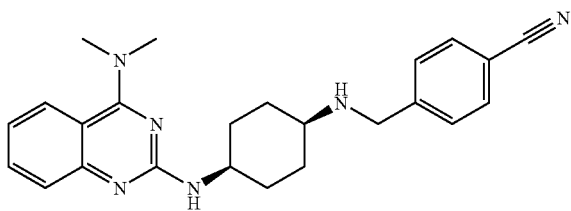<br>2CF₃CO₂H | 401.2 (M + H) | 2.76 |
| 3267 | 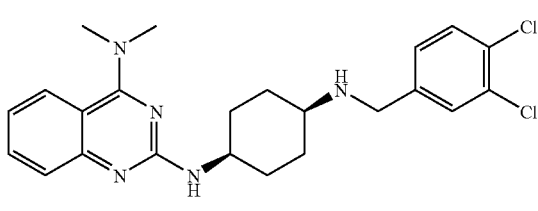<br>2CF₃CO₂H | 444.4 (M + H) | 3.17 |
| 3268 | 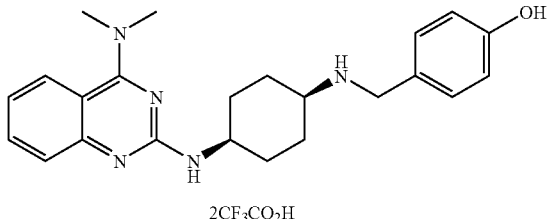<br>2CF₃CO₂H | 392.4 (M + H) | 2.61 |
| 3269 | 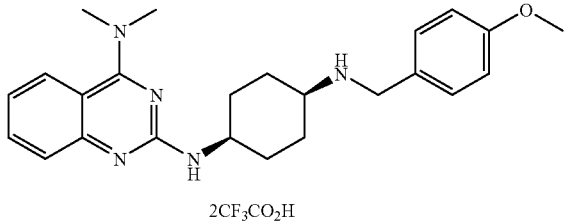<br>2CF₃CO₂H | 406.4 (M + H) | 2.86 |
| 3270 | 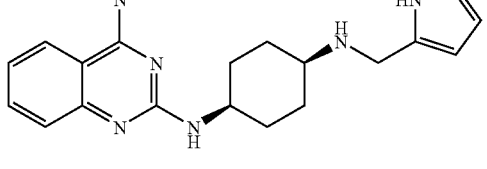<br>3CF₃CO₂H | 365.4 (M + H) | 2.61 |
| 3271 | 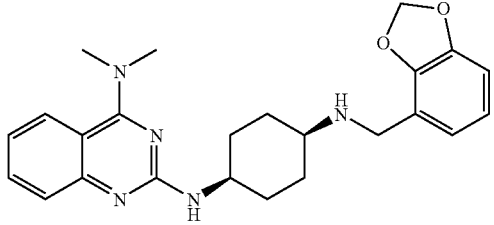<br>2CF₃CO₂H | 420.4 (M + H) | 2.83 |

-continued

| Example No. | Structure | ESI-MS | Retention Time (min) |
|---|---|---|---|
| 3272 | 2CF₃CO₂H | 466.4 (M + H) | 3.10 |
| 3273 | 2CF₃CO₂H | 514.4 (M + H) | 3.13 |
| 3274 | 2CF₃CO₂H | 444.4 (M + H) | 3.17 |
| 3275 | 2CF₃CO₂H | 466.4 (M + H) | 2.86 |
| 3276 | 2CF₃CO₂H | 456.2 (M + H) | 3.22 |

-continued
| Example No. | Structure | ESI-MS | Retention Time (min) |
|---|---|---|---|
| 3277 | 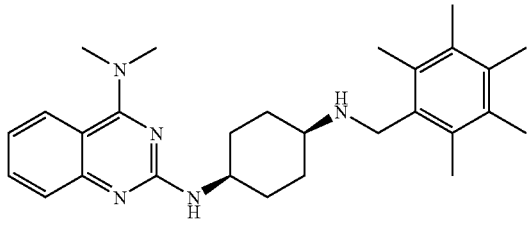<br>2CF₃CO₂H | 446.6 (M + H) | 3.45 |
| 3278 | 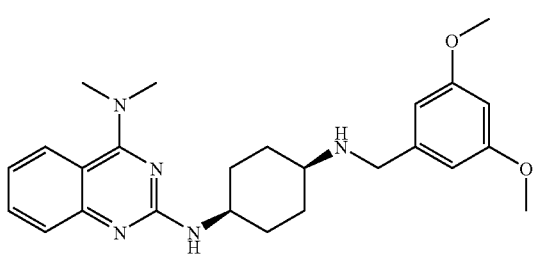<br>2CF₃CO₂H | 436.4 (M + H) | 2.95 |
| 3279 | 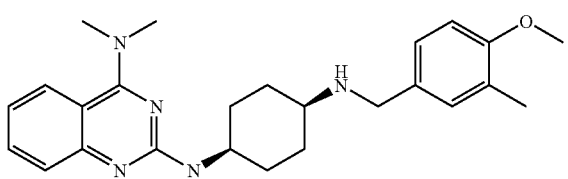<br>2CF₃CO₂H | 420.2 (M + H) | 3.03 |
| 3280 | 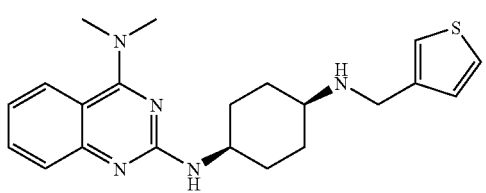<br>2CF₃CO₂H | 382.4 (M + H) | 2.72 |
| 3281 | 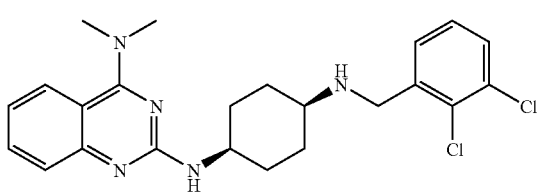<br>2CF₃CO₂H | 444.4 (M + H) | 3.07 |
| 3282 | 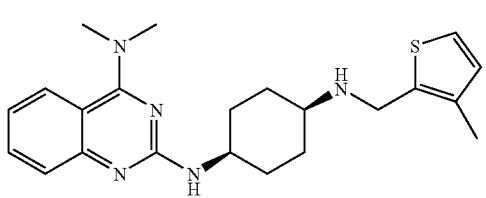<br>2CF₃CO₂H | 396.2 (M + H) | 2.79 |

-continued

| Example No. | Structure | ESI-MS | Retention Time (min) |
|---|---|---|---|
| 3283 | 2CF₃CO₂H | 412.4 (M + H) | 2.95 |
| 3284 | 3CF₃CO₂H | 493.4 (M + H) | 3.57 |
| 3285 | 2CF₃CO₂H | 508.2 (M + H) | 3.52 |
| 3286 | 2CF₃CO₂H | 469.6 (M + H) | 2.76 |
| 3287 | 3CF₃CO₂H | 493.2 (M + H) | 3.17 |

| Example No. | Structure | ESI-MS | Retention Time (min) |
|---|---|---|---|
| 3288 | 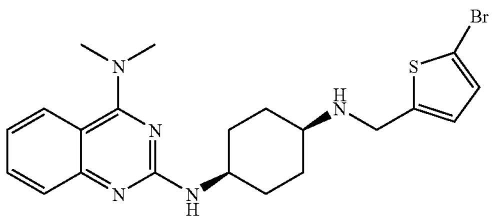 | 460.2 (M + H) | 2.95 |
| 3289 | 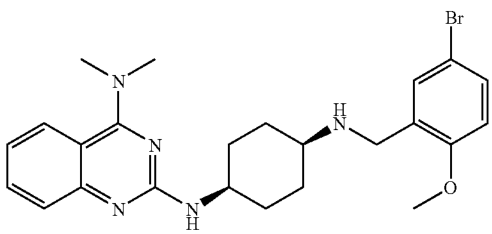 | 484.2 (M + H) | 3.14 |
| 3290 | 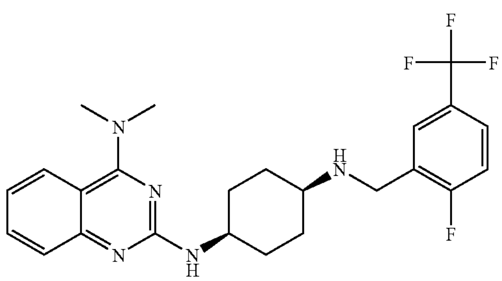 | 462.2 (M + H) | 3.11 |
| 3291 | 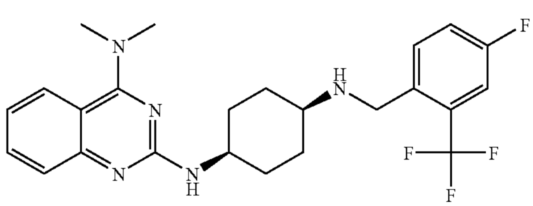 | 462.2 (M + H) | 3.11 |
| 3292 | 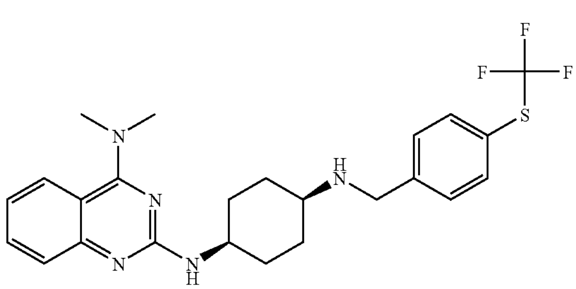 | 476.4 (M + H) | 3.39 |

-continued

| Example No. | Structure | ESI-MS | Retention Time (min) |
|---|---|---|---|
| 3293 | 2CF₃CO₂H | 420.4 (M + H) | 3.05 |
| 3294 | 2CF₃CO₂H | 464.2 (M + H) | 3.21 |
| 3295 | 2CF₃CO₂H | 424.2 (M + H) | 2.94 |
| 3296 | 3CF₃CO₂H | 419.4 (M + H) | 2.51 |
| 3297 | 3CF₃CO₂H | 366.4 (M + H) | 2.26 |

-continued

| Example No. | Structure | ESI-MS | Retention Time (min) |
|---|---|---|---|
| 3298 | (structure) 2CF₃CO₂H | 424.2 (M + H) | 2.93 |
| 3299 | (structure) 2CF₃CO₂H | 442.4 (M + H) | 2.97 |
| 3300 | (structure) 2CF₃CO₂H | 478.2 (M + H) | 3.19 |
| 3301 | (structure) 2CF₃CO₂H | 462.2 (M + H) | 3.05 |
| 3302 | (structure) 2CF₃CO₂H | 476.4 (M + H) | 3.20 |

-continued
| Example No. | Structure | ESI-MS | Retention Time (min) |
|---|---|---|---|
| 3303 | 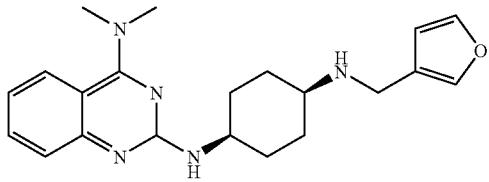 2CF₃CO₂H | 366.4 (M + H) | 2.64 |
| 3304 | 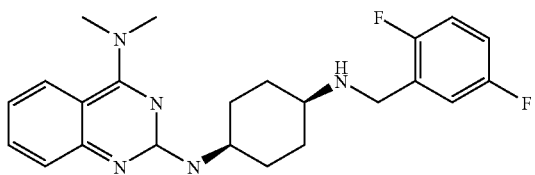 2CF₃CO₂H | 412.4 (M + H) | 2.85 |
| 3305 | 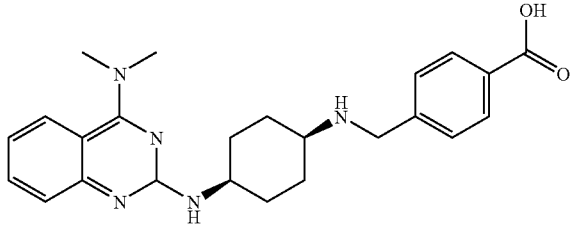 2CF₃CO₂H | 420.4 (M + H) | 2.67 |
| 3306 | 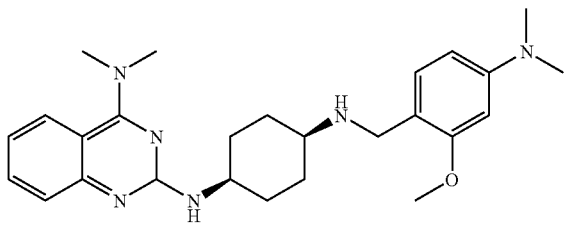 3CF₃CO₂H | 449.4 (M + H) | 2.74 |
| 3307 | 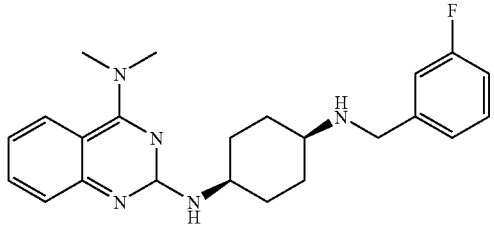 2CF₃CO₂H | 394.4 (M + H) | 2.86 |

-continued
| Example No. | Structure | ESI-MS | Retention Time (min) |
|---|---|---|---|
| 3308 | 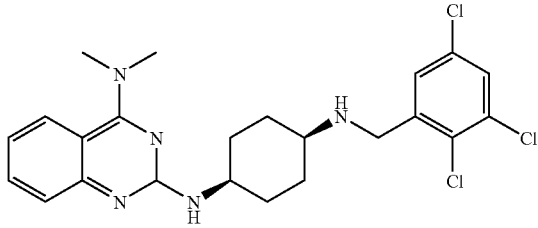*2CF₃CO₂H* | 478.2 (M + H) | 3.38 |
| 3309 | 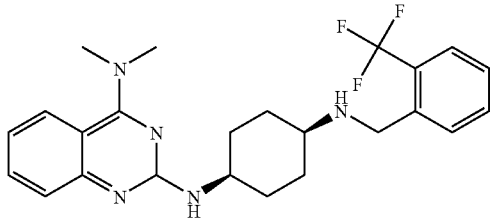*2CF₃CO₂H* | 444.4 (M + H) | 3.09 |
| 3310 | 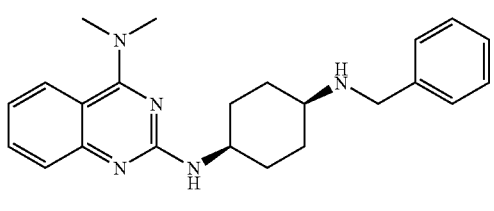*2CF₃CO₂H* | 376.4 (M + H) | 2.82 |
| 3311 | 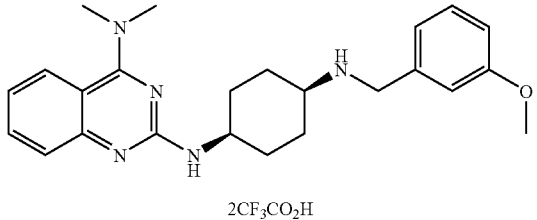*2CF₃CO₂H* | 406.4 (M + H) | 2.87 |
| 3312 | 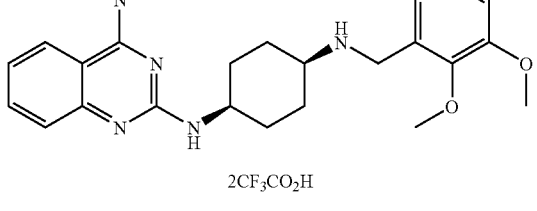*2CF₃CO₂H* | 436.4 (M + H) | 2.91 |
| 3313 | 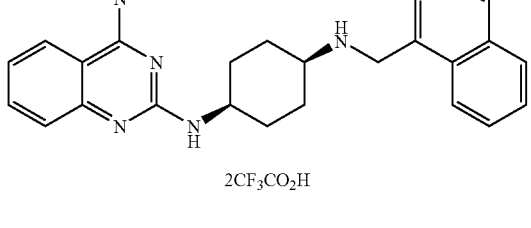*2CF₃CO₂H* | 426.2 (M + H) | 3.13 |

-continued
| Example No. | Structure | ESI-MS | Retention Time (min) |
|---|---|---|---|
| 3314 | 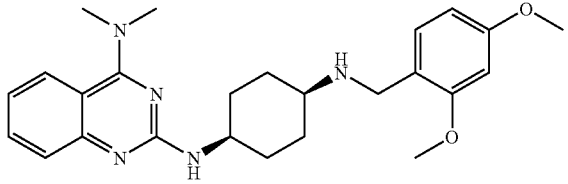 2CF₃CO₂H | 436.4 (M + H) | 2.99 |
| 3315 | 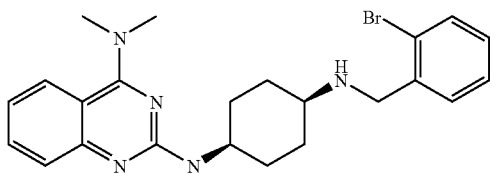 2CF₃CO₂H | 454.0 (M + H) | 2.97 |
| 3316 | 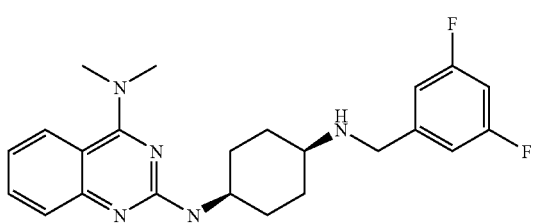 2CF₃CO₂H | 412.4 (M + H) | 2.92 |
| 3317 | 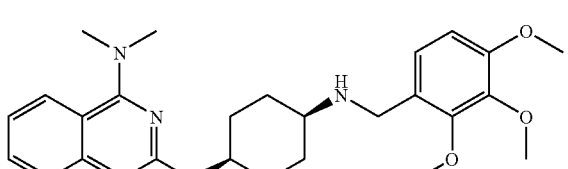 2CF₃CO₂H | 466.4 (M + H) | 2.95 |
| 3318 | 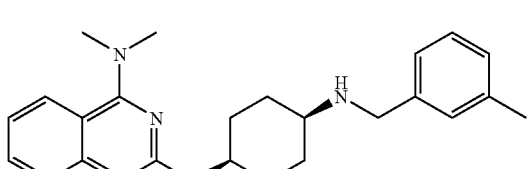 2CF₃CO₂H | 390.4 (M + H) | 2.95 |
| 3319 | 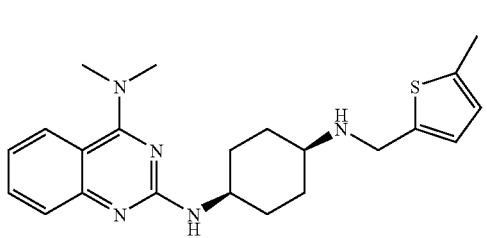 2CF₃CO₂H | 396.2 (M + H) | 2.89 |

-continued
| Example No. | Structure | ESI-MS | Retention Time (min) |
|---|---|---|---|
| 3320 | 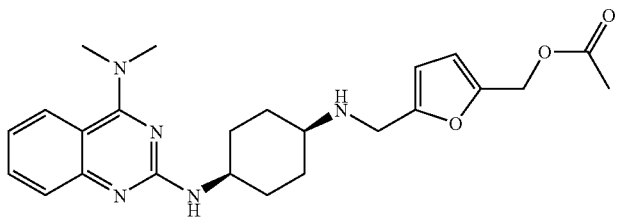<br>2CF₃CO₂H | 438.2 (M + H) | 2.76 |
| 3321 | 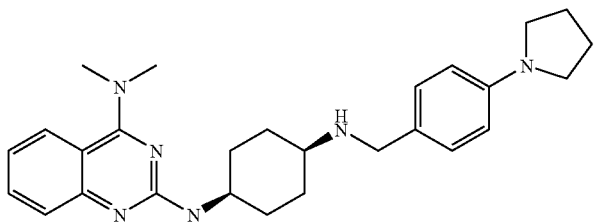<br>3CF₃CO₂H | 445.4 (M + H) | 3.16 |
| 3322 | 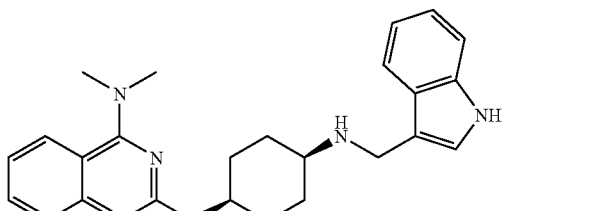<br>3CF₃CO₂H | 415.4 (M + H) | 2.96 |
| 3323 | 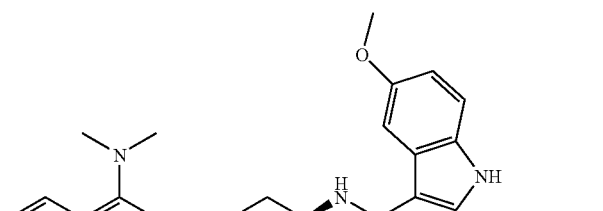<br>3CF₃CO₂H | 445.4 (M + H) | 2.96 |
| 3324 | 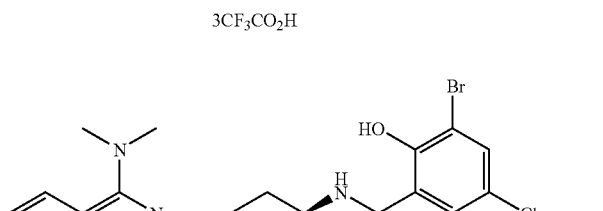<br>2CF₃CO₂H | 504.2 (M + H) | 3.11 |

-continued
| Example No. | Structure | ESI-MS | Retention Time (min) |
|---|---|---|---|
| 3325 | 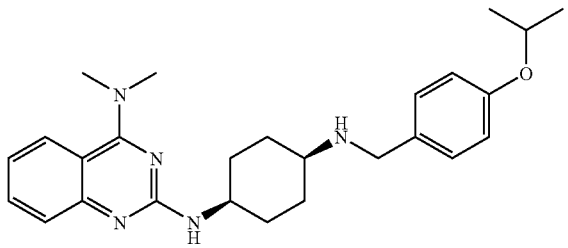 2CF$_3$CO$_2$H | 434.4 (M + H) | 3.17 |
| 3326 | 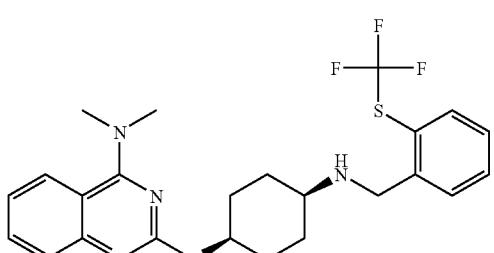 2CF$_3$CO$_2$H | 476.2 (M + H) | 3.27 |
| 3327 | 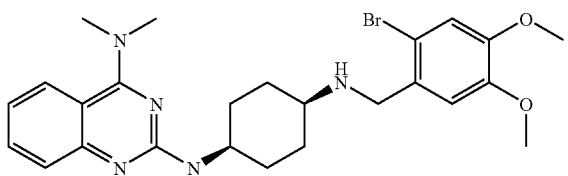 2CF$_3$CO$_2$H | 514.4 (M + H) | 3.07 |
| 3328 | 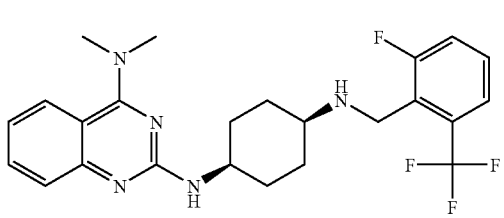 2CF$_3$CO$_2$H | 462.2 (M + H) | 2.99 |
| 3329 | 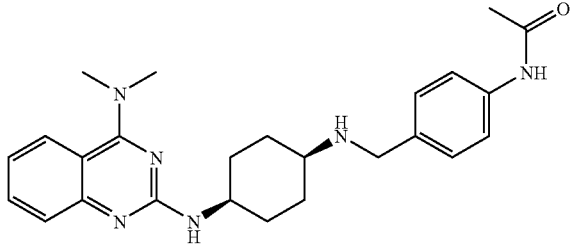 2CF$_3$CO$_2$H | 433.2 (M + H) | 2.63 |

-continued

| Example No. | Structure | ESI-MS | Retention Time (min) |
|---|---|---|---|
| 3330 | 2CF₃CO₂H | 518.4 (M + H) | 3.63 |
| 3331 | 2CF₃CO₂H | 500.4 (M + H) | 3.09 |
| 3332 | 3CF₃CO₂H | 379.4 (M + H) | 2.77 |
| 3333 | 2CF₃CO₂H | 460.2 (M + H) | 3.31 |

-continued

| Example No. | Structure | ESI-MS | Retention Time (min) |
|---|---|---|---|
| 3334 | 2CF$_3$CO$_2$H | 512.4 (M + H) | 3.51 |
| 3335 | 2CF$_3$CO$_2$H | 512.6 (M + H) | 3.51 |
| 3336 | 2CF$_3$CO$_2$H | 476.2 (M + H) | 3.39 |
| 3337 | 2CF$_3$CO$_2$H | 448.4 (M + H) | 3.42 |
| 3338 | 2CF$_3$CO$_2$H | 404.4 (M + H) | 3.17 |

-continued

| Example No. | Structure | ESI-MS | Retention Time (min) |
|---|---|---|---|
| 3339 | 2CF₃CO₂H | 444.4 (M + H) | 3.13 |
| 3340 | 2CF₃CO₂H | 462.2 (M + H) | 3.21 |
| 3341 | 2CF₃CO₂H | 424.2 (M + H) | 2.97 |
| 3342 | 2CF₃CO₂H | 444.6 (M + H) | 3.16 |
| 3343 | 2CF₃CO₂H | 469.4 (M + H) | 3.47 |

-continued

| Example No. | Structure | ESI-MS | Retention Time (min) |
|---|---|---|---|
| 3344 | 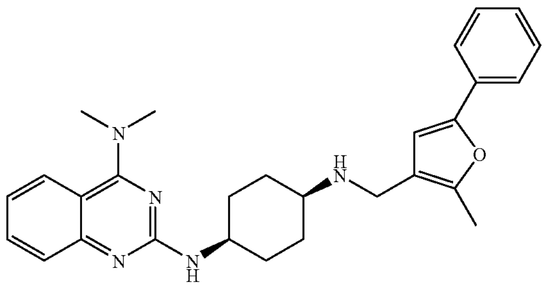 | 456.4 (M + H) | 3.47 |
| 3345 | 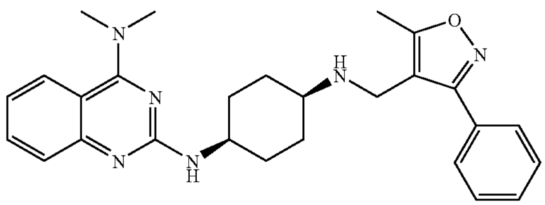 | 457.4 (M + H) | 3.09 |
| 3346 | 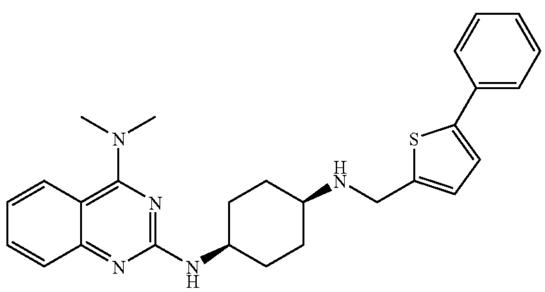 | 458.2 (M + H) | 3.37 |
| 3347 | 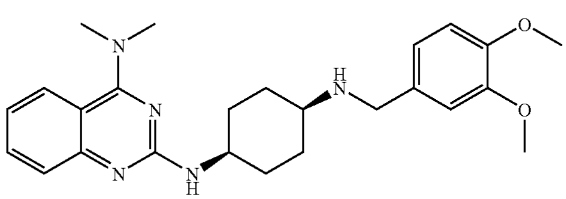 | 436.4 (M + H) | 2.83 |
| 3348 | 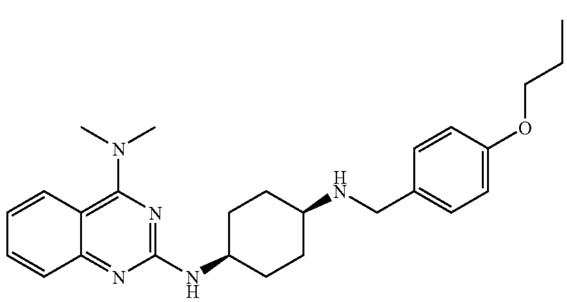 | 434.4 (M + H) | 3.30 |

-continued

| Example No. | Structure | ESI-MS | Retention Time (min) |
|---|---|---|---|
| 3349 | 2CF₃CO₂H | 494.4 (M + H) | 2.98 |
| 3350 | 2CF₃CO₂H | 406.4 (M + H) | 2.80 |
| 3351 | 2CF₃CO₂H | 460.4 (M + H) | 3.20 |
| 3352 | 2CF₃CO₂H | 390.4 (M + H) | 2.97 |
| 3353 | 2CF₃CO₂H | 444.2 (M + H) | 3.01 |

-continued
| Example No. | Structure | ESI-MS | Retention Time (min) |
|---|---|---|---|
| 3354 | 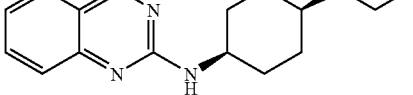<br>3CF$_3$CO$_2$H | 380.2 (M + H) | 2.27 |
| 3355 | 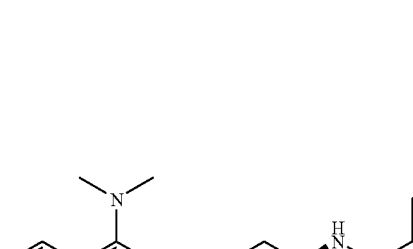<br>2CF$_3$CO$_2$H | 491.4 (M + H) | 2.55 |
| 3356 | <br>2CF$_3$CO$_2$H | 410.4 (M + H) | 3.05 |
| 3357 | 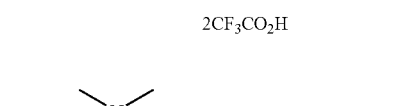<br>2CF$_3$CO$_2$H | 422.2 (M + H) | 2.69 |
| 3358 | 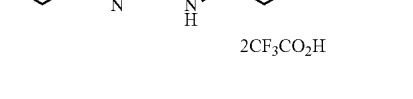<br>2CF$_3$CO$_2$H | 418.6 (M + H) | 3.36 |

-continued
| Example No. | Structure | ESI-MS | Retention Time (min) |
|---|---|---|---|
| 3359 | 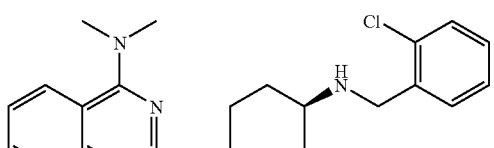<br>2CF₃CO₂H | 410.4 (M + H) | 2.97 |
| 3360 | 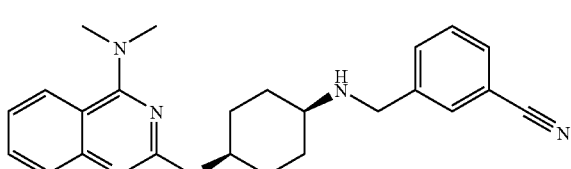<br>2CF₃CO₂H | 401.2 (M + H) | 2.81 |
| 3361 | 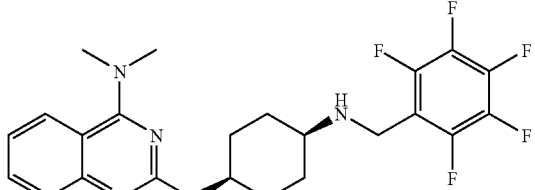<br>2CF₃CO₂H | 466.2 (M + H) | 3.01 |
| 3362 | 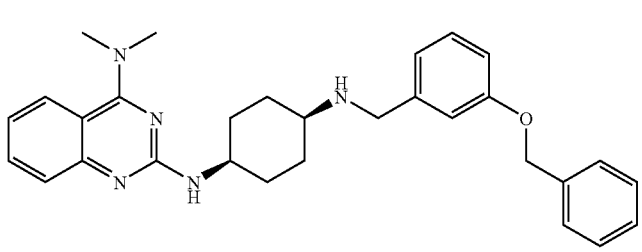<br>2CF₃CO₂H | 482.4 (M + H) | 3.43 |
| 3363 | 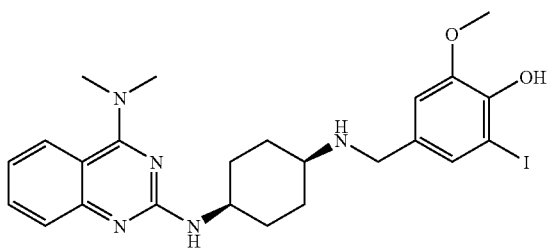<br>2CF₃CO₂H | 548.4 (M + H) | 3.03 |

-continued

| Example No. | Structure | ESI-MS | Retention Time (min) |
|---|---|---|---|
| 3364 | 3CF₃CO₂H | 543.6 (M + H) | 3.95 |
| 3365 | 2CF₃CO₂H | 478.4 (M + H) | 3.64 |
| 3366 | 2CF₃CO₂H | 478.4 (M + H) | 3.29 |
| 3367 | 2CF₃CO₂H | 434.4 (M + H) | 3.20 |
| 3368 | 2CF₃CO₂H | 442.4 (M + H) | 3.09 |

-continued
| Example No. | Structure | ESI-MS | Retention Time (min) |
|---|---|---|---|
| 3369 | 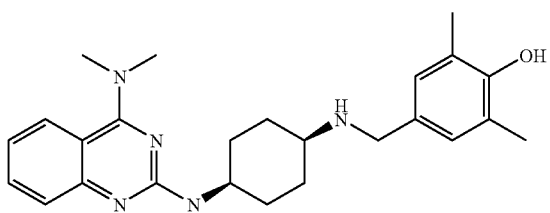<br>2CF₃CO₂H | 420.4 (M + H) | 2.87 |
| 3370 | 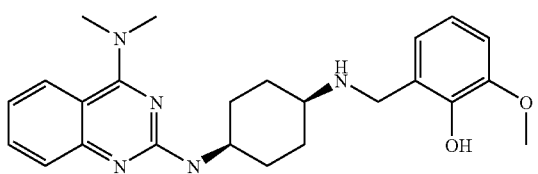<br>2CF₃CO₂H | 422.2 (M + H) | 2.79 |
| 3371 | 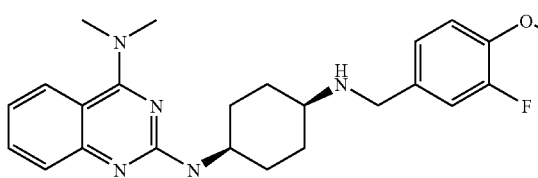<br>2CF₃CO₂H | 424.2 (M + H) | 2.96 |
| 3372 | 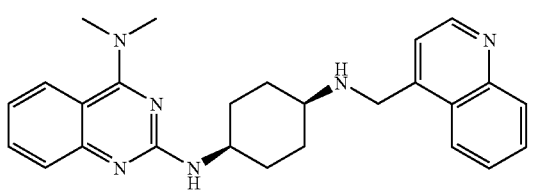<br>3CF₃CO₂H | 427.2 (M + H) | 2.53 |
| 3373 | 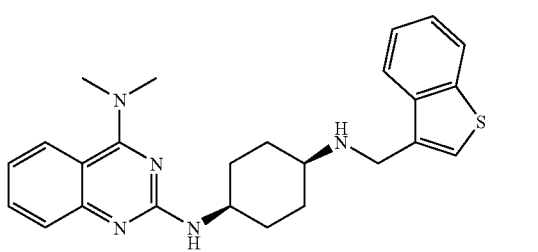<br>2CF₃CO₂H | 432.4 (M + H) | 3.12 |

-continued

| Example No. | Structure | ESI-MS | Retention Time (min) |
|---|---|---|---|
| 3374 | 3CF$_3$CO$_2$H | 447.4 (M + H) | 2.45 |
| 3375 | 2CF$_3$CO$_2$H | 408.2 (M + H) | 3.02 |
| 3376 | 2CF$_3$CO$_2$H | 496.4 (M + H) | 2.81 |
| 3377 | 2CF$_3$CO$_2$H | 400.2 (M + H) | 2.81 |
| 3378 | 2CF$_3$CO$_2$H | 520.2 (M + H) | 3.14 |

-continued

| Example No. | Structure | ESI-MS | Retention Time (min) |
|---|---|---|---|
| 3379 | 2CF₃CO₂H | 410.4 (M + H) | 3.12 |
| 3380 | 2CF₃CO₂H | 496.4 (M + H) | 3.40 |
| 3381 | 2CF₃CO₂H | 496.4 (M + H) | 3.17 |
| 3382 | 2CF₃CO₂H | 462.2 (M + H) | 3.19 |

-continued

| Example No. | Structure | ESI-MS | Retention Time (min) |
|---|---|---|---|
| 3383 | 2CF₃CO₂H | 462.2 (M + H) | 3.28 |
| 3384 | 2CF₃CO₂H | 440.4 (M + H) | 2.74 |
| 3385 | 2CF₃CO₂H | 454.2 (M + H) | 2.89 |
| 3386 | 2CF₃CO₂H | 404.4 (M + H) | 3.09 |
| 3387 | 2CF₃CO₂H | 482.2 (M + H) | 3.29 |

-continued

| Example No. | Structure | ESI-MS | Retention Time (min) |
|---|---|---|---|
| 3388 | 3CF₃CO₂H | 458.4 (M + H) | 2.99 |
| 3389 | 2CF₃CO₂H | 452.2 (M + H) | 3.40 |
| 3390 | 2CF₃CO₂H | 560.2 (M + H) | 3.73 |
| 3391 | 2CF₃CO₂H | 416.4 (M + H) | 2.99 |
| 3392 | 2CF₃CO₂H | 518.6 (M + H) | 4.08 |

| Example No. | Structure | ESI-MS | Retention Time (min) |
|---|---|---|---|
| 3393 | 2CF₃CO₂H | 436.4 (M + H) | 2.95 |
| 3394 | 2CF₃CO₂H | 434.4 (M + H) | 3.30 |
| 3395 | CF₃CO₂H | 440.4 (M + H) | 4.26 |
| 3396 | CF₃CO₂H | 458.2 (M + H) | 4.39 |
| 3397 | CF₃CO₂H | 480.4 (M + H) | 4.37 |

-continued
| Example No. | Structure | ESI-MS | Retention Time (min) |
|---|---|---|---|
| 3398 | 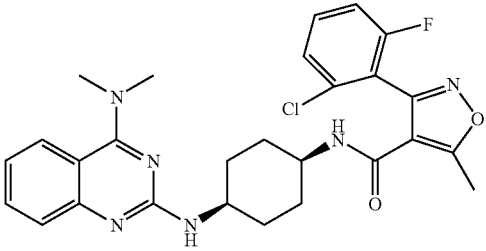 CF$_3$CO$_2$H | 523.6 (M + H) | 4.15 |
| 3399 | 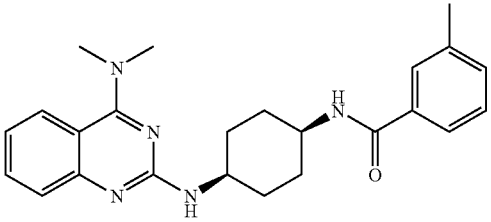 CF$_3$CO$_2$H | 404.4 (M + H) | 3.46 |
| 3400 | 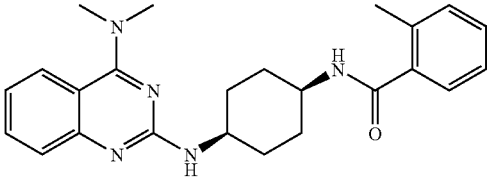 CF$_3$CO$_2$H | 404.4 (M + H) | 3.75 |
| 3401 | 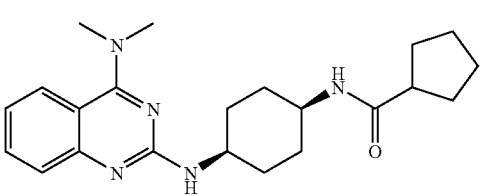 CF$_3$CO$_2$H | 382.4 (M + H) | 3.65 |
| 3402 | 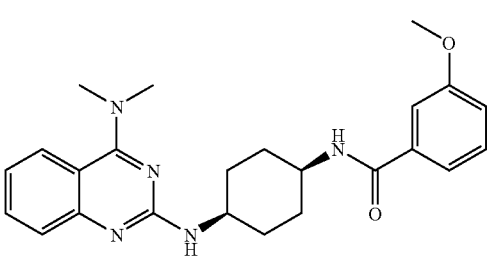 CF$_3$CO$_2$H | 420.4 (M + H) | 3.81 |

-continued

| Example No. | Structure | ESI-MS | Retention Time (min) |
|---|---|---|---|
| 3403 | CF₃CO₂H | 381.2 (M + H) | 3.33 |
| 3404 | CF₃CO₂H | 404.4 (M + H) | 3.93 |
| 3405 | CF₃CO₂H | 435.2 (M + H) | 3.40 |
| 3406 | CF₃CO₂H | 484.4 (M + H) | 4.15 |
| 3407 | CF₃CO₂H | 469.4 (M + H) | 4.20 |

-continued

| Example No. | Structure | ESI-MS | Retention Time (min) |
|---|---|---|---|
| 3408 | CF₃CO₂H | 436.2 (M + H) | 3.88 |
| 3409 | CF₃CO₂H | 434.4 (M + H) | 3.91 |
| 3410 | CF₃CO₂H | 558.4 (M + H) | 4.92 |
| 3411 | 2CF₃CO₂H | 483.4 (M + H) | 4.08 |
| 3412 | CF₃CO₂H | 396.2 (M + H) | 3.68 |

-continued

| Example No. | Structure | ESI-MS | Retention Time (min) |
|---|---|---|---|
| 3413 | CF₃CO₂H | 454.2 (M + H) | 3.70 |
| 3414 | 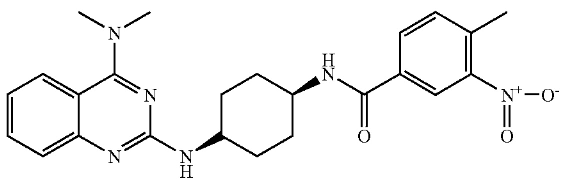 | 449.4 (M + H) | 4.09 |
| 3415 | CF₃CO₂H | 476.2 (M + H) | 4.33 |
| 3416 | CF₃CO₂H | 476.4 (M + H) | 3.60 |
| 3417 | CF₃CO₂H | 476.4 (M + H) | 4.23 |

-continued

| Example No. | Structure | ESI-MS | Retention Time (min) |
|---|---|---|---|
| 3418 | 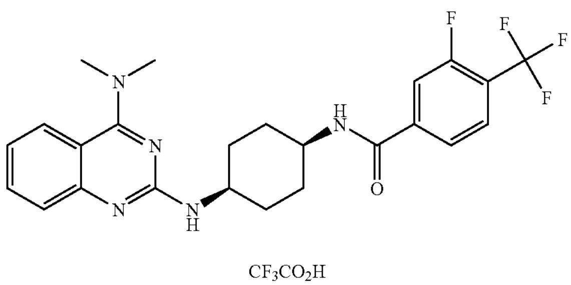 | 476.4 (M + H) | 4.38 |
| 3419 | 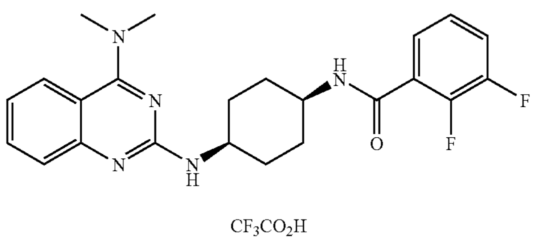 | 426.2 (M + H) | 3.87 |
| 3420 | 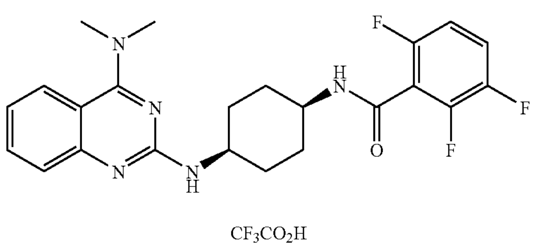 | 444.4 (M + H) | 3.86 |
| 3421 | 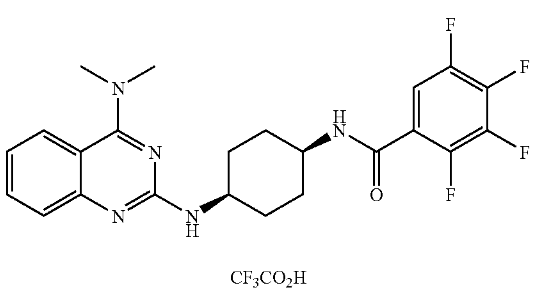 | 462.2 (M + H) | 4.15 |
| 3422 | 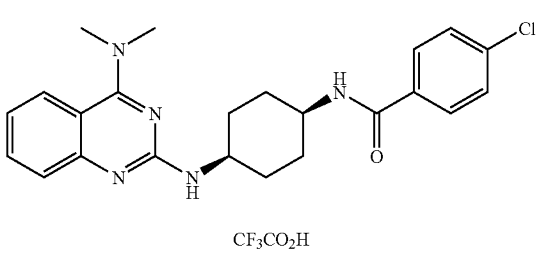 | 424.2 (M + H) | 4.06 |

-continued

| Example No. | Structure | ESI-MS | Retention Time (min) |
|---|---|---|---|
| 3423 | CF₃CO₂H | 450.4 (M + H) | 4.03 |
| 3424 | CF₃CO₂H | 434.2 (M + H) | 3.75 |
| 3425 | CF₃CO₂H | 426.2 (M + H) | 3.88 |
| 3426 | CF₃CO₂H | 450.4 (M + H) | 3.64 |
| 3427 | CF₃CO₂H | 450.4 (M + H) | 3.55 |

-continued

| Example No. | Structure | ESI-MS | Retention Time (min) |
|---|---|---|---|
| 3428 | (4-dimethylamino-quinazolin-2-yl)-amino-cyclohexyl-NH-C(O)-(4-ethylphenyl); CF₃CO₂H | 418.6 (M + H) | 4.17 |
| 3429 | (4-dimethylamino-quinazolin-2-yl)-amino-cyclohexyl-NH-C(O)-(4-ethoxyphenyl); CF₃CO₂H | 404.4 (M + H) | 4.03 |
| 3430 | (4-dimethylamino-quinazolin-2-yl)-amino-cyclohexyl-NH-C(O)-(3,5-dichlorophenyl); CF₃CO₂H | 458.2 (M + H) | 4.45 |
| 3431 | (4-dimethylamino-quinazolin-2-yl)-amino-cyclohexyl-NH-C(O)-(3-cyanophenyl); CF₃CO₂H | 415.4 (M + H) | 3.76 |
| 3432 | (4-dimethylamino-quinazolin-2-yl)-amino-cyclohexyl-NH-C(O)-(4-pentylphenyl); CF₃CO₂H | 474.4 (M + H) | 5.06 |
| 3433 | (4-dimethylamino-quinazolin-2-yl)-amino-cyclohexyl-NH-C(O)-CH₂-(thiophen-3-yl); CF₃CO₂H | 410.2 (M + H) | 3.64 |

-continued

| Example No. | Structure | ESI-MS | Retention Time (min) |
|---|---|---|---|
| 3434 | 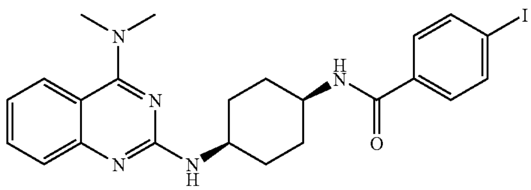 | 516.2 (M + H) | 4.24 |
| 3435 | 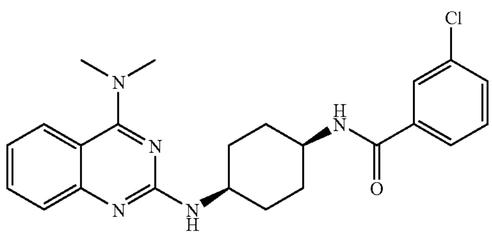 | 424.2 (M + H) | 4.09 |
| 3436 | 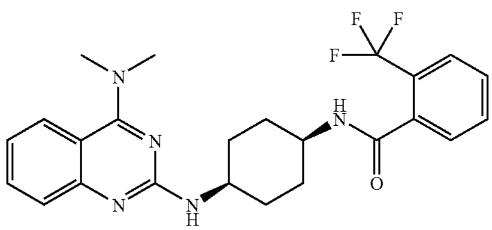 | 458.2 (M + H) | 3.89 |
| 3437 | 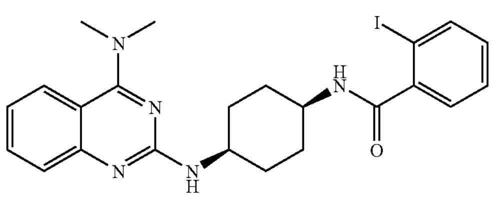 | 516.2 (M + H) | 3.88 |
| 3438 | 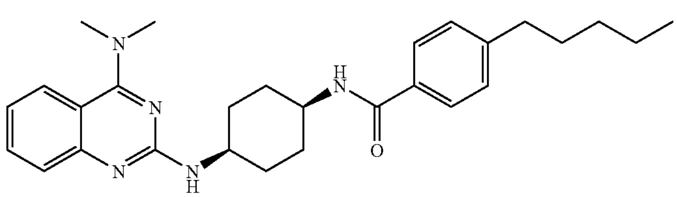 | 460.4 (M + H) | 4.86 |
| 3439 | 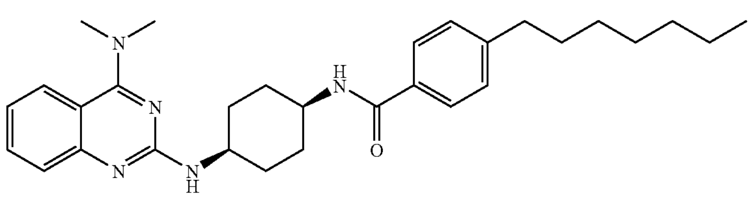 | 488.4 (M + H) | 4.70 |

-continued

| Example No. | Structure | ESI-MS | Retention Time (min) |
|---|---|---|---|
| 3440 | 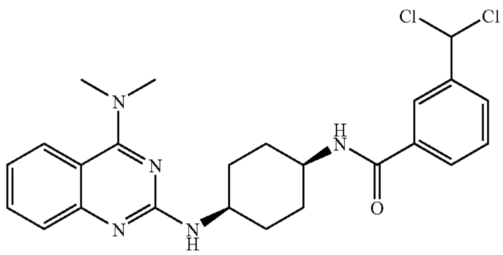 | 472.4 (M + H) | 4.29 |
| 3441 | 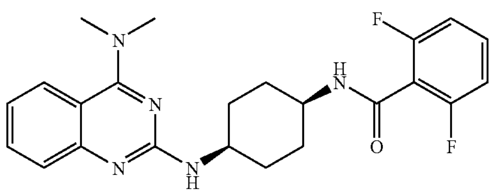 | 426.2 (M + H) | 3.69 |
| 3442 | 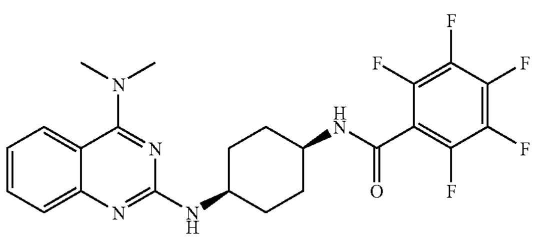 | 480.2 (M + H) | 4.16 |
| 3443 | 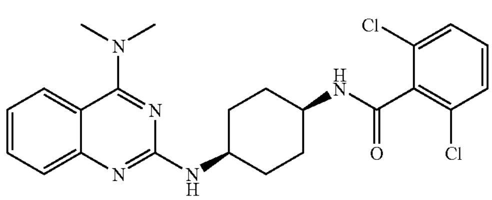 | 458.2 (M + H) | 3.91 |
| 3444 | 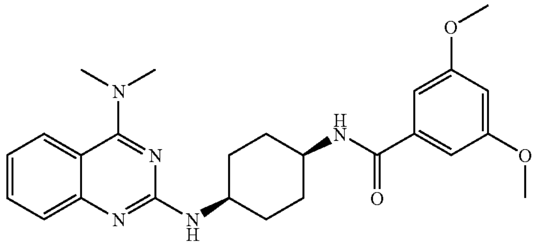 | 450.4 (M + H) | 3.95 |

-continued
| Example No. | Structure | ESI-MS | Retention Time (min) |
|---|---|---|---|
| 3445 | 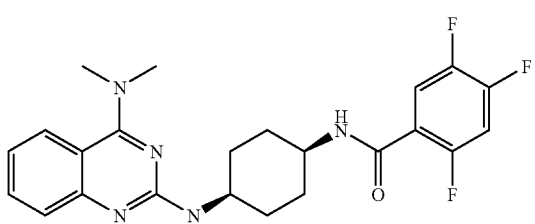 CF3CO2H | 444.4 (M + H) | 4.01 |
| 3446 | 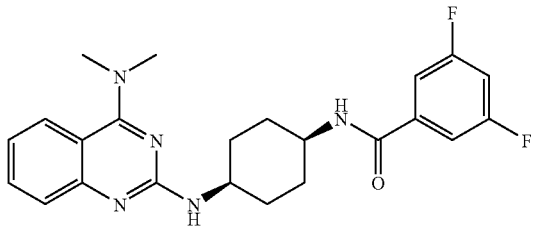 CF3CO2H | 426.2 (M + H) | 4.00 |
| 3447 | 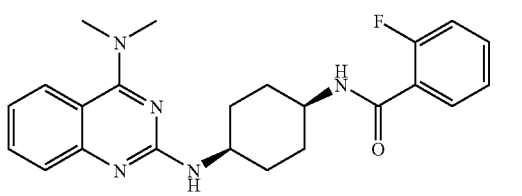 CF3CO2H | 408.4 (M + H) | 3.75 |
| 3448 | 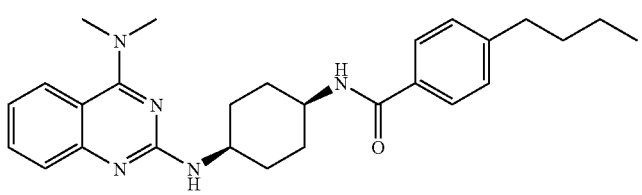 CF3CO2H | 446.6 (M + H) | 4.65 |
| 3449 | 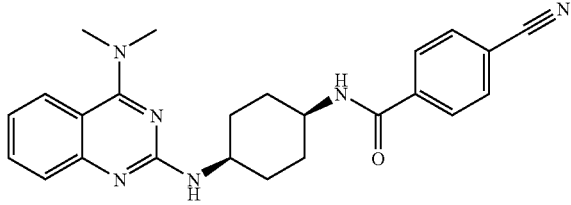 CF3CO2H | 415.2 (M + H) | 3.75 |

-continued

| Example No. | Structure | ESI-MS | Retention Time (min) |
|---|---|---|---|
| 3450 | CF$_3$CO$_2$H | 420.4 (M + H) | 3.91 |
| 3451 | CF$_3$CO$_2$H | 490.4 (M + H) | 4.99 |
| 3452 | CF$_3$CO$_2$H | 504.4 (M + H) | 5.16 |
| 3453 | CF$_3$CO$_2$H | 444.4 (M + H) | 4.00 |
| 3454 | CF$_3$CO$_2$H | 396.2 (M + H) | 3.85 |

-continued

| Example No. | Structure | ESI-MS | Retention Time (min) |
|---|---|---|---|
| 3455 | [Structure: quinazoline with dimethylamino, cyclohexyl-NH linker, amide to 3,5-bis(trifluoromethyl)benzene; CF₃CO₂H salt] | 526.6 (M + H) | 4.69 |
| 3456 | [Structure: quinazoline with dimethylamino, cyclohexyl-NH linker, amide to 4-fluorobenzene; CF₃CO₂H salt] | 408.4 (M + H) | 3.30 |
| 3457 | [Structure: quinazoline with dimethylamino, cyclohexyl-NH linker, amide to 3,4,5-trimethoxybenzene; CF₃CO₂H salt] | 480.4 (M + H) | 3.76 |
| 3458 | [Structure: quinazoline with dimethylamino, cyclohexyl-NH linker, amide to 2,4-difluorobenzene; CF₃CO₂H salt] | 426.2 (M + H) | 3.86 |
| 3459 | [Structure: quinazoline with dimethylamino, cyclohexyl-NH linker, amide to 2-chlorobenzene; CF₃CO₂H salt] | 424.2 (M + H) | 3.76 |

-continued
| Example No. | Structure | ESI-MS | Retention Time (min) |
|---|---|---|---|
| 3460 | 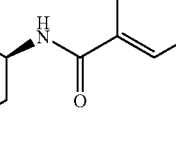 CF₃CO₂H | 440.4 (M + H) | 4.05 |
| 3461 | 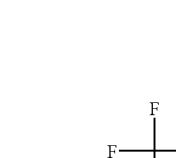 CF₃CO₂H | 458.4 (M + H) | 4.25 |
| 3462 | 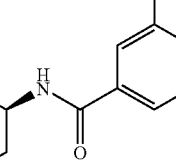 CF₃CO₂H | 408.2 (M + H) | 3.84 |
| 3463 |  CF₃CO₂H | 458.2 (M + H) | 4.25 |
| 3464 | 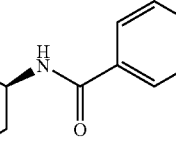 CF₃CO₂H | 446.6 (M + H) | 4.44 |

-continued

| Example No. | Structure | ESI-MS | Retention Time (min) |
|---|---|---|---|
| 3465 | (4-dimethylamino-quinazolin-2-ylamino-cyclohexyl)-N-(3-bromobenzamide) · CF₃CO₂H | 470.2 (M + H) | 4.13 |
| 3466 | (4-dimethylamino-quinazolin-2-ylamino-cyclohexyl)-N-(2-fluoro-4-trifluoromethyl-benzamide) · CF₃CO₂H | 479.2 (M + H) | 4.25 |
| 3467 | (4-dimethylamino-quinazolin-2-ylamino-cyclohexyl)-N-(2-fluoro-6-trifluoromethyl-benzamide) · CF₃CO₂H | 476.2 (M + H) | 3.92 |
| 3468 | (4-dimethylamino-quinazolin-2-ylamino-cyclohexyl)-N-(2,5-bis-trifluoromethyl-benzamide) · CF₃CO₂H | 526.4 (M + H) | 4.31 |
| 3469 | (4-dimethylamino-quinazolin-2-ylamino-cyclohexyl)-N-(2,4-dichloro-5-fluoro-benzamide) · CF₃CO₂H | 476.2 (M + H) | 4.15 |

-continued
| Example No. | Structure | ESI-MS | Retention Time (min) |
|---|---|---|---|
| 3470 | 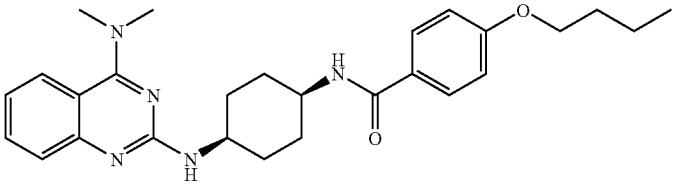 CF$_3$CO$_2$H | 462.2 (M + H) | 4.48 |
| 3471 | 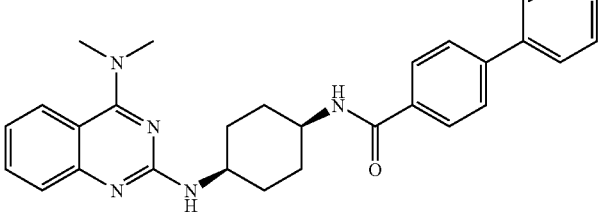 CF$_3$CO$_2$H | 466.4 (M + H) | 4.45 |
| 3472 | 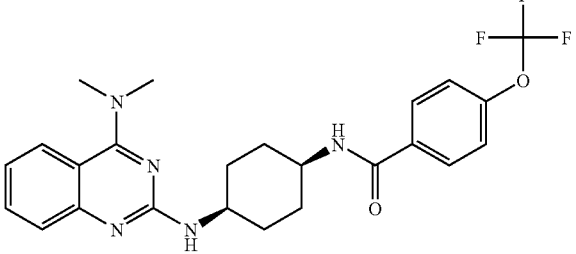 CF$_3$CO$_2$H | 474.4 (M + H) | 4.29 |
| 3473 | 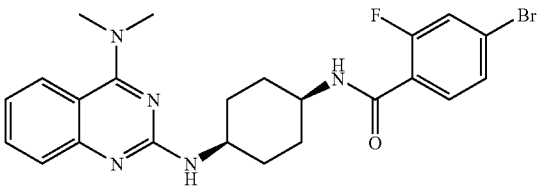 CF$_3$CO$_2$H | 486.2 (M + H) | 4.32 |
| 3474 | 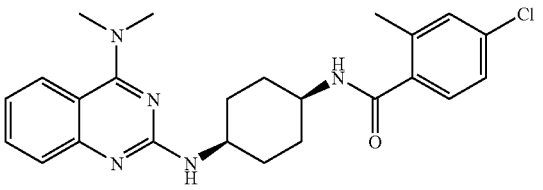 CF$_3$CO$_2$H | 438.4 (M + H) | 4.32 |

-continued
| Example No. | Structure | ESI-MS | Retention Time (min) |
|---|---|---|---|
| 3475 | 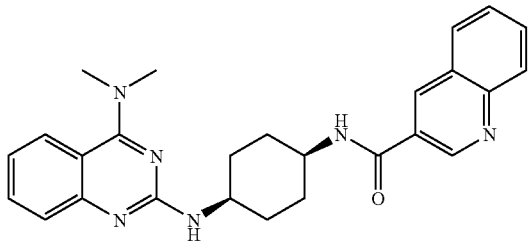<br>2CF₃CO₂H | 441.4 (M + H) | 3.75 |
| 3476 | 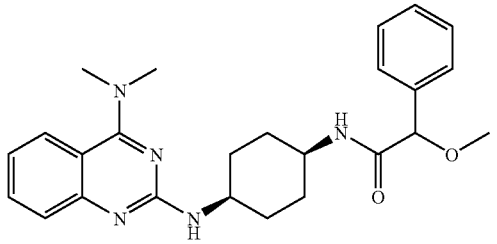<br>CF₃CO₂H | 434.4 (M + H) | 4.10 |
| 3477 | 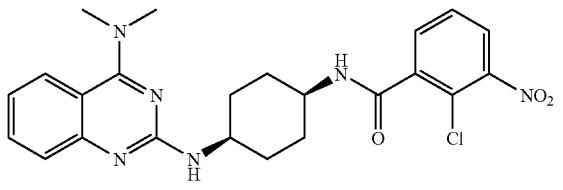<br>CF₃CO₂H | 469.4 (M + H) | 4.19 |
| 3478 | 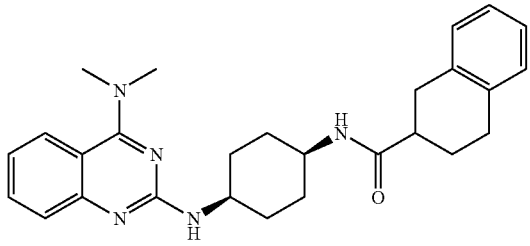<br>CF₃CO₂H | 444.4 (M + H) | 4.36 |
| 3479 | 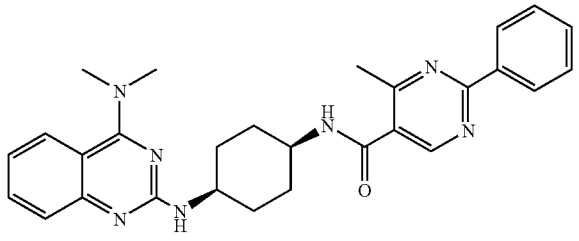<br>3CF₃CO₂H | 482.4 (M + H) | 4.35 |

-continued

| Example No. | Structure | ESI-MS | Retention Time (min) |
|---|---|---|---|
| 3480 | CF₃CO₂H | 482.4 (M + H) | 4.64 |
| 3481 | CF₃CO₂H | 502.2 (M + H) | 4.37 |
| 3482 | CF₃CO₂H | 458.2 (M + H) | 4.08 |
| 3483 | 2CF₃CO₂H | 465.4 (M + H) | 3.66 |
| 3484 | CF₃CO₂H | 404.4 (M + H) | 4.03 |

-continued

| Example No. | Structure | ESI-MS | Retention Time (min) |
|---|---|---|---|
| 3485 | CF₃CO₂H | 469.4 (M + H) | 4.23 |
| 3486 | 2CF₃CO₂H | 447.4 (M + H) | 3.94 |
| 3487 | 2CF₃CO₂H | 456.2 (M + H) | 4.07 |
| 3488 | CF₃CO₂H | 432.4 (M + H) | 3.99 |
| 3489 | 2CF₃CO₂H | 441.3 (M + H) | 1.70 |

-continued

| Example No. | Structure | ESI-MS | Retention Time (min) |
|---|---|---|---|
| 3490 | CF$_3$CO$_2$H | 440.2 (M + H) | 4.57 |
| 3491 | CF$_3$CO$_2$H | 393.4 (M + H) | 4.01 |
| 3492 | 2CF$_3$CO$_2$H | 497.4 (M + H) | 4.45 |
| 3493 | CF$_3$CO$_2$H | 470.2 (M + H) | 2.40 |
| 3494 | 2CF$_3$CO$_2$H | 439.4 (M + H) | 1.92 |

-continued

| Example No. | Structure | ESI-MS | Retention Time (min) |
|---|---|---|---|
| 3495 | 2CF$_3$CO$_2$H | 407.4 (M + H) | 2.30 |
| 3496 | 2CF$_3$CO$_2$H | 469.5 (M + H) | 2.27 |
| 3497 | 2CF$_3$CO$_2$H | 439.4 (M + H) | 1.93 |
| 3498 | 2CF$_3$CO$_2$H | 407.4 (M + H) | 1.62 |
| 3499 | CF$_3$CO$_2$H | 416.3 (M + H) | 2.34 |

-continued
| Example No. | Structure | ESI-MS | Retention Time (min) |
|---|---|---|---|
| 3500 | 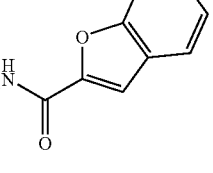 CF₃CO₂H | 460.4 (M + H) | 2.46 |
| 3501 | 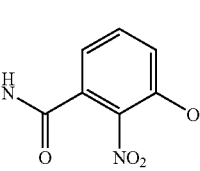 CF₃CO₂H | 465.4 (M + H) | 4.13 |
| 3502 | 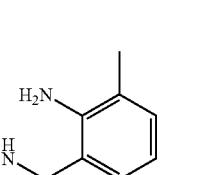 2CF₃CO₂H | 419.4 (M + H) | 3.87 |
| 3503 | 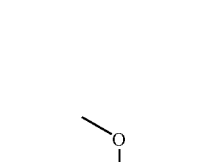 CF₃CO₂H | 450.4 (M + H) | 3.97 |
| 3504 | 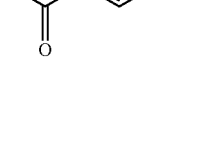 CF₃CO₂H | 406.2 (M + H) | 2.18 |

-continued

| Example No. | Structure | ESI-MS | Retention Time (min) |
|---|---|---|---|
| 3505 | CF$_3$CO$_2$H | 470.4 (M + H) | 4.74 |
| 3506 | CF$_3$CO$_2$H | 466.4 (M + H) | 3.83 |
| 3507 | 2CF$_3$CO$_2$H | 441.2 (M + H) | 4.38 |
| 3508 | 2CF$_3$CO$_2$H | 441.2 (M + H) | 3.62 |
| 3509 | CF$_3$CO$_2$H | 454.5 (M + H) | 2.44 |

-continued

| Example No. | Structure | ESI-MS | Retention Time (min) |
|---|---|---|---|
| 3510 | CF₃CO₂H | 384.4 (M + H) | 3.67 |
| 3511 | CF₃CO₂H | 502.2 (M + H) | 4.37 |
| 3512 | CF₃CO₂H | 480.5 (M + H) | 2.18 |
| 3513 | CF₃CO₂H | 380.2 (M + H) | 3.81 |
| 3514 | 2CF₃CO₂H | 463.2 (M + H) | 4.23 |

-continued
| Example No. | Structure | ESI-MS | Retention Time (min) |
|---|---|---|---|
| 3515 | 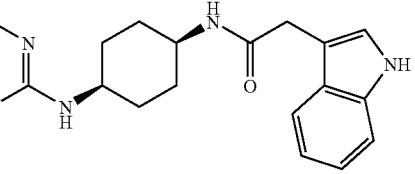<br>2CF$_3$CO$_2$H | 443.4 (M + H) | 2.12 |
| 3516 | 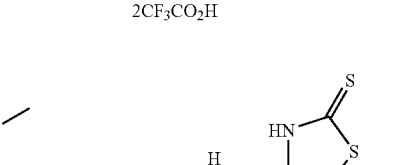<br>CF$_3$CO$_2$H | 431.1 (M + H) | 1.90 |
| 3517 | 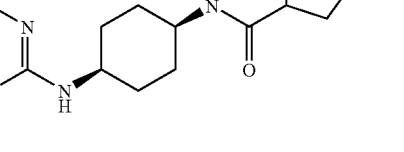<br>CF$_3$CO$_2$H | 474.4 (M + H) | 5.05 |
| 3518 | 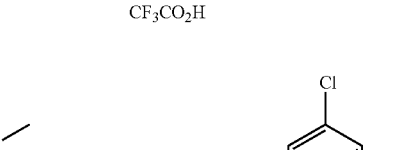<br>CF$_3$CO$_2$H | 440.5 (M + H) | 2.33 |
| 3519 | 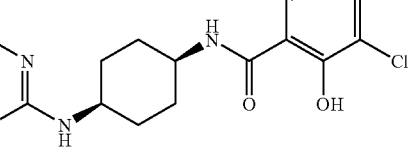<br>CF$_3$CO$_2$H | 440.5 (M + H) | 2.33 |

-continued

| Example No. | Structure | ESI-MS | Retention Time (min) |
|---|---|---|---|
| 3520 | 2CF₃CO₂H | 391.1 (M + H) | 1.59 |
| 3521 | CF₃CO₂H | 474.4 (M + H) | 4.53 |
| 3522 | CF₃CO₂H | 429.3 (M + H) | 2.41 |
| 3523 | 2CF₃CO₂H | 429.3 (M + H) | 2.41 |
| 3524 | CF₃CO₂H | 494.6 (M + H) | 2.59 |
| 3525 | CF₃CO₂H | 518.5 (M + H) | 2.96 |

-continued

| Example No. | Structure | ESI-MS | Retention Time (min) |
|---|---|---|---|
| 3526 | (dimethylamino-quinazoline, NH-cyclohexyl-NH-C(=O)-CH(OH)-phenyl) · CF₃CO₂H | 420.4 (M + H) | 2.19 |
| 3527 | (dimethylamino-quinazoline, NH-cyclohexyl-NH-C(=O)-CH(OH)-phenyl) · CF₃CO₂H | 420.4 (M + H) | 2.19 |
| 3528 | (isopropylamino-quinazoline, NH-cyclohexyl-NH-CH₂-(4-bromo-2-trifluoromethoxyphenyl)) · 2CF₃CO₂H | 552.0 (M + H) | 2.45 |
| 3529 | (cyclopropylmethylamino-quinazoline, NH-cyclohexyl-NH-CH₂-(4-bromo-2-trifluoromethoxyphenyl)) · 2CF₃CO₂H | 564.2 (M + H) | 2.48 |
| 3530 | (cyclohexylmethylamino-quinazoline, NH-cyclohexyl-NH-CH₂-(4-bromo-2-trifluoromethoxyphenyl)) · 2CF₃CO₂H | 606.0 (M + H) | 2.86 |

-continued
| Example No. | Structure | ESI-MS | Retention Time (min) |
|---|---|---|---|
| 3531 | 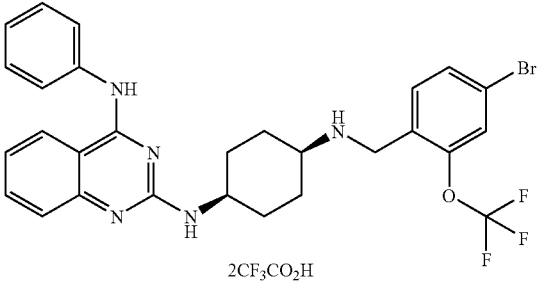<br>2CF₃CO₂H | 586.2 (M + H) | 3.20 |
| 3532 | 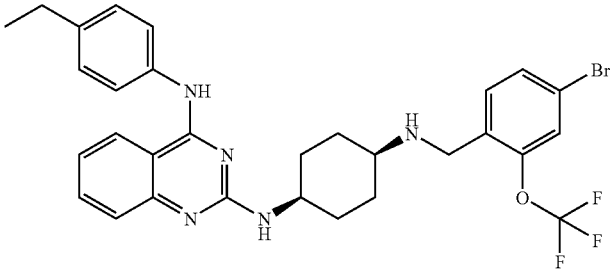<br>2CF₃CO₂H | 614.4 (M + H) | 2.76 |
| 3533 | 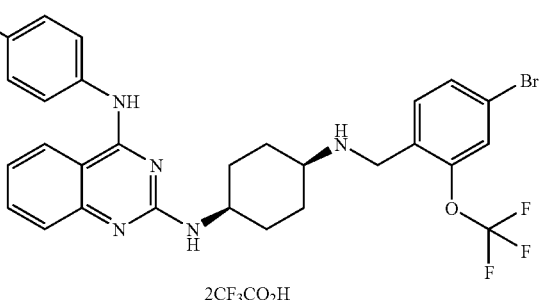<br>2CF₃CO₂H | 620.0 (M + H) | 2.68 |
| 3534 | 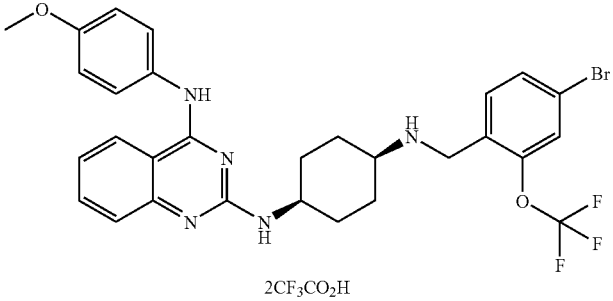<br>2CF₃CO₂H | 616.0 (M + H) | 2.56 |
| 3535 | 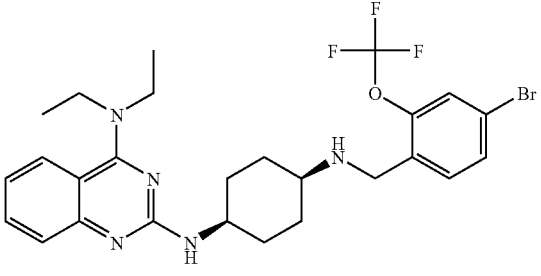<br>2CF₃CO₂H | 566.0 (M + H) | 2.54 |

-continued
| Example No. | Structure | ESI-MS | Retention Time (min) |
|---|---|---|---|
| 3536 | 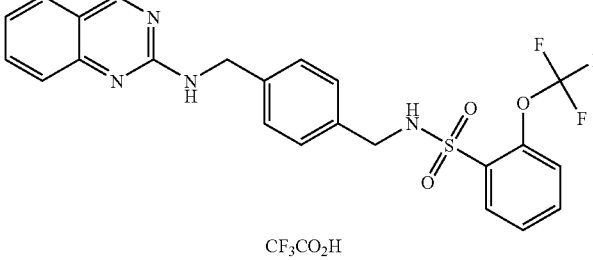 CF$_3$CO$_2$H | 532.2 (M + H) | 3.35 |
| 3537 | 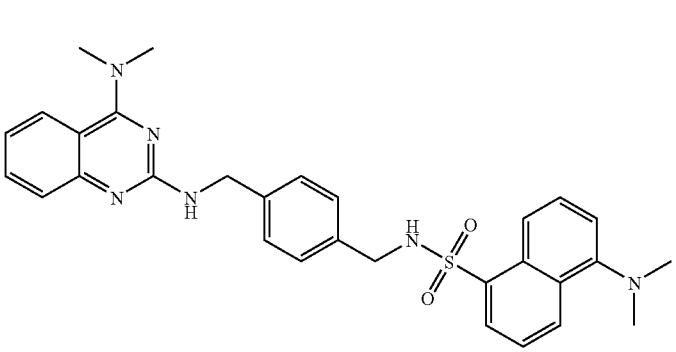 2CF$_3$CO$_2$H | 514.4 (M + H) | 3.11 |
| 3538 | 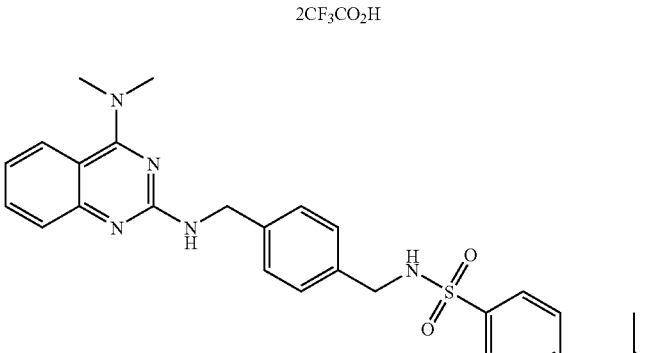 CF$_3$CO$_2$H | 505.2 (M + H) | 2.98 |
| 3539 | 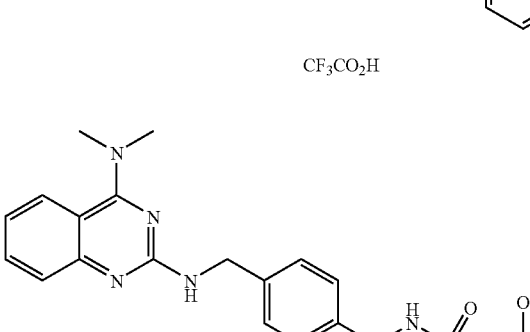 CF$_3$CO$_2$H | 556 (M + H) | 3.37 |

-continued

| Example No. | Structure | ESI-MS | Retention Time (min) |
|---|---|---|---|
| 3540 | 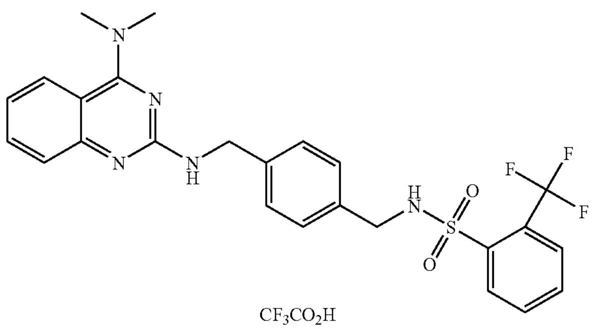 | 516.4 (M + H) | 3.39 |
| 3541 | 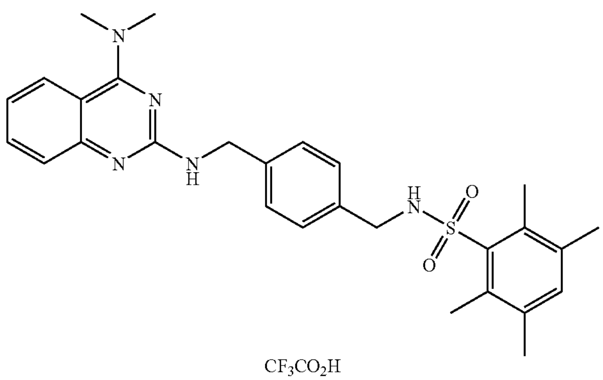 | 504.4 (M + H) | 3.61 |
| 3542 | 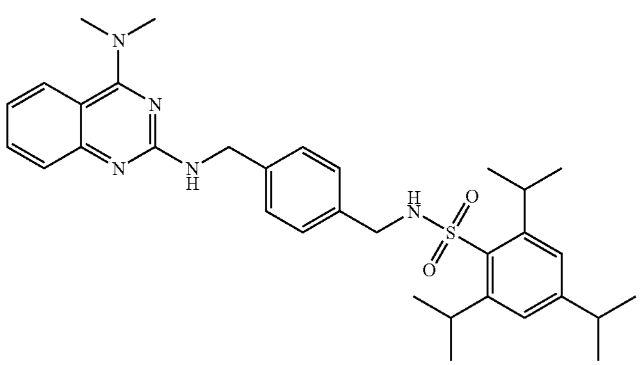 | 574.4 (M + H) | 4.27 |
| 3543 | 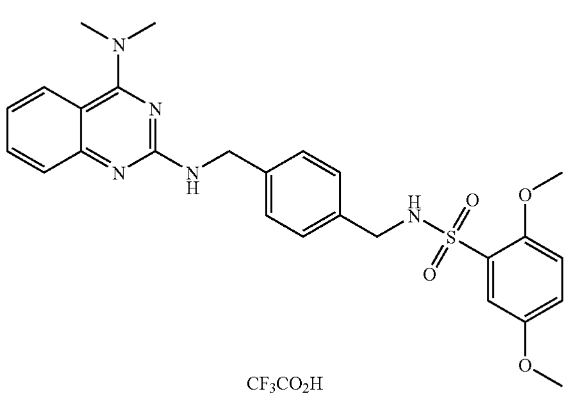 | 508.2 (M + H) | 3.17 |

-continued

| Example No. | Structure | ESI-MS | Retention Time (min) |
|---|---|---|---|
| 3544 | CF₃CO₂H | 644.2 (M + H) | 3.63 |
| 3545 | CF₃CO₂H | 520.4 (M + H) | 3.56 |
| 3546 | CF₃CO₂H | 504.2 (M + H) | 3.25 |
| 3547 | 2CF₃CO₂H | 513.4 (M + H) | 2.86 |

-continued

| Example No. | Structure | ESI-MS | Retention Time (min) |
|---|---|---|---|
| 3548 | CF₃CO₂H | 616.2 (M + H) | 3.73 |
| 3549 | 2CF₃CO₂H | 450.4 (M + H) | 2.79 |
| 3550 | CF₃CO₂H | 466.2 (M + H) | 3.35 |
| 3551 | 2CF₃CO₂H | 465.2 (M + H) | 3.34 |
| 3552 | CF₃CO₂H | 451.4 (M + H) | 3.83 |

-continued

| Example No. | Structure | ESI-MS | Retention Time (min) |
|---|---|---|---|
| 3553 | CF₃CO₂H | 451.2 (M + H) | 4.10 |
| 3554 | CF₃CO₂H | 563.2 (M + H) | 4.33 |
| 3555 | 2CF₃CO₂H | 468.4 (M + H) | 3.66 |
| 3556 | 2CF₃CO₂H | 467.4 (M + H) | 2.85 |
| 3557 | CF₃CO₂H | 515.4 (M + H) | 3.52 |

-continued
| Example No. | Structure | ESI-MS | Retention Time (min) |
|---|---|---|---|
| 3558 | 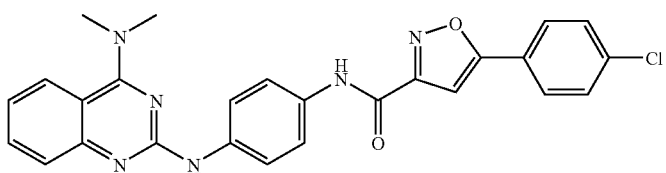 CF₃CO₂H | 485.2 (M + H) | 3.40 |
| 3559 | 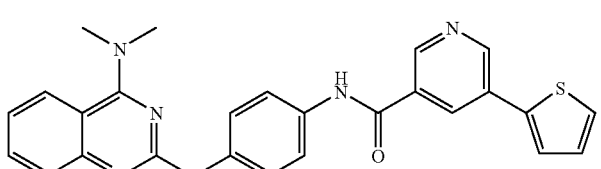 2CF₃CO₂H | 467.4 (M + H) | 3.90 |
| 3560 | 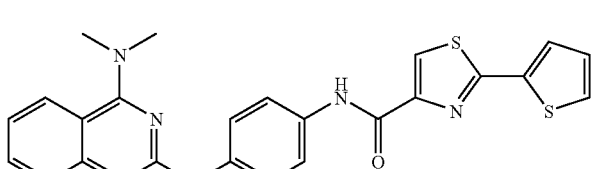 CF₃CO₂H | 473.4 (M + H) | 4.17 |
| 3561 | 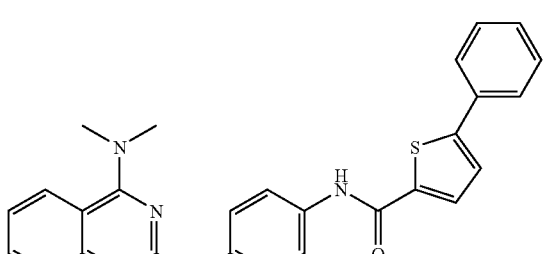 CF₃CO₂H | 467.4 (M + H) | 3.57 |
| 3562 | 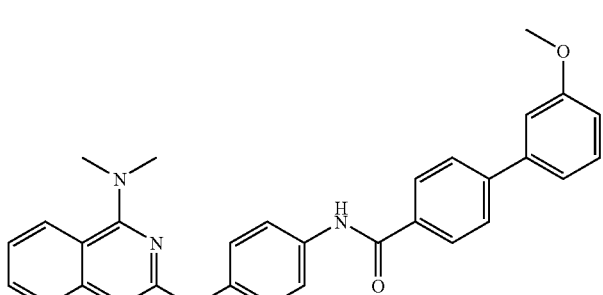 CF₃CO₂H | 490.2 (M + H) | 4.00 |

-continued
| Example No. | Structure | ESI-MS | Retention Time (min) |
|---|---|---|---|
| 3563 | 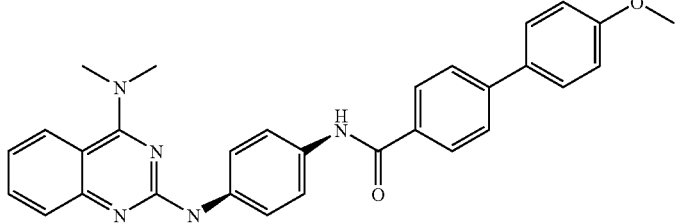 CF₃CO₂H | 490.2 (M + H) | 3.99 |
| 3564 | 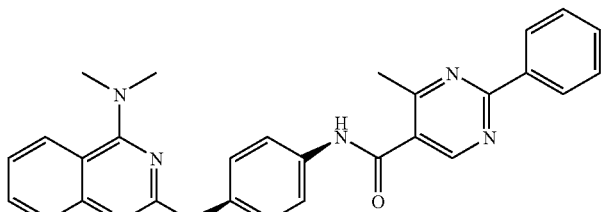 2CF₃CO₂H | 476.2 (M + H) | 3.76 |
| 3565 | 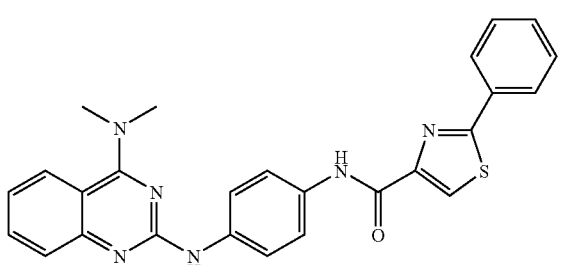 CF₃CO₂H | 467.2 (M + H) | 4.07 |
| 3566 | 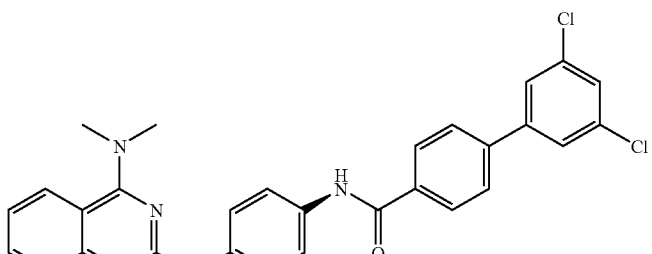 CF₃CO₂H | 528.2 (M + H) | 4.53 |
| 3567 | 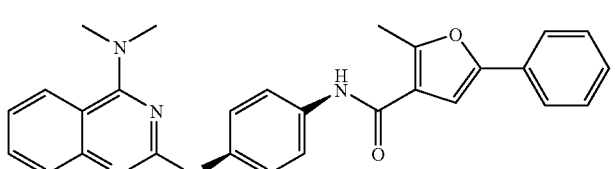 CF₃CO₂H | 464.2 (M + H) | 4.11 |

-continued

| Example No. | Structure | ESI-MS | Retention Time (min) |
|---|---|---|---|
| 3568 | (structure) CF₃CO₂H | 494.0 (M + H) | 3.43 |
| 3564 | (structure) CF₃CO₂H | 444.0 (M + H) | 3.03 |
| 3570 | (structure) CF₃CO₂H | 552.0 (M + H) | 3.30 |
| 3571 | (structure) CF₃CO₂H | 510.0 (M + H) | 3.37 |

-continued

| Example No. | Structure | ESI-MS | Retention Time (min) |
|---|---|---|---|
| 3572 | (structure) CF₃CO₂H | 562.0 (M + H) | 3.66 |
| 3573 | (structure) CF₃CO₂H | 622.0 (M + H) | 3.61 |
| 3574 | (structure) CF₃CO₂H | 588.0 (M + H) | 3.59 |
| 3575 | (structure) CF₃CO₂H | 510.0 (M + H) | 3.31 |

-continued

| Example No. | Structure | ESI-MS | Retention Time (min) |
|---|---|---|---|
| 3576 | CF₃CO₂H | 562.0 (M + H) | 3.61 |
| 3577 | CF₃CO₂H | 510.0 (M + H) | 3.35 |
| 3578 | CF₃CO₂H | 597.0 (M + H) | 3.55 |

-continued

| Example No. | Structure | ESI-MS | Retention Time (min) |
|---|---|---|---|
| 3579 | 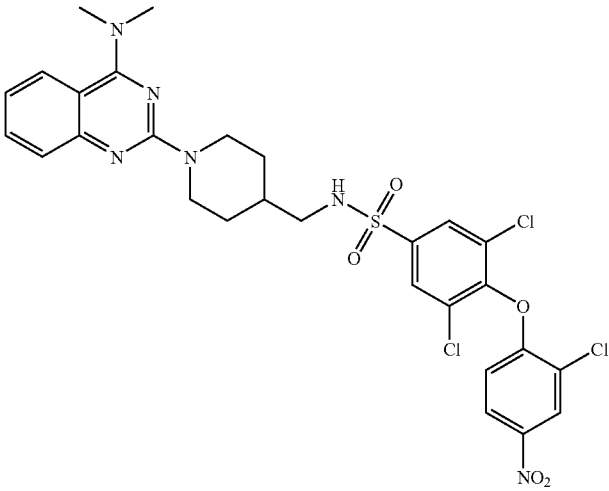 CF$_3$CO$_2$H | 665.0 (M + H) | 4.02 |

Assay Procedures

Compounds identified and disclosed throughout this patent document were assayed according to the protocols found in co-pending patent application having U.S. Ser. No. 09/826,509, which is incorporated herein by reference.

Example 3580

Preparation of Endogenous MCH Receptor

The endogenous human MCH receptor was obtained by PCR using genomic DNA as template and rTth polymerase (Perkin Elmer) with the buffer system provided by the manufacturer, 0.25 μM of each primer, and 0.2 mM of each 4 nucleotides. The cycle condition was 30 cycles of 94° C. for 1 min, 56° C. for 1 min and 72° C. for 1 min and 20 sec.

The 5' PCR primer contained a HindIII site with the sequence:

5'-GTGAAGCTTGCCTCTGGTGCCTGCAGGAGG-3' (SEQ.ID.NO.:1)

and the 3' primer contained an EcoRI site with the sequence:

(SEQ. ID. NO.:2)
5'-GCAGAATTCCCGGTGGCGTGTTGTGGTGCCC-3'.

The 1.3 kb PCR fragment was digested with HindIII and EcoRI and cloned into HindIII-EcoRI site of CMVp expression vector. Later the cloning work by Lakaye et al showed that there is an intron the coding rgion of the gene. Thus the 5' end of the cDNA was obtained by 5' RACE PCR using Clontech's marathon-ready hypothalamus cDNA as template and the manufacturer's recommended protocol for cycling condition. The 5' RACE PCR for the first and second round PCR were as follows:

(SEQ. ID. NO.:3)
5'-CATGAGCTGGTGGATCATGAAGGG-3'
and (SEQ. ID. NO.:4)
5'-ATGAAGGGCATGCCCAGGAGAAAG-3'.

Nucleic acid and amino acid sequences were thereafter determined and verified with the published sequences found on GenBank having Accession Number U71092.

Example 3581

Preparation of Non-Endogenous, Constitutively Active MCH Receptor

Preparation of a non-endogenous version of the human MCH receptor was accomplished by creating a MCH-IC3-SST2 mutation (see; SEQ.ID.NO.:5 for nucleic acid sequence, and SEQ.ID.NO.:6 for amino acid sequence). Blast result showed that MCH receptor had the highest sequence homology to known SST2 receptor. Thus the third intracellular loop ("IC3") of MCH receptor was replaced with that of the IC3 of SST2 receptor to see if the chimera would show constitutive activity.

The BamHI-BstEII fragment containing IC3 of MCH receptor was replaced with synthetic oligonucleotides that contained the IC3 of SST2. The PCR sense mutagenesis primer used had the following sequence:

(SEQ. ID. NO.:7)
5'-GATCCTGCAGAAGGTGAAGTCCTCTGGAATCCGAGTGGGCTCCTCTA
AGAGGAAGAAGTCTGAGAAGAAG-3' and the antisense primer had the following sequence:

```
                                           (SEQ. ID. NO.:8)
5'-GTGACCTTCTTCTCAGACTTCTTCCTCTTAGAGGAGCCCACTCGGAT

TCCAGAGGACTTCACCTTCTGCAG-3'.
```

The endogenous MCH receptor cDNA was used as a template.

Example 3582

GPCR Fusion Protein Preparation

MCH Receptor-Giα Fusion Protein construct was made as follows: primers were designed for endogenous MCH receptor was as follows:

```
                            (SEQ. ID. NO.:9; sense)
     5'-GTGAAGCTTGCCCGGGCAGGATGGACCTGG-3'

(SEQ. ID. NO.:10; anitsense)
     5'-ATCTAGAGGTGCCTTTGCTTTCTG-3'.
```

The sense and anti-sense primers included the restriction sites for KB4 and XbaI, respectively.

PCR was utilized to secure the respective receptor sequences for fusion within the Giα universal vector disclosed above, using the following protocol for each: 100 ng cDNA for MCH receptor was added to separate tubes containing 2 ul of each primer (sense and anti-sense), 3 uL of 10 mM dNTPs, 10 uL of 10XTaqPlus™ Precision buffer, 1 uL of TaqPlus™ Precision polymerase (Stratagene: #600211), and 80 uL of water. Reaction temperatures and cycle times for MCH receptor were as follows: the initial denaturing step was done it 94° C. for five minutes, and a cycle of 94° C. for 30 seconds; 55° C. for 30 seconds; 72° C. for two minutes. A final extension time was done at 72° C. for ten minutes. PCR product for was run on a 1% agarose gel and then purified (data not shown). The purified product was digested with KB4 and XbaI (New England Biolabs) and the desired inserts will be isolated, purified and ligated into the Gi universal vector at the respective restriction site. The positive clones was isolated following transformation and determined by restriction enzyme digest; expression using 293 cells was accomplished following the protocol set forth infra. Each positive clone for MCH receptor: Gi-Fusion Protein was sequenced and made available for the direct identification of candidate compounds. (See, SEQ.ID.NO.:11 for nucleic acid sequence and SEQ.ID.NO.:12 for amino acid sequence).

Endogenous version of MCH receptor was fused upstream from the G protein Gi and is located at nucleotide 1 through 1,059 (see, SEQ.ID.NO.:11) and amino acid residue 1 through 353 (see, SEQ.ID.NO.:12). With respect to the MCH receptor, 2 amino acid residues (an equivalent of 6 nucleotides) were placed in between the endogenous (or non-endogenous) GPCR and the start codon for the G protein Giα. Therefore, the Gi protein is located at nucleotide 1,066 through 2,133 (see, SEQ.ID.NO.:11) and at amino acid residue 356 through 709 (see, SEQ.ID.NO.:12). Those skilled in the art are credited with the ability to select techniques for constructing a GPCR Fusion Protein where the G protein is fused to the 3' end of the GPCR of interest.

Example 3583

Assay for Determination of Constitutive Activity of Non-Endogenous GPCRs

A. Intracellular $IP_3$ Accumulation Assay

On day 1, cells comprising the receptors (endogenous and/or non-endogenous) can be plated onto 24 well plates, usually $1 \times 10^5$ cells/well (although his umber can be optimized. On day 2 cells can be transfected by firstly mixing 0.25 ug DNA in 50 ul serum free DMEM/well and 2 ul lipofectamine in 50 µl serum-free DMEM/well. The solutions are gently mixed and incubated for 15-30 min at room temperature. Cells are washed with 0.5 ml PBS and 400 µl of serum free media is mixed with the transfection media and added to the cells. The cells are then incubated for 3-4 hrs at 37° C./5% $CO_2$ and then the transfection media is removed and replaced with 1 ml/well of regular growth media. On day 3 the cells are labeled with $^3$H-myo-inositol. Briefly, the media is removed and the cells are washed with 0.5 ml PBS. Then 0.5 ml inositol-free/serum free media (GIBCO BRL) is added/well with 0.25 µCi of $^3$H-myo-inositol/well and the cells are incubated for 16-18 hrs o/n at 37° C./5% $CO_2$. On Day 4 the cells are washed with 0.5 ml PBS and 0.45 ml of assay medium is added containing inositol-free/serum free media 10 µM pargyline 10 mM lithium chloride or 0.4 ml of assay medium and 50 ul of 10× ketanserin (ket) to final concentration of 10 µM. The cells are then incubated for 30 min at 37° C. The cells are then washed with 0.5 ml PBS and 200 µl of fresh/ice cold stop solution (1M KOH; 18 mM Na-borate; 3.8 mM EDTA) is added/well. The solution is kept on ice for 5-10 min or until cells were lysed and then neutralized by 200 µl of fresh/ice cold neutralization sol. (7.5% HCL). The lysate is then transferred into 1.5 ml eppendorf tubes and 1 ml of chloroform/methanol (1:2) is added/tube. The solution is vortexed for 15 sec and the upper phase is applied to a Biorad AG1-X8™ anion exchange resin (100-200 mesh). Firstly, the resin is washed with water at 1:1.25 W/V and 0.9 ml of upper phase is loaded onto the column. The column is washed with 10 mls of 5 mM myo-inositol and 10 ml of 5 mM Na-borate/60 mM Na-formate. The inositol tris phosphates are eluted into scintillation vials containing 10 ml of scintillation cocktail with 2 ml of 0.1 M formic acid/1 M ammonium formate. The columns are regenerated by washing with 10 ml of 0.1 M formic acid/3M ammonium formate and rinsed twice with $H_2O$ and stored at 4° C. in water.

Reference is made to FIG. 1. FIG. 1 provides an illustration of $IP_3$ production from several non-endogenous, constitutively activated version of MCH receptor as compared with the endogenous version of this receptor. When compared to the endogenous version of MCH receptor ("MCH-R wt"), MCH-IC3-SST2 evidenced about a 27% increase in $IP_3$ accumulation.

Example 3584

Determination of Compound Using [$^{35}$S]GTPγS Assay

Direct identification of candidate compounds was initially screened using [$^{35}$S]GTPγS Assay (see, Example 6 of co-pending patent application Ser. No. 09/826,509). Preferably, an MCH receptor: Gi Fusion Protein was utilized, according to Example 6(2) of co-pending patent application Ser. No. 09/826,509. Several lead hits were identified utilizing [$^{35}$S] GTPγS Assay.

Example 3585

High Throughput Functional Screening: FLIPR™

Subsequently, a functional based assay was used to confirm the lead hits, referred to as FLIPR™ (the Fluorometric Imaging Plate Reader) and FDSS6000™ (Functional Drug Screening System). This assay utilized a non-endogenous version of the MCH receptor, which was created by swapping the third intracellular loop of the MCH receptor with that of the SST2 receptor (see Example 2(B)(2) of patent application Ser. No. 09/826,509).

The FLIPR and FDSS assays are able to detect intracellular $Ca^{2+}$ concentration in cells, which can be utilized to assess receptor activation and determine whether a candidate compound is an, for example, antagonist, inverse agonist or agonist to a Gq-coupled receptor. The concentration of free $Ca^{2+}$ in the cytosol of any cell is extremely low, whereas its concentration in the extracellular fluid and endoplasmic reticulum (ER) is very high. Thus, there is a large gradient tending to drive $Ca^{2+}$ into the cytosol across both the plasma membrane and ER. The FLIPR™ and FDSS6000™ systems (Molecular Devices Corporation, HAMAMATSU Photonics K.K.) are designed to perform functional cell-based assays, such as the measurement of intracellular calcium for high-throughput screening. The measurement of fluorescent is associated with calcium release upon activation of the Gq-coupled receptors. Gi or Go coupled receptors are not as easily monitored through the FLIPR™ and FDSS6000™ systems because these G proteins do not couple with calcium signal pathways.

To confirm the lead hits identified using the [$^{35}$S]GTPγS assay, Fluorometric Imaging Plate Reader system was used to allow for rapid, kinetic measurements of intracellular fluorescence in 96 well microplates (or 384 well microplates). Simultaneous measurements of fluorescence in all wells can be made by FLIPR or FDSS6000™, every second with high sensitivity and precision. These systems are ideal for measuring cell-based functional assays such as monitoring the intracellular calcium fluxes that occur within seconds after activation of the Gq coupled receptor.

Briefly, the cells are seeded into 96 well at $5.5 \times 10^4$ cells/well with complete culture media (Dulbecco's Modified Eagle Medium with 10% fetal bovine serum, 2 mM L-glutamine, 1 mM sodium pyruvate and 0.5 mg/ml G418, pH 7.4) for the assay next day. On the day of assay, the media is removed and the cells are incubated with 100 μl of loading buffer (4 μM Fluo4-AM in complete culture media containing 2.5 mM Probenicid, 0.5 mg/ml and 0.2% bovine serum albumin) in 5% $CO_2$ incubator at 37° C. for 1 hr. The loading buffer is removed, and the cells are washed with wash buffer (Hank's Balanced Salt Solution containing 2.5 mM Probenicid, 20 mM HEPES, 0.5 mg/ml and 0.2% bovine serum albumin, pH 7.4)). One hundred fifty μl of wash buffer containing various concentrations of test compound are added to the cells, and the cells are incubated in 5% $CO_2$ incubator at 37° C. for 30 min. Fifty μl of wash buffer containing various concentration of MCH are added to each well, and transient changes in [$Ca^{2+}$]i evoked by MCH are monitored using the FLIPR or FDSS in 96 well plates at Ex. 488 nm and Em. 530 nm for 290 second. When antagonist activity of compound is tested, 50 nM of MCH is used.

Use of FLIPR™ and FDSS6000™ can be accomplished by following manufacturer's instruction (Molecular Device Corporation and HAMAMATSU Photonics K.K.).

The results were shpwn below.

| Compound No. | IC$_{50}$ value (nM) |
|---|---|
| Example 41 | 6 |
| Example 42 | 19 |

It is intended that each of the patents, applications, printed publications, and other published documents mentioned or referred to in this specification be herein incorporated by reference in their entirety.

Those skilled in the art will appreciate that numerous changes and modifications may be made to the preferred embodiments of the invention and that such changes and modifications may be made without departing from the spirit of the invention. It is therefore intended that the appended claims cover all such equivalent variations as fall within the true spirit and scope of the invention.

What is claimed is:

1. A compound selected from the group consisting of

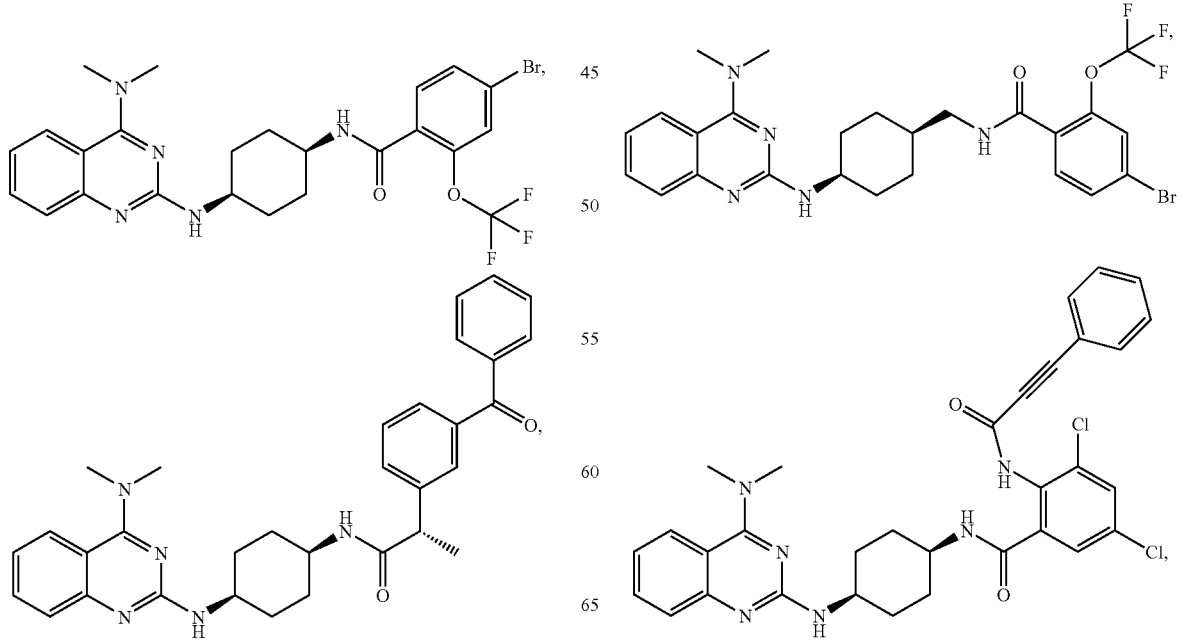

-continued
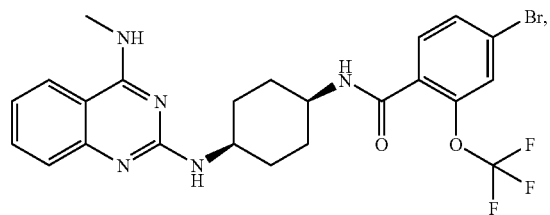
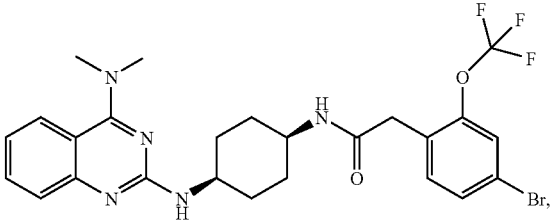
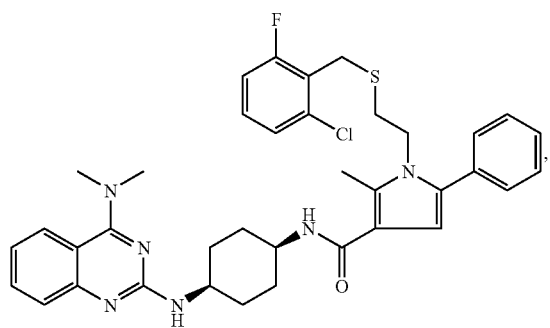
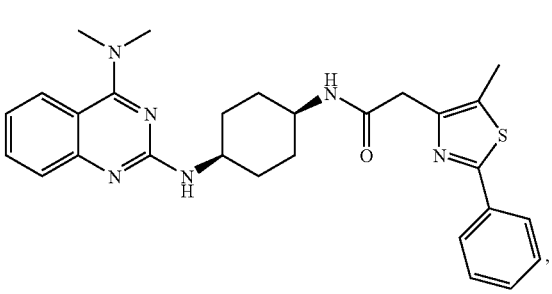
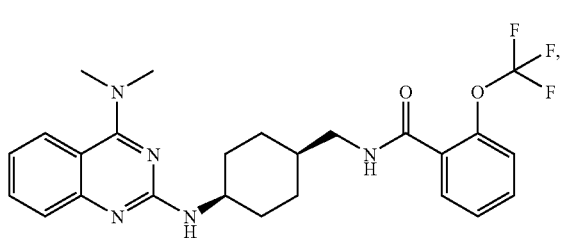
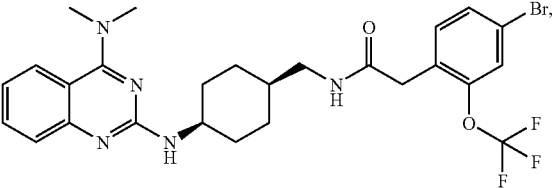
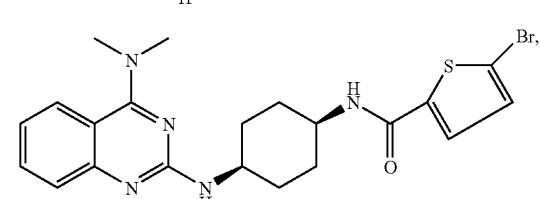
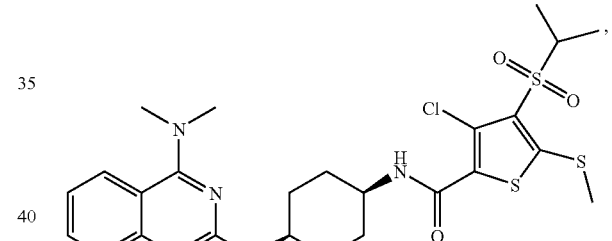
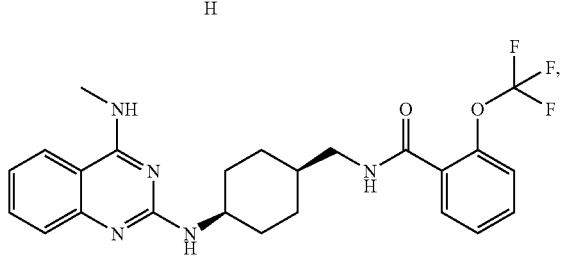
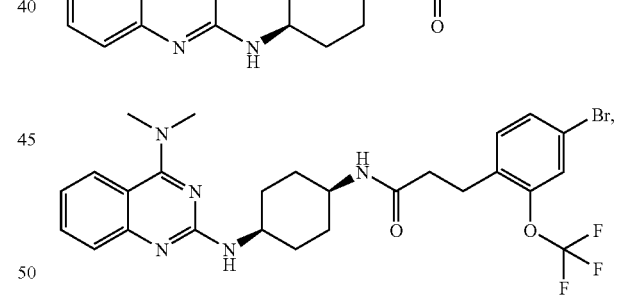
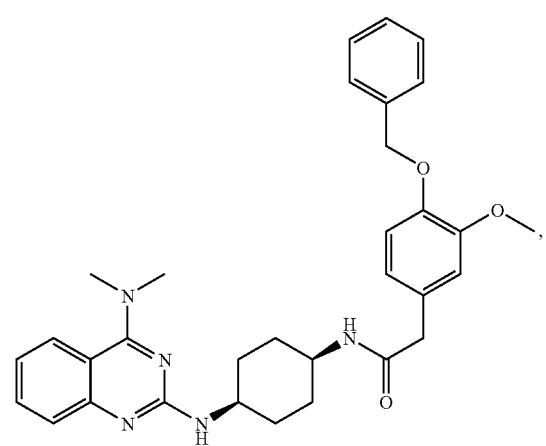
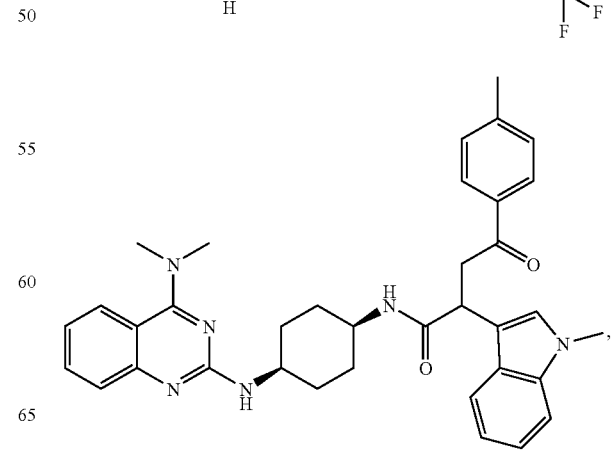

-continued
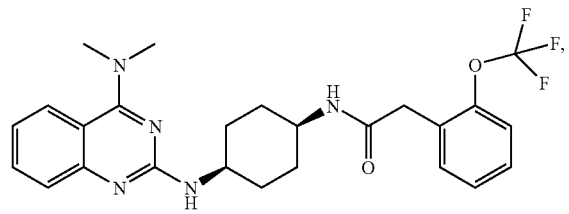
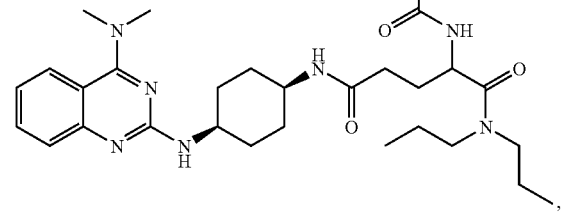
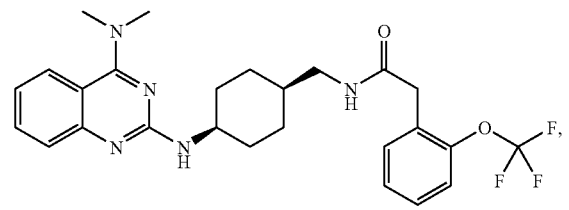
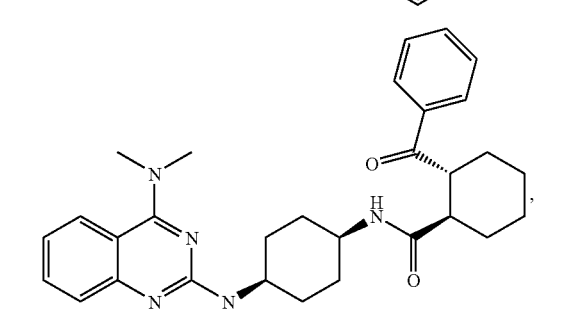
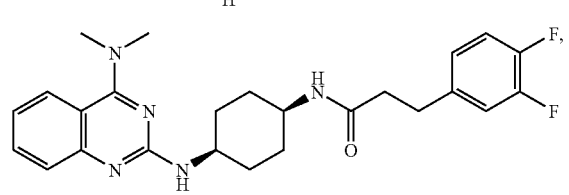
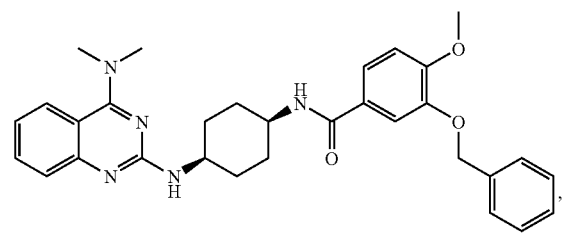
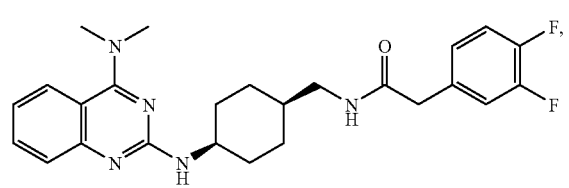
-continued
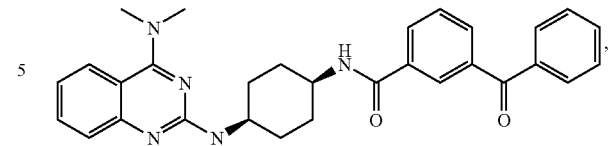
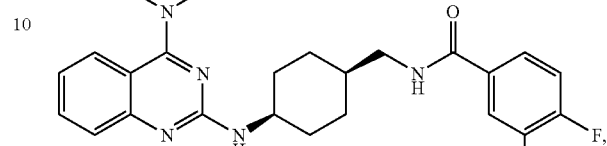
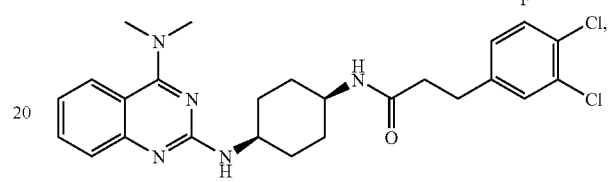
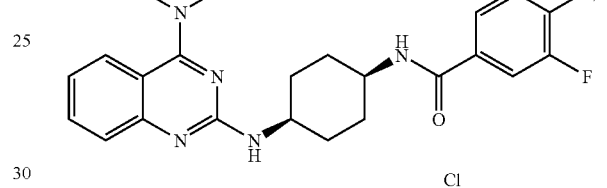
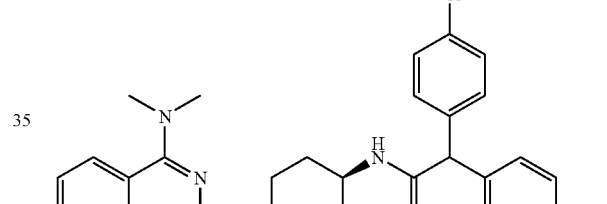
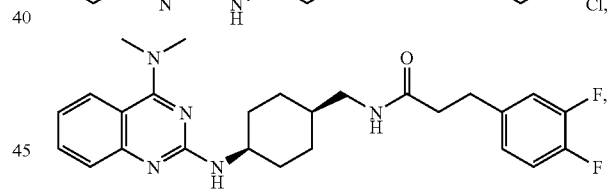
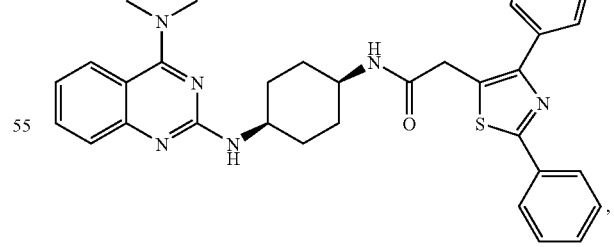
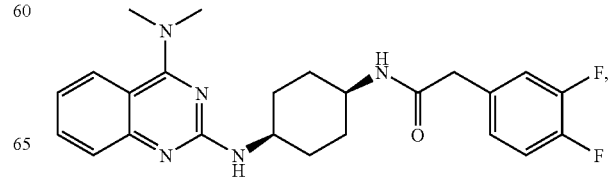

-continued
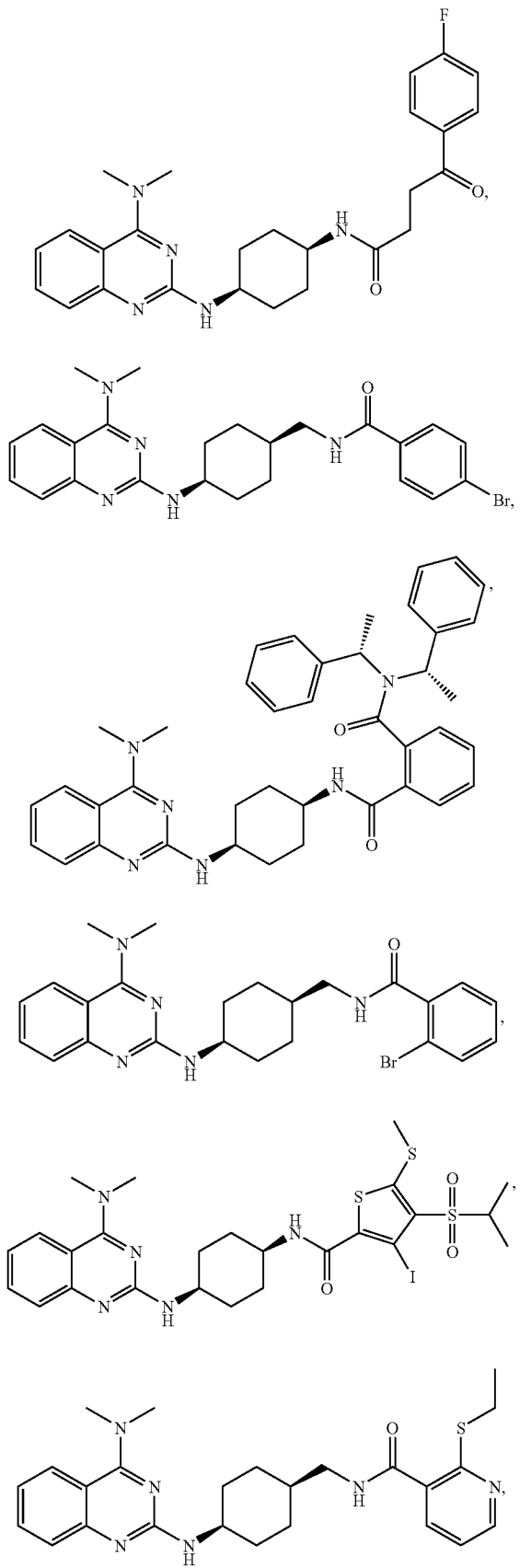
-continued
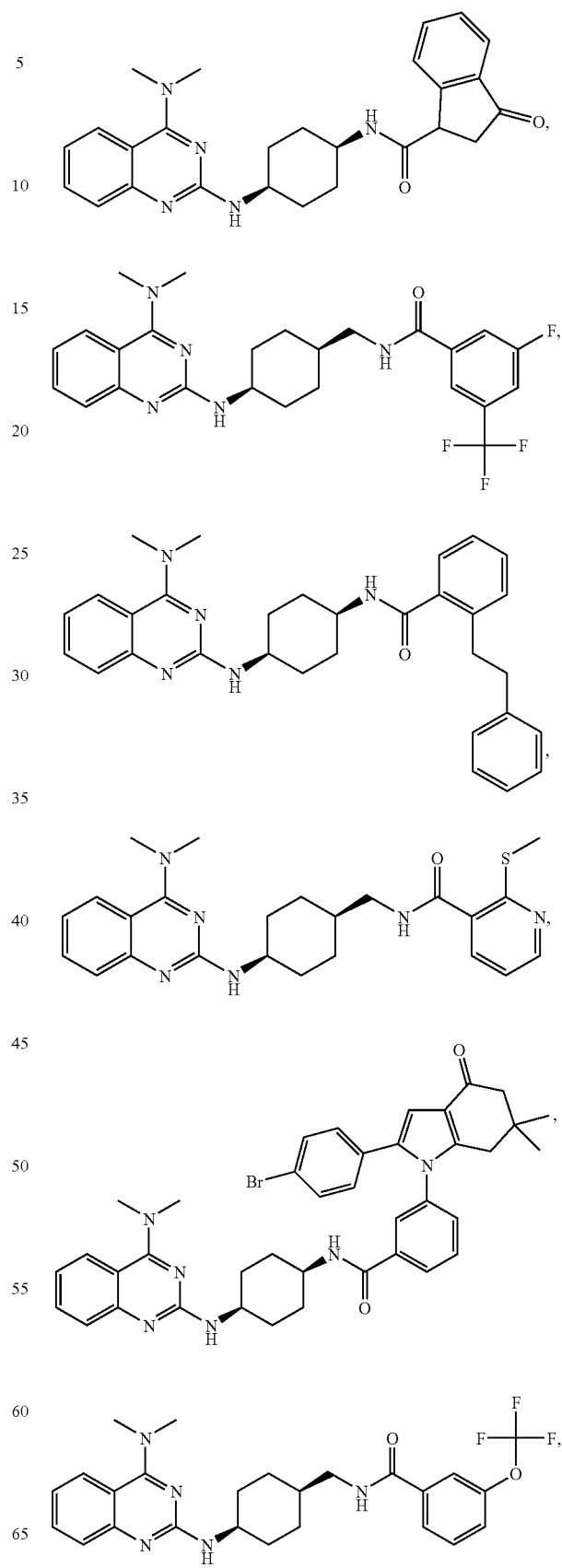

-continued
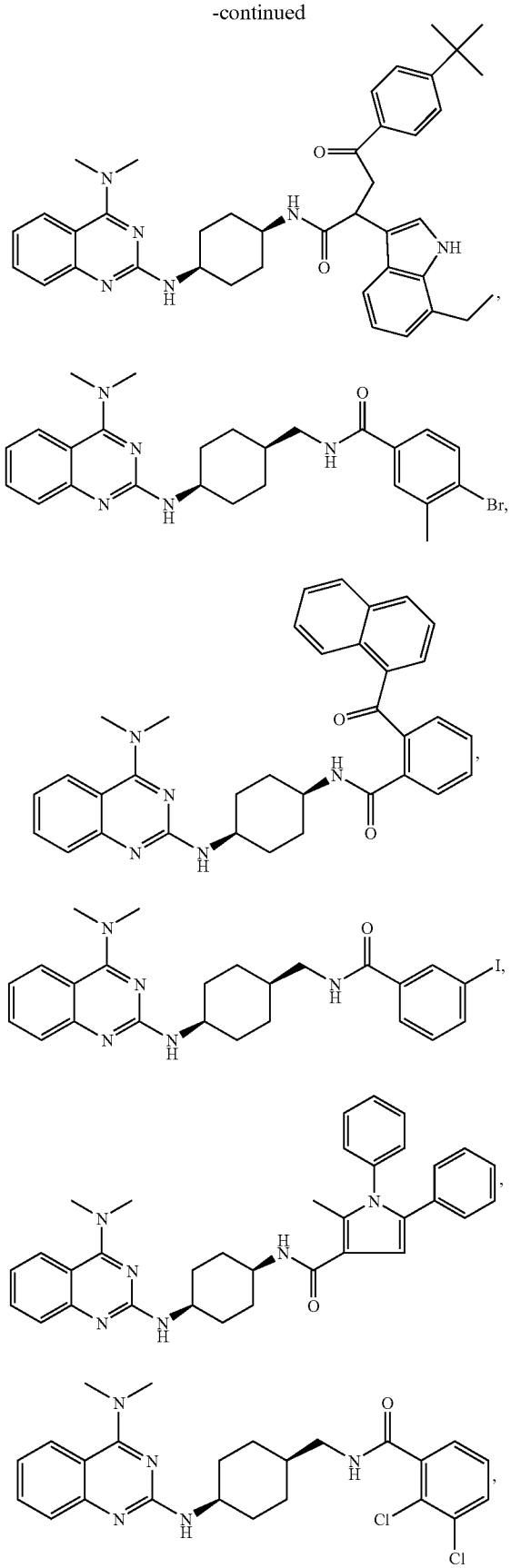
-continued
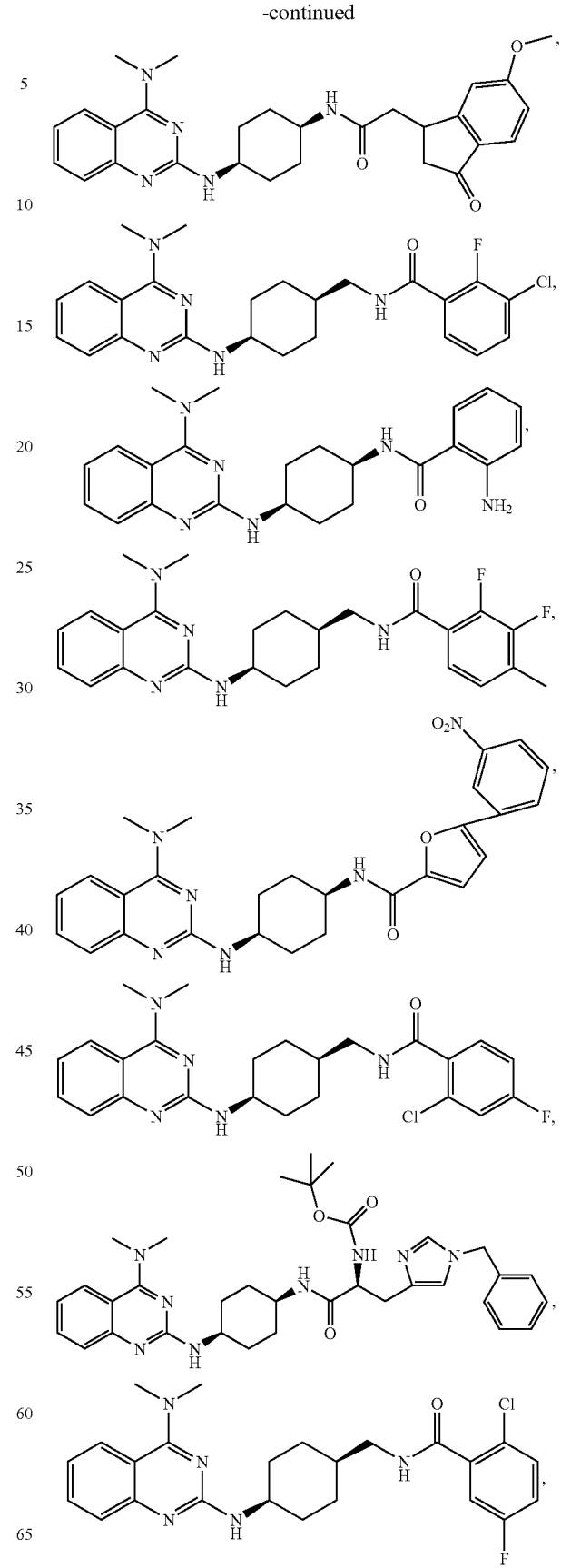

-continued
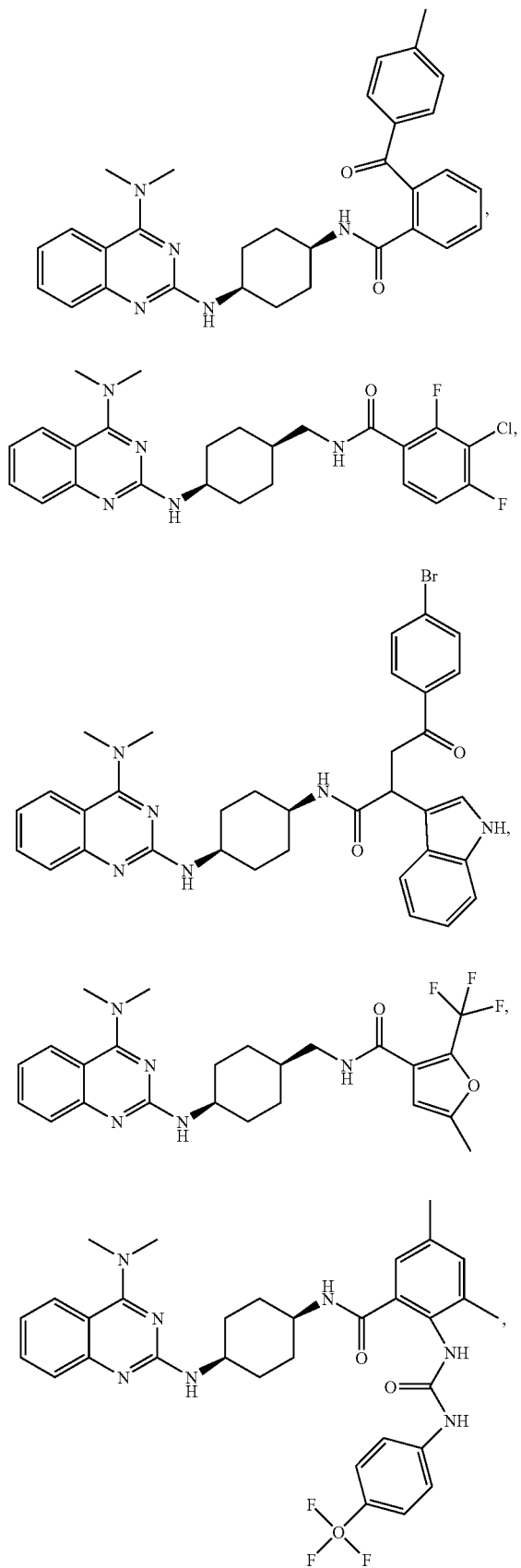
-continued
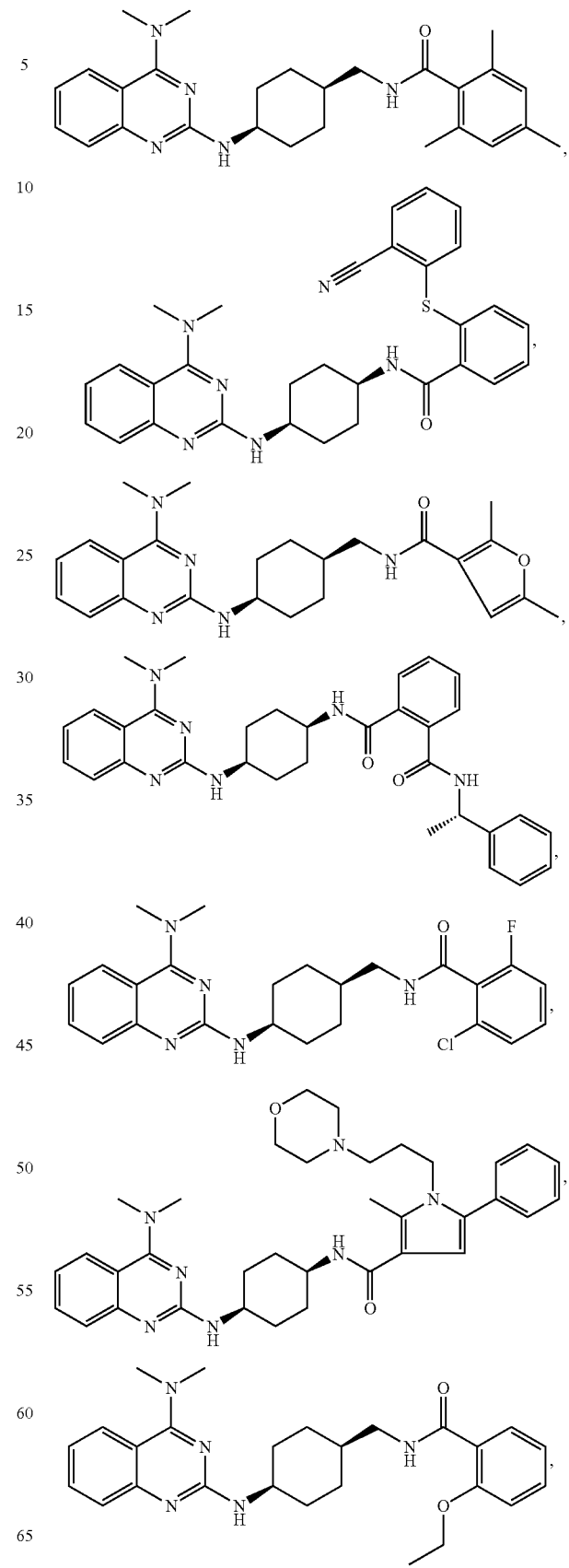

1835
-continued
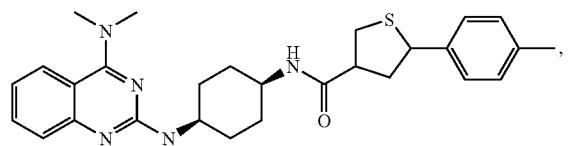
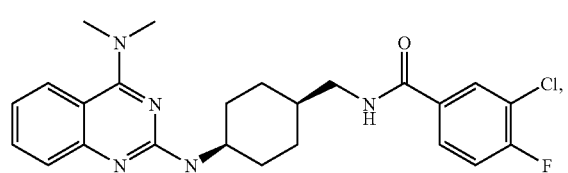
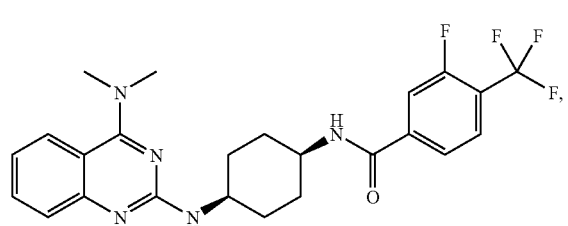
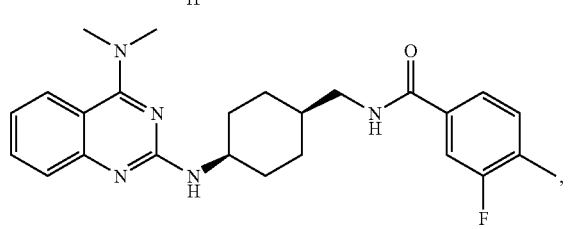
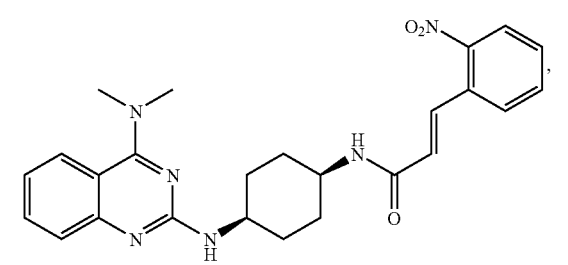
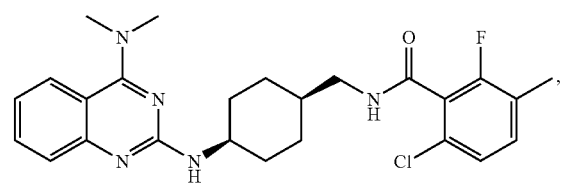
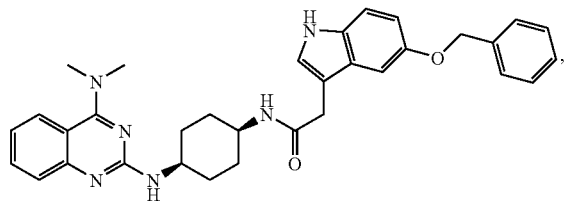
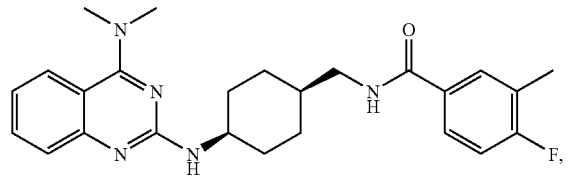

1837                                                                  1838
-continued                                                        -continued
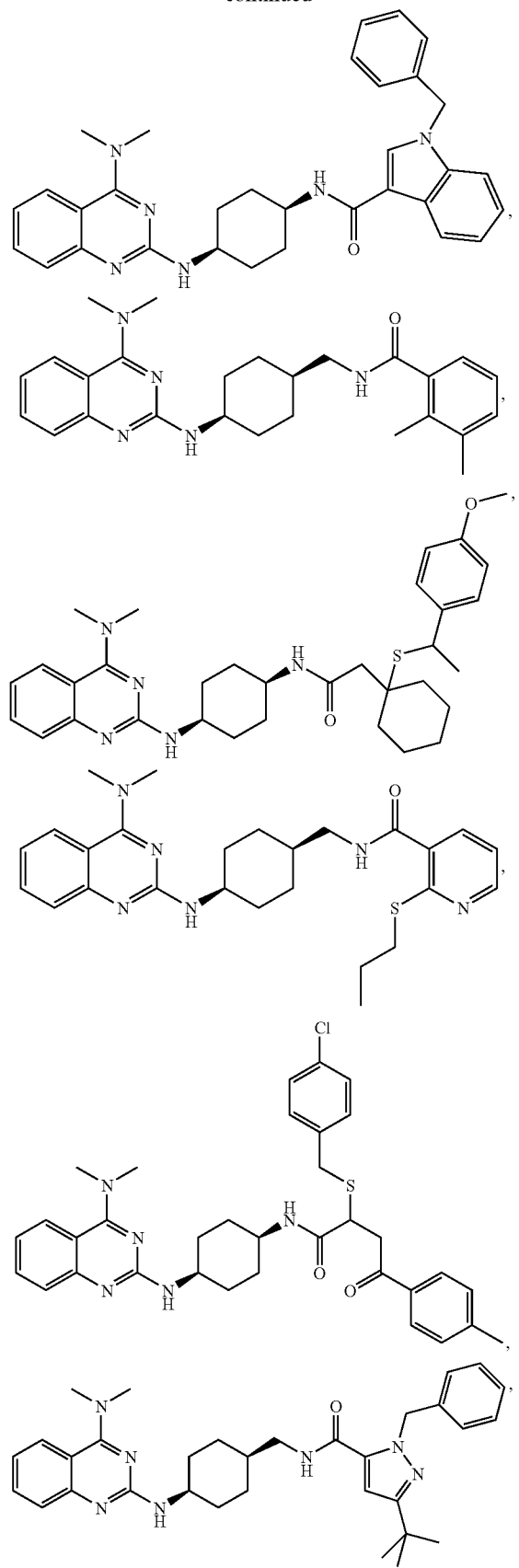
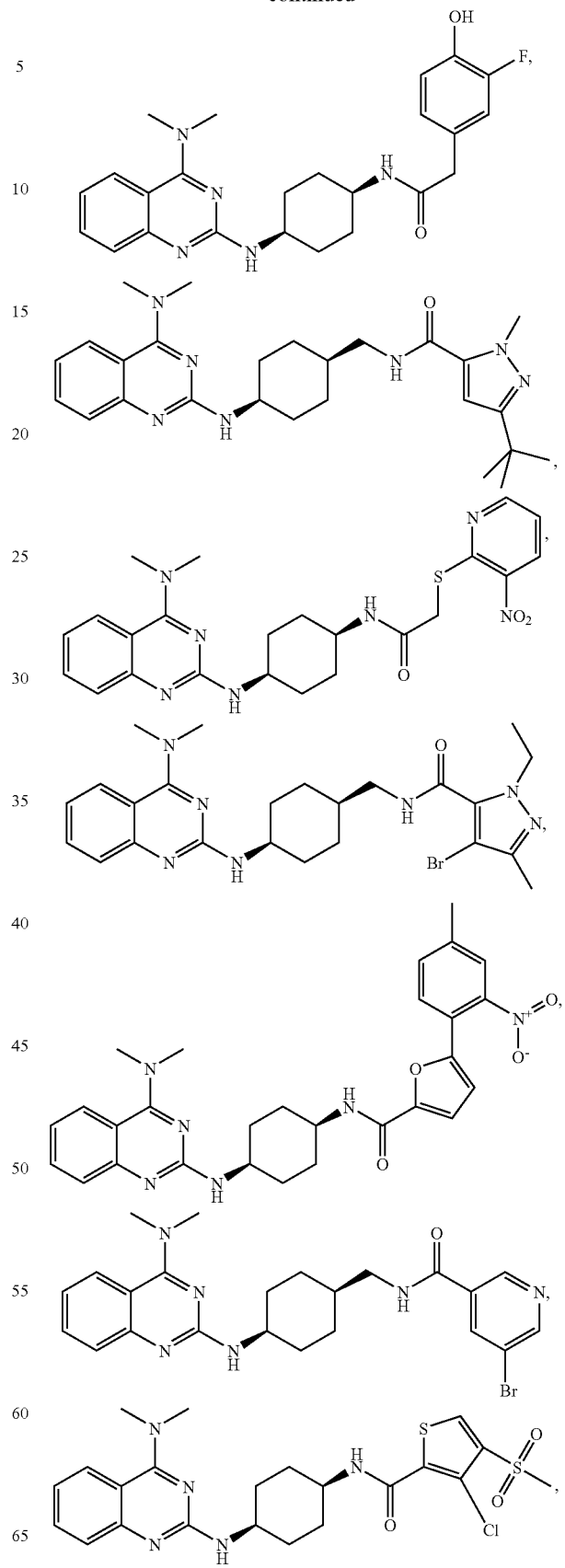

-continued
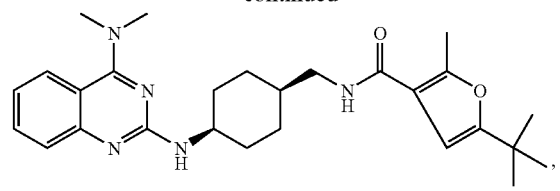
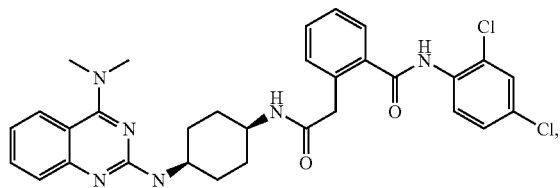
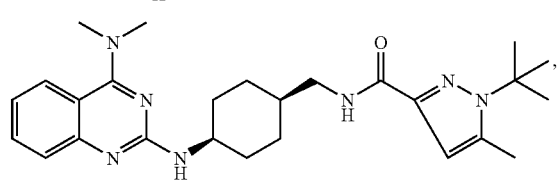
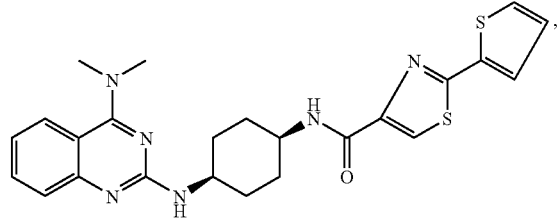
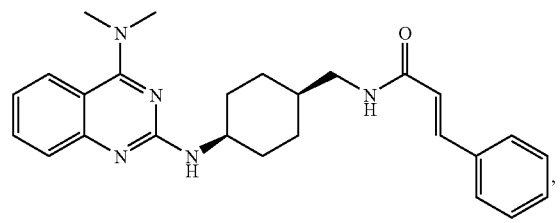
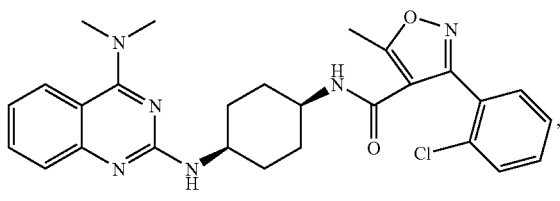
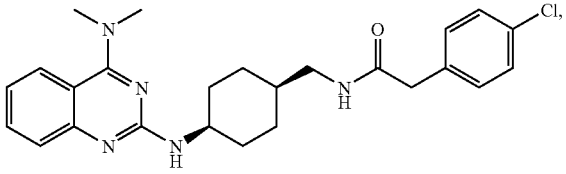
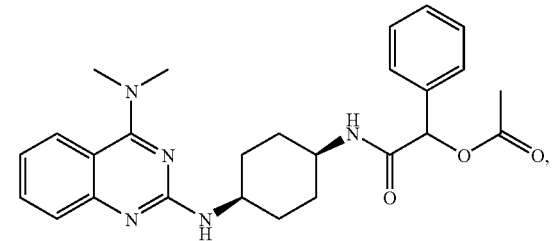
-continued
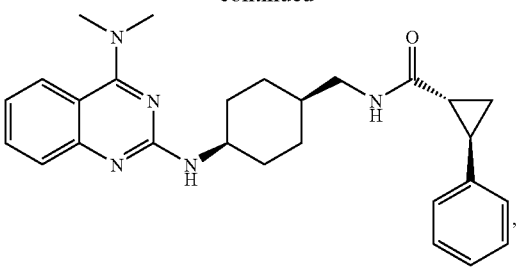
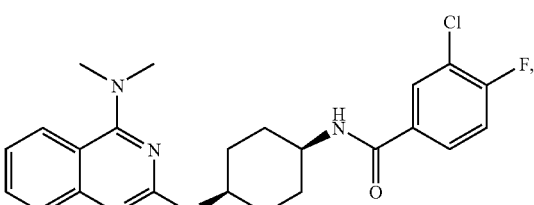
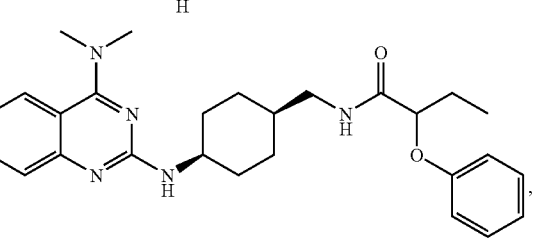
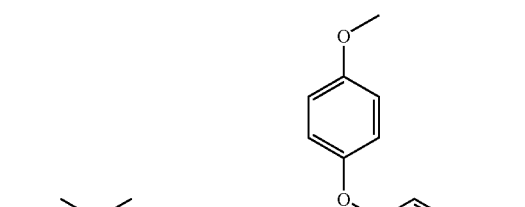
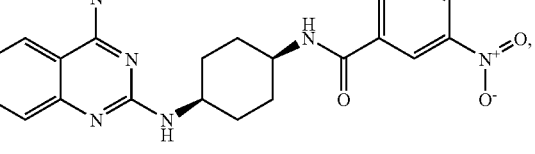
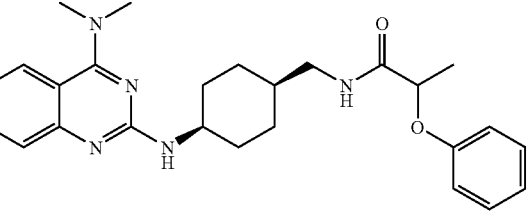
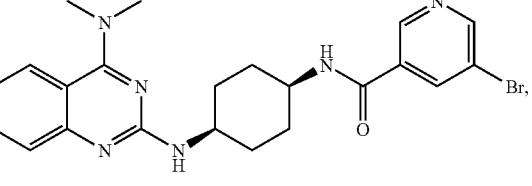
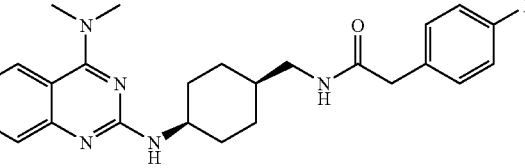

1841
-continued
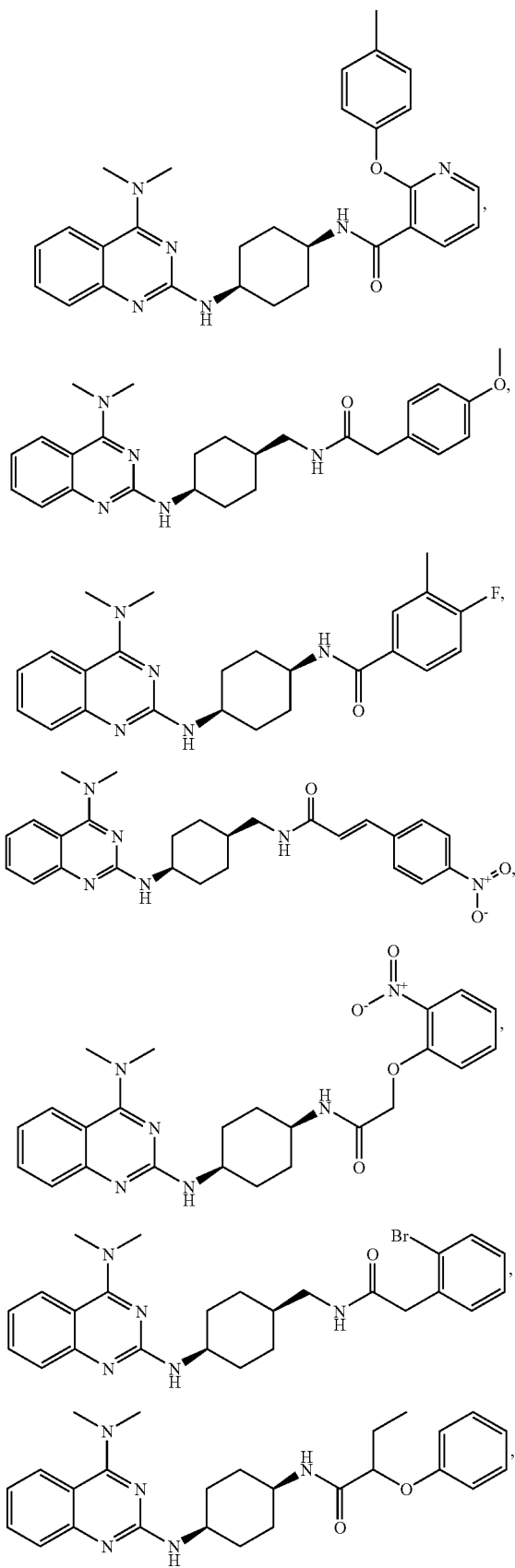
1842
-continued
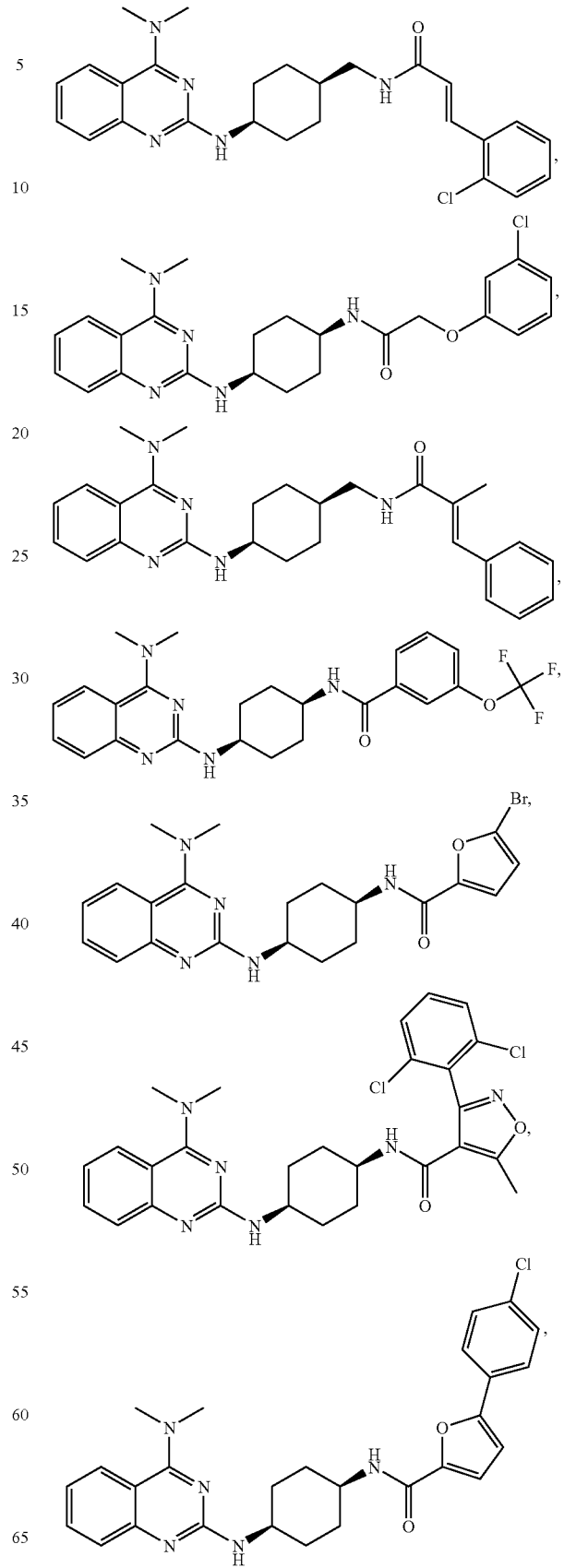

-continued
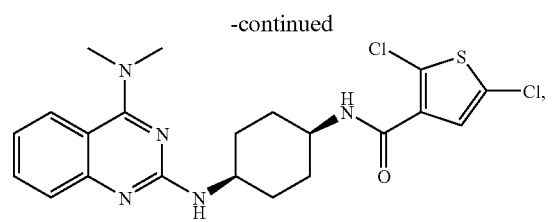
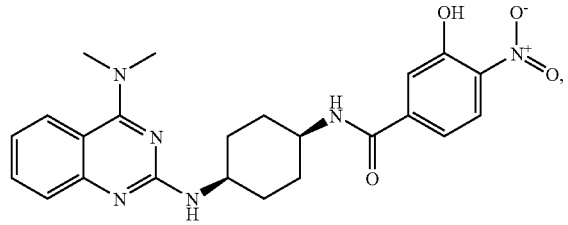
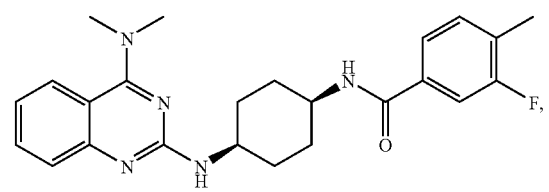
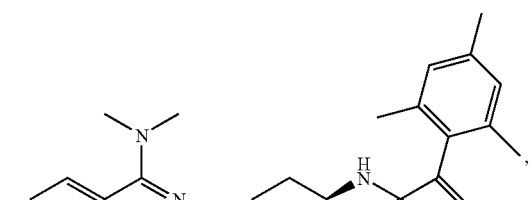
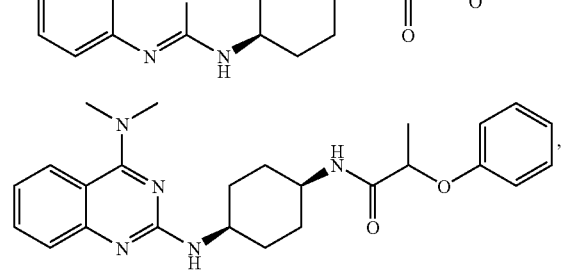
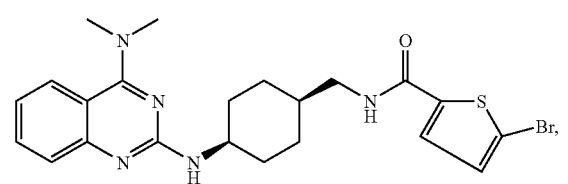
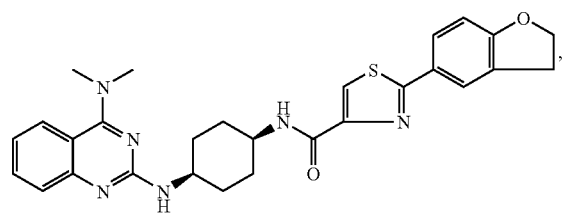
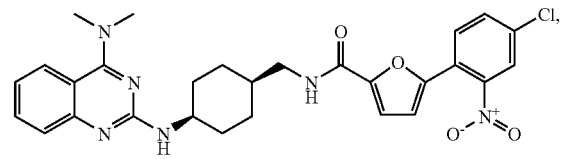
-continued
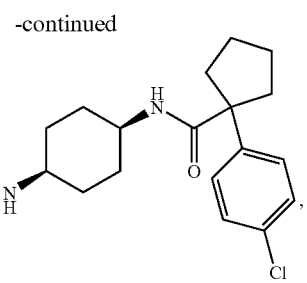
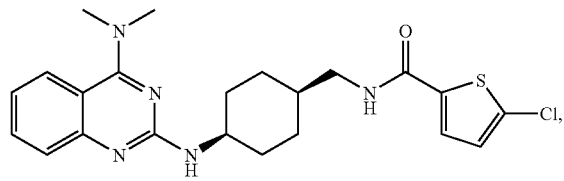
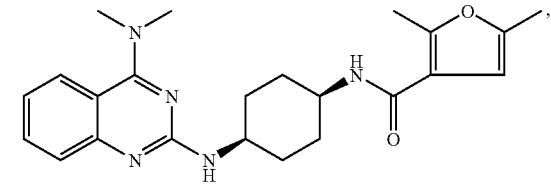
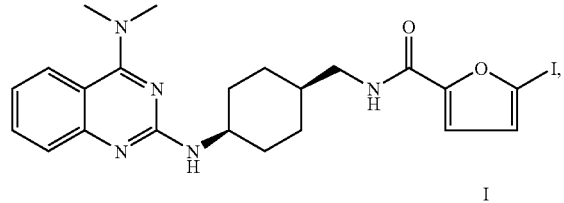
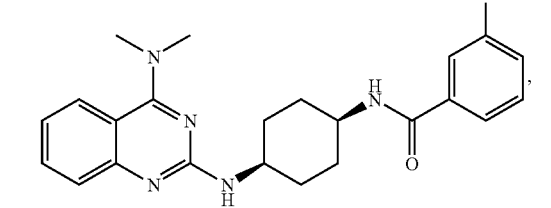
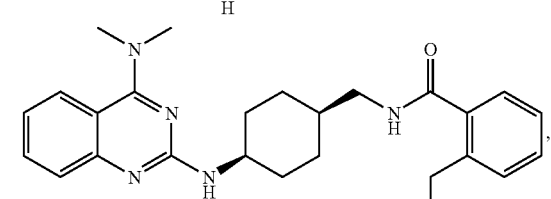
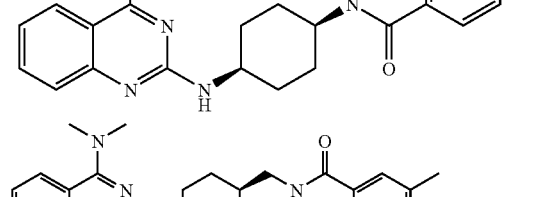
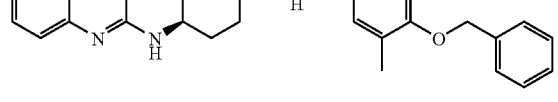

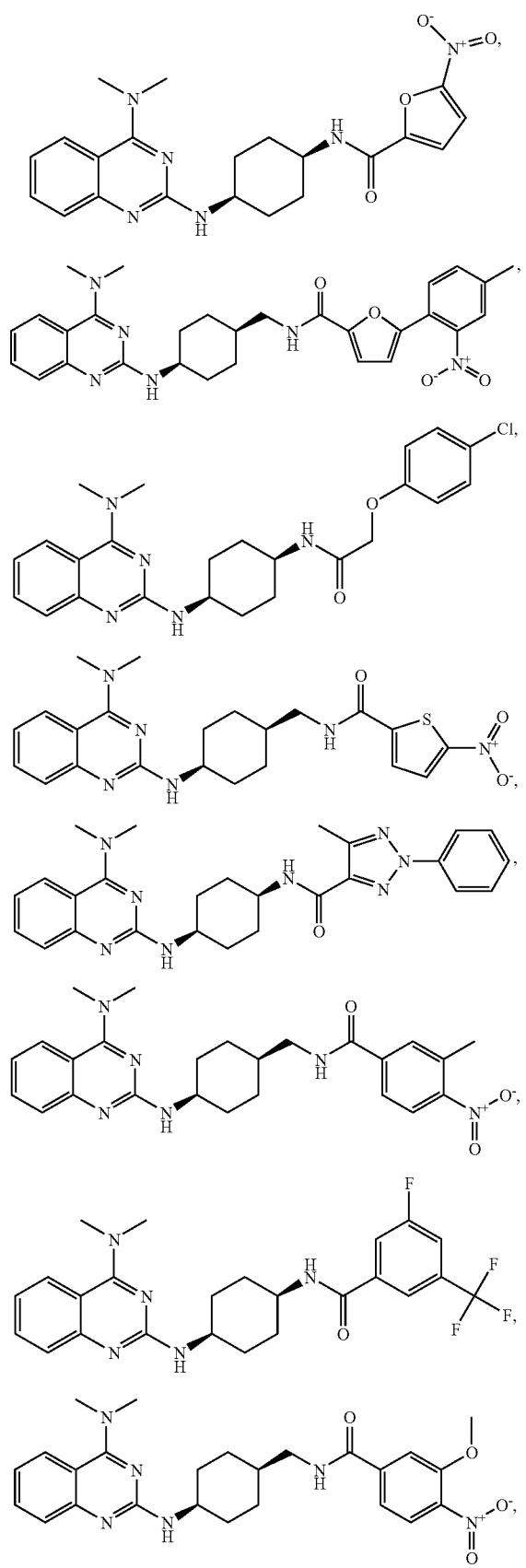
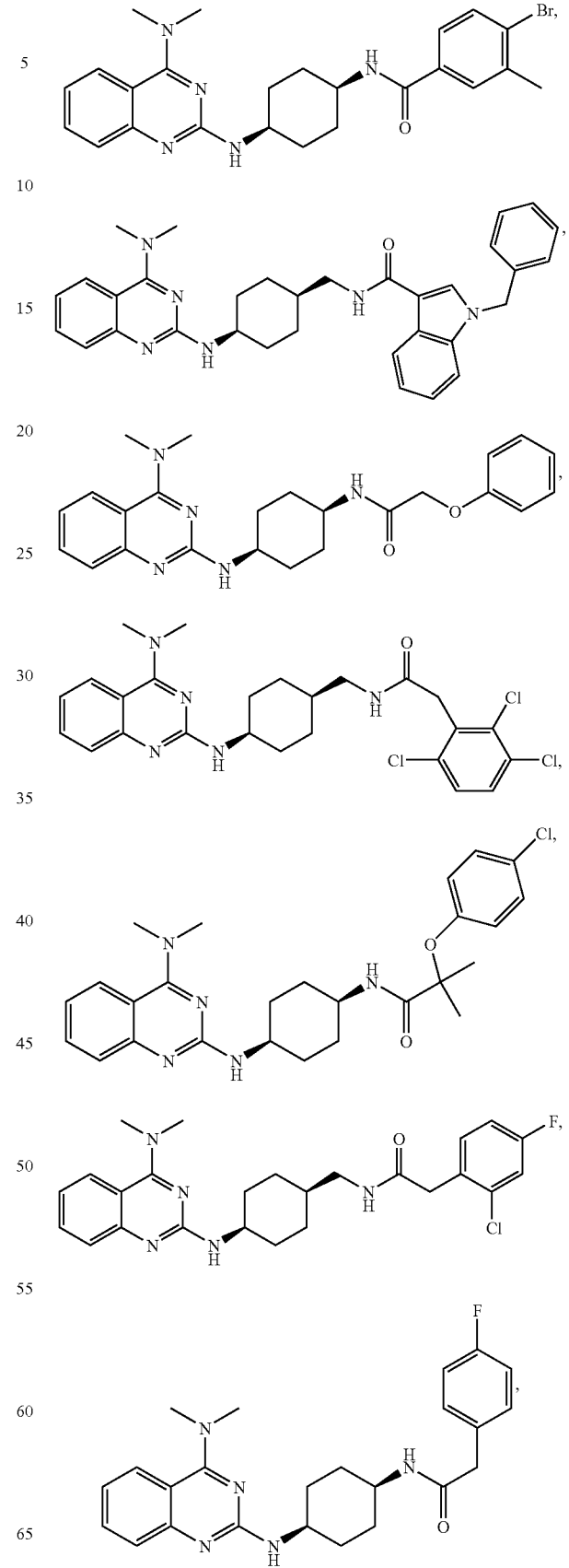

1847
-continued
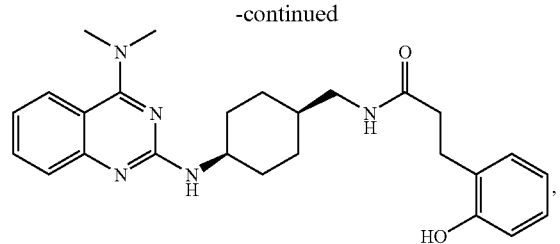
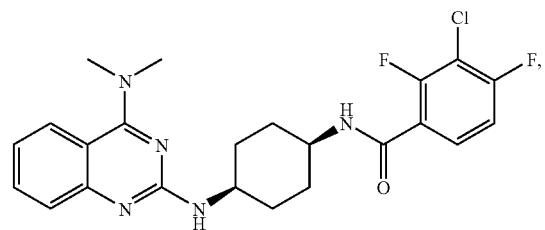
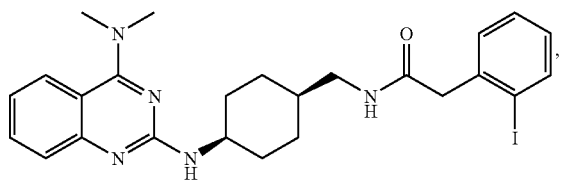
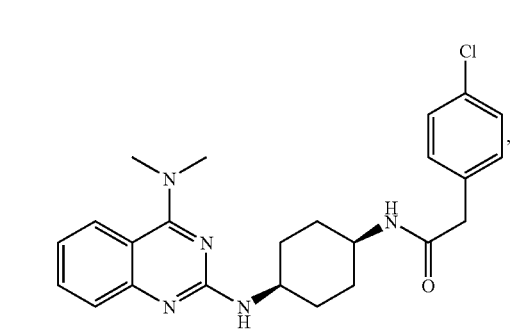
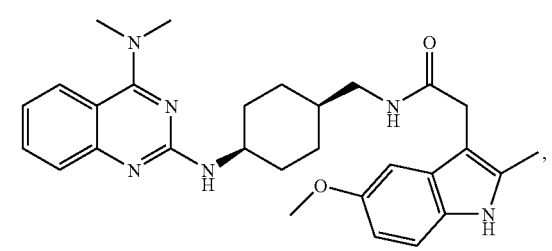
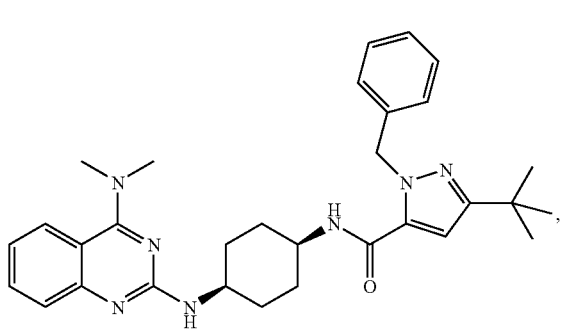
1848
-continued
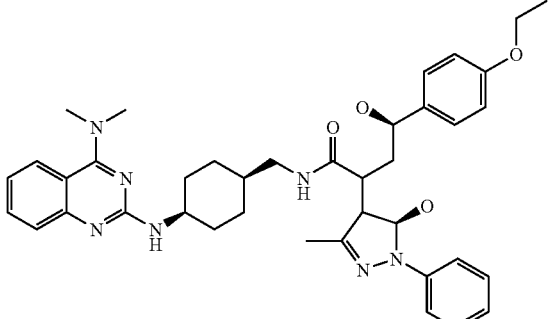
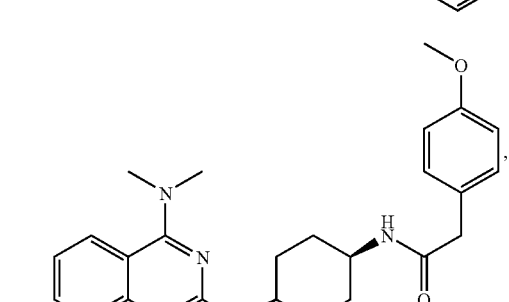
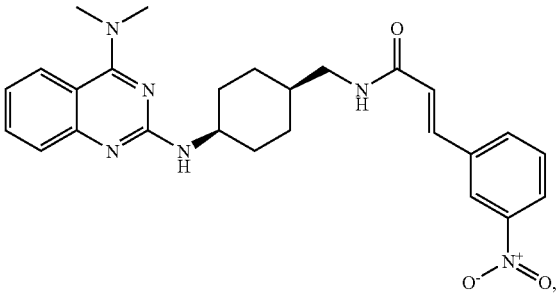
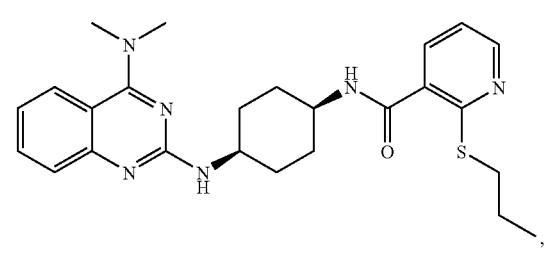
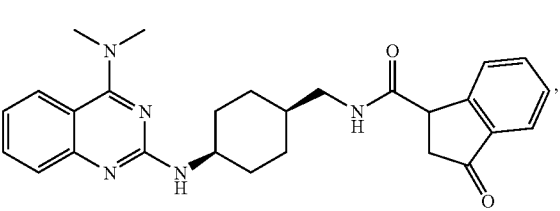
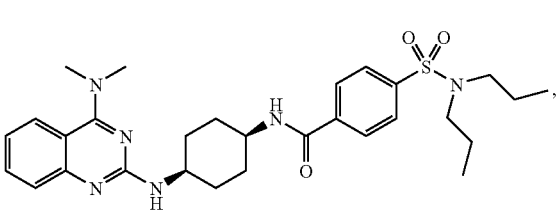

1849
-continued
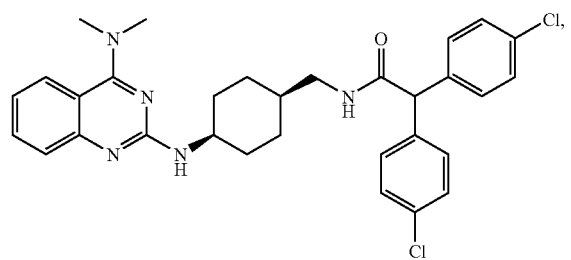
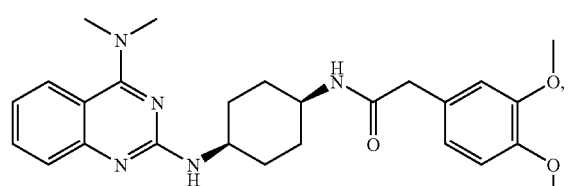
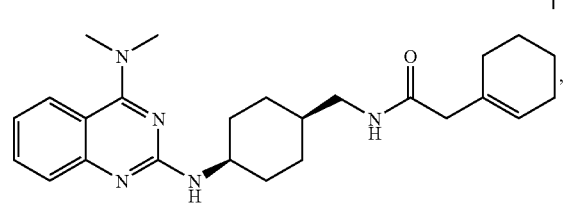
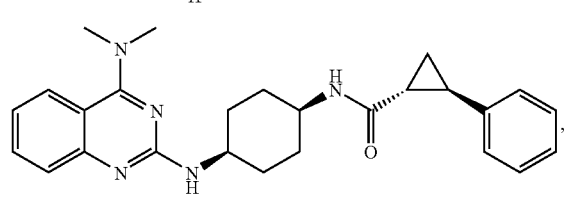
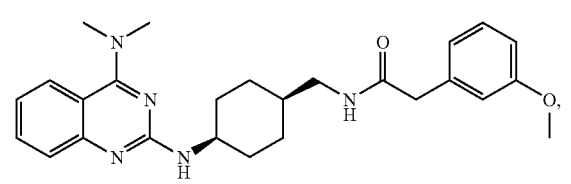
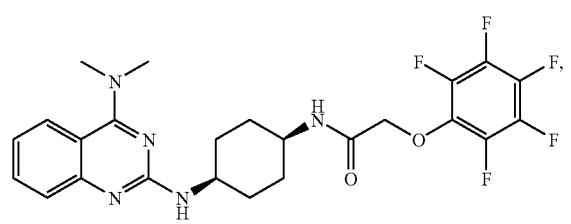
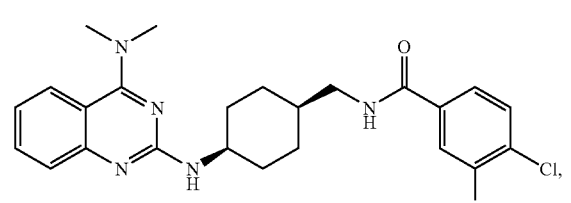
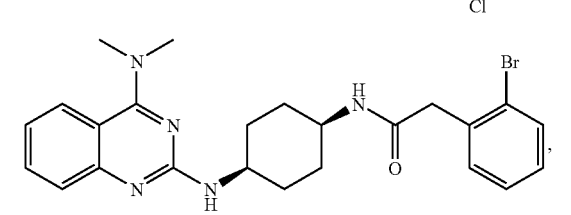
1850
-continued
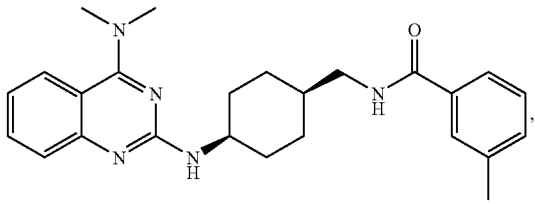
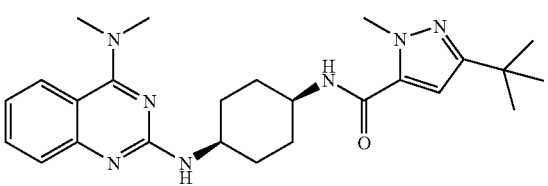
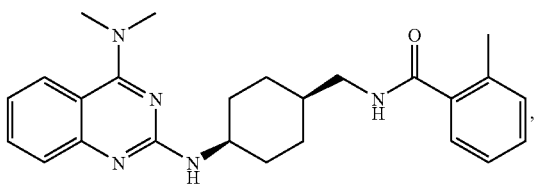
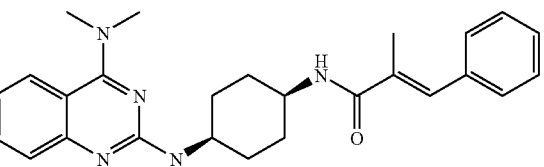
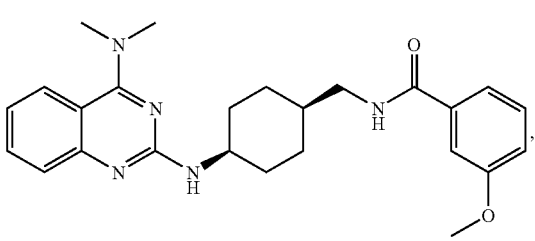
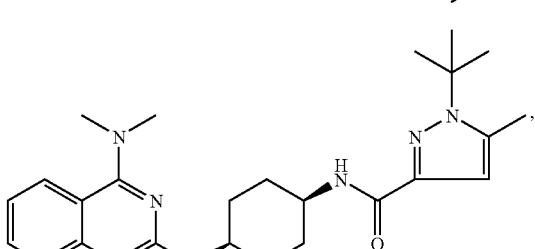
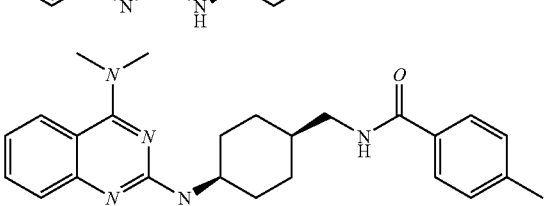
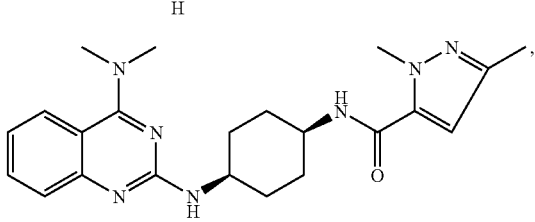

1851
-continued
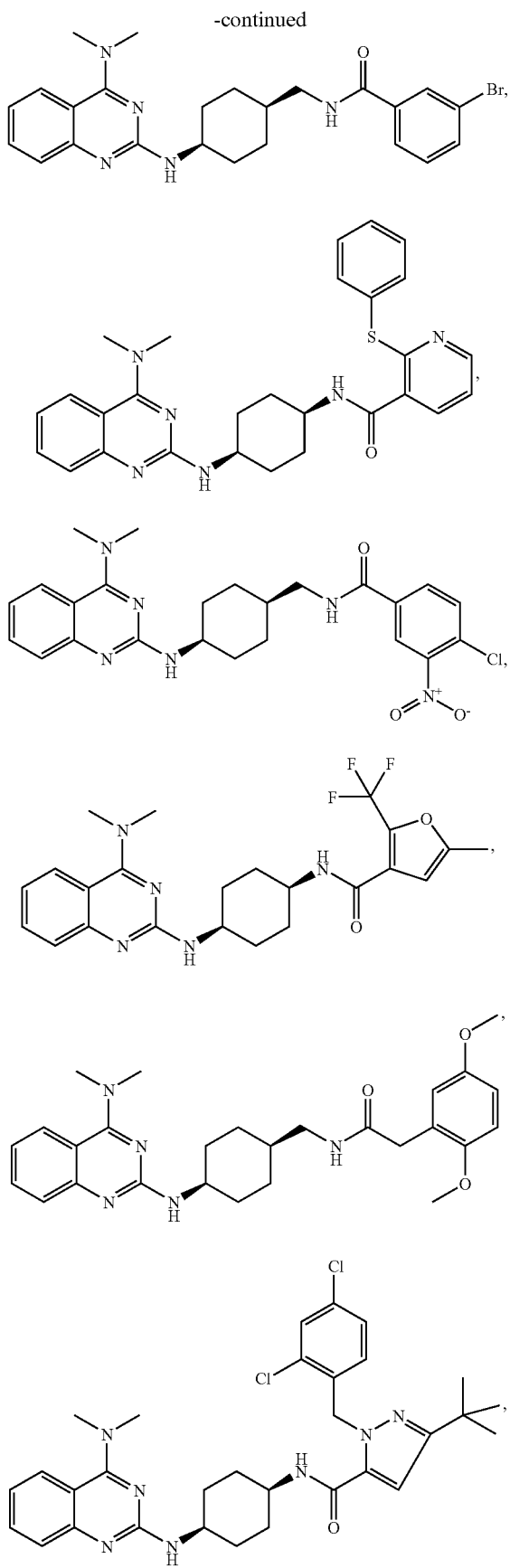
1852
-continued
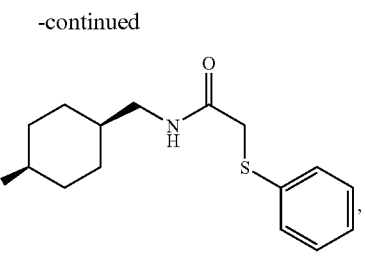
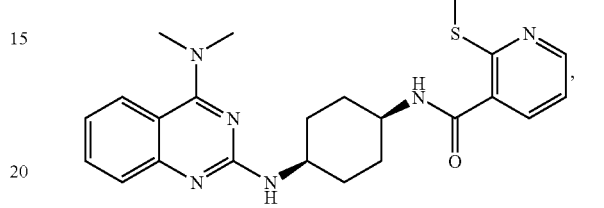
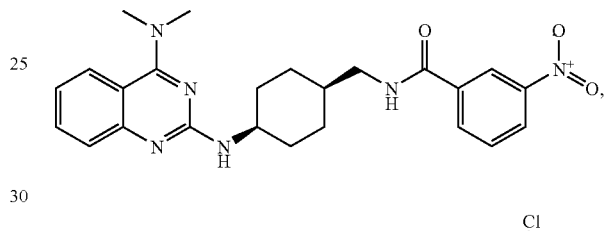
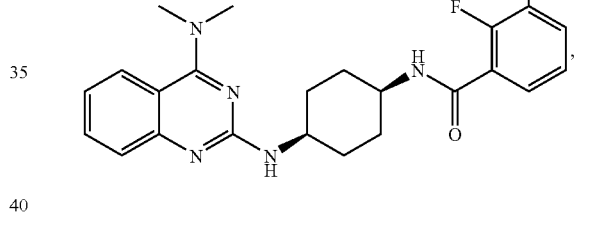
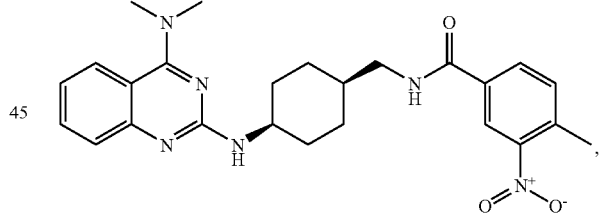
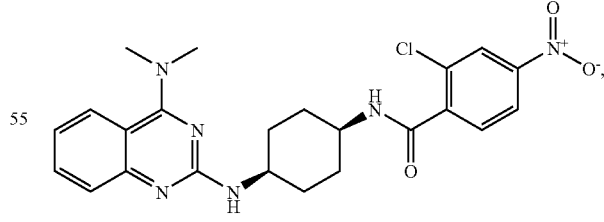
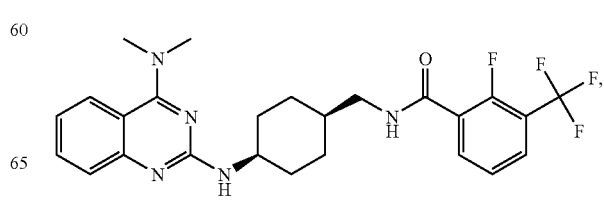

1853
-continued
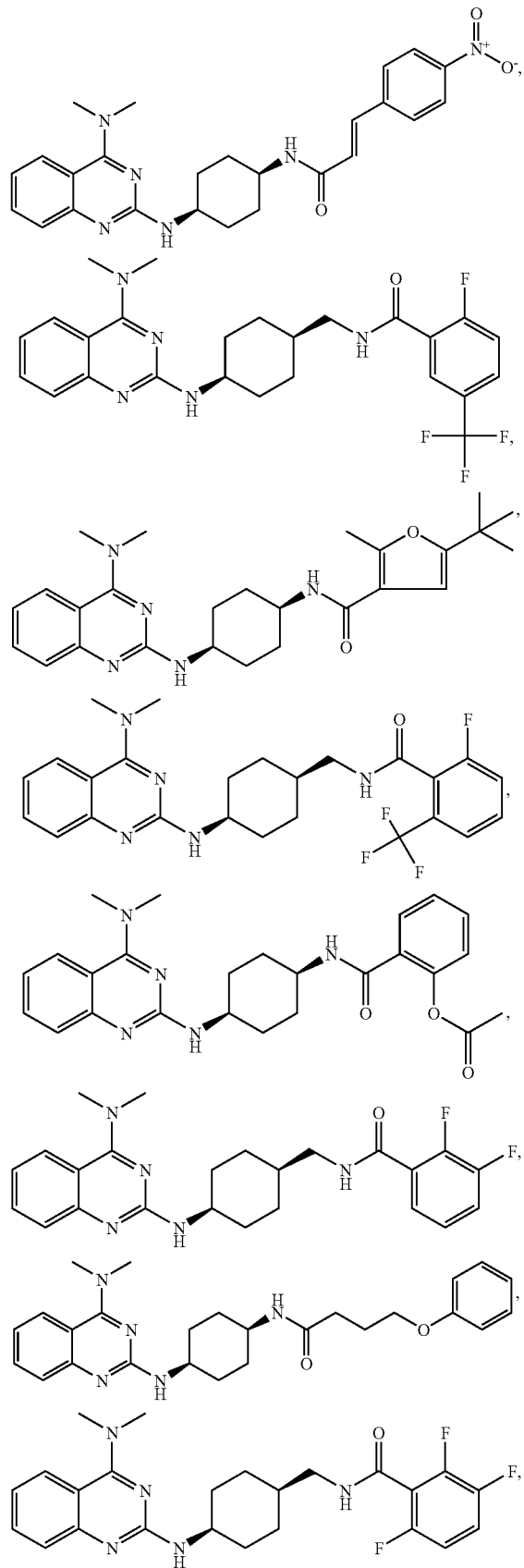
1854
-continued
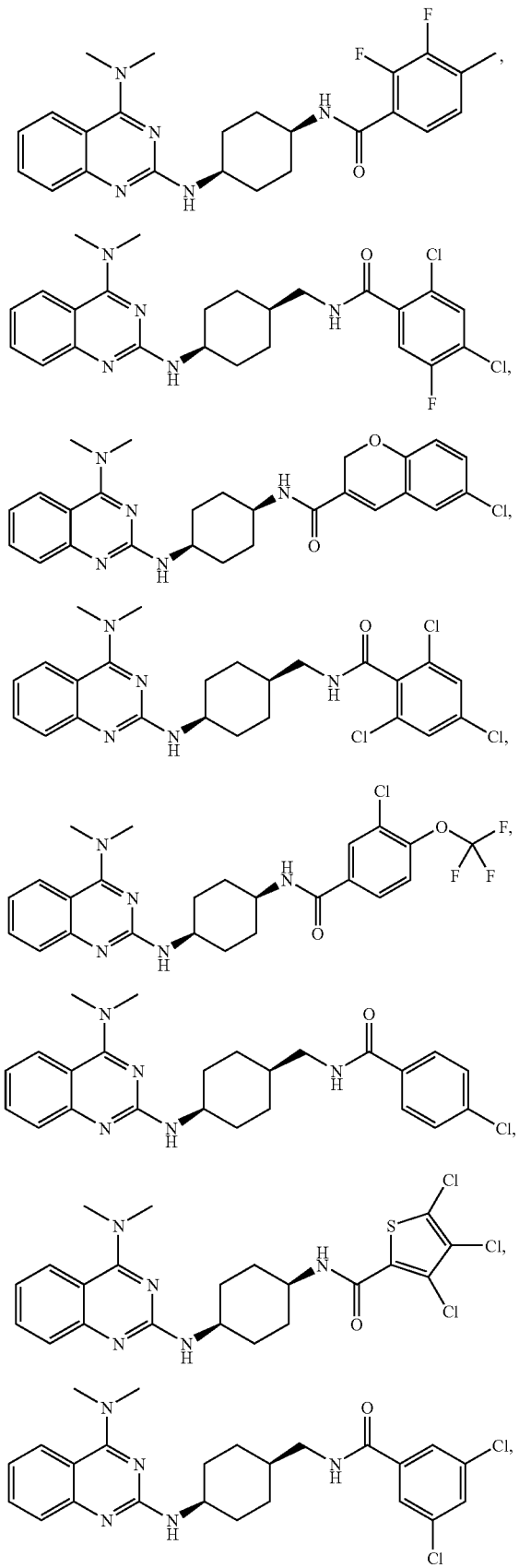

1855
-continued
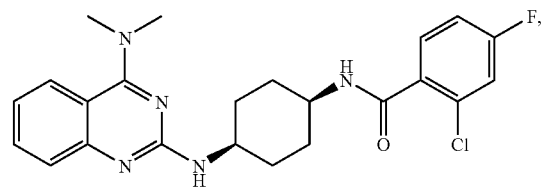
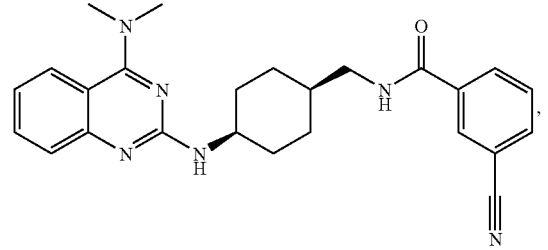
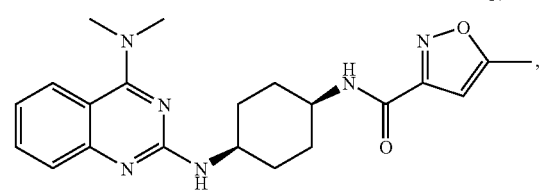
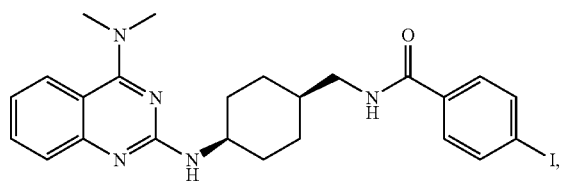
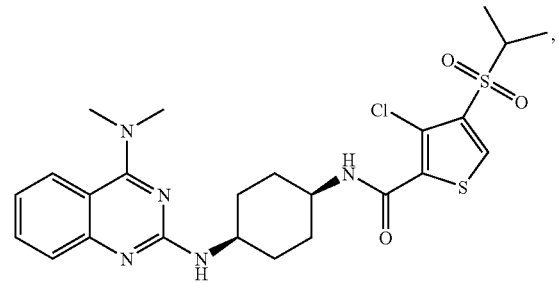
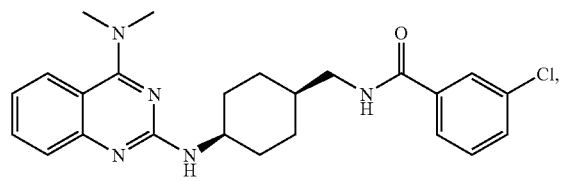
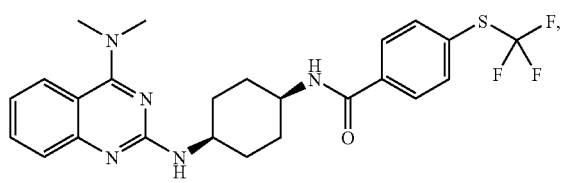
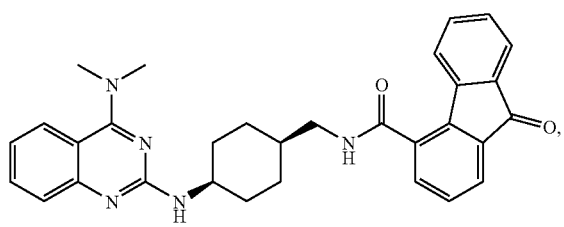
1856
-continued
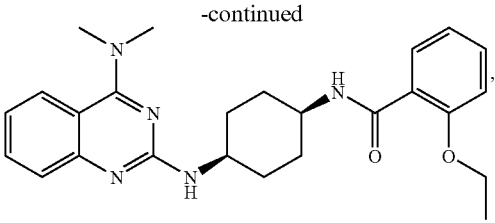
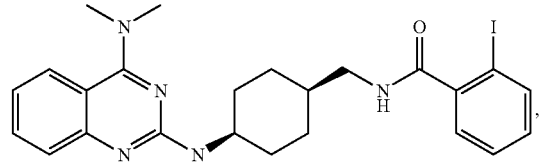
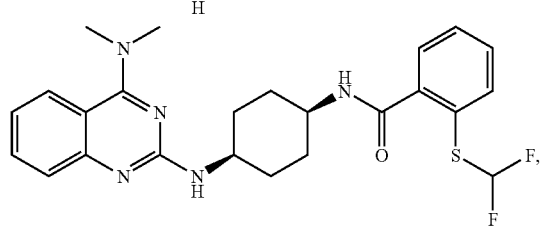
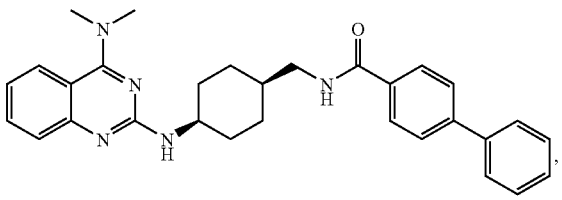
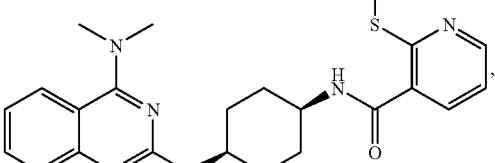
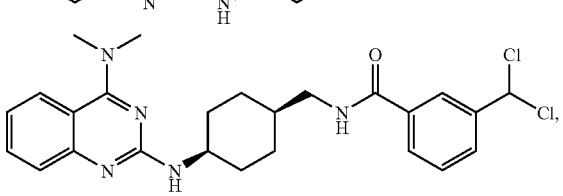
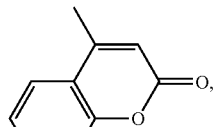
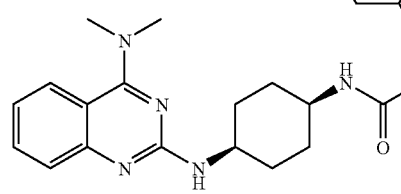
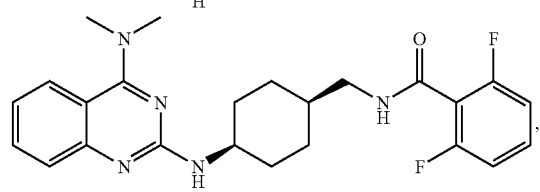

1857
-continued
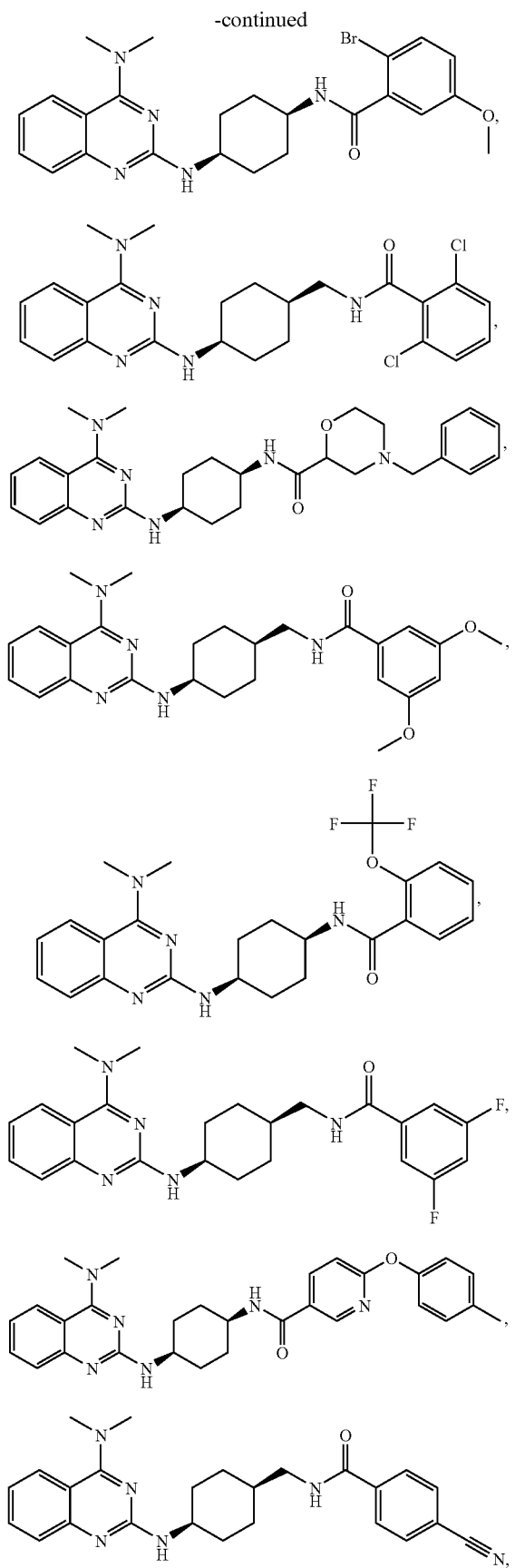
1858
-continued
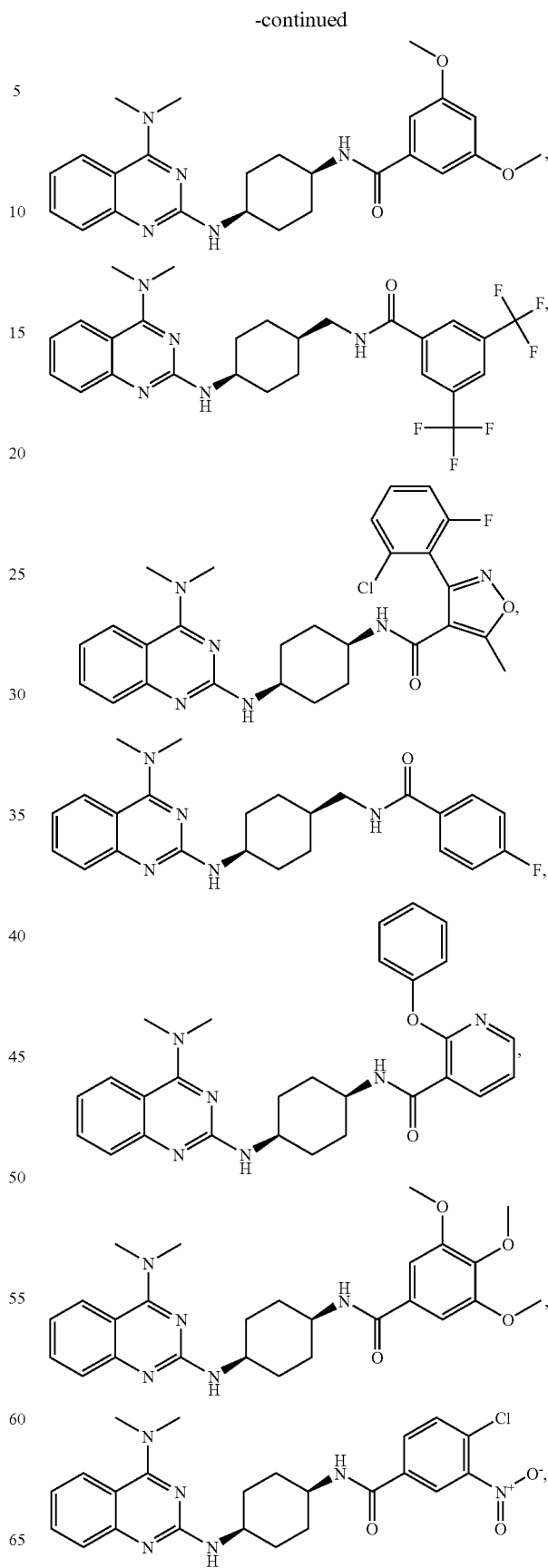

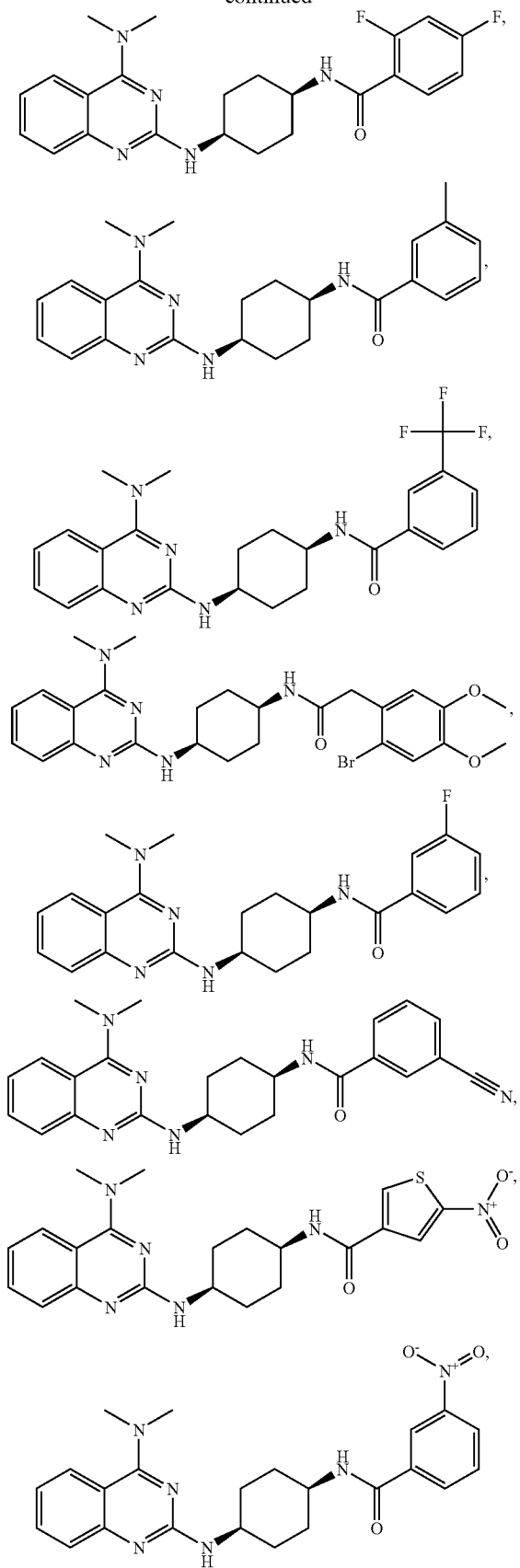
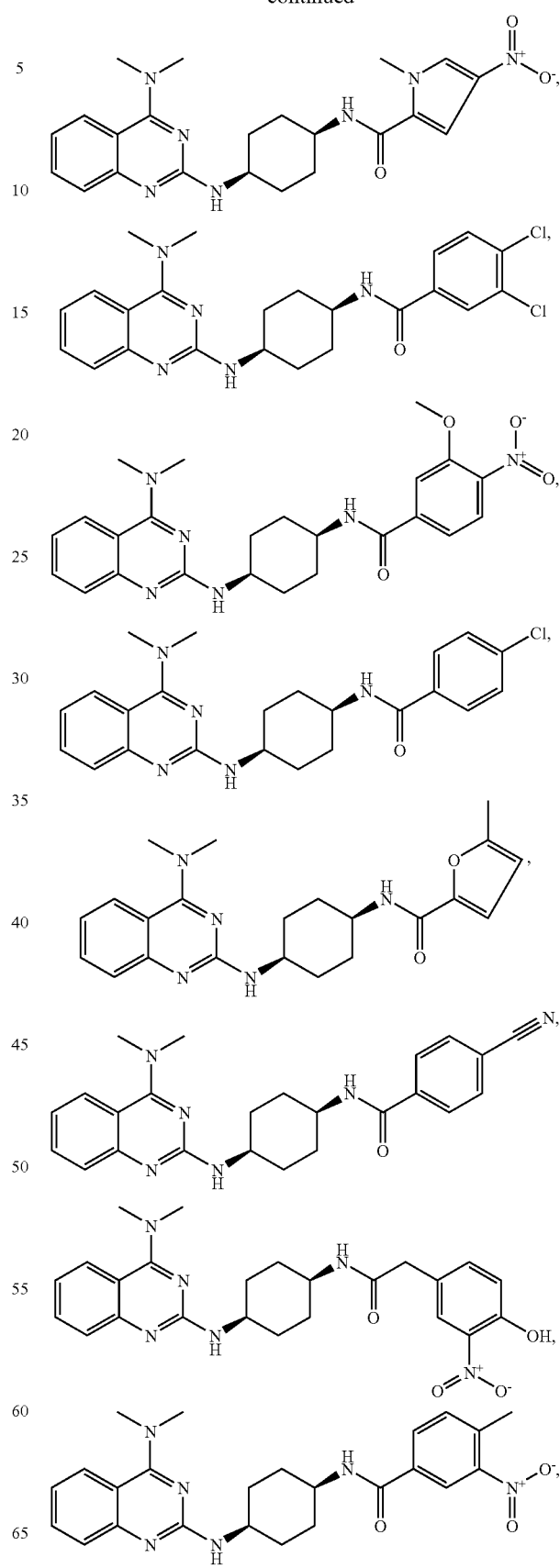

-continued
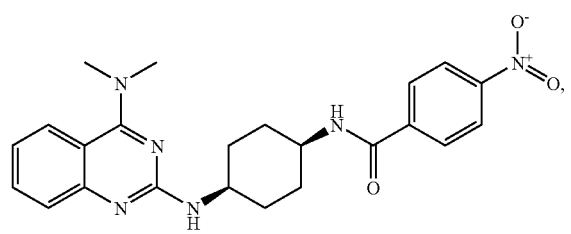
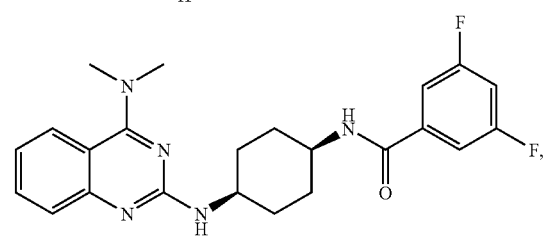
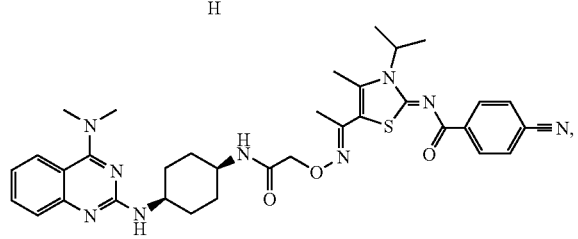
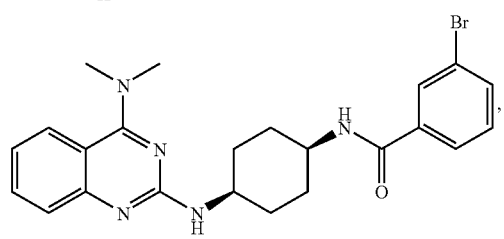
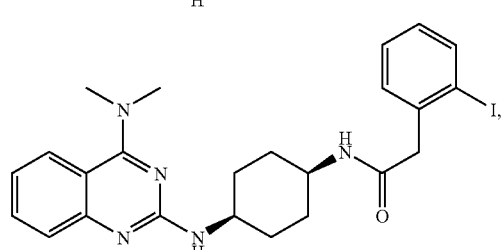
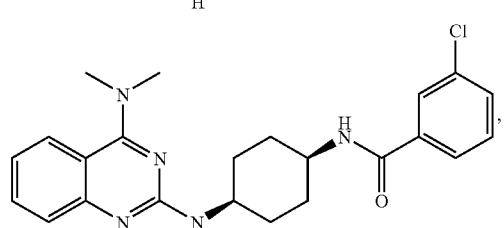
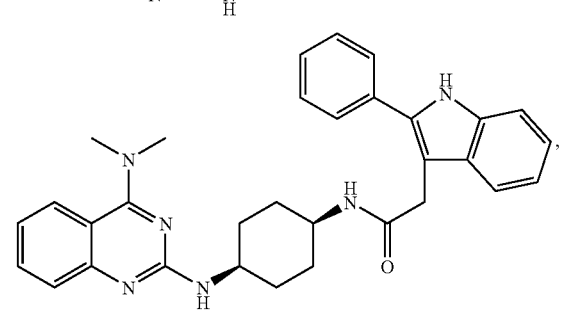
-continued
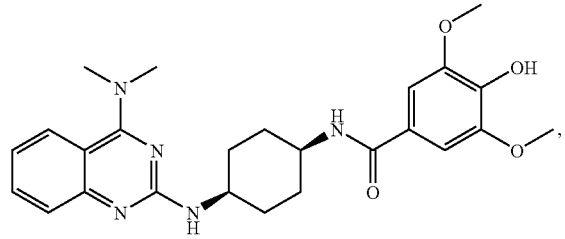
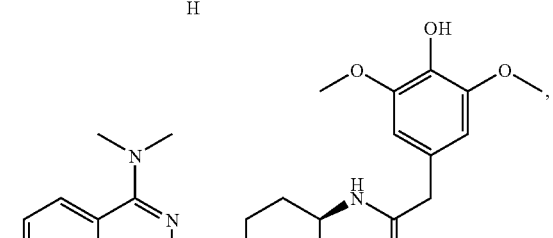
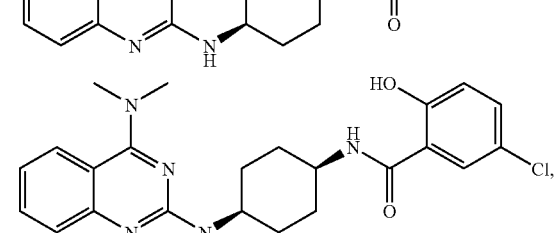
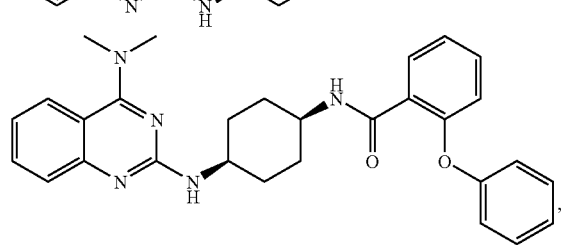
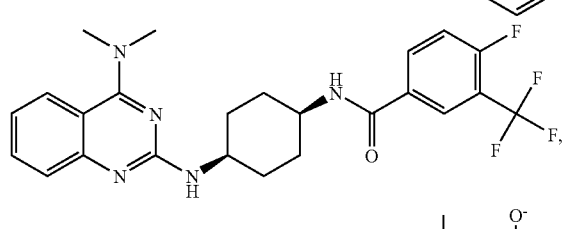
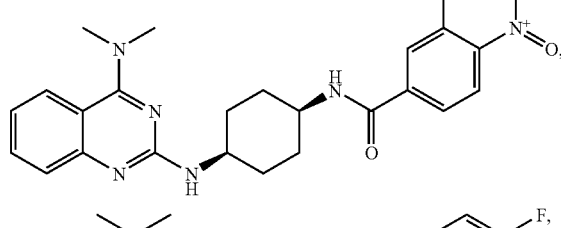
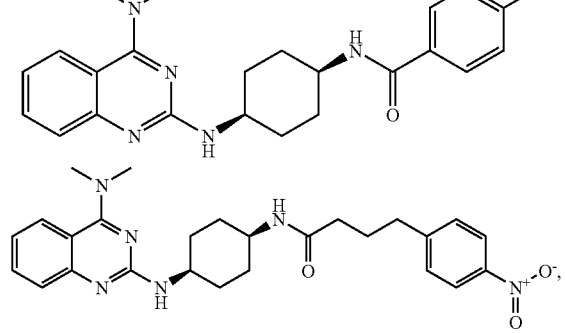

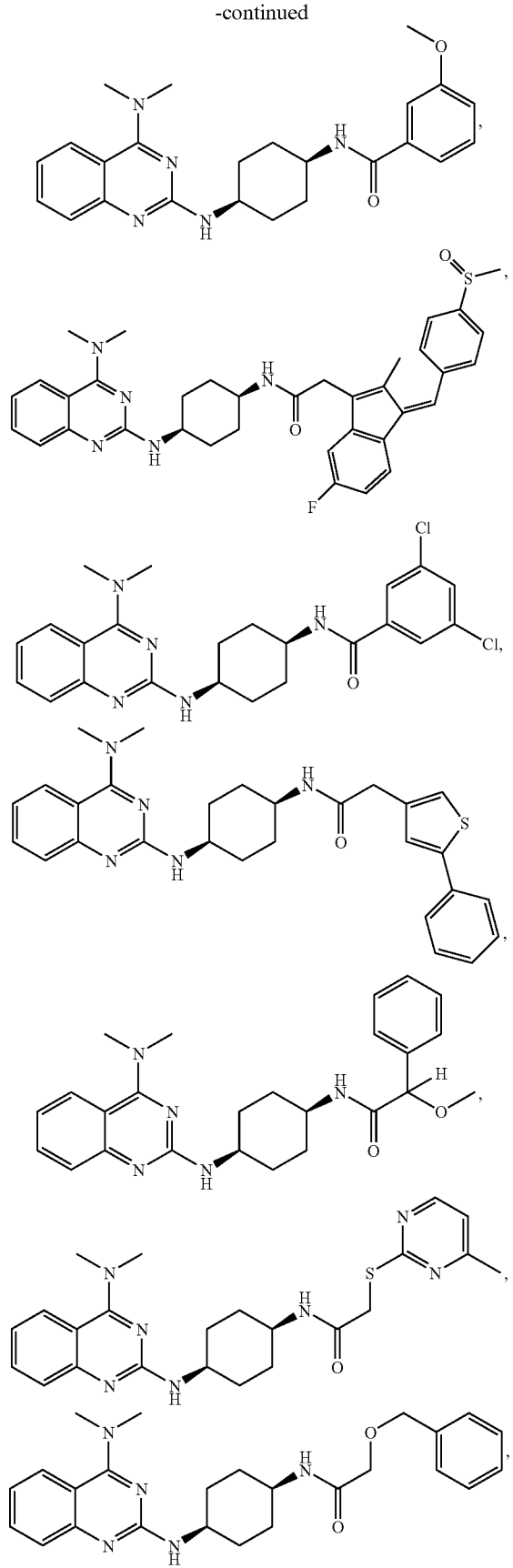
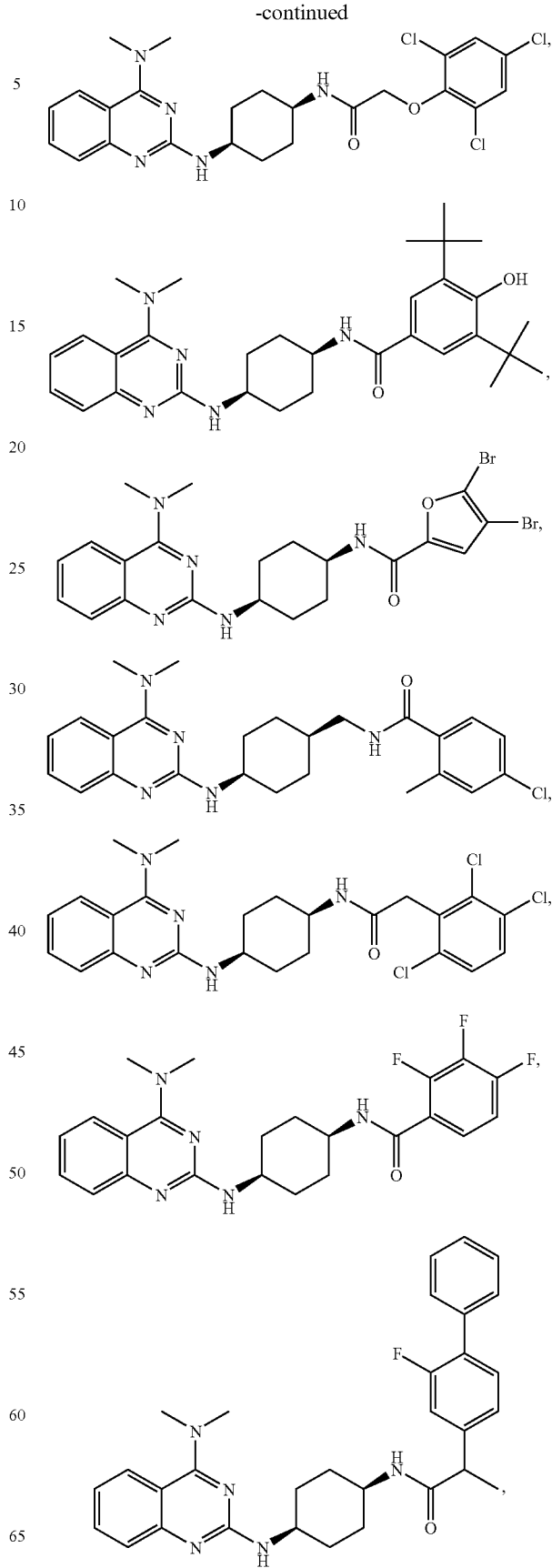

-continued
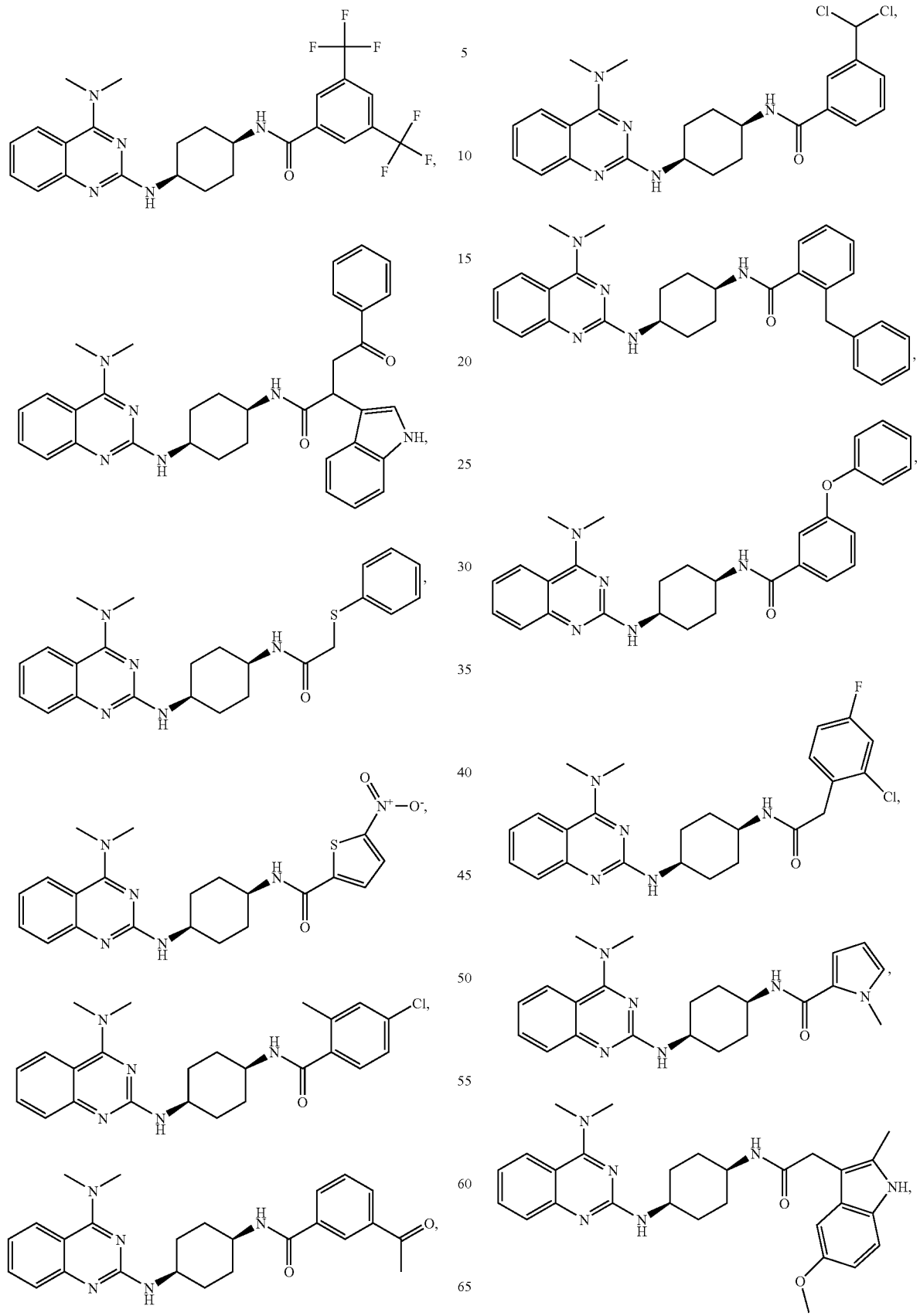

-continued
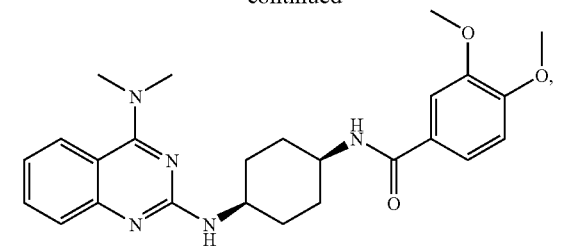
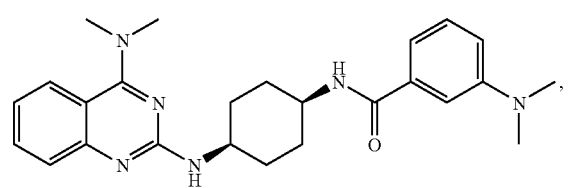
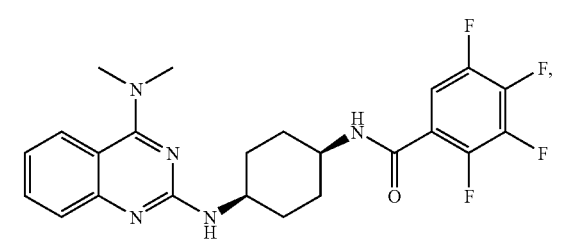
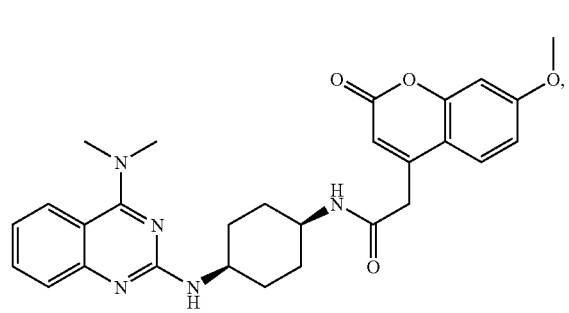
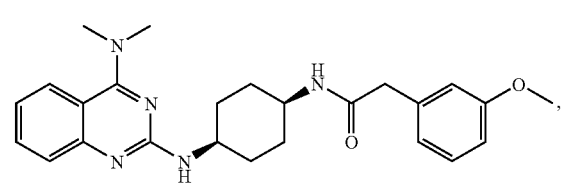
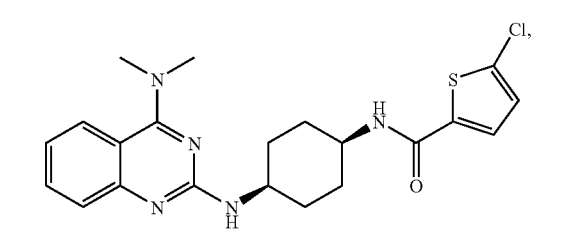
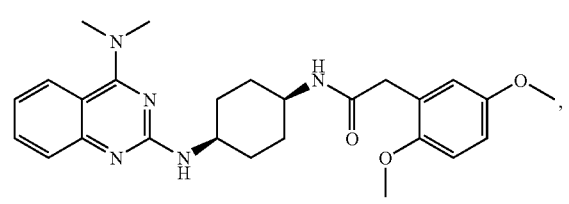
-continued
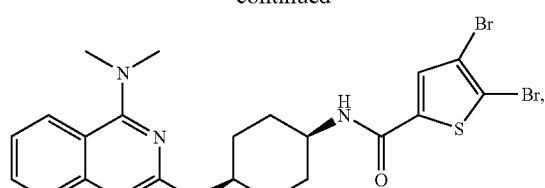
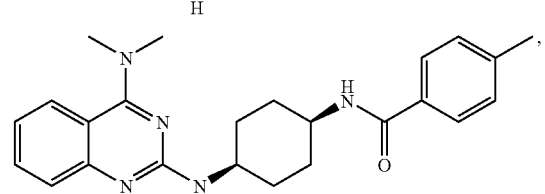
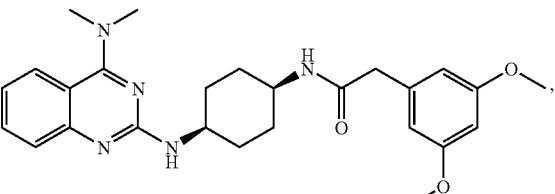
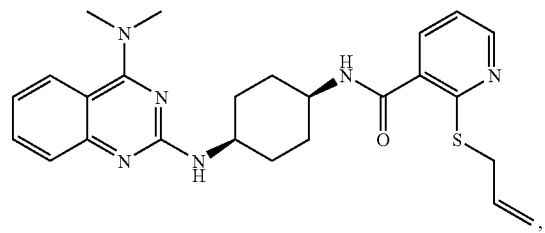
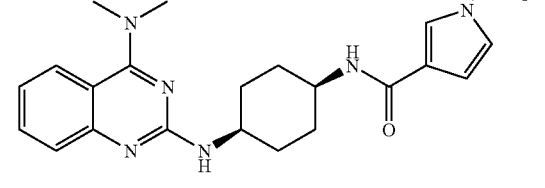
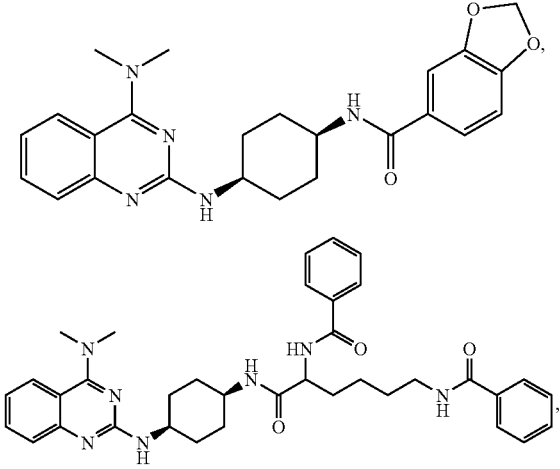

-continued
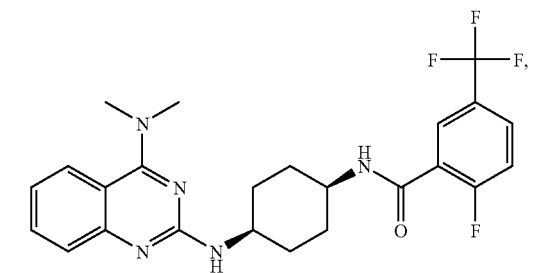
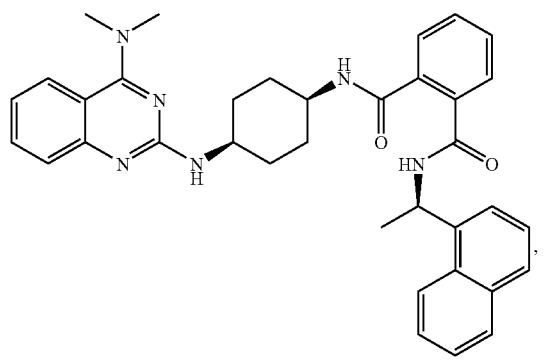
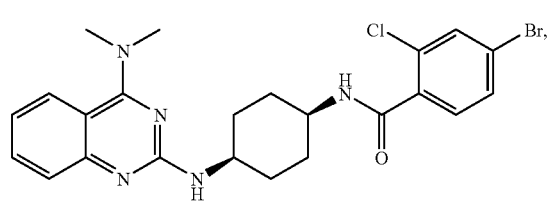
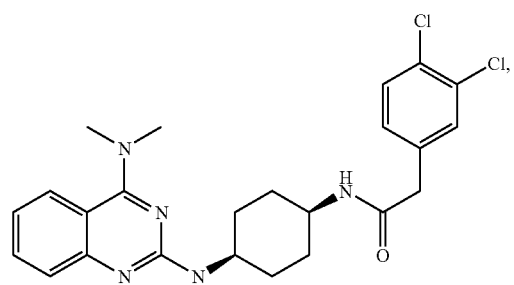
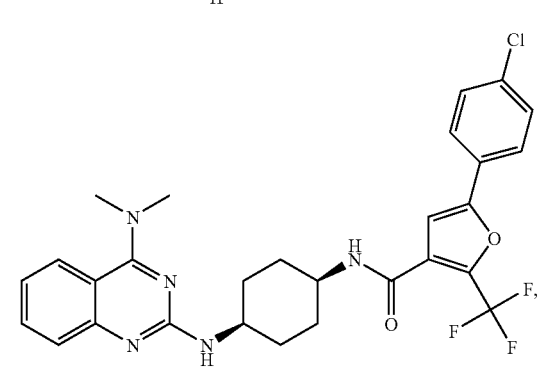
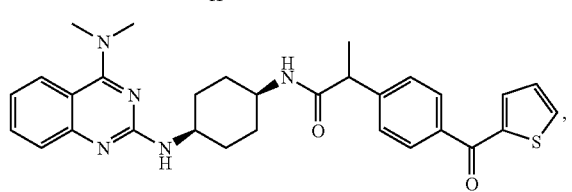
-continued
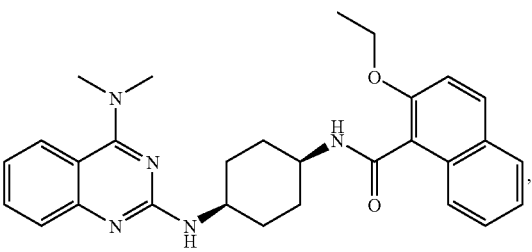
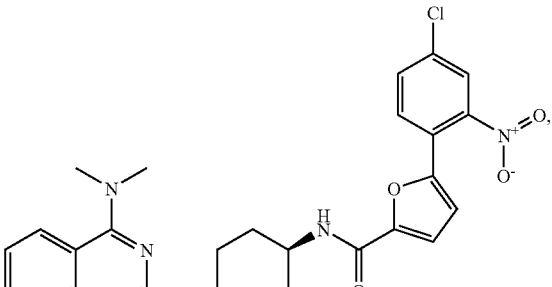
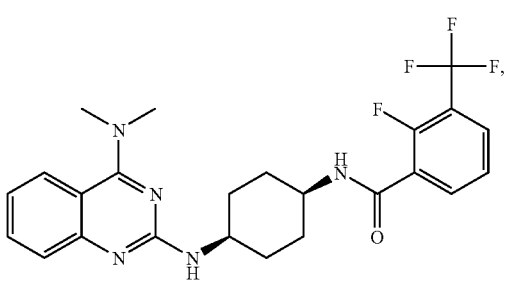
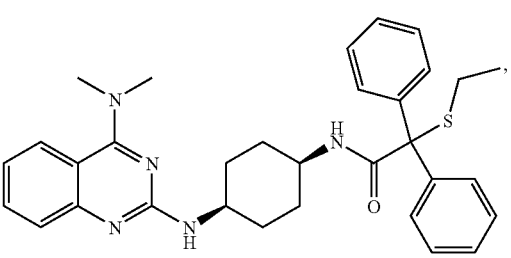
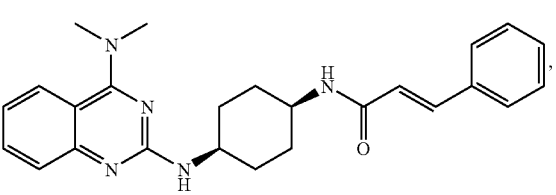
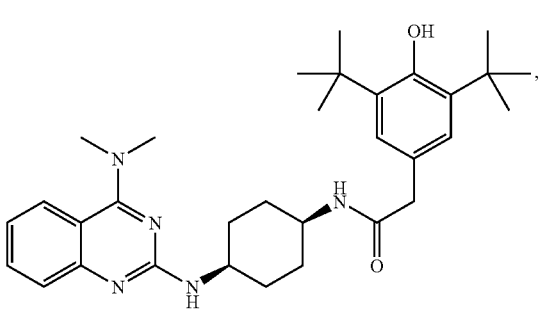

-continued
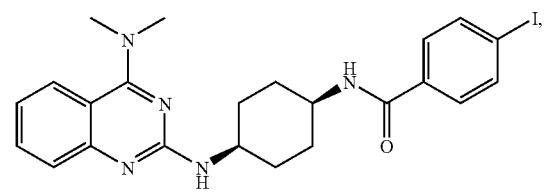
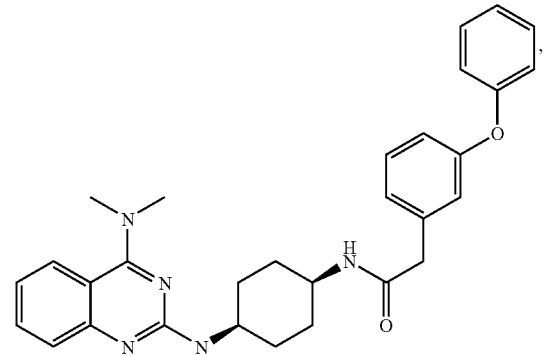
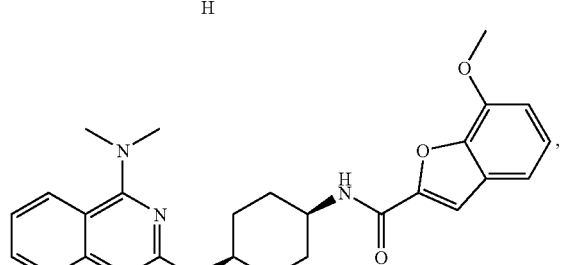
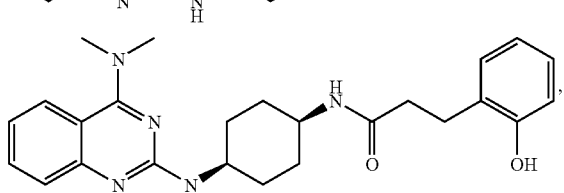
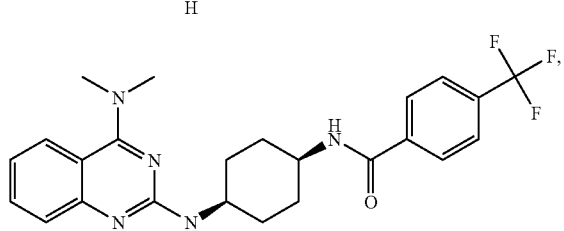
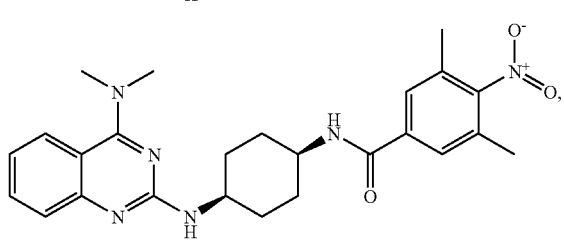
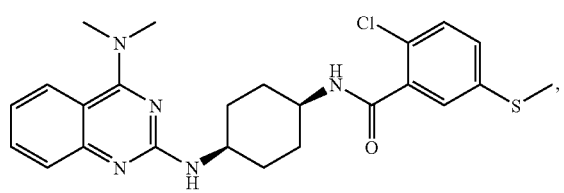
-continued
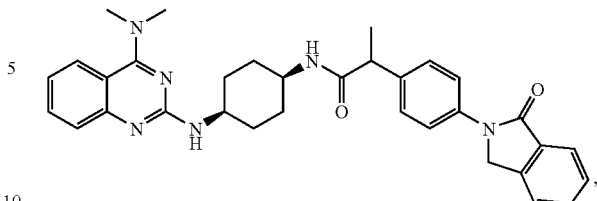
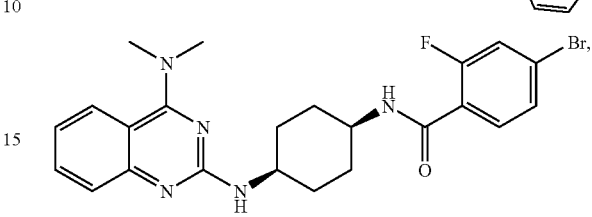
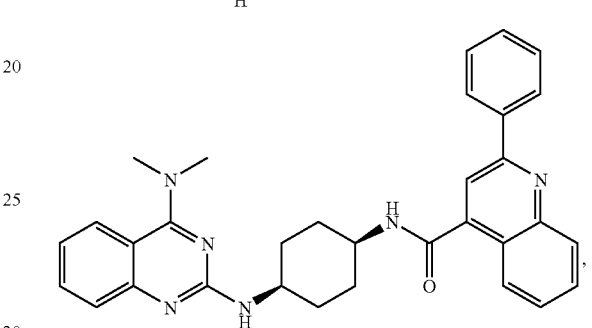
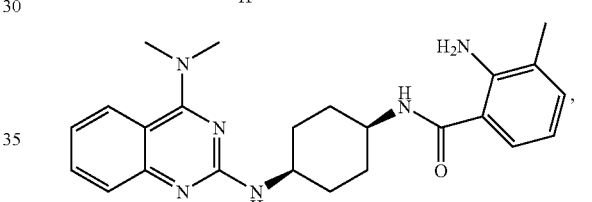
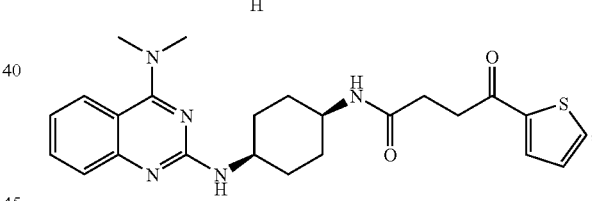
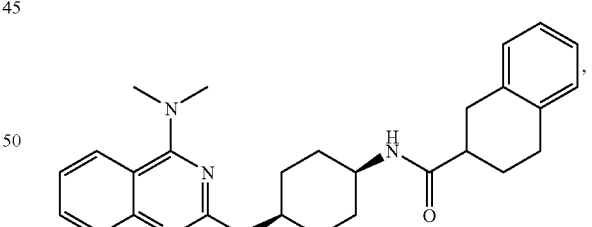
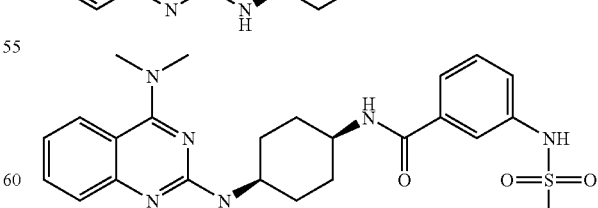
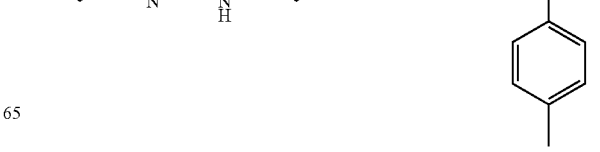

1873
-continued
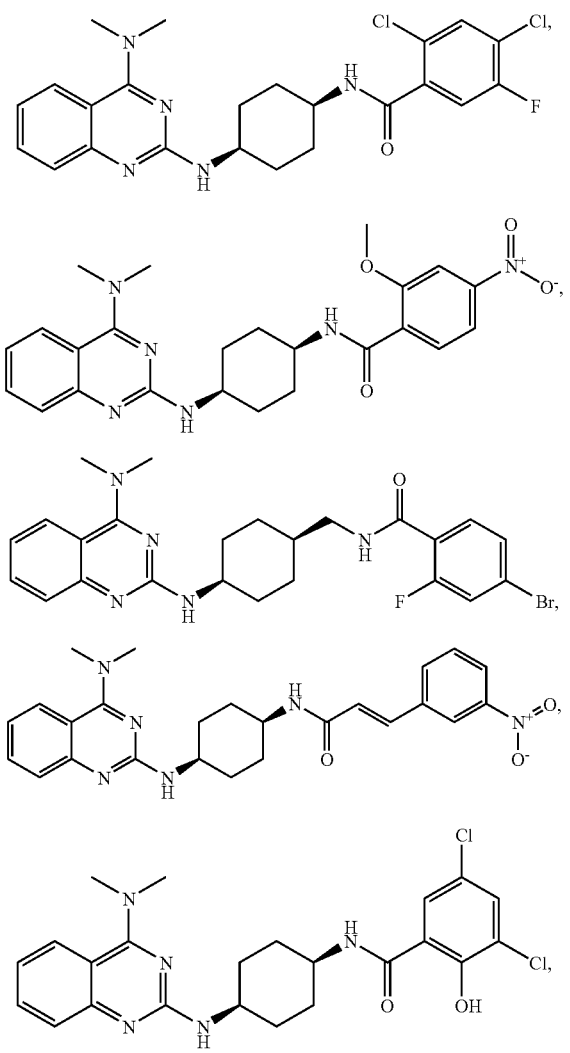
1874
-continued
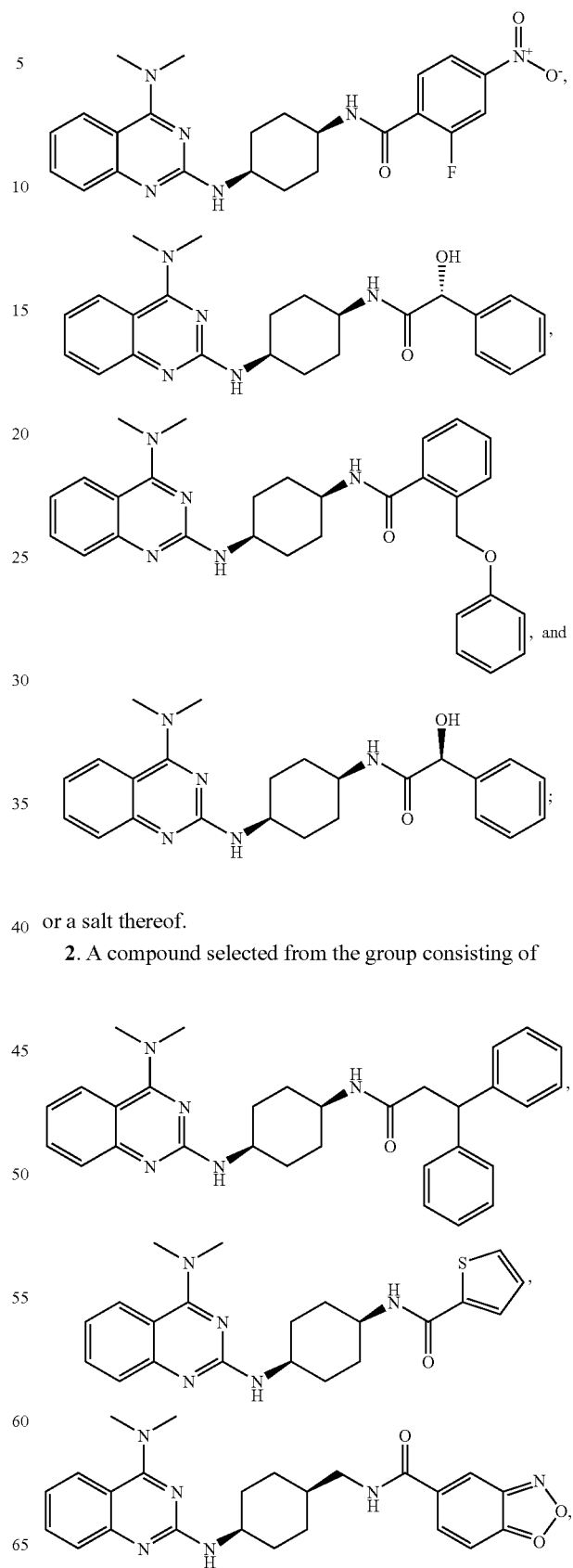
or a salt thereof.
2. A compound selected from the group consisting of

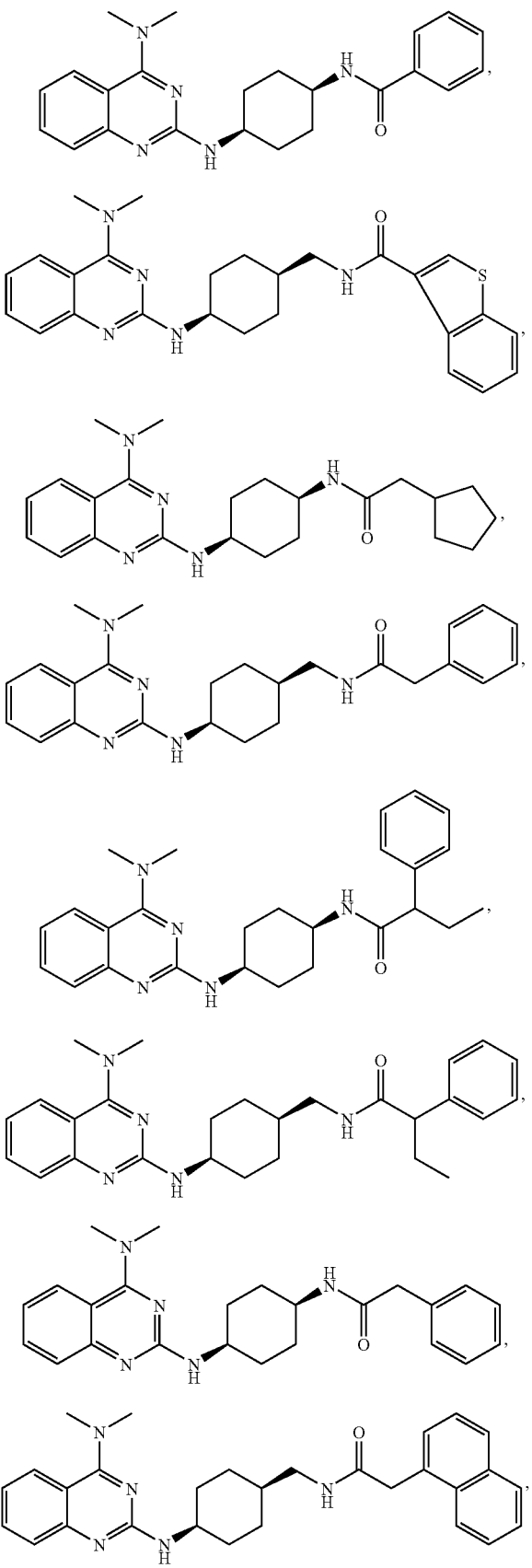
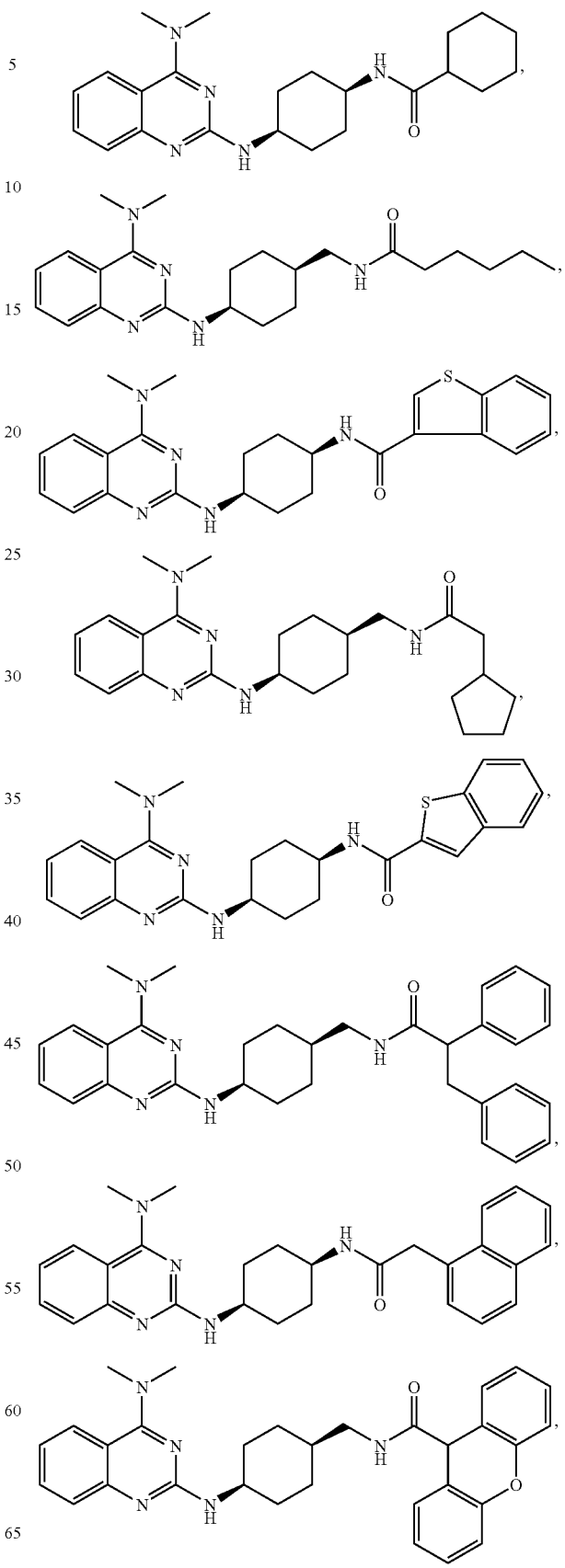

1877
-continued
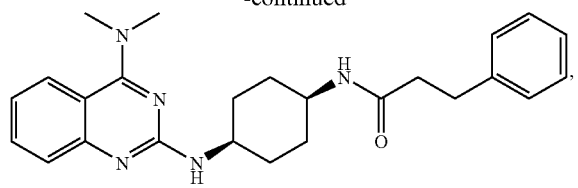
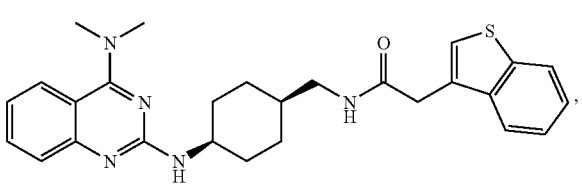
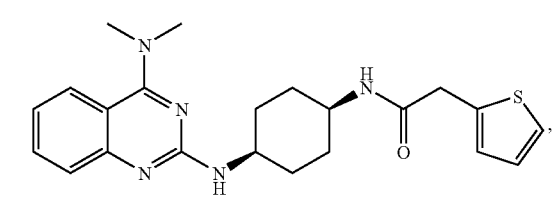
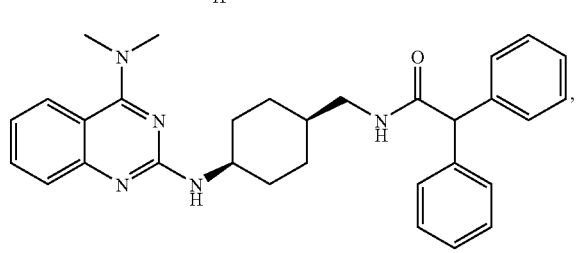
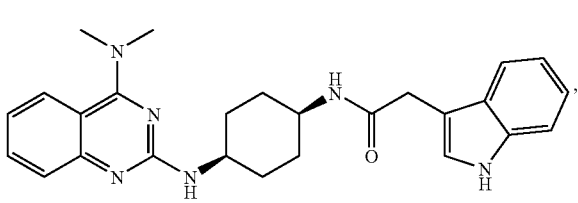
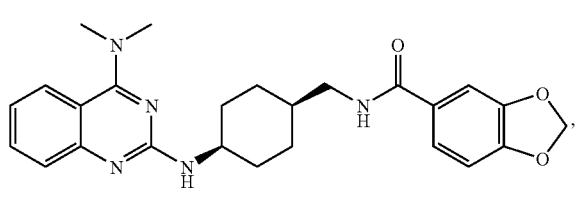
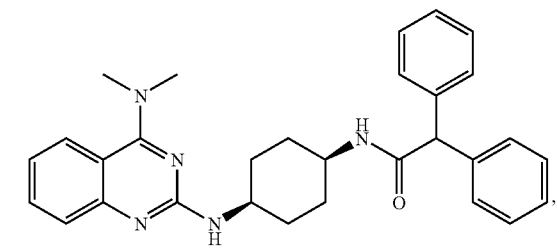
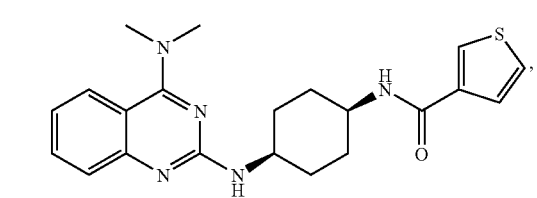
1878
-continued
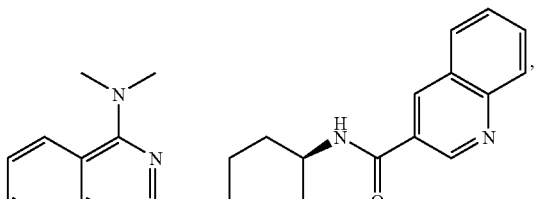
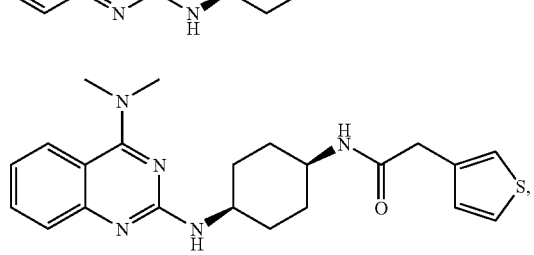
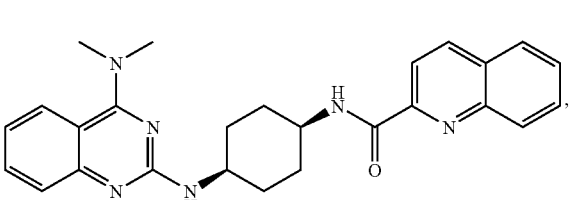
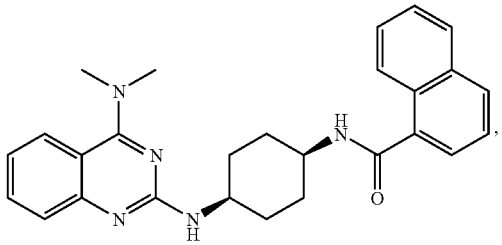
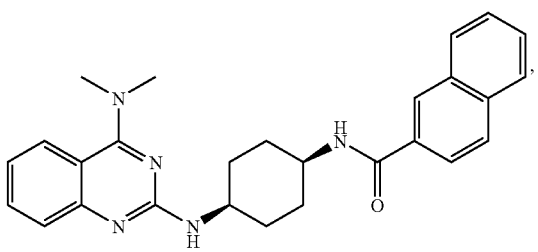
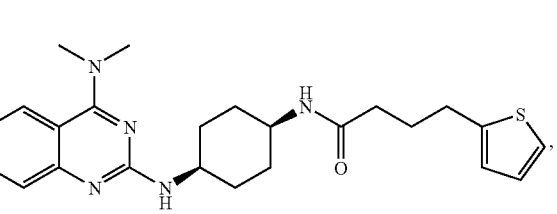
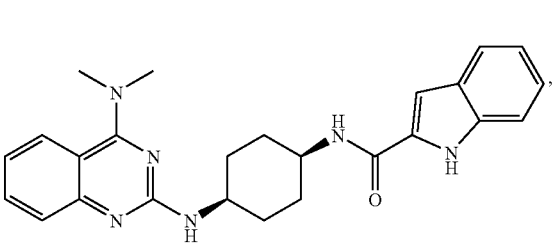

1879
-continued
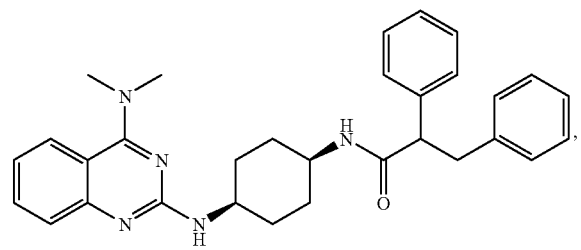
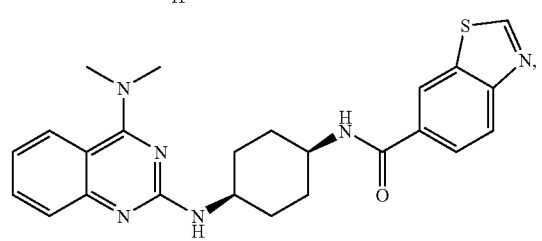
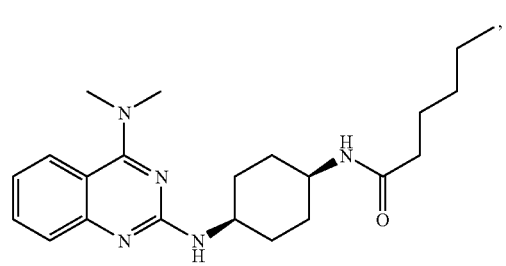
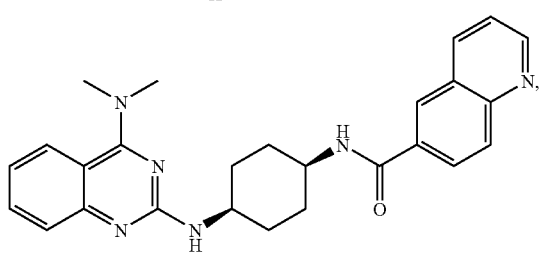
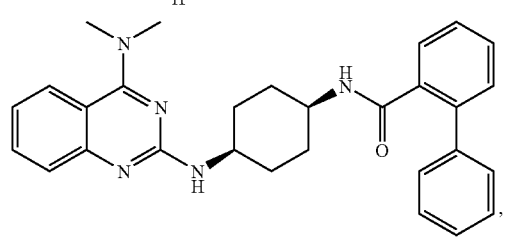
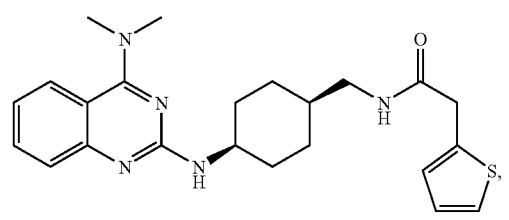
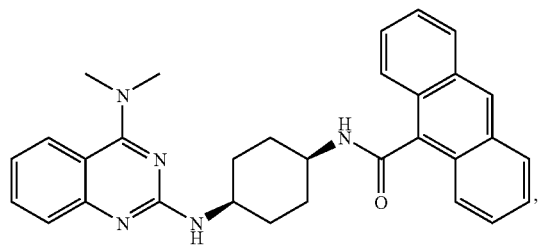
1880
-continued
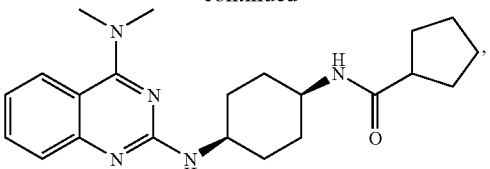
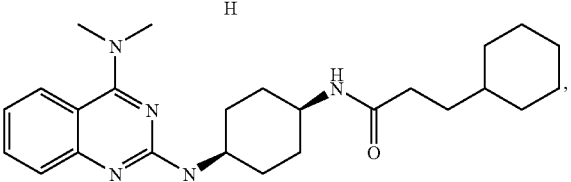
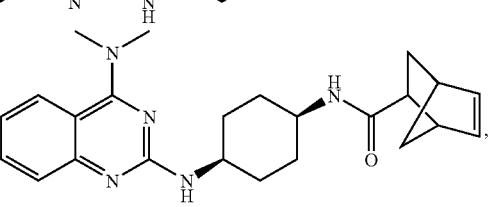
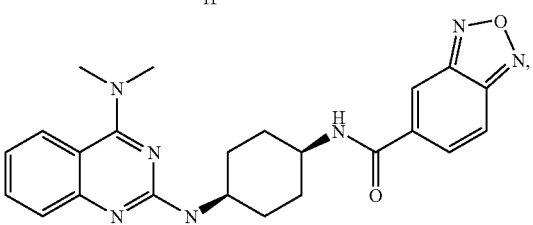
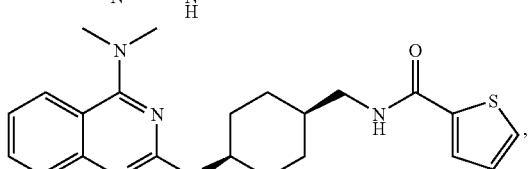
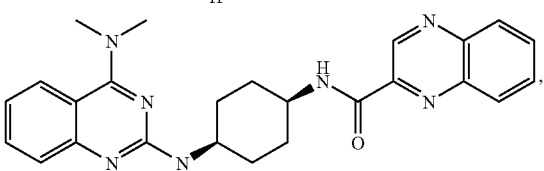
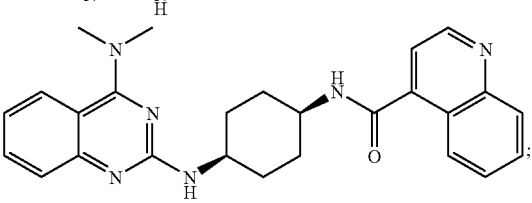
or a salt thereof.
3. A compound selected from the group consisting of
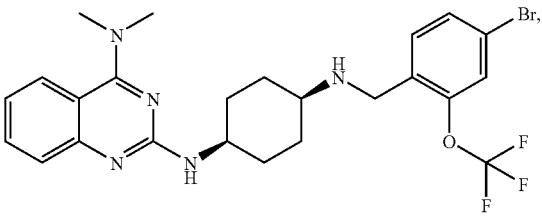

-continued

-continued
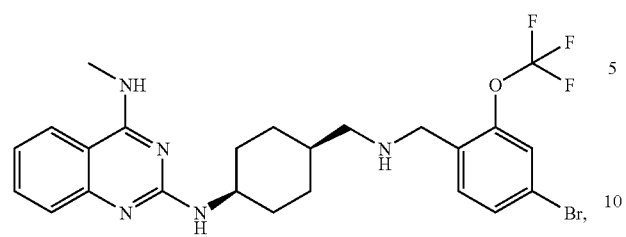
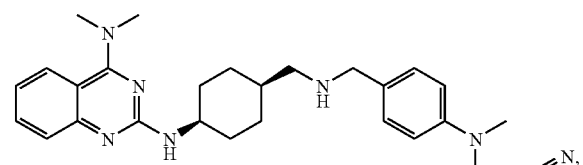
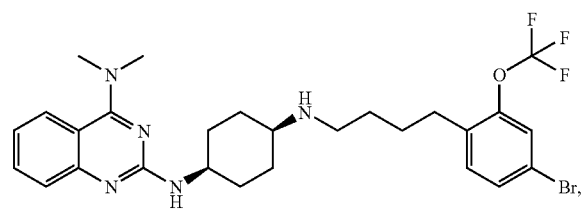
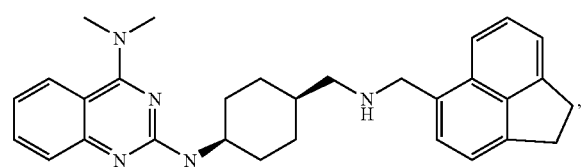
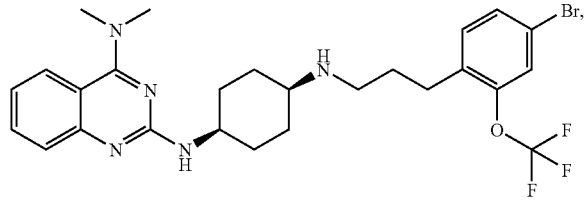
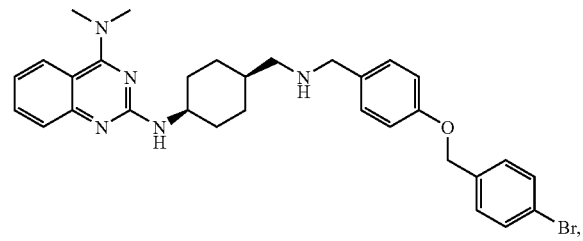
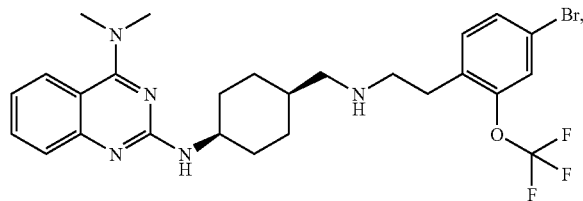
-continued
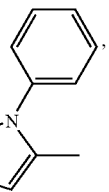
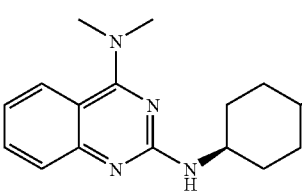
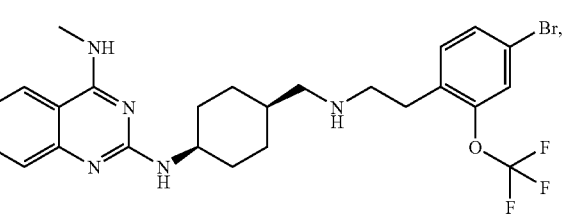
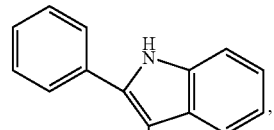
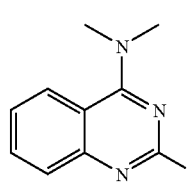
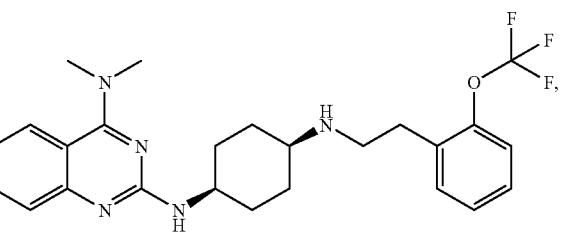
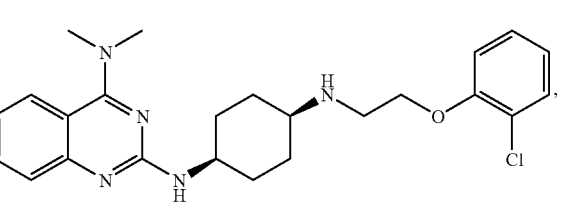
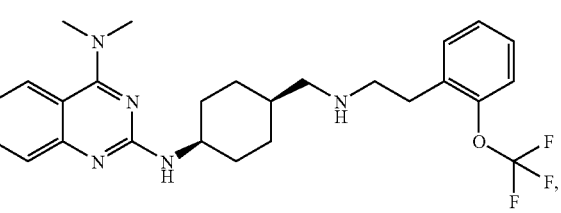

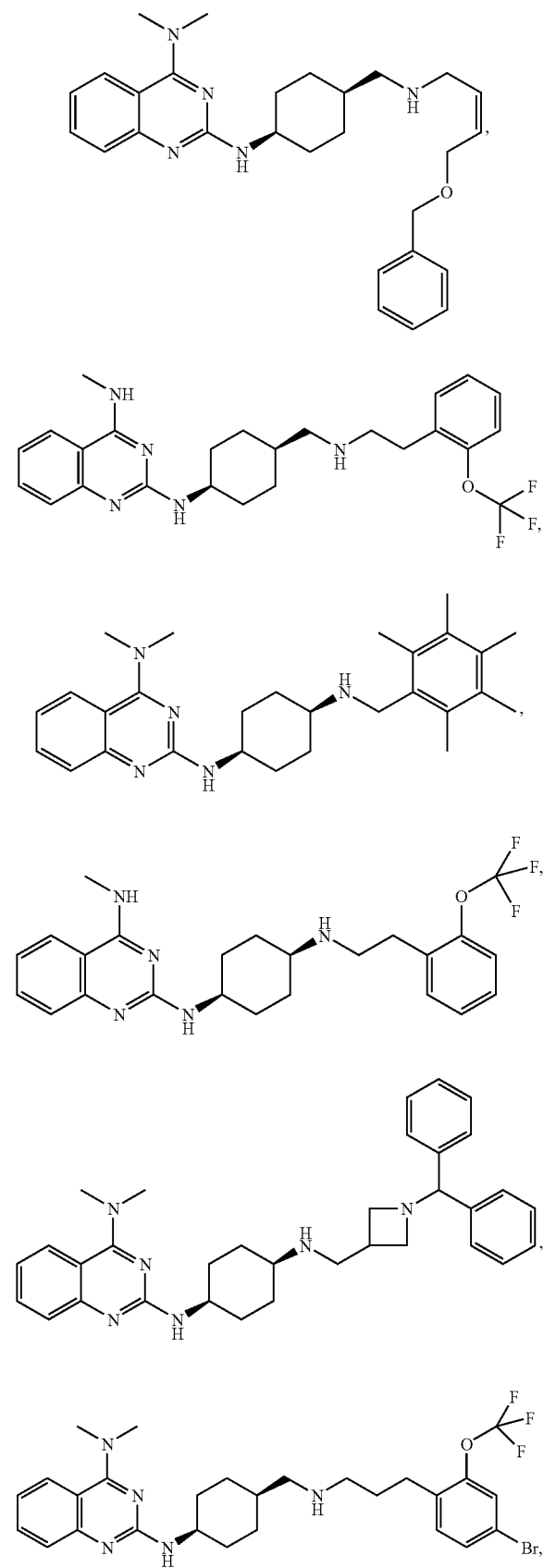

1887
-continued
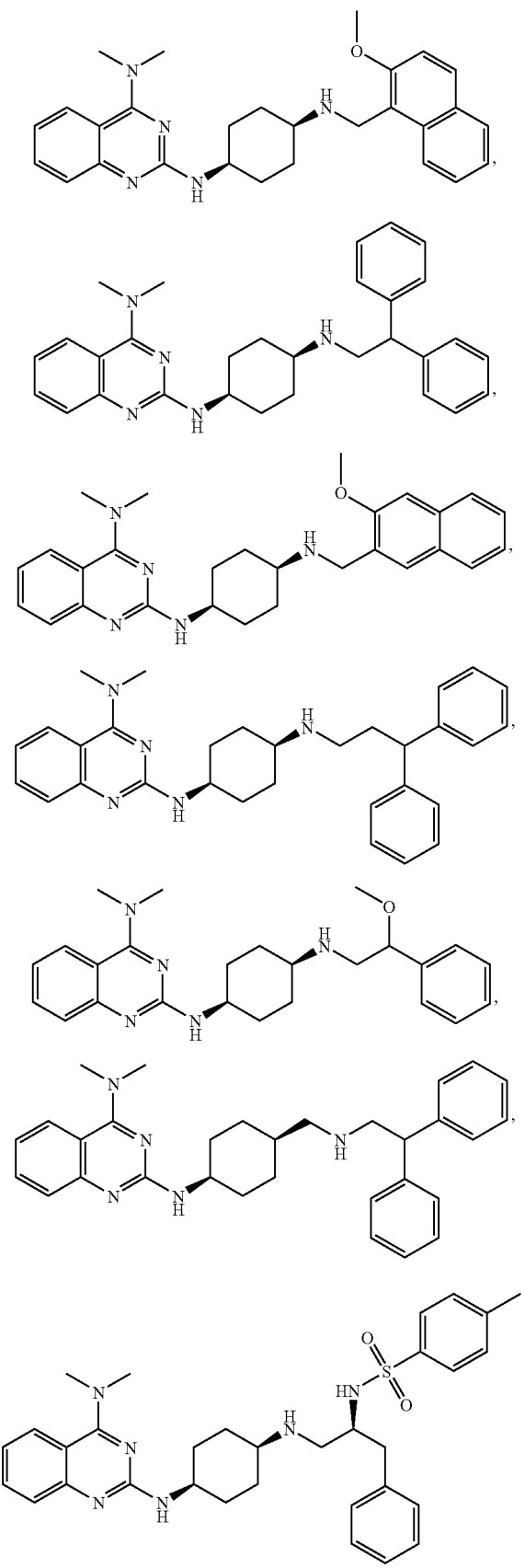
1888
-continued
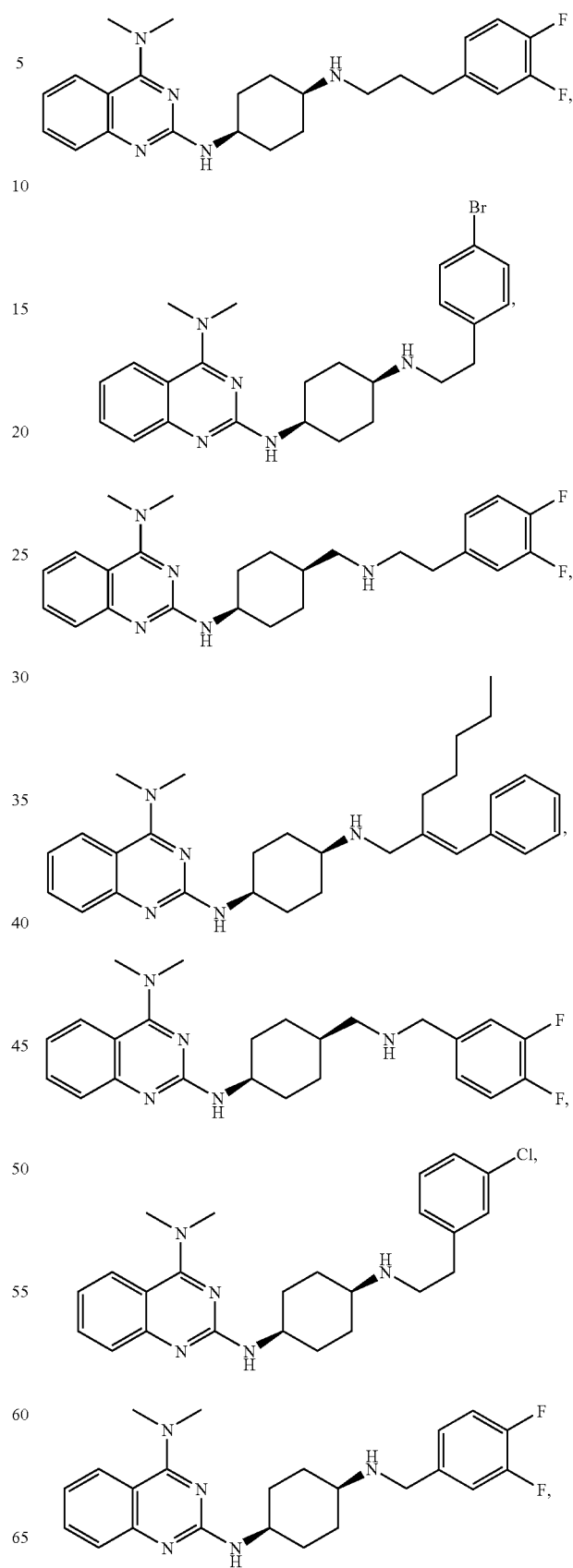

1889
-continued
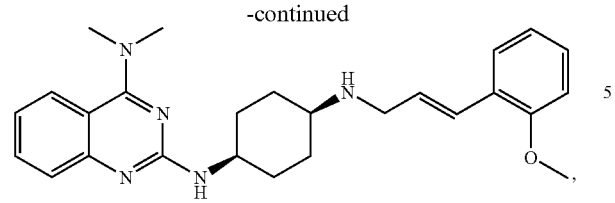
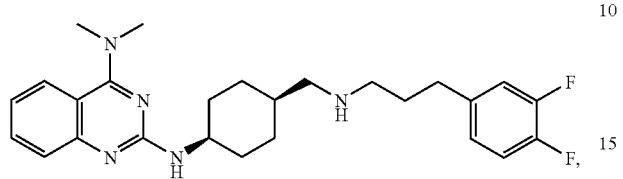
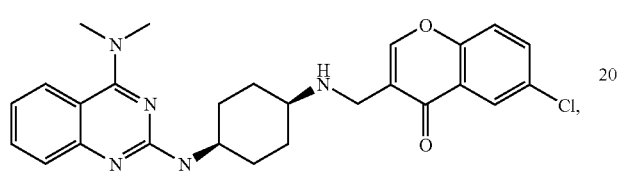
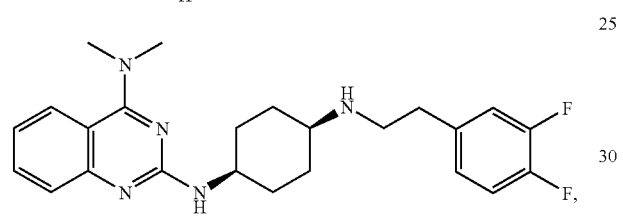
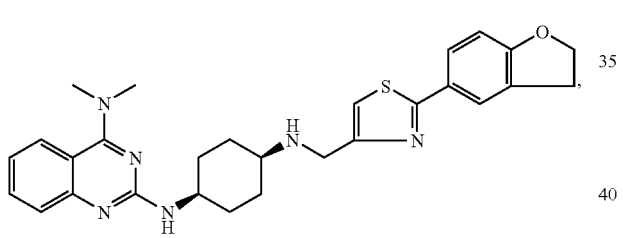
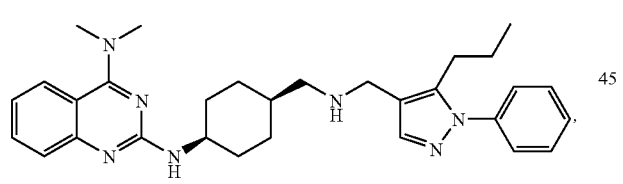
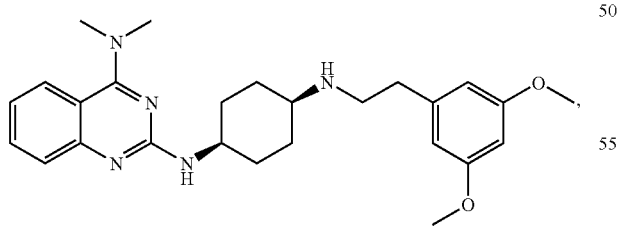
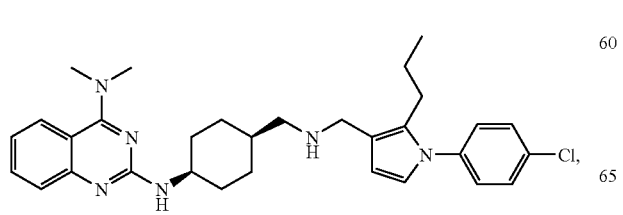
1890
-continued
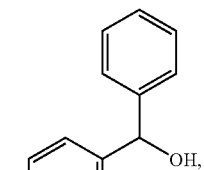
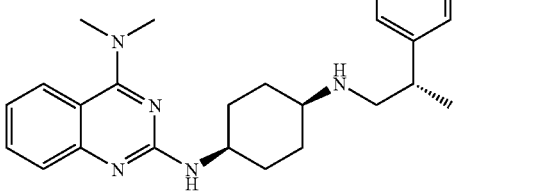
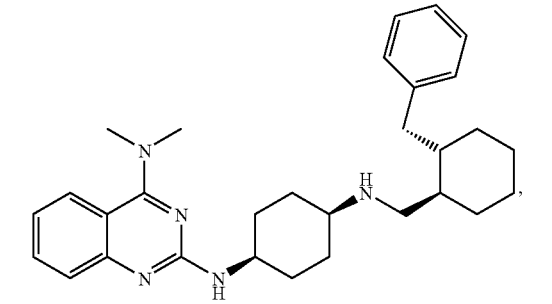
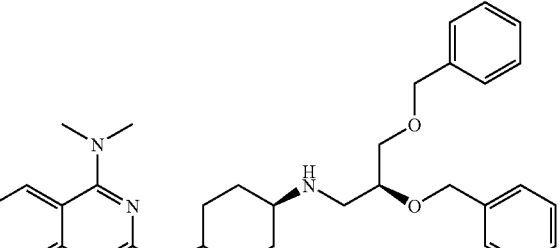
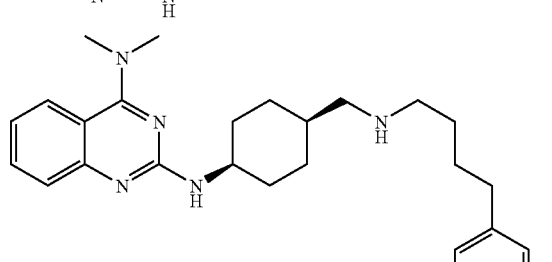
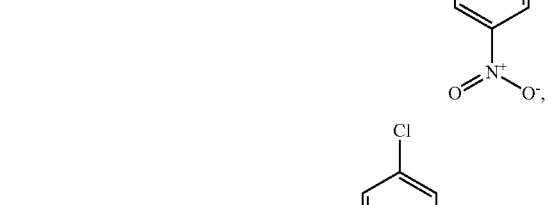
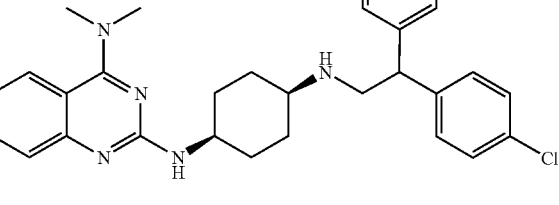

1891
-continued
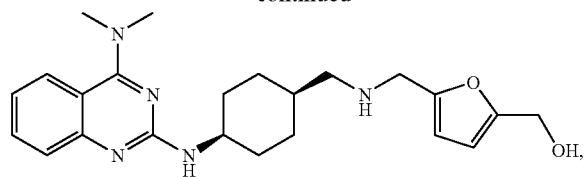
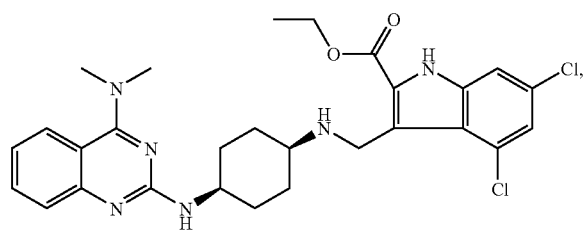
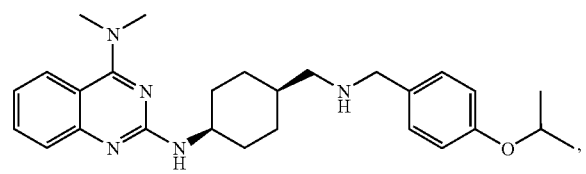
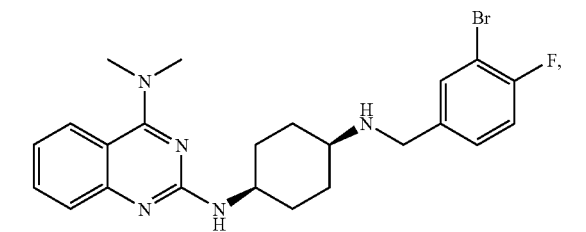
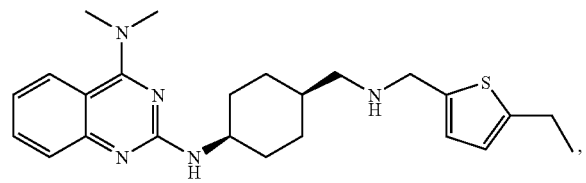
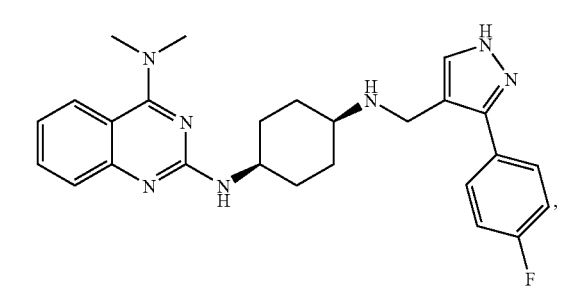
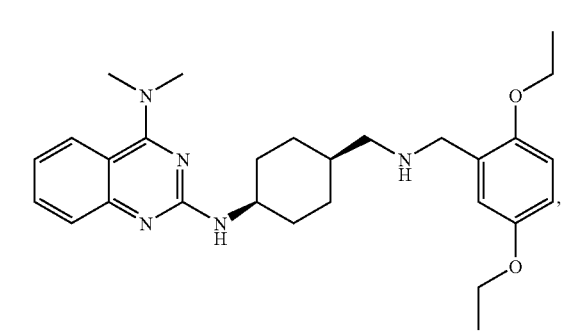
1892
-continued
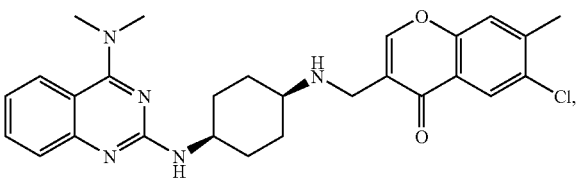
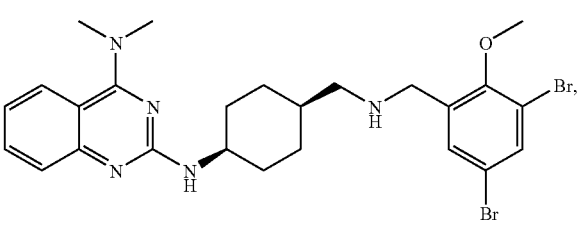
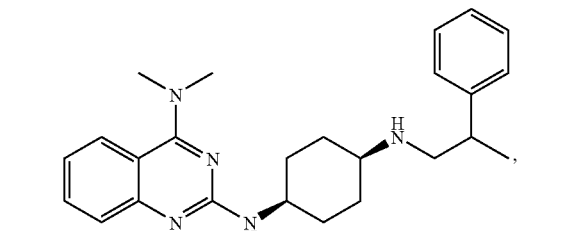
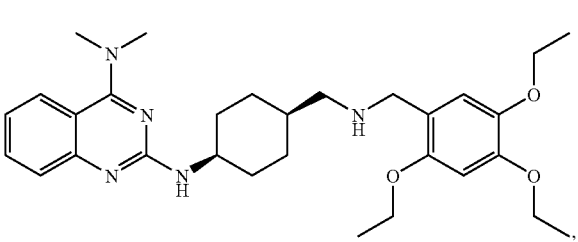
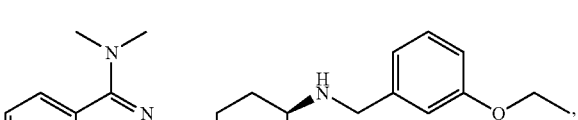
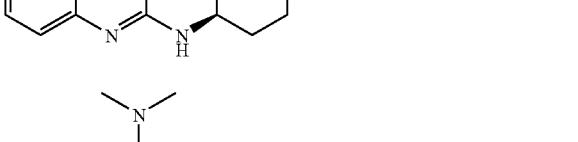
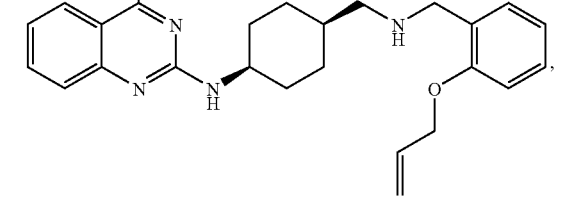
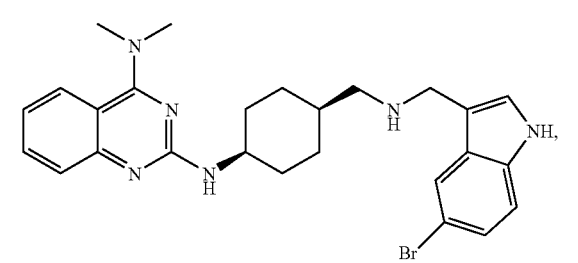

1893
-continued
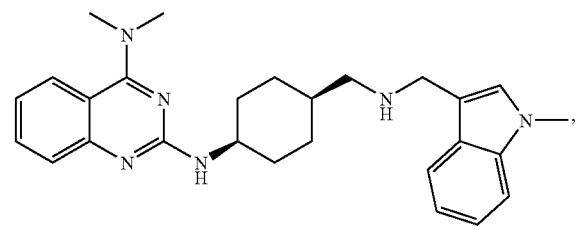
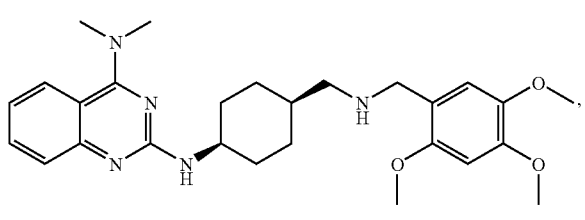
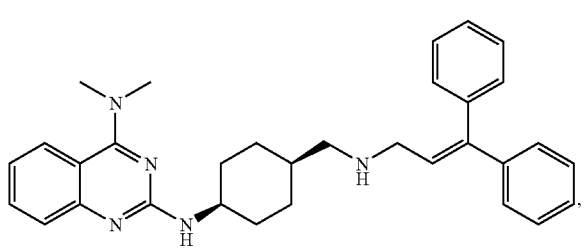
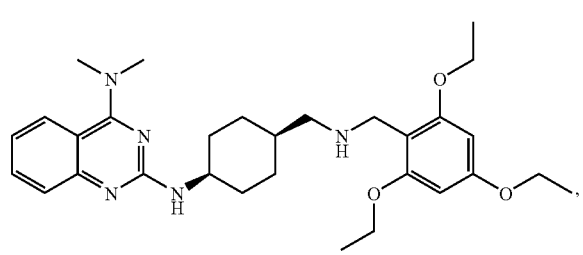
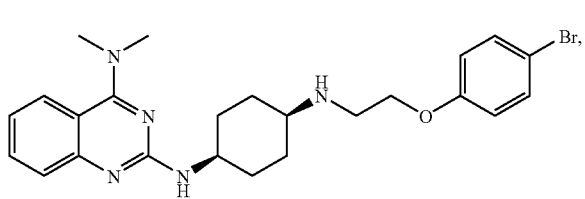
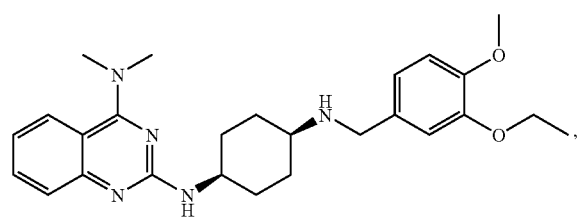
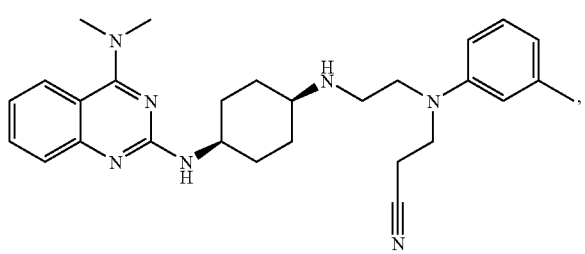
1894
-continued
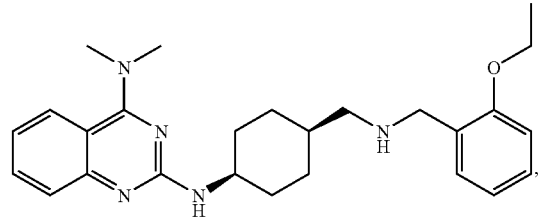
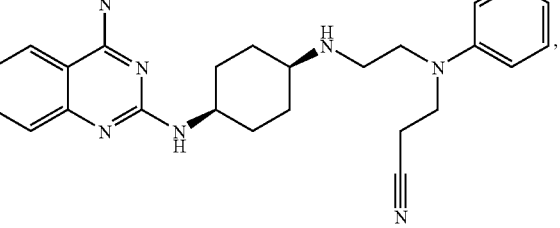
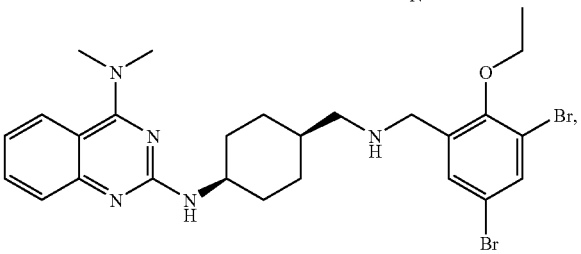
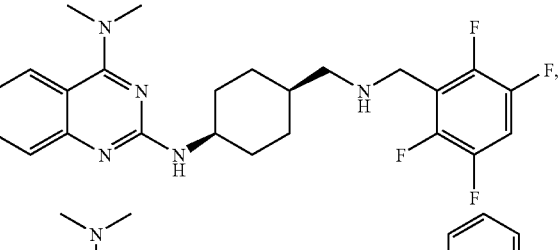
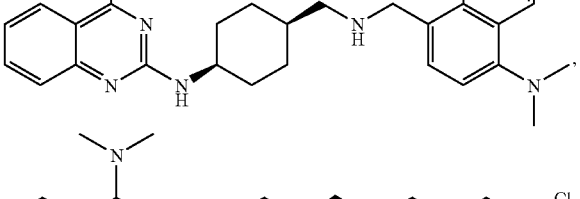
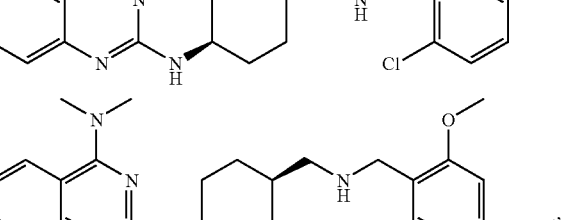
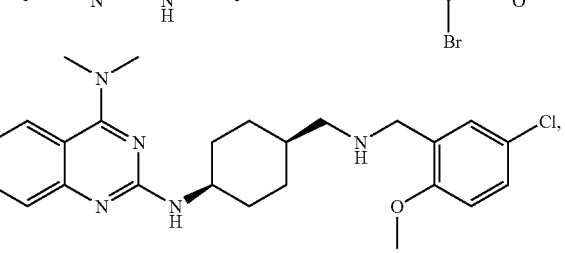

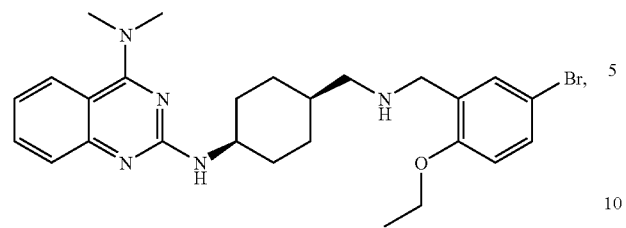
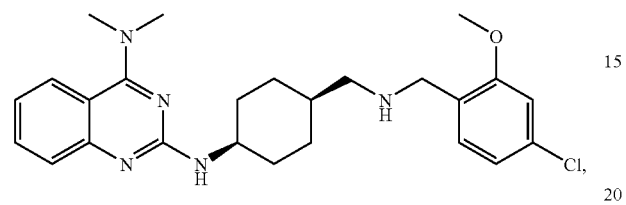
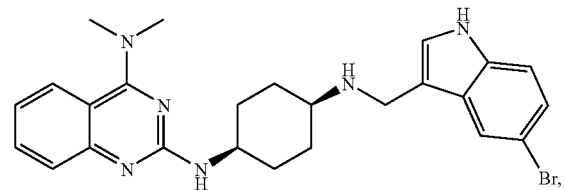
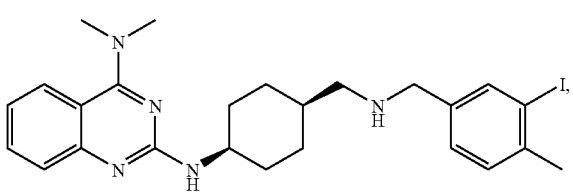
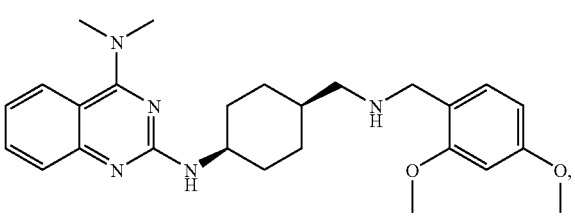
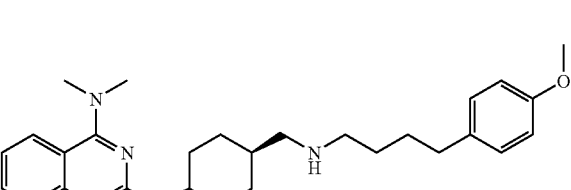
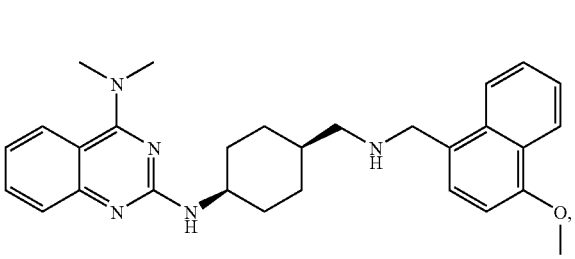
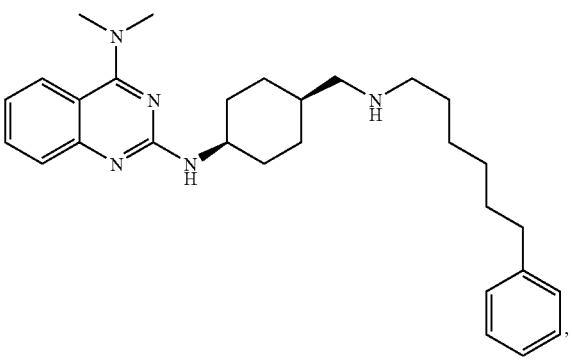
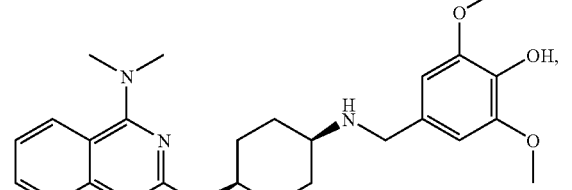
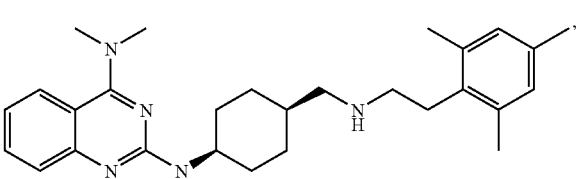
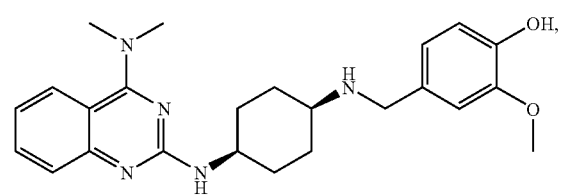
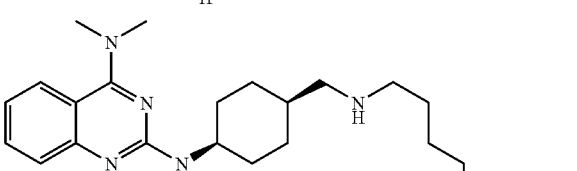
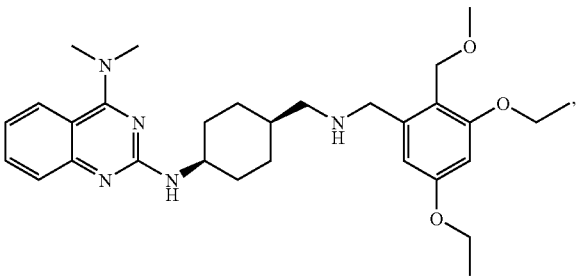

1897
-continued
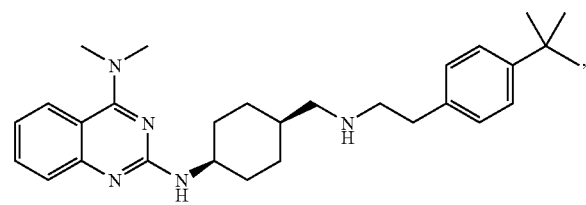
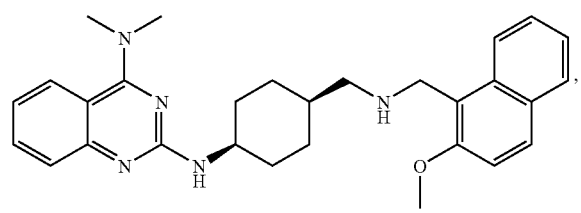
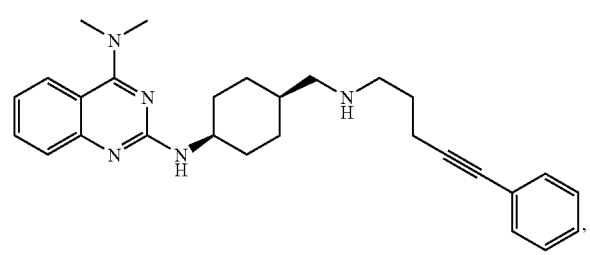
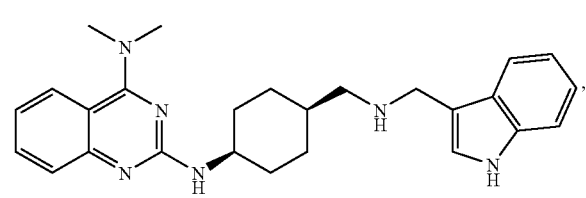
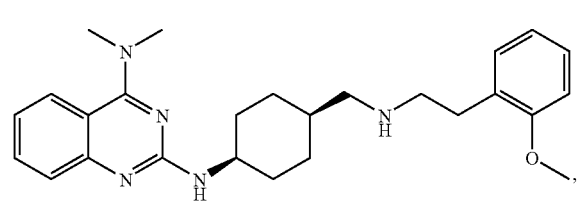
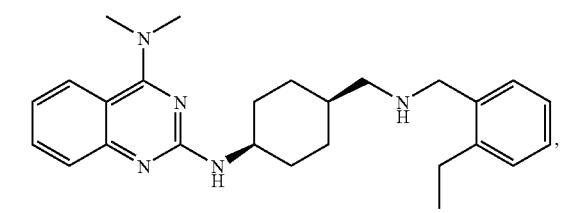
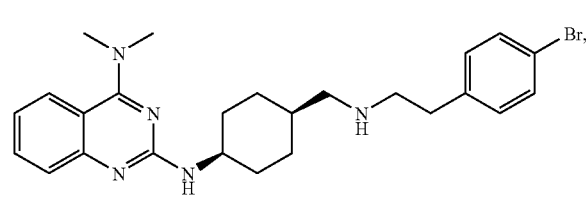
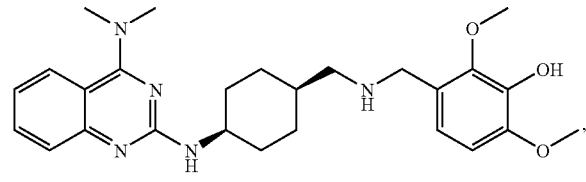
1898
-continued
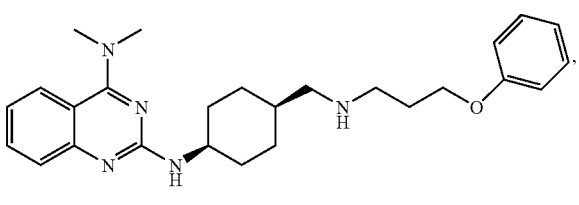
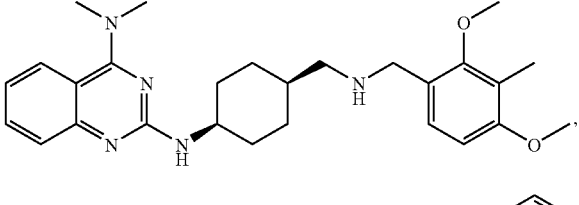
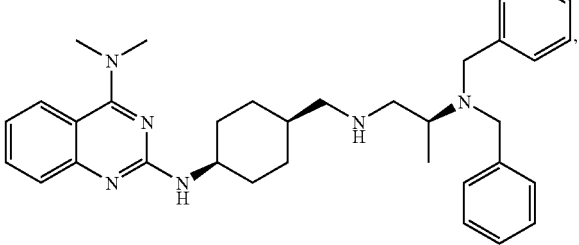
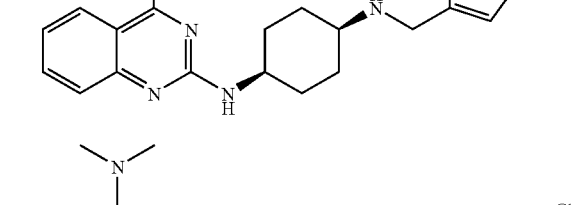
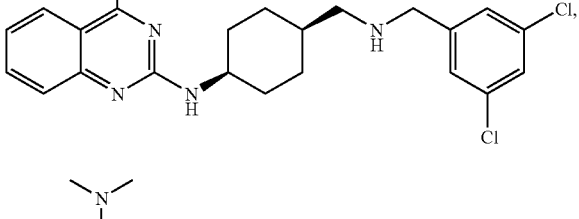
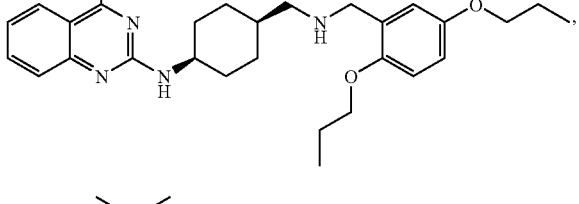

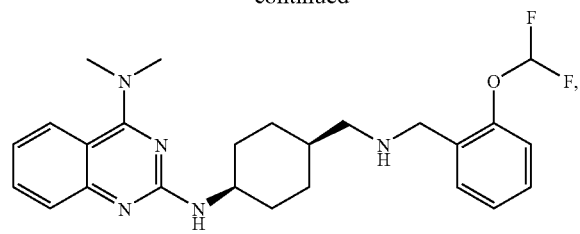
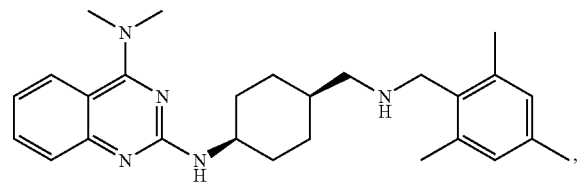
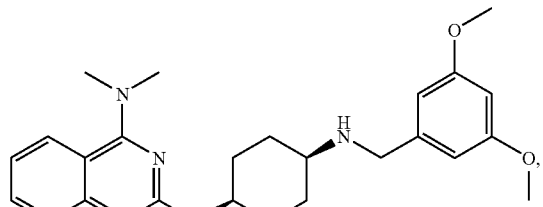
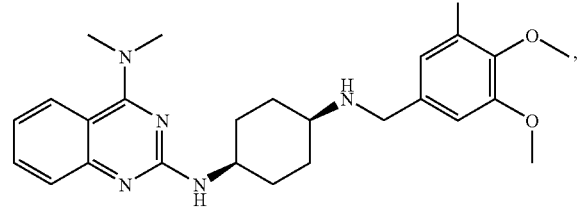
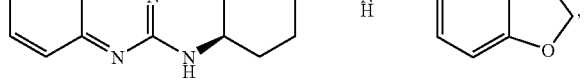
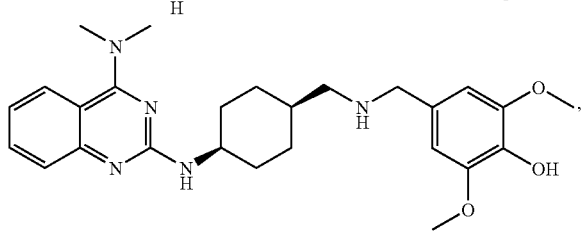

-continued
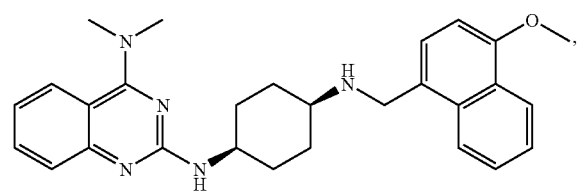
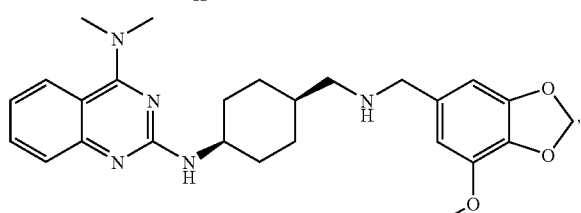
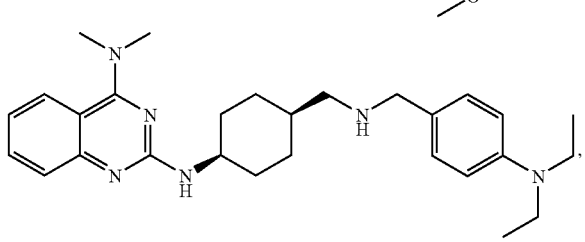
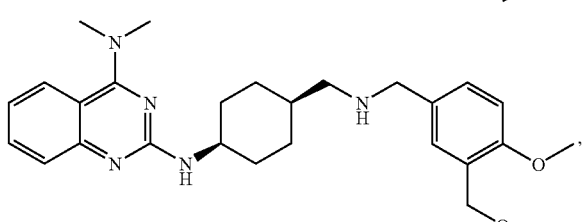
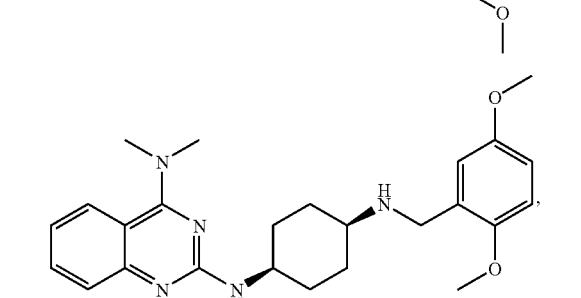
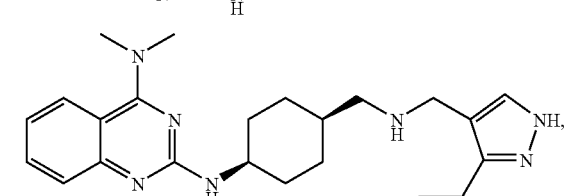
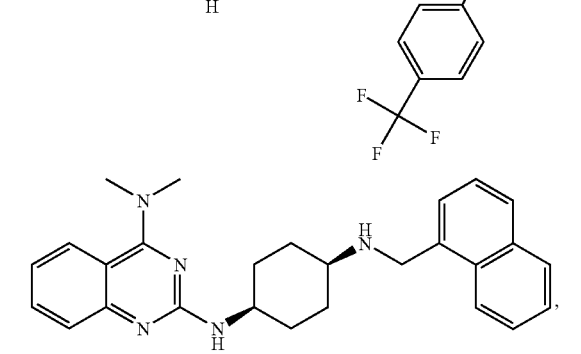
-continued
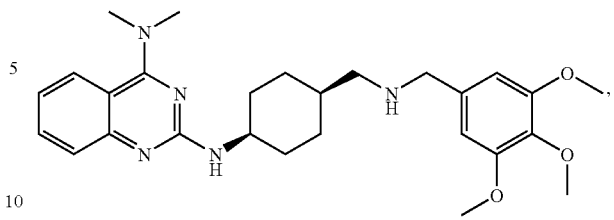
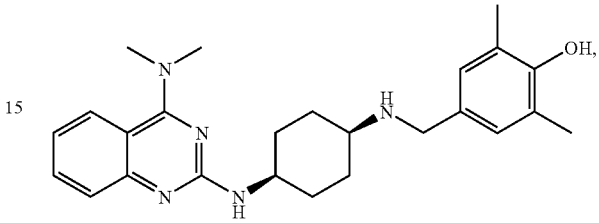
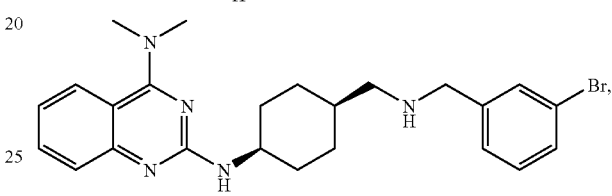
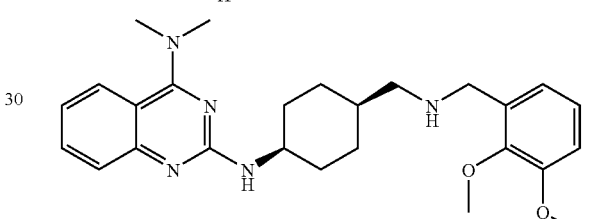
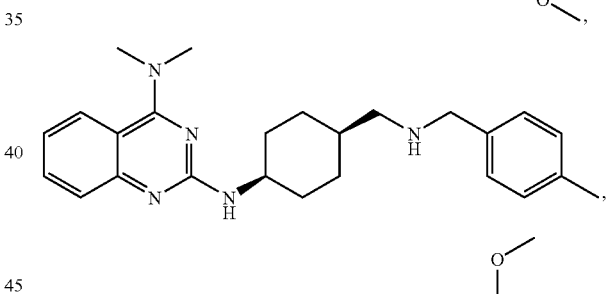
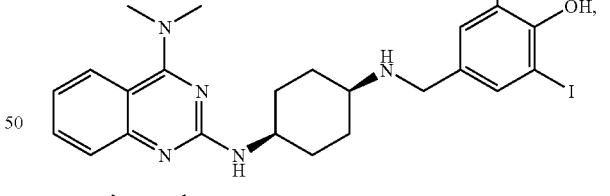
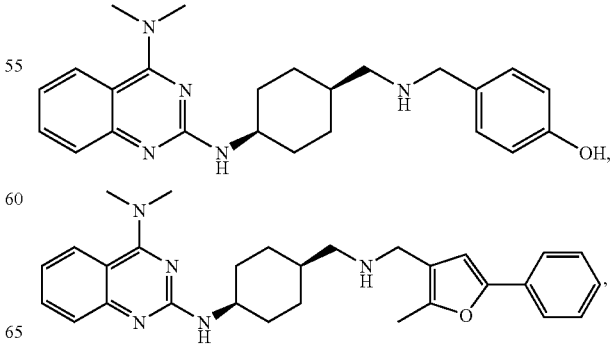

-continued
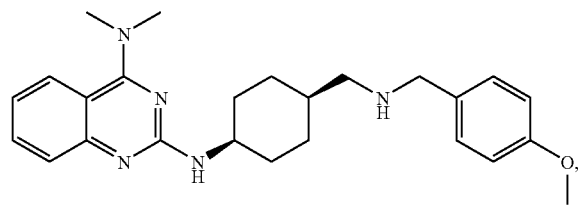
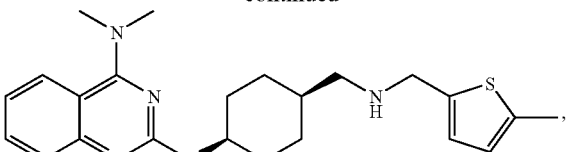
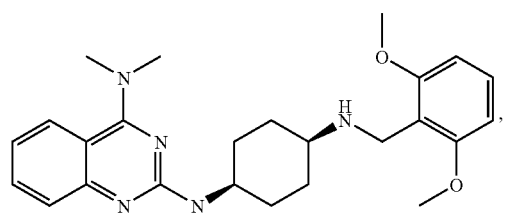
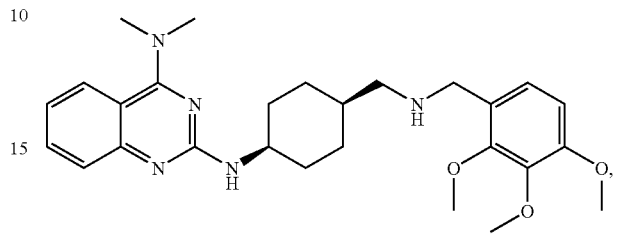
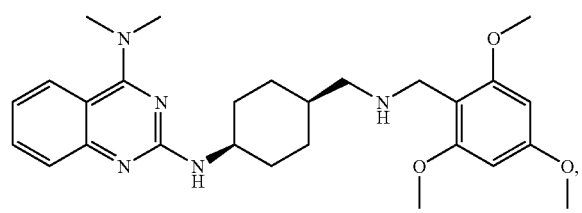
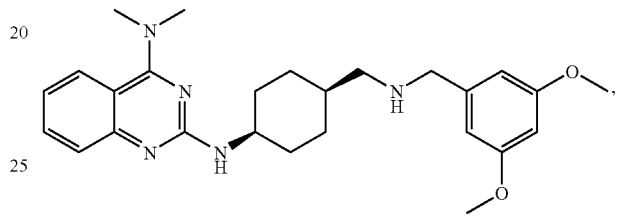
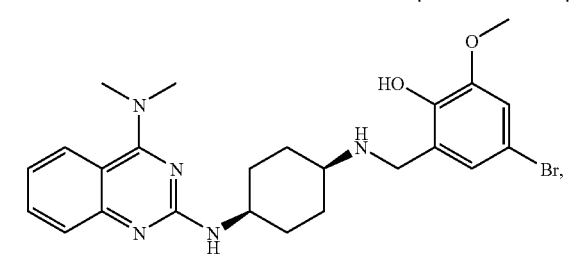
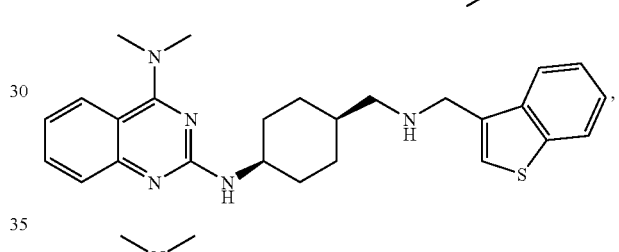
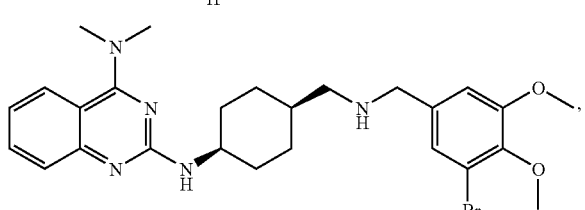
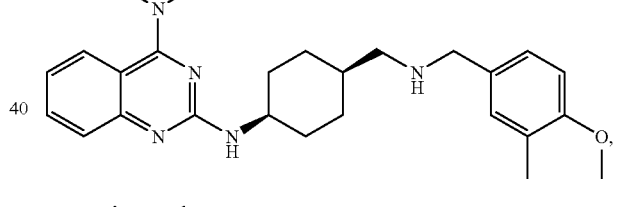
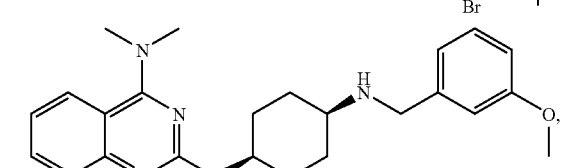
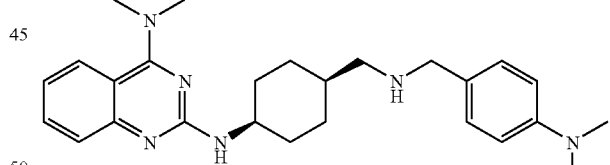
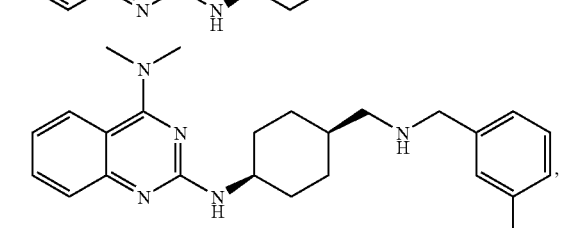
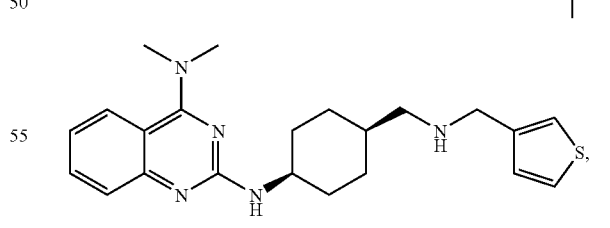
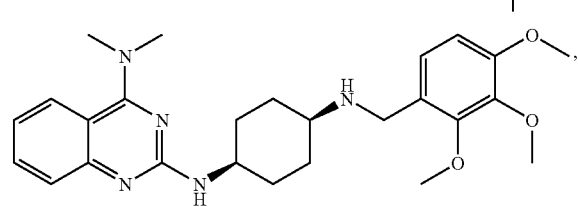
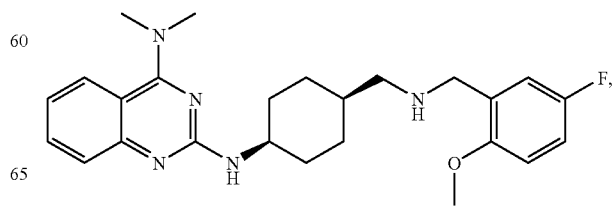

-continued
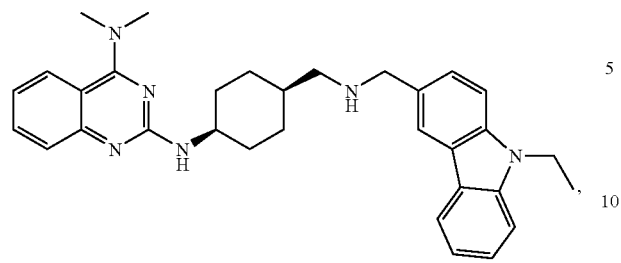
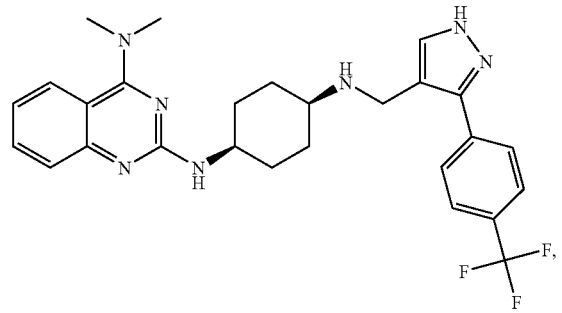
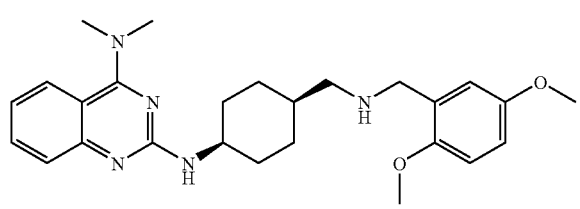
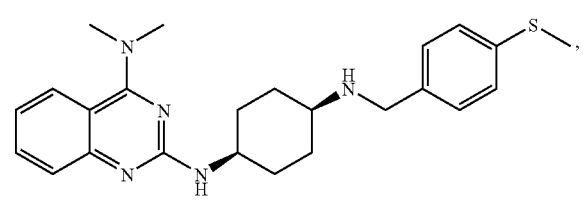
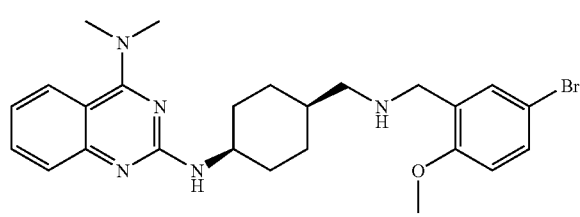
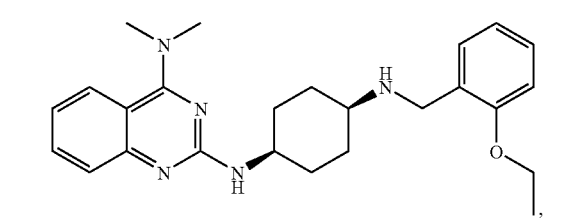
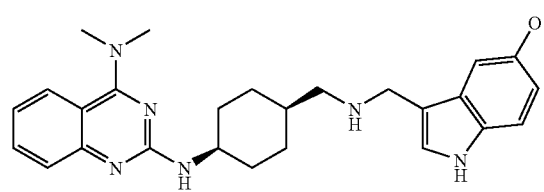
-continued
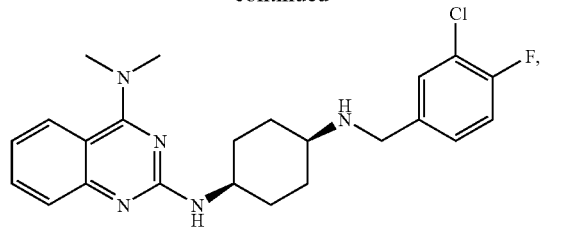
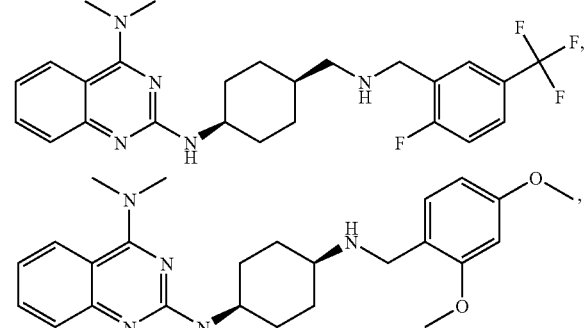
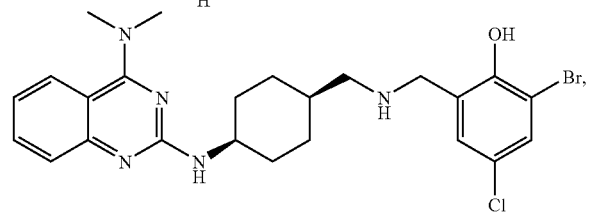
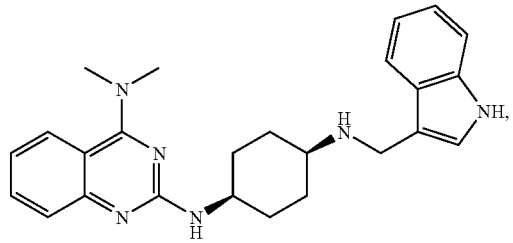
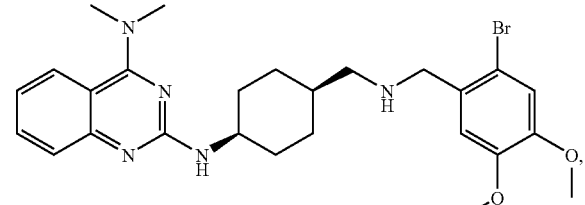
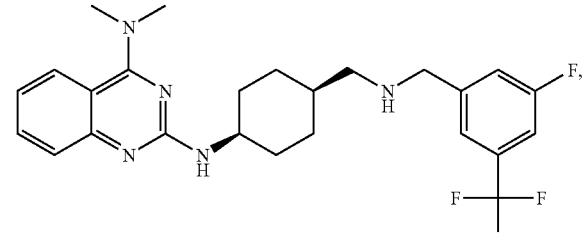
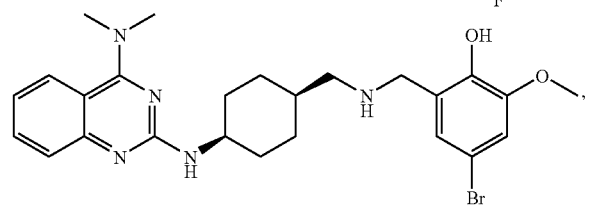

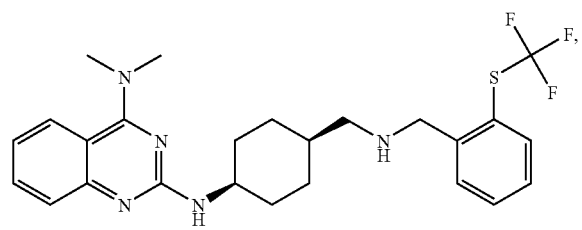
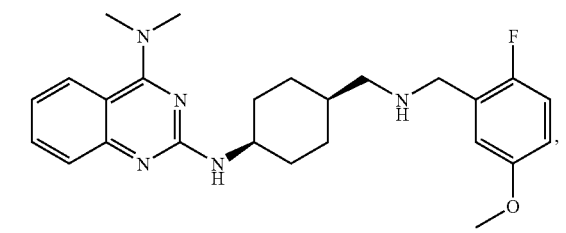
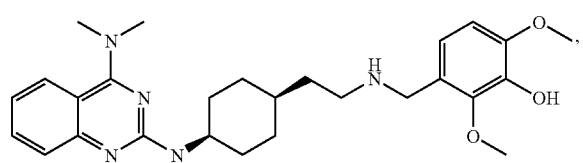
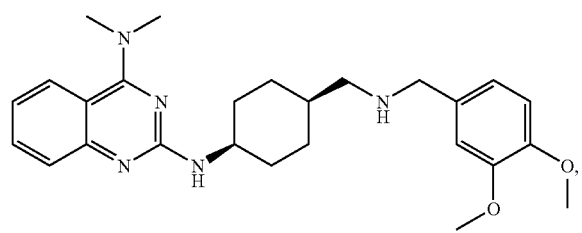
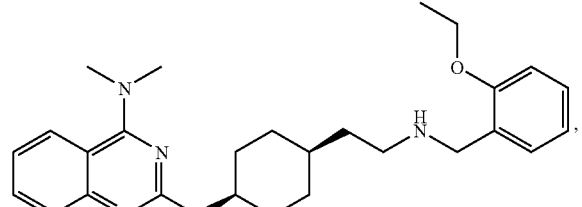
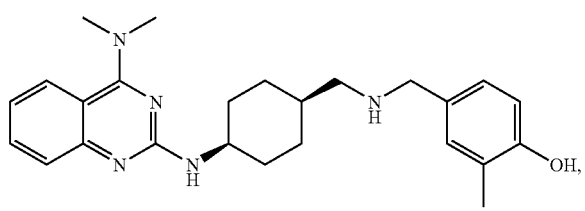
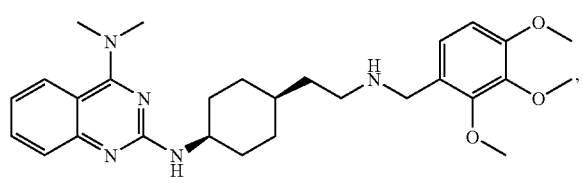
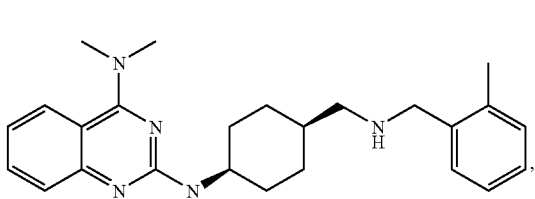
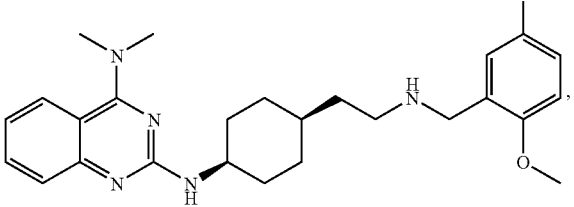
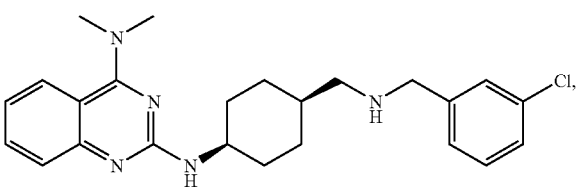
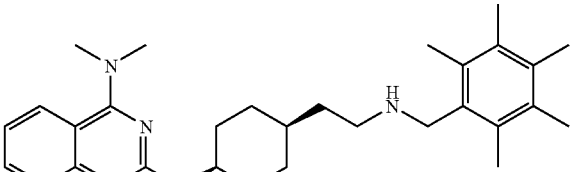
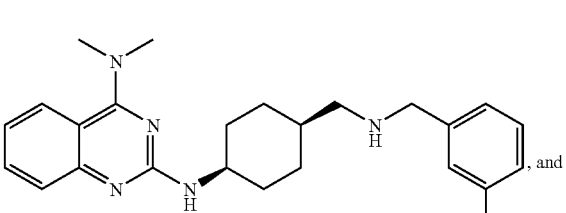
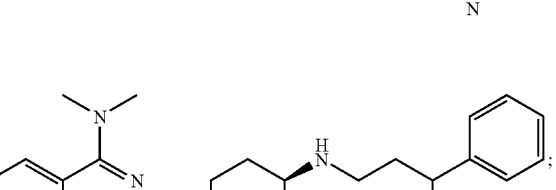
or a salt thereof.

4. A compound selected from the group consisting of
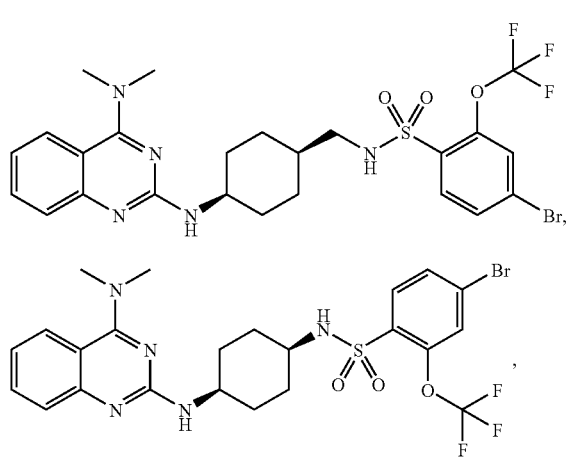
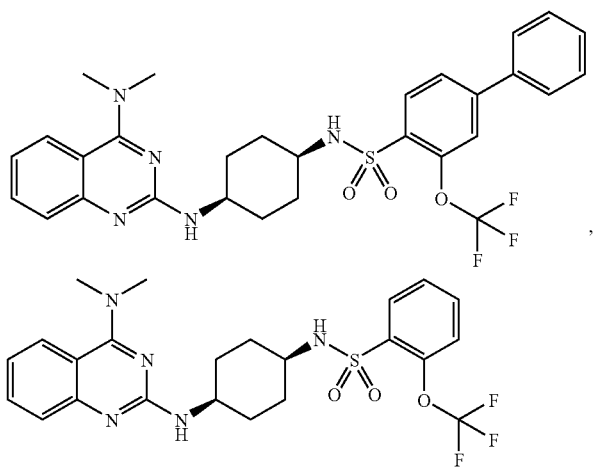
or a salt thereof.
* * * * *